US012723045B2

(12) United States Patent
McGowan et al.

(10) Patent No.: US 12,723,045 B2
(45) Date of Patent: Sep. 1, 2026

(54) TRICYCLIC DERIVATIVES AND RELATED USES

(71) Applicant: MOMA Therapeutics, Inc., Cambridge, MA (US)

(72) Inventors: Meredeth A. McGowan, Bedford, MA (US); John R. Butler, Thousand Oaks, CA (US); Momar Toure, Burlington, MA (US); Haoxuan Wang, Somerville, MA (US); Timothy J. Guzi, Sudbury, MA (US); Yonghong Bai, Lexington, MA (US); Michael H. Reutershan, Acton, MA (US); Xin Yan, Newton Highlands, MA (US); Laurie B. Schenkel, Belmont, MA (US); Cen Gao, Carmel, IN (US); Brian Alexander Sosa-Alvarado, Cambridge, MA (US)

(73) Assignee: MOMA Therapeutics, Inc., Cambridge, MA (US)

( * ) Notice: Subject to any disclaimer, the term of this patent is extended or adjusted under 35 U.S.C. 154(b) by 0 days.

(21) Appl. No.: 19/274,255

(22) Filed: Jul. 18, 2025

(65) Prior Publication Data

US 2025/0346600 A1 Nov. 13, 2025

Related U.S. Application Data

(63) Continuation of application No. PCT/US2024/045640, filed on Sep. 6, 2024.

(60) Provisional application No. 63/537,426, filed on Sep. 8, 2023, provisional application No. 63/654,502, filed on May 31, 2024, provisional application No. 63/684,749, filed on Aug. 19, 2024.

(51) Int. Cl.

| | |
|---|---|
| ***C07D 471/16*** | (2006.01) |
| ***A61K 31/437*** | (2006.01) |
| ***A61K 31/4375*** | (2006.01) |
| ***A61K 31/551*** | (2006.01) |
| ***C07D 487/16*** | (2006.01) |
| ***C07D 498/16*** | (2006.01) |
| ***C07D 519/00*** | (2006.01) |

(52) U.S. Cl.

CPC .......... *C07D 471/16* (2013.01); *A61K 31/437* (2013.01); *A61K 31/4375* (2013.01); *A61K 31/551* (2013.01); *C07D 487/16* (2013.01); *C07D 498/16* (2013.01); *C07D 519/00* (2013.01)

(58) Field of Classification Search

CPC .................................................... C07D 471/16

See application file for complete search history.

(56) References Cited

U.S. PATENT DOCUMENTS

| | | | |
|---|---|---|---|
| 11,530,413 | B2 | 12/2022 | Billy et al. |
| 2006/0089378 | A1 | 4/2006 | Xia et al. |
| 2007/0015812 | A1 | 1/2007 | Boehringer et al. |
| 2016/0185777 | A1 | 6/2016 | Hartman et al. |
| 2017/0158691 | A1 | 6/2017 | Hartman et al. |

FOREIGN PATENT DOCUMENTS

| | | | |
|---|---|---|---|
| CN | 102134243 | A | 7/2011 |
| CN | 102166215 | A | 8/2011 |
| CN | 103087067 | A | 5/2013 |
| CN | 118684676 | A | 9/2024 |
| CN | 118684677 | A | 9/2024 |
| WO | WO 2002/012242 | A2 | 2/2002 |
| WO | WO 2003/035065 | A1 | 5/2003 |
| WO | WO 2004/064778 | A2 | 8/2004 |
| WO | WO 2004/069162 | A2 | 8/2004 |
| WO | WO 2009/038812 | A1 | 3/2009 |
| WO | WO 2009/138440 | A1 | 11/2009 |
| WO | WO 2013/055984 | A1 | 4/2013 |
| WO | WO 2016/038045 | A1 | 3/2016 |
| WO | WO 2016/086200 | A1 | 6/2016 |
| WO | WO 2019/016772 | A2 | 1/2019 |
| WO | WO 2019/157014 | A1 | 8/2019 |
| WO | WO 2019/177975 | A1 | 9/2019 |
| WO | WO 2022/249060 | A1 | 12/2022 |

(Continued)

OTHER PUBLICATIONS

Ames, B. et al., "Methods for detecting carcinogens and mutagens with the *Salmonella*/mammalian-microsome mutagenicity test," Mutat Res. Dec. 1975;31(6):pp. 347-364.

(Continued)

*Primary Examiner* — Svetlana M Ivanova

(74) *Attorney, Agent, or Firm* — Fenwick & West LLP; Heidi Erlacher; Christine McCain

(57) ABSTRACT

The present disclosure relates to compounds of Formula (I'):

(I')

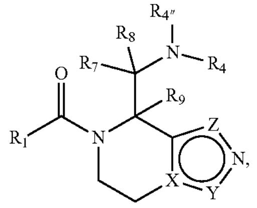

and to their prodrugs, pharmaceutically acceptable salts, pharmaceutical compositions, methods of use, and methods for their preparation. The compounds disclosed herein are useful for modulating Werner Helicase (WRN) activity and may be used in the treatment of disorders in which WRN activity is implicated, such as cancer.

21 Claims, No Drawings

(56) References Cited

FOREIGN PATENT DOCUMENTS

| | | | |
|---|---|---|---|
| WO | WO 2023/062575 | A1 | 4/2023 |
| WO | WO 2024/010782 | A1 | 1/2024 |
| WO | WO 2024/010784 | A1 | 1/2024 |
| WO | WO 2024/028169 | A1 | 2/2024 |
| WO | WO 2024/079623 | A1 | 4/2024 |
| WO | WO 2024/105553 | A1 | 5/2024 |
| WO | WO 2024/105610 | A1 | 5/2024 |
| WO | WO 2024/120378 | A2 | 6/2024 |
| WO | WO 2024/140597 | A1 | 7/2024 |
| WO | WO 2024/155884 | A1 | 7/2024 |
| WO | WO 2024/187049 | A1 | 9/2024 |
| WO | WO 2024/199108 | A1 | 10/2024 |
| WO | WO 2024/199109 | A1 | 10/2024 |
| WO | WO 2024/220887 | A1 | 10/2024 |
| WO | WO 2024/230828 | A1 | 11/2024 |
| WO | WO 2024/235292 | A1 | 11/2024 |
| WO | WO 2024/246862 | A1 | 12/2024 |
| WO | WO 2024/246863 | A1 | 12/2024 |
| WO | WO 2024/254511 | A2 | 12/2024 |
| WO | WO 2024/254602 | A1 | 12/2024 |
| WO | WO 2024/255765 | A1 | 12/2024 |
| WO | WO 2024/255790 | A1 | 12/2024 |
| WO | WO 2024/259048 | A2 | 12/2024 |
| WO | WO 2025/002413 | A1 | 1/2025 |
| WO | WO 2025/014846 | A1 | 1/2025 |
| WO | WO 2025/014877 | A2 | 1/2025 |
| WO | WO 2025/040168 | A1 | 2/2025 |
| WO | WO 2025/045145 | A1 | 3/2025 |
| WO | WO 2025/049746 | A1 | 3/2025 |
| WO | WO 2025/054488 | A1 | 3/2025 |
| WO | WO 2025/073792 | A1 | 4/2025 |

OTHER PUBLICATIONS

André, T. et al., "Antitumor activity and safety of dostarlimab monotherapy in patients with mismatch repair deficient solid tumors: a nonrandomized controlled trial," JAMA Netw Open. 2023;6(11), 15 pages.
André, T. et al., "Nivolumab plus Ipilimumab in Microsatellite-Instability-High Metastatic Colorectal Cancer," N Engl J Med. Nov. 27, 2024;391(21), pp. 2014-2026.
Baltgalvis, K. A. et al., "Chemoproteomic discovery of a covalent allosteric inhibitor of WRN helicase," Nature 629.8011 (2024): pp. 435-442.
Behan, F. M. et al., "Prioritization of cancer therapeutic targets using CRISPR-Cas9 screens," Nature, Apr. 10, 2019;568: pp. 511-516.
Bonneville R. et al., " Landscape of microsatellite instability across 39 cancer types," JCO Precis Oncol. 2017; 15 pages.
CAS RN 1072096-59-3, Date retrieved: Oct. 7, 2022, 1 page.
CAS RN 1072097-06-3, Date retrieved: Oct. 7, 2022, 1 page.
CAS RN 1072097-46-1, Date retrieved: Oct. 7, 2022, 1 page.
CAS RN 1072097-50-7, Date retrieved: Oct. 7, 2022, 1 page.
CAS RN 1072097-66-5, Date retrieved: Oct. 7, 2022, 1 page.
CAS RN 1072097-88-1, Date retrieved: Oct. 7, 2022, 1 page.
CAS RN 1072097-97-2, Date retrieved: Oct. 7, 2022, 1 page.
CAS RN 1072098-14-6, Date retrieved: Oct. 7, 2022, 1 page.
CAS RN 1072098-70-4, Date retrieved: Oct. 7, 2022, 1 page.
CAS RN 1072104-18-7, Date retrieved: Oct. 7, 2022, 1 page.
CAS RN 1072104-25-6, Date retrieved: Oct. 7, 2022, 1 page.
CAS RN 1072104-33-6, Date retrieved: Oct. 7, 2022, 1 page.
CAS RN 1151660-73-9, Date entered STN: Jul. 12, 2015, Date retrieved: Oct. 7, 2022, 1 page.
CAS RN 1151660-74-0, Date entered STN: Jul. 12, 2015, Date retrieved: Oct. 7, 2022, 1 page.
CAS RN 1151660-75-1, Date entered STN: Jul. 12, 2015, Date retrieved: Oct. 7, 2022, 1 page.
CAS RN 1151660-76-2, Date entered STN: Jul. 12, 2015, Date retrieved: Oct. 7, 2022, 1 page.
CAS RN 1151660-90-0, Date entered STN: Jul. 12, 2015, Date retrieved: Oct. 7, 2022, 1 page.
CAS RN 1151660-91-1, Date entered STN: Jul. 12, 2015, Date retrieved: Oct. 7, 2022, 1 page.
CAS RN 1357104-18-7, Date retrieved: Oct. 7, 2022, 1 page.
CAS RN 1357104-19-8, Date retrieved: Oct. 7, 2022, 1 page.
CAS RN 1357104-20-1, Date retrieved: Oct. 7, 2022, 1 page.
CAS RN 1357104-21-2, Date retrieved: Oct. 7, 2022, 1 page.
CAS RN 1357104-27-8, Date retrieved: Oct. 7, 2022, 1 page.
CAS RN 1357104-28-9, Date retrieved: Oct. 7, 2022, 1 page.
CAS RN 1357104-29-0, Date retrieved: Oct. 7, 2022, 1 page.
CAS RN 1357104-30-3, Date retrieved: Oct. 7, 2022, 1 page.
CAS RN 1370438-74-6, Date retrieved: Oct. 7, 2022, 1 page.
CAS RN 1427532-76-0, Date retrieved: Oct. 7, 2022, 1 page.
CAS RN 1430216-79-7, Date retrieved: Oct. 7, 2022, 1 page.
CAS RN 1430217-07-4, Date retrieved: Oct. 7, 2022, 1 page.
CAS RN 1430217-08-5, Date retrieved: Oct. 7, 2022, 1 page.
CAS RN 1430218-38-4, Date retrieved: Oct. 7, 2022, 1 page.
CAS RN 157397-44-9, Date retrieved: Oct. 7, 2022, 1 page.
CAS RN 157397-45-0, Date retrieved: Oct. 7, 2022, 1 page.
CAS RN 1627900-25-7, Date retrieved: Oct. 7, 2022, 1 page.
CAS RN 1627900-30-4, Date retrieved: Oct. 7, 2022, 1 page.
CAS RN 1798911-72-4, Date entered STN: Jul. 12, 2015, Date retrieved: Oct. 7, 2022, 1 page.
CAS RN 2389183-01-9, Date retrieved: Oct. 7, 2022, 1 page.
CAS RN 2411776-77-5, Date retrieved: Oct. 7, 2022, 1 page.
CAS RN 2411776-80-0, Date retrieved: Oct. 7, 2022, 1 page.
CAS RN 2411776-81-1, Date retrieved: Oct. 7, 2022, 1 page.
CAS RN 2650139-22-1, Date entered STN: Jul. 7, 2021, Date retrieved: Oct. 7, 2022, 1 page.
CAS RN 2728722-49-2, Date entered STN: Nov. 10, 2021, Date retrieved: Oct. 7, 2022, 1 page.
CAS RN 2730123-40-5, Date retrieved: Oct. 7, 2022, 1 page.
CAS RN 2730123-41-6, Date retrieved: Oct. 7, 2022, 1 page.
CAS RN 2730123-63-2, Date retrieved: Oct. 7, 2022, 1 page.
CAS RN 2730123-72-3, Date retrieved: Oct. 7, 2022, 1 page.
CAS RN 2730123-93-8, Date retrieved: Oct. 7, 2022, 1 page.
CAS RN 2761674-58-0, Date entered STN: Mar. 8, 2022, Date retrieved: Oct. 7, 2022, 1 page.
CAS RN 2769721-02-8, Date retrieved: Oct. 7, 2022, 1 page.
CAS RN 2769721-03-9, Date retrieved: Oct. 7, 2022, 1 page.
CAS RN 645415-37-8, Date retrieved: Oct. 7, 2022, 1 page.
CAS RN 645415-38-9, Date retrieved: Oct. 7, 2022, 1 page.
CAS RN 645415-41-4, Date retrieved: Oct. 7, 2022, 1 page.
CAS RN 645415-42-5, Date retrieved: Oct. 7, 2022, 1 page.
CAS RN 645415-43-6, Date retrieved: Oct. 7, 2022, 1 page.
CAS RN 645415-44-7, Date retrieved: Oct. 7, 2022, 1 page.
CAS RN 645415-45-8, Date retrieved: Oct. 7, 2022, 1 page.
CAS RN 645415-46-9, Date retrieved: Oct. 7, 2022, 1 page.
CAS RN 693235-20-0, Date retrieved: Oct. 7, 2022, 1 page.
CAS RN 914604-96-9, Date retrieved: Oct. 7, 2022, 1 page.
CAS RN 914604-98-1, Date retrieved: Oct. 7, 2022, 1 page.
CAS RN 914605-01-9, Date retrieved: Oct. 7, 2022, 1 page.
Chan, E. M. et al., "WRN helicase is a synthetic lethal target in microsatellite unstable cancers," Nature 568.7753 (2019): pp. 551-556.
Czejka, M. et al., "Pharmacokinetics of irinotecan in combination with biweekly cetuximab in patients with advanced colorectal cancer," Anticancer Res. Jun. 2010;30(6):pp. 2355-2360.
Diaz, L. et al., "Pembrolizumab versus chemotherapy for microsatellite instability-high or mismatch repair-deficient .metastatic colorectal cancer," (Keynote-177): final analysis of a randomised, open-label, phase 3 study. The Lancet. Oncology, May 2022;23(5), pp. 659-670.
Eisenhauer, E. A. et al., "New response evaluation criteria in solid tumours: revised RECIST guideline (version 1.1)," Eur J Cancer. Jan. 2009;45(2):pp. 228-247.
Engleman, K.. "MOMA Therapeutics Announces Initiation of Phase 1 Clinical Trial for MOMA-313, a Novel Polymerase Theta Helicase Inhibitor," Momatx.com, Aug. 19, 2024, 6 pages.
Engleman, K. "MOMA Therapeutics Provides Corporate Update and Announces Exclusive License Agreement for Selective PARP1 Inhibitor," Businneswire.com, Jan. 8, 2025, 6 pages.

(56) References Cited

OTHER PUBLICATIONS

Erickson, B.K. et al., "Active Instrument Engagement Combined with a Real-Time Database Search for Improved Performance of Sample Multiplexing Workflows," J Proteome Res. Mar. 1, 2019;18(3):pp. 1299-1306.
Ferretti, S. et al., "Discovery of WRN inhibitor HRO761 with synthetic lethality in MSI cancers," Nature, Apr. 24, 2024;629, pp. 443-449.
Food and Drug Administration (FDA) "Jemperli Prescribing Information," received initial U.S. Approval in 2021, 28 pages [Online] [Retrieved on Aug. 2024] <URL: https://www.accessdata.fda.gov/drugsatfda_docs/label/2022/761174s002lbl.pdf>.
Food and Drug Administration (FDA) "Keytruda Prescribing Information," received initial U.S. Approval in 2014, 106 pages [Online] [Retrieved on Sep. 2024] <URL: https://www.accessdata.fda.gov/drugsatfda_docs/label/2021/125514s096lbl.pdf>.
Food and Drug Administration (FDA) "Opdivo Prescribing Information," received initial U.S. Approval in 2014, 129 pages [Online] [Retrieved on Sep. 2024] <URL: https://www.accessdata.fda.gov/drugsatfda_docs/label/2022/125554s112lbl.pdf>.
Food and Drug Administration (FDA), "For healthcare professionals: FDA's examples of drugs that interact with CYP enzymes and transporter systems," Updated Mar. 8, 2024, 7 pages [Online] [Retrieved on Jun. 4, 2024] <URL: https://www.fda.gov/clrugs/drug-interactions-labeling/healthcare-professionals-fdas-examples-drugs-interact-cyp-enzymes-and-transporter-systems>.
Food and Drug Administration (FDA), "Guidance for Industry S9 Nonclinical Evaluation for Anticancer Pharmaceuticals," Mar. 2010, 12 pages [Online] [Retrieved 2024] <URL: https://www.fda.gov/regulatory-information/search-fda-guidance-documents/s9-nonclinical-evaluation-anticancer-pharmaceuticals>.
Geoerger, B. et al..,"Pembrolizumab in paediatric patients with advanced melanoma or a PD-L1-positive, advanced, relapsed, or refractory solid tumour or lymphoma (Keynote-051): interim analysis of an open-label, single-arm, phase 1-2 trial," Lancet Oncol. Jan. 2020;21(1):pp. 121-133.
Ghandi, M. et al., "Next-generation characterization of the Cancer Cell Line Encyclopedia," Nature. May 23, 2019;569, pp. 503-508.
Gottlieb, H. E. et al., "NMR chemical shifts of common laboratory solvents as trace impurities," Journal of organic chemistry 62.21 (1997): pp. 7512-7515.
Jones, R. D. et al., "PhRMA CPCDC initiative on predictive models of human pharmacokinetics, part 2: comparative assessment of prediction methods of human volume of distribution," J Pharm Sci. Oct. 2011;100(10):pp. 4074-4089.
Kategaya, L. et al., "Werner syndrome helicase is required for survival of cancer cells with microsatellite instability," iScience. Mar. 29, 2019;13, pp. 488-497.
Krippendorff, B. F. et al., "Mechanism-Based Inhibition: Deriving KI and kinact Directly from Time-Dependent IC50 Values," Journal of Biomolecular Screening. Mar. 28, 2009;14(8), pp. 913-923.
Le, D. T. et al., "Pembrolizumab for previously treated, microsatellite instability-high/mismatch repair-deficient advanced colorectal cancer: final analysis of Keynote-164," Eur J Cancer. 2023;186:pp. 185-195.
Le, D. T. et al., "Phase II open-label study of pembrolizumab in treatment-refractory, microsatellite instability-high/mismatch repair-deficient metastatic colorectal cancer: Keynote-164," J Clin Oncol. 2020;38(1):pp. 11-19.
Lebel, M. et al., "A deletion within the murine Werner syndrome helicase induces sensitivity to inhibitors of topoisomerase and loss of cellular proliferative capacity," Proc Natl Acad Sci U S A. Oct. 27, 1998;95(22):pp. 13097-13102.
Lee, V. et al., "Mismatch Repair Deficiency and Response to Immune Checkpoint Blockade," The Oncologist, Jul. 13, 2016; 21(10), pp. 1200-1211.
Lieb, Simone et al., "Werner syndrome helicase is a selective vulnerability of microsatellite instability-high tumor cells," eLIFE 8, Mar. 25, 2019, 22 pages.
Lombardo, F. et al., "Comprehensive assessment of human pharmacokinetic prediction based on in vivo animal pharmacokinetic data, part 1: volume of distribution at steady state," J Clin Pharmacol. Feb. 2013b;53(2):pp. 167-177.
Lombardo, F. et al., "Comprehensive assessment of human pharmacokinetic prediction based on in vivo animal pharmacokinetic data, part 2: clearance," J Clin Pharmacol. Feb. 2013a;53(2):pp. 178-191.
Maio, M. et al., "Pembrolizumab in micro-satellite instability high or mismatch repair deficient cancers: updated analysis from the phase II Keynote-158 study," Ann Oncol. 2022;33(9):pp. 929-938.
Marabelle, A. et al., "Efficacy of pembrolizumab in patients with noncolorectal high microsatellite instability/mismatch repair-deficient cancer: results from the phase II Keynote-158 study," J Clin Oncol. 2020;38:pp. 1-10.
Mathijssen, R. et al., "Irinotecan pharmacokinetics-pharmacodynamics: the clinical relevance of prolonged exposure to SN-38," Br J Cancer. Jul. 9, 2002;87, pp. 144-150.
Mengoli, V. et al., "WRN helicase and mismatch repair complexes independently and synergistically disrupt cruciform DNA structures," EMBO J. Feb. 1, 2023;42(3), 16 pages.
Middha, S. et al., "Reliable Pan-Cancer Microsatellite Instability Assessment by Using Targeted Next-Generation Sequencing Data," JCO Precis Oncol. Oct. 3, 2017;1, pp. 1-17.
Moghaddam, M. F. et al., "A proposed screening paradigm for discovery of covalent inhibitor drugs," Drug Metab Lett. 2014;8(1):pp. 19-30.
Mouradov, D. et al., "Colorectal cancer cell lines are representative models of the main molecular subtypes of primary cancer," Cancer Res. Jun. 15, 2014;74(12):pp. 3238-3247.
Oaknin, A. et al., "Safety and antitumor activity of dostarlimab in patients with advanced or recurrent DNA mismatch repair deficient/microsatellite instability-high (dMMR/MSI-H) or proficient/stable (MMRp/MSS) endometrial cancer: interim results from GARNET—a phase I, single-arm study," J Immunother Cancer. Jan. 21, 2022, 10 pages.
Oaknin, A. et al., "Safety, efficacy, and biomarker analyses of dostarlimab in patients with endometrial cancer: interim results of the phase I GARNET study," Clin Cancer Res. 2023;29(22):pp. 4564-4574.
Oaknin, A. et al., "Clinical activity and safety of the anti-programmed death 1 monoclonal antibody dostarli-mab for patients with recurrent or advanced mismatch repair-deficient endometrial cancer: a nonrandomized phase 1 clinical trial," JAMA Oncol. 2020;6(11):pp. 1766-1772.
Oken, M. M. et al., "Toxicity and response criteria of the Eastern Cooperative Oncology Group," Am J Clin Oncol. Dec. 1982;5(6):pp. 649-655.
Pharmaceutical Technology, "Bayer and MOMA Therapeutics partner for oncology programme" Oct. 8, 2024, 4 pages [Online] [Retrieved on Aug. 6, 2025] <URL: https://www.pharmaceutical-technology.com/news/bayer-moma-therapeutics-partner/>.
Picco, G. et al., "Novel WRN helicase inhibitors selectively target microsatellite-unstable cancer cells," Cancer discovery 14.8 (2024): pp. 1457-1475.
Poynter, J. N. et al., "Molecular characterization of MSI-H colorectal cancer by MLHI promoter methylation, immunohistochemistry, and mismatch repair germline mutation screening," Cancer Epidemiology, Biomarkers & Prevention. Nov. 1, 2008. 17(11), pp. 3208-3215.
Rappsilber, J. et al. "Protocol for micro-purification, enrichment, pre-fractionation and storage of peptides for proteomics using StageTips," Nature Protocols. Aug. 2, 2007;2, pp. 1896-1906.
Ring, B. J. et al., "PhRMA CPCDC initiative on predictive models of human pharmacokinetics, part 3: comparative assessement of prediction methods of human clearance," J Pharm Sci. Oct. 2011;100(10):pp. 4090-4110.
Rossi, M. L. et al. "Roles of Werner syndrome protein in protection of genome integrity," DNA Repair (Amst). Mar. 2, 2010;9(3):pp. 331-344.

(56) References Cited

OTHER PUBLICATIONS

Ryan, A.J. et al., Camptothecin cytotoxicity in mammalian cells is associated with the induction of persistent double strand breaks in replicating DNA. Nucleic Acids Research. Jun. 25, 1991; 19, pp. 3295-3300.

Scher, H. I. et al., "Trial Design and Objectives for Castration-Resistant Prostate Cancer: Updated Recommendations From the Prostate Cancer Clinical Trials Working Group 3," J Clin Oncol. Apr. 20, 2016;34(12):pp. 1402-1418.

Seymour, L. et al., "iRECIST: guidelines for response criteria for use in trials testing immunotherapeutics," Lancet Oncol. Mar. 2017;18(3):pp. 143-152.

Sygnature Discovery, "Unwinding the complexities of helicases," 2024, 1 page.

Van Wietmarschen, N. et al., "Repeat expansions confer WRN dependence in microsatellite-unstable cancers," Nature. Sep. 30 2020;586(7828):pp. 292-298.

Xia, L. et al., "Recent progress and challenges in screening and characterization of UGT1A1 inhibitors," Acta Pharm Sin B. Mar. 2019;9(2): pp. 258-278.

Ziv, Y. et al., "Chromatin relaxation in response to DNA double-strand breaks is modulated by a novel ATM- and KAP-1 dependent pathway," Nat. Cell Biol., Jul. 23, 2006; 8: pp. 870-876.

TRICYCLIC DERIVATIVES AND RELATED USES

RELATED APPLICATIONS

This application is a continuation of International Patent Application No. PCT/US2024/045640, filed on Sep. 6, 2024, which claims priority to, and the benefit of, U.S. Provisional Application No. 63/537,426, filed on Sep. 8, 2023; U.S. Provisional Application No. 63/654,502, filed on May 31, 2024; and U.S. Provisional Application No. 63/684,749, filed on Aug. 19, 2024, the entire contents of which are incorporated herein by reference.

BACKGROUND

The present disclosure relates to small molecule modulators of Werner helicase (WRN), designed for the treatment of a disease or disorder (e.g., cancer).

Genome instability is a hallmark of cancer, achieved through loss of DNA mismatch repair in numerous tumor types such as colorectal, gastric, endometrial, neuroendocrine, breast, ovarian, cervical, uterine, liver, prostate, cholangiocarcinoma, thyroid, pancreatic, uveal melanoma, esophageal, glioblastoma, and lung cancers identified as deficient in these pathways. This DNA mismatch repair deficiency (dMMR) leads to a high mutational burden genome-wide, but it is mainly characterized by insertions and deletions at repetitive DNA sequences across the genome known as microsatellites. The resulting phenotype is known as microsatellite instability, and the most severe of which may be graded as microsatellite instability high (MSI-H). Microsatellite instability is sometimes annotated using 3 categories (i.e., microsatellite stable (MSS), microsatellite instability low (MSI-L), and MSI-H) and sometimes as a binary (i.e., MSS or MSI). Thus, MSI-H patients can sometimes be annotated as MSI. Tumor status of dMMR is determined by presence/absence of MMR proteins MLH1, MSH2, MSI 6, and/or PMS2 via immunohistochemistry, while MSI is determined by targeted molecular diagnostics of tumor DNA.

Standard of care for dMMR/MSI-H solid tumors includes 5-Fluorouracil-containing chemotherapeutic regimens and/or checkpoint inhibitors. These chemotherapeutic regimens have modest long term response rates and can be poorly tolerated by patients. Anti-PD1 therapies have been approved as a first-line therapy in MSI-H cancers, taking advantage of tumor-specific neoantigens created by high mutation levels. Despite treatment with anti-PD-1 checkpoint inhibitors, about half of dMMR/MSI tumors do not respond, thus alternative therapies are needed.

In parallel, functional genomics screens identified the essentiality of the WRN helicase in MSI-H cells. Furthermore, the mechanism of WRN helicase essentiality in MSI-H cancer cells has been elucidated, as WRN resolves repetitive large-scale TA dinucleotide expansions that uniquely occur in MSI-H cells at recurrent locations in the genome. These expanded TA dinucleotide repeats form secondary DNA structures that must be resolved by the WRT helicase during DNA replication in order for the cell to duplicate its DNA and divide properly. In the absence of WRN helicase activity, these toxic DNA structures persist, leading to chromosomal breakage at these sites and subsequent cell cycle arrest and cell death. As such, in the absence of WRN helicase activity, a DNA damage-mediated anti-proliferative and pro-apoptotic effect is observed exclusively in MSI-H tumors but not in normal tissues with functioning mismatch repair (MMR). Thus, inhibition of the WRN helicase is an ideal strategy for the treatment of MMR-deficient and/or MSI-H tumors.

The disclosure arises from a need to provide further compounds for the modulation of WRN activity with improved therapeutic potential. In particular, compounds with improved physicochemical, pharmacological and/or pharmaceutical properties.

SUMMARY

In some aspects, the present disclosure provides a compound of Formula (I'):

(I')

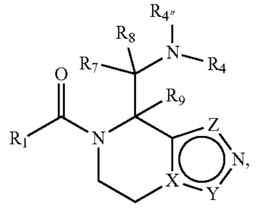

or a pharmaceutically acceptable salt, oxide, solvate, clathrate, hydrate, stereoisomer, or tautomer thereof, wherein:

X is N or C;

Y is $NR_2$ or $CR_2$;

Z is $NR_3$ or $CR_3$;

$R_1$ is $C_1$-$C_6$ alkyl, $C_2$-$C_6$ alkenyl, $C_2$-$C_6$ alkynyl, $C_1$-$C_6$, haloalkyl $C_3$-$C_{10}$ cycloalkyl, $C_6$-$C_{10}$ aryl, 5- to 10-membered heteroaryl, or 3- to 10-membered heterocyclyl, wherein the $C_1$-$C_6$ alkyl, $C_2$-$C_6$ alkenyl, $C_2$-$C_6$ alkynyl, $C_1$-$C_6$ haloalkyl, $C_3$-$C_{10}$ cycloalkyl, $C_6$-$C_{10}$ aryl, 5- to 10-membered heteroaryl, or 3- to 10-membered heterocyclyl is optionally substituted with one or more $R_{1a}$;

each $R_{1a}$ independently is oxo, halo, cyano, —OH, —$NH_2$, —$NO_2$, —NH($C_1$-$C_6$ alkyl), —N($C_1$-$C_6$ alkyl)$_2$, —NH—C(O)($C_1$-$C_6$ alkyl), —S($C_1$-$C_6$ alkyl), —S(O)$_2$($C_1$-$C_6$ alkyl), —S(O)$_2$($NH_2$), —C(O)(H), —C(O)$NH_2$, —O(3- to 10-membered heterocyclyl), $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, $C_3$-$C_{10}$ cycloalkyl, $C_6$-$C_{10}$ aryl, 5- to 10-membered heteroaryl, or 3-to 10-membered heterocyclyl, wherein the —NH($C_1$-$C_6$ alkyl), —N($C_1$-$C_6$ alkyl)$_2$ —NH—C(O)($C_1$-$C_6$ alkyl), —S($C_1$-$C_6$ alkyl), —S(O)$_2$($C_1$-$C_6$ alkyl), —O(3- to 10-membered heterocyclyl), $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, $C_3$-$C_{10}$ cycloalkyl, $C_6$-$C_{10}$ aryl, 5-to 10-membered heteroaryl, or 3- to 10-membered heterocyclyl is optionally substituted with one or more $R_{1b}$;

each $R_{1b}$ independently is oxo, halo, cyano, —OH, —O($C_1$-$C_6$ alkyl, —O($C_1$-$C_6$ haloalkyl), —O($C_2$-$C_6$ alkenyl), —O($C_2$-$C_6$ alkynyl), —$NH_2$, —NH($C_1$-$C_6$ alkyl), —N($C_1$-$C_6$ alkyl)$_2$, —NH($C_1$-$C_6$ haloalkyl), —S($C_1$-$C_6$ alkyl), —S(O)$_2$($C_1$-$C_6$ alkyl), —C(O)$NH_2$, $C_1$-$C_6$ alkyl $C_3$-$C_{10}$ cycloalkyl, or 3-to 10-membered heterocyclyl optionally substituted with oxo;

$R_2$ is $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_3$-$C_{10}$ cycloalkyl, $C_6$-$C_{10}$ aryl, 5- to 10-membered heteroaryl, or 3- to 10-membered heterocyclyl, wherein the $C_1$-$C_6$ alkyl, $C_3$-$C_{10}$ cycloalkyl, $C_6$-$C_{10}$ aryl, 5- to 10-membered heteroaryl, or 3- to 10-membered heterocyclyl is optionally substituted with one or more $R_{2a}$;

each $R_{2a}$ independently is oxo, halo, cyano, —OH, —$NH_2$, —NH($C_1$-$C_6$ alkyl), —N($C_1$-$C_6$ alkyl)$_2$, —SH, —$S(O)_2NH_2$, —$SF_5$, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, —S($C_1$-$C_6$ haloalkyl), —S($C_1$-$C_6$ alkyl), $C_3$-$C_{10}$ cycloalkyl, $C_6$-$C_{10}$ aryl, 5- to 10-membered heteroaryl, or 3- to 10-membered heterocyclyl, wherein the 1-$C_6$ alkyl, $C_2$-$C_6$ alkenyl, $C_2$-$C_6$ alkynyl, $C_1$-$C_6$ alkoxy, $C_1$-$C_6$ haloalkyl, —S($C_1$-$C_6$ haloalkyl), —S($C_1$-$C_6$ alkyl), $C_3$-$C_{10}$ cycloalkyl, $C_6$-$C_1$ aryl, 5- to 10-membered heteroaryl, or 3- to 10-membered heterocyclyl is optionally substituted with one or more $R_{2a1}$;

each $R_{2a1}$ independently is oxo, halo, cyano, —OH, —$NH_2$, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, —NH—C(O)($C_1$-$C_6$ alkyl), —C(O)$NH_2$, or —OC(O)($C_1$-$C_6$ alkyl), wherein the $C_1$-$C_6$ alkyl, $C_2$-$C_6$ alkenyl, $C_2$-$C_6$ alkynyl, $C_1$-$C_6$ alkoxy, $C_1$-$C_6$ haloalkyl or $C_1$-$C_6$ alkyl is optionally substituted with one or more —OH;

$R_3$ and $R_4$, together with the atoms to which they are attached, form a 6- to 10-membered heterocyclyl, wherein the heterocyclyl optionally comprises one or more additional N, O, or S and is optionally substituted with one or more $R_{3a}$;

each $R_{3a}$ independently is cyano, halo, —OH, —$NH_2$, —NH($C_1$-$C_6$ alkyl), —N($C_1$-$C_6$ alkyl)$_2$, —N($C_1$-$C_6$ alkyl)($C_1$-$C_6$ haloalkyl), —NH—C(O)($C_1$-$C_6$ alkyl), —O($C_3$-$C_{10}$ cycloalkyl), —O(3- to 10-membered heterocyclyl), $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_1$-$C_6$ haloalkoxy, $C_3$-$C_{10}$ cycloalkyl, 3- to 10-membered heterocyclyl, 5- to 10-membered heteroaryl, —S(O)(=NH)($C_1$-$C_6$ alkyl), —$SO_2$($C_1$-$C_6$ alkyl), —S($C_1$-$C_6$ alkyl), or —S($C_1$-$C_6$ haloalkyl), wherein the —NH($C_1$-$C_6$ alkyl), —N($C_1$-$C_6$ alkyl)$_2$, —N($C_1$-$C_6$ alkyl)($C_1$-$C_6$ haloalkyl), —NH—C(O)($C_1$-$C_6$ alkyl), —O($C_3$-$C_{10}$ cycloalkyl), —O(3- to 10-membered heterocyclyl), $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_1$-$C_6$ haloalkoxy, $C_3$-$C_{10}$ cycloalkyl, 3- to 10-membered heterocyclyl, 5- to 10-membered heteroaryl, —S(O)(=NH)($C_1$-$C_6$ alkyl), —$SO_2$($C_1$-$C_6$ alkyl), —S($C_1$-$C_6$ alkyl), or —S($C_1$-$C_6$ haloalkyl) is optionally substituted with one or more oxo, cyano, 3- to 10-membered heterocyclyl, —C(O)($C_1$-$C_6$ alkyl), 5- to 10-membered heteroaryl optionally substituted with $C_1$-$C_6$ alkyl, $C_1$-$C_6$ alkyl optionally substituted with $C_1$-$C_6$ alkoxy, —N($R_{3a1}$)CO($R_{3a2}$), —O($C_3$-$C_{10}$ cycloalkyl), —O($C_6$-$C_{10}$ aryl), —O(5- to 10-membered heteroaryl), or —O(3- to 10-membered heterocyclyl), or two $R_{3a}$, together with the atoms to which they are attached, form a $C_3$-$C_{10}$ cycloalkyl or 3- to 10-membered heterocyclyl, wherein the cycloalkyl or heterocyclyl is optionally substituted with one or more $C_3$-$C_{10}$ cycloalkyl, 3- to 10-membered heterocyclyl, $C_1$-$C_{10}$ aryl, or 5- to 10-membered heteroaryl, wherein the cycloalkyl, heterocyclyl, aryl, or heteroaryl is optionally substituted with one or more $C_1$-$C_6$ alkyl;

$R_{3a1}$ and $R_{3a2}$, together with the atoms to which they are attached form a 3- to 10-membered heterocyclyl;

$R_{4''}$ is

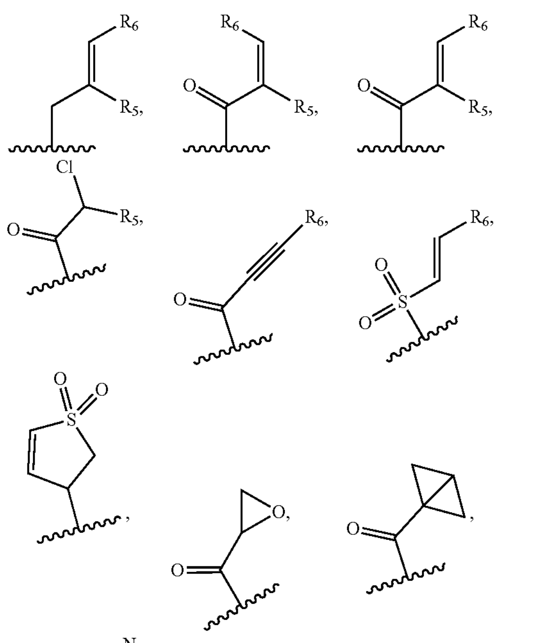

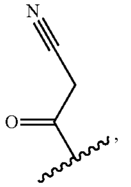

or

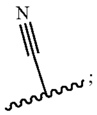

$R_5$ is H, halo, cyano, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy, $R_6$ is H, halo, cyano, —$SO_2$($C_1$-$C_6$ alkyl), $C_1$-$C_6$ alkyl, $C_2$-$C_6$ alkenyl, $C_2$-$C_6$ alkynyl, or $C_1$-$C_6$ alkoxy, wherein the alkyl, alkenyl, alkynyl, or alkoxy is optionally substituted with one or more —OH, —O($C_1$-$C_6$ alkyl), —$NH_2$, —NH($C_1$-$C_6$ alkyl), or —N($C_1$-$C_6$ alkyl)$_2$, or $R_5$ and $R_6$, together with the atoms to which they are attached, form a $C_4$-$C_{10}$ cycloalkenyl; and each $R_7$, $R_8$, and $R_9$ independently is H, cyano, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy, wherein the alkyl, alkenyl, alkynyl, haloalkyl, or alkoxy is optionally substituted with one or more oxo, halo, cyano, —OH, —$NH_2$, $C_1$-$C_6$ alkoxy, —NH($C_1$-$C_6$ alkyl), —N($C_1$-$C_6$ alkyl)$_2$, —NH($C_1$-$C_6$ haloalkyl), or —S($C_1$-$C_6$ alkyl), or $R_7$ and $R_8$, together with the atoms to which they are attached, form a $C_3$-$C_{10}$ cycloalkyl or 3- to 10-membered heterocyclyl.

In some aspects, the present disclosure provides a compound of Formula (I'):

(I')

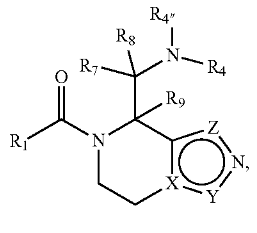

or a pharmaceutically acceptable salt, oxide, solvate, clathrate, hydrate, stereoisomer, or tautomer thereof, wherein:

X is N or C;

Y is $NR_2$ or $CR_2$;

Z is $NR_3$ or $CR_3$;

$R_1$ is $C_1$-$C_6$ alkyl, $C_2$-$C_6$ alkenyl, $C_2$-$C_6$ alkynyl, $C_1$-$C_6$ haloalkyl, $C_3$-$C_{10}$ cycloalkyl, $C_6$-$C_{10}$ aryl, 5- to 10-membered heteroaryl, or 3- to 10-membered heterocyclyl, wherein the $C_1$-$C_6$ alkyl, $C_2$-$C_6$ alkenyl, $C_2$-$C_6$ alkynyl, $C_1$-$C_6$ haloalkyl, $C_3$-$C_{10}$ cycloalkyl, $C_6$-$C_{10}$ aryl, 5- to 10-membered heteroaryl, or 3- to 10-membered heterocyclyl is optionally substituted with one or more $R_{1a}$;

each $R_{1a}$ independently is oxo, halo, cyano, —OH, —$NH_2$, —$NO_2$, —NH($C_1$-$C_6$ alkyl), —N($C_1$-$C_6$ alkyl)$_2$, —NH—C(O)($C_1$-$C_6$ alkyl), —S($C_1$-$C_6$ alkyl), —S(O)$_2$($C_1$-$C_6$ alkyl), —S(O)$_2$($NH_2$), —C(O)(H), —C(O)$NH_2$, —O(3- to 10-membered heterocyclyl), $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, $C_3$-$C_{10}$ cycloalkyl, $C_6$-$C_{10}$ aryl, 5- to 10-membered heteroaryl, or 3-to 10-membered heterocyclyl, wherein the —NH($C_1$-$C_6$ alkyl), —N($C_1$-$C_6$ alkyl)$_2$ —NH—C(O)($C_1$-$C_6$ alkyl), —S($C_1$-$C_6$ alkyl), —S(O)$_2$($C_1$-$C_6$ alkyl), —O(3- to 10-membered heterocyclyl), $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, $C_3$-$C_{10}$ cycloalkyl, $C_6$-$C_{10}$ aryl, 5-to 10-membered heteroaryl, or 3- to 10-membered heterocyclyl is optionally substituted with one or more $R_{1b}$;

each $R_{1b}$ independently is oxo, halo, cyano, —OH, —O($C_1$-$C_6$ alkyl), —O($C_1$-$C_6$ haloalkyl), —O($C_2$-$C_6$ alkenyl), —O($C_2$-$C_6$ alkynyl), —$NH_2$, —NH($C_1$-$C_6$ alkyl), —N($C_1$-$C_6$ alkyl)$_2$, —NH($C_1$-$C_6$ haloalkyl), —S($C_1$-$C_6$ alkyl), —S(O)$_2$($C_1$-$C_6$ alkyl), $C_1$-$C_6$ alkyl, $C_3$-$C_{10}$ cycloalkyl, or 3- to 10-membered heterocyclyl optionally substituted with oxo;

$R_2$ is $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_3$-$C_{10}$ cycloalkyl, $C_6$-$C_{10}$ aryl, 5- to 10-membered heteroaryl, or 3- to 10-membered heterocyclyl, wherein the $C_1$-$C_6$ alkyl, $C_3$-$C_{10}$ cycloalkyl, $C_6$-$C_{10}$ aryl, 5- to 10-membered heteroaryl, or 3- to 10-membered heterocyclyl is optionally substituted with one or more $R_{2a}$;

each $R_{2a}$ independently is oxo, halo, cyano, —OH, —$NH_2$, —NH($C_1$-$C_6$ alkyl), —N($C_1$-$C_6$ alkyl)$_2$, —SH, —S(O)$_2NH_2$, —$SF_5$, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, —S($C_1$-$C_6$ haloalkyl), —S($C_1$-$C_6$ alkyl), $C_3$-$C_{10}$ cycloalkyl, $C_6$-$C_{10}$ aryl, 5- to 10-membered heteroaryl, or 3- to 10-membered heterocyclyl, wherein the $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, —S($C_1$-$C_6$ haloalkyl), —S($C_1$-$C_6$ alkyl), $C_3$-$C_{10}$ cycloalkyl, $C_6$-$C_{10}$ aryl, 5- to 10-membered heteroaryl, or 3- to 10-membered heterocyclyl is optionally substituted with one or more $R_{2a1}$;

each $R_{2a1}$ independently is oxo, halo, cyano, —OH, —$NH_2$, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, —NH—C(O)($C_1$-$C_6$ alkyl), —C(O)$NH_2$, or —OC(O)($C_1$-$C_6$ alkyl), wherein the $C_1$-$C_6$ alkyl, $C_2$-$C_6$ alkenyl, $C_2$-$C_6$ alkynyl, $C_1$-$C_6$ alkoxy, $C_1$-$C_6$ haloalkyl or $C_1$-$C_6$ alkyl is optionally substituted with one or more —OH;

$R_3$ and $R_4$, together with the atoms to which they are attached, form a 6- to 10-membered heterocyclyl, wherein the heterocyclyl optionally comprises one or more additional N, O, or S and is optionally substituted with one or more $R_{3a}$;

each $R_{3a}$ independently is cyano, halo, —OH, —$NH_2$, —NH($C_1$-$C_6$ alkyl), —N($C_1$-$C_6$ alkyl)$_2$, —N($C_1$-$C_6$ alkyl)($C_1$-$C_6$ haloalkyl), —NH—C(O)($C_1$-$C_6$ alkyl), —O($C_3$-$C_{10}$ cycloalkyl), —O(3- to 10-membered heterocyclyl), $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_1$-$C_6$ haloalkoxy, $C_3$-$C_{10}$ cycloalkyl, 3- to 10-membered heterocyclyl, $C_6$-$C_{10}$ aryl, 5- to 10-membered heteroaryl, —S(O)(=NH)($C_1$-$C_6$ alkyl), —$SO_2$($C_1$-$C_6$ alkyl), —S($C_1$-$C_6$ alkyl), or —S($C_1$-$C_6$ haloalkyl), wherein the alkyl, alkenyl, alkynyl, haloalkyl, alkoxy, haloalkoxy, —O($C_3$-$C_{10}$ cycloalkyl), —O(3- to 10-membered heterocyclyl), heterocycle, cycloalkyl, aryl, or heteroaryl is optionally substituted with one or more oxo, —CN, $C_1$-$C_6$ alkoxy, —C(O)($C_1$-$C_6$ alkyl), —N($R_{3a1}$)CO($R_{3a2}$), —O($C_3$-$C_{10}$ cycloalkyl), —O($C_6$-$C_{10}$ aryl), —O(5- to 10-membered heteroaryl), —O(3- to 10-membered heterocyclyl), $C_3$-$C_{10}$ cycloalkyl, 3- to 10-membered heterocyclyl, $C_6$-$C_{10}$ aryl, or 5- to 10-membered heteroaryl, wherein the cycloalkyl, aryl, heteroaryl, or heterocyclyl is optionally substituted with one or more $C_1$-$C_6$ alkyl, or two $R_{3a}$, together with the atoms to which they are attached, form a $C_3$-$C_{10}$ cycloalkyl or 3- to 10-membered heterocyclyl, wherein the cycloalkyl or heterocyclyl is optionally substituted with one or more $C_3$-$C_{10}$ cycloalkyl, 3- to 10-membered heterocyclyl, $C_6$-$C_{10}$ aryl, or 5- to 10-membered heteroaryl, wherein the cycloalkyl, heterocyclyl, aryl, or heteroaryl is optionally substituted with one or more $C_1$-$C_6$ alkyl;

$R_{3a1}$ and $R_{3a2}$, together with the atoms to which they are attached form a 3- to 10-membered heterocyclyl;

$R_{4''}$ is

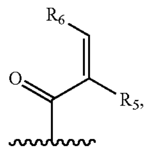
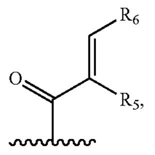
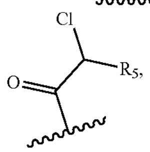
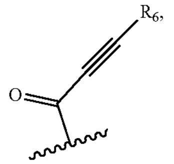
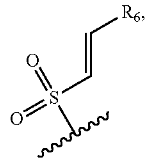
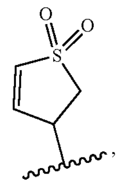,
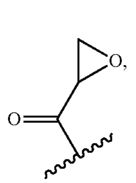
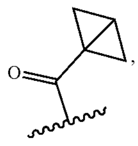,
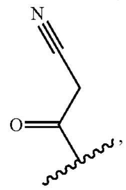, or
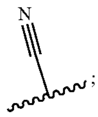;

$R_5$ is H, halo, cyano, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy;

$R_6$ is H, halo, cyano, $C_1$-$C_6$ alkyl, $C_2$-$C_6$ alkenyl, $C_2$-$C_6$ alkynyl, or $C_1$-$C_6$ alkoxy, wherein the alkyl, alkenyl, alkynyl, or alkoxy is optionally substituted with one or more —$NH_2$, —NH($C_1$-$C_6$ alkyl), or —N($C_1$-$C_6$ alkyl)$_2$, or $R_5$ and $R_6$, together with the atoms to which they are attached, form a $C_4$-$C_{10}$ cycloalkenyl; and each $R_7$, $R_8$, and $R_9$ independently is H, cyano, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy, wherein the alkyl, alkenyl, alkynyl, haloalkyl, or alkoxy is optionally substituted with one or more oxo, halo, cyano, —OH, —$NH_2$, $C_1$-$C_6$ alkoxy, —NH($C_1$-$C_6$ alkyl), —N($C_1$-$C_6$ alkyl)$_2$, —NH($C_1$-$C_6$ haloalkyl), or —S($C_1$-$C_6$ alkyl), or $R_7$ and $R_8$, together with the atoms to which they are attached, form a $C_3$-$C_{10}$ cycloalkyl or 3- to 10-membered heterocyclyl.

In some aspects, the present disclosure provides a compound of Formula (I'):

(I')

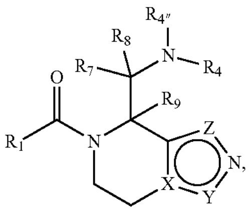

or a pharmaceutically acceptable salt, oxide, solvate, clathrate, hydrate, stereoisomer, or tautomer thereof, wherein:

X is N or C;

Y is $NR_2$ or $CR_2$;

Z is $NR_3$ or $CR_3$;

$R_1$ is $C_1$-$C_6$ alkyl, $C_2$-$C_6$ alkenyl, $C_2$-$C_6$ alkynyl, $C_1$-$C_6$ haloalkyl $C_3$-$C_{10}$ cycloalkyl, $C_6$-$C_{10}$ aryl, 5- to 10-membered heteroaryl, or 3- to 10-membered heterocyclyl, wherein the $C_1$-$C_6$ alkyl, $C_2$-$C_6$ alkenyl, $C_2$-$C_6$ alkynyl, $C_1$-$C_6$ haloalkyl, $C_3$-$C_{10}$ cycloalkyl, $C_6$-$C_{10}$ aryl, 5- to 10-membered heteroaryl, or 3- to 10-membered heterocyclyl is optionally substituted with one or more $R_{1a}$;

each $R_{1a}$ independently is oxo, halo, cyano, —OH, —$NH_2$, —$NO_2$, —NH($C_1$-$C_6$ alkyl), —N($C_1$-$C_6$ alkyl)$_2$, —NH—C(O)($C_1$-$C_6$ alkyl), —S($C_1$-$C_6$ alkyl), —S(O)$_2$($C_1$-$C_6$ alkyl), —S(O)$_2$($NH_2$), —C(O)(H), —C(O)$NH_2$, —O(3- to 10-membered heterocyclyl), $C_1$-$C_6$ alkyl, $C_2$-$C_6$ alknyl, $C_2$-$C_6$ alkynyl, $C_1$-$C_6$ alkoxy, $C_1$-$C_6$ haloalkyl, $C_3$-$C_{10}$ cycloalkyl, $C_6$-$C_{10}$ aryl, 5- to 10-membered heteroaryl, or 3-to 10-membered heterocyclyl, wherein the —NH($C_1$-$C_6$ alkyl), —N($C_1$-$C_6$ alkyl)$_2$ —NH—C(O)($C_1$-$C_6$ alkyl), —S($C_1$-$C_6$ alkyl), —S(O)$_2$($C_1$-$C_6$ alkyl), —O(3- to 10-membered heterocyclyl), $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, $C_3$-$C_{10}$ cycloalkyl, $C_6$-$C_{10}$ aryl, 5-to 10-membered heteroaryl, or 3- to 10-membered heterocyclyl is optionally substituted with one or more $R_{1b}$;

each $R_{1b}$ independently is oxo, halo, cyano, —OH, —O($C_1$-$C_6$ alkyl), —O($C_1$-$C_6$ haloalkyl), —O($C_2$-$C_6$ alkenyl), —O($C_2$-$C_6$ alkynyl), —$NH_2$, —NH($C_1$-$C_6$ alkyl), —N($C_1$-$C_6$ alkyl)$_2$, —NH($C_1$-$C_6$ haloalkyl), —S($C_1$-$C_6$ alkyl), —S(O)$_2$($C_1$-$C_6$ alkyl), $C_1$-$C_6$ alkyl, $C_3$-$C_{10}$ cycloalkyl, or 3- to 10-membered heterocyclyl optionally substituted with oxo;

$R_2$ is $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_3$-$C_{10}$ cycloalkyl, $C_6$-$C_{10}$ aryl, 5- to 10-membered heteroaryl, or 3- to 10-membered heterocyclyl, wherein the $C_1$-$C_6$ alkyl, $C_3$-$C_{10}$ cycloalkyl, $C_6$-$C_{10}$ aryl, 5- to 10-membered heteroaryl, or 3- to 10-membered heterocyclyl is optionally substituted with one or more $R_2$;

each $R_{2a}$ independently is oxo, halo, cyano, —OH, —$NH_2$, —NH($C_1$-$C_6$ alkyl), —N($C_1$-$C_6$ alkyl)$_2$, —SH, —S(O)$_2NH_2$, —$SF_5$, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, —S($C_1$-$C_6$ haloalkyl), —S($C_1$-$C_6$ alkyl), $C_3$-$C_{10}$ cycloalkyl, $C_6$-$C_{10}$ aryl, 5- to 10-membered heteroaryl, or 3- to 10-membered heterocyclyl, wherein the $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, —S($C_1$-$C_6$ haloalkyl), —S($C_1$-$C_6$ alkyl), $C_3$-$C_{10}$ cycloalkyl, $C_6$-$C_{10}$ aryl, 5- to 10-membered heteroaryl, or 3- to 10-membered heterocyclyl is optionally substituted with one or more $R_{2a1}$;

each $R_{2a1}$ independently is oxo, halo, cyano, —OH, —$NH_2$, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, —NH—C(O)($C_1$-$C_6$ alkyl), —C(O)$NH_2$, or —OC(O)($C_1$-$C_6$ alkyl), wherein the $C_1$-$C_6$ alkyl, $C_2$-$C_6$ alkenyl, $C_2$-$C_6$ alkynyl, $C_1$-$C_6$ alkoxy, $C_1$-$C_6$ haloalkyl or $C_1$-$C_6$ alkyl is optionally substituted with one or more —OH;

$R_3$ and $R_4$, together with the atoms to which they are attached, form a 6- to 10-membered heterocyclyl, wherein the heterocyclyl optionally comprises one or more additional N, O, or S and is optionally substituted with one or more $R_{3a}$;

each $R_{3a}$ independently is cyano, halo, —OH, —$NH_2$, —NH($C_1$-$C_6$ alkyl), —N($C_1$-$C_6$ alkyl)$_2$, —N($C_1$-$C_6$ alkyl)($C_1$-$C_6$ haloalkyl), —NH—C(O)($C_1$-$C_6$ alkyl), —O($C_3$-$C_{10}$ cycloalkyl), $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_1$-$C_6$ haloalkoxy, $C_3$-$C_{10}$ cycloalkyl, 3- to 10-membered heterocyclyl, —S(O)(=NH)($C_1$-$C_6$ alkyl), $SO_2$($C_1$-$C_6$ alkyl), —S($C_1$-$C_6$ alkyl), or —S($C_1$-$C_6$ haloalkyl), wherein the alkyl is optionally substituted with one or more —N($R_{3a1}$)CO($R_{3a2}$), —O($C_3$-$C_{10}$ cycloalkyl), —O($C_6$-$C_{10}$ aryl), —O(5- to 10-membered heteroaryl), or —O(3- to 10-membered heterocyclyl), wherein the cycloalkyl, aryl, heteroaryl, or heterocyclyl is optionally substituted with one or more $C_1$-$C_6$ alkyl, or two $R_{3a}$, together with the atoms to which they are attached, form a $C_3$-$C_{10}$ cycloalkyl or 3- to 10-membered heterocyclyl;

$R_{3a1}$ and $R_{3a2}$, together with the atoms to which they are attached form a 3- to 10-membered heterocyclyl;

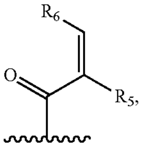
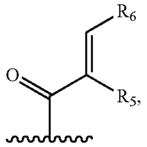
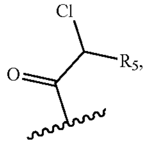
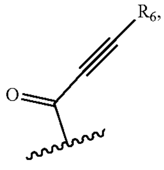
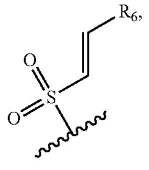

-continued

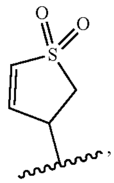,

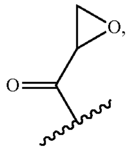

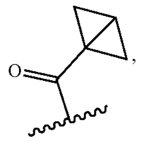,

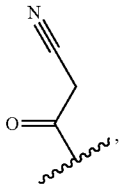, or 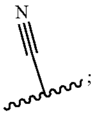;

$R_5$ is H, halo, cyano, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy;

$R_6$ is H, halo, cyano, $C_1$-$C_6$ alkyl, $C_2$-$C_6$ alkenyl, $C_2$-$C_6$ alkynyl, or $C_1$-$C_6$ alkoxy, wherein the alkyl, alkenyl, alkynyl, or alkoxy is optionally substituted with one or more —$NH_2$, —NH($C_1$-$C_6$ alkyl), or —N($C_1$-$C_6$ alkyl)$_2$, or $R_5$ and $R_6$, together with the atoms to which they are attached, form a $C_4$-$C_{10}$ cycloalkenyl; and each $R_7$, $R_8$, and $R_9$ independently is H, cyano, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy, wherein the alkyl, alkenyl, alkynyl, haloalkyl, or alkoxy is optionally substituted with one or more oxo, halo, cyano, —OH, —$NH_2$, $C_1$-$C_6$ alkoxy, —NH($C_1$-$C_6$ alkyl), —N($C_1$-$C_6$ alkyl)$_2$, —NH($C_1$-$C_6$ haloalkyl), or —S($C_1$-$C_6$ alkyl), or $R_7$ and $R_8$, together with the atoms to which they are attached, form a $C_3$-$C_{10}$ cycloalkyl or 3- to 10-membered heterocyclyl.

In some aspects, the compound of Formula (I') is a compound of Formula (I):

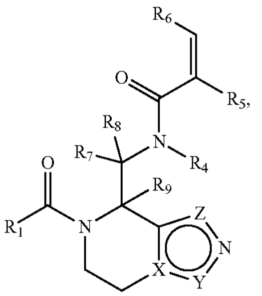

(I)

or a pharmaceutically acceptable salt, oxide, solvate, clathrate, hydrate, stereoisomer, or tautomer thereof.

In some aspects, the present disclosure provides a compound obtainable by, or obtained by, a method for preparing a compound as described herein (e.g., a method comprising one or more steps described in any one of Schemes 1-18).

In some aspects, the present disclosure provides a pharmaceutical composition comprising a compound of the present disclosure, or a pharmaceutically acceptable salt thereof, and one or more pharmaceutically acceptable excipient, diluent, or carrier, or a combination thereof.

In some aspects, the present disclosure provides an intermediate as described herein, being suitable for use in a method for preparing a compound as described herein (e.g., the intermediate is selected from the intermediates described in the Examples).

In some aspects, the present disclosure provides a method of modulating Werner helicase (WRN) activity (e.g., in vitro or in vivo), comprising contacting a cell with an effective amount of a compound of the present disclosure or a pharmaceutically acceptable salt thereof.

In some aspects, the present disclosure provides a method of treating or preventing a disease or disorder disclosed herein in a subject in need thereof, comprising administering to the subject a therapeutically effective amount of a compound of the present disclosure or a pharmaceutically acceptable salt thereof, or a pharmaceutical composition of the present disclosure.

In some aspects, the present disclosure provides a method of treating a disease or disorder disclosed herein in a subject in need thereof, comprising administering to the subject a therapeutically effective amount of a compound of the present disclosure or a pharmaceutically acceptable salt thereof, or a pharmaceutical composition of the present disclosure.

In some aspects, the present disclosure provides a compound of the present disclosure or a pharmaceutically acceptable salt thereof for use in modulating WRN activity (e.g., in vitro or in vivo).

In some aspects, the present disclosure provides a compound of the present disclosure or a pharmaceutically acceptable salt thereof for use in treating or preventing a disease or disorder disclosed herein.

In some aspects, the present disclosure provides a compound to the present disclosure or a pharmaceutically acceptable salt thereof for use in treating a disease or disorder disclosed herein.

In some aspects, the present disclosure provides use of a compound of the present disclosure or a pharmaceutically acceptable salt thereof in the manufacture of a medicament for modulating WRN activity (e.g., in vitro or in vivo).

In some aspects, the present disclosure provides use of a compound of the present disclosure or a pharmaceutically acceptable salt thereof in the manufacture of a medicament for treating or preventing a disease or disorder disclosed herein.

In some aspects, the present disclosure provides use of a compound of the present disclosure or a pharmaceutically acceptable salt thereof in the manufacture of a medicament for treating a disease or disorder disclosed herein.

In some aspects, the present disclosure provides a method of preparing a compound of the present disclosure.

In some aspects, the present disclosure provides a method of preparing a compound, comprising one or more steps described herein.

Unless otherwise defined, all technical and scientific terms used herein have the same meaning as commonly understood by one of ordinary skill in the art to which this disclosure belongs. In the specification, the singular forms also include the plural unless the context clearly dictates otherwise. Although methods and materials similar or equivalent to those described herein can be used in the practice or testing of the present disclosure, suitable methods and materials are described below. All publications, patent applications, patents and other references mentioned herein are incorporated by reference. The references cited herein are not admitted to be prior art to the claimed invention. In the case of conflict, the present specification, including definitions, will control. In addition, the materials, methods and examples are illustrative only and are not intended to be limiting. In the case of conflict between the chemical structures an names of the compounds disclosed herein, the chemical structures will control.

Other features and advantages of the disclosure will be apparent from the following detailed description and claims.

DETAILED DESCRIPTION

The present disclosure relates to octahydro-tetraazabenzoazulene derivatives, prodrugs, and pharmaceutically acceptable salts thereof, which may modulate Werner helicase (WRN) activity and are accordingly useful in methods of treatment of the human or animal body. The present disclosure also relates to processes for the preparation of these compounds, to pharmaceutical compositions comprising them and to their use in the treatment of disorders in which WRN is implicated, such as cancer.

Definitions

Unless otherwise stated, the following terms used in the specific tion and claims have the following meanings set out below.

Without wishing to be limited by this statement, it is understood that, while various options for variables are described herein, the disclosure intends to encompass operable embodiments having combinations of the options. The disclosure may be interpret d as excluding the non-operable embodiments caused by certain combinations of the options. For example, while various options for variables X, Y, Z, $R_1$, $R_{1a}$, $R_{1b}$, $R_2$, $R_{2a}$, $R_{2a1}$, $R_3$, $R_{3a}$, $R_{3a1}$, $R_{3a2}$, $R_4$, $R_{4''}$, $R_5$, $R_6$, $R_7$, $R_8$, and $R_9$ are described herein, the disclosure may be interpreted as excl ding structures for non-operable compound caused by certain combinations of variables X, Y, Z, $R_1$, $R_{1a}$, $R_{1b}$, $R_2$, $R_{2a}$, $R_{2a1}$, $R_3$, $R_{3a}$, $R_{3a1}$, $R_{3a2}$, $R_4$, $R_{4''}$, $R_5$, $R_6$, $R_7$, $R_8$, and $R_9$.

As used herein, "alkyl", "$C_1$, $C_2$, $C_3$, $C_4$, $C_5$ or $C_6$ alkyl" or "$C_1$-$C_6$ alkyl" is intended to include $C_1$, $C_2$, $C_3$, $C_4$, $C_5$ or $C_6$ straight chain (linear) saturated aliphatic hydrocarbon groups and $C_3$, $C_4$, $C_5$ or $C_6$ branched saturated aliphatic hydrocarbon groups. For example, $C_1$-$C_6$ alkyl is intends to include $C_1$, $C_2$, $C_3$, $C_4$, $C_5$ and $C_6$ alkyl groups. Examples of alkyl include, moieties having from one to six carbon atoms, such as, but not limited to, methyl, ethyl, n-propyl, i-propyl, n-butyl, s-butyl, t-butyl, n-pentyl, i-pentyl, or n-hexyl. In some embodiments, a straight chain or branched alkyl has six or fewer carbon atoms (e.g., $C_1$-$C_6$ for straight chain, $C_3$-$C_6$ for branched chain), and in another embodiment, a straight chain or branched alkyl as four or fewer carbon atoms.

As used herein, the term "optionally substituted alkyl" refers to unsubstituted alkyl or alkyl having designated substituents replacing one or more hydrogen atoms on one or more carbons of the hydrocarbon backbone. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxy carbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

As used herein, the term "alkenyl" includes unsaturated aliphatic groups analogous in length and possible substitution to the alkyls described above, but that contain at least one double bond. For example, the term "alkenyl" includes straight chain alkenyl groups (e.g., ethenyl, propenyl, butenyl, pentenyl, hexenyl, heptenyl, octenyl, nonenyl, decen 1), and branched alkenyl groups. In certain embodiments, a straight chain or branched alkenyl group has six or fewer carbon atoms in its backbone (e.g., $C_2$-$C_6$ for straight chain, $C_3$-$C_6$ for branched chain). The term "$C_2$-$C_6$" includes alkenyl groups containing two to six carbon atoms. The term "$C_3$-$C_6$" includes alkenyl groups containing three to six carbon atoms.

As used herein, the term "optionally substituted alkenyl" refer to unsubstituted alkenyl or alkenyl having designated substituents replacing one or more hydrogen atoms on one or more hydrocarbon backbone carbon atoms. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, heterocyclyl, alkylaryl, or an aromatic or heteroaromatic moiety.

As used herein, the term "alkynyl" includes unsaturated aliphatic groups analogous in length and possible substitution to the alkyls described above, but which contain at least one triple bond. For example, "alkynyl" includes straight chain alkynyl groups (e.g., ethynyl, propynyl, butynyl, pentynyl, hexynyl, heptynyl, octynyl, nonynyl, decynyl), and ranched alkynyl groups. In certain embodiments, a straight chain or branched alkynyl group has ix or fewer carbon atoms in its backbone (e.g., $C_2$-$C_6$ for straight chain, $C_3$-$C_6$ for branched chain). The term "$C_2$-$C_6$" includes alkynyl groups containing two to six carbon atoms. The term "$C_3$-$C_6$" includes alkynyl groups containing three to six carbon atoms. As used herein, "$C_2$-$C_6$ alkenylene linker" or "$C_2$-$C_6$ alkynylene linker" is intended to include $C_2$, $C_3$, $C_4$, $C_5$ or $C_6$ chain (linear or branched) divalent unsaturated aliphatic hydrocarbon groups. For example, $C_2$-$C_6$ alkenylene linker is intended to include $C_2$, $C_3$, $C_4$, $C_5$ and $C_6$ alkenylene linker groups.

As used herein, the term "optionally substituted alkynyl" refer to unsubstituted alkynyl or alkynyl having designated substituents replacing one or more hydrogen atoms on one or more hydrocarbon backbone carbon atoms. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

Other optionally substituted moieties (such as optionally substituted cycloalkyl, heterocyclyl, aryl, or heteroaryl) include both the unsubstituted moieties and the moieties having one or more of the designated substituents. For example, substituted heterocyclyl includes those substituted with one or more alkyl groups, such as 2,2,6,6-tetramethyl-piperidinyl and 2,2,6,6-tetramethyl-1,2,3,6-tetrahydro-pyridinyl.

As used herein, the term "cycloalkyl" refers to a saturated or partially unsaturated hydrocarbon monocyclic or polycyclic (e.g., fused, bridged, or spiro rings) system having 3 to 30 carbon atoms (e.g., $C_3$-$C_{12}$, $C_3$-$C_{10}$, or $C_3$-$C_8$). Examples of cycloalkyl include, but are not limited to, cyclopropyl, cyclobutyl, cyclopentyl, cyclohexyl, cycloheptyl, cyclooctyl, cyclopentenyl, cyclohexenyl, cycloheptenyl, 1,2,3,4-tetrahydronaphthalenyl, and adamantyl. In the case of polycyclic cycloalkyl, only one of the rings in the cycloalkyl needs to be non-aromatic.

As used herein, the term "heterocyclyl" refers to a saturated or partially unsaturated 3-8 membered monocyclic, 7-12 membered bicyclic (fused, bridged, or spiro rings), or 11-14 membered tricyclic ring system (fused, bridged, or spiro rings) having ne or more heteroatoms (such as O, N, S, P, or Se), e.g., 1 or 1-2 or 1-3 or 1-4 or 1-5 or 1-6 heteroatoms, or e.g., 1, 2, 3, 4, 5, or 6 heteroatoms, independently selected from the group consisting of nitrogen, oxygen and sulfur, unless specified otherwise. Examples of heterocyclyl groups incl de, but are not limited to, piperidinyl, piperazinyl, pyrrolidinyl, dioxanyl, tetrahydrofuranyl, isoindolinyl, indolinyl, imidazolidinyl, pyrazolidinyl, oxazolidinyl, isoxazolidinyl, thiazolidinyl, oxiranyl, azetidinyl, oxetanyl, thietanyl, 1,2,3,6-tetrahydropyridinyl, tetrahydropyranyl, dihydropyranyl, pyranyl, morpholinyl, tetrahydrothiopyranyl, 1,4-diazepanyl, 1,4-oxazepanyl, 2-oxa-5-azabicyclo[2.2.1]heptanyl, 2,5-diazabicyclo[2.2.1]heptanyl, 2-oxa-6-azaspiro[3.3]heptanyl, 2,6-diazaspiro[3.3]heptanyl, 1,4-dioxa-8-azaspiro[4.5]decanyl, 1,4-dioxaspiro[4.5]decanyl, 1-oxaspiro[4.5]decanyl, 1-azaspiro[4.5]decanyl, 3'H-spiro[cyclohexane-1,1'-isobenzofuran]-yl, 7'H-spiro[cyclohexane-1,5'-furo[3,4-b]pyridin]-yl, 3'H-spiro[cyclohexane-1,1'-furo[3,4-c]pyridin]-yl, 3-azabicyclo[3.1.0]hexanyl, 3-azabicyclo[3.1.0]hexan-3-yl, 1,4,5,6-tetrahydropyrrolo[3,4-c]pyrazolyl, 3,4,5,6,7,8-hexahydropyrido[4,3-d]pyrimidinyl, 4,5,6,7-tetrahydro-1H-pyrazolo[3,4 -c]pyridinyl, 5,6,7,8-tetrahydropyrido[4,3-d]pyrimidinyl, 2-azaspiro[3.3]heptanyl, 2-methyl-2-azaspiro[3.3]heptanyl, 2-azaspiro[3.5]nonanyl, 2-methyl-2-azaspiro[3.5]nonanyl, 2-azaspiro[4.5]decanyl, 2-methyl-2-azaspiro[4.5]decanyl, 2-oxa-azaspiro[3.4]octanyl, 2-oxa-azaspiro[3.4]octan-6-yl, 5,6-dihydro-4H-cyclopenta[b]thiophenyl, and the like. In the case of multicyclic heterocyclyl, only one of the rings in the heterocyclyl needs to be non-aromatic (e.g., 4,5,6,7-tetrahydrobenzo[c]isoxazolyl).

It is understood that when a variable has two attachments to the rest of the formula of the compound, the two attachments could be at the same atom or different atoms of the variable. For example, when a variable (e.g., variable X) is cycloalkyl or heterocyclyl and has two attachments to the rest of the formula of the compound, the two attachments could be at the same atom or different atoms of the cycloalkyl or heterocyclyl.

As used herein, the term "aryl" includes groups with aromaticity, including "conjugated," or multicyclic systems with one or more aromatic rings and do not contain any heteroatom in the ring structure. The term aryl includes both monovalent species and divalent species. Examples of aryl groups include, but are not limited to, phenyl, biphenyl, naphthyl and the like.

As used herein, the term "heteroaryl" is intended to include a stable 5-, 6-, or 7-membered monocyclic or 7-, 8-, 9-, 10-, 11- or 12-membered bicyclic aromatic heterocyclic ring which consists of carbon atoms and one or more heteroatoms, e.g., 1 or 1-2 or 1-3 or 1-4 or 1-5 or 1-6 heteroatoms, or e.g., 1, 2, 3, 4, 5, or 6 heteroatoms, independently selected from the group consisting of nitrogen, oxygen and sulfur. The nitrogen atom may be substituted or unsubstituted (i.e., N or NR wherein R is H or other substituents, as defined). The nitrogen and sulfur heteroatoms may optionally be oxidized (i.e., N→O and $S(O)_p$, where p 1 or 2). It is to be noted that total number of S and O atoms in the aromatic heterocycle is not more than 1. Examples of heteroaryl groups include pyrrole, furan, thiophene, thiazole, isothiazole, imidazole, triazole, tetrazole, pyrazole, oxazole, isoxazole, isothiazole, pyridine, pyrazine, pyridazine, pyrimidine, and the like. Heteroaryl groups can also be fused or bridged with alicyclic or heterocyclic rings, which are not aromatic so as to form a multicyclic system (e.g., 4,5,6,7-tetrahydrobenzo[c]isoxazolyl).

Furthermore, the terms "aryl" and "heteroaryl" include multicyclic aryl and heteroaryl groups, e.g., tricyclic, bicyclic, e.g., naphthalene, benzoxazole, benzodioxazole, benzothiazole, benzoimidazole, benzothiophene, quinoline, isoquinoline, naphthridine, indole, benzofuran, purine, benzofuran, deazapurine, or indolizine.

The cycloalkyl, heterocyclyl, aryl, or heteroaryl ring can be substituted at one or more ring positions (e.g., the ring-forming carbon or heteroatom such as N) with such substituents as described above, for example, alkyl, alkenyl, alkynyl, halogen, hydroxyl, alkoxy, alkylcarbonyloxy, arylcarbonyloxy, alkoxycarbonyloxy, aryloxycarbonyloxy, carboxylate, alkylcarbonyl, alkylaminocarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl and heteroaryl groups can also be fused or bridged with alicyclic or heterocyclic rings, which are not aromatic so as to form a multicyclic system (e.g., tetralin, methylenedioxyphenyl such as benzo[d][1,3]dioxole-5-yl).

As used herein, the term "about" refers to a recited amount, value, or duration±10% or less of said amount, value, or duration. In some embodiments, "about" refers to a recited amount, value, or duration±10%, ±8%, ±6%, f 5%, ±4%, ±2%, ±1%, or ±0.5%. In other embodiments, "about" refers to a recited amount, value, or duration±1%, +8%, ±6%, ±5%, ±4%, or ±2%. In other embodiments, "about" refers to a recited amount, value, or duration±5%. In some embodiments, "about" refers to a listed amount, value, or duration±2% or ±1%. For example, in some embodiments, when the term "about" is used when reciting a temperature or temperature range, these terms refer to the recited temperature or temperature range±5° C., ±2° C., or ±1° C. In other embodiments, the term "about" refers to the recited temperature or temperature range±2° C.

As used herein, the term "substituted," means that any one or more hydrogen atoms on the designated atom is replaced with a selection from the indicated groups, provided that the designated atom's normal valency is not exceeded, and that the substitution results in a stable compound. When a substituent is oxo or keto (i.e., =O), then 2 hydrogen atoms on the atom are replaced. Keto substituents are not present on aromatic moieties. Rin double bonds, as used herein, are double bonds that are formed between two adjacent ring a oms (e.g., C=C, C=N or N=N). "Stable compound" and "stable structure" are meant to indicate a compound that is sufficiently robust to survive isolation to a useful degree of purity from a reaction mixture, and formulation into an efficacious therapeutic agent.

When a bond to a substituent is shown to cross a bond connecting two atoms in a ring, then such substituent may be bonded to any atom in the ring. When a substituent is listed without indicating the atom via which such substituent is bonded to the rest of the compound of a given formula, then such substituent may be bonded via any atom in such formula. Combinations of substituents and/or variables are permissible, but only if such combinations result in stable compounds.

When any variable (e.g., R) occurs more than one time in any constituent or formula for a compound, its definition at each occurrence is independent of its definition at every other occurrence. Thus, for example, if a group is shown to be substituted with 0-2 R moieties, then the group may optionally be substituted with up to two R moieties and R at each occurrence is selected independently from the definition of R. Also, combinations of substituents and/or variables are permissible, but only if such combinations result in stable compounds.

As used herein, the term "hydroxy" or "hydroxyl" includes groups with an —OH or —O—.

As used herein, the term "halo" or "halogen" refers to fluoro, chloro, bromo and iodo.

The term "haloalkyl" or "haloalkoxyl" refers to an alkyl or alkoxyl substituted with one or more halogen atoms.

As used herein, the term "optionally substituted haloalkyl" refers to unsubstituted haloalkyl having designated substituents replacing one or more hydrogen atoms on one or more hydrocarbon backbone carbon atoms. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

As used herein, the term "alkoxy" or "alkoxyl" includes substituted and unsubstituted alkyl, alkenyl and alkynyl groups covalently linked to an oxygen atom. Examples of alkoxy groups or alkoxyl radicals include, but are not limited to, methoxy, ethoxy, isopropyloxy, propoxy, butoxy and pentoxy groups. Examples of substituted alkoxy groups include halogenated alkoxy groups. The alkoxy groups can be substituted with groups such as alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties. Examples of halogen substituted alkoxy groups include, but are not limited to, fluoromethoxy, difluoromethoxy, trifluoromethoxy, chloromethoxy, dichloromethoxy and trichloromethoxy.

As used herein, the expressions "one or more of A, B, or C," "one or more A, B, or C," "one or more of A, B, and C," "one or more A, B, and C," "selected from the group consisting of A, B, and C", "selected from A, B, and C", and the like are used interchangeably and all refer to a selection from a group consisting of A, B, and/or C, i.e., one or more As, one or more Bs, one or more Cs, or any combination thereof, unless indicated otherwise.

It is to be understood that the present disclosure provides metho is for the synthesis of the compounds of any of the Formulae described herein. The present disclosure also provides detailed methods for the synthesis of various disclosed compounds of the present disclosure according to the following schemes as well as those shown in the Examples.

It is to be understood that, throughout the description, where compositions are described as having, including, or comprising specific components, it is contemplated that compositions also consist essentially of, or consist of, the recited components. Similarly, where methods or processes are described as having, including, or comprising specific process steps, the processes also consist essentially of, or consist of, the recited processing steps. Further, it should be understood that the order of steps order for performing certain actions is immaterial so long as the invention remains operable. Moreover, two or more steps or actions can be conducted simultaneously.

It is to be understood that the synthetic processes of the disclosure can tolerate a wide variety of functional groups, therefore various substituted starting materials can be used. The processes generally provide the desired final compound at or near the end of the overall process, although it may be desirable in certain instances to further convert the compound to a pharmaceutically acceptable salt thereof.

It is to be understood that compounds of the present disclosure can be prepared in a variety of ways using commercially available starting materials, compounds known in the literature, or from readily prepared intermediates, by employing standard synthetic methods and procedures either known to those skilled in the art, or which will be apparent to the skilled artisan in light of the teachings herein. Standard synthetic methods and procedures for t e preparation of organic molecules and functional group transformations and manipulations c n be obtained from the relevant scientific literature or from standard textbooks in the field. Although not limited to any one or several sources, classic texts such as Smith, M. B., March, J., *March's Advanced Organic Chemistry: Reactions, Mechanisms, and Structure,* 5th edition, John Wiley & Sons: New York, 2001; Greene, T.W., Wuts, P.G. M., *Protective Groups in Organic Synthesis,* 3rd edition, John Wiley & Sons: New York, 1999; R. Larock, *Comprehensive Organic Transformations*, VCH Publishers (1989); L. Fieser and M. Fieser, *Fieser and Fieser's Reagents for organic Synthesis*, John Wiley and Sons (1994); and L. Paquette, ed., *Encyclopedia of Reagents for organic Synthesis*, John Wiley and Sons (1995), incorporated by reference herein, are useful and recognized reference textbooks of organic synthesis known to those in the art One of ordinary skill in the art will note that, during the reaction sequences and synthetic schemes described herein, the order of certain steps may be changed, such as the introduction and removal of protecting groups. One of ordinary skill in the art will recognize that certain groups may require protection from the reaction conditions via the use of protecting groups. Protecting groups may also be used to differentiate similar functional groups in molecules. A list of protecting groups and how to introduce and remove these groups can be found in Greene, T.W., Wuts, P.G. M., *Protective Groups in Organic Synthesis,* $3^{rd}$ edition, John Wiley & Sons: New York, 1999.

It is to be understood that, unless otherwise stated, any description of a method of treatment or prevention includes use of the compounds to provide such treatment or prevention as is described herein. It is to be further understood, unless otherwise stated, any description of a method of treatment or prevention includes use of the compounds to prepare a medicament to treat or prevent such condition. The treatment or prevention includes treatment or prevention of human or non-human animals including rodents and other disease models.

It is to be understood that, unless otherwise stated, any description of a method of treatment includes use of the compounds to provide such treatment as is described herein. It is to be further understood, unless otherwise stated, any description of a method of treatment includes use of the compounds to prepare a medicament to treat such condition. The treatment includes treatment of human or non-human animals including rodents and other disease models.

As used herein, the term "subject" includes human and non-human animals, as well as cell lines, cell cultures, tissues, and organs. In some embodiments, the subject is a mammal. The mammal can be e.g., a human or appropriate non-human mammal, such as primate, mouse, rat, dog, cat, cow, horse, goat, camel, sheep or a pig. The subject can also be a bird or fowl. In some embodiments, the subject is a human.

As used herein, the term "subject in need thereof" refers to a subject having a disease or having an increased risk of developing the disease. A subject in need thereof can be one who has been previously diagnosed or identified as having a disease or disorder disclosed herein. A subject in need thereof can also be one who is suffering from a disease or disorder disclosed herein. Alternatively, a subject in need thereof can be one who has an increase risk of developing such disease or disorder relative to the population at large (i.e., a subject who is predisposed to developing such disorder relative to the population at large). A subject in need thereof can have a refractory or resistant a disease or disorder disclosed herein (i.e., a disease or disorder disclosed herein that does not respond or has not yet responded to treatment). The subject may be resistant at start of treatment or may become resistant during treatment. In some embodiments, the subject in need thereof received and failed all known effective therapies for a disease or disorder disclosed herein. In some embodiments, the subject in need thereof received at least one prior therapy.

As used herein, the term "treating" or "treat" describes the management and care of a patient for the purpose of combating a disease, condition, or disorder and includes the administration of a compound of the present disclosure, or a pharmaceutically acceptable salt, polymorph or solvate thereof, to alleviate the symptoms or complications of a disease, condition or disorder, or to eliminate the disease, condition or disorder. The term "treat" can also include treatment of a cell in vitro or an animal model. It is to be appreciated that references to "treating" or "treatment" include the alleviation of established symptoms of a condition. "Treating" or "treatment" of a state, disorder or condition therefore includes: (1) preventing or delaying the appearance of clinical symptoms of the state, disorder or condition developing in a human that may be afflicted with or predisposed to the state, disorder or condition but does not yet experience or display clinical or subclinical symptoms of the state, disorder or condition, (2) inhibiting the state, disorder or condition, i.e., arresting, reducing or delaying the development of the disease or a relapse thereof (in case of maintenance treatment) or at least one clinical or subclinical symptom thereof, or (3) relieving or attenuating the disease, i.e., causing regression of the state, disorder or condition or at least one of its clinical or subclinical symptoms.

It is to be understood that a compound of the present disclosure, or a pharmaceutically acceptable salt, polymorph or solvate thereof, can or may also be used to prevent a relevant disease, condition or disorder, or used to identify suitable candidates for such purposes.

As used herein, the term "preventing," "prevent," or "protecting against" describes reducing or eliminating the onset of the symptoms or complications of such disease, condition or disorder.

It is to be understood that one skilled in the art may refer to general reference texts for detailed descriptions of known techniques discussed herein or equivalent techniques. These texts include Ausubel et al., *Current Protocols in Molecular Biology*, John Wiley and Sons, Inc. (2005); Sambrook et al., *Molecular Cloning, A Laboratory Manual* ($3^{rd}$ edition), Cold Spring Harbor Press, Cold Spring Harbor, New York (2000); Coligan et al., *Current Protocols in Immunology*, John Wiley & Sons, N.Y.; Enna et al., *Current Protocols in Pharmacology*, John Wiley & Sons, N.Y.; Fingl et al., *The Pharmacological Basis of Therapeutics* (1975), Remington's *Pharmaceutical Sciences*, Mack Publishing Co., Easton, PA, $18^{th}$ edition (1990). These texts can, of course, also be referred to in making or using an aspect of the disclosure.

It is to be understood that the present disclosure also provides pharmaceutical compositions comprising any compound described herein in combination with one or more pharmaceutically acceptable excipient, diluent, adjuvant, carrier, or a combination thereof.

As used herein, the term "pharmaceutical composition" is a formulation containing the compounds of the present disclosure in a form suitable for administration to a subject. In one embodiment, the pharmaceutical composition is in bulk or in unit dosage form. The unit dosage form is any of a variety of forms, including, for example, a capsule, an IV bag, a tablet, a single pump on an aerosol inhaler or a vial. The quantity of active ingredient (e.g., a formulation of the disclosed compound or salt, hydrate, solvate or isomer thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, inhalational, buccal, sublingual, intrapleural, intrathecal, intranasal, and the like. Dosage forms for the topical or transdermal administration of a compound of this disclosure include powders, sprays, ointments, pastes, creams, lotions, gels, solutions, patches and inhalants. In one embodiment, the active compound is mixed under sterile conditions with a pharmaceutically acceptable carrier, and with any preservatives, buffers, or propellants that are required.

As used herein, the term "pharmaceutically acceptable" refers to those compounds, anions, cations, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

It is to be understood that a pharmaceutical composition of the disclosure is formulated to be compatible with its intended route of administration. Examples of routes of administration include parenteral, e.g., intravenous, intradermal, subcutaneous, oral (e.g., ingestion), inhalation, transdermal (topical), and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

It is to be understood that a compound or pharmaceutical composition of the disclosure can be administered to a subject in many of the well-known methods currently used for chemotherapeutic treatment. For example, a compound of the disclosure may be injected into the blood stream or body cavities or taken orally or applied through the skin with patches. The dose chosen should be sufficient to constitute effective treatment but not so high as to cause unacceptable side effects. The state of the disease condition (e.g., a disease or disorder disclosed herein) and the health of the patient should preferably be closely monitored during and for a reasonable period after treatment.

As used herein, the term "therapeutically effective amount", refers to an amount of a pharmaceutical agent to treat, ameliorate, or prevent an identified disease or condition, or to exhibit a detectable therapeutic or inhibitory effect. The effect can be detected by any assay method known in the art. The precise effective amount for a subject will depend upon the subject's body weight, size, and health; the nature and extent of the condition; and the therapeutic or combination of therapeutics selected for administration. The dosage may vary within this range depending upon the dosage form employed, sensitivity of the patient, and the route of administration.

Dosage and administration are adjusted to provide sufficient levels of the active agent(s) or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

The pharmaceutical compositions containing active compounds of the present disclosure may be manufactured in a manner that is generally known, e.g., by means of conventional mixing, dissolving, granulating, dragee-making, levigating, emulsifying, encapsulating, entrapping, or lyophilizing processes. Pharmaceutical compositions may be formulated in a conventional manner using one or more pharmaceutically acceptable carriers comprising excipients and/or auxiliaries that facilitate processing of the active compounds into preparations that can be used pharmaceutically. Of course, the appropriate formulation is dependent upon the route of administration chosen.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), cyclodextrins and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol and sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible pharmaceutically acceptable carrier. They can be enclosed in gelatin capsules or compressed into tablets. For the purpose of oral therapeutic administration, the active compound c n be incorporated with excipients and used in the form of tablets, troches, capsules or sachets. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, orange flavoring.

For administration by inhalation, the compounds are delivered in the form of an aerosol spray from pressured container or dispenser, which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays, powders or suppositories. For transdermal administration, the active compounds are formulated into ointments, salves, gels, or creams as generally known in the art.

The active compounds can be prepared with pharmaceutically acceptable carriers that will protect the compound against rapid elimination from the body, such as a controlled release formulation, including implants and microencapsulated delivery systems. Biodegradable, biocompatible polymers can be used, such as ethylene vinyl acetate, pol anhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the disclosure are dictated by and directly dependent on the unique characteristics of the active compound and the particular therapeutic effect to be achieved.

It is to be understood that the pharmaceutical compositions can be included in a container, pack, or dispenser together with instructions for administration.

It is to be understood that, for the compounds of the present disclosure being capable of further forming salts, all of these forms are also contemplated within the scope of the claimed disclosure.

As used herein, the term "pharmaceutically acceptable salts" refer to derivatives of the compounds of the present disclosure wherein the parent compound is modified by making acid or base salts thereof. Examples of pharmaceutically acceptable salts include, but are not limited to, mineral organic acid salts of basic residues such as amines, alkali organic salts of acidic residues such as carboxylic acids, and the like. The pharmaceutically acceptable salts include the conventional non-toxic salts or the quaternary ammonium salts of the parent compound formed, for example, from non-toxic inorganic organic acids. For example, such conventional non-toxic salts include, but are not limited to, those derived from inorganic and organic acids selected from 2-acetoxybenzoic, 2-hydroxyethane sulfonic, acetic, ascorbic, benzene sulfonic, benzoic, bicarbonic, carbonic, citric, edetic, ethane disulfonic, 1,2-ethane sulfonic, fumaric, glucoheptonic, gluconic, glutamic, glycolic, glycollyarsanilic, hexylresorcinic, hydrabamic, hydrobromic, hydrochloric, hydroiodic, hydroxymaleic, hydroxynaphthoic, isethionic, lactic, lactobionic, lauryl sulfonic, maleic, malic, mandelic, methane sulfonic, napsylic, nitric, oxalic, pamoic, pantothenic, phenylacetic, phosphoric, polygalacturonic, propionic, salicylic, stearic, subacetic, succinic, sulfamic, sulfanilic, sulfuric, tannic, tartaric, toluene sulfonic, and the commonly occurring amine acids, e.g., glycine, alanine, phenylalanine, arginine, etc.

In some embodiments, the pharmaceutically acceptable salt is a sodium salt, a potassium salt, a calcium salt, a magnesium salt, a diethylamine salt, a choline salt, a meglumine salt, a benzathine salt, a tromethamine salt, an ammonia salt, an arginine salt, or a lysine salt.

Other examples of pharmaceutically acceptable salts include hexanoic acid, cyclopentane propionic acid, pyruvic acid, malonic acid, 3-(4-hydroxybenzoyl)benzoic acid, cinnamic acid, 4-chlorobenzenesulfonic acid, 2-naphthalenesulfonic acid, 4-toluenesulfonic acid, camphorsulfonic acid, 4-methylbicyclo-[2.2.2]-oct-2-ene-1-carboxylic acid, 3-phenylpropionic acid, trimethylacetic acid, tertiary butylacetic acid, muconic acid, and the like. The present disclosure also encompasses salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like. In the salt form, it is understood that the ratio of the compound to the cation or anion of the salt can be 1:1, or any ratio other than 1:1, e.g., 3:1, 2:1, 1:2, or 1:3.

The compounds, or pharmaceutically acceptable salts thereof, are administered orally, nasally, transdermally, pulmonary, inhalationally, buccally, sublingually, intraperitoneally, subcutaneously, intramuscularly, intravenously, rectally, intrapleurally, intrathecally and parenterally. In one embodiment, the compound is administered orally.

The dosage regimen utilizing the compounds is selected in accordance with a variety of factors including type, species, age, weight, sex and medical condition of the patient; the severity of the condition to be treated; the route of administration; the renal and hepatic function of the patient; and the particular compound or salt thereof employed.

Techniques for formulation and administration of the disclosed compounds of the disclosure can be found in *Remington: the Science and Practice of Pharmacy,* $19^{th}$ edition, Mack Publishing Co., Easton, PA (1995). In an embodiment, the compounds described herein, and the pharmaceutically acceptable salts thereof, are used in pharmaceutical preparations in combination with a pharmaceutically acceptable carrier or diluent. Suitable pharmaceutically acceptable carriers include inert solid fillers or diluents and sterile aqueous organic solutions. The compounds will be present in such pharmaceutical compositions in amounts sufficient to provide the desired dosage amount in the range described herein.

All percentages and ratios used herein, unless otherwise indicated, are by weight. Other features and advantages of the present disclosure are apparent from the different examples. The provided examples illustrate different components and methodology useful in practicing the present disclosure. The examples do not limit the claimed disclosure. Based on the present disclosure the skilled artisan can identify and employ other components and methodology useful for practicing the present disclosure.

In the synthetic schemes described herein, compounds may be drawn with one particular configuration for simplicity. Such particular configurations are not to be construed as limiting the disclosure to one or another isomer, tautomer, regioisomer or stereoisomer, nor does it exclude mixtures of isomers, tautomers, regioisomers or stereoisomers; however, it will be understood that a given isomer, tautomer, regioisomer or stereoisomer may have a higher level of activity than another isomer, tautomer, regioisomer or stereoisomer.

All publications and patent documents cited herein are incorporated herein by reference as if each such publication or document was specifically and individually indicated to be incorporated herein by reference. Citation of publications and patent documents is not intended as an admission that any is pertinent prior art, nor does it constitute any admission as to the contents or date of the same. The invention having now been described by way of written description, those of skill in the art will recognize that the invention can be practiced in a variety of embodiments and that the foregoing description and examples below are for purposes of illustration and not limitation of the claims that follow.

As use herein, the phrase "compound of the disclosure" refers to those compounds which are disclosed herein, both generically and specifically.

Compounds of the Present Disclosure

In some aspects, the present disclosure provides a compound of Formula (I'):

(I')

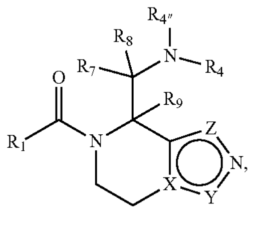

or a pharmaceutically acceptable salt, oxide, solvate, clathrate, hydrate, stereoisomer, or tautomer thereof, wherein:

X is N or C;

Y is $NR_2$ or $CR_2$;

Z is $NR_3$ or $CR_3$;

$R_1$ is $C_1$-$C_6$ alkyl, $C_2$-$C_6$ alkenyl, $C_2$-$C_6$ alkynyl, $C_1$-$C_6$ haloalkyl, $C_3$-$C_{10}$ cycloalkyl, $C_6$-$C_{10}$ aryl, 5- to 10-membered heteroaryl, or 3- to 10-membered heterocyclyl, wherein the $C_1$-$C_6$ alkyl, $C_2$-$C_6$ alkenyl, $C_2$-$C_6$ alkynyl, $C_1$-$C_6$ haloalkyl, $C_3$-$C_{10}$ cycloalkyl, $C_6$-$C_{10}$ aryl, 5- to 10-membered heteroaryl, or 3- to 10-membered heterocyclyl is optionally substituted with one or more $R_{1a}$;

each $R_{1a}$ independently is oxo, halo, cyano, —OH, —$NH_2$, —$NO_2$, —NH($C_1$-$C_6$ alkyl), —N($C_1$-$C_6$ alkyl)$_2$, —NH—C(O)($C_1$-$C_6$ alkyl), —S($C_1$-$C_6$ alkyl), —S(O)$_2$($C_1$-$C_6$ alkyl). —S(O)$_2$($NH_2$), —C(O)(H), —C(O)$NH_2$, —O(3- to 10-membered heterocyclyl), $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, $C_3$-$C_{10}$ cycloalkyl, $C_6$-$C_{10}$ aryl, 5- to 10-membered heteroaryl, or 3-to 10-membered heterocyclyl, wherein the —NH($C_1$-$C_6$ alkyl), —N($C_1$-$C_6$ alkyl)$_2$ —NH—C(O)($C_1$-$C_6$ alkyl), —S($C_1$-$C_6$ alkyl), —S(O)$_2$($C_1$-$C_6$ alkyl), —O(3- to 10-membered heterocyclyl), $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, $C_3$-$C_{10}$ cycloalkyl, $C_6$-$C_{10}$ aryl, 5-to 10-membered heteroaryl, or 3- to 10-membered heterocyclyl is option ally substituted with one or more $R_{1b}$;

each $R_{1b}$ independently is oxo, halo, cyano, —OH, —O($C_1$-$C_6$ alkyl), —O($C_1$-$C_6$ haloalkyl), —O($C_2$-$C_6$ alkenyl), —O($C_2$-$C_6$ alkynyl), —$NH_2$, —NH($C_1$-$C_6$ alkyl), —N($C_1$-$C_6$ alkyl)$_2$, —NH($C_1$-$C_6$ haloalkyl), —S($C_1$-$C_6$ alkyl), —S(O)$_2$($C_1$-$C_6$ alkyl), —C(O)$NH_2$, $C_1$-$C_6$ alkyl, $C_3$-$C_{10}$ cycloalkyl, or 3-to 10-membered heterocyclyl optionally substituted with oxo;

$R_2$ is $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_3$-$C_{10}$ cycloalkyl, $C_6$-$C_{10}$ aryl, 5- to 10-membered heteroaryl, or 3- to 10-membered heterocyclyl, wherein the $C_1$-$C_6$ alkyl, $C_3$-$C_{10}$ cycloalkyl, $C_6$-$C_{10}$ aryl, 5- to 10-membered heteroaryl, or 3- to 10-membered heterocyclyl is optionally substituted with one or more $R_{2a}$;

each $R_{2a}$ independently is oxo, halo, cyano, —OH, —$NH_2$, —NH($C_1$-$C_6$ alkyl), —N($C_1$-$C_6$ alkyl)$_2$, —SH, —S(O)$_2$$NH_2$, —$SF_5$, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, —S($C_1$-$C_6$ haloalkyl), —S($C_1$-$C_6$ alkyl), $C_3$-$C_{10}$ cycloalkyl, $C_6$-$C_{10}$ aryl, 5- to 10-membered heteroaryl, or 3- to 10-membered heterocyclyl, wherein the $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, —S($C_1$-$C_6$ haloalkyl), —S($C_1$-$C_6$ alkyl), $C_3$-$C_{10}$ cycloalkyl, $C_6$-$C_{10}$ aryl, 5- to 10-membered heteroaryl, or 3- to 10-membered heterocyclyl is optionally substituted with one or more $R_{2a1}$;

each $R_{2a1}$ independently is oxo, halo, cyano, —OH, —$NH_2$, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, —NH—C(O)($C_1$-$C_6$ alkyl), —C(O))$NH_2$, or —OC(O)($C_1$-$C_6$ alkyl), wherein the $C_1$-$C_6$ alkyl, $C_2$-$C_6$ alkenyl, $C_2$-$C_6$ alkynyl, $C_1$-$C_6$ alkoxy, $C_1$-$C_6$ haloalkyl or $C_1$-$C_6$ alkyl is optionally substituted with one or more —OH;

$R_3$ and $R_4$, together with the atoms to which they are attached, form a 6- to 10-membered heterocyclyl, wherein the heterocyclyl optionally comprises one or more additional N, O, or S and is optionally substituted with one or more $R_{3a}$;

each $R_{3a}$ independently is cyano, halo, —OH, —$NH_2$, —NH($C_1$-$C_6$ alkyl), —N($C_1$-$C_6$ alkyl)$_2$, —N($C_1$-$C_6$ alkyl)($C_1$-$C_6$ haloalkyl), —NH—C(O)($C_1$-$C_6$ alkyl), —O($C_3$-$C_{10}$ cycloalkyl), —O(3- to 10-membered heterocyclyl), $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_1$-$C_6$ haloalkoxy, $C_3$-$C_{10}$ cycloalkyl, 3- to 10-membered heterocyclyl, 5- to 10-membered heteroaryl, —S(O)(=NH)($C_1$-$C_6$ alkyl), —$SO_2$($C_1$-$C_6$ alkyl), —S($C_1$-$C_6$ alkyl), or —S($C_1$-$C_6$ haloalkyl), wherein the —NH($C_1$-$C_6$ alkyl), —N($C_1$-$C_6$ alkyl)$_2$, —N($C_1$-$C_6$ alkyl)($C_1$-$C_6$ haloalkyl), —NH—C(O)($C_1$-$C_6$ alkyl), —O($C_3$-$C_{10}$ cycloalkyl), —O(3- to 10-membered heterocyclyl), $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_1$-$C_6$ haloalkoxy, $C_3$-$C_{10}$ cycloalkyl, 3- to 10-membered heterocyclyl, 5- to 10-membered heteroaryl, —S(O)(=NH)($C_1$-$C_6$ alkyl), —$SO_2$($C_1$-$C_6$ alkyl), —S($C_1$-$C_6$ alkyl), or —S($C_1$-$C_6$ haloalkyl) is optionally substituted with one or more oxo, cyano, 3- to 10-membered heterocyclyl, —C(O)($C_1$-$C_6$ alkyl), 5- to 10-membered heteroaryl optionally substituted with $C_1$-$C_6$ alkyl, $C_1$-$C_6$ alkyl optionally substituted with $C_1$-$C_6$ alkoxy, —N($R_{3a1}$)CO($R_{3a2}$), —O($C_3$-$C_{10}$ cycloalkyl), —O($C_6$-$C_{10}$ aryl), —O(5- to 10-membered heteroaryl), or —O(3- to 10-membered heterocyclyl), or two $R_{3a}$, together with the atoms to which they are attached, form a $C_3$-$C_{10}$ cycloalkyl or 3- to 10-membered heterocyclyl, wherein the cycloalkyl or heterocyclyl is optionally substituted with one or more $C_3$-$C_{10}$ cycloalkyl, 3- to 10-membered heterocyclyl, $C_1$-$C_{10}$ aryl, or 5- to 10-membered heteroaryl, wherein the cycloalkyl, heterocyclyl, aryl, or heteroaryl is optionally substituted with one or more $C_1$-$C_6$ alkyl;

$R_{3a1}$ and $R_{3a2}$, together with the atoms to which they are attached, form a 3- to 10-membered heterocyclyl;

$R_{4''}$ is

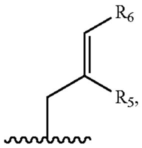
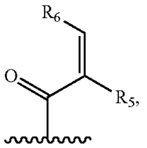
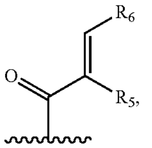
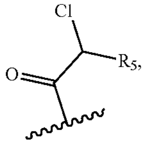
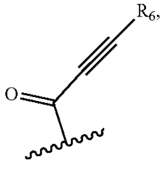
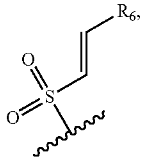
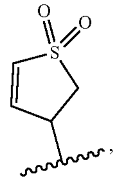
,
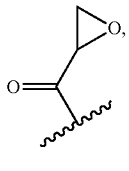
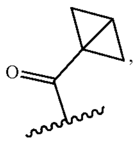
,
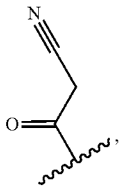
, or
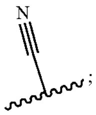
;

$R_5$ is H, halo, cyano, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy, $R_6$ is H, halo, cyano, —$SO_2$($C_1$-$C_6$ alkyl), $C_1$-$C_6$ alkyl, $C_2$-$C_6$ alkenyl, $C_2$-$C_6$ alkynyl, or $C_1$-$C_6$ alkoxy, wherein the alkyl, alkenyl, alkynyl, or alkoxy is optionally substituted with one or more —OH, —O($C_1$-$C_6$ alkyl), —$NH_2$, —NH($C_1$-$C_6$ alkyl), or —N($C_1$-$C_6$ alkyl), or $R_5$ and $R_6$, together with the atoms to which they are attached, form a $C_4$-$C_{10}$ cycloalkenyl; and each $R_7$, $R_8$, and $R_9$ independently is H, cyano, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy, wherein the alkyl, alkenyl, alkynyl, haloalkyl, or alkoxy is optionally substituted with one or more oxo, halo, cyano, —OH, —$NH_2$, $C_1$-$C_6$ alkoxy, —NH($C_1$-$C_6$ alkyl), —N($C_1$-$C_6$ alkyl)$_2$, —NH($C_1$-$C_6$ haloalkyl), or —S($C_1$-$C_6$ alkyl), or $R_7$ and $R_8$, together with the atoms to which they are attached, form a $C_3$-$C_{10}$ cycloalkyl or 3- to 10-membered heterocyclyl.

In some aspects, the present disclosure provides a compound of Formula (I'):

(I')

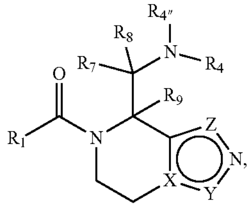

or a pharmaceutically acceptable salt, oxide, solvate, clathrate, hydrate, stereoisomer, or tautomer thereof, wherein:

X is N or C;

Y is $NR_2$ or $CR_2$;

Z is $NR_3$ or $CR_3$;

$R_1$ is $C_1$-$C_6$ alkyl, $C_2$-$C_6$ alkenyl, $C_2$-$C_6$ alkynyl, $C_1$-$C_6$ haloalkyl, $C_3$-$C_{10}$ cycloalkyl, $C_6$-$C_{10}$ aryl, 5- to 10-membered heteroaryl, or 3- to 10-membered heterocyclyl, wherein the $C_1$-$C_6$ alkyl, $C_2$-$C_6$ alkenyl, $C_2$-$C_6$ alkynyl, $C_1$-$C_6$ haloalkyl, $C_3$-$C_{10}$ cycloalkyl, $C_6$-$C_{10}$ aryl, 5- to 10-membered heteroaryl, or 3- to 10-membered heterocyclyl is optionally substituted with one or more $R_{1a}$;

each $R_{1a}$ independently is oxo, halo, cyano, —OH, —$NH_2$, —$NO_2$, —NH($C_1$-$C_6$ alkyl), —N($C_1$-$C_6$ alkyl)$_2$, —NH—C(O)($C_1$-$C_6$ alkyl), —S($C_1$-$C_6$ alkyl), —S(O)$_2$($C_1$-$C_6$ alkyl), —S(O)$_2$($NH_2$), —C(O)(H), —C(O)$NH_2$, —O(3- to 10-membered heterocyclyl), $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, $C_3$-$C_{10}$ cycloalkyl, $C_6$-$C_{10}$ aryl, 5- to 10-membered heteroaryl, or 3-to 10-membered heterocyclyl, wherein the —NH($C_1$-$C_6$ alkyl), —N($C_1$-$C_6$ alkyl)$_2$ —NH—C(O)($C_1$-$C_6$ alkyl), —S($C_1$-$C_6$ alkyl), —S(O)$_2$($C_1$-$C_6$ alkyl), —O(3- to 10-membered heterocyclyl), $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, $C_3$-$C_{10}$ cycloalkyl, $C_6$-$C_{10}$ aryl, 5-to 10-membered heteroaryl, or 3- to 10-membered heterocyclyl is optionally substituted with one or more $R_{1b}$;

each $R_{1b}$ independently is oxo, halo, cyano, —OH, —O($C_1$-$C_6$ alkyl, —O($C_1$-$C_6$ haloalkyl), —O($C_2$-$C_6$ alkenyl), —O($C_2$-$C_6$ alkynyl), —$NH_2$, —NH($C_1$-$C_6$ alkyl), —N($C_1$-C alkyl)$_2$, —NH($C_1$-$C_6$ haloalkyl), —S($C_1$-$C_6$ alkyl), —S(O)$_2$($C_1$-$C_6$ alkyl), $C_1$-$C_6$ alkyl, $C_3$-$C_{10}$ cycloalkyl, or 3- to 10-membered heterocyclyl optionally substituted with oxo;

$R_2$ is $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_3$-$C_{10}$ cycloalkyl, $C_6$-$C_{10}$ aryl, 5- to 10-membered heteroaryl, or 3- to 10-membered heterocyclyl, wherein the $C_1$-$C_6$ alkyl, $C_3$-$C_{10}$ cycloalkyl, $C_6$-$C_{10}$ aryl, 5- to 10-membered heteroaryl, or 3- to 10-membered heterocyclyl is optionally substituted with one or more $R_{2a}$;

each $R_{2a}$ independently is oxo, halo, cyano, —OH, —$NH_2$, —NH($C_1$-$C_6$ alkyl), —N($C_1$-$C_6$ alkyl)$_2$, —SH, —S(O)$_2$NH$_2$, —$SF_5$, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, —S($C_1$-$C_6$ haloalkyl), —S($C_1$-$C_6$ alkyl), $C_3$-$C_{10}$ cycloalkyl, $C_6$-$C_{10}$ aryl, 5- to 10-membered heteroaryl, or 3- to 10-membered heterocyclyl, wherein the $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, —S($C_1$-$C_6$ haloalkyl), —S($C_1$-$C_6$ alkyl), $C_3$-$C_{10}$ cycloalkyl, $C_6$-$C_{10}$ aryl, 5- to 10-membered heteroaryl, or 3- to 10-membered heterocyclyl is optionally substituted with one or more $R_{2a1}$;

each $R_{2a1}$ independently is oxo, halo, cyano, —OH, —$NH_2$, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, —NH—C(O)($C_1$-$C_6$ alkyl), —C(O)NH$_2$, or —OC(O)($C_1$-$C_6$ alkyl), wherein the $C_1$-$C_6$ alkyl, $C_2$-$C_6$ alkenyl, $C_2$-$C_6$ alkynyl, $C_1$-$C_6$ alkoxy, $C_1$-$C_6$ haloalkyl or $C_1$-$C_6$ alkyl is optionally substituted with one or more —OH;

$R_3$ and $R_4$, together with the atoms to which they are attached, form a 6- to 10-membered heterocyclyl, wherein the heterocyclyl optionally comprises one or more additional N, O, or S and is optionally substituted with one or more $R_{3a}$;

each $R_{3a}$ independently is cyano, halo, —OH, —$NH_2$, —NH($C_1$-$C_6$ alkyl), —N($C_1$-$C_6$ alkyl)$_2$, —N($C_1$-$C_6$ alkyl)($C_1$-$C_6$ haloalkyl), —NH—C(O)($C_1$-$C_6$ alkyl), —O($C_3$-$C_{10}$ cycloalkyl), —O(3- to 10-membered heterocyclyl), $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_1$-$C_6$ haloalkoxy, $C_3$-$C_{10}$ cycloalkyl, 3- to 10-membered heterocyclyl, $C_6$-$C_{10}$ aryl, 5- to 10-membered heteroaryl, —S(O)(=NH)($C_1$-$C_6$ alkyl), —SO$_2$($C_1$-$C_6$ alkyl), S($C_1$-$C_6$ alkyl), or —S($C_1$-$C_6$ haloalkyl), wherein the alkyl, alkenyl, alkynyl, haloalkyl, alkoxy, haloalkoxy, —O($C_3$-$C_{10}$ cycloalkyl), —O(3- to 10-membered heterocyclyl), heterocycle, cycloalkyl, aryl, or heteroaryl is optionally substituted with one or more oxo, —CN, $C_1$-$C_6$ alkoxy, —C(O)($C_1$-$C_6$ alkyl), —N($R_{3a1}$)CO($R_{3a2}$), —O($C_3$-$C_{10}$ cycloalkyl), —O($C_6$-$C_{10}$ aryl), —O(5- to 10-membered heteroaryl), —O(3- to 10-membered heterocyclyl), $C_3$-$C_{10}$ cycloalkyl, 3- to 10-membered heterocyclyl, $C_6$-$C_{10}$ aryl, or 5- to 10-membered heteroaryl, wherein the cycloalkyl, aryl, heteroaryl, or heterocyclyl is optionally substituted with one or more $C_1$-$C_6$ alkyl, or two $R_{3a}$, together with the atoms to which they are attached, for a $C_3$-$C_{10}$ cycloalkyl or 3- to 10-membered heterocyclyl, wherein the cycloalkyl or heterocyclyl is optionally substituted with one or more $C_3$-$C_{10}$ cycloalkyl, 3- to 10-membered heterocyclyl, $C_1$-$C_{10}$ aryl, or 5- to 10-membered heteroaryl, wherein the cycloalkyl, heterocyclyl, aryl, or heteroaryl is optionally substituted with one or more $C_1$-$C_6$ alkyl;

$R_{3a1}$ and $R_{3a2}$, together with the atoms to which they are attached form a 3- to 10-membered heterocyclyl;

$R_{4''}$ is

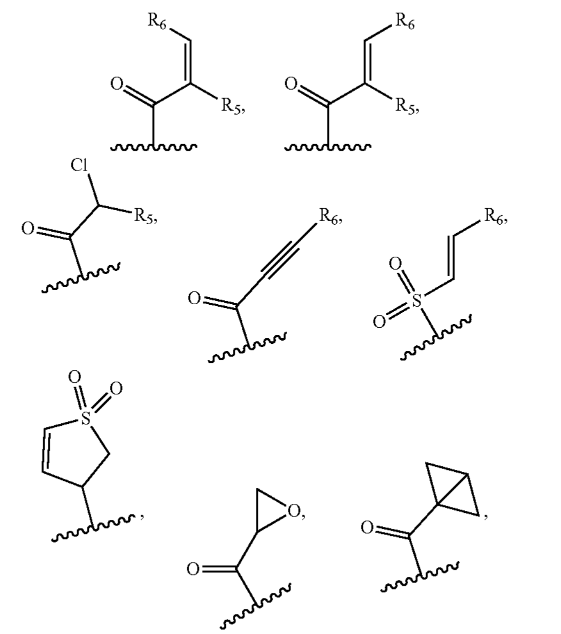

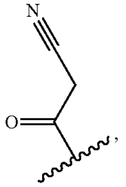

or

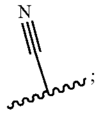

$R_5$ is H, halo, cyano, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy;

$R_6$ is H, halo, cyano, $C_1$-$C_6$ alkyl, $C_2$-$C_6$ alkenyl, $C_2$-$C_6$ alkynyl, or $C_1$-$C_6$ alkoxy, wherein the alkyl, alkenyl, alkynyl, or alkoxy is optionally substituted with one or more —$NH_2$, —NH($C_1$-$C_6$ alkyl), or —N($C_1$-$C_6$ alkyl)$_2$, or $R_5$ and $R_6$, together with the atoms to which they are attached, form a $C_4$-$C_{10}$ cycloalkenyl; and each $R_7$, $R_8$, and $R_9$ independently is H, cyano, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy, wherein the alkyl, alkenyl, alkynyl, haloalkyl, or alkoxy is optionally substituted with one or more oxo, halo, cyano, —OH, —$NH_2$, $C_1$-$C_6$ alkoxy, —NH($C_1$-$C_6$ alkyl), —N($C_1$-$C_6$ alkyl)$_2$, —NH($C_1$-$C_6$ haloalkyl), or —S($C_1$-$C_6$ alkyl), or $R_7$ and $R_8$, together with the atoms to which they are attached, form a $C_3$-$C_{10}$ cycloalkyl or 3- to 10-membered heterocyclyl.

In some aspects, the present disclosure provides a compound of Formula (I'):

(I')

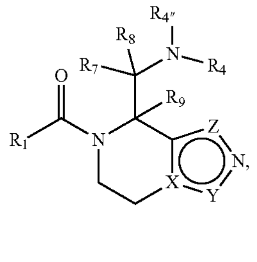

or a pharmaceutically acceptable salt, oxide, solvate, clathrate, hydrate, stereoisomer, or tautomer thereof, wherein:

X is N or C;

Y is $NR_2$ or $CR_2$;

Z is $NR_3$ or $CR_3$;

$R_1$ is $C_1$-$C_6$ alkyl, $C_2$-$C_6$ alkenyl, $C_2$-$C_6$ alkynyl, $C_1$-$C_6$ haloalkyl, $C_3$-$C_{10}$ cycloalkyl, $C_6$-$C_{10}$ aryl, 5- to 10-membered heteroaryl, or 3- to 10-membered heterocyclyl, wherein the $C_1$-$C_6$ alkyl, $C_2$-$C_6$ alkenyl, $C_2$-$C_6$ alkynyl, $C_1$-$C_6$ haloalkyl, $C_3$-$C_{10}$ cycloalkyl, $C_6$-$C_{10}$ aryl, 5- to 10-membered heteroaryl, or 3- to 10-membered heterocyclyl is optionally substituted with one or more $R_{1a}$;

each $R_{1a}$ independently is oxo, halo, cyano, —OH, —$NH_2$, —$NO_2$, —NH($C_1$-$C_6$ alkyl), —N($C_1$-$C_6$ alkyl)$_2$, —NH—C(O)($C_1$-$C_6$ alkyl), —S($C_1$-$C_6$ alkyl), —S(O)$_2$($C_1$-$C_6$ alkyl) —S(O)$_2$($NH_2$), —C(O)(H), —C(O)$NH_2$, —O(3- to 10-membered heterocyclyl), $C_1$-$C_6$ alkyl, $C_2$-$C_5$ alkenyl, $C_2$-$C_6$ alkynyl, $C_1$-$C_6$ alkoxy, $C_1$-$C_6$ haloalkyl, $C_3$-$C_{10}$ cycloalkyl, $C_6$-$C_{10}$ aryl, 5- to 10-membered heteroaryl, or 3-to 10-membered heterocyclyl, wherein the —NH($C_1$-$C_6$ alkyl), —N($C_1$-$C_6$ alkyl)$_2$ —NH—C(O)($C_1$-$C_6$ alkyl), —S($C_1$-$C_6$ alkyl), —S(O)$_2$($C_1$-$C_6$ alkyl), —O(3- to 10-membered heterocyclyl), $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, $C_3$-$C_{10}$ cycloalkyl, $C_6$-$C_{10}$ aryl, 5-to 10-membered heteroaryl, or 3- to 10-membered heterocyclyl is optionally substituted with one or more $R_{1b}$;

each $R_{1b}$ independently is oxo, halo, cyano, —OH, —O($C_1$-$C_6$ alkyl), —O($C_1$-$C_6$ haloalkyl), —O($C_2$-$C_6$ alkenyl), —O($C_2$-$C_6$ alkynyl), —$NH_2$, —NH($C_1$-$C_6$ alkyl), —N($C_1$-$C_6$ alkyl)$_2$, —NH($C_1$-$C_6$ haloalkyl), —S($C_1$-$C_6$ alkyl), —S(O)$_2$($C_1$-$C_6$ alkyl), $C_1$-$C_6$ alkyl, $C_3$-$C_{10}$ cycloalkyl, or 3- to 10-membered heterocyclyl optionally substituted with oxo;

$R_2$ is $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_3$-$C_{10}$ cycloalkyl, $C_6$-$C_{10}$ aryl, 5- to 10-membered heteroaryl, or 3- to 10-membered heterocyclyl, wherein the $C_1$-$C_6$ alkyl, $C_3$-$C_{10}$ cycloalkyl, $C_6$-$C_{10}$ aryl, 5- to 10-membered heteroaryl, or 3- to 10-membered heterocyclyl is optionally substituted with one or more $R_{2a}$;

each $R_{2a}$ independently is oxo, halo, cyano, —OH, —$NH_2$, —NH($C_1$-$C_6$ alkyl), —N($C_1$-$C_6$ alkyl)$_2$, —SH, —S(O)$_2NH_2$, —$SF_5$, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, —S($C_1$-$C_6$ haloalkyl), —S($C_1$-$C_6$ alkyl), $C_3$-$C_{10}$ cycloalkyl, $C_6$-$C_{10}$ aryl, 5- to 10-membered heteroaryl, or 3- to 10-membered heterocyclyl, wherein the $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, —S($C_1$-$C_6$ haloalkyl), —S($C_1$-$C_6$ alkyl), $C_3$-$C_{10}$ cycloalkyl, $C_6$-$C_{10}$ aryl, 5- to 10-membered heteroaryl, or 3- to 10-membered heterocyclyl is optionally substituted with one or more $R_{2a1}$;

each $R_{2a1}$ independently is oxo, halo, cyano, —OH, —$NH_2$, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, —NH—C(O)($C_1$-$C_6$ alkyl), —C(O)$NH_2$, or —OC(O)($C_1$-$C_6$ alkyl), wherein the $C_1$-$C_6$ alkyl, $C_2$-$C_6$ alkenyl, $C_2$-$C_6$ alkynyl, $C_1$-$C_6$ alkoxy, $C_1$-$C_6$ haloalkyl or $C_1$-$C_6$ alkyl is optionally substituted with one or more —OH;

$R_3$ and $R_4$, together with the atoms to which they are attached, form a 6- to 10-membered heterocyclyl, wherein the heterocyclyl optionally comprises one or more additional N, O, or S and is optionally substituted with one or more $R_{3a}$;

each $R_{3a}$ independently is cyano, halo, —OH, —$NH_2$, —NH($C_1$-$C_6$ alkyl), —N($C_1$-$C_6$ alkyl)$_2$, —N($C_1$-$C_6$ alkyl)($C_1$-$C_6$ haloalkyl), —NH—C(O)($C_1$-$C_6$ alkyl), —O($C_3$-$C_{10}$ cycloalkyl), $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_1$-$C_6$ haloalkoxy, $C_3$-$C_{10}$ cycloalkyl, 3- to 10-membered heterocyclyl, —S(O)(=NH)($C_1$-$C_6$ alkyl), —$SO_2$($C_1$-$C_6$ alkyl), —S($C_1$-$C_6$ alkyl), or —S($C_1$-$C_6$ haloalkyl), wherein the alkyl is optionally substituted with one or more —N($R_{3a1}$)CO($R_{3a2}$), —O($C_3$-$C_{10}$ cycloalkyl), —O($C_6$-$C_{10}$ aryl), —O(5- to 10-membered heteroaryl), or —O(3- to 10-membered heterocyclyl), wherein the cycloalkyl, aryl, heteroaryl, or heterocyclyl is optionally substituted with one or more $C_1$-$C_6$ alkyl, or two $R_{3a}$, together with the atoms to which they are attached, form a $C_3$-$C_{10}$ cycloalkyl or 3- to 10-membered heterocyclyl, wherein the cycloalkyl or heterocyclyl is optionally substituted with one or more $C_3$-$C_{10}$ cycloalkyl, 3- to 10-membered heterocyclyl, $C_1$-$C_{10}$ aryl, or 5- to 10-membered heteroaryl, wherein the cycloalkyl, heterocyclyl, aryl, or heteroaryl is optionally substituted with one or more $C_1$-$C_6$ alkyl;

$R_{3a1}$ and $R_{3a2}$, together with the atoms to which they are attached, form a 3- to 10-membered heterocyclyl;

$R_{4''}$ is

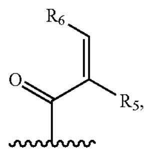
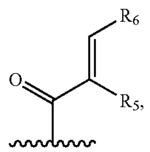
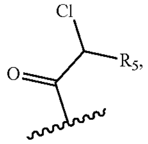
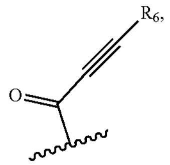
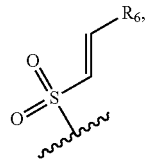
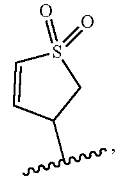
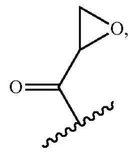
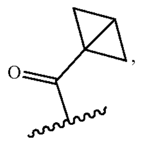
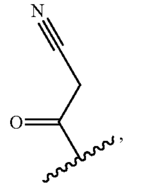
or
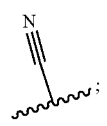

$R_5$ is H, halo, cyano, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy;

$R_6$ is H, halo, cyano, $C_1$-$C_6$ alkyl, $C_2$-$C_6$ alkenyl, $C_2$-$C_6$ alkynyl, or $C_1$-$C_6$ alkoxy, wherein the alkyl, alkenyl, alkynyl, or alkoxy is optionally substituted with one or more —$NH_2$, —NH($C_1$-$C_6$ alkyl), or —N($C_1$-$C_6$ alkyl)$_2$, or $R_5$ and $R_6$, together with the atoms to which they are attached, form a $C_4$-$C_{10}$ cycloalkenyl; and each $R_7$, $R_8$, and $R_9$ independently is H, cyano, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy, wherein the alkyl, alkenyl, alkynyl, haloalkyl, or alkoxy is optionally substituted with one or more oxo, halo, cyano, —OH, —$NH_2$, $C_1$-$C_6$ alkoxy, —NH($C_1$-$C_6$ alkyl), —N($C_1$-$C_6$ alkyl)$_2$, —NH($C_1$-$C_6$ haloalkyl), or —S($C_1$-$C_6$ alkyl), or $R_7$ and $R_8$, together with the atoms to which they are attached, form a $C_3$-$C_{10}$ cycloalkyl or 3- to 10-membered heterocyclyl.

In some embodiments, the compound is of Formula (I'), wherein:

X is N or C;

Y is $NR_2$ or $CR_2$;

Z is $NR_3$ or $CR_3$;

$R_1$ is $C_3$-$C_{10}$ cycloalkyl, $C_6$-$C_{10}$ aryl, or 5- to 10-membered heteroaryl, wherein $C_3$-$C_{10}$ cycloalkyl, $C_6$-$C_{10}$ aryl, or 5- to 10-membered heteroaryl is optionally substituted with one or more $R_{1a}$;

each $R_{1a}$ independently is oxo, halo, cyano, —OH, —$NH_2$, —NH($C_1$-$C_6$ alkyl), —$NO_2$, —S($C_1$-$C_6$ alkyl), —S(O)$_2$($NH_2$), —C(O)$NH_2$, —O(3- to 10-membered heterocyclyl), $C_1$-$C_6$ alkyl, $C_1$-$C_6$ alkoxy, $C_1$-$C_6$ haloalkyl, $C_3$-$C_{10}$ cycloalkyl, 5- to 10-membered heteroaryl, or 3- to 10-membered heterocyclyl, wherein the —NH ($C_1$-$C_6$ alkyl), —S($C_1$-$C_6$ alkyl), —O(3- to 10-membered heterocyclyl), $C_1$-$C_6$ alkyl, $C_1$-$C_6$ alkoxy, $C_1$-$C_6$ haloalkyl, $C_3$-$C_{10}$ cycloalkyl, 5- to 10-membered heteroaryl, or 3- to 10-membered heterocyclyl is optionally substituted with one or more $R_{1b}$;

each $R_{1b}$ independently is halo, cyano, —OH, —O($C_1$-$C_6$ alkyl), —C(O)$NH_2$, or 3- to 10-membered heterocyclyl; $R_2$ is $C_1$-$C_6$ alkyl, $C_3$-$C_{10}$ cycloalkyl, $C_6$-$C_{10}$ aryl, or 5- to 10-membered heteroaryl, wherein the $C_1$-$C_6$ alkyl, $C_3$-$C_{10}$ cycloalkyl, $C_6$-$C_{10}$ aryl, or 5- to 10-membered heteroaryl is optionally substituted with one or more $R_{2a}$;

each $R_{2a}$ independently is halo, cyano, —OH, —$NH_2$, $C_1$-$C_6$ alkyl, $C_6$-$C_{10}$ aryl, $C_3$-$C_{10}$ cycloalkyl, $C_1$-$C_6$ alkoxy, $C_1$-$C_6$ haloalkyl, —S($C_1$-$C_6$ alkyl), wherein the $C_1$-$C_6$ alkyl, $C_6$-$C_{10}$ aryl, $C_3$-$C_{10}$ cycloalkyl, $C_1$-$C_6$ alkoxy, $C_1$-$C_6$ haloalkyl, or —S($C_1$-$C_6$ alkyl) is optionally substituted with one or more $R_{2a1}$;

each $R_{2a1}$ independently is halo or —OH;

each $R_{3a}$ independently is halo, —OH, —O($C_3$-$C_{10}$ cycloalkyl), —O(3- to 10-membered heterocyclyl), $C_1$-$C_6$ alkyl, $C_1$-$C_6$ alkoxy, 5- to 10-membered heteroaryl, wherein the —O($C_3$-$C_{10}$ cycloalkyl), —O(3- to 10-membered heterocyclyl), $C_1$-$C_6$ alkyl, $C_1$-$C_6$ alkoxy, 5- to 10-membered heteroaryl is optionally substituted with one or more oxo, cyano, 3- to 10-membered heterocyclyl, —C(O)($C_1$-$C_6$ alkyl), 5- to 10-membered heteroaryl optionally substituted with $C_1$-$C_6$ alkyl, or $C_1$-$C_6$ alkyl optionally substituted with $C_1$-$C_6$ alkoxy, or two $R_{3a}$, together with the atoms to which they are attached, form a $C_3$-$C_{10}$ cycloalkyl or 3- to 10-membered heterocyclyl, wherein the $C_3$-$C_{10}$ cycloalkyl or 3- to 0-membered heterocyclyl is optionally substituted with one or more 5- to 10-membered heteroaryl, wherein the 5- to 10-membered heteroaryl is optionally substituted with one or ore $C_1$-$C_6$ alkyl;

$R_{4''}$ is

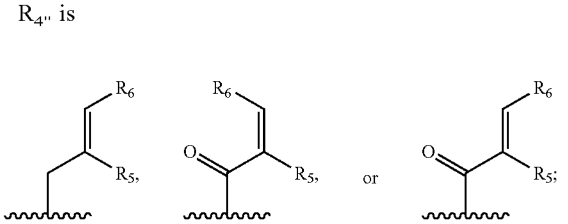

$R_5$ is H or halo, $R_6$ is H, halo, —$SO_2$($C_1$-$C_6$ alkyl), or $C_1$-$C_6$ alkyl optionally substituted with one or more —O($C_1$-$C_6$ alkyl), or —N($C_1$-$C_6$ alkyl)$_2$, or $R_5$ and $R_6$, together with the atoms to which they are attached, form a $C_4$-$C_{10}$ cycloalkenyl; and each $R_7$, $R_8$, and $R_9$ independently is H or $C_1$-$C_6$ alkyl.

In some aspects, the present disclosure provides a compound of Formula (I):

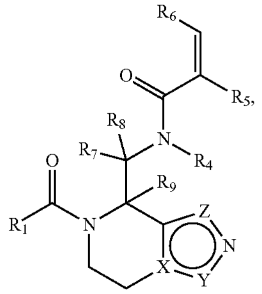

(I)

or a pharmaceutically acceptable salt, oxide, solvate, clathrate, hydrate, stereoisomer, or tautomer thereof, wherein:

X is N or C;

Y is $NR_2$ or $CR_2$;

Z is $NR_3$ or $CR_3$;

$R_1$ is $C_1$-$C_6$ alkyl, $C_2$-$C_6$ alkenyl, $C_2$-$C_6$ alkynyl, $C_1$-$C_6$ haloalkyl, $C_3$-$C_{10}$ cycloalkyl, $C_6$-$C_{10}$ aryl, 5- to 10-membered heteroaryl, or 3- to 10-membered heterocyclyl, wherein the $C_1$-$C_6$ alkyl, $C_2$-$C_6$ alkenyl, $C_2$-$C_6$ alkynyl, $C_1$-$C_6$ haloalkyl, $C_3$-$C_{10}$ cycloalkyl, $C_6$-$C_{10}$ aryl, 5- to 10-membered heteroaryl, or 3- to 10-membered heterocyclyl is optionally substituted with one or more $R_{1a}$;

each $R_{1a}$ independently is oxo, halo, cyano, —OH, —$NH_2$, —$NO_2$, —NH—C(O)($C_1$-$C_6$ alkyl), —S($C_1$-$C_6$ alkyl), —S(O)$_2$($C_1$-$C_6$ alkyl), —S(O)$_2$($NH_2$), —C(O)(H), —C(O)$NH_2$, —O(3- to 10-membered heterocyclyl), $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, $C_3$-$C_{10}$ cycloalkyl, $C_6$-$C_{10}$ aryl, 5- to 10-membered heteroaryl, or 3- to 10-membered heterocyclyl, wherein the —NH—C(O)($C_1$-$C_6$ alkyl), —S($C_1$-$C_6$ alkyl), —S(O)$_2$($C_1$-$C_6$ alkyl), —O(3- to 10-membered heterocyclyl), $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, $C_3$-$C_{10}$ cycloalkyl, $C_6$-$C_{10}$ aryl, 5- to 10-membered heteroaryl, or 3- to 10-membered heterocyclyl is optionally substituted with one or more $R_{1b}$;

each $R_{1b}$ independently is oxo, halo, cyano, —OH, —O($C_1$-$C_6$ alkyl, —O($C_1$-$C_6$ haloalkyl), —O($C_2$-$C_6$ alkenyl), —O($C_2$-$C_6$ alkynyl), —$NH_2$, —NH($C_1$-$C_6$ alkyl), —N($C_1$-$C_6$ alkyl)$_2$, —NH($C_1$-$C_6$ haloalkyl), —S(O)$_2$($C_1$-$C_6$ alkyl), $C_1$-$C_6$ alkyl, $C_3$-$C_{10}$ cycloalkyl, or 3- to 10-membered heterocyclyl optionally substituted with oxo;

$R_2$ is $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_3$-$C_{10}$ cycloalkyl, $C_6$-$C_{10}$ aryl, 5- to 10-membered heteroaryl, or 3- to 10-membered heterocyclyl, wherein the $C_1$-$C_6$ alkyl, $C_3$-$C_{10}$ cycloalkyl, $C_6$-$C_{10}$ aryl, 5- to 10-membered heteroaryl, or 3- to 10-membered heterocyclyl is optionally substituted with one or more $R_{2a}$;

each $R_{2a}$ independently is oxo, halo, cyano, —OH, —$NH_2$, —NH($C_1$-$C_6$ alkyl), —N($C_1$-$C_6$ alkyl)$_2$, —SH, —S(O)$_2$NH$_2$, —$SF_5$, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, —S($C_1$-$C_6$ haloalkyl), —S($C_1$-$C_6$ alkyl), $C_3$-$C_{10}$ cycloalkyl, $C_6$-$C_{10}$ aryl, 5- to 10-membered heteroaryl, or 3- to 10-membered heterocyclyl, wherein the 1-$C_6$ alkyl, $C_2$-$C_6$ alkenyl, $C_2$-$C_6$ alkynyl, $C_1$-$C_6$ alkoxy, $C_1$-$C_6$ haloalkyl, —S($C_1$-$C_6$ haloalkyl), —S($C_1$-$C_6$ alkyl), $C_3$-$C_{10}$ cycloalkyl, $C_6$-$C_{10}$ aryl, 5- to 10-membered heteroaryl, or 3- to 10-membered heterocyclyl is optionally substituted with one or more $R_{2a1}$;

each $R_{2a1}$ independently is oxo, halo, cyano, —OH, —$NH_2$, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, —NH—C(O)($C_1$-$C_6$ alkyl), —C(O)NH$_2$, or —OC(O)($C_1$-$C_6$ alkyl), wherein the $C_1$-$C_6$ alkyl, $C_2$-$C_6$ alkenyl, $C_2$-$C_6$ alkynyl, $C_1$-$C_6$ alkoxy, $C_1$-$C_6$ haloalkyl or $C_1$-$C_6$ alkyl is optionally substituted with one or more —OH;

$R_3$ and $R_4$, together with the atoms to which they are attached, form a 6- to 10-membered heterocyclyl, wherein the heterocyclyl optionally comprises one or more additional N, O, or S and is optionally substituted with one or more $R_{3a}$;

each $R_{3a}$ independently is cyano, halo, —OH, —$NH_2$, —NH($C_1$-$C_6$ alkyl), —N($C_1$-$C_6$ alkyl)$_2$, —N($C_1$-$C_6$ alkyl)($C_1$-$C_6$ haloalkyl), —NH—C(O)($C_1$-$C_6$ alkyl), —O($C_3$-$C_{10}$ cycloalkyl), —O(3- to 10-membered heterocyclyl), $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_1$-$C_6$ haloalkoxy, $C_3$-$C_{10}$ cycloalkyl, 3- to 10-membered heterocyclyl, $C_6$-$C_{10}$ aryl, 5- to 10-membered heteroaryl, —S(O)(=NH)($C_1$-$C_6$ alkyl), —SO$_2$($C_1$-$C_6$ alkyl), —S($C_1$-$C_6$ alkyl), or —S($C_1$-$C_6$ haloalkyl), wherein the alkyl, alkenyl, alkynyl, haloalkyl, alkoxy, haloalkoxy, —O($C_3$-$C_{10}$ cycloalkyl), —O(3- to 10-membered heterocyclyl), heterocycle, cycloalkyl, aryl, or heteroaryl is optionally substituted with one or more oxo, —CN, $C_1$-$C_6$ alkoxy, —C(O)($C_1$-$C_6$ alkyl), —N($R_{3a1}$)CO($R_{3a2}$), —O($C_3$-$C_{10}$ cycloalkyl), —O($C_6$-$C_{10}$ aryl), —O(5- to 10-membered heteroaryl), —O(3- to 10-membered heterocyclyl), $C_3$-$C_{10}$ cycloalkyl, 3- to 10-membered heterocyclyl, $C_6$-$C_{10}$ aryl, or 5- to 10-membered heteroaryl, wherein the cycloalkyl, aryl, heteroaryl, or heterocyclyl is optionally substituted with one or more $C_1$-$C_6$ alkyl, or two $R_{3a}$, together with the atoms to which they are attached, form a $C_3$-Cia cycloalkyl or 3- to 10-membered heterocyclyl, wherein the cycloalkyl or heterocyclyl is optionally substituted with one or more $C_3$-$C_{10}$ cycloalkyl, 3- to 10-membered heterocyclyl, $C_1$-$C_{10}$ aryl, or 5- to 10-membered heteroaryl, wherein the cycloalkyl, heterocyclyl, aryl, or heteroaryl is optionally substituted with one or more $C_1$-$C_6$ alkyl;

$R_{3a1}$ and $R_{3a2}$, together with the atoms to which they are attached, form a 3- to 10-membered heterocyclyl;

$R_5$ is H, halo, cyano, or $C_1$-$C_6$ alkyl;

$R_6$ is H, halo, cyano, $C_1$-$C_6$ alkyl, or $C_1$-$C_6$ alkoxy, wherein the alkyl or alkoxy is optionally substituted with one or more —$NH_2$, —NH($C_1$-$C_6$ alkyl), or —N($C_1$-$C_6$ alkyl)$_2$, or $R_5$ and $R_6$, together with the atoms to which they are attached, form a $C_4$-$C_{10}$ cycloalkenyl; and each $R_7$, $R_8$, and $R_9$ independently is H, cyano, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy, wherein the alkyl, alkenyl, alkynyl, haloalkyl, or alkoxy is optionally substituted with one or more oxo, halo, cyano, —OH, —$NH_2$, $C_1$-$C_6$ alkoxy, —NH($C_1$-$C_6$ alkyl), —N($C_1$-$C_6$ alkyl)$_2$, —NH($C_1$-$C_6$ haloalkyl), or —S($C_1$-$C_6$ alkyl), or $R_7$ and $R_8$, together with the atoms to which they are attached, form a $C_3$-$C_{10}$ cycloalkyl or 3- to 10-membered heterocyclyl.

In some aspects, the present disclosure provides a compound of Formula (I):

(I)

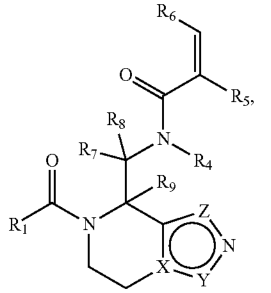

or a pharmaceutically acceptable salt, oxide, solvate, clathrate, hydrate, stereoisomer, or tautomer thereof, wherein:

X is N or C;

Y is NR$_2$ or CR$_2$;

Z is NR$_3$ or CR$_3$;

$R_1$ is $C_1$-$C_6$ alkyl, $C_2$-$C_6$ alkenyl, $C_2$-$C_6$ alkynyl, $C_1$-$C_6$ haloalkyl, $C_3$-$C_{10}$ cycloalkyl, $C_6$-$C_{10}$ aryl, 5- to 10-membered heteroaryl, or 3- to 10-membered heterocyclyl, wherein the $C_1$-$C_6$ alkyl, $C_2$-$C_6$ alkenyl, $C_2$-$C_6$ alkynyl, $C_1$-$C_6$ haloalkyl, $C_3$-$C_{10}$ cycloalkyl, $C_6$-$C_{10}$ aryl, 5- to 10-membered heteroaryl, or 3- to 10-membered heterocyclyl is optionally substituted with one or more $R_{1a}$;

each $R_{1a}$ independently is oxo, halo, cyano, —OH, —$NH_2$, —$NO_2$, —NH—C(O)($C_1$-$C_6$ alkyl), —S($C_1$-$C_6$ alkyl), —S(O)$_2$($C_1$-$C_6$ alkyl), —S(O)$_2$(NH$_2$), —C(O)(H), —C(O)NH$_2$, —O(3- to 10-membered heterocyclyl), $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, $C_3$-$C_{10}$ cycloalkyl, $C_6$-$C_{10}$ aryl, 5- to 10-membered heteroaryl, or 3- to 10-membered heterocyclyl, wherein the —NH—C(O)($C_1$-$C_6$ alkyl), —S($C_1$-$C_6$ alkyl), —S(O)$_2$($C_1$-$C_6$ alkyl), —O(3- to 10-membered heterocyclyl), $C_1$-$C_6$ alkyl, $C_2$-$C_6$ alkenyl, $C_2$-$C_6$ alkynyl, $C_1$-$C_6$ alkoxy, 1-$C_6$ haloalkyl, $C_3$-$C_{10}$ cycloalkyl, $C_6$-$C_{10}$ aryl, 5- to 10-membered heteroaryl, or 3- to 10-membered heterocyclyl is optionally substituted with one or more $R_{1b}$;

each $R_{1b}$ independently is oxo, halo, cyano, —OH, —O($C_1$-$C_6$ alkyl), —O($C_1$-$C_6$ haloalkyl), —O($C_2$-$C_6$ alkenyl), —O($C_2$-$C_6$ alkynyl), —$NH_2$, —NH($C_1$-$C_6$ alkyl), —N($C_1$-$C_6$ alkyl)$_2$, —NH($C_1$-$C_6$ haloalkyl), —$S(O)_2(C_1$-$C_6$ alkyl), $C_1$-$C_6$ alkyl, $C_3$-$C_{10}$ cycloalkyl, or 3- to 10-membered heterocyclyl optionally substituted with oxo;

$R_2$ is $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_3$-$C_{10}$ cycloalkyl, $C_6$-$C_{10}$ aryl, 5- to 10-membered heteroaryl, or 3- to 10-membered heterocyclyl, wherein the $C_1$-$C_6$ alkyl, $C_3$-$C_{10}$ cycloalkyl, $C_6$-$C_{10}$ aryl, 5- to 10-membered heteroaryl, or 3- to 10-membered heterocyclyl is optionally substituted with one or more $R_{2a}$;

each $R_{2a}$ independently is oxo, halo, cyano, —OH, —$NH_2$, —$NH(C_1$-$C_6$ alkyl), —$N(C_1$-$C_6$ alkyl$)_2$, —SH, —$S(O)_2NH_2$, —$SF_5$, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, —$S(C_1$-$C_6$ haloalkyl), —$S(C_1$-$C_6$ alkyl), $C_3$-$C_{10}$ cycloalkyl, $C_6$-$C_{10}$ aryl, 5- to 10-membered heteroaryl, or 3- to 10-membered heterocyclyl, wherein the $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, —$S(C_1$-$C_6$ haloalkyl), —$S(C_1$-$C_6$ alkyl), $C_3$-$C_{10}$ cycloalkyl, $C_6$-$C_{10}$ aryl, 5- to 10-membered heteroaryl, or 3- to 10-membered heterocyclyl is optionally substituted with one or more $R_{2a1}$;

each $R_{2a1}$ independently is oxo, halo, cyano, —OH, —$NH_2$, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, —NH—$C(O)(C_1$-$C_6$ alkyl), —$C(O)NH_2$, or —$OC(O)(C_1$-$C_6$ alkyl), wherein the $C_1$-$C_6$ alkyl, $C_2$-$C_6$ alkenyl, $C_2$-$C_6$ alkynyl, $C_1$-$C_6$ alkoxy, $C_1$-$C_6$ haloalkyl or $C_1$-$C_6$ alkyl is optionally substituted with one or more —OH;

$R_3$ and $R_4$, together with the atoms to which they are attached, form a 6- to 10-membered heterocyclyl, wherein the heterocyclyl optionally comprises one or more additional N, O, or S and is optionally substituted with one or more $R_{3a}$;

each $R_{3a}$ independently is cyano, halo, —OH, —$NH_2$, —$NH(C_1$-$C_6$ alkyl), —$N(C_1$-$C_6$ alkyl$)_2$, —$N(C_1$-$C_6$ alkyl)$(C_1$-$C_6$ haloalkyl), —NH—$C(O)(C_1$-$C_6$ alkyl), —$O(C_3$-$C_{10}$ cycloalkyl), $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_1$-$C_6$ haloalkoxy, $C_3$-$C_{10}$ cycloalkyl, 3- to 10-membered heterocyclyl, —S(O)(=NH)$(C_1$-$C_6$ alkyl), —$SO_2(C_1$-$C_6$ alkyl), —$S(C_1$-$C_6$ alkyl), or —$S(C_1$-$C_6$ haloalkyl), wherein the alkyl is optionally substituted with one or more —$N(R_{3a1})CO(R_{3a2})$, —$O(C_3$-$C_{10}$ cycloalkyl), —$O(C_6$-$C_{10}$ aryl), —O(5- to 10-membered heteroaryl), or —O(3- to 10-membered heterocyclyl), wherein the cycloalkyl, aryl, heteroaryl, or heterocyclyl is optionally substituted with one or more $C_1$-$C_6$ alkyl, or two $R_{3a}$, together with the atoms to which they are attached, form a $C_3$-$C_{10}$ cycloalkyl or 3- to 10-membered heterocyclyl;

$R_{3a1}$ and $R_{3a2}$, together with the atoms to which they are attached form a 3- to 10-membered heterocyclyl;

$R_5$ is H, halo, cyano, or $C_1$-$C_6$ alkyl;

$R_6$ is H, halo, cyano, $C_1$-$C_6$ alkyl, or $C_1$-$C_6$ alkoxy, wherein the alkyl or alkoxy is optionally substituted with one or more —$NH_2$, —$NH(C_1$-$C_6$ alkyl), or —$N(C_1$-$C_6$ alkyl$)_2$, or $R_5$ and $R_6$, together with the atoms to which they are attached, form a $C_4$-$C_{10}$ cycloalkenyl; and each $R_7$, $R_8$, and $R_9$ independently is H, cyano, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy, wherein the alkyl, alkenyl, alkynyl, haloalkyl, or alkoxy is optionally substituted with one or more oxo, halo, cyano, —OH, —$NH_2$, $C_1$-$C_6$ alkoxy, —$NH(C_1$-$C_6$ alkyl), —$N(C_1$-$C_6$ alkyl$)_2$, —$NH(C_1$-$C_6$ haloalkyl), or —$S(C_1$-$C_6$ alkyl), or $R_7$ and $R_8$, together with the atoms to which they are attached, form a $C_3$-$C_{10}$ cycloalkyl or 3- to 10-membered heterocyclyl.

In some aspects, the present disclosure provides a compound of Formula (I):

(I)

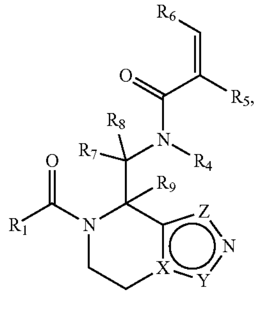

or a pharmaceutically acceptable salt, oxide, solvate, clathrate, hydrate, stereoisomer, or tautomer thereof, wherein:

X is N or C;

Y is $NR_2$ or $CR_2$;

Z is $NR_3$ or $CR_3$;

$R_1$ is $C_1$-$C_6$ alkyl, $C_2$-$C_6$ alkenyl, $C_2$-$C_6$ alkynyl, $C_1$-$C_6$ haloalkyl, $C_3$-$C_{10}$ cycloalkyl, $C_6$-$C_{10}$ aryl, 5- to 10-membered heteroaryl, or 3- to 10-membered heterocyclyl, wherein the $C_1$-$C_6$ alkyl, $C_2$-$C_6$ alkenyl, $C_2$-$C_6$ alkynyl, $C_1$-$C_6$ haloalkyl, $C_3$-$C_{10}$ cycloalkyl, $C_6$-$C_{10}$ aryl, 5- to 10-membered heteroaryl, or 3- to 10-membered heterocyclyl is optionally substituted with one or more $R_{1a}$;

each $R_{1a}$ independently is oxo, halo, cyano, —OH, —$NH_2$, —$NO_2$, —$NH(C_1$-$C_6$ alkyl), —$N(C_1$-$C_6$ alkyl$)_2$, —NH—$C(O)(C_1$-$C_6$ alkyl), —$S(C_1$-$C_6$ alkyl), —$S(O)_2(C_1$-$C_6$ alkyl) —$S(O)_2(NH_2)$, —C(O)(H), —$C(O)NH_2$, —O(3- to 10-membered heterocyclyl), $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, $C_3$-$C_{10}$ cycloalkyl, $C_6$-$C_{10}$ aryl, 5- to 10-membered heteroaryl, or 3-to 10-membered heterocyclyl, wherein the —$NH(C_1$-$C_6$ alkyl), —$N(C_1$-$C_6$ alkyl$)_2$, —NH—$C(O)(C_1$-$C_6$ alkyl), —$S(C_1$-$C_6$ alkyl), —$S(O)_2(C_1$-$C_6$ alkyl), —O(3- to 10-membered heterocyclyl), $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, $C_3$-$C_{10}$ cycloalkyl, $C_6$-$C_{10}$ aryl, 5-to 10-membered heteroaryl, or 3- to 10-membered heterocyclyl is optionally substituted with one or more $R_{1b}$;

each $R_{1b}$ independently is oxo, halo, cyano, —OH, —$O(C_1$-$C_6$ alkyl, —$O(C_1$-$C_6$ haloalkyl), —$O(C_2$-$C_6$ alkenyl), —$O(C_2$-$C_6$ alkynyl); —$NH_2$, —$NH(C_1$-$C_6$ alkyl), —$N(C_1$-C alkyl$)_2$, —$NH(C_1$-$C_6$ haloalkyl), —$S(C_1$-$C_6$ alkyl), —$S(O)_2(C_1$-$C_6$ alkyl), —$C(O)NH_2$, $C_1$-$C_6$ alkyl $C_3$-$C_{10}$ cycloalkyl, or 3-to 10-membered heterocyclyl optionally substituted with oxo;

$R_2$ is $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_3$-$C_{10}$ cycloalkyl, $C_6$-$C_{10}$ aryl, 5- to 10-membered heteroaryl, or 3- to 10-membered heterocyclyl, wherein the $C_1$-$C_6$ alkyl, $C_3$-$C_{10}$ cycloalkyl, $C_6$-$C_{10}$ aryl, 5- to 10-membered heteroaryl, or 3- to 10-membered heterocyclyl is optionally substituted with one or more R a;

each $R_{2a}$ independently is oxo, halo, cyano, —OH, —$NH_2$, —$NH(C_1$-$C_6$ alkyl), —$N(C_1$-$C_6$ alkyl$)_2$, —SH, —$S(O)_2NH_2$, —$SF_5$, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, —S($C_1$-$C_6$ haloalkyl), —S($C_1$-$C_6$ alkyl), $C_3$-$C_{10}$ cycloalkyl, $C_6$-$C_{10}$ aryl, 5- to 10-membered heteroaryl, or 3- to 10-membered heterocyclyl, wherein the $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, —S($C_1$-$C_6$ haloalkyl), —S($C_1$-$C_6$ alkyl), $C_3$-$C_{10}$ cycloalkyl, $C_6$-$C_{10}$ aryl, 5- to 10-membered heteroaryl, or 3- to 10-membered heterocyclyl is optionally substituted with one or more $R_{2a1}$;

each $R_{2a1}$ independently is oxo, halo, cyano, —OH, —$NH_2$, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, —NH—C(O)($C_1$-$C_6$ alkyl), —C(O)$NH_2$, or —OC(O)($C_1$-$C_6$ alkyl), wherein the $C_1$-$C_6$ alkyl, $C_2$-$C_6$ alkenyl, $C_2$-$C_6$ alkynyl, $C_1$-$C_6$ alkoxy, $C_1$-$C_6$ haloalkyl or $C_1$-$C_6$ alkyl is optionally substituted with one or more —OH;

$R_3$ and $R_4$, together with the atoms to which they are attached, form a 6- to 10-membered heterocyclyl, wherein the heterocyclyl optionally comprises one or mor additional N, O, or S and is optionally substituted with one or more $R_{3a}$;

each $R_{3a}$ independently is cyano, halo, —OH, —$NH_2$, —NH($C_1$-$C_6$ alkyl), —N($C_1$-$C_6$ alkyl)$_2$, —N($C_1$-$C_6$ alkyl)($C_1$-$C_6$ haloalkyl), —NH—C(O)($C_1$-$C_6$ alkyl), —O($C_3$-$C_{10}$ cycloalkyl), —O(3- to 10-membered heterocyclyl), $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_1$-$C_6$ haloalkoxy, $C_3$-$C_{10}$ cycloalkyl, 3- to 10-membered heterocyclyl, 5- to 10-membered heteroaryl, —S(O)(=NH)($C_1$-$C_6$ alkyl), —$SO_2$($C_1$-$C_6$ alkyl), —S($C_1$-$C_6$ alkyl), or —S($C_1$-$C_6$ haloalkyl), wherein the —NH($C_1$-$C_6$ alkyl), —N($C_1$-$C_6$ alkyl)$_2$, —N($C_1$-$C_6$ alkyl)($C_1$-$C_6$ haloalkyl), —NH—C(O)($C_1$-$C_6$ alkyl), —O($C_3$-$C_{10}$ cycloalkyl), —O(3- to 10-membered heterocyclyl), $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_1$-$C_6$ haloalkoxy, $C_3$-$C_{10}$ cycloalkyl, 3- to 10-membered heterocyclyl, 5- to 10-membered heteroaryl, —S(O)(=NH)($C_1$-$C_6$ alkyl), —$SO_2$($C_1$-$C_6$ alkyl), —S($C_1$-$C_6$ alkyl), or —S($C_1$-$C_6$ haloalkyl), is optionally substituted with one or more oxo, cyano, 3- to 10-membered heterocyclyl, —C(O)($C_1$-$C_6$ alkyl), 5- to 10-membered heteroaryl optionally substituted with $C_1$-$C_6$ alkyl, $C_1$-$C_6$ alkyl optionally substituted with $C_1$-$C_6$ alkoxy, —N($R_{3a1}$)CO($R_{3a2}$), —O($C_3$-$C_{10}$ cycloalkyl), —O($C_6$-$C_{10}$ aryl), —O(5- to 10-membered heteroaryl), or —O(3- to 10-membered heterocyclyl), or two $R_{3a}$, together with the atoms to which they are attached, form a $C_3$-$C_{10}$ cycloalkyl or 3- to 10-membered heterocyclyl, wherein the cycloalkyl or heterocyclyl is optionally substituted with one or more $C_3$-$C_{10}$ cycloalkyl, 3- to 10-membered heterocyclyl, $C_1$-$C_{10}$ aryl, or 5- to 10-membered heteroaryl, wherein the cycloalkyl, heterocyclyl, aryl, or heteroaryl is optionally substituted with one or more $C_1$-$C_6$ alkyl;

$R_{3a1}$ and $R_{3a2}$, together with the atoms to which they are attached form a 3- to 10-membered heterocyclyl;

$R_5$ is H, halo, cyano, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy;

$R_6$ is H, halo, cyano, —$SO_2$($C_1$-$C_6$ alkyl), $C_1$-$C_6$ alkyl, $C_2$-$C_6$ alkenyl, $C_2$-$C_6$ alkynyl, or $C_1$-$C_6$ alkoxy, wherein the alkyl, alkenyl, alkynyl, or alkoxy is optionally substituted with one or more —OH, —O($C_1$-$C_6$ alkyl), —$NH_2$, —NH($C_1$-$C_6$ alkyl), or —N($C_1$-$C_6$ alkyl)$_2$, or $R_5$ and $R_6$, together with the atoms to which they are attached, form a $C_4$-$C_{10}$ cycloalkenyl; and each $R_7$, $R_8$, and $R_9$ independently is H, cyano, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy, wherein the alkyl, alkenyl, alkynyl, haloalkyl, or alkoxy is optionally substituted with one or more oxo, halo, cyano, —OH, —$NH_2$, $C_1$-$C_6$ alkoxy, —NH($C_1$-$C_6$ alkyl), —N($C_1$-$C_6$ alkyl)$_2$, —NH($C_1$-$C_6$ haloalkyl), or —S($C_1$-$C_6$ alkyl), or $R_7$ and $R_8$, together with the atoms to which they are attached, form a $C_3$-$C_{10}$ cycloalkyl or 3- to 10-membered heterocyclyl.

In some embodiments, the compound is of Formula (I), wherein:

X is C;

Y is $NR_2$;

Z is $CR_3$;

$R_1$ is $C_3$-$C_{10}$ cycloalkyl, $C_6$-$C_{10}$ aryl, or 5- to 10-membered heteroaryl, wherein the $C_3$-$C_{10}$ cycloalkyl, $C_6$-$C_{10}$ aryl, or 5- to 10-membered heteroaryl is optionally substituted with one or more $R_{1a}$;

each $R_{1a}$ independently is oxo, cyano, —C(O)$NH_2$, —O(3- to 10-membered heterocyclyl), halo, —OH, —$NH_2$, $C_1$-$C_6$ alkyl, $C_1$-$C_6$ alkoxy, $C_1$-$C_6$ haloalkyl, or 3- to 10-membered heterocyclyl, wherein the —O(3- to 10-membered heterocyclyl), $C_1$-$C_6$ alkyl, $C_1$-$C_6$ alkoxy, $C_1$-$C_6$ haloalkyl, or 3- to 10-membered heterocyclyl is optionally substituted with one or more $R_{1b}$;

each $R_{1b}$ independently is —O($C_1$-$C_6$ alkyl) or 3- to 10-membered heterocyclyl;

$R_2$ is $C_6$-$C_{10}$ aryl or 5- to 10-membered heteroaryl, wherein the $C_6$-$C_{10}$ aryl or 5- to 10-membered heteroaryl is optionally substituted with one or more $R_{2a}$;

each $R_{2a}$ independently is halo, —OH, —$NH_2$, $C_1$-$C_6$ alkyl, $C_1$-$C_6$ alkoxy, $C_1$-$C_6$ haloalkyl, or $C_3$-$C_{10}$ cycloalkyl, wherein the $C_1$-$C_6$ alkyl, $C_1$-$C_6$ alkoxy, $C_1$-$C_6$ haloalkyl, or $C_3$-$C_{10}$ cycloalkyl is optionally substituted with one or more $R_{2a1}$;

each $R_{2a1}$ independently is halo;

$R_3$ and $R_4$, together with the atoms to which they are attached, form a 6- to 10-membered heterocyclyl, wherein the heterocyclyl optionally comprises one or mor additional O or N and is optionally substituted with one or more $R_{3a}$;

each $R_{3a}$ independently is halo, $C_1$-$C_6$ alkyl, $C_1$-$C_6$ alkoxy, —O($C_1$-$C_{10}$ cycloalkyl), or —O(3- to 10-membered heterocyclyl), wherein the alkoxy, heteroaryl, cycloalkyl or heterocyclyl is optionally substituted with one or more oxo, —CN, —C(O)($C_1$-$C_6$ alkyl), $C_1$-$C_6$ alkoxy, $C_3$-$C_{10}$ cycloalkyl, or 5- to 10-membered heteroaryl, or two $R_{3a}$, together with the atoms to which they are attached, form a 3- to 10-membered heterocyclyl optionally substituted with one or more 5- to 10-membered heteroaryl optionally substituted with one or more $C_1$-$C_6$ alkyl;

$R_5$ is H or halo;

$R_6$ is H or $C_1$-$C_6$ alkyl optionally substituted with —N($C_1$-$C_6$ alkyl)$_2$, or $R_5$ and $R_6$, together with the atoms to which they are attached, form a $C_4$-$C_{10}$ cycloalkenyl; and each $R_7$, $R_8$, and $R_9$ independently is H or $C_1$-$C_6$ alkyl.

In some embodiments, the compound is of Formula (I), wherein:

X is C;

Y is $NR_2$;

Z is $CR_3$;

$R_1$ is $C_3$-$C_{10}$ cycloalkyl, $C_6$-$C_{10}$ aryl, or 5- to 10-membered heteroaryl, wherein the $C_3$-$C_{10}$ cycloalkyl, $C_6$-$C_{10}$ aryl, or 5- to 10-membered heteroaryl is optionally substituted with one or more $R_{1a}$;

each $R_{1a}$ independently is oxo, cyano, —C(O)$NH_2$, —O(3- to 10-membered heterocyclyl), halo, —OH, —$NH_2$, $C_1$-$C_6$ alkyl, $C_1$-$C_6$ alkoxy, $C_1$-$C_6$ haloalkyl, or 3- to 10-membered heterocyclyl, wherein the —O(3- to 10-membered heterocyclyl), $C_1$-$C_6$ alkyl, $C_1$-$C_6$ alkoxy, $C_1$-$C_6$ haloalkyl, or 3- to 10-membered heterocyclyl is optionally substituted with one or more $R_{1b}$;

each $R_{1b}$ independently is —O($C_1$-$C_6$ alkyl) or 3- to 10-membered heterocyclyl;

$R_2$ is $C_6$-$C_{10}$ aryl or 5- to 10-membered heteroaryl, wherein the $C_6$-$C_{10}$ aryl or 5- to 10-membered heteroaryl is optionally substituted with one or more $R_{2a}$;

each $R_{2a}$ independently is halo, —OH, —$NH_2$, $C_1$-$C_6$ alkyl, $C_1$-$C_6$ alkoxy, $C_1$-$C_6$ haloalkyl, or $C_3$-$C_{10}$ cycloalkyl, wherein the $C_1$-$C_6$ alkyl, $C_1$-$C_6$ alkoxy, $C_1$-$C_6$ haloalkyl, or $C_3$-$C_{10}$ cycloalkyl is optionally substituted with one or more $R_{2a1}$;

each $R_{2a1}$ independently is halo;

$R_3$ and $R_4$, together with the atoms to which they are attached, form a 6- to 10-membered heterocyclyl, wherein the heterocyclyl optionally comprises one or more additional O or N and is optionally substituted with one or more $R_{3a}$;

each $R_{3a}$ independently is halo, $C_1$-$C_6$ alkyl, $C_1$-$C_6$ alkoxy, or —O($C_3$-$C_{10}$ cycloalkyl);

$R_5$ is H or halo;

$R_6$ is H or $C_1$-$C_6$ alkyl optionally substituted with —N($C_1$-$C_6$ alkyl)$_2$, or $R_5$ and $R_6$, together with the atoms to which they are attached, form a $C_4$-$C_{10}$ cycloalkenyl; and each $R_7$, $R_8$, and $R_9$ independently is H or $C_1$-$C_6$ alkyl.

It is understood that, for a compound of the present disclosure, variables X, Y, Z, $R_1$, $R_{1a}$, $R_{1b}$, $R_2$, $R_{2a}$, $R_{2a1}$, $R_3$, $R_{3a}$, $R_{3a1}$, $R_{3a2}$, $R_{4''}$, $R_5$, $R_6$, $R_7$, $R_8$, and $R_9$ can each be, where applicable, selected from the groups described herein, and any group described here n for any of variables X, Y, Z, $R_1$, $R_{1a}$, $R_{1b}$, $R_2$, $R_{2a}$, $R_{2a1}$, $R_3$, $R_{3a}$, $R_{3a1}$, $R_{3a2}$, $R_{4''}$, $R_5$, $R_6$, $R_7$, $R_8$, and $R_9$ can be combined, where applicable, with any group described herein for one or more of the remainder of variables X, Y, Z, $R_1$, $R_{1a}$, $R_{1b}$, $R_2$, $R_{2a}$, $R_{2a1}$, $R_3$, $R_{3a}$, $R_{3a1}$, $R_{3a2}$, $R_{4''}$, $R_5$, $R_6$, $R_7$, $R_8$ and $R_9$.

In some embodiments, X is N or C.

In some embodiments, X is N. In some embodiments, X is C.

In some embodiments, Y is $NR_2$ or $CR_2$.

In some embodiments, Y is $NR_2$. In some embodiments, Y is $CR_2$.

In some embodiments, Z is $NR_3$ or $CR_3$.

In some embodiments, Z is $NR_3$.

In some embodiments, Z is $CR_3$.

In some embodiments, $R_1$ is $C_1$-$C_6$ alkyl, $C_2$-$C_6$ alkenyl, $C_2$-$C_6$ alkynyl, $C_1$-$C_6$ haloalkyl, $C_3$-$C_{10}$ cycloalkyl, $C_6$-$C_{10}$ aryl, 5- to 10-membered heteroaryl, or 3- to 10-membered heterocyclyl, wherein the $C_1$-$C_6$ alkyl, $C_2$-$C_6$ alkenyl, $C_2$-$C_6$ alkynyl, $C_1$-$C_6$ haloalkyl, $C_3$-$C_{10}$ cycloalkyl, $C_6$-$C_{10}$ aryl, 5- to 10-membered heteroaryl, or 3- to 10-membered heterocyclyl is optionally substituted with one or more $R_{1a}$.

In some embodiments, $R_1$ is $C_1$-$C_6$ alkyl, $C_2$-$C_6$ alkenyl, $C_2$-$C_6$ alkynyl, $C_1$-$C_6$ haloalkyl, $C_3$-$C_{10}$ cycloalkyl, $C_6$-$C_{10}$ aryl, 5- to 10-membered heteroaryl, or 3- to 10-membered heterocyclyl.

In some embodiments, $R_1$ is $C_1$-$C_6$ alkyl, $C_2$-$C_6$ alkenyl, $C_2$-$C_6$ alkynyl, or $C_1$-$C_6$ haloalkyl, wherein the $C_1$-$C_6$ alkyl, $C_2$-$C_6$ alkenyl, $C_2$-$C_6$ alkynyl, or $C_1$-$C_6$ haloalkyl is optionally substituted with one or more $R_{1a}$.

In some embodiments, $R_1$ is $C_1$-$C_6$ alkyl, $C_2$-$C_6$ alkenyl, $C_2$-$C_6$ alkynyl, or $C_1$-$C_6$ haloalkyl.

In some embodiments, $R_1$ is $C_1$-$C_6$ alkyl.

In some embodiments, $R_1$ is $C_1$-$C_6$ alkyl optionally substituted with one or more $R_{1a}$.

In some embodiments, $R_1$ is $C_1$-$C_6$ alkyl substituted with one or more $R_{1a}$.

In some embodiments, $R_1$ is methyl. In some embodiment, $R_1$ is ethyl. In some embodiments, $R_1$ is propyl. In some embodiments, $R_1$ is butyl. In some embodiments, $R_1$ is pentyl.

In some embodiments, $R_1$ is hexyl. In some embodiments, $R_1$ is isopropyl. In some embodiments, $R_1$ is isobutyl. In some embodiments, $R_1$ is isopentyl. In some embodiments, $R_1$ is isohexyl. In some embodiments, $R_1$ is secbutyl. In some embodiments, $R_1$ is secpentyl. In some embodiments, $R_1$ is sechexyl. In some embodiments, $R_1$ is tertbutyl.

In some embodiments, $R_1$ is $C_2$-$C_6$ alkenyl (e.g., ethenyl, propenyl, butenyl).

In some embodiments, $R_1$ is $C_2$-$C_6$ alkenyl (e.g., ethenyl, propenyl, butenyl) optionally substituted with one or more $R_{1a}$.

In some embodiments, $R_1$ is $C_2$-$C_6$ alkenyl (e.g., ethenyl, propynyl, butenyl) substituted with one or more $R_{1a}$.

In some embodiments, $R_1$ is $C_2$-$C_6$ alkynyl (e.g., ethynyl, propynyl, butynyl).

In some embodiments, $R_1$ is $C_2$-$C_6$ alkynyl (e.g., ethynyl, propynyl, butynyl) optionally substituted with one or more $R_{1a}$.

In some embodiments, $R_1$ is $C_2$-$C_6$ alkynyl (e.g., ethynyl, propynyl, butynyl) substituted with one or more $R_{1a}$.

In some embodiments, $R_1$ is $C_1$-$C_6$ haloalkyl.

In some embodiments, $R_1$ is $C_1$-$C_6$ haloalkyl optionally substituted with one or more $R_{1a}$.

In some embodiments, $R_1$ is $C_1$-$C_6$ haloalkyl substituted with on or more $R_{1a}$.

In some embodiments, $R_1$ is halomethyl. In some embodiments, 1 is haloethyl. In some embodiments, $R_1$ is halopropyl. In some embodiments, $R_1$ is halobutyl. In some embodiments, $R_1$ is halopentyl. In some embodiments, $R_1$ is halohexyl.

In some embodiments, $R_1$ is $C_3$-$C_{10}$ cycloalkyl, $C_6$-$C_{10}$ aryl, 5- to 10-membered heteroaryl, or 3- to 10-membered heterocyclyl, wherein the $C_3$-$C_{10}$ cycl alkyl, $C_6$-$C_{10}$ aryl, 5- to 10-membered heteroaryl, or 3- to 10-membered heterocyclyl is optional y substituted with one or more $R_{1a}$.

In some embodiments, $R_1$ is $C_3$-$C_{10}$ cycloalkyl, $C_6$-$C_{10}$ aryl, 5- to 10-membered heteroaryl, or 3- to 10-membered heterocyclyl.

In some embodiments, $R_1$ is $C_3$-$C_{10}$ cycloalkyl.

In some embodiments, $R_1$ is $C_3$-$C_{10}$ cycloalkyl optionally substituted with one or more $R_{1a}$.

In some embodiments, $R_1$ is $C_3$-$C_{10}$ cycloalkyl substituted with one or more $R_{1a}$.

In some embodiments, $R_1$ is $C_3$-$C_7$ cycloalkyl.

In some embodiments, $R_1$ is $C_3$-$C_7$ cycloalkyl optionally substituted with one or more $R_{1a}$.

In some embodiments, $R_1$ is $C_3$-$C_7$ cycloalkyl substituted with one or more $R_{1a}$.

In some embodiments, $R_1$ is $C_6$-$C_{10}$ aryl.

In some embodiments, $R_1$ is $C_6$-$C_{10}$ aryl optionally substituted with one or more $R_{1a}$.

In some embodiments, $R_1$ is $C_6$-$C_{10}$ aryl substituted with one or ore $R_{1a}$.

In some embodiments, $R_1$ is $C_6$ aryl.

In some embodiments, $R_1$ is $C_6$ aryl optionally substituted with one or more $R_{1a}$.

In some embodiments, $R_1$ is $C_6$ aryl substituted with one or more $R_{1a}$.

In some embodiments, $R_1$ is 5- to 10-membered heteroaryl.

In some embodiments, $R_1$ is 5- to 10-membered heteroaryl optionally substituted with one or more $R_{1a}$.

In some embodiments, $R_1$ is 5- to 10-membered heteroaryl substituted with one or more $R_{1a}$.

In some embodiments, $R_1$ is 6- to 9-membered heteroaryl.

In some embodiments, $R_1$ is 6- to 9-membered heteroaryl optionally substituted with one or more $R_{1a}$.

In some embodiments, $R_1$ is 6- to 9-membered heteroaryl substituted with one or more $R_{1a}$.

In some embodiments, $R_1$ is 9-membered heteroaryl.

In some embodiments, $R_1$ is 9-membered heteroaryl optionally substituted with one or more $R_{1a}$.

In some embodiments, $R_1$ is 9-membered heteroaryl substituted with one or more $R_{1a}$.

In some embodiments, $R_1$ is 5- or 6-membered heteroaryl.

In some embodiments, $R_1$ is 5- or 6-membered heteroaryl optionally substituted with one or more $R_{1a}$.

In some embodiments, $R_1$ is 5- or 6-membered heteroaryl substituted with one or more $R_{1a}$.

In some embodiments, $R_1$ is 3- to 10-membered heterocyclyl.

In some embodiments, $R_1$ is 3- to 10-membered heterocyclyl optionally substituted with one or more $R_{1a}$.

In some embodiments, $R_1$ is 3- to 10-membered heterocyclyl substituted with one or more $R_{1a}$.

In some embodiments, $R_1$ is $C_3$-$C_{10}$ cycloalkyl, $C_6$-$C_{10}$ aryl or 5- to 10-membered heteroaryl.

In some embodiments, $R_1$ is $C_3$-$C_{10}$ cycloalkyl, $C_6$-$C_{10}$ aryl or 5- to 10-membered heteroaryl, wherein the $C_3$-$C_{10}$ cycloalkyl, $C_6$-$C_{10}$ aryl, or 5- to 10 membered heteroaryl is optionally substituted with one or more $R_{1a}$.

In some embodiments, $R_1$ is $C_3$-$C_{10}$ cycloalkyl, $C_6$-$C_{10}$ aryl, or 5- to 10-membered heteroaryl, wherein the $C_3$-$C_{10}$ cycloalkyl, $C_6$-$C_{10}$ aryl, or 5- to 10-membered heteroaryl is substituted with one or more $R_{1a}$.

In some embodiments, $R_1$ is:

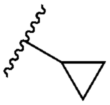 , 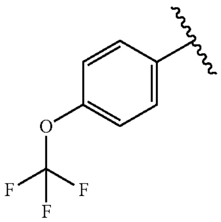 ,

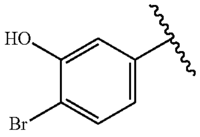 , 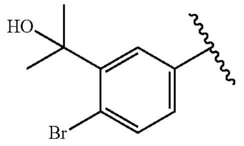 ,

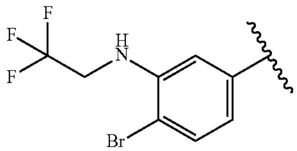 , 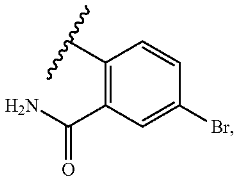

-continued

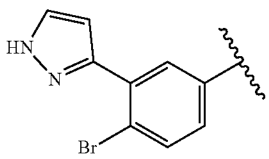 , 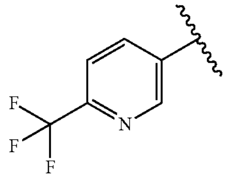 ,

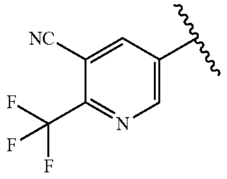 , 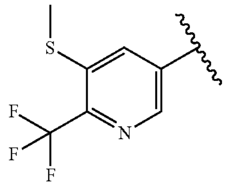 ,

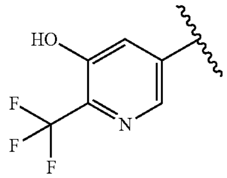 , 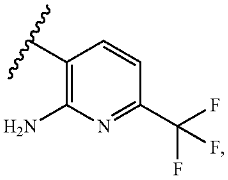

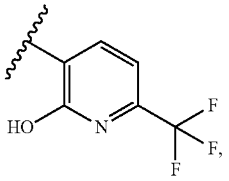 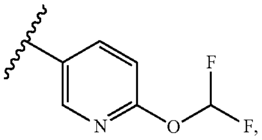

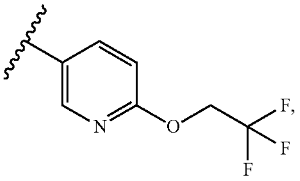 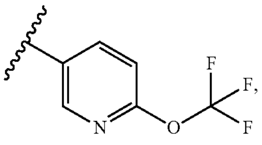

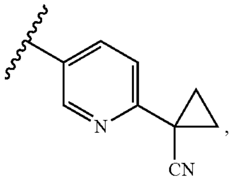 , 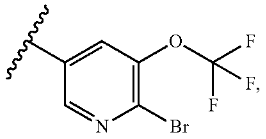

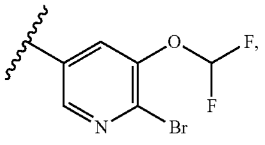 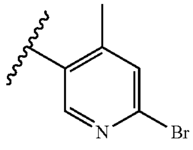 ,

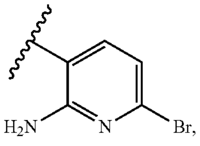 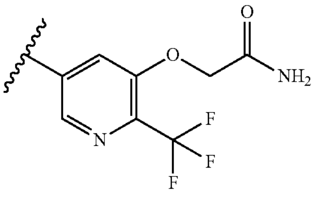 ,

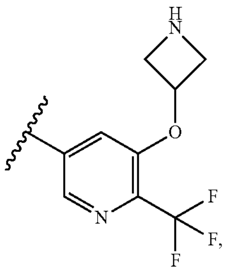 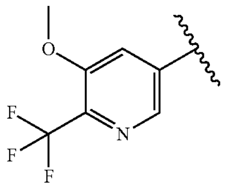 ,

-continued
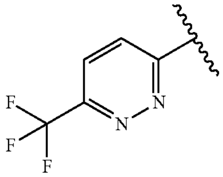, 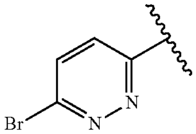,
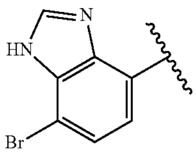, 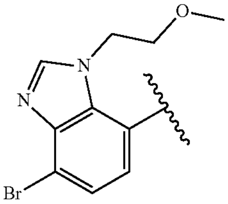,
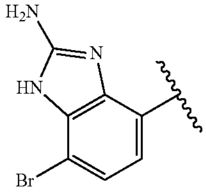, 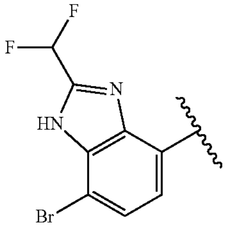,
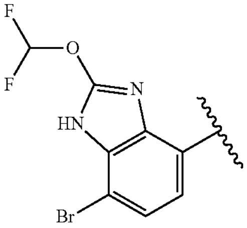, 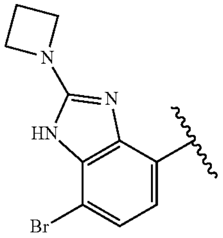,
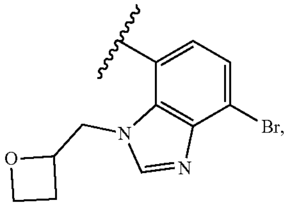
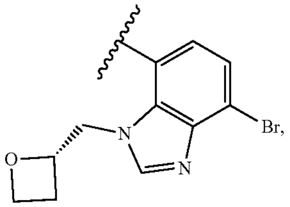
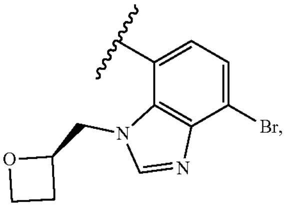 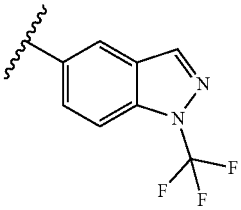,
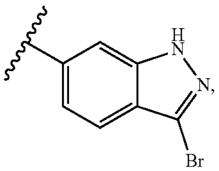 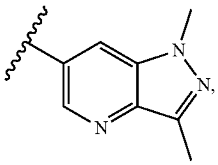
-continued
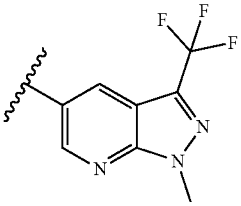, 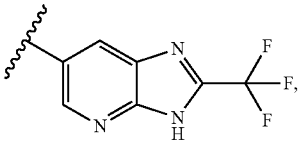
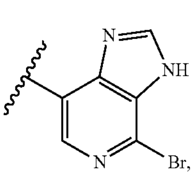 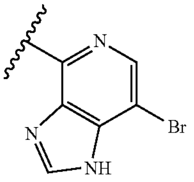,
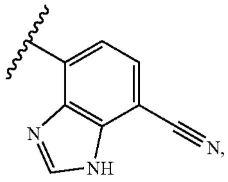 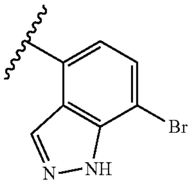,
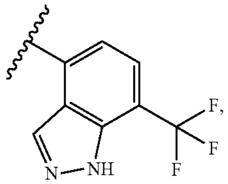 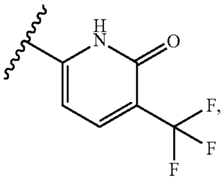
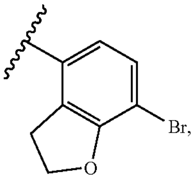 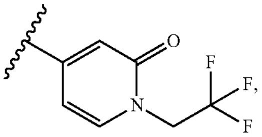
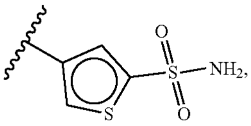 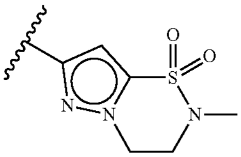, or
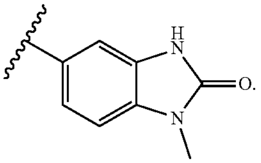
In some embodiments, $R_1$ is:
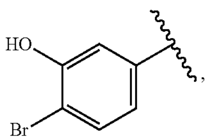 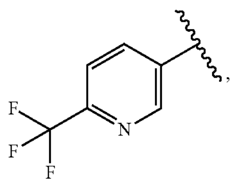
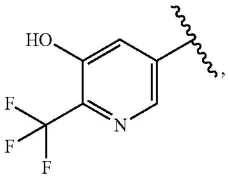 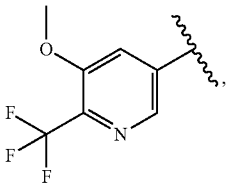

-continued
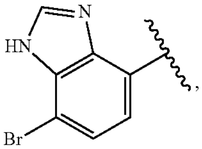,
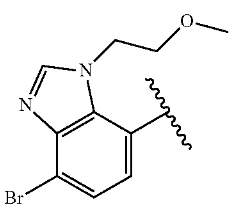,
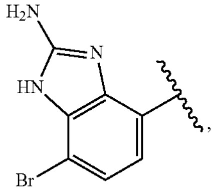,
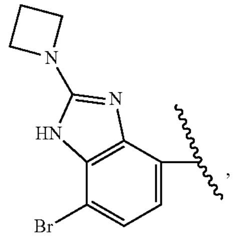,
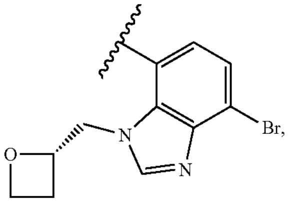
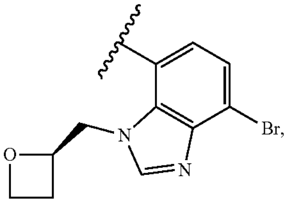
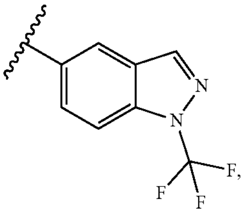
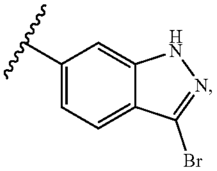
or
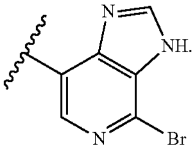
In some embodiments, $R_1$ is:
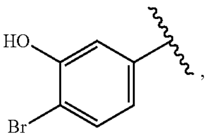,
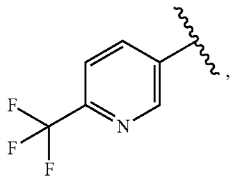,
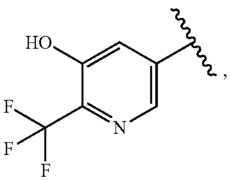,
or
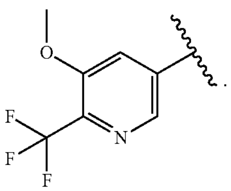.
In some embodiments, $R_1$ is:
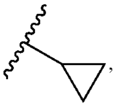
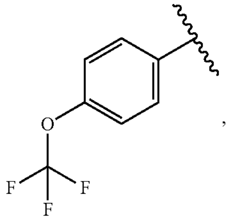,
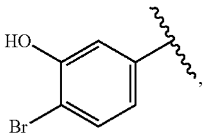
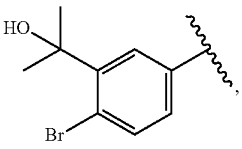
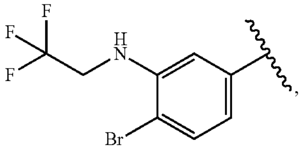
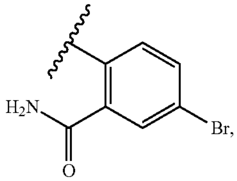
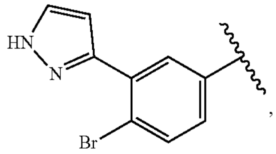,
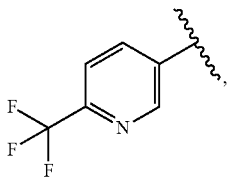
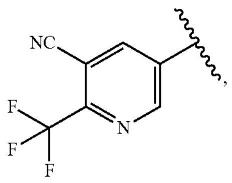
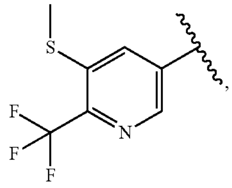
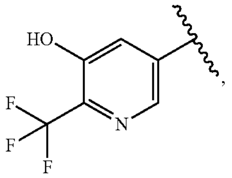
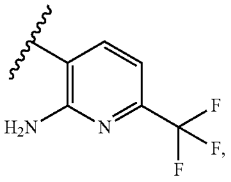
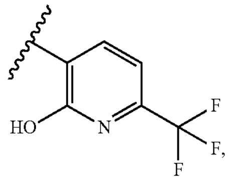
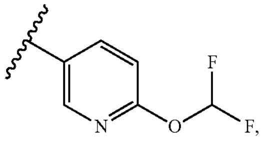
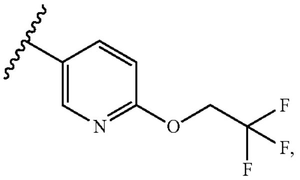
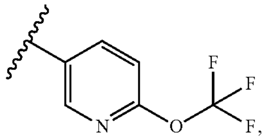
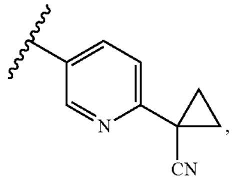
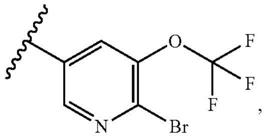, -continued
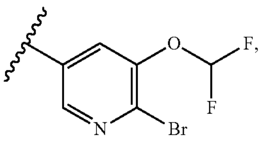
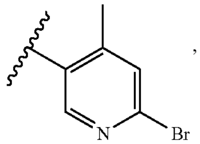
,
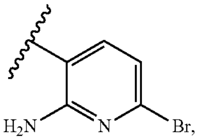
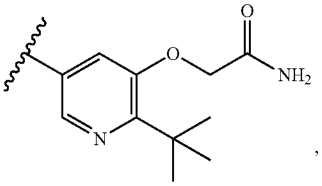
,
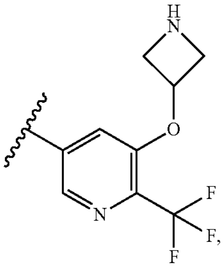
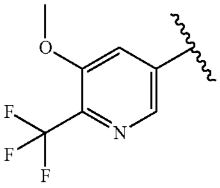
,
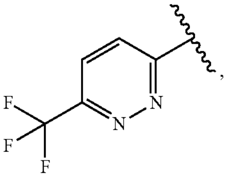
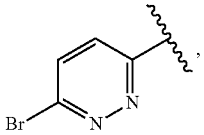
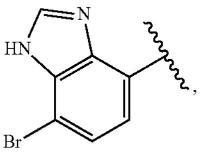
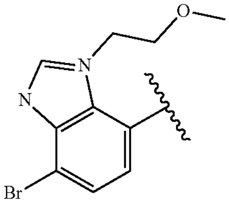
,
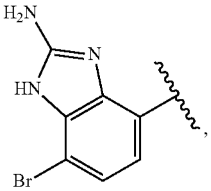
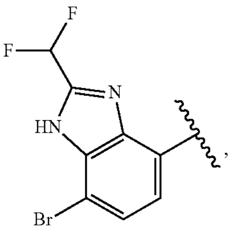
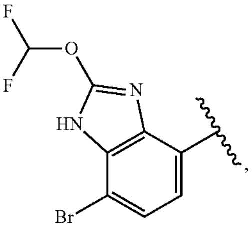
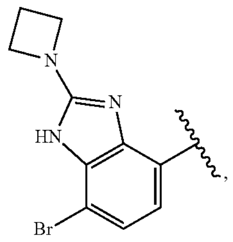
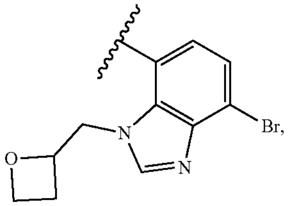
-continued
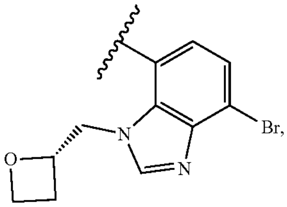
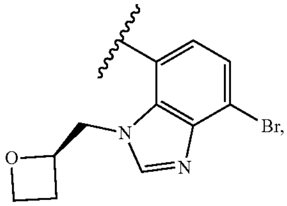
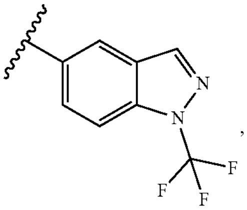
,
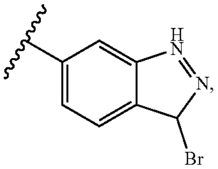
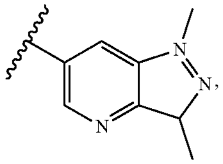
,
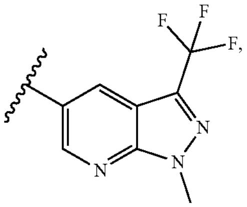
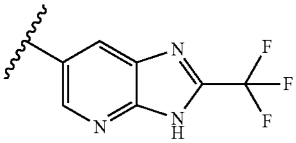
,
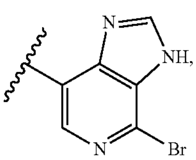
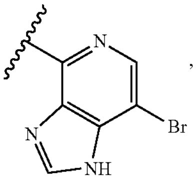
,
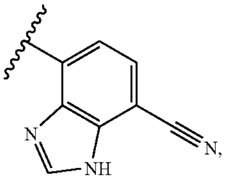
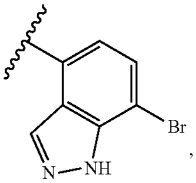
,
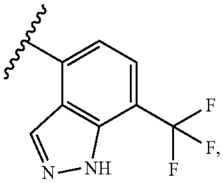
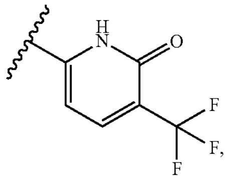
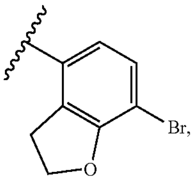
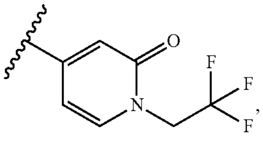
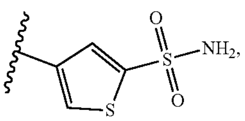
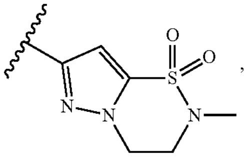
, or -continued
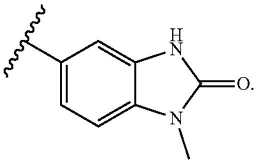 [SMILES: *c1ccc2c(c1)[nH]c(=O)n2C]
In some embodiments, $R_1$ is:
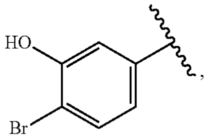,
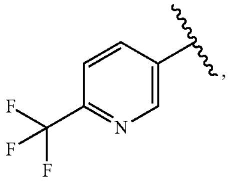,
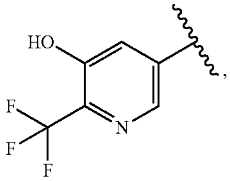,
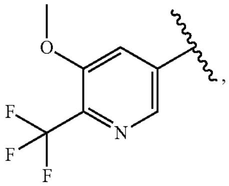,
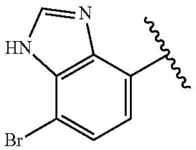,
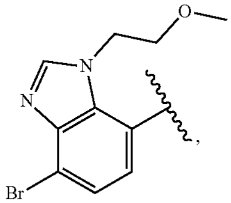,
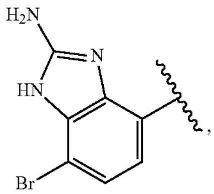,
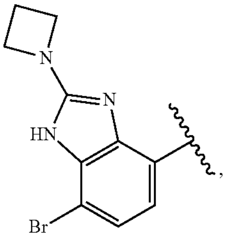,
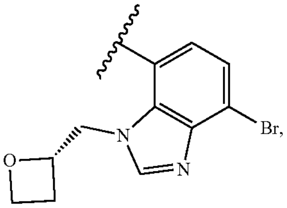
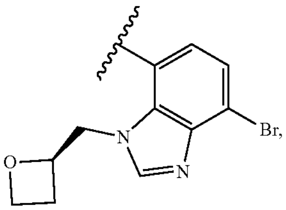
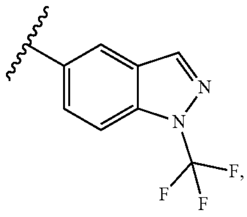
-continued
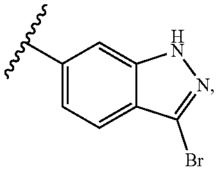
or
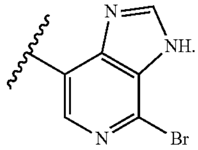
In some embodiments, $R_1$ is:
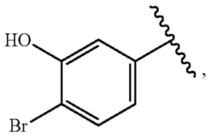,
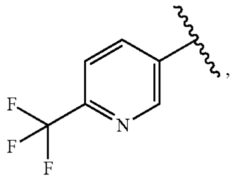,
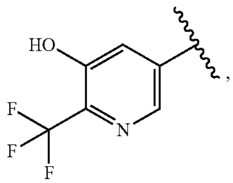,
or
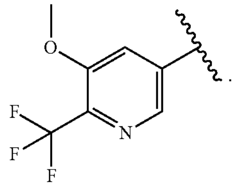.
In some embodiments, $R_1$ is:
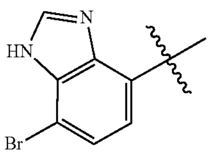,
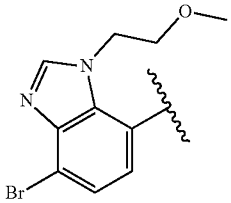,
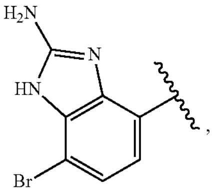,
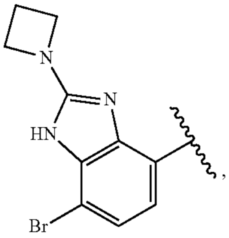,
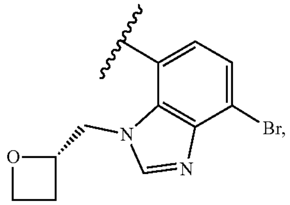
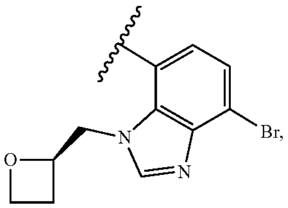
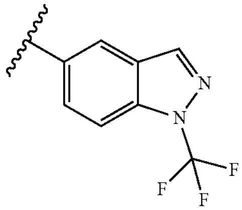, -continued
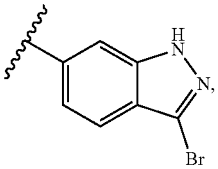 or 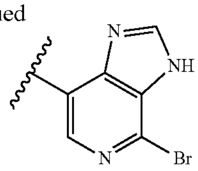,
In some embodiments, $R_1$ is:
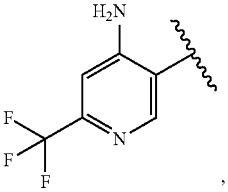, 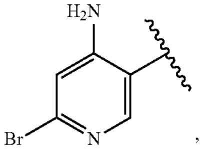,
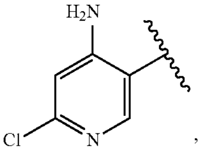, 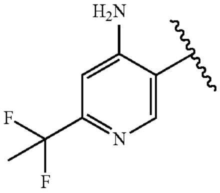,
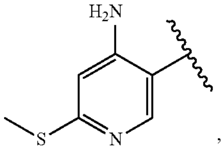, 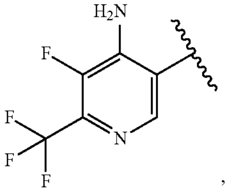,
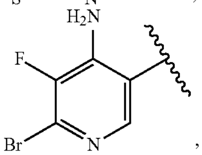, 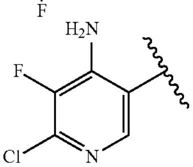,
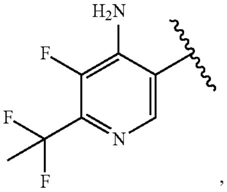, 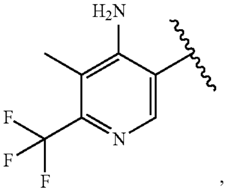,
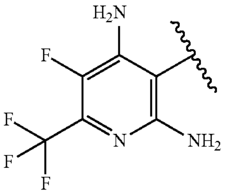, or 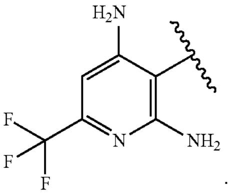.
In some embodiments, $R_1$ is:
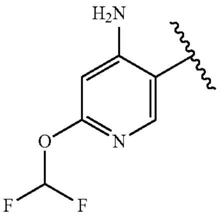, 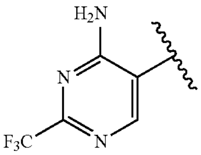,
-continued
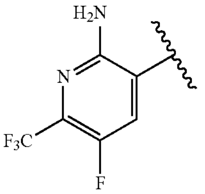, 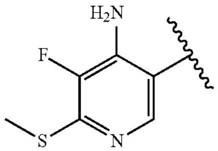,
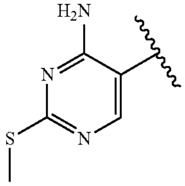, 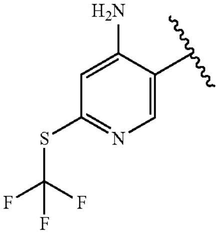, or
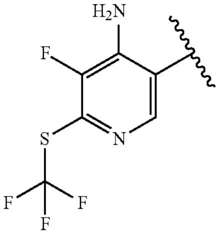.
In some embodiments, $R_1$ is:
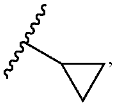, 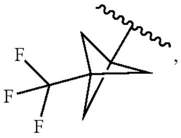, 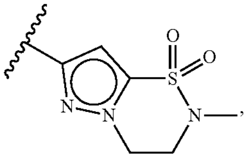
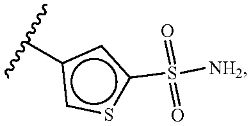 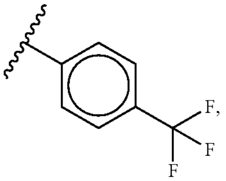
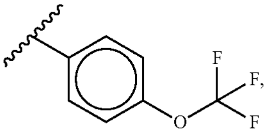 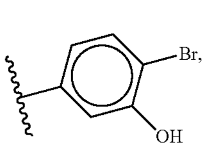
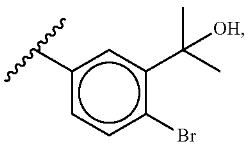 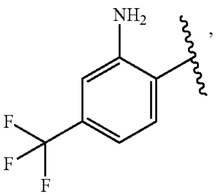,
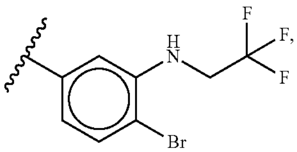

-continued
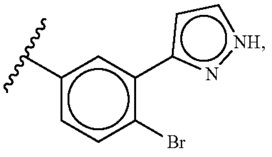
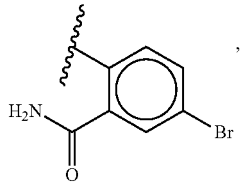
,
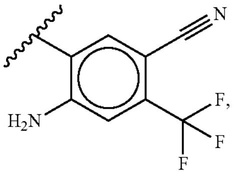
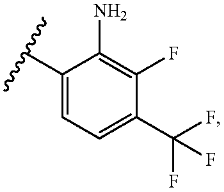
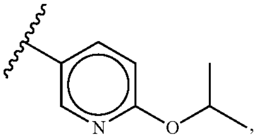
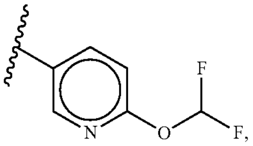
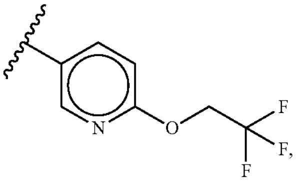
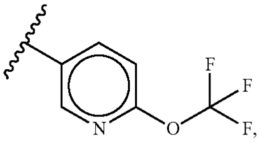
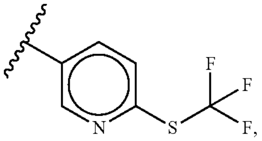
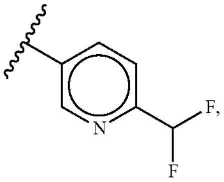
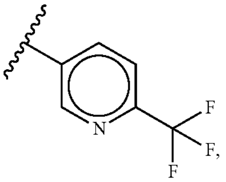
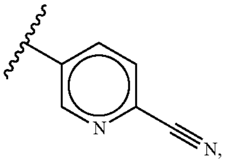
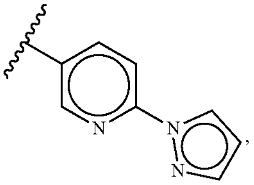
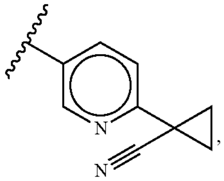
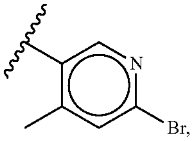
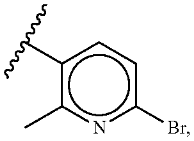
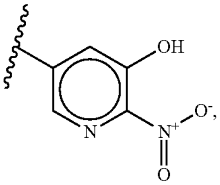
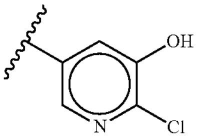
,
-continued
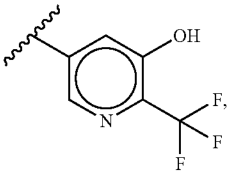
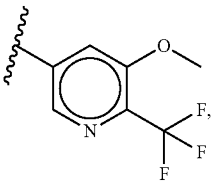
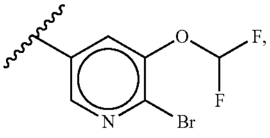
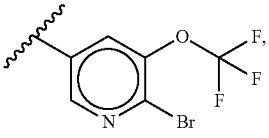
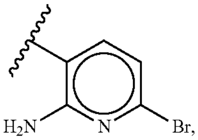
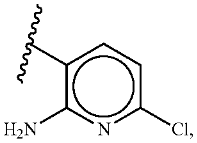
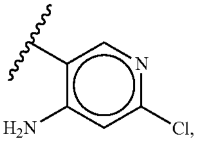
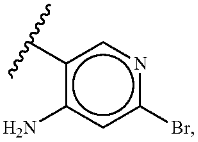
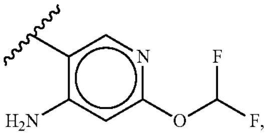
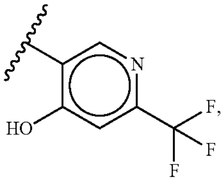
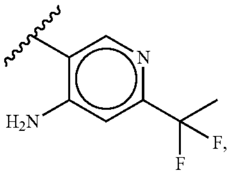
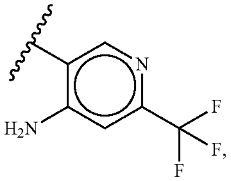
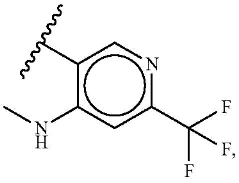
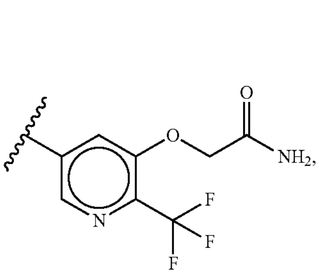
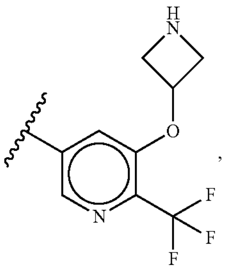
,
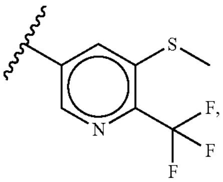
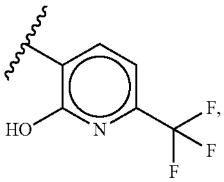

-continued
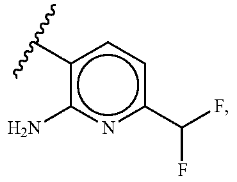
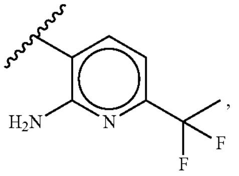
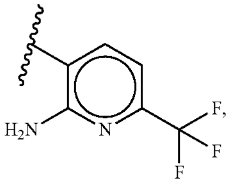
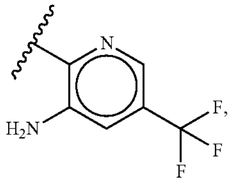
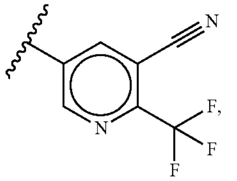
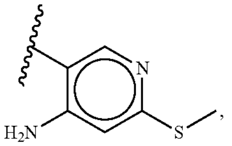
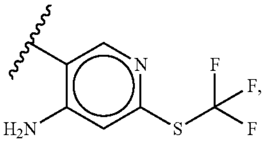
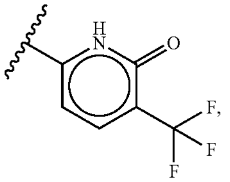
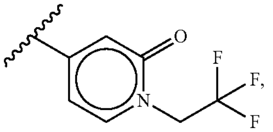
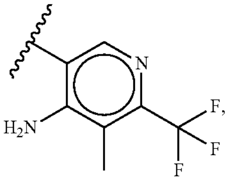
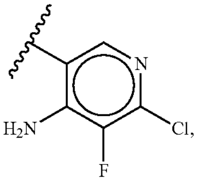
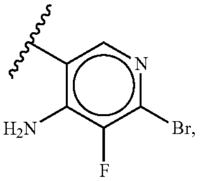
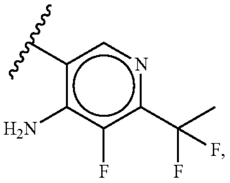
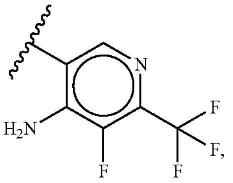
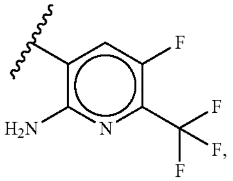
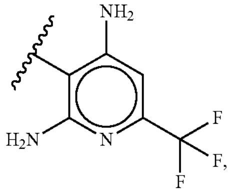
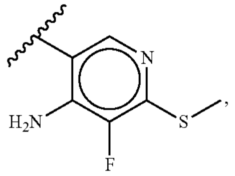
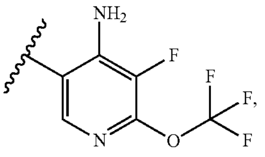
-continued
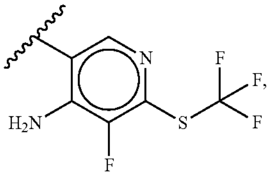
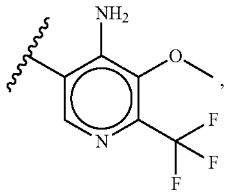
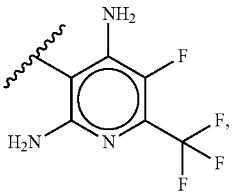
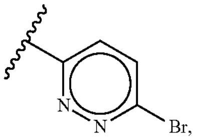
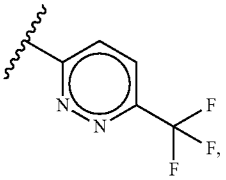
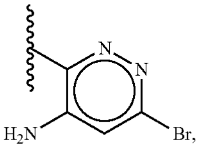
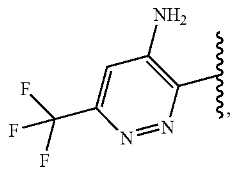
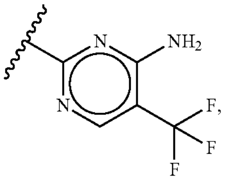
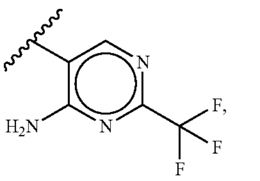
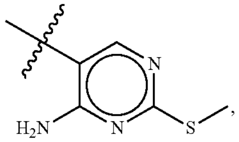
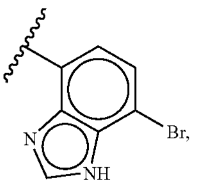
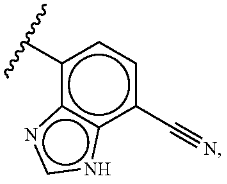
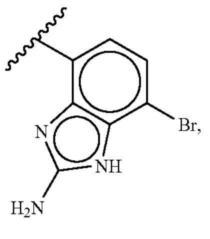
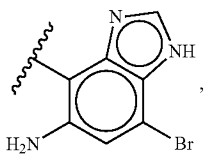
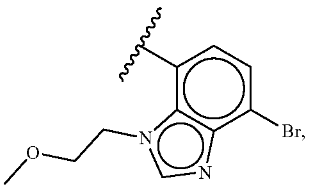

-continued

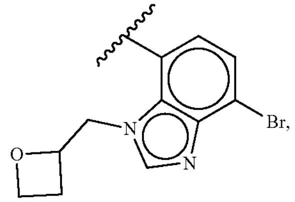
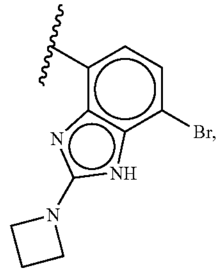
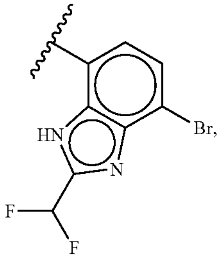
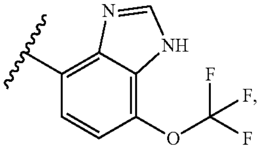
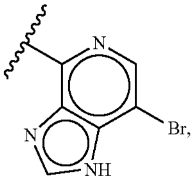
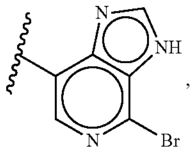
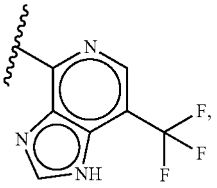
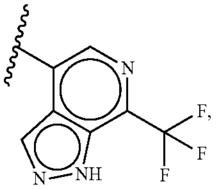
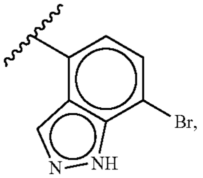
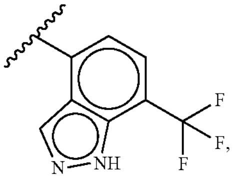
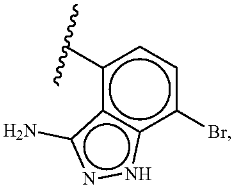
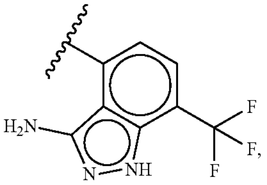
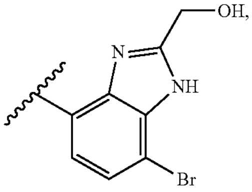
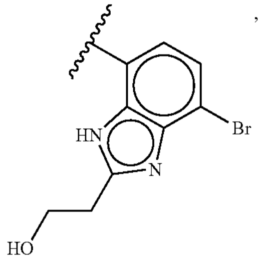

-continued

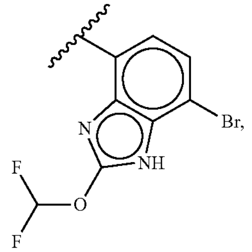
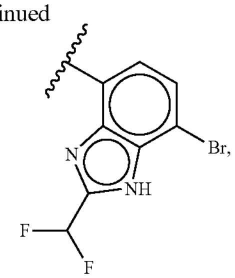
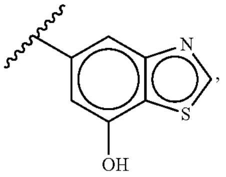
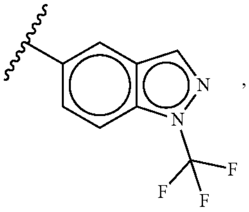
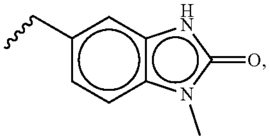
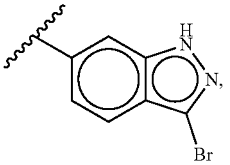
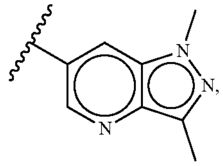
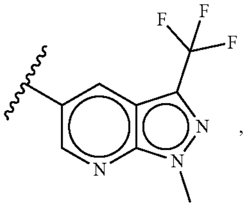
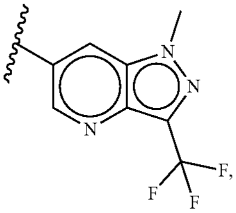
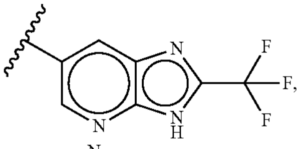
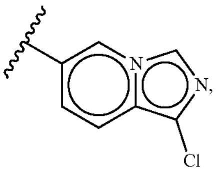
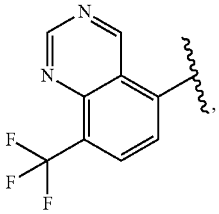

or

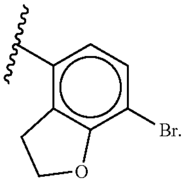

In some embodiments, $R_1$ is $C_3$-$C_{10}$ cycloalkyl, $C_6$-$C_{10}$ aryl, or 5- to 10-membered heteroaryl, wherein $C_3$-$C_{10}$ cycloalkyl, $C_6$-$C_{10}$ aryl, or 5- to 10-membered heteroaryl is optionally substituted with one or more $R_{1a}$;

each $R_{1a}$ independently is oxo, halo, cyano, —OH, —$NH_2$, —NH($C_1$-$C_6$ alkyl), —$NO_2$, —S($C_1$-$C_6$ alkyl), —$S(O)_2(NH_2)$, —C(O)$NH_2$, —O(3- to 10-membered heterocyclyl), $C_1$-$C_6$ alkyl, $C_1$-$C_6$ alkoxy, $C_1$-$C_6$ haloalkyl, $C_3$-$C_{10}$ cycloalkyl, 5- to 10-membered heteroaryl or 3- to 10-membered heterocyclyl, wherein the —NH($C_1$-$C_6$ alkyl), —S($C_1$-$C_6$ alkyl), —O(3- to 10-membered heterocyclyl), $C_1$-$C_6$ alkyl, $C_1$-$C_6$ alkoxy, $C_1$-$C_6$ haloalkyl, $C_3$-$C_{10}$ cycloalkyl, 5- to 10-membered heteroaryl, or 3- to 10-membered heterocyclyl is optionally substituted with one or more $R_{1b}$; and each $R_{1b}$ independently is halo, cyano, —OH, —O($C_1$-$C_6$ alkyl), —C(O)$NH_2$, or 3- to 10-membered heterocyclyl.

In some embodiments, $R_1$ is $C_3$-$C_{10}$ cycloalkyl, $C_6$-$C_{10}$ aryl, or 5- to 10-membered heteroaryl, wherein $C_3$-$C_{10}$ cycloalkyl, $C_6$-$C_{10}$ aryl, or 5- to 10-membered heteroaryl is optionally substituted with one or more $R_{1a}$;

each $R_{1a}$ independently is oxo, fluoro, chloro, bromo, cyano, —OH, —$OCH_3$, —$OCHF_2$, —$OCF_3$, —$OCH_2CF_3$, —$OCH(CH_3)_2$, —$OCH_2C(O)NH_2$, —$SCH_3$, —$SCF_3$, —$NH_2$, —$NH(CH_3)$, —NH($CH_2CF_3$), —$NO_2$, $CH_3$, —$CH_2OH$, —$(CH_2)_2OH$, —$(CH_2)_2OCH_3$, —$CHF_2$, —$CF_2CH_3$, —$CH_2CF_3$, —$CF_3$, —$S(O)_2(NH_2)$, —C(O)$NH_2$,

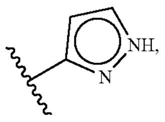

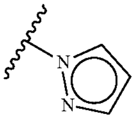

,

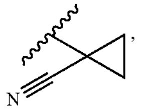

,

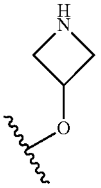

,

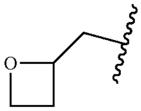

, or

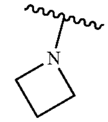

.

In some embodiments, $R_1$ is:

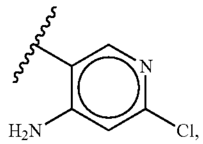

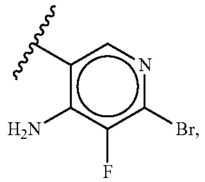

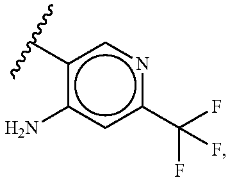

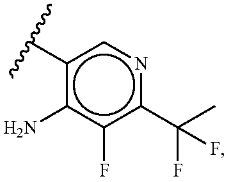

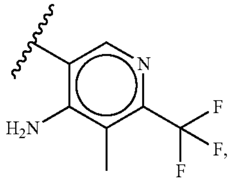

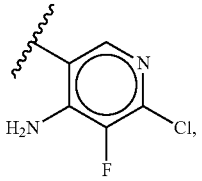

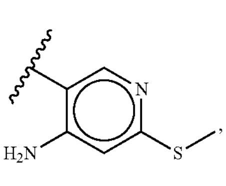

,

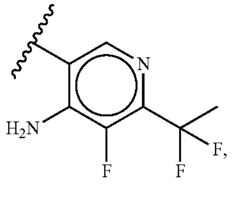

-continued

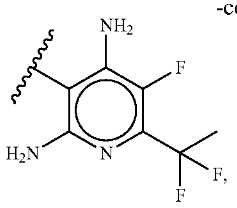

or

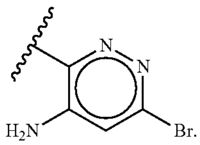

In some embodiments, each $R_{1a}$ independently is halo, —$NH_2$, —S($C_1$-$C_6$ alkyl), $C_1$-$C_6$ alkyl, or $C_1$-$C_6$ haloalkyl.

In some embodiments, each $R_{1a}$ independently is fluoro, chloro, bromo, —$NH_2$, —$SCH_3$, —$CH_3$, —$CF_3$, or —$CF_2CH_3$.

In some embodiments, each $R_{1a}$ independently is oxo, halo, cyano, —OH, —$NH_2$, —$NO_2$, —NH($C_1$-$C_6$ alkyl), —N($C_1$-$C_6$ alkyl)$_2$ —NH—C(O)($C_1$-$C_6$ alkyl), —S($C_1$-$C_6$ alkyl), —$S(O)_2$($C_1$-$C_6$ alkyl), —$S(O)_2(NH_2)$, —C(O)(H), —C(O)$NH_2$, —O(3- to 10-membered heterocyclyl), $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, $C_3$-$C_{10}$ cycloalkyl, $C_6$-$C_{10}$ aryl, 5- to 10-membered heteroaryl, or 3- to 10-membered heterocyclyl, wherein the —NH($C_1$-$C_6$ alkyl), —N($C_1$-$C_6$ alkyl)$_2$ —NH—C(O)($C_1$-$C_6$ alkyl), —S($C_1$-$C_6$ alkyl), —$S(O)_2$($C_1$-$C_6$ alkyl), —O(3- to 10-membered heterocyclyl), $C_1$-$C_6$ alkyl, $C_2$-$C_6$ alkenyl, $C_2$-$C_6$ alkynyl, $C_1$-$C_6$ alkoxy $C_1$-$C_6$ haloalkyl, $C_3$-$C_{10}$ cycloalkyl, $C_6$-$C_{10}$ aryl, 5- to 10-membered heteroaryl, or 3- to 10-membered heterocyclyl is optionally substituted with one or more $R_{1b}$.

In some embodiments, each $R_{1a}$ independently is oxo, halo, cyano, —OH, —$NH_2$, —$NO_2$, —NH($C_1$-$C_6$ alkyl), —N($C_1$-$C_6$ alkyl)$_2$ —NH—C(O)($C_1$-$C_6$ alkyl), —S($C_1$-$C_6$ alkyl), —$S(O)_2$($C_1$-$C_6$ alkyl), —$S(O)_2(NH_2)$, —C(O)(H), —C(O)$NH_2$, —O(3- to 10-membered heterocyclyl), $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, $C_3$-$C_{10}$ cycloalkyl, $C_6$-$C_{10}$ aryl, 5- to 10-membered heteroaryl, or 3- to 10-membered heterocyclyl, wherein the NH($C_1$-$C_6$ alkyl), —N($C_1$-$C_6$ alkyl)$_2$ —NH—C(O)($C_1$-$C_6$ alkyl), —S($C_1$-$C_6$ alkyl), —$S(O)_2$($C_1$-$C_6$ alkyl), —O(3- to 10-membered heterocyclyl), $C_1$-$C_6$ alkyl, $C_2$-$C_6$ alkenyl, $C_2$-$C_6$ alkynyl, $C_1$-$C_6$ alkoxy $C_1$-$C_6$ haloalkyl, $C_3$-$C_{10}$ cycloalkyl, $C_6$-$C_{10}$ aryl, 5- to 10-membered heteroaryl, or 3- to 10-membered heterocyclyl is substituted with one or more $R_{1b}$.

In some embodiments, each $R_{1a}$ independently is oxo, halo, cyano, —OH, —$NH_2$, —$NO_2$, —NH($C_1$-$C_6$ alkyl), —N($C_1$-$C_6$ alkyl)$_2$ —NH—C(O)($C_1$-$C_6$ alkyl), —S($C_1$-$C_6$ alkyl), —$S(O)_2$($C_1$-$C_6$ alkyl), —$S(O)_2(NH_2)$, —C(O)(H), —C(O)$NH_2$, —O(3- to 10-membered heterocyclyl), $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, $C_3$-$C_{10}$ cycloalkyl, $C_6$-$C_{10}$ aryl, 5- to 10-membered heteroaryl, or 3- to 10-membered heterocyclyl.

In some embodiments, each $R_{1a}$ independently is oxo, halo, cyano, —OH, —$NH_2$, —$NO_2$, —NH—C(O)($C_1$-$C_6$ alkyl), —S($C_1$-$C_6$ alkyl), —C(O)H, —C(O)$NH_2$, —O(3- to 10 membered heterocyclyl), $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, $C_3$-$C_{10}$ cycloalkyl, $C_6$-$C_{10}$ aryl, 5- to 10-membered heteroaryl, or 3- to 10-membered heterocyclyl, wherein the —O(3- to 10-membered heterocyclyl), —NH—C(O)($C_1$-$C_6$ alkyl), —S($C_1$-$C_6$ alkyl), —C(O)H, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, $C_3$-$C_{10}$ cycloalkyl, $C_6$-$C_{10}$ aryl, 5- to 10-membered heteroaryl, or 3- to 10-membered heterocyclyl is optionally substituted with one or more $R_{1b}$.

In some embodiments, each $R_{1a}$ independently is oxo, halo, cyano, —OH, —$NH_2$, —$NO_2$, —NH—C(O)($C_1$-$C_6$ alkyl), —S($C_1$-$C_6$ alkyl), —C(O)H, —C(O)$NH_2$, —O(3- to 10 membered heterocyclyl), $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, $C_3$-$C_{10}$ cycloalkyl, $C_6$-$C_{10}$ aryl, 5- to 10-membered heteroaryl, or 3- to 10-membered heterocyclyl.

In some embodiments, each $R_{1a}$ independently is oxo.

In some embodiments, each $R_{1a}$ independently is halo.

In some embodiments, each $R_{1a}$ independently is F, Cl, Br, or. In some embodiments, each $R_{1a}$ independently is F, Cl, or Br. In some embodiments, each $R_{1a}$ is dependently is F or Cl.

In some embodiments, each $R_{1a}$ independently is F. In some embodiments, each $R_{1a}$ independently is Cl. In some embodiments, each $R_{1a}$ independently is Er. In some embodiments, each $R_{1a}$ independently is I.

In some embodiments, each $R_{1a}$ independently is cyano.

In some embodiments, each $R_{1a}$ independently is —OH.

In some embodiments, each $R_{1a}$ independently is —$NH_2$.

In some embodiments, each $R_{1a}$ independently is —$NO_2$.

In some embodiments, each $R_{1a}$ independently is —NH—C(O)($C_1$-$C_6$ alkyl).

In some embodiments, each $R_{1a}$ independently is —NH—C(O)($C_1$-$C_6$ alkyl), wherein-the —NH—C(O)($C_1$-$C_6$ alkyl) is optionally substituted with one or more $R_{1b}$.

In some embodiments, each $R_{1a}$ independently is —NH—C(O)($C_1$-$C_6$ alkyl), wherein the —NH—C(O)($C_1$-$C_6$ alkyl) is substituted with one or more $R_{1b}$.

In some embodiments, each $R_{1a}$ independently is —S($C_1$-$C_6$ alkyl).

In some embodiments, each $R_{1a}$ independently is —S($C_1$-$C_6$ alkyl), wherein the —S($C_1$-$C_6$ alkyl) is optionally substituted with one or more $R_{1b}$.

In some embodiments, each $R_{1a}$ independently is —S($C_1$-$C_6$ alkyl), wherein the —S($C_1$-$C_6$ alkyl) is substituted with one or more $R_{1b}$.

In some embodiments, each $R_{1a}$ independently is —S(O)$_2$($C_1$-$C_6$ alkyl).

In some embodiments, each $R_{1a}$ independently is —S(O)$_2$($C_1$-$C_6$ alkyl), wherein the —S(O)$_2$($C_1$-$C_6$ alkyl) is optionally substituted with one or more $R_{1b}$.

In some embodiments, each $R_{1a}$ independently is —S(O)$_2$($C_1$-$C_6$ alkyl), wherein the —S(O)$_2$($C_1$-$C_6$ alkyl) is substituted with one or more $R_{1b}$.

In some embodiments, each $R_{1a}$ independently is —S(O)$_2$($NH_2$).

In some embodiments, each $R_{1a}$ independently is —C(O)(H).

In some embodiments, each $R_{1a}$ independently is —C(O)$NH_2$.

In some embodiments, each $R_{1a}$ independently is —O(3- to 10-membered heterocyclyl).

In some embodiments, each $R_{1a}$ independently is —O(3- to 10-membered heterocyclyl), wherein the —O(3- to 10-membered heterocyclyl) is optionally substituted with one or more $R_{1b}$.

In some embodiments, each $R_{1a}$ independently is —O(3- to 10 membered heterocyclyl), wherein the —O(3- to 10-membered heterocyclyl) is substituted with one or more $R_{1b}$.

In some embodiments, each $R_{1a}$ independently is $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, $C_3$-$C_{10}$ cycloalkyl, $C_6$-$C_{10}$ aryl, 5- to 10-membered heteroaryl, or 3- to 10-membered heterocyclyl, wherein the $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, $C_3$-$C_{10}$ cycloalkyl, $C_6$-$C_{10}$ aryl, 5- to 10-membered heteroaryl, or 3- to 10-membered heterocyclyl is optionally substituted with one or more $R_{1b}$.

In some embodiments, each $R_{1a}$ independently is $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, $C_3$-$C_{10}$ cycloalkyl, $C_6$-$C_{10}$ aryl, 5- to 10-membered heteroaryl, or 3- to 10-membered heterocyclyl.

In some embodiments, each $R_{1a}$ independently is $C_1$-$C_6$ alkyl, $C_2$-$C_6$ alkenyl, $C_2$-$C_6$ alkynyl, $C_1$-$C_6$ alkoxy, or $C_1$-$C_6$ haloalkyl, wherein the $C_1$-$C_6$ alkyl, $C_2$-$C_6$ alkenyl, $C_2$-$C_6$ alkynyl, $C_1$-$C_6$ alkoxy, or $C_1$-$C_6$ haloalkyl is optionally substituted with one or more $R_{1b}$.

In some embodiments, each $R_{1a}$ independently is $C_1$-$C_6$ alkyl, $C_2$-$C_6$ alkenyl, $C_2$-$C_6$ alkynyl, $C_1$-$C_6$ alkoxy, or $C_1$-$C_6$ haloalkyl.

In some embodiments, each $R_{1a}$ independently is $C_1$-$C_6$ alkyl.

In some embodiments, each $R_{1a}$ independently is $C_1$-$C_6$ alkyl optionally substituted with one or more $R_{1b}$.

In some embodiments, each $R_{1a}$ independently is $C_1$-$C_6$ alkyl substituted with one or more Rib.

In some embodiments, each $R_{1a}$ independently is methyl. In some embodiments, each $R_{1a}$ independently is ethyl. In some embodiments, each $R_{1a}$ independently is propyl. In some embodiments, each $R_{1a}$ independently is butyl. In some embodiments, ach $R_{1a}$ independently is pentyl. In some embodiments, each $R_{1a}$ independently is hexyl. In some embodiments, each $R_{1a}$ independently is isopropyl. In some embodiments, each $R_{1a}$ independently is isobutyl. In some embodiments, each $R_{1a}$ independently is isopentyl. In some embodiments, each $R_{1a}$ independently is isohexyl. In some embodiments, each $R_{1a}$ independently is secbutyl. In some embodiments, each $R_{1a}$ independently is secpentyl. In some embodiments, each $R_{1a}$ independently is sechexyl. In some embodiments, each $R_{1a}$ independently is tertbutyl.

In some embodiments, each $R_{1a}$ independently is $C_2$-$C_6$ alkenyl.

In some embodiments, each $R_{1a}$ independently is $C_2$-$C_6$ alkenyl optionally substituted with one or more $R_{1b}$.

In some embodiments, each $R_{1a}$ independently is $C_2$-$C_6$ alkenyl substituted with one or more $R_{1b}$.

In some embodiments, each $R_{1a}$ independently is $C_2$-$C_6$ alkynyl.

In some embodiments, each $R_{1a}$ independently is $C_2$-$C_6$ alkynyl optionally substituted with one or more $R_{1b}$.

In some embodiments, each $R_{1a}$ independently is $C_2$-$C_6$ alkynyl substituted with one or more $R_{1b}$.

In some embodiments, each $R_{1a}$ independently is $C_1$-$C_6$ alkoxy.

In some embodiments, each $R_{1a}$ independently is $C_1$-$C_6$ alkoxy optionally substituted with one or more $R_{1b}$.

In some embodiments, each $R_{1a}$ independently is $C_1$-$C_6$ alkoxy substituted with one or more Rib.

In some embodiments, each $R_{1a}$ independently is $C_1$-$C_6$ haloalkyl.

In some embodiments, each $R_{1a}$ independently is $C_1$-$C_6$ haloalkyl optionally substituted with one or more $R_{1b}$.

In some embodiments, each $R_{1a}$ independently is $C_1$-$C_6$ haloalkyl substituted with one or more $R_{1b}$.

In some embodiments, each $R_{1a}$ independently is halomethyl. In some embodiments, each $R_{1a}$ independently is haloethyl. In some embodiments, each $R_{1a}$ independently is halopropyl. In some embodiments, each $R_{1a}$ independently is halobutyl. In some embodiments, each $R_{1a}$ independently is halopentyl. In some embodiments, each $R_{1a}$ independently is halohexyl.

In some embodiments, each $R_{1a}$ independently is $C_3$-$C_{10}$ cycloalkyl, $C_6$-$C_{10}$ aryl, 5- to 10-membered heteroaryl, or 3- to 10-membered heterocyclyl, wherein the 3-$C_{10}$ cycloalkyl, $C_6$-$C_{10}$ aryl, 5- to 10-membered heteroaryl, or 3- to 10-membered heterocyclyl is optionally substituted with one or more $R_{1b}$.

In some embodiments, each $R_{1a}$ independently is $C_3$-$C_{10}$ cycloalkyl, $C_6$-$C_{10}$ aryl, 5- to 10-membered heteroaryl, or 3- to 10-membered heterocyclyl.

In some embodiments, each $R_{1a}$ independently is $C_3$-$C_{10}$ cycloalkyl.

In some embodiments, each $R_{1a}$ independently is $C_3$-$C_{10}$ cycloalkyl optionally substituted with one or more $R_{1b}$.

In some embodiments, each $R_{1a}$ independently is $C_3$-$C_{10}$ cycloalkyl substituted with one or more $R_{1b}$.

In some embodiments, each $R_{1a}$ independently is $C_3$-$C_7$ cycloalkyl.

In some embodiments, each $R_{1a}$ independently is $C_3$-$C_7$ cycloalkyl optionally substituted with one or more $R_{1b}$.

In some embodiments, each $R_{1a}$ independently is $C_3$-$C_7$ cycloalkyl substituted with one or more $R_{1b}$.

In some embodiments, each $R_{1a}$ independently is 3- to 10-membered heterocyclyl.

In some embodiments, each $R_{1a}$ independently is 3- to 10-membered heterocyclyl optionally substituted with one or more $R_{1b}$.

In some embodiments, each $R_{1a}$ independently is 3- to 10-membered heterocyclyl substituted with one or more $R_{1b}$.

In some embodiments, each $R_{1a}$ independently is 3- to 7-membered heterocyclyl.

In some embodiments, each $R_{1a}$ independently is 3- to 7-membered heterocyclyl optionally substituted with one or more $R_{1b}$.

In some embodiments, each $R_{1a}$ independently is 3- to 7-membered heterocyclyl substituted with one or more $R_{1b}$.

In some embodiments, each $R_{1a}$ independently is $C_6$-$C_{10}$ aryl.

In some embodiments, each $R_{1a}$ independently is $C_6$-$C_{10}$ aryl optionally substituted with one or more $R_{1b}$.

In some embodiments, each $R_{1a}$ independently is $C_6$-$C_{10}$ aryl substituted with one or more Rib.

In some embodiments, each $R_{1a}$ independently is $C_6$ aryl.

In some embodiments, each $R_{1a}$ independently is CO aryl optionally substituted with one or more $R_{1b}$.

In some embodiments, each $R_{1a}$ independently is $C_6$ aryl substituted with one or more $R_{1b}$.

In some embodiments, each $R_{1a}$ independently is 5- to 10-membered heteroaryl.

In some embodiments, each $R_{1a}$ independently is 5- to 10-membered heteroaryl optionally substituted with one or more $R_{1b}$.

In some embodiments, each $R_{1a}$ independently is 5- to 10-membered heteroaryl substituted with one or more $R_{1b}$.

In some embodiments, each $R_{1a}$ independently is 5- or 6-membered heteroaryl.

In some embodiments, each $R_{1a}$ independently is 5- or 6-membered heteroaryl optionally substituted with one or more $R_{1b}$.

In some embodiments, each $R_{1a}$ independently is 5- or 6-membered heteroaryl substituted with one or more $R_{1b}$.

In some embodiments, each $R_{1a}$ independently is halo, —OH, —$NH_2$, —NH($C_1$-$C_6$ alkyl), —S($C_1$-$C_6$ alkyl), $C_1$-$C_6$ alkyl, $C_1$-$C_6$ alkoxy, $C_1$-$C_6$ haloalkyl, or 3- to 10-membered heterocyclyl.

In some embodiments, each $R_{1a}$ independently is halo, —OH, —$NH_2$, —NH($C_1$-$C_6$ alkyl), —S($C_1$-$C_6$ alkyl), $C_1$-$C_6$ alkyl, $C_1$-$C_6$ alkoxy, $C_1$-$C_6$ haloalkyl, or 3- to 10-membered heterocyclyl, wherein the —NH($C_1$-$C_6$ alkyl), —S($C_1$-$C_6$ alkyl), $C_1$-$C_6$ alkyl, $C_1$-$C_6$ alkoxy, $C_1$-$C_6$ haloalkyl, or 3-to 10-membered heterocyclyl is optionally substituted with one or more $R_{1b}$.

In some embodiments, each $R_{1a}$ independently is oxo, cyano, —C(O)$NH_2$, —O(3- to 10-membered heterocyclyl), halo, —OH, —$NH_2$, $C_1$-$C_6$ alkyl, $C_1$-$C_6$ alkoxy, $C_1$-$C_6$ haloalkyl, or 3- to 10-membered heterocyclyl, wherein the —O(3- to 10-membered heterocyclyl), $C_1$-$C_6$ alkyl, $C_1$-$C_6$ alkoxy, $C_1$-$C_6$ haloalkyl, or 3- to 10-membered heterocyclyl is substituted with one or more $R_{1b}$.

In some embodiments, each $R_{1a}$ independently is oxo, cyano, —O($CH_2$)C(O)$NH_2$, —O— azetidinyl, —$OCF_3$, —C(O)$NH_2$, —$CH_2CF_3$, —C($CH_3$)$_2$(OH), —$OCHF_2$, —$CH_3$, —OH, Br, —$CF_3$, —$CHF_2$, —($CH_2$)$_2$—$OCH_3$, —$NH_2$, —NH—$CH_2$—$CF_3$, —($CH_2$)-oxetanyl, azetidinyl, pyrazolyl, cyclopropyl, —S($O_2$)($NH_2$), —$SCH_3$, or —$OCH_3$.

In some embodiments, each $R_{1b}$ independently is oxo, halo, cyano, —OH, —O($C_1$-$C_6$ alkyl), —O($C_1$-$C_6$ haloalkyl), —O($C_2$-$C_6$ alkenyl), —O($C_2$-$C_6$ alkynyl), —$NH_2$, —N($C_1$-$C_6$ alkyl), —N($C_1$-$C_6$ alkyl)$_2$, —NH($C_1$-$C_6$ haloalkyl), —S($C_1$-$C_6$ alkyl), —S(O)$_2$($C_1$-$C_6$ alkyl), $C_1$-$C_6$ alkyl, $C_3$-$C_{10}$ cycloalkyl, or 3- to 10-membered heterocyclyl optionally substituted with oxo.

In some embodiments, each $R_{1b}$ independently is oxo, halo, cyano, —OH, —O($C_1$-$C_6$ alkyl), —O($C_1$-$C_6$ haloalkyl), —O($C_2$-$C_6$ alkenyl), —O($C_2$-$C_6$ alkynyl), —$NH_2$, —S($C_1$-$C_6$ alkyl), —S(O)$_2$($C_1$-$C_6$ alkyl), $C_1$-$C_6$ alkyl, $C_3$-$C_{10}$ cycloalkyl, or 3- to 10-membered heterocyclyl optionally substituted with oxo.

In some embodiments, each $R_{1b}$ independently is oxo, halo, cyano, —OH, —O($C_1$-$C_6$ alkyl), —O($C_1$-$C_6$ haloalkyl), —O($C_2$-$C_6$ alkenyl), —O($C_2$-$C_6$ alkynyl), —$NH_2$, —S(i-$C_6$ alkyl), —S(O)$_2$($C_1$-$C_6$ alkyl), $C_1$-$C_6$ alkyl, $C_3$-$C_{10}$ cycloalkyl, or 3- to 10-membered heterocyclyl.

In some embodiments, each $R_{1b}$ independently is oxo, halo, cyano, —OH, —O($C_1$-$C_6$ alkyl), —O($C_1$-$C_6$ haloalkyl), —O($C_2$-$C_6$ alkenyl), —O($C_2$-$C_6$ alkynyl), —$NH_2$, —N($C_1$-$C_6$ alkyl), —N($C_1$-$C_6$ alkyl)$_2$, —NH($C_1$-$C_6$ haloalkyl), —S($C_1$-$C_6$ alkyl), —S(O)$_2$($C_1$-$C_6$ alkyl), —C(O)$NH_2$, $C_1$-$C_6$ alkyl, $C_3$-$C_{10}$ cycloalkyl, or 3- to 10-membered heterocyclyl optionally substitute with oxo.

In some embodiments, each $R_{1b}$ independently is oxo, halo, cyano, —OH, —O($C_1$-$C_6$ alkyl), —O($C_1$-$C_6$ haloalkyl), —O($C_2$-$C_6$ alkenyl), —O($C_2$-$C_6$ alkynyl), —$NH_2$, —NH($C_1$-$C_6$ alkyl), —N($C_1$-$C_6$ alkyl)$_2$, —NH($C_1$-$C_6$ haloalkyl), —S($C_1$-$C_6$ alkyl), —S(O)$_2$($C_1$-$C_6$ alkyl), —C(O)$NH_2$, $C_1$-$C_6$ alkyl, $C_3$-$C_{10}$ cycloalkyl, or 3- to 10-membered heterocyclyl substituted with oxo.

In some embodiments, each $R_{1b}$ independently is oxo, halo, cyano, —OH, —O($C_1$-$C_6$ alkyl), —O($C_1$-$C_6$ haloalkyl), —O($C_2$-$C_6$ alkenyl), —O($C_2$-$C_6$ alkynyl), —$NH_2$, —N($C_1$-$C_6$ alkyl), —N($C_1$-$C_6$ alkyl)$_2$, —NH($C_1$-$C_6$ haloalkyl), —S($C_1$-$C_6$ alkyl), —S(O)$_2$($C_1$-$C_6$ alkyl), —C(O)$NH_2$, $C_1$-$C_6$ alkyl, $C_3$-$C_{10}$ cycloalkyl, or 3- to 10-membered heterocyclyl.

In some embodiments, each $R_{1b}$ independently is oxo.

In some embodiments, each $R_{1b}$ independently is halo.

In some embodiments, each $R_{1b}$ independently is F, Cl, Br, or I. In some embodiments, each $R_{1b}$ independently is F, Cl, or Br. In some embodiments, each $R_{1b}$ independently is F or Cl.

In some embodiments, each $R_{1b}$ independently is F. In some embodiments, each Rib independently is Cl. In some embodiments, each $R_{1b}$ independently is Br. In some embodiments, each $R_{1b}$ independently is I.

In some embodiments, each $R_{1b}$ independently is cyano.

In some embodiments, each $R_{1b}$ independently is —OH.

In some embodiments, each $R_{1b}$ independently is —O($C_1$-$C_6$ alkyl).

In some embodiments, each $R_{1b}$ independently is —O($C_1$-$C_6$ haloalkyl).

In some embodiments, each $R_{1b}$ independently is —O($C_2$-$C_6$ alkenyl).

In some embodiments, each $R_{1b}$ independently is —O($C_2$-$C_6$ alkyl).

In some embodiments, each $R_{1b}$ independently is —$NH_2$, —NH($C_1$-$C_6$ alkyl), —N($C_1$-$C_6$ alkyl)$_2$, or —NH($C_1$-$C_6$ haloalkyl).

In some embodiments, each $R_{1b}$ independently is —$NH_2$.

In some embodiments, each $R_{1b}$ independently is —NH ($C_1$-$C_6$ alkyl).

In some embodiments, each $R_{1b}$ independently is —N($C_1$-$C_6$ alkyl)$_2$.

In some embodiments, each $R_{1b}$ independently is —NH ($C_1$-$C_6$ haloalkyl).

In some embodiments, each $R_{1b}$ independently is —S($C_1$-$C_6$ alkyl).

In some embodiments, each $R_{1b}$ independently is —S(O)$_2$($C_1$-$C_6$ alkyl).

In some embodiments, each $R_{1b}$ independently is —C(O) $NH_2$.

In some embodiments, each $R_{1b}$ independently is $C_1$-$C_6$ alkyl.

In some embodiments, each $R_{1b}$ independently is $C_3$-$C_{10}$ cycloalkyl.

In some embodiments, each $R_{1b}$ independently is $C_3$-$C_7$ cycloalkyl.

In some embodiments, each $R_{1b}$ independently is 3- to 10-membered heterocyclyl.

In some embodiments, each $R_{1b}$ independently is 3- to 10-membered heterocyclyl optionally substituted with oxo.

In some embodiments, each $R_{1b}$ independently is 3- to 10-membered heterocyclyl substituted with oxo.

In some embodiments, each $R_{1b}$ independently is 3- to 7-membered heterocyclyl.

In some embodiments, each $R_{1b}$ independently is 3- to 7-membered heterocyclyl optionally substituted with oxo.

In some embodiments, each $R_{1b}$ independently is —O($C_1$-$C_6$ alkyl) or 3- to 10-membered heterocyclyl.

In some embodiments, each $R_{1b}$ independently is —$OCH_3$ or oxetanyl.

In some embodiments, $R_2$ is $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_3$-$C_{10}$ cycloalkyl, $C_6$-$C_{10}$ aryl, 5- to 10-membered heteroaryl, or 3- to 10-membered heterocyclyl, wherein the $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_3$-$C_{10}$ cycloalkyl, $C_6$-$C_{10}$ aryl, 5- to 10-membered heteroaryl, or 3- to 10-membered heterocyclyl is optionally substituted with one or more $R_{2a}$.

In some embodiments, $R_2$ is $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_3$-$C_{10}$ cycloalkyl, $C_6$-$C_{10}$ aryl, 5- to 10-membered heteroaryl, or 3- to 10-membered heterocyclyl.

In some embodiments, $R_2$ is $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy wherein the $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy is optionally substituted with one or more $R_{2a}$.

In some embodiments, $R_2$ is $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy.

In some embodiments, $R_2$ is $C_1$-$C_6$ alkyl.

In some embodiments, $R_2$ is $C_1$-$C_6$ alkyl optionally substituted with one or more $R_{2a}$.

In some embodiments, $R_2$ is $C_1$-$C_6$ alkyl substituted with one or more $R_{2a}$.

In some embodiments, $R_2$ is methyl. In some embodiments, $R_2$ is ethyl. In some embodiments, $R_2$ is propyl. In some embodiments, $R_2$ is butyl. In some embodiments, $R_2$ is pentyl. In some embodiments, $R_2$ is hexyl. In some embodiments, $R_2$ is isopropyl. In some embodiments, $R_2$ is isobutyl. In some embodiments, $R_2$ is isopentyl. In some embodiments, $R_2$ is isohexyl. In some embodiments, $R_2$ is secbutyl. In some embodiments, $R_2$ is secpentyl. In some embodiments, $R_2$ is sechexyl. In some embodiments, $R_2$ is tertbutyl.

In some embodiments, $R_2$ is $C_2$-$C_6$ alkenyl (e.g., ethenyl, propenyl, butenyl).

In some embodiments, $R_2$ is $C_2$-$C_6$ alkenyl (e.g., ethenyl, propenyl, butenyl) optionally substituted with one or more $R_{2a}$.

In some embodiments, $R_2$ is $C_2$-$C_6$ alkenyl (e.g., ethenyl, propenyl, butenyl) substituted with one or more $R_{2a}$.

In some embodiments, $R_2$ is $C_2$-$C_6$ alkynyl (e.g., ethynyl, propynyl, butynyl).

In some embodiments, $R_2$ is $C_2$-$C_6$ alkynyl (e.g., ethynyl, propynyl, butynyl) optionally substituted with one or more $R_{2a}$.

In some embodiments, $R_2$ is $C_2$-$C_6$ alkynyl (e.g., ethynyl, propynyl, butynyl) substituted with one or more $R_{2a}$.

In some embodiments, $R_2$ is $C_1$-$C_6$ haloalkyl.

In some embodiments, $R_2$ is $C_1$-$C_6$ haloalkyl optionally substituted with one or more $R_{2a}$.

In some embodiments, $R_2$ is $C_1$-$C_6$ haloalkyl substituted with one or more $R_{2a}$.

In some embodiments, $R_2$ is halomethyl. In some embodiments, is haloethyl. In some embodiments, $R_2$ is halopropyl. In some embodiments, $R_2$ is halobutyl. In some embodiments, $R_2$ is halopentyl. In some embodiments, $R_2$ is halohexyl.

In some embodiments, $R_2$ is $C_1$-$C_6$ alkoxy.

In some embodiments, $R_2$ is $C_1$-$C_6$ alkoxy optionally substituted with one or more $R_{2a}$.

In some embodiments, $R_2$ is $C_1$-$C_6$ alkoxy substituted with one or more $R_{2a}$.

In some embodiments, $R_2$ is methoxy. In some embodiments, $R_2$ is ethoxy. In some embodiments, $R_2$ is propoxy. In some embodiments, $R_2$ is butoxy. In some embodiments, $R_2$ is pentoxy. In some embodiments, $R_2$ is hexoxy.

In some embodiments, $R_2$ is $C_3$-$C_{10}$ cycloalkyl, $C_6$-$C_{10}$ aryl, 5- to 10-membered heteroaryl, or 3- to 10-membered heterocyclyl, wherein the $C_3$-$C_{10}$ cycl alkyl, $C_6$-$C_{10}$ aryl, 5- to 10-membered heteroaryl, or 3- to 10-membered heterocyclyl is optionality substituted with one or more $R_{2a}$.

In some embodiments, $R_2$ is $C_3$-$C_{10}$ cycloalkyl, $C_6$-$C_{10}$ aryl, 5- to 10-membered heteroaryl, or 3- to 10-membered heterocyclyl.

In some embodiments, $R_2$ is $C_3$-$C_{10}$ cycloalkyl.

In some embodiments, $R_2$ is $C_3$-$C_{10}$ cycloalkyl optionally substituted with one or more $R_{2a}$.

In some embodiments, $R_2$ is $C_3$-$C_{10}$ cycloalkyl substituted with one or more $R_{2a}$.

In some embodiments, $R_2$ is $C_3$-$C_7$ cycloalkyl.

In some embodiments, $R_2$ is $C_3$-$C_7$ cycloalkyl optionally substituted with one or more $R_{2a}$.

In some embodiments, $R_2$ is $C_3$-$C_7$ cycloalkyl substituted with or e or more $R_{2a}$.

In some embodiments, $R_2$ is $C_6$-$C_{10}$ aryl.

In some embodiments, $R_2$ is $C_6$-$C_{10}$ aryl optionally substituted with one or more $R_{2a}$.

In some embodiments, $R_2$ is $C_6$-$C_{10}$ aryl substituted with one or more $R_{2a}$.

In some embodiments, $R_2$ is $C_6$ aryl.

In some embodiments, $R_2$ is $C_6$ aryl optionally substituted with one or more $R_{2a}$.

In some embodiments, $R_2$ is $C_6$ aryl substituted with one or more $R_{2a}$.

In some embodiments, $R_2$ is 5- to 10-membered heteroaryl.

In some embodiments, $R_2$ is 5- to 10-membered heteroaryl optionally substituted with one or more $R_{2a}$.

In some embodiments, $R_2$ is 5- to 10-membered heteroaryl substituted with one or more $R_{2a}$.

In some embodiments, $R_2$ is 5- or 6-membered heteroaryl.

In some embodiments, $R_2$ is 5- or 6-membered heteroaryl optionally substituted with one or more $R_{2a}$.

In some embodiments, $R_2$ is 5- or 6-membered heteroaryl substituted with one or more $R_{2a}$.

In some embodiments, $R_2$ is 6-membered heteroaryl.

In some embodiments, $R_2$ is 6-membered heteroaryl optionally substituted with one or more $R_{2a}$.

In some embodiments, $R_2$ is 6-membered heteroaryl substituted with one or more $R_{2a}$.

In some embodiments, $R_2$ is 3- to 10-membered heterocyclyl.

In some embodiments, $R_2$ is 3- to 10-membered heterocyclyl optionally substituted with one or more $R_{2a}$.

In some embodiments, $R_2$ is 3- to 10-membered heterocyclyl substituted with one or more $R_{2a}$.

In some embodiments, $R_2$ is $C_6$-$C_{10}$ aryl or 5- to 10-membered heteroaryl, wherein the $C_6$-$C_{10}$ aryl or 5- to 10-membered heteroaryl.

In some embodiments, $R_2$ is $C_6$-$C_{10}$ aryl or 5- to 10-membered heteroaryl, wherein the $C_6$-$C_{10}$ aryl or 5- to 10-membered heteroaryl is optionally substituted with one or more $R_{2a}$.

In some embodiments, $R_2$ is $C_6$-$C_{10}$ aryl or 5- to 10-membered heteroaryl, wherein the $C_6$-$C_{10}$ aryl or 5- to 10-membered heteroaryl is substituted with one or more $R_{2a}$.

In some embodiments, $R_2$ is:

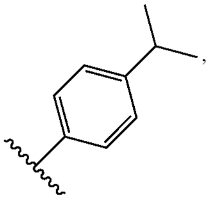,
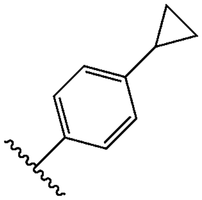,
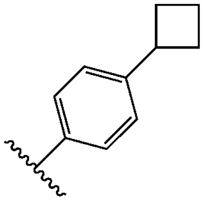,
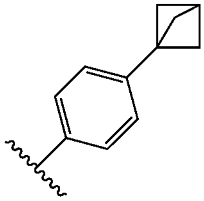,
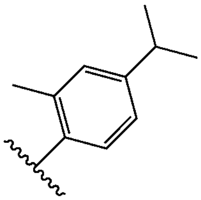,
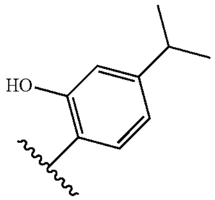,

-continued

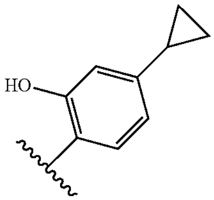,
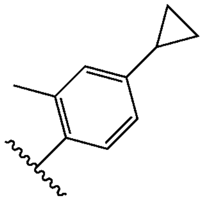,
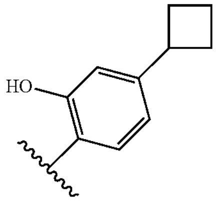,
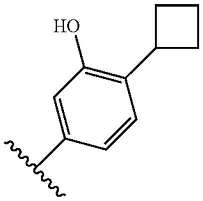,
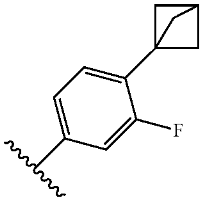,
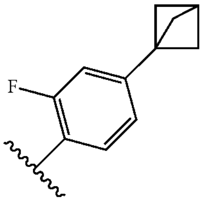,
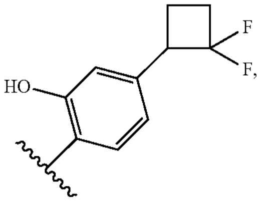
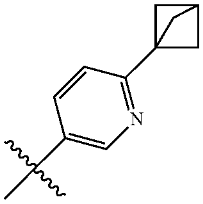,
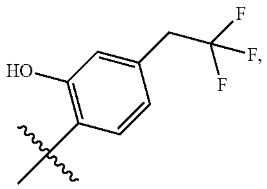
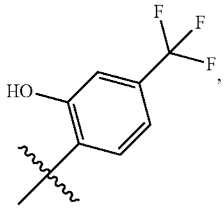
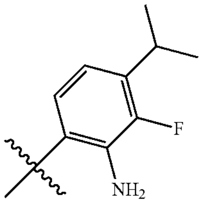,
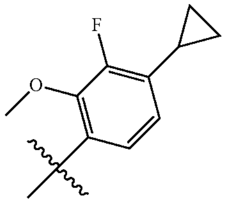,
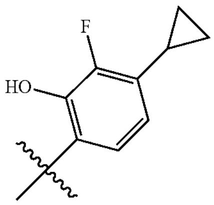,
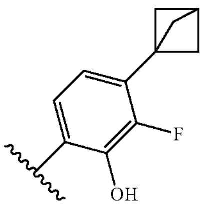,
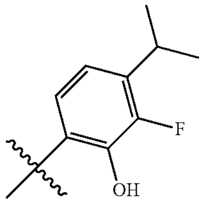,
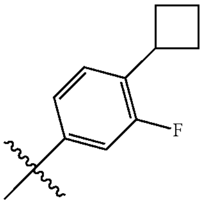, or -continued
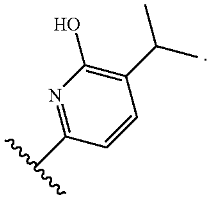
In some embodiments, $R_2$ is
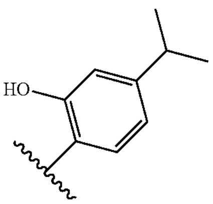
,
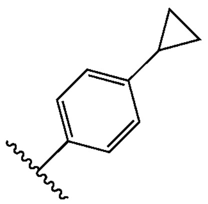
,
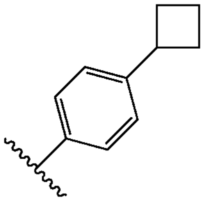
,
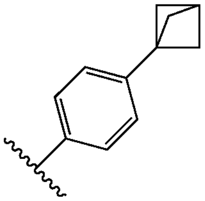
.
In some embodiments, $R_2$ is:
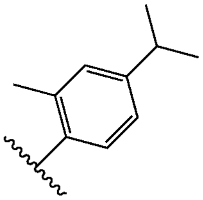
,
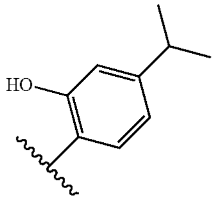
,
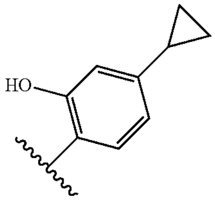
,
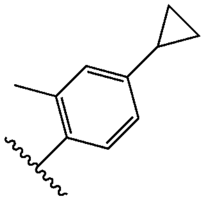
,
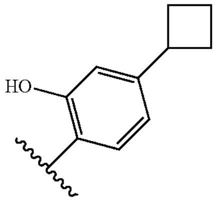
,
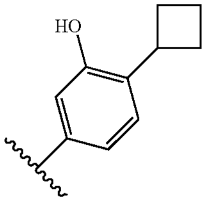
,
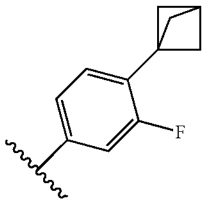
,
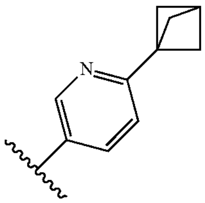
, or
-continued
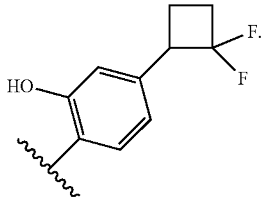
In some embodiments, $R_2$ is
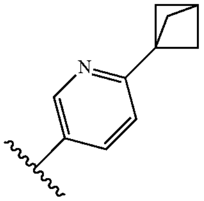
or
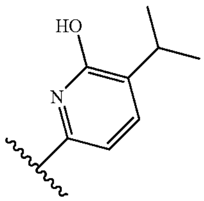
.
In some embodiments, $R_2$ is:
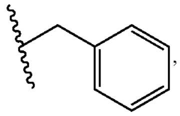
,
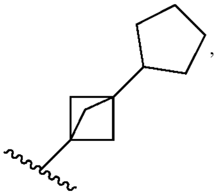
,
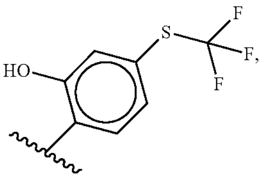
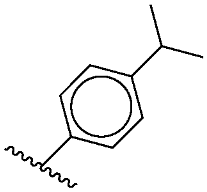
,
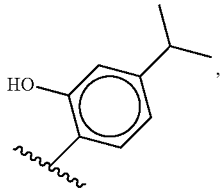
,
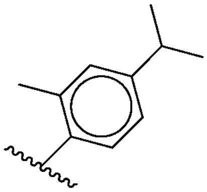
,
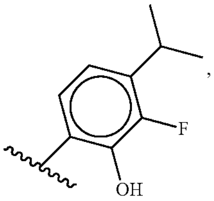
,
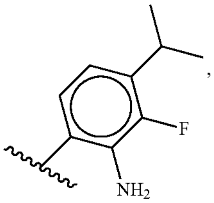
,
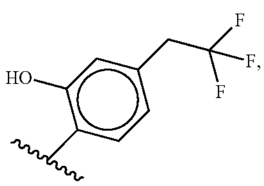
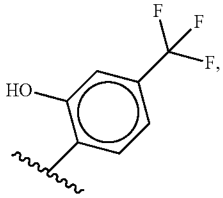

-continued

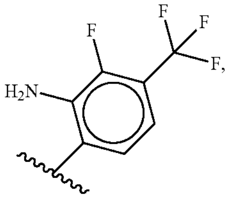

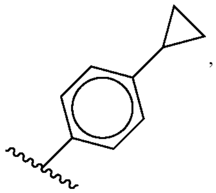
,

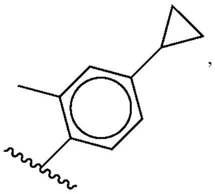
,

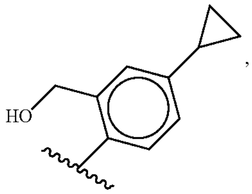
,

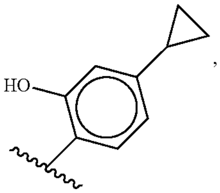
,

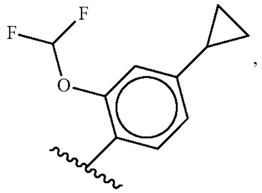
,

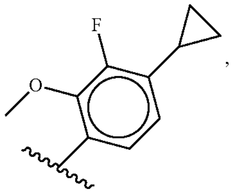
,

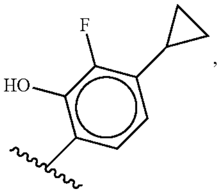
,

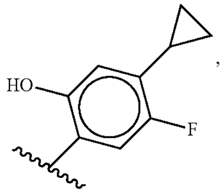
,

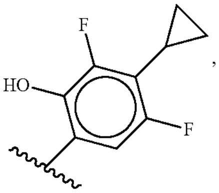
,

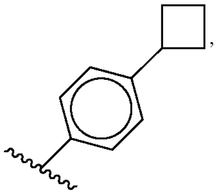
,

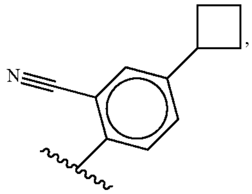
,

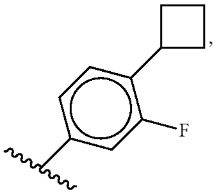
,

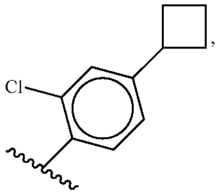
,

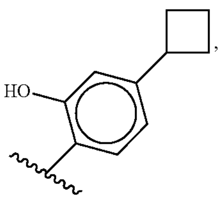
,

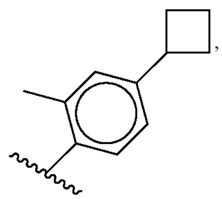
,

-continued

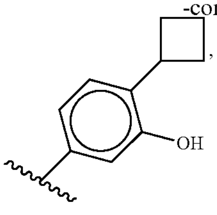
,

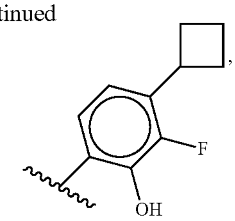
,

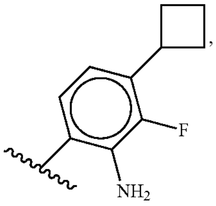
,

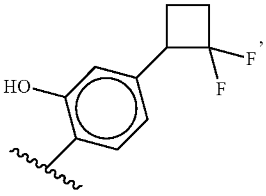
,

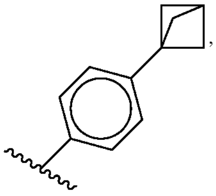
,

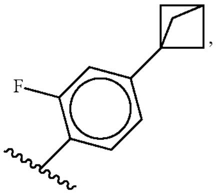
,

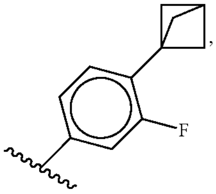
,

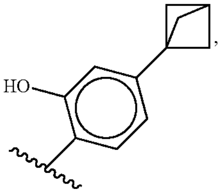
,

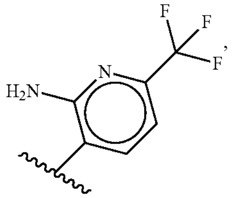
,

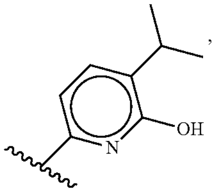
,

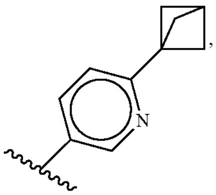
, or

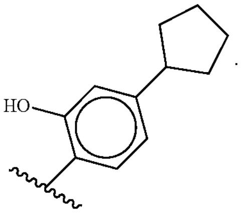
.

In some embodiments, $R_2$ is $C_1$-$C_6$ alkyl, $C_3$-$C_{10}$ cycloalkyl, $C_6$-$C_{10}$ aryl, or 5- to 10-membered heteroaryl, wherein the $C_1$-$C_6$ alkyl, $C_3$-$C_{10}$ cycloalkyl, $C_6$-$C_{10}$ aryl, or 5- to 10-membered heteroaryl is optionally substituted with one or more $R_{2a}$;

each $R_{2a}$ independently is halo, cyano, —OH, —$NH_2$, $C_1$-$C_6$ alkyl, $C_6$-$C_{10}$ aryl, $C_3$-$C_{10}$ cycloalkyl, $C_1$-$C_6$ alkoxy, $C_1$-$C_6$ haloalkyl, —S($C_1$-$C_6$ alkyl), wherein the $C_1$-$C_6$ alkyl, $C_6$-$C_{10}$ aryl, $C_3$-$C_{10}$ cycloalkyl, $C_1$-$C_6$ alkoxy, $C_1$-$C_6$ haloalkyl, or —S($C_1$-$C_6$ alkyl) is optionally substituted with one or more $R_{2a1}$; and each $R_{2a1}$ independently is halo or —OH.

In some embodiments, $R_2$ is $C_1$-$C_6$ alkyl, $C_3$-$C_{10}$ cycloalkyl, $C_6$-$C_{16}$ aryl, or 5- to 10-membered heteroaryl, wherein the $C_1$-$C_6$ alkyl, $C_3$-$C_{10}$ cycloalkyl, $C_6$-$C_{10}$ aryl, or 5- to 10-membered heteroaryl is optionally substituted with one or more $R_{2a}$; and each $R_{2a}$ independently is fluoro, chloro, cyano, —OH, —$NH_2$, phenyl, cyclopropyl, cyclobutyl, cyclopentyl, $-OCH_3$, $-OCHF_2$, $-SCF_3$, $-CH_3$, $-CH(CH_3)_2$, $-H_2OH$, $-CF_3$, $-CH(CF_3)_2$,

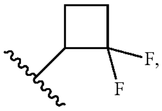
, or
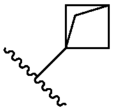
.

In some embodiments, $R_2$ is

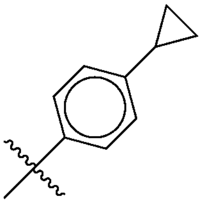
,
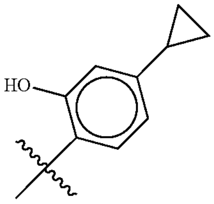
, or
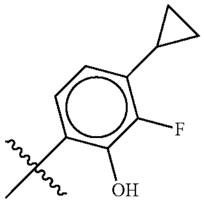
,

In some embodiments, each $R_{2a}$ independently halo, —OH, or $C_3$-$C_{10}$ cycloalkyl.

In some embodiments, each $R_{2a}$ independently is fluoro, —OH, or cyclopropyl.

In some embodiments, each $R_{2a}$ independently is oxo, halo, cyano, —OH, $-NH_2$, —NH($C_1$-$C_6$ alkyl), —N($C_1$-$C_6$ alkyl)$_2$, —SH, $-S(O)_2NH_2$, $-SF_5$, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, —S($C_1$-$C_6$ alkyl), —S($C_1$-$C_6$ haloalkyl), $C_3$-$C_{10}$ cycloalkyl, $C_6$-$C_{10}$ aryl, 5- to 10-membered heteroaryl, or 3- to 10-membered heterocyclyl, wherein the $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, —S($C_1$-$C_6$ alkyl), —S($C_1$-$C_6$ haloalkyl), $C_3$-$C_{10}$ cycloalkyl, $C_6$-$C_{10}$ aryl, 5- to 10-membered heteroaryl, or 3- to 10-membered heterocyclyl is optionally substituted with one or more $R_{2a1}$.

In some embodiments, each $R_{2a}$ independently is oxo, halo, cy no, —OH, $-NH_2$, —NH($C_1$-$C_6$ alkyl), —N($C_1$-$C_6$ alkyl)$_2$, —SH, $-S(O)_2NH_2$, $-SF_5$, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, —S($C_1$-$C_6$ alkyl), —S($C_1$-$C_6$ haloalkyl), $C_3$-$C_{10}$ cycloalkyl, $C_6$-$C_{10}$ aryl, 5- to 10-membered heteroaryl, or 3- to 10-membered heterocyclyl.

In some embodiments, each $R_{2a}$ independently is oxo.

In some embodiments, each $R_{2a}$ independently is halo.

In some embodiments, each $R_{2a}$ independently is F, Cl, Br, or I. In some embodiments, each $R_{2a}$ independently is F, Cl, or Br. In some embodiments, each $R_{2a}$ independently is F or Cl.

In some embodiments, each $R_{2a}$ independently is F. In some embodiments, each $R_{2a}$ independently is Cl. In some embodiments, each $R_{2a}$ independently is Br. In some embodiments, each $R_{2a}$ independently is I.

In some embodiments, each $R_{2a}$ independently is cyano.

In some embodiments, each $R_{2a}$ independently is —OH.

In some embodiments, each $R_{2a}$ independently is $-NH_2$.

In some embodiments, each $R_{2a}$ independently is —NH ($C_1$-$C_6$ alkyl).

In some embodiments, each $R_{2a}$ independently is —N($C_1$-$C_6$ alkyl)$_2$.

In some embodiments, each $R_{2a}$ independently is —SH.

In some embodiments, each $R_{2a}$ independently is $-S(O)_2NH_2$.

In some embodiments, each $R_{2a}$ independently is $-SF_5$.

In some embodiments, each $R_{2a}$ independently is $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, —S($C_1$-$C_6$ alkyl), or —S($C_1$-$C_6$ haloalkyl), wherein the $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, —S($C_1$-$C_6$ alkyl), or —S($C_1$-$C_6$ haloalkyl) is optionally substituted with one or more $R_{2a1}$.

In some embodiments, each $R_{2a}$ independently is $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, —S($C_1$-$C_6$ alkyl), or —S($C_1$-$C_6$ haloalkyl).

In some embodiments, each $R_{2a}$ independently is $C_1$-$C_6$ alkyl.

In some embodiments, each $R_{2a}$ independently is $C_1$-$C_6$ alkyl optionally substituted with one or more $R_{2a1}$.

In some embodiments, each $R_{2a}$ independently is $C_1$-$C_6$ alkyl substituted with one or more $R_{2a1}$.

In some embodiments, each $R_{2a}$ independently is methyl. In sore embodiments, each $R_{2a}$ independently is ethyl. In some embodiments, each $R_{2a}$ independently is propyl. In some embodiments, each $R_{2a}$ independently is butyl. In some embodiments, each $R_{2a}$ independently is pentyl. In some embodiments, each $R_{2a}$ independently is hexyl. In some embodiments, each $R_{2a}$ independently is isopropyl. In some embodiments, each $R_{2a}$ independently is isobutyl. In some embodiments, each $R_{2a}$ independently is isopentyl. In some embodiments, each $R_{2a}$ independently is isohexyl. In some embodiments, each $R_{2a}$ independently is secbutyl. In some embodiments, each $R_{2a}$ independently is secpentyl. In some embodiments, each $R_{2a}$ independently is sechexyl. In some embodiments, each $R_{2a}$ independently is tertbutyl.

In some embodiments, each $R_{2a}$ independently is $C_2$-$C_6$ alkenyl.

In some embodiments, each $R_{2a}$ independently is $C_2$-$C_6$ alkenyl optionally substituted with one or more $R_{2a1}$.

In some embodiments, each $R_{2a}$ independently is $C_2$-$C_6$ alkenyl substituted with one or more $R_{2a1}$.

In some embodiments, each $R_{2a}$ independently is $C_2$-$C_6$ alkynyl.

In some embodiments, each $R_{2a}$ independently is $C_2$-$C_6$ alkynyl optionally substituted with one or more $R_{2a1}$.

In some embodiments, each $R_{2a}$ independently is $C_2$-$C_6$ alkynyl substituted with one or more $R_{2a1}$.

In some embodiments, each $R_{2a}$ independently is $C_1$-$C_6$ haloalkyl.

In some embodiments, each $R_{2a}$ independently is $C_1$-$C_6$ haloalkyl optionally substituted with one or more $R_{2a1}$.

In some embodiments, each $R_{2a}$ independently is $C_1$-$C_6$ haloalkyl substituted with one or more $R_{2a1}$.

In some embodiments, each $R_{2a}$ independently is halomethyl. In some embodiments, each $R_{2a}$ independently is haloethyl. In some embodiments, each $R_{2a}$ independently is halopropyl. In some embodiments, each $R_{2a}$ independently is halobutyl. In some embodiments, each $R_{2a}$ independently is halopentyl. In some embodiments, each $R_{2a}$ independently is halohexyl.

In some embodiments, each $R_{2a}$ independently is $C_1$-$C_6$ alkoxy.

In some embodiments, each $R_{2a}$ independently is $C_1$-$C_6$ alkoxy optionally substituted with one or more $R_{2a1}$.

In some embodiments, each $R_{2a}$ independently is $C_1$-$C_6$ alkoxy substituted with one or more $R_{2a1}$.

In some embodiments, each $R_{2a}$ independently is methoxy. In some embodiments, each $R_{2a}$ independently is ethoxy. In some embodiments, each $R_{2a}$ independently is propoxy. In some embodiments, each $R_{2a}$ independently is butoxy. In some embodiments, each $R_{2a}$ independently is pentoxy. In some embodiments, each $R_{2a}$ independently is hexoxy.

In some embodiments, each $R_{2a}$ independently is —S($C_1$-$C_6$ alkyl).

In some embodiments, each $R_{2a}$ independently is —S($C_1$-$C_6$ alkyl), wherein the $C_1$-$C_6$ alkyl is optionally substituted with one or more $R_{2a1}$.

In some embodiments, each $R_{2a}$ independently is —S($C_1$-$C_6$ alkyl), wherein the $C_1$-$C_6$ alkyl is substituted with one or more $R_{2a1}$.

In some embodiments, each $R_{2a}$ independently is —S($C_1$-$C_6$ haloalkyl).

In some embodiments, each $R_{2a}$ independently is —S($C_1$-$C_6$ haloalkyl), wherein the $C_1$-$C_6$ haloalkyl is optionally substituted with one or more $R_{2a1}$.

In some embodiments, each $R_{2a}$ independently is —S($C_1$-$C_6$ haloalkyl), wherein the $C_1$-$C_6$ haloalkyl is substituted with one or more $R_{2a1}$.

In some embodiments, each $R_{2a}$ independently is $C_3$-$C_{10}$ cycloallyl, $C_6$-$C_{10}$ aryl, 5- to 10-membered heteroaryl, or 3- to 10-membered heterocyclyl, wherein the $C_3$-$C_{10}$ cycloalkyl, $C_6$-$C_{10}$ aryl, 5- to 10-membered heteroaryl, or 3- to 10-membered heterocycyl is optionally substituted with one or more $R_{2a1}$.

In some embodiments, each $R_{2a}$ independently is $C_3$-$C_{10}$ cycloalkyl, $C_6$-$C_{10}$ aryl, 5- to 10-membered heteroaryl, or 3- to 10-membered heterocyclyl.

In some embodiments, each $R_{2a}$ independently is $C_3$-$C_{10}$ cycloalkyl.

In some embodiments, each $R_{2a}$ independently is $C_3$-$C_{10}$ cycloalkyl optionally substituted with one or more $R_{2a1}$.

In some embodiments, each $R_{2a}$ independently is $C_3$-$C_{10}$ cycloalkyl substituted with one or more $R_{2a1}$.

In some embodiments, each $R_{2a}$ independently is $C_3$-$C_7$ cycloalkyl.

In some embodiments, each $R_{2a}$ independently is $C_3$-$C_7$ cycloalkyl optionally substituted with one or more $R_{2a1}$.

In some embodiments, each $R_{2a}$ independently is $C_3$-$C_7$ cycloalkyl substituted with one or more $R_{2a1}$.

In some embodiments, each $R_{2a}$ independently is 3- to 10-membered heterocyclyl.

In some embodiments, each $R_{2a}$ independently is 3- to 10-membered heterocyclyl optionally substituted with one or more $R_{2a1}$.

In some embodiments, each $R_{2a}$ independently is 3- to 10-membered heterocyclyl substituted with one or more $R_{2a1}$.

In some embodiments, each $R_{2a}$ independently is 3- to 7-membered heterocyclyl.

In some embodiments, each $R_{2a}$ independently is 3- to 7-membered heterocyclyl optionally substituted with one or more $R_{2a1}$.

In some embodiments, each $R_{2a}$ independently is 3- to 7-membered heterocyclyl substituted with one or more $R_{2a1}$.

In some embodiments, each $R_{2a}$ independently is $C_6$-$C_{10}$ aryl.

In some embodiments, each $R_{2a}$ independently is $C_6$-$C_{10}$ aryl optionally substituted with one or more $R_{2a1}$.

In some embodiments, each $R_{2a}$ independently is $C_6$-$C_{10}$ aryl substituted with one or more $R_{2a1}$.

In some embodiments, each $R_{2a}$ independently is $C_6$ aryl.

In some embodiments, each $R_{2a}$ independently is $C_6$ aryl optionally substituted with one or more $R_{2a1}$.

In some embodiments, each $R_{2a}$ independently is $C_6$ aryl substituted with one or more $R_{2a1}$.

In some embodiments, each $R_{2a}$ independently is 5- to 10-membered heteroaryl.

In some embodiments, each $R_{2a}$ independently is 5- to 10-membered heteroaryl optionally substituted with one or more $R_{2a1}$.

In some embodiments, each $R_{2a}$ independently is 5- to 10-membered heteroaryl substituted with one or more $R_{2a1}$.

In some embodiments, each $R_{2a}$ independently is 5- or 6-membered heteroaryl.

In some embodiments, each $R_{2a}$ independently is 5- or 6-membered heteroaryl optionally substituted with one or more $R_{2a1}$.

In some embodiments, each $R_{2a}$ independently is 5- or 6-membered heteroaryl substituted with one or more $R_{2a1}$.

In some embodiments, each $R_{2a}$ independently is halo, —OH, —$H_2$, $C_1$-$C_6$ alkyl, $C_1$-$C_6$ alkoxy, $C_1$-$C_6$ haloalkyl, or $C_3$-$C_{10}$ cycloalkyl, wherein the $C_1$-$C_6$ allyl, $C_1$-$C_6$ alkoxy, $C_1$-$C_6$ haloalkyl, or $C_3$-$C_{10}$ cycloalkyl is optionally substituted with one or mor $R_{2a1}$.

In some embodiments, each $R_{2a}$ independently is methyl, isopropyl, —$CH_2CF_3$, —$CF_3$, —$NH_2$, —$OCH_3$, cyclobutyl, cyclopropyl, —OH, -(cyclopropyl)-$F_2$, F, or bicyclo[1.1.1] pentane.

In some embodiments, each $R_{2a1}$ independently is oxo, halo, cyano, —OH, —$NH_2$, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, —NH—C(O)($C_1$-$C_6$ alkyl), —C(O)$NH_2$, or —OC(O)($C_1$-$C_6$ alkyl), wherein the $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, —NH—C(O)($C_1$-$C_6$ alkyl), or —OC(O)($C_1$-$C_6$ alkyl) is optionally substituted with one or more —OH.

In some embodiments, each $R_{2a1}$ independently is oxo, halo, cyano, —OH, —$NH_2$, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, —H—C(O)($C_1$-$C_6$ alkyl), —C(O)$NH_2$, or —OC(O)($C_1$-$C_6$ alkyl).

In some embodiments, each $R_{2a1}$ independently is oxo, halo, cyano, —OH, —$NH_2$, —NH—C(O)($C_1$-$C_6$ alkyl), —C(O)$NH_2$, or —OC(O)($C_1$-$C_6$ alkyl), wherein the —NH—C(O)($C_1$-$C_6$ alkyl) or —OC(O)($C_1$-$C_6$ alkyl) is optionally substituted with one or more —OH.

In some embodiments, each $R_{2a1}$ independently is oxo, halo, cyano, —OH, —$NH_2$, —NH—C(O)($C_1$-$C_6$ alkyl), —C(O)$NH_2$, or —OC(O)($C_1$-$C_6$ alkyl).

In some embodiments, each $R_{2a1}$ independently is oxo.

In some embodiments, each $R_{2a1}$ independently is halo.

In some embodiments, each $R_{2a1}$ independently is F, Cl, Br, or. In some embodiments, each $R_{2a1}$ independently is F, Cl, or Br. In some embodiments, each $R_{2a1}$ independently is F or Cl.

In some embodiments, each $R_{2a1}$ independently is F. In some embodiments, each $R_{2a1}$ independently is Cl. In some embodiments, each $R_{2a1}$ independently is r. In some embodiments, each $R_{2a1}$ independently is I.

In some embodiments, each $R_{2a1}$ independently is cyano.

In some embodiments, each $R_{2a1}$ independently is —OH.

In some embodiments, each $R_{2a1}$ independently is —$NH_2$.

In some embodiments, each $R_{2a1}$ independently is —C(O)$NH_2$.

In some embodiments, each $R_{2a1}$ independently is —NH—C(O)($C_1$-$C_6$ alkyl).

In some embodiments, each $R_{2a1}$ independently is —NH—C(O)($C_1$-$C_6$ alkyl), wherein the —OC(O)($C_1$-$C_6$ alkyl) is optionally substituted with one or more —OH.

In some embodiments, each $R_{2a1}$ independently is —NH—C(O)($C_1$-$C_6$ alkyl), wherein the —OC(O)($C_1$-$C_6$ alkyl) is substituted with one or more —OH.

In some embodiments, each $R_{2a1}$ independently is —OC(O)($C_1$-$C_6$ alkyl).

In some embodiments, each $R_{2a1}$ independently is —OC(O)($C_1$-$C_6$ alkyl), wherein the —OC(O)($C_1$-$C_6$ alkyl) is optionally substituted with one or more —OH.

In some embodiments, each $R_{2a1}$ independently is —OC(O)($C_1$-$C_6$ alkyl), wherein the —OC(O)($C_1$-$C_6$ alkyl) is substituted with one or more —OH.

In some embodiments, each $R_{2a1}$ independently is $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy, wherein the $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy is optionally substituted with one or more —OH.

In some embodiments, each $R_{2a1}$ independently is $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy.

In some embodiments, each $R_{2a1}$ independently is $C_1$-$C_6$ alkyl.

In some embodiments, each $R_{2a1}$ independently is $C_1$-$C_6$ alkyl optionally substituted with one or more —OH.

In some embodiments, each $R_{2a1}$ independently is $C_1$-$C_6$ alkyl substituted with one or more —OH.

In some embodiments, each $R_{2a1}$ independently is methyl. In some embodiments, each $R_{2a1}$ independently is ethyl. In some embodiments, each $R_{2a1}$ independently is propyl. In some embodiments, each $R_{2a1}$ independently is butyl. In some embodiments, each $R_{2a1}$ independently is pentyl. In some embodiments, each $R_{2a1}$ independently is hexyl. In some embodiments, each $R_{2a1}$ independently is isopropyl. In some embodiments, each $R_{2a1}$ independently is isobutyl. In some embodiments, each $R_{2a1}$ independently is isopentyl. In some embodiments, each $R_{2a1}$ independently is isohexyl. In some embodiments, each $R_{2a1}$ independently is secbutyl. In some embodiments, each $R_{2a1}$ independently is secpentyl. In some embodiments, each $R_{2a1}$ independently is sechexyl. In some embodiments, each $R_{2a1}$ independently is tertbutyl.

In some embodiments, each $R_{2a1}$ independently is $C_2$-$C_6$ alkenyl.

In some embodiments, each $R_{2a1}$ independently is $C_2$-$C_6$ alkenyl optionally substituted with one or more —OH.

In some embodiments, each $R_{2a1}$ independently is $C_2$-$C_6$ alkenyl substituted with one or more —OH.

In some embodiments, each $R_{2a1}$ independently is $C_2$-$C_6$ alkynyl.

In some embodiments, each $R_{2a1}$ independently is $C_2$-$C_6$ alkynyl optionally substituted with one or more —OH.

In some embodiments, each $R_{2a1}$ independently is $C_2$-$C_6$ alkynyl substituted with one or more —OH.

In some embodiments, each $R_{2a1}$ independently is $C_1$-$C_6$ haloalkyl.

In some embodiments, each $R_{2a1}$ independently is $C_1$-$C_6$ haloalkyl optionally substituted with one or more —OH.

In some embodiments, each $R_{2a1}$ independently is $C_1$-$C_6$ haloalkyl substituted with one or more —OH.

In some embodiments, each $R_{2a1}$ independently is halomethyl. In some embodiments, each $R_{2a1}$ independently is haloethyl. In some embodiments, each $R_{2a1}$ is dependently is halopropyl. In some embodiments, each $R_{2a1}$ independently is halobutyl. In some embodiments, each $R_{2a1}$ independently is halopentyl. In some embodiments, each $R_{2a1}$ independently is halohexyl.

In some embodiments, each $R_{2a1}$ independently is $C_1$-$C_6$ alkoxy.

In some embodiments, each $R_{2a1}$ independently is $C_1$-$C_6$ alkoxy optionally substituted with one or more —OH.

In some embodiments, each $R_{2a1}$ independently is $C_1$-$C_6$ alkoxy substituted with one or more —OH.

In some embodiments, each $R_{2a1}$ independently is methoxy. In some embodiments, each $R_{2a1}$ independently is ethoxy. In some embodiments, each $R_{2a1}$ independently is propoxy. In some embodiments, each $R_{2a1}$ independently is butoxy. In some embodiments, each $R_{2a1}$ independently is pentoxy. In some embodiments, each $R_{2a1}$ independently is hexoxy.

In some embodiments, each $R_{2a1}$ independently is F.

In some embodiments, $R_3$ and $R_4$, together with the atoms to which they are attached, form a 6- to 10-membered heterocyclyl, wherein the heterocyclyl optionally comprises one or more additional N, O, or S and is optionally substituted with one or more $R_{3a}$.

In some embodiments, $R_3$ and $R_4$, together with the atoms to which they are attached, form a 6- to 10-membered heterocyclyl, wherein the heterocyclyl optionally comprises one or more additional N, O, or S and is substituted with one or more $R_{3a}$.

In some embodiments, $R_3$ and $R_4$, together with the atoms to which they are attached, form a 6- to 10-membered heterocyclyl, wherein the heterocyclyl optionally comprises one or more additional N, O, or S.

In some embodiments, $R_3$ and $R_4$, together with the atoms to which they are attached, form a 6- to 10-membered heterocyclyl, wherein the heterocyclyl optionally comprises one or more additional O or N and is optionally substituted with one or more $R_{3a}$.

In some embodiments, $R_3$ and $R_4$, together with the atoms to which they are attached, form a 6- to 10-membered heterocyclyl, wherein the heterocyclyl option ally comprises one or more additional O or N and is substituted with one or more $R_{3a}$.

In some embodiments, $R_3$ and $R_4$, together with the atoms to which they are attached, form a 6- to 10-membered heterocyclyl, wherein the heterocyclyl optionally comprises one or more additional O or N.

In some embodiments, $R_3$ and $R_4$, together with the atoms to which they are attached, form a 6- to 10-membered heterocyclyl, wherein the heterocyclyl optionally comprises one or more additional O and is optionally substituted with one or more $R_{3a}$.

In some embodiments, $R_3$ and $R_4$, together with the atoms to which they are attached, form a 6- to 10-membered heterocyclyl, wherein the heterocyclyl optionally comprises one or more additional O and is substituted with one or more $R_{3a}$.

In some embodiments, $R_3$ and $R_4$, together with the atoms to which they are attached, form a 6- to 10-membered heterocyclyl, wherein the heterocyclyl optionally comprises one or more additional O.

In some embodiments, $R_3$ and $R_4$, together with the atoms to which they are attached, form a 6- to 10-membered heterocyclyl optionally substituted with one or more $R_{3a}$.

In some embodiments, $R_3$ and $R_4$, together with the atoms to which they are attached, form a 6- to 10-membered heterocyclyl substituted with one or more $R_3$.

In some embodiments, $R_3$ and $R_4$, together with the atoms to which they are attached, form a 6- to 10-membered heterocyclyl.

In some embodiments, $R_3$ and $R_4$, together with the atoms to which they are attached, form a 6-membered heterocyclyl, wherein the heterocyclyl optionally comprises one or more additional N, O, or S and is optionally substituted with one or more $R_{3a}$.

In some embodiments, $R_3$ and $R_4$, together with the atoms to which they are attached, form a 6-membered heterocyclyl, wherein the heterocyclyl optionally comprises one or more additional N, O, or S and is substituted with one or more $R_{3a}$.

In some embodiments, $R_3$ and $R_4$, together with the atoms to which they are attached, form a 6-membered heterocyclyl, wherein the heterocyclyl optionally comprises one or more additional N, O, or S.

In some embodiments, $R_3$ and $R_4$, together with the atoms to which they are attached, form a 6-membered heterocyclyl, wherein the heterocyclyl optionally comprises one or more additional O and is optionally substituted with one or more $R_{3a}$.

In some embodiments, $R_3$ and $R_4$, together with the atoms to which they are attached, form a 6-membered heterocyclyl, wherein the heterocyclyl optionally comprises one or more additional O and is substituted with one or more $R_{3a}$.

In some embodiments, $R_3$ and $R_4$, together with the atoms to which they are attached, form a 6-membered heterocyclyl, wherein the heterocyclyl optionally comprises one or more additional O.

In some embodiments, $R_3$ and $R_4$, together with the atoms to which they are attached, form a 6-membered heterocyclyl optionally substituted with one or more $R_{3a}$.

In some embodiments, $R_3$ and $R_4$, together with the atoms to which they are attached, form a 6-membered heterocyclyl substituted with one or more $R_{3a}$.

In some embodiments, $R_3$ and $R_4$, together with the atoms to which they are attached, form a 6-membered heterocyclyl.

In some embodiments, $R_3$ and $R_4$, together with the atoms to which they are attached, form a 7-membered heterocyclyl, wherein the heterocyclyl optionally comprises one or more additional N, O, or S and is optionally substituted with one or more $R_{3a}$.

In some embodiments, $R_3$ and $R_4$, together with the atoms to which they are attached, form a 7-membered heterocyclyl, wherein the heterocyclyl optionally comprises one or more additional N, O, or S and is substituted with one or more $R_{3a}$.

In some embodiments, $R_3$ and $R_4$, together with the atoms to which they are attached, form a 7-membered heterocyclyl, wherein the heterocyclyl optionally comprises one or more additional N, O, or S.

In some embodiments, $R_3$ and $R_4$, together with the atoms to which they are attached, form a 7-membered heterocyclyl, wherein the heterocyclyl optionally comprises one or more additional O and is optionally substituted with one or more $R_{3a}$.

In some embodiments, $R_3$ and $R_4$, together with the atoms to w ich they are attached, form a 7-membered heterocyclyl, wherein the heterocyclyl optionally comprises one or more additional O and is substituted with one or more $R_{3a}$.

In some embodiments, $R_3$ and $R_4$, together with the atoms to which they are attached, form a 7-membered heterocyclyl, wherein the heterocyclyl optionally comprises one or more additional O.

In some embodiments, $R_3$ and $R_4$, together with the atoms to which they are attached, form a 7-membered heterocyclyl optionally substituted with one or more $R_{3a}$.

In some embodiments, $R_3$ and $R_4$, together with the atoms to which they are attached, form a 7-membered heterocyclyl substituted with one or more $R_{3a}$.

In some embodiments, $R_3$ and $R_4$, together with the atoms to which they are attached, form a 7-membered heterocyclyl.

In some embodiments, $R_3$ and $R_4$, together with the atoms to which they are attached, form a 8-membered heterocyclyl, wherein the heterocyclyl optionally comprises one or more additional N, O, or S and is optionally substituted with one or more $R_{3a}$.

In some embodiments, $R_3$ and $R_4$, together with the atoms to which they are attached, form a 8-membered heterocyclyl, wherein the heterocyclyl optionally comprises one or more additional N, O, or S and is substituted with one or more $R_{3a}$.

In some embodiments, $R_3$ and $R_4$, together with the atoms to which they are attached, form a 8-membered heterocyclyl, wherein the heterocyclyl optionally comprises one or more additional N, O, or S.

In some embodiments, $R_3$ and $R_4$, together with the atoms to which they are attached, form a 8-membered heterocyclyl, wherein the heterocyclyl optionally comprises one or more additional O and is optionally substituted with one or more $R_{3a}$.

In some embodiments, $R_3$ and $R_4$, together with the atoms to which they are attached, form a 8-membered heterocyclyl, wherein the heterocyclyl optionally comprises one or more additional O and is substituted with one or more $R_{3a}$.

In some embodiments, $R_3$ and $R_4$, together with the atoms to which they are attached, form a 8-membered heterocyclyl, wherein the heterocyclyl optionally comprises one or more additional O.

In some embodiments, $R_3$ and $R_4$, together with the atoms to which they are attached, form a 8-membered heterocyclyl optionally substituted with one or more $R_{3a}$.

In some embodiments, $R_3$ and $R_4$, together with the atoms to which they are attached, form a 8-membered heterocyclyl substituted with one or more $R_{3a}$.

In some embodiments, $R_3$ and $R_4$, together with the atoms to which they are attached, form a 8-membered heterocyclyl.

In some embodiments, $R_3$ and $R_4$, together with the atoms to which they are attached, form a 9-membered heterocyclyl, wherein the heterocyclyl optionally comprises one or more additional N, O, or S and is optionally substituted with one or more $R_{3a}$.

In some embodiments, $R_3$ and $R_4$, together with the atoms to which they are attached, form a 9-membered heterocyclyl, wherein the heterocyclyl optionally comprises one or more additional N, O, or S and is substituted with one or more $R_{3a}$.

In some embodiments, $R_3$ and $R_4$, together with the atoms to which they are attached, form a 9-membered heterocyclyl, wherein the heterocyclyl optionally comprises one or more additional N, O, or S.

In some embodiments, $R_3$ and $R_4$, together with the atoms to which they are attached, form a 9-membered heterocyclyl, wherein the heterocyclyl optionally comprises one or more additional O and is optionally substituted with one or more $R_{3a}$.

In some embodiments, $R_3$ and $R_4$, together with the atoms to which they are attached, form a 9-membered heterocyclyl, wherein the heterocyclyl optionally comprises one or more additional O and is substituted with one or more $R_{3a}$.

In some embodiments, $R_3$ and $R_4$, together with the atoms to which they are attached, form a 9-membered heterocyclyl, wherein the heterocyclyl optionally comprises one or more additional O.

In some embodiments, $R_3$ and $R_4$, together with the atoms to which they are attached, form a 9-membered heterocyclyl optionally substituted with one or more $R_{3a}$.

In some embodiments, $R_3$ and $R_4$, together with the atoms to which they are attached, form a 9-membered heterocyclyl substituted with one or more $R_{3a}$.

In some embodiments, $R_3$ and $R_4$, together with the atoms to which they are attached, form a 9-membered heterocyclyl.

In some embodiments, $R_3$ and $R_4$, together with the atoms to which they are attached, form a 10-membered heterocyclyl, wherein the heterocyclyl optionally comprises one or more additional N, O, or S and is optionally substituted with one or more $R_{3a}$.

In some embodiments, $R_3$ and $R_4$, together with the atoms to which they are attached, form a 10-membered heterocyclyl, wherein the heterocyclyl optionally comprises one or more additional N, O, or S and is substituted with one or more $R_{3a}$.

In some embodiments, $R_3$ and $R_4$, together with the atoms to which they are attached, form a 10-membered heterocyclyl, wherein the heterocyclyl optionally comprises one or more additional N, O, or S.

In some embodiments, $R_3$ and $R_4$, together with the atoms to which they are attached, form a 10-membered heterocyclyl, wherein the heterocyclyl optionally comprises one or more additional O and is optionally substituted with one or more $R_{3a}$.

In some embodiments, $R_3$ and $R_4$, together with the atoms to which they are attached, form a 10-membered heterocyclyl, wherein the heterocyclyl optionally comprises one or more additional O and is substituted with one or more $R_{3a}$.

In some embodiments, $R_3$ and $R_4$, together with the atoms to which they are attached, form a 10-membered heterocyclyl, wherein the heterocyclyl optionally comprises one or more additional O.

In some embodiments, $R_3$ and $R_4$, together with the atoms to which they are attached, form a 10-membered heterocyclyl optionally substituted with one or more $R_3$ In some embodiments, $R_3$ and $R_4$, together with the atoms to which they are attached, form a 10-membered heterocyclyl substituted with one or more $R_{3a}$.

In some embodiments, $R_3$ and $R_4$, together with the atoms to which they are attached, form a 10-membered heterocyclyl.

In some embodiments, each $R_{3a}$ independently is cyano, halo, —OH, —$NH_2$, —NH($C_1$-$C_6$ alkyl), —N($C_1$-$C_6$ alkyl)$_2$, —N($C_1$-$C_6$ alkyl)($C_1$-$C_6$ haloalkyl), —NH—C(O)($C_1$-$C_6$ alkyl), —O($C_3$-$C_{10}$ cycloalkyl), —O(3- to 10-membered heterocyclyl), $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_1$-$C_6$ haloalkoxy, $C_3$-$C_{10}$ cycloalkyl, 3- to 1-membered heterocyclyl, $C_6$-$C_{10}$ aryl, 5- to 10-membered heteroaryl, —S(O)(═NH)($C_1$-$C_6$ alkyl), —$SO_2$($C_1$-$C_6$ alkyl), —S($C_1$-$C_6$ alkyl), or —S($C_1$-$C_6$ haloalkyl), wherein the alkyl, alkenyl, alknyl, haloalkyl, alkoxy, haloalkoxy, —O($C_3$-$C_{10}$ cycloalkyl), —O(3- to 10-membered heterocyclyl), heterocycle, cycloalkyl, aryl, or heteroaryl is optionally substituted with one or more oxo, —CN, $C_1$-$C_6$ alkoxy, —C(O)($C_1$-$C_6$ alkyl), —N($R_{3a1}$)CO($R_{3a2}$), —O($C_3$-$C_{10}$ cycloalkyl), —O($C_6$-$C_{10}$ aryl), —O(5- to 10-membered heteroaryl), —O(3- to 10-membered heterocyclyl), $C_3$-$C_{10}$ cycloalkyl, 3- to 10-membered heterocyclyl, $C_6$-$C_{10}$ aryl, or 5- to 10-membered heteroaryl, wherein the cycloalkyl, aryl, heteroaryl, or heterocyclyl is optionally substituted with one or more $C_1$-$C_6$ alkyl.

, In some embodiments, each $R_{3a}$ independently is cyano, halo, —OH, —$NH_2$, —NH($C_1$-$C_6$ alkyl), —N($C_1$-$C_6$ alkyl)$_2$, —N($C_1$-$C_6$ alkyl)($C_1$-$C_6$ haloalkyl), —NH—C(O)($C_1$-$C_6$ alkyl), —O($C_3$-$C_{10}$ cycloalkyl), $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_1$-$C_6$ haloalkoxy, $C_3$-$C_{10}$ cycloalkyl, 3- to 10-membered heterocyclyl, —S(O)(═NH)($C_1$-$C_6$ alkyl), —$SO_2$($C_1$-$C_6$ alkyl), —S($C_1$-$C_6$ alkyl), or —S($C_1$-$C_6$ haloalkyl), wherein the alkyl is optionally substituted with one or more —N($R_{3a1}$)CO($R_{3a2}$), —O($C_3$-$C_{10}$ cycloalkyl), —O($C_6$-$C_{10}$ aryl), —O(5- to 10-membered heteroaryl), or —O(3- to 10-membered heterocyclyl), wherein the cycloalkyl, aryl, heteroaryl, or heterocyclyl is optionally substituted with one or more $C_1$-$C_6$ alkyl.

In some embodiments, each $R_{3a}$ independently is cyano, halo, —OH, —$NH_2$, —NH($C_1$-$C_6$ alkyl), —N($C_1$-$C_6$ alkyl)$_2$, —N($C_1$-$C_6$ alkyl)($C_1$-$C_6$ haloalkyl), —NH—C(O)($C_1$-$C_6$ alkyl), —O($C_3$-$C_{10}$ cycloalkyl), $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_1$-$C_6$ haloalkoxy, $C_3$-$C_{10}$ cycloalkyl, 3- to 10-membered heterocyclyl, —S(O)(═NH)($C_1$-$C_6$ alkyl), —$SO_2$($C_1$-$C_6$ alkyl), —S($C_1$-$C_6$ alkyl), or —S($C_1$-$C_6$ haloalkyl), wherein the alkyl is optionally substituted with one or more —N($R_{3a1}$)CO($R_{3a2}$), —O($C_3$-$C_{10}$ cycloalkyl), —O($C_6$-$C_{10}$ aryl), —O(5- to 10-membered heteroaryl), or —O(3- to 10-membered heterocyclyl).

In some embodiments, each $R_{3a}$ independently is cyano, halo, —OH, —$NH_2$, —NH—C(O)($C_1$-$C_6$ alkyl), —NH($C_1$-$C_6$ alkyl), —N($C_1$-$C_6$ alkyl)$_2$, —N($C_1$-$C_6$ alkyl)($C_1$-$C_6$ haloalkyl), —O($C_3$-$C_{10}$ cycloalkyl), $C_1$-$C_6$ alkyl optionally substituted with —N($R_{3a1}$)CO($R_{3a2}$), $C_2$-$C_6$ alkenyl, $C_2$-$C_6$ alkynyl, $C_1$-$C_6$ haloalkyl, $C_1$-$C_6$ alkoxy, $C_1$-$C_6$ haloalkoxy, 3- to 10-membered heterocyclyl, —S(O)(═NH)($C_1$-$C_6$ alkyl), —$SO_2$($C_1$-$C_6$ alkyl), —S($C_1$-$C_6$ alkyl), or —S($C_1$-$C_6$ haloalkyl); or two $R_{3a}$, together with the atoms to which they are attached, form a $C_3$-$C_{10}$ cycloalkyl or 3- to 10-membered heterocyclyl.

In some embodiments, each $R_{3a}$ independently is cyano, halo, —OH, —$NH_2$, —NH—C(O)($C_1$-$C_6$ alkyl), —NH($C_1$-$C_6$ alkyl), —N($C_1$-$C_6$ alkyl)$_2$, —N($C_1$-$C_6$ alkyl)($C_1$-$C_6$ haloalkyl), —O($C_3$-$C_{10}$ cycloalkyl), $C_1$-$C_6$ alkyl optionally substituted with —N($R_{3a1}$)CO($R_{3a2}$), $C_2$-$C_6$ alkenyl, $C_2$-$C_6$ alkynyl, $C_1$-$C_6$ haloalkyl, $C_1$-$C_6$ alkoxy, $C_1$-$C_6$ haloalkoxy, 3- to 10-membered heterocyclyl, —S(O)(═NH)($C_1$-$C_6$ alkyl), —$SO_2$($C_1$-$C_6$ alkyl), —S($C_1$-$C_6$ alkyl), or —S($C_1$-$C_6$ haloalkyl).

In some embodiments, two $R_{3a}$, together with the atoms to which they are attached, form a $C_3$-$C_{10}$ cycloalkyl or 3- to 10-membered heterocyclyl, wherein the cycloalkyl or heterocyclyl is optionally substituted with one or more $C_3$-$C_{10}$ cycloalkyl, 3- to 10-membered heterocyclyl, $C_6$-$C_{10}$ aryl, or 5- to 10-membered heteroaryl, wherein the cycloalkyl, heterocyclyl, aryl, or heteroaryl is optionally substituted with one or more $C_1$-$C_6$ alkyl.

In some embodiments, two $R_{3a}$, together with the atoms to which they are attached, form a $C_3$-$C_{10}$ cycloalkyl or 3- to 10-membered heterocyclyl.

In some embodiments, two $R_{3a}$, together with the atoms to which they are attached, form a $C_3$-$C_{10}$ cycloalkyl.

In some embodiments, two $R_{3a}$, together with the atoms to which they are attached, form a 3- to 10-membered heterocyclyl.

In some embodiments, two $R_{3a}$, together with the atoms to which they are attached, form a 3- to 10-membered heterocyclyl optionally substituted with one or more 5- to 10-membered heteroaryl optionally substituted with one or more $C_1$-$C_6$ alkyl.

In some embodiments, two $R_{3a}$, together with the atoms to which they are attached, form a 3- to 10-membered heterocyclyl substituted with one or more 5- to 10-membered heteroaryl substituted with one or more $C_1$-$C_6$ alkyl.

In some embodiments, two $R_{3a}$, together with the atoms to which they are attached, form cyclopropyl or azetidinyl substituted with

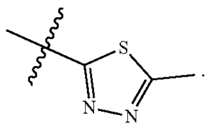 [SMILES: *c1nnc(C)s1]

In some embodiments, each $R_{3a}$ independently is cyano.

In some embodiments, each $R_{3a}$ independently is halo.

In some embodiments, each $R_{3a}$ independently is —OH.

In some embodiments, each $R_{3a}$ independently is —$NH_2$.

In some embodiments, each $R_{3a}$ independently is F, Cl, Br, or I. In some embodiments, each $R_{3a}$ independently is F, Cl, or Br. In some embodiments, each $R_{3a}$ independently is F or Cl.

In some embodiments, each $R_{3a}$ independently is F. In some embodiments, each $R_{3a}$ independently is Cl. In some embodiments, each $R_{3a}$ independently is Br. In some embodiments, each $R_{3a}$ independently is I.

In some embodiments, each $R_{3a}$ independently is —NH—C(O)($C_1$-$C_6$ alkyl).

In some embodiments, each $R_{3a}$ independently is —NH($C_1$-$C_6$ alkyl), —N($C_1$-$C_6$ alkyl)$_2$, or —N($C_1$-$C_6$ alkyl)($C_1$-$C_6$ haloalkyl).

In some embodiments, each $R_{3a}$ independently is —NH($C_1$-$C_6$ alkyl).

In some embodiments, each $R_{3a}$ independently is —N($C_1$-$C_6$ alkyl)$_2$.

In some embodiments, each $R_{3a}$ independently is —N($C_1$-$C_6$ alkyl)($C_1$-$C_6$ haloalkyl).

In some embodiments, each $R_{3a}$ independently is —S($C_1$-$C_6$ alkyl).

In some embodiments, each $R_{3a}$ independently is —S($C_1$-$C_6$ haloalkyl).

In some embodiments, each $R_{3a}$ independently is —S(O)(=NH)($C_1$-$C_6$ alkyl).

In some embodiments, each $R_{3a}$ independently is —$SO_2$($C_1$-$C_6$ alkyl).

In some embodiments, each $R_{3a}$ independently is $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, or $C_1$-$C_6$ haloalkoxy.

In some embodiments, each $R_{3a}$ independently is $C_1$-$C_6$ alkyl.

In some embodiments, each $R_{3a}$ independently is $C_1$-$C_6$ alkyl optionally substituted with one or more —N($R_{3a1}$)CO($R_{3a2}$), —O($C_3$-$C_{10}$ cycloalkyl), —O($C_6$-$C_{10}$ aryl), —O(5- to 10-membered heteroaryl), or —O(3- to 10-membered heterocyclyl).

In some embodiments, each $R_{3a}$ independently is $C_1$-$C_6$ alkyl optionally substituted with one or more —N($R_{3a1}$)CO($R_{3a2}$).

In some embodiments, each $R_{3a}$ independently is $C_1$-$C_6$ alkyl optionally substituted with one or more —P($C_3$-$C_{11}$ cycloalkyl).

In some embodiments, each $R_{3a}$ independently is $C_1$-$C_6$ alkyl optionally substituted with one or more —O($C_6$-$C_{10}$ aryl).

In some embodiments, each $R_{3a}$ independently is $C_1$-$C_6$ alkyl optionally substituted with one or more —O(5- to 10-membered heteroaryl).

In some embodiments, each $R_{3a}$ independently is $C_1$-$C_6$ alkyl optionally substituted with one or more —O(3- to 10-membered heterocyclyl).

In some embodiments, each $R_{3a}$ independently is methyl. In some embodiments, each $R_{3a}$ independently is ethyl. In some embodiments, each $R_{3a}$ independently is propyl. In some embodiments, each $R_{3a}$ independently is butyl. In some embodiments, each $R_{3a}$ independently is pentyl. In some embodiments, each $R_{3a}$ independently is hexyl. In some embodiments, each $R_{3a}$ independently is isopropyl. In some embodiments, each $R_{3a}$ independently is isobutyl. In some embodiments, each $R_{3a}$ independently is isopentyl. In some embodiment, each $R_{3a}$ independently is isohexyl. In some embodiments, each $R_{3a}$ independently is secbutyl. In some embodiments, each $R_{3a}$ independently is secpentyl. In some embodiments, each $R_{3a}$ independently is sechexyl. In some embodiments, each $R_{3a}$ independently is tertbutyl.

In some embodiments, each $R_{3a}$ independently is $C_2$-$C_6$ alkenyl.

In some embodiments, each $R_{3a}$ independently is $C_2$-$C_6$ alkynyl.

In some embodiments, each $R_{3a}$ independently is $C_1$-$C_6$ haloalkyl.

In some embodiments, each $R_{3a}$ independently is halomethyl. In Some embodiments, each $R_{3a}$ independently is haloethyl. In some embodiments, each $R_{3a}$ independently is halopropyl. In some embodiments, each $R_{3a}$ independently is halobutyl. In some embodiments, each $R_{3a}$ independently is halopentyl. In some embodiments, each $R_{3a}$ independently is halohexyl.

In some embodiments, each $R_{3a}$ independently is $C_1$-$C_6$ alkoxy.

In some embodiments, each $R_{3a}$ independently is methoxy. In some embodiments, each $R_{3a}$ independently is ethoxy. In some embodiments, each $R_{3a}$ independently is propoxy. In some embodiments, each $R_{3a}$ independently is butoxy. In some embodiments, ach $R_{3a}$ independently is pentoxy. In some embodiments, each $R_{3a}$ independently is hexoxy.

In some embodiments, each $R_{3a}$ independently is $C_1$-$C_6$ haloalkoxy.

In some embodiments, each $R_{3a}$ independently is halomethoxy. In some embodiments, each $R_{3a}$ independently is haloethoxy. In some embodiments, each $R_{3a}$ independently is halopropoxy. In some embodiments, each $R_{3a}$ independently is halobutoxy. In some embodiments, each $R_{3a}$ independently is halopentoxy. In some embodiments, each $R_{3a}$ independently is halohexoxy.

In some embodiments, each $R_{3a}$ independently is $C_3$-$C_{10}$ cycloalkyl or 3- to 10-membered heterocyclyl.

In some embodiments, each $R_{3a}$ independently is —O($C_3$-$C_{10}$ cycloalkyl) or —(O)(3- to 10-membered heterocyclyl).

In some embodiments, each $R_{3a}$ independently is —O($C_3$-$C_{10}$ cycloalkyl) or —(O)(3- to 10-membered heterocyclyl), wherein the cycloalkyl or heterocyclyl is optionally substituted with one or more —C(O)($C_1$-$C_6$ alkyl) or —CN.

In some embodiments, each $R_{3a}$ independently is —O($C_3$-$C_{10}$ cycloalkyl).

In some embodiments, each $R_{3a}$ independently is —O($C_3$-$C_{10}$ cycloalkyl) optionally substituted with —CN.

In some embodiments, each $R_{3a}$ independently is —O($C_3$-$C_{10}$ cycloalkyl) substituted with —CN.

In some embodiments, each $R_{3a}$ independently is —(O)(3- to 10-membered heterocyclyl).

In some embodiments, each $R_{3a}$ independently is —(O)(3- to 10 membered heterocyclyl) optionally substituted with —C(O)($C_1$-$C_6$ alkyl).

In some embodiments, each $R_{3a}$ independently is —(O)(3- to 10 membered heterocyclyl) substituted with —C(O)($C_1$-$C_6$ alkyl).

In some embodiments, each $R_{3a}$ independently is 5- to 10-membered heteroaryl optionally substituted with oxo.

In some embodiments, each $R_{3a}$ independently is 5- to 10-membered heteroaryl substituted with oxo.

In some embodiments, each $R_{3a}$ independently is $C_1$-$C_6$ alkoxy optionally substituted with one or more $C_1$-$C_6$ alkoxy, $C_3$-$C_{10}$ cycloalkyl, or 5- to 10-membered heteroaryl.

In some embodiments, each $R_{3a}$ independently is $C_1$-$C_6$ alkoxy optionally substituted with one or more $C_1$-$C_6$ alkoxy or $C_3$-$C_{10}$ cycloalkyl.

In some embodiments, each $R_{3a}$ independently is $C_1$-$C_6$ alkoxy substituted with $C_1$-$C_6$ alkoxy and $C_3$-$C_{10}$ cycloalkyl.

In some embodiments, each $R_{3a}$ independently is $C_1$-$C_6$ alkoxy substituted with 5- to 10-membered heteroaryl.

In some embodiments, each $R_{3a}$ independently is halo, $C_1$-$C_6$ alkyl, $C_1$-$C_6$ alkoxy, or —O($C_3$-$C_{10}$ cycloalkyl).

In some embodiments, each $R_{3a}$ independently is halo, —OH, —O($C_3$-$C_{10}$ cycloalkyl), —O(3- to 10-membered heterocyclyl), $C_1$-$C_6$ alkyl, $C_1$-$C_6$ alkoxy, 5- to 10-membered heteroaryl, wherein the —O($C_3$-$C_{10}$ cycloalkyl), —O(3- to 10-membered heterocyclyl) $C_1$-$C_6$ alkyl, $C_1$-$C_6$ alkoxy, 5- to 10-membered heteroaryl is optionally substituted with one or more oxo, cyano, 3-to 10-membered heterocyclyl, —C(O)($C_1$-$C_6$ alkyl), 5- to 10-membered heteroaryl optionally substituted with $C_1$-$C_6$ alkyl, or $C_1$-$C_6$ alkyl optionally substituted with $C_1$-$C_6$ alkoxy.

In some embodiments, each $R_{3a}$ independently is F, $CH_3$, —OH, —$OCH_3$, —O(cyclopropyl),

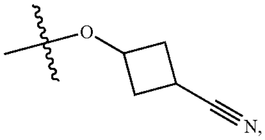

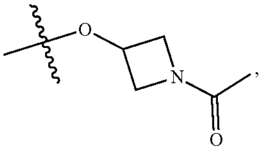 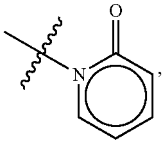

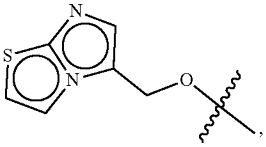 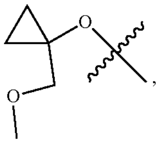

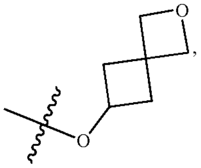 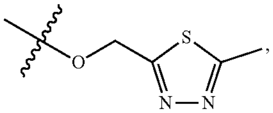

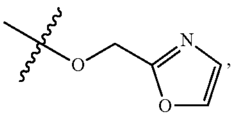 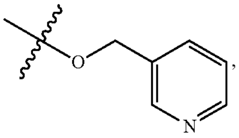

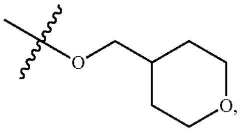 or 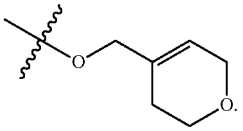

In some embodiments, each $R_{3a}$ independently is F, $CH_3$, —$OCH_3$, or —O(cyclopropyl).

In some embodiments, each $R_{3a}$ independently is halo, $C_1$-$C_6$ alkyl, or $C_1$-$C_6$ alkoxy.

In some embodiments, each $R_{3a}$ independently is F, $CH_3$, or —$OCH_3$.

In some embodiments, $R_{3a1}$ and $R_{3a2}$, together with the atoms to which they are attached, form a 3- to 10-membered heterocyclyl.

In some embodiments, $R_{4''}$ is

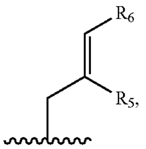 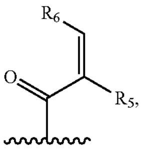 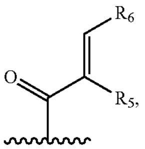

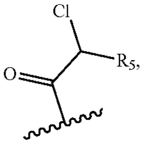 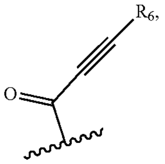 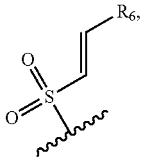

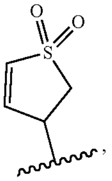 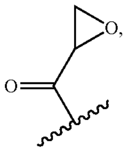 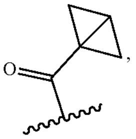

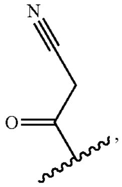 or 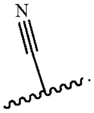

In some embodiments, $R_{4''}$ is

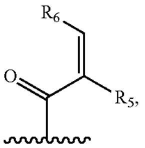 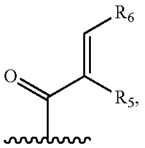

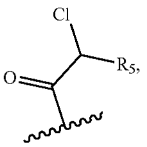 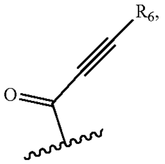 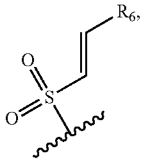

-continued
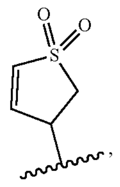
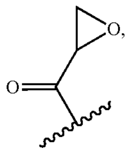
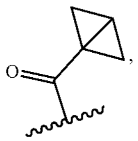
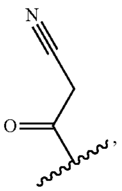
or
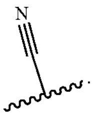
In some embodiments, $R_{4''}$ is
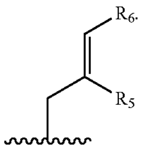
In some embodiments, $R_{4''}$ is
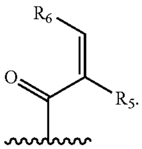
In some embodiments, $R_{4''}$ is
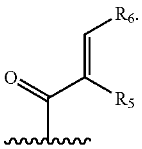
In some embodiments, $R_{4''}$ is
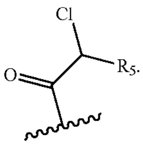
In some embodiments, $R_{4''}$ is
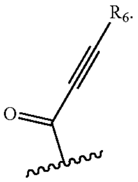
In some embodiments, $R_{4''}$ is
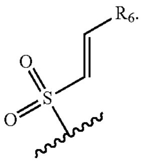
In some embodiments, $R_{4''}$ is
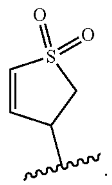 [SMILES: *C1C=CS(=O)(=O)C1]
In some embodiments, $R_{4''}$ is
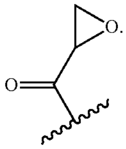
In some embodiments, $R_{4''}$ is
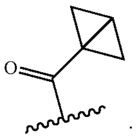
In some embodiments, $R_{4''}$ is
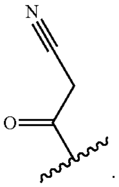 [SMILES: *C(=O)CC#N]

In some embodiments, $R_{4''}$ is

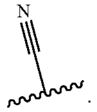

In some embodiments, $R_{4''}$ is

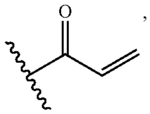, 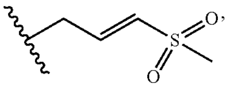, 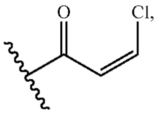

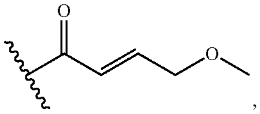, 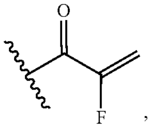,

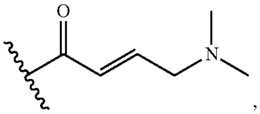, or 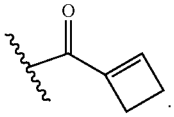.

In some embodiments, $R_5$ is H, halo, cyano, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy.

In some embodiments, $R_5$ is H.

In some embodiments, $R_5$ is halo or cyano.

In some embodiments, $R_5$ is halo.

In some embodiments, $R_5$ is F, Cl, Br, or I. In some embodiments, $R_5$ is F, Cl, or Br. In some embodiments, $R_5$ is F or Cl.

In some embodiments, $R_5$ is F. In some embodiments, $R_5$ is Cl. In some embodiments, $R_5$ is Br. In some embodiments, $R_5$ is I.

In some embodiments, $R_5$ is cyano.

In some embodiments, $R_5$ is H or halo.

In some embodiments, $R_5$ is H or F.

In some embodiments, $R_5$ is $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy.

In some embodiments, $R_5$ is $C_1$-$C_6$ alkyl. In some embodiments, $R_5$ is $C_2$-$C_6$ alkenyl. In some embodiments, $R_5$ is $C_2$-$C_6$ alkynyl. In some embodiments, $R_5$ is $C_1$-$C_6$ haloalkyl. In some embodiments, $R_5$ is $C_1$-$C_6$ alkoxy.

In some embodiments, $R_6$ is H, halo, cyano, $C_1$-$C_6$ alkyl, $C_2$-$C_6$ alkenyl, $C_2$-$C_6$ alkynyl, or $C_1$-$C_6$ alkoxy, wherein the alkyl, alkenyl, alkynyl, or alkoxy is optionally substituted with one or more —$NH_2$, —NH($C_1$-$C_6$ alkyl), or —N($C_1$-$C_6$ alkyl)$_2$.

In some embodiments, $R_6$ is H, halo, cyano, $C_1$-$C_6$ alkyl, $C_2$-$C_6$ alkenyl, $C_2$-$C_6$ alkynyl, or $C_1$-$C_6$ alkoxy.

In some embodiments, $R_6$ is H, halo, cyano, —$SO_2$($C_1$-$C_6$ alkyl), $C_1$-$C_6$ alkyl, $C_2$-$C_6$ alkenyl, $C_2$-$C_6$ alkynyl, or $C_1$-$C_6$ alkoxy, wherein the alkyl, alkenyl, alkynyl, or alkoxy is optionally substituted with one or more —OH, —O($C_1$-$C_6$ alkyl), —$NH_2$, —NH($C_1$-$C_6$ alkyl), or —N($C_1$-$C_6$ alkyl)$_2$.

In some embodiments, $R_6$ is H, halo, cyano, —$SO_2$($C_1$-$C_6$ alkyl), $C_1$-$C_6$ alkyl, $C_2$-$C_6$ alkenyl, $C_2$-$C_6$ alkynyl, or $C_1$-$C_6$ alkoxy, wherein the alkyl, alkenyl, alkynyl, or alkoxy is substituted with one or more —OH, —O($C_1$-$C_6$ alkyl), —$NH_2$, —NH($C_1$-$C_6$ alkyl), or —N($C_1$-$C_6$ alkyl)$_2$.

In some embodiments, $R_6$ is H, halo, cyano, —$SO_2$($C_1$-$C_6$ alkyl), $C_1$-$C_6$ alkyl, $C_2$-$C_6$ alkenyl, $C_2$-$C_6$ alkynyl, or $C_1$-$C_6$ alkoxy.

In some embodiments, $R_6$ is H, chloro, —$SO_2$($C_1$-$C_6$ alkyl), or $C_1$-$C_6$ alkyl optionally substituted with —N($C_1$-$C_6$ alkyl)$_2$ or —O($C_1$-$C_6$ alkyl).

In some embodiments, $R_6$ is H, chloro, —$SO_2$($C_1$-$C_6$ alkyl), or $C_1$-$C_6$ alkyl substituted with —N($C_1$-$C_6$ alkyl)$_2$ or —O($C_1$-$C_6$ alkyl).

In some embodiments, $R_6$ is H, chloro, —$SO_2$($C_1$-$C_6$ alkyl), or $C_1$-$C_6$ alkyl.

In some embodiments, $R_6$ is H.

In some embodiments, $R_6$ is halo, or cyano.

In some embodiments, $R_6$ is halo.

In some embodiments, $R_6$ is F, Cl, Br, or I. In some embodiments, $R_6$ is F, Cl, or Br. In some embodiments, $R_6$ is F or Cl.

In some embodiments, $R_6$ is F. In some embodiments, $R_6$ is Cl. In some embodiments, $R_6$ is Br. In some embodiments, $R_6$ is I.

In some embodiments, $R_6$ is cyano.

In some embodiments, $R_6$ is —$SO_2$($C_1$-$C_6$ alkyl).

In some embodiments, $R_6$ is $C_1$-$C_6$ alkyl.

In some embodiments, $R_6$ is $C_1$-$C_6$ alkyl optionally substituted with —OH.

In some embodiments, $R_6$ is $C_1$-$C_6$ alkyl substituted with —OH.

In some embodiments, $R_6$ is $C_1$-$C_6$ alkyl optionally substituted with —O($C_1$-$C_6$ alkyl).

In some embodiments, $R_6$ is $C_1$-$C_6$ alkyl substituted with —O($C_1$-$C_6$ alkyl).

In some embodiments, $R_6$ is $C_1$-$C_6$ alkyl optionally substituted with —$NH_2$.

In some embodiments, $R_6$ is $C_1$-$C_6$ alkyl substituted with —$NH_2$.

In some embodiments, $R_6$ is $C_1$-$C_6$ alkyl.

In some embodiments, $R_6$ is $C_1$-$C_6$ alkyl optionally substituted with —NH($C_1$-$C_6$ alkyl).

In some embodiments, $R_6$ is $C_1$-$C_6$ alkyl substituted with —NH($C_1$-$C_6$ alkyl).

In some embodiments, $R_6$ is $C_1$-$C_6$ alkyl.

In some embodiments, $R_6$ is $C_1$-$C_6$ alkyl optionally substituted with —N($C_1$-$C_6$ alkyl)$_2$.

In some embodiments, $R_6$ is $C_1$-$C_6$ alkyl substituted with —N($C_1$-$C_6$ alkyl)$_2$.

In some embodiments, $R_6$ is $C_1$-$C_6$ alkoxy.

In some embodiments, $R_6$ is $C_2$-$C_6$ alkenyl optionally substitute with one or more —$NH_2$, —NH($C_1$-$C_6$ alkyl), or —N($C_1$-$C_6$ alkyl)$_2$.

In some embodiments, $R_6$ is $C_2$-$C_6$ alkenyl optionally substituted with one or more OH, —O($C_1$-$C_6$ alkyl), —$NH_2$, —NH($C_1$-$C_6$ alkyl), or —N($C_1$-$C_6$ alkyl)$_2$.

In some embodiments, $R_6$ is $C_2$-$C_6$ alkenyl.

In some embodiments, $R_6$ is $C_2$-$C_6$ alkynyl optionally substituted with one or more —$NH_2$, —NH($C_1$-$C_6$ alkyl), or —N($C_1$-$C_6$ alkyl)$_2$.

In some embodiments, $R_6$ is $C_2$-$C_6$ alkynyl optionally substitute with one or more OH, —O($C_1$-$C_6$ alkyl), —$NH_2$, —NH($C_1$-$C_6$ alkyl), or —N($C_1$-$C_6$ alkyl)$_2$.

In some embodiments, $R_6$ is $C_2$-$C_6$ alkynyl.

In some embodiments, $R_6$ is $C_1$-$C_6$ alkoxy optionally substituted with one or more —$NH_2$, —NH($C_1$-$C_6$ alkyl), or —N($C_1$-$C_6$ alkyl)$_2$.

In some embodiments, $R_6$ is $C_1$-$C_6$ alkoxy optionally substituted with one or more OH, —O($C_1$-$C_6$ alkyl), —$NH_2$, —NH($C_1$-$C_6$ alkyl), or —N($C_1$-$C_6$ alkyl)$_2$.

In some embodiments, $R_6$ is $C_1$-$C_6$ alkoxy.

In some embodiments, $R_5$ and $R_6$, together with the atoms to which they are attached, form a $C_4$-$C_{10}$ cycloalkenyl.

In some embodiments, $R_5$ and $R_6$, together with the atoms to which they are attached, form a $C_4$ cycloalkenyl.

In some embodiments, $R_5$ and $R_6$, together with the atoms to which they are attached, form a $C_5$ cycloalkenyl.

In some embodiments, $R_5$ and $R_6$, together with the atoms to which they are attached, form a $C_6$ cycloalkenyl.

In some embodiments, $R_5$ and $R_6$, together with the atoms to which they are attached, form a $C_7$ cycloalkenyl.

In some embodiments, $R_5$ and $R_6$, together with the atoms to which they are attached, form a $C_8$ cycloalkenyl.

In some embodiments, $R_5$ and $R_6$, together with the atoms to which they are attached, form a $C_9$ cycloalkenyl.

In some embodiments, $R_5$ and $R_6$, together with the atoms to which they are attached, form a $C_{10}$ cycloalkenyl.

In some embodiments, each $R_7$, $R_8$, and $R_9$ independently is H, cyano, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy, wherein the alkyl, alkenyl, alkynyl, haloalkyl, or alkoxy is optionally substituted with one or more oxo, halo, cyano, —OH, —$NH_2$, $C_1$-$C_6$ alkoxy, —NH($C_1$-$C_6$ alkyl), —N($C_1$-$C_6$ alkyl)$_2$, —NH($C_1$-$C_6$ haloalkyl), or —S($C_1$-$C_6$ alkyl), or $R_7$ and $R_8$, together with the atoms to which they are attached, form a $C_3$-$C_{10}$ cycloalkyl or 3- to 10-membered heterocyclyl.

In some embodiments, each $R_7$, $R_8$, and $R_9$ independently is H, cyano, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy, wherein the alkyl, alkenyl, alkynyl, haloalkyl, or alkoxy is optionally substituted with one or more oxo, halo, cyano, —OH, —$NH_2$, $C_1$-$C_6$ alkoxy, —NH($C_1$-$C_6$ alkyl), —N($C_1$-$C_6$ alkyl)$_2$, —NH($C_1$-$C_6$ haloalkyl), or —S($C_1$-$C_6$ alkyl).

In some embodiments, each $R_7$, $R_8$, and $R_9$ independently is H, cyano, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy.

In some embodiments, each $R_7$, $R_8$, and $R_9$ independently is H, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy.

In some embodiments, each $R_7$, $R_8$, and $R_9$ independently is H.

In some embodiments, each $R_7$, $R_8$, and $R_9$ independently is $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy.

In some embodiments, $R_7$ is H, cyano, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy.

In some embodiments, $R_7$ is H, cyano, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy, wherein the alkyl, alkenyl, alkynyl, haloalkyl, or alkoxy is optionally substituted with one or more oxo, halo, cyano, —OH, —$NH_2$, $C_1$-$C_6$ alkoxy, —NH($C_1$-$C_6$ alkyl), —N($C_1$-$C_6$ alkyl)$_2$, —NH($C_1$-$C_6$ haloalkyl), or —S($C_1$-$C_6$ alkyl).

In some embodiments, $R_7$ is H, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy.

In some embodiments, $R_7$ is H.

In some embodiments, $R_7$ is H or $C_1$-$C_6$ alkyl.

In some embodiments, $R_7$ is cyano.

In some embodiments, $R_7$ is $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy.

In some embodiments, $R_7$ is $C_1$-$C_6$ alkyl.

In some embodiments, $R_7$ is methyl. In some embodiments, $R_7$ is ethyl. In some embodiments, $R_7$ is propyl. In some embodiments, $R_7$ is butyl. In some embodiments, $R_7$ is pentyl. In some embodiments, $R_7$ is hexyl. In some embodiments, $R_7$ is isopropyl. In some embodiments, $R_7$ is isobutyl. In some embodiments, $R_7$ is isopentyl. In some embodiments, $R_7$ is isohexyl. In some embodiments, $R_7$ is secbutyl. In some embodiments, $R_7$ is secpentyl. In some embodiments, $R_7$ is sechexyl. In some embodiments, $R_7$ is tertbutyl.

In some embodiments, $R_7$ is $C_2$-$C_6$ alkenyl (e.g., ethenyl, propenyl, butenyl).

In some embodiments, $R_7$ is $C_2$-$C_6$ alkynyl (e.g., ethynyl, propynyl, butynyl).

In some embodiments, $R_7$ is $C_1$-$C_6$ haloalkyl.

In some embodiments, $R_7$ is halomethyl. In some embodiments, $R_7$ is haloethyl. In some embodiments, $R_7$ is halopropyl. In some embodiments, $R_7$ is halobutyl. In some embodiments, $R_7$ is halopentyl. In some embodiments, $R_7$ is halohexyl.

In some embodiments, $R_7$ is $C_1$-$C_6$ alkoxy.

In some embodiments, $R_7$ is methoxy. In some embodiments, $R_7$ is ethoxy. In some embodiments, $R_7$ is propoxy. In some embodiments, $R_7$ is butoxy. In some embodiments, $R_7$ is pentoxy. In some embodiments, $R_7$ is hexoxy.

In some embodiments, $R_8$ is H, cyano, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy, wherein the alkyl, alkenyl, alkynyl, haloalkyl, or alkoxy is optionally substituted with one or more oxo, halo, cyano, —OH, —$NH_2$, $C_1$-$C_6$ alkoxy, —NH($C_1$-$C_6$ alkyl), —N($C_1$-$C_6$ alkyl)$_2$, —NH($C_1$-$C_6$ haloalkyl), or —S($C_1$-$C_6$ alkyl).

In some embodiments, $R_8$ is H, cyano, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy.

In some embodiments, $R_8$ is H, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy.

In some embodiments, $R_8$ is H.

In some embodiments, $R_8$ is H or $C_1$-$C_6$ alkyl.

In some embodiments, $R_8$ is cyano.

In some embodiments, $R_8$ is $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy.

In some embodiments, $R_8$ is $C_1$-$C_6$ alkyl.

In some embodiments, $R_8$ is methyl. In some embodiment, $R_8$ is ethyl. In some embodiments, $R_8$ is propyl. In some embodiments, $R_8$ is butyl. In some embodiments, $R_8$ is pentyl. In some embodiments, $R_8$ is hexyl. In some embodiments, $R_8$ is isopropyl. In some embodiments, $R_8$ is isobutyl. In some embodiments, $R_8$ is isopentyl. In some embodiments, $R_8$ is isohexyl. In some embodiments, $R_8$ is secbutyl. In some embodiments, $R_8$ is secpentyl. In some embodiments, $R_8$ is sechexyl. In some embodiments, $R_8$ is tertbutyl.

In some embodiments, $R_8$ is $C_2$-$C_6$ alkenyl (e.g., ethenyl, propenyl, butenyl).

In some embodiments, $R_8$ is $C_2$-$C_6$ alkynyl (e.g., ethynyl, propynyl, butynyl).

In some embodiments, $R_8$ is $C_1$-$C_6$ haloalkyl.

In some embodiments, $R_8$ is halomethyl. In some embodiments, $R_8$ is haloethyl. In some embodiments, $R_8$ is halopropyl. In some embodiments, $R_8$ is halobutyl. In some embodiments, $R_8$ is halopentyl. In some embodiments, $R_8$ is halohexyl.

In some embodiments, $R_8$ is $C_1$-$C_6$ alkoxy.

In some embodiments, $R_8$ is methoxy. In some embodiments, $R_8$ is ethoxy. In some embodiments, $R_8$ is propoxy. In some embodiments, $R_8$ is butoxy. In some embodiments, $R_8$ is pentoxy. In some embodiments, $R_8$ is hexoxy.

In some embodiments, $R_9$ is H, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy, wherein the alkyl, alkenyl, alkynyl, haloalkyl, or alkoxy is optionally substituted with one or more oxo, halo, cyano, —OH, —$NH_2$, $C_1$-$C_6$ alkoxy, —NH($C_1$—C alkyl), —N($C_1$-$C_6$ alkyl)$_2$, —NH($C_1$-$C_6$ haloalkyl), or —S($C_1$-$C_6$ alkyl).

In some embodiments, $R_9$ is H, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy.

In some embodiments, $R_9$ is H, cyano, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy.

In some embodiments, $R_9$ is H.

In some embodiments, $R_9$ is H or $C_1$-$C_6$ alkyl.

In some embodiments, $R_9$ is cyano.

In some embodiments, $R_9$ is $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy.

In some embodiments, $R_9$ is $C_1$-$C_6$ alkyl.

In some embodiments, $R_9$ is methyl. In some embodiments, $R_9$ is ethyl. In some embodiments, $R_9$ is propyl. In some embodiments, $R_9$ is butyl. In some embodiments, $R_9$ is pentyl. In some embodiments, $R_9$ is hexyl. In some embodiments, $R_9$ is isopropyl. In some embodiments, $R_9$ is isobutyl. In some embodiments, $R_9$ is isopentyl. In some embodiments, $R_9$ is isohexyl. In some embodiments, $R_9$ is secbutyl. In some embodiments, $R_9$ is secpentyl. In some embodiments, $R_9$ is sechexyl. In some embodiments, $R_9$ is tertbutyl.

In some embodiments, $R_9$ is $C_2$-$C_6$ alkenyl (e.g., ethenyl, propenyl, butenyl).

In some embodiments, $R_9$ is $C_2$-$C_6$ alkynyl (e.g., ethynyl, propynyl, butynyl).

In some embodiments, $R_9$ is $C_1$-$C_6$ haloalkyl.

In some embodiments, $R_9$ is halomethyl. In some embodiments, $R_9$ is haloethyl. In some embodiments, $R_9$ is halopropyl. In some embodiments, $R_9$ is halobutyl. In some embodiments, $R_9$ is halopentyl. In some embodiments, $R_9$ is halohexyl.

In some embodiments, $R_9$ is $C_1$-$C_6$ alkoxy.

In some embodiments, $R_9$ is methoxy. In some embodiments $R_9$ is ethoxy. In some embodiments, $R_9$ is propoxy. In some embodiments, $R_9$ is butoxy. In some embodiments, $R_9$ is pentoxy. In some embodiments, $R_9$ is hexoxy.

In some embodiments, $R_7$ and $R_8$, together with the atoms to which they are attached, form a $C_3$-$C_{10}$ cycloalkyl or 3- to 10-membered heterocyclyl.

In some embodiments, $R_7$ and $R_8$, together with the atoms to which they are attached, form a $C_3$-$C_{10}$ cycloalkyl.

In some embodiments, $R_7$ and $R_8$, together with the atoms to which they are attached, form a 3- to 10-membered heterocyclyl.

In some embodiments, the compound of Formula (I) is of Formula (II-a), (II-b), (II-c), (II-d), or (II-e):

(II-a)

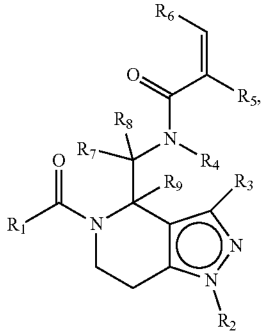

(II-b)

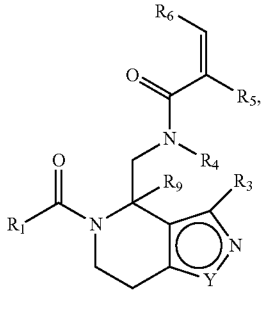

-continued (II-c)

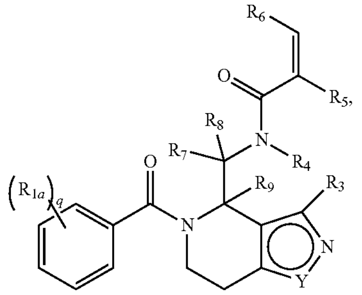

(II-d)

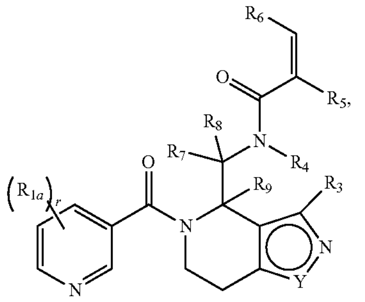

or (II-e)

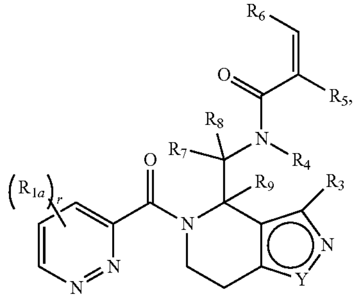

or a pharmaceutically acceptable salt, solvate, clathrate, hydrate, stereoisomer, or tautomer thereof, wherein q is 0, 1, 2, 3, 4, or 5; and r is 0, 1, 2, 3, or 4.

In some embodiments, the compound of Formula (I) is of Formula (II-a) or (II-b) wherein $R_1$ is 5- to 10-membered heteroaryl.

In some embodiments, the compound of Formula (I) is of Formula (II-a1), (II-b1), (II-c1), (II-d1), or (II-e):

(II-a1)

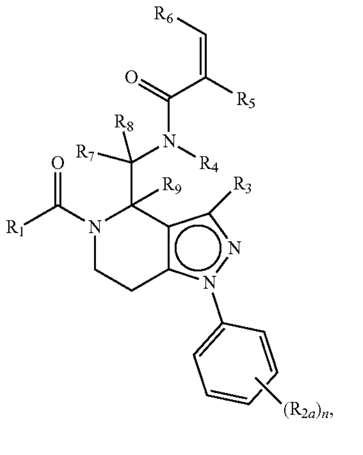

-continued (II-b1)

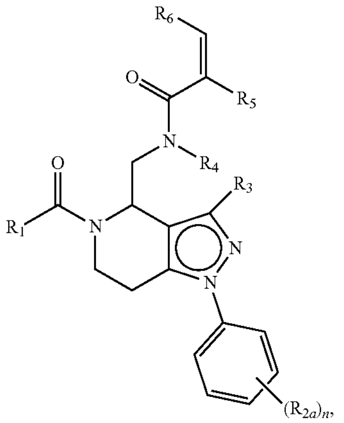

(II-c1)

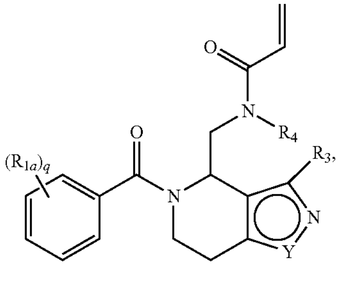

(II-d1)

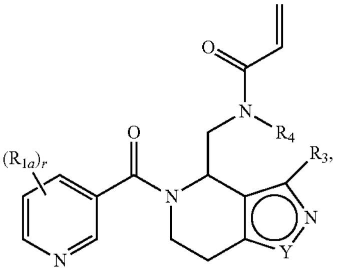

or (II-e1)

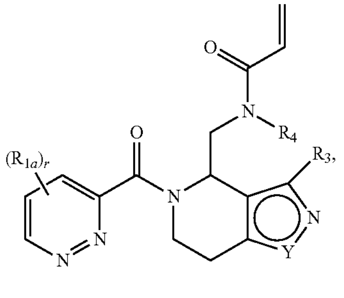

or a pharmaceutically acceptable salt, solvate, clathrate, hydrate, stereoisomer, or tautomer thereof, wherein n is 0, 1, 2, 3, 4, or 5; q is 0, 1, 2, 3, 4, or 5; and r is 0, 1, 2, 3, or 4.

In some embodiments, the compound of Formula (I) is of Formula (II-a1) or (II-b1) wherein $R_1$ is 5- to 10-membered heteroaryl.

In some embodiments, the compound of Formula (I) is of Formula (III-a'), (III-b'), or (III-c'):

(III-a')

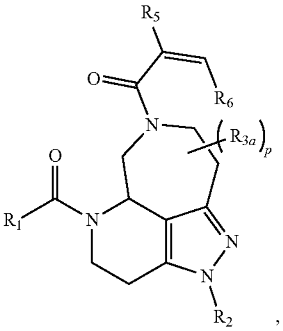

, (III-b')

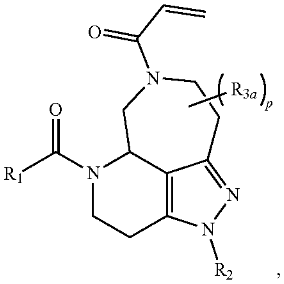

, or (III-c')

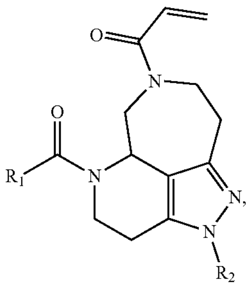

or a pharmaceutically acceptable salt, solvate, clathrate, hydrate, stereoisomer, or tautomer thereof, wherein p is 0, 1, 2, 3, 4, 5, or 6.

In some embodiments, the compound of Formula (I) is of Formula (III-a), (III-b), or (III-c):

(III-a)

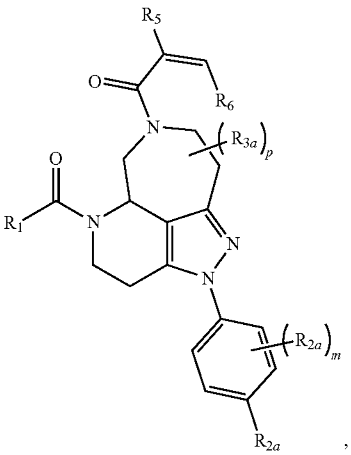

,

-continued
(III-b)
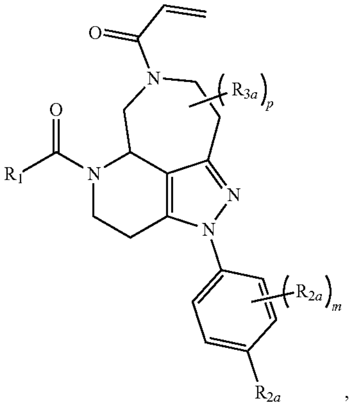
, or
(III-c)
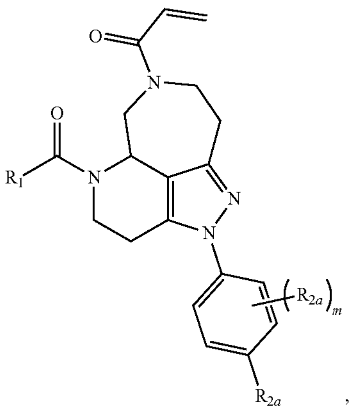
,
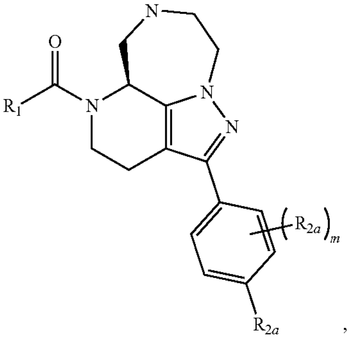
,
or a pharmaceutically acceptable salt, solvate, clathrate, hydrate, stereoisomer, or tautomer thereof, wherein m is 0, 1, 2, 3, or 4 and p is 0, 1, 2, 3, 4, 5, or 6.
In some embodiments, the compound of Formula (I) is of Formula (III-a'''), (III-b'''), (III-c'''), (III-a''), (III-b''), or (III-c''):
(III-a''')
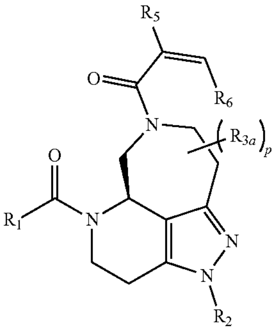
,
(III-b''')
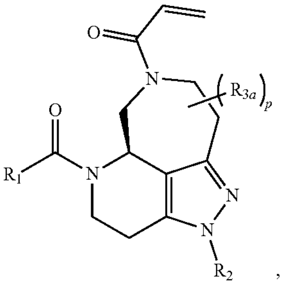
,
(III-c''')
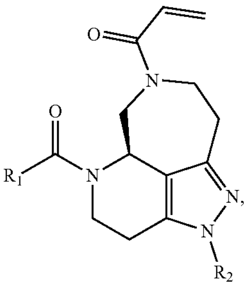
(III-a'')
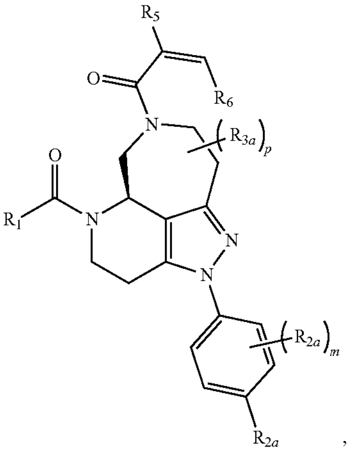
, -continued (III-b″)

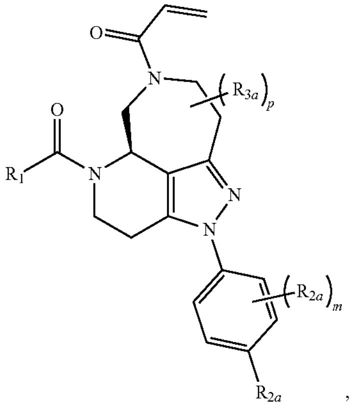

, or (VIII-c′)

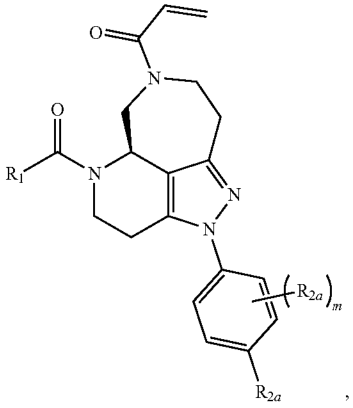

, or a pharmaceutically acceptable salt, solvate, clathrate, hydrate, stereoisomer, or tautomer thereof, wherein m is 0, 1, 2, 3, or 4 and p is 0, 1, 2, 3, 4, 5, or 6.

In some embodiments, the compound of Formula (I) is of Formula (III-a'), (III-b'), (III-c'), (III-a), (III-b), or (III-c) wherein $R_1$ is 5- to 10-membered heteroaryl.

In some embodiments, the compound of Formula (I) is of Formula (III-a'''), (III-b'''), (III-c'''), (III-a''), (III-b''), or (III-c'') wherein $R_1$ is 5- to 10-membered heteroaryl.

In some embodiments, the compound of Formula (I) is of Formula (IV-a), (IV-b), or (IV-c):

(IV-g)

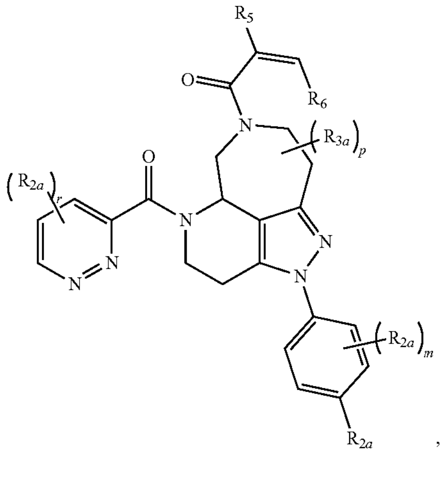

,

-continued (IV-h)

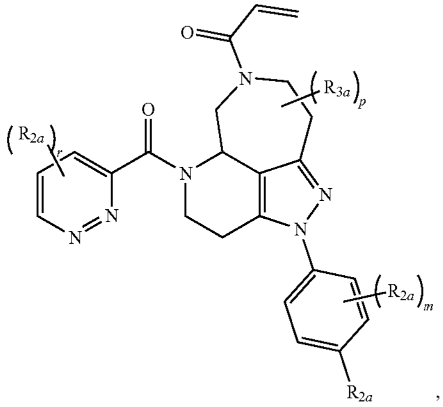

, or (IV-i)

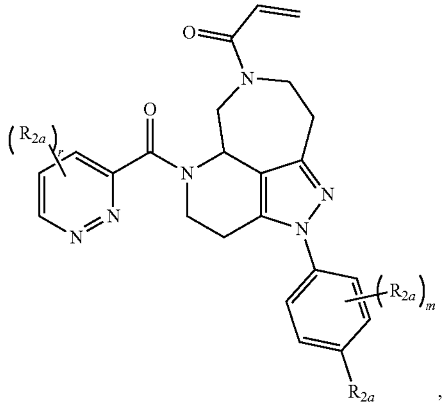

, or a pharmaceutically acceptable salt, solvate, clathrate, hydrate, stereoisomer, or tautomer thereof, wherein m is 0, 1, 2, 3, or 4; p is 0, 1, 2, 3, 4, 5, or 6; and q is 0, 1, 2, 3, 4, or 5.

In some embodiments, the compound of Formula (I) is of Formula (IV-d), (IV-e), or (IV-f):

(IV-g)

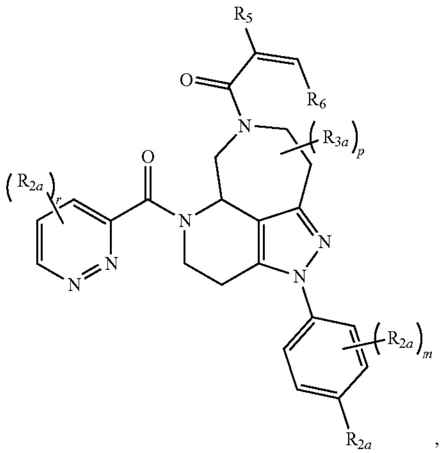

,

-continued (IV-h)

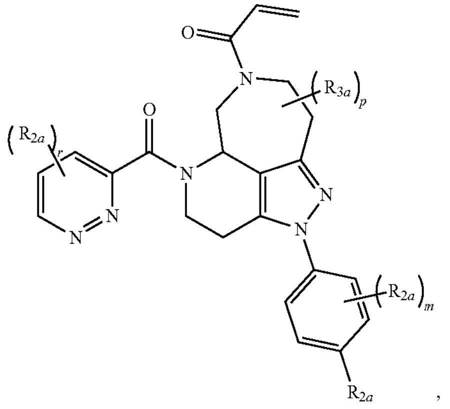

, or (IV-i)

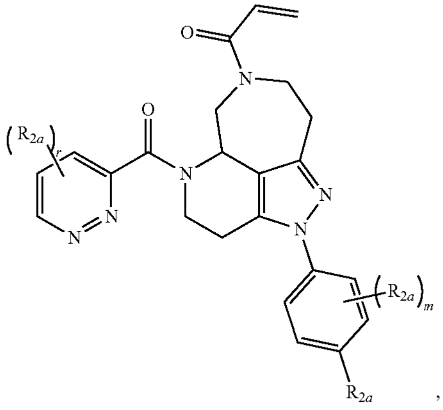

, or a pharmaceutically acceptable salt, solvate, clathrate, hydrate, stereoisomer, or tautomer thereof, wherein m is 0, 1, 2, 3, or 4; p is 0, 1, 2, 3, 4, 5, or 6; and r is 0, 1, 2, 3, or 4.

In some embodiments, the compound of Formula (I) is of Formula (IV-g), (IV-h), or (IV-i):

(IV-g)

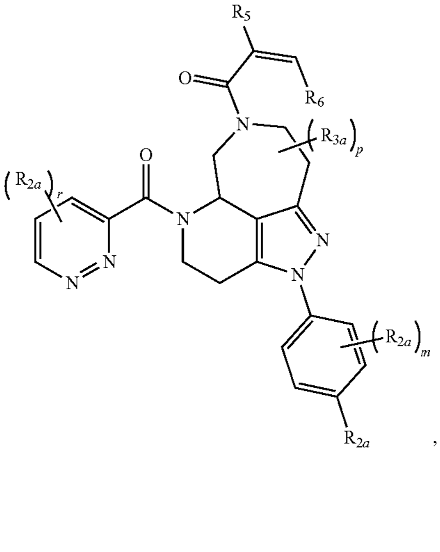

,

-continued (IV-h)

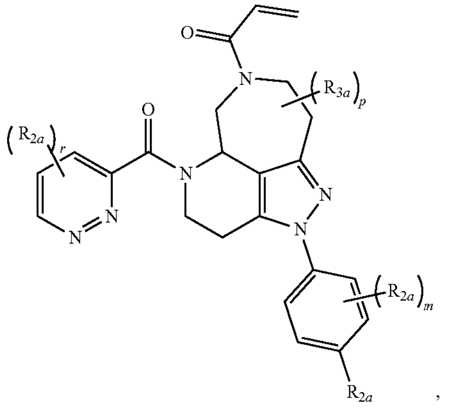

, or (IV-i)

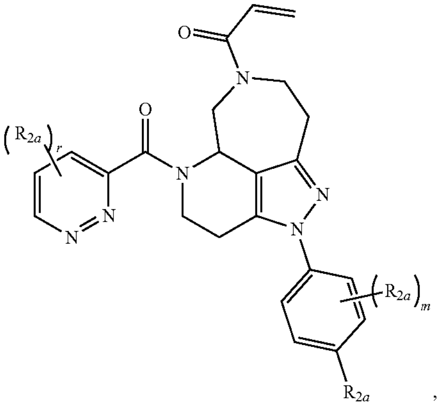

, or a pharmaceutically acceptable salt, solvate, clathrate, hydrate, stereoisomer, or tautomer thereof, wherein m is 0, 1, 2, 3, or 4; p is 0, 1, 2, 3, 4, 5, or 6; and r is 0, 1, 2, 3, or 4.

In some embodiments, the compound of Formula (I) is of Formula (IV-a), (IV-b), (IV-c), (IV-d), (IV-e), (IV-f), (IV-g), (IV-h), or (IV-i), wherein each $R_{2a}$ independently is halo, —OH, or $C_3$-$C_{10}$ cycloalkyl.

In some embodiments, the compound of Formula (I) is of Formula (IV-a), (IV-b), (IV-c), (IV-d), (IV-e), (IV-f), (IV-g), (IV-h), or (IV-i), wherein each $R_{2a}$ independently is fluoro, —OH, or cyclopropyl.

In some embodiments, the compound of Formula (I) is of Formula (IV-a), (IV-b), (IV-c), (IV-d), (IV-e), (IV-f), (IV-g), (IV-h), or (IV-i), wherein each $R_{1a}$ independently is halo, —$NH_2$, —S($C_1$-$C_6$ alkyl), $C_1$-$C_6$ alkyl, or $C_1$-$C_6$ haloalkyl.

In some embodiments, the compound of Formula (I) is of Formula (IV-a), (IV-b), (IV-c), (IV-d), (IV-e), (IV-f), (IV-g), (IV-h), or (IV-i), wherein each $R_{1a}$ independently is fluoro, chloro, bromo, —$NH_2$, —$SCH_3$, —$CH_3$, —$CF_3$, or —$CF_2CH_3$.

In some embodiments, the compound of Formula (I) is of Formula (IV-a'), (IV-b'), (IV-c'), (IV-d'), (IV-e'), (IV-f'), (IV-g'), (IV-h'), or (IV-i'):

-continued
(IV-a')
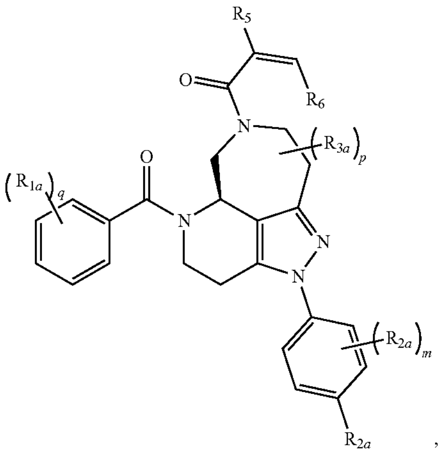
(IV-b')
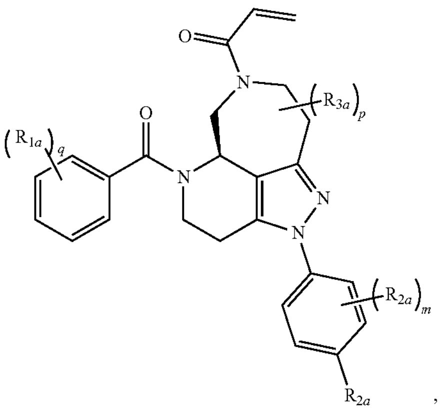
(IV-c')
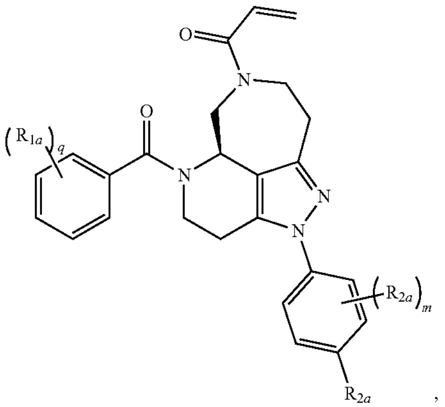
(IV-d')
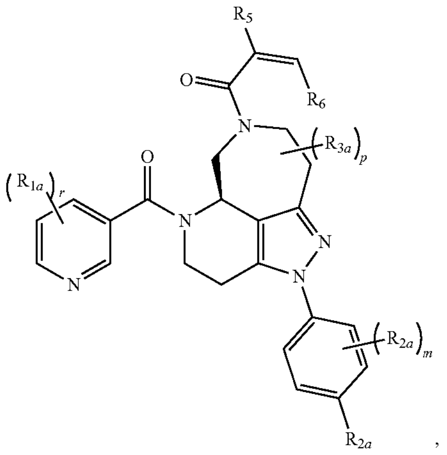
(IV-e')
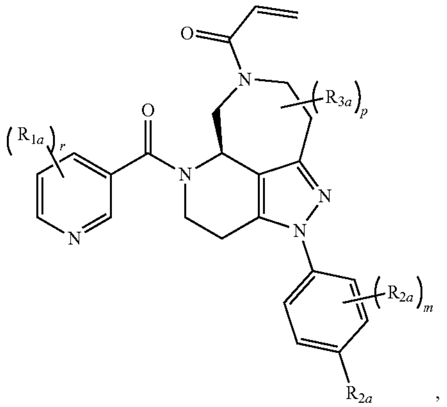
(IV-f')
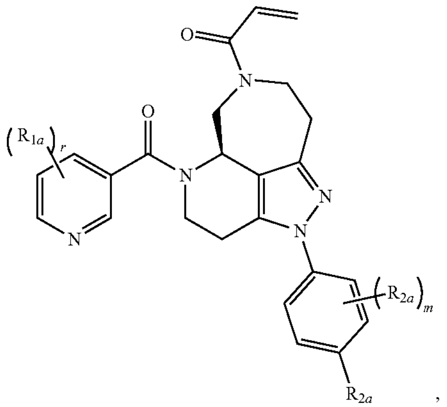

-continued (IV-g')

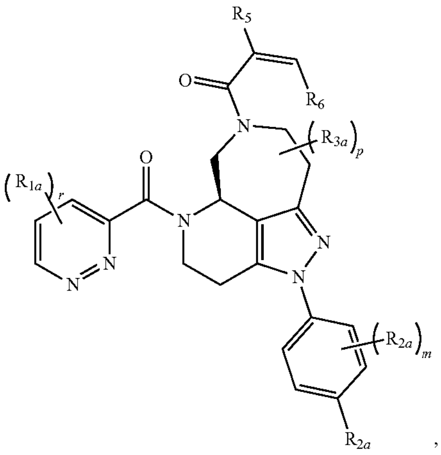

, (IV-h')

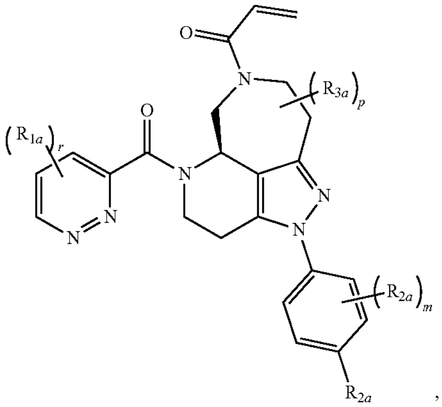

, or (IV-i')

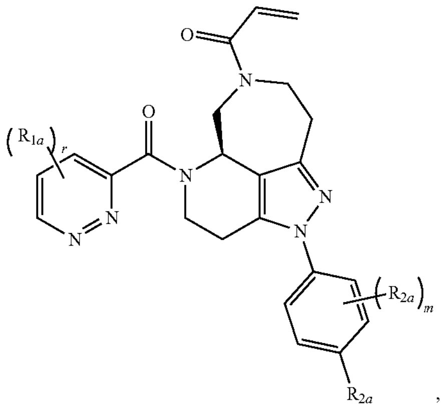

, or a pharmaceutically acceptable salt, solvate, clathrate, hydrate, stereoisomer, or tautomer thereof, wherein m is 0, 1, 2, 3, or 4; p is 0, 1, 2, 3, 4, 5, or 6; and r is 0, 2, 3, or 4.

In some embodiments, the compound of Formula (I) is of Formula (IV-a'), (IV-b'), (IV-c'), (IV-d'), (IV-e'), (IV-f'), (IV-g'), (IV-h'), or (IV-i'), wherein each $R_{2a}$ independently is halo, —OH, or $C_3$-$C_{10}$ cycloalkyl.

In some embodiments, the compound of Formula (I) is of Formula (IV-a'), (IV-b'), (IV-c'), (IV-d'), (IV-e'), (IV-f'), (IV-g'), (IV-h'), or (IV-i'), wherein each a independently is fluoro, —OH, or cyclopropyl.

In some embodiments, the compound of Formula (I) is of Form IIa (IV-a'), (IV-b'), (IV-c'), (IV-d'), (IV-e'), (IV-f'), (IV-g'), (IV-h'), or (IV-i'), wherein each $R_{1a}$ independently is halo, —$NH_2$, —S($C_1$-$C_6$ alkyl), $C_1$-$C_6$ alkyl, or $C_1$-$C_6$ haloalkyl.

In some embodiments, the compound of Formula (I) is of Formula (IV-a'), (IV-b'), (IV-c'), (IV-d'), (IV-e'), (IV-f'), or (IV-g'), (IV-h'), or (IV-i'), wherein each $R_{1a}$ independently is fluoro, chloro, bromo, —$NH_2$, —$SCH_3$, —$CH_3$, —$CF_3$, or —$CF_2CH_3$.

In some embodiments, the compound of Formula (I) is of Formula (V-a) or (V-b):

(V-a)

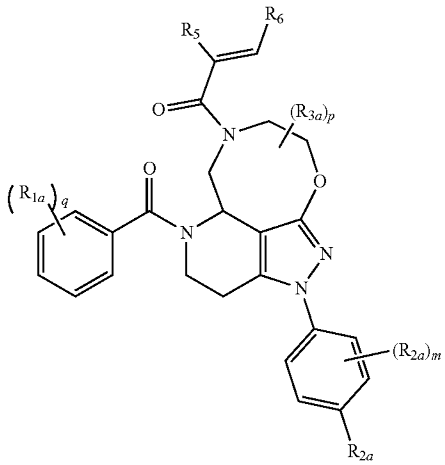

or (V-b)

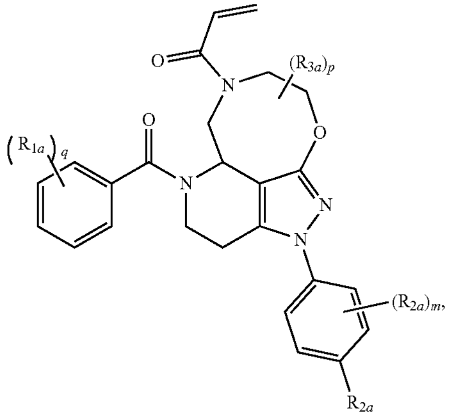

or a pharmaceutically acceptable salt, solvate, clathrate, hydrate, stereoisomer, or tautomer thereof, wherein m is 0, 1, 2, 3, or 4; p is 0, 1, 2, 3, 4, 5, or 6; and q is 0, 1, 2, 3, 4, or 5.

In some embodiments, the compound of Formula (I) is of Formula (V-c) or (V-d):

(V-c)

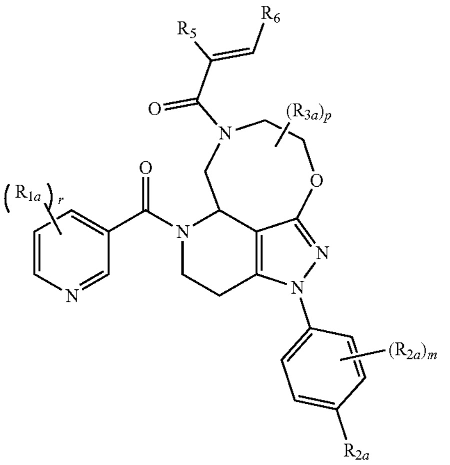

or (V-d)

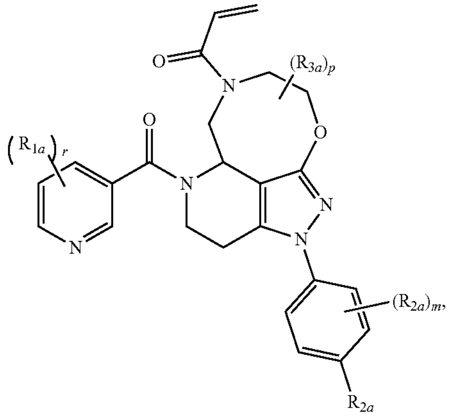

or a pharmaceutically acceptable salt, solvate, clathrate, hydrate, stereoisomer, or tautomer thereof, wherein m is 0, 1, 2, 3, or 4; p is 0, 1, 2, 3, 4, 5, or 6; and r is 0, 1, 2, 3, or 4.

In some embodiments, the compound of Formula (I) is of Formula (V-a'), (V-b'), (V-c'), or (V-d'):

(V-a')

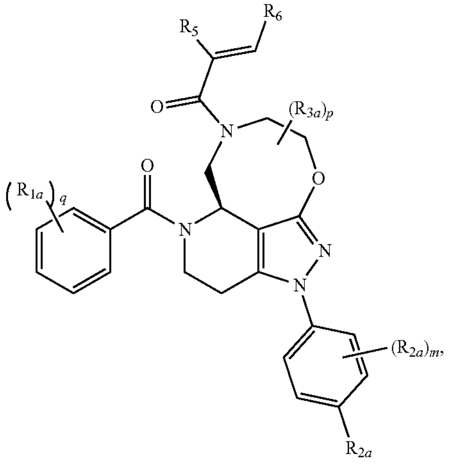

-continued (V-b')

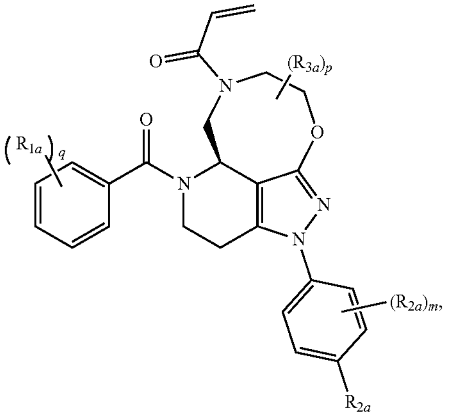

(V-c')

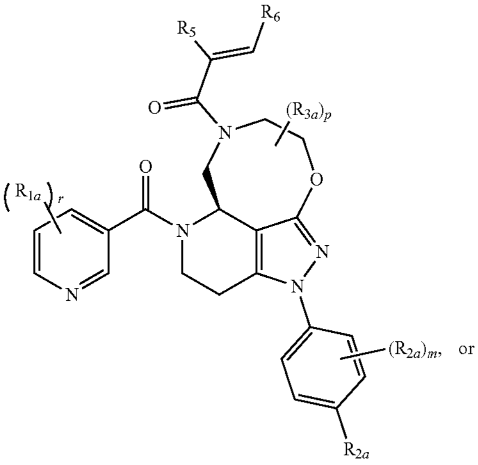

or (V-d')

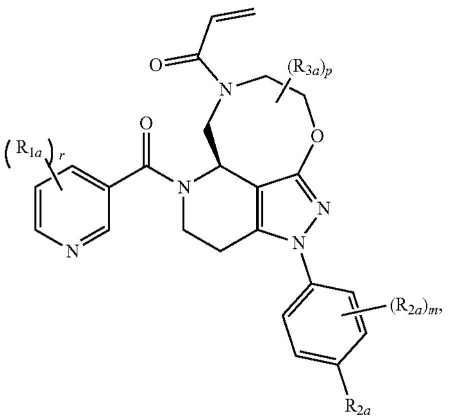

or a pharmaceutically acceptable salt, solvate, clathrate, hydrate, stereoisomer, or tautomer thereof, wherein m is 0, 1, 2, 3, or 4; p is 0, 1, 2, 3, 4, 5, or 6; q is 0, 1, 2, 3, 4, or 5; and r is 0, 1, 2, 3, or 4.

In some embodiments, the compound of Formula (I) is of Formula (VI-a) or (VI-b):

(VI-a)

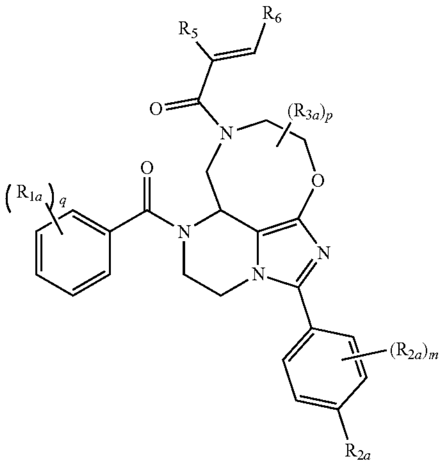

or (VI-b)

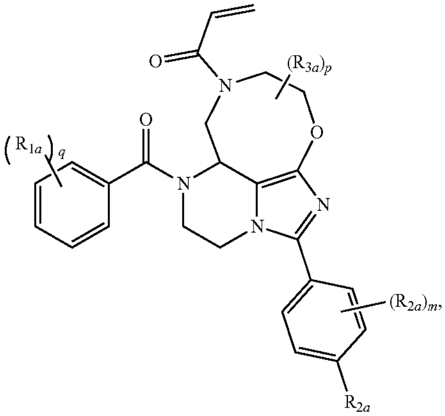

or a pharmaceutically acceptable salt, solvate, clathrate, hydrate, stereoisomer, or tautomer thereof, wherein m is 0, 1, 2, 3, or 4; p is 0, 1, 2, 3, 4, 5, or 6; and q is 0, 1, 2, 3, 4, or 5.

In some embodiments, the compound of Formula (I) is of Formula (VI-c) or (VI-d):

(VI-c)

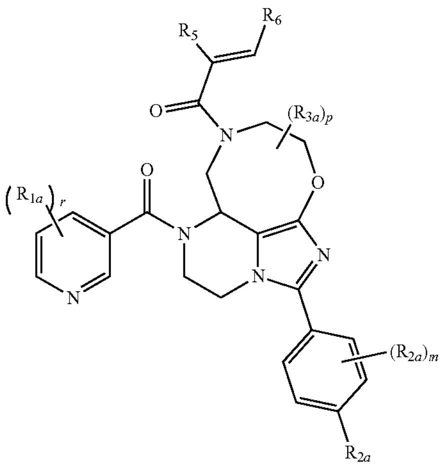

or

-continued (VI-d)

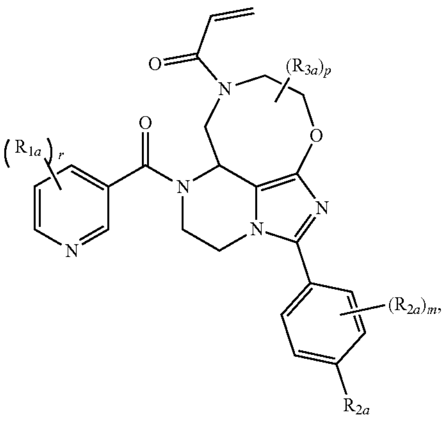

or a pharmaceutically acceptable salt, solvate, clathrate, hydrate, stereoisomer, or tautomer thereof, wherein m is 0, 1, 2, 3, or 4; p is 0, 1, 2, 3, 4, 5, or 6; and r is 0, 1, 2, 3, or 4.

In some embodiments, the compound of Formula (I) is of Formula (VI-a'), (VI-b'), (VI-c'), or (VI-d')

(VI-a')

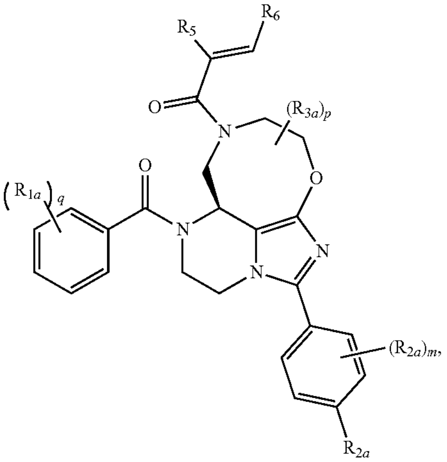

(VI-b')

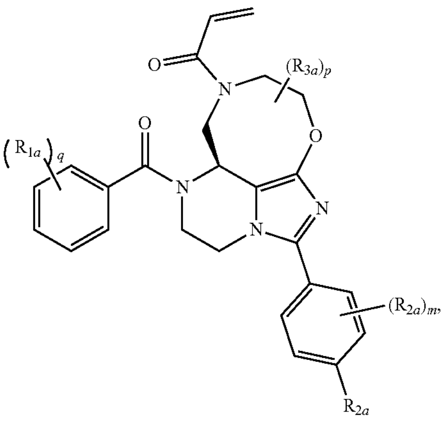

-continued (VI-c')

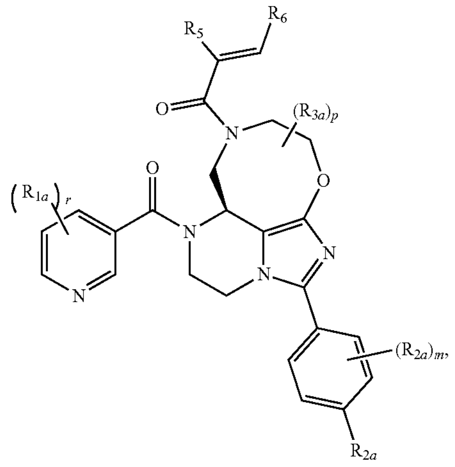

or (VI-d')

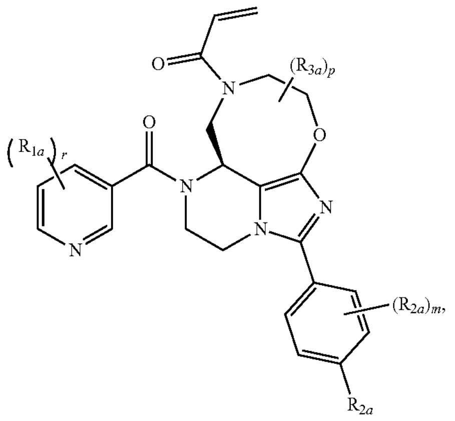

or a pharmaceutically acceptable salt, solvate, clathrate, hydrate, stereoisomer, or tautomer thereof, wherein m is 0, 1, 2, 3, or 4; p is 0, 1, 2, 3, 4, 5, or 6; q is 0, 1, 2, 3, 4, or 5; and r is 0, 1, 2, 3, or 4.

In some embodiments, the compound of Formula (I) is of Formula (VII-a) or (VII-b):

(VII-a)

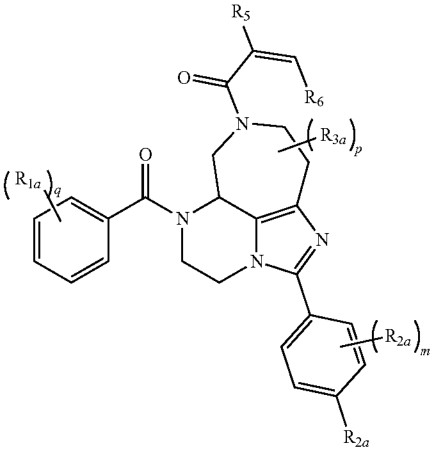

or

-continued (VII-b)

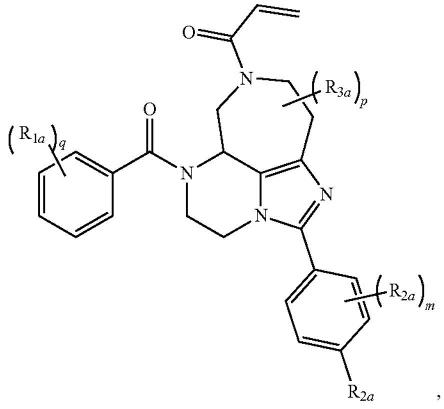

, or a pharmaceutically acceptable salt, solvate, clathrate, hydrate, stereoisomer, or tautomer thereof, wherein m is 0, 1, 2, 3, or 4; p is 0, 1, 2, 3, 4, 5, or 6; and q is 0, 1, 2, 3, 4, or 5.

In some embodiments, the compound of Formula (I) is of Formula (VII-c) or (VII-d):

(VII-c)

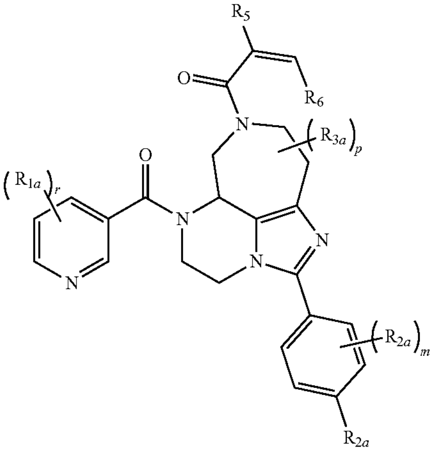

or (VII-d)

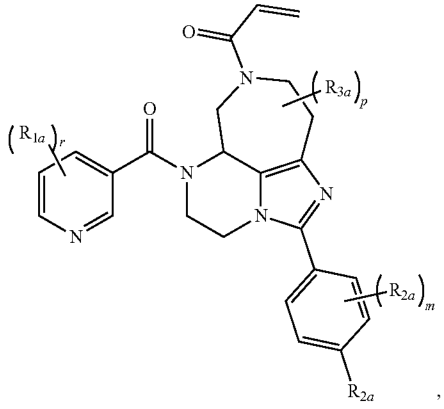

, or a pharmaceutically acceptable salt, solvate, clathrate, hydrate, stereoisomer, or tautomer thereof, wherein m is 0, 1, 2, 3, or 4; p is 0, 1, 2, 3, 4, 5, or 6; and r is 0, 1, 2, 3, or 4.

In some embodiments, the compound of Formula (I) is of Formula (VII-a'), (VII-b'), (VII-c'), or (VII-d'):

(VII-a')

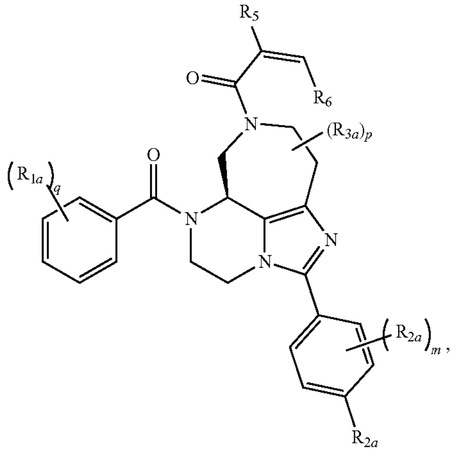

(VII-b')

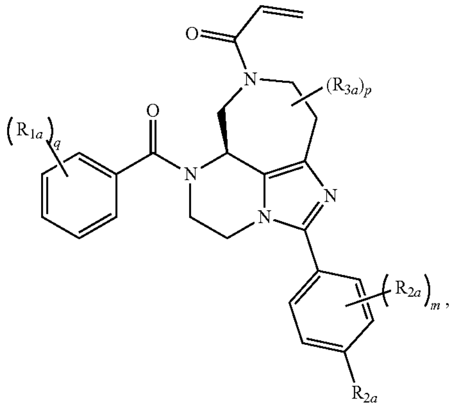

(VII-c')

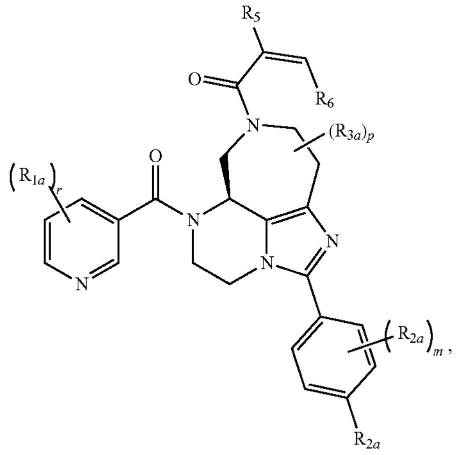

or

-continued (VII-d')

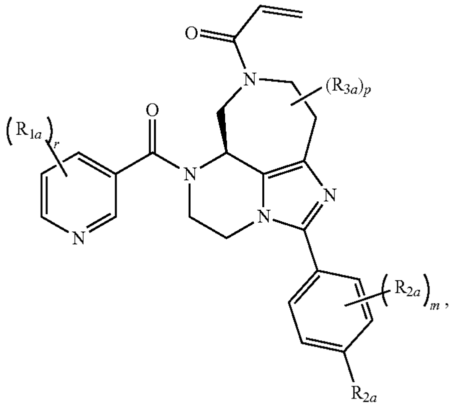

or a pharmaceutically acceptable salt, solvate, clathrate, hydrate, stereoisomer, or tautomer thereof, wherein m is 0, 1, 2, 3, or 4; p is 0, 1, 2, 3, 4, 5, or 6; q is 0, 1, 2, 3, 4, or 5; and r is 0, 1, 2, 3, or 4.

In some embodiments, the compound of Formula (I) is of Formula (VIII-a) or (VIII-b):

(VIII-a)

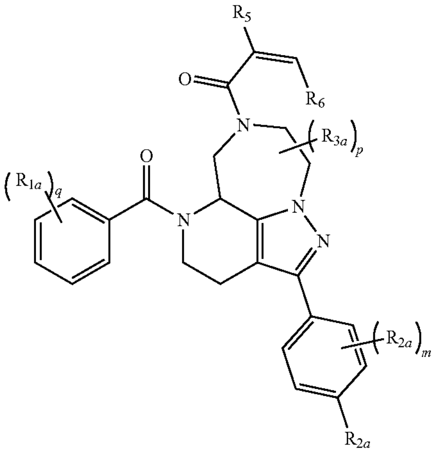

or (VIII-b)

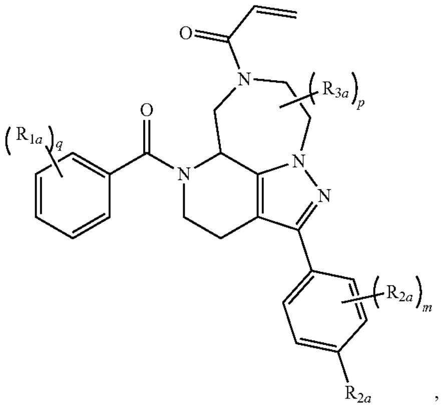

, or a pharmaceutically acceptable salt, solvate, clathrate, hydrate, stereoisomer, or tautomer thereof, wherein m is 0, 1, 2, 3, or 4; p is 0, 1, 2, 3, 4, 5, or 6; and q is 0, 1, 2, 3, 4, or 5.

In some embodiments, the compound of Formula (I) is of Formula (VIII-c) or (VIII-d):

(VIII-c)

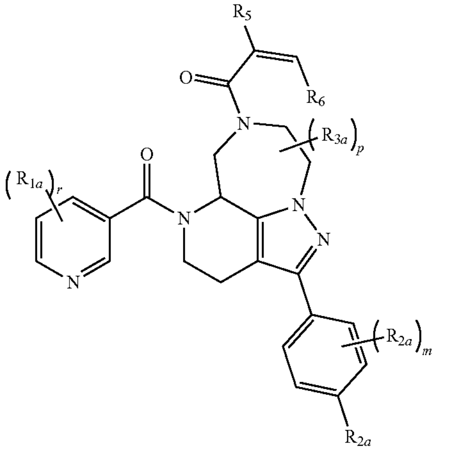

or (VIII-d)

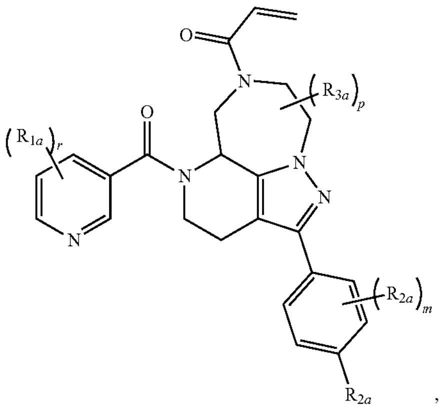

, or a pharmaceutically acceptable salt, solvate, clathrate, hydrate, stereoisomer, or tautomer thereof, wherein m is 0, 1, 2, 3, or 4; p is 0, 1, 2, 3, 4, 5, or 6; and r is 0, 1, 2, 3, or 4.

In some embodiments, the compound of Formula (I) is of Formula (VIII-a'), (VIII-b'), (VIII-c'), or (VIII-d'):

(VIII-a')

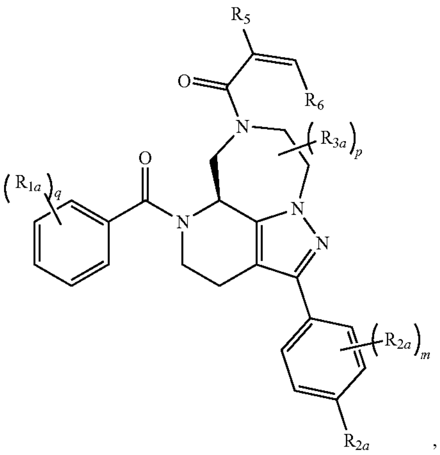

,

-continued (VIII-b')

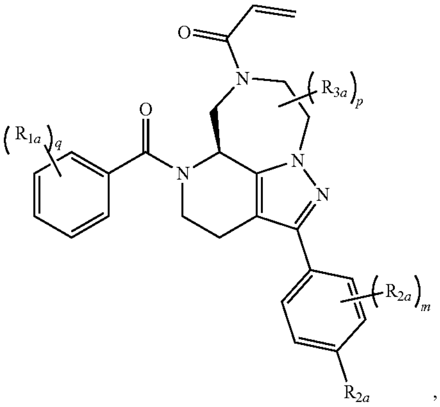

, (VIII-c')

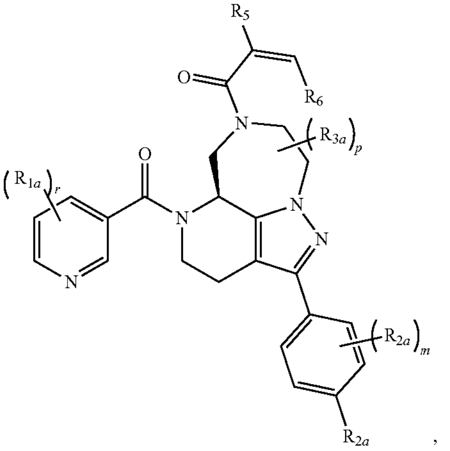

, or (VIII-d')

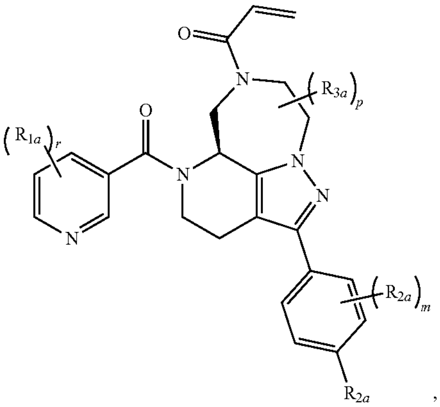

, or a pharmaceutically acceptable salt, solvate, clathrate, hydrate, stereoisomer, or tautomer thereof, wherein m is 0, 1, 2, 3, or 4; p is 0, 1, 2, 3, 4, 5, or 6; q is 0, 1, 2, 3, 4, or 5; and r is 0, 1, 2, 3, or 4.

In some embodiments, n is 0, 1, 2, 3, 4, or 5.

In some embodiments, n is 1, 2, 3, 4, or 5.

In some embodiments, n is 0. In some embodiments, n is 1. In some embodiments, n is 2. In some embodiments, n is 3. In some embodiments, n is 4. In some embodiments, n is 5.

In some embodiments, n is 1 or 2.

In some embodiments, m is 0, 1, 2, 3, or 4.

In some embodiments, m is 1, 2, 3, or 4.

In some embodiments, m is 0. In some embodiments, m is 1. In some embodiments, m is 2. In some embodiments, m is 3. In some embodiments, m is 4.

In some embodiments, p is 0, 1, 2, 3, 4, 5, or 6.

In some embodiments, p is 1, 2, 3, 4, 5, or 6.

In some embodiments, p is 0. In some embodiments, p is 1. In some embodiments, p is 2. In some embodiments, p is 3. In some embodiments, p is 4. In some embodiments, p is 5. In some embodiments, p is 6.

In some embodiments, p is 1 or 2.

In some embodiments, q is 0, 1, 2, 3, 4, or 5.

In some embodiments, q is 1, 2, 3, 4, or 5.

In some embodiments, q is 0. In some embodiments, q is 1. In some embodiments, q is 2. In some embodiments, q is 3. In some embodiments, q is 4. In some embodiments, q is 5.

In some embodiments, q is 1 or 2.

In some embodiments, r is 1, 2, 3, or 4.

In some embodiments, r is 0. In some embodiments, r is 1. In some embodiments, r is 2. In some embodiments, r is 3. In some embodiments, r is 4.

In some embodiments, r is 1 or 2.

In some embodiments, r is 3; m is 1; and p is 0.

In some embodiments, the compound is selected from the compounds described in Table 1, or a prodrug or pharmaceutically acceptable salt thereof.

In some embodiments, the compound is selected from the compounds described in Table 1, or a pharmaceutically acceptable salt thereof.

In some embodiments, the compound is selected from the prodrugs of compounds described in Table 1, or a pharmaceutically acceptable salt thereof.

In some embodiments, the compound is selected from the compounds described in Table 1.

In some embodiments, the compound of Table 1 comprises one (S) stereocenter.

In some embodiments, the compound of Table 1 comprises one (R) stereocenter.

In some embodiments, the compound of Table 1 comprises one (S) stereocenter and one (R) stereocenter.

In some embodiments, the compound of Table 1 comprises two (S) stereocenters.

In some embodiments, the compound of Table 1 comprises two (R) stereocenters.

In some embodiments, the compound is selected from the compounds described in Table 2, or a prodrug or pharmaceutically acceptable salt thereof.

In some embodiments, the compound is selected from the compounds described in Table 2, or a pharmaceutically acceptable salt thereof.

In some embodiments, the compound is selected from the prodrugs of compounds described in Table 2, or a pharmaceutically acceptable salt thereof.

In some embodiments, the compound is selected from the compounds described in Table 2.

In some embodiments, the compound of Table 2 comprises one (S) stereocenter.

In some embodiments, the compound of Table 2 comprises one (R) stereocenter.

In some embodiments, the compound of Table 2 comprises one (S) stereocenter and one (R) stereocenter.

In some embodiments, the compound of Table 2 comprises two (S) stereocenters.

In some embodiments, the compound of Table 2 comprises two (R) stereocenters.

In some embodiments, the compound is selected from the compounds described in Table 1A, or a prodrug or pharmaceutically acceptable salt thereof.

In some embodiments, the compound is selected from the compounds described in Table 1A, or a pharmaceutically acceptable salt thereof.

In some embodiments, the compound is selected from the prodrugs of compounds described in Table 1A, or a pharmaceutically acceptable salt thereof.

In some embodiments, the compound is selected from the compounds described in Table 1A.

In some embodiments, the compound is selected from the compounds described in Table 2A, or a prodrug or pharmaceutically acceptable salt thereof.

In some embodiments, the compound is selected from the compounds described in Table 2A, or a pharmaceutically acceptable salt thereof.

In some embodiments, the compound is selected from the prodrugs of compounds described in Table 2A, or a pharmaceutically acceptable salt thereof.

In some embodiments, the compound is selected from the compounds described in Table 2A.

TABLE 1

| Compound No | Example No. | Name | Structure |
|---|---|---|---|
| 1 | A-4 | 1-(2-(4-cyclopropylphenyl)-5-(5-hydroxy-6-(trifluoromethyl)nicotinoyl)-2,3,4,5,5a,6,8,9-octahydro-7H-1,2,5,7-tetraazabenzo[cd]azulen-7-yl)prop-2-en-1-one | 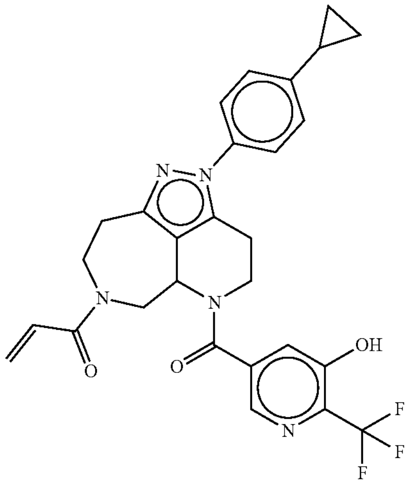 |

TABLE 1-continued

| Compound No | Example No. | Name | Structure |
|---|---|---|---|
| 2 | A-5 | 1-(5-(7-bromo-1H-benzo[d]imidazole-4-carbonyl)-2-(2-hydroxy-4-(2,2,2-trifluoroethyl)phenyl)-2,3,4,5,5a,6,8,9-octahydro-7H-1,2,5,7-tetraazabenzo[cd]azulen-7-yl)prop-2-en-1-one | 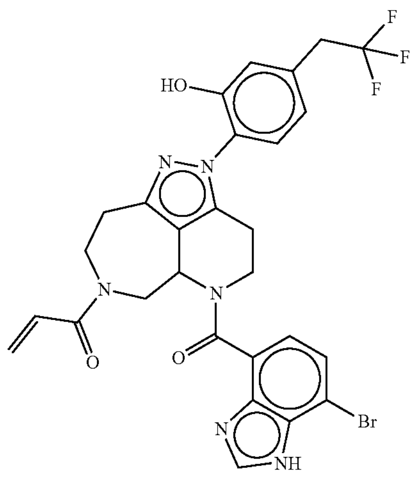 |
| 3 | A-6 | 1-(5-(7-bromo-1H-benzo[d]imidazole-4-carbonyl)-2-(2-hydroxy-4-(trifluoromethyl)phenyl)-2,3,4,5,5a,6,8,9-octahydro-7H-1,2,5,7-tetraazabenzo[cd]azulen-7-yl)prop-2-en-1-one | 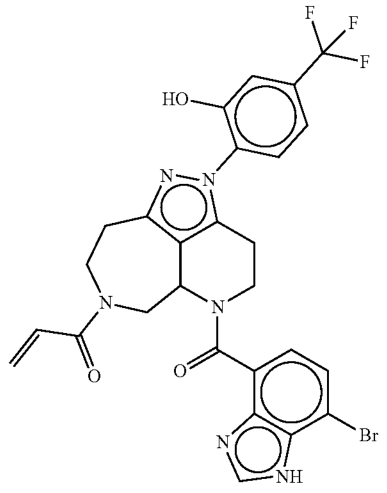 |
| 4 | A-7 | 1-(2-(4-(bicyclo[1.1.1]pentan-1-yl)phenyl)-5-(7-bromo-1H-benzo[d]imidazole-4-carbonyl)-2,3,4,5,5a,6,8,9-octahydro-7H-1,2,5,7-tetraazabenzo[cd]azulen-7-yl)prop-2-en-1-one | 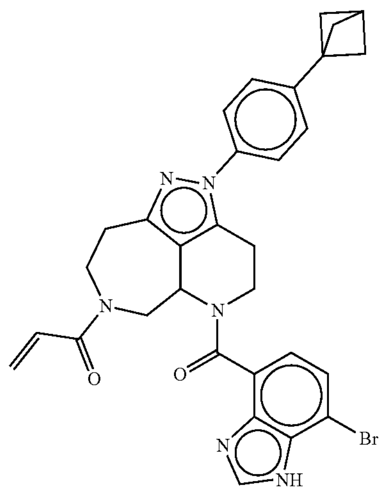 |

TABLE 1-continued

| Compound No | Example No. | Name | Structure |
|---|---|---|---|
| 5 | A-8 | 1-(5-(7-bromo-1H-benzo[d]imidazole-4-carbonyl)-2-(4-cyclopropyl-2-hydroxyphenyl)-2,3,4,5,5a,6,8,9-octahydro-7H-1,2,5,7-tetraazabenzo[cd]azulen-7-yl)prop-2-en-1-one | 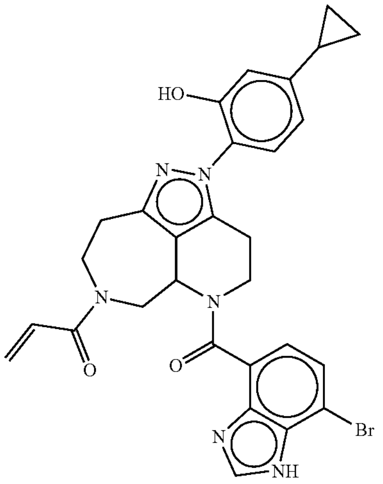 |
| 6 | A-9 | 1-(5-(7-bromo-1H-benzo[d]imidazole-4-carbonyl)-2-(4-(2,2-difluorocyclobutyl)-2-hydroxyphenyl)-2,3,4,5,5a,6,8,9-octahydro-7H-1,2,5,7-tetraazabenzo[cd]azulen-7-yl)prop-2-en-1-one | 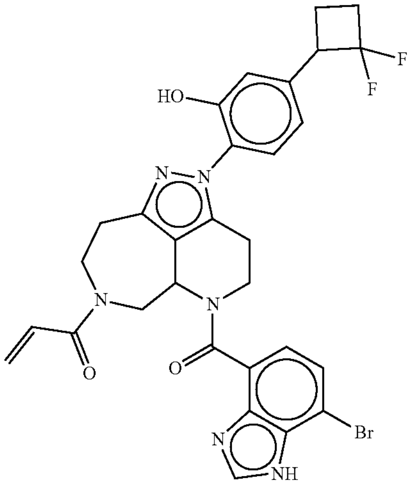 |
| 7 | B-2 | 1-(5-(7-bromo-1H-benzo[d]imidazole-4-carbonyl)-2-(4-isopropylphenyl)-2,3,4,5,5a,6,8,9-octahydro-7H-1,2,5,7-tetraazabenzo[cd]azulen-7-yl)prop-2-en-1-one | 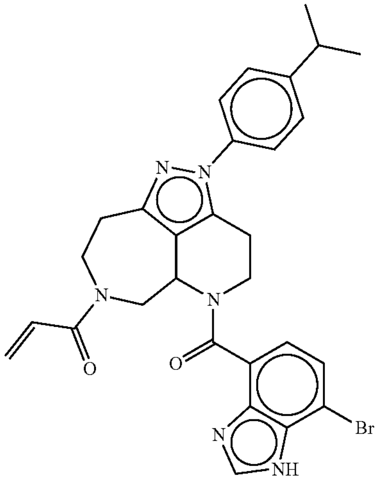 |

TABLE 1-continued

| Compound No | Example No. | Name | Structure |
| --- | --- | --- | --- |
| 8 | B-3 | 1-(5-(2-amino-7-bromo-1H-benzo[d]imidazole-4-carbonyl)-2-(4-isopropylphenyl)-2,3,4,5,5a,6,8,9-octahydro-7H-1,2,5,7-tetraazabenzo[cd]azulen-7-yl)prop-2-en-1-one | 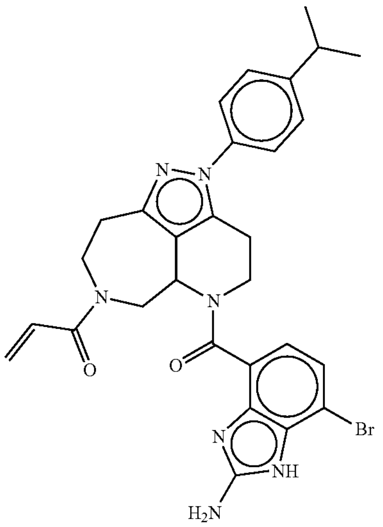 |
| 9 | B-4 | 1-(5-(2-(azetidin-1-yl)-7-bromo-1H-benzo[d]imidazole-4-carbonyl)-2-(4-isopropylphenyl)-2,3,4,5,5a,6,8,9-octahydro-7H-1,2,5,7-tetraazabenzo[cd]azulen-7-yl)prop-2-en-1-one | 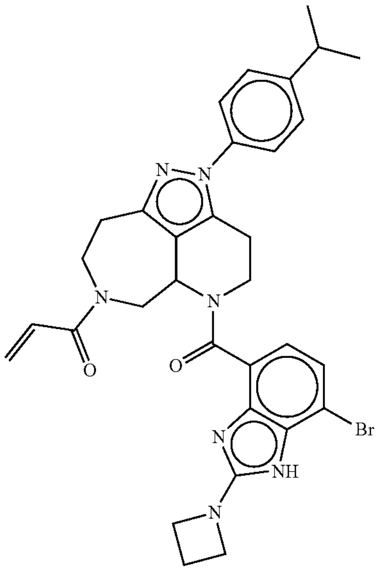 |
| 10 | B-5 | 1-(5-(7-bromo-1H-imidazo[4,5-c]pyridine-4-carbonyl)-2-(4-isopropylphenyl)-2,3,4,5,5a,6,8,9-octahydro-7H-1,2,5,7-tetraazabenzo[cd]azulen-7-yl)prop-2-en-1-one | 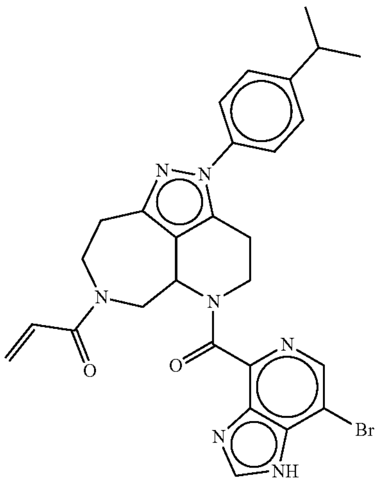 |

TABLE 1-continued

| Compound No | Example No. | Name | Structure |
|---|---|---|---|
| 11 | B-6 | 1-(2-(4-isopropylphenyl)-5-(1-(trifluoromethyl)-1H-indazole-5-carbonyl)-2,3,4,5,5a,6,8,9-octahydro-7H-1,2,5,7-tetraazabenzo[cd]azulen-7-yl)prop-2-en-1-one | 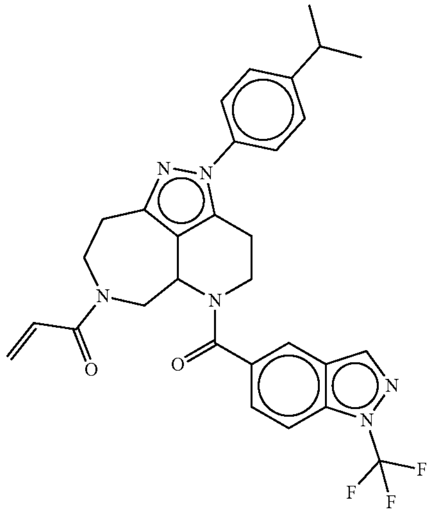 |
| 12 | B-7 | 1-(2-(4-isopropylphenyl)-5-(5-methoxy-6-(trifluoromethyl)nicotinoyl)-2,3,4,5,5a,6,8,9-octahydro-7H-1,2,5,7-tetraazabenzo[cd]azulen-7-yl)prop-2-en-1-one | 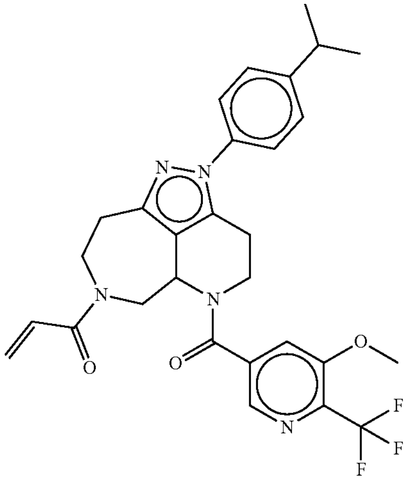 |
| 13 | B-8 | 1-(2-(4-isopropylphenyl)-5-(6-(trifluoromethyl)nicotinoyl)-2,3,4,5,5a,6,8,9-octahydro-7H-1,2,5,7-tetraazabenzo[cd]azulen-7-yl)prop-2-en-1-one | 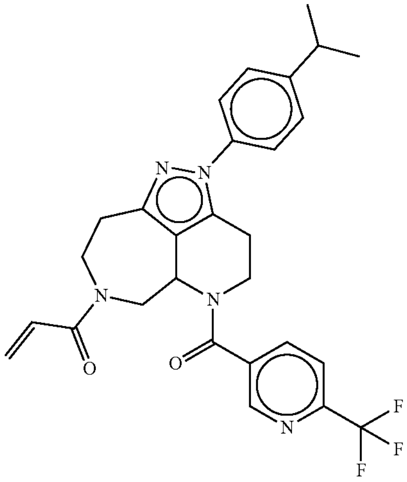 |

TABLE 1-continued

| Compound No | Example No. | Name | Structure |
|---|---|---|---|
| 14 | B-9 | 1-(5-(5-hydroxy-6-(trifluoromethyl)nicotinoyl)-2-(4-isopropylphenyl)-2,3,4,5,5a,6,8,9-octahydro-7H-1,2,5,7-tetraazabenzo[cd]azulen-7-yl)prop-2-en-1-one | 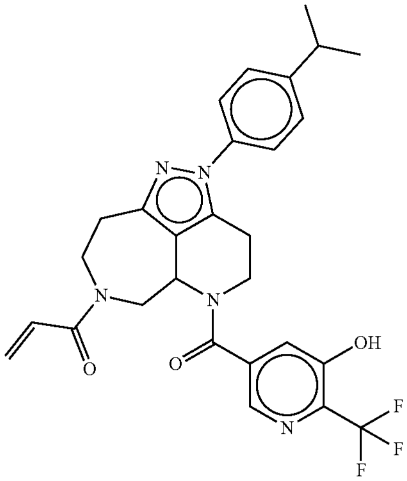 |
| 15 | B-10 | 1-(5-(7-bromo-1H-benzo[d]imidazole-4-carbonyl)-2-(4-isopropylphenyl)-2,3,4,5,5a,6,8,9-octahydro-7H-1,2,5,7-tetraazabenzo[cd]azulen-7-yl)-4-(dimethylamino)but-2-en-1-one | 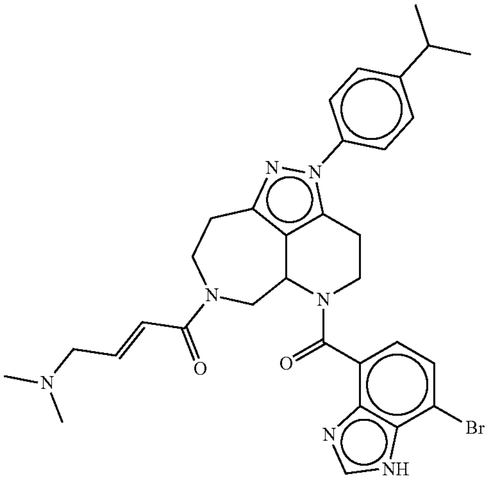 |
| 16 | B-11 | (7-bromo-1H-benzo[d]imidazol-4-yl)(7-(cyclobut-1-ene-1-carbonyl)-2-(4-isopropylphenyl)-2,3,4,5a,6,7,8,9-octahydro-5H-1,2,5,7-tetraazabenzo[cd]azulen-5-yl)methanone | 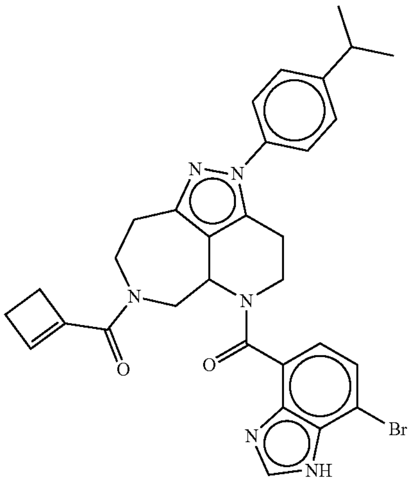 |

TABLE 1-continued

| Compound No | Example No. | Name | Structure |
|---|---|---|---|
| 17 | B-12 | 1-(5-(7-bromo-1H-benzo[d]imidazole-4-carbonyl)-2-(4-isopropylphenyl)-2,3,4,5,5a,6,8,9-octahydro-7H-1,2,5,7-tetraazabenzo[cd]azulen-7-yl)-2-fluoroprop-2-en-1-one | 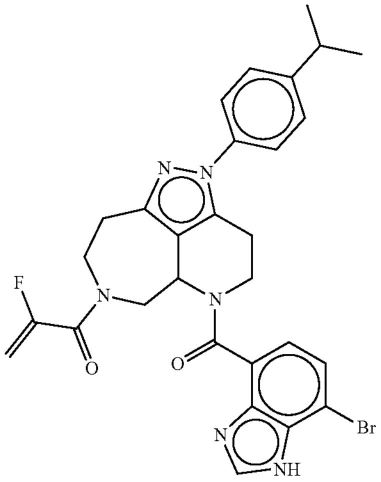 |
| 18 | B-13 | 4-(7-acryloyl-2-(4-cyclopropylphenyl)-3,4,5,5a,6,7,8,9-octahydro-2H-1,2,5,7-tetraazabenzo[cd]azulene-5-carbonyl)-1H-benzo[d]imidazole-7-carbonitrile | 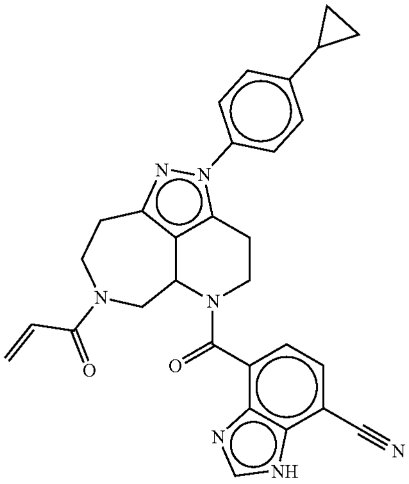 |
| 19 | C-1 | 1-(2-(4-(bicyclo[1.1.1]pentan-1-yl)phenyl)-5-(7-(trifluoromethyl)-1H-indazole-4-carbonyl)-2,3,4,5,5a,6,8,9-octahydro-7H-1,2,5,7-tetraazabenzo[cd]azulen-7-yl)prop-2-en-1-one | 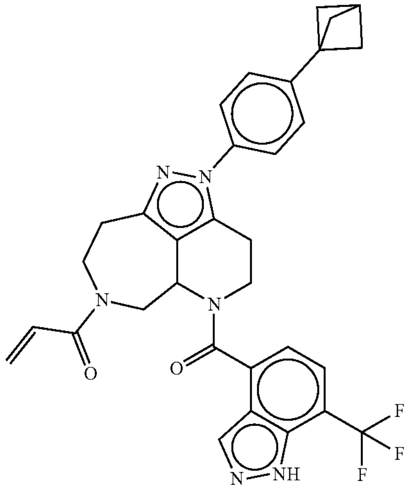 |

TABLE 1-continued

| Compound No | Example No. | Name | Structure |
|---|---|---|---|
| 20 | C-2 | 1-(5-(7-bromo-1H-benzo[d]imidazole-4-carbonyl)-2-(2-hydroxy-4-isopropylphenyl)-2,3,4,5,5a,6,8,9-octahydro-7H-1,2,5,7-tetraazabenzo[cd]azulen-7-yl)prop-2-en-1-one | 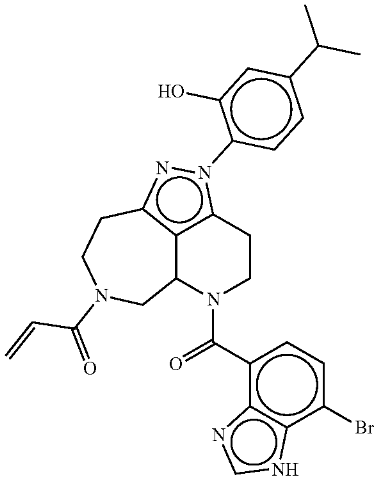 |
| 21 | C-3 | 1-(2-(2-hydroxy-4-isopropylphenyl)-5-(5-hydroxy-6-(trifluoromethyl)nicotinoyl)-2,3,4,5,5a,6,8,9-octahydro-7H-1,2,5,7-tetraazabenzo[cd]azulen-7-yl)prop-2-en-1-one | 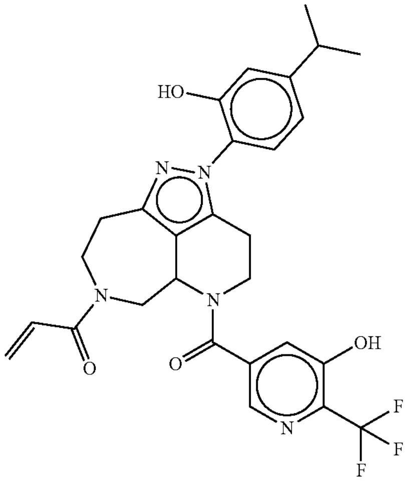 |
| 22 | C-4 | 1-(5-(4-bromo-3H-imidazo[4,5-c]pyridine-7-carbonyl)-2-(2-hydroxy-4-isopropylphenyl)-2,3,4,5,5a,6,8,9-octahydro-7H-1,2,5,7-tetraazabenzo[cd]azulen-7-yl)prop-2-en-1-one | 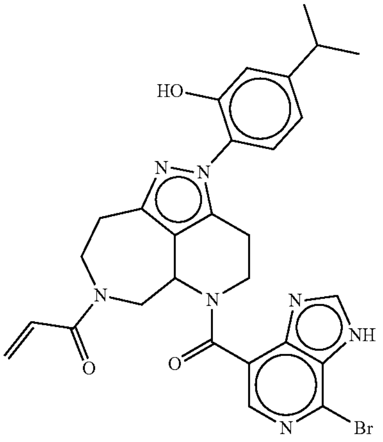 |

TABLE 1-continued

| Compound No | Example No. | Name | Structure |
|---|---|---|---|
| 23 | C-5 | 1-(5-(7-bromo-1H-benzo[d]imidazole-4-carbonyl)-2-(4-cyclobutyl-2-hydroxyphenyl)-2,3,4,5,5a,6,8,9-octahydro-7H-1,2,5,7-tetraazabenzo[cd]azulen-7-yl)prop-2-en-1-one | 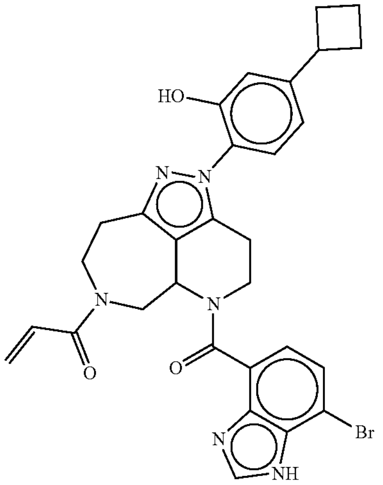 |
| 24 | C-6 | 1-(5-(3-bromo-1H-indazole-6-carbonyl)-2-(4-cyclobutyl-2-hydroxyphenyl)-2,3,4,5,5a,6,8,9-octahydro-7H-1,2,5,7-tetraazabenzo[cd]azulen-7-yl)prop-2-en-1-one | 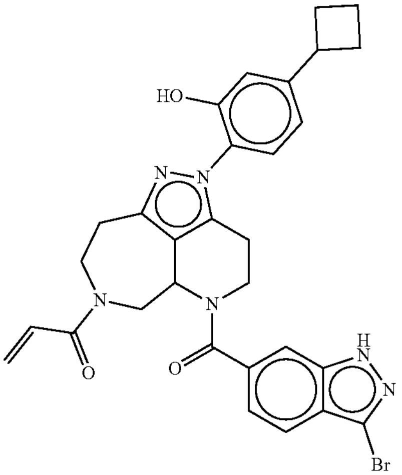 |
| 25 | C-7 | 1-(2-(4-cyclobutyl-2-hydroxyphenyl)-5-(5-hydroxy-6-(trifluoromethyl)nicotinoyl)-2,3,4,5,5a,6,8,9-octahydro-7H-1,2,5,7-tetraazabenzo[cd]azulen-7-yl)prop-2-en-1-one | 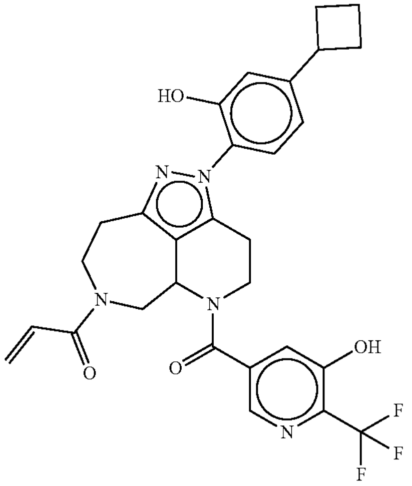 |

TABLE 1-continued

| Compound No | Example No. | Name | Structure |
|---|---|---|---|
| 26 | C-8 | 1-(2-(4-cyclobutylphenyl)-5-(5-hydroxy-6-(trifluoromethyl)nicotinoyl)-2,3,4,5,5a,6,8,9-octahydro-7H-1,2,5,7-tetraazabenzo[cd]azulen-7-yl)prop-2-en-1-one | 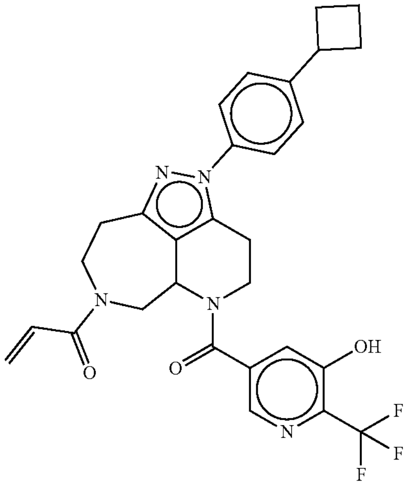 |
| 27 | C-9 | 1-(5-(7-bromo-1H-benzo[d]imidazole-4-carbonyl)-2-(4-cyclobutylphenyl)-9-methoxy-2,3,4,5,5a,6,8,9-octahydro-7H-1,2,5,7-tetraazabenzo[cd]azulen-7-yl)prop-2-en-1-one | 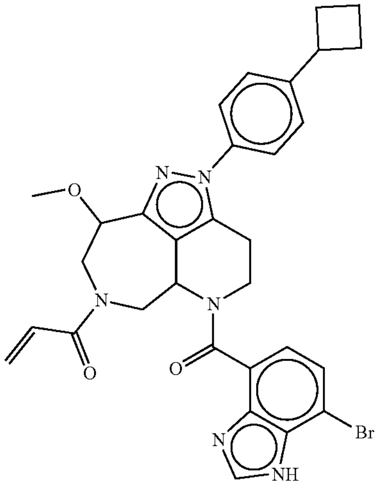 |
| 28 | C-10 | 1-(5-(7-bromo-1H-benzo[d]imidazole-4-carbonyl)-2-(4-cyclobutylphenyl)-9-fluoro-2,3,4,5,5a,6,8,9-octahydro-7H-1,2,5,7-tetraazabenzo[cd]azulen-7-yl)prop-2-en-1-one | 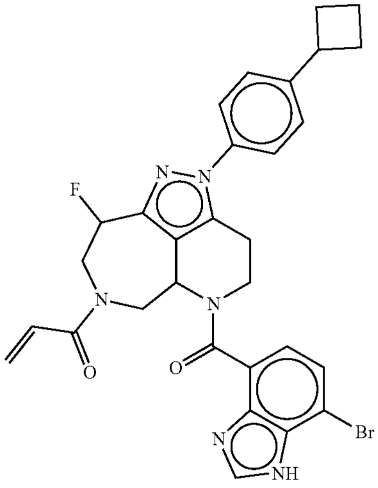 |

TABLE 1-continued

| Compound No | Example No. | Name | Structure |
|---|---|---|---|
| 29 | D-1 | 1-(2-(6-(bicyclo[1.1.1]pentan-1-yl)pyridin-3-yl)-5-(7-bromo-1H-benzo[d]imidazole-4-carbonyl)-2,3,4,5,5a,6,8,9-octahydro-7H-1,2,5,7-tetraazabenzo[cd]azulen-7-yl)prop-2-en-1-one | 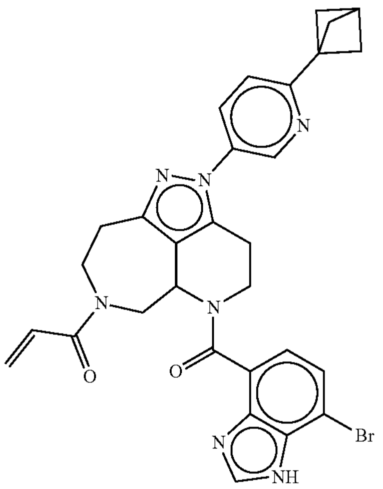 |
| 30 | D-2 | 1-(2-(4-(bicyclo[1.1.1]pentan-1-yl)-2-fluorophenyl)-5-(7-bromo-1H-benzo[d]imidazole-4-carbonyl)-2,3,4,5,5a,6,8,9-octahydro-7H-1,2,5,7-tetraazabenzo[cd]azulen-7-yl)prop-2-en-1-one | 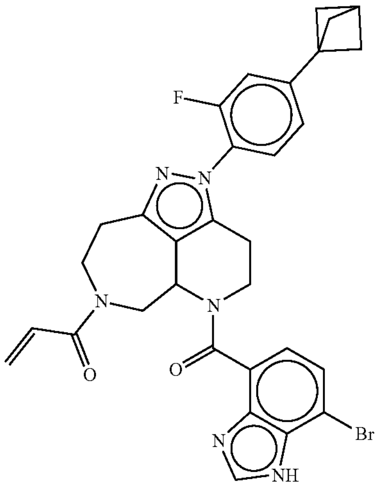 |
| 31 | E-2 | 1-(5-(7-bromo-1H-benzo[d]imidazole-4-carbonyl)-2-(2-hydroxy-4-isopropylphenyl)-9-methyl-2,3,4,5,5a,6,8,9-octahydro-7H-1,2,5,7-tetraazabenzo[cd]azulen-7-yl)prop-2-en-1-one | 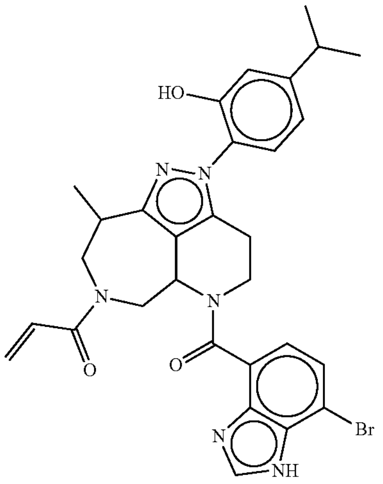 |

TABLE 1-continued

| Compound No | Example No. | Name | Structure |
|---|---|---|---|
| 32 | E-1 | 1-(5-(7-bromo-1H-benzo[d]imidazole-4-carbonyl)-2-(2-hydroxy-4-isopropylphenyl)-9-methyl-2,3,4,5,5a,6,8,9-octahydro-7H-1,2,5,7-tetraazabenzo[cd]azulen-7-yl)prop-2-en-1-one | 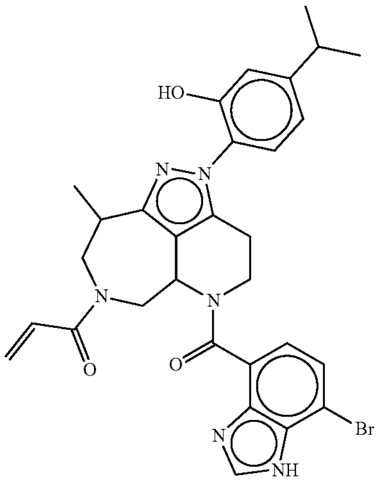 |
| 33 | E-3 | 1-(5-(7-bromo-1H-benzo[d]imidazole-4-carbonyl)-2-(4-isopropylphenyl)-9-methyl-2,3,4,5,5a,6,8,9-octahydro-7H-1,2,5,7-tetraazabenzo[cd]azulen-7-yl)prop-2-en-1-one | 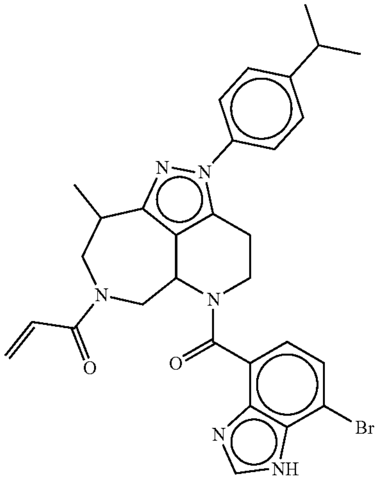 |
| 34 | E-4 | 1-(5-(7-bromo-1H-benzo[d]imidazole-4-carbonyl)-2-(4-isopropylphenyl)-9-methyl-2,3,4,5,5a,6,8,9-octahydro-7H-1,2,5,7-tetraazabenzo[cd]azulen-7-yl)prop-2-en-1-one | 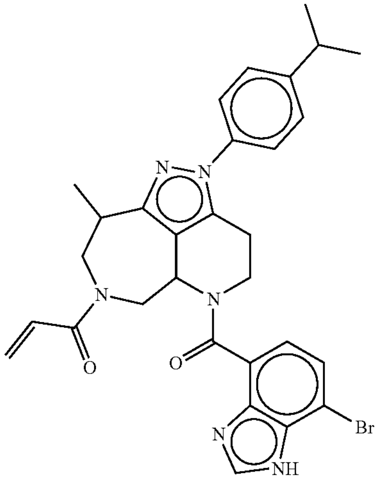 |

TABLE 1-continued

| Compound No | Example No. | Name | Structure |
|---|---|---|---|
| 35 | F-1 | 1-(6-(4-bromo-3-hydroxybenzoyl)-1-(4-isopropyl-2-methylphenyl)-1,5,5a,6,7,8-hexahydropyrazolo[3,4,5-de][1,7]naphthyridin-4(3H)-yl)prop-2-en-1-one | 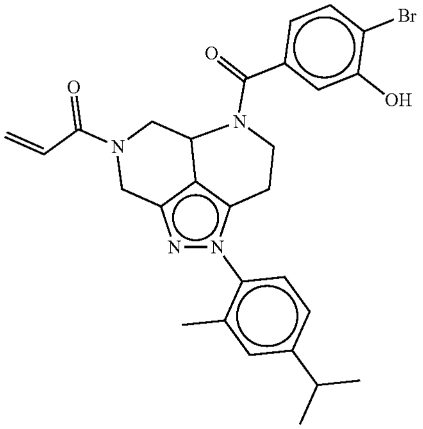 |
| 36 | F-2 | 1-(5-(4-bromo-3-hydroxybenzoyl)-2-(4-isopropyl-2-methylphenyl)-2,4,5,5a,6,8,9,11-octahydro-10-oxa-1,2,5,7-tetraazacyclonona[cd]inden-7(3H)-yl)prop-2-en-1-one | 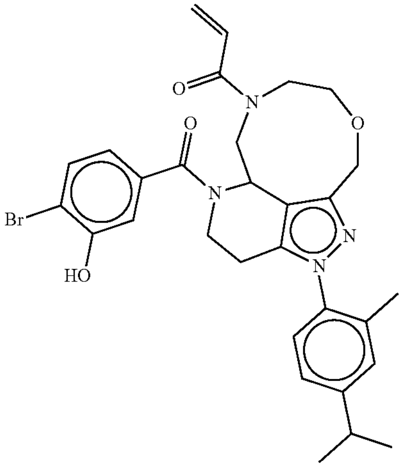 |
| 37 | F-3 | 1-(5-(4-bromo-3-hydroxybenzoyl)-2-(4-isopropylphenyl)-4,5,5a,6,8,9-hexahydro-1,5,7,9a-tetraazabenzo[cd]azulen-7(3H)-yl)prop-2-en-1-one | 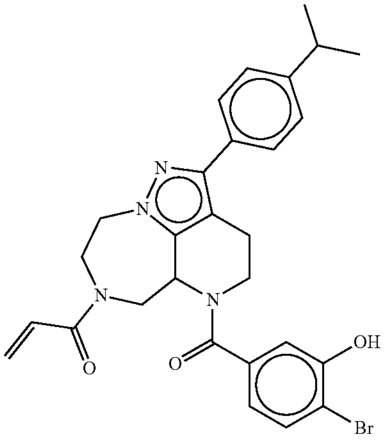 |

TABLE 1-continued

| Compound No | Example No. | Name | Structure |
|---|---|---|---|
| 38 | F-4 | 1-(5-(7-bromo-1H-benzo[d]imidazole-4-carbonyl)-2-(4-isopropylphenyl)-4,5,5a,6,8,9-hexahydro-1,2a,5,7-tetraazabenzo[cd]azulen-7(3H)-yl)prop-2-en-1-one | 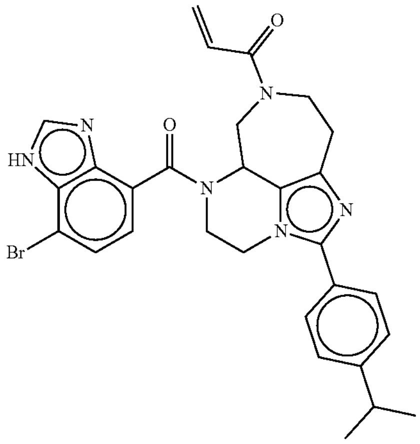 |
| 39 | K-3 | 1-(5-(7-bromo-1H-benzo[d]imidazole-4-carbonyl)-2-(4-cyclobutyl-2-hydroxyphenyl)-2,3,4,5,5a,6,8,9-octahydro-7H-10-oxa-1,2,5,7-tetraazacycloocta[cd]inden-7-yl)prop-2-en-1-one | 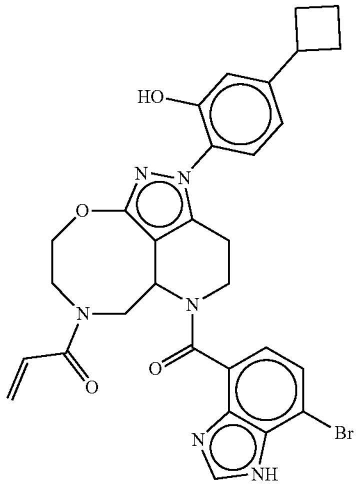 |
| 40 | K-4 | 1-(5-(3-bromo-1H-indazole-6-carbonyl)-2-(4-cyclobutyl-2-hydroxyphenyl)-2,3,4,5,5a,6,8,9-octahydro-7H-10-oxa-1,2,5,7-tetraazacycloocta[cd]inden-7-yl)prop-2-en-1-one | 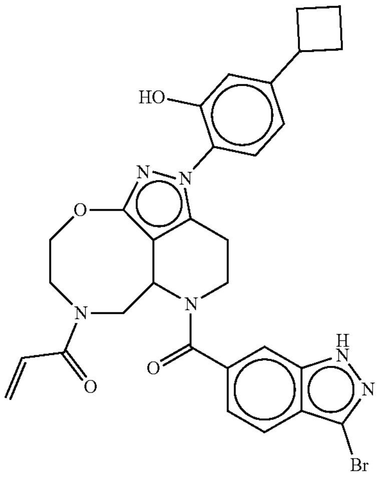 |

TABLE 1-continued

| Compound No | Example No. | Name | Structure |
|---|---|---|---|
| 41 | K-5 | 1-(5-(7-bromo-1H-benzo[d]imidazole-4-carbonyl)-2-(4-cyclobutylphenyl)-2,3,4,5,5a,6,8,9-octahydro-7H-10-oxa-1,2,5,7-tetraazacycloocta[cd]inden-7-yl)prop-2-en-1-one | 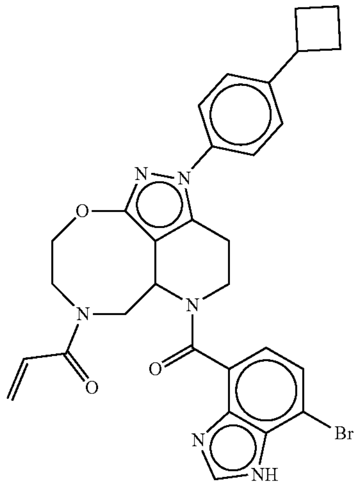 |
| 42 | K-6 | 1-(5-(7-bromo-1H-indazole-4-carbonyl)-2-(4-cyclobutylphenyl)-2,3,4,5,5a,6,8,9-octahydro-7H-10-oxa-1,2,5,7-tetraazacycloocta[cd]inden-7-yl)prop-2-en-1-one | 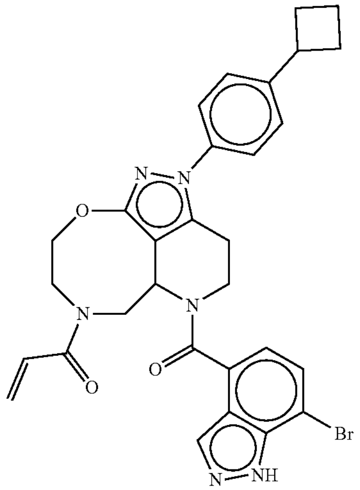 |
| 43 | K-7 | 1-(2-(4-(bicyclo[1.1.1]pentan-1-yl)phenyl)-5-(7-bromo-1H-benzo[d]imidazole-4-carbonyl)-2,3,4,5,5a,6,8,9-octahydro-7H-10-oxa-1,2,5,7-tetraazacycloocta[cd]inden-7-yl)prop-2-en-1-one | 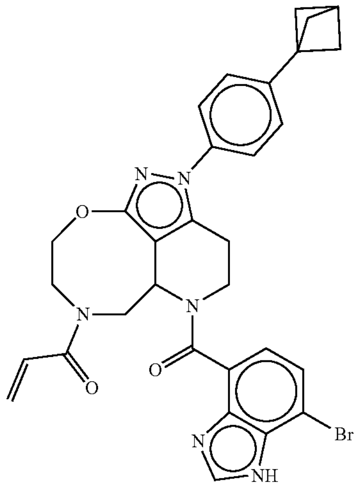 |

TABLE 1-continued

| Compound No | Example No. | Name | Structure |
| --- | --- | --- | --- |
| 44 | K-8 | 1-(5-(7-bromo-1H-benzo[d]imidazole-4-carbonyl)-2-(2-hydroxy-4-isopropylphenyl)-2,3,4,5,5a,6,8,9-octahydro-7H-10-oxa-1,2,5,7-tetraazacycloocta[cd]inden-7-yl)prop-2-en-1-one | 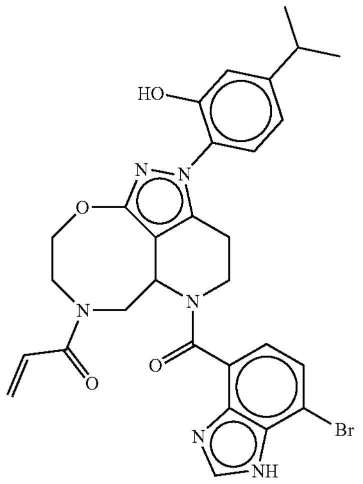 |
| 45 | K-9 | 1-(2-(2-hydroxy-4-isopropylphenyl)-5-(5-hydroxy-6-(trifluoromethyl)nicotinoyl)-2,3,4,5,5a,6,8,9-octahydro-7H-10-oxa-1,2,5,7-tetraazacycloocta[cd]inden-7-yl)prop-2-en-1-one | 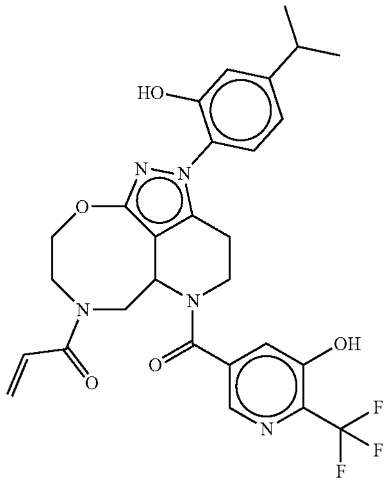 |
| 46 | K-10 | 1-(5-(7-bromo-1H-benzo[d]imidazole-4-carbonyl)-2-(4-isopropylphenyl)-2,3,4,5,5a,6,8,9-octahydro-7H-10-oxa-1,2,5,7-tetraazacycloocta[cd]inden-7-yl)prop-2-en-1-one | 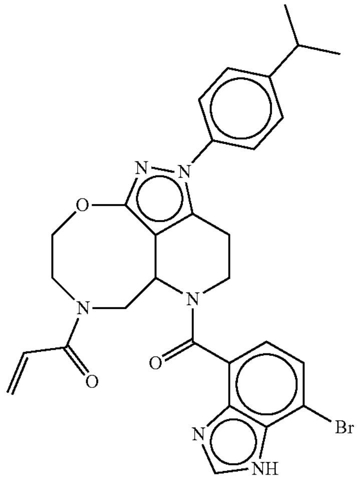 |

TABLE 1-continued

| Compound No | Example No. | Name | Structure |
|---|---|---|---|
| 47 | K-11 | 1-(5-(5-hydroxy-6-(trifluoromethyl)nicotinoyl)-2-(4-isopropylphenyl)-2,3,4,5,5a,6,8,9-octahydro-7H-10-oxa-1,2,5,7-tetraazacycloocta[cd]inden-7-yl)prop-2-en-1-one | 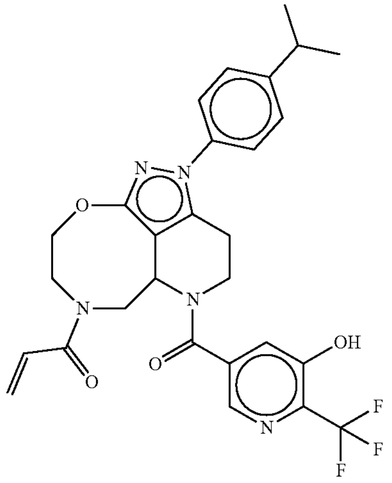 |
| 48 | K-12 | 1-(5-(4-bromo-3-hydroxybenzoyl)-2-(4-isopropylphenyl)-2,3,4,5,5a,6,8,9-octahydro-7H-10-oxa-1,2,5,7-tetraazacycloocta[cd]inden-7-yl)prop-2-en-1-one | 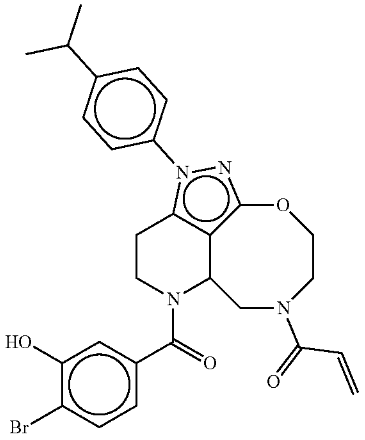 |
| 49 | K-13 | 1-(5-(7-bromo-1H-benzo[d]imidazole-4-carbonyl)-2-(4-cyclopropylphenyl)-2,3,4,5,5a,6,8,9-octahydro-7H-10-oxa-1,2,5,7-tetraazacycloocta[cd]inden-7-yl)prop-2-en-1-one | 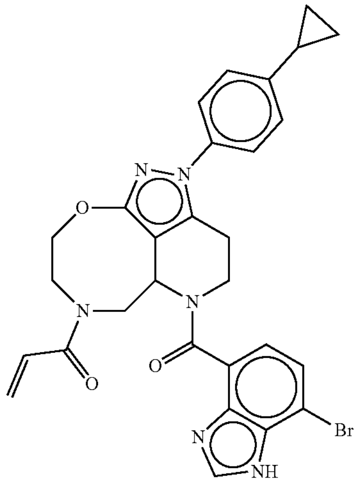 |

TABLE 1-continued

| Compound No | Example No. | Name | Structure |
|---|---|---|---|
| 50 | K-14 | 1-(2-(4-cyclopropylphenyl)-5-(7-(trifluoromethyl)-1H-indazole-4-carbonyl)-2,3,4,5,5a,6,8,9-octahydro-7H-10-oxa-1,2,5,7-tetraazacycloocta[cd]inden-7-yl)prop-2-en-1-one | 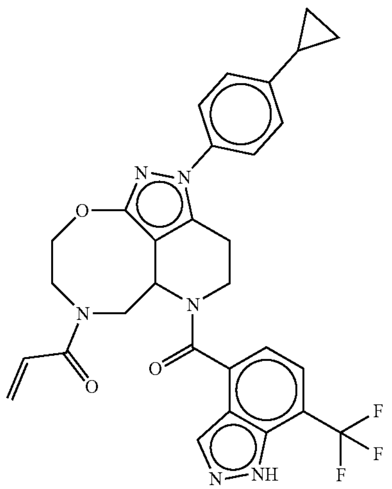 |
| 51 | K-15 | 1-(5-(7-bromo-1H-benzo[d]imidazole-4-carbonyl)-2-(4-cyclobutylphenyl)-2,3,4,5,5a,6,8,9-octahydro-7H-10-oxa-1,2,5,7-tetraazacycloocta[cd]inden-7-yl)-4-(dimethylamino)but-2-en-1-one | 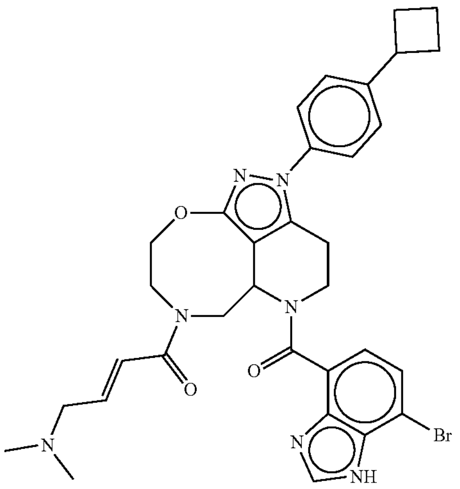 |
| 52 | K-16a | 1-(5-(7-bromo-1H-benzo[d]imidazole-4-carbonyl)-2-(4-isopropylphenyl)-9-methyl-2,3,4,5,5a,6,8,9-octahydro-7H-10-oxa-1,2,5,7-tetraazacycloocta[cd]inden-7-yl)prop-2-en-1-one | 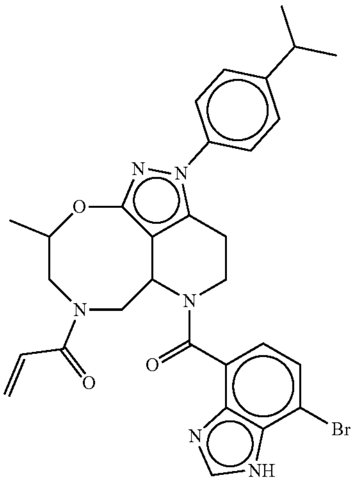 |

TABLE 1-continued

| Compound No | Example No. | Name | Structure |
|---|---|---|---|
| 53 | K-16b | 1-(5-(7-bromo-1H-benzo[d]imidazole-4-carbonyl)-2-(4-isopropylphenyl)-9-methyl-2,3,4,5,5a,6,8,9-octahydro-7H-10-oxa-1,2,5,7-tetraazacycloocta[cd]inden-7-yl)prop-2-en-1-one | 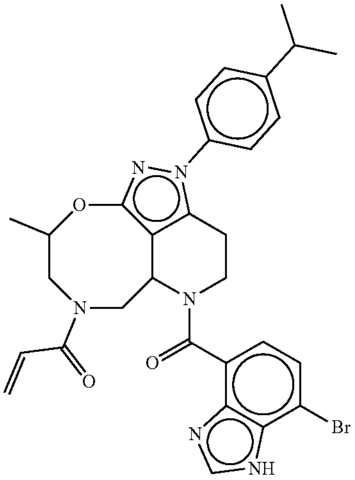 |
| 54 | K-17a | 1-(5-(7-bromo-1H-benzo[d]imidazole-4-carbonyl)-9-fluoro-2-(4-isopropylphenyl)-2,3,4,5,5a,6,8,9-octahydro-7H-10-oxa-1,2,5,7-tetraazacycloocta[cd]inden-7-yl)prop-2-en-1-one | 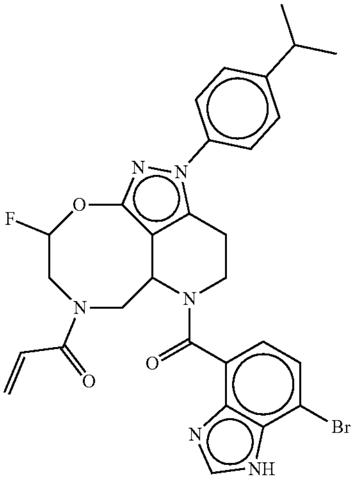 |
| 55 | K-17b | 1-(5-(7-bromo-1H-benzo[d]imidazole-4-carbonyl)-9-fluoro-2-(4-isopropylphenyl)-2,3,4,5,5a,6,8,9-octahydro-7H-10-oxa-1,2,5,7-tetraazacycloocta[cd]inden-7-yl)prop-2-en-1-one | 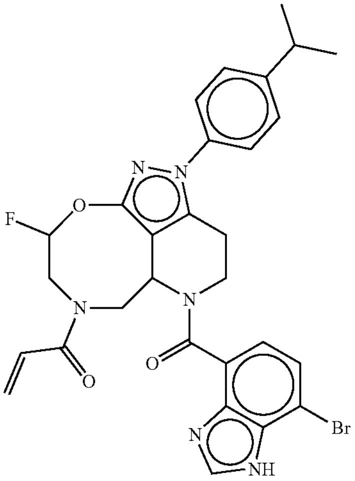 |

TABLE 1-continued

| Compound No | Example No. | Name | Structure |
|---|---|---|---|
| 56 | K-18 | 1-(5-(7-bromo-1H-benzo[d]imidazole-4-carbonyl)-2-(4-isopropylphenyl)-10-methyl-2,4,5,5a,6,8,9,10-octahydro-1,2,5,7,10-pentaazacycloocta[cd]inden-7(3H)-yl)prop-2-en-1-one | 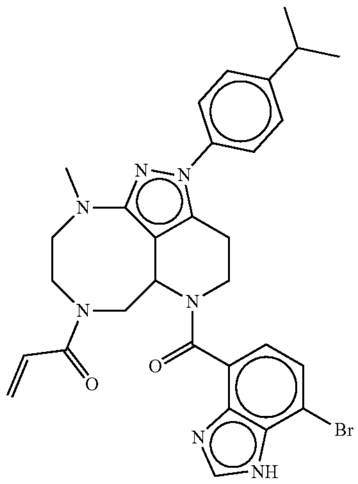 |
| 57 | L-8 | 1-(2-(2-amino-3-fluoro-4-isopropylphenyl)-5-(5-hydroxy-6-(trifluoromethyl)nicotinoyl)-2,3,4,5,5a,6,8,9-octahydro-7H-1,2,5,7-tetraazabenzo[cd]azulen-7-yl)prop-2-en-1-one | 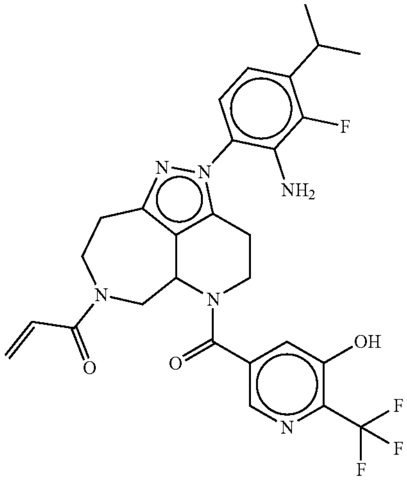 |
| 58 | B-9-1 | 6-(7-acryloyl-2-(4-isopropylphenyl)-3,4,5,5a,6,7,8,9-octahydro-2H-1,2,5,7-tetraazabenzo[cd]azulene-5-carbonyl)-3-(trifluoromethyl)pyridin-2(1H)-one | 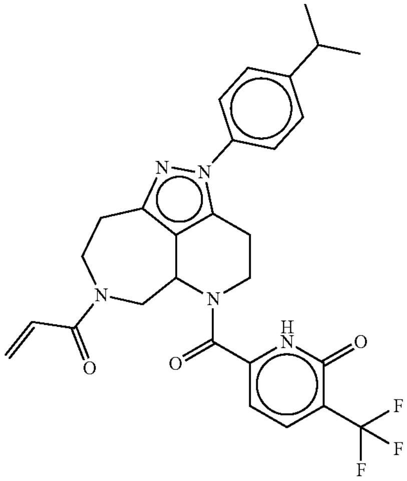 |

TABLE 1-continued

| Compound No | Example No. | Name | Structure |
| --- | --- | --- | --- |
| 59 | B-9-3 | 2-((5-(7-acryloyl-2-(4-isopropylphenyl)-3,4,5,5a,6,7,8,9-octahydro-2H-1,2,5,7-tetraazabenzo[cd]azulene-5-carbonyl)-2-(trifluoromethyl)pyridin-3-yl)oxy)acetamide | 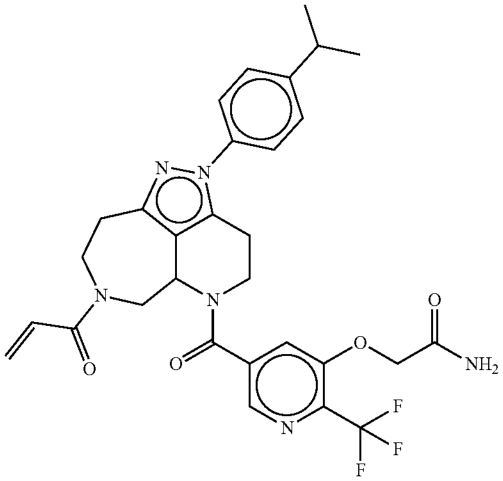 |
| 60 | B-15 | 1-(5-(5-(azetidin-3-yloxy)-6-(trifluoromethyl) nicotinoyl)-2-(4-isopropylphenyl)-2,3,4,5,5a,6,8,9-octahydro-7H-1,2,5,7-tetraazabenzo[cd]azulen-7-yl)prop-2-en-1-one | 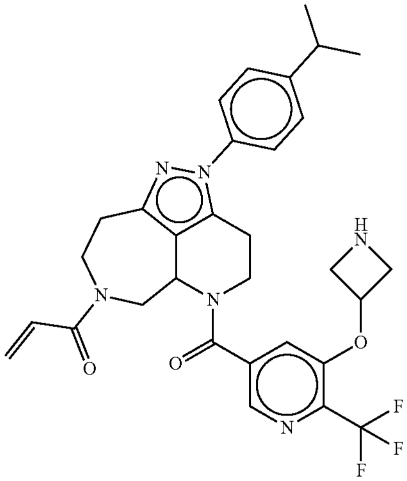 |
| 61 | B-9-2 | 2-(7-acryloyl-2-(4-isopropylphenyl)-3,4,5,5a,6,7,8,9-octahydro-2H-1,2,5,7-tetraazabenzo[cd]azulene-5-carbonyl)-5-bromobenzamide | 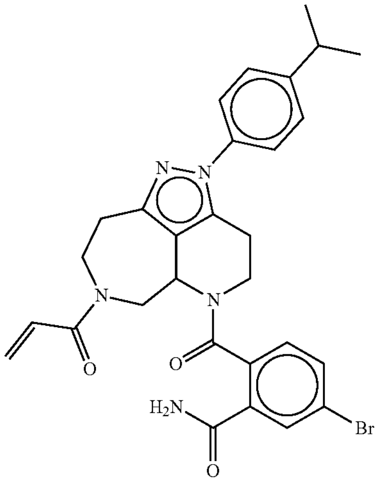 |

TABLE 1-continued

| Compound No | Example No. | Name | Structure |
|---|---|---|---|
| 62 | C-6-9 | 1-(5-(6-bromo-5-(trifluoromethoxy) nicotinoyl)-2-(4-cyclobutyl-2-hydroxyphenyl)-2,3,4,5,5a,6,8,9-octahydro-7H-1,2,5,7-tetraazabenzo[cd]azulen-7-yl)prop-2-en-1-one | 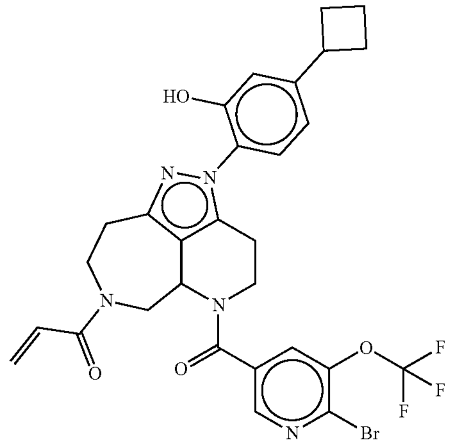 |
| 63 | L-10 | 1-(2-(4-cyclopropyl-3-fluoro-2-methoxyphenyl)-5-(5-hydroxy-6-(trifluoromethyl) nicotinoyl)-2,3,4,5,5a,6,8,9-octahydro-7H-1,2,5,7-tetraazabenzo[cd]azulen-7-yl)prop-2-en-1-one | 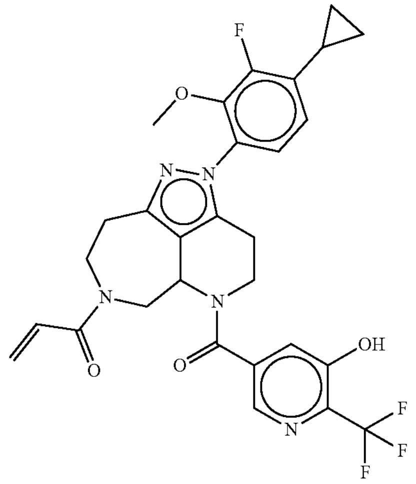 |
| 64 | L-1-10 | 1-(2-(3-fluoro-2-hydroxy-4-isopropylphenyl)-5-(5-hydroxy-6-(trifluoromethyl) nicotinoyl)-2,3,4,5,5a,6,8,9-octahydro-7H-1,2,5,7-tetraazabenzo[cd]azulen-7-yl)prop-2-en-1-one | 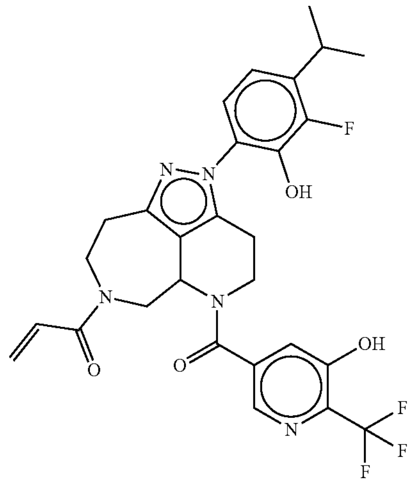 |

TABLE 1-continued

| Compound No | Example No. | Name | Structure |
|---|---|---|---|
| 65 | B-9-4 | 1-(5-(7-bromo-2,3-dihydrobenzofuran-4-carbonyl)-2-(4-isopropylphenyl)-2,3,4,5,5a,6,8,9-octahydro-7H-1,2,5,7-tetraazabenzo[cd]azulen-7-yl)prop-2-en-1-one | 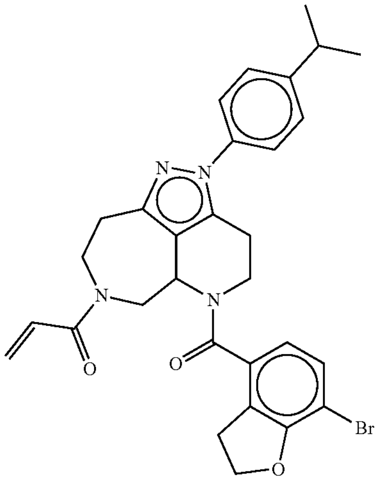 |
| 66 | D-4 | 1-(2-(4-cyclobutyl-3-fluorophenyl)-5-(5-hydroxy-6-(trifluoromethyl) nicotinoyl)-2,3,4,5,5a,6,8,9-octahydro-7H-1,2,5,7-tetraazabenzo[cd]azulen-7-yl)prop-2-en-1-one | 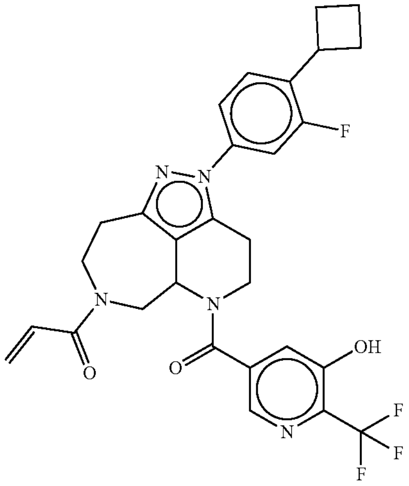 |
| 67 | A-4-1 | 1-(5-(2-amino-6-(trifluoromethyl) nicotinoyl)-2-(4-cyclopropylphenyl)-2,3,4,5,5a,6,8,9-octahydro-7H-1,2,5,7-tetraazabenzo[cd]azulen-7-yl)prop-2-en-1-one | 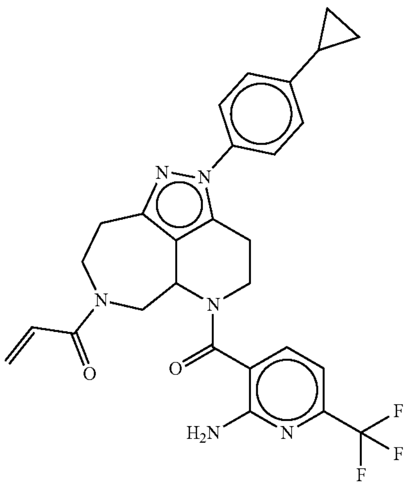 |

TABLE 1-continued

| Compound No | Example No. | Name | Structure |
|---|---|---|---|
| 68 | A-4-12 | 4-(7-acryloyl-2-(4-cyclopropylphenyl)-3,4,5,5a,6,7,8,9-octahydro-2H-1,2,5,7-tetraazabenzo[cd]azulene-5-carbonyl)-1-(2,2,2-trifluoroethyl)pyridin-2(1H)-one | 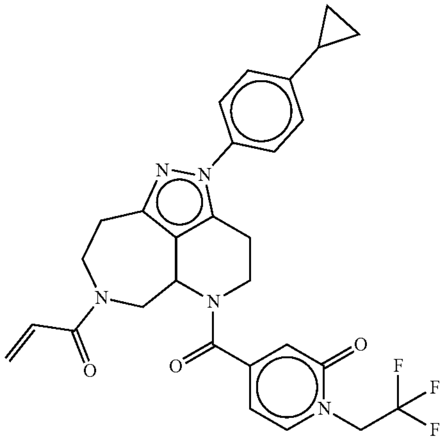 |
| 69 | A-4-3 | 1-(2-(4-cyclopropylphenyl)-5-(6-(difluoromethoxy)nicotinoyl)-2,3,4,5,5a,6,8,9-octahydro-7H-1,2,5,7-tetraazabenzo[cd]azulen-7-yl)prop-2-en-1-one | 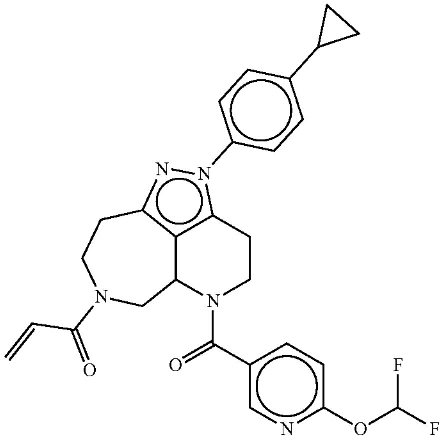 |
| 70 | A-4-6 | 5-(7-acryloyl-2-(4-cyclopropylphenyl)-3,4,5,5a,6,7,8,9-octahydro-2H-1,2,5,7-tetraazabenzo[cd]azulene-5-carbonyl)-1-methyl-1,3-dihydro-2H-benzo[d]imidazol-2-one | 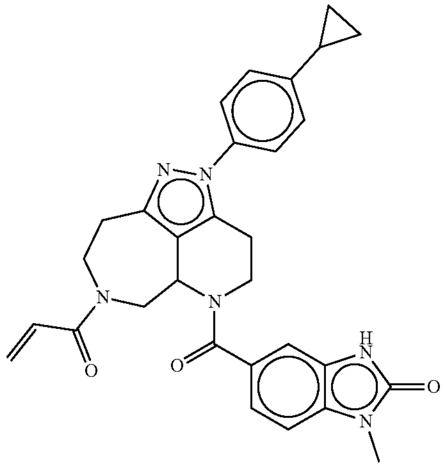 |

TABLE 1-continued

| Compound No | Example No. | Name | Structure |
|---|---|---|---|
| 71 | L-4 | 1-(2-(2-amino-4-cyclobutyl-3-fluorophenyl)-5-(5-hydroxy-6-(trifluoromethyl) nicotinoyl)-2,3,4,5,5a,6,8,9-octahydro-7H-1,2,5,7-tetraazabenzo[cd]azulen-7-yl)prop-2-en-1-one | 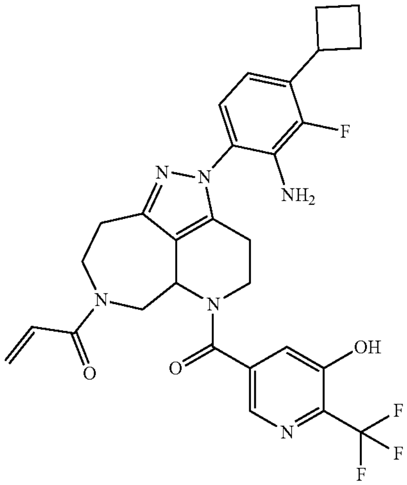 [SMILES: C=CC(=O)N1CCc2nn(-c3ccc(C4CCC4)c(F)c3N)c3c2C(C1)N(C(=O)c1cnc(C(F)(F)F)c(O)c1)CC3] |
| 72 | L-11-2 | 1-(2-(4-cyclobutyl-2-hydroxyphenyl)-5-(5-hydroxy-6-(trifluoromethyl) nicotinoyl)-9-methoxy-2,3,4,5,5a,6,8,9-octahydro-7H-1,2,5,7-tetraazabenzo[cd]azulen-7-yl)prop-2-en-1-one | 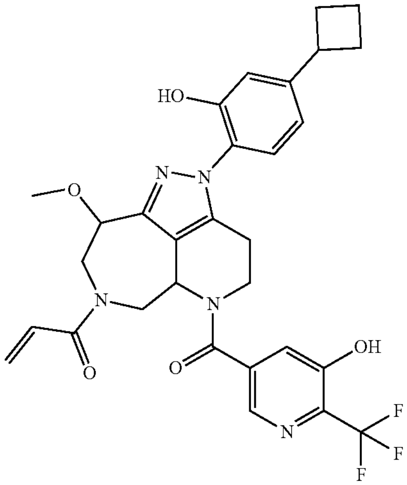 [SMILES: C=CC(=O)N1CC(OC)c2nn(-c3ccc(C4CCC4)cc3O)c3c2C(C1)N(C(=O)c1cnc(C(F)(F)F)c(O)c1)CC3] |
| 73 | | 1-(5-(4-bromo-1-(2-methoxyethyl)-1H-benzo[d]imidazole-7-carbonyl)-2-(4-isopropylphenyl)-2,3,4,5,5a,6,8,9-octahydro-7H-1,2,5,7-tetraazabenzo[cd]azulen-7-yl)prop-2-en-1-one | 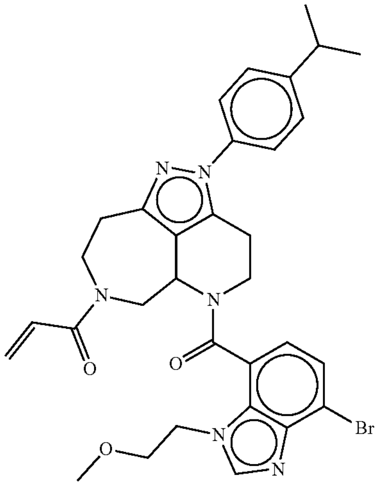 |

TABLE 1-continued

| Compound No | Example No. | Name | Structure |
| --- | --- | --- | --- |
| 74 | C-11-9 | 1-(2-(4-cyclobutyl-2-hydroxyphenyl)-5-(6-(difluoromethoxy) nicotinoyl)-2,3,4,5,5a,6,8,9-octahydro-7H-1,2,5,7-tetraazabenzo[cd]azulen-7-yl)prop-2-en-1-one | 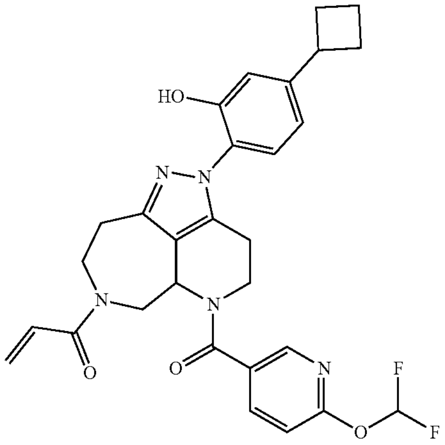 [SMILES: C=CC(=O)N1CCc2nn(-c3ccc(C4CCC4)cc3O)c3c2C(C1)N(C(=O)c1ccc(OC(F)F)nc1)CC3] |
| 75 | C-16 | 1-(5-(7-bromo-2-(hydroxymethyl)-1H-benzo[d]imidazole-4-carbonyl)-2-(4-cyclobutyl-2-hydroxyphenyl)-2,3,4,5,5a,6,8,9-octahydro-7H-1,2,5,7-tetraazabenzo[cd]azulen-7-yl)prop-2-en-1-one | 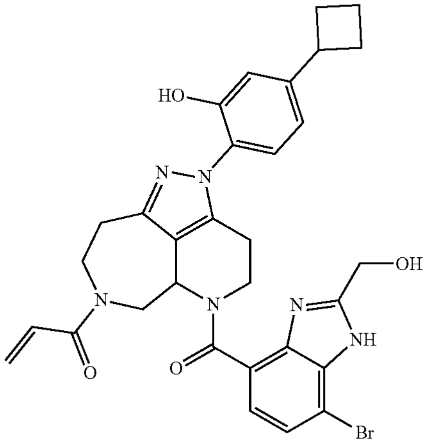 [SMILES: C=CC(=O)N1CCc2nn(-c3ccc(C4CCC4)cc3O)c3c2C(C1)N(C(=O)c1ccc(Br)c2[nH]c(CO)nc12)CC3] |
| 76 | C-11-8 | 1-(5-(2-amino-6-(trifluoromethyl) nicotinoyl)-2-(4-cyclobutyl-2-hydroxyphenyl)-2,3,4,5,5a,6,8,9-octahydro-7H-1,2,5,7-tetraazabenzo[cd]azulen-7-yl)prop-2-en-1-one | 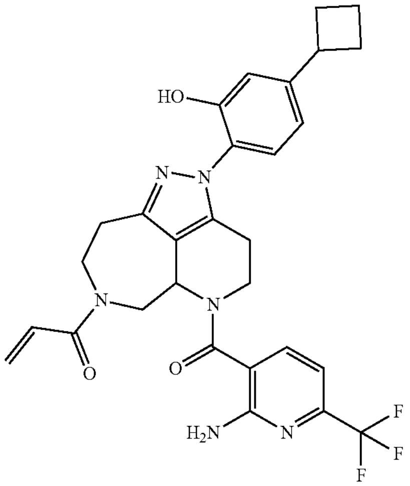 [SMILES: C=CC(=O)N1CCc2nn(-c3ccc(C4CCC4)cc3O)c3c2C(C1)N(C(=O)c1ccc(C(F)(F)F)nc1N)CC3] |

TABLE 1-continued

| Compound No | Example No. | Name | Structure |
| --- | --- | --- | --- |
| 78 | | 1-(2-(4-cyclobutyl-2-hydroxyphenyl)-5-(7-(trifluoromethoxy)-1H-benzo[d]imidazole-4-carbonyl)-2,3,4,5,5a,6,8,9-octahydro-7H-1,2,5,7-tetraazabenzo[cd]azulen-7-yl)prop-2-en-1-one | 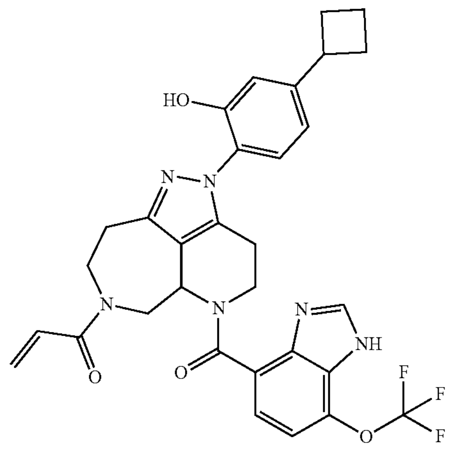 [SMILES: C=CC(=O)N1CCc2nn(-c3ccc(C4CCC4)cc3O)c3c2C(C1)N(C(=O)c1ccc(OC(F)(F)F)c2[nH]cnc12)CC3] |
| 79 | | 1-(2-(4-cyclobutyl-2-hydroxyphenyl)-5-(5-hydroxy-6-(trifluoromethyl) nicotinoyl)-9-methyl-2,3,4,5,5a,6,8,9-octahydro-7H-1,2,5,7-tetraazabenzo[cd]azulen-7-yl)prop-2-en-1-one | 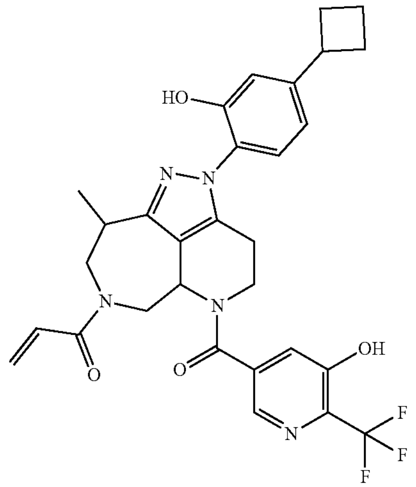 [SMILES: C=CC(=O)N1CC(C)c2nn(-c3ccc(C4CCC4)cc3O)c3c2C(C1)N(C(=O)c1cnc(C(F)(F)F)c(O)c1)CC3] |
| 81 | | 1-(5-(5-hydroxy-6-(trifluoromethyl) nicotinoyl)-2-(4-isopropylphenyl)-6-methyl-2,3,4,5,5a,6,8,9-octahydro-7H-1,2,5,7-tetraazabenzo[cd]azulen-7-yl)prop-2-en-1-one | 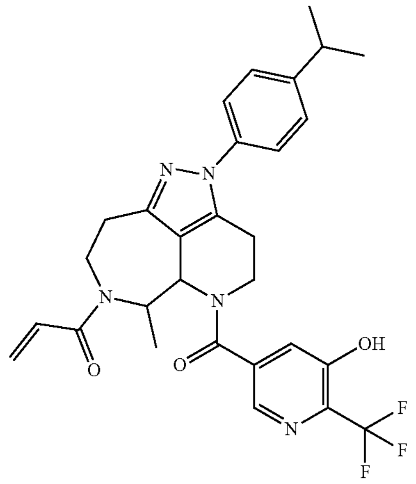 [SMILES: C=CC(=O)N1CCc2nn(-c3ccc(C(C)C)cc3)c3c2C(C1C)N(C(=O)c1cnc(C(F)(F)F)c(O)c1)CC3] |

TABLE 1-continued

| Compound No | Example No. | Name | Structure |
|---|---|---|---|
| 82 | | 1-(5-(4-bromo-1-((oxetan-2-yl)methyl)-1H-benzo[d]imidazole-7-carbonyl)-2-(4-isopropylphenyl)-2,3,4,5,5a,6,8,9-octahydro-7H-1,2,5,7-tetraazabenzo[cd]azulen-7-yl)prop-2-en-1-one | 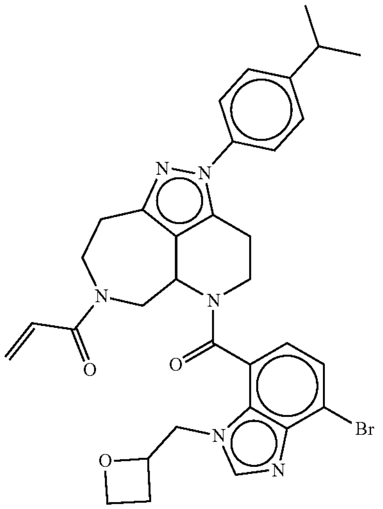 |
| 83 | | 1-(5-(4-bromo-1-((oxetan-2-yl)methyl)-1H-benzo[d]imidazole-7-carbonyl)-2-(4-isopropylphenyl)-2,3,4,5,5a,6,8,9-octahydro-7H-1,2,5,7-tetraazabenzo[cd]azulen-7-yl)prop-2-en-1-one | 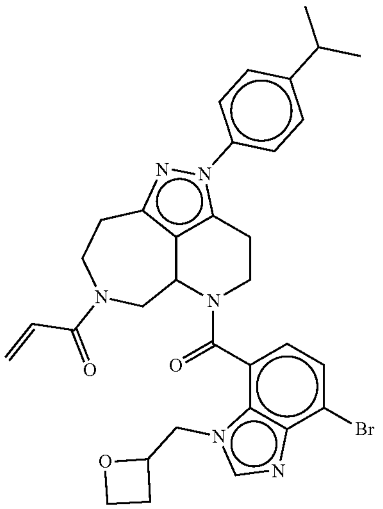 |
| 84 | D-3 | 1-(2-(4-(bicyclo[1.1.1]pentan-1-yl)-3-fluorophenyl)-5-(7-bromo-1H-benzo[d]imidazole-4-carbonyl)-2,3,4,5,5a,6,8,9-octahydro-7H-1,2,5,7-tetraazabenzo[cd]azulen-7-yl)prop-2-en-1-one | 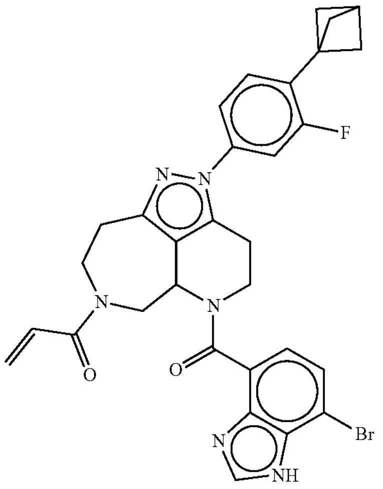 |

TABLE 1-continued

| Compound No | Example No. | Name | Structure |
|---|---|---|---|
| 86 | F-5 | 1-(2-(4-cyclobutylphenyl)-5-(5-hydroxy-6-(trifluoromethyl)nicotinoyl)-4,5,5a,6,8,9-hexahydro-1,2a,5,7-tetraazabenzo[cd]azulen-7(3H)-yl)prop-2-en-1-one | 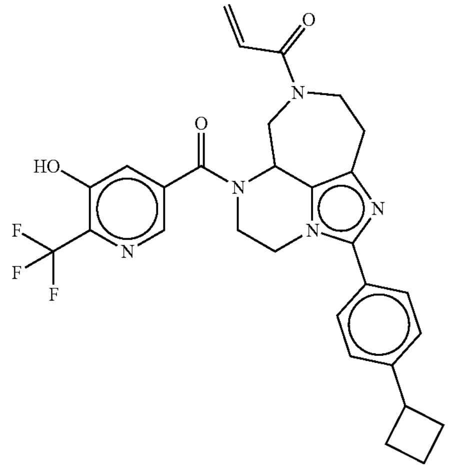 |
| 87 | C-6-1 | 1-(5-(7-bromo-1H-indazole-4-carbonyl)-2-(4-cyclobutyl-2-hydroxyphenyl)-2,3,4,5,5a,6,8,9-octahydro-7H-1,2,5,7-tetraazabenzo[cd]azulen-7-yl)prop-2-en-1-one | 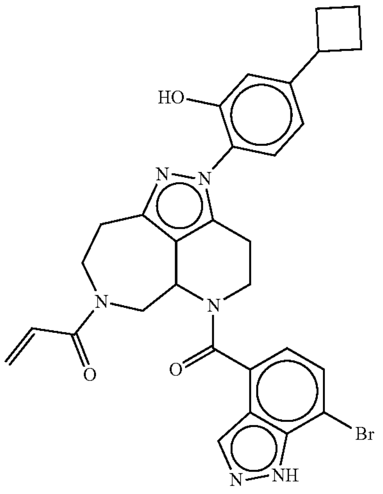 |
| 88 | C-31 | 1-(5-(7-bromo-2-(difluoromethoxy)-1H-benzo[d]imidazole-4-carbonyl)-2-(4-cyclobutyl-2-hydroxyphenyl)-2,3,4,5,5a,6,8,9-octahydro-7H-1,2,5,7-tetraazabenzo[cd]azulen-7-yl)prop-2-en-1-one | 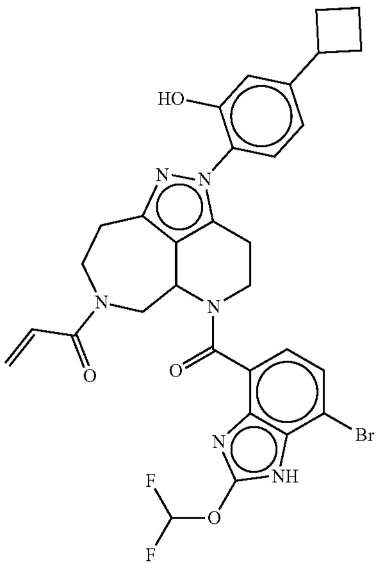 |

TABLE 1-continued

| Compound No | Example No. | Name | Structure |
|---|---|---|---|
| 89 | C-32 | 1-(2-(4-cyclobutyl-2-hydroxyphenyl)-5-(5-(methylthio)-6-(trifluoromethyl) nicotinoyl)-2,3,4,5,5a,6,8,9-octahydro-7H-1,2,5,7-tetraazabenzo[cd]azulen-7-yl)prop-2-en-1-one | 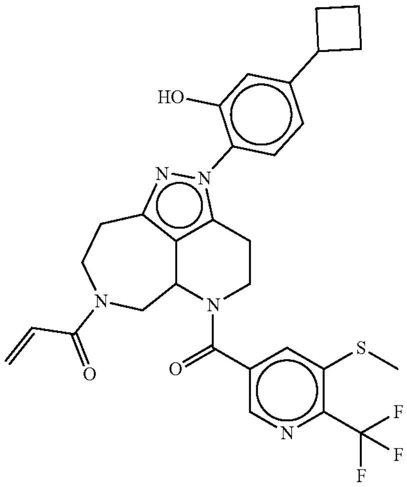 |
| 90 | C-6-2 | 1-(5-(4-bromo-2-(difluoromethyl)-1H-benzo[d]imidazole-7-carbonyl)-2-(4-cyclobutyl-2-hydroxyphenyl)-2,3,4,5,5a,6,8,9-octahydro-7H-1,2,5,7-tetraazabenzo[cd]azulen-7-yl)prop-2-en-1-one | 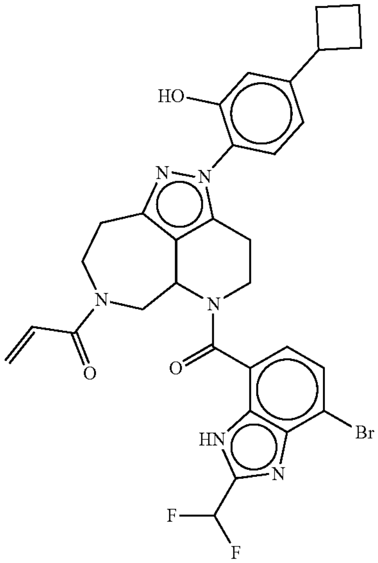 |
| 91 | L-9-2 | 1-(2-(4-cyclobutyl-3-hydroxyphenyl)-5-(5-hydroxy-6-(trifluoromethyl) nicotinoyl)-2,3,4,5,5a,6,8,9-octahydro-7H-1,2,5,7-tetraazabenzo[cd]azulen-7-yl)prop-2-en-1-one | 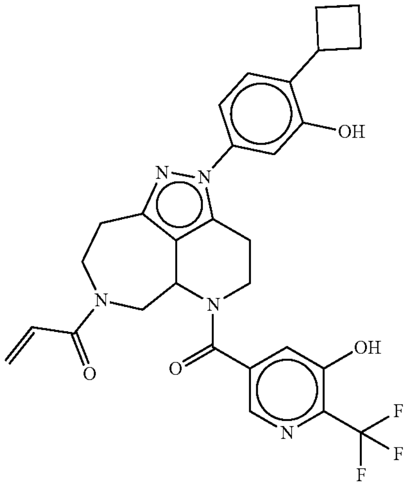 |

TABLE 1-continued

| Compound No | Example No. | Name | Structure |
|---|---|---|---|
| 92 | A-29 | 1-(2-(4-(bicyclo[1.1.1]pentan-1-yl)-2-hydroxyphenyl)-5-(5-hydroxy-6-(trifluoromethyl) nicotinoyl)-2,3,4,5,5a,6,8,9-octahydro-7H-1,2,5,7-tetraazabenzo[cd]azulen-7-yl)prop-2-en-1-one | 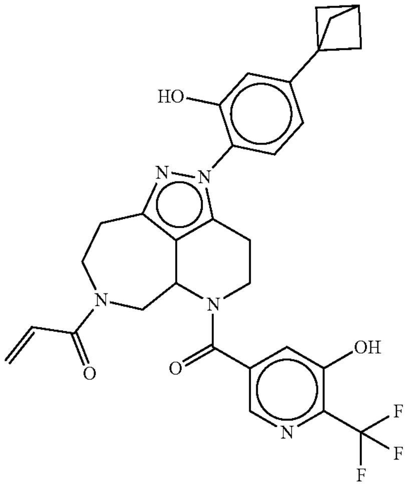 |
| 93 | C-6-3 | 1-(2-(4-cyclobutyl-2-hydroxyphenyl)-5-(6-(trifluoromethoxy) nicotinoyl)-2,3,4,5,5a,6,8,9-octahydro-7H-1,2,5,7-tetraazabenzo[cd]azulen-7-yl)prop-2-en-1-one | 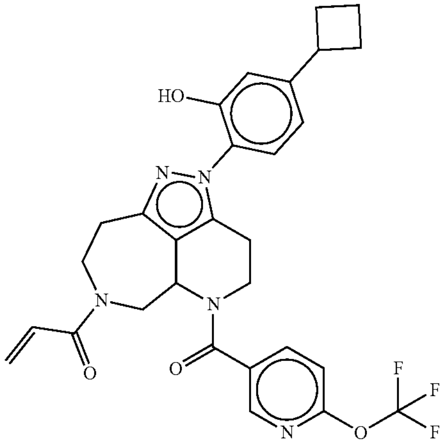 |
| 94 | C-6-4 | 1-(5-(6-bromo-5-(difluoromethoxy) nicotinoyl)-2-(4-cyclobutyl-2-hydroxyphenyl)-2,3,4,5,5a,6,8,9-octahydro-7H-1,2,5,7-tetraazabenzo[cd]azulen-7-yl)prop-2-en-1-one | 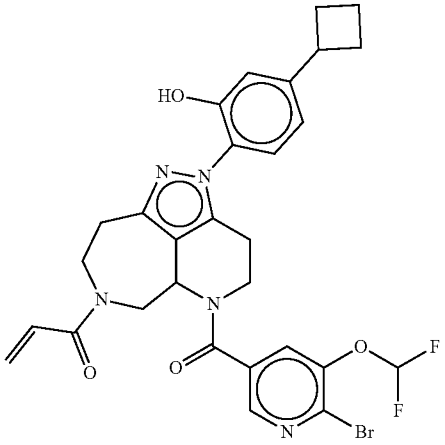 |

TABLE 1-continued

| Compound No | Example No. | Name | Structure |
|---|---|---|---|
| 95 | C-6-5 | 1-(5-(7-bromo-1H-imidazo[4,5-c]pyridine-4-carbonyl)-2-(4-cyclobutyl-2-hydroxyphenyl)-2,3,4,5,5a,6,8,9-octahydro-7H-1,2,5,7-tetraazabenzo[cd]azulen-7-yl)prop-2-en-1-one | 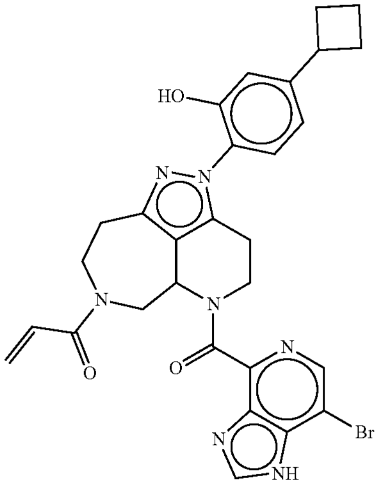 |
| 96 | C-6-6 | 1-(2-(4-cyclobutyl-2-hydroxyphenyl)-5-(6-(trifluoromethyl) nicotinoyl)-2,3,4,5,5a,6,8,9-octahydro-7H-1,2,5,7-tetraazabenzo[cd]azulen-7-yl)prop-2-en-1-one | 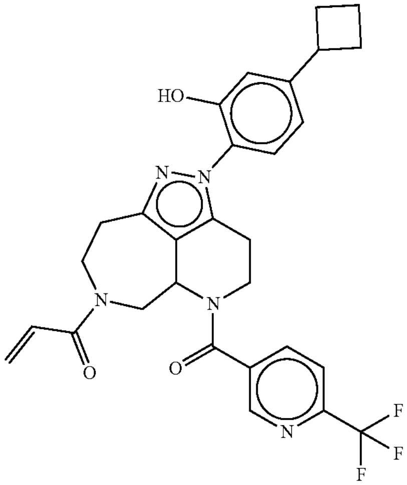 |
| 97 | C-6-7 | 1-(2-(4-cyclobutyl-2-hydroxyphenyl)-5-(7-(trifluoromethyl)-1H-indazole-4-carbonyl)-2,3,4,5,5a,6,8,9-octahydro-7H-1,2,5,7-tetraazabenzo[cd]azulen-7-yl)prop-2-en-1-one | 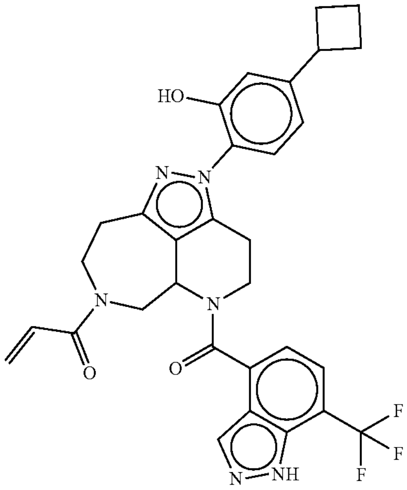 |

TABLE 1-continued

| Compound No | Example No. | Name | Structure |
| --- | --- | --- | --- |
| 98 | A-4-23 | 1-(5-(6-(1H-pyrazol-1-yl)nicotinoyl)-2-(4-cyclopropylphenyl)-2,3,4,5,5a,6,8,9-octahydro-7H-1,2,5,7-tetraazabenzo[cd]azulen-7-yl)prop-2-en-1-one | 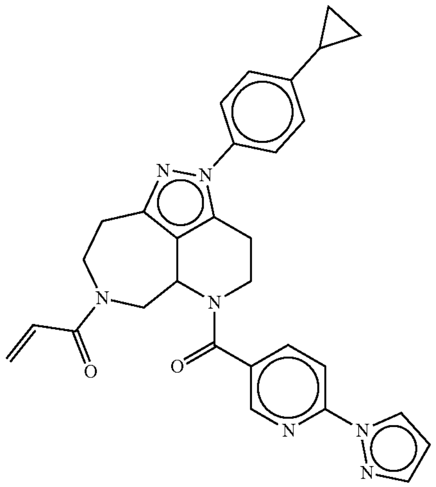 |
| 100 | L-1 | 1-(2-(4-cyclopropyl-3-fluoro-2-hydroxyphenyl)-5-(5-hydroxy-6-(trifluoromethyl) nicotinoyl)-2,3,4,5,5a,6,8,9-octahydro-7H-1,2,5,7-tetraazabenzo[cd]azulen-7-yl)prop-2-en-1-one | 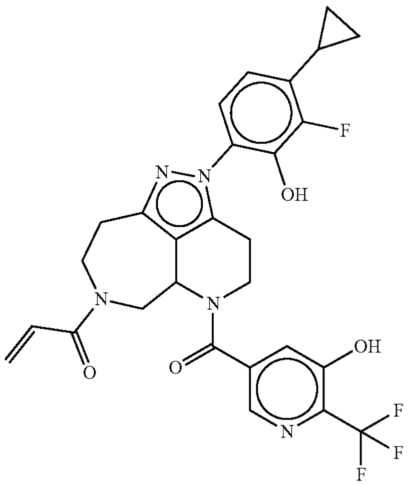 |
| 101 | L-1-9 | 1-(2-(4-(bicyclo[1.1.1]pentan-1-yl)-3-fluoro-2-hydroxyphenyl)-5-(5-hydroxy-6-(trifluoromethyl) nicotinoyl)-2,3,4,5,5a,6,8,9-octahydro-7H-1,2,5,7-tetraazabenzo[cd]azulen-7-yl)prop-2-en-1-one | 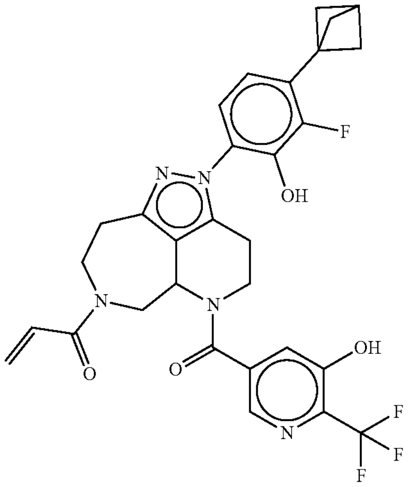 |

TABLE 1-continued

| Compound No | Example No. | Name | Structure |
|---|---|---|---|
| 102 | B-2-3 | 1-(5-(4-bromo-3-(2-hydroxypropan-2-yl)benzoyl)-2-(4-isopropylphenyl)-2,3,4,5,5a,6,8,9-octahydro-7H-1,2,5,7-tetraazabenzo[cd]azulen-7-yl)prop-2-en-1-one | 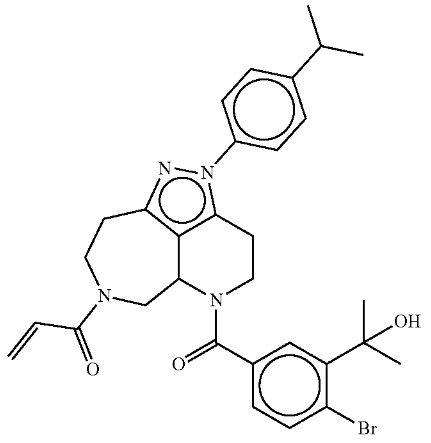 |
| 103 | K-19 | 1-(5-(7-bromo-1H-benzo[d]imidazole-4-carbonyl)-2-(4-cyclopropyl-2-methylphenyl)-2,3,4,5,5a,6,8,9-octahydro-7H-10-oxa-1,2,5,7-tetraazacycloocta[cd]inden-7-yl)prop-2-en-1-one | 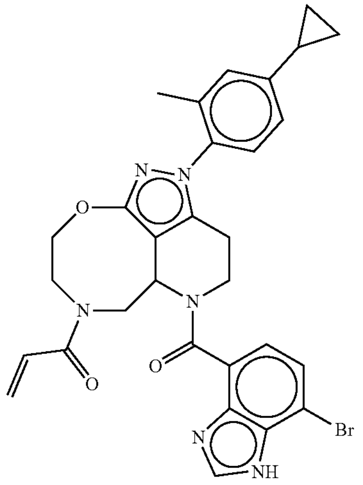 |
| 104 | B-14 | 1-(5-(4-bromo-3-((2,2,2-trifluoroethyl)amino)benzoyl)-2-(4-isopropylphenyl)-2,3,4,5,5a,6,8,9-octahydro-7H-1,2,5,7-tetraazabenzo[cd]azulen-7-yl)prop-2-en-1-one | 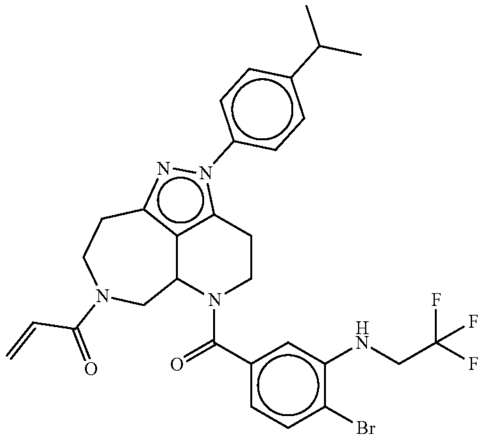 |

TABLE 1-continued

| Compound No | Example No. | Name | Structure |
|---|---|---|---|
| 105 | K-20 | 1-(5-(7-bromo-1H-benzo[d]imidazole-4-carbonyl)-2-(6-hydroxy-5-isopropylpyridin-2-yl)-2,3,4,5,5a,6,8,9-octahydro-7H-10-oxa-1,2,5,7-tetraazacycloocta[cd]inden-7-yl)prop-2-en-1-one | 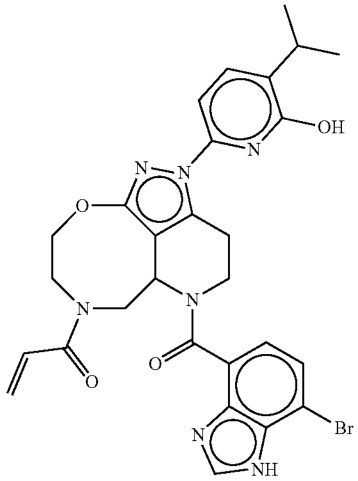 |
| 106 | B-2-4 | 1-(5-(4-bromo-3-(1H-pyrazol-3-yl)benzoyl)-2-(4-isopropylphenyl)-2,3,4,5,5a,6,8,9-octahydro-7H-1,2,5,7-tetraazabenzo[cd]azulen-7-yl)prop-2-en-1-one | 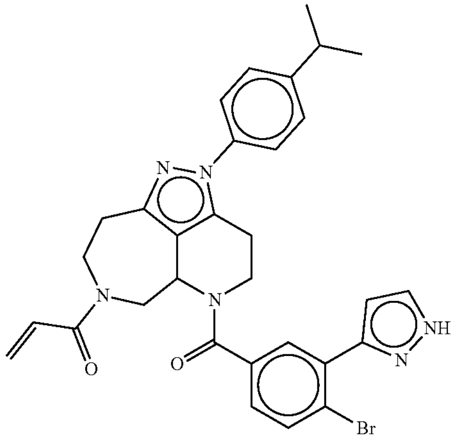 |
| 107 | C-6-8 | 1-(2-(4-cyclobutyl-2-hydroxyphenyl)-5-(4-(trifluoromethoxy)benzoyl)-2,3,4,5,5a,6,8,9-octahydro-7H-1,2,5,7-tetraazabenzo[cd]azulen-7-yl)prop-2-en-1-one | 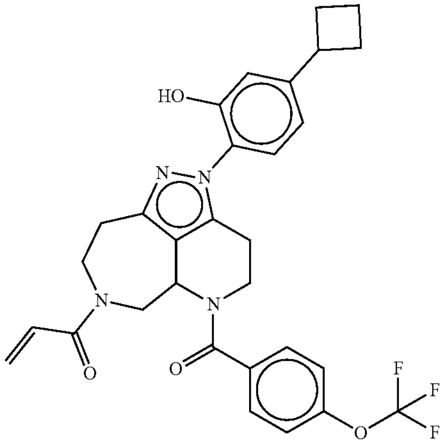 |

TABLE 1-continued

| Compound No | Example No. | Name | Structure |
|---|---|---|---|
| 108 | A-4-13 | 1-(5-(6-bromopyridazine-3-carbonyl)-2-(4-cyclopropylphenyl)-2,3,4,5,5a,6,8,9-octahydro-7H-1,2,5,7-tetraazabenzo[cd]azulen-7-yl)prop-2-en-1-one | 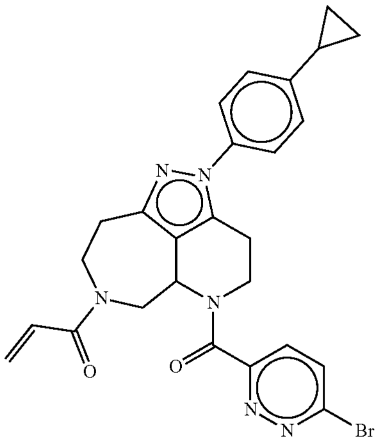 |
| 109 | A-4-2 | 1-(2-(4-cyclopropylphenyl)-5-(2-hydroxy-6-(trifluoromethyl) nicotinoyl)-2,3,4,5,5a,6,8,9-octahydro-7H-1,2,5,7-tetraazabenzo[cd]azulen-7-yl)prop-2-en-1-one | 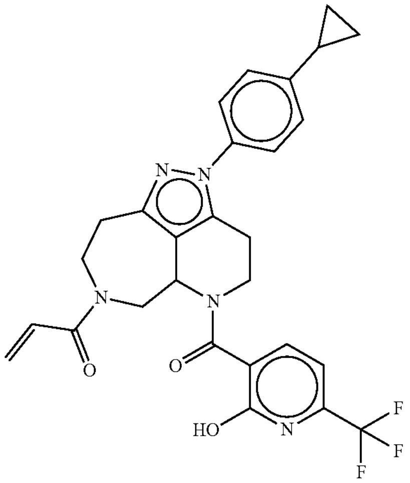 |
| 110 | A-4-10 | 1-(2-(4-cyclopropylphenyl)-5-(1,3-dimethyl-1H-pyrazolo[4,3-b]pyridine-6-carbonyl)-2,3,4,5,5a,6,8,9-octahydro-7H-1,2,5,7-tetraazabenzo[cd]azulen-7-yl)prop-2-en-1-one | 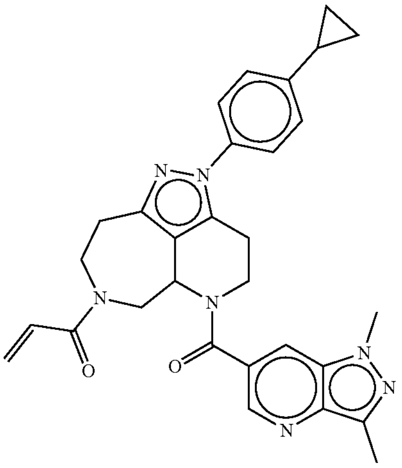 |

TABLE 1-continued

| Compound No | Example No. | Name | Structure |
|---|---|---|---|
| 111 | A-4-4 | 1-(2-(4-cyclopropylphenyl)-5-(1-methyl-3-(trifluoromethyl)-1H-pyrazolo[3,4-b]pyridine-5-carbonyl)-2,3,4,5,5a,6,8,9-octahydro-7H-1,2,5,7-tetraazabenzo[cd]azulen-7-yl)prop-2-en-1-one | 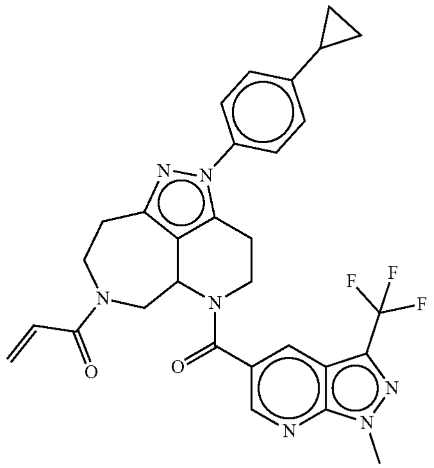 |
| 112 | A-4-9 | 5-(7-acryloyl-2-(4-cyclopropylphenyl)-3,4,5,5a,6,7,8,9-octahydro-2H-1,2,5,7-tetraazabenzo[cd]azulene-5-carbonyl)-2-(trifluoromethyl)nicotino nitrile | 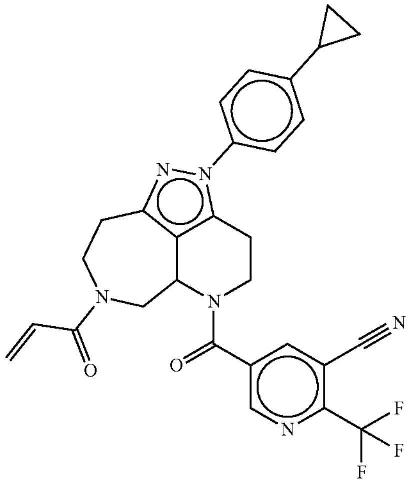 |
| 113 | A-4-17 | 1-(5-(6-bromo-4-methylnicotinoyl)-2-(4-cyclopropylphenyl)-2,3,4,5,5a,6,8,9-octahydro-7H-1,2,5,7-tetraazabenzo[cd]azulen-7-yl)prop-2-en-1-one | 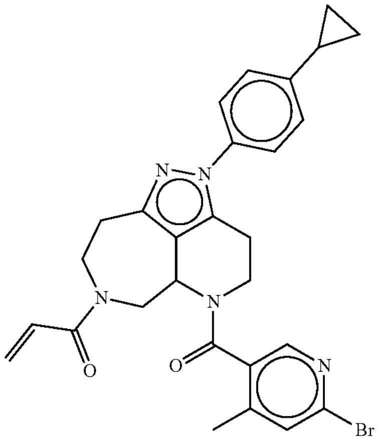 |

TABLE 1-continued

| Compound No | Example No. | Name | Structure |
|---|---|---|---|
| 114 | A-4-15 | 1-(5-(6-bromo-2-methylnicotinoyl)-2-(4-cyclopropylphenyl)-2,3,4,5,5a,6,8,9-octahydro-7H-1,2,5,7-tetraazabenzo[cd]azulen-7-yl)prop-2-en-1-one | 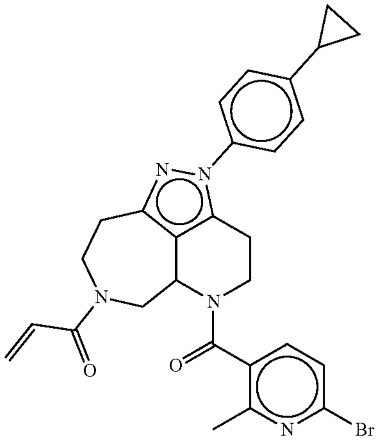 |
| 115 | A-4-14 | 1-(2-(4-cyclopropylphenyl)-5-(6-(trifluoromethyl) pyridazine-3-carbonyl)-2,3,4,5,5a,6,8,9-octahydro-7H-1,2,5,7-tetraazabenzo[cd]azulen-7-yl)prop-2-en-1-one | 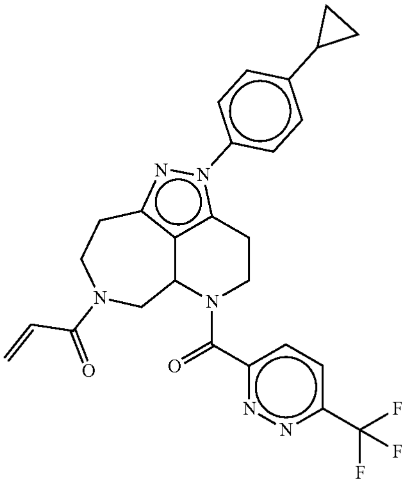 |
| 116 | A-4-5 | 1-(2-(4-cyclopropylphenyl)-5-(2-methyl-1,1-dioxido-3,4-dihydro-2H-pyrazolo[1,5-e][1,2,5]thiadiazine-7-carbonyl)-2,3,4,5,5a,6,8,9-octahydro-7H-1,2,5,7-tetraazabenzo[cd]azulen-7-yl)prop-2-en-1-one | 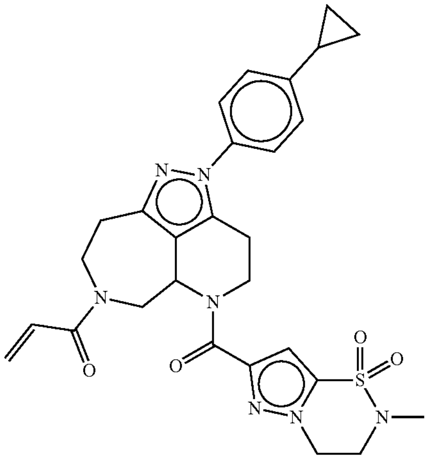 |

TABLE 1-continued

| Compound No | Example No. | Name | Structure |
|---|---|---|---|
| 117 | A-4-16 | 1-(5-(2-amino-6-bromonicotinoyl)-2-(4-cyclopropylphenyl)-2,3,4,5,5a,6,8,9-octahydro-7H-1,2,5,7-tetraazabenzo[cd]azulen-7-yl)prop-2-en-1-one | 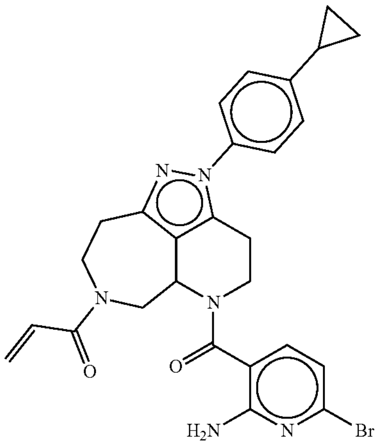 |
| 118 | A-4-19 | 1-(2-(4-cyclopropylphenyl)-5-(6-(2,2,2-trifluoroethoxy)nicotinoyl)-2,3,4,5,5a,6,8,9-octahydro-7H-1,2,5,7-tetraazabenzo[cd]azulen-7-yl)prop-2-en-1-one | 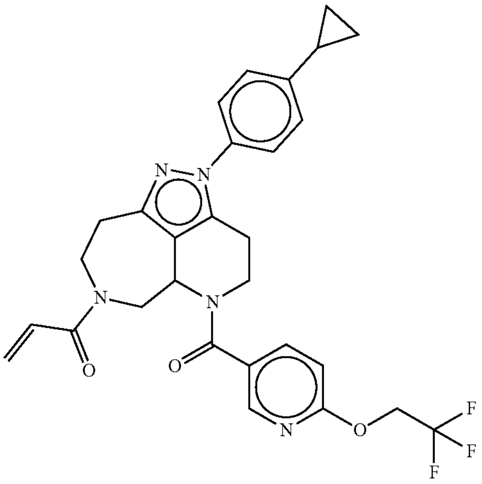 |
| 119 | A-4-22 | 1-(5-(7-acryloyl-2-(4-cyclopropylphenyl)-3,4,5,5a,6,7,8,9-octahydro-2H-1,2,5,7-tetraazabenzo[cd]azulene-5-carbonyl)pyridin-2-yl)cyclopropane-1-carbonitrile | 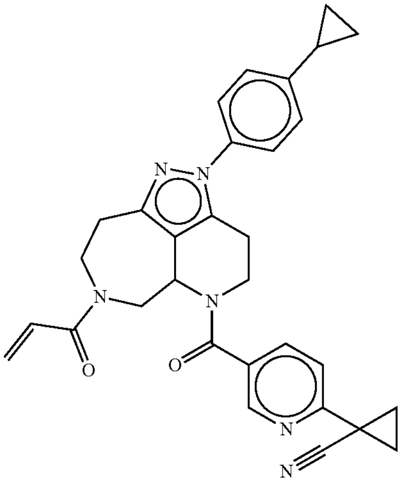 |

TABLE 1-continued

| Compound No | Example No. | Name | Structure |
|---|---|---|---|
| 120 | A-4-18 | 1-(2-(4-cyclopropylphenyl)-5-(5-hydroxy-6-nitronicotinoyl)-2,3,4,5,5a,6,8,9-octahydro-7H-1,2,5,7-tetraazabenzo[cd]azulen-7-yl)prop-2-en-1-one | 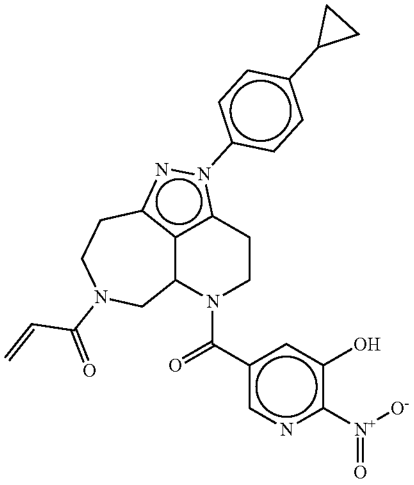 |
| 121 | A-4-11 | 1-(2-(4-cyclopropylphenyl)-5-(3-(trifluoromethyl)bicyclo[1.1.1]pentane-1-carbonyl)-2,3,4,5,5a,6,8,9-octahydro-7H-1,2,5,7-tetraazabenzo[cd]azulen-7-yl)prop-2-en-1-one | 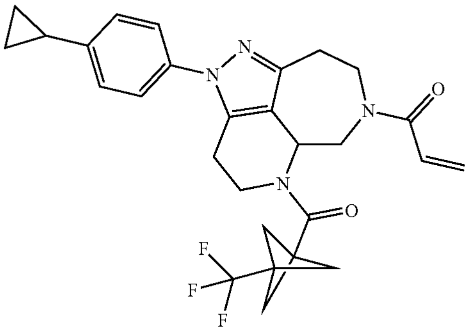 [SMILES: C=CC(=O)N1CCc2nn(-c3ccc(C4CC4)cc3)c3c2C(C1)N(C(=O)C12CC(C(F)(F)F)(C1)C2)CC3] |
| 122 | A-4-20 | 1-(2-(4-cyclopropylphenyl)-5-(6-isopropoxynicotinoyl)-2,3,4,5,5a,6,8,9-octahydro-7H-1,2,5,7-tetraazabenzo[cd]azulen-7-yl)prop-2-en-1-one | 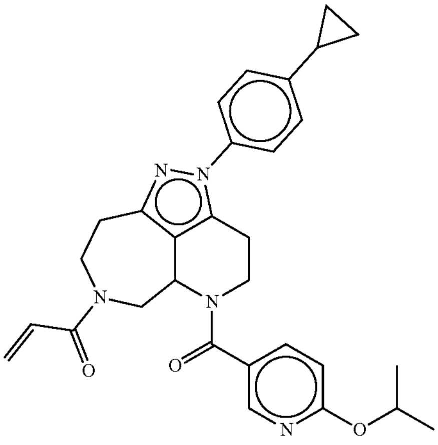 |

TABLE 1-continued

| Compound No | Example No. | Name | Structure |
|---|---|---|---|
| 123 | A-4-21 | 5-(7-acryloyl-2-(4-cyclopropylphenyl)-3,4,5,5a,6,7,8,9-octahydro-2H-1,2,5,7-tetraazabenzo[cd]azulene-5-carbonyl)picolinonitrile | 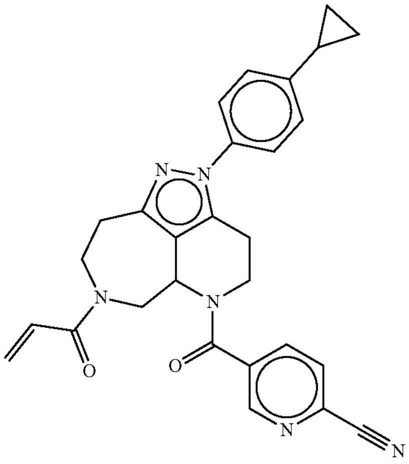 |
| 124 | A-4-7 | 1-(2-(4-cyclopropylphenyl)-5-(2-(trifluoromethyl)-3H-imidazo[4,5-b]pyridine-6-carbonyl)-2,3,4,5,5a,6,8,9-octahydro-7H-1,2,5,7-tetraazabenzo[cd]azulen-7-yl)prop-2-en-1-one | 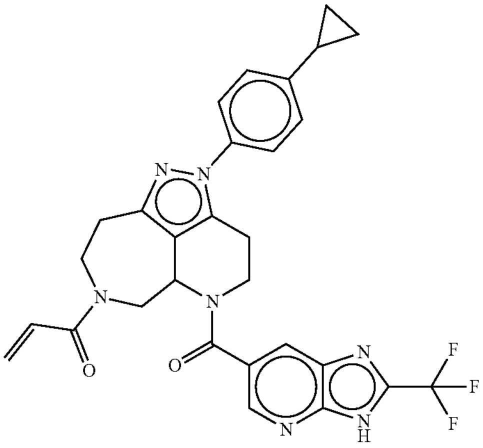 |
| 125 | A-4-8 | 4-(7-acryloyl-2-(4-cyclopropylphenyl)-3,4,5,5a,6,7,8,9-octahydro-2H-1,2,5,7-tetraazabenzo[cd]azulene-5-carbonyl)thiophene-2-sulfonamide | 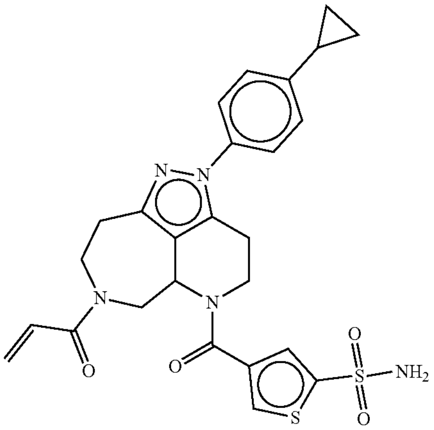 |

TABLE 1-continued

| Compound No | Example No. | Name | Structure |
|---|---|---|---|
| 126 | A-4-24 | 1-(2-(4-cyclopropylphenyl)-5-(6-(difluoromethyl) nicotinoyl)-2,3,4,5,5a,6,8,9-octahydro-7H-1,2,5,7-tetraazabenzo[cd]azulen-7-yl)prop-2-en-1-one | 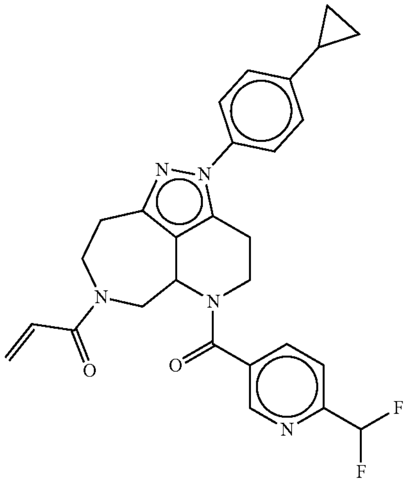 |
| 128 | A-4-25 | 1-(5-(4-amino-6-(trifluoromethyl) nicotinoyl)-2-(4-cyclopropylphenyl)-2,3,4,5,5a,6,8,9-octahydro-7H-1,2,5,7-tetraazabenzo[cd]azulen-7-yl)prop-2-en-1-one | 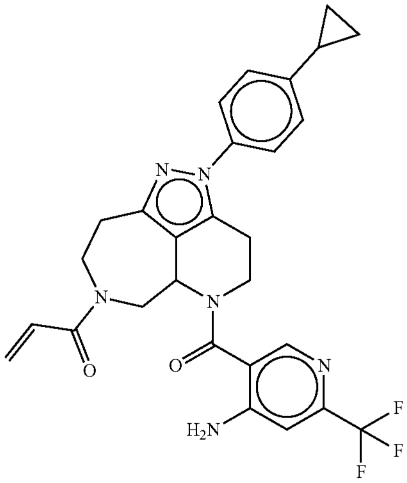 |
| 129 | C-22 | 1-(5-(4-amino-6-(trifluoromethyl) nicotinoyl)-2-(4-cyclobutylphenyl)-9-cyclopropoxy-2,3,4,5,5a,6,8,9-octahydro-7H-1,2,5,7-tetraazabenzo[cd]azulen-7-yl)prop-2-en-1-one | 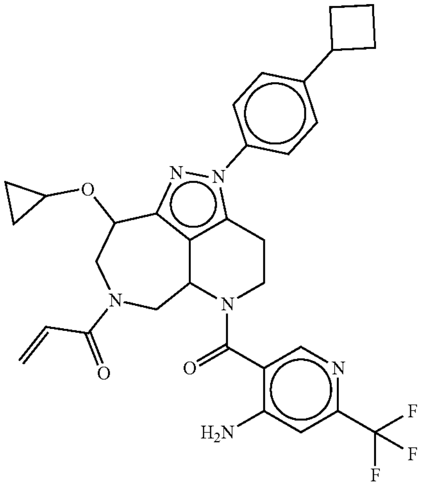 |

TABLE 1-continued

| Compound No | Example No. | Name | Structure |
|---|---|---|---|
| 130 | E-11 | 1-(5-(4-amino-6-(trifluoromethyl)nicotinoyl)-2-(4-cyclobutyl-2-hydroxyphenyl)-9-methyl-2,3,4,5,5a,6,8,9-octahydro-7H-1,2,5,7-tetraazabenzo[cd]azulen-7-yl)prop-2-en-1-one | 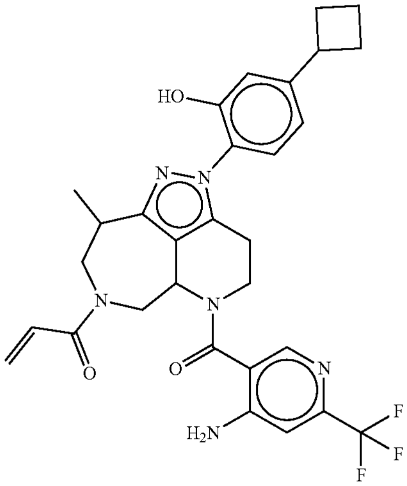 |
| 131 | A-34 | 1-(5-(3-amino-7-bromo-1H-indazole-4-carbonyl)-2-(4-cyclopropylphenyl)-2,3,4,5,5a,6,8,9-octahydro-7H-1,2,5,7-tetraazabenzo[cd]azulen-7-yl)prop-2-en-1-one | 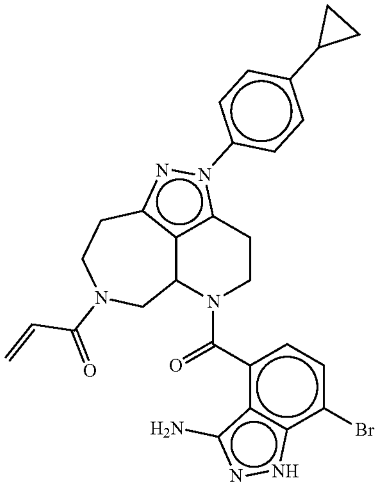 |
| 132 | C-11 | 1-(5-(4-amino-6-bromonicotinoyl)-2-(4-cyclobutyl-2-hydroxyphenyl)-2,3,4,5,5a,6,8,9-octahydro-7H-1,2,5,7-tetraazabenzo[cd]azulen-7-yl)prop-2-en-1-one | 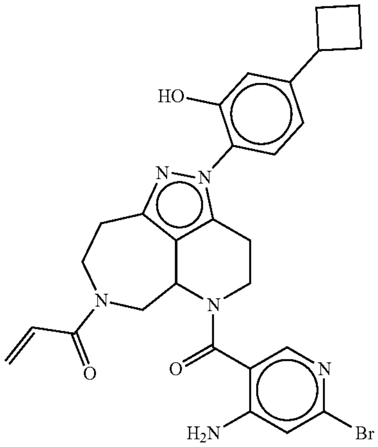 |

TABLE 1-continued

| Compound No | Example No. | Name | Structure |
|---|---|---|---|
| 133 | A-7-1 | 1-(5-(4-amino-6-(trifluoromethyl) nicotinoyl)-2-(4-(bicyclo[1.1.1]pentan-1-yl)phenyl)-2,3,4,5,5a,6,8,9-octahydro-7H-1,2,5,7-tetraazabenzo[cd]azulen-7-yl)prop-2-en-1-one | 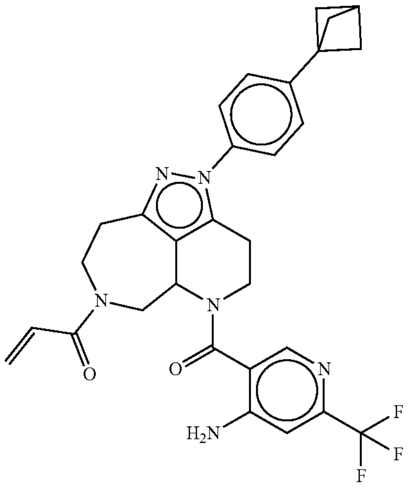 |
| 134 | C-11-1 | 1-(5-(4-amino-5-fluoro-6-(trifluoromethyl)nicotinoyl)-2-(4-cyclobutyl-2-hydroxyphenyl)-2,3,4,5,5a,6,8,9-octahydro-7H-1,2,5,7-tetraazabenzo[cd]azulen-7-yl)prop-2-en-1-one | 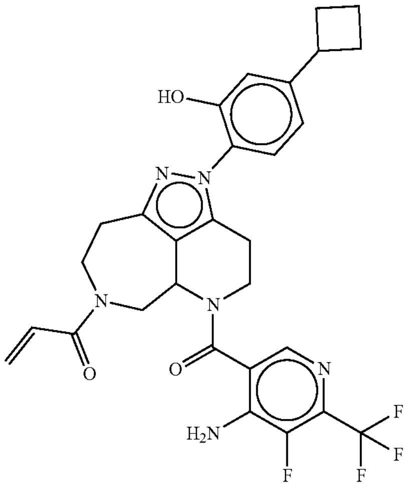 |
| 135 | E-10 | 1-(5-(4-amino-6-(trifluoromethyl) nicotinoyl)-2-(4-cyclobutyl-2-hydroxyphenyl)-9-methyl-2,3,4,5,5a,6,8,9-octahydro-7H-1,2,5,7-tetraazabenzo[cd]azulen-7-yl)prop-2-en-1-one | 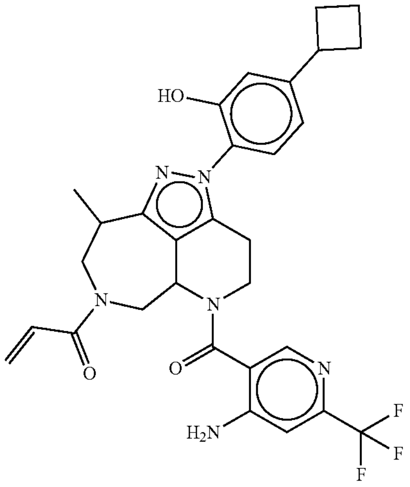 |

TABLE 1-continued

| Compound No | Example No. | Name | Structure |
|---|---|---|---|
| 136 | L-9 | 1-(2-(2-amino-6-(trifluoromethyl)pyridin-3-yl)-5-(7-bromo-2-(difluoromethyl)-1H-benzo[d]imidazole-4-carbonyl)-2,3,4,5,5a,6,8,9-octahydro-7H-1,2,5,7-tetraazabenzo[cd]azulen-7-yl)prop-2-en-1-one | 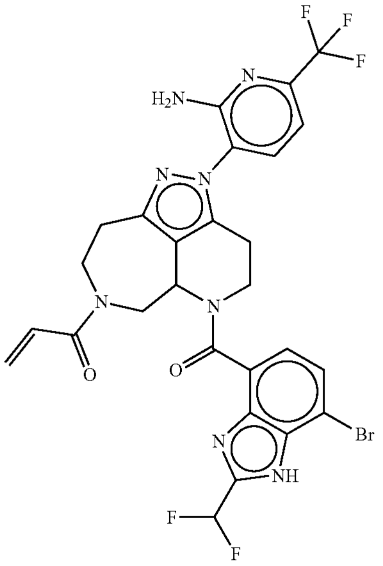 |
| 137 | C-11-10 | 1-(5-(4-bromo-3H-imidazo[4,5-c]pyridine-7-carbonyl)-2-(4-cyclobutyl-2-hydroxyphenyl)-2,3,4,5,5a,6,8,9-octahydro-7H-1,2,5,7-tetraazabenzo[cd]azulen-7-yl)prop-2-en-1-one | 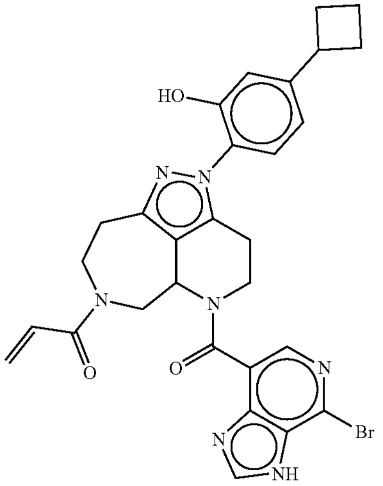 |
| 138 | C-11-2 | 1-(5-(4-amino-6-(trifluoromethyl)nicotinoyl)-2-(4-cyclobutyl-2-hydroxyphenyl)-2,3,4,5,5a,6,8,9-octahydro-7H-1,2,5,7-tetraazabenzo[cd]azulen-7-yl)prop-2-en-1-one | 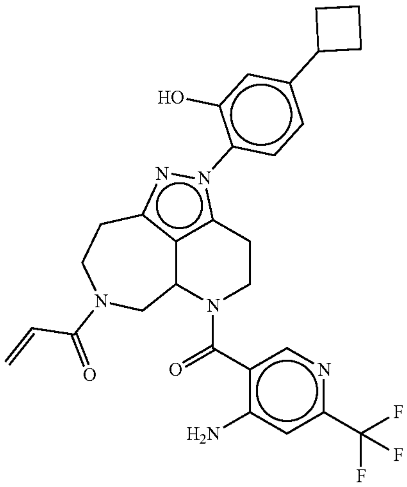 |

TABLE 1-continued

| Compound No | Example No. | Name | Structure |
|---|---|---|---|
| 139 | L-1-7 | 1-(5-(4-amino-6-(trifluoromethyl) nicotinoyl)-2-(4-cyclobutyl-3-fluoro-2-hydroxyphenyl)-2,3,4,5,5a,6,8,9-octahydro-7H-1,2,5,7-tetraazabenzo[cd]azulen-7-yl)prop-2-en-1-one | 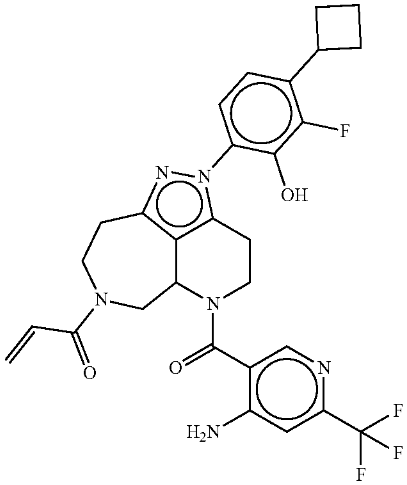 |
| 140 | C-11-3 | 1-(5-(6-chloro-5-hydroxynicotinoyl)-2-(4-cyclobutyl-2-hydroxyphenyl)-2,3,4,5,5a,6,8,9-octahydro-7H-1,2,5,7-tetraazabenzo[cd]azulen-7-yl)prop-2-en-1-one | 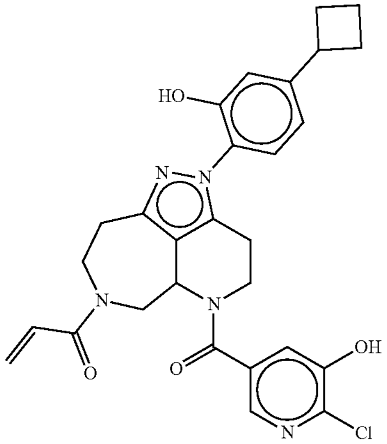 |
| 141 | L-1-8 | 1-(2-(4-cyclobutyl-3-fluoro-2-hydroxyphenyl)-5-(5-hydroxy-6-(trifluoromethyl) nicotinoyl)-2,3,4,5,5a,6,8,9-octahydro-7H-1,2,5,7-tetraazabenzo[cd]azulen-7-yl)prop-2-en-1-one | 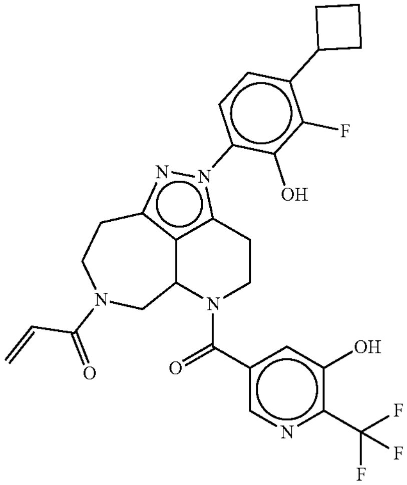 |

TABLE 1-continued

| Compound No | Example No. | Name | Structure |
|---|---|---|---|
| 142 | C-11-4 | 1-(5-(3-amino-5-(trifluoromethyl)picolinoyl)-2-(4-cyclobutyl-2-hydroxyphenyl)-2,3,4,5,5a,6,8,9-octahydro-7H-1,2,5,7-tetraazabenzo[cd]azulen-7-yl)prop-2-en-1-one | 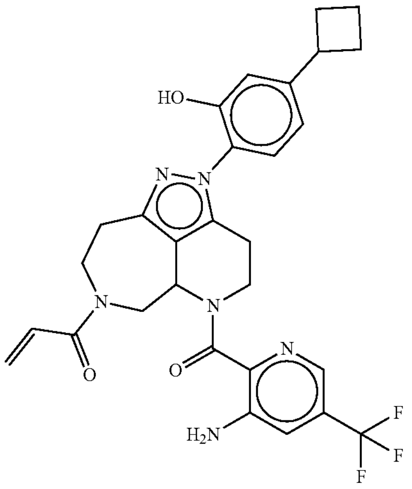 |
| 143 | A-25 | 1-(5-(7-bromo-2-(difluoromethyl)-1H-benzo[d]imidazole-4-carbonyl)-2-(4-cyclopropyl-2-hydroxyphenyl)-2,3,4,5,5a,6,8,9-octahydro-7H-1,2,5,7-tetraazabenzo[cd]azulen-7-yl)prop-2-en-1-one | 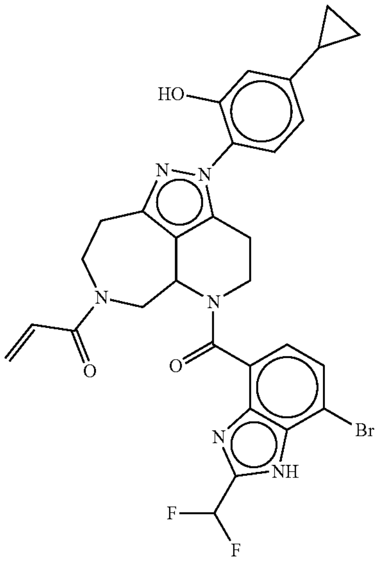 |
| 144 | C-11-5 | 1-(5-(4-amino-6-chloronicotinoyl)-2-(4-cyclobutyl-2-hydroxyphenyl)-2,3,4,5,5a,6,8,9-octahydro-7H-1,2,5,7-tetraazabenzo[cd]azulen-7-yl)prop-2-en-1-one | 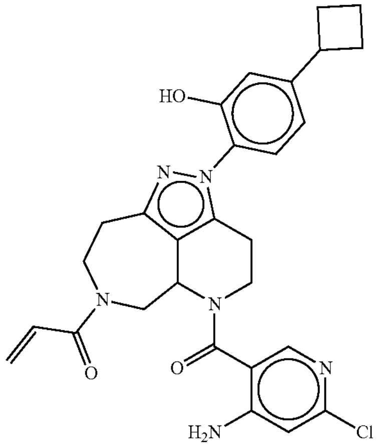 |

TABLE 1-continued

| Compound No | Example No. | Name | Structure |
|---|---|---|---|
| 145 | C-12-1 | 1-(2-(4-cyclobutyl-2-hydroxyphenyl)-5-(1,3-dimethyl-1H-pyrazolo[4,3-b]pyridine-6-carbonyl)-2,3,4,5,5a,6,8,9-octahydro-7H-1,2,5,7-tetraazabenzo[cd]azulen-7-yl)prop-2-en-1-one | 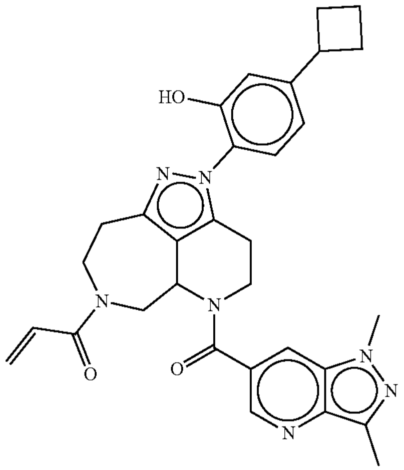 |
| 146 | C-11-6 | 1-(5-(2-amino-6-(difluoromethyl)nicotinoyl)-2-(4-cyclobutyl-2-hydroxyphenyl)-2,3,4,5,5a,6,8,9-octahydro-7H-1,2,5,7-tetraazabenzo[cd]azulen-7-yl)prop-2-en-1-one | 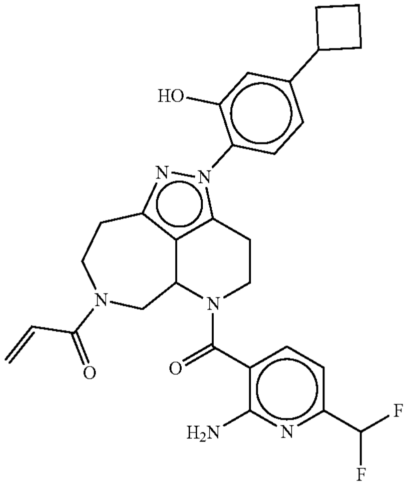 |
| 147 | C-8-3 | 1-(5-(3-amino-7-(trifluoromethyl)-1H-indazole-4-carbonyl)-2-(4-cyclobutylphenyl)-2,3,4,5,5a,6,8,9-octahydro-7H-1,2,5,7-tetraazabenzo[cd]azulen-7-yl)prop-2-en-1-one | 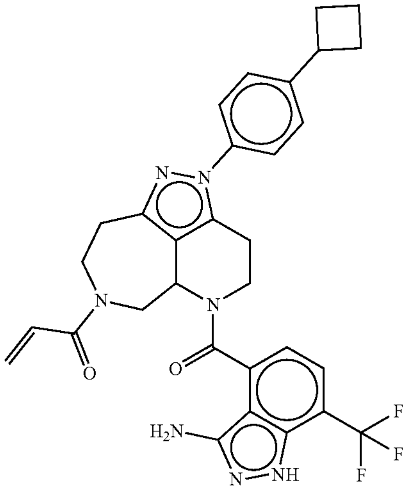 |

TABLE 1-continued

| Compound No | Example No. | Name | Structure |
|---|---|---|---|
| 148 | C-33 | 1-(5-(4-bromo-2-(2-hydroxyethyl)-1H-benzo[d]imidazole-7-carbonyl)-2-(4-cyclobutyl-2-hydroxyphenyl)-2,3,4,5,5a,6,8,9-octahydro-7H-1,2,5,7-tetraazabenzo[cd]azulen-7-yl)prop-2-en-1-one | 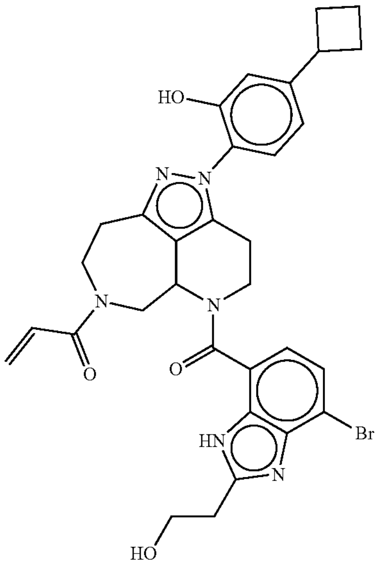 |
| 149 | C-11-7 | 1-(2-(4-cyclobutyl-2-hydroxyphenyl)-5-(4-hydroxy-6-(trifluoromethyl) nicotinoyl)-2,3,4,5,5a,6,8,9-octahydro-7H-1,2,5,7-tetraazabenzo[cd]azulen-7-yl)prop-2-en-1-one | 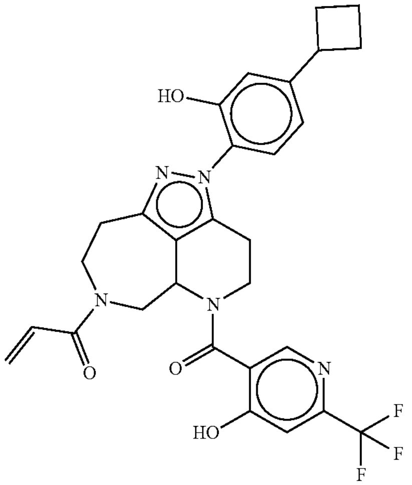 |
| 150 | B-2-1 | 1-(5-(4-amino-6-(trifluoromethyl) nicotinoyl)-2-(4-isopropylphenyl)-2,3,4,5,5a,6,8,9-octahydro-7H-1,2,5,7-tetraazabenzo[cd]azulen-7-yl)prop-2-en-1-one | 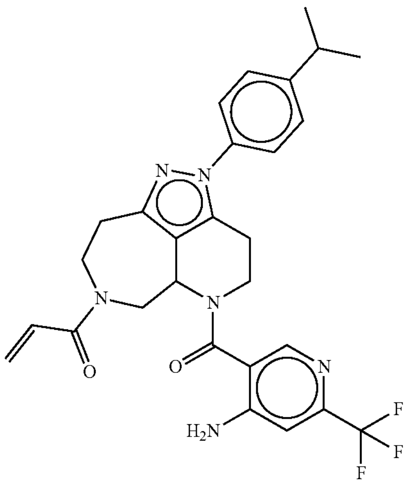 |

TABLE 1-continued

| Compound No | Example No. | Name | Structure |
|---|---|---|---|
| 151 | C-13 | 1-(2-(4-cyclobutyl-2-hydroxyphenyl)-5-(7-(trifluoromethyl)-1H-pyrazolo[3,4-c]pyridine-4-carbonyl)-2,3,4,5,5a,6,8,9-octahydro-7H-1,2,5,7-tetraazabenzo[cd]azulen-7-yl)prop-2-en-1-one | 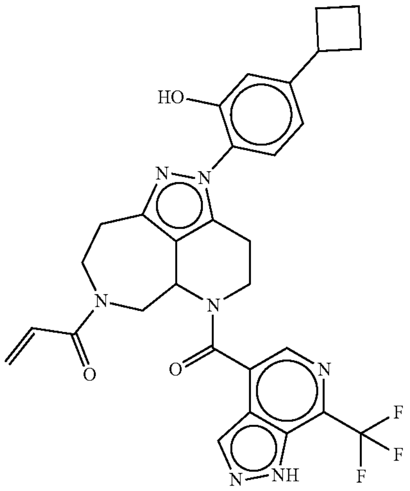 |
| 152 | A-7-2 | 1-(5-(2-amino-6-(trifluoromethyl)nicotinoyl)-2-(4-(bicyclo[1.1.1]pentan-1-yl)phenyl)-2,3,4,5,5a,6,8,9-octahydro-7H-1,2,5,7-tetraazabenzo[cd]azulen-7-yl)prop-2-en-1-one | 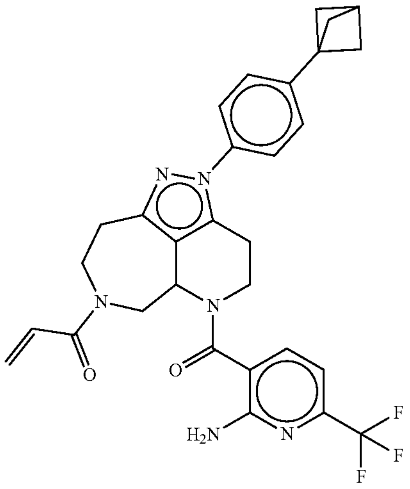 |
| 153 | C-14 | 1-(2-(4-cyclobutyl-2-hydroxyphenyl)-5-(7-hydroxybenzo[d]thiazole-5-carbonyl)-2,3,4,5,5a,6,8,9-octahydro-7H-1,2,5,7-tetraazabenzo[cd]azulen-7-yl)prop-2-en-1-one | 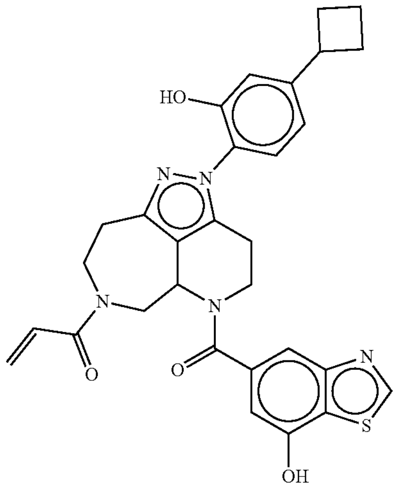 |

TABLE 1-continued

| Compound No | Example No. | Name | Structure |
|---|---|---|---|
| 154 | C-34 | 1-(2-(4-cyclobutyl-2-hydroxyphenyl)-5-(7-(trifluoromethyl)-1H-imidazo[4,5-c]pyridine-4-carbonyl)-2,3,4,5,5a,6,8,9-octahydro-7H-1,2,5,7-tetraazabenzo[cd]azulen-7-yl)prop-2-en-1-one | 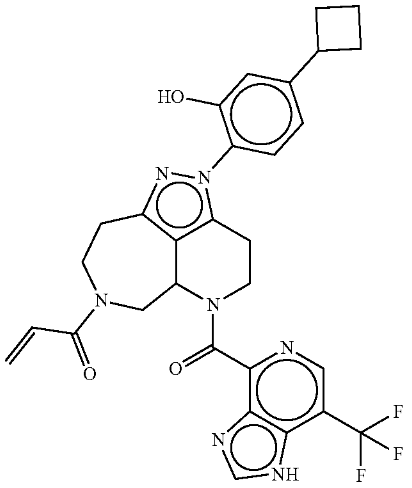 |
| 155 | C-24 | 1-(5-(2-amino-6-(1,1-difluoroethyl)nicotinoyl)-2-(4-cyclobutyl-2-hydroxyphenyl)-2,3,4,5,5a,6,8,9-octahydro-7H-1,2,5,7-tetraazabenzo[cd]azulen-7-yl)prop-2-en-1-one | 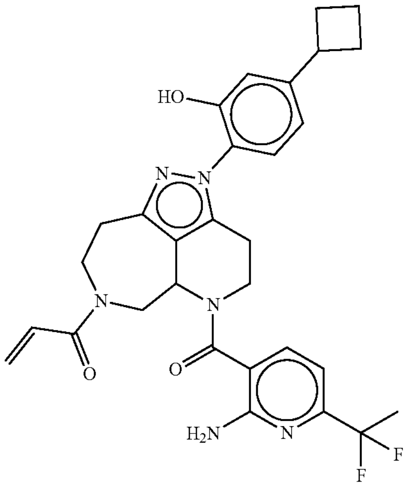 |
| 156 | C-22-2 | 1-(2-(4-cyclobutylphenyl)-5-(5-hydroxy-6-(trifluoromethyl) nicotinoyl)-9-methoxy-2,3,4,5,5a,6,8,9-octahydro-7H-1,2,5,7-tetraazabenzo[cd]azulen-7-yl)prop-2-en-1-one | 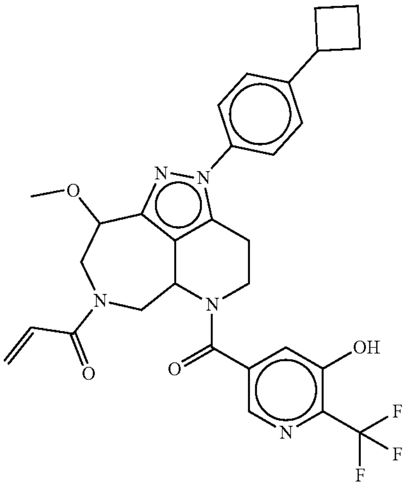 |

TABLE 1-continued

| Compound No | Example No. | Name | Structure |
|---|---|---|---|
| 157 | C-12-2 | 1-(2-(4-cyclobutyl-2-hydroxyphenyl)-5-(6-((trifluoromethyl)thio) nicotinoyl)-2,3,4,5,5a,6,8,9-octahydro-7H-1,2,5,7-tetraazabenzo[cd]azulen-7-yl)prop-2-en-1-one | 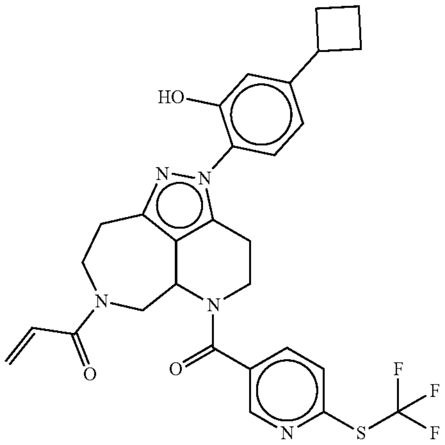 |
| 158 | C-8-4 | 1-(5-(3-amino-7-bromo-1H-indazole-4-carbonyl)-2-(4-cyclobutylphenyl)-2,3,4,5,5a,6,8,9-octahydro-7H-1,2,5,7-tetraazabenzo[cd]azulen-7-yl)prop-2-en-1-one | 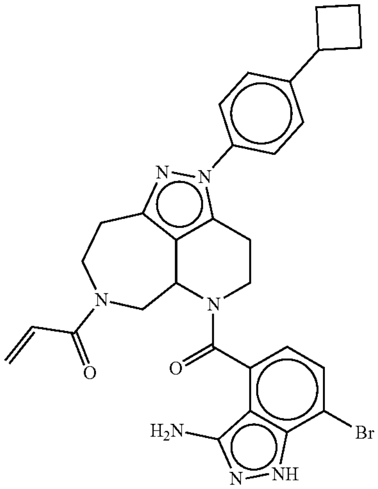 |
| 159 | C-11-12 | 1-(5-(4-amino-5-(trifluoromethyl) pyrimidine-2-carbonyl)-2-(4-cyclobutyl-2-hydroxyphenyl)-2,3,4,5,5a,6,8,9-octahydro-7H-1,2,5,7-tetraazabenzo[cd]azulen-7-yl)prop-2-en-1-one | 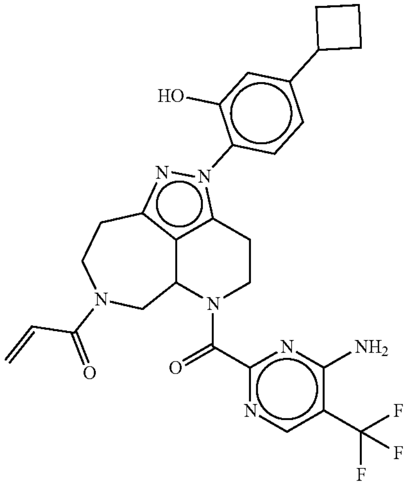 |

TABLE 1-continued

| Compound No | Example No. | Name | Structure |
|---|---|---|---|
| 160 | C-27 | 1-(5-(7-bromo-2-(difluoromethyl)-1H-benzo[d]imidazole-4-carbonyl)-2-(4-cyclobutylphenyl)-9-hydroxy-2,3,4,5,5a,6,8,9-octahydro-7H-1,2,5,7-tetraazabenzo[cd]azulen-7-yl)prop-2-en-1-one | 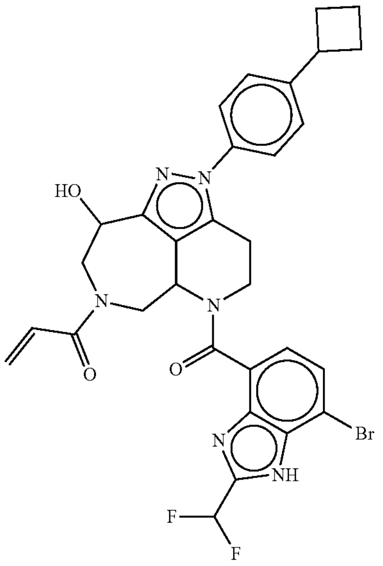 |
| 161 | C-8-1 | 1-(5-(4-amino-2-(trifluoromethyl) pyrimidine-5-carbonyl)-2-(4-cyclobutylphenyl)-2,3,4,5,5a,6,8,9-octahydro-7H-1,2,5,7-tetraazabenzo[cd]azulen-7-yl)prop-2-en-1-one | 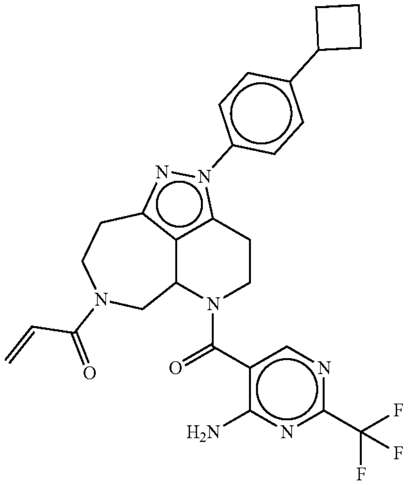 |
| 162 | A-4-32 | 1-(5-(4-amino-6-chloronicotinoyl)-2-(4-cyclopropylphenyl)-2,3,4,5,5a,6,8,9-octahydro-7H-1,2,5,7-tetraazabenzo[cd]azulen-7-yl)prop-2-en-1-one | 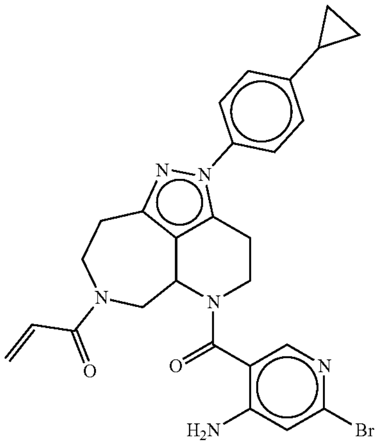 |

TABLE 1-continued

| Compound No | Example No. | Name | Structure |
|---|---|---|---|
| 163 | A-10 | 1-(5-(4-amino-6-(trifluoromethyl) nicotinoyl)-2-(4-cyclopropyl-2-hydroxyphenyl)-2,3,4,5,5a,6,8,9-octahydro-7H-1,2,5,7-tetraazabenzo[cd]azulen-7-yl)prop-2-en-1-one | 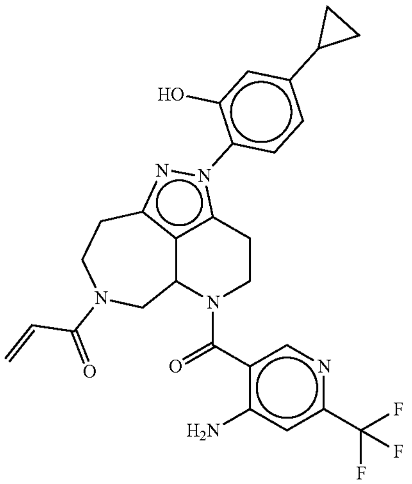 |
| 164 | C-11-11 | 1-(5-(4-amino-6-(difluoromethoxy) nicotinoyl)-2-(4-cyclobutyl-2-hydroxyphenyl)-2,3,4,5,5a,6,8,9-octahydro-7H-1,2,5,7-tetraazabenzo[cd]azulen-7-yl)prop-2-en-1-one | 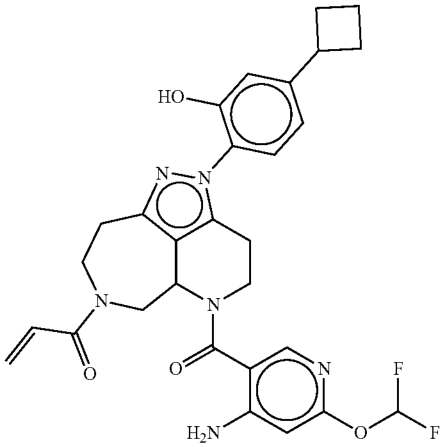 |
| 165 | C-15 | 1-(5-(2-amino-5-fluoro-6-(trifluoromethyl) nicotinoyl)-2-(4-cyclobutyl-2-hydroxyphenyl)-2,3,4,5,5a,6,8,9-octahydro-7H-1,2,5,7-tetraazabenzo[cd]azulen-7-yl)prop-2-en-1-one | 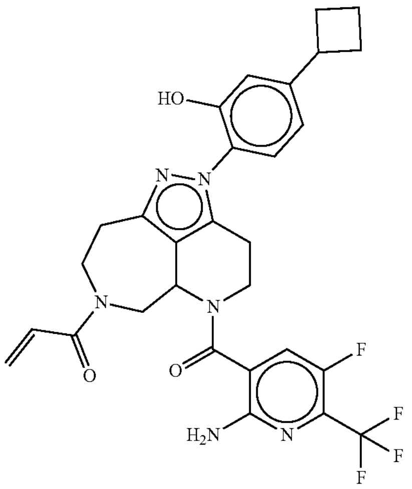 |

TABLE 1-continued

| Compound No | Example No. | Name | Structure |
|---|---|---|---|
| 166 | A-4-26 | 1-(5-(4-amino-6-bromonicotinoyl)-2-(4-cyclopropylphenyl)-2,3,4,5,5a,6,8,9-octahydro-7H-1,2,5,7-tetraazabenzo[cd]azulen-7-yl)prop-2-en-1-one | 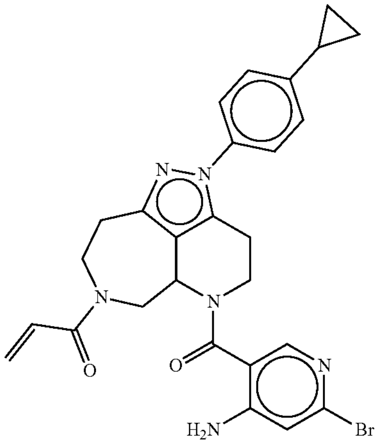 |
| 167 | A-4-27 | 1-(5-(2-amino-6-chloronicotinoyl)-2-(4-cyclopropylphenyl)-2,3,4,5,5a,6,8,9-octahydro-7H-1,2,5,7-tetraazabenzo[cd]azulen-7-yl)prop-2-en-1-one | 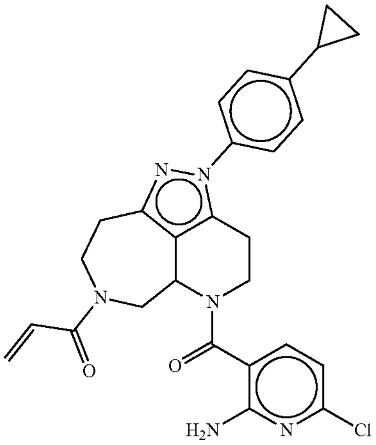 |
| 168 | E-8 | 1-(5-(4-amino-6-(trifluoromethyl)nicotinoyl)-2-(4-isopropylphenyl)-6-methyl-2,3,4,5,5a,6,8,9-octahydro-7H-1,2,5,7-tetraazabenzo[cd]azulen-7-yl)prop-2-en-1-one | 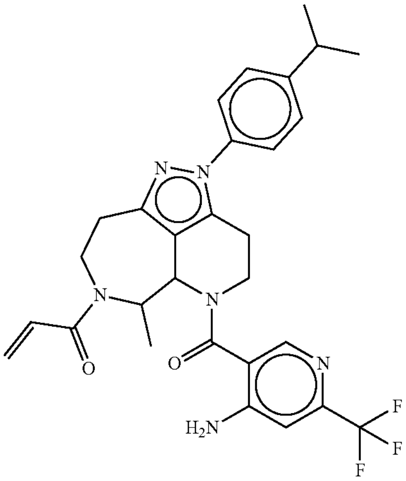 |

TABLE 1-continued

| Compound No | Example No. | Name | Structure |
|---|---|---|---|
| 169 | C-26 | 1-(5-(7-bromo-1H-benzo[d]imidazole-4-carbonyl)-2-(4-cyclobutylphenyl)-2,3,4,5,5a,6-hexahydro-1,2,5,7-tetraazaspiro[benzo[cd]azulene-9,1'-cyclopropan]-1(9a),2a-dien-7(8H)-yl)prop-2-en-1-one | 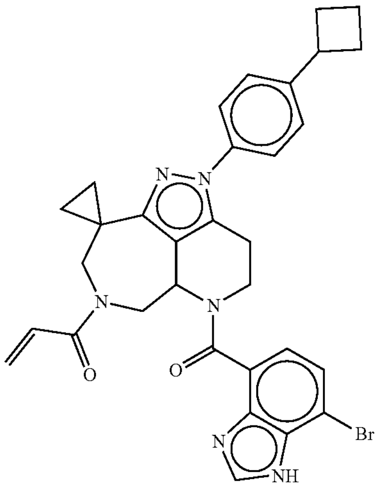 |

TABLE 2

| Compound No | Example No. | Name | Structure |
|---|---|---|---|
| 170 | B-2-2 | 1-(5-(cyclopropanecarbonyl)-2-(4-isopropylphenyl)-2,3,4,5,5a,6,8,9-octahydro-7H-1,2,5,7-tetraazabenzo[cd]azulen-7-yl)prop-2-en-1-one | 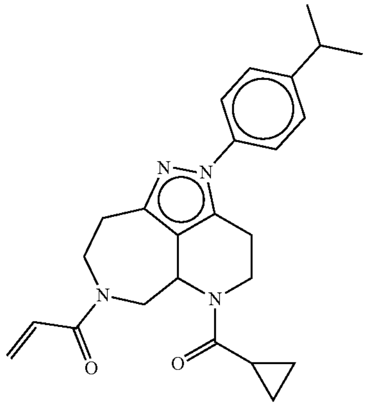 |
| 171 | C-20 | 2-(7-acryloyl-5-(4-amino-6-(trifluoromethyl) nicotinoyl)-3,4,5,5a,6,7,8,9-octahydro-2H-1,2,5,7-tetraazabenzo[cd]azulen-2-yl)-5-cyclobutylbenzonitrile | 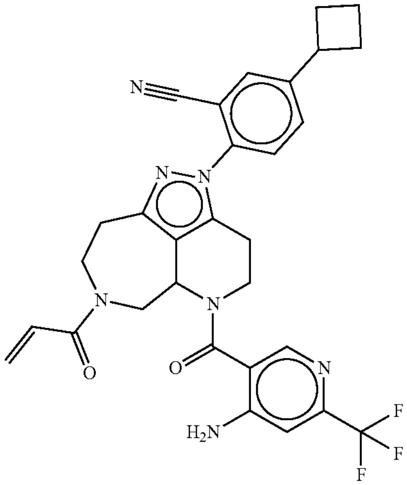 |

TABLE 2-continued

| Compound No | Example No. | Name | Structure |
|---|---|---|---|
| 172 | A-10-1 | 1-(5-(2-amino-6-(trifluoromethyl) nicotinoyl)-2-(4-cyclopropyl-2-hydroxyphenyl)-2,3,4,5,5a,6,8,9-octahydro-7H-1,2,5,7-tetraazabenzo[cd]azulen-7-yl)prop-2-en-1-one | 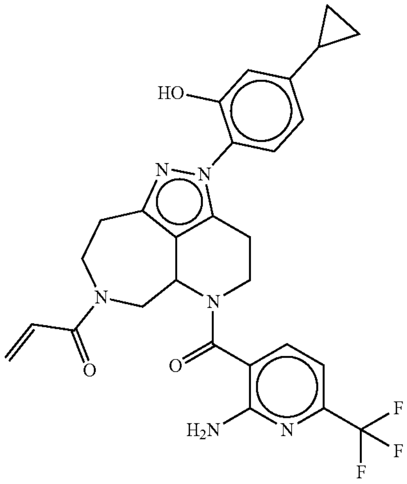 |
| 173 | C-29 | 1-(5-(2-amino-6-(trifluoromethyl) nicotinoyl)-2-(2-hydroxy-4-isopropylphenyl)-2,3,4,5,5a,6,8,9-octahydro-7H-1,2,5,7-tetraazabenzo[cd]azulen-7-yl)prop-2-en-1-one | 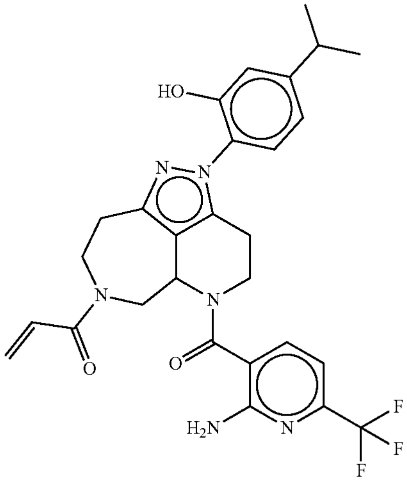 |
| 174 | C-28 | 1-(5-(7-bromo-2-(difluoromethyl)-1H-benzo[d]imidazole-4-carbonyl)-2-(2-hydroxy-4-isopropylphenyl)-2,3,4,5,5a,6,8,9-octahydro-7H-1,2,5,7-tetraazabenzo[cd]azulen-7-yl)prop-2-en-1-one | 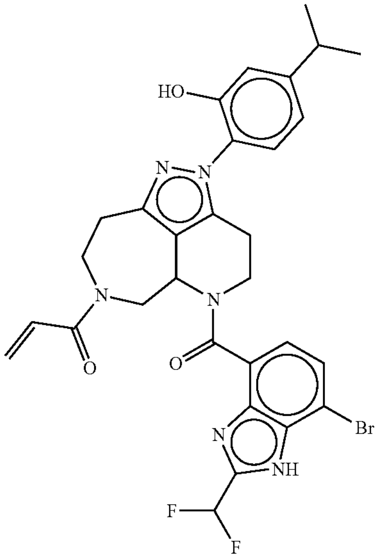 |

TABLE 2-continued

| Compound No | Example No. | Name | Structure |
|---|---|---|---|
| 175 | A-25-1 | 1-(2-(4-cyclopropyl-2-hydroxyphenyl)-5-(5-hydroxy-6-(trifluoromethyl) nicotinoyl)-2,3,4,5,5a,6,8,9-octahydro-7H-1,2,5,7-tetraazabenzo[cd]azulen-7-yl)prop-2-en-1-one | 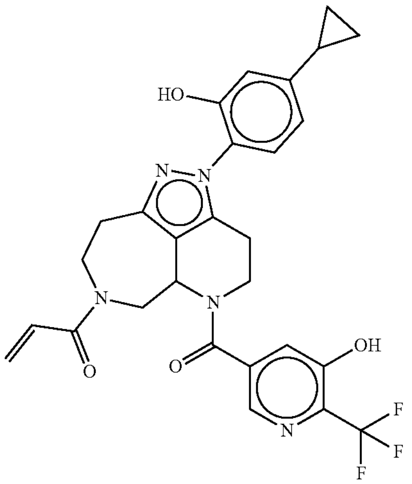 |
| 176 | C-30 | 1-(2-(2-hydroxy-4-isopropylphenyl)-5-(7-(trifluoromethyl)-1H-pyrazolo[3,4-c]pyridine-4-carbonyl)-2,3,4,5,5a,6,8,9-octahydro-7H-1,2,5,7-tetraazabenzo[cd]azulen-7-yl)prop-2-en-1-one | 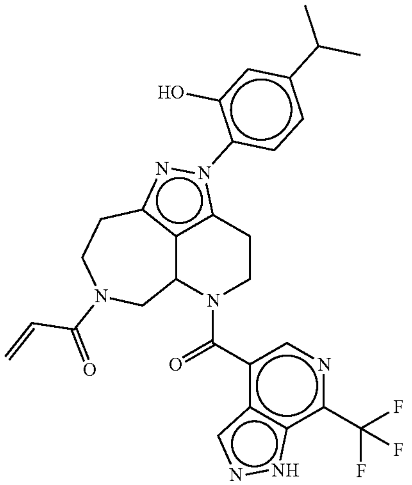 |
| 177 | A-24 | 1-(5-(4-amino-6-(difluoromethoxy) nicotinoyl)-2-(4-cyclopropylphenyl)-2,3,4,5,5a,6,8,9-octahydro-7H-1,2,5,7-tetraazabenzo[cd]azulen-7-yl)prop-2-en-1-one | 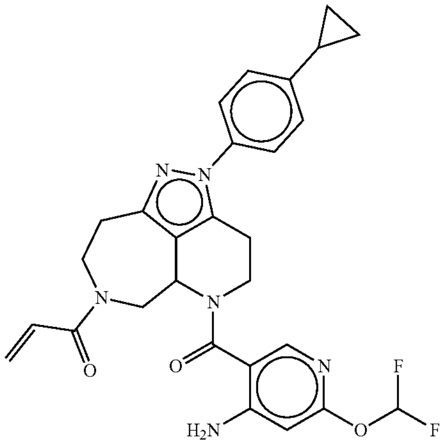 |

TABLE 2-continued

| Compound No | Example No. | Name | Structure |
|---|---|---|---|
| 178 | A-4-29 | 1-(5-(4-amino-5-fluoro-6-(trifluoromethyl) nicotinoyl)-2-(4-cyclopropylphenyl)-2,3,4,5,5a,6,8,9-octahydro-7H-1,2,5,7-tetraazabenzo[cd]azulen-7-yl)prop-2-en-1-one | 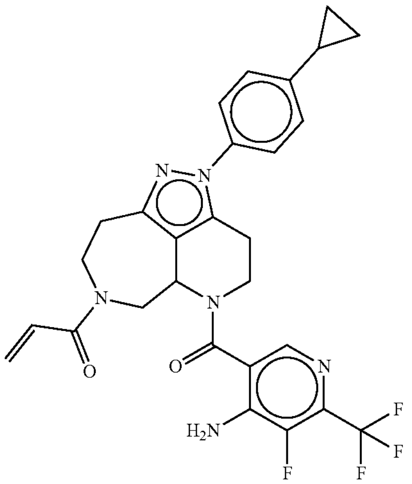 |
| 179 | A-33 | 1-(2-(4-cyclopropylphenyl)-5-(4-(methylamino)-6-(trifluoromethyl) nicotinoyl)-2,3,4,5,5a,6,8,9-octahydro-7H-1,2,5,7-tetraazabenzo[cd]azulen-7-yl)prop-2-en-1-one | 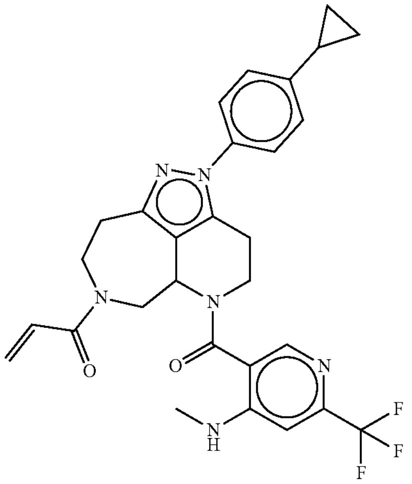 |
| 180 | A-5-1 | 1-(5-(4-amino-6-(trifluoromethyl) nicotinoyl)-2-(2-hydroxy-4-(2,2,2-trifluoroethyl)phenyl)-2,3,4,5,5a,6,8,9-octahydro-7H-1,2,5,7-tetraazabenzo[cd]azulen-7-yl)prop-2-en-1-one | 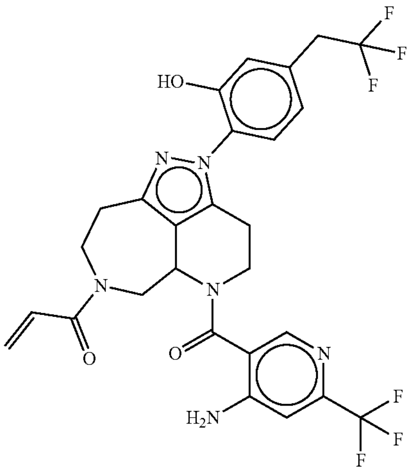 |

TABLE 2-continued

| Compound No | Example No. | Name | Structure |
|---|---|---|---|
| 181 | A-4-28 | 1-(5-(4-amino-6-chloro-5-fluoronicotinoyl)-2-(4-cyclopropylphenyl)-2,3,4,5,5a,6,8,9-octahydro-7H-1,2,5,7-tetraazabenzo[cd]azulen-7-yl)prop-2-en-1-one | 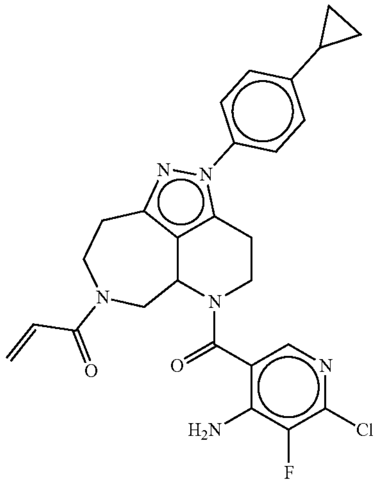 |
| 182 | A-4-30 | 1-(5-(4-amino-6-bromo-5-fluoronicotinoyl)-2-(4-cyclopropylphenyl)-2,3,4,5,5a,6,8,9-octahydro-7H-1,2,5,7-tetraazabenzo[cd]azulen-7-yl)prop-2-en-1-one | 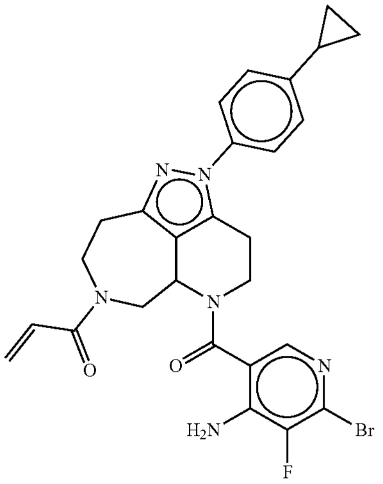 |
| 183 | A-14 | 1-(5-(4-amino-6-(1,1-difluoroethyl)nicotinoyl)-2-(4-cyclopropylphenyl)-2,3,4,5,5a,6,8,9-octahydro-7H-1,2,5,7-tetraazabenzo[cd]azulen-7-yl)prop-2-en-1-one | 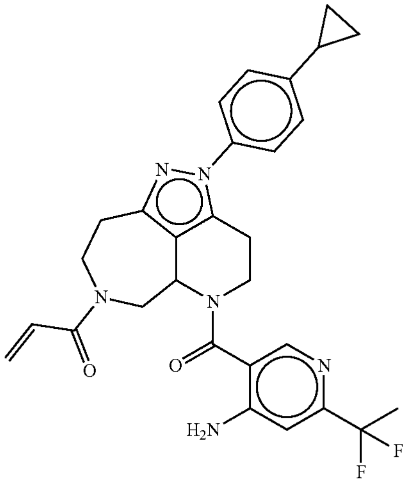 |

TABLE 2-continued

| Compound No | Example No. | Name | Structure |
|---|---|---|---|
| 184 | A-22 | 1-(5-(4-amino-6-(trifluoromethyl) nicotinoyl)-2-(4-cyclopropylphenyl)-9-hydroxy-2,3,4,5,5a,6,8,9-octahydro-7H-1,2,5,7-tetraazabenzo[cd]azulen-7-yl)prop-2-en-1-one | 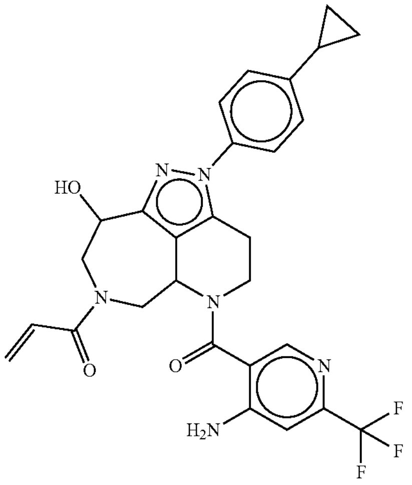 |
| 185 | C-35 | 1-(2-(4-cyclobutylphenyl)-5-(1-methyl-3-(trifluoromethyl)-1H-pyrazolo[4,3-b]pyridine-6-carbonyl)-2,3,4,5,5a,6,8,9-octahydro-7H-1,2,5,7-tetraazabenzo[cd]azulen-7-yl)prop-2-en-1-one | 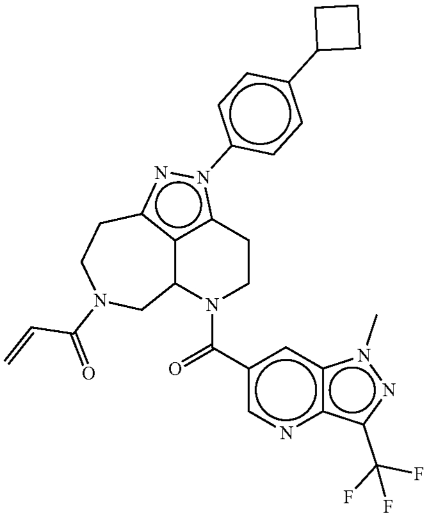 |
| 186 | A-16 | 1-(2-(4-cyclopropylphenyl)-5-(2,4-diamino-6-(trifluoromethyl) nicotinoyl)-2,3,4,5,5a,6,8,9-octahydro-7H-1,2,5,7-tetraazabenzo[cd]azulen-7-yl)prop-2-en-1-one | 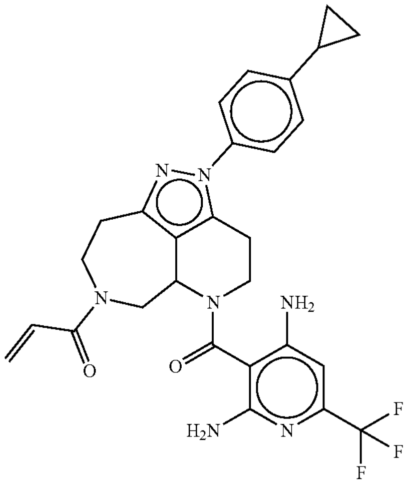 |

TABLE 2-continued

| Compound No | Example No. | Name | Structure |
|---|---|---|---|
| 187 | C-22-1 | 1-(5-(4-amino-6-(trifluoromethyl) nicotinoyl)-2-(4-cyclopropylphenyl)-9-methoxy-2,3,4,5,5a,6,8,9-octahydro-7H-1,2,5,7-tetraazabenzo[cd]azulen-7-yl)prop-2-en-1-one | 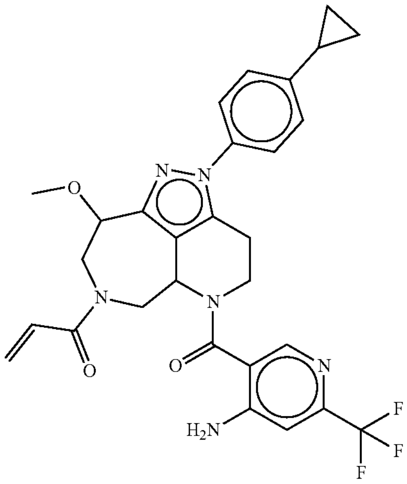 |
| 188 | A-28 | 1-(5-(5-amino-7-bromo-1H-benzo[d]imidazole-4-carbonyl)-2-(4-cyclopropylphenyl)-2,3,4,5,5a,6,8,9-octahydro-7H-1,2,5,7-tetraazabenzo[cd]azulen-7-yl)prop-2-en-1-one | 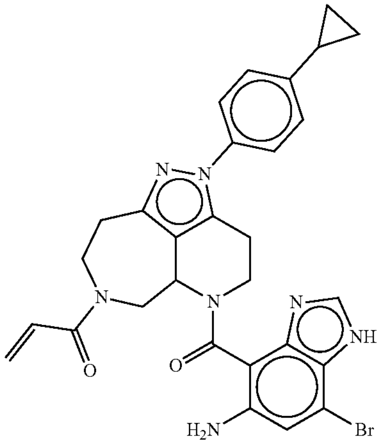 |
| 189 | E-6 | 1-(5-(4-amino-6-(trifluoromethyl) nicotinoyl)-2-(4-cyclopropyl-2-hydroxyphenyl)-9-methyl-2,3,4,5,5a,6,8,9-octahydro-7H-1,2,5,7-tetraazabenzo[cd]azulen-7-yl)prop-2-en-1-one | 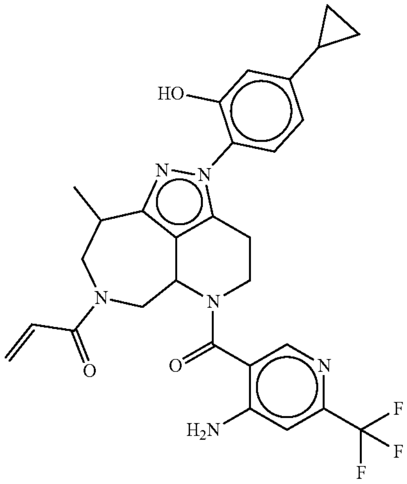 |

TABLE 2-continued

| Compound No | Example No. | Name | Structure |
|---|---|---|---|
| 190 | E-7 | 1-(5-(4-amino-6-bromonicotinoyl)-2-(4-cyclopropyl-2-hydroxyphenyl)-9-methyl-2,3,4,5,5a,6,8,9-octahydro-7H-1,2,5,7-tetraazabenzo[cd]azulen-7-yl)prop-2-en-1-one | 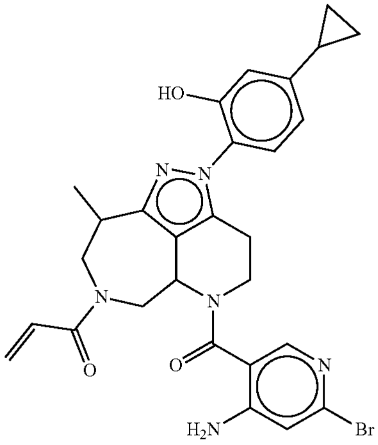 |
| 191 | A-10-2 | 1-(5-(4-amino-6-bromonicotinoyl)-2-(4-cyclopropyl-2-hydroxyphenyl)-2,3,4,5,5a,6,8,9-octahydro-7H-1,2,5,7-tetraazabenzo[cd]azulen-7-yl)prop-2-en-1-one | 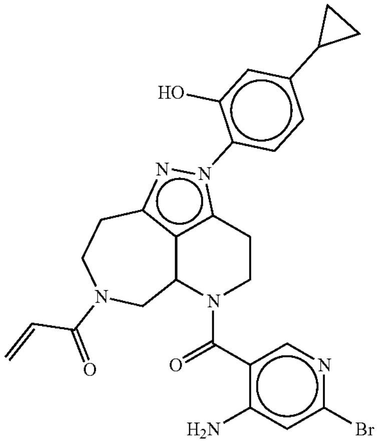 |
| 192 | A-10-12 | 1-(5-(4-amino-6-(difluoromethoxy) nicotinoyl)-2-(4-cyclopropyl-2-hydroxyphenyl)-2,3,4,5,5a,6,8,9-octahydro-7H-1,2,5,7-tetraazabenzo[cd]azulen-7-yl)prop-2-en-1-one | 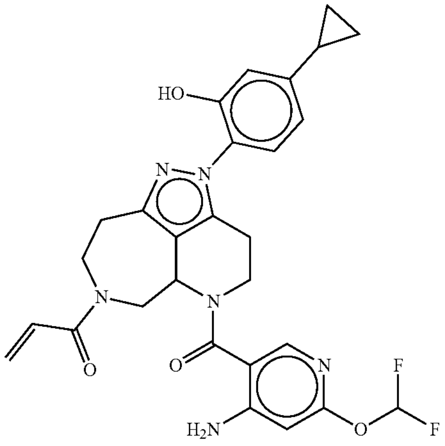 |

TABLE 2-continued

| Compound No | Example No. | Name | Structure |
|---|---|---|---|
| 193 | A-10-3 | 1-(5-(2-amino-6-bromonicotinoyl)-2-(4-cyclopropyl-2-hydroxyphenyl)-2,3,4,5,5a,6,8,9-octahydro-7H-1,2,5,7-tetraazabenzo[cd]azulen-7-yl)prop-2-en-1-one | 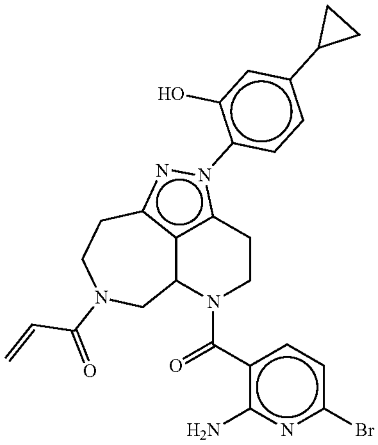 |
| 194 | A-13 | 1-(5-(4-amino-5-fluoro-6-(trifluoromethyl) nicotinoyl)-2-(4-cyclopropyl-2-hydroxyphenyl)-2,3,4,5,5a,6,8,9-octahydro-7H-1,2,5,7-tetraazabenzo[cd]azulen-7-yl)prop-2-en-1-one | 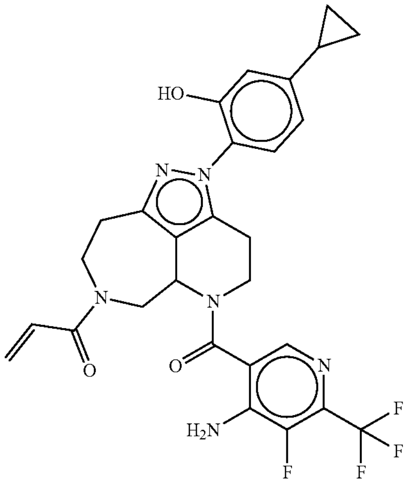 |
| 195 | E-5 | 1-(5-(4-amino-6-(trifluoromethyl) nicotinoyl)-2-(4-cyclopropyl-2-hydroxyphenyl)-9-methyl-2,3,4,5,5a,6,8,9-octahydro-7H-1,2,5,7-tetraazabenzo[cd]azulen-7-yl)prop-2-en-1-one | 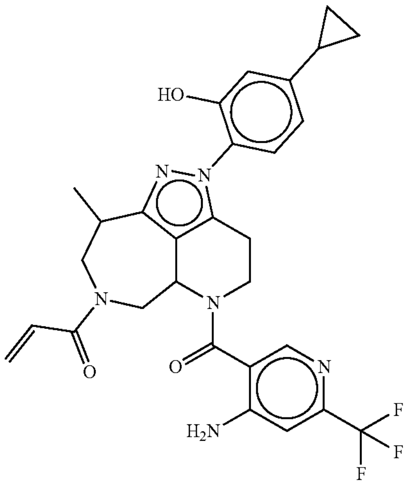 |

TABLE 2-continued

| Compound No | Example No. | Name | Structure |
| --- | --- | --- | --- |
| 196 | A-10-4 | 1-(5-(4-amino-6-chloronicotinoyl)-2-(4-cyclopropyl-2-hydroxyphenyl)-2,3,4,5,5a,6,8,9-octahydro-7H-1,2,5,7-tetraazabenzo[cd]azulen-7-yl)prop-2-en-1-one | 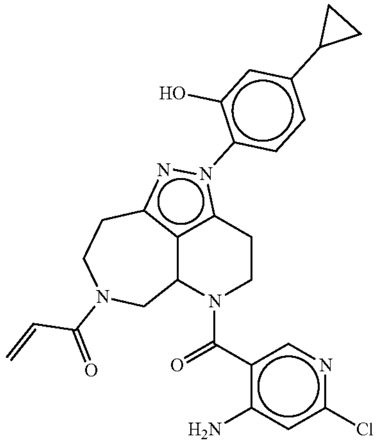 |
| 197 | A-10-5 | 1-(5-(4-amino-2-(trifluoromethyl) pyrimidine-5-carbonyl)-2-(4-cyclopropyl-2-hydroxyphenyl)-2,3,4,5,5a,6,8,9-octahydro-7H-1,2,5,7-tetraazabenzo[cd]azulen-7-yl)prop-2-en-1-one | 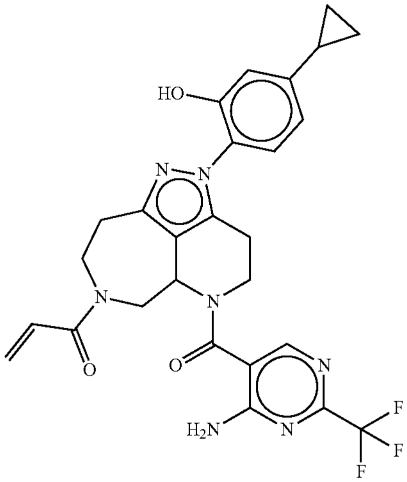 |
| 198 | C-25 | 3-((7-acryloyl-5-(4-amino-6-(trifluoromethyl) nicotinoyl)-2-(4-cyclobutylphenyl)-3,4,5,5a,6,7,8,9-octahydro-2H-1,2,5,7-tetraazabenzo[cd]azulen-9-yl)oxy)cyclobutane-1-carbonitrile | 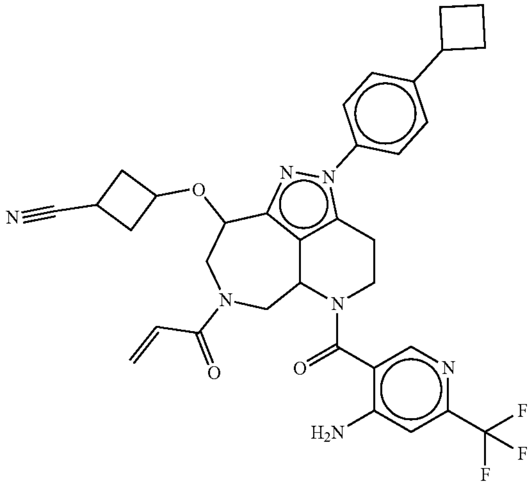 |

TABLE 2-continued

| Compound No | Example No. | Name | Structure |
| --- | --- | --- | --- |
| 199 | A-10-6 | 1-(5-(2-amino-6-chloronicotinoyl)-2-(4-cyclopropyl-2-hydroxyphenyl)-2,3,4,5,5a,6,8,9-octahydro-7H-1,2,5,7-tetraazabenzo[cd]azulen-7-yl)prop-2-en-1-one | 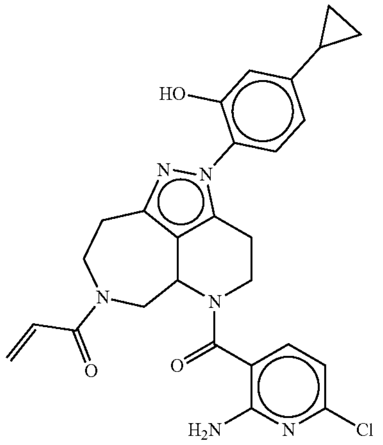 |
| 200 | A-26 | 1-(5-(2-amino-5-fluoro-6-(trifluoromethyl)nicotinoyl)-2-(4-cyclopropyl-2-hydroxyphenyl)-2,3,4,5,5a,6,8,9-octahydro-7H-1,2,5,7-tetraazabenzo[cd]azulen-7-yl)prop-2-en-1-one | 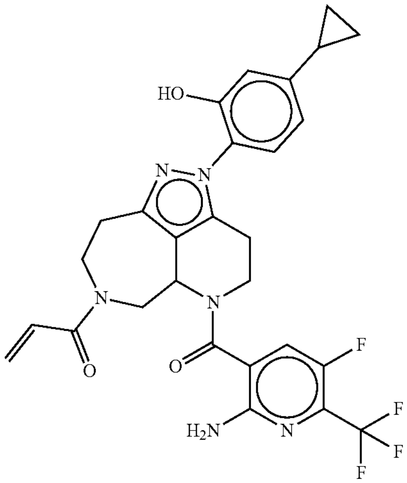 |
| 201 | L-6 | 1-(5-(4-amino-6-(trifluoromethyl)nicotinoyl)-2-benzyl-2,3,4,5,5a,6,8,9-octahydro-7H-1,2,5,7-tetraazabenzo[cd]azulen-7-yl)prop-2-en-1-one | 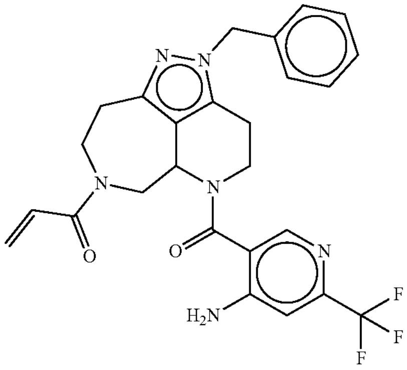 |

TABLE 2-continued

| Compound No | Example No. | Name | Structure |
|---|---|---|---|
| 202 | A-10-7 | 1-(5-(4-amino-6-bromo-5-fluoronicotinoyl)-2-(4-cyclopropyl-2-hydroxyphenyl)-2,3,4,5,5a,6,8,9-octahydro-7H-1,2,5,7-tetraazabenzo[cd]azulen-7-yl)prop-2-en-1-one | 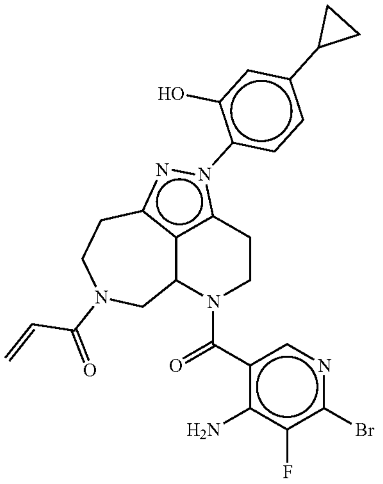 |
| 203 | L-1-2 | 1-(5-(4-amino-6-(trifluoromethyl) nicotinoyl)-2-(4-cyclopropyl-3-fluoro-2-hydroxyphenyl)-2,3,4,5,5a,6,8,9-octahydro-7H-1,2,5,7-tetraazabenzo[cd]azulen-7-yl)prop-2-en-1-one | 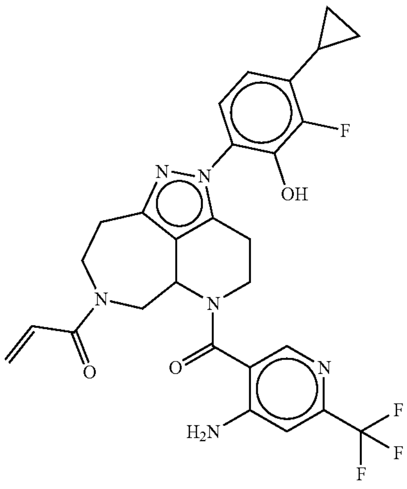 |
| 204 | A-4-33 | 1-(5-(4-amino-2-(methylthio)pyrimidine-5-carbonyl)-2-(4-cyclopropylphenyl)-2,3,4,5,5a,6,8,9-octahydro-7H-1,2,5,7-tetraazabenzo[cd]azulen-7-yl)prop-2-en-1-one | 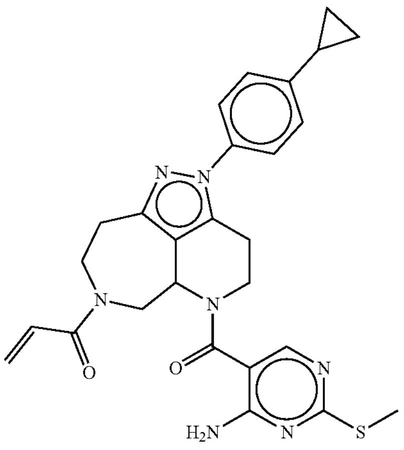 |

TABLE 2-continued

| Compound No | Example No. | Name | Structure |
|---|---|---|---|
| 205 | C-25-6 | 1-(9-((1-acetylazetidin-3-yl)oxy)-2-(4-cyclobutylphenyl)-5-(6-(trifluoromethyl) nicotinoyl)-2,3,4,5,5a,6,8,9-octahydro-7H-1,2,5,7-tetraazabenzo[cd]azulen-7-yl)prop-2-en-1-one | 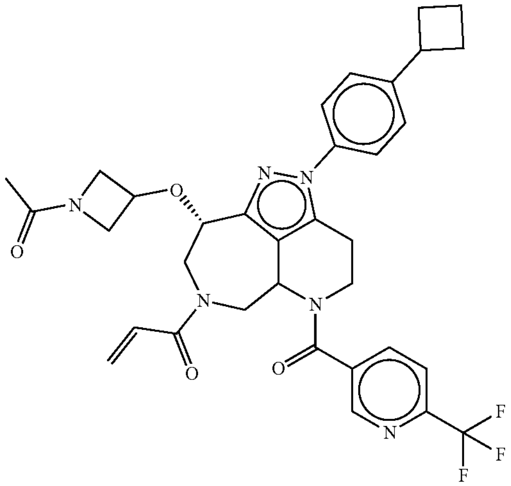 |
| 206 | A-12 | 1-(5-(4-amino-6-(1,1-difluoroethyl)-5-fluoronicotinoyl)-2-(4-cyclopropyl-2-hydroxyphenyl)-2,3,4,5,5a,6,8,9-octahydro-7H-1,2,5,7-tetraazabenzo[cd]azulen-7-yl)prop-2-en-1-one | 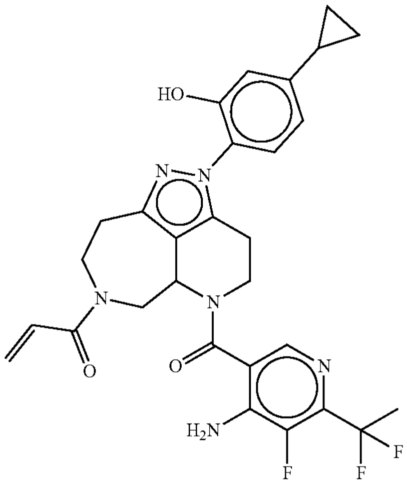 |
| 207 | A-10-8 | 5-(7-acryloyl-2-(4-cyclopropyl-2-hydroxyphenyl)-3,4,5,5a,6,7,8,9-octahydro-2H-1,2,5,7-tetraazabenzo[cd]azulene-5-carbonyl)-4-amino-2-(trifluoromethyl) benzonitrile | 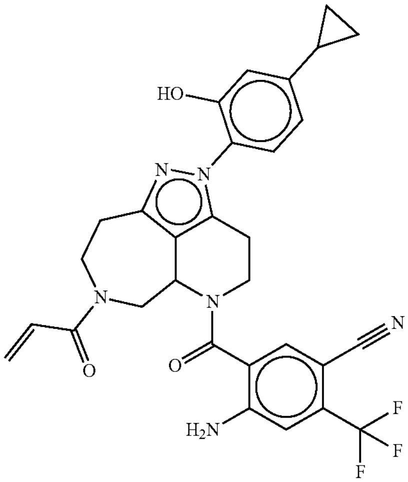 |

TABLE 2-continued

| Compound No | Example No. | Name | Structure |
|---|---|---|---|
| 208 | A-18 | 1-(5-(4-amino-5-methyl-6-(trifluoromethyl) nicotinoyl)-2-(4-cyclopropyl-2-hydroxyphenyl)-2,3,4,5,5a,6,8,9-octahydro-7H-1,2,5,7-tetraazabenzo[cd]azulen-7-yl)prop-2-en-1-one | 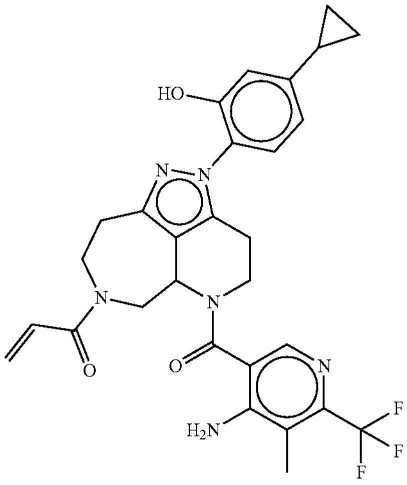 |
| 209 | A-27 | 1-(5-(4-amino-6-((trifluoromethyl)thio) nicotinoyl)-2-(4-cyclopropyl-2-hydroxyphenyl)-2,3,4,5,5a,6,8,9-octahydro-7H-1,2,5,7-tetraazabenzo[cd]azulen-7-yl)prop-2-en-1-one | 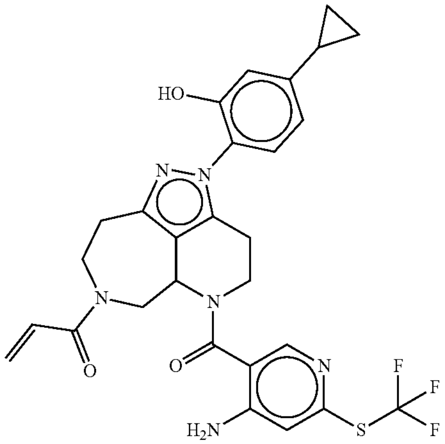 |
| 210 | A-10-9 | 1-(5-(4-amino-6-chloro-5-fluoronicotinoyl)-2-(4-cyclopropyl-2-hydroxyphenyl)-2,3,4,5,5a,6,8,9-octahydro-7H-1,2,5,7-tetraazabenzo[cd]azulen-7-yl)prop-2-en-1-one | 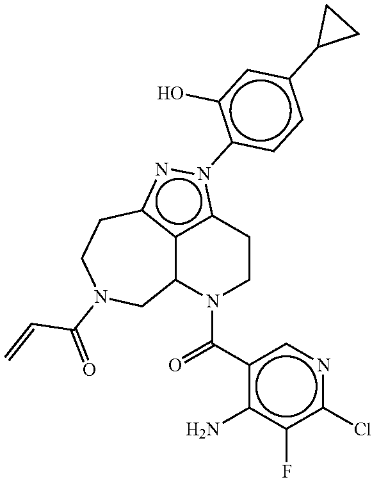 |

TABLE 2-continued

| Compound No | Example No. | Name | Structure |
|---|---|---|---|
| 211 | A-17 | 1-(5-(4-amino-6-(methylthio)nicotinoyl)-2-(4-cyclopropyl-2-hydroxyphenyl)-2,3,4,5,5a,6,8,9-octahydro-7H-1,2,5,7-tetraazabenzo[cd]azulen-7-yl)prop-2-en-1-one | 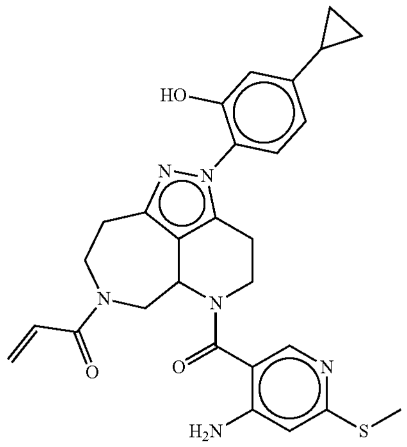 |
| 212 | A-31 | 1-(5-(6-amino-4-bromo-1H-benzo[d]imidazole-7-carbonyl)-2-(4-cyclopropyl-2-hydroxyphenyl)-2,3,4,5,5a,6,8,9-octahydro-7H-1,2,5,7-tetraazabenzo[cd]azulen-7-yl)prop-2-en-1-one | 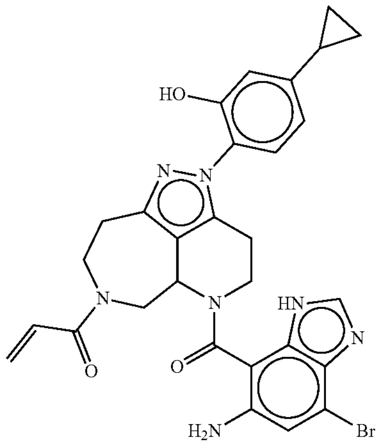 |
| 213 | A-10-10 | 1-(2-(4-cyclopropyl-2-hydroxyphenyl)-5-(6-(trifluoromethyl) nicotinoyl)-2,3,4,5,5a,6,8,9-octahydro-7H-1,2,5,7-tetraazabenzo[cd]azulen-7-yl)prop-2-en-1-one | 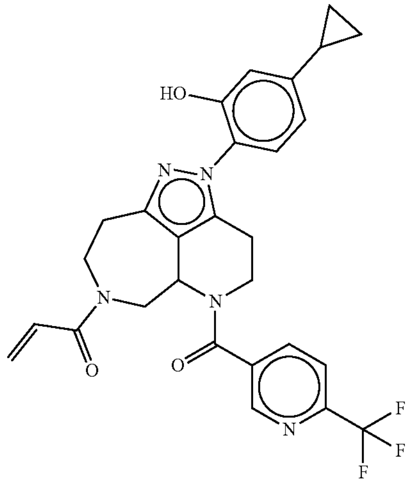 |

TABLE 2-continued

| Compound No | Example No. | Name | Structure |
|---|---|---|---|
| 214 | A-30 | 1-(5-(4-amino-5-fluoro-6-((trifluoromethyl)thio)nicotinoyl)-2-(4-cyclopropyl-2-hydroxyphenyl)-2,3,4,5,5a,6,8,9-octahydro-7H-1,2,5,7-tetraazabenzo[cd]azulen-7-yl)prop-2-en-1-one | 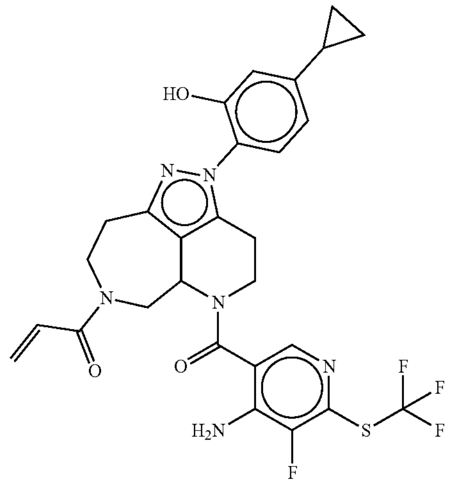 |
| 215 | L-1-5 | 1-(5-(4-amino-6-bromonicotinoyl)-2-(4-cyclopropyl-3-fluoro-2-hydroxyphenyl)-2,3,4,5,5a,6,8,9-octahydro-7H-1,2,5,7-tetraazabenzo[cd]azulen-7-yl)prop-2-en-1-one | 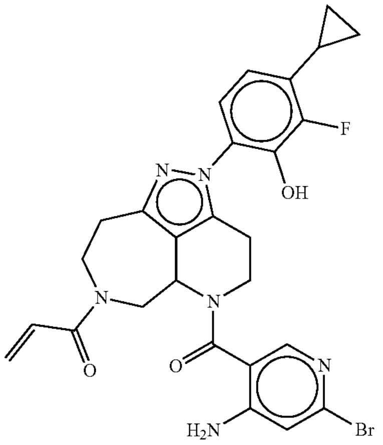 |
| 216 | A-32 | 1-(5-(4-amino-5-methoxy-6-(trifluoromethyl)nicotinoyl)-2-(4-cyclopropyl-2-hydroxyphenyl)-2,3,4,5,5a,6,8,9-octahydro-7H-1,2,5,7-tetraazabenzo[cd]azulen-7-yl)prop-2-en-1-one | 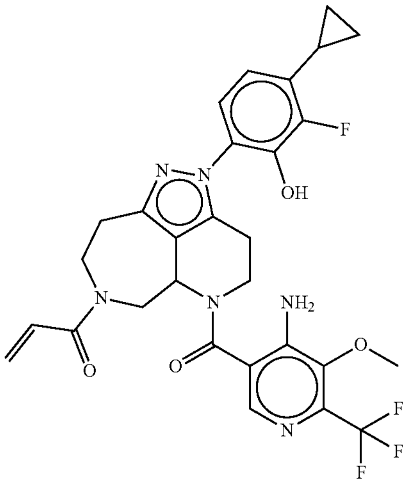 |

TABLE 2-continued

| Compound No | Example No. | Name | Structure |
|---|---|---|---|
| 217 | L-1-11 | 1-(5-(4-amino-6-(trifluoromethyl) nicotinoyl)-2-(4-cyclopentyl-2-hydroxyphenyl)-2,3,4,5,5a,6,8,9-octahydro-7H-1,2,5,7-tetraazabenzo[cd]azulen-7-yl)prop-2-en-1-one | 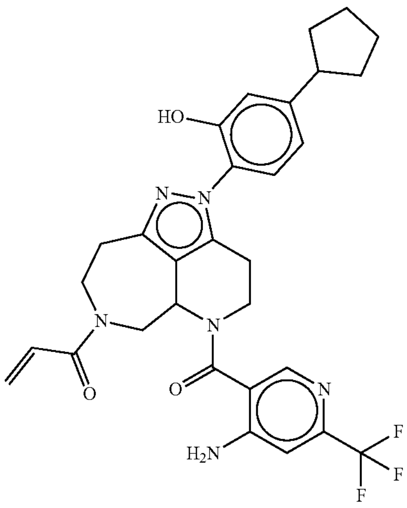 |
| 218 | L-1-1 | 1-(5-(4-amino-5-fluoro-6-(trifluoromethyl) nicotinoyl)-2-(4-cyclopropyl-3-fluoro-2-hydroxyphenyl)-2,3,4,5,5a,6,8,9-octahydro-7H-1,2,5,7-tetraazabenzo[cd]azulen-7-yl)prop-2-en-1-one | 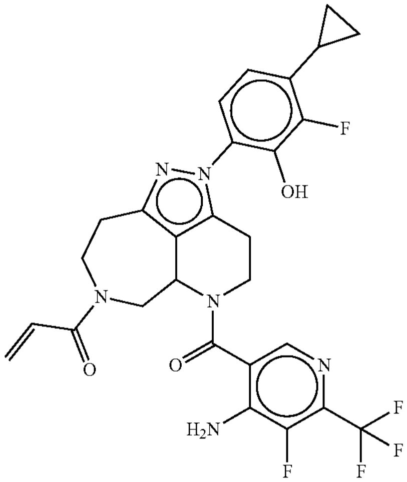 |
| 219 | L-7 | 1-(5-(4-amino-6-(trifluoromethyl) nicotinoyl)-2-(3-cyclopentylbicyclo[1.1.1] pentan-1-yl)-2,3,4,5,5a,6,8,9-octahydro-7H-1,2,5,7-tetraazabenzo[cd]azulen-7-yl)prop-2-en-1-one | 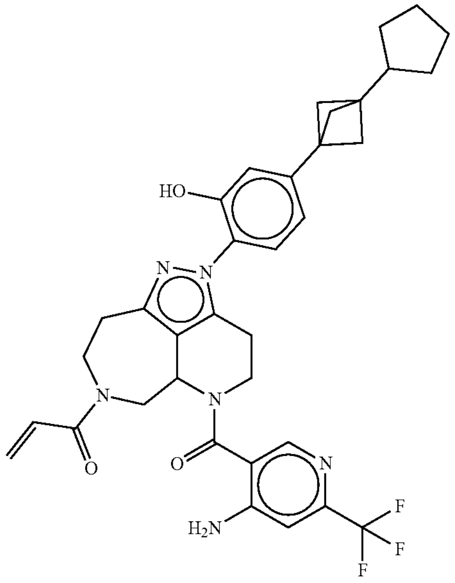 |

TABLE 2-continued

| Compound No | Example No. | Name | Structure |
|---|---|---|---|
| 220 | A-15 | 1-(2-(4-cyclopropylphenyl)-5-(2,4-diamino-5-fluoro-6-(trifluoromethyl)nicotinoyl)-2,3,4,5,5a,6,8,9-octahydro-7H-1,2,5,7-tetraazabenzo[cd]azulen-7-yl)prop-2-en-1-one | 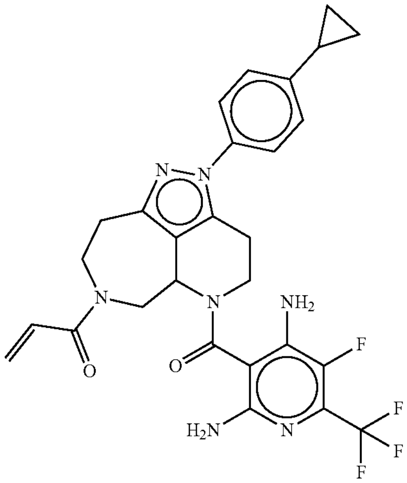 |
| 221 | E-9 | 1-(5-(4-amino-6-(trifluoromethyl)nicotinoyl)-2-(4-cyclopropyl-2-hydroxyphenyl)-6-methyl-2,3,4,5,5a,6,8,9-octahydro-7H-1,2,5,7-tetraazabenzo[cd]azulen-7-yl)prop-2-en-1-one | 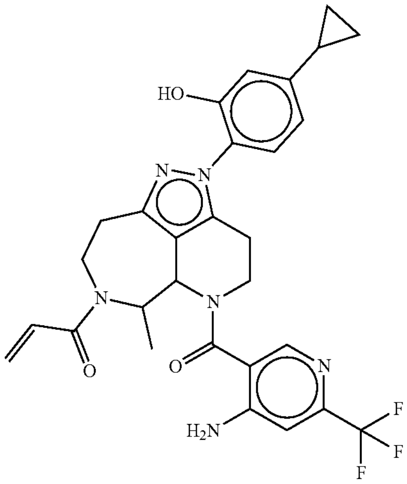 |
| 222 | L-11-1 | 3-((7-acryloyl-5-(4-amino-6-(trifluoromethyl)nicotinoyl)-2-(4-cyclopropyl-2-hydroxyphenyl)-3,4,5,5a,6,7,8,9-octahydro-2H-1,2,5,7-tetraazabenzo[cd]azulen-9-yl)oxy)cyclobutane-1-carbonitrile | 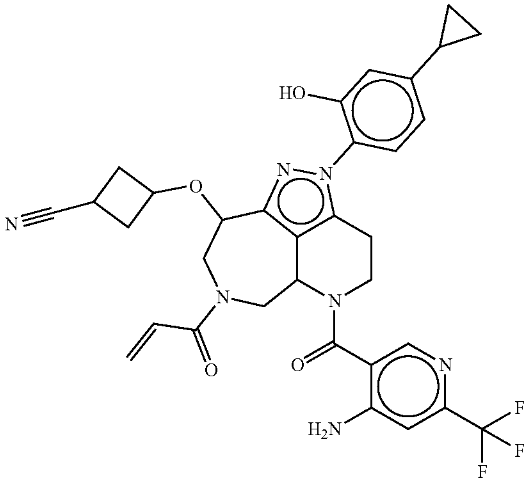 |

TABLE 2-continued

| Compound No | Example No. | Name | Structure |
|---|---|---|---|
| 223 | A-17-1 | 1-(5-(4-amino-5-fluoro-6-(methylthio)nicotinoyl)-2-(4-cyclopropyl-2-hydroxyphenyl)-2,3,4,5,5a,6,8,9-octahydro-7H-1,2,5,7-tetraazabenzo[cd]azulen-7-yl)prop-2-en-1-one | 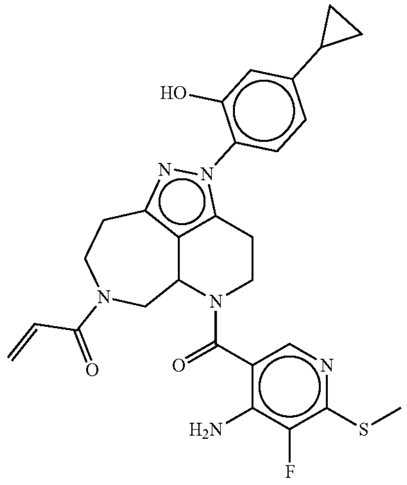 |
| 224 | L-2 | 1-(5-(4-amino-6-(trifluoromethyl) nicotinoyl)-2-(4-cyclopropyl-5-fluoro-2-hydroxyphenyl)-2,3,4,5,5a,6,8,9-octahydro-7H-1,2,5,7-tetraazabenzo[cd]azulen-7-yl)prop-2-en-1-one | 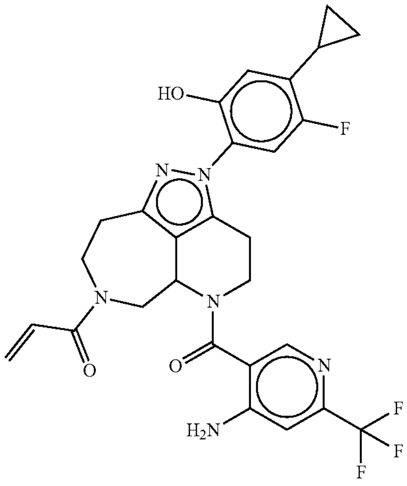 |
| 225 | A-19 | 1-(5-(4-amino-6-(trifluoromethyl) nicotinoyl)-2-(4-cyclopropyl-2-(hydroxymethyl)phenyl)-2,3,4,5,5a,6,8,9-octahydro-7H-1,2,5,7-tetraazabenzo[cd]azulen-7-yl)prop-2-en-1-one | 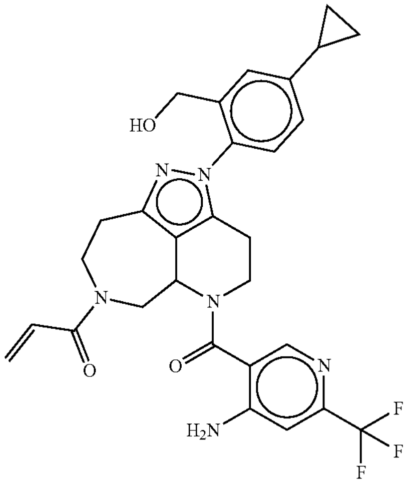 |

TABLE 2-continued

| Compound No | Example No. | Name | Structure |
|---|---|---|---|
| 226 | L-5 | 1-(5-(4-amino-6-(trifluoromethyl)nicotinoyl)-2-(2-hydroxy-4-((trifluoromethyl)thio)phenyl)-2,3,4,5,5a,6,8,9-octahydro-7H-1,2,5,7-tetraazabenzo[cd]azulen-7-yl)prop-2-en-1-one | 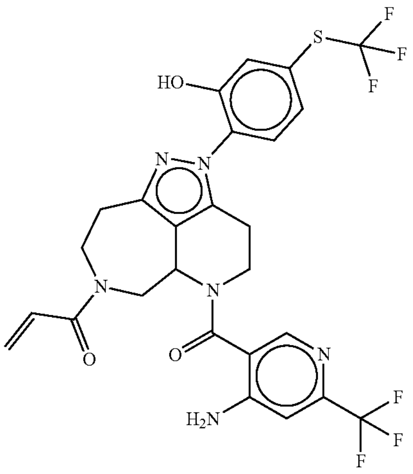 |
| 227 | L-1-3 | 1-(5-(4-amino-6-(1,1-difluoroethyl)-5-fluoronicotinoyl)-2-(4-cyclopropyl-3-fluoro-2-hydroxyphenyl)-2,3,4,5,5a,6,8,9-octahydro-7H-1,2,5,7-tetraazabenzo[cd]azulen-7-yl)prop-2-en-1-one | 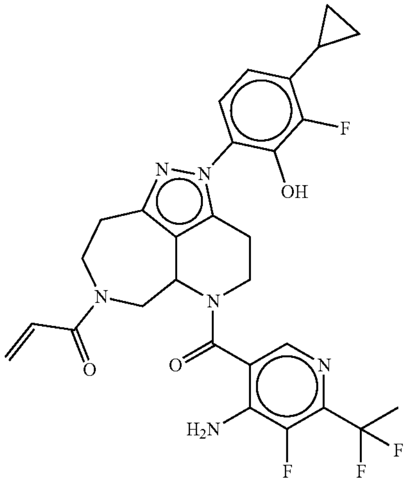 |
| 228 | A-11 | 1-(5-(4-amino-6-bromopyridazine-3-carbonyl)-2-(4-cyclopropyl-2-hydroxyphenyl)-2,3,4,5,5a,6,8,9-octahydro-7H-1,2,5,7-tetraazabenzo[cd]azulen-7-yl)prop-2-en-1-one | 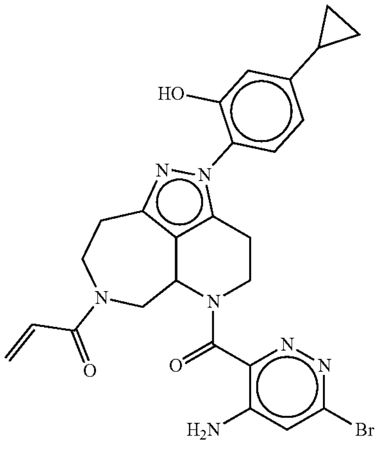 |

TABLE 2-continued

| Compound No | Example No. | Name | Structure |
|---|---|---|---|
| 229 | L-1-4 | 1-(5-(4-amino-6-bromo-5-fluoronicotinoyl)-2-(4-cyclopropyl-3-fluoro-2-hydroxyphenyl)-2,3,4,5,5a,6,8,9-octahydro-7H-1,2,5,7-tetraazabenzo[cd]azulen-7-yl)prop-2-en-1-one | 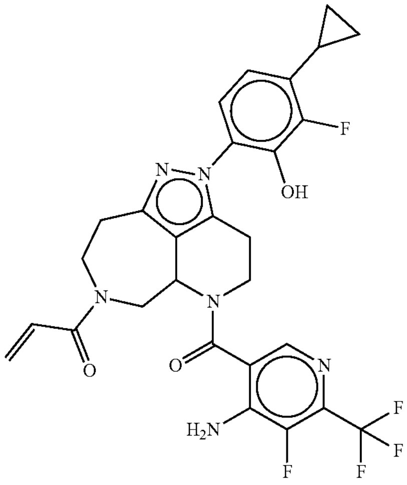 |
| 230 | A-23 | 1-(2-(3-cyclopentylbicyclo[1.1.1]pentan-1-yl)-5-(2,4-diamino-6-(trifluoromethyl)nicotinoyl)-2,3,4,5,5a,6,8,9-octahydro-7H-1,2,5,7-tetraazabenzo[cd]azulen-7-yl)prop-2-en-1-one | 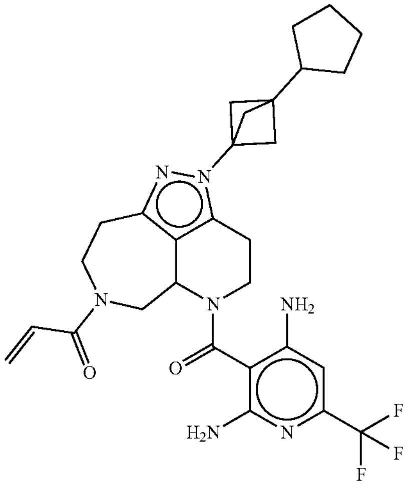 |
| 231 | L-11 | 1-(7-acryloyl-2-(4-cyclopropylphenyl)-5-(4-(trifluoromethyl)benzoyl)-3,4,5,5a,6,7,8,9-octahydro-2H-1,2,5,7-tetraazabenzo[cd]azulen-9-yl)pyridin-2(1H)-one | 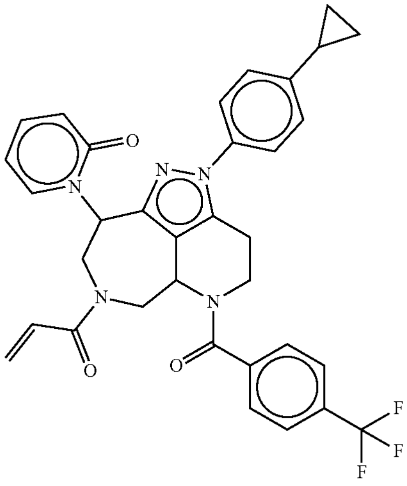 |

TABLE 2-continued

| Compound No | Example No. | Name | Structure |
|---|---|---|---|
| 232 | | 1-(5-(4-amino-6-(trifluoromethyl) nicotinoyl)-9-cyclopropoxy-2-(4-cyclopropyl-2-hydroxyphenyl)-2,3,4,5,5a,6,8,9-octahydro-7H-1,2,5,7-tetraazabenzo[cd]azulen-7-yl)prop-2-en-1-one | 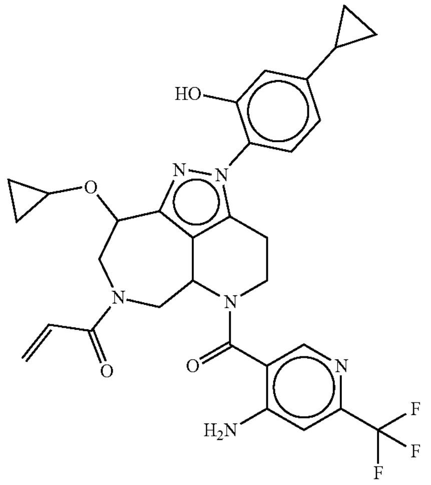 |
| 233 | | 1-(5'-(4-amino-6-(trifluoromethyl) nicotinoyl)-2'-(4-cyclopropylphenyl)-1-(5-methyl-1,3,4-thiadiazol-2-yl)-2',3',4',5',5a',6'-hexahydro-1',2',5',7'-tetraazaspiro[azetidine-3,9'-benzo[cd]azulen]-1'(9a'),2a'-dien-7'(8'H)-yl)prop-2-en-1-one | 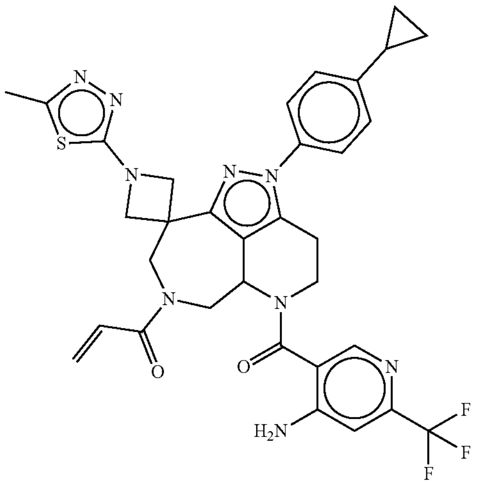 |
| 234 | C-25-7 | 1-(2-(4-cyclopropylphenyl)-9-(imidazo[2,1-b]thiazol-5-ylmethoxy)-5-(6-(trifluoromethyl) nicotinoyl)-2,3,4,5,5a,6,8,9-octahydro-7H-1,2,5,7-tetraazabenzo[cd]azulen-7-yl)prop-2-en-1-one | 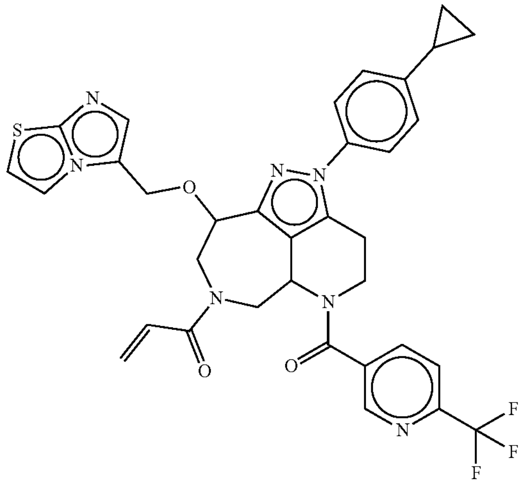 |

TABLE 2-continued

| Compound No | Example No. | Name | Structure |
|---|---|---|---|
| 235 | C-25-8 | 1-(2-(4-cyclopropylphenyl)-9-(1-(methoxymethyl) cyclopropoxy)-5-(6-(trifluoromethyl) nicotinoyl)-2,3,4,5,5a,6,8,9-octahydro-7H-1,2,5,7-tetraazabenzo[cd]azulen-7-yl)prop-2-en-1-one | 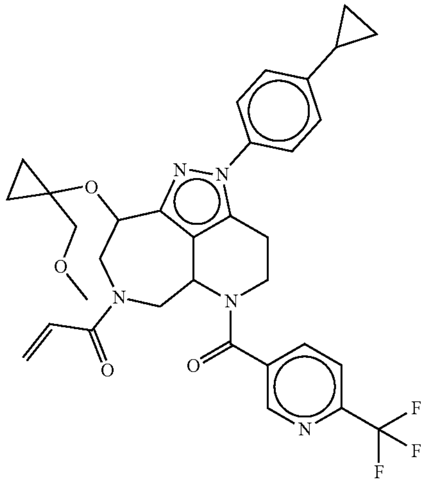 |
| 236 | C-8-2 | 1-(5-(1-chloroimidazo[1,5-a]pyridine-6-carbonyl)-2-(4-cyclobutylphenyl)-2,3,4,5,5a,6,8,9-octahydro-7H-1,2,5,7-tetraazabenzo[cd]azulen-7-yl)prop-2-en-1-one | 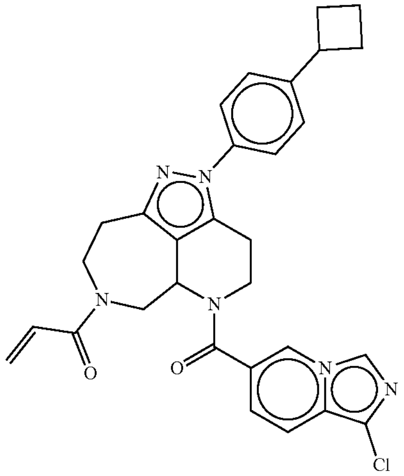 |
| 237 | F-6 | 1-(5-(7-bromo-2-(difluoromethyl)-1H-benzo[d]imidazole-4-carbonyl)-2-(4-cyclobutylphenyl)-4,5,5a,6,8,9-hexahydro-1,2a,5,7-tetraazabenzo[cd]azulen-7(3H)-yl)prop-2-en-1-one | 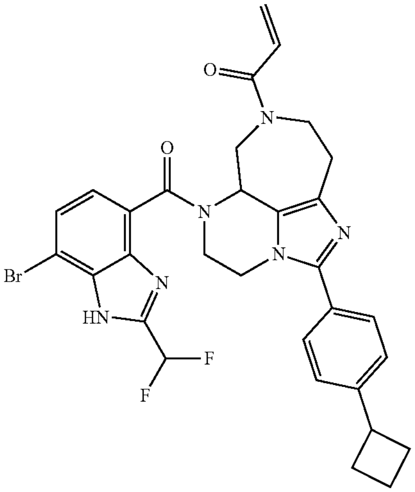 [SMILES: C=CC(=O)N1CCc2nc(-c3ccc(C4CCC4)cc3)n3c2C(C1)N(C(=O)c1ccc(Br)c2[nH]c(C(F)F)nc12)CC3] |

TABLE 2-continued

| Compound No | Example No. | Name | Structure |
|---|---|---|---|
| 238 | F-7 | 1-(5-(4-amino-6-(trifluoromethyl)nicotinoyl)-2-(4-cyclobutylphenyl)-4,5,5a,6,8,9-hexahydro-1,2a,5,7-tetraazabenzo[cd]azulen-7(3H)-yl)prop-2-en-1-one | 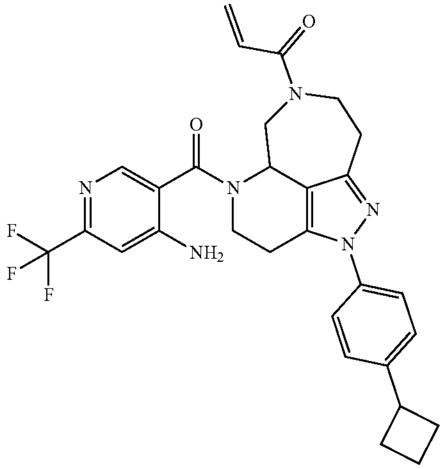 [SMILES: C=CC(=O)N1CCc2nn(-c3ccc(C4CCC4)cc3)c3c2C(C1)N(C(=O)c1cnc(C(F)(F)F)cc1N)CC3] |
| 239 | C-17 | 1-(5-(4-amino-6-(trifluoromethyl)nicotinoyl)-2-(4-cyclobutyl-2-hydroxyphenyl)-2,3,4,5,5a,6,8,9-octahydro-7H-1,2,5,7-tetraazabenzo[cd]azulen-7-yl)-4-methoxybut-2-en-1-one | 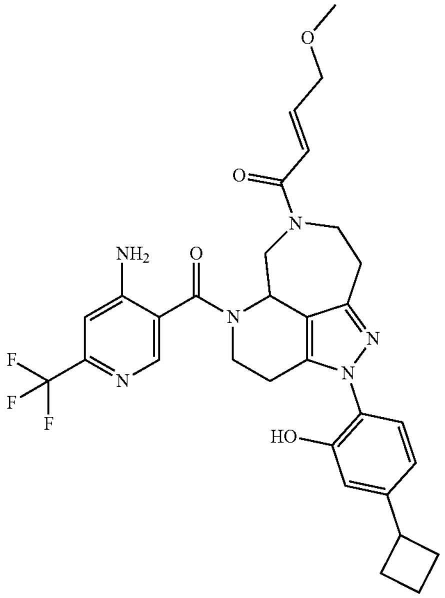 [SMILES: COC/C=C/C(=O)N1CCc2nn(-c3ccc(C4CCC4)cc3O)c3c2C(C1)N(C(=O)c1cnc(C(F)(F)F)cc1N)CC3] |
| 240 | C-19 | 1-(5-(4-amino-6-(trifluoromethyl)nicotinoyl)-2-(4-cyclobutyl-2-methylphenyl)-2,3,4,5,5a,6,8,9-octahydro-7H-1,2,5,7-tetraazabenzo[cd]azulen-7-yl)prop-2-en-1-one | 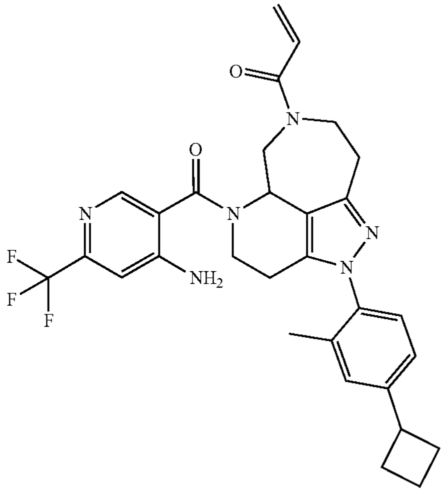 [SMILES: C=CC(=O)N1CCc2nn(-c3ccc(C4CCC4)cc3C)c3c2C(C1)N(C(=O)c1cnc(C(F)(F)F)cc1N)CC3] |

TABLE 2-continued

| Compound No | Example No. | Name | Structure |
|---|---|---|---|
| 241 | C-21 | 1-(5-(4-amino-6-(trifluoromethyl) nicotinoyl)-2-(2-chloro-4-cyclobutylphenyl)-2,3,4,5,5a,6,8,9-octahydro-7H-1,2,5,7-tetraazabenzo[cd]azulen-7-yl)prop-2-en-1-one | 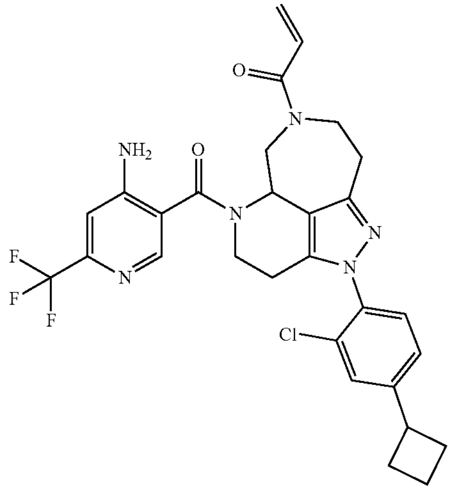 [SMILES: C=CC(=O)N1CCc2nn(-c3ccc(C4CCC4)cc3Cl)c3c2C(C1)N(C(=O)c1cnc(C(F)(F)F)cc1N)CC3] |
| 242 | C-23 | 1-(2-(4-cyclobutyl-2-hydroxyphenyl)-5-(8-(trifluoromethyl) quinazoline-5-carbonyl)-2,3,4,5,5a,6,8,9-octahydro-7H-1,2,5,7-tetraazabenzo[cd]azulen-7-yl)prop-2-en-1-one | 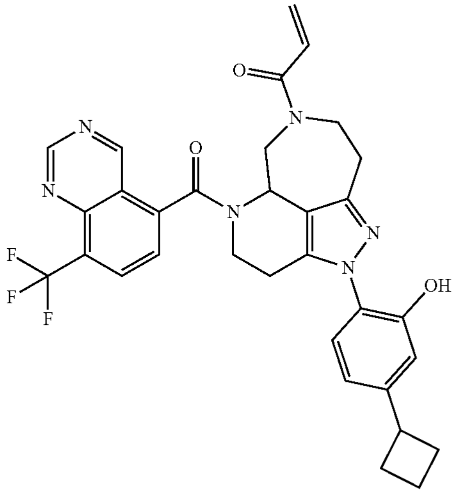 [SMILES: C=CC(=O)N1CCc2nn(-c3ccc(C4CCC4)cc3O)c3c2C(C1)N(C(=O)c1ccc(C(F)(F)F)c2ncncc12)CC3] |
| 243 | C-18 | 1-(5-(4-amino-6-(trifluoromethyl) nicotinoyl)-2-(4-cyclobutylphenyl)-2,3,4,5,5a,6,8,9-octahydro-7H-1,2,5,7-tetraazabenzo[cd]azulen-7-yl)-3-chloroprop-2-en-1-one | 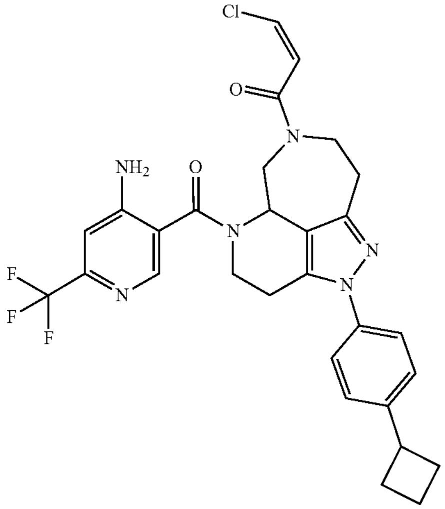 [SMILES: Nc1cc(C(F)(F)F)ncc1C(=O)N1CCc2c3c(nn2-c2ccc(C4CCC4)cc2)CCN(C(=O)/C=C\Cl)CC31] |

TABLE 2-continued

| Compound No | Example No. | Name | Structure |
|---|---|---|---|
| 244 | L-9-1 | 1-(5-(4-amino-6-(trifluoromethyl) nicotinoyl)-2-(4-cyclopropyl-3,5-difluoro-2-hydroxyphenyl)-2,3,4,5,5a,6,8,9-octahydro-7H-1,2,5,7-tetraazabenzo[cd]azulen-7-yl)prop-2-en-1-one | 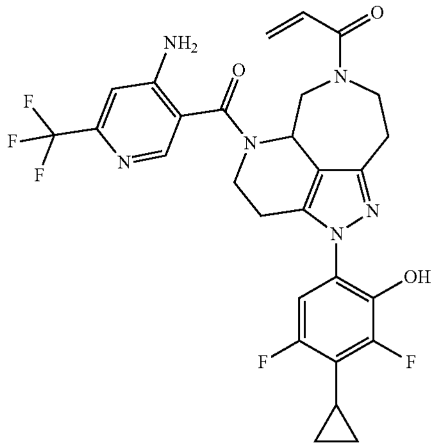 [SMILES: C=CC(=O)N1CCc2nn(-c3cc(F)c(C4CC4)c(F)c3O)c3c2C(C1)N(C(=O)c1cnc(C(F)(F)F)cc1N)CC3] |
| 245 | A-10-11 | 1-(5-(2-amino-4-(trifluoromethyl)benzoyl)-2-(4-cyclopropyl-2-hydroxyphenyl)-2,3,4,5,5a,6,8,9-octahydro-7H-1,2,5,7-tetraazabenzo[cd]azulen-7-yl)prop-2-en-1-one | 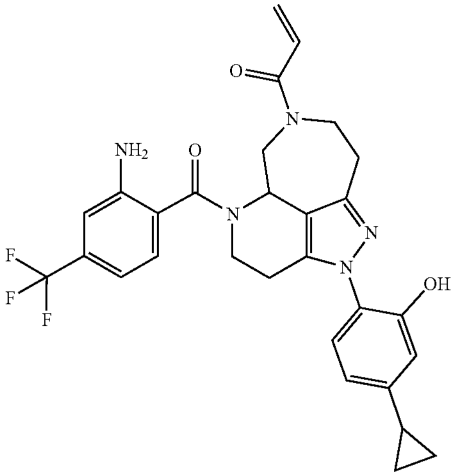 [SMILES: C=CC(=O)N1CCc2nn(-c3ccc(C4CC4)cc3O)c3c2C(C1)N(C(=O)c1ccc(C(F)(F)F)cc1N)CC3] |
| 246 | C-25-5 | 1-(9-((2-oxaspiro[3.3]heptan-6-yl)oxy)-5-(4-amino-6-(trifluoromethyl) nicotinoyl)-2-(4-cyclobutylphenyl)-2,3,4,5,5a,6,8,9-octahydro-7H-benzo[cd]azulen-7-yl)prop-2-en-1-one | 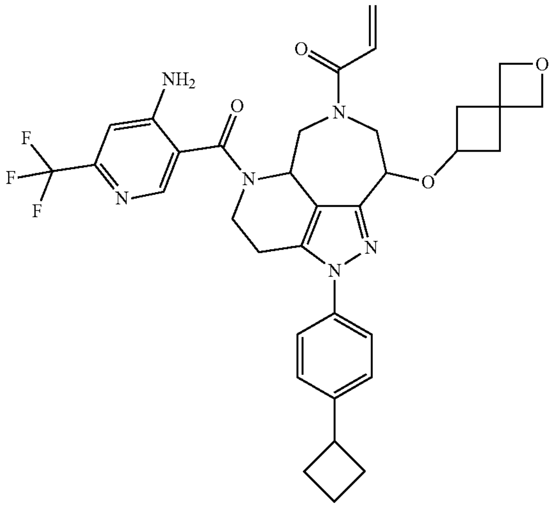 [SMILES: C=CC(=O)N1CC(OC2CC3(COC3)C2)c2nn(-c3ccc(C4CCC4)cc3)c3c2C(C1)N(C(=O)c1cnc(C(F)(F)F)cc1N)CC3] |

TABLE 2-continued

| Compound No | Example No. | Name | Structure |
|---|---|---|---|
| 247 | A-10-14 | 1-(5-(4-amino-5-fluoro-6-(trifluoromethoxy)nicotinoyl)-2-(4-cyclopropyl-2-hydroxyphenyl)-2,3,4,5,5a,6,8,9-octahydro-7H-1,2,5,7-tetraazabenzo[cd]azulen-7-yl)prop-2-en-1-one | 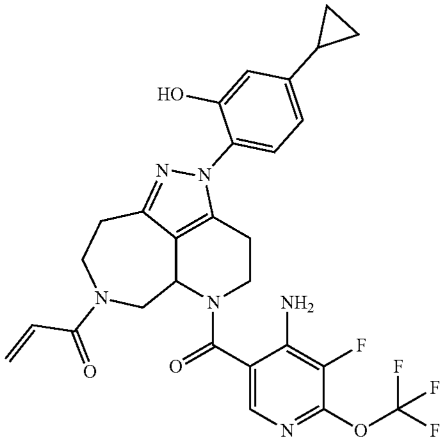 [SMILES: C=CC(=O)N1CCc2nn(-c3ccc(C4CC4)cc3O)c3c2C(C1)N(C(=O)c1cnc(OC(F)(F)F)c(F)c1N)CC3] |
| 248 | A-35 | 1-(5-(4-amino-6-(trifluoromethyl)pyridazine-3-carbonyl)-2-(4-cyclopropyl-2-hydroxyphenyl)-2,3,4,5,5a,6,8,9-octahydro-7H-1,2,5,7-tetraazabenzo[cd]azulen-7-yl)prop-2-en-1-one | 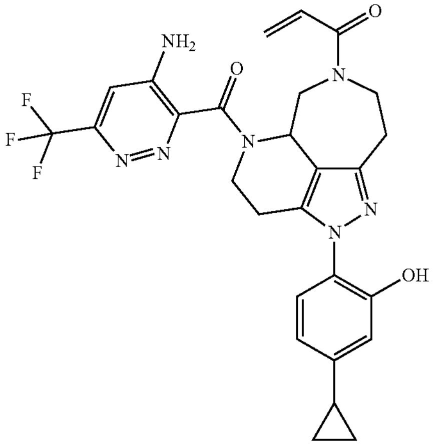 [SMILES: C=CC(=O)N1CCc2nn(-c3ccc(C4CC4)cc3O)c3c2C(C1)N(C(=O)c1nnc(C(F)(F)F)cc1N)CC3] |
| 249 | C-25-3 | 1-(5-(4-amino-6-(trifluoromethyl)nicotinoyl)-2-(4-cyclopropylphenyl)-9-((5-methyl-1,3,4-thiadiazol-2-yl)methoxy)-2,3,4,5,5a,6,8,9-octahydro-7H-1,2,5,7-tetraazabenzo[cd]azulen-7-yl)prop-2-en-1-one | 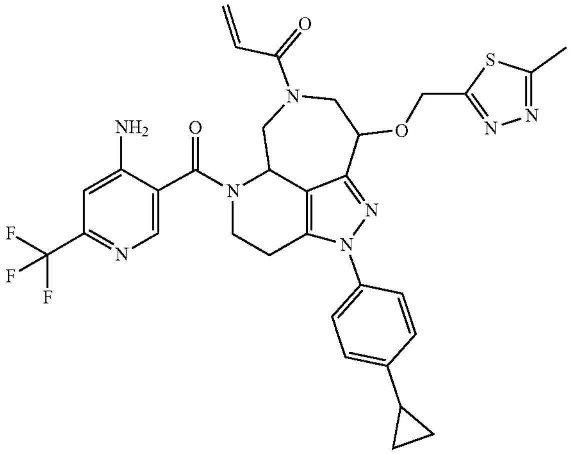 [SMILES: C=CC(=O)N1CC(OCc2nnc(C)s2)c2nn(-c3ccc(C4CC4)cc3)c3c2C(C1)N(C(=O)c1cnc(C(F)(F)F)cc1N)CC3] |

TABLE 2-continued

| Compound No | Example No. | Name | Structure |
|---|---|---|---|
| 250 | C-25-1 | 1-(5-(4-amino-6-(trifluoromethyl)nicotinoyl)-2-(4-cyclopropylphenyl)-9-(oxazol-2-ylmethoxy)-2,3,4,5,5a,6,8,9-octahydro-7H-1,2,5,7-tetraazabenzo[cd]azulen-7-yl)prop-2-en-1-one | 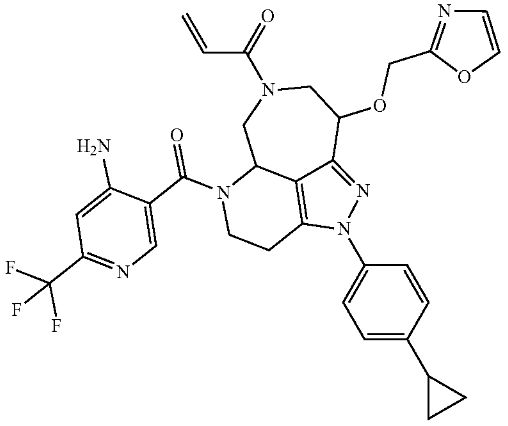 [SMILES: C=CC(=O)N1CC(OCc2ncco2)c2nn(-c3ccc(C4CC4)cc3)c3c2C(C1)N(C(=O)c1cnc(C(F)(F)F)cc1N)CC3] |
| 251 | C-25-2 | 1-(5-(4-amino-6-(trifluoromethyl)nicotinoyl)-2-(4-cyclopropylphenyl)-9-(pyridin-3-ylmethoxy)-2,3,4,5,5a,6,8,9-octahydro-7H-1,2,5,7-tetraazabenzo[cd]azulen-7-yl)prop-2-en-1-one | 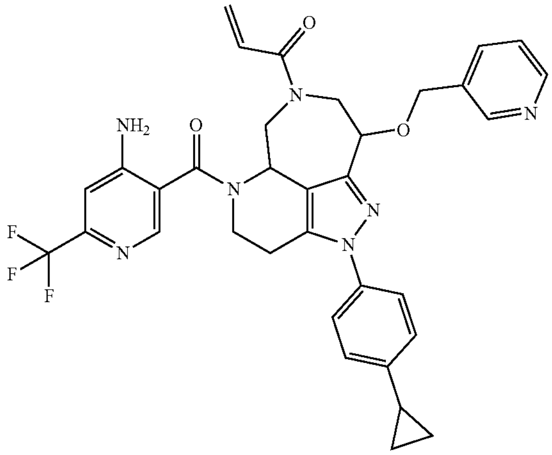 [SMILES: C=CC(=O)N1CC(OCc2cccnc2)c2nn(-c3ccc(C4CC4)cc3)c3c2C(C1)N(C(=O)c1cnc(C(F)(F)F)cc1N)CC3] |
| 252 | A-20 | 1-(5-(4-amino-6-(trifluoromethyl)nicotinoyl)-2-(4-cyclopropyl-2-(difluoromethoxy)phenyl)-2,3,4,5,5a,6,8,9-octahydro-7H-1,2,5,7-tetraazabenzo[cd]azulen-7-yl)prop-2-en-1-one | 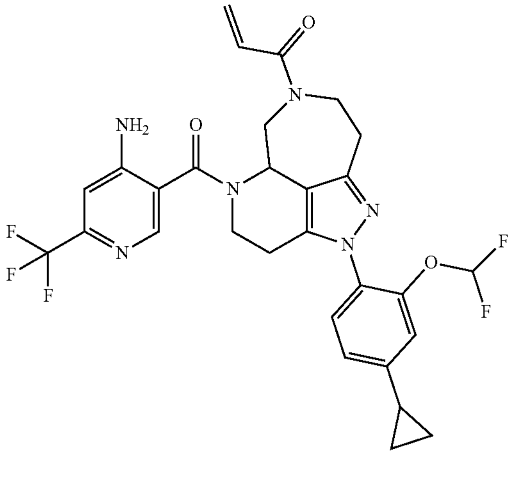 [SMILES: C=CC(=O)N1CCc2nn(-c3ccc(C4CC4)cc3OC(F)F)c3c2C(C1)N(C(=O)c1cnc(C(F)(F)F)cc1N)CC3] |

TABLE 2-continued

| Compound No | Example No. | Name | Structure |
|---|---|---|---|
| 253 | L-2-1 | 1-[7-[4-amino-6-(1,1-difluoroethyl)-5-fluoro-pyridine-3-carbonyl]-3-(4-cyclopropyl-5-fluoro-2-hydroxy-phenyl)-2,3,7,10-tetrazatricyclo[6.4.1.04,13]trideca-1,4(13)-dien-10-yl]prop-2-en-1-one | 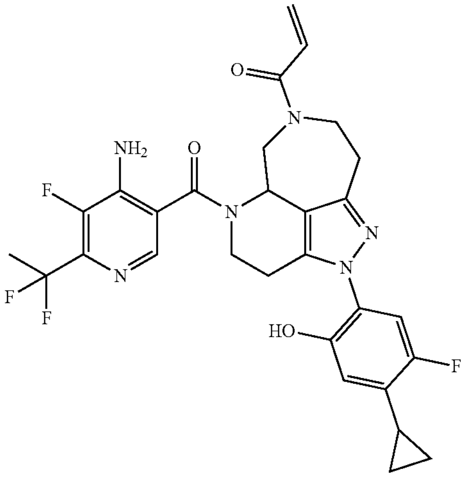 [SMILES: C=CC(=O)N1CCc2nn(-c3cc(F)c(C4CC4)cc3O)c3c2C(C1)N(C(=O)c1cnc(C(C)(F)F)c(F)c1N)CC3] |
| 254 | L-3 | 1-(5-(4-amino-5-fluoro-6-(trifluoromethoxy) nicotinoyl)-2-(4-cyclopropyl-5-fluoro-2-hydroxyphenyl)-2,3,4,5,5a,6,8,9-octahydro-7H-1,2,5,7-tetraazabenzo[cd]azulen-7-yl)prop-2-en-1-one | 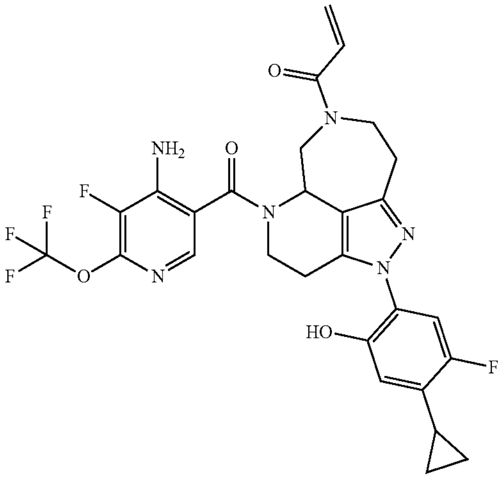 [SMILES: C=CC(=O)N1CCc2nn(-c3cc(F)c(C4CC4)cc3O)c3c2C(C1)N(C(=O)c1cnc(OC(F)(F)F)c(F)c1N)CC3] |
| 255 | C-25-4 | 1-(5-(4-amino-6-(trifluoromethyl) nicotinoyl)-2-(4-cyclopropylphenyl)-9-((tetrahydro-2H-pyran-4-yl)methoxy)-2,3,4,5,5a,6,8,9-octahydro-7H-1,2,5,7-tetraazabenzo[cd]azulen-7-yl)prop-2-en-1-one | 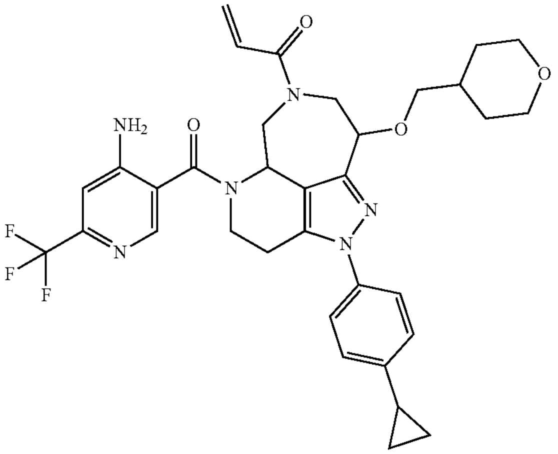 [SMILES: C=CC(=O)N1CC(OCC2CCOCC2)c2nn(-c3ccc(C4CC4)cc3)c3c2C(C1)N(C(=O)c1cnc(C(F)(F)F)cc1N)CC3] |

TABLE 2-continued

| Compound No | Example No. | Name | Structure |
|---|---|---|---|
| 256 | A-21 | 1-(5-(4-amino-6-(trifluoromethyl) nicotinoyl)-2-(4-cyclopropyl-2-(trifluoromethyl)phenyl)-2,3,4,5,5a,6,8,9-octahydro-7H-1,2,5,7-tetraazabenzo[cd]azulen-7-yl)prop-2-en-1-one | 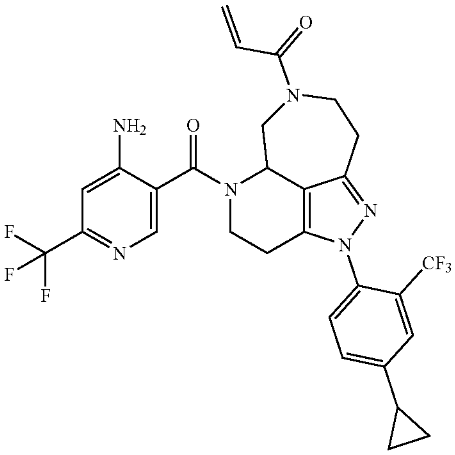 [SMILES: C=CC(=O)N1CCc2nn(-c3ccc(C4CC4)cc3C(F)(F)F)c3c2C(C1)N(C(=O)c1cnc(C(F)(F)F)cc1N)CC3] |
| 257 | L-12 | (4-amino-6-(trifluoromethyl)pyridin-3-yl)(2-(4-cyclopropyl-2-hydroxyphenyl)-7-(3-(methylsulfonyl)allyl)-3,4,6,7,8,9-hexahydro-2H-1,2,5,7-tetraazabenzo[cd]azulen-5(5aH)-yl)methanone | 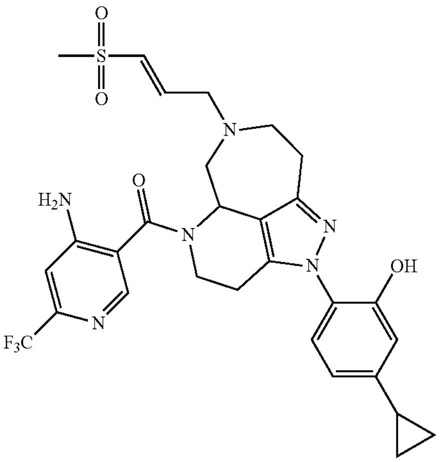 [SMILES: CS(=O)(=O)/C=C/CN1CCc2nn(-c3ccc(C4CC4)cc3O)c3c2C(C1)N(C(=O)c1cnc(C(F)(F)F)cc1N)CC3] |
| 258 | L-1-6 | 1-(5-(4-amino-5-fluoro-6-(trifluoromethoxy) nicotinoyl)-2-(4-cyclopropyl-3-fluoro-2-hydroxyphenyl)-2,3,4,5,5a,6,8,9-octahydro-7H-1,2,5,7-tetraazabenzo[cd]azulen-7-yl)prop-2-en-1-one | 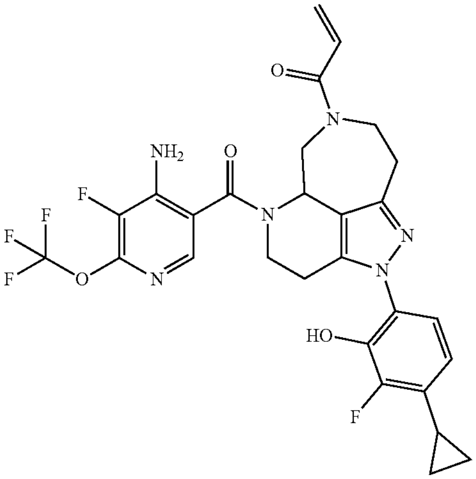 [SMILES: C=CC(=O)N1CCc2nn(-c3ccc(C4CC4)c(F)c3O)c3c2C(C1)N(C(=O)c1cnc(OC(F)(F)F)c(F)c1N)CC3] |

TABLE 2-continued

| Compound No | Example No. | Name | Structure |
|---|---|---|---|
| 259 | A-10-13 | 1-(5-(2-amino-3-fluoro-4-(trifluoromethyl)benzoyl)-2-(4-cyclopropyl-2-hydroxyphenyl)-2,3,4,5,5a,6,8,9-octahydro-7H-1,2,5,7-tetraazabenzo[cd]azulen-7-yl)prop-2-en-1-one | 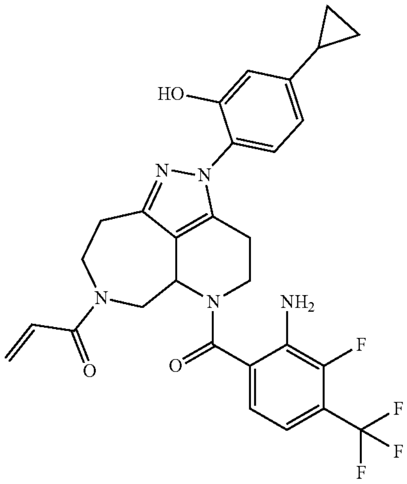 [SMILES: C=CC(=O)N1CCc2nn(-c3ccc(C4CC4)cc3O)c3c2C(C1)N(C(=O)c1ccc(C(F)(F)F)c(F)c1N)CC3] |
| 260 | C-25-9 | 1-(5-(4-amino-6-(trifluoromethyl) nicotinoyl)-2-(4-cyclobutylphenyl)-9-((3,6-dihydro-2H-pyran-4-yl)methoxy)-2,3,4,5,5a,6,8,9-octahydro-7H-1,2,5,7-tetraazabenzo[cd]azulen-7-yl)prop-2-en-1-one | 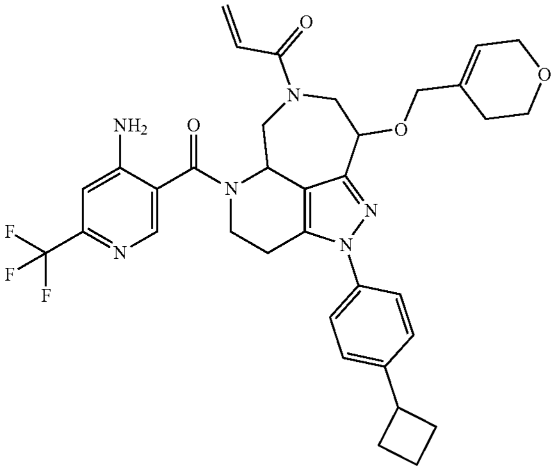 [SMILES: C=CC(=O)N1CC(OCC2=CCOCC2)c2nn(-c3ccc(C4CCC4)cc3)c3c2C(C1)N(C(=O)c1cnc(C(F)(F)F)cc1N)CC3] |

TABLE 1A

| Compound No. | Name | Structure |
|---|---|---|
| 1A | (R)-1-(2-(4-cyclopropylphenyl)-5-(5-hydroxy-6-(trifluoromethyl)nicotinoyl)-2,3,4,5,5a,6,8,9-octahydro-7H-1,2,5,7-tetraazabenzo[cd]azulen-7-yl)prop-2-en-1-one | 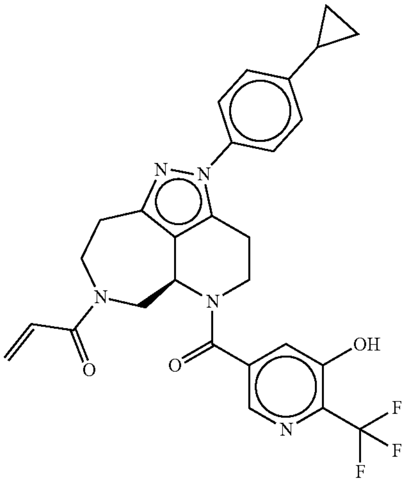 |

TABLE 1A-continued

| Compound No. | Name | Structure |
|---|---|---|
| 4A | (R)-1-(2-(4-(bicyclo[1.1.1]pentan-1-yl)phenyl)-5-(7-bromo-1H-benzo[d]imidazole-4-carbonyl)-2,3,4,5,5a,6,8,9-octahydro-7H-1,2,5,7-tetraazabenzo[cd]azulen-7-yl)prop-2-en-1-one | 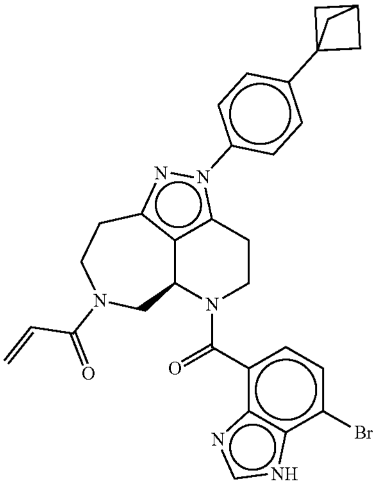 |
| 5A | (R)-1-(5-(7-bromo-1H-benzo[d]imidazole-4-carbonyl)-2-(4-cyclopropyl-2-hydroxyphenyl)-2,3,4,5,5a,6,8,9-octahydro-7H-1,2,5,7-tetraazabenzo[cd]azulen-7-yl)prop-2-en-1-one | 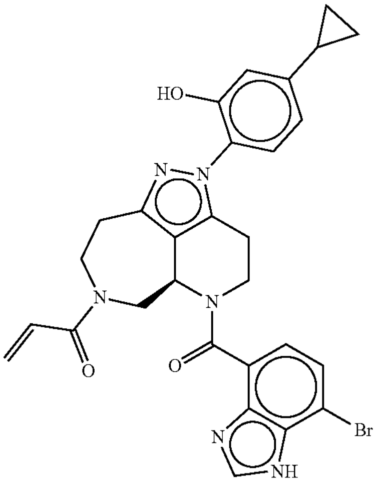 |
| 7A | (R)-1-(5-(7-bromo-1H-benzo[d]imidazole-4-carbonyl)-2-(4-isopropylphenyl)-2,3,4,5,5a,6,8,9-octahydro-7H-1,2,5,7-tetraazabenzo[cd]azulen-7-yl)prop-2-en-1-one | 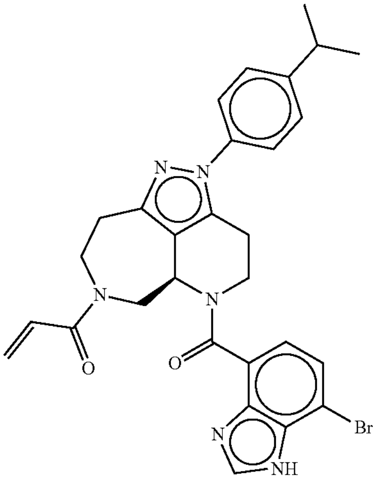 |

TABLE 1A-continued

| Compound No. | Name | Structure |
| --- | --- | --- |
| 8A | (R)-1-(5-(2-amino-7-bromo-1H-benzo[d]imidazole-4-carbonyl)-2-(4-isopropylphenyl)-2,3,4,5,5a,6,8,9-octahydro-7H-1,2,5,7-tetraazabenzo[cd]azulen-7-yl)prop-2-en-1-one | 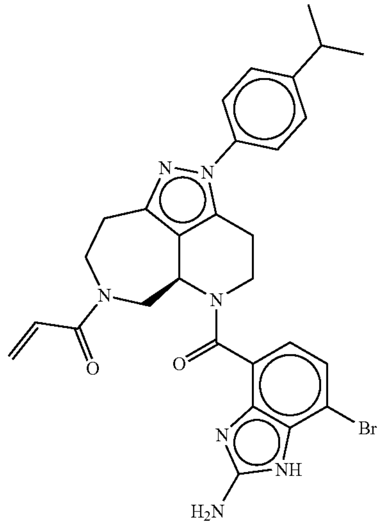 |
| 9A | (R)-1-(5-(2-(azetidin-1-yl)-7-bromo-1H-benzo[d]imidazole-4-carbonyl)-2-(4-isopropylphenyl)-2,3,4,5,5a,6,8,9-octahydro-7H-1,2,5,7-tetraazabenzo[cd]azulen-7-yl)prop-2-en-1-one | 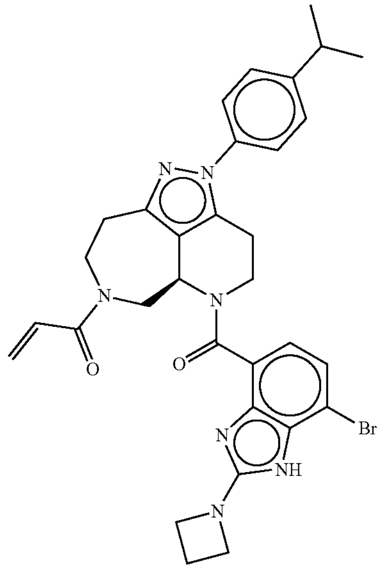 |
| 10A | (R)-1-(5-(7-bromo-1H-imidazo[4,5-c]pyridine-4-carbonyl)-2-(4-isopropylphenyl)-2,3,4,5,5a,6,8,9-octahydro-7H-1,2,5,7-tetraazabenzo[cd]azulen-7-yl)prop-2-en-1-one | 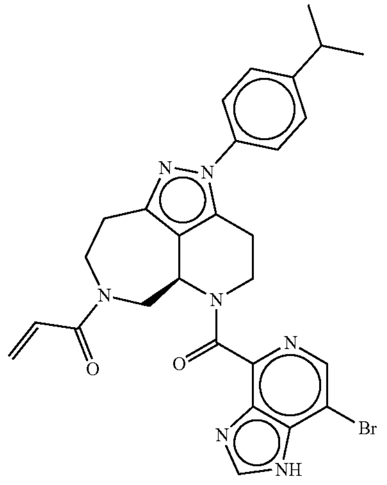 |

TABLE 1A-continued

| Compound No. | Name | Structure |
|---|---|---|
| 11A | (R)-1-(2-(4-isopropylphenyl)-5-(1-(trifluoromethyl)-1H-indazole-5-carbonyl)-2,3,4,5,5a,6,8,9-octahydro-7H-1,2,5,7-tetraazabenzo[cd]azulen-7-yl)prop-2-en-1-one | 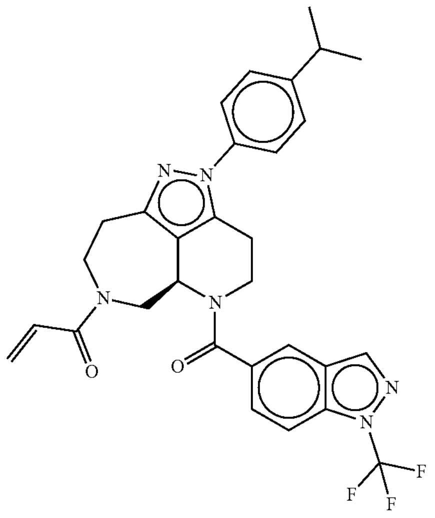 |
| 12A | (R)-1-(2-(4-isopropylphenyl)-5-(5-methoxy-6-(trifluoromethyl)nicotinoyl)-2,3,4,5,5a,6,8,9-octahydro-7H-1,2,5,7-tetraazabenzo[cd]azulen-7-yl)prop-2-en-1-one | 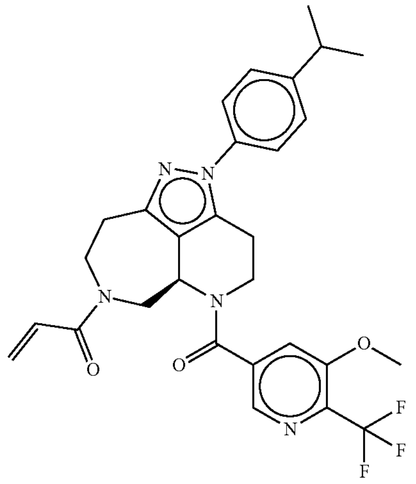 |
| 13A | (R)-1-(2-(4-isopropylphenyl)-5-(6-(trifluoromethyl)nicotinoyl)-2,3,4,5,5a,6,8,9-octahydro-7H-1,2,5,7-tetraazabenzo[cd]azulen-7-yl)prop-2-en-1-one | 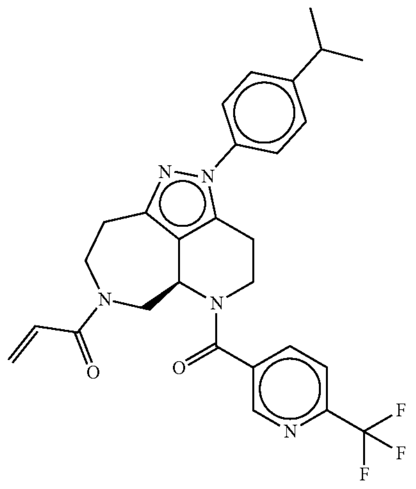 |

TABLE 1A-continued

| Compound No. | Name | Structure |
|---|---|---|
| 14A | (R)-1-(5-(5-hydroxy-6-(trifluoromethyl)nicotinoyl)-2-(4-isopropylphenyl)-2,3,4,5,5a,6,8,9-octahydro-7H-1,2,5,7-tetraazabenzo[cd]azulen-7-yl)prop-2-en-1-one | 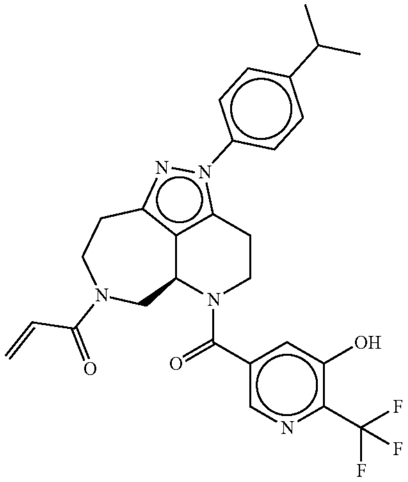 |
| 15A | (R)-1-(5-(7-bromo-1H-benzo[d]imidazole-4-carbonyl)-2-(4-isopropylphenyl)-2,3,4,5,5a,6,8,9-octahydro-7H-1,2,5,7-tetraazabenzo[cd]azulen-7-yl)-4-(dimethylamino)but-2-en-1-one | 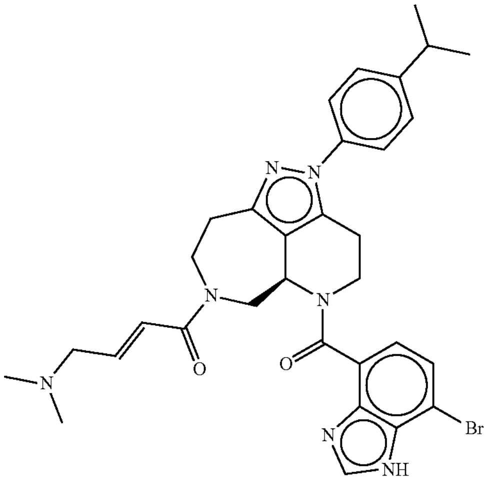 |
| 16A | (R)-(7-bromo-1H-benzo[d]imidazol-4-yl)(7-(cyclobut-1-ene-1-carbonyl)-2-(4-isopropylphenyl)-2,3,4,5a,6,7,8,9-octahydro-5H-1,2,5,7-tetraazabenzo[cd]azulen-5-yl)methanone | 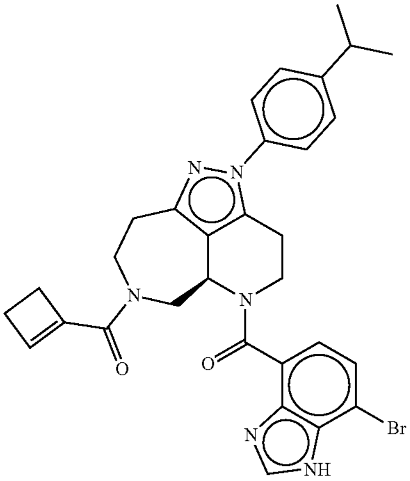 |

TABLE 1A-continued

| Compound No. | Name | Structure |
|---|---|---|
| 17A | (R)-1-(5-(7-bromo-1H-benzo[d]imidazole-4-carbonyl)-2-(4-isopropylphenyl)-2,3,4,5,5a,6,8,9-octahydro-7H-1,2,5,7-tetraazabenzo[cd]azulen-7-yl)-2-fluoroprop-2-en-1-one | 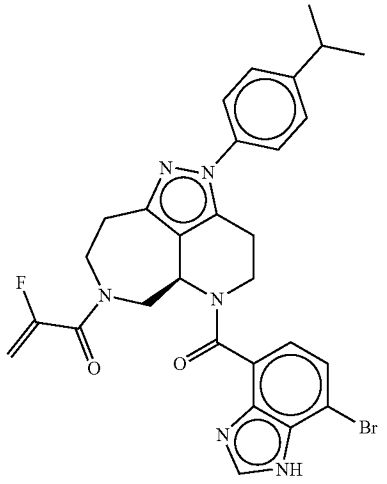 |
| 18A | (R)-4-(7-acryloyl-2-(4-cyclopropylphenyl)-3,4,5,5a,6,7,8,9-octahydro-2H-1,2,5,7-tetraazabenzo[cd]azulene-5-carbonyl)-1H-benzo[d]imidazole-7-carbonitrile | 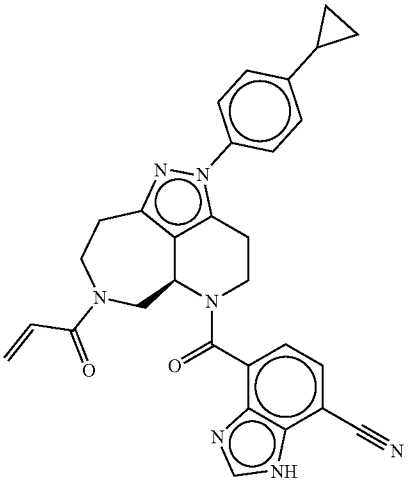 |
| 19A | (R)-1-(2-(4-(bicyclo[1.1.1]pentan-1-yl)phenyl)-5-(7-(trifluoromethyl)-1H-indazole-4-carbonyl)-2,3,4,5,5a,6,8,9-octahydro-7H-1,2,5,7-tetraazabenzo[cd]azulen-7-yl)prop-2-en-1-one | 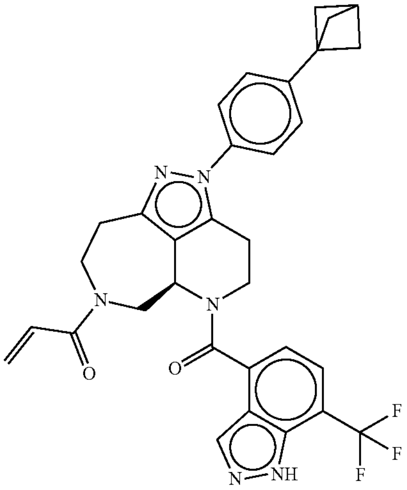 |

TABLE 1A-continued

| Compound No. | Name | Structure |
|---|---|---|
| 20A | (R)-1-(5-(7-bromo-1H-benzo[d]imidazole-4-carbonyl)-2-(2-hydroxy-4-isopropylphenyl)-2,3,4,5,5a,6,8,9-octahydro-7H-1,2,5,7-tetraazabenzo[cd]azulen-7-yl)prop-2-en-1-one | 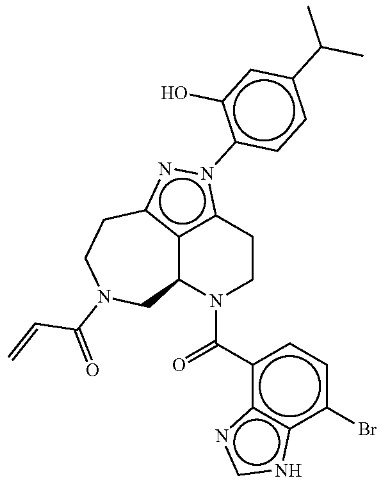 |
| 21A | (R)-1-(2-(2-hydroxy-4-isopropylphenyl)-5-(5-hydroxy-6-(trifluoromethyl)nicotinoyl)-2,3,4,5,5a,6,8,9-octahydro-7H-1,2,5,7-tetraazabenzo[cd]azulen-7-yl)prop-2-en-1-one | 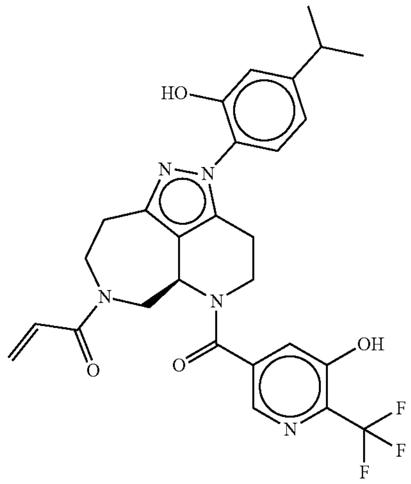 |
| 22A | (R)-1-(5-(4-bromo-3H-imidazo[4,5-c]pyridine-7-carbonyl)-2-(2-hydroxy-4-isopropylphenyl)-2,3,4,5,5a,6,8,9-octahydro-7H-1,2,5,7-tetraazabenzo[cd]azulen-7-yl)prop-2-en-1-one | 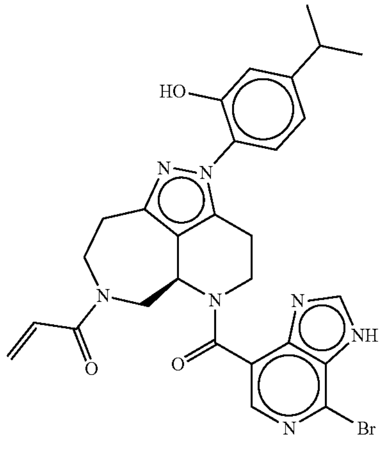 |

TABLE 1A-continued

| Compound No. | Name | Structure |
|---|---|---|
| 23A | (R)-1-(5-(7-bromo-1H-benzo[d]imidazole-4-carbonyl)-2-(4-cyclobutyl-2-hydroxyphenyl)-2,3,4,5,5a,6,8,9-octahydro-7H-1,2,5,7-tetraazabenzo[cd]azulen-7-yl)prop-2-en-1-one | 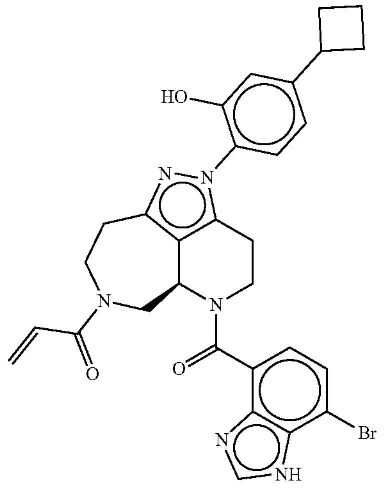 |
| 24A | (R)-1-(5-(3-bromo-1H-indazole-6-carbonyl)-2-(4-cyclobutyl-2-hydroxyphenyl)-2,3,4,5,5a,6,8,9-octahydro-7H-1,2,5,7-tetraazabenzo[cd]azulen-7-yl)prop-2-en-1-one | 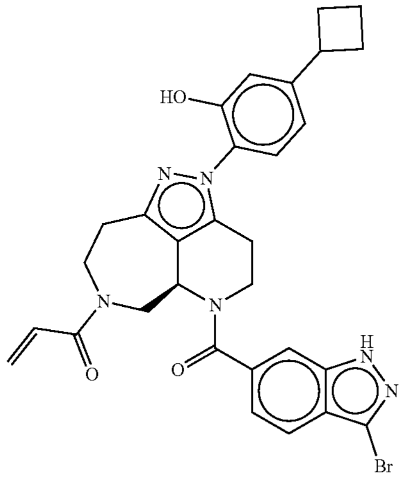 |
| 25A | (R)-1-(2-(4-cyclobutyl-2-hydroxyphenyl)-5-(5-hydroxy-6-(trifluoromethyl)nicotinoyl)-2,3,4,5,5a,6,8,9-octahydro-7H-1,2,5,7-tetraazabenzo[cd]azulen-7-yl)prop-2-en-1-one | 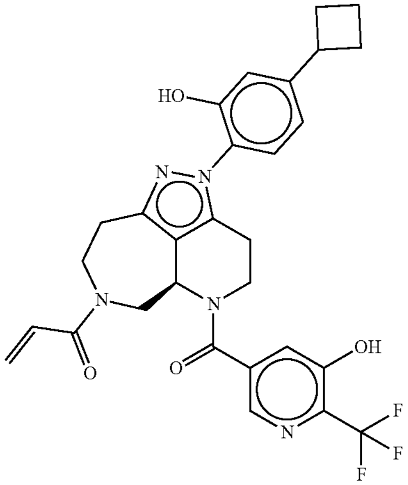 |

TABLE 1A-continued

| Compound No. | Name | Structure |
| --- | --- | --- |
| 26A | (R)-1-(2-(4-cyclobutylphenyl)-5-(5-hydroxy-6-(trifluoromethyl)nicotinoyl)-2,3,4,5,5a,6,8,9-octahydro-7H-1,2,5,7-tetraazabenzo[cd]azulen-7-yl)prop-2-en-1-one | 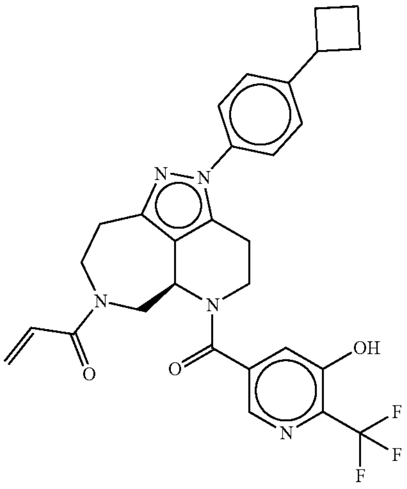 |
| 38A | (S)-1-(5-(7-bromo-1H-benzo[d]imidazole-4-carbonyl)-2-(4-isopropylphenyl)-4,5,5a,6,8,9-hexahydro-1,2a,5,7-tetraazabenzo[cd]azulen-7(3H)-yl)prop-2-en-1-one | 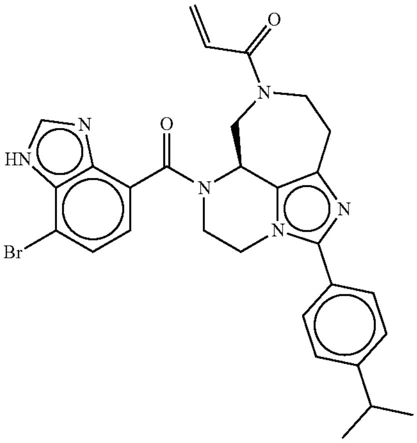 |
| 62A | (R)-1-(5-(6-bromo-5-(trifluoromethoxy)nicotinoyl)-2-(4-cyclobutyl-2-hydroxyphenyl)-2,3,4,5,5a,6,8,9-octahydro-7H-1,2,5,7-tetraazabenzo[cd]azulen-7-yl)prop-2-en-1-one | 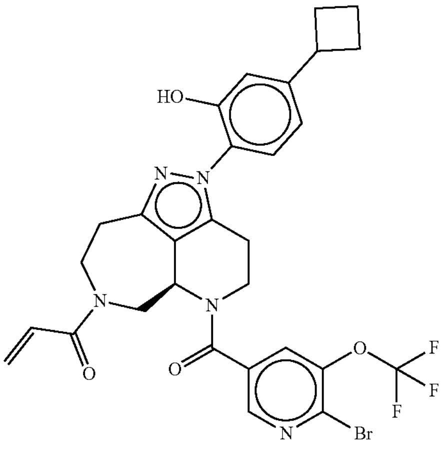 |

TABLE 1A-continued

| Compound No. | Name | Structure |
|---|---|---|
| 67A | (R)-1-(5-(2-amino-6-(trifluoromethyl) nicotinoyl)-2-(4-cyclopropylphenyl)-2,3,4,5,5a,6,8,9-octahydro-7H-1,2,5,7-tetraazabenzo[cd]azulen-7-yl)prop-2-en-1-one | 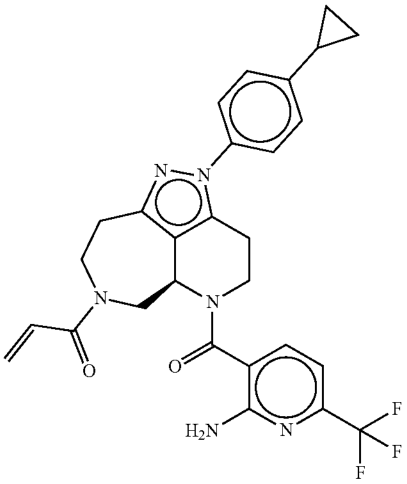 |
| 68A | (R)-4-(7-acryloyl-2-(4-cyclopropylphenyl)-3,4,5,5a,6,7,8,9-octahydro-2H-1,2,5,7-tetraazabenzo[cd]azulene-5-carbonyl)-1-(2,2,2-trifluoroethyl)pyridin-2(1H)-one | 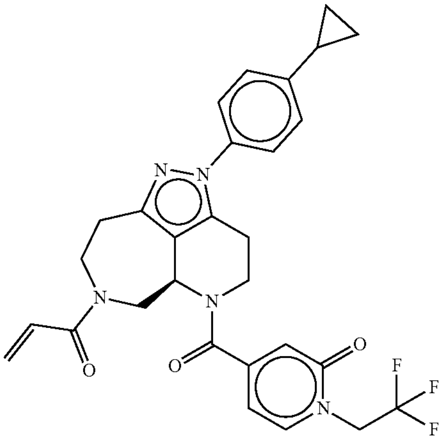 |
| 69A | (R)-1-(2-(4-cyclopropylphenyl)-5-(6-(difluoromethoxy) nicotinoyl)-2,3,4,5,5a,6,8,9-octahydro-7H-1,2,5,7-tetraazabenzo[cd]azulen-7-yl)prop-2-en-1-one | 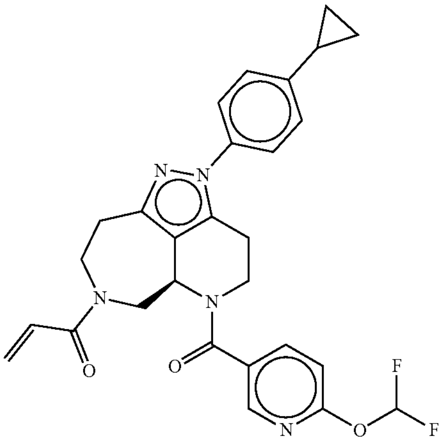 |

TABLE 1A-continued

| Compound No. | Name | Structure |
|---|---|---|
| 70A | (R)-5-(7-acryloyl-2-(4-cyclopropylphenyl)-3,4,5,5a,6,7,8,9-octahydro-2H-1,2,5,7-tetraazabenzo[cd]azulene-5-carbonyl)-1-methyl-1,3-dihydro-2H-benzo[d]imidazol-2-one | 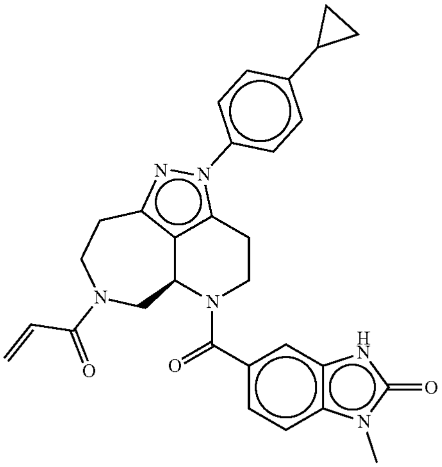 |
| 71A | (R)-1-(2-(2-amino-4-cyclobutyl-3-fluorophenyl)-5-(5-hydroxy-6-(trifluoromethyl)nicotinoyl)-2,3,4,5,5a,6,8,9-octahydro-7H-1,2,5,7-tetraazabenzo[cd]azulen-7-yl)prop-2-en-1-one | 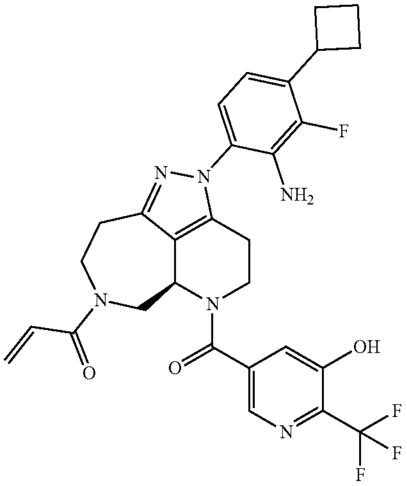 [SMILES: C=CC(=O)N1CCc2nn(-c3ccc(C4CCC4)c(F)c3N)c3c2[C@H](C1)N(C(=O)c1cnc(C(F)(F)F)c(O)c1)CC3] |
| 74A | (R)-1-(2-(4-cyclobutyl-2-hydroxyphenyl)-5-(6-(difluoromethoxy) nicotinoyl)-2,3,4,5,5a,6,8,9-octahydro-7H-1,2,5,7-tetraazabenzo[cd]azulen-7-yl)prop-2-en-1-one | 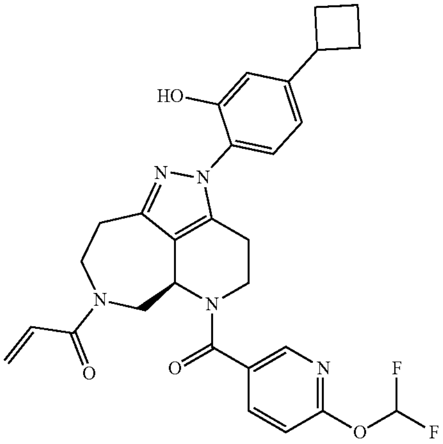 [SMILES: C=CC(=O)N1CCc2nn(-c3ccc(C4CCC4)cc3O)c3c2[C@H](C1)N(C(=O)c1ccc(OC(F)F)nc1)CC3] |

TABLE 1A-continued

| Compound No. | Name | Structure |
|---|---|---|
| 75A | (R)-1-(5-(7-bromo-2-(hydroxymethyl)-1H-benzo[d]imidazole-4-carbonyl)-2-(4-cyclobutyl-2-hydroxyphenyl)-2,3,4,5,5a,6,8,9-octahydro-7H-1,2,5,7-tetraazabenzo[cd]azulen-7-yl)prop-2-en-1-one | 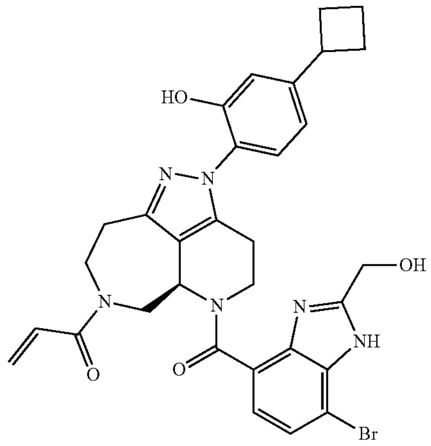 [SMILES: C=CC(=O)N1CCc2nn(-c3ccc(C4CCC4)cc3O)c3c2[C@H](C1)N(C(=O)c1ccc(Br)c2[nH]c(CO)nc12)CC3] |
| 76A | (R)-1-(5-(2-amino-6-(trifluoromethyl)nicotinoyl)-2-(4-cyclobutyl-2-hydroxyphenyl)-2,3,4,5,5a,6,8,9-octahydro-7H-1,2,5,7-tetraazabenzo[cd]azulen-7-yl)prop-2-en-1-one | 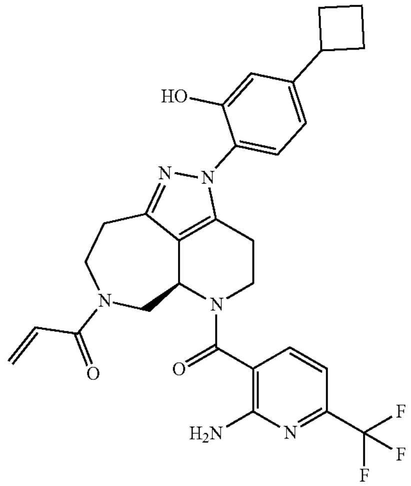 [SMILES: C=CC(=O)N1CCc2nn(-c3ccc(C4CCC4)cc3O)c3c2[C@H](C1)N(C(=O)c1ccc(C(F)(F)F)nc1N)CC3] |
| 86A | (S)-1-(2-(4-cyclobutylphenyl)-5-(5-hydroxy-6-(trifluoromethyl)nicotinoyl)-4,5,5a,6,8,9-hexahydro-1,2a,5,7-tetraazabenzo[cd]azulen-7(3H)-yl)prop-2-en-1-one | 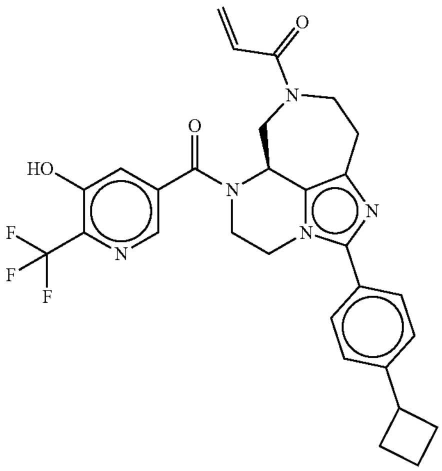 |

TABLE 1A-continued

| Compound No. | Name | Structure |
|---|---|---|
| 87A | (R)-1-(5-(7-bromo-1H-indazole-4-carbonyl)-2-(4-cyclobutyl-2-hydroxyphenyl)-2,3,4,5,5a,6,8,9-octahydro-7H-1,2,5,7-tetraazabenzo[cd]azulen-7-yl)prop-2-en-1-one | 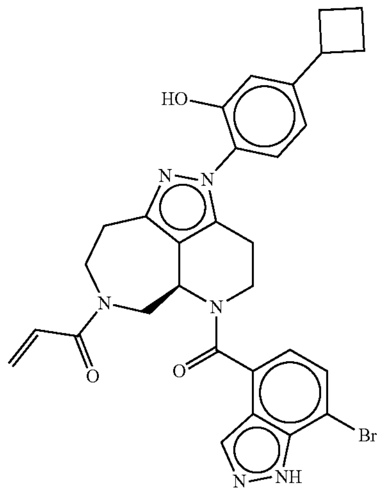 |
| 88A | (R)-1-(5-(7-bromo-2-(difluoromethoxy)-1H-benzo[d]imidazole-4-carbonyl)-2-(4-cyclobutyl-2-hydroxyphenyl)-2,3,4,5,5a,6,8,9-octahydro-7H-1,2,5,7-tetraazabenzo[cd]azulen-7-yl)prop-2-en-1-one | 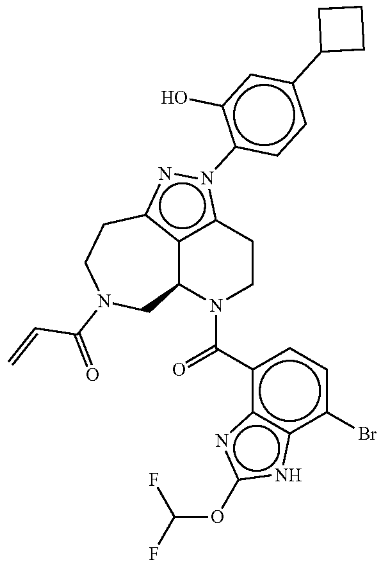 |
| 89A | (R)-1-(2-(4-cyclobutyl-2-hydroxyphenyl)-5-(5-(methylthio)-6-(trifluoromethyl)nicotinoyl)-2,3,4,5,5a,6,8,9-octahydro-7H-1,2,5,7-tetraazabenzo[cd]azulen-7-yl)prop-2-en-1-one | 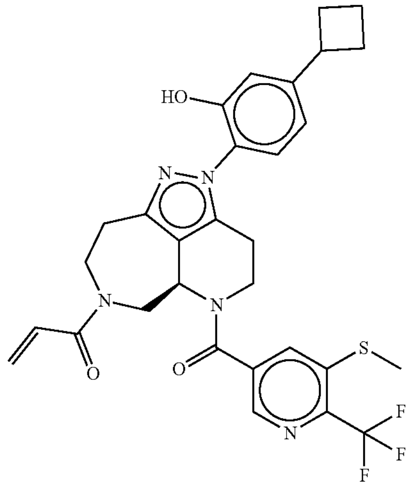 |

TABLE 1A-continued

| Compound No. | Name | Structure |
|---|---|---|
| 90A | (R)-1-(5-(4-bromo-2-(difluoromethyl)-1H-benzo[d]imidazole-7-carbonyl)-2-(4-cyclobutyl-2-hydroxyphenyl)-2,3,4,5,5a,6,8,9-octahydro-7H-1,2,5,7-tetraazabenzo[cd]azulen-7-yl)prop-2-en-1-one | 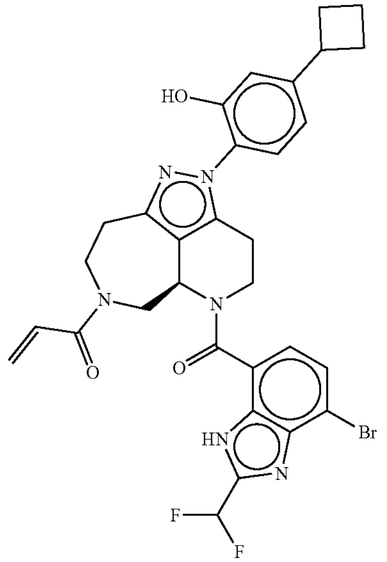 |
| 91A | (R)-1-(2-(4-cyclobutyl-3-hydroxyphenyl)-5-(5-hydroxy-6-(trifluoromethyl)nicotinoyl)-2,3,4,5,5a,6,8,9-octahydro-7H-1,2,5,7-tetraazabenzo[cd]azulen-7-yl)prop-2-en-1-one | 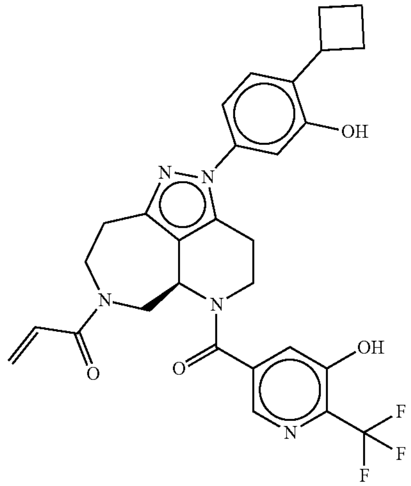 |
| 92A | (R)-1-(2-(4-(bicyclo[1.1.1]pentan-1-yl)-2-hydroxyphenyl)-5-(5-hydroxy-6-(trifluoromethyl)nicotinoyl)-2,3,4,5,5a,6,8,9-octahydro-7H-1,2,5,7-tetraazabenzo[cd]azulen-7-yl)prop-2-en-1-one | 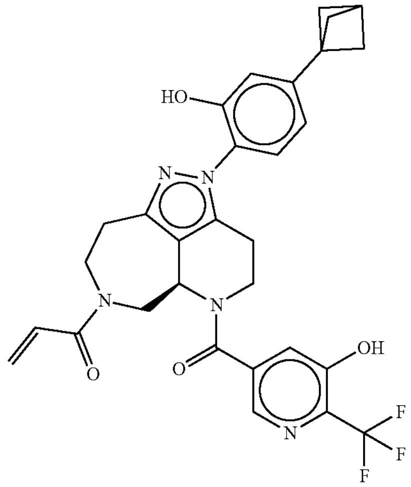 |

TABLE 1A-continued

| Compound No. | Name | Structure |
|---|---|---|
| 93A | (R)-1-(2-(4-cyclobutyl-2-hydroxyphenyl)-5-(6-(trifluoromethoxy)nicotinoyl)-2,3,4,5,5a,6,8,9-octahydro-7H-1,2,5,7-tetraazabenzo[cd]azulen-7-yl)prop-2-en-1-one | 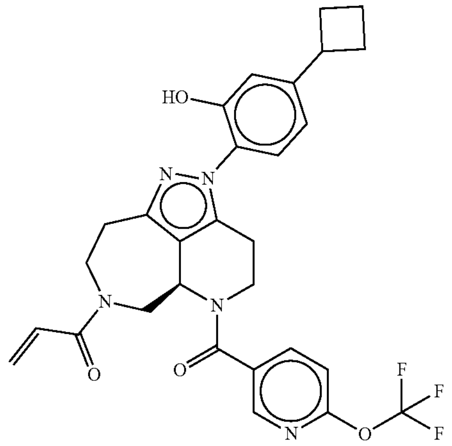 |
| 94A | (R)-1-(5-(6-bromo-5-(difluoromethoxy)nicotinoyl)-2-(4-cyclobutyl-2-hydroxyphenyl)-2,3,4,5,5a,6,8,9-octahydro-7H-1,2,5,7-tetraazabenzo[cd]azulen-7-yl)prop-2-en-1-one | 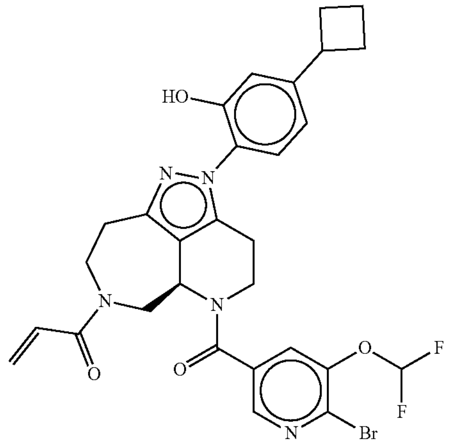 |
| 95A | (R)-1-(5-(7-bromo-1H-imidazo[4,5-c]pyridine-4-carbonyl)-2-(4-cyclobutyl-2-hydroxyphenyl)-2,3,4,5,5a,6,8,9-octahydro-7H-1,2,5,7-tetraazabenzo[cd]azulen-7-yl)prop-2-en-1-one | 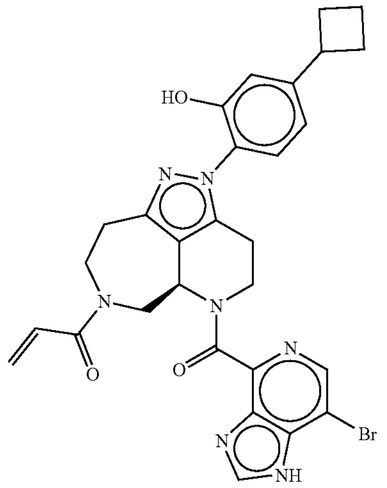 |

TABLE 1A-continued

| Compound No. | Name | Structure |
| --- | --- | --- |
| 96A | (R)-1-(2-(4-cyclobutyl-2-hydroxyphenyl)-5-(6-(trifluoromethyl)nicotinoyl)-2,3,4,5,5a,6,8,9-octahydro-7H-1,2,5,7-tetraazabenzo[cd]azulen-7-yl)prop-2-en-1-one | 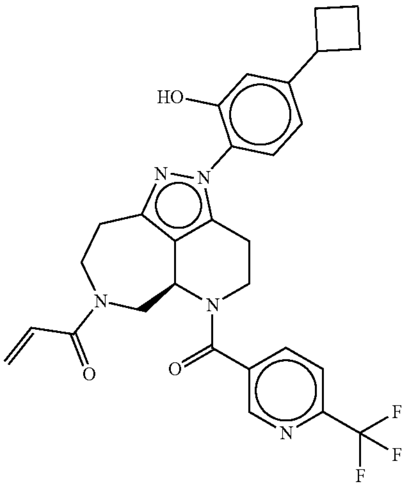 |
| 97A | (R)-1-(2-(4-cyclobutyl-2-hydroxyphenyl)-5-(7-(trifluoromethyl)-1H-indazole-4-carbonyl)-2,3,4,5,5a,6,8,9-octahydro-7H-1,2,5,7-tetraazabenzo[cd]azulen-7-yl)prop-2-en-1-one | 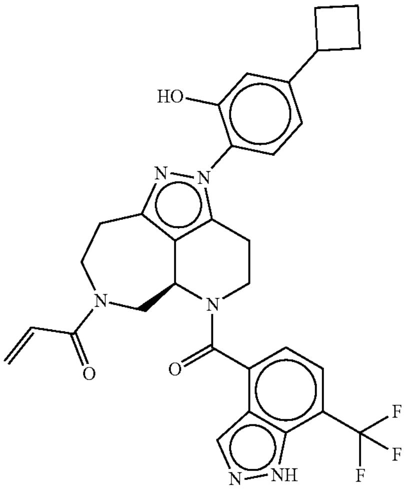 |
| 98A | (R)-1-(5-(6-(1H-pyrazol-1-yl)nicotinoyl)-2-(4-cyclopropylphenyl)-2,3,4,5,5a,6,8,9-octahydro-7H-1,2,5,7-tetraazabenzo[cd]azulen-7-yl)prop-2-en-1-one | 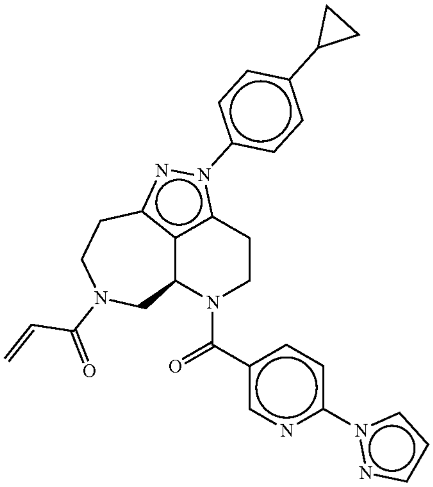 |

TABLE 1A-continued

| Compound No. | Name | Structure |
| --- | --- | --- |
| 100A | (R)-1-(2-(4-cyclopropyl-3-fluoro-2-hydroxyphenyl)-5-(5-hydroxy-6-(trifluoromethyl)nicotinoyl)-2,3,4,5,5a,6,8,9-octahydro-7H-1,2,5,7-tetraazabenzo[cd]azulen-7-yl)prop-2-en-1-one | 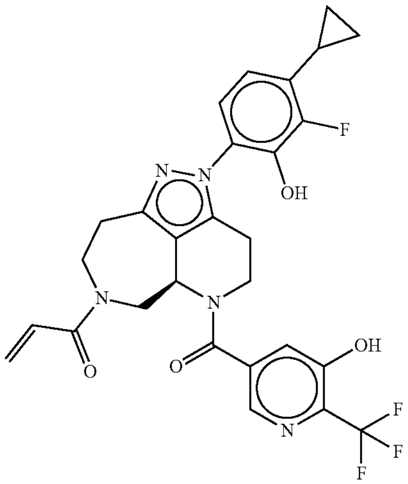 |
| 101A | (R)-1-(2-(4-(bicyclo[1.1.1]pentan-1-yl)-3-fluoro-2-hydroxyphenyl)-5-(5-hydroxy-6-(trifluoromethyl)nicotinoyl)-2,3,4,5,5a,6,8,9-octahydro-7H-1,2,5,7-tetraazabenzo[cd]azulen-7-yl)prop-2-en-1-one | 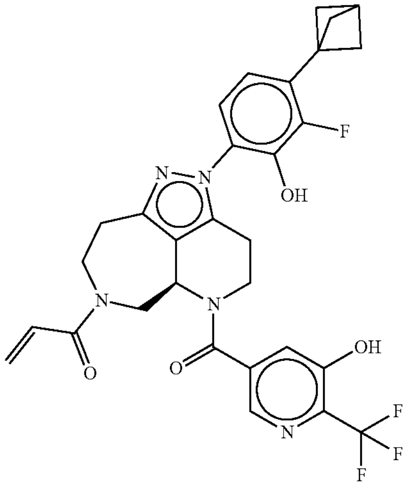 |
| 102A | (R)-1-(5-(4-bromo-3-(2-hydroxypropan-2-yl)benzoyl)-2-(4-isopropylphenyl)-2,3,4,5,5a,6,8,9-octahydro-7H-1,2,5,7-tetraazabenzo[cd]azulen-7-yl)prop-2-en-1-one | 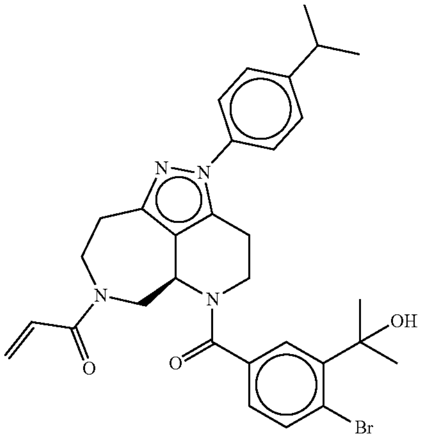 |

TABLE 1A-continued

| Compound No. | Name | Structure |
|---|---|---|
| 104A | (R)-1-(5-(4-bromo-3-((2,2,2-trifluoroethyl)amino)benzoyl)-2-(4-isopropylphenyl)-2,3,4,5,5a,6,8,9-octahydro-7H-1,2,5,7-tetraazabenzo[cd]azulen-7-yl)prop-2-en-1-one | 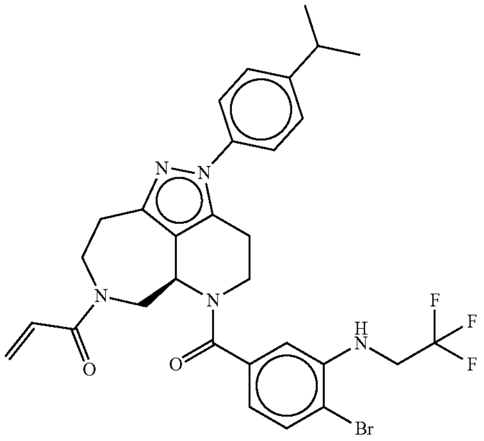 |
| 106A | (R)-1-(5-(4-bromo-3-(1H-pyrazol-3-yl)benzoyl)-2-(4-isopropylphenyl)-2,3,4,5,5a,6,8,9-octahydro-7H-1,2,5,7-tetraazabenzo[cd]azulen-7-yl)prop-2-en-1-one | 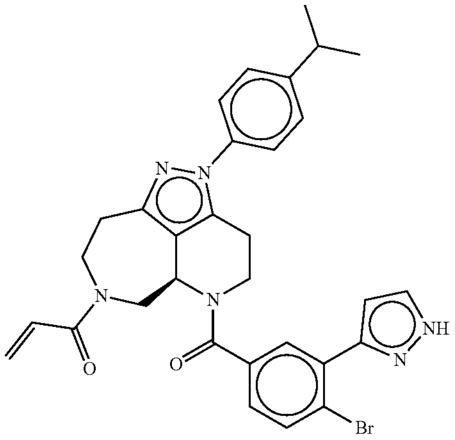 |
| 107A | (R)-1-(2-(4-cyclobutyl-2-hydroxyphenyl)-5-(4-(trifluoromethoxy)benzoyl)-2,3,4,5,5a,6,8,9-octahydro-7H-1,2,5,7-tetraazabenzo[cd]azulen-7-yl)prop-2-en-1-one | 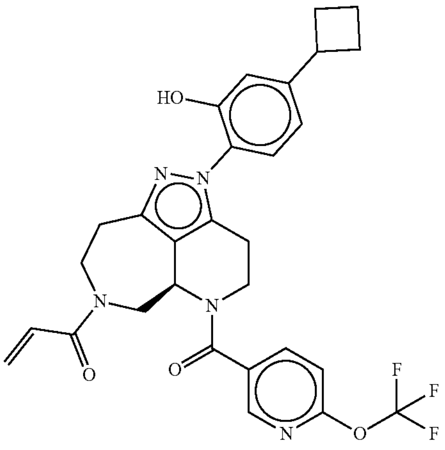 |

TABLE 1A-continued

| Compound No. | Name | Structure |
|---|---|---|
| 108A | (R)-1-(5-(6-bromopyridazine-3-carbonyl)-2-(4-cyclopropylphenyl)-2,3,4,5,5a,6,8,9-octahydro-7H-1,2,5,7-tetraazabenzo[cd]azulen-7-yl)prop-2-en-1-one | 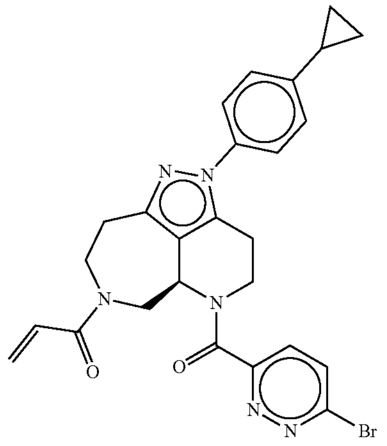 |
| 109A | (R)-1-(2-(4-cyclopropylphenyl)-5-(2-hydroxy-6-(trifluoromethyl)nicotinoyl)-2,3,4,5,5a,6,8,9-octahydro-7H-1,2,5,7-tetraazabenzo[cd]azulen-7-yl)prop-2-en-1-one | 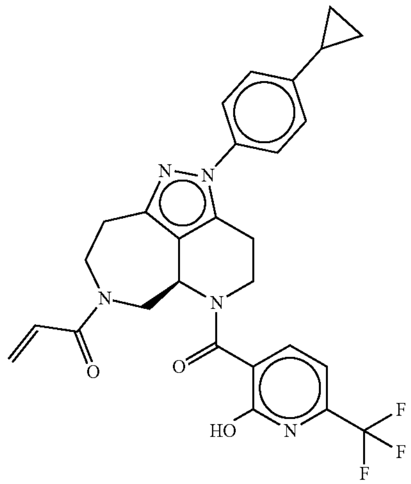 |
| 110A | (R)-1-(2-(4-cyclopropylphenyl)-5-(1,3-dimethyl-1H-pyrazolo[4,3-b]pyridine-6-carbonyl)-2,3,4,5,5a,6,8,9-octahydro-7H-1,2,5,7-tetraazabenzo[cd]azulen-7-yl)prop-2-en-1-one | 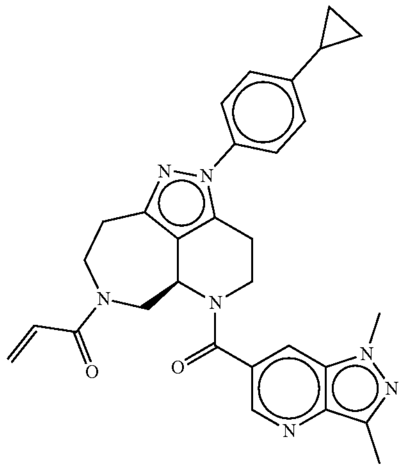 |

TABLE 1A-continued

| Compound No. | Name | Structure |
|---|---|---|
| 111A | (R)-1-(2-(4-cyclopropylphenyl)-5-(1-methyl-3-(trifluoromethyl)-1H-pyrazolo[3,4-b]pyridine-5-carbonyl)-2,3,4,5,5a,6,8,9-octahydro-7H-1,2,5,7-tetraazabenzo[cd]azulen-7-yl)prop-2-en-1-one | 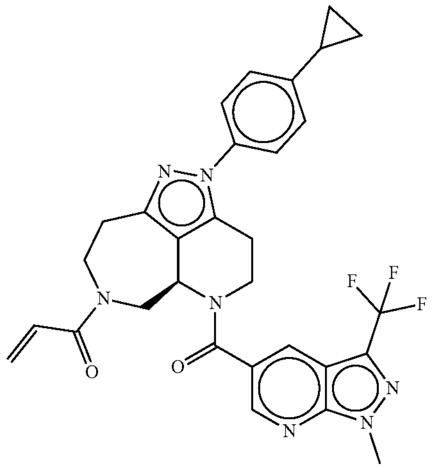 |
| 112A | (R)-5-(7-acryloyl-2-(4-cyclopropylphenyl)-3,4,5,5a,6,7,8,9-octahydro-2H-1,2,5,7-tetraazabenzo[cd]azulene-5-carbonyl)-2-(trifluoromethyl) nicotinonitrile | 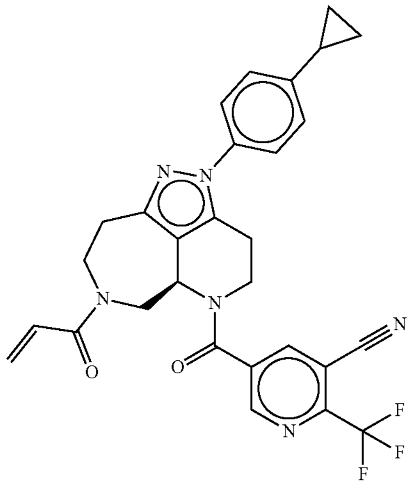 |
| 113A | (R)-1-(5-(6-bromo-4-methylnicotinoyl)-2-(4-cyclopropylphenyl)-2,3,4,5,5a,6,8,9-octahydro-7H-1,2,5,7-tetraazabenzo[cd]azulen-7-yl)prop-2-en-1-one | 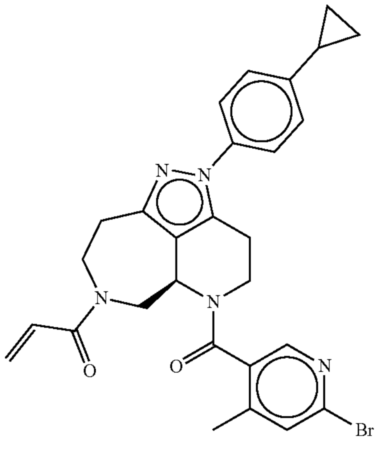 |

TABLE 1A-continued

| Compound No. | Name | Structure |
| --- | --- | --- |
| 114A | (R)-1-(5-(6-bromo-2-methylnicotinoyl)-2-(4-cyclopropylphenyl)-2,3,4,5,5a,6,8,9-octahydro-7H-1,2,5,7-tetraazabenzo[cd]azulen-7-yl)prop-2-en-1-one | 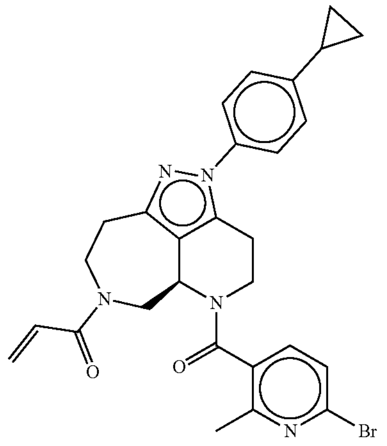 |
| 115A | (R)-1-(2-(4-cyclopropylphenyl)-5-(6-(trifluoromethyl)pyridazine-3-carbonyl)-2,3,4,5,5a,6,8,9-octahydro-7H-1,2,5,7-tetraazabenzo[cd]azulen-7-yl)prop-2-en-1-one | 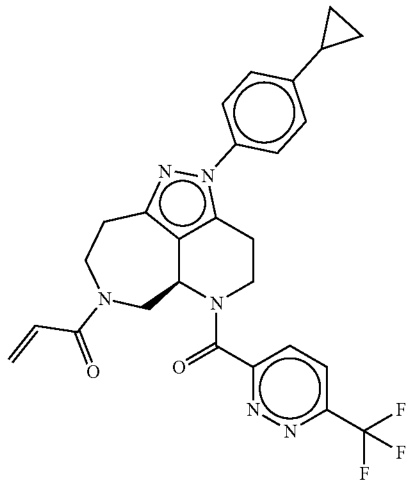 |
| 116A | (R)-1-(2-(4-cyclopropylphenyl)-5-(2-methyl-1,1-dioxido-3,4-dihydro-2H-pyrazolo[1,5-e][1,2,5]thiadiazine-7-carbonyl)-2,3,4,5,5a,6,8,9-octahydro-7H-1,2,5,7-tetraazabenzo[cd]azulen-7-yl)prop-2-en-1-one | 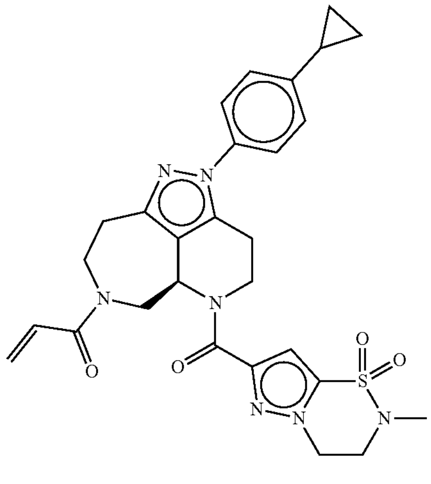 |

TABLE 1A-continued

| Compound No. | Name | Structure |
| --- | --- | --- |
| 117A | (R)-1-(5-(2-amino-6-bromonicotinoyl)-2-(4-cyclopropylphenyl)-2,3,4,5,5a,6,8,9-octahydro-7H-1,2,5,7-tetraazabenzo[cd]azulen-7-yl)prop-2-en-1-one | 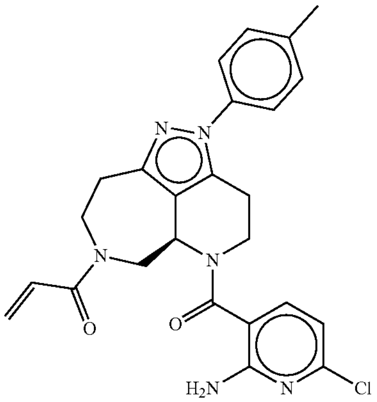 |
| 118A | (R)-1-(2-(4-cyclopropylphenyl)-5-(6-(2,2,2-trifluoroethoxy)nicotinoyl)-2,3,4,5,5a,6,8,9-octahydro-7H-1,2,5,7-tetraazabenzo[cd]azulen-7-yl)prop-2-en-1-one | 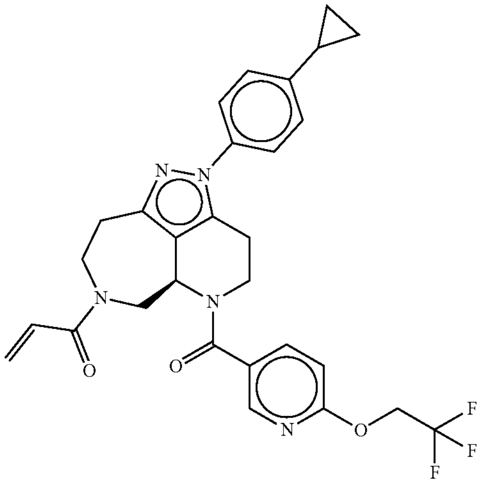 |
| 119A | (R)-1-(5-(7-acryloyl-2-(4-cyclopropylphenyl)-3,4,5,5a,6,7,8,9-octahydro-2H-1,2,5,7-tetraazabenzo[cd]azulene-5-carbonyl)pyridin-2-yl)cyclopropane-1-carbonitrile | 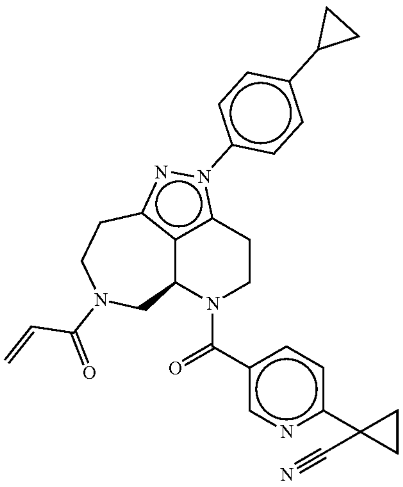 |

TABLE 1A-continued

| Compound No. | Name | Structure |
| --- | --- | --- |
| 120A | (R)-1-(2-(4-cyclopropylphenyl)-5-(5-hydroxy-6-nitronicotinoyl)-2,3,4,5,5a,6,8,9-octahydro-7H-1,2,5,7-tetraazabenzo[cd]azulen-7-yl)prop-2-en-1-one | 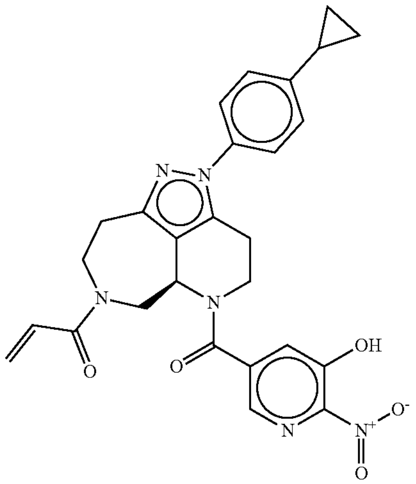 |
| 121A | (R)-1-(2-(4-cyclopropylphenyl)-5-(3-(trifluoromethyl)bicyclo[1.1.1]pentane-1-carbonyl)-2,3,4,5,5a,6,8,9-octahydro-7H-1,2,5,7-tetraazabenzo[cd]azulen-7-yl)prop-2-en-1-one | 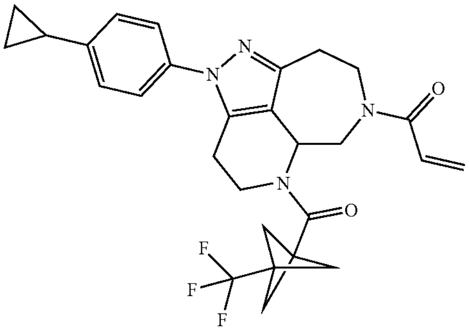 [SMILES: C=CC(=O)N1CCc2nn(-c3ccc(C4CC4)cc3)c3c2C(C1)N(C(=O)C12CC(C(F)(F)F)(C1)C2)CC3] |
| 122A | (R)-1-(2-(4-cyclopropylphenyl)-5-(6-isopropoxynicotinoyl)-2,3,4,5,5a,6,8,9-octahydro-7H-1,2,5,7-tetraazabenzo[cd]azulen-7-yl)prop-2-en-1-one | 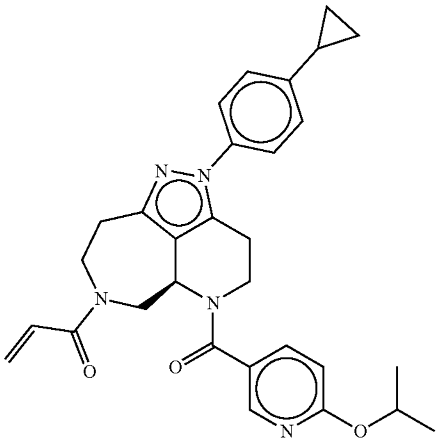 |

TABLE 1A-continued

| Compound No. | Name | Structure |
| --- | --- | --- |
| 123A | (R)-5-(7-acryloyl-2-(4-cyclopropylphenyl)-3,4,5,5a,6,7,8,9-octahydro-2H-1,2,5,7-tetraazabenzo[cd]azulene-5-carbonyl)picolinonitrile | 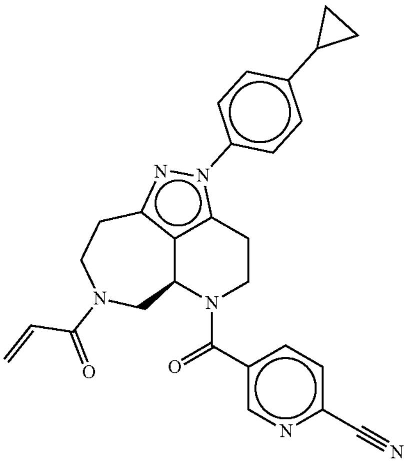 |
| 124A | (R)-1-(2-(4-cyclopropylphenyl)-5-(2-(trifluoromethyl)-3H-imidazo[4,5-b]pyridine-6-carbonyl)-2,3,4,5,5a,6,8,9-octahydro-7H-1,2,5,7-tetraazabenzo[cd]azulen-7-yl)prop-2-en-1-one | 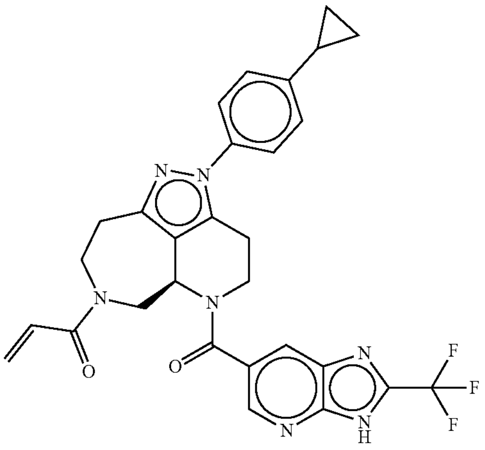 |
| 125A | (R)-4-(7-acryloyl-2-(4-cyclopropylphenyl)-3,4,5,5a,6,7,8,9-octahydro-2H-1,2,5,7-tetraazabenzo[cd]azulene-5-carbonyl)thiophene-2-sulfonamide | 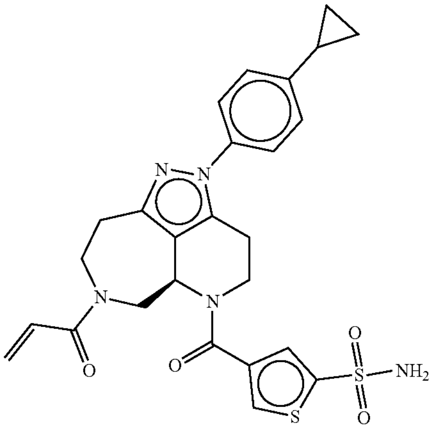 |

TABLE 1A-continued

| Compound No. | Name | Structure |
| --- | --- | --- |
| 126A | (R)-1-(2-(4-cyclopropylphenyl)-5-(6-(difluoromethyl)nicotinoyl)-2,3,4,5,5a,6,8,9-octahydro-7H-1,2,5,7-tetraazabenzo[cd]azulen-7-yl)prop-2-en-1-one | 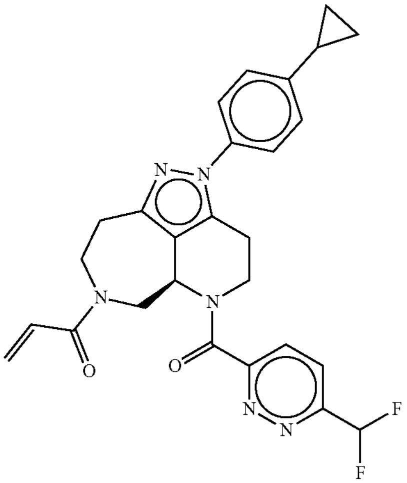 |
| 128A | (R)-1-(5-(4-amino-6-(trifluoromethyl)nicotinoyl)-2-(4-cyclopropylphenyl)-2,3,4,5,5a,6,8,9-octahydro-7H-1,2,5,7-tetraazabenzo[cd]azulen-7-yl)prop-2-en-1-one | 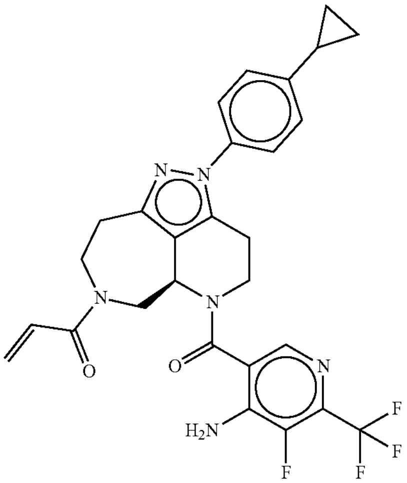 |
| 131A | (R)-1-(5-(3-amino-7-bromo-1H-indazole-4-carbonyl)-2-(4-cyclopropylphenyl)-2,3,4,5,5a,6,8,9-octahydro-7H-1,2,5,7-tetraazabenzo[cd]azulen-7-yl)prop-2-en-1-one | 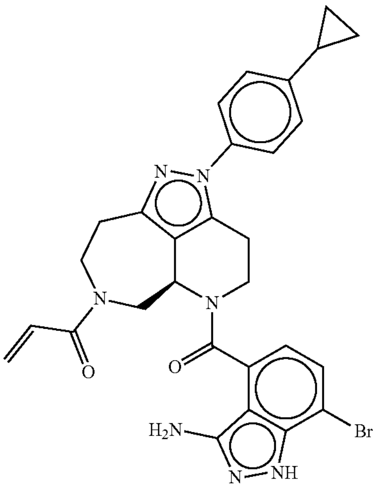 |

TABLE 1A-continued

| Compound No. | Name | Structure |
|---|---|---|
| 132A | (R)-1-(5-(4-amino-6-bromonicotinoyl)-2-(4-cyclobutyl-2-hydroxyphenyl)-2,3,4,5,5a,6,8,9-octahydro-7H-1,2,5,7-tetraazabenzo[cd]azulen-7-yl)prop-2-en-1-one | 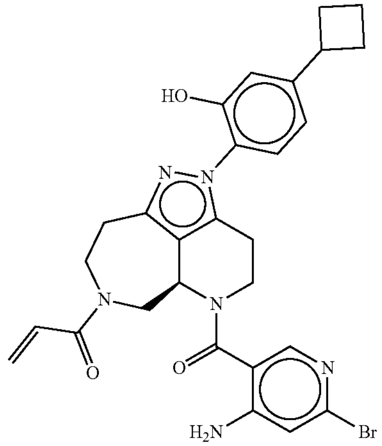 |
| 133A | (R)-1-(5-(4-amino-6-(trifluoromethyl)nicotinoyl)-2-(4-(bicyclo[1.1.1]pentan-1-yl)phenyl)-2,3,4,5,5a,6,8,9-octahydro-7H-1,2,5,7-tetraazabenzo[cd]azulen-7-yl)prop-2-en-1-one | 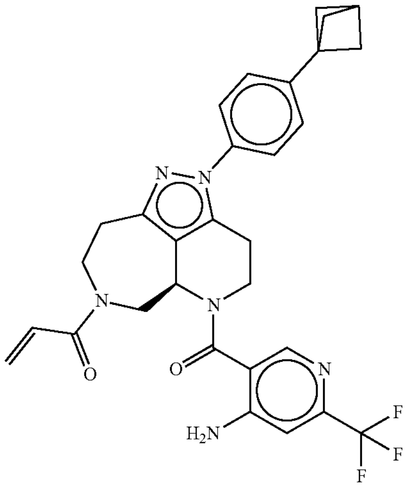 |
| 134A | (R)-1-(5-(4-amino-5-fluoro-6-(trifluoromethyl)nicotinoyl)-2-(4-cyclobutyl-2-hydroxyphenyl)-2,3,4,5,5a,6,8,9-octahydro-7H-1,2,5,7-tetraazabenzo[cd]azulen-7-yl)prop-2-en-1-one | 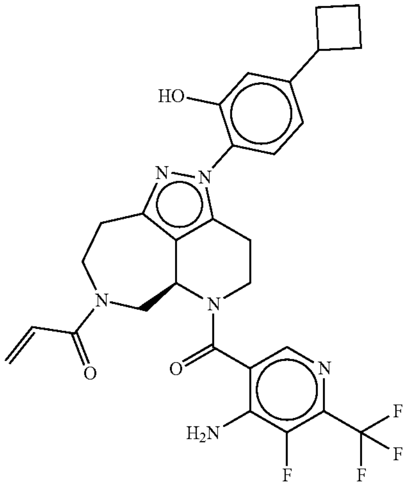 |

TABLE 1A-continued

| Compound No. | Name | Structure |
|---|---|---|
| 137A | (R)-1-(5-(4-bromo-3H-imidazo[4,5-c]pyridine-7-carbonyl)-2-(4-cyclobutyl-2-hydroxyphenyl)-2,3,4,5,5a,6,8,9-octahydro-7H-1,2,5,7-tetraazabenzo[cd]azulen-7-yl)prop-2-en-1-one | 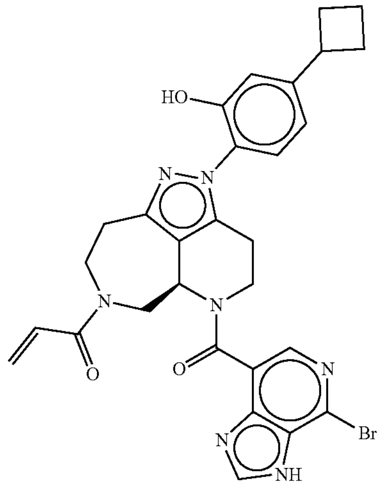 |
| 138A | (R)-1-(5-(4-amino-6-(trifluoromethyl)nicotinoyl)-2-(4-cyclobutyl-2-hydroxyphenyl)-2,3,4,5,5a,6,8,9-octahydro-7H-1,2,5,7-tetraazabenzo[cd]azulen-7-yl)prop-2-en-1-one | 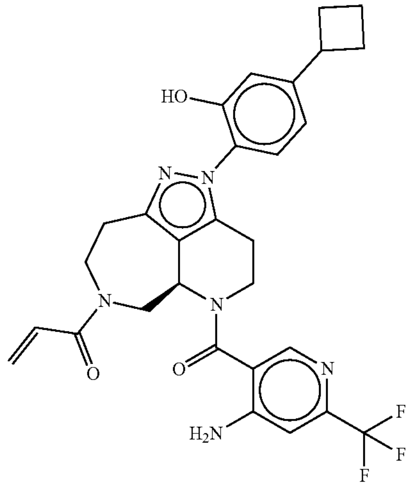 |
| 139A | (R)-1-(5-(4-amino-6-(trifluoromethyl)nicotinoyl)-2-(4-cyclobutyl-3-fluoro-2-hydroxyphenyl)-2,3,4,5,5a,6,8,9-octahydro-7H-1,2,5,7-tetraazabenzo[cd]azulen-7-yl)prop-2-en-1-one | 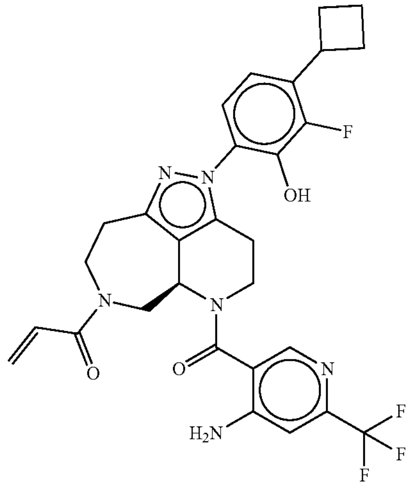 |

TABLE 1A-continued

| Compound No. | Name | Structure |
|---|---|---|
| 140A | (R)-1-(5-(6-chloro-5-hydroxynicotinoyl)-2-(4-cyclobutyl-2-hydroxyphenyl)-2,3,4,5,5a,6,8,9-octahydro-7H-1,2,5,7-tetraazabenzo[cd]azulen-7-yl)prop-2-en-1-one | 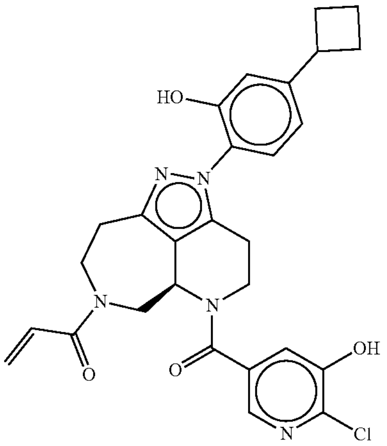 |
| 141A | (R)-1-(2-(4-cyclobutyl-3-fluoro-2-hydroxyphenyl)-5-(5-hydroxy-6-(trifluoromethyl)nicotinoyl)-2,3,4,5,5a,6,8,9-octahydro-7H-1,2,5,7-tetraazabenzo[cd]azulen-7-yl)prop-2-en-1-one | 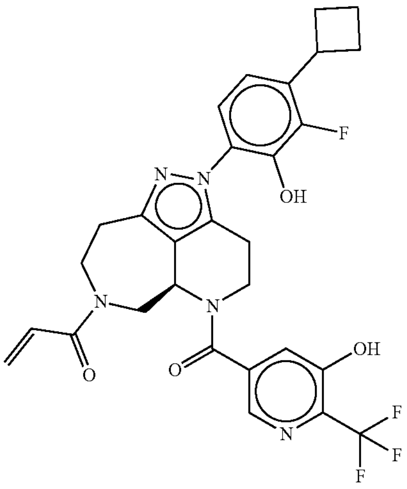 |
| 142A | (R)-1-(5-(3-amino-5-(trifluoromethyl)picolinoyl)-2-(4-cyclobutyl-2-hydroxyphenyl)-2,3,4,5,5a,6,8,9-octahydro-7H-1,2,5,7-tetraazabenzo[cd]azulen-7-yl)prop-2-en-1-one | 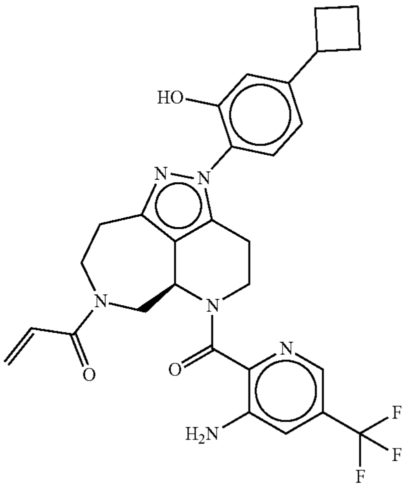 |

TABLE 1A-continued

| Compound No. | Name | Structure |
| --- | --- | --- |
| 143A | (R)-1-(5-(7-bromo-2-(difluoromethyl)-1H-benzo[d]imidazole-4-carbonyl)-2-(4-cyclopropyl-2-hydroxyphenyl)-2,3,4,5,5a,6,8,9-octahydro-7H-1,2,5,7-tetraazabenzo[cd]azulen-7-yl)prop-2-en-1-one | 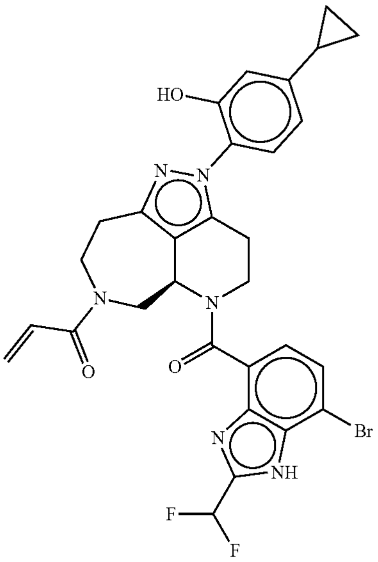 |
| 144A | (R)-1-(5-(4-amino-6-chloronicotinoyl)-2-(4-cyclobutyl-2-hydroxyphenyl)-2,3,4,5,5a,6,8,9-octahydro-7H-1,2,5,7-tetraazabenzo[cd]azulen-7-yl)prop-2-en-1-one | 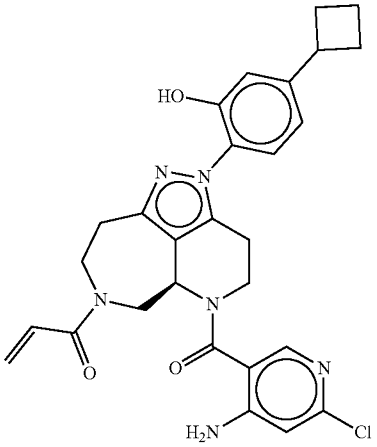 |
| 145A | (R)-1-(2-(4-cyclobutyl-2-hydroxyphenyl)-5-(1,3-dimethyl-1H-pyrazolo[4,3-b]pyridine-6-carbonyl)-2,3,4,5,5a,6,8,9-octahydro-7H-1,2,5,7-tetraazabenzo[cd]azulen-7-yl)prop-2-en-1-one | 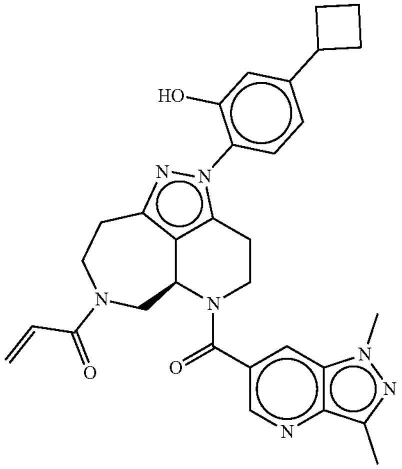 |

TABLE 1A-continued

| Compound No. | Name | Structure |
|---|---|---|
| 146A | (R)-1-(5-(2-amino-6-(difluoromethyl)nicotinoyl)-2-(4-cyclobutyl-2-hydroxyphenyl)-2,3,4,5,5a,6,8,9-octahydro-7H-1,2,5,7-tetraazabenzo[cd]azulen-7-yl)prop-2-en-1-one | 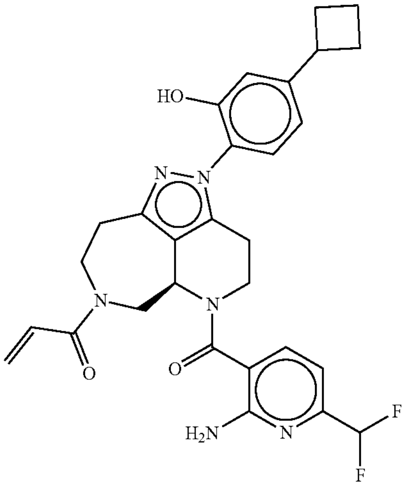 |
| 147A | (R)-1-(5-(3-amino-7-(trifluoromethyl)-1H-indazole-4-carbonyl)-2-(4-cyclobutylphenyl)-2,3,4,5,5a,6,8,9-octahydro-7H-1,2,5,7-tetraazabenzo[cd]azulen-7-yl)prop-2-en-1-one | 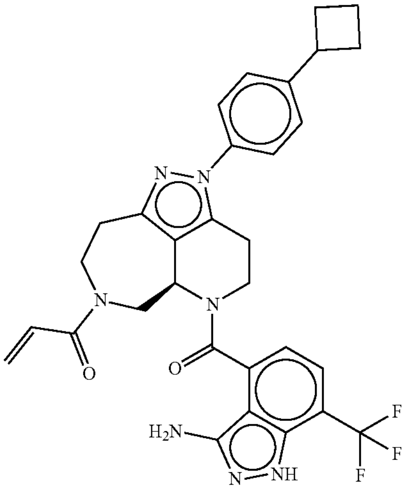 |
| 148A | (R)-1-(5-(4-bromo-2-(2-hydroxyethyl)-1H-benzo[d]imidazole-7-carbonyl)-2-(4-cyclobutyl-2-hydroxyphenyl)-2,3,4,5,5a,6,8,9-octahydro-7H-1,2,5,7-tetraazabenzo[cd]azulen-7-yl)prop-2-en-1-one | 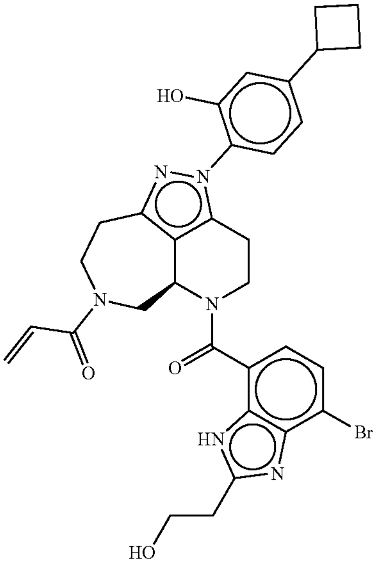 |

TABLE 1A-continued

| Compound No. | Name | Structure |
| --- | --- | --- |
| 149A | (R)-1-(2-(4-cyclobutyl-2-hydroxyphenyl)-5-(4-hydroxy-6-(trifluoromethyl)nicotinoyl)-2,3,4,5,5a,6,8,9-octahydro-7H-1,2,5,7-tetraazabenzo[cd]azulen-7-yl)prop-2-en-1-one | 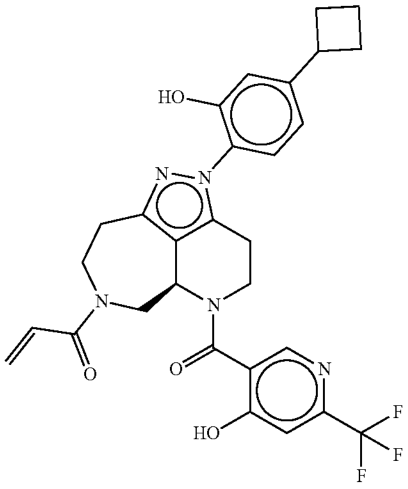 |
| 150A | (R)-1-(5-(4-amino-6-(trifluoromethyl)nicotinoyl)-2-(4-isopropylphenyl)-2,3,4,5,5a,6,8,9-octahydro-7H-1,2,5,7-tetraazabenzo[cd]azulen-7-yl)prop-2-en-1-one | 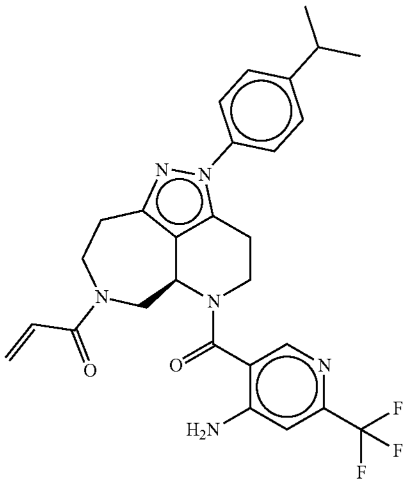 |
| 151A | (R)-1-(2-(4-cyclobutyl-2-hydroxyphenyl)-5-(7-(trifluoromethyl)-1H-pyrazolo[3,4-c]pyridine-4-carbonyl)-2,3,4,5,5a,6,8,9-octahydro-7H-1,2,5,7-tetraazabenzo[cd]azulen-7-yl)prop-2-en-1-one | 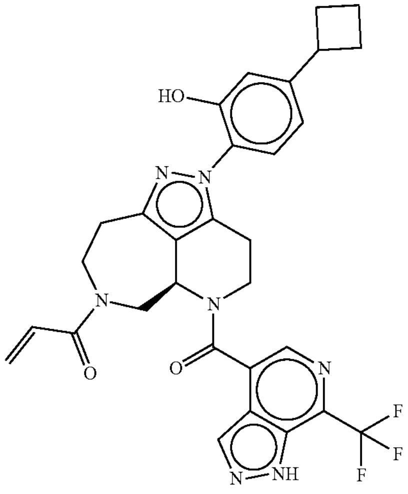 |

TABLE 1A-continued

| Compound No. | Name | Structure |
|---|---|---|
| 152A | (R)-1-(5-(2-amino-6-(trifluoromethyl)nicotinoyl)-2-(4-(bicyclo[1.1.1]pentan-1-yl)phenyl)-2,3,4,5,5a,6,8,9-octahydro-7H-1,2,5,7-tetraazabenzo[cd]azulen-7-yl)prop-2-en-1-one | 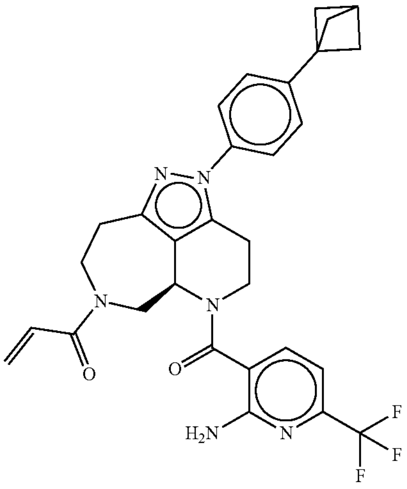 |
| 153A | (R)-1-(2-(4-cyclobutyl-2-hydroxyphenyl)-5-(7-hydroxybenzo[d]thiazole-5-carbonyl)-2,3,4,5,5a,6,8,9-octahydro-7H-1,2,5,7-tetraazabenzo[cd]azulen-7-yl)prop-2-en-1-one | 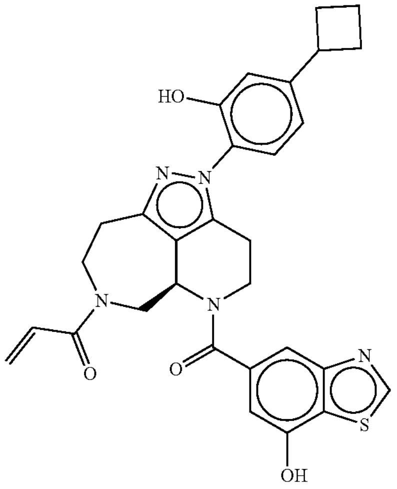 |
| 154A | (R)-1-(2-(4-cyclobutyl-2-hydroxyphenyl)-5-(7-(trifluoromethyl)-1H-imidazo[4,5-c]pyridine-4-carbonyl)-2,3,4,5,5a,6,8,9-octahydro-7H-1,2,5,7-tetraazabenzo[cd]azulen-7-yl)prop-2-en-1-one | 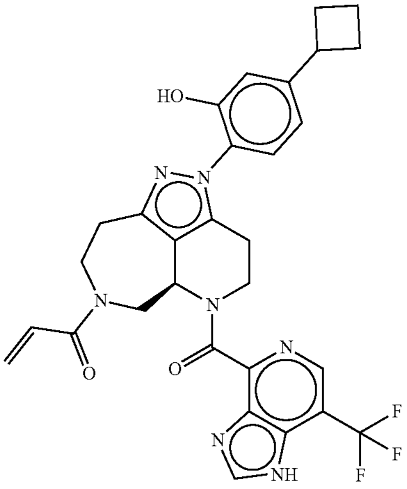 |

TABLE 1A-continued

| Compound No. | Name | Structure |
| --- | --- | --- |
| 155A | (R)-1-(5-(2-amino-6-(1,1-difluoroethyl)nicotinoyl)-2-(4-cyclobutyl-2-hydroxyphenyl)-2,3,4,5,5a,6,8,9-octahydro-7H-1,2,5,7-tetraazabenzo[cd]azulen-7-yl)prop-2-en-1-one | 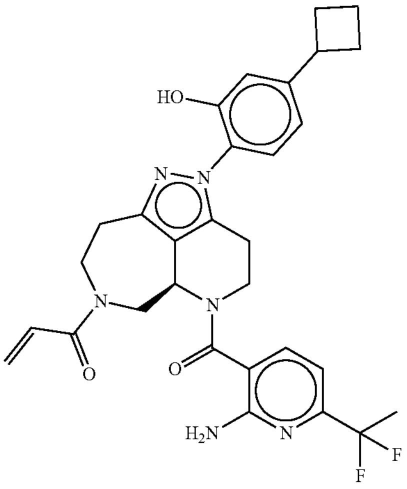 |
| 157A | (R)-1-(2-(4-cyclobutyl-2-hydroxyphenyl)-5-(6-((trifluoromethyl)thio) nicotinoyl)-2,3,4,5,5a,6,8,9-octahydro-7H-1,2,5,7-tetraazabenzo[cd]azulen-7-yl)prop-2-en-1-one | 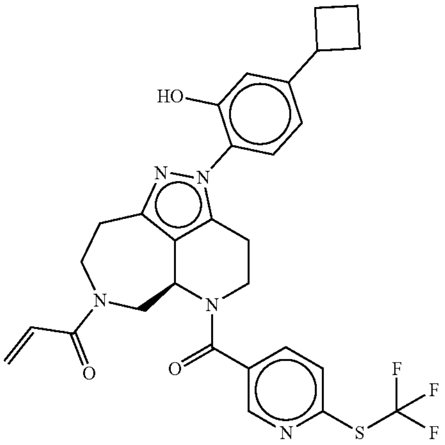 |
| 158A | (R)-1-(5-(3-amino-7-bromo-1H-indazole-4-carbonyl)-2-(4-cyclobutylphenyl)-2,3,4,5,5a,6,8,9-octahydro-7H-1,2,5,7-tetraazabenzo[cd]azulen-7-yl)prop-2-en-1-one | 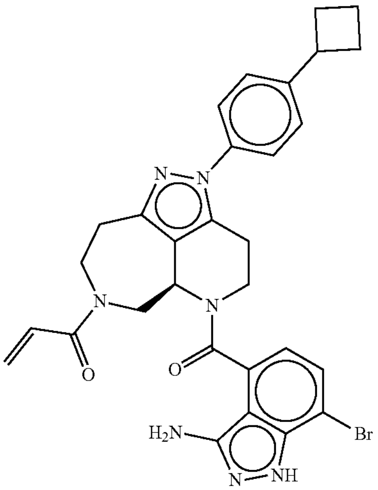 |

TABLE 1A-continued

| Compound No. | Name | Structure |
| --- | --- | --- |
| 159A | (R)-1-(5-(4-amino-5-(trifluoromethyl) pyrimidine-2-carbonyl)-2-(4-cyclobutyl-2-hydroxyphenyl)-2,3,4,5,5a,6,8,9-octahydro-7H-1,2,5,7-tetraazabenzo[cd]azulen-7-yl)prop-2-en-1-one | 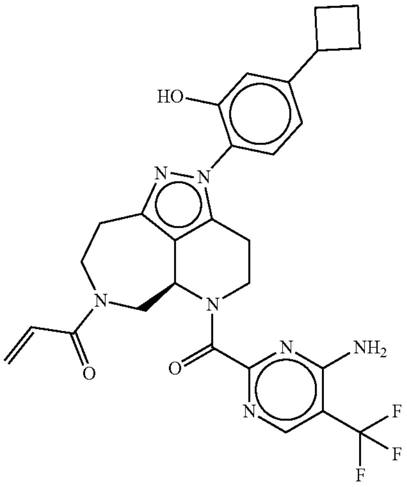 |
| 161A | (R)-1-(5-(4-amino-2-(trifluoromethyl) pyrimidine-5-carbonyl)-2-(4-cyclobutylphenyl)-2,3,4,5,5a,6,8,9-octahydro-7H-1,2,5,7-tetraazabenzo[cd]azulen-7-yl)prop-2-en-1-one | 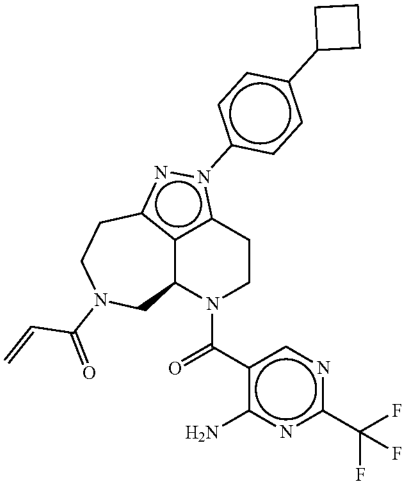 |
| 162A | (R)-1-(5-(4-amino-6-chloronicotinoyl)-2-(4-cyclopropylphenyl)-2,3,4,5,5a,6,8,9-octahydro-7H-1,2,5,7-tetraazabenzo[cd]azulen-7-yl)prop-2-en-1-one | 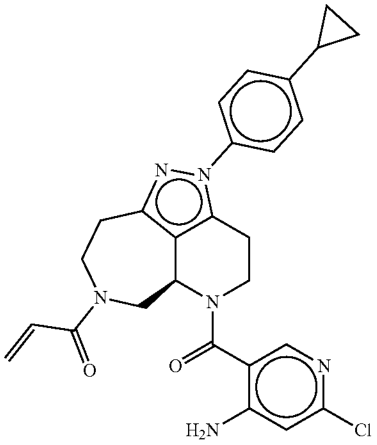 |

TABLE 1A-continued

| Compound No. | Name | Structure |
|---|---|---|
| 163A | (R)-1-(5-(4-amino-6-(trifluoromethyl)nicotinoyl)-2-(4-cyclopropyl-2-hydroxyphenyl)-2,3,4,5,5a,6,8,9-octahydro-7H-1,2,5,7-tetraazabenzo[cd]azulen-7-yl)prop-2-en-1-one | 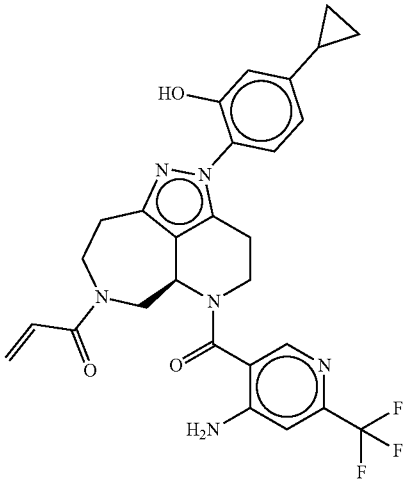 |
| 164A | (R)-1-(5-(4-amino-6-(difluoromethoxy) nicotinoyl)-2-(4-cyclobutyl-2-hydroxyphenyl)-2,3,4,5,5a,6,8,9-octahydro-7H-1,2,5,7-tetraazabenzo[cd]azulen-7-yl)prop-2-en-1-one | 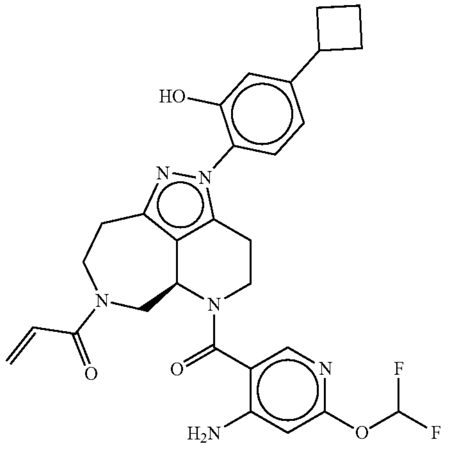 |
| 165A | (R)-1-(5-(2-amino-5-fluoro-6-(trifluoromethyl) nicotinoyl)-2-(4-cyclobutyl-2-hydroxyphenyl)-2,3,4,5,5a,6,8,9-octahydro-7H-1,2,5,7-tetraazabenzo[cd]azulen-7-yl)prop-2-en-1-one | 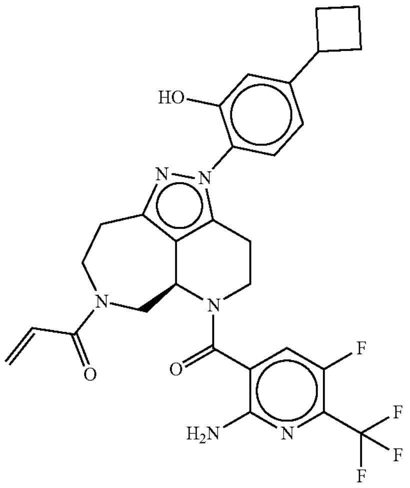 |

TABLE 1A-continued

| Compound No. | Name | Structure |
|---|---|---|
| 166A | (R)-1-(5-(4-amino-6-bromonicotinoyl)-2-(4-cyclopropylphenyl)-2,3,4,5,5a,6,8,9-octahydro-7H-1,2,5,7-tetraazabenzo[cd]azulen-7-yl)prop-2-en-1-one | 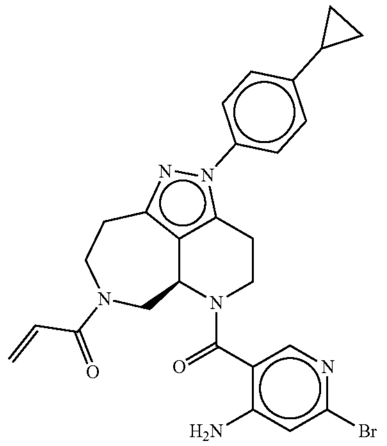 |
| 167A | (R)-1-(5-(2-amino-6-chloronicotinoyl)-2-(4-cyclopropylphenyl)-2,3,4,5,5a,6,8,9-octahydro-7H-1,2,5,7-tetraazabenzo[cd]azulen-7-yl)prop-2-en-1-one | 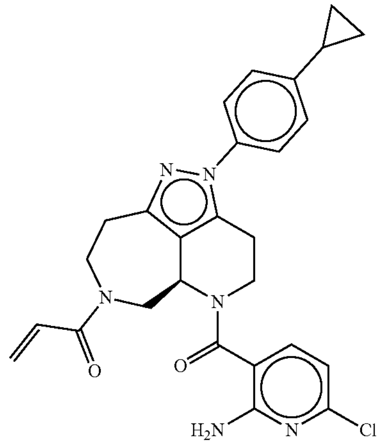 |

TABLE 2A

| Compound No. | Name | Structure |
|---|---|---|
| 172A | (R)-1-(5-(2-amino-6-(trifluoromethyl)nicotinoyl)-2-(4-cyclopropyl-2-hydroxyphenyl)-2,3,4,5,5a,6,8,9-octahydro-7H-1,2,5,7-tetraazabenzo[cd]azulen-7-yl)prop-2-en-1-one | 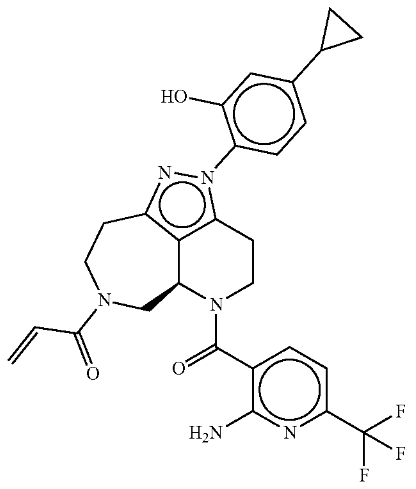 |

TABLE 2A-continued

| Compound No. | Name | Structure |
| --- | --- | --- |
| 173A | (R)-1-(5-(2-amino-6-(trifluoromethyl)nicotinoyl)-2-(2-hydroxy-4-isopropylphenyl)-2,3,4,5,5a,6,8,9-octahydro-7H-1,2,5,7-tetraazabenzo[cd]azulen-7-yl)prop-2-en-1-one | 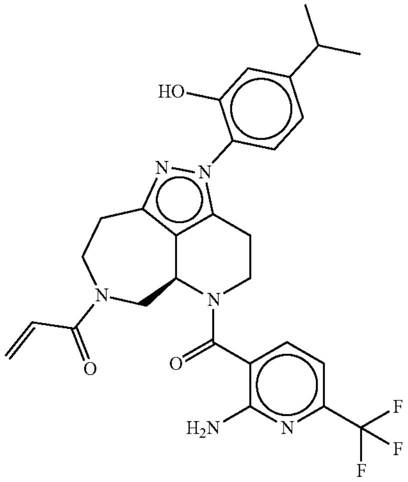 |
| 175A | (R)-1-(2-(4-cyclopropyl-2-hydroxyphenyl)-5-(5-hydroxy-6-(trifluoromethyl)nicotinoyl)-2,3,4,5,5a,6,8,9-octahydro-7H-1,2,5,7-tetraazabenzo[cd]azulen-7-yl)prop-2-en-1-one | 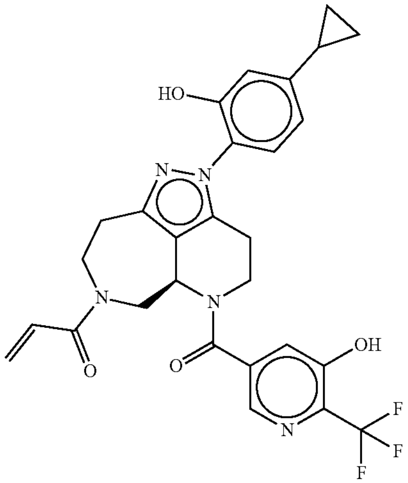 |
| 177A | (R)-1-(5-(4-amino-6-(difluoromethoxy)nicotinoyl)-2-(4-cyclopropylphenyl)-2,3,4,5,5a,6,8,9-octahydro-7H-1,2,5,7-tetraazabenzo[cd]azulen-7-yl)prop-2-en-1-one | 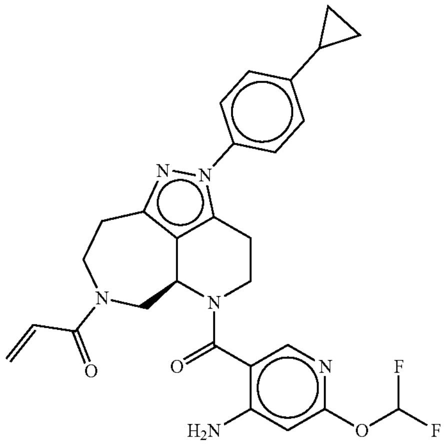 |

TABLE 2A-continued

| Compound No. | Name | Structure |
|---|---|---|
| 178A | (R)-1-(5-(4-amino-5-fluoro-6-(trifluoromethyl)nicotinoyl)-2-(4-cyclopropylphenyl)-2,3,4,5,5a,6,8,9-octahydro-7H-1,2,5,7-tetraazabenzo[cd]azulen-7-yl)prop-2-en-1-one | 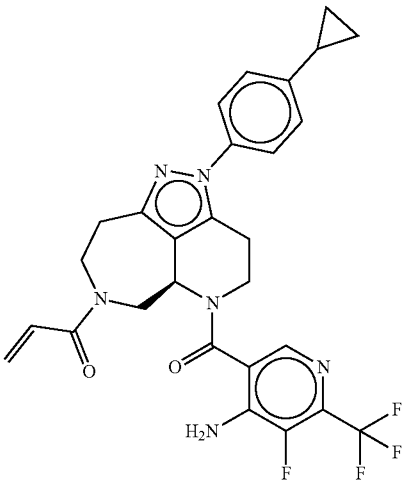 |
| 179A | (R)-1-(2-(4-cyclopropylphenyl)-5-(4-(methylamino)-6-(trifluoromethyl)nicotinoyl)-2,3,4,5,5a,6,8,9-octahydro-7H-1,2,5,7-tetraazabenzo[cd]azulen-7-yl)prop-2-en-1-one | 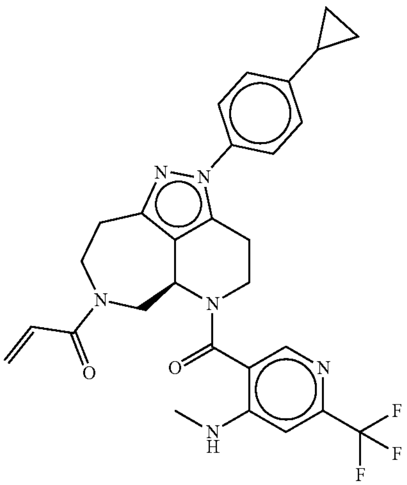 |
| 181A | (R)-1-(5-(4-amino-6-chloro-5-fluoronicotinoyl)-2-(4-cyclopropylphenyl)-2,3,4,5,5a,6,8,9-octahydro-7H-1,2,5,7-tetraazabenzo[cd]azulen-7-yl)prop-2-en-1-one | 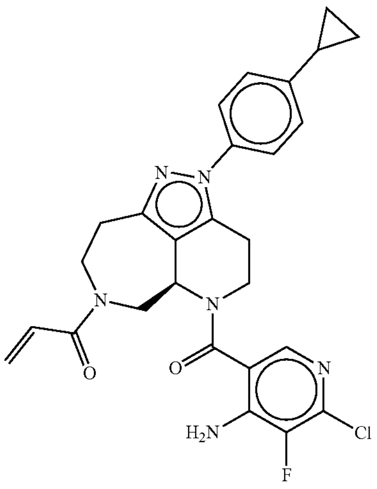 |

TABLE 2A-continued

| Compound No. | Name | Structure |
| --- | --- | --- |
| 182A | (R)-1-(5-(4-amino-6-bromo-5-fluoronicotinoyl)-2-(4-cyclopropylphenyl)-2,3,4,5,5a,6,8,9-octahydro-7H-1,2,5,7-tetraazabenzo[cd]azulen-7-yl)prop-2-en-1-one | 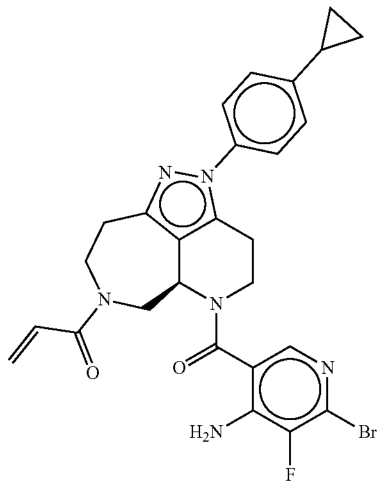 |
| 183A | (R)-1-(5-(4-amino-6-(1,1-difluoroethyl)nicotinoyl)-2-(4-cyclopropylphenyl)-2,3,4,5,5a,6,8,9-octahydro-7H-1,2,5,7-tetraazabenzo[cd]azulen-7-yl)prop-2-en-1-one | 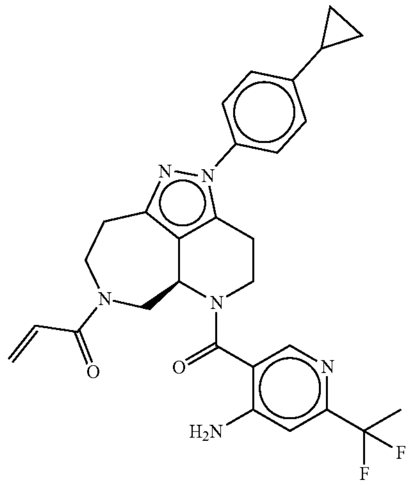 |
| 185A | (R)-1-(2-(4-cyclobutylphenyl)-5-(1-methyl-3-(trifluoromethyl)-1H-pyrazolo[4,3-b]pyridine-6-carbonyl)-2,3,4,5,5a,6,8,9-octahydro-7H-1,2,5,7-tetraazabenzo[cd]azulen-7-yl)prop-2-en-1-one | 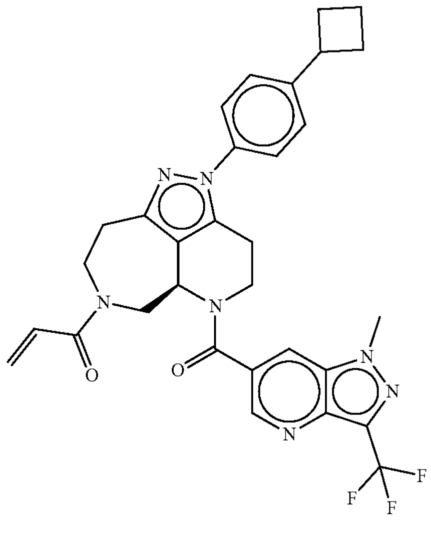 |

TABLE 2A-continued

| Compound No. | Name | Structure |
|---|---|---|
| 186A | (R)-1-(2-(4-cyclopropylphenyl)-5-(2,4-diamino-6-(trifluoromethyl)nicotinoyl)-2,3,4,5,5a,6,8,9-octahydro-7H-1,2,5,7-tetraazabenzo[cd]azulen-7-yl)prop-2-en-1-one | 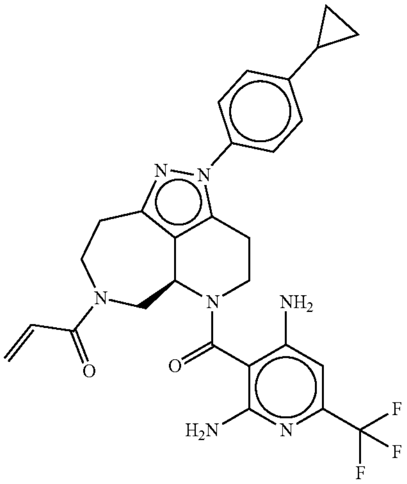 |
| 191A | (R)-1-(5-(4-amino-6-bromonicotinoyl)-2-(4-cyclopropyl-2-hydroxyphenyl)-2,3,4,5,5a,6,8,9-octahydro-7H-1,2,5,7-tetraazabenzo[cd]azulen-7-yl)prop-2-en-1-one | 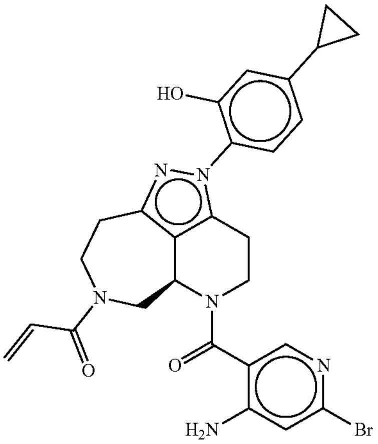 |
| 192A | (R)-1-(5-(4-amino-6-(difluoromethoxy)nicotinoyl)-2-(4-cyclopropyl-2-hydroxyphenyl)-2,3,4,5,5a,6,8,9-octahydro-7H-1,2,5,7-tetraazabenzo[cd]azulen-7-yl)prop-2-en-1-one | 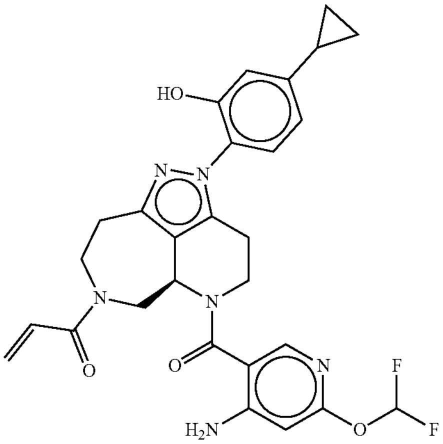 |

TABLE 2A-continued

| Compound No. | Name | Structure |
|---|---|---|
| 193A | (R)-1-(5-(2-amino-6-bromonicotinoyl)-2-(4-cyclopropyl-2-hydroxyphenyl)-2,3,4,5,5a,6,8,9-octahydro-7H-1,2,5,7-tetraazabenzo[cd]azulen-7-yl)prop-2-en-1-one | 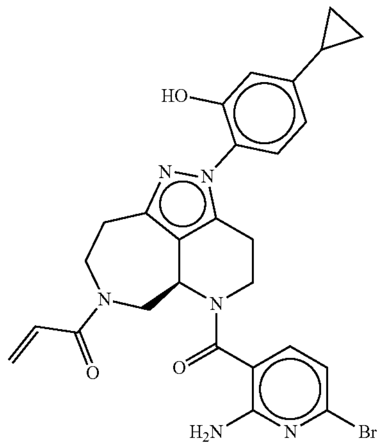 |
| 194A | (R)-1-(5-(4-amino-5-fluoro-6-(trifluoromethyl) nicotinoyl)-2-(4-cyclopropyl-2-hydroxyphenyl)-2,3,4,5,5a,6,8,9-octahydro-7H-1,2,5,7-tetraazabenzo[cd]azulen-7-yl)prop-2-en-1-one | 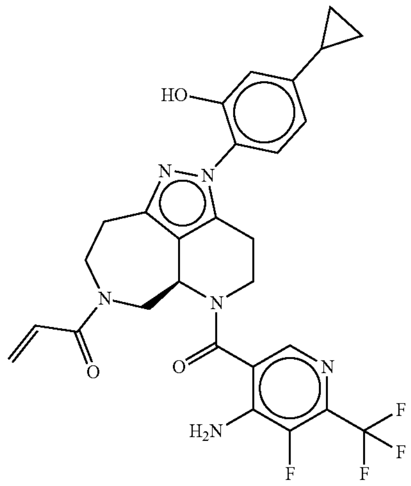 |
| 196A | (R)-1-(5-(4-amino-6-chloronicotinoyl)-2-(4-cyclopropyl-2-hydroxyphenyl)-2,3,4,5,5a,6,8,9-octahydro-7H-1,2,5,7-tetraazabenzo[cd]azulen-7-yl)prop-2-en-1-one | 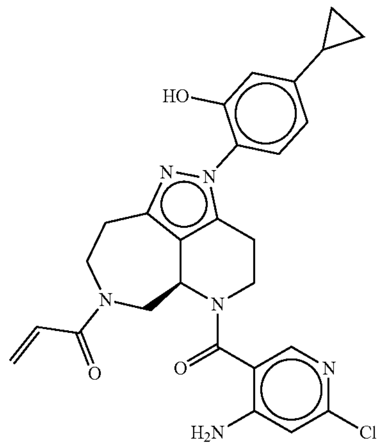 |

TABLE 2A-continued

| Compound No. | Name | Structure |
| --- | --- | --- |
| 197A | (R)-1-(5-(4-amino-2-(trifluoromethyl)pyrimidine-5-carbonyl)-2-(4-cyclopropyl-2-hydroxyphenyl)-2,3,4,5,5a,6,8,9-octahydro-7H-1,2,5,7-tetraazabenzo[cd]azulen-7-yl)prop-2-en-1-one | 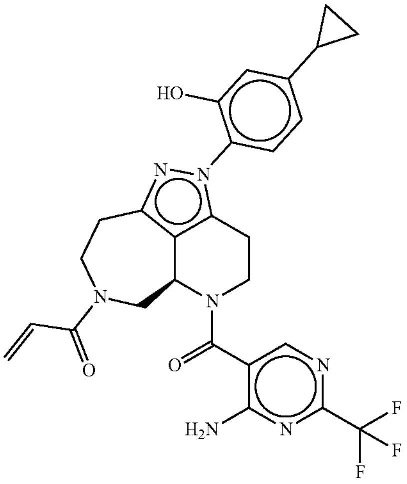 |
| 199A | (R)-1-(5-(2-amino-6-chloronicotinoyl)-2-(4-cyclopropyl-2-hydroxyphenyl)-2,3,4,5,5a,6,8,9-octahydro-7H-1,2,5,7-tetraazabenzo[cd]azulen-7-yl)prop-2-en-1-one | 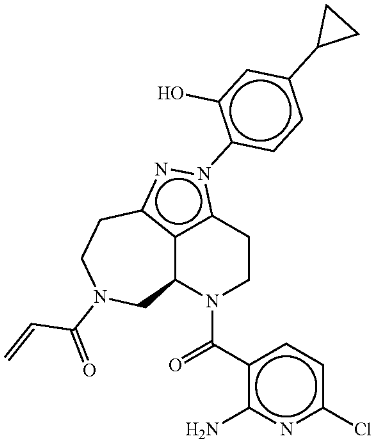 |
| 200A | (R)-1-(5-(2-amino-5-fluoro-6-(trifluoromethyl)nicotinoyl)-2-(4-cyclopropyl-2-hydroxyphenyl)-2,3,4,5,5a,6,8,9-octahydro-7H-1,2,5,7-tetraazabenzo[cd]azulen-7-yl)prop-2-en-1-one | 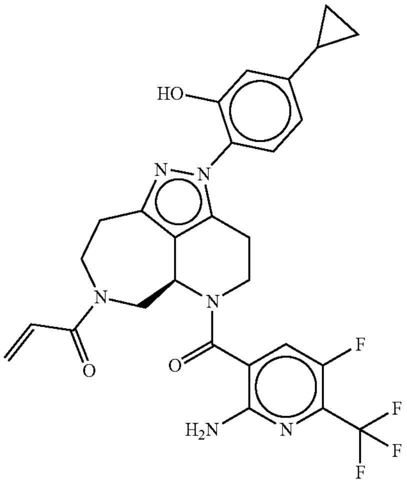 |

TABLE 2A-continued

| Compound No. | Name | Structure |
| --- | --- | --- |
| 202A | (R)-1-(5-(4-amino-6-bromo-5-fluoronicotinoyl)-2-(4-cyclopropyl-2-hydroxyphenyl)-2,3,4,5,5a,6,8,9-octahydro-7H-1,2,5,7-tetraazabenzo[cd]azulen-7-yl)prop-2-en-1-one | 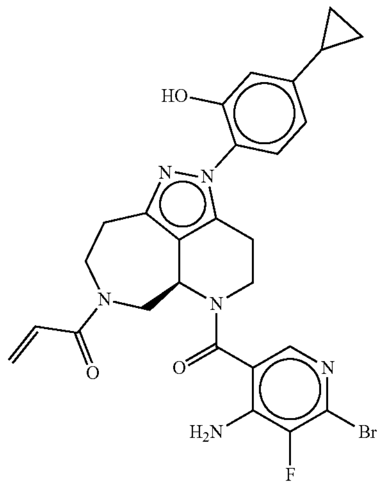 |
| 203A | (R)-1-(5-(4-amino-6-(trifluoromethyl)nicotinoyl)-2-(4-cyclopropyl-3-fluoro-2-hydroxyphenyl)-2,3,4,5,5a,6,8,9-octahydro-7H-1,2,5,7-tetraazabenzo[cd]azulen-7-yl)prop-2-en-1-one | 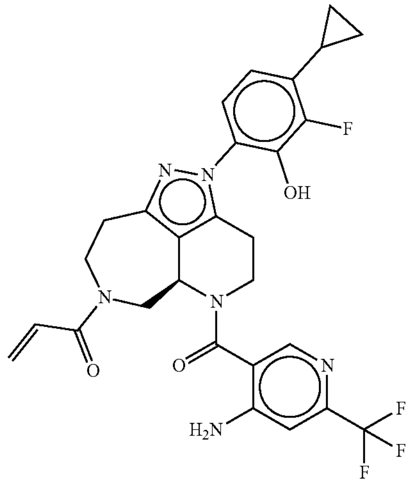 |
| 204A | (R)-1-(5-(4-amino-2-(methylthio)pyrimidine-5-carbonyl)-2-(4-cyclopropylphenyl)-2,3,4,5,5a,6,8,9-octahydro-7H-1,2,5,7-tetraazabenzo[cd]azulen-7-yl)prop-2-en-1-one | 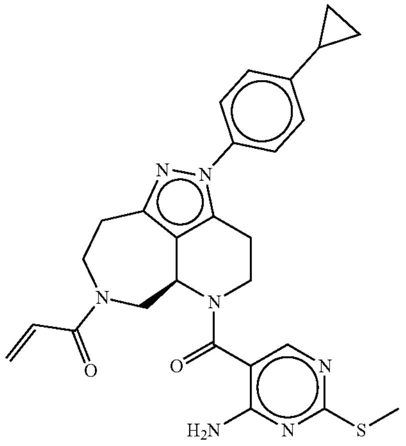 |

TABLE 2A-continued

| Compound No. | Name | Structure |
| --- | --- | --- |
| 206A | (R)-1-(5-(4-amino-6-(1,1-difluoroethyl)-5-fluoronicotinoyl)-2-(4-cyclopropyl-2-hydroxyphenyl)-2,3,4,5,5a,6,8,9-octahydro-7H-1,2,5,7-tetraazabenzo[cd]azulen-7-yl)prop-2-en-1-one | 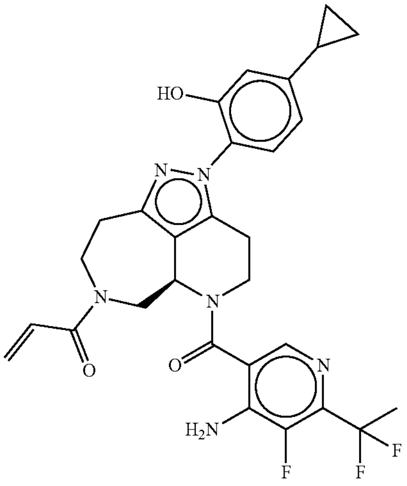 |
| 207A | (R)-5-(7-acryloyl-2-(4-cyclopropyl-2-hydroxyphenyl)-3,4,5,5a,6,7,8,9-octahydro-7H-1,2,5,7-tetraazabenzo[cd]azulene-5-carbonyl)-4-amino-2-(trifluoromethyl) benzonitrile | 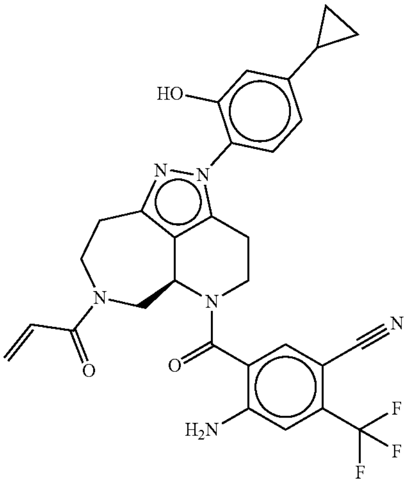 |
| 208A | (R)-1-(5-(4-amino-5-methyl-6-(trifluoromethyl)nicotinoyl)-2-(4-cyclopropyl-2-hydroxyphenyl)-2,3,4,5,5a,6,8,9-octahydro-7H-1,2,5,7-tetraazabenzo[cd]azulen-7-yl)prop-2-en-1-one | 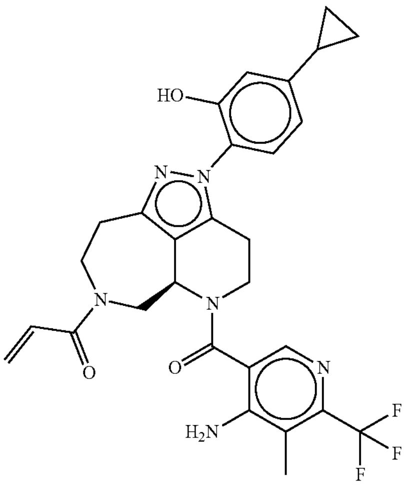 |

TABLE 2A-continued

| Compound No. | Name | Structure |
|---|---|---|
| 209A | (R)-1-(5-(4-amino-6-((trifluoromethyl)thio)nicotinoyl)-2-(4-cyclopropyl-2-hydroxyphenyl)-2,3,4,5,5a,6,8,9-octahydro-7H-1,2,5,7-tetraazabenzo[cd]azulen-7-yl)prop-2-en-1-one | 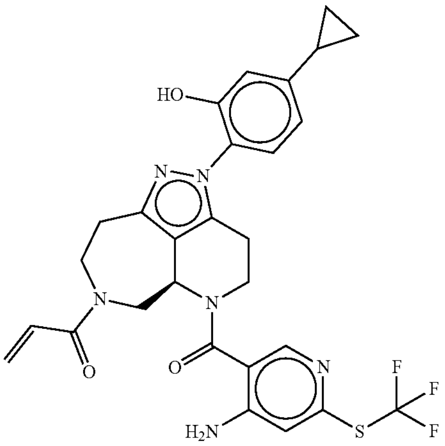 |
| 210A | (R)-1-(5-(4-amino-6-chloro-5-fluoronicotinoyl)-2-(4-cyclopropyl-2-hydroxyphenyl)-2,3,4,5,5a,6,8,9-octahydro-7H-1,2,5,7-tetraazabenzo[cd]azulen-7-yl)prop-2-en-1-one | 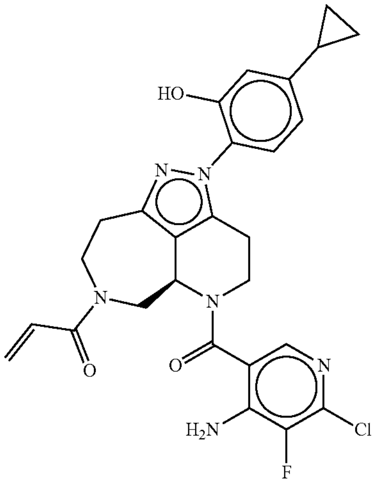 |
| 211A | (R)-1-(5-(4-amino-6-(methylthio)nicotinoyl)-2-(4-cyclopropyl-2-hydroxyphenyl)-2,3,4,5,5a,6,8,9-octahydro-7H-1,2,5,7-tetraazabenzo[cd]azulen-7-yl)prop-2-en-1-one | 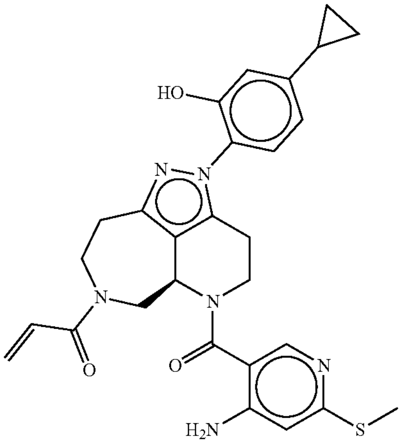 |

TABLE 2A-continued

| Compound No. | Name | Structure |
| --- | --- | --- |
| 213A | (R)-1-(2-(4-cyclopropyl-2-hydroxyphenyl)-5-(6-(trifluoromethyl)nicotinoyl)-2,3,4,5,5a,6,8,9-octahydro-7H-1,2,5,7-tetraazabenzo[cd]azulen-7-yl)prop-2-en-1-one | 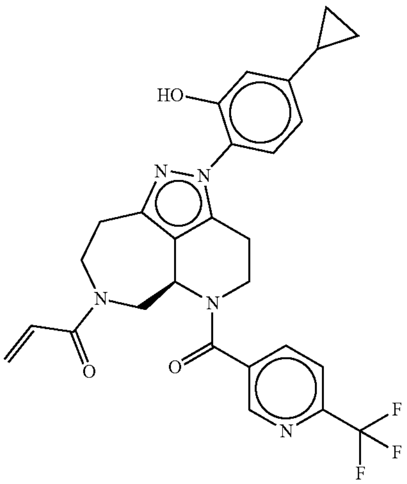 |
| 214A | (R)-1-(5-(4-amino-5-fluoro-6-((trifluoromethyl)thio)nicotinoyl)-2-(4-cyclopropyl-2-hydroxyphenyl)-2,3,4,5,5a,6,8,9-octahydro-7H-1,2,5,7-tetraazabenzo[cd]azulen-7-yl)prop-2-en-1-one | 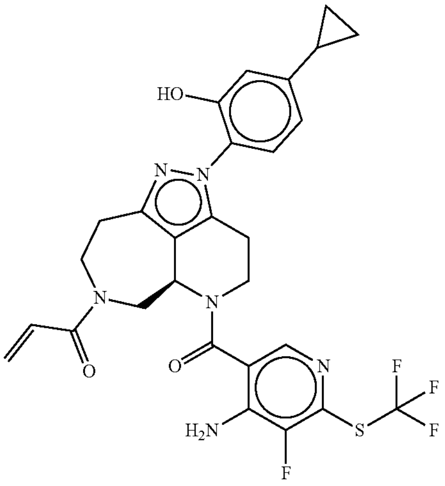 |
| 215A | (R)-1-(5-(4-amino-6-bromonicotinoyl)-2-(4-cyclopropyl-3-fluoro-2-hydroxyphenyl)-2,3,4,5,5a,6,8,9-octahydro-7H-1,2,5,7-tetraazabenzo[cd]azulen-7-yl)prop-2-en-1-one | 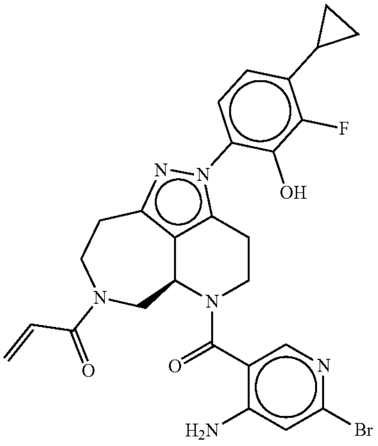 |

TABLE 2A-continued

| Compound No. | Name | Structure |
| --- | --- | --- |
| 216A | (R)-1-(5-(4-amino-5-methoxy-6-(trifluoromethyl)nicotinoyl)-2-(4-cyclopropyl-2-hydroxyphenyl)-2,3,4,5,5a,6,8,9-octahydro-7H-1,2,5,7-tetraazabenzo[cd]azulen-7-yl)prop-2-en-1-one | 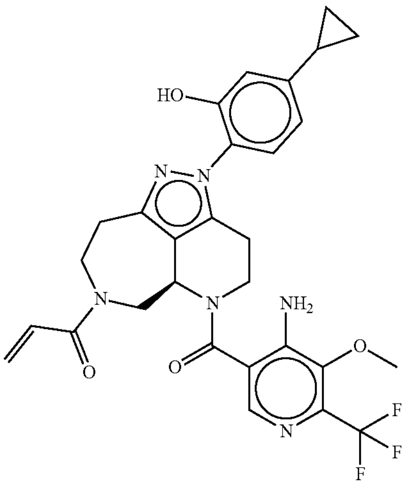 |
| 218A | (R)-1-(5-(4-amino-5-fluoro-6-(trifluoromethyl)nicotinoyl)-2-(4-cyclopropyl-3-fluoro-2-hydroxyphenyl)-2,3,4,5,5a,6,8,9-octahydro-7H-1,2,5,7-tetraazabenzo[cd]azulen-7-yl)prop-2-en-1-one | 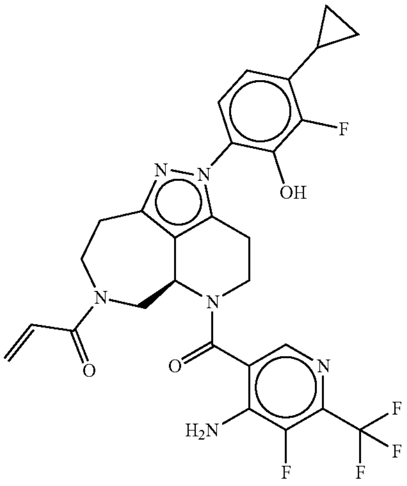 |
| 220A | (R)-1-(2-(4-cyclopropylphenyl)-5-(2,4-diamino-5-fluoro-6-(trifluoromethyl)nicotinoyl)-2,3,4,5,5a,6,8,9-octahydro-7H-1,2,5,7-tetraazabenzo[cd]azulen-7-yl)prop-2-en-1-one | 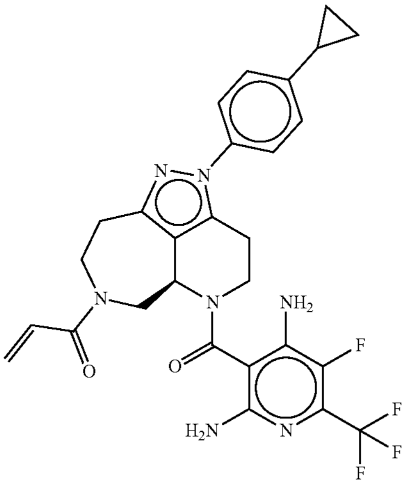 |

TABLE 2A-continued

| Compound No. | Name | Structure |
| --- | --- | --- |
| 223A | (R)-1-(5-(4-amino-5-fluoro-6-(methylthio)nicotinoyl)-2-(4-cyclopropyl-2-hydroxyphenyl)-2,3,4,5,5a,6,8,9-octahydro-7H-1,2,5,7-tetraazabenzo[cd]azulen-7-yl)prop-2-en-1-one | 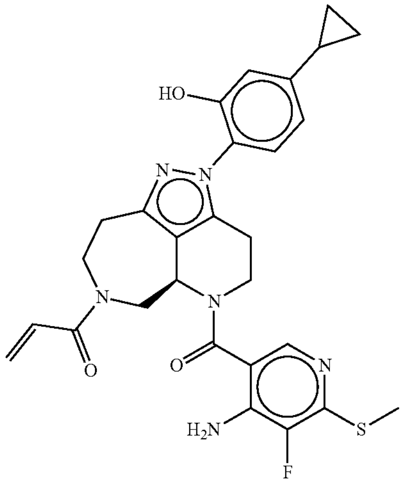 |
| 227A | (R)-1-(5-(4-amino-6-(1,1-difluoroethyl)-5-fluoronicotinoyl)-2-(4-cyclopropyl-3-fluoro-2-hydroxyphenyl)-2,3,4,5,5a,6,8,9-octahydro-7H-1,2,5,7-tetraazabenzo[cd]azulen-7-yl)prop-2-en-1-one | 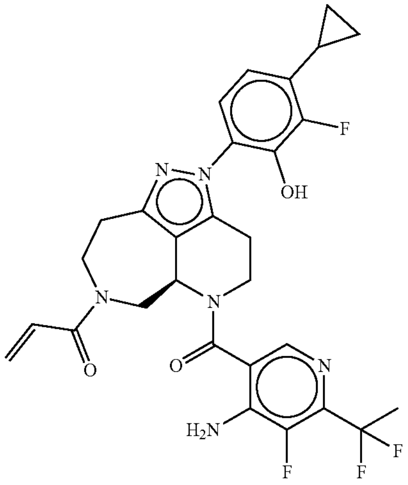 |
| 228A | (R)-1-(5-(4-amino-6-bromopyridazine-3-carbonyl)-2-(4-cyclopropyl-2-hydroxyphenyl)-2,3,4,5,5a,6,8,9-octahydro-7H-1,2,5,7-tetraazabenzo[cd]azulen-7-yl)prop-2-en-1-one | 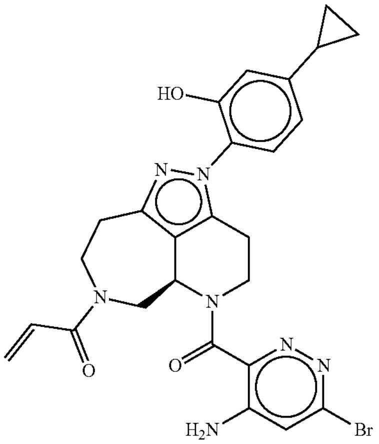 |

TABLE 2A-continued

| Compound No. | Name | Structure |
|---|---|---|
| 229A | (R)-1-(5-(4-amino-6-bromo-5-fluoronicotinoyl)-2-(4-cyclopropyl-3-fluoro-2-hydroxyphenyl)-2,3,4,5,5a,6,8,9-octahydro-7H-1,2,5,7-tetraazabenzo[cd]azulen-7-yl)prop-2-en-1-one | 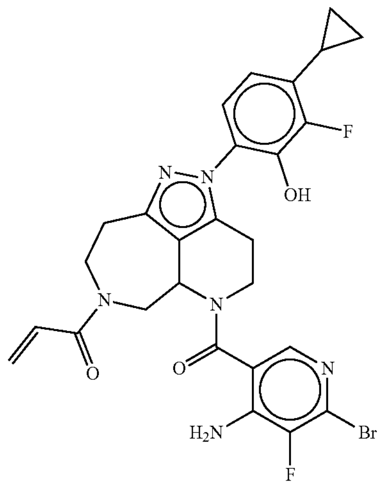 |
| 236A | (R)-1-(5-(1-chloroimidazo[1,5-a]pyridine-6-carbonyl)-2-(4-cyclobutylphenyl)-2,3,4,5,5a,6,8,9-octahydro-7H-1,2,5,7-tetraazabenzo[cd]azulen-7-yl)prop-2-en-1-one | 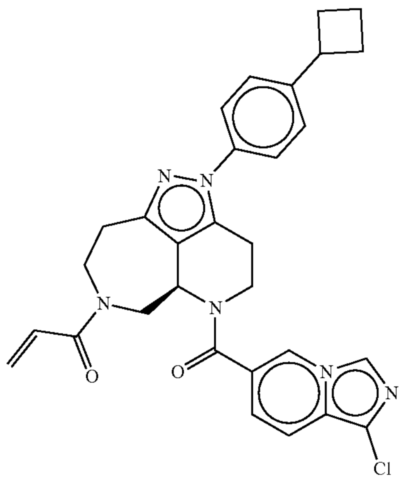 |
| 237A | (S)-1-(5-(7-bromo-2-(difluoromethyl)-1H-benzo[d]imidazole-4-carbonyl)-2-(4-cyclobutylphenyl)-4,5,5a,6,8,9-hexahydro-1,2a,5,7-tetraazabenzo[cd]azulen-7(3H)-yl)prop-2-en-1-one | 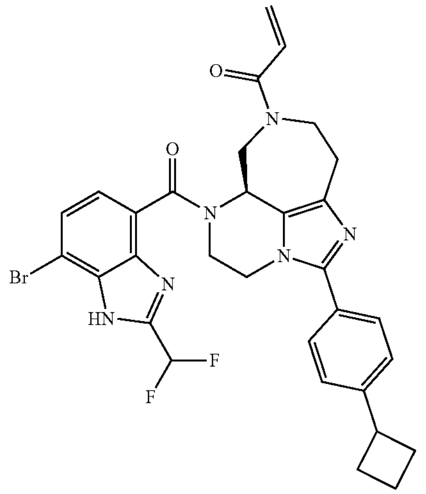 [SMILES: C=CC(=O)N1CCc2nc(-c3ccc(C4CCC4)cc3)n3c2[C@H](C1)N(C(=O)c1ccc(Br)c2[nH]c(C(F)F)nc12)CC3] |

TABLE 2A-continued

| Compound No. | Name | Structure |
|---|---|---|
| 238A | (S)-1-(5-(4-amino-6-(trifluoromethyl)nicotinoyl)-2-(4-cyclobutylphenyl)-4,5,5a,6,8,9-hexahydro-1,2a,5,7-tetraazabenzo[cd]azulen-7(3H)-yl)prop-2-en-1-one | 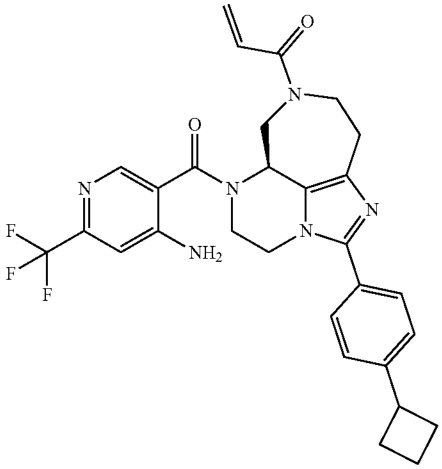 [SMILES: C=CC(=O)N1CCc2nc(-c3ccc(C4CCC4)cc3)n3c2[C@H](C1)N(C(=O)c1cnc(C(F)(F)F)cc1N)CC3] |
| 239A | (R,E)-1-(5-(4-amino-6-(trifluoromethyl)nicotinoyl)-2-(4-cyclobutyl-2-hydroxyphenyl)-2,3,4,5,5a,6,8,9-octahydro-7H-1,2,5,7-tetraazabenzo[cd]azulen-7-yl)-4-methoxybut-2-en-1-one | 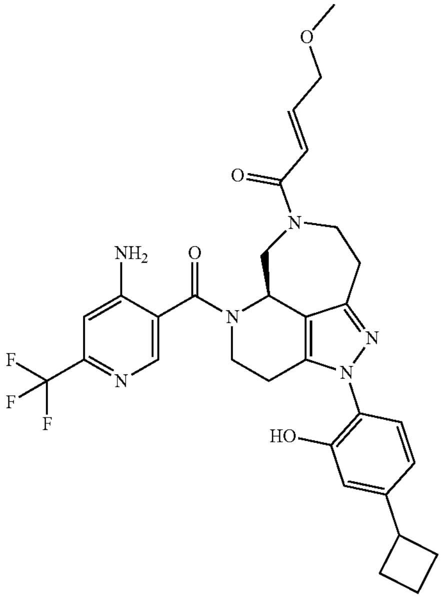 [SMILES: COC/C=C/C(=O)N1CCc2nn(-c3ccc(C4CCC4)cc3O)c3c2[C@H](C1)N(C(=O)c1cnc(C(F)(F)F)cc1N)CC3] |
| 242A | (R)-1-(2-(4-cyclobutyl-2-hydroxyphenyl)-5-(8-(trifluoromethyl)quinazoline-5-carbonyl)-2,3,4,5,5a,6,8,9-octahydro-7H-1,2,5,7-tetraazabenzo[cd]azulen-7-yl)prop-2-en-1-one | 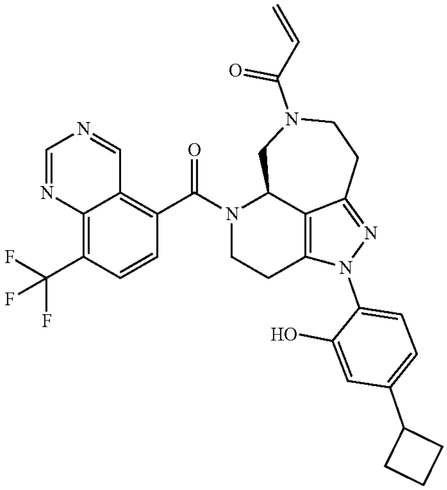 [SMILES: C=CC(=O)N1CCc2nn(-c3ccc(C4CCC4)cc3O)c3c2[C@H](C1)N(C(=O)c1ccc(C(F)(F)F)c2ncncc12)CC3] |

TABLE 2A-continued

| Compound No. | Name | Structure |
| --- | --- | --- |
| 243A | (R,Z)-1-(5-(4-amino-6-(trifluoromethyl)nicotinoyl)-2-(4-cyclobutylphenyl)-2,3,4,5,5a,6,8,9-octahydro-7H-1,2,5,7-tetraazabenzo[cd]azulen-7-yl)-3-chloroprop-2-en-1-one | 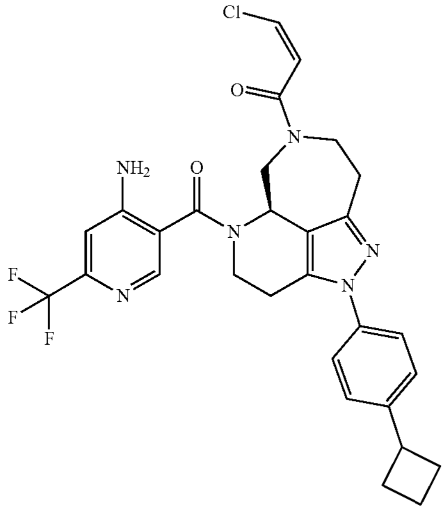 [SMILES: Nc1cc(C(F)(F)F)ncc1C(=O)N1CCc2c3c(nn2-c2ccc(C4CCC4)cc2)CCN(C(=O)/C=C\Cl)C[C@@H]31] |
| 244A | (R)-1-(5-(4-amino-6-(trifluoromethyl)nicotinoyl)-2-(4-cyclopropyl-3,5-difluoro-2-hydroxyphenyl)-2,3,4,5,5a,6,8,9-octahydro-7H-1,2,5,7-tetraazabenzo[cd]azulen-7-yl)prop-2-en-1-one | 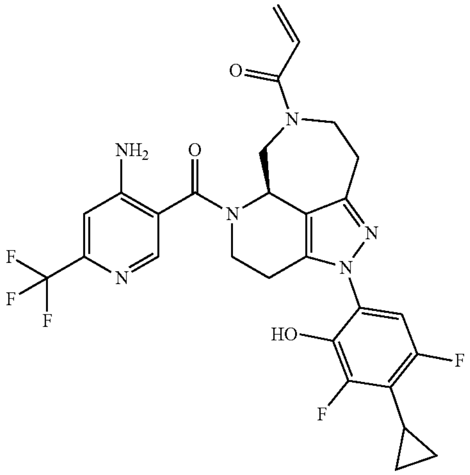 [SMILES: C=CC(=O)N1CCc2nn(-c3cc(F)c(C4CC4)c(F)c3O)c3c2[C@H](C1)N(C(=O)c1cnc(C(F)(F)F)cc1N)CC3] |
| 245A | (R)-1-(5-(2-amino-4-(trifluoromethyl)benzoyl)-2-(4-cyclopropyl-2-hydroxyphenyl)-2,3,4,5,5a,6,8,9-octahydro-7H-1,2,5,7-tetraazabenzo[cd]azulen-7-yl)prop-2-en-1-one | 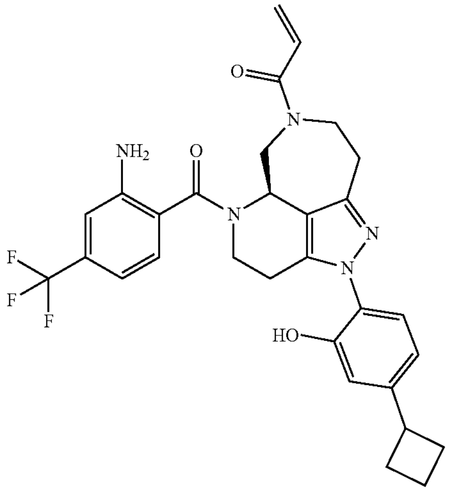 [SMILES: C=CC(=O)N1CCc2nn(-c3ccc(C4CCC4)cc3O)c3c2[C@H](C1)N(C(=O)c1ccc(C(F)(F)F)cc1N)CC3] |

TABLE 2A-continued

| Compound No. | Name | Structure |
|---|---|---|
| 247A | (R)-1-(5-(4-amino-5-fluoro-6-(trifluoromethoxy)nicotinoyl)-2-(4-cyclopropyl-2-hydroxyphenyl)-2,3,4,5,5a,6,8,9-octahydro-7H-1,2,5,7-tetraazabenzo[cd]azulen-7-yl)prop-2-en-1-one | 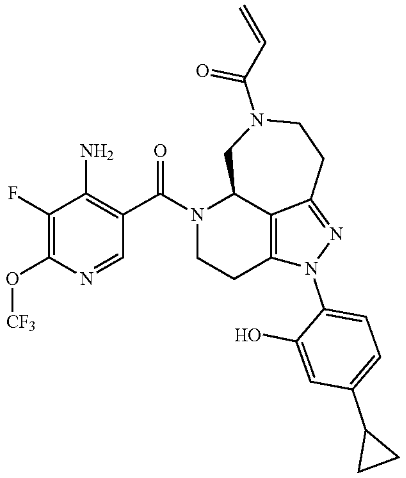 [SMILES: C=CC(=O)N1CCc2nn(-c3ccc(C4CC4)cc3O)c3c2[C@H](C1)N(C(=O)c1cnc(OC(F)(F)F)c(F)c1N)CC3] |
| 248A | (R)-1-(5-(4-amino-6-(trifluoromethyl)pyridazine-3-carbonyl)-2-(4-cyclopropyl-2-hydroxyphenyl)-2,3,4,5,5a,6,8,9-octahydro-7H-1,2,5,7-tetraazabenzo[cd]azulen-7-yl)prop-2-en-1-one | 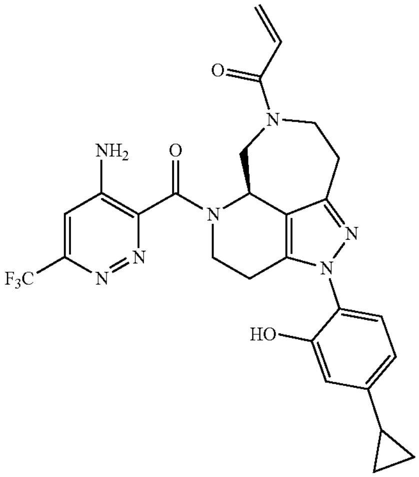 [SMILES: C=CC(=O)N1CCc2nn(-c3ccc(C4CC4)cc3O)c3c2[C@H](C1)N(C(=O)c1nnc(C(F)(F)F)cc1N)CC3] |
| 258A | (R)-1-(5-(4-amino-5-fluoro-6-(trifluoromethoxy)nicotinoyl)-2-(4-cyclopropyl-3-fluoro-2-hydroxyphenyl)-2,3,4,5,5a,6,8,9-octahydro-7H-1,2,5,7-tetraazabenzo[cd]azulen-7-yl)prop-2-en-1-one | 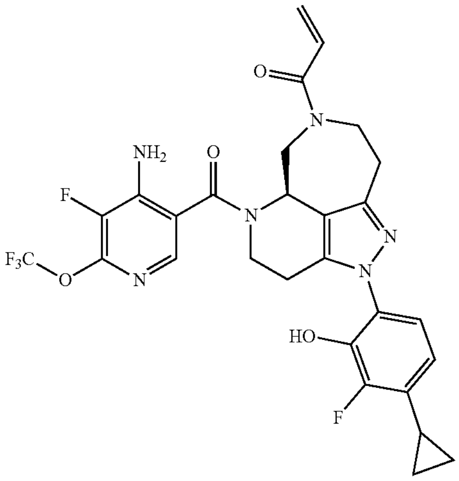 [SMILES: C=CC(=O)N1CCc2nn(-c3ccc(C4CC4)c(F)c3O)c3c2[C@H](C1)N(C(=O)c1cnc(OC(F)(F)F)c(F)c1N)CC3] |

TABLE 2A-continued

| Compound No. | Name | Structure |
| --- | --- | --- |
| 259A | (R)-1-(5-(2-amino-3-fluoro-4-(trifluoromethyl)benzoyl)-2-(4-cyclopropyl-2-hydroxyphenyl)-2,3,4,5,5a,6,8,9-octahydro-7H-1,2,5,7-tetraazabenzo[cd]azulen-7-yl)prop-2-en-1-one | 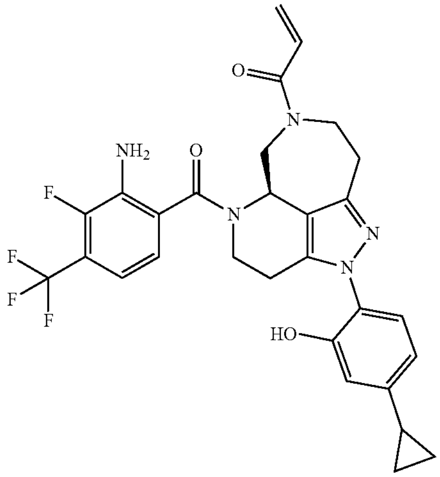 [SMILES: C=CC(=O)N1CCc2nn(-c3ccc(C4CC4)cc3O)c3c2[C@H](C1)N(C(=O)c1ccc(C(F)(F)F)c(F)c1N)CC3] |

In some embodiments, the compound is a pharmaceutically acceptable salt of any one of the compounds described in Table 1.

In some aspects, the present disclosure provides a compound being an isotopic derivative (e.g., isotopically labeled compound) of any one of the compounds of the Formulae disclosed herein.

In some embodiments, the compound is an isotopic derivative of any one of the compounds described in Table 1, or a prodrug or pharmaceutically acceptable salt thereof.

In some embodiments, the compound is an isotopic derivative of any one of the compounds described in Table 1, or a pharmaceutically acceptable salt thereof.

In some embodiments, the compound is an isotopic derivative f any one of prodrugs of the compounds described in Table 1, or a pharmaceutically acceptable salt thereof.

In some embodiments, the compound is an isotopic derivative of any one of the compounds described in Table 1.

In some embodiments, the compound is a pharmaceutically acceptable salt of any one of the compounds described in Table 2.

In some embodiments, the compound is an isotopic derivative of any one of the compounds described in Table 2, or a prodrug or pharmaceutically acceptable salt thereof.

In some embodiments, the compound is an isotopic derivative of any one of the compounds described in Table 2, or a pharmaceutically acceptable salt thereof.

In some embodiments, the compound is an isotopic derivative of any one of prodrugs of the compounds described in Table 2, or a pharmaceutically acceptable salt thereof.

In some embodiments, the compound is an isotopic derivative of any one of the compounds described in Table 2.

In some embodiments, the compound is a pharmaceutically acceptable salt of any one of the compounds described in Table 1A.

In some embodiments, the compound is an isotopic derivative of any one of the compounds described in Table 1A, or a prodrug or pharmaceutically acceptable salt thereof.

In some embodiments, the compound is an isotopic derivative of any one of the compounds described in Table 1A, or a pharmaceutically acceptable salt thereof.

In some embodiments, the compound is an isotopic derivative of any one of prodrugs of the compounds described in Table 1A, or a pharmaceutically acceptable salt thereof.

In some embodiments, the compound is an isotopic derivative of any one of the compounds described in Table 1A.

In some embodiments, the compound is a pharmaceutically acceptable salt of any one of the compounds described in Table 2A.

In some embodiments, the compound is an isotopic derivative of any one of the compounds described in Table 2A, or a prodrug or pharmaceutically acceptable salt thereof.

In some embodiments, the compound is an isotopic derivative of any one of the compounds described in Table 2A, or a pharmaceutically acceptable salt thereof.

In some embodiments, the compound is an isotopic derivative f any one of prodrugs of the compounds described in Table 2A, or a pharmaceutically acceptable salt thereof.

In some embodiments, the compound is an isotopic derivative of any one of the compounds described in Table 2A.

In some embodiments, the compound is selected from Compound Nos. 5, 14, 21, 23, 25, 26, 27, 32, 67, 87, or 92, or a prodrug or pharmaceutically acceptable salt thereof.

In some embodiments, the compound is selected from Compound Nos 5, 14, 21, 23, 25, 26, 27, 32, 67, 87, or 92, or a pharmaceutically acceptable salt thereof.

In some embodiments, the compound is selected from Compound Nos 5, 14, 21, 23, 25, 26, 27, 32, 67, 87, or 92.

In some embodiments, the compound is selected from Compound Nos. 128, 163, 166, 178, 182, 183, 184, 186, 187, 190, 191, 194, 195, 196, 202, 203, 206, 208, 210, 211, 218, 220, or 228, or a prodrug or pharmaceutically acceptable salt thereof.

In some embodiments, the compound is selected from Compound Nos. 128, 163, 166, 178, 182, 183, 184, 186, 187, 190, 191, 194, 195, 196, 202, 203, 206, 208, 210, 211, 218, 220, or 228, or a pharmaceutically acceptable salt thereof.

In some embodiments, the compound is selected from Compound Nos. 128, 163, 166, 178, 182, 183, 184, 186, 187, 190, 191, 194, 195, 196, 202, 203, 206, 208, 210, 211, 218, 220, or 228.

In some embodiments, the compound is selected from Compound Nos. 128A, 163A, 166A, 178A, 182A, 183A, 186A, 191A, 194A, 196A, 202A, 203A, 206A, 208A, 210A, 211A, 218A, 220A, or 228A, or a prodrug or pharmaceutically acceptable salt thereof.

In some embodiments, the compound is selected from Compound Nos. 128A, 163A, 166A, 178A, 182A, 183A, 186A, 191A, 194A, 196A, 202A, 203A, 206A, 208A, 210A, 211A, 218A, 220A, or 228A, or a pharmaceutically acceptable salt thereof.

In some embodiments, the compound is selected from Compound Nos. 128A, 163A, 166A, 178A, 182A, 183A, 186A, 191A, 194A, 196A, 202A, 203A, 206A, 208A, 210A, 211A, 218A, 220A, or 228A.

In some embodiments, the compound is selected from Compound Nos. 5, 14, 21, 23, 25, 26, 27, 32, 67, 87, 92, 128, 163, 166, 178, 182, 183, 184, 186, 187, 190, 191, 194, 195, 196, 202, 203, 206, 208, 210, 211, 218, 220, or 228, or a prodrug or pharmaceutically acceptable salt thereof.

In some embodiments, the compound is selected from Compound Nos. 5, 14, 21, 23, 25, 26, 27, 32, 67, 87, 92, 128, 163, 166, 178, 182, 183, 184, 186, 187, 190, 191, 194, 195, 196, 202, 203, 206, 208, 210, 211, 218, 220, or 228, or a pharmaceutically acceptable salt thereof.

In some embodiments, the compound is selected from 5, 14, 21, 23, 25, 26, 27, 32, 67, 87, 92, 128, 163, 166, 178, 182, 183, 184, 186, 187, 190, 191, 194, 195, 196, 202, 203, 206, 208, 210, 211, 218, 220, or 228.

In some embodiments, the compound is selected from Compound Nos. 128, 163, 166, 178, 182, 183, 184, 186, 187, 190, 191, 194, 195, 196, 202, 203, 206, 208, 210, 211, 218, 220, or 228, or a prodrug or pharmaceutically acceptable salt thereof.

In some embodiments, the compound is selected from Compound Nos. 128, 163, 166, 178, 182, 183, 184, 186, 187, 190, 191, 194, 195, 196, 202, 203, 206, 208, 210, 211, 218, 220, or 228, or a pharmaceutically acceptable salt thereof.

In some embodiments, the compound is selected from Compound Nos. 128, 163, 166, 178, 182, 183, 184, 186, 187, 190, 191, 194, 195, 196, 202, 203, 206, 208, 210, 211, 218, 220, or 228.

In some embodiments, the compound is selected from Compound Nos. 128, 163, 178, 191, 194, 202, 203, 206, 208, 210, 218, or 228, or a prodrug or pharmaceutically acceptable salt thereof.

In some embodiments, the compound is selected from Compound Nos. 128, 163, 178, 191, 194, 202, 203, 206, 208, 210, 218, or 228, or a pharmaceutically acceptable salt thereof.

In some embodiments, the compound is selected from Compound Nos. 128, 163, 178, 191, 194, 202, 203, 206, 208, 210, 218, or 228.

In some embodiments, the compound is Compound No. 128 or a prodrug or pharmaceutically acceptable salt thereof. In some embodiments, the compound is Compound No. 163 or a prodrug or pharmaceutically acceptable salt thereof. In some embodiments, the compound is Compound No. 178 or a prodrug or pharmaceutically acceptable salt thereof. In some embodiments, the compound is Compound No. 191 or a prodrug or pharmaceutically acceptable salt thereof. In some embodiments, the compound is Compound No. 194 or a prodrug or pharmaceutically acceptable salt thereof. In some embodiments, the compound is Compound No. 202 or a prodrug or pharmaceutically acceptable salt thereof. In some embodiments, the compound is Compound No. 203 or a prodrug or pharmaceutically acceptable salt thereof. In some embodiments, the compound is Compound No. 206 or a prodrug or pharmaceutically acceptable salt thereof. In some embodiments, the compound is Compound No. 208 or a prodrug or pharmaceutically acceptable salt thereof. In some embodiments, the compound is Compound No. 210 or a prodrug or pharmaceutically acceptable salt thereof. In some embodiments, the compound is Compound No. 218 or a prodrug or pharmaceutically acceptable salt thereof. In some embodiments, the compound is Compound No. 228 or a prodrug or pharmaceutically acceptable salt thereof.

In some embodiments, the compound is Compound No. 128 or a pharmaceutically acceptable salt thereof. In some embodiments, the compound is Compound No. 163 or a pharmaceutically acceptable salt thereof. In some embodiments, the compound is Compound No. 178 or a pharmaceutically acceptable salt thereof. In some embodiments, the compound is Compound No. 191 or a pharmaceutically acceptable salt thereof. In some embodiments, the compound is Compound No. 194 or a pharmaceutically acceptable salt thereof. In some embodiments, the compound is Compound No. 202 or a pharmaceutically acceptable salt thereof. In some embodiments, the compound is Compound No. 203 or a pharmaceutically acceptable salt thereof. In some embodiments, the compound is Compound No. 206 or a pharmaceutically acceptable salt thereof. In some embodiments, the compound is Compound No. 208 or a pharmaceutically acceptable salt thereof. In some embodiments, the compound is Compound No. 210 or a pharmaceutically acceptable salt thereof. In some embodiments, the compound is Compound No. 218 or a pharmaceutically acceptable salt thereof. In some embodiments, the compound is Compound No. 228 or a pharmaceutically acceptable salt thereof.

In some embodiments, the compound is Compound No. 128. In some embodiments, the compound is Compound No. 163. In some embodiments, the compound is Compound No. 178. In some embodiments, the compound is Compound No. 191. In some embodiments, the compound is Compound No. 194. In some embodiments, the compound is Compound No. 202. In some embodiments, the compound is Compound No. 203. In some embodiments, the compound is Compound No. 206. In some embodiments, the compound is Compound No. 208. In some embodiments, the compound is Compound No. 210. In some embodiments, the compound is Compound No. 218. In some embodiments, the compound is Compound No. 228.

In some embodiments, the compound is selected from Compound Nos. 128A, 163A, 178A, 191A, 194A, 202A, 203A, 206A, 208A, 210A, 218A, or 28A, or a prodrug or pharmaceutically acceptable salt thereof.

In some embodiments, the compound is selected from Compound Nos. 128A, 163A, 178A, 191A, 194A, 202A, 203A, 206A, 208A, 210A, 218A, or 228A, or a pharmaceutically acceptable salt thereof.

In some embodiments, the compound is selected from Compound Nos. 128A, 163A, 178A, 191A, 194A, 202A, 203A, 206A, 208A, 210A, 218A, or 228A.

In some embodiments, the compound is Compound No. 128A or a prodrug or pharmaceutically acceptable salt thereof. In some embodiments, the compound is Compound No. 163A or a prodrug or pharmaceutically acceptable salt thereof. In some embodiments, the compound is Compound No. 178A or a prodrug or pharmaceutically acceptable salt thereof. In some embodiments, the compound is Compound No. 191A or a prodrug or pharmaceutically acceptable salt thereof. In some embodiments, the compound is Compound No. 194A or a prodrug or pharmaceutically acceptable salt thereof. In some embodiments, the compound is Compound No. 202A or a prodrug or pharmaceutically acceptable salt thereof. In some embodiments, the compound is Compound No. 203A or a prodrug or pharmaceutically acceptable salt thereof. In some embodiments, the compound is Compound No. 206A or a prodrug or pharmaceutically acceptable salt thereof. In some embodiments, the compound is Compound No. 208A or a prodrug or pharmaceutically acceptable salt thereof. In some embodiments, the compound is Compound No. 210A or a prodrug or pharmaceutically acceptable salt thereof. In some embodiments, the compound is Compound No. 218A or a prodrug or pharmaceutically acceptable salt thereof. In some embodiments, the compound is Compound No. 228A or a prodrug or pharmaceutically acceptable salt thereof.

In some embodiments, the compound is Compound No. 1284 or a pharmaceutically acceptable salt thereof. In some embodiments, the compound is Compound No. 163A or a pharmaceutically acceptable salt thereof. In some embodiments, the compound is Compound No. 178A or a pharmaceutically acceptable salt thereof. In some embodiments, the compound is Compound No. 191A or a pharmaceutically acceptable salt thereof. In some embodiments, the compound is Compound No. 194A or a pharmaceutically acceptable salt thereof. In some embodiments, the compound is Compound No. 202A or a pharmaceutically acceptable salt thereof. In some embodiments, the compound is Compound No. 203A or a pharmaceutically acceptable salt thereof. In some embodiments, the compound is Compound No. 206A or a pharmaceutically acceptable salt thereof. In some embodiments, the compound is Compound No. 208A or a pharmaceutically acceptable salt thereof. In some embodiments, the compound is Compound No. 210A or a pharmaceutically acceptable salt thereof. In some embodiments, the compound is Compound No. 218A or a pharmaceutically acceptable salt thereof. In some embodiments, the compound is Compound No. 228A or a pharmaceutically acceptable salt thereof.

In some embodiments, the compound is Compound No. 128A. In some embodiments, the compound is Compound No. 163A. In some embodiments, the compound is Compound No. 178A. In some embodiments, the compound is Compound No. 191A. In some embodiments, the compound is Compound No. 194A. In some embodiments, the compound is Compound No. 202A. In some embodiments, the compound is Compound No. 203A. In some embodiments, the compound is Compound No. 206A. In some embodiments, the compound is Compound No. 208A. In some embodiments, the compound is Compound No. 210A. In some embodiments, the compound is Compound No. 218A. In some embodiments, the compound is Compound No. 228A.

It is understood that the isotopic derivative can be prepared using any of a variety of art-recognized techniques. For example, the isotopic derivative can generally be prepared by carrying out the procedures disclosed in the Schemes and/or in the Examples described herein, by substituting an isotopically labeled reagent for a non-isotopically labeled reagent.

In some embodiments, the isotopic derivative is a deuterium labeled compound.

In some embodiments, the isotopic derivative is a deuterium labeled compound of any one of the compounds of the Formulae disclosed herein.

The term "isotopic derivative", as used herein, refers to a derivative of a compound in which one or more atoms are isotopically enriched or labelled. For example, an isotopic derivative of a compound of Formula (I) is isotopically enriched with regard to, or labelled with, one or more isotopes as compared to the corresponding compound of Formula (I). In some embodiments, the isotopic derivative is enriched with regard to, or labelled with, one or ore atoms selected from $^{2}H$, $^{13}C$, $^{14}C$, $^{15}N$, $^{18}O$, $^{29}Si$, $^{31}P$, and $^{34}S$. In some embodiments, the isotopic derivative is a deuterium labeled compound (i.e., being enriched with $^{2}H$ with regard to one or more atoms thereof). In some embodiments, the compound is a $^{18}F$ labeled compound. In some embodiments, the compound is a $^{123}I$ labeled compound, a $^{124}I$ labeled compound, a $^{125}I$ labeled compound, a $^{129}I$ labeled compound, a $^{131}I$ labeled compound, a $^{135}I$ labeled compound, or any combination thereof. In some embodiments, the compound is a $^{33}S$ labeled compound, a $^{34}S$ labeled compound, a $^{35}S$ labeled compound, a $^{36}S$ labeled compound, or any combination thereof.

It is understood that the $^{18}F$, $^{123}I$, $^{124}I$, $^{125}I$, $^{129}I$, $^{131}I$, $^{135}I$, $^{32}S$, $^{34}S$, $^{35}S$, and/or $^{36}S$ labeled compound, can be prepared using any of a variety of art-recognized techniques. For example, the labeled compound can generally be prepared by carrying out the procedures disclosed in the Schemes and/or in the Examples described herein, by substituting a $^{18}F$, $^{123}I$, $^{124}I$, $^{125}I$, $^{129}I$, $^{131}I$, $^{135}I$, $^{3}S$, $^{34}S$, $^{35}S$, and/or $^{36}S$ labeled reagent for a non-isotope labeled reagent.

A compound of the invention or a pharmaceutically acceptable salt or solvate thereof that contains one or more of the aforementioned $^{18}F$, $^{123}I$, $^{124}I$, $^{125}I$, $^{129}I$, $^{131}I$, $^{135}I$, $^{32}S$, $^{34}S$, $^{35}S$, and $^{36}S$ atom(s) is within the scope of the invention. Further, substitution with isotope (e.g., $^{18}F$, $^{123}I$, $^{124}I$, $^{125}I$, $^{129}I$, $^{131}I$, $^{135}I$, $^{3}S$, $^{34}S$, $^{35}S$, and/or $^{36}S$) may afford certain therapeutic advantages resulting from greater metabolic stability, e.g., increased in vivo half-life or reduced dosage requirements.

For the avoidance of doubt it is to be understood that, where in this specification a group is qualified by "described herein", the said group encompasses the first occurring and broadest definition as well as each and all of the particular definitions for that gr up.

The various functional groups and substituents making up the compounds of the Formula (I) are typically chosen such that the molecular weight of the compound does not exceed 1000 daltons. More usually, the molecular weight of the compound will be less than 900, for example less than 800, or less than 750, or less than 700, or less than 650 daltons. More conveniently, the molecular weight is less than 600 and, for example, is 550 daltons or les.

A suitable pharmaceutically acceptable salt of a compound of the disclosure is, for example, an acid-addition salt of a compound of the disclosure which is sufficiently basic, for example, an acid-addition salt with, for example, an inorganic organic acid, for example hydrochloric, hydrobromic, sulfuric, phosphoric, trifluoroacetic, formic citric methane sulfonate or maleic acid. In addition, a suitable pharmaceutically acceptable salt of a compound of the disclosure which is sufficiently acidic is an alkali metal salt, for example a sodium or potassium salt, an alkaline earth metal salt, for example a calcium or magnesium salt, an ammonium salt or a salt with an organic base which affords a pharmaceutically acceptable cation, for example a salt with methylamine, dimethylamine, diethylamine, trimethylamine, piperidine, morpholine or tris-(2-hydroxyethyl)amine.

It will be understood that the compounds of any one of the Formulae disclosed herein and any pharmaceutically acceptable salts thereof, comprise stereoisomers, mixtures of stereoisomers, polymorphs of all isomeric forms of said compounds.

It will be understood that while compounds disclosed herein may be presented in one particular configuration. Such particular configuration is not to be construed as limiting the disclosure to one or another isomer, tautomer, regioisomer or stereoisomer, nor does it exclude mixtures of isomers, tautomers, regioisomers or stereoisomers. In some embodiments, the presentation of a compound herein in a particular configuration intends to encompass, and to refer to, each of the available isomers, tautomers, regioisomers, and stereoisomers of the compound, or any mixture thereof; while the presentation further intends to refer to the specific configuration of the compound.

It will be understood that while compounds disclosed herein may be presented without specified configuration (e.g., without specified stereochemistry). Such presentation intends to encompass all available isomers, tautomers, regioisomers, and stereoisomers of the compound. In some embodiments, the presentation of a compound herein without specified configuration intends to refer to each of the available isomers, tautomers, regioisomers, and stereoisomers of the compound, or any mixture thereof.

As used herein, the term "isomerism" means compounds that have identical molecular formulae but differ in the sequence of bonding of their atoms or in the arrangement of their atoms in space. Isomers that differ in the arrangement of their atoms in space are termed "stereoisomers." Stereoisomers that are not mirror images of one another are termed "diastereoisomers," and stereoisomers that are non-superimposable mirror images of each other are termed "enantiomers" or sometimes optical isomers. A mixture containing equal amounts of individual enantiomeric forms of opposite chirality is termed a "racemic mixture."

As used herein, the term "chiral center" refers to a carbo atom bonded to four nonidentical substituents.

As used herein, the term "chiral isomer" means a compound with at least one chiral center. Compounds with more than one chiral center may exist either as an individual diastereomer or as a mixture of diastereomers, termed "diastereomeric mixture." When one chiral center is present, a stereoisomer may be characterized by the absolute configuration (R or S) of that chiral center. Absolute configuration refers to the arrangement in space of the substituents attached to the chiral center. The substituents attached to the chiral center under consideration are ranked in accordance with the *Sequence Rule* of Cahn, Ingold and Prelog. (Cahn et al., *Angew. Chem. Inter. Edit.* 1966, 5, 385; errata 511; Cahn et al., *Angew. Chem.* 1966, 78, 413; Cahn and Ingold, *J. Chem. Soc.* 1951 (London), 612; Cahn et al., *Experientia* 1956, 12, 81; Cahn, *J. Chem. Educ.* 1964, 41, 116).

As used herein, the term "geometric isomer" means the diastereomers that owe their existence to hindered rotation about double bonds or a cycloalkyl linker (e.g., 1,3-cyclobutyl). These configurations are differentiated in their names by the prefixes cis and trans, or Z and E, which indicate that the groups are on the same or opposite side of the double bond in the molecule according to the Cahn-Ingold-Prelog rules.

It is to be understood that the compounds of the present disclosure may be depicted as different chiral isomers or geometric isomers. It is also to be understood that when compounds have chiral isomeric or geometric isomeric forms, all isomeric forms are intended to be included in the scope of the present disclosure, and the naming of the compounds does not exclude any isomeric forms, it being understood that not all isomers may have the same level of activity.

It is to be understood that the structures and other compounds discussed in this disclosure include all atropic isomers thereof. It is also to be understood that not all atropic isomers may have the same level of activity.

As used herein, the term "atropic isomers" are a type of stereoisomer in which the atoms of two isomers are arranged differently in space. Atropic isomers owe their existence to a restricted rotation caused by hindrance of rotation of large groups about a central bond. Such atropic isomers typically exist as a mixture, however as a result of recent advances in chromatography techniques, it has been possible to separate mixtures of two atropic isomers in select cases.

As used herein, the term "tautomer" is one of two or more structural isomers that exist in equilibrium and is readily converted from one isomeric form to another. This conversion results in the formal migration of a hydrogen atom accompanied by a switch of adjacent conjugated double bonds. Tautomers exist as a mixture of a tautomeric set in solution. In solutions where tautomerization is possible, a chemical equilibrium of the tautomers will be reached. The exact ratio of the tautomers depends on several factors, including temperature, solvent and pH. The concept of tautomers that are interconvertible by tautomerisations is called tautomerism. Of the various types of tautomerism that are possible, two are commonly observed. In keto-enol tautomerism a simultaneous shift of electrons and a hydrogen atom occurs. Ring-chain tautomerism arises as a result of the aldehyde group (—CHO) in a sugar chain molecule reacting with one of the hydroxy groups (—OH) in the same molecule to give it a cyclic (ring-shaped) form as exhibited by glucose.

It is to be understood that the compounds of the present disclosure may be depicted as different tautomers. It should also be understood that when compounds have tautomeric forms, all tautomeric forms are intended to be included in the scope of the present disclosure, and the naming of the compounds does not exclude any tautomer form. It will be understood that certain tautomers may have a higher level of activity than others.

Compounds that have the same molecular formula but differ in the nature or sequence of bonding of their atoms or the arrangement of their atoms in space are termed "isomers". Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterised by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The compounds of this disclosure may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see discussion in Chapter of "Advanced Organic Chemistry", 4th edition J. March, John Wiley and Sons, New York 2001), for example by synthesis from optically active starting materials or by resolution of a racemic form. Some of the compounds of the disclosure may have geometric isomeric centers (E- and Z-isomers). It is to be understood that the present disclosure encompasses all optical, diastereoisomers and geometric isomers and mixtures thereof that possess WRN inhibitory activity.

The present disclosure also encompasses compounds of the disclosure as defined herein which comprise one or more isotopic substitutions.

It is to be understood that the compounds of any Formula described herein include the compounds themselves, as well as their salts, and their solvates, if applicable. A salt, for example, can be formed between an anion and a positively charged group (e.g., amino) on a substituted compound disclosed herein. Suitable anions include chloride, bromide, iodide, sulfate, bisulfate, sulfamate, nitrate, phosphate, citrate, methanesulfonate, trifluoroacetate, glutamate, glucuronate, glutarate, malate, maleate, succinate, fumarate, tartrate, tosylate, salicylate, lactate, naphthalenesulfonate, and acetate (e.g., trifluoroacetate).

As used herein, the term "pharmaceutically acceptable anion" refers to an anion suitable for forming a pharmaceutically acceptable salt. Likewise, a salt can a so be formed between a cation and a negatively charged group (e.g., carboxylate) on a substituted compound disclosed herein. Suitable cations include sodium ion, potassium ion, magnesium ion, calcium ion, and an ammonium cation such as tetramethylammonium ion or diethylamine ion. The substituted compounds disclosed herein also include those salts containing quaternary nitrogen atoms.

It is to be understood that the compounds of the present disclosure, for example, the salts of the compounds, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

As used herein, the term "solvate" means solvent addition forms that contain either stoichiometric or non-stoichiometric amounts of solvent. Some compounds have a tendency to trap a fixed molar ratio of solvent molecules in the crystalline solid state, thus forming a solvate. If the solvent is water the solvate formed is a hydrate; and if the solvent is alcohol, the solvate formed is an alcoholate. Hydrates are formed by the combination of one or more molecules of water with one molecule of the substance in which the water retains its molecular state as $H_2O$.

As used herein, the term "analog" refers to a chemical compound that is structurally similar to another but differs slightly in composition (as in the replacement of one atom by an atom of a different element or in the presence of a particular functional group, or the replacement of one functional group by another functional group). Thus, an analog is a compound that is similar or comparable in function and appearance, but not in structure origin to the reference compound.

As used herein, the term "derivative" refers to compounds t at have a common core structure and are substituted with various groups as described herein.

As used herein, the term "bioisostere" refers to a compound resulting from the exchange of an atom or of a group of atoms with another, broadly similar, atom or group of atoms. The objective of a bioisosteric replacement is to create a new compound with similar biological properties to the parent compound. The bioisosteric replacement may be physicochemically or topologically based. Examples of carboxylic acid bioisosteres include, but are not limited to, acyl sulfonamides, tetrazoles, sulfonates and phosphonates. See, e.g., Patani and LaVöie, *Chem. Rev.* 96, 3147-3176, 1996.

It is also to be understood that certain compounds of any one of the Formulae disclosed herein may exist in solvated as well as unsolvated forms such as, for example, hydrated forms. A suitable pharmaceutically acceptable solvate is, for example, a hydrate such as hemi-hydrate, a mono-hydrate, a di-hydrate or a tri-hydrate. It is to be understood that the disclosure encompasses all such solvated forms that possess WRN activity.

It is also to be understood that certain compounds of any one f the Formulae disclosed herein may exhibit polymorphism, and that the disclosure encompasses all such forms, or mixtures thereof, which possess WRN activity. It is generally known that crystalline materials may be analysed using conventional techniques such as X-Ray Powder Diffraction analysis, Differential Scanning Calorimetry, Thermal Gravimetric Analysis, Diffuse Reflectance Infrared Fourier Transform (DRIFT) spectroscopy, Near Infrared (NIR) spectroscopy, solution and/or solid state nuclear magnetic resonance spectroscopy. The water content of such crystalline materials may be determined by Karl Fischer analysis.

Compounds of any one of the Formulae disclosed herein may exist in a number of different tautomeric forms and references to compounds of Formula (I) include all such forms. For the avoidance of doubt, where a compound can exist in one of several tautomeric forms, and only one is specifically described or shown, all others are nevertheless embraced by Formula (I). Examples of tautomeric forms include keto-, enol-, and enolate-forms, as in, for example, the following tautomeric pairs: keto/enol (illustrated below), imine/enamine, amide/imino alcohol, amidine/amidine, nitroso/oxime, thioketone/enethiol, and nitro/aci-nitro.

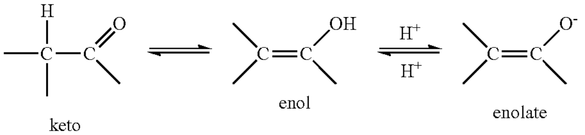

keto enol enolate

Compounds of any one of the Formulae disclosed herein containing an amine function may also form N-oxides. A reference herein to a compound of Formula (I) that contains an amine function also includes the N-oxide. Where a compound contains several amine functions, one or more than one nitrogen atom may be oxidized to form an N-oxide. Particular examples of N-oxides are the N-oxides of a tertiary amine or a nitrogen atom of a nitrogen-containing heterocycle. N-oxides can be formed by treatment of the corresponding amine with an oxidizing agent such as hydrogen peroxide or a peracid (e.g. a peroxycarboxylic acid), see for example Advanced Organic Chemistry, by Jerry March, 4th Edition, Wiley Interscience, pages. More particularly, N-oxides can be made by the procedure of L. W. Deady (Syn. Comm. 1977, 7, 509-514) in which the amine compound is reacted with meta-chloroperoxybenzoic acid (mCPBA), for example, in an inert solvent such as dichloromethane.

The compounds of any one of the Formulae disclosed herein may be administered in the form of a prodrug which is broken down in the human or animal body to release a compound of the disclosure. A prodrug may be used to alter the physical properties and/or the pharmacokinetic properties of a compound of the disclosure. A prodrug can be formed when the compound of the disclosure contains a suitable group or substituent to which a property-modifying group can be attached. Examples of prodrugs include derivatives containing in vivo cleavable alkyl or acyl substituents at the ester or amide group in any one of the Formulae disclosed herein.

Accordingly, the present disclosure includes those compounds of any one of the Formulae disclosed herein as defined hereinbefore when made available by organic synthesis and when made available within the human or animal body by way of cleavage of a prodrug thereof. Accordingly, the present disclosure includes those compounds of any one of the Formulae disclosed herein that are produced by organic synthetic means and also such compounds that are produced in the human or animal body by way of metabolism of a precursor compound, that is a compound of any one of the Formulae disclosed herein may be a synthetically-produced compound or a metabolically-produced compound.

A suitable pharmaceutically acceptable prodrug of a compound of anyone of the Formulae disclosed herein is one that is based on reasonable medical judgment as being suitable for administration to the human or animal body without undesirable pharmacological activities and without undue toxicity. Various forms of prodrug have been described, for example in the following documents: a) Methods in Enzymology, Vol. 42, p. 309-396, edited by K. Widder, et al. (Academic Press, 1985); b) Design of Pro-drugs, edited by H. Bundgaard, (Elsevier, 1985); c) A Textbook of Drug Design and Development, edited by Krogsgaard-Larsen and H. Bundgaard, Chapter 5 “Design and Application of Prodrugs”, by H. Bundgaard p. 113-191 (1991); d) H. Bundgaard, Advanced Drug Delivery Reviews, 8, 1-38 (1992); e) H. Bundgaard, et al., Journal of Pharmaceutical Sciences, 77, 285 (1988); f) N. Kakeya, et al., Chem. Pham. Bull., 32, 692 (1984); g) T. Higuchi and V. Stella, “Pro-Drugs as Novel Delivery Systems”, A.C.S. Symposium Series, Volume 14; and h) E. Roche (editor), “Bioreversible Carriers in Drug Design”, Pergamon Press, 1987.

A suitable pharmaceutically acceptable prodrug of a compound of anyone of the Formulae disclosed herein that possesses a hydroxy group is, for example, an in vivo cleavable ester or ether thereof. An in vivo cleavable ester or ether of a compound of any one of the Formulae disclosed herein containing a hydroxy group is, for example, a pharmaceutically acceptable ester or ether which is cleaved in the human or animal body to produce the parent hydroxy compound. Suitable pharmaceutically acceptable ester forming groups for a hydroxy group include inorganic esters such as phosphate esters (including phosphoramidic cyclic esters). Further suitable pharmaceutically acceptable ester forming groups for a hydroxy group include $C_1$-$C_{10}$ alkanoyl groups such as acetyl, benzoyl, phenylacetyl and substituted benzoyl and phenylacetyl groups, $C_1$-$C_{10}$ alkoxycarbonyl groups such as ethoxycarbonyl, N,N—($C_1$-$C_6$ alkyl)$_2$carbamoyl, 2-dialkylaminoacetyl and 2-carboxyacetyl groups. Examples of ring substituents on the phenylacetyl and benzoyl groups include aminomethyl, N-alkylaminomethyl, N,N-dialkylaminomethyl, morpholinomethyl, piperazin-1-ylmethyl and 4-($C_1$-$C_4$ alkyl)piperazin-1-ylmethyl. Suitable pharmaceutically acceptable ether forming groups for a hydroxy group include α-acyloxyalkyl groups such as acetoxymethyl and pivaloyloxymethyl groups.

A suitable pharmaceutically acceptable prodrug of a compound of any one of the Formulae disclosed herein that possesses a carboxy group is, for example, an in vivo cleavable amide thereof, for example an amide formed with an amine such as ammonia, a $C_{1-4}$alkylamine such as methylamine, a ($C_1$-$C_4$ alkyl)$_2$amine such as dimethylamine, N-ethyl-N-methylamine or diethylamine, a $C_1$-$C_4$ alkoxy-$C_2$-$C_4$ alkylamine such as 2-methoxyethylamine, a phenyl-$C_1$-$C_4$ alkylamine such as benzylamine and amino acids such as glycine or an ester thereof.

A suitable pharmaceutically acceptable prodrug of a compound of any one of the Formulae disclosed herein that possesses an amino group is, for example, an in vivo cleavable amide derivative thereof. Suitable pharmaceutically acceptable amides from an amino group include, for example an amide formed with $C_1$-$C_{10}$ alkanoyl groups such as an acetyl, benzoyl, phenylacetyl and substituted benzoyl and phenylacetyl groups. Examples of ring substituents on the phenylacetyl and benzoyl groups include aminomethyl, N-alkylaminomethyl, N,N-dialkylaminomethyl, morpholinomethyl, piperazin-1-ylmethyl and 4-($C_1$-$C_4$ alkyl)piperazin-1-ylmethyl.

The in vivo effects of a compound of any one of the Formulae disclosed herein may be exerted in part by one or more metabolites that are formed within the human or animal body after administration of a compound of any one of the Formulae disclosed herein. As stated hereinbefore, the in vivo effects of a compound of any one of the Formulae disclosed herein may also be exerted by way of metabolism of a precursor compound (a prodrug).

Suitably, the present disclosure excludes any individual compounds not possessing the biological activity defined herein.

Methods of Synthesis

In some aspects, the present disclosure provides a method of preparing a compound of the present disclosure.

In some aspects, the present disclosure provides a method of a compound, comprising one or more steps as described herein.

In some aspects, the present disclosure provides a compound obtainable by, or obtained by, or directly obtained by a method for preparing a compound as described herein.

In some aspects, the present disclosure provides an intermediate as described herein, being suitable for use in a method for preparing a compound as described herein.

The compounds of the present disclosure can be prepared by any suitable technique known in the art. Particular processes for the preparation of these compounds are described further in the accompanying examples.

In the description of the synthetic methods described herein and in any referenced synthetic methods that are used to prepare the starting materials, it is to be understood that all proposed reaction conditions, including choice of solvent, reaction atmosphere, reaction temperature, duration of the experiment and workup procedures, can be selected by a person skilled in the art.

It is understood by one skilled in the art of organic synthesis that the functionality present on various portions of the molecule must be compatible with the reagents and reaction conditions utilized.

It will be appreciated that during the synthesis of the compounds of the disclosure in the processes defined herein, or during the synthesis of certain starting materials, it may be desirable to protect certain substituent groups to prevent their undesired reaction. The skilled chemist will appreciate when such protection is required, and how such protecting groups may be put in place, and later removed. For examples of protecting groups see one of the any general texts on the subject, for example, ‘Protective Groups in Organic Synthesis' by Theodora Green (publisher: John Wiley & Sons). Protecting groups may be removed by any convenient method described in the literature or known to the skilled chemist as appropriate for the removal of the protecting group in question, such methods being chosen so as to effect removal of the protecting group with the minimum disturbance of groups elsewhere in the molecule. Thus, if reactants include, for example, groups such as amino, carboxy or hydroxy it may be desirable to protect the group in some of the reactions mentioned herein.

By way of example, a suitable protecting group for an amino or alkylamino group is, for example, an acyl group, for example an alkanoyl group such as acetyl, n alkoxycarbonyl group, for example a methoxycarbonyl, ethoxycarbonyl, or t-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed by, for example, hydrolysis with a suitable base such as an alkali metal hydroxide, for example lithium or sodium hydroxide. Alternatively an acyl group such as a tert-butoxycarbonyl group may be removed, for example, by treatment with a suitable acid as hydrochloric, sulfuric or phosphoric acid or trifluoroacetic acid and an arylmethoxycarbonyl group such as a benzyloxycarbonyl group may be removed, for example, by hydrogenation over a catalyst such as palladium on carbon, or by treatment with a Lewis acid for example boron tris(trifluoroacetate). A suitable alternative protecting group for a primary amino group is, for example, a phthaloyl group which may be removed by treat ent with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium, sodium hydroxide or ammonia. Alternatively an arylmethyl group such as a benzyl group may be removed, for example, by hydrogenation over a catalyst such as palladium on carbon.

A suitable protecting group for a carboxy group is, for example, an esterifying group, for example a methyl or an ethyl group which may be removed, for example, by hydrolysis with a base such as sodium hydroxide, or for example a tert-butyl group which may be removed, for example, by treatment with an acid, for example an organic acid such as trifluoroacetic acid, or for example a benzyl group which may be removed, for example, by hydrogenation over a catalyst such as palladium on carbon.

Once a compound of Formula (I) has been synthesized by any ore of the processes defined herein, the processes may then further comprise the additional steps of: (i) removing any protecting groups present; (ii) converting the compound Formula (I) into another compound of Formula (I); (iii) forming a pharmaceutically acceptable salt, hydrate or solvate thereof; and/or (iv) forming a prodrug thereof.

The resultant compounds of Formula (I) can be isolated and purified using techniques well known in the art.

In some embodiments, the reaction of the compounds is carried out in the presence of a suitable solvent, which is preferably inert under the respective reaction conditions. Examples of suitable solvents comprise but are not limited to hydrocarbons, such as hexane, petroleum ether, benzene, toluene or xylene; chlorinated hydrocarbons, such as trichlorethylene, 1,2-dichloroethane, tetrachloromethane, chloroform or dichloromethane; alcohols, such as methanol, ethanol, isopropanol, n-propanol, n-butanol or tert-butanol; ethers, such as diethyl ether, diisopropyl ether, tetrahydrofuran (THF), 2-methyltetrahydrofuran, cyclopentylmethyl ether (CPME), methyl tert-butyl ether (MTBE) or dioxane; glycol ethers, such as ethylene glycol monomethyl or monoethyl ether or ethylene glycol dimethyl ether (diglyme); ketones, such as acetone, methylisobutylketone (MIBK) or butanone; amides, such as acetamide, dimethylacetamide, dimethylformamide (DMF) or N-methylpyrrolidinone (NMP); nitriles, such as acetonitrile; sulfoxides, such as dimethyl sulfoxide (DMSO); nitro compounds, such as nitromethane or nitrobenzene; esters, such as ethyl acetate or methyl acetate, or mixtures of the said solvents or mixtures with water.

The reaction temperature is suitably between about −100° C. and 300° C., depending on the reaction step and the conditions used.

Reaction times are generally in the range between a fraction of a minute and several days, depending on the reactivity of the respective compounds and the respective reaction conditions. Suitable reaction times are readily determinable by methods known in the art, for example reaction monitoring. Based on the reaction temperatures given above, suitable reaction times generally lie in the range between 10 minutes and 48 hours.

Moreover, by utilizing the procedures described herein, in conjunction with ordinary skills in the art, additional compounds of the present disclosure can be readily prepared. Those skilled in the art will readily understand that known variations of the conditions and processes of the following preparative procedures can be used to prepare these compounds.

As will be understood by the person skilled in the art of organic synthesis, compounds of the present disclosure are readily accessible by various synthetic routes, some of which are exemplified in the accompanying examples. The skilled person will easily recognize which kind of reagents and reactions conditions are to be used and how they are to be applied and adapted in any particular instance—wherever necessary or useful—in order to obtain the compounds of the present disclosure. Furthermore, some of the compounds of the present disclosure can readily be synthesized by reacting other compounds of the present disclosure under suitable conditions, for instance, by converting one particular functional group being present in compound of the present disclosure, or a suitable precursor molecule thereof, into another one by applying standard synthetic methods, like reduction, oxidation, addition or substitution reactions; those methods are well known to the skilled person. Likewise, the skilled person will apply—whenever necessary or useful—synthetic protecting (or protective) groups; suitable protecting groups as well as methods for introducing and removing them are well-known to the person skilled in the art of chemical synthesis and are described, in more detail, in, e.g., P. G. M. Wuts, T. W. Greene, "Greene's Protective Groups in Organic Synthesis", 4th edition (2006) (John Wiley & Sons).

General routes for the preparation of a compound of the application are described in Schemes 1-18 herein.

Scheme 1
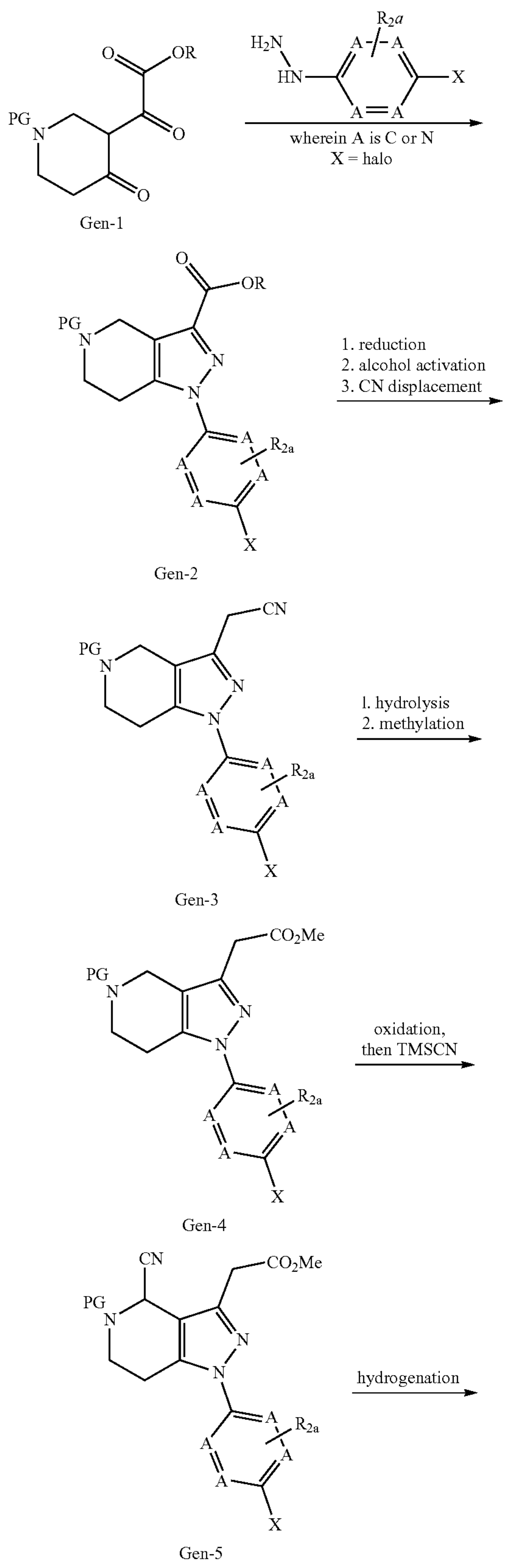
-continued
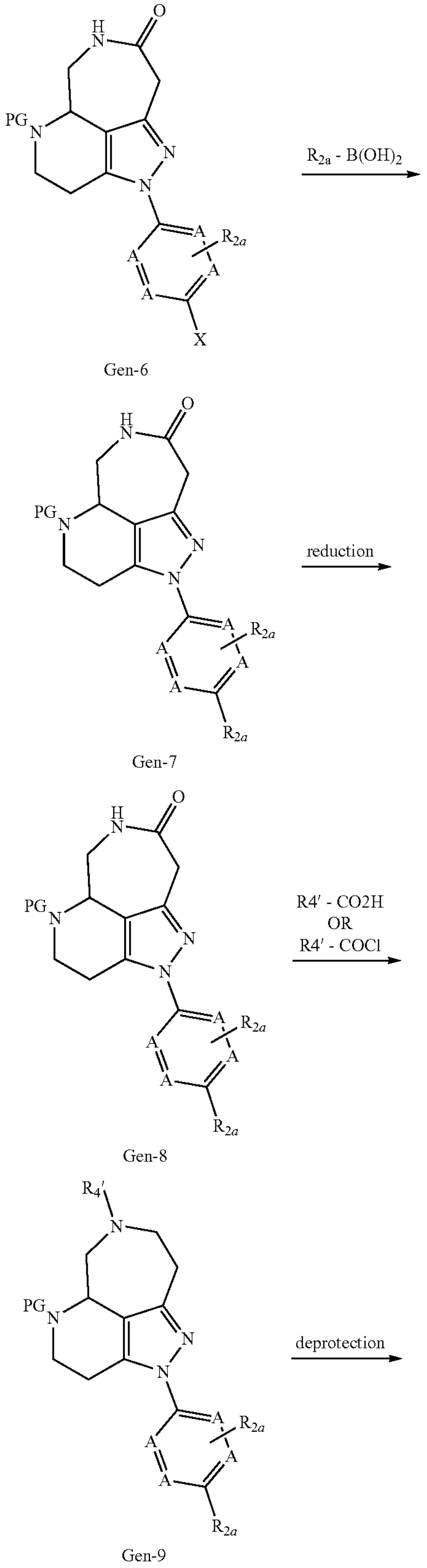

-continued

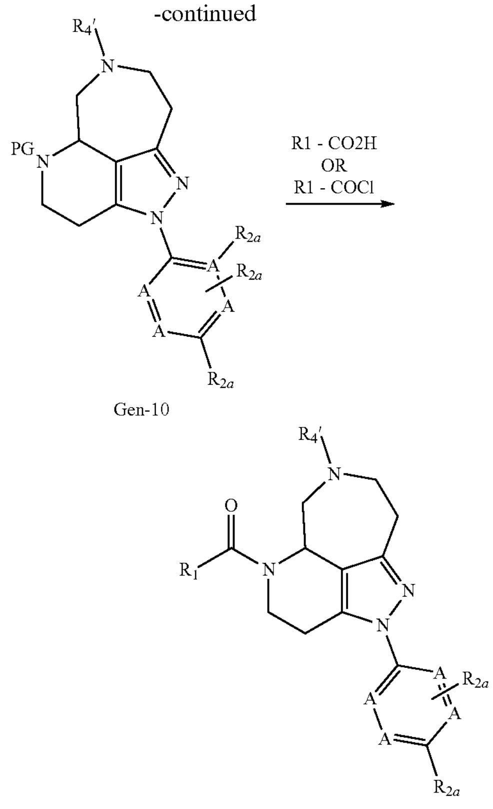

Gen-10

Gen-A

Compounds of the formula Gen-A can be prepared by the synthetic route depicted in Scheme 1, wherein A is C or N; X is halo; and PG is a protecting group. Amine-protected bis-carbonyl ester Gen-1 can be combined with a halo-functionalized hydrazine to form pyrazole ester Gen-2. Ester Gen-2 can then be reduced to the corresponding primary alcohol (e.g., with the use of DIBAL-H) and the resulting primary alcohol transformed to the O-mesylate (e.g., with the use of methanesulfonic anhydride and a base, e.g., triethylamine). The resulting mesylate can then be displaced with a cyanide nucleophile (e.g., with trimethylsilyl cyanide) t afford Gen-3. Gen-3 can then be subjected to hydrolysis conditions (e.g., through the use of a hydroxide base like sodium hydroxide) to afford the corresponding carboxylic acid, which can then be transformed to the corresponding methyl ester through the use of a base and iodomethane to afford Gen-4. Gen-4 can then to oxidized to the corresponding imine (e.g., through the use of $TEMPO^+$ $BF4^-$) and a cyanide nucleophile (e.g., TMSCN) can be added to afford Gen-5. Nitrile Gen-5 can then be reduced to the corresponding primary amine with a suitable catalyst (e.g., with Raney Nickel) and this resulting primary amine can cyclize in situ or through the use of additional base (e.g., potassium carbonate) to afford lactam Gen-6. Gen-6 can then be cross-coupled using palladium catalysis with a boronic acid or ester (e.g., through Suzuki coupling conditions with a standard catalyst system and base) to afford Gen-7. It is noted that intermediates Gen-2, Gen-3, or Gen-4 can also alternatively be used in a cross-coupling reaction to functionalize the halogen (e.g., in a cross-coupling reaction with a suitable catalyst) and the resulting intermediates can be advanced through the analogous synthetic sequence depicted in Scheme 1. Gen-7 can then be reduced (e.g., through the use of borane tetrahydrofuran complex) to afford amine Gen-8. Amine Gen-8 can then be functionalized with a suitable carboxylic acid ((e.g., using standard amide coupling conditions, or acid chloride or sulfonyl chloride using a suitable base) to provide Gen-9. Gen-9 can then be deprotected using standard protecting group deprotection conditions (e.g., a Boc group can be removed via treatment with acid, e.g., trifluoroacetic acid) to afford Gen-10. Amine Gen-10 can then be coupled with a carboxylic acid using amide coupling conditions (e.g., HOBT and EDC and a suitable base) to afford Gen-A. In some cases, Gen-10 can be combined with an acid chloride and a suitable base to afford Gen-A. At any point in the synthetic route, the intermediate or final compound may undergo chiral and/or diastereomer separation and a single enantiomer or diastereomer can be carried through the remaining steps of the route.

Scheme 2

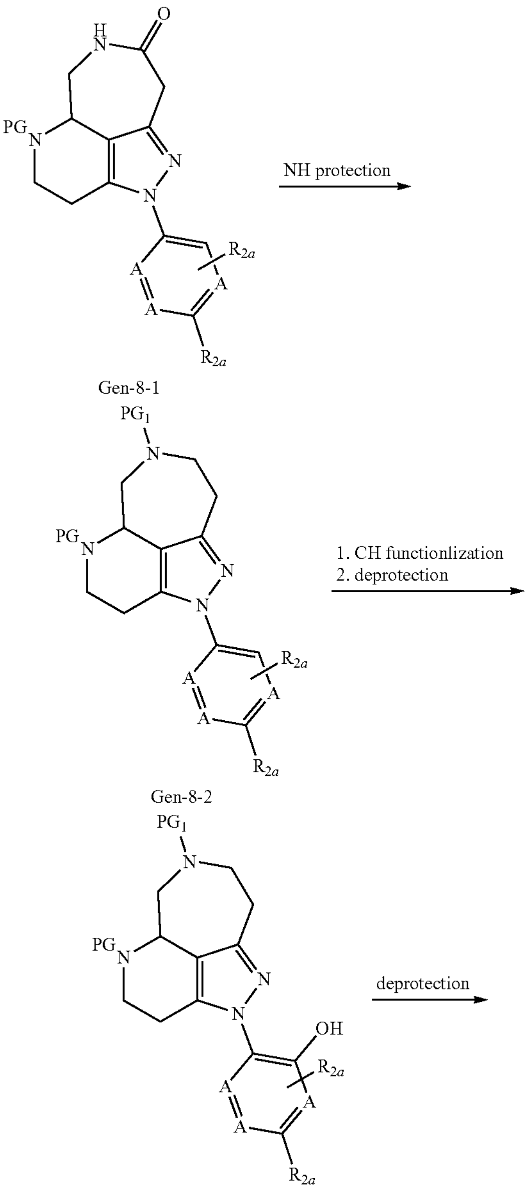

Gen-8-1

Gen-8-2

Gen-8-3

-continued

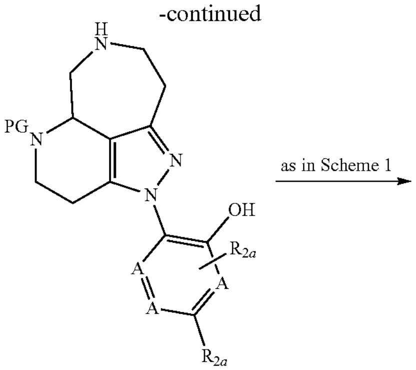

Gen-8-4

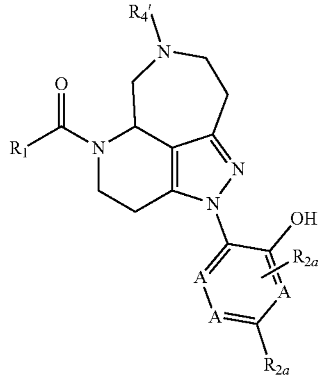

Gen-A-1

Compounds of the formula Gen-A-1 can be prepared by the synthetic route depicted in Scheme 2, wherein A is C or N and PG is a protecting group. In some instances, a compound of the structure Gen-8-1 can be protected with a suitable protecting group to form Gen-8-2, which can then be functionalized at an aryl carbon at the ortho position to prov de phenol Gen-8-3 (e.g., Gen-8-2 can be treated with a palladium catalyst and acetic acid to form the ortho-acetate, which can then be hydrolyzed using a suitable base to provide phenol Gen-8-3). Gen-8-3 can then be deprotected to form Gen-8-4, which can proceed to Gen-9 as described in Scheme 1. In some steps of Scheme 1, the phenol may become esterified, and the resulting ester can be cleaved through the use of a suitable base (e.g., lithium hydroxide) to provide compounds of Gen-A-1.

Scheme 3

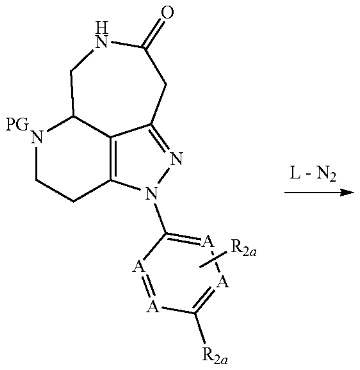

Gen-7

-continued

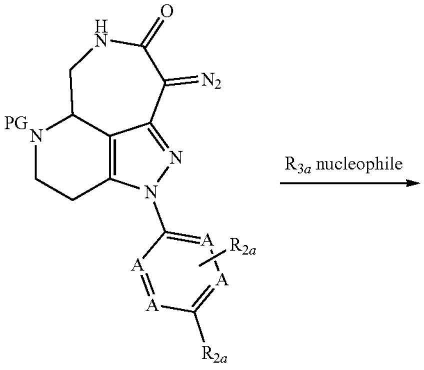

Gen-7-1

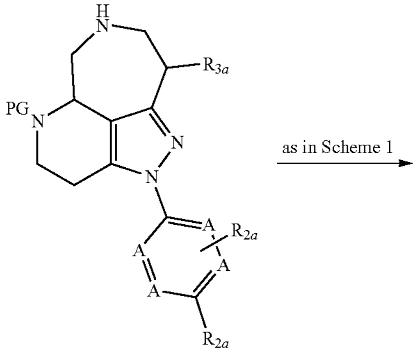

Gen-7-2

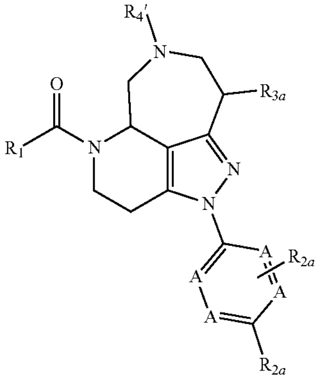

Gen-A-2

Compounds of the formula Gen-A-2 can be prepared by the synthetic route depicted in Scheme 3, wherein A is C or N and PG is a protecting group. In some instances, intermediate Gen-7 can be functionalized at the benzylic position to form azide Gen-7-1 (e.g., through the use of 4-methylbenzenesulfonyl azide solution). Azide Gen-7-1 could then be functionalized with a nucleophile (e.g., MeOH could be added to provide Gen-7-2 where $R_{3a}$ is —$OCH_3$). Gen-7-2 could then be advanced to Gen-A-2 via the synthetic sequence depicted in Scheme 1.

Scheme 4

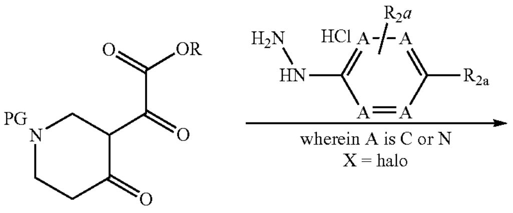

Gen-1

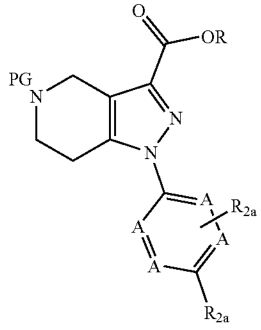

Gen-2'

Compounds of the formula Gen-2' can be prepared by the synthetic route depicted in Scheme 4, wherein A is C or N; X is halo; and PG is a protecting group. In some cases, the hydrazine employed in step 1 of scheme 1 already contains the $R_{2a}$ group in place of a halogen, and the resulting Gen-2' is carried through the rest of the route depicted in scheme 1, forgoing the coupling step to introduce $R_{2a}$ at the halogen position.

Scheme 5

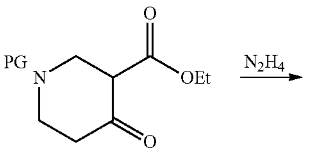

Gen-11

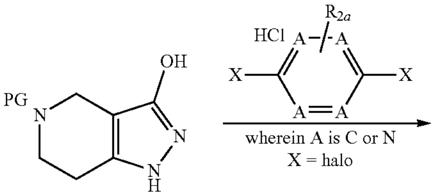

Gen-12

-continued

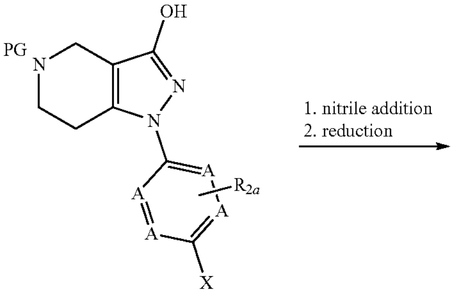

Gen-13

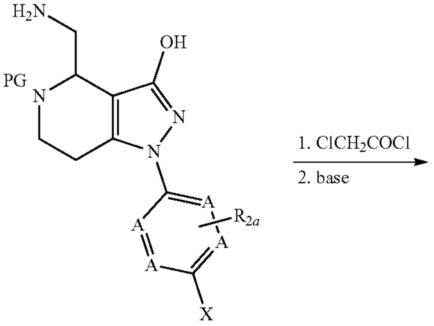

Gen-14

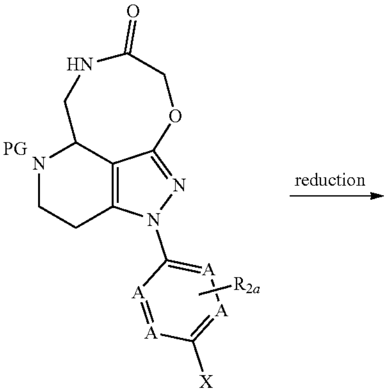

Gen-15

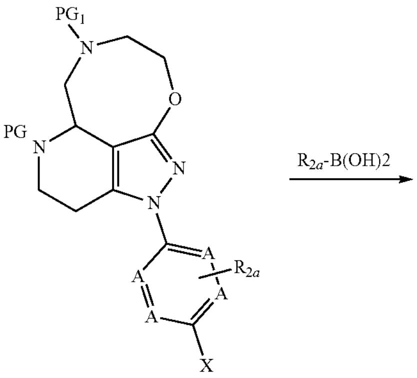

Gen-16

-continued

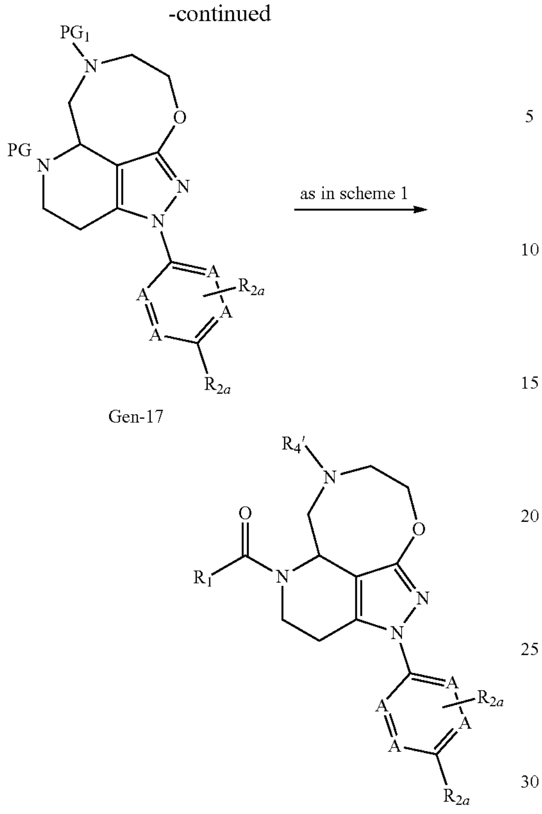

Gen-17

Gen-B

Compounds of the formula Gen-B can be prepared by the synthetic route depicted in Scheme 5, wherein A is C or N; X is halo; and PG is a protecting group. Keto-ester Gen-11 can be combined with hydrazine to form pyrazole Gen-12. Gen-12 can then be combined with a suitable substituted bis-halogenated aryl or heteroaryl ring in a cross-coupling reaction (e.g., through the use of a copper catalyst and cesium carbonate) to provide Gen-13. Gen-13 can then be oxidized to the corresponding imine (e.g., through the use of $TEMPO^+$ $BF4^-$ and a cyanide nucleophile, e.g., TMSCN) can be added to afford the corresponding nitrile, which can then be reduced (e.g., through the use of sodium borohydride) to afford the primary amine Gen-14. Amino alcohol Gen-14 can then be cyclized through the use of chloroacetyl chloride and a base to afford cyclic lactam Gen-15. Gen-15 can then be reduced to the secondary amine (e.g., through the use of sodium borohydride) and the resulting amine protected with a suitable orthogonal protecting group to provide Gen-16. Gen-16 can then undergo a cross-coupling reaction to functionalize the remaining halogen (e.g., Gen-16 can engage in a Suzuki reaction with a palladium catalyst and corresponding boronic acid or ester to provide Gen-17). Intermediate Gen-17 can then engage in analogous steps to Schemes 2 and 1 in the above examples to provide compounds of the structure of Gen-B. It is noted that Gen-15 can also alternatively be used in a cross-coupling reaction to functionalize the halogen (e.g., in a cross-coupling reaction with a suitable catalyst) and the resulting intermediates can be advanced in an analogous fashion.

Scheme 6

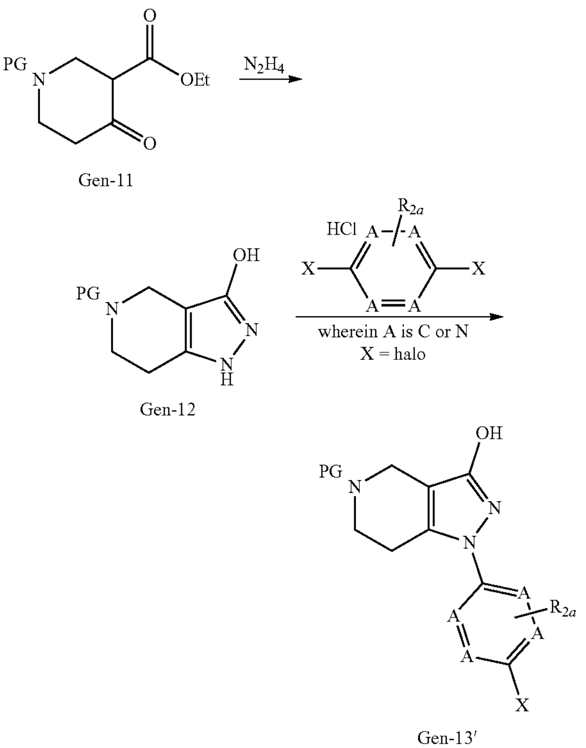

Gen-11

Gen-12

Gen-13'

Compounds of the formula Gen-13' can be prepared by the synthetic route depicted in Scheme 6, wherein A is C or N; X is halo; and PG is a protecting group. In some cases, Gen-12 can be combined with a suitable substituted halogenated aryl or heteroaryl ring already functionalized with one or more $R_{2a}$ group in the cross-coupling reaction (e.g., through the use of a copper catalyst and cesium carbonate) to provide Gen-13', which can be advanced through an analogous synthetic sequence of Scheme 5.

Scheme 7

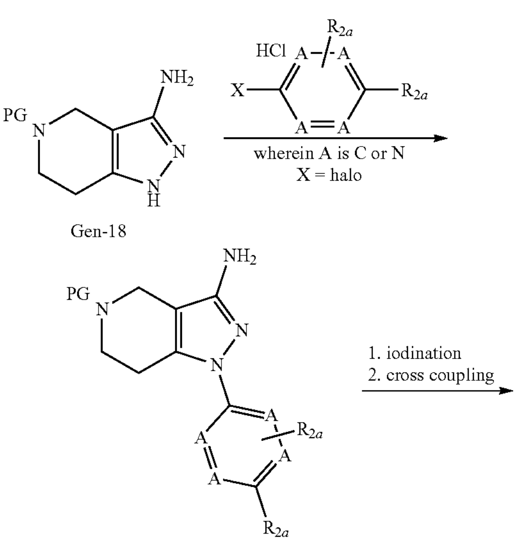

Gen-18

Gen-19

-continued

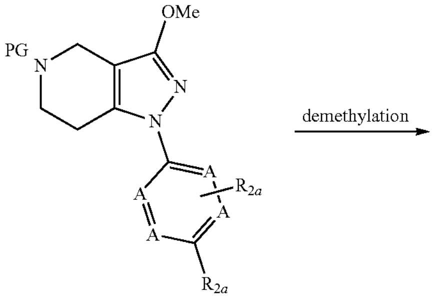

Gen-20

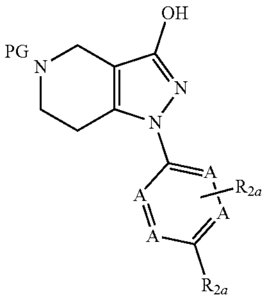

Gen-13'

Compounds of the formula Gen-13' can be prepared by the synthetic route depicted in Scheme 7, wherein A is C or N; X is halo; and PG is a protecting group. In some cases, Gen-13' can be accessed via amino-pyrazole Gen-18, which can be cross-coupled with a halogenated aryl or heteroaryl ring (e.g., through the use of copper catalysis) to afford Gen-19. Gen-19 can then be transformed to the halogenated pyrazole (e.g., through the use of iodine and isoamyl nitrite to afford the iodinated pyrazole) and the subsequent halogen can engage in cross-coupling reaction with a suitable alcohol (e.g., methanol under copper catalysis) to afford en-20. Gen-20 can then be transformed to Gen-13' through the use of a demethylating reagent (e.g., lithium tri-sec-butylhydroborate). Gen-13' can then engage in a synthetic route analogous to those described in Scheme 5 to afford compounds of the structure of Gen-B.

Scheme 8

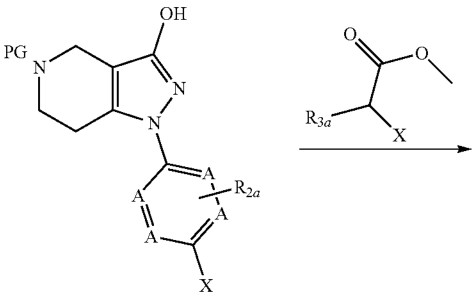

Gen-13

-continued

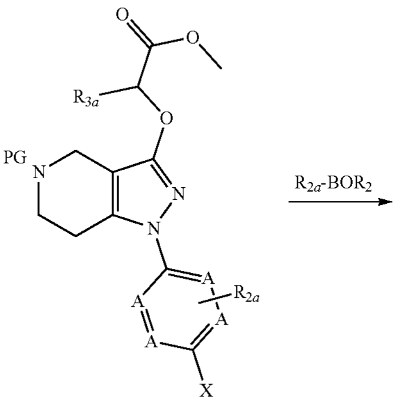

Gen-21

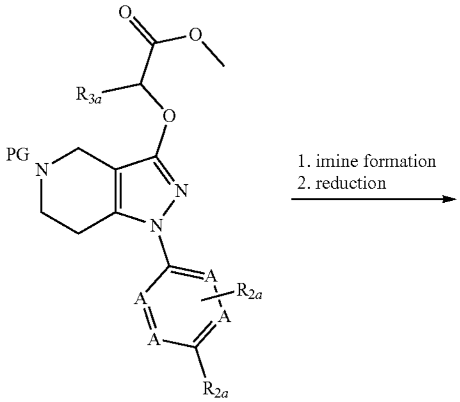

Gen-22

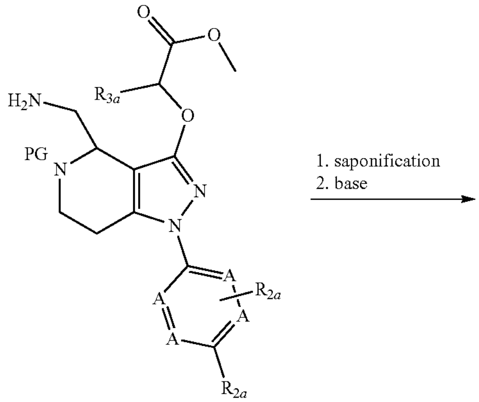

Gen-23

-continued

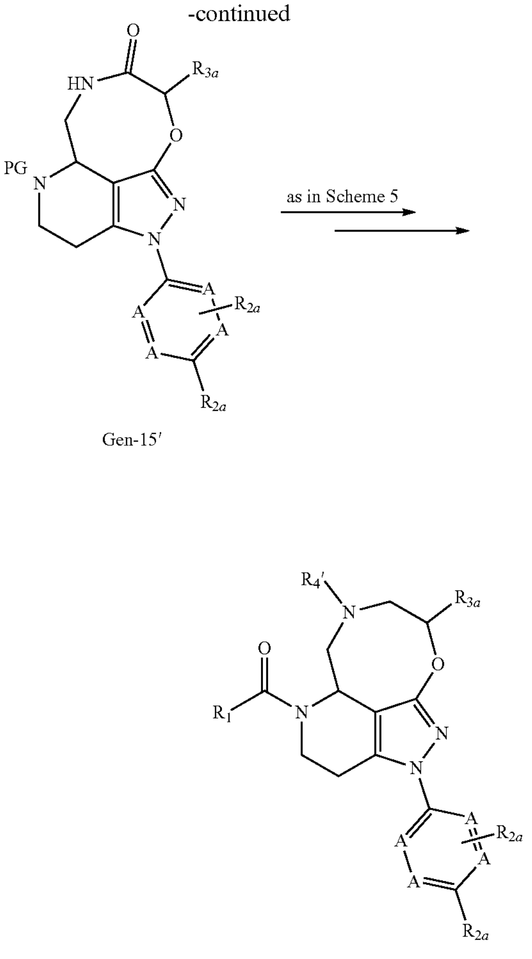

Gen-15′

Gen-B-1

Scheme 9

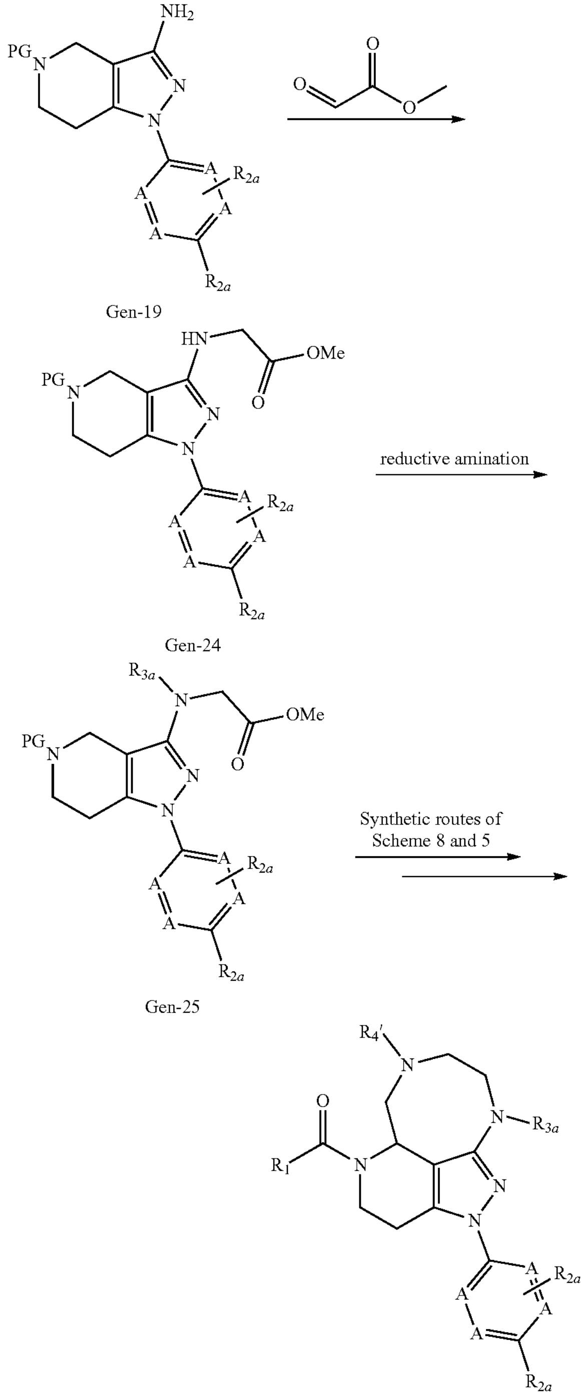

Gen-19

Gen-24

Gen-25

Gen-C

Compounds of the formula Gen-B-1 can be prepared by the synthetic route depicted in Scheme 8, wherein A is C or N; X is halo; and PG is a protecting group. In some instances, heterocyclic phenol Gen-13 can be alkylated with an alpha-halo carboxylic ester (e.g., with ethyl 2-bromopropanoate). The resulting ester Gen-21 can then be cross-coup ed with a suitable cross-coupling partner (e.g., Gen-21 could react with a boronic acid under palladium-catalyzed Suzuki conditions) to afford Gen-22. Ester Gen-22 can then be oxidized to the corresponding imine (e.g., through the use of $TEMPO^+$ $BF4^-$, and a cyanide nucleophile, e.g., TMSCN) can be added to afford the corresponding nitrile, which can then be reduced (e.g., through the use of sodium borohydride) to afford the primary amine Gen-23. Amine Gen-23 can then be saponified to the corresponding carboxylic acid (e.g., via reaction with lithium hydroxide) and the resulting amino acid can be cyclized via use of a base and a standard peptide coupling reagent to afford lactam Gen-15'. Lactam Gen-15' could then engage in synthetic routes analog us to those described in Scheme 5 starting from Gen-15.

Compounds of the formula Gen-C can be prepared by the synthetic route depicted in Scheme 9, wherein A is C or N and PG is a protecting group. In some cases, Gen-19 can be reacted with an oxoacetate (e.g., methyl 2-oxoacetate) under reductive amination conditions (e.g., through the use of sodium borohydride) to provide secondary amine Gen-24. The amine Gen-24 can then be functionalized by an additional reductive amination (e.g., by using for aldehyde and palladium on carbon) to afford Gen-25. Gen-25 can then be used in place of Gen-22 in synthetic routes analogous to those described in Schemes 8 and 5 to advance to compounds of the formula Gen-C.

Scheme 10

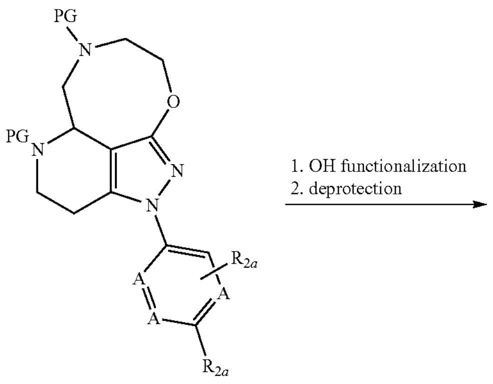

Gen-17'

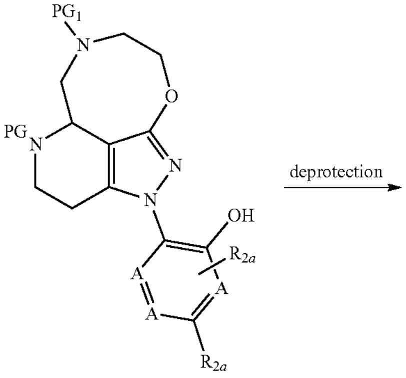

Gen-26

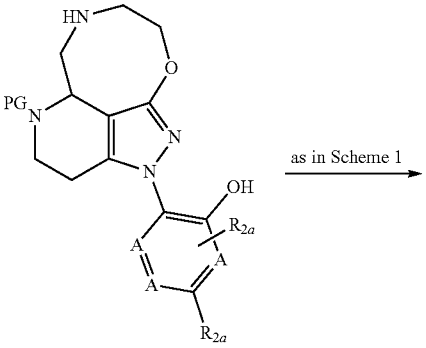

Gen-27

-continued

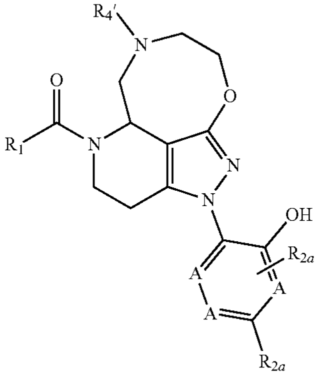

Gen-B-2

Compounds of the formula Gen-B-2 can be prepared by the synthetic route depicted in Scheme 10, wherein A is C or N and PG is a protecting group. In some instances, a compound of the structure of Gen-17' can be functionalized at an aryl carbon at the ortho position to provide phenol Gen-26 (e.g., Gen-17' can be treated with a palladium catalyst a d acetic acid to form the ortho-acetate, which can then be hydrolyzed using a suitable base to provide phenol Gen-26). Gen-26 can then be deprotected to form Gen-27, which can proceed to Gen-B-2 as described in Scheme 1. In some steps of Scheme 1, the phenol may become esterified, and the resulting ester can be cleaved through the use of a suitable base, for example lithium hydroxide, to provide compounds of Gen-B-2.

Scheme 11

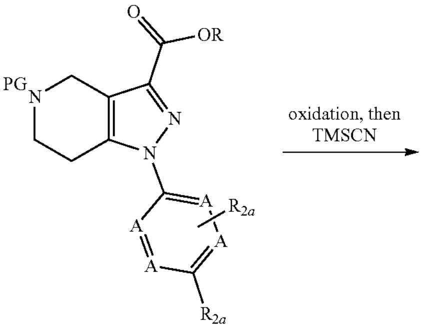

Gen-2'

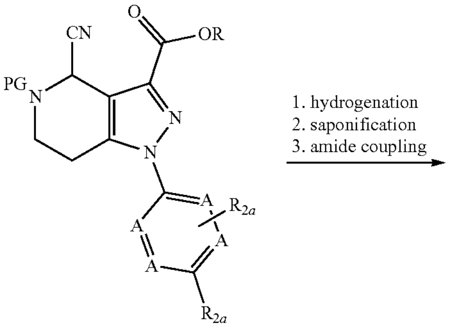

Gen-28

-continued

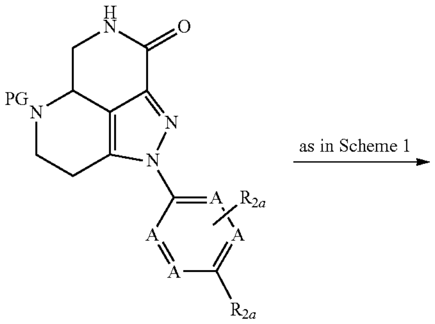

Gen-29

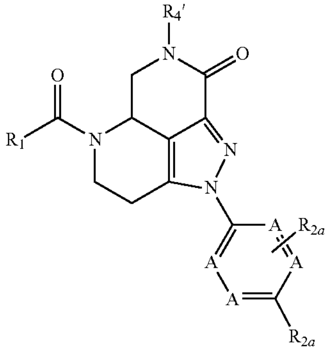

Gen-C

Compounds of the formula Gen-C can be prepared by the synthetic route depicted in Scheme 11, wherein A is C or N and PG is a protecting group. In s me cases, Gen-2' can be directly oxidized to the corresponding imine (e.g., through the use of TEMPO$^+$ BF4$^-$, and a cyanide nucleophile, e.g., TMSCN) can be added to afford Gen-28. Nitrile Gen-28 can then be reduced to the corresponding primary amine with a suitable catalyst (e.g., with Raney Nickel). The ester can then be saponified, (e.g., through the use of a base like lithium hydroxide) and the resulting amino-acid can be cyclized to the lactam (e.g., through the use of standard amide coupling reagents) to lactam Gen-29. Lactam Gen-29 can then engage in analogous sequence to Schemes 1-4 to afford compounds of the structure Gen-C.

Scheme 12

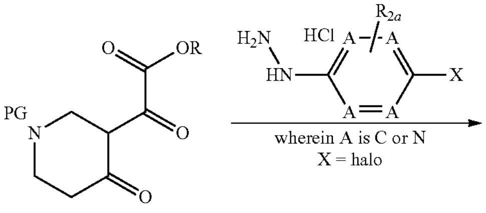

Gen-1

-continued

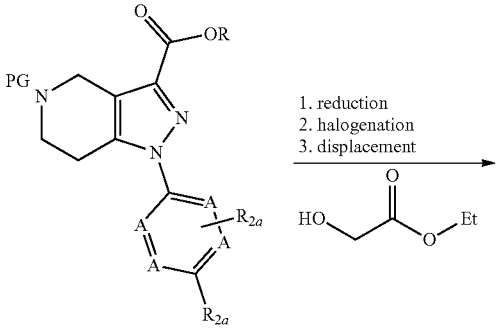

Gen-2'

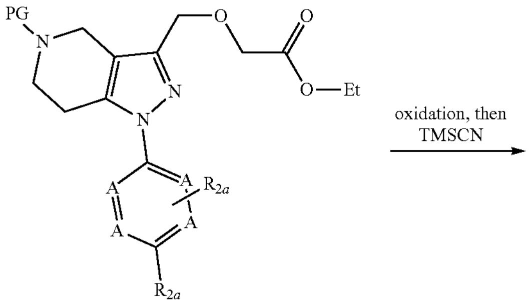

Gen-30

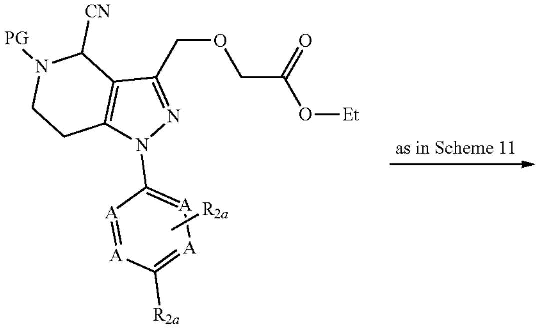

Gen-31

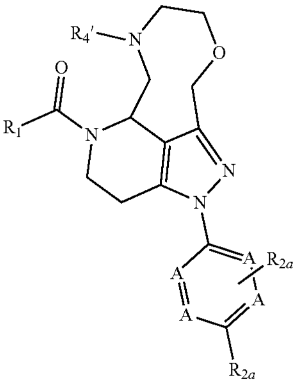

Gen-D

Compounds of the formula Gen-D can be prepared by the synthetic route depicted in Scheme 12, wherein A is C or N; X is halo; and PG is a protecting group. In some cases, Gen-2' can be reduced to the primary alcohol (e.g., through the use of DIBAL-H) and the resulting alcohol can be transformed to the alkyl halide (e.g., through the use of triphenylphosphine and 1,2-dibromo-1,1,2,2-tetrachloroethane) to afford the alkyl bromide. The halide can then be displaced with a nucleophile (e.g., ethyl 2-hydroxyacetate)

to afford esters of the formula Gen-30. Gen-30 can then be oxidized to the corresponding imine (e.g., through the use of $TEMPO^+BF4^-$, and a cyanide nucleophile, e.g., TMSCN) can be added to afford Gen-31. Nitrile Gen-31 can then be advanced to compounds of the structure Gen-D by employing synthetic steps analogous to those described in Scheme 11.

Scheme 13

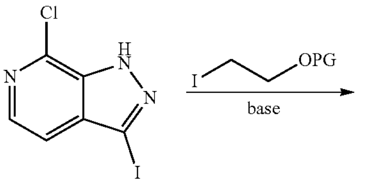

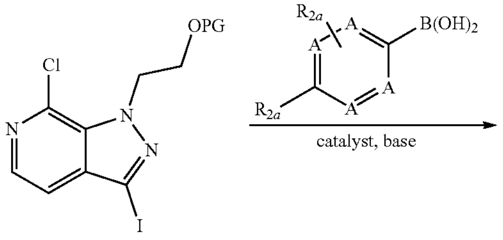

Gen-32

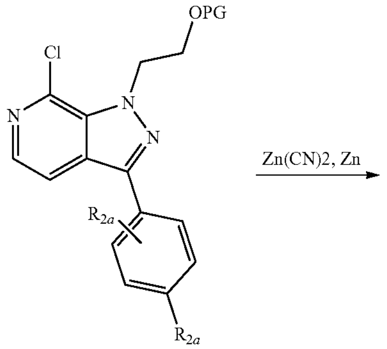

Gen-33

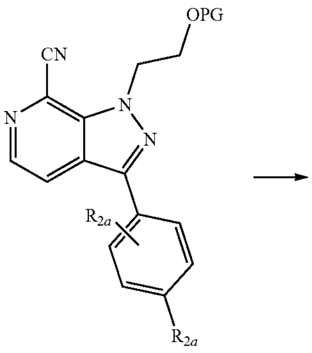

Gen-34

-continued

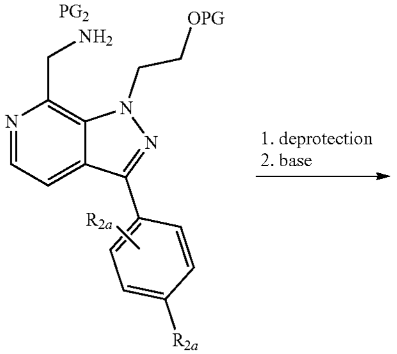

Gen-35

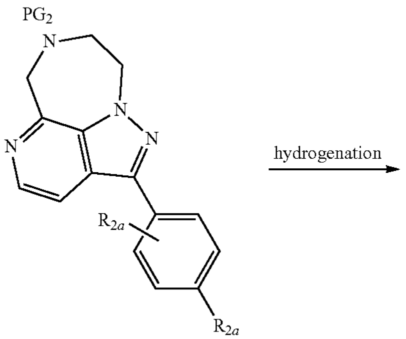

Gen-36

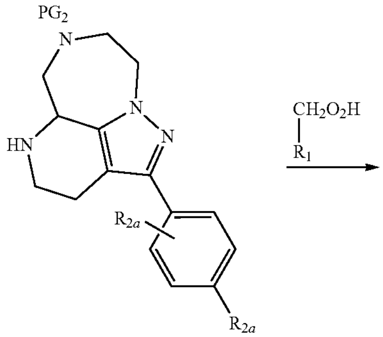

Gen-37

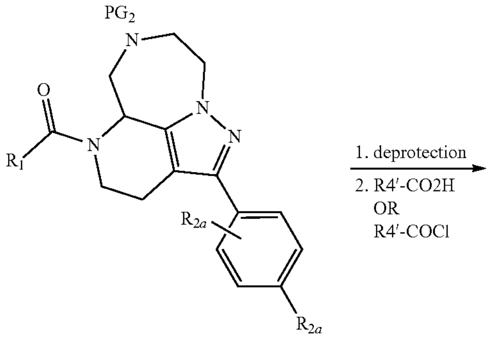

Gen-38

-continued

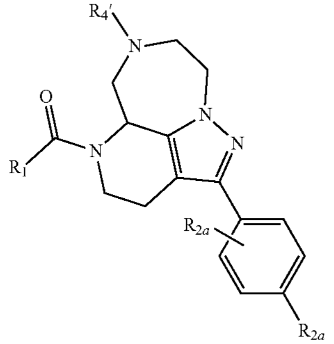

Gen-E

Compounds of the formula Gen-E can be prepared by the synthetic route depicted in Scheme 13, wherein A is C or N and PG is a protecting group. In some cases, 7-chloro-1H-pyrazolo[3,4-c]pyridine may be N-functionalized with an alkyl halide to afford a compound of Gen-32. Aryl iodide Gen-32 can then be reacted with a boronic acid or ester under cross-coupling conditions, (e.g., with the use of a palladium catalyst under Suzuki conditions) to afford aryl pyrazole Gen-33. Gen-33 can then be elaborated to a nitrile through the use of zinc cyanide to afford Gen-34. Gen-34 can then be reduced to the corresponding prima amine (e.g., through the use of DIBAL-H) and subsequently protected with a suitable amine protecting group. The alcohol can then be deprotected (e.g., a silyl protecting group can be removed through the use of TBAF) and the subsequent primary alcohol can be activated (e.g., with the use of triphenylphosphine) and displaced intramolecularly with the protected amine to afford the cyclized compound Gen-36. Gen-36 can then be partially hydrogenated (e.g., with the use of platinum oxide under an atmosphere of hydrogen gas) to afford pyrazole Gen-37. Gen-37 can then engage in an amide couple at the secondary amine to afford amide Gen-38. Gen-38 can then be deprotected to afford a secondary amine, which can then be functionalized with a suitable carboxylic acid (e.g., using standard amide coupling conditions, or acid chloride or sulfonyl chloride using a suitable base), to provide compounds of the formula Gen-E.

Scheme 14

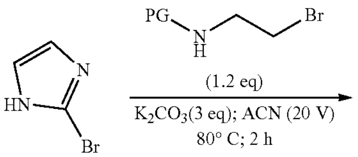

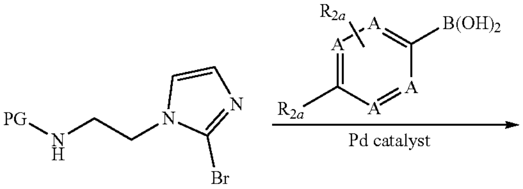

-continued

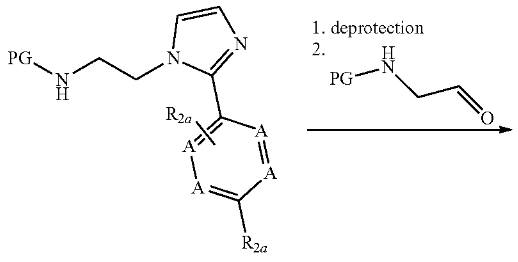

Gen-39

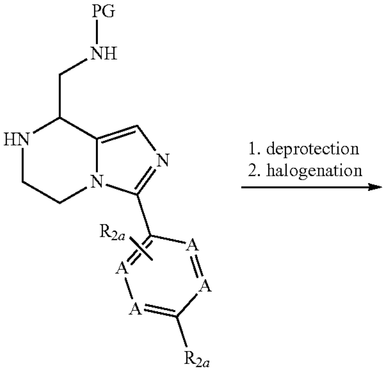

Gen-40

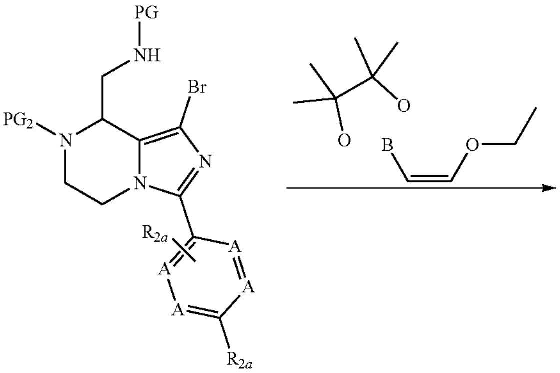

Gen-41

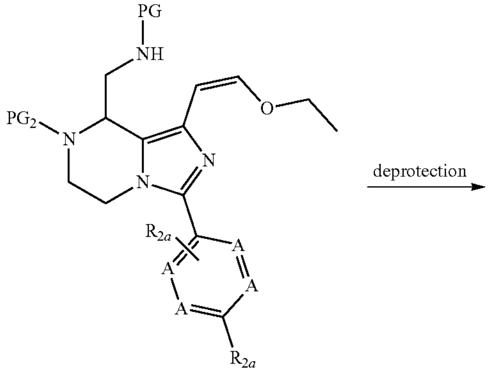

Gen-42

-continued

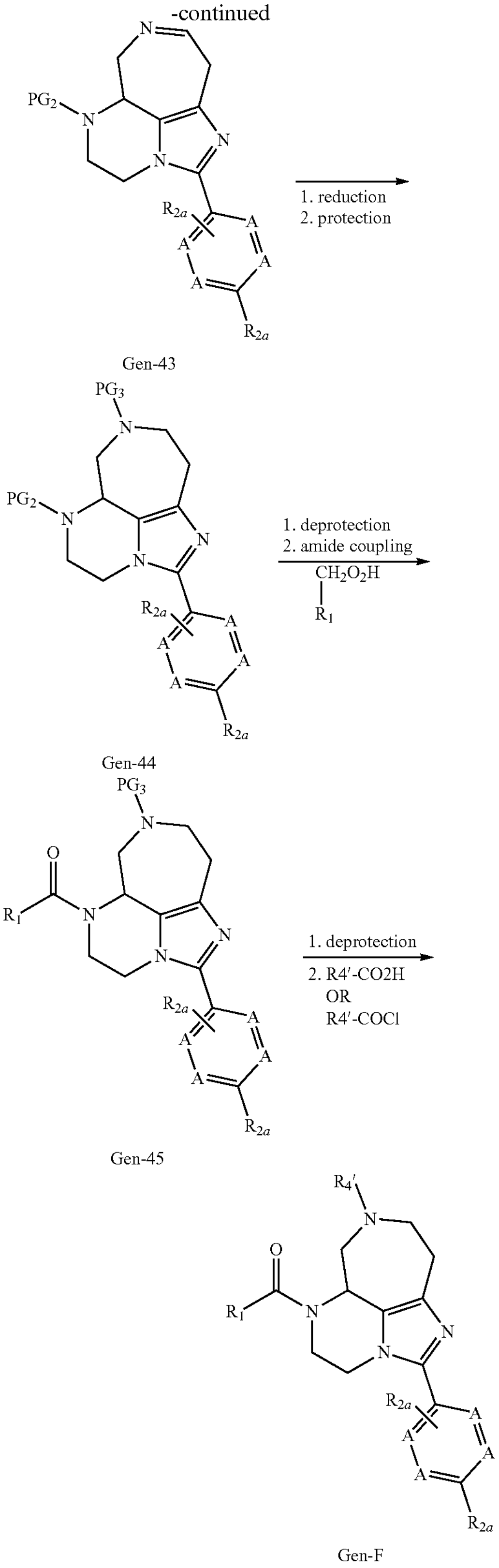

Gen-43

Gen-44

Gen-45

Gen-F

In some cases, a compound of the formula Gen-F can be obtained by following the sequence described in Scheme 14. 2-bromo-1H-imidazole can be reacted with a protected (2-bromoethyl) carbamate to afford a protected 2-(2-bromo- 1H-imidazol-1-yl)ethan-1-amine. This heteroaryl bromide can then engage in a cross coupling reaction with a suitable coupling partner (e.g., the bromo-imidazole can be coupled with an aryl or heteroaryl boronic acid or ester under Suzuki conditions to afford aryl imidazoles of the structure of Gen-39). Amine Gen-39 can then be deprotected (e.g., a Boc group can be removed through the use of acid) and the resulting primary amine can engage in a cyclization reaction with a protected amine-bearing aldehyde to afford diamine Gen-40. The resulting secondary amine can then be protected, and the imidazole can undergo a bromination reaction (e.g., through the use of NBS). The resulting aryl bromide can then engage in a cross-coupling reaction with an enol-ether boronic ester or acid (e.g., under palladium-catalyzed conditions) to afford Gen-42. Gen-42 can be deprotected both at the primary amine and at the enol ether (e.g., the primary amine may be protected by a phthalan ide derivative, which can be removed through the use of ammonia, and aldehyde can be revealed from the enol ether under acidic conditions). The resulting amino-aldehyde can undergo intramolecular imine formation to provide Gen-43. Imine Gen-43 can then be reduced to the amine (e.g., through the use of sodium borohydride) and the resulting amine protected with a suitable protecting group to afford Gen-44. Gen-44 can then undergo amine deprotection at the alternate secondary amine through the use of an orthogonal, compatible protecting group and standard deprotection conditions (e.g., an N-alkyl nitrobenzenesulfonamide could be removed by treating with 4-methoxy-benzenethiol). The resulting free secondary amine can then engage with a carboxylic acid or acid chloride (e.g., a carboxylic acid can undergo amide coupling under standard conditions) to afford amide Gen-45. Gen-45 can then be deprotected to afford a secondary amine (e.g., a Boc group can be removed by treatment with acid) and the resulting amine can then be functionalized with a suitable carboxylic acid (e.g., using standard amide coupling conditions, or acid chloride or sulfonyl chloride using a suitable base), to provide compounds of the formula Gen-F.

Scheme 15

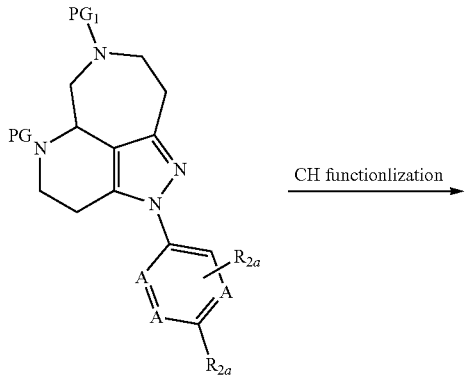

Gen-8-2

-continued

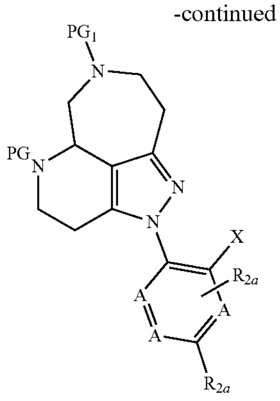

Gen-8-5 cross-coupling
functionalization

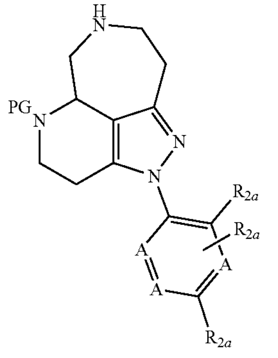

Gen-8-6 as in Scheme 1

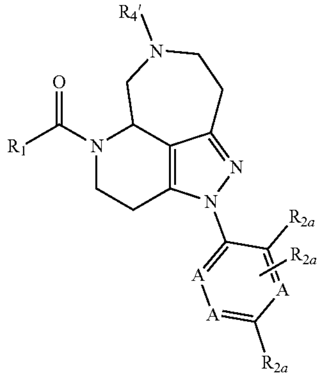

Gen-A

Scheme 16

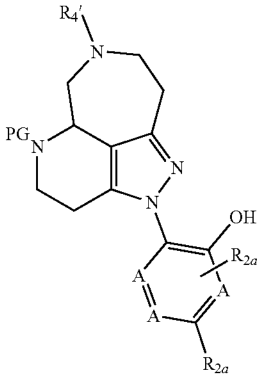

Gen-8-7 functionalization

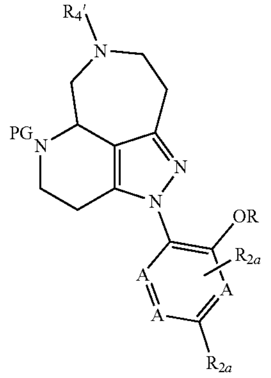

Gen-8-8 as in Scheme 1

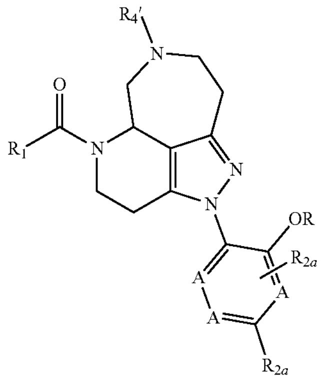

Gen-A-3

Compounds of the formula Gen-A can also be prepared by the synthetic route depicted in Scheme 15, wherein Gen-8-2 can be functionalized at the ortho position to provide either Gen-8-6 directly, or to provide halide Gen-8-5 (e.g., Gen-8-2 can be treated with a rhodium complex and iodobenzenediacetate to provide Gen-8-5 wherein x=I). Gen-8-5 can then be further functionalized under standard cross-coupling conditions with a suitable coupling partner, for example to provide an alkylated analog. In some cases, this added group can be further functionalized to a final $R^{2a}$. Gen-8-6 can then be elaborated to provide compounds of the formula Gen-A in an analogous manner to general Scheme 1.

In some cases, compounds of the formula Gen-8-7 (prepared as described in Scheme 2) can be further functionalized on the phenol oxygen to provide intermediates of the formula Gen-8-8 (for example, the phenol can be treated with sodium chloro(difluoro)acetate to provide the corresponding difluoromethoxyphenol, which can then be elaborated to provide compounds of the formula Gen-A-3 through the general route described in Scheme 1.

Scheme 17

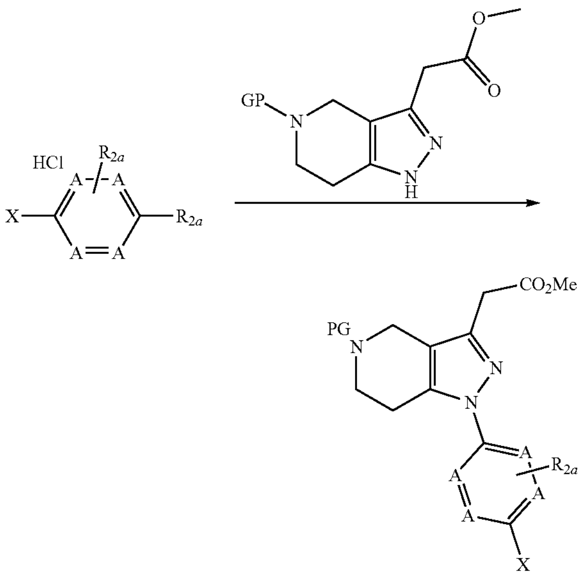

Gen-4

In some cases, intermediates of the formula Gen-4 can be prepared via cross-coupling of a protected methyl 2-(4,5,6,7-tetrahydro-1H-pyrazolo[4,3-c]pyridin-3-yl)acetate with a suitable coupling partner and the use of a metal catalyst, for example a copper catalyst. Esters Gen-4 can then be elaborated as in Schemes 1 and 2 to final compounds.

Scheme 18

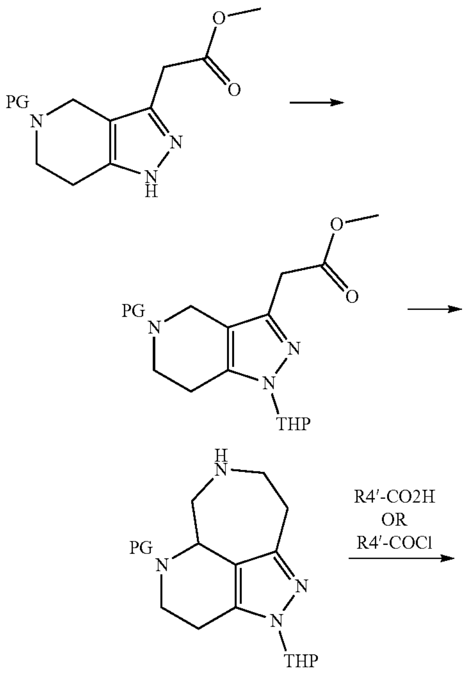

Gen-8-1

-continued

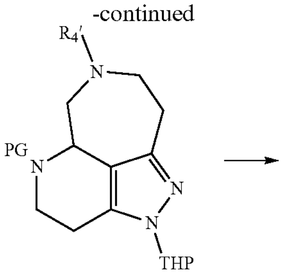

Gen-12

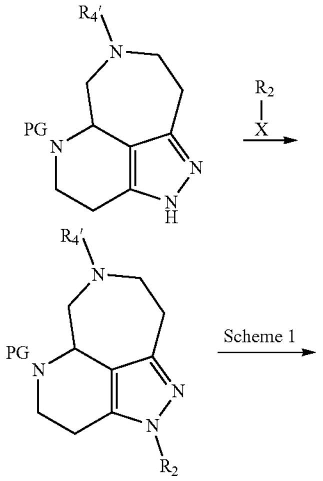

Gen-9-1

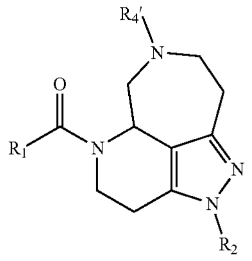

Gen-A-4

In some cases, a protected methyl 2-(4,5,6,7-tetrahydro-1H-pyrazolo[4,3-c]pyridin-3-yl)acetate can be further protected with an orthogonal protecting group, or example a THP group on the azole nitrogen. This protected pyrazole can then undergo analogous steps to those described in general Scheme 1 to provide compounds of Gen-8-1. Amine Gen-8-1 can then be functionalized with a suitable carboxylic acid (e.g., using standard amide coupling conditions, or acid chloride or sulfonyl chloride using a suitable base) to provide Gen-12. Gen-12 can then be deprotected at the pyrazole to afford the free pyrazole, which can engage in a cross-coupling reaction with a suitable alkyl or aryl coupling partner or alkylated with a suitable alkyl halide. Gen-9-1 can then be elaborated to compounds of the formula Gen-A-4 via steps analogous to those depicted in general Scheme 1.

Biological Assays

Compounds designed, selected and/or optimized by methods described above, once produced, can be characterized using a variety of assays known to those skilled in the art to determine whether the compounds have biological activity. For example, the molecules can be characterized by conventional assays, including but not limited to those assays described below, to determine whether they have a predicted activity, binding activity and/or binding specificity.

Furthermore, high-throughput screening can be used to speed up analysis using such assays. As a result, it can be possible to rapidly screen the molecules described herein for activity, using techniques known in the art. General methodologies for performing high-throughput screening are described, for example, in Devlin (1998) High Throughput Screening, Marcel Dekker; and U.S. Pat. No. 5,763,263. High-throughput assays can use one or more different assay techniques including, but not limited to, those described below.

Various in vitro or in vivo biological assays are may be suitable for detecting the effect of the compounds of the present disclosure. These in vitro or in vivo biological assays can include, but are not limited to, enzymatic activity assays, electrophoretic mobility shift assays, reporter gene assays, in vitro cell viability assays, and the assays described herein.

In some embodiments, the biological assay is described in the Examples herein.

In some embodiments, the Werner helicase construct is produced and purified for use in the biological assay.

In some embodiments, WRN activity may be measured using ap ATPase assay.

In some embodiments, Full length WRN protein (aa 2-1432) may be used in the ATPase assay.

In some embodiments, the compound may be incubated with the protein under optimized conditions.

In some embodiments, control wells may be utilized to included compounds which show no inhibition of WRN and compounds which show maximum inhibition of WRN.

In some embodiments, the inhibition may be observed with luminescence was (e.g., on a PHERAstar) followed by a data fit to obtain $IC_{50}$ values.

In some embodiments, the compounds may be incubated with a cancer cell line (e.g., a colon carcinoma line). In some embodiments, the incubation may take place for a period of time at a specified temperature. In some embodiments, luminescence quantification of activity may be performed followed by a fit (e.g., linear least squares fit) to provide $IC_{50}$ values.

In some embodiments, the biological assay is completed more than one time (e.g., in duplicate) and the reported $IC_{50}$ is an average.

Pharmaceutical Compositions

In some aspects, the present disclosure provides a pharmaceutical composition comprising a compound of the present disclosure as an active ingredient. In some embodiments, the present disclosure provides a pharmaceutical composition comprising at least one compound of each of the formulae described herein, or a pharmaceutically acceptable salt or solvate thereof, and one or more pharmaceutically acceptable carrier, diluent, adjuvant, excipient, or a combination thereof. In some embodiments, the present disclosure provides a pharmaceutical composition comprising a compound described in Table 1 or Table 2. In some embodiments, the present disclosure provides a pharmaceutical composition comprising at least one compound select d from Table 1 or Table 2. In some embodiments, the present disclosure provides a pharmaceutic 1 composition comprising a compound described in Table 1A or Table 2A. In some embodiments, the present disclosure provides a pharmaceutical composition comprising at least one compound selected from Table 1A or Table 2A.

In some embodiments, the present disclosure provides a pharmaceutical composition comprising Compound No. 128, 163, 166, 178, 182, 183, 184, 186, 187, 190, 191, 194, 195, 196, 202, 203, 206, 208, 210, 211, 218, 220, or 228. In some embodiments, the present disclosure provides a pharmaceutical composition comprising at least one compound selected from Compound Nos. 128, 163, 166, 178, 182, 183, 184, 186, 187, 190, 191, 194, 195, 196, 202, 203, 206, 208, 210, 211, 218, 220, and 228.

In some embodiments, the present disclosure provides a pharmaceutical composition comprising Compound No. 128A, 163A, 166A, 178A, 182A, 183A, 186A, 191A, 194A, 196A, 202A, 203A, 206A, 208A, 210A, 211A, 218A, 220A, or 228A. In some embodiments, the present disclosure provides a pharmaceutical composition comprising at least one compound selected from Compound Nos. 128A, 163A, 166A, 178A, 182A, 183A, 186A, 191A, 194A, 196A, 202A, 203A, 206A, 208A, 210A, 211A, 218A, 220A, and 228A.

In some embodiments, the present disclosure provides a pharmaceutical composition comprising Compound No. 128, 163, 178, 191, 194, 202, 203, 206, 208, 210, 218, or 228. In some embodiments, the present disclosure provides a pharmaceutical composition comprising at least one compound selected from Compound Nos. 128, 163, 178, 191, 194, 202, 203, 206, 208, 210, 218, and 228.

In some embodiments, the present disclosure provides a pharmaceutical composition comprising Compound No. 128. In some embodiments, the present disclosure provides a pharmaceutical composition comprising Compound No. 163. In some embodiments, the present disclosure provides a pharmaceutical composition comprising Compound No. 178. In some embodiments, the present disclosure provides a pharmaceutical composition comprising Compound No. 191. In some embodiments, the present disclosure provides a pharmaceutical composition comprising Compound No. 194. In some embodiments, the present disclosure provides a pharmaceutical composition comprising Compound No. 202. In some embodiments, the present disclosure provides a pharmaceutical composition comprising Compound No. 203. In some embodiments, the present disclosure provides a pharmaceutical composition comprising Compound No. 206. In some embodiments, the present disclosure provides a pharmaceutical composition comprising Compound No. 208. In some embodiment, the present disclosure provides a pharmaceutical composition comprising Compound No. 210. In some embodiments, the present disclosure provides a pharmaceutical composition comprising Compound No. 218. In some embodiments, the present disclosure provides a pharmaceutical composition comprising Compound No. 228.

In some embodiments, the present disclosure provides a pharmaceutical composition comprising Compound No. 128A, 163A, 178A, 191A, 194A, 202A, 203A, 206A, 208A, 210A, 218A, or 228A. In some embodiments, the present disclosure provides a pharmaceutical composition comprising at least one compound selected from Compound Nos. 128A, 163A, 178A, 191A, 194A, 202A, 203A, 206A, 208A, 210A, 218A, and 228A.

In some embodiments, the present disclosure provides a pharmaceutical composition comprising Compound No. 128A. In some embodiments, the present disclosure provides a pharmaceutical composition comprising Compound No. 163A. In some embodiments, the present disclosure provides a pharmaceutical composition comprising Compound No. 178A. In some embodiments, the present disclosure provides a pharmaceutical composition comprising Compound No. 191A. In some embodiments, the present disclosure provides a pharmaceutical composition comprising Compound No. 194A. In some embodiments, the present disclosure provides a pharmaceutical composition comprising Compound No. 202. In some embodiments, the present disclosure provides a pharmaceutical composition comprising Compound No. 203A. In some embodiments, the present disclosure provides a pharmaceutical composition comprising Compound No. 206A. In some embodiments, the present disclosure provides a pharmaceutical composition comprising Compound No. 208A. In some embodiments, the present disclosure provides a pharmaceutical composition comprising Compound No. 210A. In some embodiments, the present disclosure provides a pharmaceutical composition comprising Compound No. 218A. In some embodiments, the present disclosure provides a pharmaceutical composition comprising Compound No. 228A.

As used herein, the term "composition" is intended to encompass a product comprising the specified ingredients in the specified amounts, as well as any product which results, directly or indirectly, from combination of the specified ingredients in the specified amounts.

The compounds of present disclosure can be formulated for or 1 administration in forms such as tablets, capsules (each of which includes sustained release or timed release formulations), pills, powders, granules, elixirs, tinctures, suspensions, syrups and emulsions. The compounds of present disclosure on can also be formulated for intravenous (bolus or in-fusion), intraperitoneal, topical, subcutaneous, intramuscular or transdermal (e.g., patch) administration, all using forms well known to those of ordinary skill in the pharmaceutical arts.

The formulation of the present disclosure may be in the form of an aqueous solution comprising an aqueous vehicle. The aqueous vehicle component may comprise water and at least one pharmaceutically acceptable excipient. Suitable acceptable excipients include those selected from the group consisting of a solubility enhancing agent, chelating agent, preservative, tonicity agent, viscosity/suspending agent, buffer, and pH modifying agent, and a mixture thereof.

Any suitable solubility enhancing agent can be used. Examples of a solubility enhancing agent include cyclodextrin, such as those selected from the group consisting of hydroxypropyl-β-cyclodextrin, methyl-β-cyclodextrin, randomly methylated-β-cyclodextrin, ethylated-β-cyclodextrin, triacetyl-β-cyclodextrin, peracetylated-β-cyclodextrin, carboxymethyl-β-cyclodextrin, hydroxyethyl-β-cyclodextrin, 2-hydroxy-3-(trimethylammonio)propyl-β-cyclodextrin, glucosyl-β-cyclodextrin, sulfated β-cyclodextrin (S-β-CD), maltosyl-β-cyclodextrin, β-cyclodextrin sulfobutyl ether, branched-β-cyclodextrin, hydroxypropyl-γ-cyclodextrin, randomly methylated-γ-cyclodextrin, and trimethyl-γ-cyclodextrin, and mixtures thereof.

Any suitable chelating agent can be used. Examples of a suitable chelating agent include those selected from the group consisting of ethylenediaminetetraacetic ac d and metal salts thereof, disodium edetate, trisodium edetate, and tetrasodium edetate, and mixtures thereof.

Any suitable preservative can be used. Examples of a preservative include those selected from the group consisting of quaternary ammonium salts such as benzalkonium halides (preferably benzalkonium chloride), chlorhexidine gluconate, benzethonium chloride, cetyl pyridinium chloride, benzyl bromide, phenylmercury nitrate, phenylmercury acetate, phenylmercury neodecanoate, merthiolate, methylparaben, propylparaben, sorbic acid, potassium sorbate, sodium benzoate, sodium propionate, ethyl p-hydroxybenzoate, propylaminopropyl biguanide, and butyl-p-hydroxybenzoate, and sorbic acid, and mixtures thereof.

The aqueous vehicle may also include a tonicity agent to adjust the tonicity (osmotic pressure). The tonicity agent can be selected from the group consisting of a glycol (such as propylene glycol, diethylene glycol, triethylene glycol), glycerol, dextrose, glycerin, mannitol, potassium chloride, and sodium chloride, and a mixture thereof.

The aqueous vehicle may also contain a viscosity/suspending agent. Suitable viscosity/suspending agents include those selected from the group consisting of cellulose derivatives, such as methyl cellulose, ethyl cellulose, hydroxyethylcellulose, polyethylene glycols (such as polyethylene glycol 300, polyethylene glycol 400), carboxymethyl cellulose, hydroxypropylmethyl cellulose, and cross-linked acrylic acid polymers (carbomers), such as polymers of acrylic acid cross-linked with polyalkenyl ethers or divinyl glycol (Carbopols—such as Carbopol 934, Carbopol 934P, Carbopol 971, Carbopol 974 and Carbopol 974P), and a mixture thereof.

In order to adjust the formulation to an acceptable pH (typically a pH range of about 5.0 to about 9.0, more preferably about 5.5 to about 8.5, particularly about 6.0 to about 8.5, about 7.0 to about 8.5, about 7.2 to about 7.7, about 7.1 to about 7.9, or about 7.5 to about 8.0), the formulation may contain a pH modifying agent. The pH modifying agent is typically a mineral acid or metal hydroxide base, selected from the group of potassium hydroxide, sodium hydroxide, and hydrochloric acid, and mixtures thereof, and preferably sodium hydroxide and/or hydrochloric acid. These acidic and/or basic pH modifying agents are added to adjust the formulation to the target acceptable pH range. Hence it may not be necessary to use both acid and base—depending on the formulation, the addition of one of the acid or base may be sufficient to bring the mixture to the desired pH range.

The aqueous vehicle may also contain a buffering agent to stabilize the pH. When used, the buffer is selected from the group consisting of a phosphate buffer (such as sodium dihydrogen phosphate and disodium hydrogen phosphate), a borate buffer (such as boric acid, or salts thereof including disodium tetraborate), a citrate buffer (such as citric acid, or salts thereof including sodium citrate), and s-aminocaproic acid, and mixtures thereof.

The formulation may further comprise a wetting agent. Suitable classes of wetting agents include those selected from the group consisting of polyoxypropylene-polyoxyethylene block copolymers (poloxamers), polyethoxylated ethers of castor oils, polyoxyethylenated sorbitan esters (polysorbates), polymers of oxyethylated octyl phenol (Tyloxapol), polyoxyl 40 stearate, fatty acid glycol esters, fatty acid glyceryl esters, sucrose fatty esters, and polyoxyethylene fatty esters, and mixtures thereof.

Oral compositions generally include an inert diluent or an edible pharmaceutically acceptable carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, orange flavoring.

According to a further aspect of the disclosure there is provided a pharmaceutical composition which comprises a compound of the disclosure as defined hereinbefore, or a pharmaceutically acceptable salt, hydrate or solvate thereof, in association with a pharmaceutically acceptable diluent or carrier.

The compositions of the disclosure may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular, intraperitoneal or intramuscular dosing or as a suppository for rectal dosing).

The compositions of the disclosure may be obtained by conventional procedures using conventional pharmaceutical excipients, well known in the art. Thus, compositions intended for oral use may contain, for example, one or more coloring, sweetening, flavoring and/or preservative agents.

An effective amount of a compound of the present disclosure for use in therapy is an amount sufficient to treat or prevent a WRN related condition referred to herein, slow its progression and/or reduce the symptoms associated with the condition.

An effective amount of a compound of the present disclosure for use in therapy is an amount sufficient to treat a WRN related condition referred to herein, slow its progression and/or reduce the symptoms associated with the condition.

The size of the dose for therapeutic or prophylactic purposes of a compound of Formula (I) will naturally vary according to the nature and severity of the conditions, the age and sex of the animal or patient and the route of administration, according to well-known principles of medicine.

Methods of Use

In some aspects, the present disclosure provides a method of modulating WRN activity, comprising contacting a cell with a compound of the present disclosure or a pharmaceutically acceptable salt thereof.

In some aspects, the present disclosure provides a method of modulating WRN activity (e.g., in vitro or in vivo), comprising contacting a cell with an effective amount of a compound of the present disclosure or a pharmaceutically acceptable salt thereof.

In some aspects, the present disclosure provides a method of modulating WRN activity (e.g., in vitro or in vivo), comprising contacting a cell with a compound of the present disclosure or a pharmaceutically acceptable salt thereof.

In some aspects, the present disclosure provides a method of treating or preventing a disease or disorder disclosed herein in a subject in need thereof, comprising administering to the subject a therapeutically effective amount of a compound of the present disclosure or a pharmaceutically acceptable salt thereof.

In some aspects, the present disclosure provides a method of treating a disease or disorder disclosed herein in a subject in need thereof, comprising administering to the subject a therapeutically effective amount of a compound of the present disclosure or a pharmaceutically acceptable salt thereof, or a pharmaceutical composition of the present disclosure.

In some aspects, the present disclosure provides a method of treating or preventing a disease or disorder disclosed herein in a subject in need thereof, comprising administering to the subject a compound of the present disclosure or a pharmaceutically acceptable salt thereof.

In some aspects, the present disclosure provides a method of treating a disease or disorder disclosed herein in a subject in need thereof, comprising administering to the subject a compound of the present disclosure or a pharmaceutically acceptable salt thereof, or a pharmaceutical composition of the present disclosure.

In some aspects, the present disclosure provides a method for inhibiting DNA repair by WRN in a cancer cell comprising contacting the cell with an effective amount of a compound of the present disclosure or a pharmaceutically acceptable salt there f, or a pharmaceutical composition of the present disclosure.

In some embodiments, the cancer is a microsatellite instable (MS) and/or mismatch repair deficient (dMMR) cancer.

In some embodiments, the cancer is a microsatellite instability-high (MSI-H) and/or mismatch repair deficient (dMMR) cancer.

In some embodiments, the cancer is a microsatellite instable (MSI) cancer. In some embodiments, the cancer is a microsatellite instability-high (M I-H) cancer. In some embodiments, the cancer is a mismatch repair deficient (dMMR) cancer In some aspects, the present disclosure provides a method for treating and/or preventing a cancer in a patient, wherein the cancer is characterized by a reduction or absence of MMR gene expression, in which MMR genes include: MLH1, PMS2, MSH2, MSH3, MSH6, MLH3, PMS1, and EPCAM, the absence of MMR genes, or reduced function of MMR proteins, comprising administering to the subject a compound of the present disclosure or a pharmaceutically acceptable salt thereof, or a pharmaceutical composition of the present disclosure.

In some aspects, the present disclosure provides a method for treating and/or preventing a cancer in a patient, wherein the cancer is characterized by a reduction or absence of MMR gene expression, in which MMR genes include: MLH1, PMS2, MSH2, MSH3, MSH6, MLH3, PMS1, and EPCAM, comprising administering to the subject a compound of the present disclosure or a pharmaceutically acceptable salt thereof, or a pharmaceutical composition of the present disclosure.

In some aspects, the present disclosure provides a method for treating and/or preventing a cancer in a patient, wherein the cancer is characterized by the absence of MMR genes, comprising administering to the subject a compound of the present disclosure or a pharmaceutically acceptable salt thereof, or a pharmaceutical composition of the present disclosure.

In some aspects, the present disclosure provides a method for treating and/or preventing a cancer in a patient, wherein the cancer is characterized by a reduced function of MMR proteins, comprising administering to the subject a compound of the present disclosure or a pharmaceutically acceptable salt thereof, or a pharmaceutical composition of the present disclosure.

In some embodiments, the disease or disorder is associated with an implicated WRN activity. In some embodiments, the disease or disorder is a disease or disorder in which WRN activity is implicated.

In some embodiments, the disease or disorder is associated with an implicated WRN activity. In some embodiments, the disease or disorder is a disease or disorder in which WRN activity is implicated.

In some embodiments, the disease or disorder is cancer.

In some aspects, the present disclosure provides a method of treating or preventing cancer in a subject in need thereof, comprising administering to the subject a therapeutically effective amount of a compound of the present disclosure or a pharmaceutically acceptable salt thereof, or a pharmaceutical composition of the present disclosure.

In some aspects, the present disclosure provides a method of treating cancer in a subject in need thereof, comprising administering to the subject a therapeutically effective amount of a compound of the present disclosure or a pharmaceutically acceptable salt thereof, or a pharmaceutical composition of the present disclosure.

In some aspects, the present disclosure provides a method of treating or preventing cancer in a subject in need thereof, comprising administering to the subject a compound of the present disclosure or a pharmaceutically acceptable salt thereof, or a pharmaceutical composition of the present disclosure.

In some aspects, the present disclosure provides a method of treating cancer in a subject in need thereof, comprising administering to the subject a compound of the present disclosure or a pharmaceutically acceptable salt thereof, or a pharmaceutical composition of the present disclosure.

In some aspects, the present disclosure provides a compound of the present disclosure or a pharmaceutically acceptable salt thereof, or a pharmaceutical composition of the present disclosure for use in modulating WRN activity.

In some aspects, the present disclosure provides a compound of the present disclosure or a pharmaceutically acceptable salt thereof for use in modulating WRN activity (e.g., in vitro or in vivo).

In some aspects, the present disclosure provides a compound of the present disclosure or a pharmaceutically acceptable salt thereof for use in modulating WRN activity (e.g., in vitro or in vivo).

In some aspects, the present disclosure provides a compound of the present disclosure or a pharmaceutically acceptable salt thereof for inhibiting DNA repair by WRN in a cell. In some embodiments, the cell is an MSI and/or MMR-deficient cell. In some embodiments, the cell is an MSI-H and/or MMR-deficient cell.

In some aspects, the present disclosure provides a compound of the present disclosure or a pharmaceutically acceptable salt thereof for use in the treatment and/or prevention of a disease in a patient, wherein the disease is characterized by overexpression of WRN.

In some aspects, the present disclosure provides a compound of the present disclosure or a pharmaceutically acceptable salt thereof for use in the treatment and/or prevention of a cancer in a patient, wherein the cancer is characterized by a reduction or absence of MMR gene expression, the absence of MMR genes, or reduced function of MMR proteins, in which MMR genes include: MLH1, PMS2, MSH2, MSH3, MSH6, MLH3, PMS1, and EPCAM.

In some embodiments, the MMR gene is MLH1.

In some embodiments, the MMR gene is PMS2.

In some embodiments, the MMR gene is MSH2.

In some embodiments, the MMR gene is MSH3.

In some embodiments, the MMR gene is MSH6.

In some embodiments, the MMR gene is MLH3.

In some embodiments, the MMR gene is PMS1.

In some embodiments, the MMR gene is EPCAM.

In some aspects, the present disclosure provides a compound of the present disclosure or a pharmaceutically acceptable salt thereof for use in the treatment and/or prevention of an MSI and/or MMR-deficient cancer in a patient.

In some aspects, the present disclosure provides a compound of the present disclosure or a pharmaceutically acceptable salt thereof for use in the treatment and/or prevention of an MSI-H and/or MMR-deficient cancer in a patient.

In some aspects, the present disclosure provides a compound of the present disclosure or a pharmaceutically acceptable salt thereof, or a pharmaceutical composition of the present disclosure for use in treating or preventing a disease or disorder.

In some aspects, the present disclosure provides a compound of the present disclosure or a pharmaceutically acceptable salt thereof for use in treating or preventing a disease or disorder disclosed herein.

In some aspects, the present disclosure provides a compound of the present disclosure or a pharmaceutically acceptable salt thereof for use in treating a disease or disorder disclosed herein.

In some aspects, the present disclosure provides a compound of the present disclosure or a pharmaceutically acceptable salt thereof for use in treating or preventing cancer in a subject in need thereof.

In some aspects, the present disclosure provides a compound of the present disclosure or a pharmaceutically acceptable salt thereof for use in treating cancer in a subject in need thereof.

In some aspects, the present disclosure provides use of a compound of the present disclosure or a pharmaceutically acceptable salt thereof in the manufacture of a medicament for modulating WRN activity (e.g., in vitro or in vivo).

In some aspects, the present disclosure provides use of a compound of the present disclosure or a pharmaceutically acceptable salt thereof in the manufacture of a medicament for treating or preventing a disease or disorder disclosed herein.

In some aspects, the present disclosure provides use of a compound of the present disclosure or a pharmaceutically acceptable salt thereof in the manufacture of a medicament for treating a disease or disorder disclosed herein.

In some aspects, the present disclosure provides use of a compound of the present disclosure or a pharmaceutically acceptable salt thereof in the manufacture of a medicament for treating or preventing cancer in a subject in need thereof.

In some aspects, the present disclosure provides use of a compound of the present disclosure or a pharmaceutically acceptable salt thereof in the manufacture of a medicament for treating cancer in a subject in need thereof.

The present disclosure provides compounds that function as modulators of WRN activity.

In some embodiments, modulation is inhibition.

Effectiveness of compounds of the disclosure can be determined by industry-accepted assays/disease models according to standard practices of elucidating the same as described in the art and are found in the current general knowledge.

The present disclosure also provides a method of treating a disease or disorder in which WRN activity is implicated in a patient in need of such treatment, said method comprising administering to said patient a therapeutically effective amount of a compound, or a pharmaceutically acceptable salt thereof, or a pharmaceutical composition as defined herein.

In some embodiments, an MSI and/or MMR-deficient cancer is colorectal cancer. In some embodiments, an MSI-H and/or MMR-deficient cancer is colorectal cancer. Colorectal cancer includes, but is not limited to, adenocarcinoma, mucinous adenocarcinoma, and signet-ring cell carcinoma. In some embodiments, an MSI and/or MMR-deficient cancer is gastric cancer. In some embodiments, an MSI-H and/or MMR-deficient cancer is gastric cancer. Gastric cancer includes, but is not limited to, adenocarcinoma, diffuse adenocarcinoma, intestinal adenocarcinoma, mixed adenosquamous carcinoma, signet ring adenocarcinoma, small cell adenocarcinoma, tubular adenocarcinoma, undifferentiated adenocarcinoma.

In some embodiments, the cancer is selected from colorectal, gastric, endometrial, neuroendocrine, breast, ovarian, cervical, uterine, liver, prostate, cholangiocarcinoma, thyroid, pancreatic, uveal melanoma, esophageal, glioblastoma, and lung cancer.

In some embodiments, the cancer is colorectal cancer.

In some embodiments, the cancer is gastric cancer.

In some embodiments, the cancer has a deficiency in a DNA dan age repair process.

In some embodiments, the cancer is sensitive to WRN inhibition.

In some embodiments, the cancer has evidence of elevated W activity.

In some embodiments, the cancer has elevated expression of WRN mRNA or protein.

In some embodiments, the cancer has elevated expression of WRN mRNA.

In some embodiments, the cancer has elevated expression of WRN protein.

In some embodiments, the cancer is classified by a genotype.

In some embodiments, the genotype has a modulated function.

In some embodiments, the modulated function is an inactivating mutation, deletion, or other genomic alteration.

In some embodiments, the genotype is loss of mRNA or protein expression.

In some embodiments, the cancer has modulated function of at least one gene.

In some embodiments, the gene is selected from MLH1, PMS2, MSH2, MSH4, MSH6, MLH3, PMS1, and EPCAM.

In some embodiments, the cancer is MSI and/or MMR-deficient cancer.

In some embodiments, the cancer is MSI-H and/or MMR-deficient cancer.

In some embodiments, the cancer is classified as an MSI and/or MMR-deficient cancer because the tumor is unable to accurately repair mismatches or small insertions or deletions in DNA via mismatch repair.

In some embodiments, the cancer is classified as an MSI-H and/pr MMR-deficient cancer because the tumor is unable to accurately repair mismatches or small insertions or deletions in DNA via mismatch repair.

In some embodiments, the mutation is in a gene that, when lost, causes MMR-deficiency.

In some embodiments, the cancer has a compromised mismatch repair pathway.

In some embodiments, the cancer with a compromised MMR is dependent on WRN activity.

In some embodiments, the cancer is a tumor. In some embodiments, the cancer is a solid tumor.

In some embodiments, the cancer is a tumor with microsatellite instability (e.g., colorectal, gastric, endometrial cancers). In some embodiments, the cancer is a TA-repeat expanded tumor.

In some aspects, the present disclosure provides a combination of a compound of the present disclosure and chemotherapy and immunotherapy for the treatment of tumors with microsatellite instability (e.g., colorectal, gastric, endometrial cancers).

In some aspects, the present disclosure provides a combination of a compound of the present disclosure and chemotherapy for the treatment of tumors with microsatellite instability (e.g., colorectal, gastric, endometrial cancers).

In some aspects, the present disclosure provides a combination of a compound of the present disclosure and immunotherapy for the treatment of tumors with microsatellite instability (e.g., colorectal, gastric, endometrial cancers).

In some aspects, the present disclosure provides a combination of a compound of the present disclosure and chemotherapy or immunotherapy for the treatment of tumors with microsatellite instability (e.g., colorectal, gastric, endometrial cancers).

In some aspects, the present disclosure provides a combination of a compound of the present disclosure and chemotherapy and immunotherapy for the treatment of TA-repeat expanded tumors.

In some aspects, the present disclosure provides a combination of a compound of the present disclosure and chemotherapy for the treatment of TA-repeat expanded tumors.

In some aspects, the present disclosure provides a combination of a compound of the present disclosure and immunotherapy for the treatment of TA-repeat expanded tumors.

In some aspects, the present disclosure provides a combination of a compound of the present disclosure and chemotherapy or immunotherapy for the treatment of TA-repeat expanded tumors.

In some embodiments, the compound of the present disclosure and chemotherapy or immunotherapy are administered in temporal proximity, sequentially, or in alternation.

In some embodiments, the compound of the present disclosure and chemotherapy or immunotherapy are administered in temporal proximity.

In some embodiments, the compound of the present disclosure and chemotherapy or immunotherapy are administered sequentially.

In some embodiments, the compound of the present disclosure and chemotherapy or immunotherapy are administered in alternation.

In some embodiments, the compound of the present disclosure and chemotherapy or immunotherapy are administered as different formulations.

Routes of Administration

Compounds of the present disclosure, or pharmaceutically acceptable salts thereof, may be administered alone as a sole therapy or can be administered in addition with one or more other substances and/or treatments. Such conjoint treatment may be achieved by way of the simultaneous, sequential or separate administration of the individual components of the treatment.

For example, therapeutic effectiveness may be enhanced by administration of an adjuvant (i.e. by itself the adjuvant may only have minimal therapeutic benefit, but in combination with another therapeutic agent, the overall therapeutic benefit to the individual is enhanced). Alternatively, by way of example only, the benefit experienced by an individual may be increased by administering the compound of Formula (I) with another therapeutic agent (which also includes a therapeutic regimen) that also has therapeutic benefit.

In the instances where the compound of the present disclosure is administered in combination with other therapeutic agents, the compound of the disclosure need not be administered via the same route as other therapeutic agents, and may, because of different physical and chemical characteristics, be administered by a different route. For example, the compound of the disclosure may be administered orally to generate and maintain good blood levels thereof, while the other therapeutic agent may be administered intravenously. The initial administration may be made according to established protocols known in the art, and then, based upon the observed effects, the dosage, modes of administration and times of administration can be modified by the skilled clinician.

The particular choice of other therapeutic agent will depend upon the diagnosis of the attending physicians and their judgment of the condition of the individual and the appropriate treatment protocol. According to this aspect of the disclosure there is provided a combination for use in the treatment of a disease in which WRN activity is implicated comprising a compound of the disclosure as defined hereinbefore, or a pharmaceutically acceptable salt thereof, and another suitable agent.

According to a further aspect of the disclosure there is provided a pharmaceutical composition which comprises a compound of the disclosure, or a pharmaceutically acceptable salt thereof, in combination with a suitable, in association with a pharmaceutically acceptable diluent or carrier.

In addition to its use in therapeutic medicine, compounds of Formula (I) and pharmaceutically acceptable salts thereof are also useful as pharmacological tools in the development and standardization of in vitro and in vivo test systems for the evaluation of the effects of modulators of WRN activity in laboratory animals such as dog, rabbits, monkeys, minipigs, rats and mice, as part of the search for new therapeutic agents.

In any of the above-mentioned pharmaceutical composition, process, method, use, medicament, and manufacturing features of the instant disclosure, any of the alternate embodiments of macromolecules of the present disclosure described herein also apply.

The compounds of the disclosure or pharmaceutical compositions comprising these compounds may be administered to a subject by any convenient route of administration, whether systemically/peripherally or topically (i.e., at the site of desired action).

Routes of administration include, but are not limited to, oral (e.g. by ingestion); buccal; sublingual; transdermal (including, e.g., by a patch, plaster, etc.); transmucosal (including, e.g., by a patch, plaster, etc.); intranasal (e.g., by nasal spray or powder); ocular (e.g., by eye drops); pulmonary (e.g., by inhalation or insufflation therapy using, e.g., via an aerosol, e.g., through the mouth or nose); rectal (e.g., by suppository or enema); vaginal (e.g., by pessary); parenteral, for example, by injection, including subcutaneous, intradermal, intramuscular, intravenous, intra-arterial, intracardiac, intrathecal, intraspinal, intracapsular, subcapsular, intraorbital, intraperitoneal, intratracheal, subcuticular, intraarticular, subarachnoid, and intrasternal; by implant of a depot or reservoir, for example, subcutaneously or intramuscularly.

"Combination therapy," "combination treatment," or "combination" refers to the use of two or more drugs or agents in treatment, e.g., the use of a compound of Formula (I) of the present disclosure together with another agent useful to treat cancer, and symptoms and manifestations of each thereof. Administration in "combination" refers to the administration of two agents (e.g., a compound of Formula (I) of the present disclosure, and another agent or treatment (e.g., chemotherapy or immunotherapy)) in any manner in which the pharmacological effects of both manifest in the subject. Thus, administration in combination does not require that a single pharmaceutical composition, the same dosage form, or even the same route of administration be used for administration of both agents or that the two agents be administered at precisely the same time. Both agents can also be formulated in a single pharmaceutically acceptable composition. In some embodiments, the each agent may be administered in temporal proximity, sequentially, or in alternation.

EXEMPLARY EMBODIMENTS—A

Exemplary Embodiment No. A1. A compound of Formula (I'):

(I')

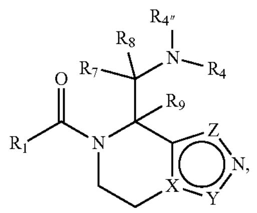

or a pharmaceutically acceptable salt, oxide, solvate, clathrate, hydrate, stereoisomer, or tautomer thereof, wherein:

X is N or C;

Y is $NR_2$ or $CR_2$;

Z is $NR_3$ or $CR_3$;

$R_1$ is $C_1$-$C_6$ alkyl, $C_2$-$C_6$ alkenyl, $C_2$-$C_6$ alkynyl, $C_1$-$C_6$ haloalkyl, $C_3$-$C_{10}$ cycloalkyl, $C_6$-$C_{10}$ aryl, 5- to 10-membered heteroaryl, or 3- to 10-membered heterocyclyl, wherein the $C_1$-$C_6$ alkyl, $C_2$-$C_6$ alkenyl, $C_2$-$C_6$ alkynyl, $C_1$-$C_6$ haloalkyl, $C_3$-$C_{10}$ cycloalkyl, $C_6$-$C_{10}$ aryl, 5- to 10-membered heteroaryl, or 3- to 10-membered heterocyclyl is optionally substituted with one or more $R_{1a}$;

each $R_{1a}$ independently is oxo, halo, cyano, —OH, —$NH_2$, —$NO_2$, —NH($C_1$-$C_6$ alkyl), —N($C_1$-$C_6$ alkyl)$_2$, —NH—C(O)($C_1$-$C_6$ alkyl), —S($C_1$-$C_6$ alkyl), —S(O)$_2$($C_1$-$C_6$ alkyl) —S(O)$_2$($NH_2$), —C(O)(H), —C(O)$NH_2$, —O(3- to 10-membered heterocyclyl), $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, $C_3$-$C_{10}$ cycloalkyl, $C_6$-$C_{10}$ aryl, 5- to 10-membered heteroaryl, or 3- to 10-membered heterocyclyl, wherein the —NH($C_1$-$C_6$ alkyl), —N($C_1$-$C_6$ alkyl)$_2$ —NH—C(O)($C_1$-$C_6$ alkyl), —S($C_1$-$C_6$ alkyl), —S(O)$_2$($C_1$-$C_6$ alkyl), —O(3- to 10-membered heterocyclyl), $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, $C_3$-$C_{10}$ cycloalkyl, $C_6$-$C_{10}$ aryl, 5- to 10-membered heteroaryl, or 3- to 10-membered heterocyclyl is optionally substituted with one or more Rib;

each $R_{1b}$ independently is oxo, halo, cyano, —OH, —O($C_1$-$C_6$ alkyl), —O($C_1$-$C_6$ haloalkyl), —O($C_2$-$C_6$ alkenyl), —O($C_2$-$C_6$ alkynyl), —$NH_2$, —NH($C_1$-$C_6$ alkyl), —N($C_1$-$C_6$ alkyl)$_2$, —NH($C_1$-$C_6$ haloalkyl), —S($C_1$-$C_6$ alkyl), —S(O)$_2$($C_1$-$C_6$ alkyl), $C_1$-$C_6$ alkyl, $C_3$-$C_{10}$ cycloalkyl, or 3- to 10-membered heterocyclyl optionally substituted with oxo;

$R_2$ is $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_3$-$C_{10}$ cycloalkyl, $C_6$-$C_{10}$ aryl, 5- to 10-membered heteroaryl, or 3- to 10-membered heterocyclyl, wherein the $C_1$-$C_6$ alkyl, $C_3$-$C_{10}$ cycloalkyl, $C_6$-$C_{10}$ aryl, 5- to 10-membered heteroaryl, or 3- to 10-membered heterocyclyl is optionally substituted with one or more R a;

each $R_{2a}$ independently is oxo, halo, cyano, —OH, —$NH_2$, —NH($C_1$-$C_6$ alkyl), —N($C_1$-$C_6$ alkyl)$_2$, —SH, —S(O)$_2$NH$_2$, —SF$_5$, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, —S($C_1$-$C_6$ haloalkyl), —S($C_1$-$C_6$ alkyl), $C_3$-$C_{10}$ cycloalkyl, $C_6$-$C_{10}$ aryl, 5- to 10-membered heteroaryl, or 3- to 10-membered heterocyclyl, wherein the $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, —S($C_1$-$C_6$ haloalkyl), —S($C_1$-$C_6$ alkyl), $C_3$-$C_{10}$ cycloalkyl, $C_6$-$C_{10}$ aryl, 5- to 10-membered heteroaryl, or 3- to 10-membered heterocyclyl is optionally substituted with one or more $R_{2a1}$;

each $R_{2a1}$ independently is oxo, halo, cyano, —OH, —$NH_2$, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, —NH—C(O)($C_1$-$C_6$ alkyl), —C(O)NH$_2$, or —OC(O)($C_1$-$C_6$ alkyl), wherein the $C_1$-$C_6$ alkyl, $C_2$-$C_6$ alkenyl, $C_2$-$C_6$ alkynyl, $C_1$-$C_6$ alkoxy, $C_1$-$C_6$ haloalkyl or $C_1$-$C_6$ alkyl is optionally substituted with one or more —OH;

$R_3$ and $R_4$, together with the atoms to which they are attached, form a 6- to 10-membered heterocyclyl, wherein the heterocyclyl optionally comprises one or more additional N, O, or S and is optionally substituted with one or more $R_{3a}$;

each $R_{3a}$ independently is cyano, halo, —OH, —$NH_2$, —NH($C_1$-$C_6$ alkyl), —N($C_1$-$C_6$ alkyl)$_2$, —N($C_1$-$C_6$ alkyl)($C_1$-$C_6$ haloalkyl), —NH—C(O)($C_1$-$C_6$ alkyl), —O($C_3$-$C_{10}$ cycloalkyl), $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_1$-$C_6$ haloalkoxy, $C_3$-$C_{10}$ cycloalkyl, 3- to 10-membered heterocyclyl, —S(O)(═NH)($C_1$-$C_6$ alkyl), —SO$_2$($C_1$-$C_6$ alkyl), —S($C_1$-$C_6$ alkyl), or —S($C_1$-$C_6$ haloalkyl), wherein the alkyl is optionally substituted with one or more —N($R_{3a1}$)CO($R_{3a2}$), —O($C_3$-$C_{10}$ cycloalkyl), —O($C_6$-$C_{10}$ aryl), —O(5- to 10-membered heteroaryl), or —O(3- to 10-membered heterocyclyl), wherein the cycloalkyl, aryl, heteroaryl, or heterocyclyl is optionally substituted with one or more $C_1$-$C_6$ alkyl, or two $R_{3a}$, together with the atoms to which they are attached, form a $C_3$-$C_{10}$ cycloalkyl or 3- to 10-membered heterocyclyl;

$R_{3a1}$ and $R_{3a2}$, together with the atoms to which they are attached, form a 3- to 10-membered heterocyclyl;

$R_{4''}$ is

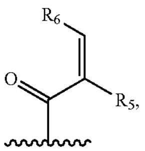
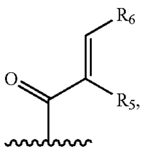

-continued

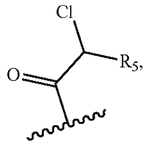
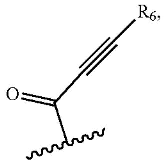
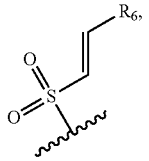
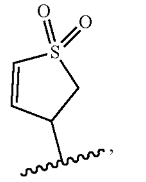
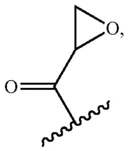
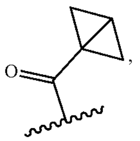
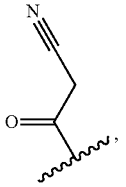
or
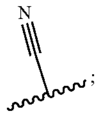

$R_5$ is H, halo, cyano, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy- $R_6$ is H, halo, cyano, $C_1$-$C_6$ alkyl, $C_2$-$C_6$ alkenyl, $C_2$-$C_6$ alkynyl, or $C_1$-$C_6$ alkoxy, wherein the alkyl, alkenyl, alkynyl, or alkoxy is optionally substituted with one or more —$NH_2$, —NH($C_1$-$C_6$ alkyl), or —N($C_1$-$C_6$ alkyl)$_2$, or $R_5$ and $R_6$, together with the atoms to which they are attached, form a $C_4$-$C_{10}$ cycloalkenyl; and each $R_7$, $R_8$, and $R_9$ independently is H, cyano, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy, wherein the alkyl, alkenyl, alkynyl, haloalkyl, or alkoxy is optionally substituted with one or more oxo, halo, cyano, —OH, —$NH_2$, $C_1$-$C_6$ alkoxy, —NH($C_1$-$C_6$ alkyl), —N($C_1$-$C_6$ alkyl)$_2$, —NH($C_1$-$C_6$ haloalkyl), or —S($C_1$-$C_6$ alkyl), or $R_7$ and $R_8$, together with the atoms to which they are attached, form a $C_3$-$C_{10}$ cycloalkyl or 3- to 10-membered heterocyclyl.

Exemplary Embodiment No. A2. A compound of Formula (I):

(I)

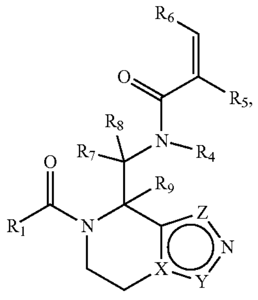

or a pharmaceutically acceptable salt, oxide, solvate, clathrate, hydrate, stereoisomer, or tautomer thereof, wherein:

X is N or C;

Y is $NR_2$ or $CR_2$;

Z is $NR_3$ or $CR_3$;

$R_1$ is $C_1$-$C_6$ alkyl, $C_2$-$C_6$ alkenyl, $C_2$-$C_6$ alkynyl, $C_1$-$C_6$ haloalkyl $C_3$-$C_{10}$ cycloalkyl, $C_6$-$C_{10}$ aryl, 5- to 10-membered heteroaryl, or 3- to 10-membered heterocyclyl, wherein the $C_1$-$C_6$ alkyl, $C_2$-$C_6$ alkenyl, $C_2$-$C_6$ alkynyl, $C_1$-$C_6$ haloalkyl, $C_3$-$C_{10}$ cycloalkyl, $C_6$-$C_{10}$ aryl, 5- to 10-membered heteroaryl, or 3- to 10-membered heterocyclyl is optionally substituted with one or more $R_{1a}$;

each $R_{1a}$ independently is oxo, halo, cyano, —OH, —$NH_2$, —$NO_2$, —H—C(O)($C_1$-$C_6$ alkyl), —S($C_1$-$C_6$ alkyl), —$S(O)_2$($C_1$-$C_6$ alkyl), —$S(O)_2(NH_2)$, —C(O)(H), —C(O)$NH_2$, —O(3- to 10-membered heterocyclyl), $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, $C_3$-$C_{10}$ cycloalkyl, $C_6$-$C_{10}$ aryl, 5- to 10-membered heteroaryl, or 3- to 10-membered heterocyclyl, wherein the —NH—C(O)($C_1$-$C_6$ alkyl), —S($C_1$-$C_6$ alkyl), —$S(O)_2$($C_1$-$C_6$ alkyl), —O(3- to 10-membered heterocyclyl), $C_1$-$C_6$ alkyl, $C_2$-$C_6$ alkenyl, $C_2$-$C_6$ alkynyl, $C_1$-$C_6$ alkoxy, 1-$C_6$ haloalkyl, $C_3$-$C_{10}$ cycloalkyl, $C_6$-$C_{10}$ aryl, 5- to 10-membered heteroaryl, or 3- to 10-membered heterocyclyl is optionally substituted with one or more $R_{1b}$;

each $R_{1b}$ independently is oxo, halo, cyano, —OH, —O($C_1$-$C_6$ alkyl), —O($C_1$-$C_6$ haloalkyl), —O($C_2$-$C_6$ alkenyl), —O($C_2$-$C_6$ alkynyl), —$NH_2$, —NH($C_1$-$C_6$ alkyl), —N($C_1$-$C_6$ $alkyl)_2$, —NH($C_1$-$C_6$ haloalkyl), —S($C_1$-$C_6$ alkyl), —$S(O)_2$($C_1$-$C_6$ alkyl), $C_1$-$C_6$ alkyl, $C_3$-$C_{10}$ cycloalkyl, or 3- to 10-membered heterocyclyl optionally substituted with oxo;

$R_2$ is $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_3$-$C_{10}$ cycloalkyl, $C_6$-$C_{10}$ aryl, 5- to 10-membered heteroaryl, or 3- to 10-membered heterocyclyl, wherein the $C_1$-$C_6$ alkyl, $C_3$-$C_{10}$ cycloalkyl, $C_6$-$C_{10}$ aryl, 5- to 10-membered heteroaryl, or 3- to 10-membered heterocyclyl is optionally substituted with one or more $R_{2a}$;

each $R_{2a}$ independently is oxo, halo, cyano, —OH, —$NH_2$, —NH($C_1$-$C_6$ alkyl), —N($C_1$-$C_6$ $alkyl)_2$, —SH, —$S(O)_2NH_2$, —$SF_5$, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, —S($C_1$-$C_6$ haloalkyl), —S($C_1$-$C_6$ alkyl), $C_3$-$C_{10}$ cycloalkyl, $C_6$-$C_{10}$ aryl, 5- to 10-membered heteroaryl, or 3- to 10-membered heterocyclyl, wherein the $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, —S($C_1$-$C_6$ haloalkyl), —S($C_1$-$C_6$ alkyl), $C_3$-$C_{10}$ cycloalkyl, $C_6$-$C_{10}$ aryl, 5- to 10-membered heteroaryl, or 3- to 10-membered heterocyclyl is optionally substituted with one or more $R_{2a1}$;

each $R_{2a1}$ independently is oxo, halo, cyano, —OH, —$NH_2$, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, —NH—C(O)($C_1$-$C_6$ alkyl), —C(O)$NH_2$, or —OC(O)($C_1$-$C_6$ alkyl), wherein the $C_1$-$C_6$ alkyl, $C_2$-$C_6$ alkenyl, $C_2$-$C_6$ alkynyl, $C_1$-$C_6$ alkoxy, $C_1$-$C_6$ haloalkyl or $C_1$-$C_6$ alkyl is optionally substituted with one or more —OH;

$R_3$ and $R_4$, together with the atoms to which they are attached, form a 6- to 10-membered heterocyclyl, wherein the heterocyclyl optionally comprises one or more additional N, O, or S and is optionally substituted with one or more $R_{3a}$;

each $R_{3a}$ independently is cyano, halo, —OH, —$NH_2$, —NH($C_1$-$C_6$ alkyl), —N($C_1$-$C_6$ $alkyl)_2$, —N($C_1$-$C_6$ alkyl)($C_1$-$C_6$ haloalkyl), —NH—C(O)($C_1$-$C_6$ alkyl), —O($C_3$-$C_{10}$ cycloalkyl), —O(3- to 10-membered heterocyclyl), $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_1$-$C_6$ haloalkoxy, $C_3$-$C_{10}$ cycloalkyl, 3- to 10-membered heterocyclyl, $C_6$-$C_{10}$ aryl, 5- to 10-membered heteroaryl, —S(O)(=NH)($C_1$-$C_6$ alkyl), —$SO_2$($C_1$-$C_6$ alkyl), —S($C_1$-$C_6$ alkyl), or —S($C_1$-$C_6$ haloalkyl), wherein the alkyl, alkenyl, alkynyl, haloalkyl, alkoxy, haloalkoxy, —O($C_3$-$C_{10}$ cycloalkyl), —O(3- to 10-membered heterocyclyl), heterocycle, cycloalkyl, aryl, or heteroaryl is optionally substituted with one or more oxo, —CN, $C_1$-$C_6$ alkoxy, —C(O)($C_1$-$C_6$ alkyl), —N($R_{3a1}$)CO($R_{3a2}$), —O($C_3$-$C_{10}$ cycloalkyl), —O($C_6$-$C_{10}$ aryl), —O(5- to 10-numbered heteroaryl), —O(3- to 10-membered heterocyclyl), $C_3$-$C_{10}$ cycloalkyl, 3- to 10-membered heterocyclyl, $C_6$-$C_{10}$ aryl, or 5- to 10-membered heteroaryl, wherein the cycloalkyl, aryl, heteroaryl, or heterocyclyl is optionally substituted with one or more $C_1$-$C_6$ alkyl, or two $R_{3a}$, together with the atoms to which they are attached, form a $C_3$-$C_{10}$ cycloalkyl or 3- to 10-membered heterocyclyl, wherein the cycloalkyl or heterocyclyl is optionally substituted with one or more $C_3$-$C_{10}$ cycloalkyl, 3- to 10-membered heterocyclyl, $C_1$-$C_{10}$ aryl, or 5- to 10-membered heteroaryl, wherein the cycloalkyl, heterocyclyl, aryl, or heteroaryl is optionally substituted with one or more $C_1$-$C_6$ alkyl;

$R_{3a1}$ and $R_{3a2}$, together with the atoms to which they are attached, form a 3- to 10-membered heterocyclyl;

$R_5$ is H, halo, cyano, or $C_1$-$C_6$ alkyl;

$R_6$ is H, halo, cyano, $C_1$-$C_6$ alkyl, or $C_1$-$C_6$ alkoxy, wherein the alkyl or alkoxy is optionally substituted with one or more —$NH_2$, —NH($C_1$-$C_6$ alkyl), or —N($C_1$-$C_6$ $alkyl)_2$, or $R_5$ and $R_6$, together with the atoms to which they are attached, form a $C_4$-$C_{10}$ cycloalkenyl; and each $R_7$, $R_8$, and $R_9$ independently is H, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy, wherein the alkyl, alkenyl, alkynyl, haloalkyl, or alkoxy is optionally substituted with one or more oxo, halo, cyano, —OH, —$NH_2$, $C_1$-$C_6$ alkoxy, —NH($C_1$-$C_6$ alkyl), —N($C_1$-$C_6$ $alkyl)_2$, —NH($C_1$-$C_6$ haloalkyl), or —S($C_1$-$C_6$ alkyl), or $R_7$ and $R_8$, together with the atoms to which they are attached, form a $C_3$-$C_{10}$ cycloalkyl or 3- to 10-membered heterocyclyl.

Exemplary Embodiment No. A3. The compound of Exemplary Embodiment No. A1 or Exemplary Embodiment No. A2, wherein:

X is C;

Y is $NR_2$;

Z is $CR_3$;

$R_1$ is $C_3$-$C_{10}$ cycloalkyl, $C_6$-$C_{10}$ aryl, or 5- to 10-membered heteroaryl, wherein the $C_3$-$C_{10}$ cycloalkyl, $C_6$-$C_{10}$ aryl, or 5- to 10-membered heteroaryl is optionally substituted with one or more $R_{1a}$;

each $R_{1a}$ independently is oxo, cyano, —C(O)$NH_2$, —$NO_2$, —O(3- to 10-membered heterocyclyl), halo, —OH, —$NH_2$, $C_1$-$C_6$ alkyl, $C_1$-$C_6$ alkoxy, $C_1$-$C_6$ haloalkyl, or 3- to 10-membered heterocyclyl, wherein the —O(3- to 10-membered heterocyclyl), $C_1$-$C_6$ alkyl, $C_1$-$C_6$ alkoxy, $C_1$-$C_6$ haloalkyl, or 3- to 10-membered heterocyclyl is optionally substituted with one or more $R_{1b}$;

each $R_{1b}$ independently is —O($C_1$-$C_6$ alkyl), —$S(O)_2$($C_1$-$C_6$ alkyl), or 3- to 10-membered heterocyclyl;

$R_2$ is $C_6$-$C_{10}$ aryl or 5- to 10-membered heteroaryl, wherein the $C_6$-$C_{10}$ aryl or 5- to 10-membered heteroaryl is optionally substituted with one or more $R_{2a}$;

each $R_{2a}$ independently is halo, —OH, —$NH_2$, $C_1$-$C_6$ alkyl, $C_1$-$C_6$ alkoxy, $C_1$-$C_6$ haloalkyl, or $C_3$-$C_{10}$ cycloalkyl, wherein the $C_1$-$C_6$ alkyl, $C_1$-$C_6$ alkoxy, $C_1$-$C_6$ haloalkyl, or $C_3$-$C_{10}$ cycloalkyl is optionally substituted with one or more $R_{2a1}$;

each $R_{2a1}$ independently is halo;

$R_3$ and $R_4$, together with the atoms to which they are attached, form a 6- to 10-membered heterocyclyl, wherein the heterocyclyl optionally comprises one or more additional O or N and is optionally substituted with one or more $R_{3a}$;

each $R_{3a}$ independently is halo, $C_1$-$C_6$ alkyl, $C_1$-$C_6$ alkoxy, or —O($C_3$-$C_{10}$ cycloalkyl);

$R_5$ is H or halo;

$R_6$ is H or $C_1$-$C_6$ alkyl optionally substituted with —N($C_1$-$C_6$ alkyl)$_2$, or $R_5$ and $R_6$, together with the atoms to which they are attached, f rm a $C_4$-$C_{10}$ cycloalkenyl; and each $R_7$, $R_8$, and $R_9$ independently is H or $C_1$-$C_6$ alkyl.

Exemplary Embodiment No. A4. The compound of any one of the preceding Exemplary Embodiments, wherein X is C.

Exemplary Embodiment No. A5. The compound of any-one of the preceding Exemplary Embodiments, wherein Y is $NR_2$.

Exemplary Embodiment No. A6. The compound of any one of the preceding Exemplary Embodiments, wherein Z is $CR_3$.

Exemplary Embodiment No. A7. The compound of any-one of the preceding Exemplary Embodiments, wherein $R_1$ is $C_3$-$C_{10}$ cycloalkyl, $C_6$-$C_{10}$ aryl, or 5- to 10-membered heteroaryl, wherein the $C_3$-$C_{10}$ cycloalkyl, $C_6$-$C_{10}$ aryl, or 5- to 10-membered heteroaryl is substituted with one or more Ria.

Exemplary Embodiment No. A8. The compound of any-one of the preceding Exemplary Embodiments, wherein $R_1$ is

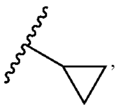,
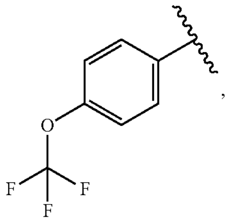,
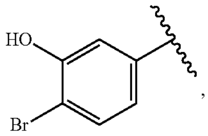,
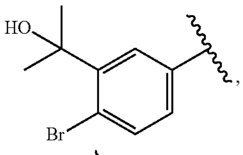,
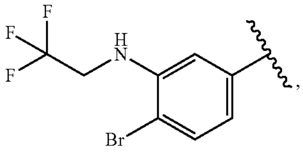,
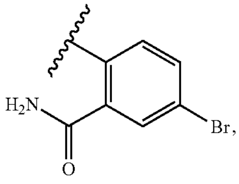,
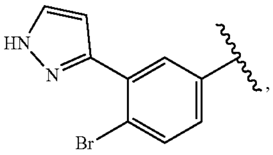,
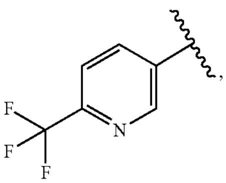,
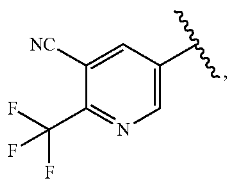, -continued

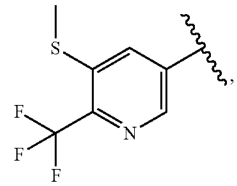,
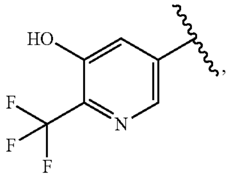,
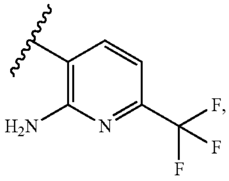,
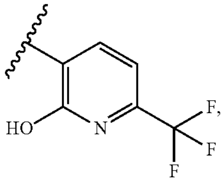,
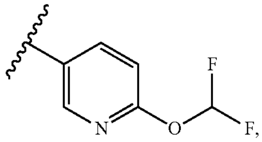,
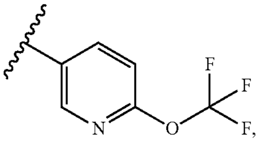,
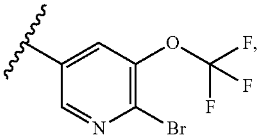,
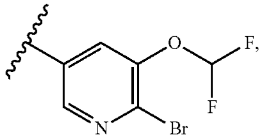,
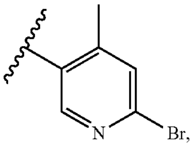,
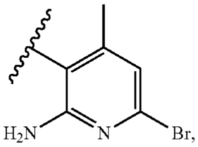,
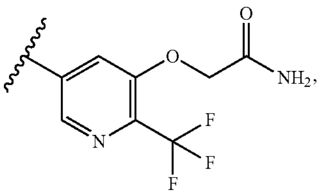,
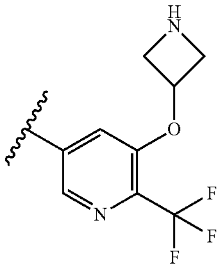,
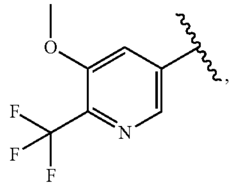,
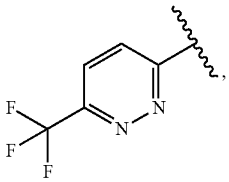,
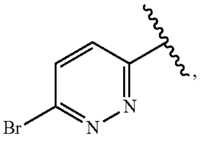,
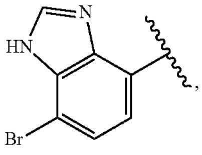,
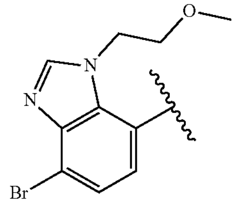,
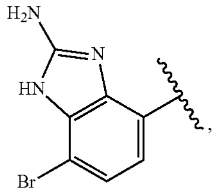, -continued

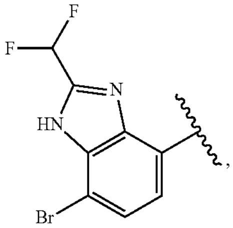,
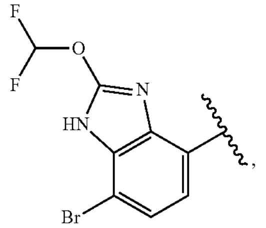,
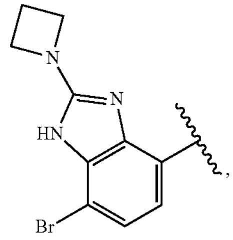,
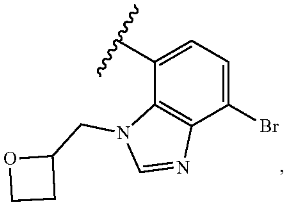,
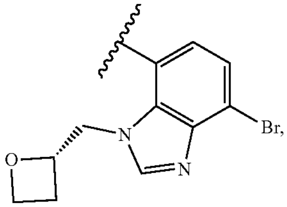,
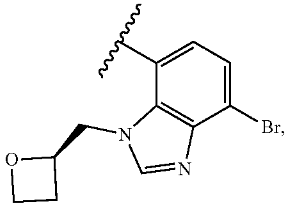,
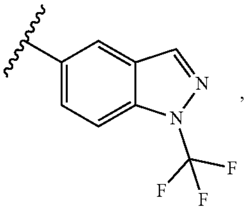,
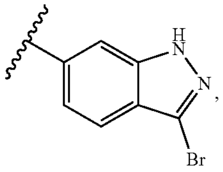,
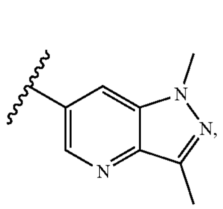,
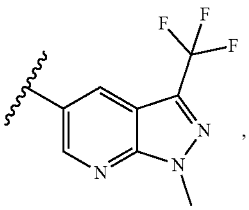,
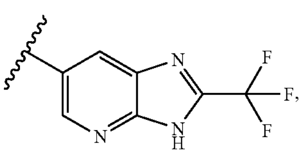,
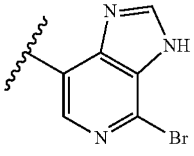,
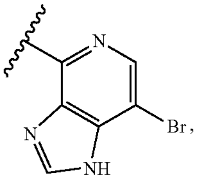,
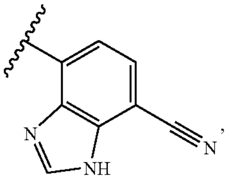,
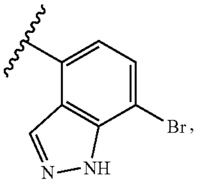,
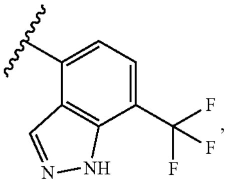, -continued

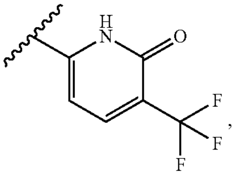,
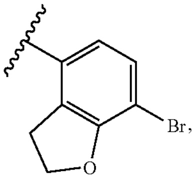,
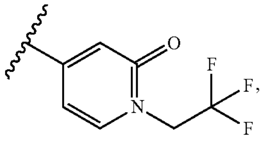,
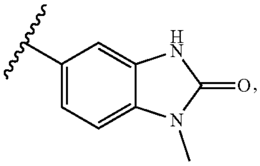,
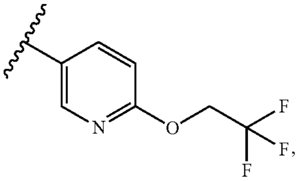,
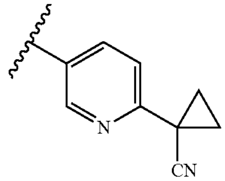,
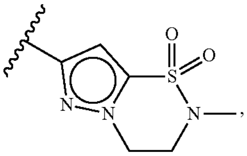, or
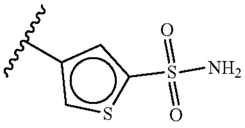.

Exemplary Embodiment No. A9. The compound of any-one of the preceding Exemplary Embodiments, wherein Ria independently is oxo, cyano, —$C(O)NH_2$, —O(3- to 10-membered heterocyclyl), halo, —OH, —$NH_2$, $C_1$-$C_6$ alkyl, $C_1$-$C_6$ alkoxy, $C_1$-$C_6$ haloalkyl, or 3- to 10-membered heterocyclyl, wherein the —O(3- to 10-membered heterocyclyl), $C_1$-$C_6$ alkyl, $C_1$-$C_6$ alkoxy, $C_1$-$C_6$ haloalkyl, or 3- to 10-membered heterocyclyl is substituted with one or more Rib.

Exemplary Embodiment No. A10. The compound of any one of the preceding Exemplary Embodiments, wherein Ria independently is oxo, cyano —$O(CH_2)C(O)NH_2$, —O—azetidinyl, —$OCF_3$, —$C(O)NH_2$, —$CH_2CF_3$, —$OCHF_2$, —$CH_3$, —OH, Br, $CF_3$, —$(CH_2)_2$—$OCH_3$, —$NH_2$, —$(CH_2)$-oxetanyl, azetidinyl, or —$OCH_3$.

Exemplary Embodiment No. A11. The compound of any one of the preceding Exemplary Embodiments, wherein $R_2$ is $C_6$-$C_{10}$ aryl or 5- to 10-membered heteroaryl, wherein the $C_6$-$C_{10}$ aryl or 5- to 10-membered heteroaryl is substituted with one or more $R_{2a}$.

Exemplary Embodiment No. A12. The compound of any one of the preceding Exemplary Embodiments, wherein $R_2$ is:

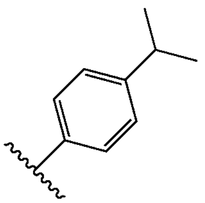,
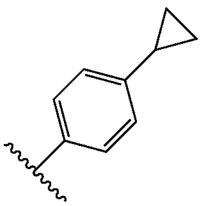,

-continued

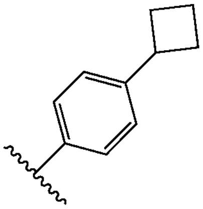,
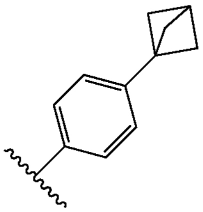,
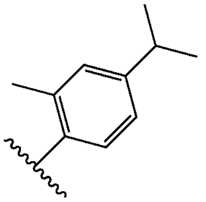,
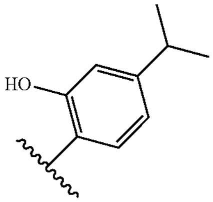,
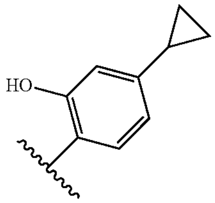,
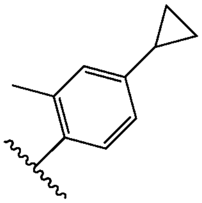,
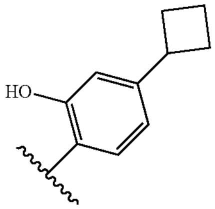,
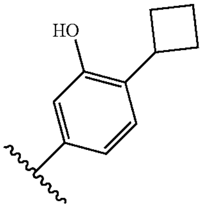,
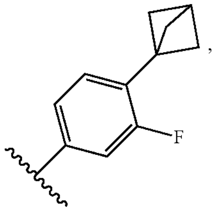,
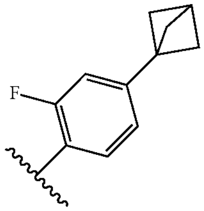,
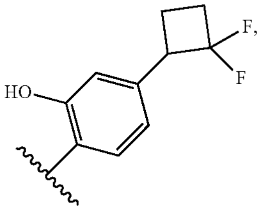
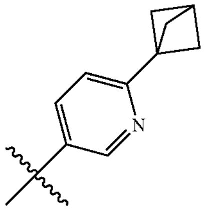,
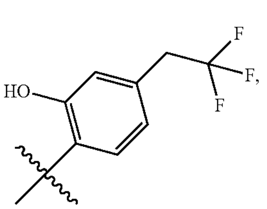
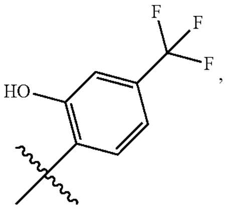
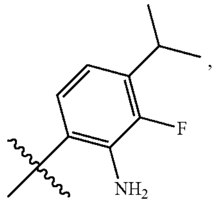,
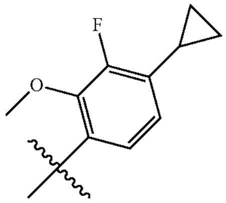, -continued

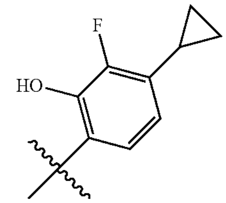,
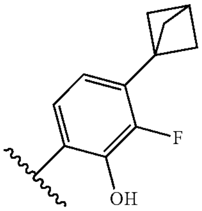,
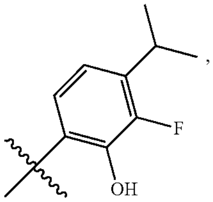,
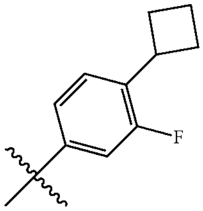, or
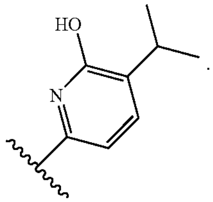.

Exemplary Embodiment No. A13. The compound of any one of the preceding Exemplary Embodiments, wherein each $R_{2a}$ independently is halo, —OH, —$NH_2$, $C_1$-$C_6$ alkyl, $C_1$-$C_6$ alkoxy, $C_1$-$C_6$ haloalkyl, or $C_3$-$C_{10}$ cycloalkyl, wherein the $C_1$-$C_6$ alkyl, $C_1$-$C_6$ alkoxy, $C_1$-$C_6$ haloalkyl, or $C_3$-$C_{10}$ cycloalkyl is optionally substituted with one or more $R_{2a1}$.

Exemplary Embodiment No. A14. The compound of any one of the preceding Exemplary Embodiments, wherein each $R_{2a}$ independently is isopropyl —$CH_2CF_3$, —$CF_3$, —$NH_2$, —$OCH_3$, cyclobutyl, cyclopropyl, —OH, -(cyclopropyl)-$F_2$, F, or bicyclo[1.1.1]pentane.

Exemplary Embodiment No. A15. The compound of any one of the preceding Exemplary Embodiments, wherein $R_3$ and $R_4$, together with the atoms to which they are attached, form a 6-membered heterocyclyl optionally substituted with one or more $R_{3a}$.

Exemplary Embodiment No. A16. The compound of any one of the preceding Exemplary Embodiments, wherein $R_3$ and $R_4$, together with the atoms to which they are attached, form a 7-membered heterocyclyl optionally substituted with one or more $R_{3a}$.

Exemplary Embodiment No. A17. The compound of any one of the preceding Exemplary Embodiments, wherein $R_3$ and $R_4$, together with the atoms to which they are attached, form a 8-membered heterocyclyl, wherein the heterocyclyl optionally comprises one or more additional O and is optionally substituted with one or more $R_{3a}$.

Exemplary Embodiment No. A18. The compound of any one of the preceding Exemplary Embodiments, wherein each $R_{3a}$ independently is halo, $C_1$-$C_6$ alkyl, or $C_1$-$C_6$ alkoxy.

Exemplary Embodiment No. A19. The compound of any one of the preceding Exemplary Embodiments, wherein each $R_{3a}$ independently is F, $CH_3$, or —$OCH_3$.

Exemplary Embodiment No. A20. The compound of any one of the preceding Exemplary Embodiments, wherein $R_5$ is H or halo.

Exemplary Embodiment No. A21. The compound of an one of the preceding Exemplary Embodiments, wherein $R_6$ is H or $C_1$-$C_6$ alkyl optionally substituted with —N($C_1$-$C_6$ alkyl)$_2$.

Exemplary Embodiment No. A22. The compound of any one of the preceding Exemplary Embodiments, wherein $R_5$ and $R_6$, together with the atoms to which they are attached, form a $C_4$ cycloalkenyl.

Exemplary Embodiment No. A23. The compound of any one of the preceding Exemplary Embodiments, wherein each $R_7$, $R_8$, and $R_9$ independently is H.

Exemplary Embodiment No. A24. The compound of any one of the preceding Exemplary Embodiments, wherein the compound is of Formula (II-a), (II-b), (II-c), or (II-d):

(II-a)

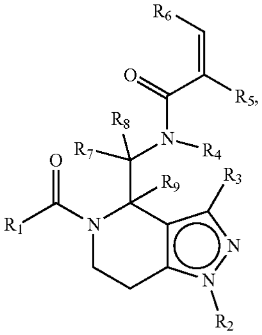

(II-b)

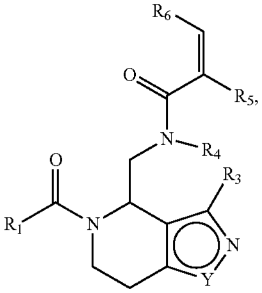

(II-c)

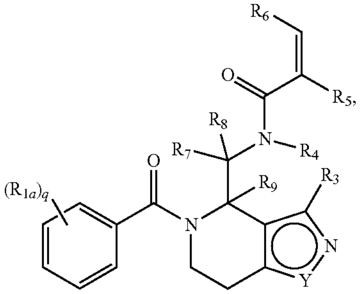

(II-d)

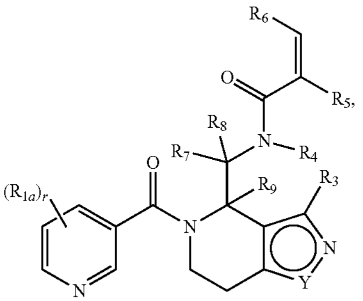

or a pharmaceutically acceptable salt, solvate, clathrate, hydrate, stereoisomer, or tautomer thereof, wherein q is 0, 1, 2, 3, 4, or 5; and r is 0, 1, 2, 3, or 4.

Exemplary Embodiment No. A25. The compound of Exemplary Embodiment No. A1 or Exemplary Embodiment No. A2, wherein the compound is of Formula (II-a1), (II-b1), (II-c1), or (II-d1):

(II-a1)

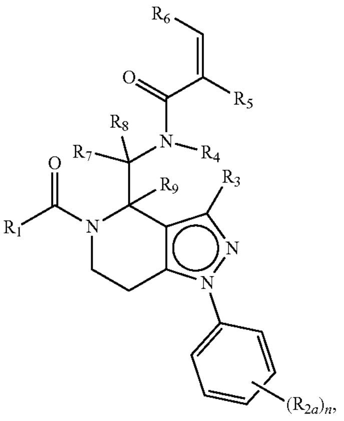

(II-b1)

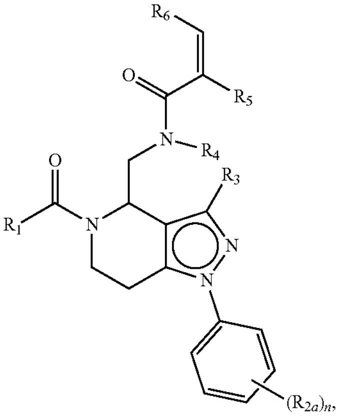

(II-c1)

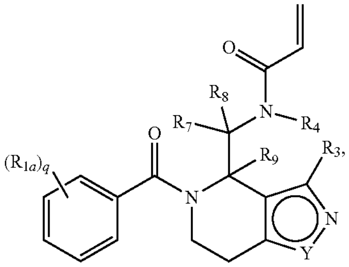

(II-d1)

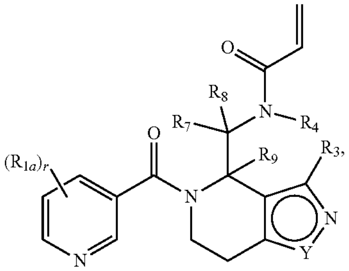

or a pharmaceutically acceptable salt, solvate, clathrate, hydrate, stereoisomer, or tautomer thereof, wherein n is 0, 1, 2, 3, 4, or 5; q is 0, 1, 2, 3, 4, or 5; and r is 0, 1, 2, 3, or 4.

Exemplary Embodiment No. A26. The compound of Exemplary Embodiment No. A1 or Exemplary Embodiment No. A2, wherein the compound is of Formula (III-a'''), (III-b'''), (III-c'''), (III-a''), (III-b''), or (III-c''):

(III-a''')

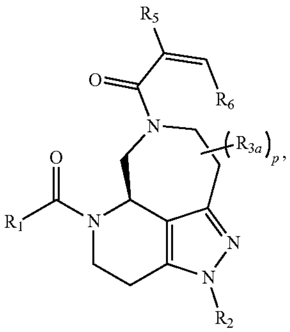

(III-b''')

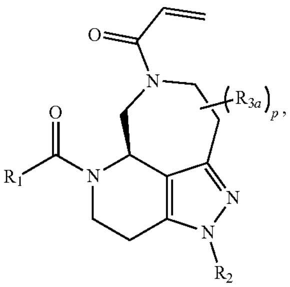

(III-c''')

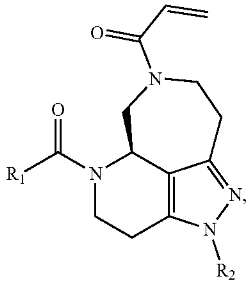

(III-a'')

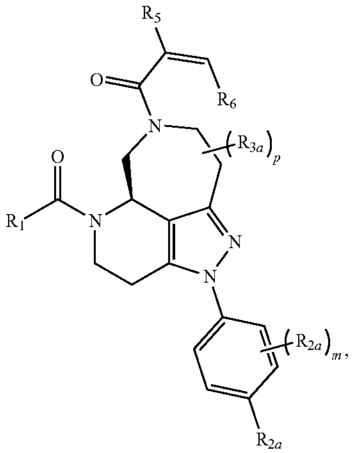

-continued (III-b'')

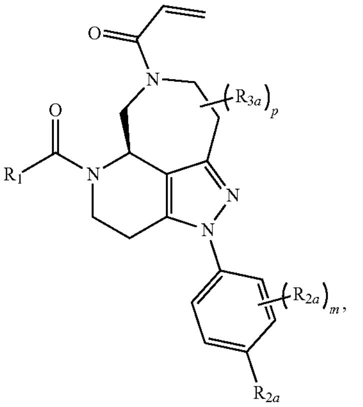

or (III-c'')

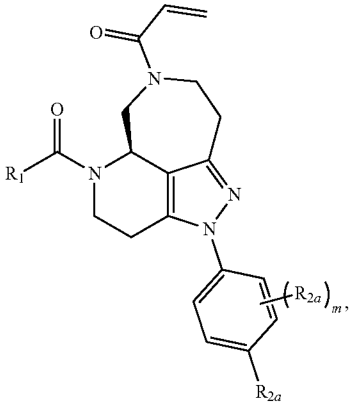

or a pharmaceutically acceptable salt, solvate, clathrate, hydrate, stereoisomer, or tautomer thereof, wherein m is 0, 1, 2, 3, or 4 and p is 0, 1, 2, 3, 4, 5, or 6.

Exemplary Embodiment No. A27. The compound of Exemplary Embodiment No. A1 or Exemplary Embodiment No. A2, wherein the compound is of Formula (IV-a'), (IV-b'), (IV-c'), (IV-d'), (IV-e'), or (IV-f'):

(IV-a')

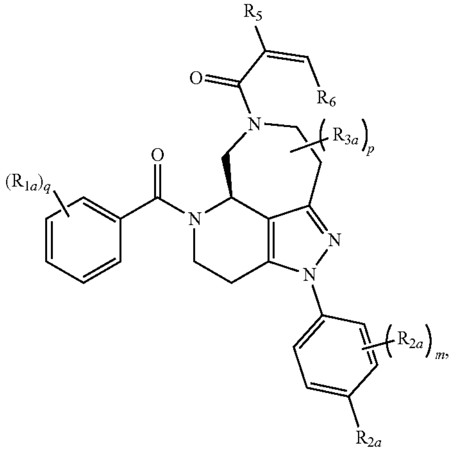

-continued
(IV-b')
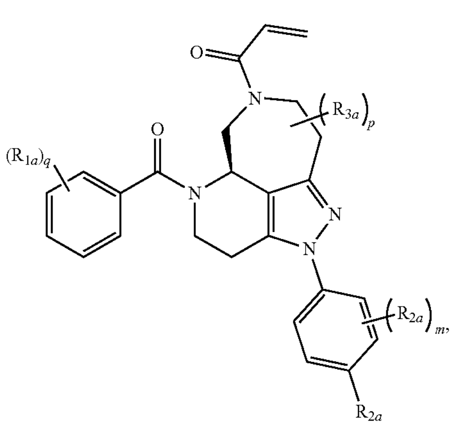
(IV-c')
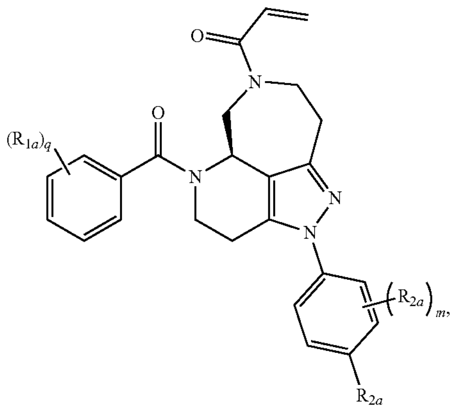
(IV-d')
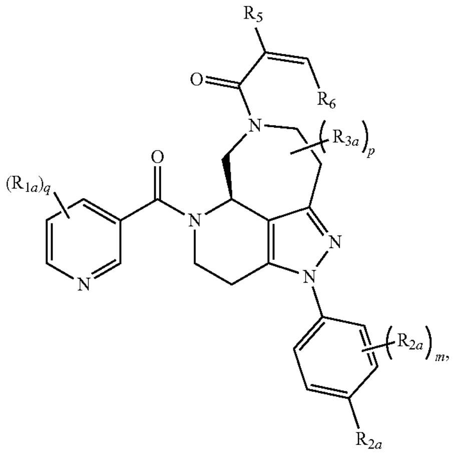
-continued
(IV-e')
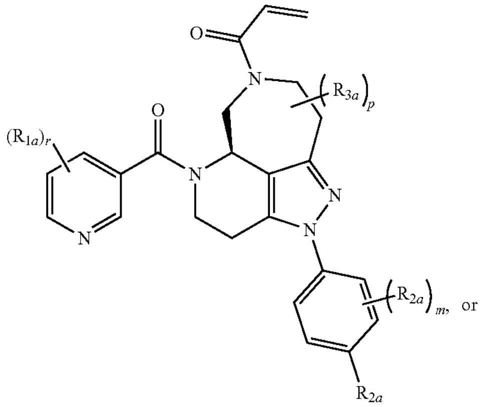
or
(IV-f')
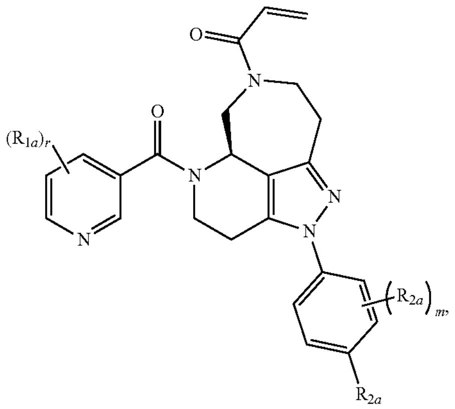
or a pharmaceutically acceptable salt, solvate, clathrate, hydrate, stereoisomer, or tautomer thereof, wherein m is 0, 1, 2, 3, or 4; p is 0, 1, 2, 3, 4, 5, or 6; and r is 0, 1, 2, 3, or 4.
Exemplary Embodiment No. A28. The compound of Exemplary Embodiment No. A1 or Exemplary Embodiment No. A2, wherein the compound is of Formula (V-a'), (V-b'), (V-c'), or (V-d'):
(V-a')
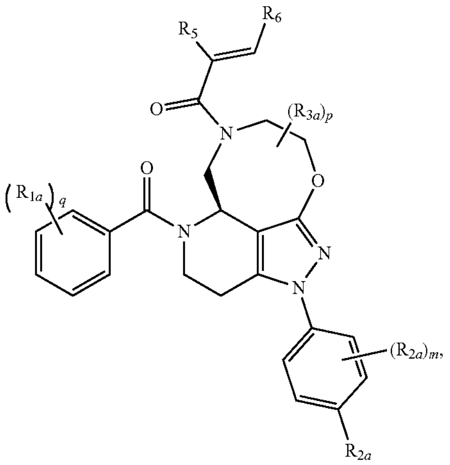

-continued
(V-b')
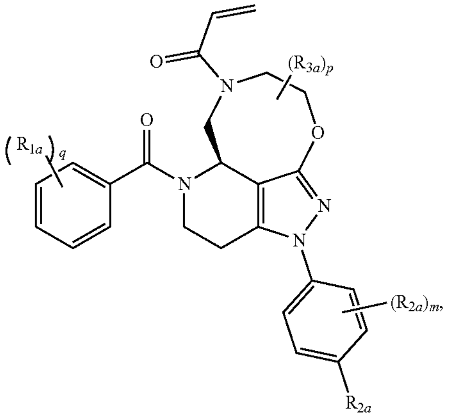
(V-c')
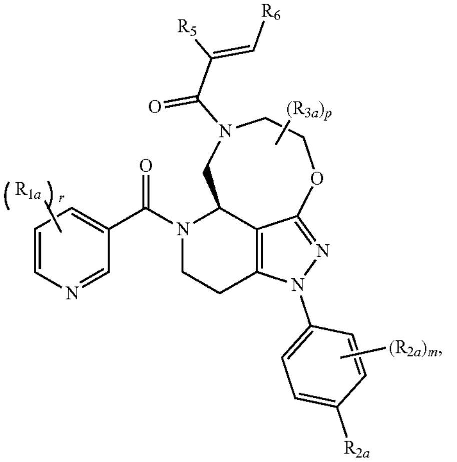
or
(V-d')
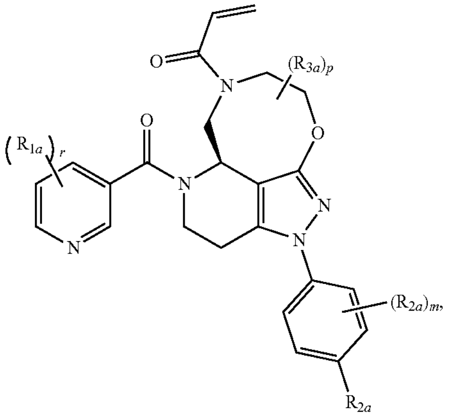
or a pharmaceutically acceptable salt, solvate, clathrate, hydrate, stereoisomer, or tautomer thereof, wherein m is 0, 1, 2, 3, or 4; p is 0, 1, 2, 3, 4, 5, or 6; q is 0, 1, 2, 3, 4, or 5; and r is 0, 1, 2, 3, or 4.
Exemplary Embodiment No. A29. The compound of Exemplary Embodiment No. A1 or Exemplary Embodiment No. A2, wherein the compound is of Formula (VI-a'), (VI-b'), (VI-c'), or (VI-d'):
(VI-a')
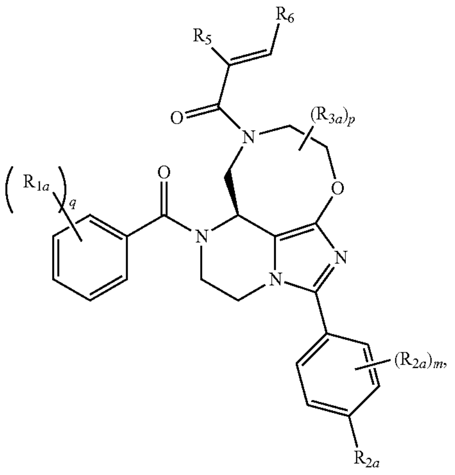
(VI-b')
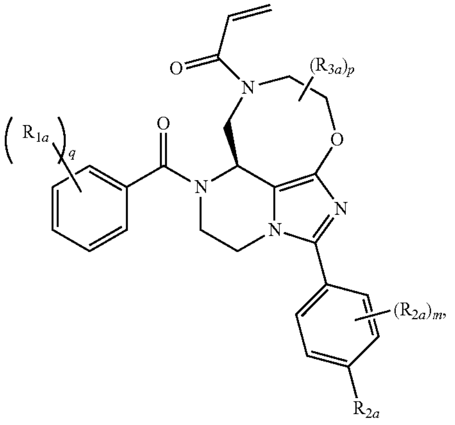
(VI-c')
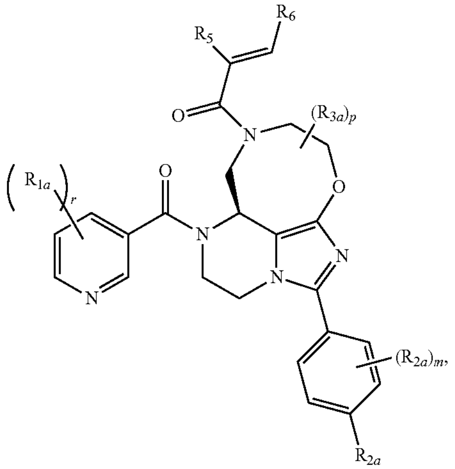
or -continued (VI-d')

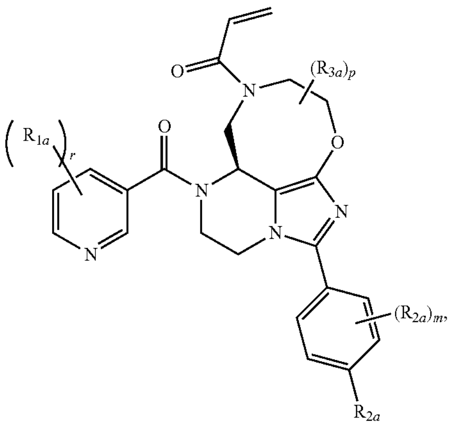

or a pharmaceutically acceptable salt, solvate, clathrate, hydrate, stereoisomer, or tautomer thereof, wherein m is 0, 1, 2, 3, or 4; p is 0, 1, 2, 3, 4, 5, or 6; q is 0, 1, 2, 3, 4, or 5; and r is 0, 1, 2, 3, or 4.

Exemplary Embodiment No. A30. The compound of Exemplary Embodiment No. A1 or Exemplary Embodiment No. A2, wherein the compound is of Formula (VII-a'), (VII-b'), (VII-c'), or (VII-d'):

(VII-a')

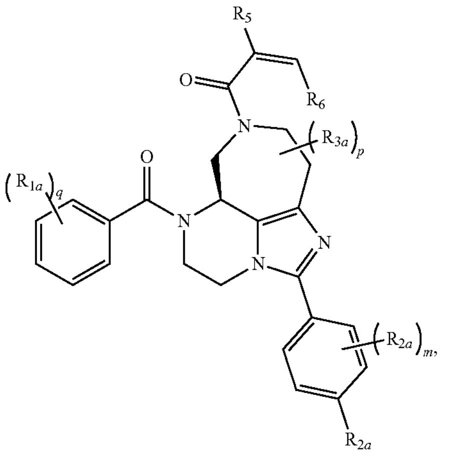

(VII-b')

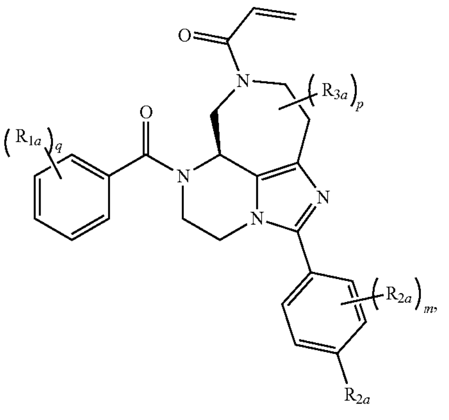

-continued (VII-c¢)

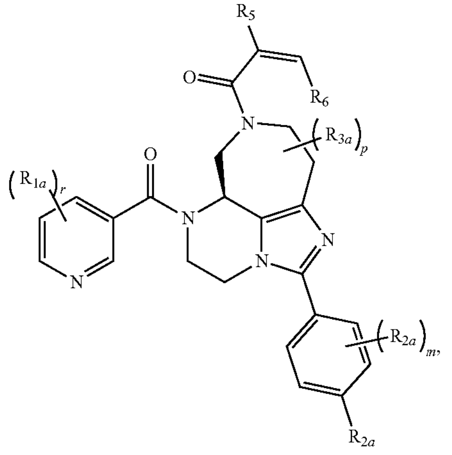

or (VII-d¢)

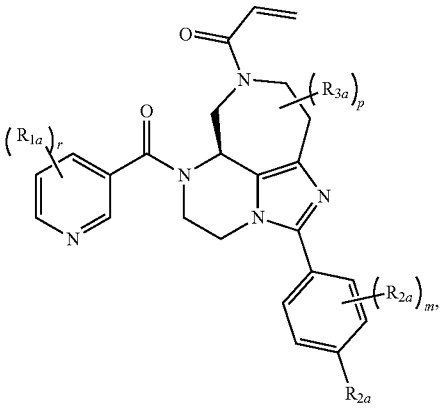

or a pharmaceutically acceptable salt, solvate, clathrate, hydrate, stereoisomer, or tautomer thereof, wherein m is 0, 1, 2, 3, or 4; p is 0, 1, 2, 3, 4, 5, or 6; q is 0, 1, 2, 3, 4, or 5; and r is 0, 1, 2, 3, or 4.

Exemplary Embodiment No. A31. The compound of Exemplary Embodiment No. A1 or Exemplary Embodiment No. A2, wherein the compound is of Formula (VIII-a'), (VIII-b'), (VIII-c'), or (VIII-d'):

(VIII-a')

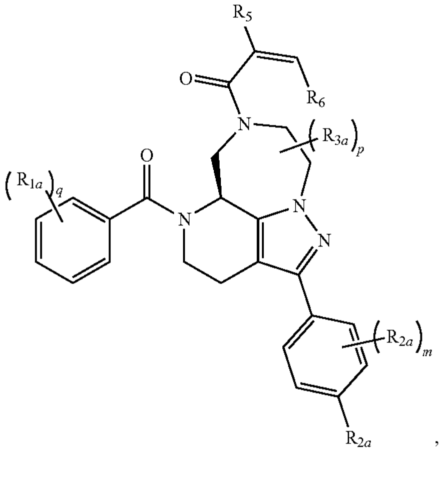

,

-continued (VIII-b')

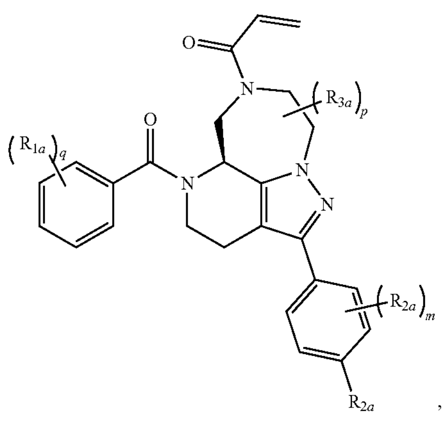

, (VIII-c')

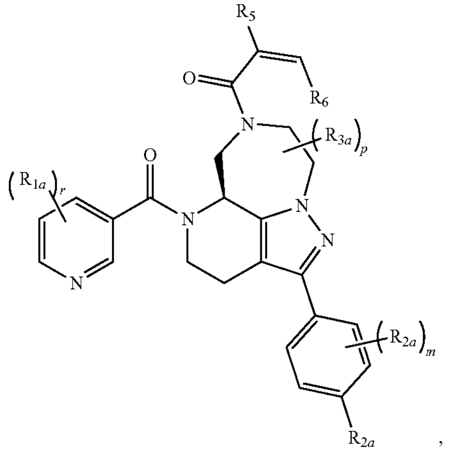

, or (VIII-d')

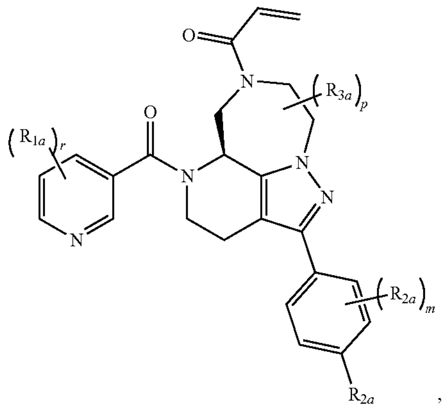

, or a pharmaceutically acceptable salt, solvate, clathrate, hydrate, stereoisomer, or tautomer thereof, wherein mis 0, 1, 2, 3, or 4; p is 0, 1, 2, 3, 4, 5, or 6; q is 0, 1, 23, 4, or 5; and r is 0, 1, 2, 3, or 4.

Exemplary Embodiment No. A32. The compound of any one of the preceding Exemplary Embodiments, wherein the compound is selected from a compound described in Table 1 or Table 2, or a pharmaceutically acceptable salt thereof.

Exemplary Embodiment No. A33. A compound obtainable by, or obtained by, a method described herein; optionally, the method comprises one or more steps described in any one of Schemes 1-14.

Exemplary Embodiment No. A34. A pharmaceutical coin position comprising the compound of any one of the preceding Exemplary Embodiments or a pharmaceutically acceptable salt thereof, and a pharmaceutically acceptable diluent or carrier.

Exemplary Embodiment No. A35. The pharmaceutical composition of Exemplary Embodiment No. A34, wherein the compound is selected from a compound described in Table 1 or Table 2.

Exemplary Embodiment No. A36. A method of modulating WRN activity, comprising contacting a cell with a compound of any one of Exemplary Embodiment Nos. A1-A33 or a pharmaceutical composition of Exemplary Embodiment No. A34 or Exemplary Embodiment No. A35.

Exemplary Embodiment No. A37. The compound of anyone of Exemplary Embodiment Nos. A1-A33 or pharmaceutical composition of Exemplary Embodiment No. A34 or Exemplary Embodiment No. A35 for use in modulating WRN activity.

Exemplary Embodiment No. A38. Use of the compound of any one of Exemplary Embodiment Nos. A1-A33 in the manufacture of a medicament for modulating WRN activity.

Exemplary Embodiment No. A39. A method of treating or preventing a disease or disorder in a subject in need thereof, comprising administering to the subject a compound of any one of Exemplary Embodiment Nos. A1-A33 or pharmaceutical composition of Exemplary Embodiment No. A34 or Exemplary Embodiment No. A35.

Exemplary Embodiment No. A40. The compound of anyone of Exemplary Embodiment Nos. A1-A33 or pharmaceutical composition of Exemplary Embodiment No. A34 or Exemplary Embodiment No. A35 for use in treating or preventing a disease or disorder.

Exemplary Embodiment No. A41. Use of the compound of any one of Exemplary Embodiment Nos. A1-A33 in the manufacture of a medicament for treating or preventing a disease or disorder.

Exemplary Embodiment No. A42. The method, compound, pharmaceutical composition, or use of any-one of Exemplary Embodiment Nos. A39-A41, wherein the disease or disorder is associated with an implicated WRN activity.

Exemplary Embodiment No. A43. The method, compound, pharmaceutical composition, or use of any one of Exemplary Embodiment Nos. A39-A42, wherein the disease or disorder is cancer.

Exemplary Embodiment No. A44. The method, compound, pharmaceutical composition, or use of any one of Exemplary Embodiment Nos. A36-A43, wherein the subject is human.

EXEMPLARY EMBODIMENTS—B

Exemplary Embodiment No. B1. A compound of Formula (I'):

(I')

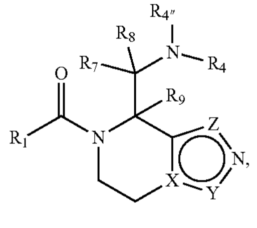

or a pharmaceutically acceptable salt, oxide, solvate, clathrate, hydrate, stereoisomer, or tautomer thereof, wherein:

X is N or C;

Y is $NR_2$ or $CR_2$;

Z is $NR_3$ or $CR_3$;

$R_1$ is $C_1$-$C_6$ alkyl, $C_2$-$C_6$ alkenyl, $C_2$-$C_6$ alkynyl, $C_1$-$C_6$ haloalkyl, $C_3$-$C_{10}$ cycloalkyl, $C_6$-$C_{10}$ aryl, 5- to 10-membered heteroaryl, or 3- to 10-membered heterocyclyl, wherein the $C_1$-$C_6$ alkyl, $C_2$-$C_6$ alkenyl, $C_2$-$C_6$ alkynyl, $C_1$-$C_6$ haloalkyl, $C_3$-$C_{10}$ cycloalkyl, $C_6$-$C_{10}$ aryl, 5- to 10-membered heteroaryl, or 3- to 10-membered heterocyclyl is optionally substituted with one or more $R_{1a}$;

each $R_{1a}$ independently is oxo, halo, cyano, —OH, —$NH_2$, —$NO_2$, —H($C_1$-$C_6$ alkyl), —N($C_1$-$C_6$ alkyl$)_2$, —NH—C(O)($C_1$-$C_6$ alkyl), —S($C_1$-$C_6$ alkyl), —S$(O)_2$($C_1$-$C_6$ alkyl) —S$(O)_2$($NH_2$), —C(O)(H), —C(O)$NH_2$, —O(3- to 10-membered heterocyclyl), $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, $C_3$-$C_{10}$ cycloalkyl, $C_6$-$C_{10}$ aryl, 5- to 10-membered heteroaryl, or 3-to 10-membered heterocyclyl, wherein the —NH($C_1$-$C_6$ alkyl), —N($C_1$-$C_6$ alkyl$)_2$ —NH—C(O)($C_1$-$C_6$ alkyl), —S($C_1$-$C_6$ alkyl), —S$(O)_2$($C_1$-$C_6$ alkyl), —O(3- to 10-membered heterocyclyl), $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, $C_3$-$C_{10}$ cycloalkyl, $C_6$-$C_{10}$ aryl, 5-to 10-membered heteroaryl, or 3- to 10-membered heterocyclyl is optionally substituted with one or more $R_{1b}$;

each $R_{1b}$ independently is oxo, halo, cyano, —OH, —O($C_1$-$C_6$ alkyl), —O($C_1$-$C_6$ haloalkyl), —O($C_2$-$C_6$ alkenyl), —O($C_2$-$C_6$ alkynyl), —$NH_2$, —NH($C_1$-$C_6$ alkyl), —N($C_1$-$C_6$ alkyl$)_2$, —NH($C_1$-$C_6$ haloalkyl), —S($C_1$-$C_6$ alkyl), —S$(O)_2$($C_1$-$C_6$ alkyl), —C(O)$NH_2$, $C_1$-$C_6$ alkyl $C_3$-$C_{10}$ cycloalkyl, or 3-to 10-membered heterocyclyl optionally substituted with oxo;

$R_2$ is $C_1$-$C_6$ alkyl, $C_2$-$C_6$ alkenyl, $C_2$-$C_6$ alkynyl, $C_1$-$C_6$ haloalkyl $C_1$-$C_6$ alkoxy, $C_3$-$C_{10}$ cycloalkyl, $C_6$-$C_{10}$ aryl, 5- to 10-membered heteroaryl, or 3- to 10-membered heterocyclyl, wherein the $C_1$-$C_6$ alkyl, $C_3$-$C_{10}$ cycloalkyl, $C_6$-$C_{10}$ aryl, 5- to 10-membered heteroaryl, or 3- to 10-membered heterocyclyl is optionally substituted with one or more $R_{2a}$;

each $R_{2a}$ independently is oxo, halo, cyano, —OH, —$NH_2$, —NH($C_1$-$C_6$ alkyl), —N($C_1$-$C_6$ alkyl$)_2$, —SH, —S$(O)_2NH_2$, —$SF_5$, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, —S($C_1$-$C_6$ haloalkyl), —S($C_1$-$C_6$ alkyl), $C_3$-$C_{10}$ cycloalkyl, $C_6$-$C_{10}$ aryl, 5- to 10-membered heteroaryl, or 3- to 10-membered heterocyclyl, wherein the $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, —S($C_1$-$C_6$ haloalkyl), —S($C_1$-$C_6$ alkyl), $C_3$-$C_{10}$ cycloalkyl, $C_6$-$C_{10}$ aryl, 5- to 10-membered heteroaryl, or 3- to 10-membered heterocyclyl is optionally substituted with one or more $R_{2a1}$;

each $R_{2a1}$ independently is oxo, halo, cyano, —OH, —$NH_2$, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, —NH—C(O)($C_1$-$C_6$ alkyl), —C(O)$NH_2$, or —OC(O)($C_1$-$C_6$ alkyl), wherein the $C_1$-$C_6$ alkyl, $C_2$-$C_6$ alkenyl, $C_2$-$C_6$ alkynyl, $C_1$-$C_6$ alkoxy, $C_1$-$C_6$ haloalkyl or $C_1$-$C_6$ alkyl is optionally substituted with one or more —OH;

$R_3$ and $R_4$, together with the atoms to which they are attached, form a 6- to 10-membered heterocyclyl, wherein the heterocyclyl optionally comprises one or more additional N, O, or S and is optionally substituted with one or more $R_{3a}$;

each $R_{3a}$ independently is cyano, halo, —OH, —$NH_2$, —NH($C_1$-$C_6$ alkyl), —N($C_1$-$C_6$ alkyl$)_2$, —N($C_1$-$C_6$ alkyl)($C_1$-$C_6$ haloalkyl), —NH—C(O)($C_1$-$C_6$ alkyl), —O($C_3$-$C_{10}$ cycloalkyl), —O(3- to 10-membered heterocyclyl), $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_1$-$C_6$ haloalkoxy, $C_3$-$C_{10}$ cycloalkyl, 3- to 10-membered heterocyclyl, 5- to 10-membered heteroaryl, —S(O)(=NH)($C_1$-$C_6$ alkyl), —$SO_2$($C_1$-$C_6$ alkyl), —S($C_1$-$C_6$ alkyl), or —S($C_1$-$C_6$ haloalkyl), wherein the —NH($C_1$-$C_6$ alkyl), —N($C_1$-$C_6$ alkyl$)_2$, —N($C_1$-$C_6$ alkyl)($C_1$-$C_6$ haloalkyl), —NH—C(O)($C_1$-$C_6$ alkyl), —O($C_3$-$C_{10}$ cycloalkyl), —O(3- to 10-membered heterocyclyl), $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_1$-$C_6$ haloalkoxy, $C_3$-$C_{10}$ cycloalkyl, 3- to 10-membered heterocyclyl, 5- to 10-membered heteroaryl, —S(O)(=NH)($C_1$-$C_6$ alkyl), —$SO_2$($C_1$-$C_6$ alkyl), —S($C_1$-$C_6$ alkyl), or —S($C_1$-$C_6$ haloalkyl) is optionally substituted with one or more oxo, cyano, 3- to 10-membered heterocyclyl, —C(O)($C_1$-$C_6$ alkyl), 5- to 10 -membered heteroaryl optionally substituted with $C_1$-$C_6$ alkyl, $C_1$-$C_6$ alkyl optionally substituted with $C_1$-$C_6$ alkoxy, —N($R_{3a1}$)CO($R_{3a2}$), —O($C_3$-$C_{10}$ cycloalkyl), —O($C_6$-$C_{10}$ aryl), —O(5- to 10-membered heteroaryl), or —O(3- to 10-membered heterocyclyl), or two $R_{3a}$, together with the atoms to which they are attached, form a $C_3$-$C_{10}$ cycloalkyl or 3- to 10-membered heterocyclyl, wherein the cycloalkyl or heterocyclyl is optionally substituted with one or more $C_3$-$C_{10}$ cycloalkyl, 3- to 10-membered heterocyclyl, $C_6$-$C_{10}$ aryl, or 5- to 10-membered heteroaryl, wherein the cycloalkyl, heterocyclyl, aryl, or heteroaryl is optionally substituted with one or more $C_1$-$C_6$ alkyl;

$R_{3a1}$ and $R_{3a2}$, together with the atoms to which they are attached, form a 3- to 10-membered heterocyclyl;

$R_{4''}$ is

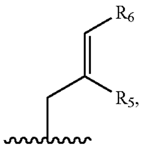 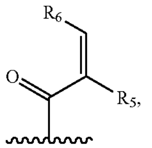 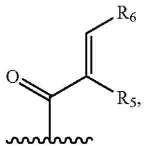 ,

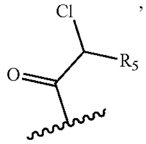 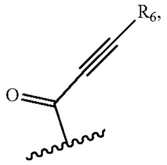 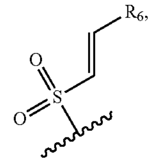

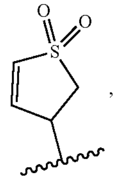 , 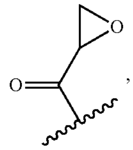 , 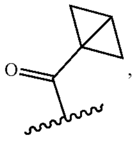 ,

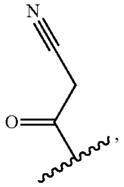 , or 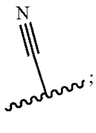 ;

$R_5$ is H, halo, cyano, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy, $R_6$ is H, halo, cyano, —$SO_2$($C_1$-$C_6$ alkyl), $C_1$-$C_6$ alkyl, $C_2$-$C_6$ alkenyl, $C_2$-$C_6$ alkynyl, or $C_1$-$C_6$ alkoxy, wherein the alkyl, alkenyl, alkynyl, or alkoxy is optionally substituted with one or more —OH, —O($C_1$-$C_6$ alkyl), —$NH_2$, —NH($C_1$-$C_6$ alkyl), or —N($C_1$-$C_6$ alkyl), or $R_5$ and $R_6$, together with the atoms to which they are attached, form a $C_4$-$C_{10}$ cycloalkenyl; and each $R_7$, $R_8$, and $R_9$ independently is H, cyano, $C_1$-$C_6$ alkyl, $C_2$—6 alkenyl, $C_2$-$C_6$ alkynyl, $C_1$-$C_6$ haloalkyl, or $C_1$-$C_6$ alkoxy, wherein the alkyl, alkenyl, alkynyl, haloalkyl, or alkoxy is optionally substituted with one or more oxo, halo, cyano, —OH, —$NH_2$, $C_1$-$C_6$ alkoxy, —NH($C_1$-$C_6$ alkyl), —N($C_1$-$C_6$ alkyl)$_2$, —NH($C_1$-$C_6$ haloalkyl), or —S($C_1$-$C_6$ alkyl), or $R_7$ and $R_8$, together with the atoms to which they are attached, form a $C_3$-$C_{10}$ cycloalkyl or 3- to 10-membered heterocyclyl.

Exemplary Embodiment No. B2. A compound of Formula (I):

(I)

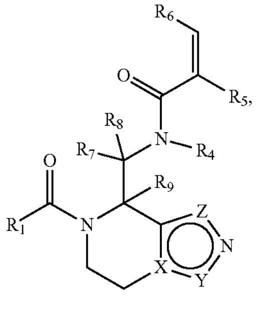

or a pharmaceutically acceptable salt, oxide, solvate, clathrate, hydrate, stereoisomer, or tautomer thereof, wherein:

X is N or C;

Y is $NR_2$ or $CR_2$;

Z is $NR_3$ or $CR_3$;

$R_1$ is $C_1$-$C_6$ alkyl, $C_2$-$C_6$ alkenyl, $C_2$-$C_6$ alkynyl, $C_1$-$C_6$ haloalkyl, $C_3$-$C_{10}$ cycloalkyl, $C_6$-$C_{10}$ aryl, 5- to 10-membered heteroaryl, or 3- to 10-membered heterocyclyl, wherein the $C_1$-$C_6$ alkyl, $C_2$-$C_6$ alkenyl, $C_2$-$C_6$ alkynyl, $C_1$-$C_6$ haloalkyl, $C_3$-$C_{10}$ cycloalkyl, $C_6$-$C_{10}$ aryl, 5- to 10-membered heteroaryl, or 3- to 10-membered heterocyclyl is optionally substituted with one or more $R_{1a}$;

each $R_{1a}$ independently is oxo, halo, cyano, —OH, —$NH_2$, —$NO_2$, —($C_1$-$C_6$ alkyl), —N($C_1$-$C_6$ alkyl)$_2$, —NH—C(O)($C_1$-$C_6$ alkyl), —S($C_1$-$C_6$ alkyl), —S(O)$_2$($C_1$-$C_6$ alkyl) —S(O)$_2$($NH_2$), —C(O)(H), —C(O)$NH_2$, —O(3- to 10-membered heterocyclyl), $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, $C_3$-$C_{10}$ cycloalkyl, $C_6$-$C_{10}$ aryl, 5- to 10-membered heteroaryl, or 3-to 10-membered heterocyclyl, wherein the —NH($C_1$-$C_6$ alkyl), —N($C_1$-$C_6$ alkyl)$_2$, —NH—C(O)($C_1$-$C_6$ alkyl), —S($C_1$-$C_6$ alkyl), —S(O)$_2$($C_1$-$C_6$ alkyl), —O(3- to 10-membered heterocyclyl), $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, $C_3$-$C_{10}$ cycloalkyl, $C_6$-$C_{10}$ aryl, 5-to 10-membered heteroaryl, or 3- to 10-membered heterocyclyl is optionally substituted with one or more $R_{1b}$;

each $R_{1b}$ independently is oxo, halo, cyano, —OH, —O($C_1$-$C_6$ alkyl, —O($C_1$-$C_6$ haloalkyl), —O($C_2$-$C_6$ alkenyl), —O($C_2$-$C_6$ alkynyl), —$NH_2$, —NH($C_1$-$C_6$ alkyl), —N($C_1$-$C_6$ alkyl)$_2$, —NH($C_1$-$C_6$ haloalkyl), —S($C_1$-$C_6$ alkyl), —S(O)$_2$($C_1$-$C_6$ alkyl), —C(O)$NH_2$, $C_1$-$C_6$ alkyl, $C_3$-$C_{10}$ cycloalkyl, or 3-to 10-membered heterocyclyl optionally substituted with oxo;

$R_2$ is $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_3$-$C_{10}$ cycloalkyl, $C_6$-$C_{10}$ aryl, 5- to 10-membered heteroaryl, or 3- to 10-membered heterocyclyl, wherein the $C_1$-$C_6$ alkyl, $C_3$-$C_{10}$ cycloalkyl, $C_6$-$C_{10}$ aryl, 5- to 10-membered heteroaryl, or 3- to 10-membered heterocyclyl is optionally substituted with one or more $R_{2a}$;

each $R_{2a}$ independently is oxo, halo, cyano, —OH, —$NH_2$, —NH($C_1$-$C_6$ alkyl), —N($C_1$-$C_6$ alkyl)$_2$, —SH, —S(O)$_2NH_2$, —$SF_5$, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, —S($C_1$-$C_6$ haloalkyl), —S($C_1$-$C_6$ alkyl), $C_3$-$C_{10}$ cycloalkyl, $C_6$-$C_{10}$ aryl, 5- to 10-membered heteroaryl, or 3- to 10-membered heterocyclyl, wherein the $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, —S($C_1$-$C_6$ haloalkyl), —S($C_1$-$C_6$ alkyl), $C_3$-$C_{10}$ cycloalkyl, $C_6$-$C_{10}$ aryl, 5- to 10-membered heteroaryl, or 3- to 10-membered heterocyclyl is optionally substituted with one or more $R_{2a1}$;

each $R_{2a1}$ independently is oxo, halo, cyano, —OH, —$NH_2$, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, —NH—C(O)($C_1$-$C_6$ alkyl), —C(O)$NH_2$, or —OC(O)($C_1$-$C_6$ alkyl), wherein the $C_1$-$C_6$ alkyl, $C_2$-$C_6$ alkenyl, $C_2$-$C_6$ alkynyl, $C_1$-$C_6$ alkoxy, $C_1$-$C_6$ haloalkyl or $C_1$-$C_6$ alkyl is optionally substituted with one or more —OH;

$R_3$ and $R_4$, together with the atoms to which they are attached, form a 6- to 10-membered heterocyclyl, wherein the heterocyclyl optionally comprises one or more additional N, O, or S and is optionally substituted with one or more $R_{3a}$;

each $R_{3a}$ independently is cyano, halo, —OH, —$NH_2$, —NH($C_1$-$C_6$ alkyl), —N($C_1$-$C_6$ alkyl)$_2$, —N($C_1$-$C_6$ alkyl)($C_1$-$C_6$ haloalkyl), —NH—C(O)($C_1$-$C_6$ alkyl), —O($C_3$-$C_{10}$ cycloalkyl), —O(3- to 10-membered heterocyclyl), $C_1$-$C_6$ alkyl, $C_2$-$C_6$ alkenyl, $C_2$-$C_6$ alkynyl, $C_1$—6 haloalkyl, $C_1$-$C_6$ alkoxy, $C_1$-$C_6$ haloalkoxy, $C_3$-$C_{10}$ cycloalkyl, 3- to 10-membered heterocyclyl, 5- to 10-membered heteroaryl, —S(O)(=NH)($C_1$-$C_6$ alkyl), —$SO_2$($C_1$-$C_6$ alkyl), —S($C_1$-$C_6$ alkyl), or —S($C_1$-$C_6$ haloalkyl), wherein the —NH($C_1$-$C_6$ alkyl), —N($C_1$-$C_6$ alkyl)$_2$, —N($C_1$-$C_6$ alkyl)($C_1$-$C_6$ haloalkyl), —NH—C(O)($C_1$-$C_6$ alkyl), —O($C_3$-$C_{10}$ cycloalkyl), —O(3- to 10-membered heterocyclyl), $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_1$-$C_6$ haloalkoxy, $C_3$-$C_{10}$ cycloalkyl, 3- to 10-membered heterocyclyl, 5- to 10-membered heteroaryl, —S(O)(=NH)($C_1$-$C_6$ alkyl), —$SO_2$($C_1$-$C_6$ alkyl), —S($C_1$-$C_6$ alkyl), or —S($C_1$-$C_6$ haloalkyl), is optionally substituted with one or more oxo, cyano, 3- to 10-membered heterocyclyl, —C(O)($C_1$-$C_6$ alkyl), 5- to 10-membered heteroaryl optionally substituted with $C_1$-$C_6$ alkyl, $C_1$-$C_6$ alkyl optionally substituted with $C_1$-$C_6$ alkoxy, —N($R_{3a1}$)CO($R_{3a2}$), —O($C_3$-$C_{10}$ cycloalkyl), —O($C_6$-$C_{10}$ aryl), —O(5- to 10-membered heteroaryl), or —O(3- to 10-membered heterocyclyl), or two $R_{3a}$, together with the atoms to which they are attached, form a $C_3$-$C_{10}$ cycloalkyl or 3- to 10-membered heterocyclyl, wherein the cycloalkyl or heterocyclyl is optionally substituted with one or more $C_3$-$C_{10}$ cycloalkyl, 3- to 10-membered heterocyclyl, $C_6$-$C_{10}$ aryl, or 5- to 10-membered heteroaryl, wherein the cycloalkyl, heterocyclyl, aryl, or heteroaryl is optionally substituted with one or more $C_1$-$C_6$ alkyl;

$R_{3a1}$ and $R_{3a2}$, together with the atoms to which they are attached form a 3- to 10-membered heterocyclyl;

$R_5$ is H, halo, cyano, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy;

$R_6$ is H, halo, cyano, —$SO_2$($C_1$-$C_6$ alkyl), $C_1$-$C_6$ alkyl, $C_2$-$C_6$ alkenyl, $C_2$-$C_6$ alkynyl, or $C_1$-$C_6$ alkoxy, wherein the alkyl, alkenyl, alkynyl, or alkoxy is optionally substituted with one or more —OH, —O($C_1$-$C_6$ alkyl), —$NH_2$, —NH($C_1$-$C_6$ alkyl), or —N($C_1$-$C_6$ alkyl), or $R_5$ and $R_6$, together with the atoms to which they are attached, form a $C_4$-$C_{10}$ cycloalkenyl; and each $R_7$, $R_8$, and $R_9$ independently is H, cyano, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy, wherein the alkyl, alkenyl, alkynyl, haloalkyl, or alkoxy is optionally substituted with one or more oxo, halo, cyano, —OH, —$NH_2$, $C_1$-$C_6$ alkoxy, —NH($C_1$-$C_6$ alkyl), —N($C_1$-$C_6$ alkyl)$_2$, —NH($C_1$-$C_6$ haloalkyl), or —S($C_1$-$C_6$ alkyl), or $R_7$ and $R_8$, together with the atoms to which they are attached, form a $C_3$-$C_{10}$ cycloalkyl or 3- to 10-membered heterocyclyl.

Exemplary Embodiment No. B3. The compound of Exemplary Embodiment No. B1 or Exemplary Embodiment No. B2, wherein:

X is N or C;

Y is $NR_2$ or $CR_2$;

Z is $NR_3$ or $CR_3$;

$R_1$ is $C_3$-$C_{10}$ cycloalkyl, $C_6$-$C_{10}$ aryl, or 5- to 10-membered heteroaryl, wherein $C_3$-$C_{10}$ cycloalkyl, $C_6$-$C_{10}$ aryl, or 5- to 10-membered heteroaryl is optionally substituted with one or more $R_{1a}$;

each $R_{1a}$ independently is oxo, halo, cyano, —OH, —$NH_2$, —NH($C_1$-$C_6$ alkyl), —$NO_2$, —S($C_1$-$C_6$ alkyl), —S(O)$_2$($NH_2$), —C(O)$NH_2$, —O(3- to 10-membered heterocyclyl), $C_1$-$C_6$ alkyl, $C_1$-$C_6$ alkoxy, $C_1$-$C_6$ haloalkyl, $C_3$-$C_{10}$ cycloalkyl, 5- to 10-membered heteroaryl, or 3- to 10-membered heterocyclyl, wherein the —NH($C_1$-$C_6$ alkyl), —S($C_1$-$C_6$ alkyl), —O(3- to 10-membered heterocyclyl), $C_1$-$C_6$ alkyl, $C_1$-$C_6$ alkoxy, $C_1$-$C_6$ haloalkyl, $C_3$-$C_{10}$ cycloalkyl, 5- to 10-membered heteroaryl, or 3- to 10-membered heterocyclyl is optionally substituted with one or more Rib; each $R_{1b}$ independently is halo, cyano, —OH, —O($C_1$-$C_6$ alkyl), —C(O)$NH_2$, or 3- to 10-membered heterocyclyl;

$R_2$ is $C_1$-$C_6$ alkyl, $C_3$-$C_{10}$ cycloalkyl, $C_6$-$C_{10}$ aryl, or 5- to 10-membered heteroaryl, wherein the $C_1$-$C_6$ alkyl, $C_3$-$C_{10}$ cycloalkyl, $C_6$-$C_{10}$ aryl, or 5- to 10-membered heteroaryl is optionally substituted with one or more $R_{2a}$;

each $R_{2a}$ independently is halo, cyano, —OH, —$NH_2$, $C_1$-$C_6$ alkyl, $C_6$-$C_{10}$ aryl, $C_3$-$C_{10}$ cycloalkyl, $C_1$-$C_6$ alkoxy, $C_1$-$C_6$ haloalkyl, —S($C_1$-$C_6$ alkyl), wherein the $C_1$-$C_6$ alkyl, $C_6$-$C_{10}$ aryl, $C_3$-$C_{10}$ cycloalkyl, $C_1$-$C_6$ alkoxy, $C_1$-$C_6$ haloalkyl, or —S($C_1$-$C_6$ alkyl) is optionally substituted with one or more $R_{2a1}$;

each $R_{2a1}$ independently is halo or —OH;

each $R_{3a}$ independently is halo, —OH, —O($C_3$-$C_{10}$ cycloalkyl), —O(3- to 10-membered heterocyclyl), $C_1$-$C_6$ alkyl, $C_1$-$C_6$ alkoxy, 5- to 10-membered heteroaryl, wherein the —O($C_3$-$C_{10}$ cycloalkyl), —O(3- to 10-membered heterocyclyl), $C_1$-$C_6$ alkyl, $C_1$-$C_6$ alkoxy, 5- to 10-membered heteroaryl is optionally substituted with one or more oxo, cyano, 3- to 10-membered heterocyclyl, —C(O)($C_1$-$C_6$ alkyl), 5- to 10-membered heteroaryl optionally substituted with $C_1$-$C_6$ alkyl, or $C_1$-$C_6$ alkyl optionally substituted with $C_1$-$C_6$ alkoxy, or two $R_{3a}$, together with the atoms to which they are attached, form a $C_3$-$C_{10}$ cycloalkyl or 3- to 10-membered heterocyclyl, wherein the $C_3$-$C_{10}$ cycloalkyl or 3- to 10-membered heterocyclyl is optionally substituted with one or more 5- to 10-membered heteroaryl, wherein the 5- to 10-membered heteroaryl is optionally substituted with one or more $C_1$-$C_6$ alkyl;

$R_{4''}$ is

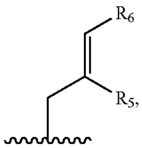,
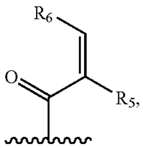, or
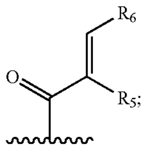;

$R_5$ is H or halo, $R_6$ is H, halo, —$SO_2$($C_1$-$C_6$ alkyl), or $C_1$-$C_6$ alkyl optionally substituted with one or more —O($C_1$-$C_6$ alkyl), or —N($C_1$-$C_6$ alkyl)$_2$, or $R_5$ and $R_6$, together with the atoms to which they are attached, form a $C_4$-$C_{10}$ cycloalkenyl; and each $R_7$, $R_8$, and $R_9$ independently is H or $C_1$-$C_6$ alkyl.

Exemplary Embodiment No. B4. The compound of any one of the preceding Exemplary Embodiments, wherein X is C.

Exemplary Embodiment No. B5. The compound of any one of the preceding Exemplary Embodiments, wherein Y is $NR_2$.

Exemplary Embodiment No. B6. The compound of any one of the preceding Exemplary Embodiments, wherein Z is $CR_3$.

Exemplary Embodiment No. B7. The compound of anyone of the preceding Exemplary Embodiments, wherein $R_1$ is $C_3$-$C_{10}$ cycloalkyl, $C_6$-$C_{10}$ aryl, or 5- to 0-membered heteroaryl, wherein the $C_3$-$C_{10}$ cycloalkyl, $C_6$-$C_{10}$ aryl, or 5- to 10-membered heteroaryl is substituted with one or more Ria.

Exemplary Embodiment No. B8. The compound of any one of the preceding Exemplary Embodiments, wherein $R_1$ is

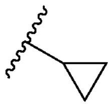,
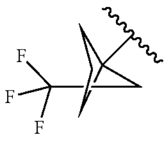,
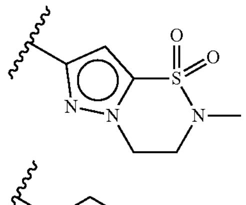,
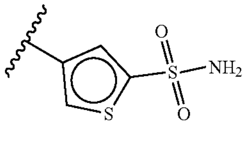,
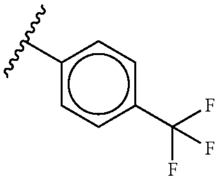,
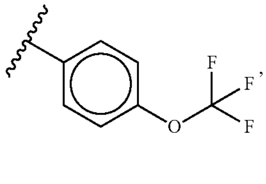,
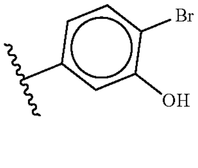, -continued
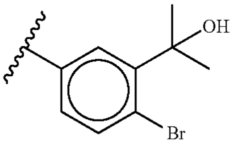,
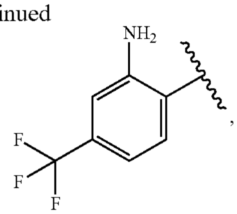,
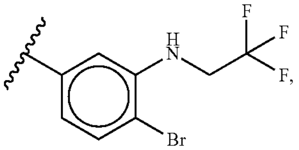
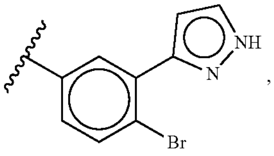,
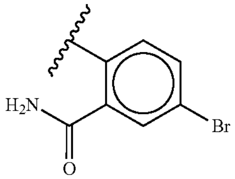,
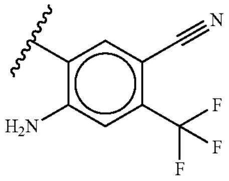,
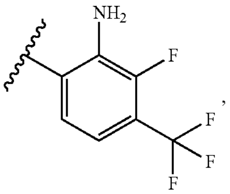,
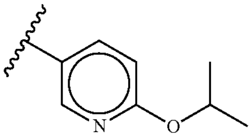,
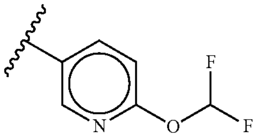,
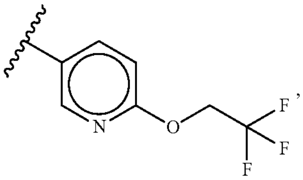,
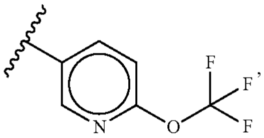,
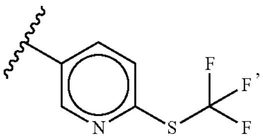,
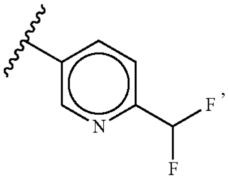,
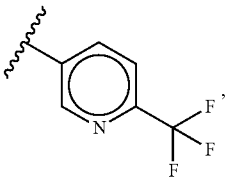,
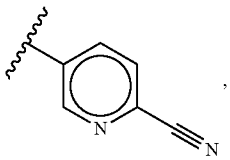,
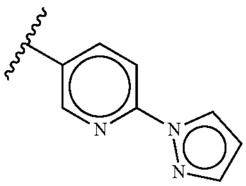,
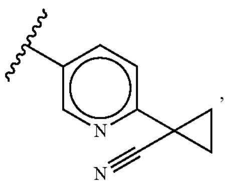,
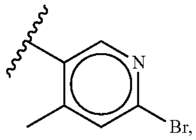,
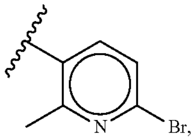
-continued
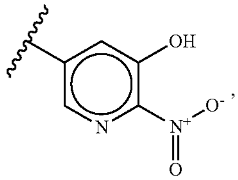,
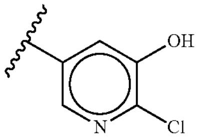,
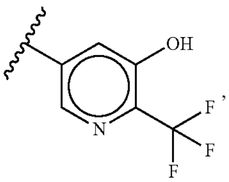,
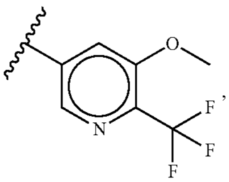,
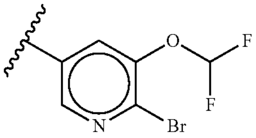,
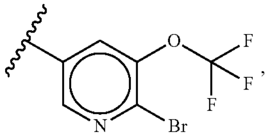,
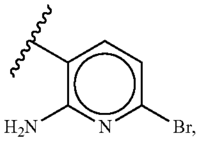
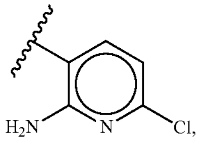
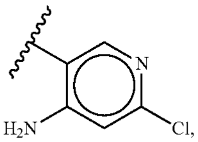
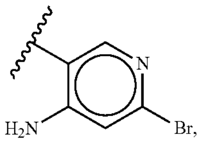
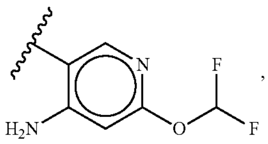,
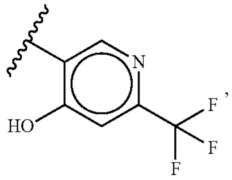,
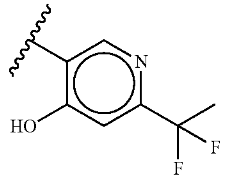,
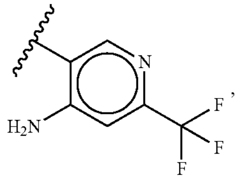,
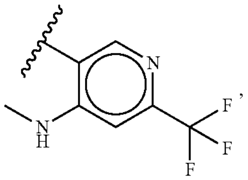,
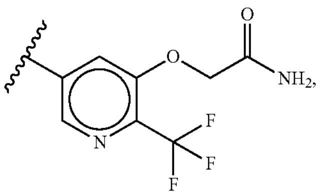

-continued
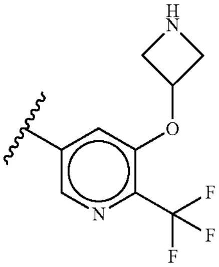,
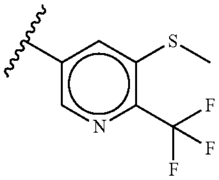,
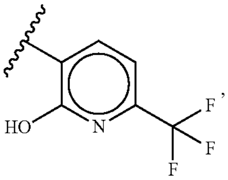,
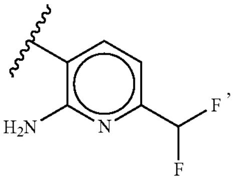,
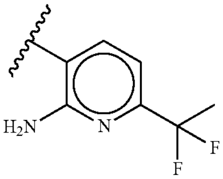,
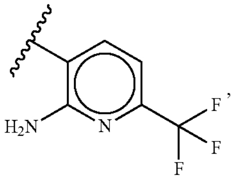,
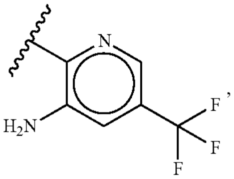,
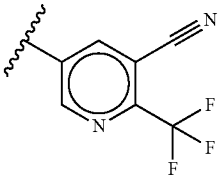,
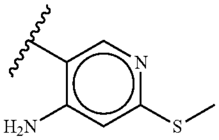,
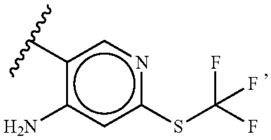,
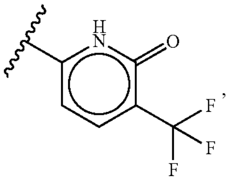,
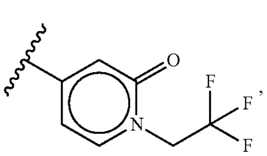,
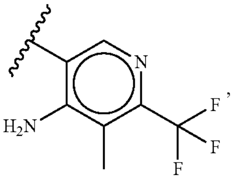,
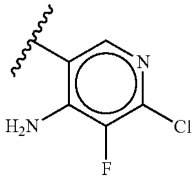,
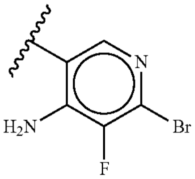,
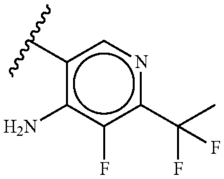,
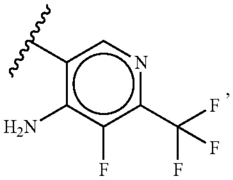,
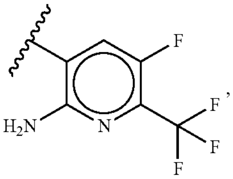,
-continued
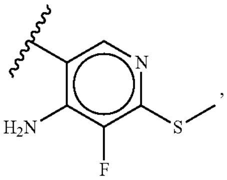,
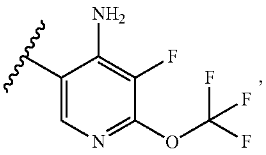,
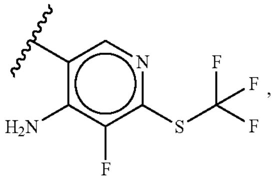,
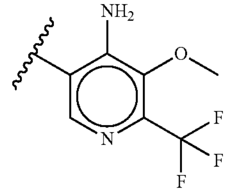,
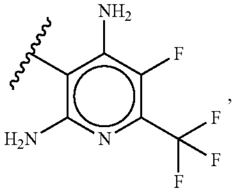,
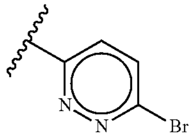,
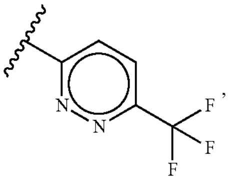,
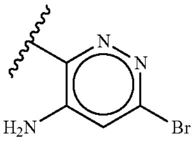,
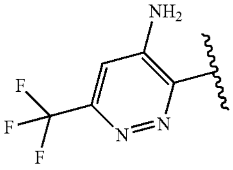,
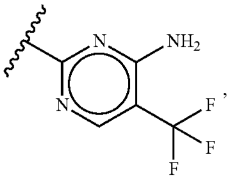,
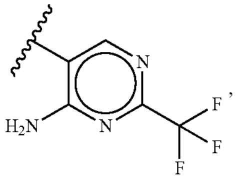,
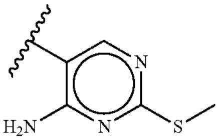,
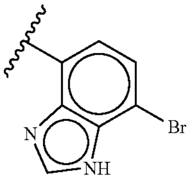,
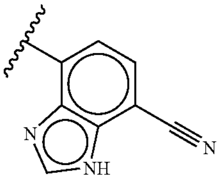,
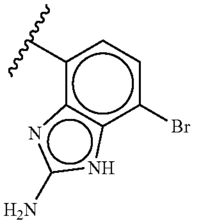,
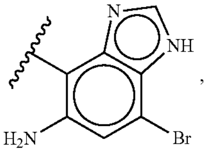,
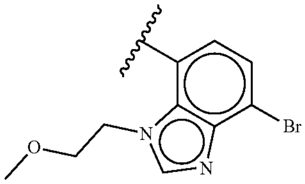, -continued

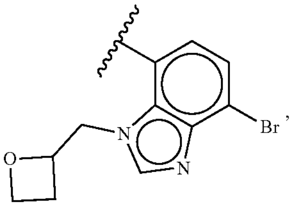

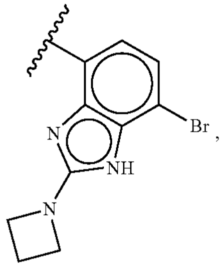

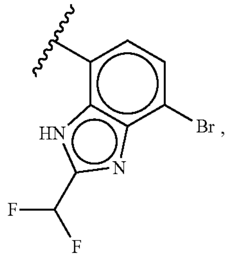

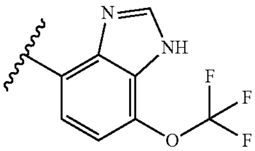

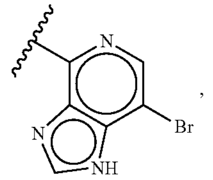

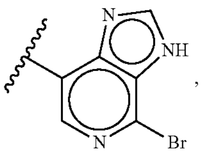

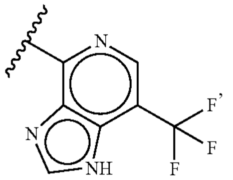

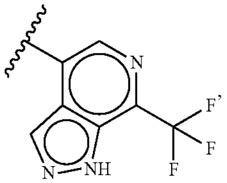

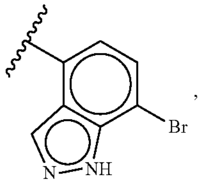

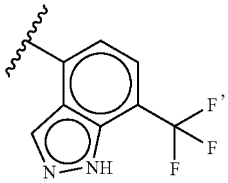

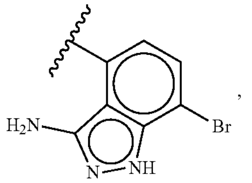

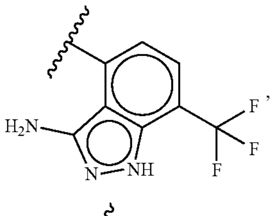

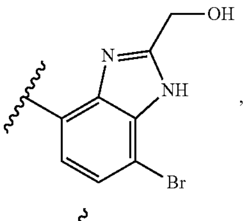

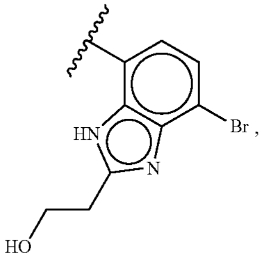

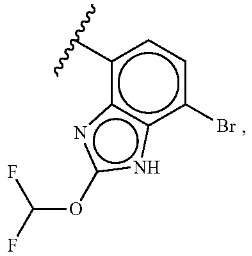

-continued

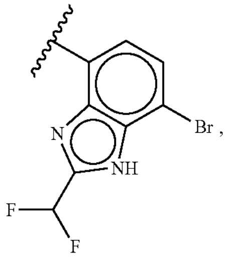

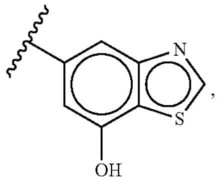

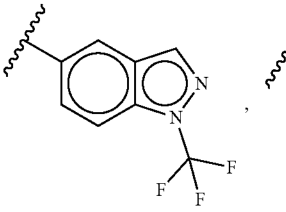

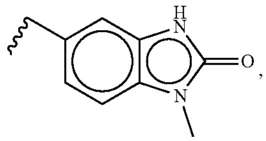

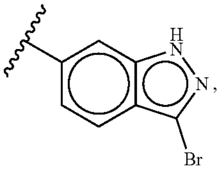

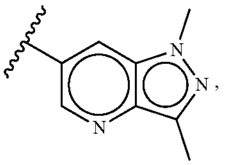

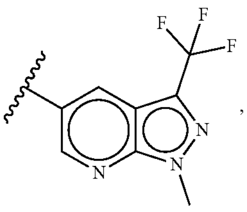

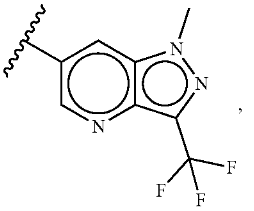

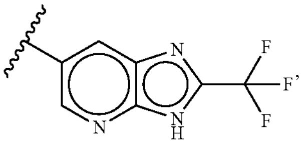

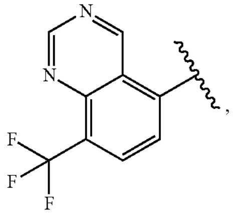

or

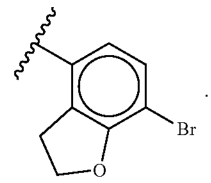

Exemplary Embodiment No. B9. The compound of any one of the preceding Exemplary Embodiments, wherein Ria independently is oxo, halo, cyano, —OH, —$NH_2$, —NH($C_1$-$C_6$ alkyl), —$NO_2$, —S($C_1$-$C_6$ alkyl), —$S(O)_2(NH_2)$, —C(O)$NH_2$, —O(3- to 10-membered heterocyclyl), $C_1$-$C_6$ alkyl, $C_1$-$C_6$ alkoxy, $C_1$-$C_6$ haloalkyl, $C_3$-$C_{10}$ cycloalkyl, 5- to 10-membered heteroaryl, or 3- to 10-membered heterocyclyl, wherein the —NH($C_1$-$C_6$ alkyl), —S($C_1$-$C_6$ alkyl), —O(3- to 10-membered heterocyclyl), $C_1$-$C_6$ alkyl, $C_1$-$C_6$ alkoxy, $C_1$-$C_6$ haloalkyl, $C_3$-$C_{10}$ cycloalkyl, 5- to 10-membered heteroaryl, or 3- to 10-membered heterocyclyl is optionally substituted with one or more Rib.

Exemplary Embodiment No. B10. The compound of any one of the preceding Exemplary Embodiments, wherein Ria independently is oxo, fluoro, chloro, bromo, cyano, —OH, —$OCH_3$, —$OCHF_2$, —$OCF_3$, —$OCH_2CF_3$, —$OCH(CH_3)_2$, —$OCH_2C(O)NH_2$, —SCH, —$SCF_3$, —$NH_2$, —$NH(CH_3)$, —$NH(CH_2CF_3)$, —$NO_2$, —$CH_3$, —$CH_2OH$, —$(CH_2)_2OH$, —$(CH_2)_2OCH_3$, —$CHF_2$, —$CF_2CH_3$, —$CH_2CF_3$, —$CF_3$, —$S(O)_2(NH_2)$, —C(O)$NH_2$,

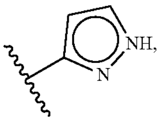, 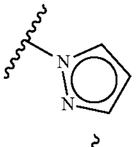, 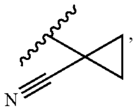, 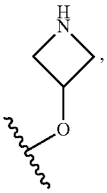, 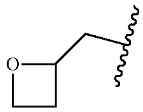, or 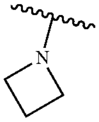.

Exemplary Embodiment No. B11. The compound of any one of the preceding Exemplary Embodiments, wherein $R_2$ is $C_1$-$C_6$ alkyl, $C_3$-$C_{10}$ cycloalkyl $C_6$-$C_{10}$ aryl, or 5- to 10-membered heteroaryl, wherein the $C_1$-$C_6$ alkyl, $C_3$-$C_{10}$ cycloalkyl, $C_6$-$C_{10}$ aryl, or 5- to 10-membered heteroaryl is optionally substituted with one or more $R_{2a}$ Exemplary Embodiment No. B12. The compound of any one of the preceding Exemplary Embodiments, wherein $R_2$ is:

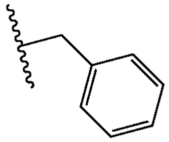, 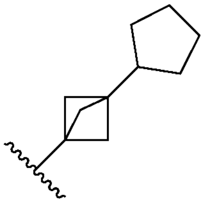,

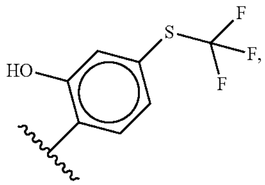 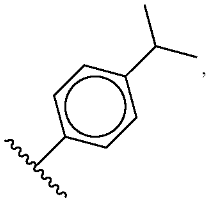,

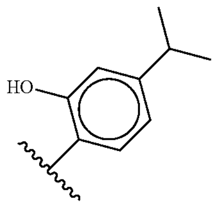, 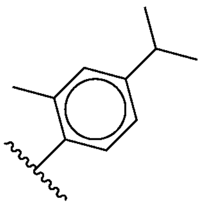,

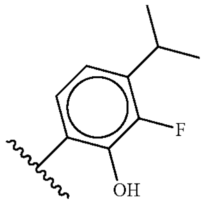, 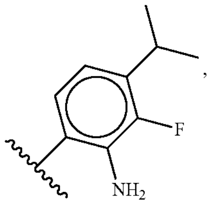,

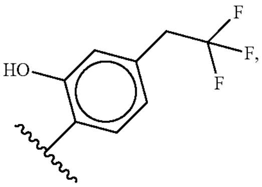 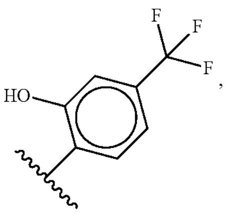,

-continued

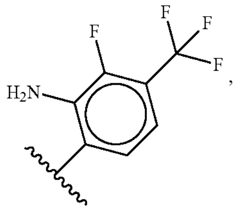, 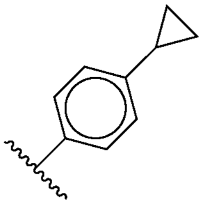,

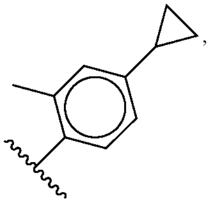, 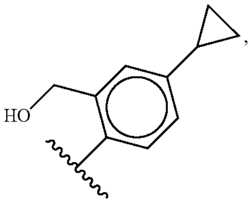,

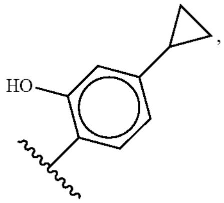, 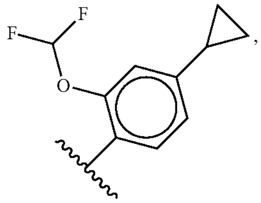,

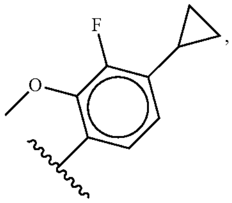, 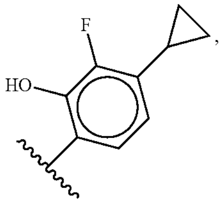,

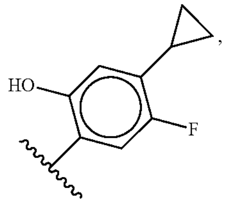, 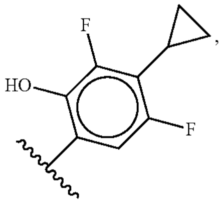,

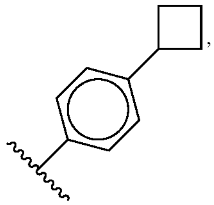, 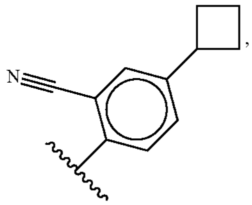,

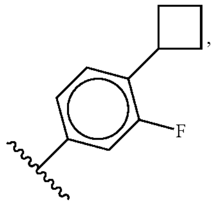, 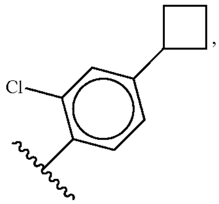,

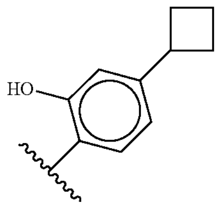, 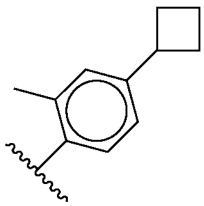,

-continued

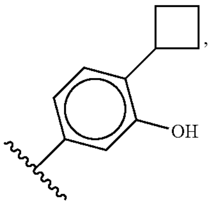

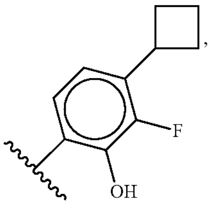

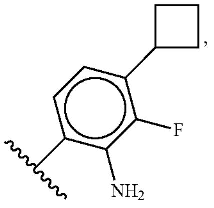

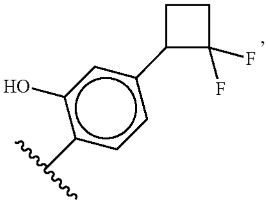

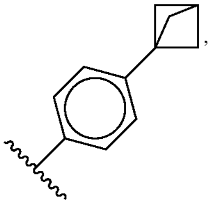

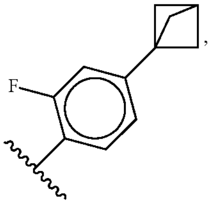

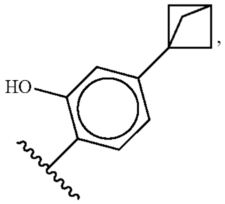

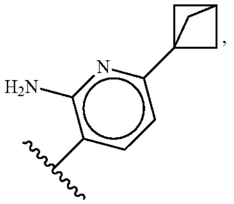

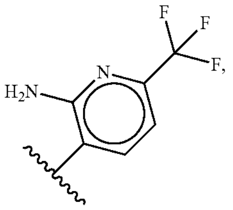

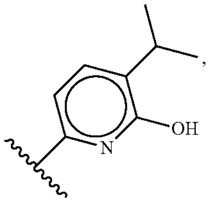

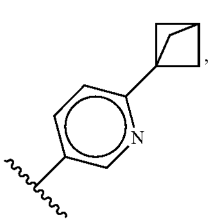

or

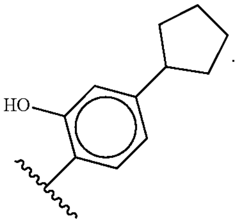

Exemplary Embodiment No. B13. The compound of any one of the preceding Exemplary Embodiments, wherein each $R_{2a}$ independently halo, cyano, —OH, —$NH_2$, $C_1$-$C_6$ alkyl, $C_6$-$C_{10}$ aryl, $C_3$-$C_{10}$ cycloalkyl, $C_1$-$C_6$ alkoxy, $C_1$-$C_6$ haloalkyl, —S($C_1$-$C_6$ alkyl), wherein the $C_1$-$C_6$ alkyl, $C_6$-$C_{10}$ aryl, $C_3$-$C_{10}$ cycloalkyl, $C_1$-$C_6$ alkoxy, $C_1$-$C_6$ haloalkyl, or —S($C_1$-$C_6$ alkyl) is optionally substituted with one or more $R_{2a1}$.

Exemplary Embodiment No. B14. The compound of any one of the preceding Exemplary Embodiments, wherein each $R_{2a}$ independently is fluoro, chloro, cyano, —OH, —$NH_2$, phenyl, cyclopropyl, cyclobutyl, cyclopentyl, —$OCH_3$, —$OCHF_2$, —$SCF_3$, —$CH_3$, —$CH(CH_3)_2$, —$CH_2OH$, —$CF_3$, —$CH(CF_3)_2$,

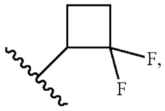

or

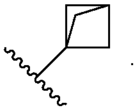

Exemplary Embodiment No. B15. The compound of an one of the preceding Exemplary Embodiments, wherein $R_3$ and $R_4$, together with the atoms t which they are attached, form a 6-membered heterocyclyl optionally substituted with one or more $R_{3a}$.

Exemplary Embodiment No. B16. The compound of any one of the preceding Exemplary Embodiments, wherein $R_3$ and $R_4$, together with the atoms to which they are attached, form a 7-membered heterocyclyl optionally substituted with one or more $R_{3a}$.

Exemplary Embodiment No. B17. The compound of any one of the preceding Exemplary Embodiments, wherein $R_3$ and $R_4$, together with the atoms to which they are attached, form a 8-membered heterocyclyl, wherein the heterocyclyl optionally comprises one or more additional O and is optionally substituted with one or more $R_{3a}$.

Exemplary Embodiment No. B18. The compound of any one of the preceding Exemplary Embodiments, wherein each $R_{3a}$ independently is halo, —OH, —O($C_3$-$C_{10}$ cycloalkyl), —O(3- to 10-membered heterocyclyl), $C_1$-$C_6$ alkyl, $C_1$-$C_6$ alkoxy, 5- to 10-membered heteroaryl, wherein the —O($C_3$-$C_{10}$ cycloalkyl), —O(3- to 10-membered heterocyclyl), $C_1$-$C_6$ alkyl, $C_1$-$C_6$ alkoxy, 5- to 10-membered heteroaryl is optionally substituted with one or more oxo, cyano, 3- to 10-membered heterocyclyl, —C(O)($C_1$-$C_6$ alkyl), 5- to 10-membered heteroaryl optionally substituted with $C_1$-$C_6$ alkyl, or $C_1$-$C_6$ alkyl optionally substituted with $C_1$-$C_6$ alkoxy.

Exemplary Embodiment No. B19. The compound of an one of the preceding Exemplary Embodiments, wherein each $R_{3a}$ independently is F, $CH_3$, —OH, —$OCH_3$, —O(cyclopropyl),

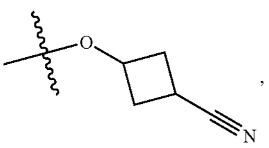

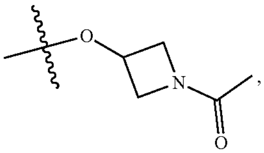

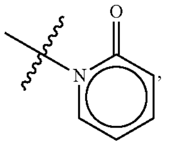

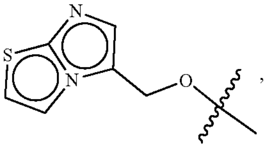

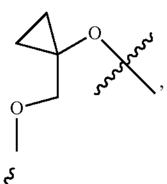

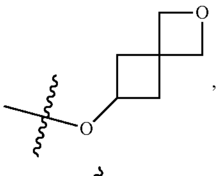

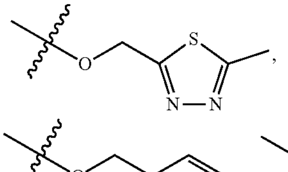

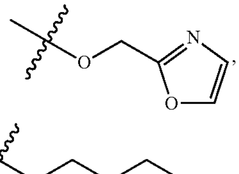

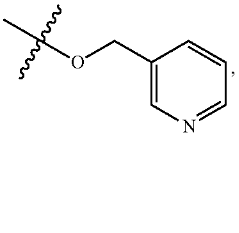

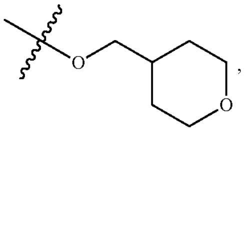

or

-continued

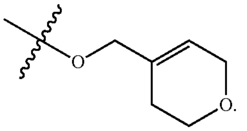

Exemplary Embodiment No. B20. The compound of any one of the preceding Exemplary Embodiments, wherein $R_5$ is H or halo.

Exemplary Embodiment No. B21. The compound of any one of the preceding Exemplary Embodiments, wherein $R_6$ is H, chloro, —$SO_2$($C_1$-$C_6$ alkyl), or $C_1$-$C_6$ alkyl optionally substituted with —N($C_1$-$C_6$ alkyl)$_2$ or —O($C_1$-$C_6$ alkyl).

Exemplary Embodiment No. B22. The compound of any one of the preceding Exemplary Embodiments, wherein $R_5$ and $R_6$, together with the atoms to which they are attached, form a $C_4$ cycloalkenyl.

Exemplary Embodiment No. B23. The compound of any one of the preceding Exemplary Embodiments, wherein each $R_7$, $R_8$, and $R_9$ independently is H.

Exemplary Embodiment No. B24. The compound of any one of the preceding Exemplary Embodiments, wherein the compound is of Formula (II-a), II-b), (II-c), (II-d), or (II-e):

(II-a)

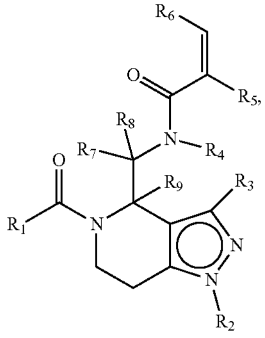

(II-b)

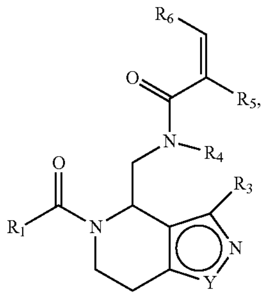

(II-c)

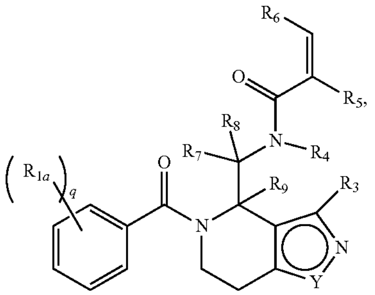

-continued (II-d)

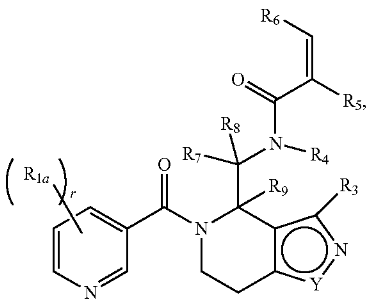

or (II-e)

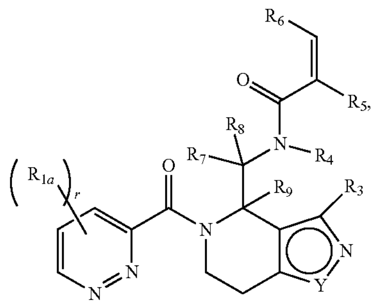

or a pharmaceutically acceptable salt, solvate, clathrate, hydrate, stereoisomer, or tautomer thereof, wherein q is 0, 1, 2, 3, 4, or 5; and r is 0, 1, 2, 3, or 4.

Exemplary Embodiment No. B25. The compound of Exemplary Embodiment No. B1 or Exemplary Embodiment No. B2, wherein the compound is of Formula (I-a1), (II-b1), (II-c1), (II-d1), or (11-e1):

(II-a1)

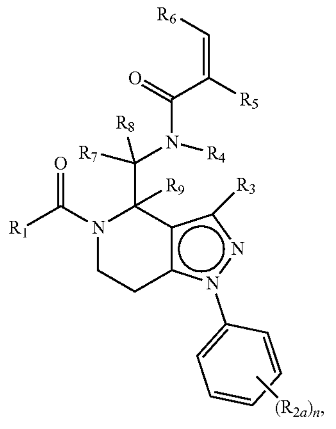

-continued
(II-b1)
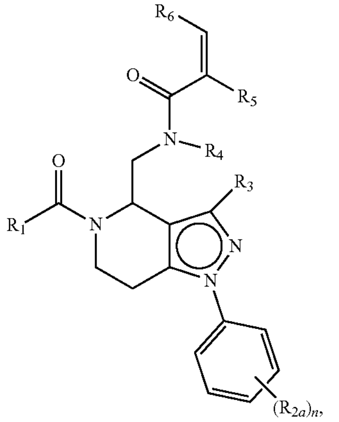
(II-c1)
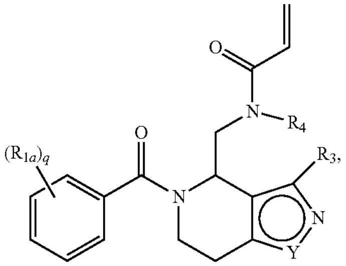
(II-d1)
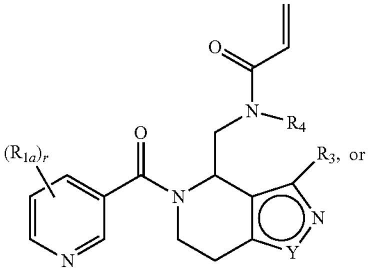
or
(II-e1)
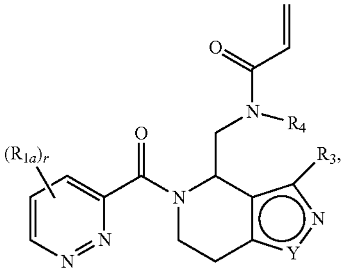
or a pharmaceutically acceptable salt, solvate, clathrate, hydrate, stereoisomer, or tautomer thereof, wherein n is 0, 1, 2, 3, 4, or 5; q is 0, 1, 2, 3, 4, or 5; and r is 0, 1, 2, 3, or 4.
Exemplary Embodiment No. B26. The compound of Exemplary Embodiment No. B1 or Exemplary Embodiment No. B2, wherein the compound is of Formula (III-a'), (III-b'), (III-c'), (III-a), (III-b), or (III-c):
(III-a')
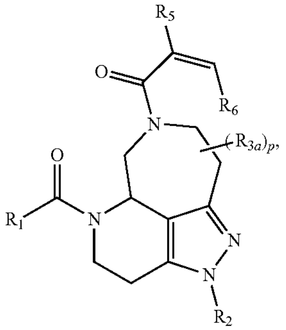
(III-b')
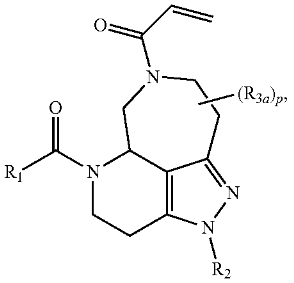
(III-c')
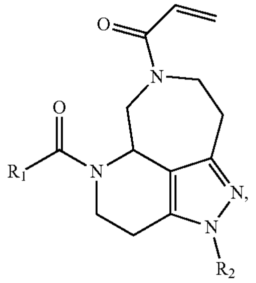
(III-a)
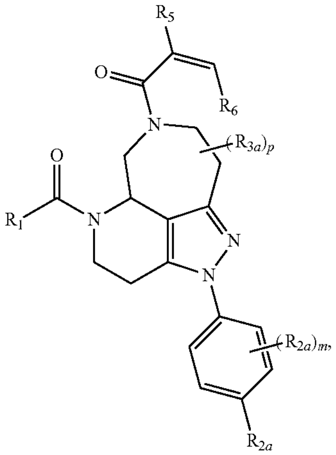

-continued (III-b)

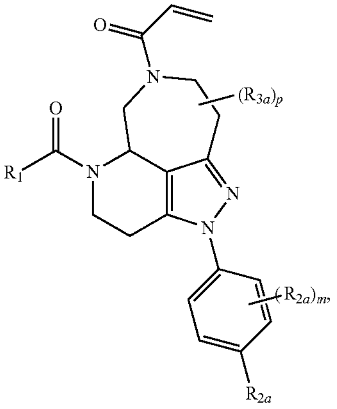

or (III-c)

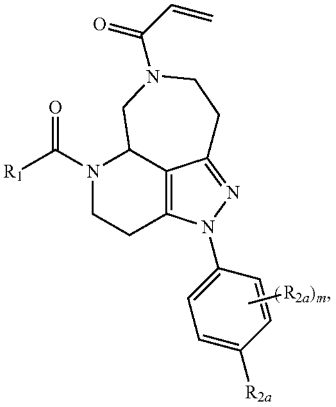

or a pharmaceutically acceptable salt, solvate, clathrate, hydrate, stereoisomer, or tautomer thereof, wherein m is 0, 1, 2, 3, or 4 and p is 0, 1, 2, 3, 4, 5, or 6.

Exemplary Embodiment No. B27. The compound of Exempla Embodiment No. B1 or Exemplary Embodiment No. B2, wherein the compound is of Formula (III-a'''), (III-b'''), (III-c'''), (III-a''), (III-b''), or (III-c''):

(III-a''')

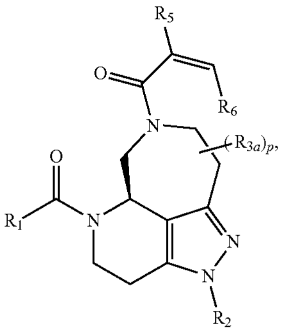

-continued (III-b''')

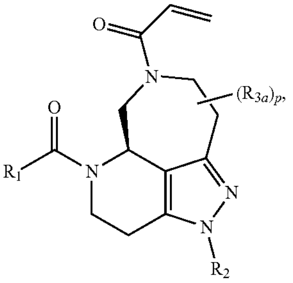

(III-c''')

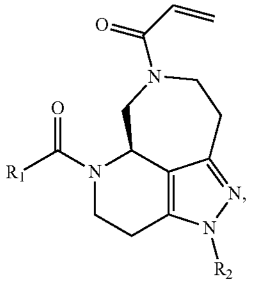

(III-a'')

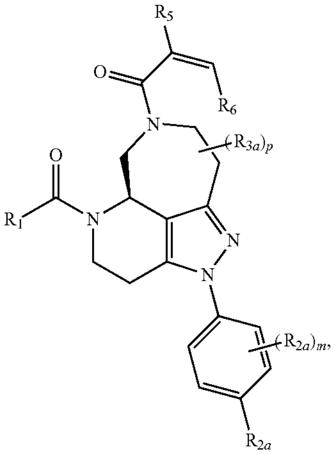

(III-b'')

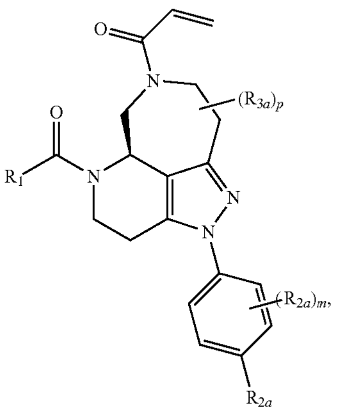

or

-continued
(III-c″)
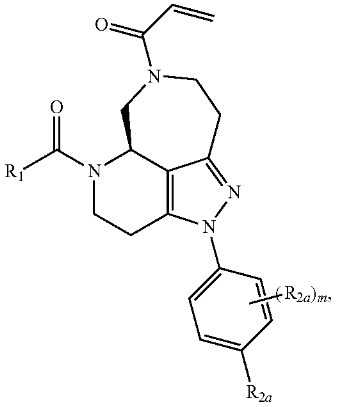
or a pharmaceutically acceptable salt, solvate, clathrate, hydrate, stereoisomer, or tautomer thereof, wherein m is 0, 1, 2, 3, or 4 and p is 0, 1, 2, 3, 4, 5, or 6.
Exemplary Embodiment No. B28. The compound of Exempla Embodiment No. B1 or Exemplary Embodiment No. B2, wherein the compound is of Formula (IV-a), (IV-b), (IV-c), (IV-d), (IV-e), (IV-f), (IV-g), (IV-h), or (IV-i):
(IV-a)
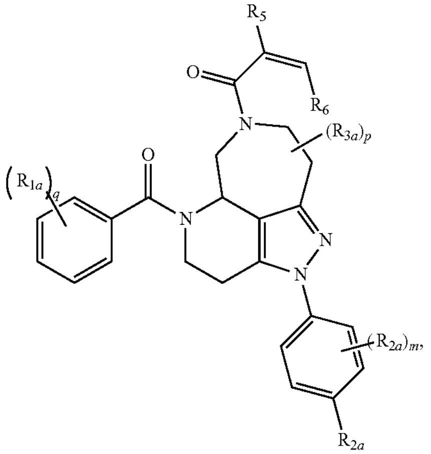
(IV-b)
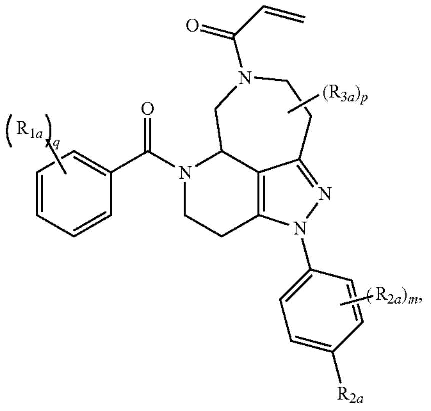
-continued
(IV-c)
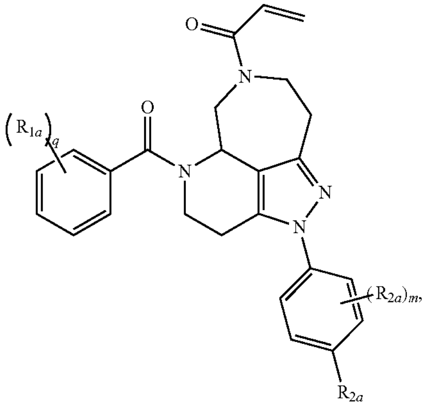
(IV-d)
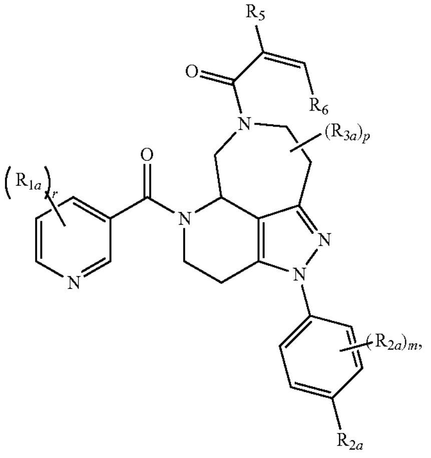
(IV-e)
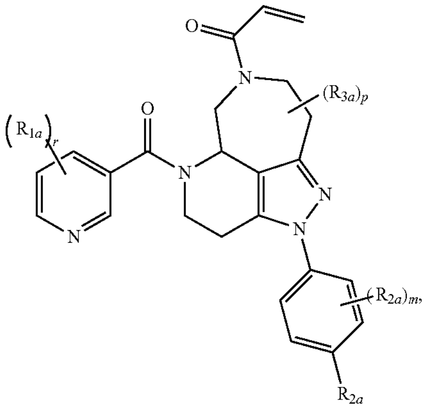

-continued
(IV-f)
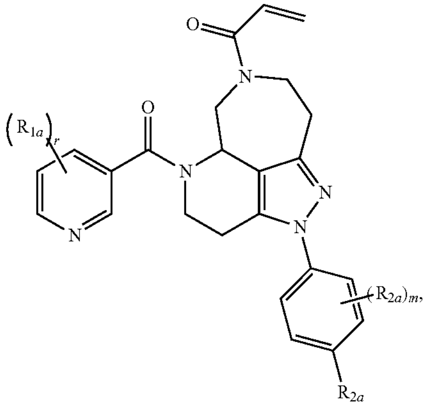
(IV-g)
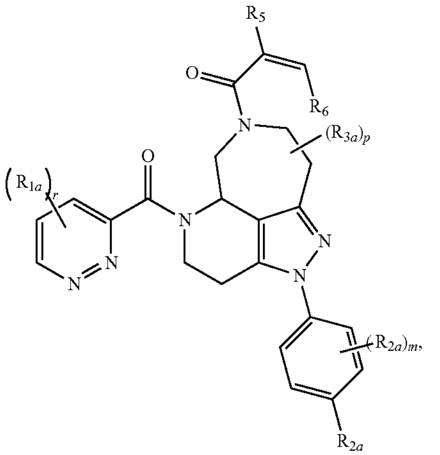
(IV-h)
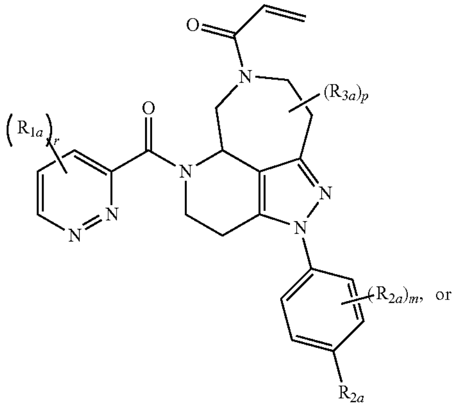
-continued
(IV-i)
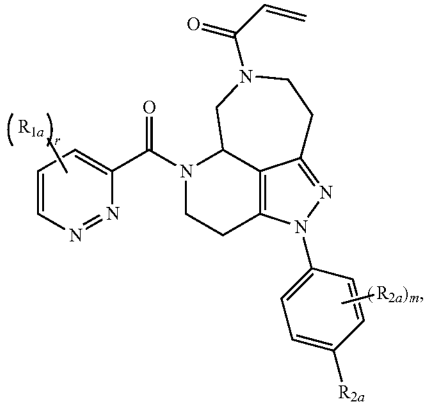
or a pharmaceutically acceptable salt, solvate, clathrate, hydrate, stereoisomer, or tautomer thereof, wherein m is 0, 1, 2, 3 or 4; p is 0, 1, 2, 3, 4, 5, 6; and r is 0, 1, 2, 3, or 4.
Exemplary Embodiment No. B29. The compound of Exemplary Embodiment No. B1 or Exemplary Embodiment No. B2, wherein the compound is of Formula (IV-a'), (IV-b'), (IV-c'), (IV-d'), (IV-e'), (IV-f'), (IV-g'), (IV-h'), or (IV-i'):
(IV-a')
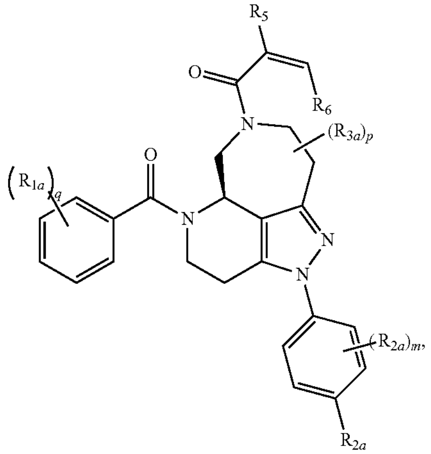
(IV-b')
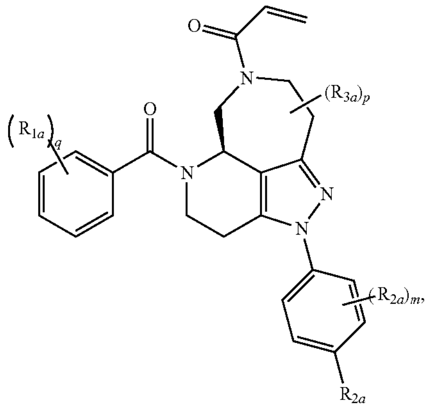

-continued
(IV-c')
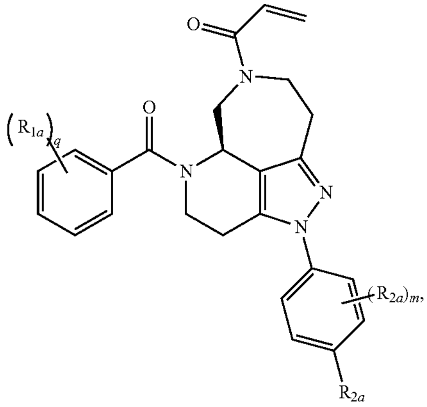
(IV-d')
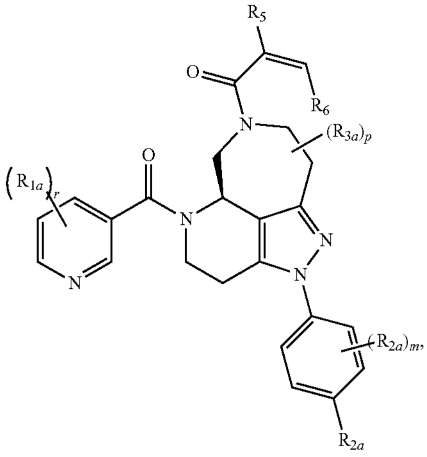
(IV-e')
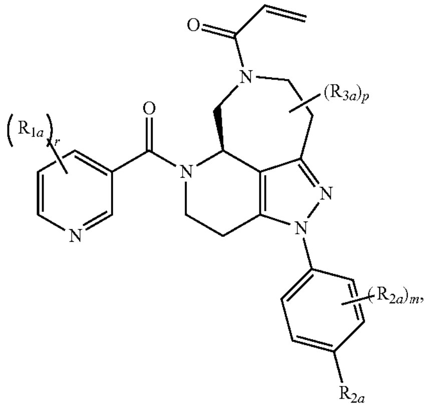
-continued
(IV-f')
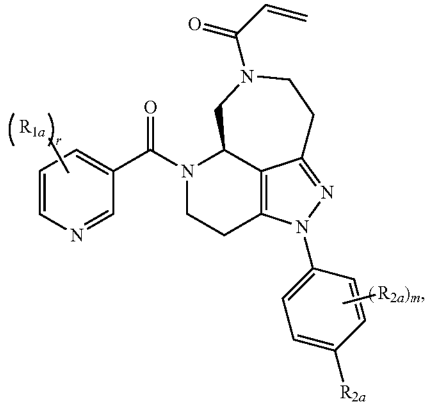
(IV-g')
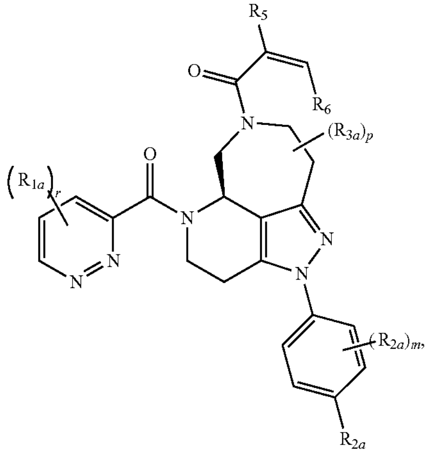
(IV-h')
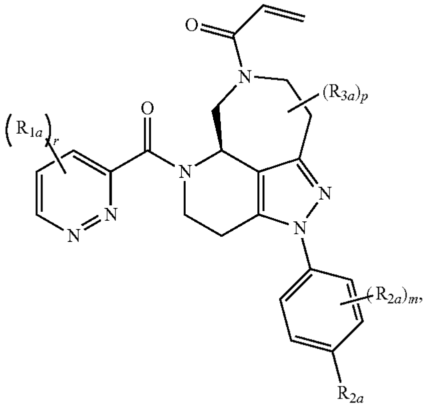
or -continued (IV-i')

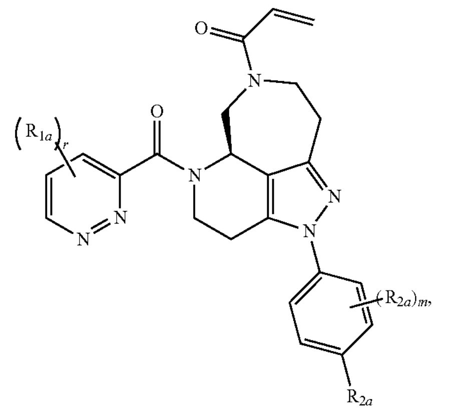

or a pharmaceutically acceptable salt, solvate, clathrate, hydrate, stereoisomer, or tautomer thereof, wherein m is 0, 1, 2, 3, or 4; p is 0, 1, 2, 3, 4, 5, or 6; and r is 0, 1, 2, 3, or 4.

Exemplary Embodiment No. B30. The compound of Exempla Embodiment No. B1 or Exemplary Embodiment No. B2, wherein the compound is of Formula (V-a'), (V-b'), (V-c'), (V-d'), (V-e'), or (V-f'):

(V-a')

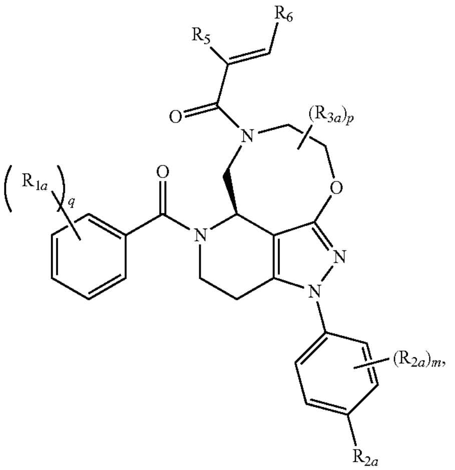

(V-b')

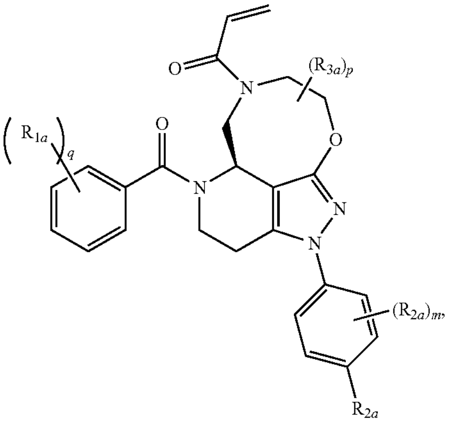

-continued (V-c')

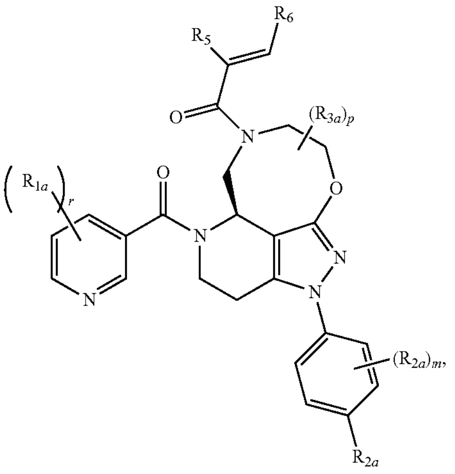

or (V-d')

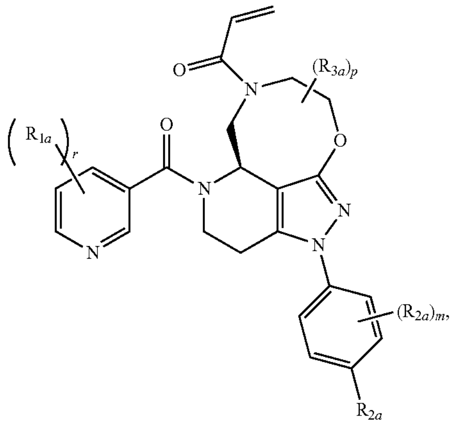

or a pharmaceutically acceptable salt, solvate, clathrate, hydrate, stereoisomer, or tautomer thereof, wherein m is 0, 1, 2, 3, or 4; p is 0, 1, 2, 3, 4, 5, or 6; q is 0, 1, 2, 3, 4, or 5; and r is 0, 1, 2, 3, or 4.

Exemplary Embodiment No. B31. The compound of Exemplary Embodiment No. B1 or Exemplary Embodiment No. B2, wherein the compound is of Formula (VI-a'), (VI-b'), (VI-c'), or (VI-d'):

(VI-a')
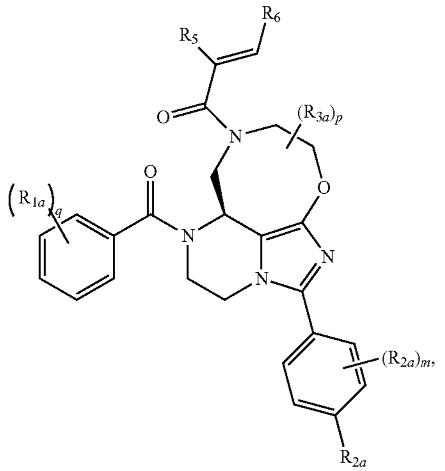
(VI-b')
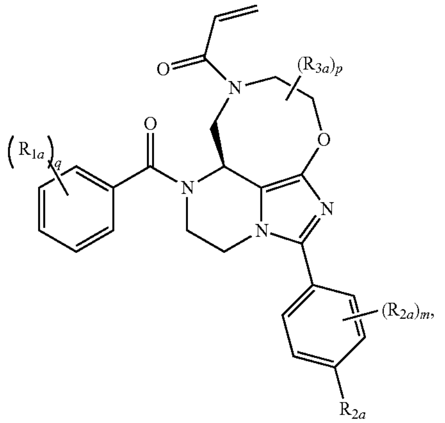
(VI-c')
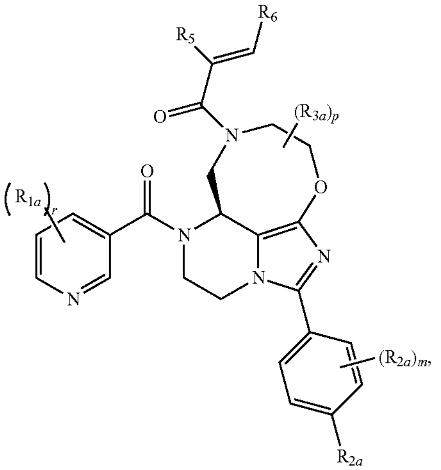
or
-continued
(VI-d')
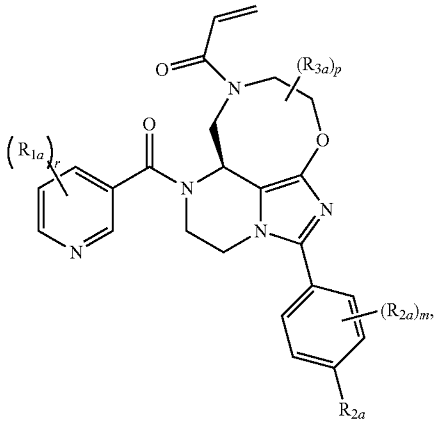
or a pharmaceutically acceptable salt, solvate, clathrate, hydrate, stereoisomer, or tautomer thereof, wherein m is 0, 1, 2, 3, or 4; p is 0, 1, 2, 3, 4, 5, or 6; q is 0, 1, 2, 3, 4, or 5; and r is 0, 1, 2, 3, or 4.
Exemplary Embodiment No. B32. The compound of Exemplary Embodiment No. B1 or Exemplary Embodiment No. B2, wherein the compound is of Formula II-a'), (VII-b'), (VII-c'), or (VII-d'):
(VII-a')
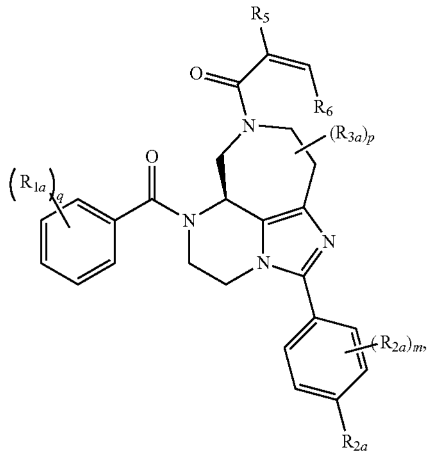
(VII-b')
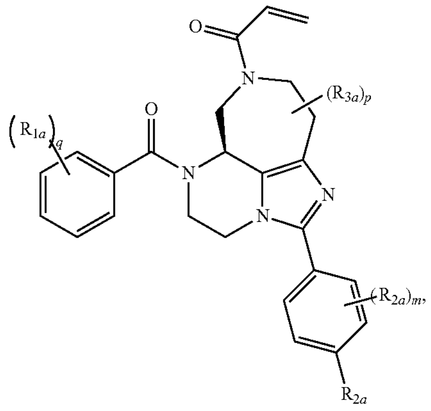

-continued (VII-c')

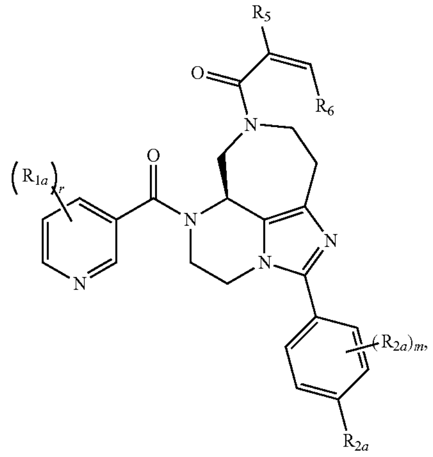

or (VII-d')

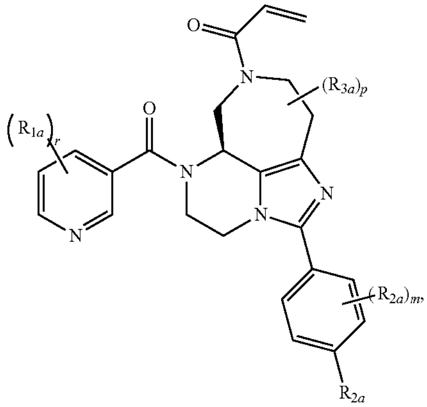

or a pharmaceutically acceptable salt, solvate, clathrate, hydrate, stereoisomer, or tautomer thereof, wherein m is 0, 1, 2, 3, or 4; p is 0, 1, 2, 3, 4, 5, or 6; q is 0, 1, 2, 3, 4, or 5; and r is 0, 1, 2, 3, or 4.

Exemplary Embodiment No. B33. The compound of Exempla Embodiment No. Bi or Exemplary Embodiment No. B2, wherein the compound is of Formula (VIII-a'), (VIII-b'), (VIII-c'), or (VIII-d'):

(VIII-a')

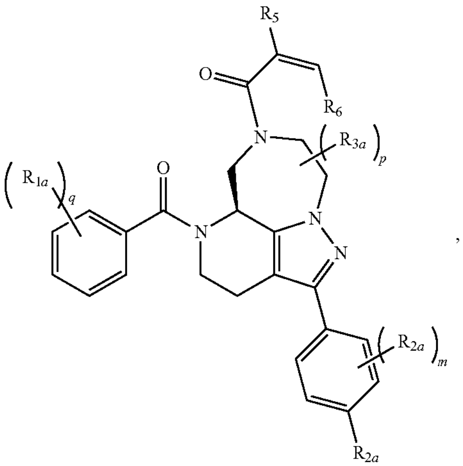

,

-continued (VIII-b')

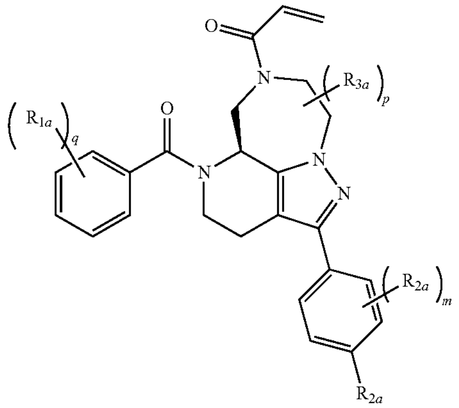

, (VIII-c')

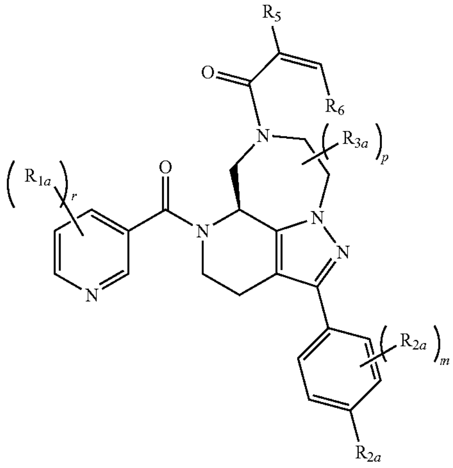

or (VIII-d')

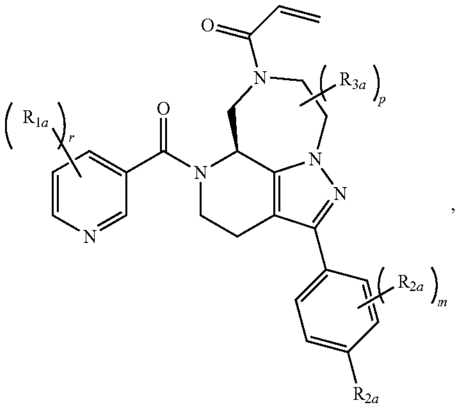

, or a pharmaceutically acceptable salt, solvate, clathrate, hydrate, stereoisomer, or tautomer thereof, wherein m is 0, 1, 2, 3, or 4; p is 0, 1, 2, 3, 4, 5, or 6; q is 0, 1, 2, 3, 4, or 5; and r is 0, 1, 2, 3, or 4.

Exemplary Embodiment No. B34. The compound of an one of the preceding Exemplary Embodiments, wherein the compound is selected from a compound described in Table 1, Table 2, Table 1A, or Table 2A, or a pharmaceutically acceptable salt thereof.

Exemplary Embodiment No. B35. The compound of any one of the preceding Exemplary Embodiments, wherein the compound is Compound No. 128, 163, 166, 178, 182, 183, 184, 186, 187, 190, 191, 194, 195, 196, 202, 203, 206, 208, 210, 21, 218, 220, or 228, or a pharmaceutically acceptable salt thereof.

Exemplary Embodiment No. B36. The compound of any one of the preceding Exemplary Embodiments, wherein the compound is Compound No. 128A, 163A, 166A, 178A, 182A, 183A, 186A, 191A, 194A, 196A, 202A, 203A, 206A, 208A, 210A, 211A, 218A, 220A, or 228A, or a pharmaceutically acceptable salt thereof.

Exemplary Embodiment No. B37. A compound obtainable by, or obtained by, a method described herein; optionally, the method comprises one or more steps described in any one of Schemes 1-18.

Exemplary Embodiment No. B38. A pharmaceutical composition comprising the compound of any one of the preceding Exemplary Embodiments or a pharmaceutically acceptable salt thereof, and a pharmaceutically acceptable diluent or carrier.

Exemplary Embodiment No. B39. The pharmaceutical composition of Exemplary Embodiment No. B38, wherein the compound is selected from a compound described in Table 1, Table 2, Table 1A, or Table 2A.

Exemplary Embodiment No. B40. The pharmaceutical composition of Exemplary Embodiment No. B38 or Exemplary Embodiment No. B39, wherein the compound is Compound No. 128, 163, 166, 178, 182, 183, 184, 186, 187, 190, 191, 194, 195, 196, 202, 203, 206, 208, 210, 211, 218, 220, or 228, or a pharmaceutically acceptable salt thereof.

Exemplary Embodiment No. B41. The pharmaceutical composition of Exemplary Embodiment No. B38 or Exemplary Embodiment No. B39, wherein the compound is Compound No. 128A, 163A, 166A, 178A, 182A, 183A, 186A, 191A, 194A, 196A, 102A, 203A, 206A, 208A, 210A, 211A, 218A, 220A, or 228A, or a pharmaceutically acceptable salt thereof.

Exemplary Embodiment No. B42. A method of modulating WRN activity, comprising contacting a cell with a compound of any one of Exemplary Embodiment Nos. B1-B37 or a pharmaceutical composition of any one of Exemplary Embodiment Nos. B38-B41.

Exemplary Embodiment No. B43. The compound of anyone of Exemplary Embodiment Nos. B1-B37 or pharmaceutical composition of any one of Exemplary Embodiment Nos. B38-B41 for use in modulating WRN activity.

Exemplary Embodiment No. B44. Use of the compound of any one of Exemplary Embodiment Nos. B1-B37 in the manufacture of a medicament for modulating WRN activity.

Exemplary Embodiment No. B45. A method of treating or preventing a disease or disorder in a subject in need thereof, comprising administering to the subject a compound of any one of Exemplary Embodiment Nos. B1-B37 or pharmaceutical composition of any one of Exemplary Embodiment Nos. B38-B41.

Exemplary Embodiment No. B46. The compound of any one of Exemplary Embodiment Nos. B1-B37 or pharmaceutical composition of any one of Exempla Embodiment Nos. B38-41 for use in treating or preventing a disease or disorder.

Exemplary Embodiment No. B47. Use of the compound of any one of Exemplary Embodiment Nos. B1-B37 in the manufacture of a medicament for treating or preventing a disease or disorder.

Exemplary Embodiment No. B48. The method, compound, pharmaceutical composition, or use of any one of Exemplary Embodiment Nos. B45-B 7, wherein the disease or disorder is associated with an implicated WRN activity.

Exemplary Embodiment No. B49. The method, compound, pharmaceutical composition, or use of any one of Exemplary Embodiment Nos. B45-B 8, wherein the disease or disorder is cancer.

Exemplary Embodiment No. B50. The method, compound, pharmaceutical composition, or use of Exemplary Embodiment No. B49, wherein the cancer is MSI, MSI-H, and/or MMR-deficient cancer.

Exemplary Embodiment No. B51. The method, compound, pharmaceutical composition, or use of Exemplary Embodiment No. B49, wherein the cancer is a TA-repeat expanded tumor.

Exemplary Embodiment No. B52. The method, compound, pharmaceutical composition, or use of any one of Exemplary Embodiment Nos. B42-B 1, wherein the subject is human.

EXAMPLES

Abbreviations $Ac_2O$ acetic anhydride
AcOH Acetic acid
Boc tert-butyloxycarbonyl
Cbz-OSu N-(Benzyloxycarbonyloxy)succinimide
CDI carbonyldiimide
COMU (1-Cyano-2-ethoxy-2-oxoethylidenaminooxy)dimethylamino-morpholino-carbenium hexafluorophosphate
$Cs_2CO_3$ cesium carbonate
dba dibenzylideneacetone
DCM Dichloromethane
DDQ 2,3-Dichloro-5,6-dicyano-1,4-benzoquinone
DIBAL-H Diisobutylaluminium hydride
DIEA, DIPEA N,N-Diisopropylethylamine
DMA dimethylamine
DMEDA N,N'-dimethylethylenediamine
DMF dimethyl formamide
dppf 1,1'-Ferrocenediyl-bis(diphenylphosphine)
EA, EtOAc ethyl acetate
EDC, EDCl (1-ethyl-3-(3-dimethylaminopropyl)carbodiimide hydrochloride
equiv., eq equivalents
equiv.; eq, eq. equivalents
EtOAc Ethyl acetate
EtOH ethanol
FA formic acid
GPhos (3-(tert-Butoxy)-2',6'-diisopropyl-6-methoxy-[1,1'-biphenyl]-2-yl)dicyclohexylphosphane
h hour(s)
HATU (1-[Bis(dimethylamino)methylene]-1H-1,2,3-triazolo[4,5-b]pyridinium 3-oxide hexafluorophosphate
HBTU N,N,N',N'-Tetramethyl-O-(1H-benzotriazol-1-yl) uronium hexafluorophosphate
HEX Hexanes
HOBT Hydroxybenzotriazole
kg kilogram
LCMS liquid chromatography-coupled mass spectrometry
LED Light-emitting diodes
LHMDS Lithium bis(trimethylsilyl)amide
MeCN or $CH_3CN$ acetonitrile
MeOH methanol
min minute(s)
MOM methoxymethyl
Mpa megapascal
$Ms_2O$ methylsulfonyl methanesulfonate mW megawatt
$Na_2SO_4$ sodium sulfate
NaOH sodium hydroxide
$NH_4HCO_3$ ammonium bicarbonate
nm nanometer
NMO N-Methylmorpholine N-oxide
NMR nuclear magnetic resonance spectrometry
PE petroleum ether
PIDA (Diacetoxyiodo)benzene
$PPh_3$ triphenylphosphine
rt room temperature
$T_3P$ Propylphosphonic anhydride
TBAF tetrabutylazanium; fluoride
TBAI tetrabutylammonium iodide
tbbpy 4,4'-Di-tert-butyl-2,2'-dipyridyl
TBP tributyl phosphate
TEA Triethylamine
TEMPO 2,2,6,6-Tetramethylpiperidine 1-Oxyl Free Radical
TFA trifluoroacetic acid
THF Tetrahydrofuran
TIPS triisopropylsilyl
TLC thin-layer chromatography
TMAD Tetramethylazodicarboxamide
TMSCN trimethylsilyl cyanide
Wt Weight
Xantphos 4,5-bis(diphenylphosphino)-9,9-dimethylxanthene
XPhos 2-Dicyclohexylphosphino-2',4',6'-triisopropylbiphenyl
XPhos Pd G2 Chloro(2-dicyclohexylphosphino-2',4',6'-triisopropyl-1,1'-biphenyl)[2-(2'-amino-1,1'-biphenyl)] palladium(II)

General Analytical Methods:

Compounds and intermediates were analyzed by one of the LCMS methods listed below. In cases where the compound contains a bromine, either both or one of the common isotope masses ($^{79}$Br and $^{81}$Br) are reported.

LCMS Method 1:

MS instrument type: SHIMADZU LCMS-2020; column: XBridge C18 2.1*30 mm, 3.5 um; mobile phase A: 0.025% $NH_3$·water in water (v/v), B: MeCN; gradient: 0.00 min 5% B—>0.80 min 95% B→0.94 min 95% B→0.95 min 5% B→1.00 min 5% B; flow rate: 2.0 mL/min; oven temperature: 40° C.; UV detection: PDA (220 nm & 254 nm).

LCMS Method 2:

MS instrument type: SHIMADZU LCMS-2020; column: Kinetex® EVO C18 2.1*30 mm 5 um; mobile phase A: 0.0375% TFA in water (v/v), B: 0.01875% TFA in MeCN (v/v); gradient: 0.00 min 5% B→0.80 min 95% B→0.95 min 95% B→0.96 min 5% B→1.00 min 5% B; flow rate: 2.0 mL/min; oven temperature: 50° C.; UV detection: PDA (220 nm & 254 nm).

LCMS Method 3:

MS instrument type: Shimadzu LCMS-2020; Column: Poroshell HPH—C18, 30*3.0 mm, 2.7 μm; Mobile phase A: water/5 mM $NH_4HCO_3$, Mobile phase B: MeCN; Flow rate: 1.2 ml/min; Gradient:10% B to 95% B in 0.7 min, hold 0.4 min; oven temperature: 40° C.; UV detection: PDA (220 nm & 254 nm).

LCMS Method 4:

MS instrument type: Shimadzu LCMS-2020; Column: Shim-pack XR-ODS, 3.0*50 mm, 2.2 μm; Mobile Phase A:water/0.05% TFA, Mobile Phase B: MeCN/0.05% TFA; Flow rate: 1.5 ml/min; Gradient:5% B to 100% B in 1.1 min, hold 0.6 min; oven temperature: 40° C.; UV detection: PDA (220 nm &-254 nm).

LCMS Method 5:

MS instrument type: Shimadzu LCMS-2020; Column: L-column, 3.0*30 mm, 2.7 m; Mobile Phase A: water/0.07% FA; Mobile Phase B: MeCN/0.1% F; Flow rate: 1.5 ml/min; Gradient: 5% B to 100% B in 1.1 min, hold 0.6 min; oven temperature: 0° C.; UV detection: PDA (220 nm & 254 nm).

Instrument Parameters $^1$H NMR and $^{13}$C NMR spectra were recorded on a 400 Hz Varian spectrometer; chemical shifts (δ) are reported relative to residual proton solvent signals. Data for NMR spectra are reported as follows: chemical shift (δ ppm), multiplicity (s=single, brs=broad singlet, d=doublet, hept=heptet, p=pentet, t=triplet, q=quartet, dd=doublet f doublets, td=triplet of doublets, m=multiplet), coupling constant (Hz), integration. In some embodiments, the compounds of the instant disclosure exits as one or more rotamers in solution, and as such the analytical NMR data may represent several rotameric mixtures.

Example 1. Synthesis of the Compounds of the Present Disclosure

Example A-1: Preparation of Tert-Butyl 2-(4-bromophenyl)-8-oxo-2,3,4,5a,6,7,8,9-octahydro-5H-1,2,5,7-tetraazabenzo[cd]azulene-5-carboxylate (Int. E)

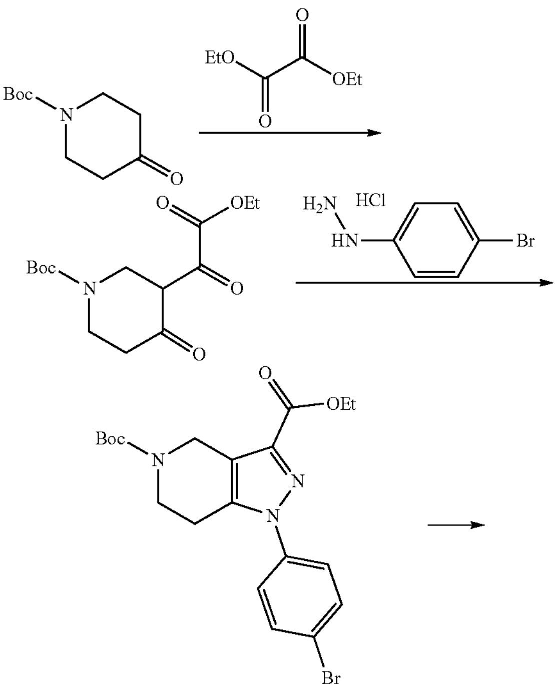

Int. A

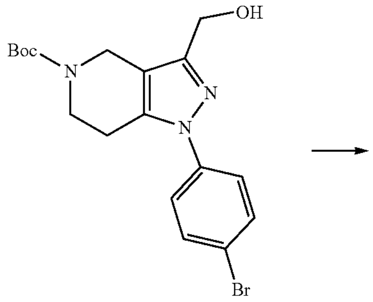

Int. B

-continued

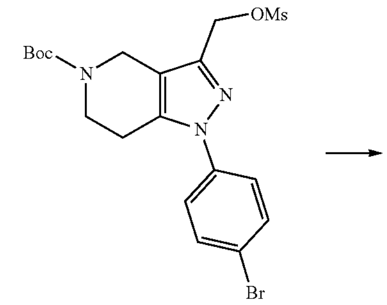

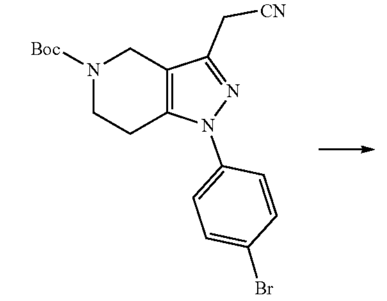

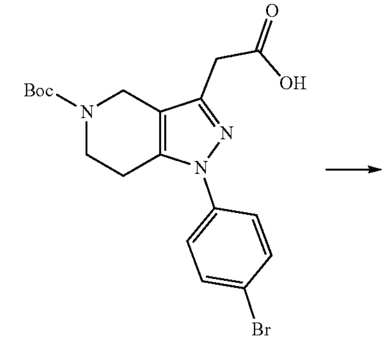

Int. C

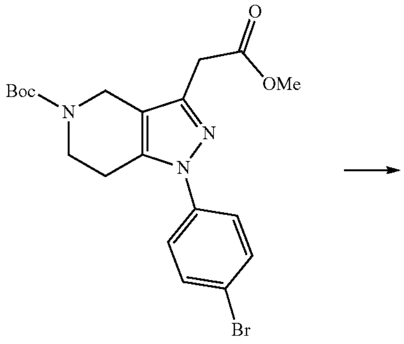

Int. D

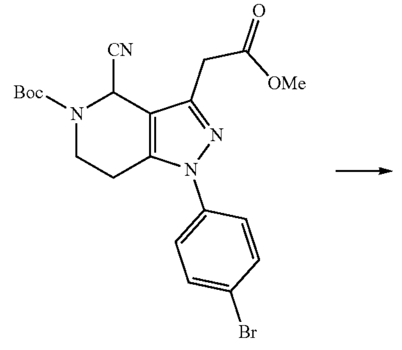

-continued

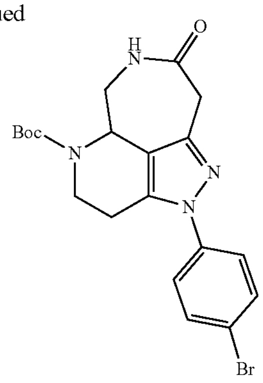

Int. E

Step 1: Synthesis of Tert-Butyl 3-(2-ethoxy-2-oxoacetyl)-4-oxopiperidine 1-carboxylate To a solution of tert-butyl 4-oxopiperidine-1-carboxylate (1.50 kg, 7.53 mol, 1.00 eq) in THE (15.0 L) was added LHMDS (1.00 M, 7.90 L, 1.05 eq) dropwise over 1 h at −5-0' C. The mixture was stirred for further 1 h at −5~0° C., after which the color of the mixture turned from yellow to orange, and then to the mixture was added diethyl oxalate (1.16 kg, 7.90 mol, 1.08 L, 1.05 eq) dropwise at 0° C. The mixture was stirred at 0° C. for 1 h. Reaction monitoring by LCMS showed tert-butyl 4-oxopiperidine-1-carboxylate was consumed completely and one main peak with the desired mass $(M+Na)^+$ was detected. The reaction mixture was quenched by addition dropwise of AcOH (1.30 L, 3.00 eq) at −5~0° C., during which time the color of the reaction mixture turned from orange to yellow. The resulting crude mixture of tert-butyl-(2-ethoxy-2-oxoacetyl)- 4-oxopiperidine-1-carboxylate was used in the next step directly without purification. LCMS: m/z=322 (M+Na)+

Step 2: Synthesis of Tert-Butyl 3-(2-ethoxy-2-oxoacetyl)-4-oxopiperidine-1-carboxylate (Int. A)

To the above solution of tert-butyl 3-(2-ethoxy-2-oxoacetyl)-4-oxopiperidine-1-carboxylate (2.25 kg, 7.52 mol, 1.00 eq) in THF (23.0 L) was added (4-bromophenyl) hydrazine hydrochloride (1.76 kg, 7.89 mol, 1.05 eq) at 0° C. The mixture was stirred at 20° C. for 16 h. LCMS monitoring indicated that tert-butyl 3-(2-ethoxy-2-oxoacetyl)-4-oxopiperidine-1-carboxylate was consumed completely and one main peak with the desired mass was detected. The reaction mixture was diluted with water (50.0 L), extracted with EtOAc (20.0 L×2), and the combined organic layers were washed with $NaHCO_3$ (20.0 L, sat. aq.), brine (20.0 L), dried over $Na_2SO_4$, filtered, and concentrated under reduced pressure to give a residue. The crude product was triturated with MeOH (30.0 L) at room temperature for 1 h. The suspension was filtered, and the filter cake was collected to give 5-(tert-butyl) 3-ethyl 1-(4-bromophenyl)-1,4,6,7-tetrahydro-5H-pyrazolo[4,3-c]pyridine-3,5-dicarboxylate (Int. A) (690 g) as a whit solid. LCMS: m/z=451 ($^{81}Br$).

Step 3: Synthesis of Tert-Butyl 1-(4-bromophenyl)-3-(hydroxymethyl)-1,4,6,7-tetrahydro-5H-pyrazolo[4,3-c]pyridine-S-carboxylate (Int. B)

The reaction was performed with 3 batches in parallel.

To a solution of 5-(tert-butyl) 3-ethyl 1-(4-bromophenyl)-1,4,6,7-tetrahydro-5H-pyrazolo[4,3-c]pyridine-3,5-dicarboxylate (180 g, 399 mmol, 1.00 eq) in THF (1.40 L) was added DIBAL-H (1.00 M, 1.00 L, 2.50 eq) dropwise at −10~-5° C. under a nitrogen atmosphere. The mixture was stirred at −5° C. for 0.5 h, and was monitored by LCMS until the starting material was consumed completely and one main peak with the desired mass was detected. The reaction mixture was quenched by addition of potassium sodium tartrate (sat, aq.) (15.0 L) at 0-5° C., then the resulting mixture was warmed to RT, and extracted with EtOAc (5.00 L×2). The combined organic layers were washed with brine (5.00 L), dried over $Na_2SO_4$, filtered, and concentrated under reduced pressure to give tert-butyl 1-(4-bromophenyl)-3-(hydroxymethyl)-1,4,6,7-tetrahydro-5H-pyrazolo[4,3-c]pyridine-5-carboxylate (Int. B) as a white solid (397 g). CMS: m/z=410 $(M+H)^+$. 1H NMR: (400 MHz, DMSO-d6) δ 7.66 (d, 2H), 7.51 (d, 2H), 5.14 (t, 1H), 4.48 (d, 2H), 4.44 (s, 2H), 3.59-3.56 (m, 2H), 2.86-2.84 (m, 2H), 1.44 (s, 9H).

Step 4: Synthesis of Tert-Butyl 1-(4-bromophenyl)-3-(((methylsulfonyl)oxy)methyl)-1,4,6,7 -tetrahydro-5H-pyrazolo[4,3-c]pyridine-5-carboxylate The reaction was performed with 2 batches in parallel.

To the solution of Int. B (200 g, 489 mmol, 1.00 eq) in THF (1.00 L) was added TEA (124 g, 1.22 mol, 170 mL, 2.50 eq) at 0° C., then $Ms_2O$ (128 g, 735 mmol, 1.50 eq) in THF (1.00 L) was added dropwise at 0° C. for 1 h. The mixture was stirred at room temperature for an additional 0.5 h, after which LCMS monitoring indicated that Int. B was consumed completely and one main peak with desired mass was detected. The reaction mixture was quenched by addition of water (5.00 L) at 0° C., and the resulting mixture was warmed to RT, and then extracted with EtOAc (3.00 L×2). The combined organic layers were dried over $Na_2SO_4$, filtered, and concentrated under reduced pressure to give tert-butyl 1-(4-bromophenyl)-3-(((methylsulfonyl)oxy)methyl)-1,4,6,7-tetrahydro-5H-pyrazolo[4,3-c]pyridine-5-carboxylate (517 g) as a brown oil which was used directly in the next step without further purification. LCMS: m/z=488 $(M+H)^+$.

Step 5: Synthesis of Tert-Butyl 1-(4-bromophenyl)-3-(cyanomethyl)-1,4,6,7-tetrahydro-5H-pyrazolo[4,3-c]pyridine-5-carboxylate The reaction was performed with 2 batches in parallel.

To the solution of tert-butyl 1-(4-bromophenyl)-3-(((methylsulfonyl)oxy)methyl)-1,4,6,7-tetrahydro-5H-pyrazolo[4,3-c]pyridine-5-carboxylate (240 g, 493 mmol 1.00 eq) in THF (1.20 L) was added TMSCN (73.4 g, 740 mmol, 92.6 mL, 1.50 eq) at room temperature, then TBAF (1.00 M, 740 mL, 1.50 eq) was added at 0° C. The mixture was stirred at room temperature for further 16 h. LCMS monitoring indicated that the starting material was consumed and one main peak with desired mass was detected. The reaction mixture was quenched by addition of water (6.00 L) at 0° C., and the resulting mixture was warmed to rt. The reaction mixture was then extracted with EtOAc (5.00 L×2), and the combined organic layers were washed with brine (5.00 L), dried over $Na_2SO_4$, filtered, and concentrated under reduced pressure to give tert-butyl 1-(4-bromophenyl)-3-(cyanomethyl)-1,4,6,7-tetrahydro-5H-pyrazolo[4,3-c]pyridine-5-carboxylate (408 g) as a brown oil, which was used into the next step directly without further purification. LCMS: m/z=419 $(M+H)^+$.

Step 6: Synthesis of 2-(1-(4-bromophenyl)-5-(tert-butoxycarbonyl)-4,5,6,7-tetrahydro-1H-pyrazolo[4,3-c]pyridin-3-yl)acetic Acid The reaction was performed with 2 batches in parallel.

To the solution of tert-butyl 1-(4-bromophenyl)-3-(cyanomethyl)-1,4,6,7-tetrahydro-5H-pyrazolo[4,3-c]pyridine-5-carboxylate (200 g, 479 mmol, 1.00 eq) in 1,4-dioxane (1.00 L) was added NaOH (4.00 M, 2.00 L, 16.7 eq) at room temperature. The mixture was stirred at 110° C. for 40 h. LCMS monitoring indicated that the starting material was consumed and one main peak with desired mass was detected. The reaction mixture was quenched by addition of HCl (1.00 M, 850 mL) to adjust pH to 4 at 0° C., after which the resulting mixture was warmed to RT, and then extracted with EtOAc (2.00 L×2). The combined organic layers were wished with brine (2.00 L), dried over $Na_2SO_4$, filtered, and concentrated under reduced pressure to give 2-(1-(4-bromophenyl)-5-(tert-butoxycarbonyl)-4,5,6,7-tetrahydro-1H-pyrazolo[4,3-c]pyridin-3-yl)acetic acid as a brown oil, which was used into the next step directly without further purification. LCMS: m/z=436 $(M+H)^+$.

Step 7: Synthesis of tert-butyl 1-(4-bromophenyl)-3-(2-methoxy-2-oxoethyl)-1,4,6,7-tetrahydro-5H-pyrazolo[4,3-c]pyridine-5-carboxylate (Int. D)

The reaction was performed in 2 batches in parallel.

To a solution of 2-(1-(4-bromophenyl)-5-(tert-butoxycarbonyl)-4,5,6,7-tetrahydro-1H-pyrazolo[4,3-c]pyridin-3-yl) acetic acid (200 g, 458 mmol, 1.00 eq) in MF (2.00 L) was added $K_2CO_3$ (126 g, 917 mmol, 2.00 eq), then $CH_3I$ (130 g, 917 mmol, 57.1 mL, 2.00 eq) was added dropwise at 0-10° C. The mixture was stirred at room temperature for 2 h. The reaction mixture was quenched by addition of water (12.0 L) and then extracted with EtOAc (4 L×2). The combined organic layers were washed with brine (6.00 L), dried over $Na_2SO_4$, filtered, and concentrated under reduced pressure to give tert-butyl 1-(4-bromphenyl)-3-(2-methoxy-2-oxoethyl)-1,4,6,7-tetrahydro-5H-pyrazolo[4,3-c]pyridine-5-carboxylate (Int. D) as a brown oil (374 g) which was used in the next step directly without further purification. LCMS: m/z=452 $(M+H)^+$. $^1H$ NMR: (400 MHz, DMSO-d6) δ 7.66 (d, 2H), 7.52 (d, 2H), 4.35 (s, 2H), 3.72 (s, 2H), 3.65 (s, 3H), 3.59-3.55 (m, 2H), 2.87-2.83 (m, 2H), 1.43 (s, 9H).

Step 8: Synthesis of Tert-Butyl 1-(4-bromophenyl)-4-cyano-3-(2=met oxy-2-oxoethyl)-1,4,6,7-tetrahydro-5H-pyrazolo[4,3-c]pyridine-5-carboxylate To a solution of Int. D (185 g, 411 mmol, 1.00 eq) in acetonitrile (1.85 L) was added AcOH (24.6 g, 411 mmol, 23.5 mL, 1.00 eq) and $TEMPO^+BF4^-$ (290 g, 0.85 mol, 4.50 eq) at room temperature, then TMSCN (163 g, 1.64 mol, 205 mL, 4.00 eq) was added dropwise at 0-10° C. The mixture was stirred at room temperature for 2 h. LCMS monitoring indicated that the starting material was consumed and one main peak with the desired mass was detected. The crude reaction mixture was poured into water (6.00 L) and extracted with ethyl acetate (2.00 L×2). The combined organic phase was concentrated under reduced pressure to give a residue. The residue was purified by column chromatography ($SiO_2$, PE/EtOAc=3/1) to provide tert-butyl 1-(4-bromophenyl)-4-cyano-3-(2-methoxy-2-oxoethyl)-1,4,6,7-tetrahydro-5H-pyrazolo[4,3-c]pyridine-5-carboxylate (95.0 g) as a white solid. LCMS: m/z=475 $(M+H)^+$ Step 9: Synthesis of Tert-Butyl 2-(4-bromophenyl)-8-oxo-2,3,4,5a,6,7,8,9-octahydro-5H-1,2,5,7-tetraazabenzo[cd]azulene-5-carboxylate (Int. E)

To prepare the reaction column, $Co/Al_2O_3$ catalyst (3.5 g) was loaded into a 5 mL fixed-bed reaction tube. The column was then purged with nitrogen three times, and the back pressure was set to 3.0 MPa to test the airtightness of the device. After confirming airtightness, the hydrogen flow rate was set to 30 mL/min, and the hydrogen pressure to 3 MPa. The catalyst was activated at 130° C. for 12 h. A 3 L flask was charged with tert-butyl 1-(4-bromophenyl)-4-cyano-3-(2-methoxy-2-oxoethyl)-1,4,6,7-tetrahydro-5H-pyrazolo[4,3-c]pyridine-5-carboxylate (71.8 g, 151 mmol) at 10° C. The flask was then charged with THF (1.36 kg) and MeOH (360 g) at 10° C. The mixture was stirred for 0.1 h at 10° C. until it became a clear solution. The backpressure regulator was then adjusted to 3.0 MPa, and the flow reactor to 110° C. The flow pump rate was adjusted to 0.3 mL/min for the solution, 20 ml/min for $H_2$. A sample was taken for analysis after hydrogenation, and LCMS showed tert-butyl 1-(4-bromophenyl)-4-cyano-3-(2-methoxy-2-oxoethyl)-1,4,6,7-tetrahydro-5H-pyrazolo[4,3-c]pyridine-5-carboxylate was consumed completely and one main peak with the desired mass was detected. After the reaction was completed, the port reactor was washed with MeOH. The reaction mixture was concentrated in vacuo to give a residue. The residue was triturated with EtOAc (350 mL) at room temperature for 30 min, and the mixture was filtered. The filter cake was collected to give tert-butyl 2-(4-bromophenyl)-8-oxo-2,3,4,5a,6,7,8,9-octahydro-5H-1,2,5,7-tetraazabenzo[cd]azulene-5-carboxylate (Int. E) (27.1 g, 60.6 mmol, 98.2% purity, 40.1% yield) as a white solid. LCMS: m/z=449 $(M+H)^+$. $^1H$ NMR: (400 MHz, DMSO-d6) δ 8.06 (brs, 1H), 7.69 (d, J=8.40 Hz, 2H), 7.51 (d, J=8.40 Hz, 2H), 4.65-4.62 (m, 1H), 4.20-4.18 (m, 1H), 3.92 (d, J=17.7 Hz, 1H), 3.59 (d, J=17.7 Hz, 1H), 3.42-3.50 (m, 1H), 3.34-3.41 (m, 1H), 2.92-3.02 (m, 1H), 2.65-2.75 (m, 2H), 1.47 (s, 9H).

Example A-2: Preparation of Acid A

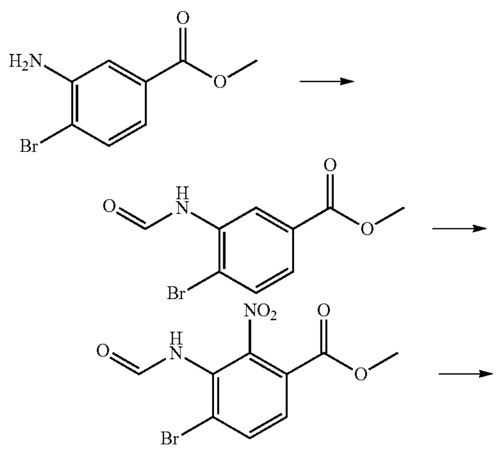

-continued

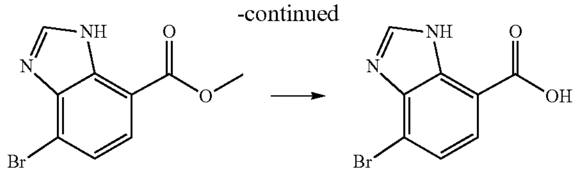

Acid A

Step 1: Synthesis of Methyl 4-bromo-3-formamidobenzoate

To a solution of $Ac_2O$ (222 g, 2.17 mol, 2.50 eq) in HCOOH (2.00 L) was added methyl 3-amino-4-bromobenzoate (200 g, 869 mmol, 1.00 eq) portion-wise at room temperature, and then the mixture was stirred at room temperature for 12 h. The reaction was monitored by LCMS, after which the reaction mixture was poured into ice water (1.50 L), filtered and the solid was dried under reduced pressure to give methyl 4-bromo-3-formamidobenzoate (213 g) as a white solid. LCMS: m/z=258.1 $(M+H)^+$, m/z=260 (M+H)+

Step 2: Synthesis of 4-bromo-3-formamido-2-nitrobenzoate

To stirring fuming nitric acid (1.49 kg, 23.7 mol, 30.0 eq) was added methyl 4-bromo-3-formamidobenzoate (204 g, 790 mmol, 1.00 eq) portion wise at −30° C. The mixture was stirred at −30° C. for 1 h. The reaction mixture was poured into ice blocks (2.00 kg×3) with stirring, diluted with water (2.00 L×3), and the product was precipitated from the water. Then the mixture was stirred for 0.5 h. After the ice blocks melted completely, the resulting mixture was filtered, and the cake was washed with water (2.00 L×2). The cake was collected and dried under reduced pressure to give 4-bromo-3-formamido-2-nitrobenzoate (200 g) as a yellow solid.

Step 3: Synthesis of Methyl 7-bromo-3H-1,3-benzodiazole-4-carboxylat

To a solution of 4-bromo-3-formamido-2-nitrobenzoate (180 g, 594 mmol, 1.00 eq) in MeOH (1.80 L) and AcOH (0.900 L) was added Fe (498 g, 8.91 mol, 15.0 eq) in portions at 70° C. The mixture was stirred at 70° C. for 4 h. The reaction mixture was then poured into water (3.60 L) and EtOAc (3.60 L), the organic phase was separated, and the aqueous phase was extracted by EtOAc (1.80 L), combined organic phase, washed with sat. $NaHCO_3$ (50 mL) and brine (500 mL), dried over $Na_2SO_4$, and concentrated to give a residue. The residue was purified by flash silica gel chromatography (ISCO®; 2000 g SepaFlash® Silica Flash Column, Eluent of 0~1% MeOH/DCM @400 mL/min) to give methyl 7-bromo-3H-1,3-benzodiazole-4-carbonylate (39.0 g) as a brown solid. LCMS: m/z=255 $(M+H)^+$. $^1H$ NMR: 400 MHz, DMSO-$d_6$ δ 12.88 (brs, 1H), 8.40 (s, 1H), 7.74 (d, J=8.0 Hz, 1H), 7.56 (d, J=8.4 Hz, 1H), 3.94 (s, 3H).

Step 4: Synthesis of 7-bromo-3H-1,3-benzodiazole-4-carboxylic acid (Acid A)

A mixture of methyl 7-bromo-3H-1,3-benzodiazole-4-carboxylate (36.0 g, 141 mmol, 1.00 eq) in HCl (aqueous, 6 N, 200 mL) was stirred at 100° C. for 4 h. The reaction mixture was then concentrated under reduced pressure to give a residue. The crude product was triturated with EtOAc (200 mL) at room temperature for 2 h, filtered and the cake was collected and dried to obtain 7-bromo-3H-1,3-benzodiazole-4-carboxylic acid (Acid A) (39.9 g, 139 mmol, 98.4% yield, 96% purity, HCl salt) as a gray solid. LCMS: m/z=240 $(M+H)^+$ $^1H$ NMR: 400 MHz, DMSO-$d_6$ δ 8.96 (s, 1H), 7.84 (d, J=8.4 Hz, 1H), 7.71 (d, J=8 Hz, 1H).

Example A-3: Preparation of Acid-B

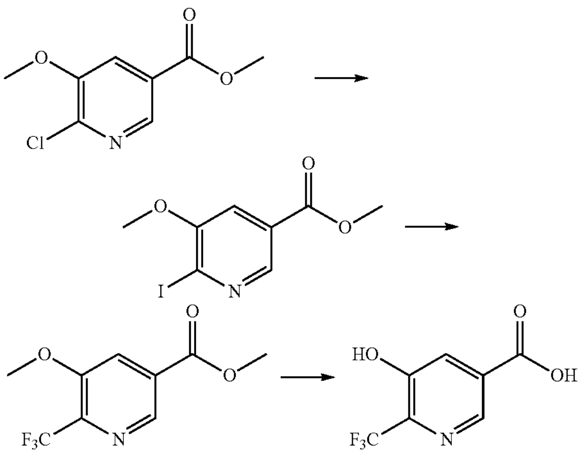

Acid B

Step 1: Synthesis of Methyl 6-iodo-5-methoxynicotinate

To a stirred solution of methyl 6-chloro-5-methoxypyridine-3-carboxylate (1 g, 5 mmol, 1 equiv) and TMSCl (0.54 g, 5 mmol, 1 equiv) in MeCN (10 mL) was added NaI (2.23 g, 14.9 mmol, 3 equiv) in portions at rt under hydrogen atmosphere. The resulting mixture was stirred overnight at 80° C. under a hydrogen atmosphere. The aqueous layer was extracted with EtOAc (2×22 mL). The resulting liquid was dried in an oven under reduced pressure. The crude methyl 6-iodo-5-methoxynicotinate (1.5 g) was used in the next step directly without further purification. LCMS: (ESI, m/z): 294 $[M+1]^+$ Step 2: Methyl 5-methoxy-6-(trifluoromethyl)nicotinate To a stirred mixture of methyl 6-iodo-5-methoxypyridine-3-carboxylate (100 mg, 0.341 mmol, 1 equiv) and CuI (454.9 mg, 2.387 mmol, 7 equiv) in DMF (2 mL) was added methyl 2,2-difluoro-2-sulfoacetate (458.9 mg, 2.387 mmol, 7 equiv) in portions at rt under nitrogen atmosphere. The resulting mixture was stirred overnight at 70° C. under a nitrogen atmosphere. The aqueous layer was extracted with EtOAc (2×25 mL). The resulting liquid was dried in an oven under reduced pressure. The resulting mixture (100 mg) was used in the next step directly without further purification. LCMS: (ESI, m/z): 236 $[M+1]^+$ Step 3: Synthesis of 5-hydroxy-6-(trifluoromethyl)nicotinic Acid (Acid B)

To a solution of methyl 5-methoxy-6-(trifluoromethyl) nicotinate (8.00 g, 1 Eq, 34.0 mmol) in HBr/AcOH (10 mL, 33% wt %) was stirred at 100° C. for 16 hour. The reaction was monitored by LCMS. The reaction mixture was concentrated to give a residue. The crude product was purified by reverse-phase flash chromatography (column, C18 silica gel; mobile phase A: 0.05% formic acid aqueous solution, mobile phase B: MeCN; eluting with a gradient of mobile phase B 10% to 50% in 10 min; detector, UV 254 nm) to afford 5-hydroxy-6-(trifluoroethyl)nicotinic acid (2.22 g, 10.7 mmol, 31.5%) as a yellow solid. LCMS: (ESI, m/z): 208 $[M+1]^+$ Example A-4: Preparation of (S or R)-1-(2-(4-cyclopropylphenyl)-5-(5-hydroxy-6-(trifluoromethyl) nicotinoyl)-2,3,4,5,5a,6,8,9-octahydro-7H-1,2,5,7-tetraazabenzo[cd]azulen-7-yl)prop-2-en-1-one

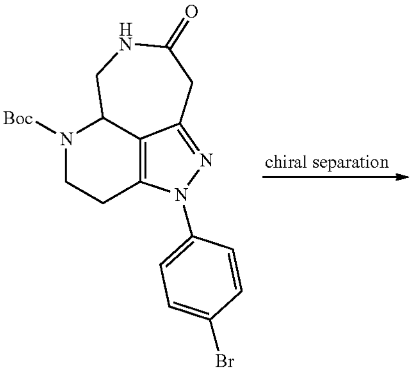

Int. E

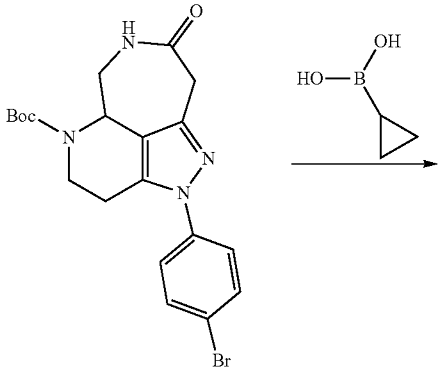

single enatiomer
Int. E-2

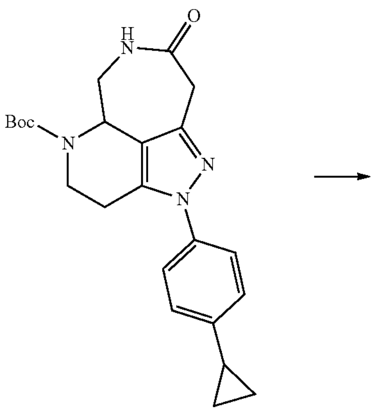

Int. EA-2

-continued

-continued

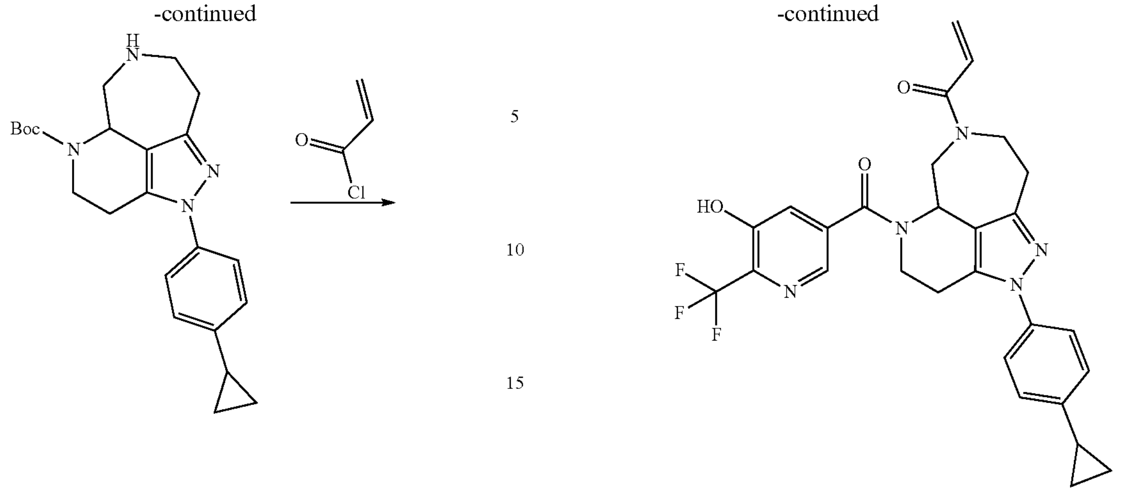

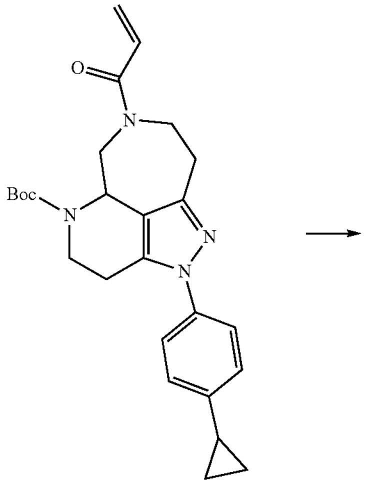

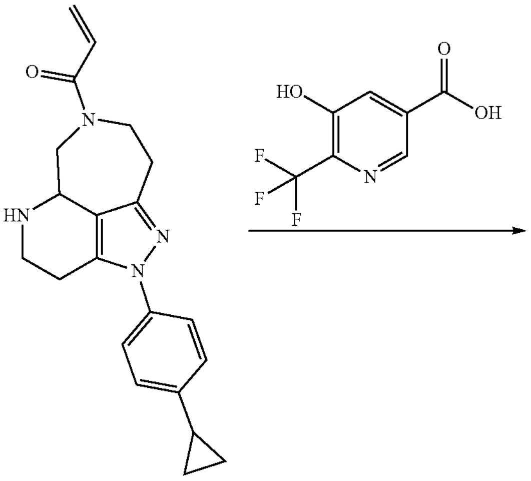

Int. F

Step 1: Chiral Separation to Afford Tert-Butyl (R or S)-2-(4-bromophenyl)-8-oxo-2,3,4,5a,6,7,8,9-octahydro-5H-1,2,5,7-tetraazabenzo[cd]azulene-5-carboxylate (Int. E-2)

Int. E (500 mg) was purified by Prep-chiral HPLC (Column: CHIRAL ART Cellulose-SC 2*25 cm, 5 m; Mobile Phase A: HEX(0.1% FA), Mobile Phase B: EtOH:DCM=1:1; Flow rate: 20 mL/min; Gradient: isocratic 40; Wave Length: UV 254/220 nm; Retention time peak 1:11 min; Retention time peak 2: 13 min; Sample Solvent: EtOH; Injection Volume: 0.71 mL; Number Of Runs: 14) to afford Int. E-2 (Peak 2, retention time 13 min, 200 mg).

On a larger scale (65 g), Int. E can be purified by chiral SFC: DAICEL CHIRALPAK IC (250 mm×50 mm, 10 um); mobile phase: [$CO_2$(Phase A)—ACN/i-PrOH (0.1% $NH_3H_2O$) (Phase B)]; B %: 60%, isocratic elution mode to provide Int. E-2 as the second-eluting enantiomer (30 g) as an off-white solid. Analytical chiral SFC: Column—Chiralcel OJ-3 50×4.6 mm I.D., 3 μm; mobile phase: [$CO_2$(Phase A)—MeOH (0.05% DEA) (Phase B)]; gradient elution 4-50% B in A; Flow rate: 3 mL/min; retention time E-2=2.2 min (second peak). (t e undesired enantiomer retention time=1.8 min).

Step 2: Synthesis of Tert-Butyl (S or R)-2-(4-cyclopropylphenyl)-8-oxo-2,3,4,5a,6,7,8,9-octahydro-5H-1,2,5,7-tetraazabenzo[cd]azulene-5-carboxylate (Int. EA-2)

To a solution of tert-butyl (S or R)-2-(4-bromophenyl)-8-oxo-2,3,4,5a,6,7,8,9-octahydro-5H-1,2,5,7-tetraazabenzo[cd]azulene-5-carboxylate (180 mg, 1 equiv., 402 mol) in toluene (3.6 mL) and water (0.9 mL) were added tricyclohexylphosphane (22.6 m, 0.2 equiv., 80.5 μmol), potassium phosphate (256 mg, 3 equiv., 1.21 mmol), cyclopropylboronic acid (69.1 mg, 2 equiv., 805 μmol) and diacetoxypalladium (9.1 mg, 0.1 equiv., 40 μmol). The reaction mixture was placed under a positive pressure of nitrogen and subjected to three backfilling cycles under high vacuum. The resulting mixture was stirred for 2 h at 100° C. under a nitrogen atmosphere, and was monitored by LCMS to completion. After the reaction mixture was cooled to RT, the mixture was filtered and rinsed with EtOAc (3×20 mL), then diluted with water (20 mL). The aqueous layer was extracted with EtOAc (2×20 mL). The combined organic layers were washed with saturated brine (3×20 mL), dried over anhydrous sodium sulfate and concentrated to give a residue. The crude product was purified by silica gel chromatography, eluting with PE:EtOAc=10:1 to give tert-butyl (R or S)-2-(4-cyclopropylphenyl)-8-oxo-2,3,4,5a,6,7,8,9-octahydro-5H-1,2,5,7-tetraazabenzo[ed]azulene-5-carboxylate (160 mg) as a yellow solid. LCMS: (ESI, m/z): 408 $[M+H]^+$ Step 3. Synthesis of Tert-Butyl (S)-2-(4-cyclopropylphenyl)-2,3,4,5a,6,7,8,9-octahydro-5H-1,2,5,7-tetraazabenzo[cd]azulene-5-carboxylate To a solution of tert-butyl (R or S)-2-(4-cyclopropylphenyl)-8-oxo-2,3,4,5a,6,7,8,9-octahydro 5H-1,2,5,7-tetraazabenzo[cd]azulene-5-carboxylate (160 mg, 1 equiv., 390 mol) in THF (3.2 mL) was added $BH_3$·THF (1.57 mL, 1M, 4 equiv., 1.57 mmol). The mixture was stirred at 60° C. for 2 h. The reaction was quenched with MeOH (20 mL) at rt. The resulting mixture was concentrated under vacuum. This resulted in tert-butyl (S or R)-2-(4-cyclopropylphenyl)-2,3,4,5a,6,7,8,9-octahydro-5H-1,2,5,7-tetraazabenzo[cd]azulene-5-carboxylate (160 mg, 406 μmol, 104%) as a crude yellow solid, which was used in the next step without further purification. LCMS: (ESI, m/z): 395 $[M+H]^+$ Step 4. Synthesis of Tert-Butyl (S or R)-7-acryloyl-2-(4-cyclopropylphenyl)-2,3,4,5a,6,7,8,9 -octahydro-5H-1,2,5,7-tetraazabenzo[cd]azulene-5-carboxylate To a solution of tert-butyl (S or R)-2-(4-cyclopropylphenyl)-2,3,4,5a,6,7,8,9-octahydro-5H-1,2,5,7-tetraazabenzo [cd]azulene-5-carboxylate (160 mg, 1 equiv., 406 gmol) in DCM (3.2 mL) was added TEA (205 mg, 283 μL, 5 equiv., 2.03 mmol). The mixture was cooled to 0° C., then acryloyl chloride (73.4 mg, 2 equiv., 811 μmol) was added dropwise to the above mixture at room temperature under a nitrogen atmosphere. The mixture was warmed to room temperature and stirred for 2 h. The reaction was monitored by LCMS. The mixture was then diluted with ice water (20 mL) and EtOAc (20 mL), and the aqueous layer was extracted with EtOAc (2×20 mL). The combined organic layers were washed with saturated brine (2×20 mL), dried over anhydrous sodium sulfate, and concentrated to give a residue. The residue was purified by flash column chromatography, eluting with EtOAc/PE (1:5) to afford tert-butyl (S or R)-7-acryloyl-2-(4-cyclopropylphenyl)-2,3,4,5a,6,7,8,9-octahydro-5H-1,2,5,7-tetraazabenzo[cd]azulene-5-carboxylate (65 mg) as a white solid. LCMS: (ESI, m/z): 449 $[M+H]^+$ Step 5: Synthesis of (S or R)-1-(2-(4-cyclopropylphenyl)-2,3,4,5,5a,6,8,9-octahydro-7H-1,2,5,7-tetraazabenzo[cd]azulen-7-yl)prop-2-en-1-one (Int. F)

A solution of tert-butyl (S or R)-7-acryloyl-2-(4-cyclopropylphenyl)-2,3,4,5a,6,7,8,9-octahydro-5H-1,2,5,7-tetraazabenzo[cd]azulene-5-carboxylate (65 mg, 1 equiv., 0.14 mmol) in DCM (1.3 mL) and TFA (0.65 mL) was stirred at room temperature for 1 h. The reaction was monitored by LCMS, after which the solvent was removed under reduced pressure. The resulting residue of (S or R)-1-(2-(4-cyclopropylphenyl)-2,3,4,5,5a,6,8,9-octahydro-7H-1,2,5,7-tetraazabenzo[cd]azulen-7-yl)prop-2-en-1-one (70 mg) as a crude yellow oil was used in the next step directly without further purification. LCMS: (ESI, m/z): 349 $[M+H]^+$ Step 6: Synthesis of (S or R)-1-(2-(4-cyclopropylphenyl)-5-(5-hydroxy-6-(trifluoromethyl)nicotinoyl)-2,3,4,5,5a,6,8,9-octahydro-7H-1,2,5,7-tetraazabenzo[cd]azulen-7-yl)prop-2-en-1-one To a solution of (S or R)-1-(2-(4-cyclopropylphenyl)-2,3,4,5,5a,6,8,9-octahydro-7H-1,2,5,7-tetraazabenzo[cd]azulen-7-yl)prop-2-en-1-one (70 mg, 1 equiv., 0.2 mmol) in DMF (1.4 mL) were added HATU (99 mg, 1.3 equiv., 0.26 mmol), 5-hydroxy-6-(trifluoromethyl)nicotinic acid (54 mg, 1.3 equiv., 0.26 mmol) and DIEA (0.21 g, 0.28 mL, 8 equiv., 1.6 mmol). The mixture was stirred at room temperature for 1 h. The reaction was monitored by LCMS, after which the mixture was diluted with water (20 mL) and EtOAc (20 mL), and the aqueous layer was extracted with EtOAc (2×20 mL). The combined organic layers were combined and washed with saturated brine (2×20 mL), dried over anhydrous sodium sulfate and concentrated to give a residue. The residue was purified by Prep-HPLC (Column: XBridge BEH Shield RP18 5 m, 30 mm*150 mm; Mobile Phase A: water (10 mmol/L $NH_4HCO_3$), Mobile Phase B: MeCN; Flow rate: 60 mL/min; Gradient: 20% B to 42% B in 10 min; Wave Length: UV 254 nm/220 nm; retention time 1: 7.97) to afford (S or R)-1-(2-(4-cyclopropylphenyl)-5-(5-hydroxy-6-(trifluoromethyl)nicotinoyl)-2,3,4,5,5a,6,8,9-octahydro-7H-1,2,5,7-tetraazabenzo[cd]azulen-7-yl)prop-2-en-1-one (13.6 mg, 25.2 μmol, 13%) as a white solid. LCMS: (ESI, m/z):538 $[M+H]^{+}$*$^1$H NMR: (400 MHz, DMSO-d6) δ 11.58 (brs, 1H), 8.27 (s, 1H), 7.57-7.49 (m, 1H), 7.48-7.34 (m, 3H), 7.18 (d, J=8.7 Hz, 2H), 6.28 (d, J=15.6 Hz, 1H), 5.80 (d, J=11.9 Hz, 11H), 5.42-5.10 (m, 1H), 4.72-4.61 (m, 1H), 4.30 (d, J=14.2 Hz, 1H), 3.80-3.69 (m, 1H), 3.47-3.37 (m, 1H), 3.23-3.10 (m, 2H), 2.95-2.74 (m, 3H), 2.58 (d, J=12.1 Hz, 1H), 2.01-1.92 (m, 1H), 1.01-0.93 (m, 2H), 0.73-0.67 (m, 2H). $^{19}$F NMR: (376 MHz, $CDCl_3$) δ −66.29.

Analytical Chiral HPLC: Column: CHIRAL ART Cellulose-SB; Column Size: 4.6*100 mm, 3 μm; Mobile Phase: Hex(0.1% FA):(EtOH:DCM=1:1)=70:30; Flow: 1.0 mL/min; Temperature: 25° C.; retention time=2.1 min.

TABLE A1

| The following Examples in Table A1 were prepared following the synthetic procedures towards Example A-4 with the following modifications in step 6: 1.5 eq of the appropriate acid was used and the reaction mixture was stirred at 50° C. for 2 h | | | | |
|---|---|---|---|---|
| Example No. | Structure | Compound Name | LCMS $[M + H]^+$ | NMR |
| A-4-1 | 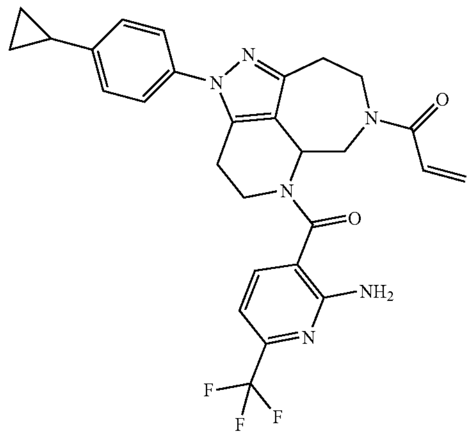 [SMILES: C=CC(=O)N1CCc2nn(-c3ccc(C4CC4)cc3)c3c2C(C1)N(C(=O)c1ccc(C(F)(F)F)nc1N)CC3] | (S or R)-1-(5-(2-amino-6-(trifluoromethyl)nicotinoyl)-2-(4-cyclopropylphenyl)-2,3,4,5,5a,6,8,9-octahydro-7H-1,2,5,7-tetraazabenzo[cd]azulen-7-yl)prop-2-en-1-one | 537 | |
| A-4-2 | 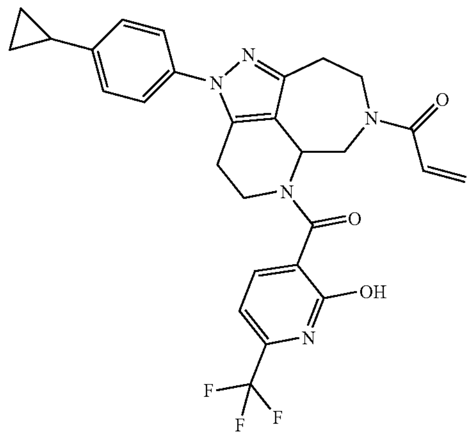 [SMILES: C=CC(=O)N1CCc2nn(-c3ccc(C4CC4)cc3)c3c2C(C1)N(C(=O)c1ccc(C(F)(F)F)nc1O)CC3] | (S or R)-1-(2-(4-cyclopropylphenyl)-5-(2-hydroxy-6-(trifluoromethyl)nicotinoyl)-2,3,4,5,5a,6,8,9-octahydro-7H-1,2,5,7-tetraazabenzo[cd]azulen-7-yl)prop-2-en-1-one | 538 | |
| A-4-3 | 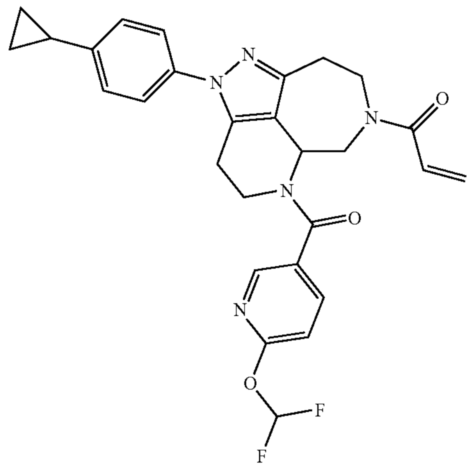 [SMILES: C=CC(=O)N1CCc2nn(-c3ccc(C4CC4)cc3)c3c2C(C1)N(C(=O)c1ccc(OC(F)F)nc1)CC3] | (S or R)-1-(2-(4-cyclopropylphenyl)-5-(6-(difluoromethoxy)nicotinoyl)-2,3,4,5,5a,6,8,9-octahydro-7H-1,2,5,7-tetraazabenzo[cd]azulen-7-yl)prop-2-en-1-one | 520 | |

TABLE A1-continued

The following Examples in Table A1 were prepared following the synthetic procedures towards Example A-4 with the following modifications in step 6: 1.5 eq of the appropriate acid was used and the reaction mixture was stirred at 50° C. for 2 h

| Example No. | Structure | Compound Name | LCMS $[M + H]^+$ | NMR |
|---|---|---|---|---|
| A-4-4 | 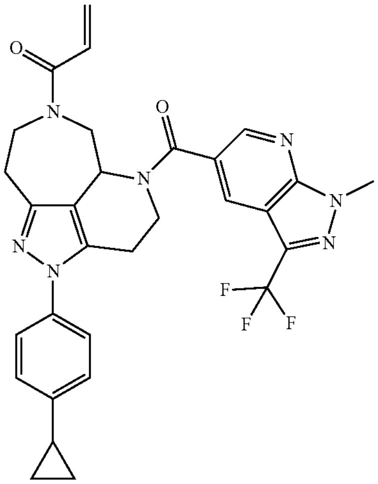 [SMILES: C=CC(=O)N1CCc2nn(-c3ccc(C4CC4)cc3)c3c2C(C1)N(C(=O)c1cnc2c(c1)c(C(F)(F)F)nn2C)CC3] | (S or R)-1-(2-(4-cyclopropylphenyl)-5-(1-methyl-3-(trifluoromethyl)-1H-pyrazolo[3,4-b]pyridine-5-carbonyl)-2,3,4,5,5a,6,8,9-octahydro-7H-1,2,5,7-tetraazabenzo[cd]azulen-7-yl)prop-2-en-1-one | 576 | $^1H$ NMR (DMSO-d6, 400 MHz) δ 8.95-8.85 (m, 1H), 8.56 (br s, 1H), 7.55-7.40 (m, 1H), 7.40 (br d, 2H, J = 8.5 Hz), 7.19 (br d, 2H, J = 8.3 Hz), 6.40-6.20 (m, 1H), 5.85-5.70 (m, 1H), 5.23 (br d, 1H, J = 8.0 Hz, 4.75-4.60 (m, 1H), 4.45-4.25 (m, 1H), 4.23 (s, 3H), 3.85-3.65 (m, 1H), 3.50-3.40 (m, 1H), 3.30-3.10 (m, 3H), 3.05-2.80 (m, 3H), 2.00-1.90 (m, 1H), 1.00-0.90 (m, 2H), 0.75-0.65 (m, 2H) |
| A-4-5 | 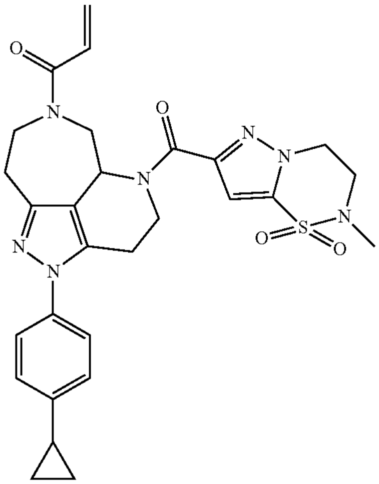 [SMILES: C=CC(=O)N1CCc2nn(-c3ccc(C4CC4)cc3)c3c2C(C1)N(C(=O)c1cc2n(n1)CCN(C)S2(=O)=O)CC3] | (S or R)-1-(2-(4-cyclopropylphenyl)-5-(2-methyl-1,1-dioxido-3,4-dihydro-2H-pyrazolo[1,5-e][1,2,5]thiadiazine-7-carbonyl)-2,3,4,5,5a,6,8,9-octahydro-7H-1,2,5,7-tetraazabenzo[cd]azulen-7-yl)prop-2-en-1-one | 562 | |
| A-4-6 | 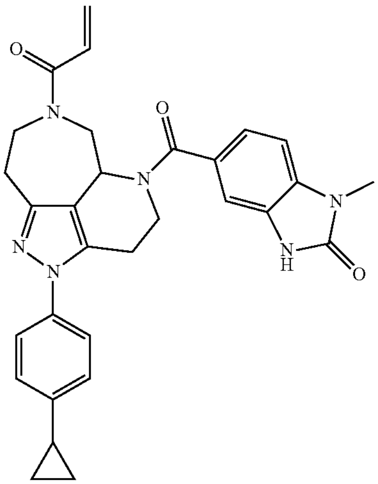 [SMILES: C=CC(=O)N1CCc2nn(-c3ccc(C4CC4)cc3)c3c2C(C1)N(C(=O)c1ccc2c(c1)[nH]c(=O)n2C)CC3] | (S or R)-5-(7-acryloyl-2-(4-cyclopropylphenyl)-3,4,5,5a,6,7,8,9-octahydro-2H-1,2,5,7-tetraazabenzo[cd]azulene-5-carbonyl)-1-methyl-1,3-dihydro-2H-benzo[d]imidazol-2-one | 523 | |

TABLE A1-continued

| The following Examples in Table A1 were prepared following the synthetic procedures towards Example A-4 with the following modifications in step 6: 1.5 eq of the appropriate acid was used and the reaction mixture was stirred at 50° C. for 2 h | | | | |
|---|---|---|---|---|
| Example No. | Structure | Compound Name | LCMS [M + H]+ | NMR |
| A-4-7 | 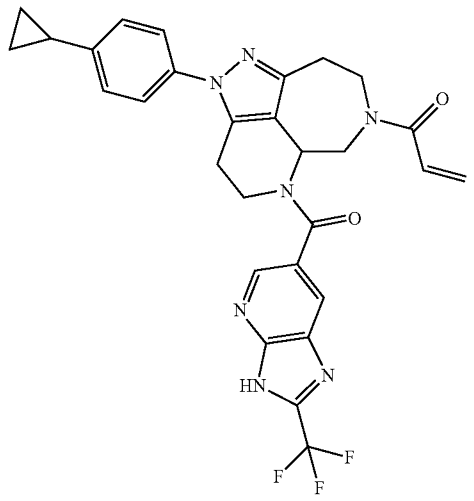 [SMILES: C=CC(=O)N1CCc2nn(-c3ccc(C4CC4)cc3)c3c2C(C1)N(C(=O)c1cnc2[nH]c(C(F)(F)F)nc2c1)CC3] | (S or R)-1-(2-(4-cyclopropylphenyl)-5-(2-(trifluoromethyl)-3H-imidazo[4,5-b]pyridine-6-carbonyl)-2,3,4,5,5a,6,8,9-octahydro-7H-1,2,5,7-tetraazabenzo[cd]azulen-7-yl)prop-2-en-1-one | 562 | |
| A-4-8 | 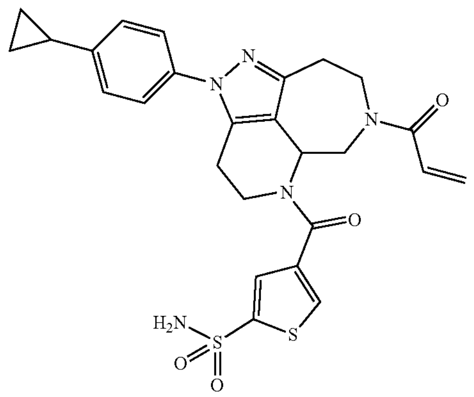 [SMILES: C=CC(=O)N1CCc2nn(-c3ccc(C4CC4)cc3)c3c2C(C1)N(C(=O)c1csc(S(N)(=O)=O)c1)CC3] | (S or R)-4-(7-acryloyl-2-(4-cyclopropylphenyl)-3,4,5,5a,6,7,8,9-octahydro-2H-1,2,5,7-tetraazabenzo[cd]azulene-5-carbonyl)thiophene-2-sulfonamide | 538 | |
| A-4-9 | 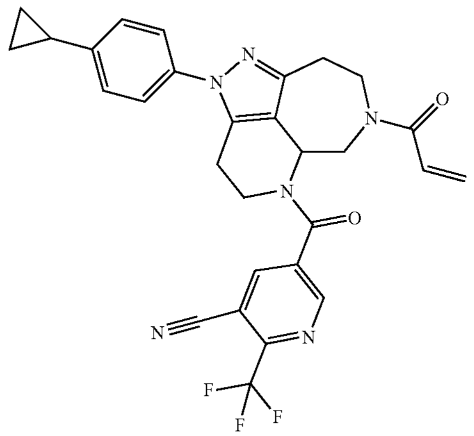 [SMILES: C=CC(=O)N1CCc2nn(-c3ccc(C4CC4)cc3)c3c2C(C1)N(C(=O)c1cnc(C(F)(F)F)c(C#N)c1)CC3] | (S or R)-5-(7-acryloyl-2-(4-cyclopropylphenyl)-3,4,5,5a,6,7,8,9-octahydro-2H-1,2,5,7-tetraazabenzo[cd]azulene-5-carbonyl)-2-(trifluoromethyl) nicotinonitrile | 547 | |

TABLE A1-continued

The following Examples in Table A1 were prepared following the synthetic procedures towards Example A-4 with the following modifications in step 6: 1.5 eq of the appropriate acid was used and the reaction mixture was stirred at 50° C. for 2 h

| Example No. | Structure | Compound Name | LCMS $[M + H]^+$ | NMR |
|---|---|---|---|---|
| A-4-10 | 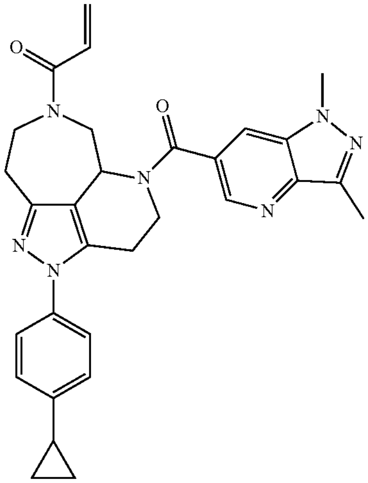 [SMILES: C=CC(=O)N1CCc2nn(-c3ccc(C4CC4)cc3)c3c2C(C1)N(C(=O)c1cnc2c(C)nn(C)c2c1)CC3] | (S or R)-1-(2-(4-cyclopropylphenyl)-5-(1,3-dimethyl-1H-pyrazolo[4,3-b]pyridine-6-carbonyl)-2,3,4,5,5a,6,8,9-octahydro-7H-1,2,5,7-tetraazabenzo[cd]azulen-7-yl)prop-2-en-1-one | 522 | |
| A-4-11 | 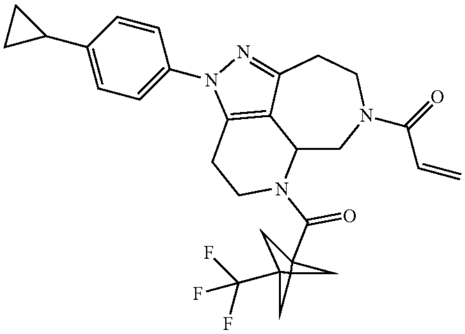 [SMILES: C=CC(=O)N1CCc2nn(-c3ccc(C4CC4)cc3)c3c2C(C1)N(C(=O)C12CC4(C(F)(F)F)CC14C2)CC3] | (S or R)-1-(2-(4-cyclopropylphenyl)-5-(3-(trifluoromethyl)bicyclo[1.1.1]pentane-1-carbonyl)-2,3,4,5,5a,6,8,9-octahydro-7H-1,2,5,7-tetraazabenzo[cd]azulen-7-yl)prop-2-en-1-one | 511 | |
| A-4-12 | 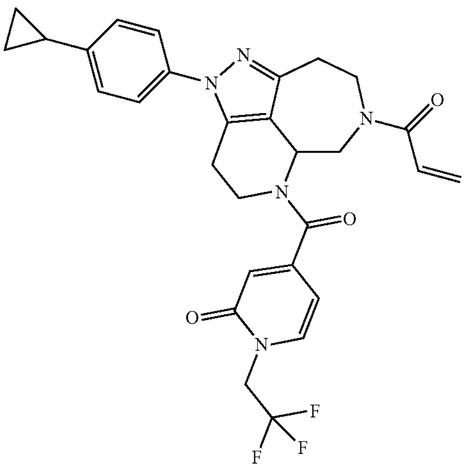 [SMILES: C=CC(=O)N1CCc2nn(-c3ccc(C4CC4)cc3)c3c2C(C1)N(C(=O)c1ccn(CC(F)(F)F)c(=O)c1)CC3] | (S or R)-4-(7-acryloyl-2-(4-cyclopropylphenyl)-3,4,5,5a,6,7,8,9-octahydro-2H-1,2,5,7-tetraazabenzo[cd]azulene-5-carbonyl)-1-(2,2,2-trifluoroethyl)pyridin-2(1H)-one | 552 | |

TABLE A1-continued

| The following Examples in Table A1 were prepared following the synthetic procedures towards Example A-4 with the following modifications in step 6: 1.5 eq of the appropriate acid was used and the reaction mixture was stirred at 50° C. for 2 h | | | | |
|---|---|---|---|---|
| Example No. | Structure | Compound Name | LCMS $[M + H]^+$ | NMR |
| A-4-13 | 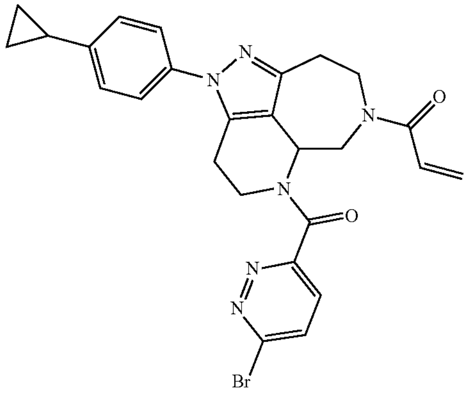 [SMILES: C=CC(=O)N1CCc2nn(-c3ccc(C4CC4)cc3)c3c2C(C1)N(C(=O)c1ccc(Br)nn1)CC3] | (S or R)-1-(5-(6-bromopyridazine-3-carbonyl)-2-(4-cyclopropylphenyl)-2,3,4,5,5a,6,8,9-octahydro-7H-1,2,5,7-tetraazabenzo[cd]azulen-7-yl)prop-2-en-1-one | 553, 555 ($^{81}Br$) | |
| A-4-14 | 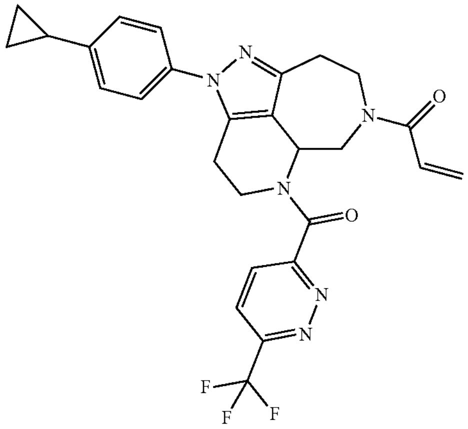 [SMILES: C=CC(=O)N1CCc2nn(-c3ccc(C4CC4)cc3)c3c2C(C1)N(C(=O)c1ccc(C(F)(F)F)nn1)CC3] | (S or R)-1-(2-(4-cyclopropylphenyl)-5-(6-(trifluoromethyl)pyridazine-3-carbonyl)-2,3,4,5,5a,6,8,9-octahydro-7H-1,2,5,7-tetraazabenzo[cd]azulen-7-yl)prop-2-en-1-one | 523 | |
| A-4-15 | 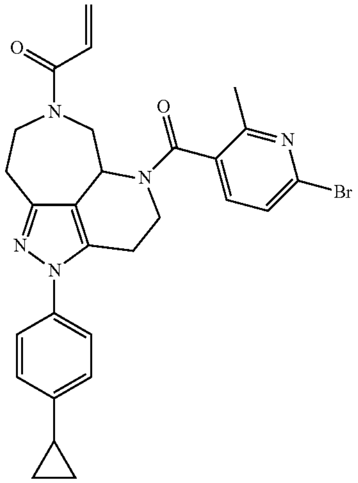 [SMILES: C=CC(=O)N1CCc2nn(-c3ccc(C4CC4)cc3)c3c2C(C1)N(C(=O)c1ccc(Br)nc1C)CC3] | (S or R)-1-(5-(6-bromo-2-methylnicotinoyl)-2-(4-cyclopropylphenyl)-2,3,4,5,5a,6,8,9-octahydro-7H-1,2,5,7-tetraazabenzo[cd]azulen-7-yl)prop-2-en-1-one | 546, 548 ($^{81}Br$) | |

TABLE A1-continued

The following Examples in Table A1 were prepared following the synthetic procedures towards Example A-4 with the following modifications in step 6: 1.5 eq of the appropriate acid was used and the reaction mixture was stirred at 50° C. for 2 h

| Example No. | Structure | Compound Name | LCMS $[M + H]^+$ | NMR |
|---|---|---|---|---|
| A-4-16 | 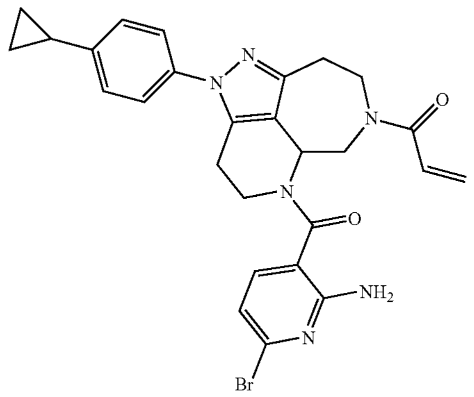 [SMILES: C=CC(=O)N1CCc2nn(-c3ccc(C4CC4)cc3)c3c2C(C1)N(C(=O)c1ccc(Br)nc1N)CC3] | (S or R)-1-(5-(2-amino-6-bromonicotinoyl)-2-(4-cyclopropylphenyl)-2,3,4,5,5a,6,8,9-octahydro-7H-1,2,5,7-tetraazabenzo[cd]azulen-7-yl)prop-2-en-1-one | 547, 549 ($^{81}$Br) | |
| A-4-17 | 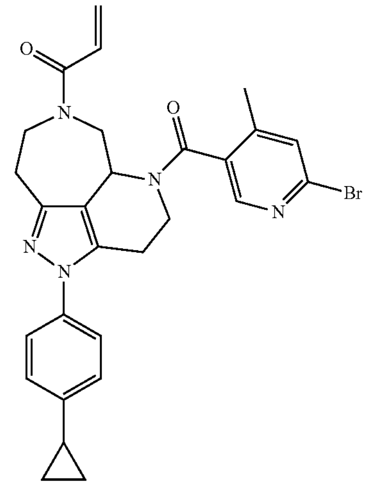 [SMILES: C=CC(=O)N1CCc2nn(-c3ccc(C4CC4)cc3)c3c2C(C1)N(C(=O)c1cnc(Br)cc1C)CC3] | (S or R)-1-(5-(6-bromo-4-methylnicotinoyl)-2-(4-cyclopropylphenyl)-2,3,4,5,5a,6,8,9-octahydro-7H-1,2,5,7-tetraazabenzo[cd]azulen-7-yl)prop-2-en-1-one | 546, 548 ($^{81}$Br) | |
| A-4-18 | 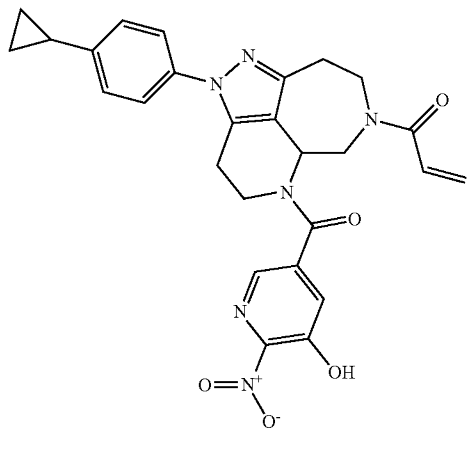 [SMILES: C=CC(=O)N1CCc2nn(-c3ccc(C4CC4)cc3)c3c2C(C1)N(C(=O)c1cnc([N+](=O)[O-])c(O)c1)CC3] | (S or R)-1-(2-(4-cyclopropylphenyl)-5-(5-hydroxy-6-nitronicotinoyl)-2,3,4,5,5a,6,8,9-octahydro-7H-1,2,5,7-tetraazabenzo[cd]azulen-7-yl)prop-2-en-1-one | 515 | |

TABLE A1-continued

| The following Examples in Table A1 were prepared following the synthetic procedures towards Example A-4 with the following modifications in step 6: 1.5 eq of the appropriate acid was used and the reaction mixture was stirred at 50° C. for 2 h | | | | |
|---|---|---|---|---|
| Example No. | Structure | Compound Name | LCMS [M + H]⁺ | NMR |
| A-4-19 | 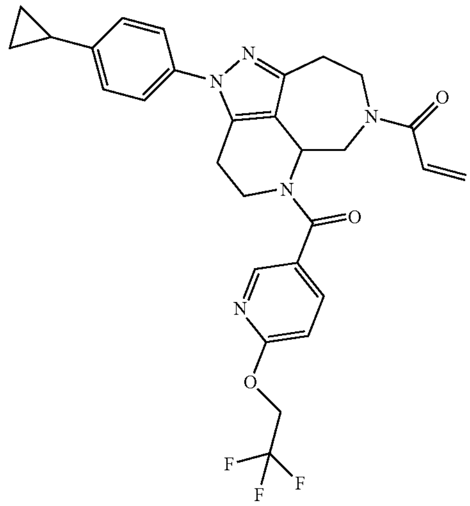 [SMILES: C=CC(=O)N1CCc2nn(-c3ccc(C4CC4)cc3)c3c2C(C1)N(C(=O)c1ccc(OCC(F)(F)F)nc1)CC3] | (S or R)-1-(2-(4-cyclopropylphenyl)-5-(6-(2,2,2-trifluoroethoxy) nicotinoyl)-2,3,4,5,5a,6,8,9-octahydro-7H-1,2,5,7-tetraazabenzo[cd]azulen-7-yl)prop-2-en-1-one | 552 | |
| A-4-20 | 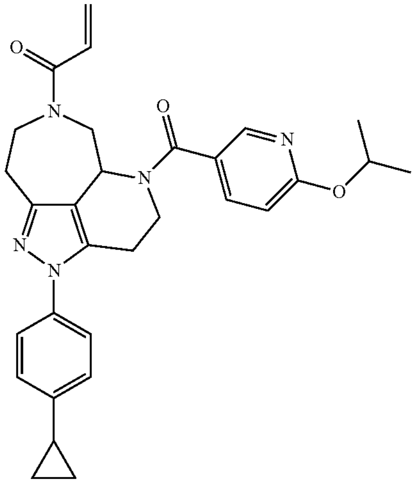 [SMILES: C=CC(=O)N1CCc2nn(-c3ccc(C4CC4)cc3)c3c2C(C1)N(C(=O)c1ccc(OC(C)C)nc1)CC3] | (S or R)-1-(2-(4-cyclopropylphenyl)-5-(6-isopropoxynicotinoyl)-2,3,4,5,5a,6,8,9-octahydro-7H-1,2,5,7-tetraazabenzo[cd]azulen-7-yl)prop-2-en-1-one | 512 | |
| A-4-21 | 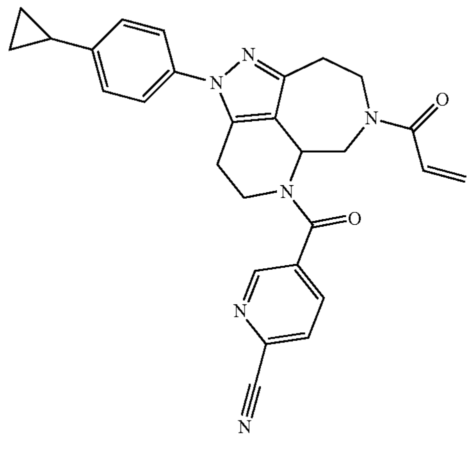 [SMILES: C=CC(=O)N1CCc2nn(-c3ccc(C4CC4)cc3)c3c2C(C1)N(C(=O)c1ccc(C#N)nc1)CC3] | (S or R)-5-(7-acryloyl-2-(4-cyclopropylphenyl)-3,4,5,5a,6,7,8,9-octahydro-2H-1,2,5,7-tetraazabenzo[cd]azulene-5-carbonyl)picolinonitrile | 479 | |

TABLE A1-continued

| The following Examples in Table A1 were prepared following the synthetic procedures towards Example A-4 with the following modifications in step 6: 1.5 eq of the appropriate acid was used and the reaction mixture was stirred at 50° C. for 2 h | | | | |
|---|---|---|---|---|
| Example No. | Structure | Compound Name | LCMS $[M + H]^+$ | NMR |
| A-4-22 | 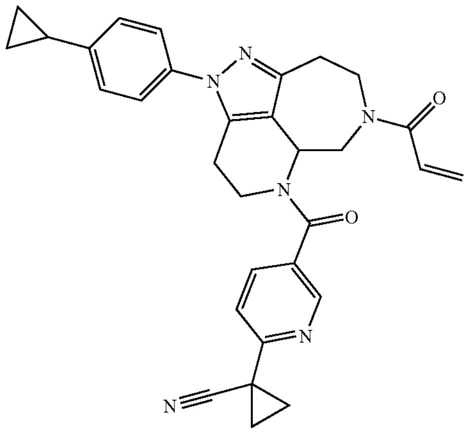 [SMILES: C=CC(=O)N1CCc2nn(-c3ccc(C4CC4)cc3)c3c2C(C1)N(C(=O)c1ccc(C2(C#N)CC2)nc1)CC3] | (S or R)-1-(5-(7-acryloyl-2-(4-cyclopropylphenyl)-3,4,5,5a,6,7,8,9-octahydro-2H-1,2,5,7-tetraazabenzo[cd]azulene-5-carbonyl)pyridin-2-yl)cyclopropane-1-carbonitrile | 519 | |
| A-4-23 | 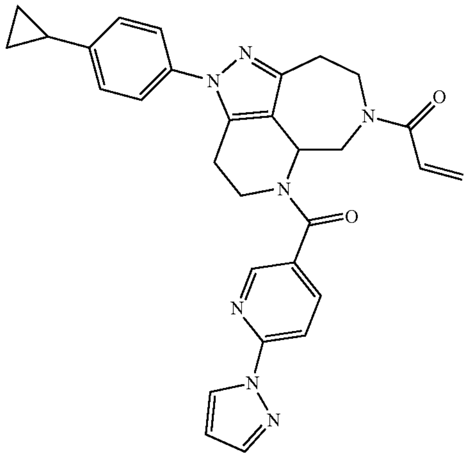 [SMILES: C=CC(=O)N1CCc2nn(-c3ccc(C4CC4)cc3)c3c2C(C1)N(C(=O)c1ccc(-n2cccn2)nc1)CC3] | (S or R)-1-(5-(6-(1H-pyrazol-1-yl)nicotinoyl)-2-(4-cyclopropylphenyl)-2,3,4,5,5a,6,8,9-octahydro-7H-1,2,5,7-tetraazabenzo[cd]azulen-7-yl)prop-2-en-1-one | 520 | $^1$H NMR (DMSO-d6, 400 MHz) δ 8.75-8.60 (m, 2H), 8.17 (dd, 1H, J = 2.2, 8.4 Hz), 8.10-7.95 (m, 1H), 7.90 (s, 1H), 7.60-7.43 (m, 1H), 7.42 (d, 2H, J = 8.5 Hz), 7.20 (d, 2H, J = 8.5 Hz), 6.65-6.60 (m, 1H), 6.35-6.20 (m, 1H), 5.85-5.65 (m, 1H), 5.25-5.10 (m, 1H), 4.80-4.60 (m, 1H), 4.40-4.25 (m, 1H), 3.95-3.85 (m, 1H), 3.50-3.35 (m, 1H), 3.35-3.10 (m, 2H), 2.95-2.75 (m, 3H), 2.70-2.55 (m, 1H), 2.00-1.90 (m, 1H), 1.00-0.90 (m, 2H), 0.75-0.65 (m, 2H) |
| A-4-24 | 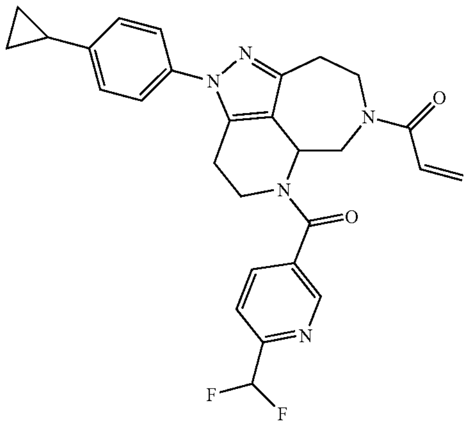 [SMILES: C=CC(=O)N1CCc2nn(-c3ccc(C4CC4)cc3)c3c2C(C1)N(C(=O)c1ccc(C(F)F)nc1)CC3] | (S or R)-1-(2-(4-cyclopropylphenyl)-5-(6-(difluoromethyl)nicotinoyl)-2,3,4,5,5a,6,8,9-octahydro-7H-1,2,5,7-tetraazabenzo[cd]azulen-7-yl)prop-2-en-1-one | 504 | |

TABLE A2

The following Examples in Table A2 were prepared in an analogous manner to Example A-4 step 6 using the corresponding carboxylic acids. The synthesis for the acid of Example A-4-29 is described in Example A-13

| Example No. | Structure | Compound Name | LCMS $[M + H]^+$ | NMR |
|---|---|---|---|---|
| A-4-25 | 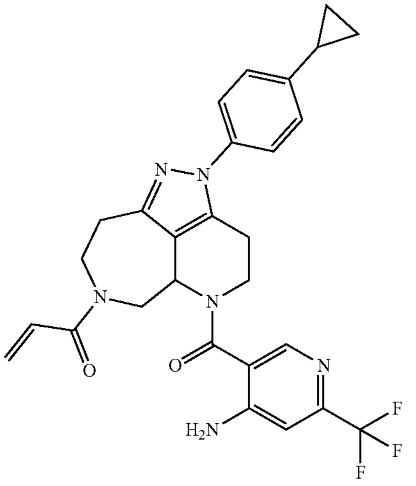 [SMILES: C=CC(=O)N1CCc2nn(-c3ccc(C4CC4)cc3)c3c2C(C1)N(C(=O)c1cnc(C(F)(F)F)cc1N)CC3] | (R or S)-1-(5-(4-amino-6-(trifluoromethyl)nicotinoyl)-2-(4-cyclopropylphenyl)-2,3,4,5,5a,6,8,9-octahydro-7H-1,2,5,7-tetraazabenzo[cd]azulen-7-yl)prop-2-en-1-one | 537 | $^1$H NMR (400 MHz, DMSO-d, ppm) δ 8.24 (s, 1H), 7.61-7.32 (m, 3H), 7.19 (d, J = 8.3 Hz, 2H), 7.10 (s, 1H), 6.95-6.54 (m, 2H), 6.41-6.10 (m, 1H), 5.90-5.69 (m, 1H), 5.31-5.08 (m, 1H), 4.85-4.56 (m, 1H), 4.54-4.15 (m, 1H), 3.82-3.57 (m, 1H), 3.45-3.30 (m, 1H), 3.25-3.03 (m, 2H), 3.03-2.73 (m, 3H), 2.71-2.56 (m, 1H), 2.10-1.86 (m, 1H), 1.12-0.82 (m, 2H), 0.80-0.60 (m, 2H) |
| A-4-26 | 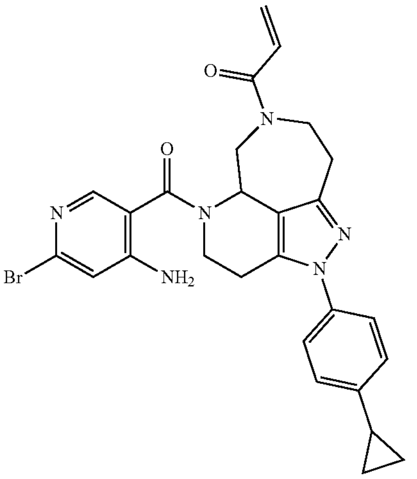 | (R or S)-1-(5-(4-amino-6-bromonicotinoyl)-2-(4-cyclopropylphenyl)-2,3,4,5,5a,6,8,9-octahydro-7H-1,2,5,7-tetraazabenzo[cd]azulen-7-yl)prop-2-en-1-one | 549 | $^1$H NMR (400 MHz, Chloroform-d) δ 7.94 (s, 1H), 7.46-7.21 (m, 2H), 7.11-7.00 (m, 2H), 6.85-6.74 (m, 1H), 6.47-6.33 (m, 1H), 5.85-5.65 (m, 1H), 5.33-5.20 (m, 1H), 5.19-5.05 (m, 1H), 4.94-4.81 (m, 1H), 4.45-4.27 (m, 1H), 4.23-4.00 (m, 1H), 3.19-3.03 (m, 2H), 3.02-2.82 (m, 3H), 2.77-2.52 (m, 2H), 1.91-1.77 (m, 1H), 1.28-1.10 (m, 2H), 1.01-0.86 (m, 2H), 0.69-0.56 (m, 2H). |
| A-4-27 | 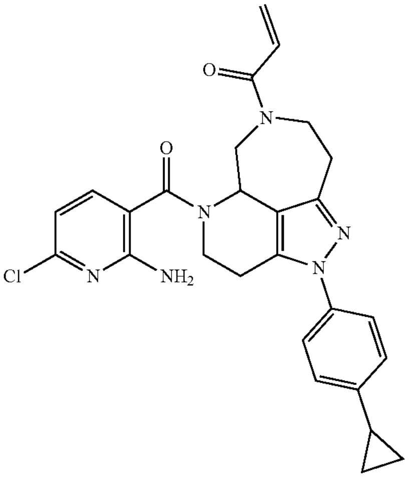 [SMILES: C=CC(=O)N1CCc2nn(-c3ccc(C4CC4)cc3)c3c2C(C1)N(C(=O)c1ccc(Cl)nc1N)CC3] | (R or S)-1-(5-(2-amino-6-chloronicotinoyl)-2-(4-cyclopropylphenyl)-2,3,4,5,5a,6,8,9-octahydro-7H-1,2,5,7-tetraazabenzo[cd]azulen-7-yl)prop-2-en-1-one | 503 | |

TABLE A2-continued

The following Examples in Table A2 were prepared in an analogous manner to Example A-4 step 6 using the corresponding carboxylic acids. The synthesis for the acid of Example A-4-29 is described in Example A-13

| Example No. | Structure | Compound Name | LCMS [M + H]+ | NMR |
|---|---|---|---|---|
| A-4-28 | 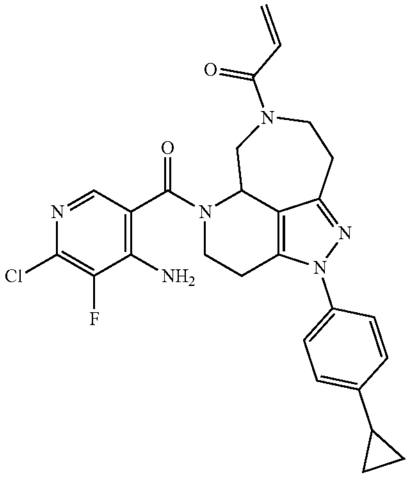 [SMILES: C=CC(=O)N1CCc2nn(-c3ccc(C4CC4)cc3)c3c2C(C1)N(C(=O)c1cnc(Cl)c(F)c1N)CC3] | (R or S)-1-(5-(4-amino-6-chloro-5-fluoronicotinoyl)-2-(4-cyclopropylphenyl)-2,3,4,5,5a,6,8,9-octahydro-7H-1,2,5,7-tetraazabenzo[cd]azulen-7-yl)prop-2-en-1-one | 521 | $^1$H NMR (400 MHz, Chloroform-d) δ 7.92 (s, 1H), 7.46-7.29 (m, 3H), 7.18-7.11 (m, 2H), 6.54-6.46 (m, 1H), 5.88-5.74 (m, 1H), 5.44-5.30 (m, 3H), 5.01-4.93 (m, 1H), 4.53-4.38 (m, 1H), 4.25-4.12 (m, 1H), 3.40-3.15 (m, 2H), 3.11-2.93 (m, 3H), 2.82-2.66 (m, 2H), 2.03-1.88 (m, 1H), 1.07-0.97 (m, 2H), 0.79-0.66 (m, 2H). |
| A-4-29 | 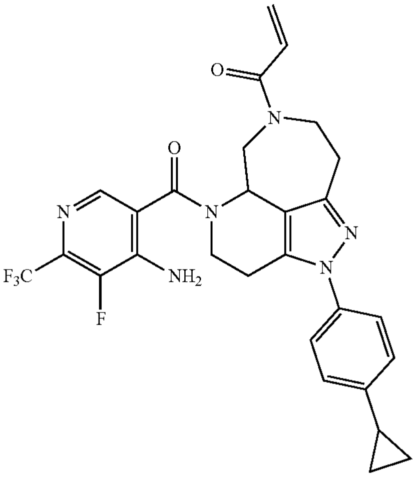 [SMILES: C=CC(=O)N1CCc2nn(-c3ccc(C4CC4)cc3)c3c2C(C1)N(C(=O)c1cnc(C(F)(F)F)c(F)c1N)CC3] | (R or S)-1-(5-(4-amino-5-fluoro-6-(trifluoromethyl)nicotinoyl)-2-(4-cyclopropylphenyl)-2,3,4,5,5a,6,8,9-octahydro-7H-1,2,5,7-tetraazabenzo[cd]azulen-7-yl)prop-2-en-1-one | 555 | $^1$H NMR (400 MHz, DMSO-$d_6$) δ 8.10 (s, 1H), 7.55-7.44 (m, 1H), 7.41-7.34 (m, 2H), 7.22-7.15 (m, 2H), 6.96 (s, 2H), 6.35-6.27 (m, 1H), 5.85-5.77 (m, 1H), 5.19-5.11 (m, 1H), 4.71-4.65 (m, 1H), 4.53-4.45 (m, 1H), 3.74-3.67 (m, 1H), 3.19-3.09 (m, 2H), 2.95-2.85 (m, 1H), 2.85-2.78 (m, 2H), 2.64-2.56 (m, 1H), 2.02-1.91 (m, 1H), 1.02-0.91 (m, 2H), 0.73-0.65 (m, 2H). |
| A-4-30 | 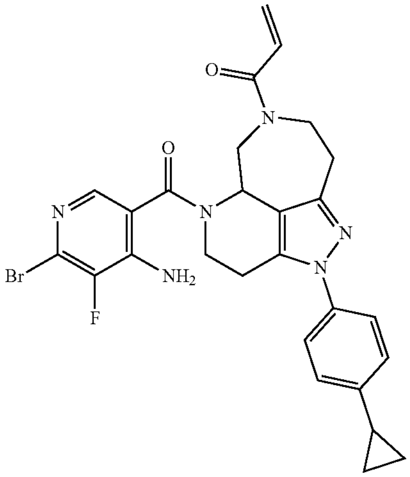 | (R or S)-1-(5-(4-amino-6-bromo-5-fluoronicotinoyl)-2-(4-cyclopropylphenyl)-2,3,4,5,5a,6,8,9-octahydro-7H-1,2,5,7-tetraazabenzo[cd]azulen-7-yl)prop-2-en-1-one | 565 | $^1$H NMR (400 MHz, Chloroform-d, ppm) δ 7.82 (brs, 1H), 7.34-7.13 (m, 2H), 7.13-6.92 (m, 2H), 6.67-6.21 (m, 1H), 5.87-5.61 (m, 1H), 5.26 (s, 3H), 4.97-3.91 (m, 3H), 3.34-2.41 (m, 7H), 1.95-1.75 (m, 1H), 1.31-0.72 (m, 3H), 0.74-0.43 (m, 2H). |

TABLE A2-continued

The following Examples in Table A2 were prepared in an analogous manner to Example A-4 step 6 using the corresponding carboxylic acids. The synthesis for the acid of Example A-4-29 is described in Example A-13

| Example No. | Structure | Compound Name | LCMS $[M + H]^+$ | NMR |
|---|---|---|---|---|
| A-4-31 | 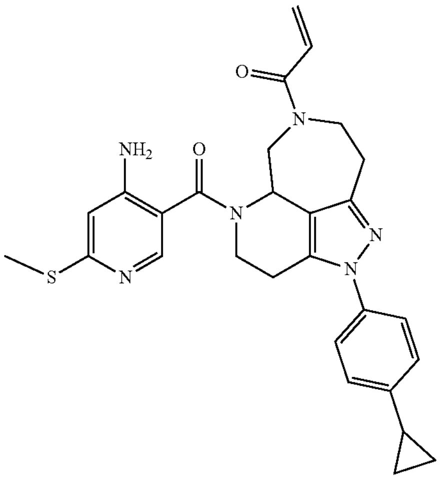 [SMILES: C=CC(=O)N1CCc2nn(-c3ccc(C4CC4)cc3)c3c2C(C1)N(C(=O)c1cnc(SC)cc1N)CC3] | (R or S)-1-(5-(4-amino-6-(methylthio)nicotinoyl)-2-(4-cyclopropylphenyl)-2,3,4,5,5a,6,8,9-octahydro-7H-1,2,5,7-tetraazabenzo[cd]azulen-7-yl)prop-2-en-1-one | 515 | 1H NMR (400 MHz, Chloroform-d) δ 7.85-7.80 (m, 1H), 7.27-7.14 (m, 2H), 7.11-7.02 (m, 2H), 6.43-6.38 (m, 1H), 5.78-5.73 (m, 1H), 5.26 (s, 3H), 4.91-4.86 (m, 1H), 4.40-4.35 (m, 1H), 4.13-4.09 (m, 1H), 3.13-3.09 (m, 2H), 2.98 (s, 3H), 2.69-2.65 (m, 2H), 1.87-1.82 (m, 1H), 1.19 (s, 1H), 0.95-0.91 (m, 2H), 0.66-0.61 (m, 2H). |
| A-4-32 | 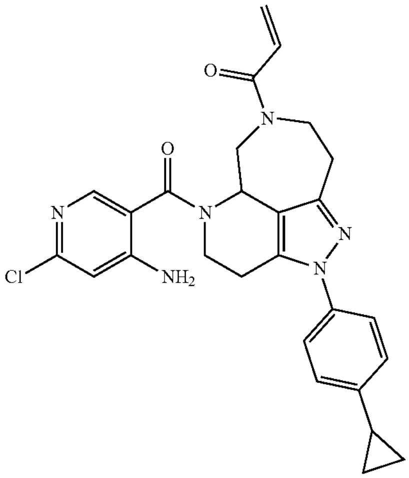 [SMILES: C=CC(=O)N1CCc2nn(-c3ccc(C4CC4)cc3)c3c2C(C1)N(C(=O)c1cnc(Cl)cc1N)CC3] | (R or S)-1-(5-(4-amino-6-chloronicotinoyl)-2-(4-cyclopropylphenyl)-2,3,4,5,5a,6,8,9-octahydro-7H-1,2,5,7-tetraazabenzo[cd]azulen-7-yl)prop-2-en-1-one | 503 | 1H NMR (400 MHz, Chloroform-d, ppm) δ 8.05 (s, 1H), 7.49-7.36 (m, 1H), 7.36-7.28 (m, 2H), 7.18-7.11 (m, 2H), 6.70 (s, 1H), 6.50 (d, J = 16.6 Hz, 1H), 5.88-5.71 (m, 1H), 5.41-5.28 (m, 1H), 5.20 (s, 2H), 5.06-4.87 (m, 1H), 4.57-4.32 (m, 1H), 4.30-4.02 (m, 1H), 3.44-2.62 (m, 7H), 1.99-1.88 (m, 1H), 1.06-0.92 (m, 2H), 0.78-0.66 (m, 2H). |
| A-4-33 | 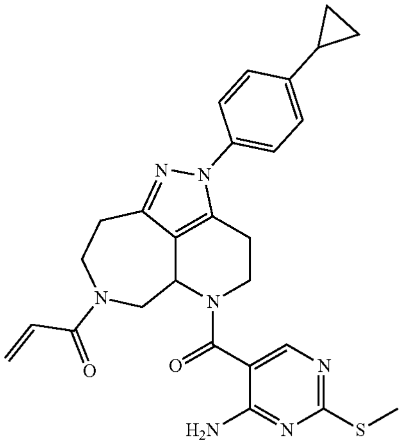 [SMILES: C=CC(=O)N1CCc2nn(-c3ccc(C4CC4)cc3)c3c2C(C1)N(C(=O)c1cnc(SC)nc1N)CC3] | (R or S)-1-(5-(4-amino-2-(methylthio)pyrimidine-5-carbonyl)-2-(4-cyclopropylphenyl)-2,3,4,5,5a,6,8,9-octahydro-7H-1,2,5,7-tetraazabenzo[cd]azulen-7-yl)prop-2-en-1-one | 516 | $^1H$ NMR (400 MHz, DMSO-$d_6$) δ 8.09 (s, 1H), 7.57-7.30 (m, 3H), 7.28-6.97 (m, 3H), 6.39-6.14 (m, 1H), 5.91-5.61 (m, 1H), 5.08 (s, 1H), 4.71-4.55 (m, 1H), 4.52-4.11 (m, 1H), 3.80 (s, 1H), 3.23-3.03 (m, 4H), 2.95-2.72 (m, 3H), 2.70-2.56 (m, 1H), 2.46 (s, 3H), 2.02-1.89 (m, 1H), 1.01-0.91 (m, 2H), 0.74-0.64 (m, 2H). |

Example A-5: Preparation of (S or R)-1-(5-(7-bromo-1H-benzo[d]imidazole-4-carbonyl)-2-(2-hydroxy-4-(2,2,2-trifluoroethyl)phenyl)-2,3,4,5,5a,6,8,9-octahydro-7H-1,2,5,7-tetraazabenzo[cd]azulen-7-yl)prop-2-en-1-one
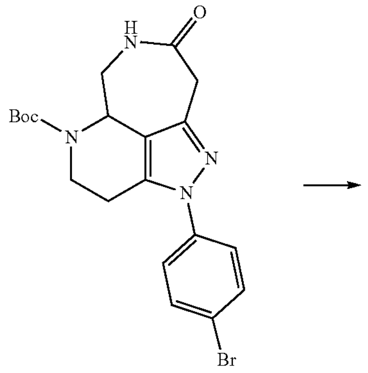
Int. E
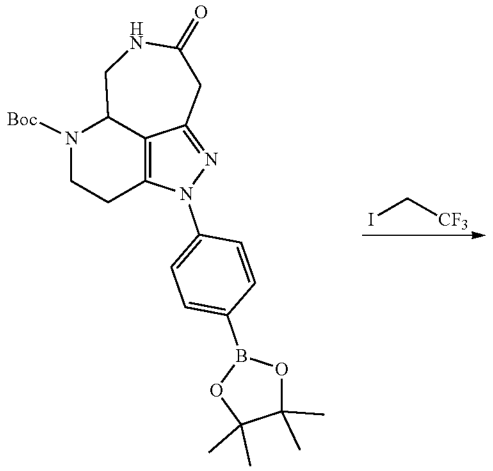
Int. E1
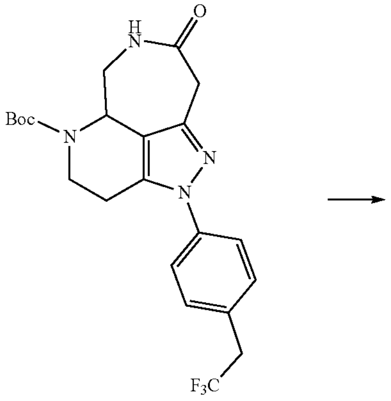
-continued
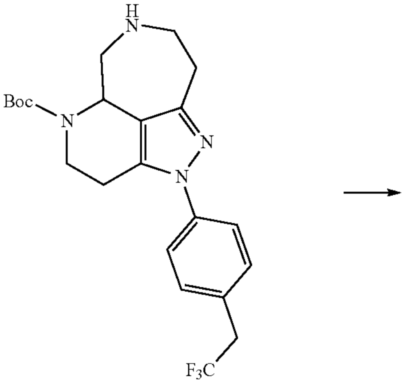
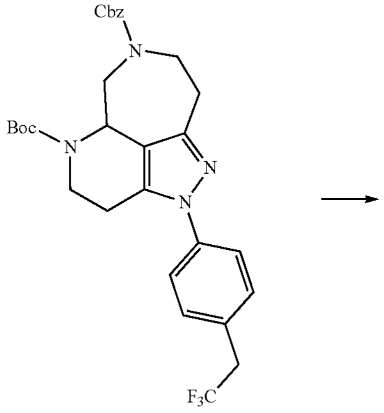
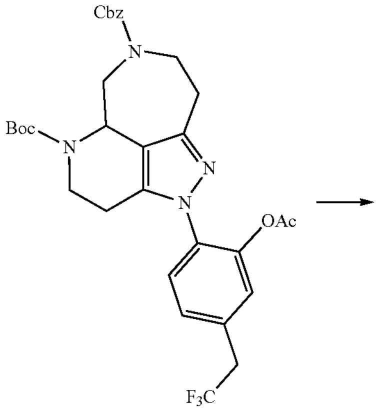
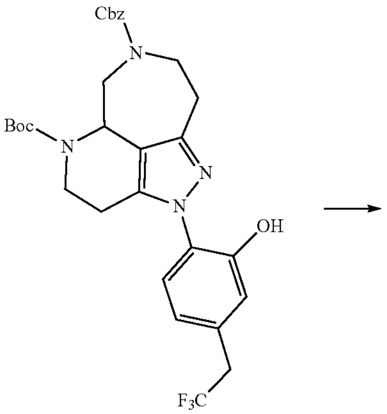

-continued

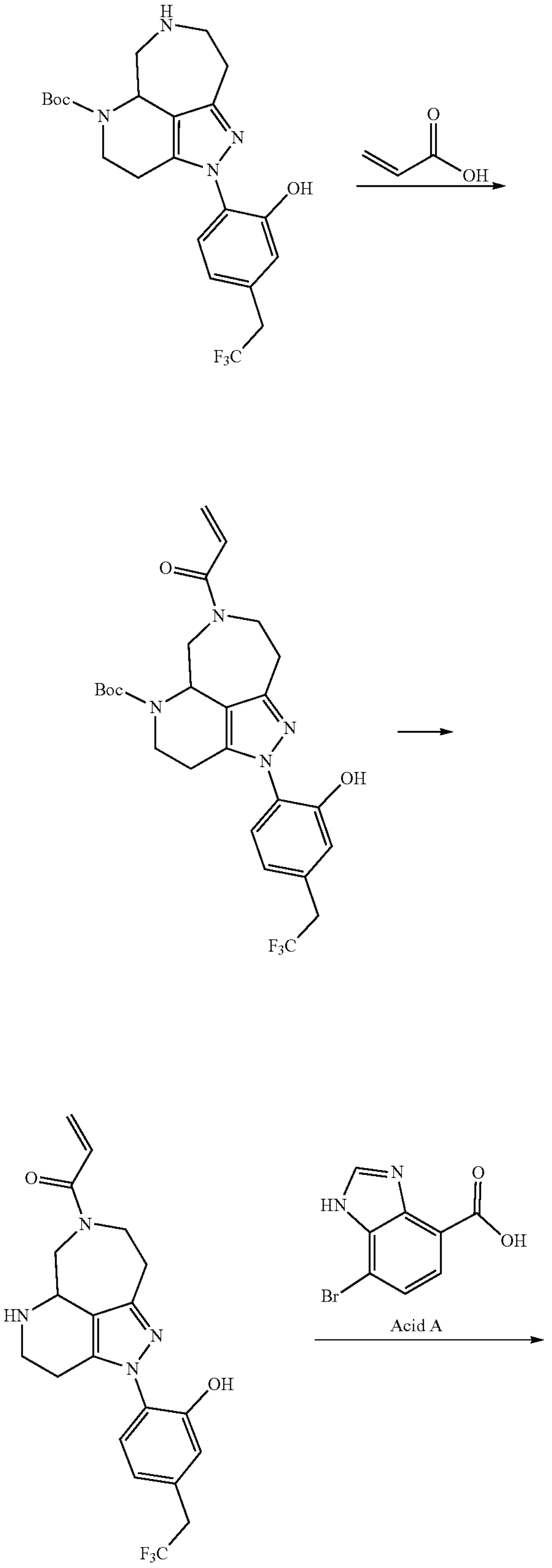

Int. E2

-continued

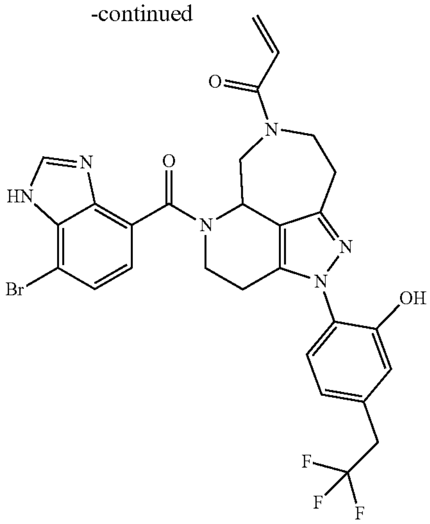

Step 1: Synthesis of Tert-Butyl 8-oxo-2-(4-(4,4,5,5-tetramethyl-1,3,2-dioxaborolan-2-yl)phenyl)-2,3,4,5a,6,7,8,9-octahydro-5H-1,2,5,7-tetraazabenzo[cd]azulene-5-carboxylate (Int. E1)

To a solution of tert-butyl 2-(4-bromophenyl)-8-oxo-2,3,4,5a,6,7,8,9-octahydro-5H-1,2,5,7-tetraazabenzo[cd]azulene-5-carboxylate (10 g, 1 equiv., 22 mmol) in 1,4-dioxane (20 mL) were added 4,4,4',4',5,5,5',5'-octamethyl-2,2'-bi(1,3,2-dioxaborolane) (11 g, 2 equiv., 45 mmol), KOAc (6.6 g, 4.2 mL, 3 equiv., 67 mmol) and $PdCl_2$(dppf) (1.6 g, 0.1 equiv., 2.2 mmol). The reaction system was purged with nitrogen×3. The resulting mixture was stirred for 80° C. at 3 h under nitrogen atmosphere. The reaction was complete based on LCMS sample analysis. After the reaction mixture was cooled to RT, the mixture was filtered and rinsed with EtOAc (3×20 mL), then diluted with water (20 mL). The aqueous layer was extracted with EtOAc (2×20 mL). The combined organic layers were washed with saturated brine (3×20 ml), dried over anhydrous sodium sulfate and concentrated to give a residue. The crude product was purified by silica gel chromatography eluting with PE:EtOAc=10:1 to give tert-butyl 8-oxo-2-(4-(4,4,5,5-tetramethyl- 1,3,2-dioxaborolan-2-yl)phenyl)-2,3,4,5a,6,7,8,9-octahydro-5H-1,2,5,7-tetraazabenzo[cd]azulene-5-carboxylate (10 g) as a brown solid. LCMS:(ESI, m/z):495 $[M+1]^+$ Step 2: Synthesis of Tert-Butyl 8-oxo-2-(4-(2,2,2-trifluoroethyl)phenyl)-2,3,4,5a,6,7,8,9-octahydro-5H-1,2,5,7-tetraazabenzo[cd]azulene-5-carboxylate To a solution of tert-butyl 8-oxo-2-(4-(4,4,5,5-tetramethyl-1,3,2-dioxaborolan-2-yl)phenyl)-2,3,4,5a,6,7,8,9-octahydro-5H-1,2,5,7-tetraazabenzo[cd]azulene-5-carboxylate (Int. E1) (2 g, 1 equiv., 4 mmol) in DMF (20 mL) were added CuCl (0.2 g, 0.0 mL, 0.5 equiv., 2 mmol), 1,1,1-trifluoro-2-iodoethane (4 g, 2 mL, 5 equiv., 0.02 mol), $Cs_2CO_3$ (2 g, 1.5 equiv., 6 mmol), water (0.3 g, 0.3 mL, 4 equiv., 0.02 mol), XPhos (0.2 g, 0.1 equiv., 0.4 mmol) and $Pd_2(dba)_3$ (0.2 g, 0.05 equiv., 0.2 mmol). The reaction system was purged with nitrogen 3. The resulting mixture was stirred overnight at 60° C. under nitrogen atmosphere. The reaction was complete based on LCMS sample analysis. After the reaction mixture was cooled to RT, the mixture was filtered and rinsed with EtOAc (3×20 mL), then diluted with water (20 mL). The aqueous layer was extracted with EtOAc (2×20 mL). The combined organic layers were washed with saturated brine (3×20 mL), dried over anhydrous sodium sulfate and concentrated to give a residue. The crude product was purified by silica gel chromatography eluting with PE:EtOAc=5:1 to give tert-butyl 8-oxo-2-(4-(2,2,2-trifluoroethyl)phenyl)-2,3,4,5a,6,7,8,9-octahydro-5H-1,2,5,7-t tetraazabenzo[cd]azulene-5-carboxylate (600 mg) as a white solid. LCMS:(ESI, m/z):451 [M+1]$^+$ Step 3: Synthesis of Tert-Butyl 2-(4-(2,2,2-trifluoroethyl)phenyl)-2,3,4,3a,6,7,8,9-octahydro-5H-1,2,5,7-tetraazabenzo[cd]azulene-5-carboxylate A solution of tert-butyl 8-oxo-2-(4-(2,2,2-trifluoroethyl)phenyl)-2,3,4,5a,6,7,8,9-octahydro-5H-1,2,5,7-tetraazabenzo[cd]azulene-5-carboxylate (600 mg, 1 equiv., 1.33 mmol) in THF (2 mL) was cooled to 0° C., then $BH_3$·THF (6.66 mL, 5 Eq, 6.66 mmol, 1 mol/L) was added slowly at 0° C. The mixture was warmed to 60° C. and stirred for 4 h. The reaction was monitored by LCMS. The reaction was quenched by the addition of MeOH (2 mL) at 0° C.; The solvent was removed under reduced pressure. This resulted in tert-butyl 2-(4-(2,2,2-trifluoroethyl)phenyl)-2,3,4,5a,6,7,8,9-octahydro-5H-1,2,5,7-tetraazabenzo[cd]azulene-5-carboxylate (580 mg, 1.33 mmol, 96.7%) as a white solid. The crude product was used in the next step directly without further purification. LCMS:(ESI, m/z): 437 [M+1]$^+$ Step 4: Synthesis of 7-Benzyl 5-(tert-butyl) 2-(4-(2,2,2-trifluoroethyl)phenyl)-3,4,5a,6,8,9-hexahydro-2H-1,2,5,7-tetraazabenzo[cd]azulene-5,7-dicarboxylate To a stirring solution of tert-butyl 2-(4-(2,2,2-trifluoroethyl)phenyl)-2,3,4,5a,6,7,8,9-octahydro-5H-1,2,5,7-tetraazabenzo[cd]azulene-5-carboxylate (650 mg 1 equiv., 1.49 mmol) in DCM (2 mL) was added TEA (1.51 g, 2.08 mL, 10 equiv., 14.9 mmol) and Cbz-OSu (1.86 g, 5 equiv., 7.45 mmol) at 40° C. The resulting mixture was stirred for 16 h at 40° C. The reaction was monitored by LCMS. After completion, the mixture was filtered and rinsed with DCM (3×5 mL), then diluted with water (10 mL). The aqueous layer was extracted with DCM (2×10 mL), dried over anhydrous sodium sulfate and concentrated to give a residue. The crude product was purified by silica gel chromatography eluting with PE:EtOAc=10:1 to give 7-benzyl 5-(tert-butyl) 2-(4-(2,2,2-trifluoroethyl)phenyl)-3,4,5a,6,8,9-hexahydro-2H-1,2,5,7-tetraazabenzo[cd]azulene-5,7-dicarboxylate (600 mg) as a white solid. LCMS:(ESI, m/z): 571 [M+1]$^+$ Step 5: Synthesis of 7-Benzyl 5-(tert-butyl) 2-(2-acetoxy-4-(2,2,2-trifluoroethyl)phenyl)-3,4,5a,6,8,9-hexahydro-2H-1,2,5,7-tetraazabenzo[cd]azulene-5,7-dicarboxylate To a solution of 7-benzyl 5-(tert-butyl) 2-(4-(2,2,2-trifluoroethyl)phenyl)-3,4,5a,6,8,9-hexahydro-2H-1,2,5,7-tetraazabenzo[cd]azulene-5,7-dicarboxylate (540 mg, 1 equiv., 946 gmol) in AcOH (54 mL) were added PIDA (610 mg, 2 equiv., 1.89 mmol) and palladium diacetate (21.2 mg, 0.1 equiv., 94.6 gmol). The mixture was stirred at 90° C. for 1 h. The reaction was monitored by LCMS. After the reaction mixture was cooled to RT, the mixture was filtered and rinsed with EtOAc (3×20 mL), then diluted with water (20 mL). The aqueous layer was extracted with EtOAc (2×20 mL). The combined organic layers were washed with sodium bicarbonate in water (3×20 mL), dried over anhydrous sodium sulfate and concentrated to give a residue. The crude product was purified by silica gel chromatography eluting with PE:EtOAc=3:1 to give 7-benzyl 5-(tert-butyl) 2-(2-acetoxy-4-(2,2,2-trifluoroethyl)phenyl)-3,4,5a,6,8,9-hexahydro-2H-1,2,5,7-tetraazabenzo[cd]azulene-5,7-dicarboxylate (200 mg) as a yellow oil. LCMS:(ESI, m/z):629 [M+1]$^+$ Step 6: Synthesis of 7-Benzyl 5-(tert-butyl) 2-(2-hydroxy-4-(2,2,2-trifluoroethyl)phenyl)-3,4,5a,6,8,9-hexahydro-2H-1,2,5,7-tetraazabenzo[cd]azulene-5,7-dicarboxylate To a solution of 7-benzyl 5-(tert-butyl) 2-(2-acetoxy-4-(2,2,2-trifluoroethyl)phenyl)-3,4,5a,6,8,9-hexahydro-2H-1,2,5,7-tetraazabenzo[cd]azulene-5,7-dicarboxylate (180 mg, 1 equiv., 286 μmol) in THF (1 mL) and water (0.5 mL) was added LiOH (10.3 g, 1.5 equiv., 429 μmol). The mixture was stirred at room temperature for 2 h. The reaction was monitored by LCMS. The mixture was acidified to pH=3 with 1 M sulfuric acid, then diluted with EtOAc (5 mL) and water (5 mL), and the aqueous layer was extracted with EtOAc (3×5 mL). The organic layers were combined and washed with saturated brine (20 mL), dried over anhydrous sodium sulfate and concentrated to afford 7-benzyl 5-(tert-butyl) 2-(2-hydroxy-4-(2,2,2-trifluoroethyl)phenyl)-3,4,5a,6,8,9-hexahydro-2H-1,2,5,7-tetraazabenzo[cd]azulene-5,7-dicarboxylate (180 mg) as a yellow solid. The crude product was used in the next step directly without further purification. LCMS:(ESI, m/z):587 [M+1]$^+$ Step 7: Synthesis of Tert-Butyl 2-(2-hydroxy-4-(2,2,2-trifluoroethyl)phenyl)-2,3,4,5a,6,7,8,9-octahydro-5H-1,2,5,7-tetraazabenzo[cd]azulene-5-carboxylate To a solution of 7-benzyl 5-(tert-butyl) 2-(2-hydroxy-4-(2,2,2-trifluoroethyl)phenyl)-3,4,5a,6,8,9-hexahydro-2H-1,2,5,7-tetraazabenzo[cd]azulene-5,7-dicarboxylate (165 mg, 1 equiv., 281 μmol) in THF (2 mL) was added Pd/C (74.8 mg, 20 wt %, 0.5 equiv., 141 mol) and $Pd(OH)_2$ (98.7 mg, 20 wt %, 0.5 equiv., 141 μmol) in a pressure tank. The mixture was hydrogenated at room temperature under 4 MPa of hydrogen pressure for 4 h. The reaction mixture was cooled to room temperature and filtered through Celite to remove insoluble solid. The filter cake was washed with EtOH (2×20 mL). The filtrate was concentrated under reduced pressure to afford tert-butyl 2-(2-hydroxy-4-(2,2,2-trifluoroethyl)phenyl)-2,3,4,5a,6,7,8,9-octahydro 5H-1,2,5,7-tetraazabenzo[cd]azulene-5-carboxylate (100 mg) as a crude yellow oil. The crude product was used in the next step directly without further purification. LCMS:(ESI, r/z):453 [M+1]$^+$ Step 8: Synthesis of Tert-Butyl 7-acryloyl-2-(2-hydroxy-4-(2,2,2-trifluoroethyl)phenyl)-2,3,4,5a,6,7,8,9-octahydro-5H-1,2,5,7-tetraazabenzo[cd]azulene-5-carboxylate To a solution of tert-butyl 2-(2-hydroxy-4-(2,2,2-trifluoroethyl)phenyl)-2,3,4,5a,6,7,8,9-octahydro-5H-1,2,5,7-tetraazabenzo[cd]azulene-5-carboxylate (90 mg, 1 equiv., 0.2 mmol) in DMF (2 mL) were added DIEA (0.10 g, 0.14 mL, 4 equiv., 0.8 mmol), acrylic acid (17 mg, 1.2 equiv., 0.24 mmol) and T3P (95 mg, 1.5 equiv., 0.3 mmol). The mixture was stirred at room temperature for 2 h. The reaction was monitored by LCMS. The mixture was diluted with water (5 mL) and EtOAc (5 mL), and the aqueous layer was extracted with EtOAc (2×5 mL). The combined organic layers were washed with saturated brine (2×20 ml), dried over anhydrous sodium sulfate and concentrated to give a residue. The residue was purified by flash column chromatography, eluting with EtOAc/PE (1:5) to afford tert-butyl 7-acryloyl-2-(2-hydroxy-4-(2,2,2-trifluoroethyl)phenyl)-2,3,4,5a,6,7,8,9-octahydro-5H-1,2,5,7-tetraazabenzo[cd]azulene-5-carboxylate (40 mg) as a yellow oil. LCMS:(ESI, m/z): 507 $[M+1]^+$ Step 9: Synthesis of 2-(3,4,5,5a,6,7,8,9-octahydro-2H-1,2,5,7-tetraazabenzo[cd]azulen-2-yl)-5-(2,2,2-trifluoroethyl)phenol (Int. E2)

The solution of tert-butyl 7-acryloyl-2-(2-hydroxy-4-(2,2,2-trifluoroethyl)phenyl)-2,3,4,5a,6,7,8,9-octahydro-5H-1,2,5,7-tetraazabenzo[cd]azulene-5-carboxylate (35 mg, 1 equiv., 69 μmol) in DCM (1.5 mL) and TFA (0.5 mL) was stirred at room temperature for 1 h. The reaction was monitored by LCMS. The solvent was removed under reduced pressure. This resulted in 2-(3,4,5,5a,6,7,8,9-octahydro-2H-1,2,5,7-tetraazabenzo[cd]azulen-2-yl)-5-(2,2,2-trifluoroethyl)phenol (Int. E2) (50 mg) as a crude yellow oil. The crude product was used in the next step directly without further purification. LCMS:(ESI, m/z): 407 $[M+1]^+$ Step 10: Synthesis of (S or R)-1-(5-(7-bromo-H-benzo[d]imidazole-4-carbonyl)-2-(2-hydroxy-4-(2,2,2-trifluoroethyl)phenyl)-2,3,4,5,5a,6,8,9-octahydro-7H-1,2,5,7-tetraazabenzo[cd]azulen-7-yl)prop-2-en-1-one To a solution of 2-(3,4,5,5a,6,7,8,9-octahydro-2H-1,2,5,7-tetraazabenzo[cd]azulen-2-yl)-5-(2,2,2-trifluoroethyl)phenol (40 mg, 1 equiv., 0.11 mmol) in DMF (1 mL) were added DIEA (73 mg, 99 μL, 5 equiv., 0.57 mmol), 7-bromo-1H-benzo[d]imidazole-4-carboxylic acid (55 mg, 2 equiv., 0.23 mmol), EDCI (44 mg, 2 equiv., 0.23 mmol) and HOBT (26 mg, 1.7 equiv., 0.19 mmol). The mixture was stirred at room temperature overnight. The reaction was monitored by LCMS. The mixture was diluted with water (20 mL) and EtOAc (20 mL), an d the aqueous layer was extracted with EtOAc (2×20 mL). The combined organic layers were washed with saturated brine (2×20 mL), dried over anhydrous sodium sulfate and concentrated to give a residue. The residue was purified by Prep-HPLC (Column: YMC Triart C18 ExRs 5 m, 30 mm*150 mm; Mobile Phase A: water (10 mmol/L $NH_4HCO_3$), Mobile Phase B: MeCN; Flow rate: 60 mL/min; Gradient: 30% B to 60% B in 8 min; Wave Length: UV 254 nm/221 nm; retention time 1: 6.8) to afford (R or S)-1-(5-(7-bromo-1H-benzo[d]imidazole-4-carbonyl)-2-(2-hydroxy-4-(2,2,2-trifluoroethyl)phenyl)-2,3,4,5,5a,6,8,9-octahydro-7H-1,2,5,7-tetraazabenzo[cd]azulen-7-yl)prop-2-en-1-one (10 mg) as a white solid. LCMS:(ESI, m/z): 631 $[M+1]^+$ The racemic compound, 1-(5-(7-bromo-1H-benzo[d]imidazole-4-carbonyl)-2-(2-hydroxy-4-(2,2,2-trifluoroethyl)phenyl)-2,3,4,5,5a,6,8,9-octahydro-7H-1,2,5,7-tetraazabenzo[cd]azulen-7-yl)prop-2-en-1-one (10 mg) was separated into constituent enantiomers by chiral HPLC separation under the condition (Column: CHIRALPAK-IE 2*25 cm, 5 μm; Mobile Phase A: HEX(0.1% FA), Mobile Phase B: EtOH:DCM=1:1; Flow rate: 20 mL/min; Gradient: isocratic 50; Wave Length: UV 254/220 nm; Sample Solvent: EtOH:DCM; Injection Volume: 2.0 mL; Number Of Runs: 1) to afford (S or R)-1-(5-(7-bromo-1H-benzo[d]imidazole-4-carbonyl)-2-(2-hydroxy-4-(2,2,2-trifluoroethyl)phenyl)-2,3,4,5,5a,6,8,9-octahydro-7-1,2,5,7-tetraazabenzo[cd]azulen-7-yl)prop-2-en-1-one (peak 1, retention time 9.2 min, 3 mg, 5.7 μmol, 30%) as a white solid. LCMS: (ESI, m/z): 631 $[M+1]^+$. $^1$H NMR: (400 MHz, Chloroform-d, ppm) δ 10.79-10.01 (m, 1H), 8.41-7.93 (m, 1H), 7.68-7.37 (m, 2H), 7.14-6.90 (m, 2H), 6.79 (brs, 1H), 6.64-6.33 (m, 1H), 5.96-5.72 (m, 1H), 5.59-5.36 (m, 1H), 5.14-4.85 (m, 1H), 4.72-3.98 (m, 1H), 3.83-2.30 (m, 11H). $^{19}$F NMR: (376 MHz, DMSO, ppm) δ 65.74

Analytical chiral HPLC: Column: CHIRAL Cellulose-SB4.6*100 mm, 3 um; Mobile Phase: HEX (0.1% FA): Mobile Phase B: EtOH:DCM=1:1; Flow rate:1.0 mL/in; Temperature:25° C.; retention time: 2.0 min.

TABLE A3

The compound of Example A-5-1 was prepared in an analogous fashion to Example A-5, using the corresponding carboxylic acid. The racemic final compound was separated using the following conditions: Column: CHIRALPAK-IC 2*25 cm, 5 μm; Mobile Phase A: HEX(0.1%F A), Mobile Phase B: ETOH: DCM = 1:1; Flow rate: 20 mL/min; Gradient: isocratic 50; Wave Length: 254/220 nm to provide the compound of the example as the second-eluting peak.

| Example No. | Structure | Compound Name | LCMS $[M + H]^+$ | NMR |
|---|---|---|---|---|
| A-5-1 | 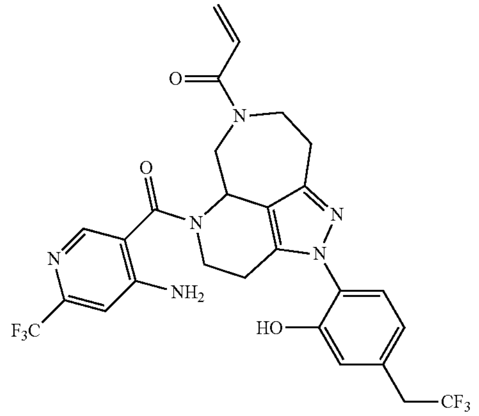 [SMILES: C=CC(=O)N1CCc2nn(-c3ccc(CC(F)(F)F)cc3O)c3c2C(C1)N(C(=O)c1cnc(C(F)(F)F)cc1N)CC3] | (R or S)-1-(5-(4-amino-6-(trifluoromethyl)nicotinoyl)-2-(2-hydroxy-4-(2,2,2-trifluoroethyl)phenyl)-2,3,4,5,5a,6,8,9-octahydro-7H-1,2,5,7-tetraazabenzo[cd]azulen-7-yl)prop-2-en-1-one | 595 | $^1$H NMR (400 MHz, CDCl3) δ 8.37 (s, 1H), 7.43-7.38 (m, 1H), 7.11-7.02 (m, 3H), 6.88-6.81 (m, 1H), 6.56-6.48 (m, 1H), 5.91-5.84 (m, 1H), 5.41-5.36 (m, 2H), 5.03-4.95 (m, 1H), 4.52-4.48 (m, 1H), 4.24-4.20 (m, 1H), 3.41-3.29 (m, 2H), 3.28-3.17 (m, 1H), 3.14-3.01 (m, 4H), 2.92-2.84 (m, 1H), 2.82-2.72 (m, 1H), 1.26 (s, 1H), 0.88-0.83 (m, 1H). |

Example A-6: Preparation of 1-(5-(7-bromo-1H-benzo[d]imidazole-4-carbonyl)-2-(2-hydroxy-4-(trifluoromethyl)phenyl)-2,3,4,5,5a,6,8,9-octahydro-7H-1,2,5,7-tetraazabenzo[cd]azulen-7-yl)prop-2-en-1-one
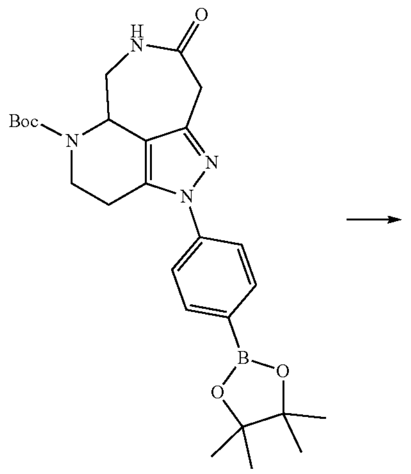
Int. E1
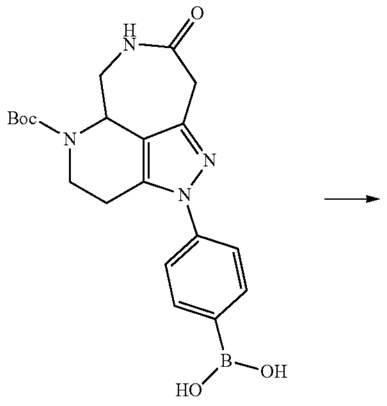
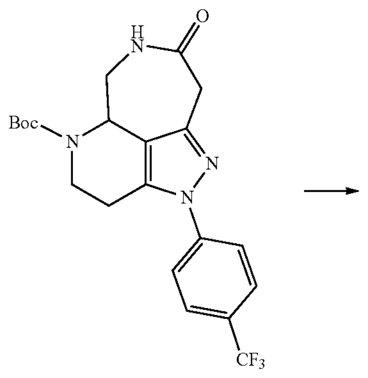
-continued
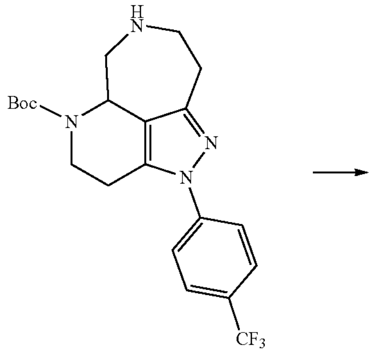
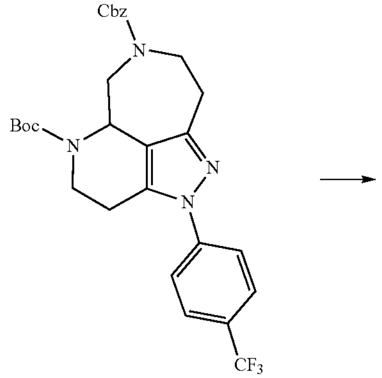
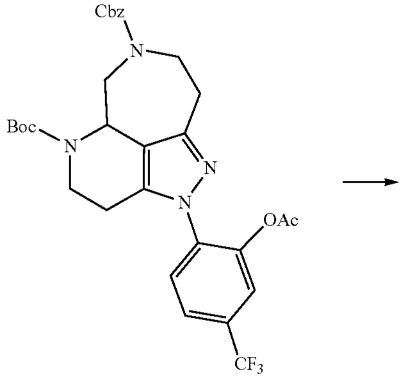
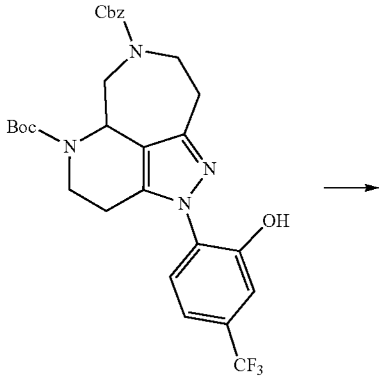

-continued

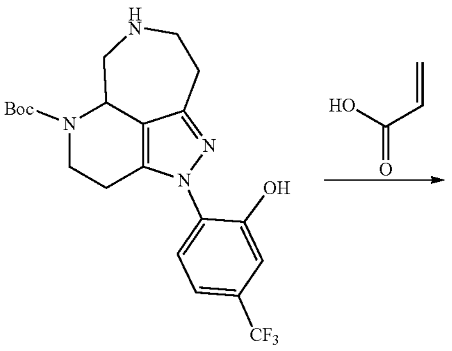

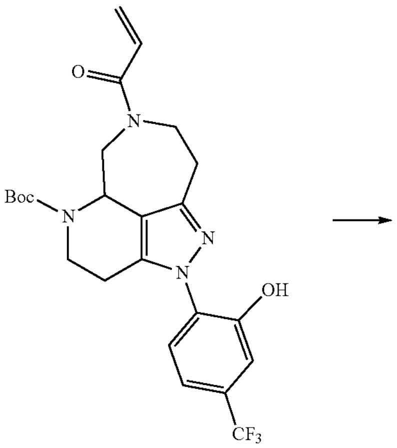

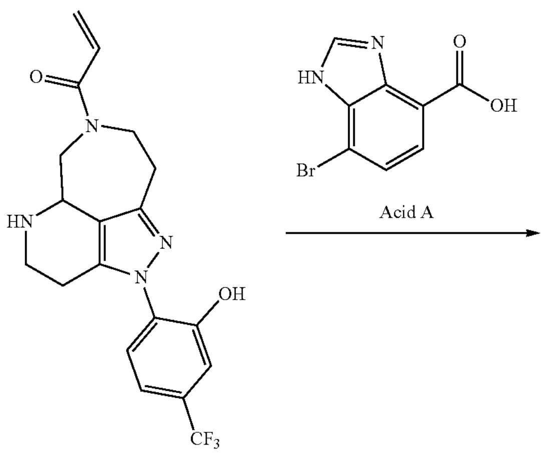

-continued

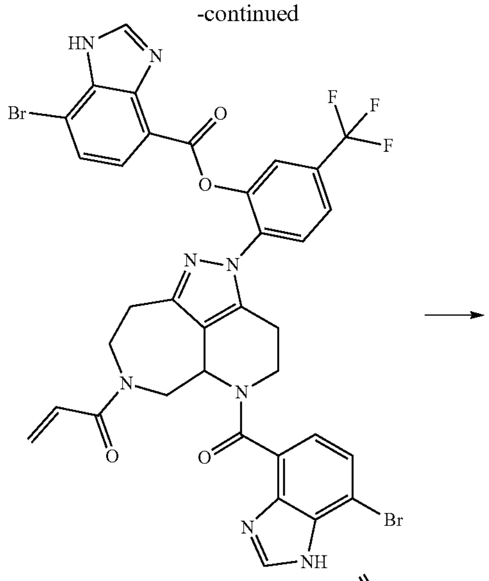

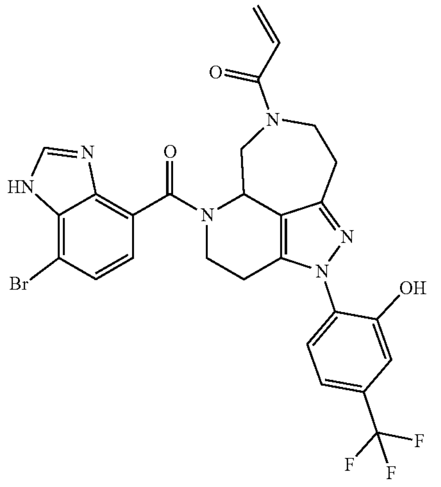

Step 1: Synthesis of (4-(5-(tert-butoxycarbonyl)-8-oxo-3,4,5,5a,6,7,8,9-octahydro-2H-1,2,5,7-tetraazabenzo[cd]azulen-2-yl)phenyl)boronic acid To a solution of tert-butyl 8-oxo-2-(4-(4,4,5,5-tetramethyl-1,3,2-dioxaborolan-2-yl)phenyl)-2,3,4,5a,6,7,8,9-octahydro-5H-1,2,5,7-tetraazabenzo[cd]azulene-5-carboxylate (3.50 g, 1 equiv., 7.08 mmol) in MeCN (35 mL) were added ammonium forma e (1.64 g, 3 equiv., 21.2 mmol) and sodium metaperiodate (3.03 g, 750 μL, 2 equiv., 14.2 mmol) The mixture was stirred for 3 h at rt. Then water (17.5 mL) was added, and the mixture was stirred for 21 h at rt. The mixture was filtered and rinsed with water (5×30 mL), and the filter cake was concentrated under vacuum to give a residue. This resulted in (4-(5-(tert-butoxycarbonyl)-8-oxo-3,4,5,5a,6,7,8,9 -octahydro-2H-1,2,5,7-tetraazabenzo[cd] azulen-2-yl)phenyl)boronic acid (4.2 g) as a crude gray solid. The crude product was used in the next step directly without further purification. LCMS: (ESI, m/z):413 $[M+H]^+$ Step 2: Synthesis of Tert-Butyl 8-oxo-2-(4-(trifluoromethyl)phenyl)-2,3,4,5a,6,7,8,9-octahydro-5H-1,2,5,7-tetraazabenzo[cd]azulene-5-carboxylate To a solution of (4-(5-(tert-butoxycarbonyl)-8-oxo-3,4,5,5a,6,7,8,9-octahydro-2H-1,2,5,7-tetraazabenzo[cd]azulen- 2-yl)phenyl)boronic acid (3.50 g, 65 wt %, 1 equiv., 5.52 mmol) in DCM (35 mL), MeOH (35 mL) and water (28 mL) were added sodium trifluoromethylsulfinate (2.58 g, 3 equiv., 16.6 mmol) and cuprous chloride (546 mg, 140 μL, 1 equiv., 5.52 mmol). The mixture was cooled to 0° C., then tert-butyl hydroperoxide, water (4.2'5 g, 4.75 mL, 70% wt, 5 equiv., 27.6 mmol) was added dropwise to the above mixture at 0° C. under nitrogen atmosphere. The mixture was warmed to 30° C. and stirred for 2 h. The reaction was monitored by LCMS. The mixture was diluted with ice water (30 mL) and EtOAc (30 mL), and the aqueous layer was extracted with EtOAc (2×30 mL). The combined organic layers were washed with saturated brine (3×30 mL), dried over anhydrous sodium sulfate and concentrated to give a residue. The residue was purified by flash column chromatography (25 g silica gel column, 75% EtOAc in PE) to afford tert-butyl 8-oxo-2-(4-(trifluoromethyl)phenyl)-2,3,4,5a,6,7,8,9-octahydro-5H-1,2,5,7-tetraazabenzo[cd]azulene-5-carboxylate (1.35 g,) as a white solid. LCMS: (ESI, m/z):437 [M+H]

Step 3: Synthesis of Tert-Butyl 2-(4-(trifluoromethyl)phenyl)-2,3,4,5a,6,7,8,9-octahydro-5H-1,2,5,7-tetraazabenzo[cd]azulene-5-carboxylate A solution of tert-butyl 8-oxo-2-(4-(trifluoromethyl)phenyl)-2,3,4,5a,6,7,8,9-octahydro-5H-1,2,5,7-tetraazabenzo [cd]azulene-5-carboxylate (800 mg, 1 equiv., 1.83 mmol) in THF (16 mL) was cooled to 0° C., then $BH_3$·THF (788 mg, 9.17 mL, 1 molar, 5 equiv., 9.17 mmol) was added dropwise to the above mixture at 0° C. under nitrogen atmosphere. The mixture was warmed to 60° C. and stirred for 2 h. The reaction was monitored by LCMS. After completion, the reaction mixture was cooled to 0° C., quenched with MeOH (20 mL). The solvent was removed under reduced pressure. This resulted in tert-butyl 2-(4-(trifluoromethyl)phenyl)-2,3,4,5a,6,7,8,9-octahydro-5H-1,2,5,7-tetraazabenzo[cd]azulene-5-carboxylate (950 mg) as a crude gray solid. The crude product was used in the next step directly without further purification. LCMS: (ESI, m/z): 423[M+H]$^+$ Step 4: Synthesis of 7-benzyl 5-(tert-butyl) 2-(4-(trifluoromethyl)phenyl)-3,4,5a,6,8,9-hexahydro-2H-1,2,5,7-tetraazabenzo[cd]azulene-5,7-dicarboxylate To a solution of tert-butyl 2-(4-(trifluoromethyl)phenyl)-2,3,4,5a,6,7,8,9-octahydro-5H-1,2,5,7-tetraazabenzo[cd] azulene-5-carboxylate (1.60 g, 85% wt, 1 equiv., 3.22 mmol) in DCM (18 mL) were added TEA (3.26 g, 4.49 mL, 10 equiv., 32.2 mmol) and Cbz-OSu (4.01 g, 5 equiv., 16.1 mmol). The mixture was stirred at 40° C. for 16 h. The mixture was diluted with ice water (30 mL) and DCM (50 mL), and the aqueous layer was extracted with DCM (2×50 mL). The organic layers were combined and washed with saturated brine (2×50 mL), dried over anhydrous sodium sulfate and concentrated to give a residue. The residue was purified by flash column chromatography (25 g silica gel column, 25% EtOAc in PE) to afford 7-benzyl 5-(tert-butyl) 2-(4-(trifluoromethyl)phenyl)-3,4,5a,6,8,9-hexahydro-2H-1,2,5,7-tetraazabenzo[cd]azulene-5,7-dicarboxylate (1.50 g) as a light yellow solid. LCMS: (ESI, m/z): 557 [M+H]$^+$ Step 5: Synthesis of 7-benzyl 5-(tert-butyl) 2-(2-acetoxy-4-(trifluoromethyl)phenyl)-3,4,5a,6,8,9-hexahydro-2H-1,2,5,7-tetraazabenzo[cd]azulene-5,7-dicarboxylate To a solution of 7-benzyl 5-(tert-butyl) 2-(4-(trifluoromethyl)phenyl)-3,4,5a,6,8,9-hexahydro-2H-1,2,5,7-tetraazabenzo[cd]azulene-5,7-dicarboxylate (800 mg, 1 equiv., 1.44 mmol) in acetone (16 mL) and AcOH (1.6 mL) were added (acetyloxy)(phenyl)-lamda3-iodanyl acetate (926 mg, 2 equiv., 2.87 mmol) and $PdOAc_2$ (32.3 mg, 0.1 equiv., 144 gmol). The mixture was stirred at 90° C. for 2 h. The mixture was diluted with water (50 mL) and EtOAc (50 mL) and the aqueous layer was extracted with EtOAc (2×50 mL). The combined organic layers were washed with saturated brine (2×50 mL), dried over anhydrous sodium sulfate aid concentrated to give a residue. The residue was purified by flash column chromatography (40 g silica gel column, 65% EtOAc in PE) to afford 7-benzyl 5-(tert-butyl) 2-(2-acetoxy-4-(trifluoromethyl)phenyl)-3,4,5a,6,8,9-hexahydro-2H-1,2,5,7-tetraazabenzo[cd]azulene-5,7-dicarboxylate (230 mg) as a yellow solid. LCMS: (ESI, m/z): 615 [M+H]$^+$ Step 6: Synthesis of 7-benzyl 5-(tert-butyl) 2-(2-hydroxy-4-(trifluoromethyl)phenyl)-3,4,5a,6,8,9-hexahydro-2H-1,2,5,7-tetraazabenzo[cd]azulene-5,7-dicarboxylate To a solution of 7-benzyl 5-(tert-butyl) 2-(2-acetoxy-4-trifluoromethyl)phenyl)-3,4,5a,6,8,9-hexahydro-2H-1,2,5,7-tetraazabenzo[cd]azulene-5,7-dicarboxylate (210 mg, 1 equiv., 342 μmol) in MeOH (4 mL) was added lithium hydroxide (32.7 mg, 20.2 μL, 4 equiv., 1.37 mmol) and water (1 mL). The mixture was stirred for 1 h at rt. The mixture was diluted with ice water (20 mL) and EtOAc (20 mL), and the aqueous layer was extracted with EtOAc (2×20 mL). The combined organic layers were washed with saturated brine (2×20 mL), dried over anhydrous sodium sulfate and concentrated to afford 7-benzyl 5-(tert-butyl) 2-(2-hydroxy-4-(trifluoromethyl)phenyl)-3,4,5a,6,8,9-hexahydro-2H-1,2,5,7-tetraazabenzo[cd]azulene-5,7-dicarboxylate (190 mg) as a yellow solid. LCMS: (ESI, m/z): 573 [M+H]$^+$ Step 7: Synthesis of Tert-Butyl 2-(2-hydroxy-4-(trifluoromethyl)phenyl)-2,3,4,5a,6,7,8,9-octahydro-5H-1,2,5,7-tetraazabenzo[cd]azulene-5-carboxylate To a solution of 7-benzyl 5-(tert-butyl) 2-(2-hydroxy-4-(trifluoromethyl)phenyl)-3,4,5a,6,8,9-hexahydro-2H-1,2,5,7-tetraazabenzo[cd]azulene-5,7-dicarboxylate (190 mg, 1 equiv., 332 μmol) in MeOH (2 mL) was added $Pd(OH)_2$ (93.2 mg, 50 wt %, 1 equiv., 332 μmol) and Pd/C (70.6 mg, 50 wt %, 1 equiv., 332 μmol). The mixture was stirred for 16 h at rt under 3 mbar $H_2$ atmosphere. The resulting mixture was filtered and the filter cake was washed with MeOH (3×10 mL). The filtrate was concentrated under reduced pressure to afford tert-butyl 2-(2-hydroxy-4-(trifluoromethyl)phenyl)-2,3,4,5a,6,7,8,9-octahydro-5H-1,2,5,7-tetraazabenzo[cd]azulene-5-carboxylate (180 mg) as a yellow solid which was used in the next step without further purification. LCMS: (ESI, m/z):439 [M+H]$^+$ Step 8: Synthesis of Tert-Butyl 7-acryloyl-2-(2-hydroxy-4-(trifluoromethyl)phenyl)-2,3,4,5a,6,7,8,9-octahydro-5H-1,2,5,7-tetraazabenzo[cd]azulene-5-carboxylate To a solution of tert-butyl 2-(2-hydroxy-4-(trifluoromethyl)phenyl)-2,3,4,5a,6,7,8,9-octahydro-5H-1,2,5,7-tetraazabenzo[cd]azulene-5-carboxylate (180 mg, 1 equiv., 411 gmol) in DMF (2 mL) was added T3P (196 mg, 1.5 equiv., 616 μmol), acrylic acid (44.4 mg, 42.2 μL, 1.5 equiv., 616 gmol) and DIEA (106 mg, 143 μL, 2 equiv., 821 μmol). The mixture was stirred for 8 h at rt. The reaction was monitored by LCMS. The mixture was diluted with ice water (10 mL) and EtOAc (10 mL), and the aqueous layer was extracted with EtOAc (2×10 mL). The combined organic layers were washed with saturated brine (2×10 mL), dried over anhydrous sodium sulfate and concentrated to give a residue. The residue was purified by flash column chromatography, eluting with EtOAc/PE (2:1) to afford tert-butyl 7-acryloyl-2-(2-hydroxy-4-(trifluoromethyl)phenyl)-2,3,4,5a,6,7,8,9-octahydro-5H-1,2,5,7-tetraazabenzo[cd]azulene-5-carboxylate (100 mg) as a white solid. LCMS: (ESI, m/z): 493 [M+H]$^+$ Step 9: Synthesis of 1-(2-(2-hydroxy-4-(trifluoromethyl)phenyl)-2,3,4,5,5a,6,8,9-octahydro-7H-1,2,5,7-tetraazabenzo[cd]azulen-7-yl)prop-2-en-1-one To a solution of tert-butyl 7-acryloyl-2-(2-hydroxy-4-(trifluoromethyl)phenyl)-2,3,4,5a,6,7,8,9-octahydro-5H-1,2,5,7-tetraazabenzo[cd]azulene-5-carboxylate (40 mg, 1 equiv., 81 μmol) in DCM (1.5 mL) was added TFA (0.5 mL). The mixture was stirred for 1 h at rt. The mixture was concentrated under reduced pressure to afford 1-(2-(2-hydroxy-4-(trifluoromethyl)phenyl)-2,3,4,5,5a,6,8,9-octahydro-7H-1,2,5,7-tetraazabenzo[cd]azulen-7-yl)prop-2-en-1-one (30 mg) as a white solid. LCMS: (ESI, m/z): 393 [M+H]$^+$ Step 10: Synthesis of 2-(7-acryloyl-5-(7-bromo-1H-benzo[d]imidazole-4-carbonyl)-3,4,5,5a,6,7,8,9-octahydro-2H-1,2,5,7-tetraazabenzo[cd]azulen-2-yl)-5-(trifluoromethyl)phenyl 7-bromo-1H-benzo[d]imidazole-4-carboxylate To a solution of 1-(2-(2-hydroxy-4-(trifluoromethyl)phenyl)-2,3,4,5,5a,6,8,9-octahydro-7H-1,2,5,7-tetraazabenzo[cd]azulen-7-yl)prop-2-en-1-one (30 mg, 1 equiv., 76 μmol) in DMF (1 mL) was added 7-bromo-1H-benzo[d]imidazole-4-carboxylic acid (37 mg, 2 equiv., 0.15 mmol), EDCI (22 mg, 1.5 equiv., 0.11 mmol), HOBT (15 mg, 1.5 equiv., 0.11 mmol) and DIEA (49 mg, 67 μL, 5 equiv., 0.38 mmol). The mixture was stirred for 5 h at rt. The reaction was monitored by LCMS. The mixture was diluted with ice water (20 mL) and EtOAc (0 mL), and the aqueous layer was extracted with EtOAc (2×20 mL). The combined organic layers were washed with saturated brine (2×20 mL), dried over anhydrous sodium sulfate and concentrated to afford 2-(7-acryloyl-5-(7-bromo-1H-benzo[d]imidazole-4-carbonyl)-3,4,5,5a,6,7,8,9-octahydro-2H-1,2,5,7-tetraazabenzo[cd]azulen-2-yl)-5-(trifluoromethyl)phenyl 7-bromo-1H-benzo[a]imidazole-4-carboxylate (20 mg) as a white solid, which was taken directly into the next step without further purification. LCMS: (ESI, m/z):837 [M+H]$^+$ Step 11: Synthesis of 1-(5-(7-bromo-1H-benzo[d]imidazole-4-carbonyl)-2-(2-hydroxy-4-(trifluoromethyl)phenyl)-2,3,4,5,5a,6,8,9-octahydro-7H-1,2,5,7-tetraazabenzo[cd]azulen-7-yl)prop-2-en-1-one To a solution of 2-(7-acryloyl-5-(7-bromo-1H-benzo[d]imidazole-4-carbonyl)-3,4,5,5a,6,7,8,9-octahydro-2H-1,2,5,7-tetraazabenzo[cd]azulen-2-yl)-5-(trifluoromethyl)phenyl 7-bromo-1H-benzo[d]imidazole-4-carboxylate (30 mg, 1 equiv., 36 μmol) in THF (0.3 mL) was added LiOH (2.6 mg, 3 equiv., 0.11 mmol) and water (0.1 mL). The mix re was stirred for 1 h at rt. The reaction was monitored by LCMS. The mixture was diluted with ice water (20 mL) and EtOAc (20 mL), and the aqueous layer was extracted with EtOAc (2×20 mL). The combined organic layers were washed with saturated brine (2×20 mL), dried over anhydrous sodium sulfate and concentrated to give a residue. After filtration, the filtrate was concentrated under reduced pressure. The crude product (30 mg) was purified by Prep-HPLC with the following conditions (Column: Sunfire C18 5 m, 30 mm*150 mm; Mobile Phase A: water 0.1% FA), Mobile Phase B: MeCN; Flow rate: 60 mL/min; Gradient: 30% B to 55% B in 8 min; Wave Length: UV 254 nm/221 nm; retention time 1: 7.68) to afford 1-(5-(7-bromo-1H-benzo[d]imidazole-4-carbonyl)-2-(2-hydroxy-4-(trifluoromethyl)phenyl)-2,3,4,5,5a,6,8,9-octahydro-7H-1,2,5,7-tetraazabenzo[cd]azulen-7-yl)prop-2-en-1-one (2.8 mg, 4.5 mol, 13%, 99.5% purity) as a white solid. LCMS: (ESI, m/z): 615 [M+H]. $^1$H NMR: (400 MHz, Chloroform-d, ppm) δ 8.61-8.18 (m, 1H), 7.67-6.96 (m, 6H), 6.62-6.32 (m, 1H), 6.04-5.67 (m, 1H), 5.57-5.35 (m, 1H), 5.16-4.85 (m, 1H), 4.71-4.49 (m, 1H), 4.44-3.95 (m, 1H), 3.40-2.62 (m, 6H), 1.34-1.15 (m, 1H), 0.95-0.69 (m, 1H).

Example A-7: Preparation of (R or S)-1-(2-(4-(bicyclo[1.1.1]pentan-1-yl)phenyl)-5-(7-bromo-1H-benzo[d]imidazole-4-carbonyl)-2,3,4,5,5a,6,8,9-octahydro-7H-1,2,5,7-tetraazabenzo[cd]azulen-7-yl)prop-2-en-1-one

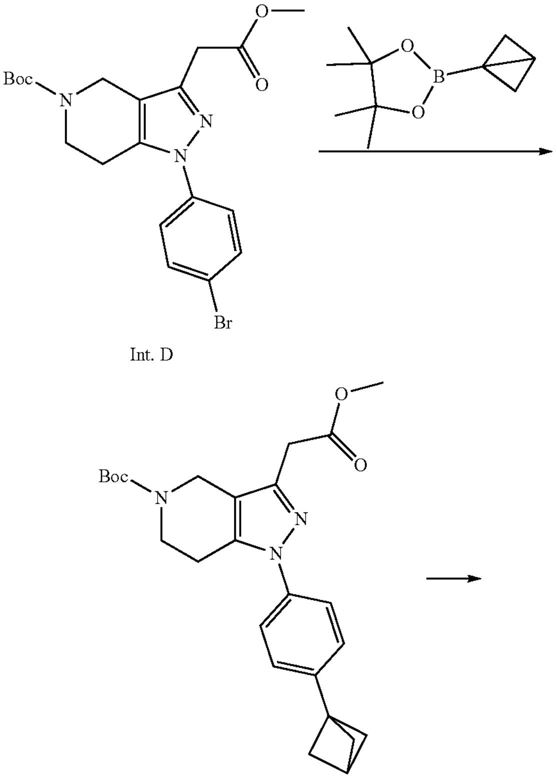

Int. D

-continued

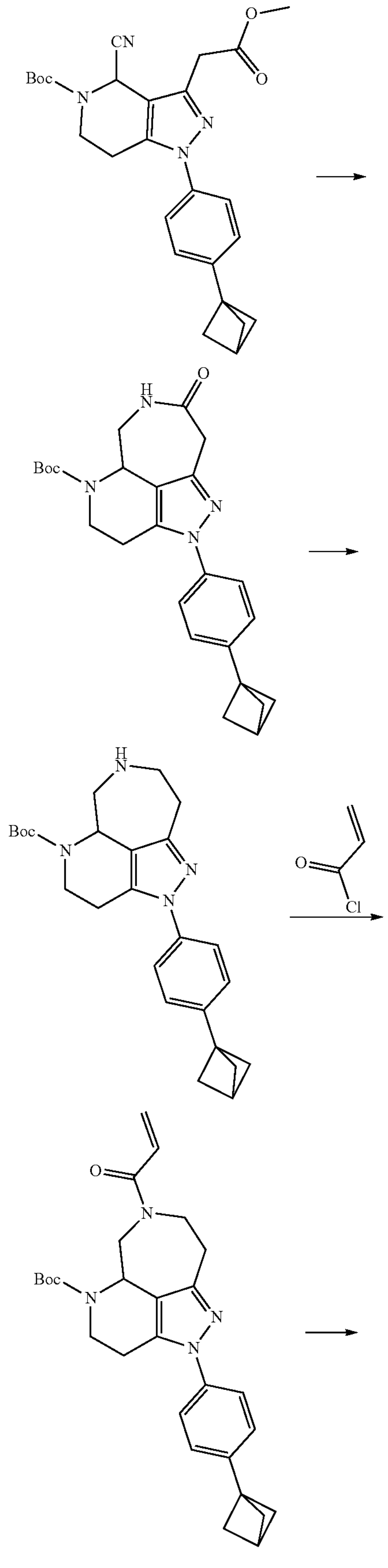

-continued

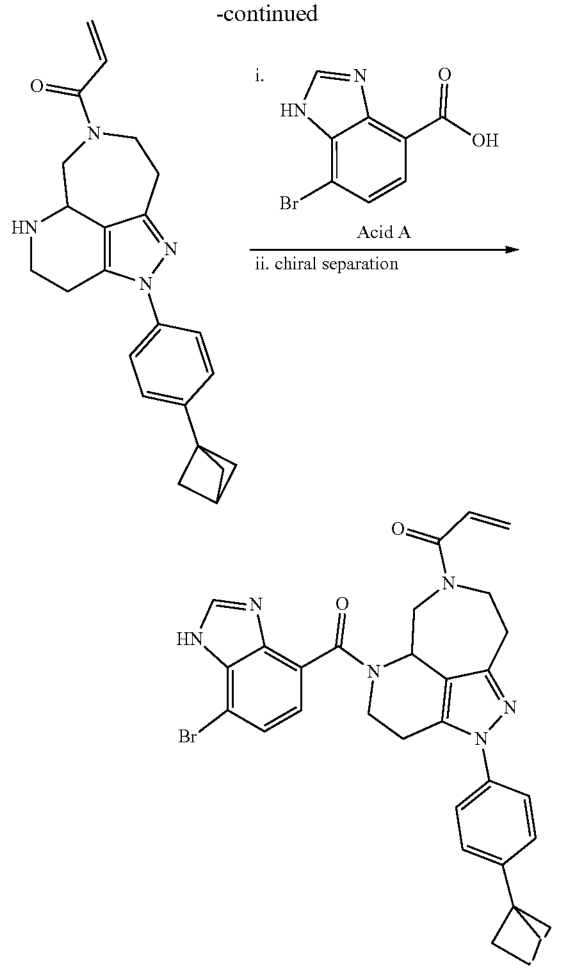

Step 1: Preparation of Tert-Butyl 1-(4-(bicyclo [1.1.1]pentan-1-yl)phenyl-3-(2-methoxy-2-oxo-ethyl)-1,4,6,7-tetrahydro-5H-pyrazolo[4,3-c]pyridine-5-carboxylate An 8 mL glass vial equipped with a magnetic stir bar was charged with (4,4'-di-t-butyl-2,2'-bipyridine)bis[3,5-difluoro-2-(5-trifluoromethyl-2-pyridinyl-kN)phenyl-kC] iridium(III) hexafluorophosphate (0.19 g, 0.05 equiv., 0.17 mmol), tert-butyl 1-(4-bromophenyl)-3-(2-methoxy-2-oxo-ethyl)-1,4,6,7-tetrahydro-5H-pyrazolo[4,3-c]pyridine-5-carboxylate (Int. D) (1.5 g, 1 equiv., 3.3 mmol) and 2-(bicyclo [1.1.1]pentan-1-yl)-4,4,5,5-tetramethyl-1,3,2-dioxaborolane (0.78 g, 1.2 equiv., 4.0 mmol). The contents were dissolved in DMF (37.5 mL) and morpholine (0.44 g, 0.43 mL, 1.5 equiv., 5.0 mmol) was added. A second vial was charged with nickel chloride, dimethoxyethane adduct (37 mg, 0.05 equiv., 0.17 mmol) and dtbbpy 45 mg, 0.05 equiv., 0.17 mmol) and the contents were dissolved in DMF (1.0 mL). The second mixture was sonicated for 30 seconds and heated afterwards to 100° C. until a clear green sol tion was obtained. Both mixtures were combined and the resulting reaction mixture was irradiated with blue LEDs (445 nm at 220 mW) for 3 h. The reaction was quenched by the addition of ater (200 mL) at rt. The resulting mixture was extracted with EtOAc (2×200 mL). The combined organic layers were washed with brine (2×200 mL) and dried over anhydrous $Na_2SO_4$. After filtration, the filtrate was concentrated under reduced pressure. The residue was purified by silica gel column chromatography, eluting with EtOAc/PE (1:5) to afford tert-butyl 1-(4-(bicyclo[1.1.1]pentan-1-yl)phenyl)-3-(2-methoxy-2-oxoethyl)-1,4,6,7-tetrahydro-5H-pyrazolo[4,3-c]pyridine-5-carboxylate (650 mg) as a yellow oil. LCMS: (ESI, m/z):438 $[M+H]^+$ Step 2. Synthesis of Tert-Butyl 1-(4-(bicyclo[1.1.1]pentan-1-yl)phenyl)-4-cyano-3-(2-methoxy-2-oxo-ethyl)-1,4,6,7-tetrahydro-5H-pyrazolo[4,3-c]pyridine-5-carboxylate To a stirred solution of tert-butyl 1-(4-(bicyclo[1.1.1]pentan-1-yl)phenyl)-3-(2-methoxy-2-oxoethyl)-1,4,6,7-tetrahydro-5H-pyrazolo[4,3-c]pyridine-5-carboxylate (650 mg, 1 equiv., 1.4 mmol) in MeCN (13 mL) was added $TEMPO^+BF^-$ (696 mg, 3 equiv., 4.46 mmol). TMSCN (590 mg, 4 equiv., 5.94 mmol) and AcOH (268 mg, 255 μL, 3 equiv., 4.46 mmol) at room temperature, and the reaction was stirred for 2 h. The reaction progress was monitored by LCMS. After completion, the reaction was quenched by the addition of water (20 mL) at rt. The resulting mixture was extracted with EtOAc (2×20 mL). The combined organic layers were washed with brine (2×20 mL) and dried over anhydrous $Na_2SO_4$. After filtration, the filtrate was concentrated under reduced pressure. The residue was purified by silica gel column chromatography, eluting with EtOAc/PE (1:5) to afford tert-butyl 1-(4-(bicyclo[1.1.1]pentan-1-yl)phenyl)-4-cyano-3-(2-methoxy-2-oxoethyl)-1,4,6,7-tetrahydro-5H-pyrazolo[4,3-c]pyridine-5-carboxylate (550 mg) as a yellow solid. LCMS: (ESI, m/z):463 $[M+H]^+$ Step 3: Synthesis of Tert-Butyl 2-(4-(bicyclo[1.1.1]pentan-1-yl)phenyl)-8-oxo-2,3,4,5a,6,7,8,9-octahydro-5H-1,2,5,7-tetraazabenzo[cd]azulene-5-carboxylate To a solution of tert-butyl 1-(4-(bicyclo[1.1.1]pentan-1-yl)phenyl)-4-cyano-3-(2-methoxy-2-oxoethyl)-1,4,6,7-tetrahydro-5H-pyrazolo[4,3-c]pyridine-5-carboxylate (600 mg, 1 equiv., 1.3 mmol) in MeOH (24 mL) was added Raney nickel (600 mg, 81.6 μL, 7.88 equiv., 10.2 mmol) in a pressure tank. The mixture was purged with nitrogen×3 and then was pressurized to 480 psi with hydrogen and was stirred at 60° C. for 12 h. The reaction mixture was cooled to rt and filtered to remove insoluble solids. The filter cake was washed with MeOH (50 mL) two times. The combined filtrate was concentrated under reduced pressure. The crude product was used in the next step directly without further purification. LCMS: (ESI, m/z):434 $[M+H]^+$ Step 4: Synthesis of Tert-Butyl 2-(4-(bicyclo[1.1.1]pentan-1-yl)phenyl)-2,3,4,5a,6,7,8,9-octahydro-5H-1,2,5,7-tetraazabenzo[cd]azulene-5-carboxylate To a stirred solution of tert-butyl 2-(4-(bicyclo[1.1.1]pentan-1-yl)phenyl)-8-oxo-2,3,4,5a,6,7,8,9-octahydro-5H-1,2,5,7-tetraazabenzo[cd]azulene-5-carboxylate (550 mg, 1 equiv., 1.27 mmol) in THF (5.5 mL) was added $BH_3$·THF (435 mg, 4 equiv., 5.06 mmol) at 60° C. and the reaction was stirred for 12 h. The reaction was then filtered, and the filtrate was concentrated under reduced pressure. The crude product was used in the next step directly without further purification. LCMS: (ESI, m/z): 421 $[M+H]^+$ Step 5: Synthesis of Tert-Butyl 7-acryloyl-2-(4-(bicyclo[1.1.1]pentan-1-yl)phenyl)-2,3,4,5a,6,7,8,9-octahydro-5H-1,2,5,7-tetraazabenzo[cd]azulene-5-carboxylate To a stirred solution of tert-butyl 2-(4-(bicyclo[1.1.1]pentan-1-yl)phenyl)-2,3,4,5a,6,7,8,9-octahydro-5H-1,2,5,7-tetraazabenzo[cd]azulene-5-carboxylate (400 mg, 1 equiv., 951 μmol) in DCM (8 mL) was added TEA (289 mg, 398 μL, 3 equiv., 2.85 mmol) and acryloyl chloride (258 mg, 3 equiv., 2.85 mmol) at room temperature and the resulting solution was stirred for 2 h. The reaction progress was monitored by LCMS. After completion, the reaction was quenched by the addition of water (20 mL) at rt. The resulting mixture was extracted with EtOAc (2×20 mL). The combined organic layers were washed with brine (2×20 mL) and dried over anhydrous $Na_2SO_4$. After filtration, the filtrate was concentrated under reduced pressure. The residue was purified by silica gel column chromatography, eluting with EtOAc/PE (1:1) to afford tert-butyl 7-acryloyl-2-(4-(bicyclo[1.1.1]pentan-1-yl)phenyl)-2,3,4,5a,6,7,8,9-octahydro-5H-1,2,5,7-tetraazabenzo[cd]azulene-5-carboxylate (130 mg) as a colorless solid. LCMS: (ESI, m/z): 475 $[M+H]^+$ Step 6: Synthesis of 1-(2-(4-(bicyclo[1.1.1]pentan-1-yl)phenyl)-2,3,4,5,5a,6,8,9-octahydro-7H-1,2,5,7-tetraazabenzo[cd]azulen-7-yl)prop-2-en-1-one (Int. G)

The solution of tert-butyl 7-acryloyl-2-(4-(bicyclo[1.1.1]pentan-1-yl)phenyl)-2,3,4,5a,6,7,8,9-octahydro-5H-1,2,5,7-tetraazabenzo[cd]azulene-5-carboxylate (130 mg, 1 equiv., 0.26 mmol) in DCM (1.95 mL) and TFA (0.65 mL) was stirred at root temperature for 1 h. The reaction was monitored by LCMS, and after completion the solvent was removed under reduced pressure. The crude product was used in the next step directly without further purification. LCMS: (ESI, m/z): 375 $[M+H]^+$ Step 7: Synthesis of (S or R)-1-(2-(4-(bicyclo[1.1.1]pentan-1-yl)phenyl)-5-(7-bromo-1H-benzo[d]imidazole-4-carbonyl)-2,3,4,5,5a,6,8,9-octahydro-7H-1,2,5,7-tetraazabenzo[cd]azulen-7-yl)prop-2-en-1-one To a stirred solution of 1-(2-(4-(bicyclo[1.1.1]pentan-1-ylphenyl)-2,3,4,5,5a,6,8,9-octahydro-7H-1,2,5,7-tetraazabenzo[cd]azulen-7-yl)prop-2-en-1-one (80 mg, 1 equiv., 0.21 mmol) in DMF (1.6 mL) was added DIEA (0.17 g, 0.22 mL, 6 equiv., 1.3 mmol), HBTU (0.12 g, 1.5 equiv., 0.32 mmol) and 7-bromo-1H-benzo[d]imidazole-4-carboxylic acid (77 mg, 1.5 equiv., 0.32 mmol) at room temperature and stirred the reaction was stirred for 2 h. The reaction was then quenched by the addition of water (20 mL) at rt. The resulting mixture was extracted with EtOAc (2×20 mL). The combined organic layers were washed with brine (2×20 mL) and dried over anhydrous $Na_2SO_4$. After filtration, the filtrate was concentrated under reduced pressure. The residue was purified by reverse-phase flash chromatography with the conditions (Column: YMC Triart C18 ExRs 5 m, 30 mm*150 mm; Mobile Phase A: water (10 mmol/L $NH_4HCO_3$), Mobile Phase B: MeCN; Flow rate: 60 mL/min; Gradient: 40% B to 63% B in 10 min; Wave Length: UV 254 nm/220 nm; retention time 1: 9.2) to afford 1-(2-(4-(bicyclo[1.1.1]pentan-1-yl)phenyl)-5-(7-bromo-1H-benzo[d]imidazole-4-carbonyl)-2,3,4,5,5a,6,8,9-octahydro- 7H-1,2,5,7-tetraazabenzo[cd]azulen-7-yl)prop-2-en-1-one (35 mg, 56 μmol, 26%) as a white solid. LCMS: (ESI, m/z):597 $[M+H]^+$ The racemic 1-(2-(4-(bicyclo[1.1.1]pentan-1-yl)phenyl)-5-(7-bromo-1H-benzo[d]imidazole-4-carbonyl)-2,3,4,5,5a,6,8,9-octahydro-7H-1,2,5,7-tetraazabenzo[cd]azulen-7-yl) prop-2-en-1-one (35 mg) was purified by Prep-chiral HPLC with the following conditions (Column: CHIRAL ART Cellulose-SB 2*25 cm, 5 μm; Mobile Phase A: HEX(0.1% FA), Mobile Phase B: EtOH:DCM=1:1; Flow rate: 40 mL/min; Gradient: isocratic 25; Wave Length: UV 254/220 nm; Injection Volume: 1.6 mL; Number Of Runs: 3) to afford (S or R)-1-(2-(4-(bicyclo[1.1.1]pentan-1-yl)phenyl)-5-(7-bromo-1H-benzo[d]imidazole-4-carbonyl)- 2,3,4,5,5a,6,8,9-octahydro-7H-1,2,5,7-tetraazabenzo[cd]azulen-7-yl) prop-2-en-1-one as the second peak (17.1 mg, 28.4 gmol, 85%, retention time 12.5 min) as a white solid. LCMS: (ESI, m/z):597 [M+H]*. $^1$H NMR:(400 MHz, Chloroform-d, ppm) δ 8.33 (s, 1H), 7.53 (d, J=7.8 Hz, 1H), 7.39-7.16 (m, 7H), 6.67 (s, 1H), 6.80-6.34 (m, 1H), 5.78 (brs, 1H), 5.36 (d, J=9.9 Hz, 1H), 5.10-4.76 (m, 1H), 4.72-4.37 (m, 1H), 4.37-3.96 (m, 1H), 3.37-2.86 (m, 4H), 2.86-2.52 (m, 2H), 2.19-1.95 (m, 6H).

TABLE A4

Examples A-7-1 and A-7-2 were prepared in an analogous fashion to Example A-7, except that HATU was used in place of HBTU in step 7. The racemic compound of Example A-7-1 was separated using the following conditions: Column-CHIRALPAK-IC 2*25 cm, 5 μm; Mobile Phase A: HEX(0.1% FA), Mobile Phase B: MeOH: DCM = 1:1; Flow rate: 20 mL/min; Gradient: isocratic 60; Wave Length: UV 254/220 nm; RT1(min): 4.7; RT2(min): 6.8 to afford the compound of Example A-7-1 as the second-eluting peak. The racemic compound of Example A-7-2 was separated using the following conditions: Column-CHIRALPAK-IC 2*25 cm, 5 μm; Mobile Phase A: HEX(0.1% FA), Mobile Phase B: MeOH: DCM = 1:1; Flow rate: 20 mL/min; Gradient: isocratic 50; Wave Length: UV 254/220 nm; RT1(min): 5.0; RT2(min): 7.1 to afford the compound of Example A-7-2 as the second-eluting peak.

| Example No. | Structure | Compound Name | LCMS $[M + H]^+$ | NMR |
|---|---|---|---|---|
| A-7-1 | 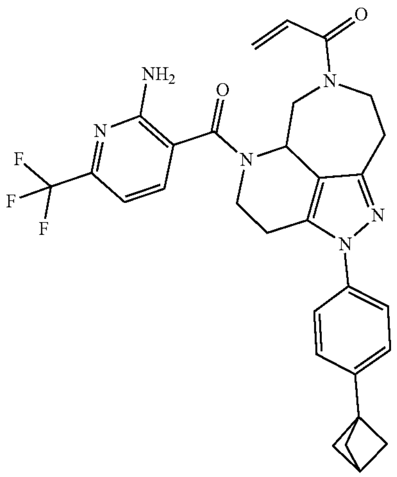 [SMILES: C=CC(=O)N1CCc2nn(-c3ccc(C45CC(C4)C5)cc3)c3c2C(C1)N(C(=O)c1ccc(C(F)(F)F)nc1N)CC3] | (R or S)-1-(5-(2-amino-6-(trifluoromethyl)nicotinoyl)-2-(4-(bicyclo[1.1.1]pentan-1-yl)phenyl)-2,3,4,5,5a,6,8,9-octahydro-7H-1,2,5,7-tetraazabenzo[cd]azulen-7-yl)prop-2-en-1-one | 563 | $^1$HNMR (400 MHz, Chloroform-d, ppm) δ 8.05-7.63 (m, 1H), 7.59-7.52 (m, 1H), 7.39-7.32 (m, 2H), 7.30-7.25 (m, 2H), 7.16-7.06 (m, 1H), 6.77-6.26 (m, 1H), 5.95-5.69 (m, 1H), 5.50-5.19 (m, 3H), 5.04-4.65 (m, 1H), 4.60-3.86 (m, 2H), 3.40-2.61 (m, 7H), 2.57 (s, 1H), 2.10 (s, 6H). |
| A-7-2 | 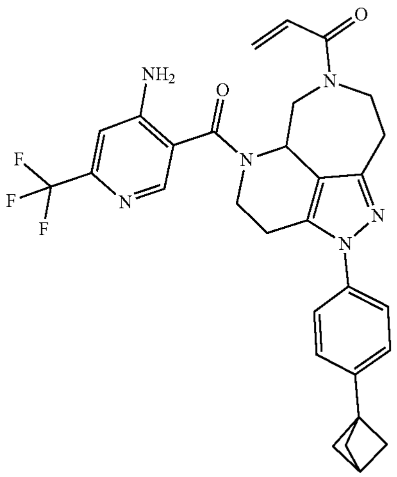 [SMILES: C=CC(=O)N1CCc2nn(-c3ccc(C45CC(C4)C5)cc3)c3c2C(C1)N(C(=O)c1cnc(C(F)(F)F)cc1N)CC3] | (R or S)-1-(5-(4-amino-6-(trifluoromethyl)nicotinoyl)-2-(4-(bicyclo[1.1.1]pentan-1-yl)phenyl)-2,3,4,5,5a,6,8,9-octahydro-7H-1,2,5,7-tetraazabenzo[cd]azulen-7-yl)prop-2-en-1-one | 563 | $^1$HNMR: (400 MHz, Chloroform-d, ppm δ 7.55 (d, J = 7.6 Hz, 1H), 7.39-7.27 (m, 4H), 7.09 (d, J = 7.6 Hz, 1H), 6.73-6.36 (m, 1H), 5.93-5.72 (m, 1H), 5.38 (s, 3H), 4.91-4.89 (m, 2H), 4.52-3.98 (m, 2H), 3.32-2.89 (m, 5H), 2.73-2.71 (m, 2H), 2.57 (s, 1H), 2.10 (s, 6H). |

Example A-8: Preparation of 1-(5-(7-bromo-1H-benzo[d]imidazole-4-carbonyl)-2-(4-cyclopropyl-2-hydroxyphenyl)-2,3,4,5,5a,6,8,9-octahydro-7H-1,2,5,7 tetraazabenzo[cd]azulen-7-yl)prop-2-en-1-one
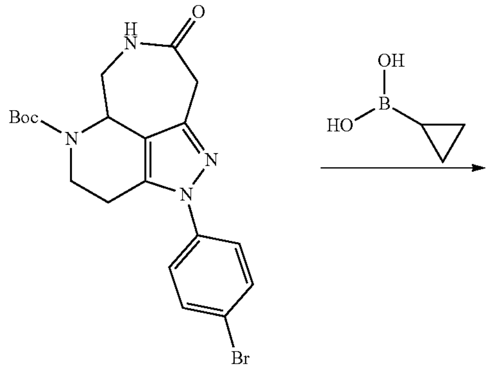
Int. E
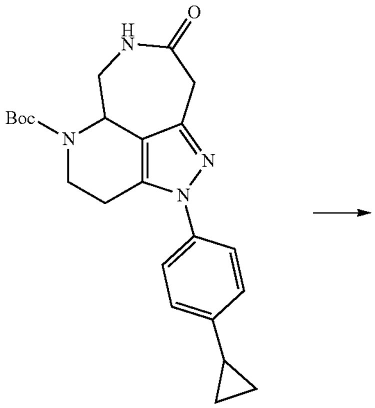
Int. E″
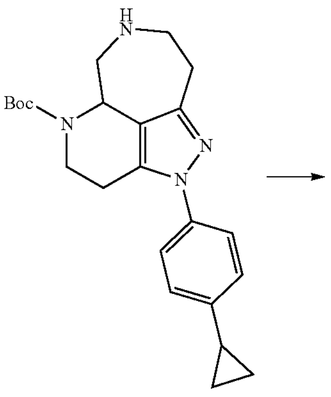
-continued
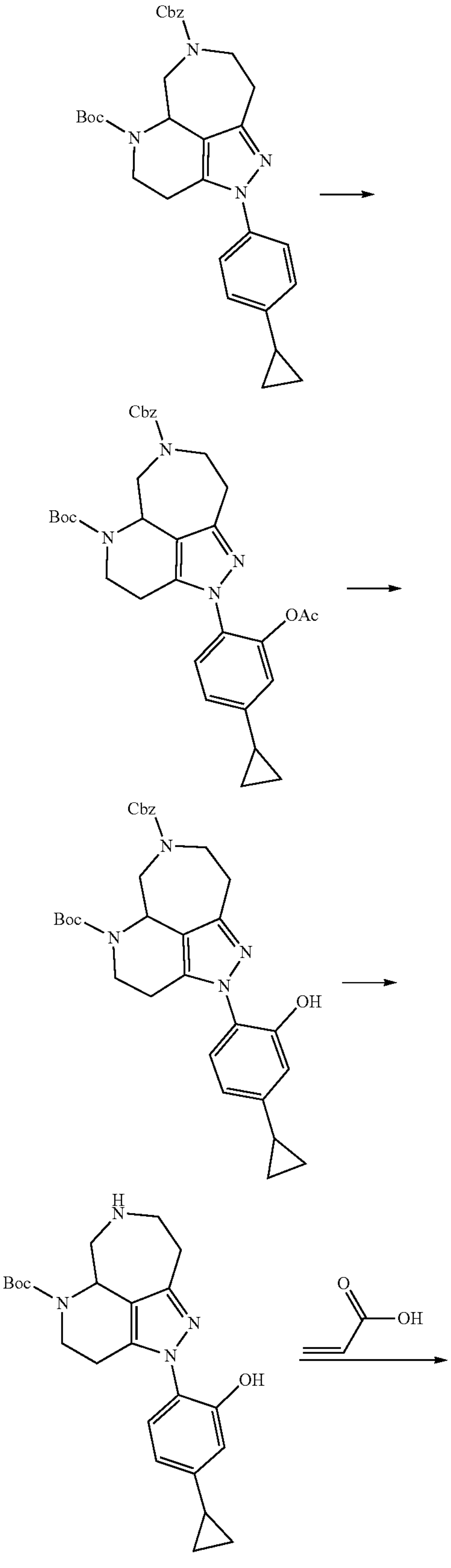

-continued

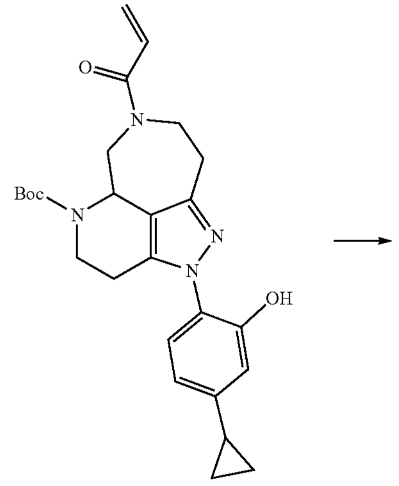

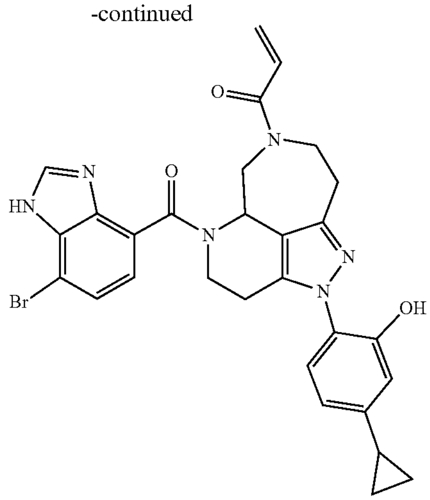

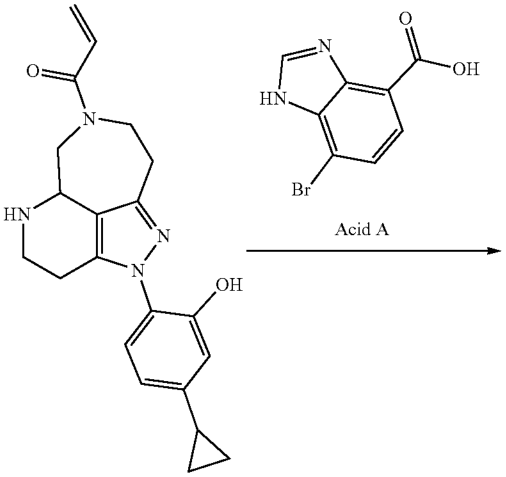

Int. H

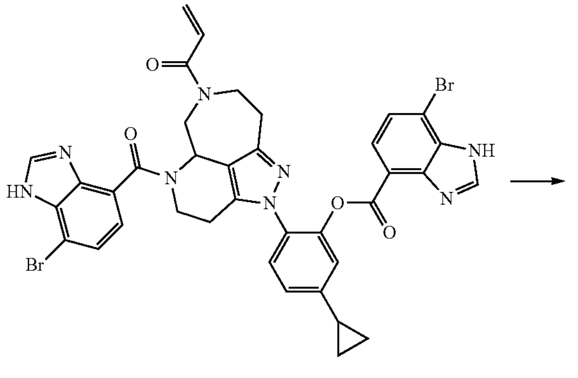

Step 1: Synthesis of Tert-Butyl 2-(4-cyclopropylphenyl)-8-oxo-2, 3, 4,5a,6,7,8,9-octahydro-5H-1,2,5,7-tetraazabenzo[cd]azulene-S-carboxylate (Int. E")

To a solution of Int. E (4.50 g, 1 equiv., 10.1 mmol) in toluene (20 mL) and water (5 mL) were added tricyclohexylphosphine (564 mg, 629 μL, 0.2 equiv., 2.01 mmol) cyclopropylboronic acid (1.73 g, 2 equiv., 20.1 mmol) potassium phosphate, tribasic (6.41 g, 2.5 mL, 3 equiv., 30.2 mmol) and palladium diacetate (226 mg, 0.1 equiv., 1.01 mmol). The reaction vessel was placed under a positive pressure of nitrogen and subjected to three backfilling cycles under high vacuum. The resulting mixture was stirred for 100° C. for 2 h under nitrogen atmosphere. The reaction was monitored by LCMS, after which the reaction mixture was cooled to rt, and the mixture was filtered and rinsed with EtOAc (3×20 mL), then diluted with water (20 mL). The aqueous layer was extracted with EtOAc (2×20 mL). The combined organic layers were washed with saturated brine (3×20 mL), dried over anhydrous sodium sulfate and concentrated to give a residue. The crude product was purified by silica gel chromatography eluting with PE:EtOAc=10:1 to give tert-butyl 2-(4-cyclopropylphenyl)-8-oxo-2,3,4,5a,6,7,8,9-octahydro-5H-1,2,5,7-tetraazabenzo[cd]azulene-5-carboxylate (4.0 g) as a yellow oil. LCMS: (ESI, m/z):409 $[M+H]^+$ Step 2: Synthesis of Tert-Butyl 2-(4-cyclopropylphenyl)-2,3,4,5a,6,7,8,9-octahydro-5H-1,2,5,7-tetraazabenzo[cd]azulene-S-carboxylate To a solution of tert-butyl 2-(4-cyclopropylphenyl)-8-oxo-2,3,4, a,6,7,8,9-octahydro-5H-1,2,5,7-tetraazabenzo[cd]azulene-5-carboxylate (4.84 g, 1 equiv., 11.8 mmol) in THE (40 mL) was added $BH_3$·THF (4.07 g, 4 equiv., 47.4 mmol). The mixture was stirred at 60° C. for 1 h. The reaction was monitored by LCMS. The solvent was removed under reduced pressure. This resulted in tert-butyl 2-(4-cyclopropylphenyl)-2,3,4,5a,6,7,8,9-octahydro-5H-1,2,5,7-tetraazabenzo[cd]azulene-5-carboxylate (4.80 g) as a white solid. The crude product was used in the next step directly without further purification. LCMS: (ESI, m/z): 395 $[M+H]^+$ Step 3: Synthesis of 7-benzyl 5-(tert-butyl) 2-(4-cyclopropylphenyl)-3,4,5a,6,8,9-hexahydro-2H-1,2,5,7-tetraazabenzo[cd]azulene-5,7-dicarboxylate To a solution of tert-butyl 2-(4-cyclopropylphenyl)-2,3,4,5a,6,7,8,9-octahydro-5H-1,2,5,7-tetraazabenzo[cd]azulene-5-carboxylate (4.20 g, 1 equiv., 10.6 mol) in DCM (40 mL) were added $K_2CO_3$ (7.36 g, 5 equiv., 53.2 mmol) and Cbz-OSu (7.96 g, equiv., 31.9 mmol). The mixture was stirred at room temperature for 16 h. The mixture was then diluted with water (20 mL) and DCM (20 mL), and the aqueous layer was extracted with DCM (2×20 mL). The combined organic layers were washed with saturated brine (2×20 mL), dried over anhydrous sodium sulfate and concentrated to give a residue. The residue was purified by flash column chromatography, eluting with EtOAc/PE (1:5) to afford 7-benzyl 5-(tert-butyl) 2-(4-cyclopropylphenyl)-3,4,5a,6,8,9-hexahydro-2H-1,2,5,7-tetraazabenzo[cd]azulene-5,7-dicarboxylate (2.83 g) as a white solid. LCMS: (ESI, m/z): 529 $[M+H]^+$ Step 4: Synthesis of 7-benzyl 5-(tert-butyl) 2-(2-acetoxy-4-cyclopropylphenyl)-3,4,5a,6,8,9-hexahydro-2H-1,2,5,7-tetraazabenzo[cd]azulene-5,7-dicarboxylate To a solution of 7-benzyl 5-(tert-butyl) 2-(4-cyclopropylphenyl)-3,4,5a,6,8,9-hexahydro-2H-1,2,5,7-tetraazabenzo[cd]azulene-5,7-dicarboxylate (2.53 g, 1 equiv., 4.79 mmol) in MeCN (25 mL) and AcOH (2.5 mL) were added (acetyloxy)(phenyl)-lamda3-iodanyl acetate (3.08 g, 2 equiv., 9.57 mmol) and palladium diacetate (107 mg, 0.1 equiv., 479 gmol). The mixture was stirred at 90° C. for 2 h. The reaction was monitored by LCMS. The mix re was diluted with water (20 mL) and EtOAc (20 mL), and the aqueous layer was extracted with EtOAc (2×20 mL). The combined organic layers were washed with saturated brine (2×20 m), dried over anhydrous sodium sulfate and concentrated to give a residue. The residue was purified by flash column chromatography, eluting with EtOAc/PE (1:5) to afford 7-benzyl 5-(t rt-butyl) 2-(2-acetoxy-4-cyclopropylphenyl)-3,4,5a,6,8,9-hexahydro-2H-1,2,5,7-tetraazabenzo[c]azulene-5,7-dicarboxylate (400 mg) as a yellow solid. LCMS: (ESI, m/z):587 $[M+H]^+$ Step 5: Synthesis of 7-benzyl 5-(tert-butyl) 2-(4-cyclopropyl-2-hydroxyphenyl)-3,4,5a,6,8,9-hexahydro-2H-1,2,5,7-tetraazabenzo[cd]azulene-5,7-dicarboxylate To a solution of 7-benzyl 5-(tert-butyl) 2-(2-acetoxy-4-cyclopropylphenyl)-3,4,5a,6,8,9-hexahydro-2H-1,2,5,7-tetraazabenzo[cd]azulene-5,7-dicarboxylate (400 mg, 1 equiv., 682 gmol) in THF (1 mL) and water (0.5 mL) was added LiOH (32.7 mg, 2 equiv., 1.36 mmol). The mixture was stirred at room temperature for 1 h. The reaction was monitored by LCMS. The mixture was acidified to pH=3 with 1 M sulfuric acid, then diluted with EtOAc (20 mL) and water (15 mL), and the aqueous layer was extracted with EtOAc (2×20 mL). The organic layers were combined and washed with saturated brine (20 mL), dried over anhydrous sodium sulfate and concentrated to afford 7-benzyl 5-(tert-butyl) 2-(4-cyclopropyl-2-hydroxyphenyl)-3,4,5a,6,8,9-hexahydro-2H-1,2,5,7-tetraazabenzo[cd]azulene-5,7-dicarboxylate (280 mg, 514 gmol, 175.4%) as a yellow solid. The crude product was used in the next step directly without further purification. LCMS: (ESI, m/z):545 $[M+H]^+$ Step 6: Synthesis of Tert-Butyl 2-(4-cyclopropyl-2-hydroxyphenyl)-2,3,4,5a,6,7,8,9-octahydro-5H-1,2,5,7-tetraazabenzo[cd]azulene-5-carboxylate To a solution of 7-benzyl 5-(tert-butyl) 2-(4-cyclopropyl-2-hydroxyphenyl)-3,4,5a,6,8,9-hexahydro-2H-1,2,5,7-tetraazabenzo[cd]azulene-5,7-dicarboxylate (250 mg, 1 equiv., 459 gmol) in THF (1 mL) were added $Pd(OH)_2/C$ (129 mg, 2 equiv., 918 mol) and Pd/C (97.7 mg, 2 equiv., 918 μmol). The mixture was purged with nitrogen for three times and then was pressurized 4 MPa with hydrogen at room temperature for 2 h. The reaction mixture was cooled to rt. The mixture was filtered and rinsed with DCM (3×20 mL), the filtrate was concentrated under vacuum to give a residue. This resulted in tert-butyl 2-(4-cyclopropyl-2-hydroxyphenyl)-2,3,4,5a,6,7,8,9-octahydro-5H-1,2,5,7-tetraazabenzo[cd]azulene-5-carboxylate (180 mg) as a crude yellow oil. The crude product was used in the next step directly without further purification. LCMS: (ESI, m/z): 411 $[M+H]^+$ Step 7: Synthesis of Tert-Butyl 7-acryloyl-2-(4-cyclopropyl-2-hydroxyphenyl)-2,3,4,5a,6,7,8,9-octahydro-5H-1,2,5,7-tetraazabenzo[cd]azulene-5-carboxylate To a solution of tert-butyl 2-(4-cyclopropyl-2-hydroxyphenyl)-2,3,4,5a,6,7,8,9-octahydro-5H-1,2,5,7-tetraazabenzo[cd]azulene-5-carboxylate (160 mg 1 equiv., 390 μmol) in DMF (2 mL) were added acrylic acid (42.1 mg, 1.5 equiv., 585 μmol) IEA (101 mg, 136 L, 2 equiv., 779 μmol) and T3P (372 mg, 50 wt %, 1.5 equiv., 585 mol). The mixture was stirred at room temperature for 1 h. The reaction was monitored by LCMS. The mixture was diluted with water (20 mL) and EtOAc (20 mL), and the aqueous layer was extracted with EtOAc (2×20 mL). The combined organic layers were washed with saturated brine (2×20 mL), dried over anhydrous sodium sulfate and concentrated to give a residue. The residue was purified by flash column chromatography, eluting with EtOAc/PE (1:5) to afford tert-butyl 7-acryloyl-2-(4-cyclopropyl-2-hydroxyphenyl)-2,3,4,5a,6,7,8,9-octahydro-5H-1,2,5,7-tetraazabenzo[cd]azulene-5-carboxylate (110 mg) as a yellow oil. LCMS: (ESI, m/z): 465 $[M+H]^+$ Step 8: Synthesis of 1-(2-(4-cyclopropyl-2-hydroxyphenyl)-2,3,4,5,5a,6,8,9-octahydro-7H-1,2,5,7-tetraazabenzo[cd]azulen-7-yl)prop-2-en-1-one (Int. H)

A solution of tert-butyl 7-acryloyl-2-(4-cyclopropyl-2-hydroxyphenyl)-2,3,4,5a,6,7,8,9-octahydro-5H-1,2,5,7-tetraazabenzo[cd]azulene-5-carboxylate (100 mg 1 equiv., 215 μmol) in DCM (1 mL) and TFA (0.5 mL) was stirred at room temperature for 30 min. The reaction was monitored by LCMS. The solvent was removed under reduced pressure. This resulted in 1-(2-(4-cyclopropyl-2-hydroxyphenyl)-2,3,4,5,5a,6,8,9-octahydro-7H-1,2,5,7-tetraazabenzo[cd]azulen- 7-yl)prop-2-en-1-one (90 mg) as a crude yellow oil. The crude product was used in the next step directly without further purification. LCMS: (ESI, m/z): 365 $[M+H]^+$ Step 9: Synthesis of 2-(7-acryloyl-5-(7-bromo-1H-benzo[d]imidazole-4-carbonyl)-3,4,5,5a,6,7,8,9-octahydro-2H-1,2,5,7-tetraazabenzo[cd]azulen-2-yl)-5 cyclopropylphenyl 7-bromo-1H-benzo[d]imidazole-4-carboxylate To a solution of 1-(2-(4-cyclopropyl-2-hydroxyphenyl)-2,3,4,5,5a,6,8,9-octahydro-7H-1,2,5,7-tetraazabenzo[cd]

azulen-7-yl)prop-2-en-1-one (50 mg, 1 equiv., 0.14 mmol) in DMF (1 mL) were added HBTU (78 mg, 1.5 equiv., 0.21 mmol), DIEA (53 mg, 7 μL, 3 equiv., 0.41 mmol) and 7-bromo-1H-benzo[d]imidazole-4-carboxylic acid (66 mg, 2 equiv., 0.27 mmol). The mixture was stirred at room temperature for 1 h. The solvent was removed under reduced pressure, resulting in 2-(7-acryloyl-5-(7-bromo-1H-benzo[d]imidazole-4-carbonyl)-3,4,5,5a,6,7,8,9-octahydro-2H-1,2,5,7-tetraazabenzo[cd]azulen-2-yl)-5-cyclopropylphenyl 7-bromo-1H-benzo[d]imidazole-4-carboxylate (30 mg, 37 μmol, 27%) as a crude yellow solid. The crude product was used in the next step directly without further purification. LCMS: (ESI, m/z):809 [M+H]$^+$ Step 10: Synthesis of 1-(5-(7-bromo-1H-benzo[d]imidazole-4-carbonyl)-2-(4-cyclopropyl-2-hydroxyphenyl)-2,3,4,5,5a,6,8,9-octahydro-7H-1,2,5,7-tetraazabenzo[cd]azulen-7-yl)prop-2-en-1-one To a solution of 2-(7-acryloyl-5-(7-bromo-1H-benzo[d]imidazole-4-carbonyl)-3,4,5,5a,6,7,8,9-octahydro-2H-1,2,5,7-tetraazabenzo[cd]azulen-2-yl)-5-cyclopropylphenyl 7-bromo-1H-benzo[d]imidazole-4-carboxylate (30 mg, 1 equiv., 37 μmol) in THE (1 mL) and water (0.5 mL) was added LiOH (1.8 mg, 2 equiv., 74 mol). The mixt re was stirred at room temperature for 1 h. The reaction was monitored by LCMS. The mixt e was diluted with water (20 mL) and EtOAc (20 mL), and the aqueous layer was extracted with EtOAc (2×20 mL). The combined organic layers were washed with saturated brine (2×20 mL), dried over anhydrous sodium sulfate and concentrated to give a residue. The residue was purified by Prep-HPLC (Column: Sunfire C18 5 m, 30 mm*150 mm; Mobile Phase A: water (0.1% FA), Mobile Phase B: MeCN; Flow rate: 60 mL/min; Gradient: 30% B to 50% B in 8 min; Wave Length: UV 254 nm/220 nm; retention time 1: 7.28) to afford racemic 1-(5-(7-bromo-1H-benzo[d]imidazole-4-carbonyl)-2-(4-cyclopropyl-2-hydroxyphenyl)-2,3,4,5,5a,6,8,9-octahydro-7H-1,2,5,7-tetraazabenzo[cd]azulen-7-yl)prop-2-en-1-one (2.0 mg, 3.4 mol, 9.2%, 99.7% purity) as a white solid. LCMS: (ESI, m/z):587 [M+H]*. $^1$H NMR: (400 MHz, Chloroform-d, ppm) δ 10.00 (brs, 1H), 8.25 (s, 1H), 7.59-7.36 (m, 1H), 7.24-7.17 (m, 1H), 6.94 (d, J=8.1 Hz, 1H), 6.72 (s, 1H), 6.60 (d, J=8.0 Hz, 1H), 6.52-6.35 (m, 1H), 5.91-5.65 (m, 1H), 5.56-5.26 (m, 1H), 4.95 (d, J=13.1 Hz, 1H), 4.61-4.39 (m, 1H), 4.35-4.07 (m, 2H), 3.41-2.91 (m, 4H), 2.89-2.57 (m, 2H), 1.96-1.72 (m, 1H), 1.06-0.87 (m, 3H), 0.68 (d, J=5.0 Hz, 2H).

Example A-9: Preparation of 1-(5-(7-bromo-1H-benzo[d]imidazole-4-carbonyl)-2-(4-(2,2-difluorocyclobutyl)-2-hydroxyphenyl)-2,3,4,5,5a,6,8,9-octahydro-7H-1,2,5,7-tetraazabenzo[cd]azulen-7-yl)prop-2-en-1-one

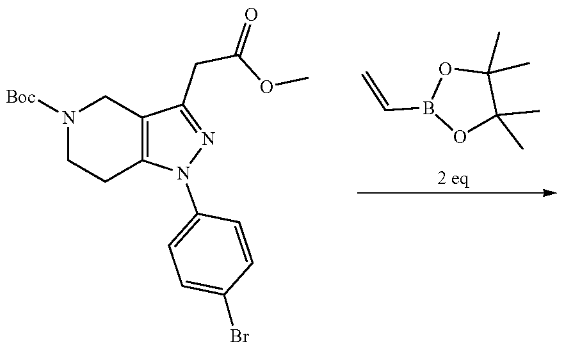

Int. D

-continued

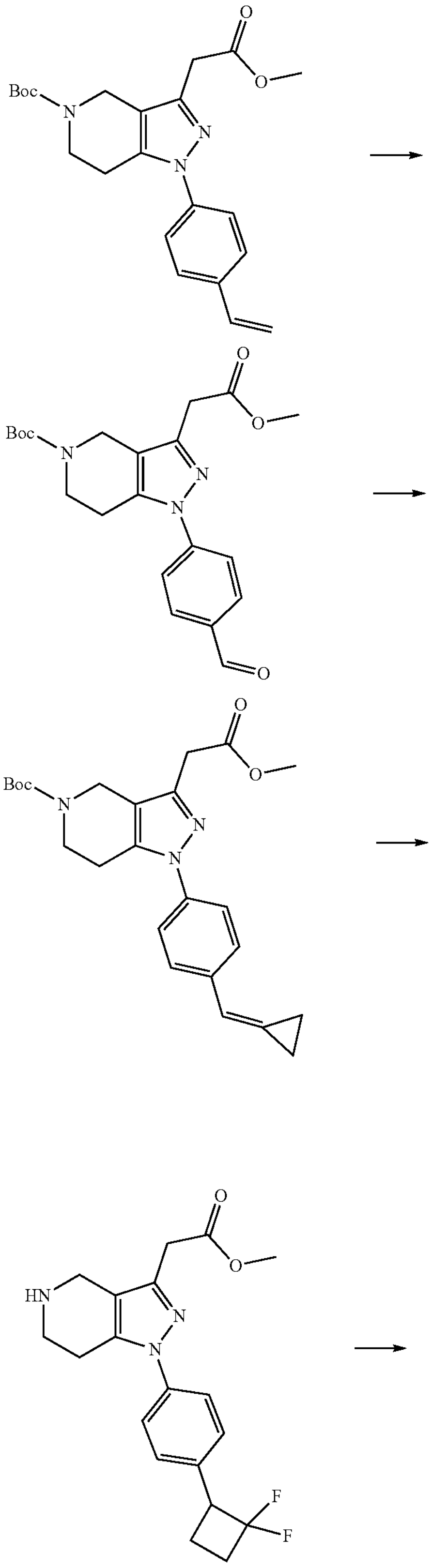

-continued
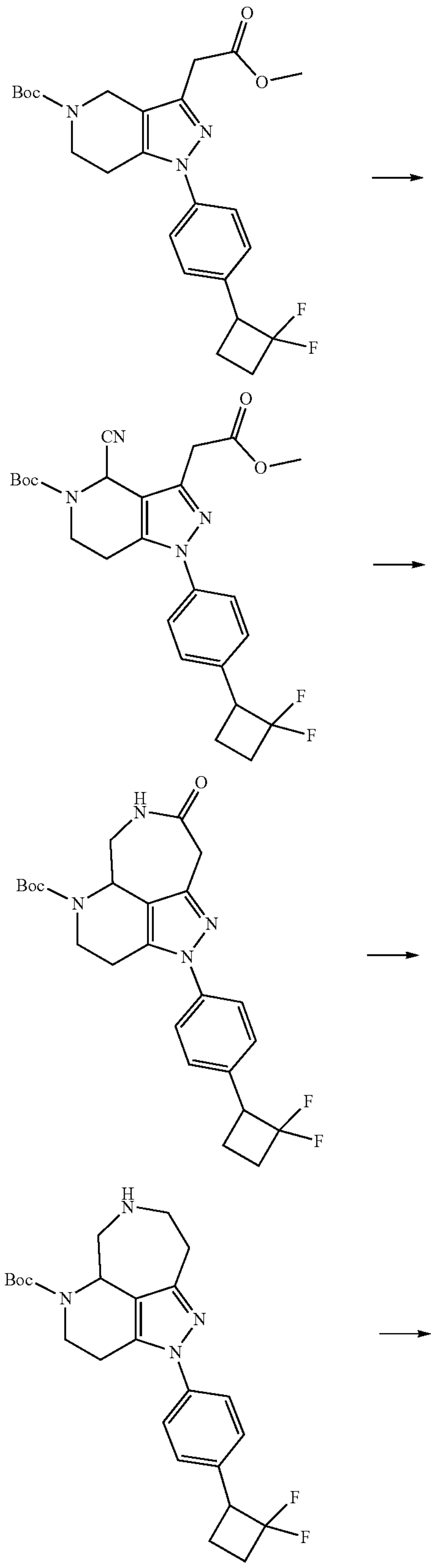
-continued
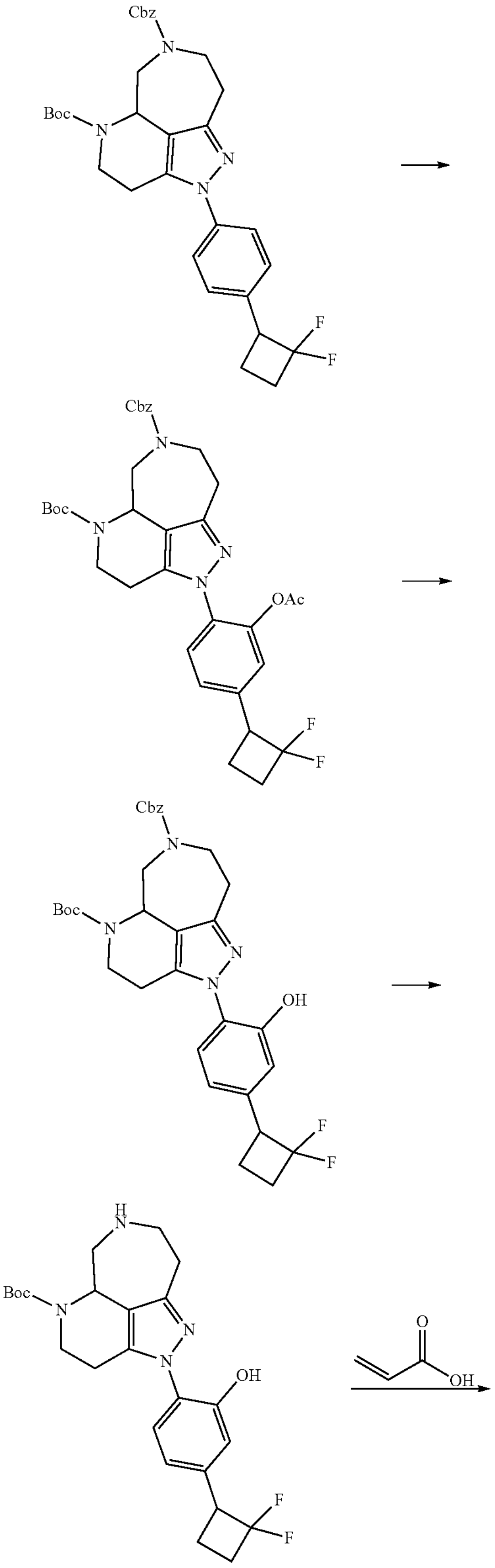

-continued

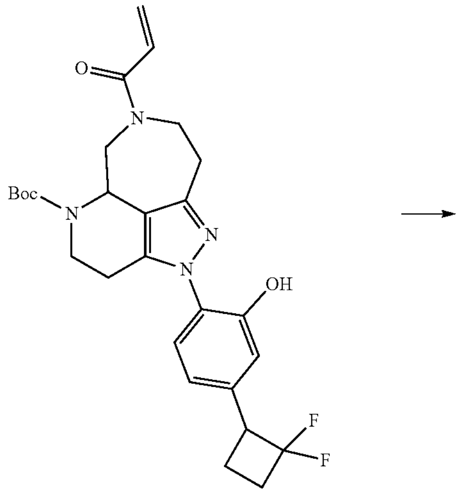

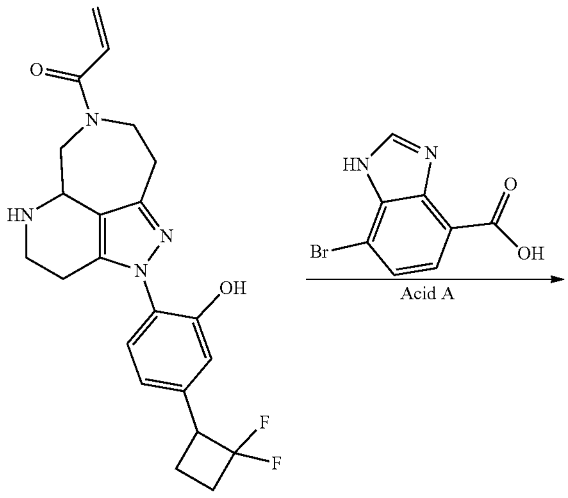

Int. I

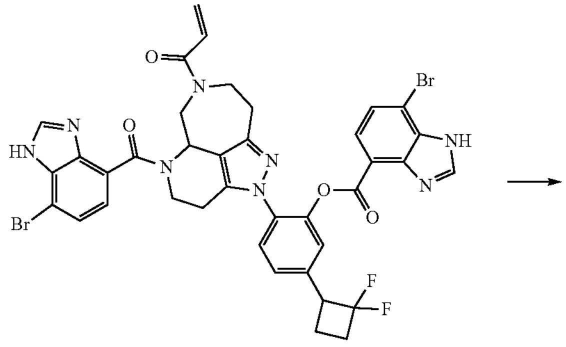

-continued

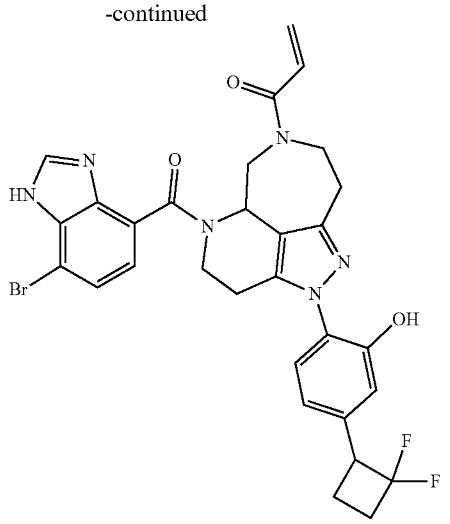

Step 1: Preparation of Tert-Butyl 3-(2-methoxy-2-oxoethyl)-1-(4-vinylphenyl)-1,4,6,7-tetrahydro-5H-pyrazolo[4,3-c]pyridine-5-carboxylate A mixture of Int. D (15.00 g, 1 equiv., 33.31 mmol), tetrakis(triphenylphosphine)palladium(0) (3.849 g, 0.1 equiv., 3.331 mmol), vinylboronic acid pinacol ester (10.26 g, 11.3 mL, 2 equiv., 66.62 mmol) and $Cs_2CO_3$ (32.56 g, 3 equiv., 99.93 mmol) in 1,4-dioxane (150 mL) and water (15 mL) was stirred for 12 h at 80° C. under nitrogen atmosphere. The resulting mixture was diluted with water (200 mL) and extracted with EtOAc (3×100 mL). The combined organic layers were washed with brine (1×100 mL) and dried over anhydrous $Na_2SO_4$. After filtration, the filtrate was concentrated under reduced pressure. The residue was purified by silica gel column chromatography, eluting with PE/EtOAc (3:1) to afford tert-butyl 3-(2-methoxy-2-oxoethyl)-1-(4-vinylphenyl)-1,4,6,7-tetrahydro-5H-pyrazolo[4,3-c]pyridine-5-carboxylate (12.5 g) as a yellow solid. LCMS:(ESI, m/z): 398 $[M+1]^+$ Step 2: Synthesis of Tert-Butyl 1-(4-formylphenyl)-3-(2-methoxy-2-oxoethyl)-1,4,6,7-tetrahydro-5H-pyrazolo[4,3-c]pyridine-5-carboxylate To a stirring mixture of tert-butyl 3-(2-methoxy-2-oxoethyl)-1-(4-vinylphenyl)-1,4,6,7-tetrahydro-5H-pyrazolo[4,3-c]pyridine-5-carboxylate (12.50 g, 1 equiv., 31.45 mmol) and NMO (7.368 g, 2 equiv., 62.9 mmol) in acetone (120 mL) and water (120 mL) was added potassium osmium oxide (VI) (1.045 g, 0.1 equiv., 3.145 mmol) in portions at room temperature under air atmosphere. After 30 min, to the above mixture was added sodium metaperiodate (20.18 g, 5.0 mL, 3 equiv., 94.35 mmol) in portions at room temperature. The resulting mixture was stirred for additional 12 h at room temperature. The reaction was quenched by the addition of $Na_2O_3S_2$. The resulting mixture was extracted with EtOAc (3×100 mL). The combined organic layers were washed with brine (1×100 mL) and dried over anhydrous $Na_2SO_4$. After filtration, the filtrate was concentrated under reduced pressure. The residue was purified by silica gel column chromatography, eluting with PE/EtOAc (2:1) to afford tert-butyl 1-(4-formylphenyl)-3-(2-methoxy-2-oxoethyl)-1,4,6,7-tetrahydro-5H-pyrazolo[4,3-c]pyridine-5-carboxylate (10 g) as a white solid. LCMS: (ESI, m/z): 400 $[M+1]^+$ Step 3: Preparation of Tert-Butyl 1-(4-(cyclopropylidenemethyl) phenyl)-3-(2-methoxy-2-oxoethyl)-1,4,6,7-tetrahydro-5H-pyrazolo[4,3-c]pyridine-5-carboxylat To a stirring mixture of 3-bromopropyl(triphenyl)phosphonium bromide (13 g, 2 equiv., 28 mmol) in THF (50 mL) was added NaH (2.2 g, 60 wt %, 4 equiv., 56 mmol) in portions at room temperature under air atmosphere. The resulting mixture was stirred for 1.5 h at 70° C. under a nitrogen atmosphere. To the above mixture was added tert-butyl 1-(4-formylphenyl)-3-(2-methoxy-2-oxoethyl)-1,4,6,7-tetrahydro-5H-pyrazolo[4,3-c]pyridine-5-carboxylate (5.6 g, 1 equiv., 14 mmol) in THF (50 mL). The resulting mixture was stirred for additional 1 h at 70° C. The reaction was quenched by the addition of saturated $NH_4Cl$ (aqueous 100 mL) at 0° C. The resulting mixture was extracted with EtOAc (3×100 mL). The combined organic layers were washed with brine (1×100 mL) and dried over anhydrous $Na_2SO_4$. After filtration, the filtrate was concentrated under reduced pressure. The residue was purified by silica gel column chromatography, eluting with PE/EtOAc (3:1) to afford tert-butyl 1-(4-cyclopropylidenemethyl) phenyl)-3-(2-methoxy-2-oxoethyl)-1,4,6,7-tetrahydro-5H-pyrazolo[4,3-]pyridine-5-carboxylate (3.5 g) as a white solid. LCMS: (ESI, m/z): 424 $[M+1]^+$ Step 4: Preparation of 2-(1-(4-(2,2-difluorocyclobutyl) phenyl)-4,5,6, 7-tetrahydro-1H-pyrazolo[4,3-c]pyridin-3-yl) acetate A mixture of 1-(Chloromethyl)-4-fluoro-1,4-diazabicyclo[2.2.2]octane-1,4-diium ditetrafluoroborate (4.39 g, 1.5 equiv., 12.4 mmol), pyridine (3.92 g, 4.01 mL, 6 equiv., 49.6 mmol) and HF-pyridine (112 g, 0.10 L, 70 wt %, 96 equiv., 793 mmol) in Toluene (50 mL) was stirred for 15 min at 40° C. under air atmosphere. To the above mixture was added tert-butyl 1-(4-(cyclopropylidenemethyl) phenyl)-3-(2-methoxy-2-oxoethyl)-1,4,6,7-tetrahydro-5H-pyrazolo[4,3-c]pyridine-5-carboxylate (3.50 g, 1 equiv., 8.26 mmol). The resulting mixture was stirred for additional 2 h at 40° C. The reaction was quenched by the addition of $NaHCO_3$ (aq. (1000 mL)). The resulting mixture was extracted with EtOAc(3×100 mL). The combined organic layers were washed with brine (100 mL) and dried over anhydrous $Na_2SO_4$. After filtration, the filtrate was concentrated under reduced pressure. The crude product as used in the next step directly without further purification. This resulted in methyl 2-(1-(4-(2,2-difluorocyclobutyl) phenyl)-4,5,6,7-tetrahydro-1H-pyrazolo[4,3-c]pyridin-3-yl) acetate (3.0 g) as a yellow solid. LCMS: (ESI, m/z): 362 $[M+1]^+$ Step 5: Preparation of Tert-Butyl 1-(4-(2,2-difluorocyclobutyl) phenyl)-3-(2-methoxy-2-oxoethyl)-1,4,6,7-tetrahydro-5H-pyrazolo[4,3-c]pyridine-5-carboxylate A mixture of methyl 2-(1-(4-(2,2-difluorocyclobutyl) phenyl)-4,5,6,7-tetrahydro-1H-pyrazolo[4,3-c]pyridin-3-yl) acetate (3.00 g, 1 equiv., 8.3 mmol), DIEA (3.22 g, 4.34 mL, 3 equiv., 24.9 mmol), $Boc_2O$ (2.72 g, 2.86 mL, 1.5 equiv., 12.5 mmol) and DMAP (101 mg, 0.1 equiv., 830 μmol) in 1,4-dioxane (50 mL) was stirred for 2 h at room temperature under air atmosphere. The resulting mixture was diluted with water (50 mL). The resulting mixture was extracted with EtOAc(3×100 mL). The combined organic layers were washed with brine (1×100 mL) and dried over anhydrous $Na_2SO_4$. After filtration, the filtrate was concentrated under reduced pressure. The residue was purified by silica gel column chromatography, eluting with PE/EtOAc (3:1) to afford tert-butyl 1-(4-(2,2-difluorocyclobutyl) phenyl)-3-(2-methoxy-2-oxoethyl)-1,4,6,7-tetrahydro- 5H-pyrazolo[4,3-c]pyridine-5-carboxylate (1.6 g) as a white solid. LCMS: (ESI, m/z): 462 $[M+1]^+$ Step 6: Preparation of Tert-Butyl 4-cyano-1-(4-(2,2-difluorocyclobutyl) phenyl)-3-(2-methoxy-2-oxoethyl)-1,4,6,7-tetrahydro-5H-pyrazolo[4,3-c]pyridine-5-carboxylate A mixture of tert-butyl 1-(4-(2,2-difluorocyclobutyl) phenyl)-3-(2-methoxy-2-oxoethyl)-1,4,6,7-tetrahydro-5H-pyrazolo[4,3-c]pyridine-5-carboxylate (1.50 g, 1 equiv., 3.25 mmol), AcOH (234 mg, 223 μL, 1.2 equiv., 3.9 mmol). TMSCN (645 mg, 813 μL, 2 equiv., 6.5 mmol) and $TEMPO^+ BF_4^-$ (2.37 g, 3 equiv., 9.75 mmol) in MeCN (20 mL) was stirred for 2 h at room temperature under a nitrogen atmosphere. The resulting mixture was diluted with water (50 mL) and extracted with EtOAc (3×50 mL). The combined organic layers were washed with brine (3×50 mL) and dried over anhydrous $Na_2SO_4$. After filtration, the filtrate was concentrated under reduced pressure. The residue was purified by silica gel column chromatography, eluting with PE/EtOAc (1:1) to afford tert-butyl 4-cyano-1-(4-(2,2-difluorocyclobutyl) phenyl)-3-(2-methoxy-2-oxoethyl)-1,4,6,7-tetrahydro-5H-pyrazolo[4,3-c]pyridine-5-carboxylate (1.5 g) as a yellow solid. LCMS: (ESI, m/z): 487 $[M+1]^+$ Step 7: Preparation of Tert-Butyl 2-(4-(2,2-difluorocyclobutyl) phenyl)-8-oxo-2,3,4,5a,6,7,8,9-octahydro-5H-1,2,5,7-tetraazabenzo[cd]azulene-5-carboxylate A mixture of tert-butyl 4-cyano-1-(4-(2,2-difluorocyclobutyl) phenyl)-3-(2-methoxy-2-oxoethyl)-1,4,6,7-tetrahydro-5H-pyrazolo[4,3-c]pyridine-5-carboxylate (1.50 g, 1 equiv., 3.08 mmol) and Raney nickel (3.62 g, 50 wt %, 492 μL, 20 equiv., 61.7 mmol) in MeOH (60 mL) was stirred for O/N at 60° C. under $H_2$ atmosphere (4 MPa). The resulting mixture was filtered, and the filter cake was washed with EtOAc (40 mL). The filtrate was concentrated under reduced pressure. The crude product was used in the next step directly without further purification. This resulted in tert-butyl 2-(4-(2,2-difluorocyclobutyl) phenyl)-8-oxo-2,3,4,5a,6,7,8,9-octahydro-5H-1,2,5,7-tetraazabenzo[cd]azulene-5-carboxylate (1.10 g) as a white solid. LCMS: (ESI, m/z): 459 $[M+1]^+$ Step 8: Preparation of Tert-Butyl 2-(4-(2,2-difluorocyclobutyl) phenyl)-2,3,4,5a,6,7,8,9-octahydro-5H-1,2,5,7-tetraazabenzo [cd]azulene-5-carboxylate A mixture of tert-butyl 2-(4-(2,2-difluorocyclobutyl) phenyl)-8-oxo-2,3,4,5a,6,7,8,9-octahydro-5H-1,2,5,7-tetraazabenzo[cd]azulene-5-carboxylate (1.00 g, equiv., 2.18 mmol) and BH3·THF (750 mg, 8.72 mL, 1 molar, 4 equiv., 8.72 mmol) in THF (20 mL) was stirred for 2 h at 60° C. under nitrogen atmosphere. The reaction was quenched by the addition of MeOH (20 mL) at rt. The resulting mixture was concentrated under reduced pressure. The residue was purified by silica gel column chromatography, eluting with PE/EtOAc (1:1) to a ford tert-butyl 2-(4-(2,2-difluorocyclobutyl) phenyl)-2,3,4,5a,6,7,8,9-octahydro-5H-1,2,5,7-tetr azabenzo [cd]azulene-5-carboxylate (650 mg) as a white solid. LCMS: (ESI, m/z): 445 [M+1]$^+$ Step 9: Preparation of 7-benzyl 5-(tert-butyl) 2-(4-(2,2-difluorocyclobutyl) phenyl)-3,4,5a,6,8,9-hexahydro-2H-1,2,5,7-tetraazabenzo[cd]azulene-5,7-dicarboxylate A mixture of tert-butyl 2-(4-(2,2-difluorocyclobutyl) phenyl)-2,3,4,5a,6,7,8,9-octahydro-5H-1,2,5,7-tetraazabenzo [cd]azulene-5-carboxylate (600 mg, 1 equiv., 1.35 mmol). TEA (820 mg, 1.13 mL, 6 equiv., 8.1 mmol) and Cbz-OSu (1.01 g, 3 equiv., 4.05 mm 1) in DCM (15 mL) was stirred for 2 h at 40° C. under nitrogen atmosphere. The resulting mixture was concentrated under reduced pressure. The residue was purified by silica gel column chromatography, eluting with PE/EtOAc (2:1) to afford 7-benzyl 5-(tert-butyl) 2-(4-(2,2-difluorocyclobutyl) phenyl)-3,4,5a,6,8,9-hexahydro-2H-1,2,5,7-tetraazabenzo[cd]azulene-5,7-dicarboxylate (670 mg) as a white solid. LCMS: (ESI, m/z): 579 [M+1]$^+$Step 10: Preparation of 7-benzyl 5-(tert-butyl) 2-(2-acetoxy-4-(2,2-difluorocyclobutyl) phenyl)-3,4,5a,6,8,9-hexahydro-2H-1,2,5,7-tetraazabenzo[cd]azulene-5,7-dicarboxylate A mixture of 7-benzyl 5-(tert-butyl) 2-(4-(2,2-difluorocyclobutyl) phenyl)-3,4,5a,6,8,9-hexahydro-2H-1,2,5,7-tetraazabenzo[cd]azulene-5,7-dicarboxylate (2.4 g, 1 equiv., 4.1 mmol), $Pd(OAc)_2$ (93 mg, 0.1 equiv., 0.41 mmol) and PIDA (2.7 g, 2 equiv., 8.3 mmol) in AcOH (4 mL) and 1,4-dioxane (40 mL) was stirred for 2 h at 90° C. under nitrogen atmosphere. The resulting mixture was diluted with saturated aqueous $NaHCO_3$ (2 mL). The resulting mixture was extracted with EtOAc (3×50 mL). The combined organic layers were washed with brine (1×50 mL) and dried over anhydrous $Na_2SO_4$. After filtration, the filtrate was concentrated under reduced pressure. The residue was purified by silica gel column chromatography, eluting with PE/EtOAc (2:1) to afford 7-benzyl 5-(tert-butyl) 2-(2-acetoxy-4-(2,2-difluorocyclobutyl) phenyl)-3,4,5a,6,8,9-hexahydro-2H-1,2,5,7-tetraazabenzo[cd]azulene-5,7-dicarboxylate (900 mg) as a yellow solid. LCMS: (ESI, m/z): 637 [M+1]$^+$ Step 11: Preparation of 7-benzyl 5-(tert-butyl) 2-(4-(2,2-difluorocyclobutyl)-2-hydroxyphenyl)-3,4,5a,6,8,9-hexahydro-2H-1,2,5,7-tetraazabenzo[cd]azulene-5,7-dicarboxylate A mixture of 7-benzyl 5-(tert-butyl) 2-(2-acetoxy-4-(2,2-difluorocyclobutyl) phenyl)-3,4,5a,6,8,9-hexahydro-2H-1,2,5,7-tetraazabenzo[cd]azulene-5,7-dicarboxylate (850 mg, 1 equiv., 1.34 mmol) and LiOH (128 mg, 2.67 mL, 2 molar, 4 equiv., 5.34 mmol) in MeOH (15 mL) was stirred for 1 h at room temperature under air atmosphere. The resulting mixture was diluted with water (15 mL). The resulting mixture was extracted with EtOAc (3×30 mL). The combined organic layers were washed with brine (1×20 mL) and dried over anhydrous $Na_2SO_4$. After filtration, the filtrate was concentrated under reduced pressure. The crude product was used in the next step directly without further purification. This resulted in 7-benzyl 5-(tert-butyl) 2-(4-(2,2-difluorocyclobutyl)-2-hydroxyphenyl)-3,4,5a,6,8,9-hexahydro-2H-1,2,5,7-tetraazabenzo[cd]azulene-5,7-dicarboxylate (790 mg,) as a white solid. LCMS: (ESI, m/z): 595 [M+1]$^+$ Step 12: Preparation of Tert-Butyl 2-(4-(2,2-difluorocyclobutyl)-2-hydroxyphenyl)-2,3,4,5a,6,7,8,9-octahydro-5H-1,2,5,7-tetraazabenzo[cd]azulene-5-carboxylate A mixture of 7-benzyl 5-(tert-butyl) 2-(4-(2,2-difluorocyclobutyl)-2-hydroxyphenyl)-3,4,5a,6,8,9-hexahydro-2H-1,2,5,7-tetraazabenzo[cd]azulene-5,7-dicarboxylate (800 mg, 1 equiv., 1.35 mmol), $Pd(OH)_2$ (756 mg, 10 wt %, 0.4 equiv., 538 μmol) and Pd/C (286 mg, 2 equiv., 2.69 mmol) in $NH_3$ in 1,4-dioxane (7M, 15 mL) was stirred for 12 h at roc m temperature under $H_2$ atmosphere. The resulting mixture was filtered, and the filter cake was washed with EtOAc (50 mL). The filtrate was concentrated under reduced pressure. The crude product was used in the next step directly without further purification. This resulted in tert-butyl 2-(4-(2,2-difluorocyclobutyl)-2-hydroxyphenyl)-2,3,4,5a,6,7,8,9-octahydro-5H-1,2,5,7-tetraazabenzo[cd]azulene-5-carboxylate (600 mg) as a white solid. LCMS: (ESI, m/z): 461 [M+1]$^+$ Step 13: Preparation of Tert-Butyl 7-acryloyl-2-(4-(2,2-difluorocyclobutyl)-2-hydroxyphenyl)-2,3,4,5a,6,7,8,9-octahydro-5H-1,2,5,7-tetraazabenzo[cd]azulene-5-carboxylate A mixture of 2-(4-(2,2-difluorocyclobutyl)-2-hydroxyphenyl)-2,3,4,5a,6,7,8,9-octahydro-5H-1,2,5,7-tetraazabenzo[cd]azulene-5-carboxylate (580 mg, 1 equiv., 1.26 mmol), propylphosphonic anhydride (601 mg, 556 μL, 1.5 equiv., 1.89 mmol), acrylic acid (136 mg, 1.5 equiv., 1.89 mmol) and DIEA (488 mg, 658 μL, 3 equiv., 3.78 mmol) in DCM (15 mL) was stirred for 2 h at room temperature under air atmosphere. The resulting mixture was diluted with water (20 mL). The resulting mixture was extracted with $CH_2Cl_2$ (3×30 mL). The combined organic layers were washed with brine (1×30 mL) and dried over anhydrous $Na_2SO_4$. After filtration, the filtrate was concentrated under reduced pressure. The residue was purified by silica gel column chromatography, eluting with PE/EtOAc (1:50) to afford tert-butyl 7-acryloyl-2-(4-(2,2 -difluorocyclobutyl)-2-hydroxyphenyl)-2,3,4,5a,6,7,8,9-octahydro-5H-1,5,7-tetraazabenzo[cd]azulene-5-carboxylate (430 mg) as a white solid. LCMI: (ESI, m/z): 515 [M+1]$^+$ Step 14: Preparation of 1-(2-(4-(2,2-difluorocyclobutyl)-2-hydroxyphenyl)-2,3,4,5,5a,6,8,9-octahydro-7H-1,2,5,7-tetraazabenzo[cd]azulen-7-yl) prop-2-en-1-one A mixture of tert-butyl 7-acryloyl-2-(4-(2,2-difluorocyclobutyl)-2-hydroxyphenyl)-2,3,4,5a,6,7,8,9-octahydro-5H-1,2,5,7-tetraazabenzo[cd]azulene-5-carboxylate (180.0 mg, 1 equiv., 349.81 gmol)- and TFA (399 mg, 270 μL, 10 equiv., 3.50 mml) in DCM (10 mL) was stirred for 2 h at room temperature under air atmosphere. The resulting mixture was concentrated under reduced pressure. The crude 1-(2-(4-(2,2-difluorocyclobutyl)-2-hydroxyphenyl)-2,3,4,5,5a,6,8,9-octahydro-7H-1,2,5,7-tetraazabenzo[cd]azulen-7-yl) prop-2-en-1-one was used in the next step directly without further purification (140 mg) as a yellow oi. LCMS: (ESI, m/z): 415 [M+1]$^+$ Step 15: Preparation of 2-(7-acryloyl-5-(7-bromo-1H-benzo[d]imidazole-4-carbonyl)-3,4,5,5a,6,7,8,9-octahydro-2H-1,2,5,7-tetraazabenzo[cd]azulen-2-yl)-5-(2,2-difluorocyclobutyl) phenyl 7-bromo-1H-benzo[d]imidazole-4-carboxylate A mixture of 1-(2-(4-(2,2-difluorocyclobutyl)-2-hydroxyphenyl)-2,3,4,5,5a,6,8,9-octahydro-7H-1,2,5,7-tetraazabenzo[cd]azulen-7-yl)prop-2-en-1-one 120 mg, 1 equiv., 290 μmol), EDC hydrochloride (EDCI) (167 mg, 3 equiv., 869 μmol), DI A (374 mg, 504 μL, 10 equiv., 2.90 mmol), HOBt (133 mg, 3 equiv., 869 gmol) and 7-bromo-1H-benzo[d]imidazole-4-carboxylic acid (209 mg, 3 equiv., 869 μmol) in DCM (4 mL) was stirred for 1 h at room temperature under air atmosphere. The resulting mixture was diluted with water (10 mL). The resulting mixture was extracted with EtOAc (3×20 mL). The combined organic layers were washed with brine (1×20 mL) and dried over anhydrous $Na_2SO_4$. After filtration, the filtrate was concentrated under reduced pressure. This resulted in 2-(7-acryloyl-5-(7-bromo-1H-benzo[d]imidazole-4-carbonyl)-3,4,5,5a,6,7,8,9-octahydro-2H-1,2,5,7-tetraazabenzo[cd]azulen-2-yl)-5-(2,2-difluorocyclobutyl) phenyl 7-bromo-1H-benzo[d]imidazole 4-carboxylate (130.0 mg) as a yellow solid, which was used directly in the next step without further purification. LCMS: (ESI, m/z): 861 $[M+1]^+$ Step 16: Preparation of (Rac)-1-(5-(7-bromo-1H-benzo[d]imidazole-4-carbonyl)-2-(4-(2,2-difluorocyclobutyl)-2-hydroxyphenyl)-2,3,4,5,5a,6,8,9-octahydro-7H-1,2,5,7-tetraazabenzo[cd]azulen-7-yl) prop-2-en-1-one A solution of 2-(7-acryloyl-5-(7-bromo-1H-benzo[d]imidazole-4-carbonyl)-3,4,5,5a,6,7,8,9-octahydro-2H-1,2,5,7-tetraazabenzo[cd]azulen-2-yl)-5-(2,2-difluorocyclobutyl) phenyl 7-bromo-1H-benzo[d]imidazole-4-carboxylate (100 mg, 1 equiv., 116 mol) and LiOH (13.9 mg, 5 equiv., 581 gmol) in THF (2 mL) and water (0.5 mL) was stirred for 12 h at room temperature under air atmosphere. The resulting mixture was diluted with water (10 mL). The resulting mixture was extracted with EtOAc (3×10 mL). The combined organic layers were washed with brine (1×20 mL) and dried over anhydrous $Na_2SO_4$. After filtration, the filtrate was concentrated under reduced pressure. The crude product was purified by Prep-HPLC (Column: XBridge BEH Shield RP18 5 m, 30 mm*150 mm; Mobile Phase A: water (10 mmol/L $NH_4HCO_3$), Mobile Phase B: MeCN; Flow rate: 60 mL/min; Gradient: 25% B to 60% in 8 min; Wave Length: UV 254 nm/220 nm; retention time 1: 6.9) to afford 1-(5-(7-bromo-1H-benzo[d]imidazole-4-carbonyl)-2-(4-(2,2-difluorocyclobutyl)-2-hydroxyphenyl)-2,3,4,5,5a,6,8,9-octahydro-7H-1,2,5,7-tetraazabenzo[cd]azulen-7-yl)prop-2-en-1-one (3.0 mg, 4.7 m 1, 4.0%) as a mixture of diastereomers as a white solid. LCMS: (ESI, m/z): 639 $[M+1]^+$. $^1H$ NMR: (400 MHz, Chloroform-d, ppm) δ 12.04-11.51 (m, 1H), 10.49-9.95 (m, 1H), 8.32-8.05 (m, 1H), 7.49-7.34 (m, 2H), 7.21-7.07 (m, 1H), 7.07-6.85 (m, 2H), 6.86-6.57 (m, 1H), 6.57-6.2 (m, 1H), 5.90-5.62 (m, 1H), 5.57-5.29 (m, 1H), 5.10-4.57 (m, 2H), 4.43 (brs, 1H), 4.00-3.69 (m, 1H), 3.55-2.83 (m, 5H), 2.79 (brs, 1H), 2.68-2.35 (m, 3H), 2.19 (brs, 1H), 2.12-1.83 (m, 1H).

Example A-10: Preparation of (R or S)-1-(5-(4-amino-6-(trifluoromethyl)nicotinoyl)-2-(4-cyclopropyl-2-hydroxyphenyl)-2,3,4,5,5a,6,8,9-octahydro-7H-1,2,5,7 tetraazabenzo[cd]azulen-7-yl)prop-2-en-1-one

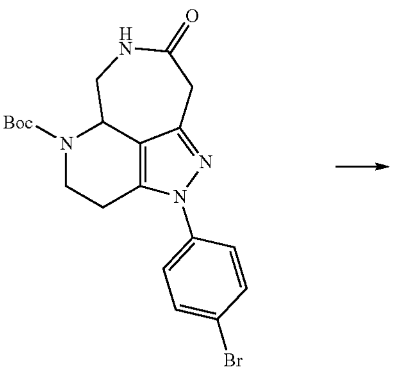

Int. E-2

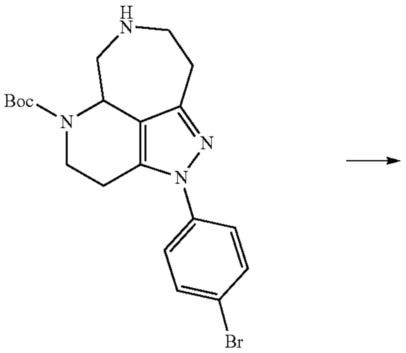

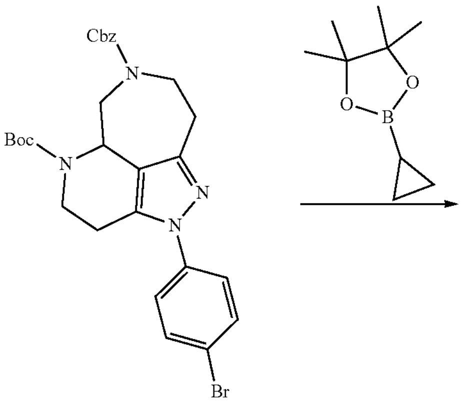

-continued
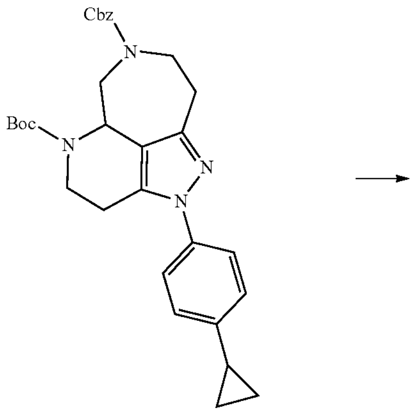
Int. E-3
-continued
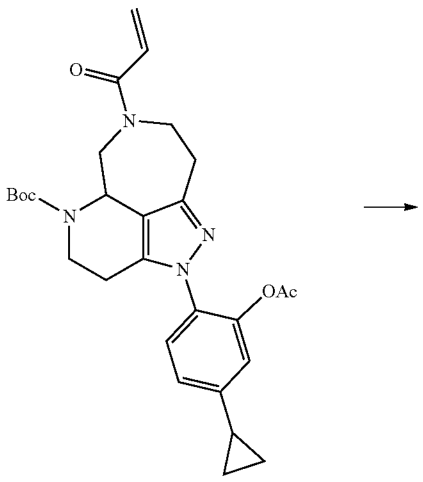
Int. E-4
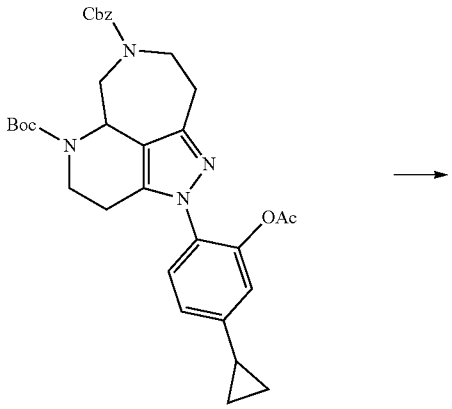
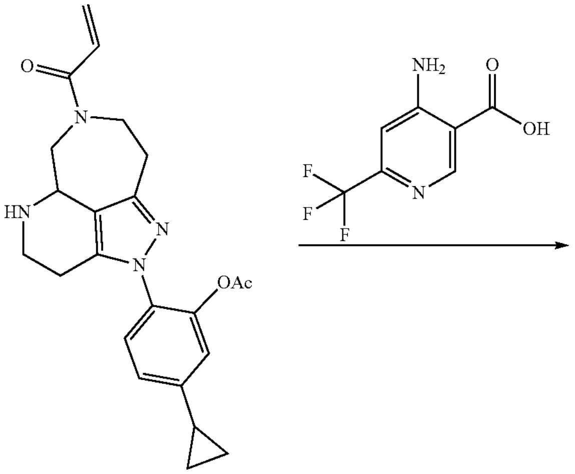
Int. H-2
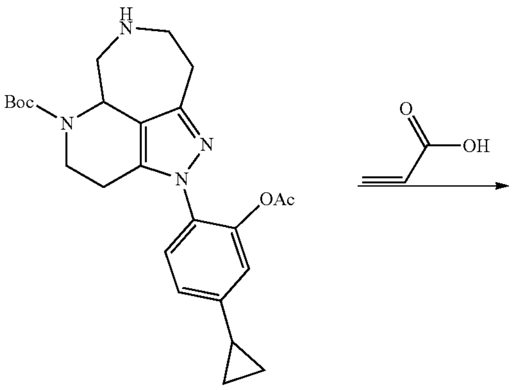
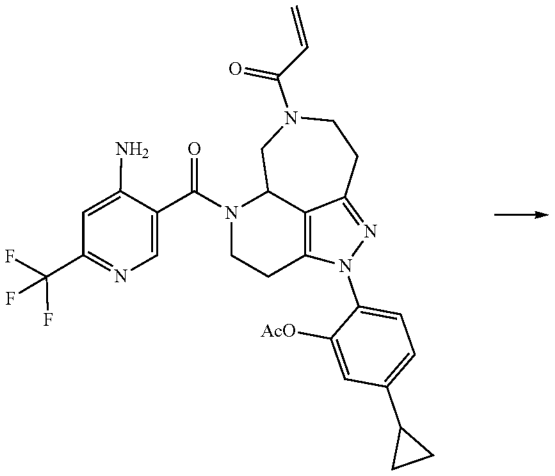

-continued

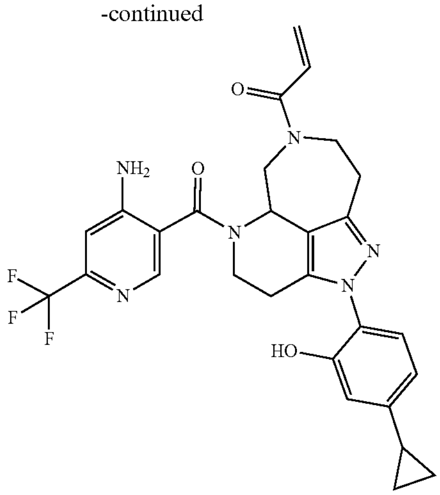

Step 1: Preparation of Tert-Butyl (R or S)-2-(4-bromophenyl)-2,3,4,5a,6,7,8,9-octahydro-5H-21,2,5,7-tetraazabenzo[cd]azulene-5-carboxylate A mixture of Int. E-2 (5.0 g, 1 equiv. 11 mmol) and $BH_3$·THF 3.8 g, 45 mL, 1 molar, 4 equiv., 45 mmol) in THF (100 mL) was stirred for 4 hours at 60° C. under a nitrogen atmosphere. The reaction was then cooled to rt and quenched by the addition of MeOH. The resulting mixture was concentrated under reduced pressure, affording tert-butyl (R or S)-2-(4-bromophenyl)-2,3,4,5a,6,7,8,9-octahydro-5H-1,2,5,7-tetraazabenzo[cd]azulene-5-carboxylate as a crude yellow solid (4.6 g) which was used in the next step without further purification. LCMS: (ESI, m/z): 433/435 $[M+1]^+$ Step 2: Preparation of 7-benzyl 5-(tert-butyl) (R or S)-2-(4-bromophenyl)-3,4,5a, 6,8,9-hexahydro-2H-1,2,5,7-tetraazabenzo[cd]azulene-5,7-dicarboxylate A mixture of tert-butyl (R or S)-2-(4-bromophenyl)-2,3,4,5a,6,7,8,9-octahydro-5H-1,2,5,7-tetraazabenzo[cd]azulene-5-carboxylate (5.1 g, crude), TEA (3.6 g, 4.9 mL, 35 mmol) and Cbz-OSu (4.4 g, 18 mmol) in DCM (100 mL) was stirred for 2 hours at 40° C. under a nitrogen atmosphere. The reaction was quenched by the addition of MeOH at room temperature. The resulting mixture was concentrated under reduced pressure. The residue was purified by silica gel column chromatography, eluting with PE/EA (1:1) to afford 7-benzyl 5-(tert-butyl) (R or S)-2-(4-bromophenyl)-3,4,5a,6,8,9-hexahydro-2H-1,2,5,7-tetraazabenzo[cd]azulene-5,7-dicarboxylate (4.9 g) as a white solid. LCMS: (ESI, m/z): 567/569 $[M+1]^+$ Step 3: Preparation of 7-benzyl 5-(tert-butyl) (R or S)-2-(4-cyclopropylphenyl)-3,4,5a,6,8,9-hexahydro-2H-1,2,5,7-tetraazabenzo[cd]azulene-5,7-dicarboxylate (Int. E-3)

A mixture of 7-benzyl 5-(tert-butyl) (R or S)-2-(4-bromophenyl-3,4,5a,6,8,9-hexahydro-2H-1,2,5,7-tetraazabenzo [cd]azulene-5,7-dicarboxylate (3.9 g, 1 equiv. 6.9 mmol), $PdCl_2$(dppf) (0.50 g, 0.1 Equiv., 0.69 mmol), 2-cyclopropyl-4,4,5,5-tetramethyl-1,3,2-dioxaborolane (2.3 g, 2 equiv., 14 mmol), silver oxide (1.6 g, 1 equiv., 6.9 mmol) and $Cs_2CO_3$ (4.5 g, 2 equiv., 14 mmol) in toluene (80 mL) was stirred for 4 hours at 90° C. under a nitrogen atmosphere. The resulting mixture was then cooled to rt and concentrated under reduced pressure. The residue was purified by silica gel column chromatography, eluting with PE/EA (1:1) to afford 7-benzyl 5-(tert-butyl) (R or S)-2-(4-cyclopropylphenyl)-3,4,5a,6,8,9-hexahydro-2H-1,2,5,7-tetraazabenzo[cd]azulene-5,7-dicarboxylate (3.5 g) as a white solid. LCMS:(ESI, m/z): 529 $[M+1]^+$ Step 4: Preparation of 7-Benzyl 5-(tert-butyl) (R or S)-2-(2-acetoxy-4-cyclopropylphenyl)-3,4,5a,6,8,9-hexahydro-2H-1,2,5,7-tetraazabenzo[cd]azulene-5,7-dicarboxylate A mixture of 7-benzyl 5-(tert-butyl) (R or S)-2-(4-cyclopropylphenyl)-3,4,5a,6,8,9-hexahydro-2H-1,2,5,7-tetraazabenzo[cd]azulene-5,7-dicarboxylate (3.5 g, 6.6 mmol), PIDA (4.3 g, 2 equiv., 13 mmol) and palladium diacetate (0.30 g, 0.2 equiv., 1.3 mmol) in MeCN (50 mL) and AcOH (25 mL) was stirred for 2 h at 90° C. under a nitrogen atmosphere. The resulting mixture was then cooled to rt and concentrated under reduced pressure, and the residue was purified by silica gel column chromatography, eluting with PE/EA (1:1) to afford 7-benzyl 5-(tert-butyl) (R or S)-2-(2-acetoxy-4-cyclopropylphenyl)-3,4,5a,6,8,9-hexahydro-2H-1,2,5,7-tetraazabenzo[cd]azulene-5,7-dicarboxylate (1:7 g) as a white solid. LCMS:(ESI, m/z): 587 $[M+1]^+$ Step 5: Preparation of Tert-Butyl (R or S)-2-(2-acetoxy-4-cyclopropylphenyl)-2,3,4,5a,6,7,8,9-octahydro-5H-1,2,5,7-tetraazabenzo[cd]azulene-5-carboxylate A mixture of 7-benzyl 5-(tert-butyl) (R or S)-2-(2-acetoxy-4-cyclopropylphenyl)-3,4,5a,6,8,9-hexahydro-2H-1,2,5,7-tetraazabenzo[cd]azulene-5,7-dicarboxylate (400 mg, 1 equiv., 682 μmol), palladium hydroxide on carbon (479 mg, 20% wt) and palladium on carbon (726 mg, 10% wt) in 1,4-dioxane (10 mL) was stirred for 12 hours at rt under a 4 MPa atmosphere of hydrogen. The resulting mixture was then filtered and the filter cake was washed with EA (20 mL×2). The filtrate was concentrated under reduced pressure, resulting in tert-butyl (R or S)-2-(2-acetoxy-4-cyclopropylphenyl)-2,3,4,5a,6,7,8,9-octahydro-5H-1,2,5,7-tetraazabenzo[cd]azulene-5-carboxylate (290 mg) as a crude yellow solid. The crude product as used in the next step directly without further purification. LCMS:(ESI, m/z): 453 $[M+1]^+$ Step 6: Preparation of Tert-Butyl (R or S)-2-(2-acetoxy-4-cyclopropylphenyl)-7-acryloyl-2,3,4,5a,6,7,8,9-octahydro-5H-1,2,5,7-tetraazabenzo[cd]azulene-5-carboxylate (Int. E-4)

A mixture of tert-butyl (R or S)-2-(2-acetoxy-4-cyclopropylphenyl)-2,3,4,5a,6,7,8,9-octahydro-5H-1,2,5,7-tetraazabenzo[cd]azulene-5-carboxylate (330 mg, 1 equiv., 729 μmol), propylphosphonic anhydride (348 mg, 322 μL, 1.5 equiv., 1.09 mmol) acrylic acid (105 mg, 2 Equiv., 1.46 mmol) and DIEA (565 mg, 762 μL, 6 Equiv., 4.38 mmol) in DMF (10 mL) was stirred for 2 hours at rt under an air atmosphere. The resulting mixture was diluted with water (20 mL), and then was extracted with EA (3×20 mL). The combined organic layers were washed with brine (1×20 mL) and dried over anhydrous sodium sulfate. After filtration, the filtrate was concentrated under reduced pressure. The residue was purified by silica gel column chromatography, eluting with PE/EA (1:1) to afford tert-butyl (R or S)-2-(2-acetoxy-4-cyclopropylphenyl)-7-acryloyl-2,3,4,5a,6,7,8,9-octahydro-5H-1,2,5,7-tetraazabenzo[cd]azulene-5-carboxylate (150 mg) as a white solid. LCMS:(ESI, m/z): 507 $[M+1]^+$ Step 7: Preparation of (R or S)-2-(7-acryloyl-3,4,5,5a,6,7,8,9-octahydro-2H-1,2,5,7-tetraazabenzo[cd]azulen-2-yl)-5-cyclopropylphenyl acetate (Int. H-2)

A mixture of tert-butyl (R or S)-2-(2-acetoxy-4-cyclopropylphenyl)-7-acryloyl-2,3,4,5a,6,7,8,9-octahydro-5H-1,2,5,7-tetraazabenzo[cd]azulene-5-carboxylate (80 mg, 1 equiv., 0.16 mmol) in DCM (2 mL) and TFA (0.4 mL) was stirred for 2 hours at rt under a nitrogen atmosphere. The resulting mixture was concentrated under reduced pressure, affording (R or S)-2-(7-acryloyl-3,4,5,5a,6,7,8,9-octahydro-2H-1,2,5,7-tetraazabenzo[cd]azulen-2-yl)-5-cyclopropylphenyl acetate (60 mg) (Int. H-2) as a crude yellow oil. The crude product was used in the next step directly without further purification. LCMS:(ESI, m/z): 407[M+1]

Step 8: Preparation of (R or S)-2-(7-acryloyl-5-(4-amino-6-(trifluoromethyl)nicotinoyl)-3,4,5,a,6,7,8,9-octahydro-2H-1,2,5,7-tetraazabenzo[cd]azulen-2-yl)-5-cyclopropylphenyl acetate A mixture of (R or S)-2-(7-acryloyl-3,4,5,5a,6,7,8,9-octahydro-2H-1,2,5,7-tetraazabenzo[cd]azulen-2-yl)-5-cyclopropylphenyl acetate (80.0 mg, crude), HATU (112.3 mg, 1.5 equiv., 295.2 μmol), 4-amino-6-(trifluoromethyl) nicotinic acid (48.68 mg, 1.2 equiv., 236.2 μmol) and DIEA (152.6 mg, 206 μL, 6 equiv., 1.181 mmol) in DCM (2 mL) was stirred for 2 hours at rt under an air atmosphere. The resulting mixture was concentrated un er reduced pressure, and the residue was purified by silica gel column chromatography, eluting with PE/EA (1:1) to afford (R or S)-2-(7-acryloyl-5-(4-amino-6-(trifluoromethyl)nicotinoyl)-3,4,5,a,6,7,8,9-octahydro-2H-1,2,5,7-tetraazabenzo[cd]azulen-2-yl)-5-cyclopropylphenyl acetate (60 mg) as a white solid. LCMS:(ESI, m/z): 595 $[M+1]^+$ Step 9: Preparation of (R or S)-1-(S-(4-amino-6-(trifluoromethyl)nicotinoyl)-2-(4-cyclopropyl-2-hydroxyphenyl)-2,3,4,5,5a,6,8,9-octahydro-7H-1,2,5,7-tetraazabenzo[cd]azulen-7-yl)prop-2-en-1-one A mixture of (R or S)-2-(7-acryloyl-5-(4-amino-6-(trifluoromethyl) nicotinoyl)-3,4,5,5a,6,7,8,9-octahydro-2H-1,2,5,7-tetraazabenzo[cd]azulen-2-yl)-5-cyclopropylphenyl acetate (55.0 mg, 1 Equiv., 92.5 μmol) and LiOH (4.4 mg, 93 μL, 2 molar, 2 equiv., 185 μmol) in THF (2 mL) was stirred for 1 h at rt under a nitrogen atmosphere. The resulting mixture was extracted with EA (2×20 mL) and the combined organic layers were washed with brine (2×20 mL) and dried over anhydrous sodium sulfate. After filtration, the filtrate was concentrated under reduced pressure. The crude product was purified by Prep-HPLC (Column: YMC Triart C18 ExRs 5 m, 30 mm*150 mm; Mobile Phase A: Water (10 mmol/$LNH_4HCO_3$), Mobile Phase B: ACN; Flow rate: 60 mL/min; Gradient: 30% B to 55% B in 10 min) to afford (R or S)-1-(5-(4-amino-6-(trifluoromethyl)nicotinoyl)-2-(4-cyclopropyl-2-hydroxyphenyl)-2,3,4,5,5a,6,8,9-octahydro-7H-1,2,5,7-tetraazabenzo[cd]azulen-7-yl)prop-2-en-1-one (7.0 mg) as a white solid. LCMS:(ESI, m/z): 553 $[M+1]^+$. $^1H$ NMR: (400 MHz, Chloroform-d) δ 10.12 (s, 1H), 0.42-8.26 (m, 1H), 7.54-7.31 (m, 1H), 7.04 (s, 1H), 7.00-6.89 (m, 1H), 6.80-6.76 (m, 1H), 0.71-6.59 (m, 1H), 6.58-6.37 (m, 1H), 5.97-5.69 (m, 1H), 5.67-5.31 (m, 3H), 5.07-4.87 (m, 1H), 4.65-4.06 (m, 2H), 3.40-2.90 (m, 5H), 2.90-2.66 (m, 2H), 1.94-1.74 (m, 1H), 106-0.88 (m, 2H), 0.86-0.60 (m, 2H).

Example A-10A: Alternative Preparation of Int. EA-2 and Int. E-3

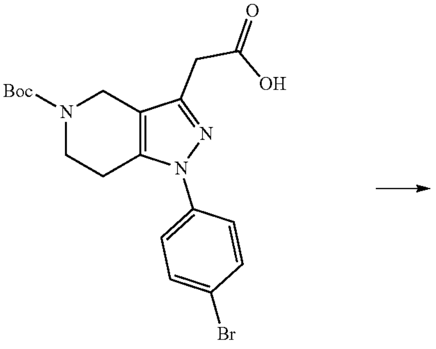

Int. C

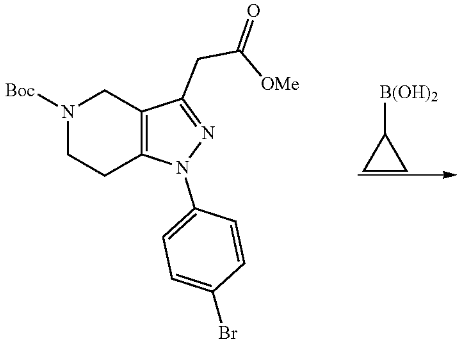

Int. D

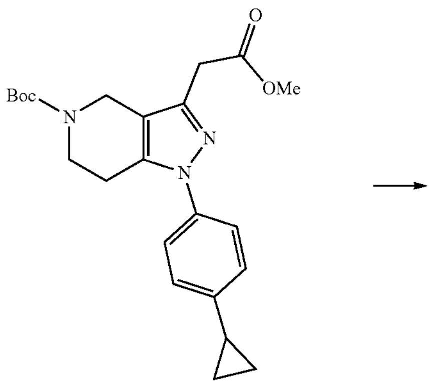

-continued

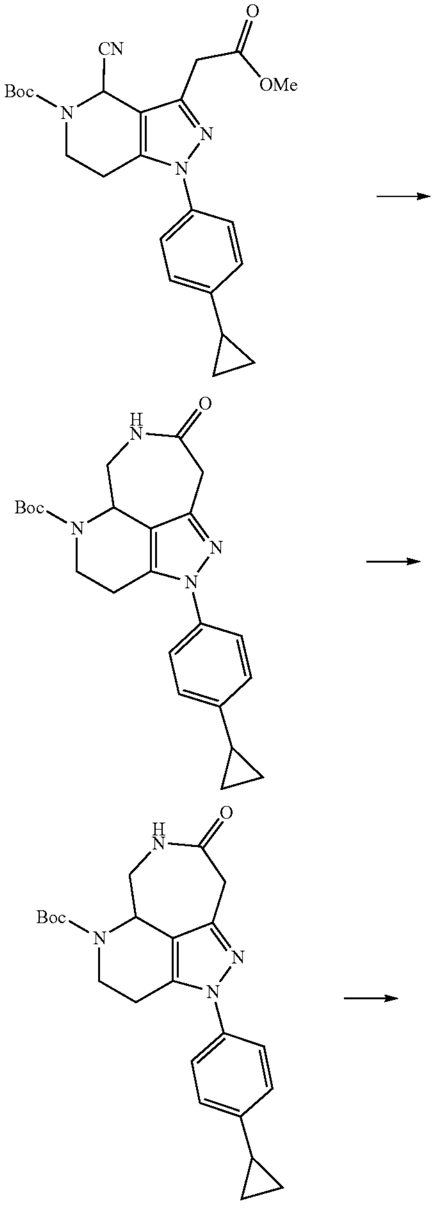

Int. EA-2

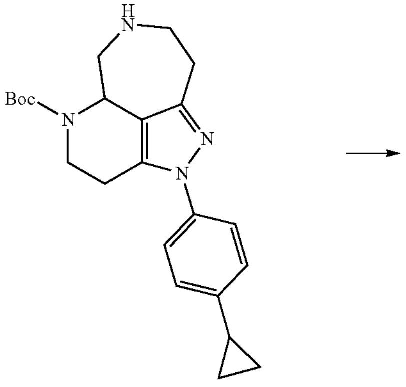

-continued

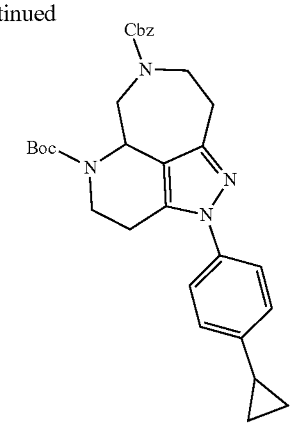

Int. E-3

Step 1: Synthesis of Tert-Butyl 1-(4-bromophenyl)-3-(2-methoxy-2-oxoethyl)-1,4,6,7-tetrahydro-5H-pyrazolo[4,3-c]pyridine-5-carboxylate To a solution of 2-(1-(4-bromophenyl)-5-(tert-butoxycarbonyl)-4,5,6,7-tetrahydro-1H-pyrazolo[4,3-c]pyridin-3-yl) acetic acid (2.40 kg, 5.50 mol, 1.00 eq.) in DMF (24.0 L) was added $K_2CO_3$ (1.52 kg, 11.0 mol, 2.00 eq) at rt, then $CH_3I$ (1.56 kg, 11.0 mol, 684 mL, 2.00 eq) was added dropwise maintaining the temperature at 0~10° C. The mixture was then stirred at rt ° C. for 2 h, after which $H_2O$ (20 L) was added to the stirring mixture at 15~25° C. The mixture was extracted with MTBE (20 L×2), and the combined organic phase was washed with brine (20 L×2), dried over $Na_2SO_4$, and concentrated under reduced pressure to give a residue. The residue was purified by column chromatography ($SiO_2$, petroleum ether/ethyl acetate=20/1 to 1/1) to obtain tert-butyl 1-(4-bromophenyl)-3-(2-methoxy-2-oxoethyl)-1,4,6,7-tetrahydro-5H-pyrazolo[4,3-c]pyridine-5-carboxylate (4.50 kg) as a brown solid. LCMS:(ESI, m/z): 452 $[M+1]^+$ Step 2: Synthesis of Tert-Butyl 1-(4-cyclopropylphenyl)-3-(2-methoxy-2-oxoethyl)-1,4,6,7-tetrahydro-5H-pyrazolo[4,3-c]pyridine-5-carboxylate To a solution of tert-butyl 1-(4-bromophenyl)-3-(2-met oxy-2-oxoethyl)-1,4,6,7-tetrahydro-5H-pyrazolo[4,3-c] pyridine-5-carboxylate (300 g, 666 mol, 1.00 eq.) and cyclopropylboronic acid (63.0 g, 733 mmol, 1.10 eq.) in toluene (3.00 and $H_2O$ (300 mL) was added $K_3PO_4$ (424 g, 2.00 mol, 3.00 eg) and Pd(dppf)$Cl_2$ (48.8 g, 66.6 mmol, 0.10 eq.) at rt, and the reaction was purged with nitrogen (×3). The resulting mixture was stirred at 100-110° C. for 2 h, after which the reaction was cooled to 20~30° C. To this mixture was then added $H_2O$ (1.00 L), and the organic phase was isolated, and the aqueous phase was extracted with EtOAc (1.00 L). The combined the organic phases were washed with brine (1.50 L×2), dried over $Na_2SO_4$, and concentrated under reduced pressure to give a residue. The residue was purified by column chromatography ($SiO_2$, eluting with PE/EA=20/1 to 1/1) to give tert-butyl 1-(4-cyclopropylphenyl)-3-(2-methoxy-2-oxoethyl)-1,4,6,7-tetrahydro-5H-pyrazolo[4,3-c]pyridine-5-carboxylate (2.60 kg) as a yellow solid. LCMS:(ESI, m/z): 412 $[M+1]^+$ Step 3: Synthesis of Tert-Butyl 4-cyano-1-(4-cyclopropylphenyl)-3-(2-methoxy-2-oxoethyl)-1,4,6,7-tetrahydro-5H-pyrazolo[4,3-c]pyridine-5-carboxylate To a solution of tert-butyl 1-(4-cyclopropylphenyl)-3-(2-methoxy-2-oxoethyl)-1,4,6,7-tetrahydro-5H-pyrazolo[4,3-c]pyridine-5-carboxylate (200 g, 486 mmol, 1.00 eq,) in MeCN (2.00 L) was added AcOH (29.2 g, 486 mmol, 27.8 mL, 1.00 eq) and $TEMPO^+ BF_4^-$ (356 g, 1.46 mol, 3.00 eq) at rt, then TMSCN (193 g, 1.94 mol, 243 mL, 4.00 eq) was added dropwise at 0~10° C. The mixture was stirred at rt for 1 h, after which the mixture was cooled to 0° C., and aqueous $Na_2SO_3$ (1.00 L) was added with stirring at 0~10° C. The mixture was then extracted with MTBE (1.00 L×2), and the combined organic phase was washed with brine (1.00 L×2), dried over $Na_2SO_4$, and concentrated under reduced pressure to give a residue. The residue was purified by column chromatography ($SiO_2$, eluting with PE/EA=3/1) to provide tert-butyl 4-cyano-1-(4-cyclopropylphenyl)-3-(2-methoxy-2-oxoethyl)-1,4,6,7-tetrahydro-5H-pyrazolo[4,3-c]pyridine-5-carboxylate (1.55 kg) as a white solid.

Step 4: Synthesis of Tert-Butyl 2-(4-cyclopropylphenyl)-8-oxo-2,3,4,5a,6,7,8,9-octahydro-5H-1,2,5,7-tetraazabenzo[cd]azulene-5-carboxylate To a solution of tert-butyl 4-cyano-1-(4-cyclopropylphenyl)-3-(2-methoxy-2-oxoethyl)-1,4,6,7-tetrahydro-5H-pyrazolo[4,3-c]pyridine-5-carboxylate (775 g, 1.78 mol, 1.00 eq, batch×2) was added Raney Ni (775 g, 13.2 mol, 7.44 eq.) in MeOH (2.00 L), and the reaction was purged with hydrogen gas (×3). The mixture was stirred at 50~60° C. under an atmosphere of hydrogen for 16 h at 4 MPa. The mixture was then cooled to 20~30° C., and the reaction solution was filtered through diatomaceous earth and subsequently concentrated under reduced pressure to give a residue. The residue was dissolved with MeOH (3.50 L) and $Na_2CO_3$ (565 g, 5.33 mol, 3.00 eq.) was added to the mixture. The mixture was stirred at 75-80° C. for 2 h, after which the mixture was filtered and concentrated under reduced pressure to give a residue. The residue was purified by column chromatography ($SiO_2$, eluting with PE/EA=3/1) to provide tert-butyl 2-(4-cyclopropylphenyl)-8-oxo-2,3,4,5a,6,7,8,9-octahydro-5H-1,2,5,7-tetraaabenzo[cd]azulene-5-carboxylate (580 g) as a white solid. LCMS:(ESI, m/z): 409 $[M+1]^+$ Step 5: Chiral Separation of Tert-Butyl 2-(4-cyclopropylphenyl)-8-oxo-2,3,4,5a,6,7,8,9-octahydro-5H-1,2,5,7-tetraazabenzo[cd]azulene-5-carboxylate To Provide Int. EA-2

The racemic tert-butyl 2-(4-cyclopropylphenyl)-8-oxo-2,3,4,5a,6,7,8,9-octahydro-5H-1,2,5,7-tetraazabenzo[cd]azulene-5-carboxylate was separated by chiral SFC (column: DAICEL CHIRALPAK AS (250 mm*50 mm, 10 um); mobile phase: [$CO_2$(phase A)—MeOH (0.1% $NH_3H_2O$) (Phase B)]; gradient: isocratic 40% B over 3 min) to provide (Tor S)-tert-butyl 2-(4-cyclopropylphenyl)-8-oxo-2,3,4,5a,6,7,8,9-octahydro-5H-1,2,5,7-tetraaabenzo[cd]azulene-5-carboxylate Int. EA-2 (270 g) as a white solid (first eluting peak, 3.1 min). LCMS:(ESI, m/z): 409 $[M+1]^+$. $^1H$ NMR (400 MHz, DMSO-d6) δ ppm 8.08 (br t, J=5.60 Hz, 1H), 7.40 (d, J=8.60 Hz, 2H), 7.19 (d, J=8.60 Hz, 2H), 4.58-4.67 (m, 1H), 4.20 (br d, J=12.00 Hz, 1H), 3.93 (d, J=17.6 Hz, 1H), 3.57 (d, J=17.6 Hz, 1H), 3.37-3.50 (m, 2H), 2.87-3.00 (m, 1H), 2.61-2.75 (m, 2H), 1.92-2.04 (m, 1H), 1.48 (s, 9H), 0.94-1.01 (m, 2H), 0.66-0.74 (m 2H). Analytical chiral SFC: Column—Chiralcel OD-3 50×4.6 mm I.D. 3 μm; Mobile phase CO2 (Phase A) abd MeOH (0.5% DEA) (Phase B); Gradient 5-40% B in A over 3 min; Flow rate: 3 mL/min. Int. EA-2 is the first-eluting peak (retention time=1.6 min). (the undesired enantiomer is the second-eluting peak, retention time=1.9 min).

Step 6: Synthesis of (R or S)-tert-butyl 2-(4-cyclopropylphenyl)-2,3,4,5a,6,7,8,9-octahydro-5H-1,2,5,7-tetraazabenzo[cd]azulene-5-carboxylate To a solution of (R or S)-tert-butyl 2-(4-cyclopropylphenyl)-8-oxo-2,3,4,5a,6,7,8,9-octahydro-5H-1,2,5,7-tetraazabenzo[cd]azulene-5-carboxylate Int. EA-2 (200 g, 489 mmol, 1.00 eq) in THF (1.00 L) was added dropwise $BH_3$·THF (1.00 M, 978 mL, 2.00 eq) at 0° C. After addition, the resulting mixture was stirred at 60° C. for 1 h. The reaction mixture was then quenched by addition of MeOH (200 mL) at 0° C., and then diluted with MeOH (4.00 L) and the mixture was concentrated under reduced pressure to give a residue. The crude (R or S)-tert-butyl 2-(4-cyclopropylphenyl)-2,3,4,5a,6,7,8,9-octahydro-5H-1,2,5,7-tetraazabenzo[cd]azulene-5-carboxylate was used directly without further purification. LCMS:(ESI, m/z): 395 [M+1]+

Step 7: Synthesis of (R or S)-7-benzyl 5-(tert-butyl) 2-(4-cyclopropylphenyl)-3,4,5a,6,8,9-hexahydro-2H-1,2,5,7-tetraazabenzo[cd]azulene-5,7-dicarboxylate (Int E-3)

To a solution of (R or S)-tert-butyl 2-(4-cyclopropylphenyl)-2,3,4,5a,6,7,8,9-octahydro-5H-1,2,5,7-tetraazabenzo[cd]azulene-5-carboxylate (167 g, 422 mmol, 1.00 eq) in DCM (1.70 L) was added TEA (214 g, 2.11 mol, 294 mL, 5.00 eq) and benzyl (2,5-dioxopyrrolidin-1-yl) carbonate (316 g, 1.27 mol, 3.00 eq). The mixture was stirred at 40° C. for 6 h, after which the reaction was then quenched by the addition of water (1.30 L) at rt and the resulting mixture was partitioned between $H_2O$ (1.30 L) and DCM (1.30 L). The water phase was extracted with DCM (650 mL), and the organic phase was separated and washed with brine (1.30 L), dried over Na2SO4, filtered and concentrated under reduced pressure to give a residue. The residue was purified by column chromatography (SiO2, Petroleum ether/Ethyl acetate=1/1) to provide (R or S)-7-benzyl 5-(tert-butyl) 2-(4-cyclopropylphenyl)-3,4,5a,6,8,9-hexahydro-2H-1,2,5,7-tetraazabenzo[cd]azulene-5,7-dicarboxylate (Int. E-3) (193 g) as an oil. LCMS:(ESI, m/z): 529 $[M+1]^+$

TABLE A5

The following Examples in Table A5 were prepared in an analogous manner to Example A-10 step 9 using the corresponding carboxylic acids. The compound of Example A-10-12 was prepared using the acid described in Example A-24. The compound of Example A-10-14 was prepared using the acid described in Example L-3.

| Example No. | Structure | Compound Name | LCMS [M + H]+ | NMR |
|---|---|---|---|---|
| A-10-1 | 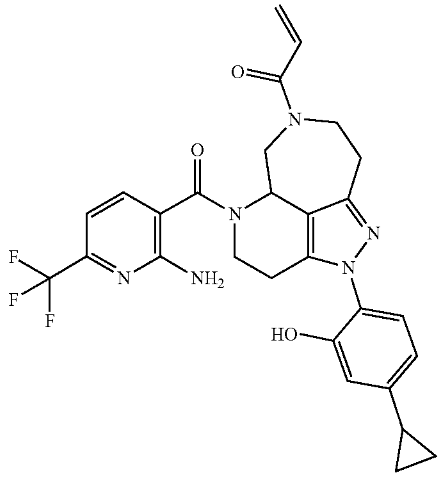 [SMILES: C=CC(=O)N1CCc2nn(-c3ccc(C4CC4)cc3O)c3c2C(C1)N(C(=O)c1ccc(C(F)(F)F)nc1N)CC3] | (R or S)-1-(5-(2-amino-6-(trifluoromethyl) nicotinoyl)-2-(4-cyclopropyl-2-hydroxyphenyl)-2,3,4,5,5a,6,8,9-octahydro-7H-1,2,5,7-tetraazabenzo[cd]azulen-7-yl)prop-2-en-1-one | 553 | $^1$H NMR (400 MHz, Chloroform-d) δ 10.11 (s, 1H), 7.56 (d, J = 7.6 Hz, 1H), 7.38 (s, 1H), 7.11 (d, J = 7.6 Hz, 1H), 6.94 (d, J = 8.4 Hz, 1H), 6.79 (d, J = 2.0 Hz, 1H), 6.67-6.61 (m, 1H), 6.52-6.46 (m 1H), 5.91-5.76 (m, 1H), 5.43-5.39 (m, 3H), 5.02-4.78 (m 1H), 4.36 (s, 1H), 4.04 (s, 1H), 3.27-2.91 (m, 5H), 2.87-2.71 (m, 2H), 1.92-1.81 (m, 1H), 1.04-0.94 (m, 2H), 0.76-0.66 (m, 2H). |
| A-10-2 | 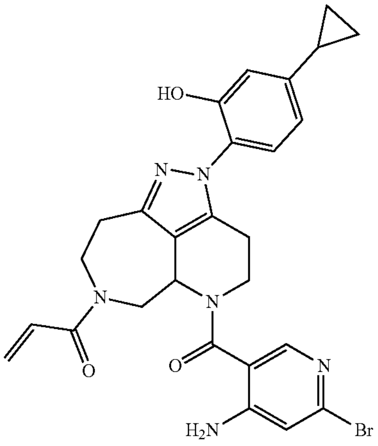 [SMILES: C=CC(=O)N1CCc2nn(-c3ccc(C4CC4)cc3O)c3c2C(C1)N(C(=O)c1cnc(Br)cc1N)CC3] | (R or S)-1-(5-(4-amino-6-bromonicotinoyl)-2-(4-cyclopropyl-2-hydroxyphenyl)-2,3,4,5,5a,6,8,9-octahydro-7H-1,2,5,7-tetraazabenzo[cd] azulen-7-yl)prop-2-en-1-one | 563 | $^1$H NMR (400 MHz, Chloroform-d) δ 10.01 (brs, 1H), 8.08-7.92 (m, 1H), 7.40-7.25 (m, 1H), 6.93-6.79 (m, 2H), 6.72 (d, J = 2.0 Hz, 1H), 6.62-6.53 (m, 1H), 6.51-6.39 (m, 1H), 5.85-5.72 (m, 1H), 5.39-5.09 (m, 2H), 5.01-4.82 (m, 1H), 4.39 (s, 1H), 4.15 (s, 1H), 3.20-2.90 (m, 5H), 2.82-2.60 (m, 2H), 1.86-1.76 (m, 1H), 0.98-0.86 (m, 2H), 0.85-0.73 (m, 1H), 0.70-0.59 (m, 2H). |
| A-10-3 | 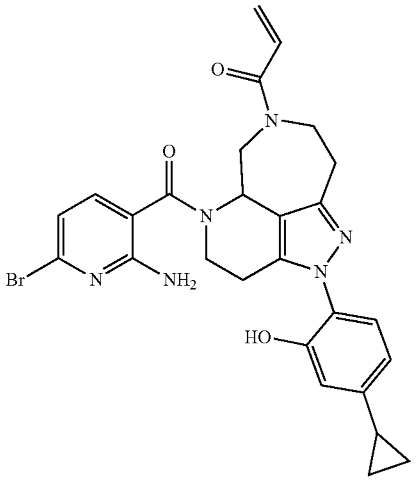 [SMILES: C=CC(=O)N1CCc2nn(-c3ccc(C4CC4)cc3O)c3c2C(C1)N(C(=O)c1ccc(Br)nc1N)CC3] | (R or S)-1-(5-(2-amino-6-bromonicotinoyl)-2-(4-cyclopropyl-2-hydroxyphenyl)-2,3,4,5,5a,6,8,9-octahydro-7H-1,2,5,7-tetraazabenzo[cd] azulen-7-yl)prop-2-en-1-one | 563 | $^1$H NMR (400 MHz, Chloroform-d) δ 7.80-7.31 (m, 1H), 7.10-6.86 (m, 2H), 6.79 (d, J = 2.0 Hz, 1H), 6.72-6.59 (m, 1H), 6.59-6.30 (m, 1H), 6.01-5.69 (m, 1H), 5.63-5.15 (m, 2H), 5.15-4.81 (m, 1H), 4.60-4.0 (m, 2H), 3.30-2.60 (m, 7H), 1.95-1.81 (m, 1H), 1.10-0.95 (m, 2H), 0.80-0.59 (m, 2H). |

TABLE A5-continued

The following Examples in Table A5 were prepared in an analogous manner to Example A-10 step 9 using the corresponding carboxylic acids. The compound of Example A-10-12 was prepared using the acid described in Example A-24. The compound of Example A-10-14 was prepared using the acid described in Example L-3.

| Example No. | Structure | Compound Name | LCMS [M + H]+ | NMR |
|---|---|---|---|---|
| A-10-4 | 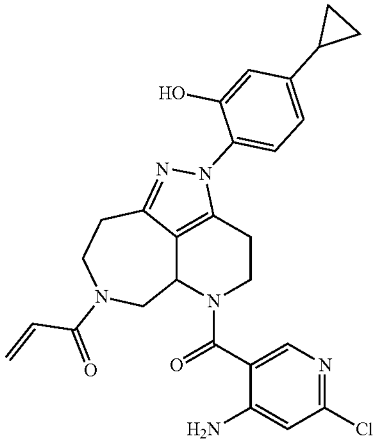 [SMILES: C=CC(=O)N1CCc2nn(-c3ccc(C4CC4)cc3O)c3c2C(C1)N(C(=O)c1cnc(Cl)cc1N)CC3] | (R or S)-1-(5-(4-amino-6-chloronicotinoyl)-2-(4-cyclopropyl-2-hydroxyphenyl)-2,3,4,5,5a,6,8,9-octahydro-7H-1,2,5,7-tetraazabenzo[cd]azulen-7-yl)prop-2-en-1-one | 519 | $^1$H NMR (400 MHz, Chloroform-d) δ 8.07 (s, 1H), 7.48-7.25 (m, 1H), 6.97-6.91 (m, 1H), 6.81-6.77 (m, 1H), 6.74-6.70 (m, 1H), 6.68-6.61 (m, 1H), 6.55-6.46 (m, 1H), 5.89-5.82 (m, 1H), 5.39-5.35 (m, 1H), 5.31-5.26 (m, 1H), 5.01-4.93 (m, 1H), 4.48-4.44 (m, 1H), 4.25-4.20 (m, 1H), 3.21-3.17 (m, 1H), 3.12-3.04 (m, 3H), 2.86-2.70 (m, 2H), 1.89-1.84 (m, 1H), 1.59-1.51 (m, 1H), 1.48-1.40 (m, 1H), 1.02-0.96 (m, 2H), 0.85-0.81 (m, 1H), 0.74-0.68 (m, 2H). |
| A-10-5 | 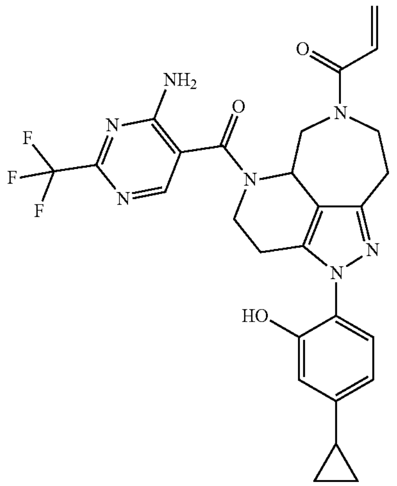 [SMILES: C=CC(=O)N1CCc2nn(-c3ccc(C4CC4)cc3O)c3c2C(C1)N(C(=O)c1cnc(C(F)(F)F)nc1N)CC3] | (S or R)-1-(5-(4-amino-2-(trifluoromethyl)pyrimidine-5-carbonyl)-2-(4-cyclopropyl-2-hydroxyphenyl)-2,3,4,5,5a,6,8,9-octahydro-7H-1,2,5,7-tetraazabenzo[cd]azulen-7-yl)prop-2-en-1-one | 554 | $^1$H NMR (400 MHz, Chloroform-d, ppm) δ 8.45-8.35 (m, 1H), 7.48-7.28 (m, 1H), 7.03-6.85 (m, 1H), 6.80 (d, J = 2.0 Hz, 1H), 6.71-6.56 (m, 1H), 6.56-6.35 (m, 1H), 6.20 (s, 2H), 5.95-5.70 (m, 1H), 5.50-5.28 (m, 1H), 4.97 (d, J = 13.4 Hz, 1H), 4.74-4.35 (m, 1H), 4.34-4.03 (m, 1H), 3.40-3.17 (m, 2H), 3.18-3.01 (m, 3H), 2.98-2.67 (m, 2H), 1.93-1.82 (m, 2H), 1.03-0.93 (m, 2H), 0.77-0.63 (m, 2H). |
| A-10-6 | 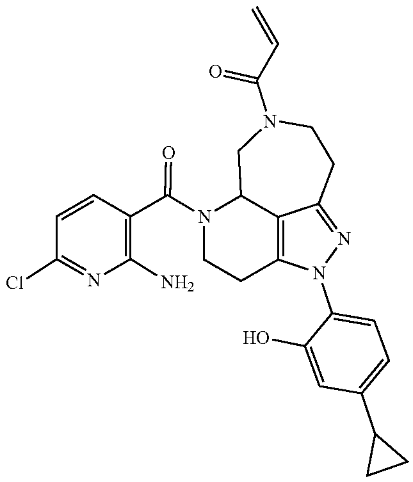 [SMILES: C=CC(=O)N1CCc2nn(-c3ccc(C4CC4)cc3O)c3c2C(C1)N(C(=O)c1ccc(Cl)nc1N)CC3] | (S or R)-1-(5-(2-amino-6-chloronicotinoyl)-2-(4-cyclopropyl-2-hydroxyphenyl)-2,3,4,5,5a,6,8,9-octahydro-7H-1,2,5,7-tetraazabenzo[cd]azulen-7-yl)prop-2-en-1-one | 519 | $^1$H NMR (400 MHz, DMSO-d6) δ 9.95 (s, 1H), 7.47 (d, J = 7.7 Hz, 1H), 7.13 (d, J = 8.2 Hz, 1H), 6.69 (s, 1H), 6.66-6.58 (m, 2H), 6.53 (s, 2H), 6.32-6.20 (m, 1H), 5.89-5.63 (m, 1H), 5.09 (s, 1H), 4.65 (s, 1H), 4.50-4.19 (m, 1H), 3.68 (s, 1H), 3.08 (s, 1H), 2.90-2.70 (m, 4H), 2.42-2.34 (m, 1H), 1.97-1.75 (m, 1H), 0.99-0.90 (m, 2H), 0.68-0.59 (m, 2H). |

TABLE A5-continued

The following Examples in Table A5 were prepared in an analogous manner to Example A-10 step 9 using the corresponding carboxylic acids. The compound of Example A-10-12 was prepared using the acid described in Example A-24. The compound of Example A-10-14 was prepared using the acid described in Example L-3.

| Example No. | Structure | Compound Name | LCMS $[M + H]^+$ | NMR |
|---|---|---|---|---|
| A-10-7 | 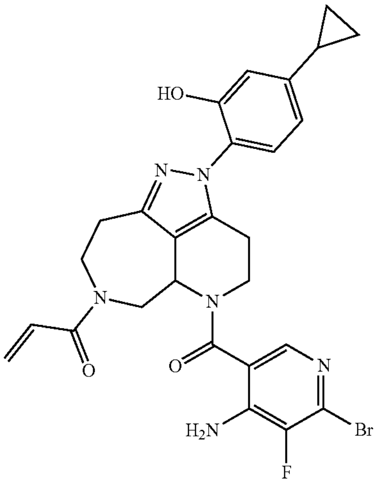 [SMILES: C=CC(=O)N1CCc2nn(-c3ccc(C4CC4)cc3O)c3c2C(C1)N(C(=O)c1cnc(Br)c(F)c1N)CC3] | (S or R)-1-(5-(4-amino-6-bromo-5-fluoronicotinoyl)-2-(4-cyclopropyl-2-hydroxyphenyl)-2,3,4,5,5a,6,8,9-octahydro-7H-1,2,5,7-tetraazabenzo[cd]azulen-7-yl)prop-2-en-1-one | 581 | $^1$H NMR (400 MHz, Chloroform-d) δ 7.97-7.90 (m, 1H), 7.38-7.34 (m, 1H), 7.00-6.90 (m, 1H), 6.82-6.77 (m, 1H), 6.68-6.61 (m, 1H), 6.55-6.40 (m, 1H), 5.90-5.75 (m, 1H), 5.51-5.47 (m, 1H), 5.38-5.34 (m, 2H), 5.01-4.93 (m, 1H), 4.51-4.43 (m, 1H), 4.26-4.18 (m, 1H), 3.38-3.15 (m, 2H), 3.14-2.91 (m, 3H), 2.87-2.71 (m, 2H), 1.93-1.82 (m, 1H), 1.04-0.94 (m, 2H), 0.76-0.67 (m, 2H). |
| A-10-8 | 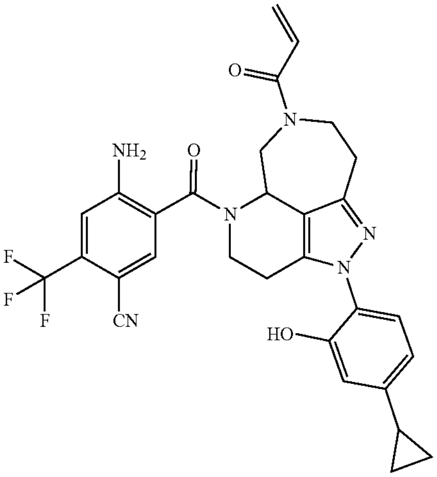 [SMILES: C=CC(=O)N1CCc2nn(-c3ccc(C4CC4)cc3O)c3c2C(C1)N(C(=O)c1cc(C#N)c(C(F)(F)F)cc1N)CC3] | (R or S)-5-(7-acryloyl-2-(4-cyclopropyl-2-hydroxyphenyl)-3,4,5,5a,6,7,8,9-octahydro-2H-1,2,5,7-tetraazabenzo[cd]azulene-5-carbonyl)-4-amino-2-(trifluoromethyl)benzonitrile | 577 | $^1$H NMR (400 MHz, DMSO-d6) δ 9.93 (s, 1H), 7.92-7.71 (m, 1H), 7.49 (s, 1H), 7.20 (s, 1H), 7.14 (d, J = 8.2 Hz, 1H), 6.89-6.65 (m, 3H), 6.61 (d, J = 8.0 Hz, 1H), 6.41-6.19 (m, 1H), 5.90-5.69 (m, 1H), 5.15 (s, 1H), 4.66 (s, 1H), 4.49-4.18 (m, 1H), 3.61 (s, 1H), 3.19-3.01 (m, 1H), 2.92-2.70 (m, 4H), 2.41-2.30 (m, 2H), 2.00-1.75 (m, 1H), 1.00-0.89 (m, 2H), 0.69-0.58 (m, 2H). |
| A-10-9 | 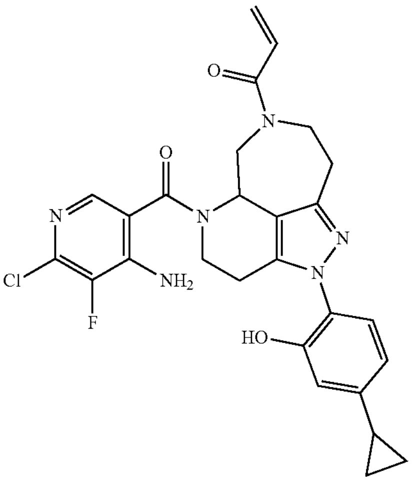 [SMILES: C=CC(=O)N1CCc2nn(-c3ccc(C4CC4)cc3O)c3c2C(C1)N(C(=O)c1cnc(Cl)c(F)c1N)CC3] | (S or R)-1-(5-(4-amino-6-chloro-5-fluoronicotinoyl)-2-(4-cyclopropyl-2-hydroxyphenyl)-2,3,4,5,5a,6,8,9-octahydro-7H-1,2,5,7-tetraazabenzo[cd]azulen-7-yl)prop-2-en-1-one | 537 | $^1$H NMR (400 MHz, Chloroform-d) δ 8.01-7.88 (m, 1H), 7.44-7.29 (m, 1H), 6.99-6.87 (m, 1H), 6.82-6.77 (m, 1H), 6.68-6.61 (m, 1H), 6.58-6.43 (m, 1H), 5.90-5.74 (m, 1H), 5.56-5.28 (m, 3H), 5.01-4.93 (m, 1H), 4.77-4.40 (m, 1H), 4.34-4.11 (m, 1H), 3.40-3.00 (m, 5H), 2.89-2.69 (m, 2H), 1.92-1.80 (m, 1H), 1.04-0.92 (m, 2H), 0.78-0.67 (m, 2H). |

TABLE A5-continued

The following Examples in Table A5 were prepared in an analogous manner to Example A-10 step 9 using the corresponding carboxylic acids. The compound of Example A-10-12 was prepared using the acid described in Example A-24. The compound of Example A-10-14 was prepared using the acid described in Example L-3.

| Example No. | Structure | Compound Name | LCMS $[M + H]^+$ | NMR |
|---|---|---|---|---|
| A-10-10 | 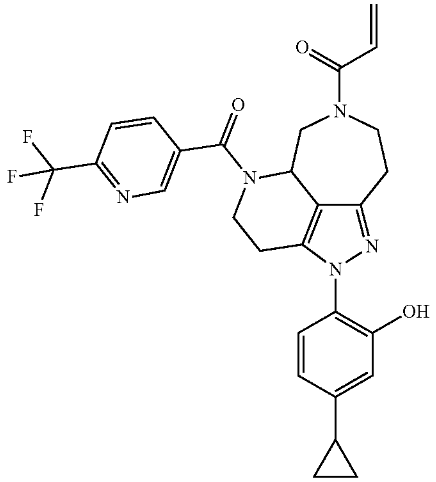 [SMILES: C=CC(=O)N1CCc2nn(-c3ccc(C4CC4)cc3O)c3c2C(C1)N(C(=O)c1ccc(C(F)(F)F)nc1)CC3] | (R or S)-1-(2-(4-cyclopropyl-2-hydroxyphenyl)-5-(6-(trifluoromethyl) nicotinoyl)-2,3,4,5,5a,6,8,9-octahydro-7H-1,2,5,7-tetraazabenzo[cd] azulen-7-yl)prop-2-en-1-one | 538 | $^1$H NMR (400 MHz, Chloroform-d) δ 10.07 (s, 1H), 8.84(s, 1H), 8.32-7.99 (m, 1H), 7.84(d, J=8.0 Hz, 1H), 7.40-7.37(m, 1H), 7.00-6.92(m, 1H), 6.79 (s, 1H), 6.67-6.62 (m, 1H), 6.53-6.49 (m, 1H), 5.89-5.87 (m, 1H), 5.43-5.41 (m, 1H), 5.00-4.97 (m, 1H), 4.54-4.51 (m, 1H), 3.92-3.90 (m, 1H), 3.24-3.02 (m, 5H), 2.82-2.74 (m, 2H), 1.90-1.83 (m, 1H), 1.01-0.96 (m, 2H), 0.73-0.69 (m, 2H). |
| A-10-11 | 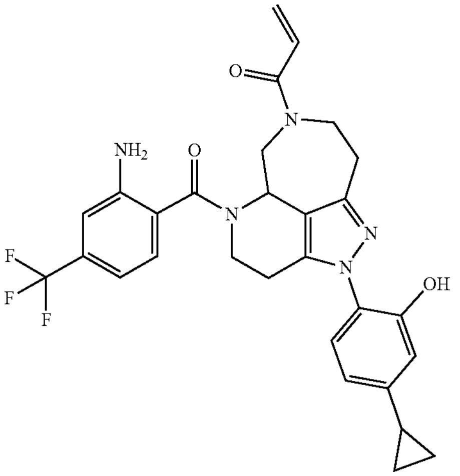 [SMILES: C=CC(=O)N1CCc2nn(-c3ccc(C4CC4)cc3O)c3c2C(C1)N(C(=O)c1ccc(C(F)(F)F)cc1N)CC3] | (S or R)-1-(5-(2-amino-4-(trifluoromethyl) benzoyl)-2-(4-cyclopropyl-2-hydroxyphenyl)-2,3,4,5,5a,6,8,9-octahydro-7H-1,2,5,7-tetraazabenzo[cd] azulen-7-yl)prop-2-en-1-one | 552 | $^1$H NMR (400 MHz, Chloroform-d) δ 7.52-7.26 (m, 1H), 7.22-7.05 (m, 2H), 6.95 (d, J = 8.3 Hz, 1H), 6.78-6.63 (m, 1H), 6.62 (d, J =7.5 Hz, 1H), 6.51-6.47 (m, 1H), 5.85 (s, 1H), 5.42 (s, 1H), 4.96 (s, 1H), 4.51 (s, 1H), 4.32-3.89 (m, 1H), 3.33-2.87 (m, 6H), 2.89-2.55 (m, 2H), 2.01-1.85 (m, 1H), 1.03-0.94 (m, 2H), 0.75-0.64 (m, 2H). |
| A-10-12 | 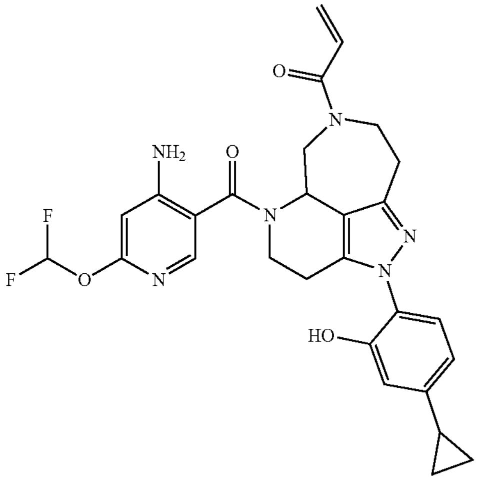 [SMILES: C=CC(=O)N1CCc2nn(-c3ccc(C4CC4)cc3O)c3c2C(C1)N(C(=O)c1cnc(OC(F)F)cc1N)CC3] | (R or S)-1-(5-(4-amino-6-(difluoromethoxy) nicotinoyl)-2-(4-cyclopropyl-2-hydroxyphenyl)-2,3,4,5,5a,6,8,9-octahydro-7H-1,2,5,7-tetraazabenzo[cd] azulen-7-yl)prop-2-en-1-one | 551 | $^1$H NMR (400 MHz, Chloroform-d, ppm) δ 10.11 (brs, 1H), 7.92 (s, 1H), 7.62-7.17 (m, 2H), 7.01-6.89 (m, 1H), 6.79 (d, J = 2.0 Hz, 1H), 6.75-6.60 (m, 1H), 6.60-6.42 (m, 1H), 6.20 (s, 1H), 5.98-5.82 (m, 1H), 5.45-5.09 (m, 3H), 5.09-4.89 (m, 1H), 4.65-4.14 (m, 2H), 3.40-2.90 (m, 5H), 2.89-2.68 (m, 2H), 1.87-1.77 (m, 1H), 1.03-0.95 (m, 2H), 0.73-0.65 (m, 2H). |

TABLE A5-continued

The following Examples in Table A5 were prepared in an analogous manner to Example A-10 step 9 using the corresponding carboxylic acids. The compound of Example A-10-12 was prepared using the acid described in Example A-24. The compound of Example A-10-14 was prepared using the acid described in Example L-3.

| Example No. | Structure | Compound Name | LCMS $[M + H]^+$ | NMR |
|---|---|---|---|---|
| A-10-14 | 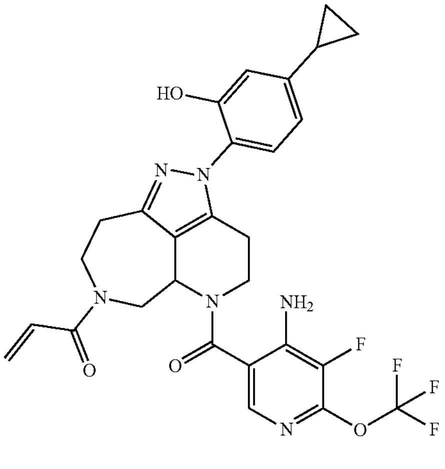 [SMILES: C=CC(=O)N1CCc2nn(-c3ccc(C4CC4)cc3O)c3c2C(C1)N(C(=O)c1cnc(OC(F)(F)F)c(F)c1N)CC3] | (R or S)-1-(5-(4-amino-5-fluoro-6-(trifluoromethoxy) nicotinoyl)-2-(4-cyclopropyl-2-hydroxyphenyl)-2,3,4,5,5a,6,8,9-octahydro-7H-1,2,5,7-tetraazabenzo[cd] azulen-7-yl)prop-2-en-1-one | 587 | $^1$H NMR (400 MHz, Chloroform-d, ppm) δ = 10.21-9.96 (m, 1H), 7.86 (s, 1H), 7.51-7.28 (m, 1H), 6.95 (d, J = 8.4 Hz, 1H), 6.80 (d, J = 1.6 Hz, 1H), 6.65 (br dd, J1 = 8.4, $J_2$ = 1.6 Hz, 1H), 6.58-6.46 (m, 1H), 5.94-5.74 (m, 1H), 5.59-5.27 (m, 3H), 4.98 (br d, J = 13.2 Hz, 1H), 4.58-4.41 (m, 1H), 4.33-4.19 (m, 1H), 3.28-3.15 (m, 2H), 3.15-3.01 (m, 3H), 2.90-2.69 (m, 2H), 1.92-1.84 (m, 1H), 1.04-0.96 (m, 2H), 0.76-0.69 (m, 2H). |
| A-10-13 | 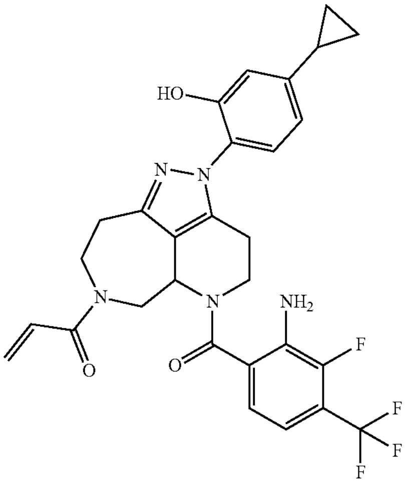 [SMILES: C=CC(=O)N1CCc2nn(-c3ccc(C4CC4)cc3O)c3c2C(C1)N(C(=O)c1ccc(C(F)(F)F)c(F)c1N)CC3] | (R or S)-1-(5-(2-amino-3-fluoro-4-(trifluoromethyl) benzoyl)-2-(4-cyclopropyl-2-hydroxyphenyl)-2,3,4,5,5a,6,8,9-octahydro-7H-1,2,5,7-tetraazabenzo[cd] azulen-7-yl)prop-2-en-1-one | 570 | $^1$H NMR (400 MHz, Chloroform-d, ppm) δ 7.47-7.32 (m, 1H), 7.10-6.89 (m, 3H), 6.79 (s, 1H), 6.66-6.60 (m, 2H), 6.56-6.40 (m, 1H), 6.10-5.70 (m, 1H), 5.43 (br s, 1H), 5.10-4.70 (m, 1H), 4.47 (br s, 1H), 4.20-3.90 (m, 1H), 3.38-2.90 (m, 5H), 2.84-2.69 (m, 2H), 1.90-1.80 (m, 1H), 1.04-0.92 (m, 2H), 0.75-0.66 (m, 2H). |

Example A-11: Preparation of (R or S)-1-(5-(4-amino-6-bromopyridazine-3-carbonyl)-2-(4-cyclopropyl-2-hydroxyphenyl)-2,3,4,5,5a,6,8,9-octahydro-7H-1,2,5,7-tetraazabenzo[cd]azulen-7-yl) prop-2-en-1-one

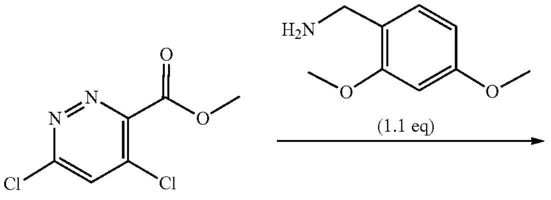

-continued

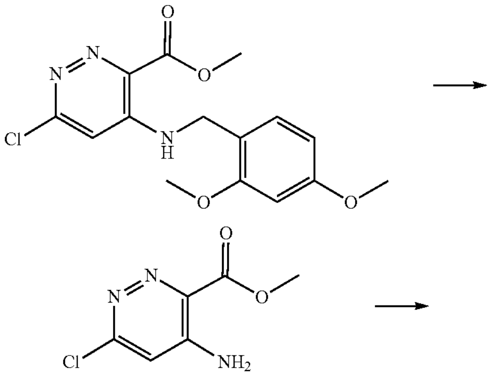

-continued

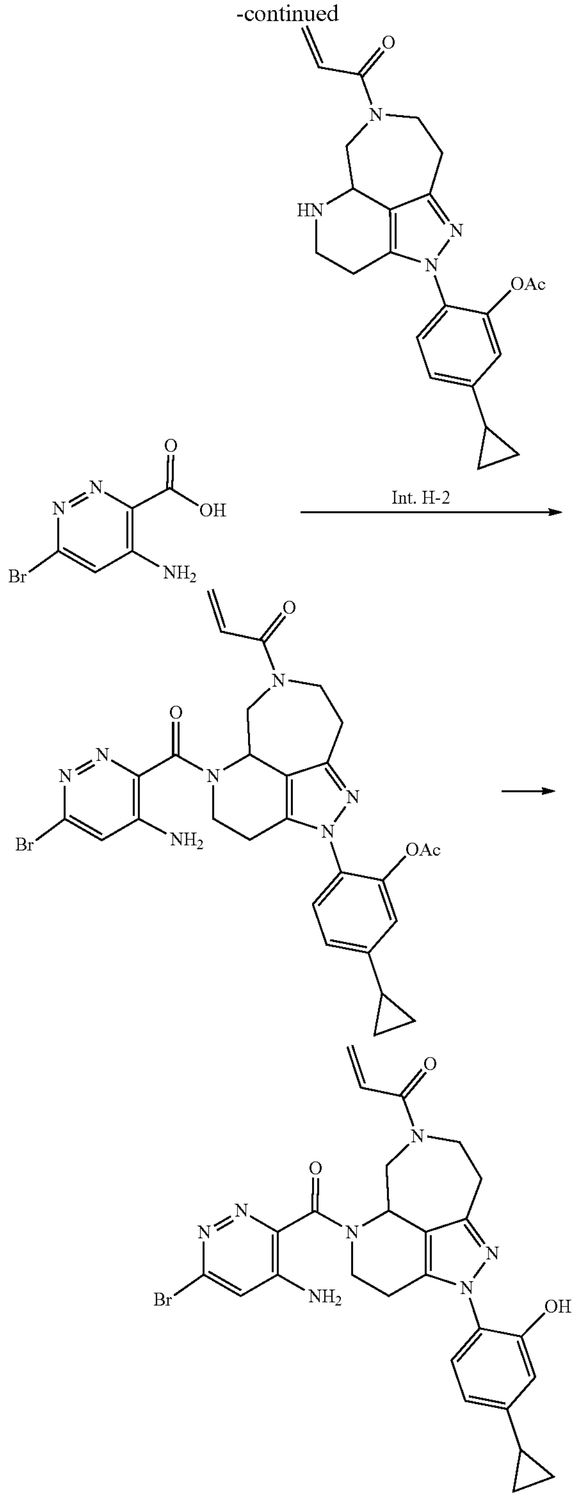

Step 1: Preparation of Methyl 6-chloro-4-((2,4-dimethoxybenzyl) amino)pyridazine-3-carboxylate To a solution of methyl 4,6-dichloropyridazine-3-carboxylate (0.0 g, 1 Equiv., 24 mmol) in MeCN (80 mL) was added N-ethyl-N-isopropylpropan-2-amine (7.8 g, 2.5 Equiv., 60 mmol). The mixture was cooled to 0° C., then (2,4-dimethoxyphenyl)methanamine (4.4 g, 1.1 Equiv., 27 mmol) was added dropwise to the above mixture at 0° C. under an atmosphere of nitrogen. The mixture was stirred at 0° C. for 1.5 hours. The mixture was then diluted with ice water (100 mL) and EA (100 mL), and the aqueous layer was extracted with EA (2×100 mL). The combined organic layers were washed with saturated brine (2×100 mL), dried over anhydrous sodium sulfate and concentrated to give a residue. The residue was purified by flash column chromatography, eluting with EA/PE (1:1) to afford methyl 6-chloro-4-((2,4-dimethoxybenzyl) amino) pyridazine-3-carboxylate (6.8 g) as a white solid. LCMS:(ESI, m/z): 338 $[M+1]^+$ Step 2: Preparation of Methyl 4-amino-6-chloropyridazine-3-carboxylate The solution methyl 6-chloro-4-((2,4-dimethoxybenzyl) amino) pyridazine-3-carboxylate (6.8 g, 1 Equiv., 19 mmol) in TFA (68 mL) was stirred at 25° C. for 12 hours. The solvent was then removed under reduced pressure, and the reaction was diluted with $H_2O$ (50 mL). The mixture was then basified to pH=8 with 1 M sodium carbonate, then diluted with EA (100 mL) and water (100 mL). The aqueous layer was extracted with EA (5×100 mL), and the combined organic layers were washed with saturated brine (2×300 mL), dried over anhydrous sodium sulfate, and concentrated to give a residue. The residue was purified by flash column chromatography, eluting with DCM/MeOH (10:1) to afford methyl 4-amino-6-chloropyridazine-1-carboxylate (3.0 g) as a white solid. LCMS:(ESI, m/z): 188 $[M+1]^+$ Step 3: Preparation of 4-amino-6-bromopyridazine-3-carboxylic Acid A solution of methyl 4-amino-6-chloropyridazine-3-carboxylate (1.5 g, 1 Equiv., 8.0 mmol) in $POBr_3$ (75 mL) was stirred at 100° C. for 12 hours. The reaction mixture was then cooled to 0° C., diluted with DCM (100 mL), and quenched with ice-water (1). The mixture was then neutralized by the addition of an aqueous sodium hydroxide solution and extracted with EA (5×500 mL). The aqueous phase was combined and concentrated to give a residue. The residue was diluted with water (20 mL). The mixture was acidified to pH=3 with 1 M Sulfuric acid, then diluted with EA (80 mL) and water (80 mL), and the aqueous layer was extracted with EA (6×80 mL). The combined organic layers were washed with saturated brine (200 mL), dried over anhydrous sodium sulfate, and concentrated to afford 4-amino-6-bromopyridazine-3-carboxylic acid (900 mg) as a crude yellow solid. The crude product was used in the next step directly without further purification. LCMS:(ESI, m/z): 218 $[M+1]^+$ Step 4: Preparation of (R or S)-2-(7-acryloyl-5-(4-amino-6-bromopyridazine-3-carbonyl)-3,4,5,5a,6,7,8,9-octahydro-2H-1, 2,5,7-tetraazabenzo[cd]azulen-2-yl)-5-cyclopropylphenyl Acetate To a solution of Int. H-2 (50 mg, 1 Equiv., 0.12 mmol) in DMA (1 mL) were added 4-amino-6-bromopyridazine-3-carboxylic acid (54 mg, 2 Equiv., 0.25 nmol), HATU (94 mg, 2 Equiv., 0.25 mmol) and DIEA (95 mg, 6 Equiv., 0.74 mmol). The mixture was stirred at rt for 12 hours, after which the mixture was diluted with water (15 mL) and EA (15 mL), and the aqueous layer was extracted with EA (2×15 mL). The organic layers were combined and washed with saturated brine (2×15 mL), dried over anhydrous sodium sulfate and concentrated to afford (R or S)-2-(7-acryloyl-5-(4-amino-6-bromopyridazine-3-carbonyl)-3,4,5,5a,6,7,8,9-octahydro-2H-1,2,5,7-tetraazabenzo[cd]azulen-2-yl)-5-cyclopropylphenyl acetate as crude yellow solid. The crude product (100 mg, crude) was used in the next step directly without further purification. LCMS:(ESI, m/z): 606 $[M+1]^+$

Step 5: Preparation of (R or S)-1-(5-(4-amino-6-bromopyridazine-3-ca bonyl)-2-(4-cyclopropyl-2-hydroxyphenyl)-2,3,4,5,5a,6,8,9-octahydro-7H-1,2,5,7-tetraazabenzo[cd]azulen-7-yl) prop-2-en-1-one To a solution of (R or S)-2-(7-acryloyl-5-(4-amino-6-bromopyridazine-3-carbonyl)-3,4,5,5a,6,7,8,9-octahydro-2H-1,2,5,7-tetraazabenzo[cd]azulen-2-yl)-5-cyclopropylphenyl acetate (100 mg, 1 Equiv., 165 μmol) in THF (2 mL) and $H_2O$ (0.5 mL) was added LiOH (11.8 mg, 3 Equiv., 495 μmol). The mixture was stirred at rt for 1 h, after which the mixture was acidified to pH=3 with 1 M Sulfuric acid, then diluted with EA (10 mL) and water (10 mL), and the aqueous layer was extracted with EA (2×10 mL). The combined organic layers were washed with saturated brine (20 mL), dried over anhydrous sodium sulfate, and concentrated to give a residue. The residue was purified by Prep-HPLC (Column: XSelect CSI Prep C18 OBD Column, 30*150 mm, 5 μm; Mobile Phase A: Water (0.1% FA), Mobile Phase B: ACN; Flow rate: 60 mL/min mL/min; Gradient: 22% B to 41% B in 9 min; Wave Length: 254 nm/220 nm nm; RT1(min): 11.03) to afford (R or S)-1-(5-(4-amino-6-bromopyridazine-3-carbonyl)-2-(4-cyclopropyl-2-hydroxyphenyl)-2,3,4,5,5a,6,8,9-octahydro-7H-1,2,5,7-tetraazabenzo [cd]azulen-7-yl) prop-2-en-1-one (7.2 mg) as a white solid. LCMS:(ESI, m/z): 564 $[M+1]^+$. $^1H$ NMR (MHz, DMSO-$d_6$) δ 9.99 (br s, 1H), 7.53-7.42 (m, 1H), 7.20-7.13 (m 1H), 7.04-6.85 (m, 3H), 6.74-6.66 (m, 1H), 6.64-6.57 (m, 1H), 6.35-6.18 (m, 1H), 5.84-5.77 (m, 1H), 5.21-5.13 (m, 1H), 4.87-4.57 (m, 1H), 4.46-4.37 (m, 1H), 3.46-3.35 (m, 1H), 3.21-3.03 (m, 1H), 2.98-2.64 (m, 3H), 2.38-2.27 (m, 1H), 1.94-1.83 (m, 1H), 1.00-0.91 (m, 2H), 0.69-0.59 (m, 2H). (some peaks obscured by solvent)

Example A-12: Preparation of (R or S)-1-(5-(4-amino-6-(1,1-difluorethyl)-5-fluoronicotinoyl)-2-(4-cyclopropyl-2-hydroxyphenyl)-2,3,4,5,5a,6,8,9-octahydro-7H-1,2,5,7-tetraazabenzo[cd]azulen-7-yl) prop-2-en-1-one

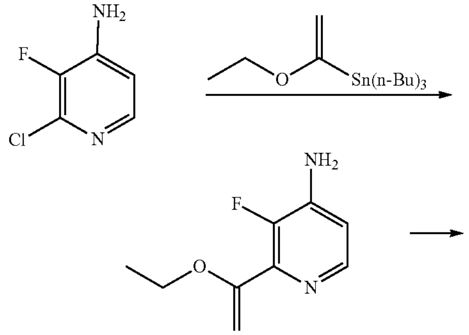

-continued

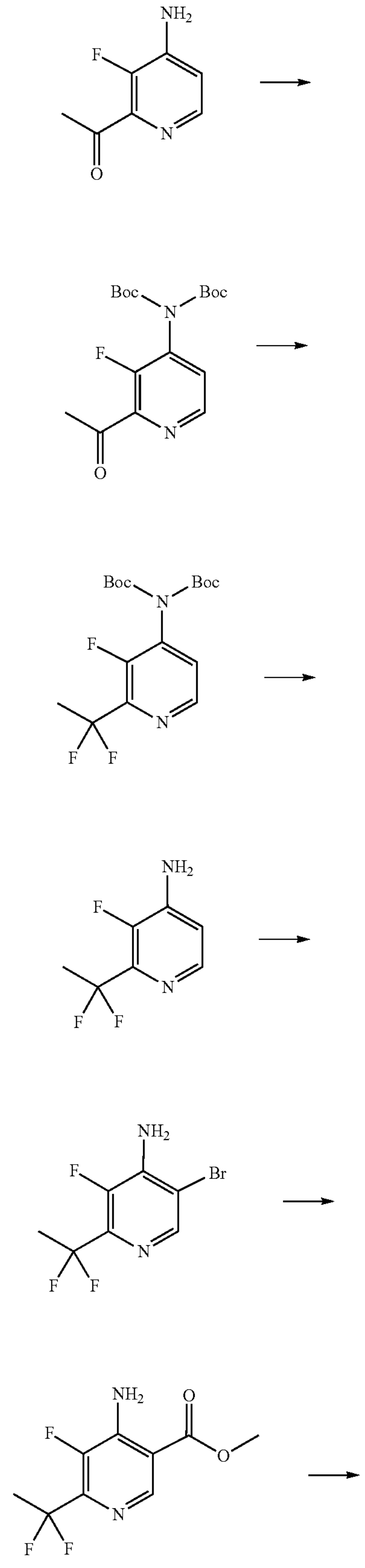

-continued

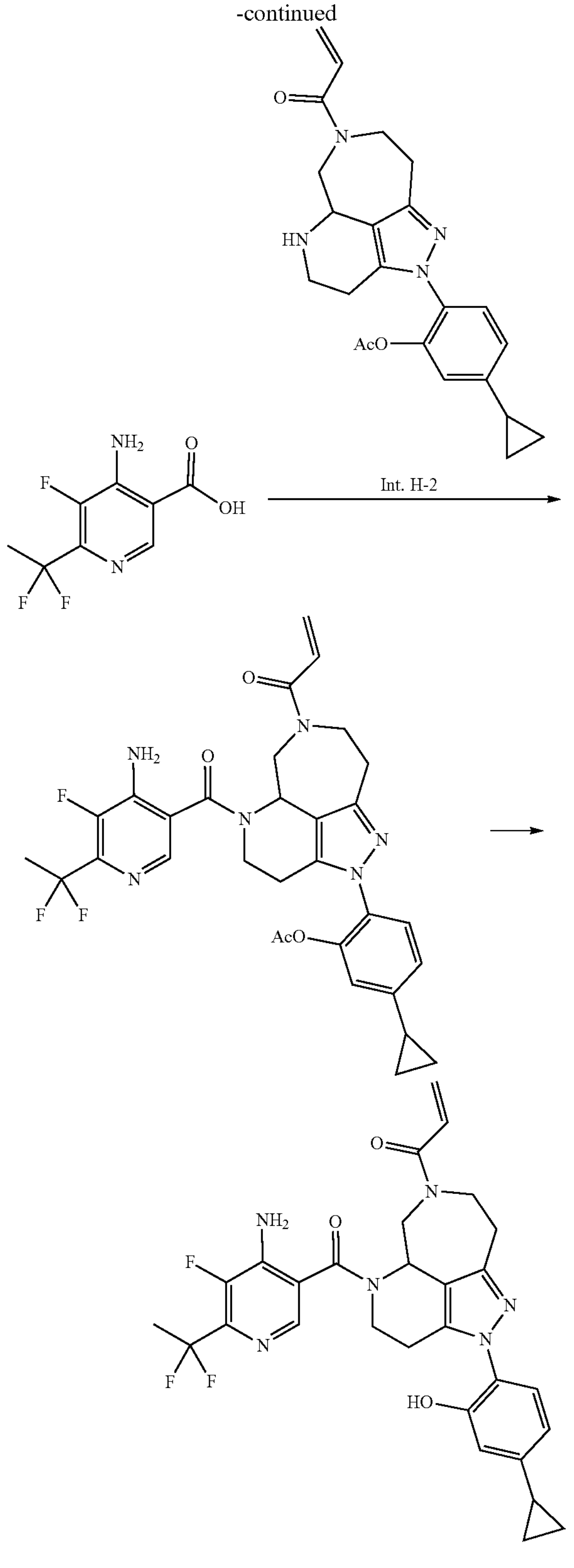

Step 1: Preparation of 2-(1-ethoxyvinyl)-3-fluoro-pyridin-4-amine

To a stirred solution of 2-chloro-3-fluoro-pyridin-4-amine (3 g 1 equiv., 20.5 mmol) in dioxane (100 mL) was added $Pd(PPh_3)_4$ (2.37 g, 0.1 equiv., 2.0 mmol) and tributyl(1-ethoxyvinyl)stannane (9.61 g, 8.99 mL, 1.3 equiv., 26.6 mmol). The mixture was purged with nitrogen (3×) and stirred at 100° C. for 12 h. After completion, the reaction was quenched by the addition of saturated aqueous potassium fluoride (150 mL) at room temperature. The resulting mixture was extracted with EA (3×50 mL). The combined organic layers were washed with brine (2×10 mL) and dried over anhydrous sodium sulfate. After filtration, the filtrate was concentrated under reduced pressure. The residue was purified by silica gel column chromatography, eluting with EA/PE (1:1) to afford 2-(1-ethoxyvinyl)-3-fluoro-pyridin-4-amine (1.7 g) as a yellow gum. LCMS: (ESI, m/z):183 $[M+H]^+$ Step 2: Preparation of 1-(4-amino-3-fluoro-2-pyridyl)ethanone To a stirred solution of 2-(1-ethoxyvinyl)-3-fluoro-pyridin-4-amine (1.7 g, 1 equiv., 9.33 mmol) in THF (4 mL) was added HCl (6 M, 2.57 equiv., 4 mL), and the reaction mixture was stirred at rt for 12 h. The pH of the mixture was adjusted to 8 by using saturated aqueous sodium bicarbonate. The resulting mixture was extracted with EA (3×20 mL). The combined organic layers were washed with brine (2×10 mL) and dried over anhydrous sodium sulfate. After filtration, the filtrate was concentrated under reduced pressure to afford 1-(4-amino-3-fluoro-2 -pyridyl)ethanone (1.4 g) as a yellow solid. LCMS: (ESI, m/z):155 $[M+H]^+$ Step 3: Preparation of Tert-Butyl N-(2-acetyl-3-fluoro-4-pyridyl)-N-tert-butoxycarbonyl-carbamate To a stirred solution of 1-(4-amino-3-fluoro-2-pyridyl) ethanone (1.4 g, 1 equiv., 9.08 mmol) in THF (12 mL) was added TEA (2.76 g, 3.79 mL, 3 equiv., 27.3 mmol) and DMAP (1.11 g, 1 equiv., 9.08 mmol). To this solution was added $Boc_2O$(5.95 g, 6.26 mL, 3 equiv., 27.3 mmol) dropwise, and the reaction mixture was stirred at 40° C. for 1 h. The reaction was then quenched by the addition of water (30 mL) at rt. The resulting mixture was extracted with EtOAc (3×20 mL), and the combined organic layers were washed with brine-(2×20 mL) and dried over anhydrous sodium sulfate. After filtration, the filtrate was concentrate under reduced pressure. The residue was purified by silica gel column chromatography, eluting with EA/PE (1:5) to afford tert-butyl N-(2-acetyl-3-fluoro-4-pyridyl)-N-tert-butoxycarbonyl-carbamate (1.1 g) as a yellow oil. LCMS: (ESI, m/z):355 $[M+H]^+$ Step 4: Preparation of Tert-Butyl N-tert-butoxycarbonyl-N-[2-(1,1-difluoroethyl)-3-fluoro-4-pyridyl] carbamate To a stirred solution of tert-butyl N-(2-acetyl-3-fluoro-4-pyridyl)-N-tert-butoxycarbonyl-carbamate (1.1 g, 1 equiv., 3.10 mmol) in DCM (20 mL) was added DAST (5.00 g, 4.10 mL, 10 equiv., 31.0 mmol) at 0° C. under an atmosphere of nitrogen, and the reaction solution was stirred at rt for 48 h. The mixture was then quenched by the addition of saturated aqueous sodium bicarbonate (30 mL) at room temperature. The resulting mixture was extracted with DCM (3×20 mL). The combined organic layers were washed with brine (2×10 mL) and dried over anhydrous sodium sulfate. After filtration, the filtrate was concentrated under reduced pressure. The residue was purified by silica gel column chromatography, eluting with EA/PE (1:3) to afford tert-butyl N-tertbutoxycarbonyl-N-[2-(1,1-difluoroethyl)-3-fluoro-4-pyridyl]carbamate (1 g) as a yellow oil. LCMS: (ESI, m/z):377 $[M+H]^+$ Step 5. Synthesis of 2-(1,1-difluoroethyl)-3-fluoro-pyridin-4-amine To a stirred solution of tert-butyl N-tert-butoxycarbonyl-N-[2-(1,1-difluoroethyl)-3-fluoro-4-pyridyl]carbamate (1 g, 1 equiv., 2.66 mmol) in DCM (5 mL) was added TFA (1.54 g, 5.07 equiv., 1 mL, 13.46 mmol), and the reaction solution was stirred at rt for 1 h. The reaction solution was quenched by the addition of saturated aqueous sodium bicarbonate (15 mL) at rt. The resulting mixture was extracted with DCM (3×10 mL), and the combined organic layers were washed with brine (2×10 mL) and dried over anhydrous sodium sulfate. After filtration, the filtrate was concentrated under reduced pressure to afford 2-(1,1-difluoroethyl) 3-fluoro-pyridin-4-amine (460 mg) as a yellow solid. LCMS: (ESI, m/z):177 $[M+H]^+$ Step 6. Synthesis of 5-bromo-2-(1,1-difluoroethyl)-3-fluoropyridin-4-amine To a stirred solution of 2-(1,1-difluoroethyl)-3-fluoro-pyridin-4-amine (460 mg, 1 equiv., 2.61 mmol) in DCM (6 mL) was added NBS (464.82 mg, 1 equiv., 2.61 mmol), and the reaction solution was stirred at 25° C. for 0.5 h. The reaction solution was purified by silica gel column chromatography, eluting with EtOAc/PE (1:4) to afford 5-bromo-2-(1,1-difluoroethyl)-3-fluoropyridin-4-amine (540 mg) as a white solid. LCMS: (ESI, m/z):255 $[M+H]^+$ Step 7. Synthesis of Methyl 4-amino-6-(1,1-difluoroethyl)-5-fluoro-pyridine-3-carboxylate To a stirred solution of 5-bromo-2-(1,1-difluoroethyl)-3-fluoropyridin-4-amine (540 mg, 1 equiv., 2.12 mmol) in MeOH (10 mL) was added TEA (643 mg, 884 L, 3 equiv., 6.35 mmol) and $Pd(dppf)Cl_2 \cdot CH_2Cl_2$ (173 mg, 0.1 equiv., 211 μmol). The mixture was purged with nitrogen 3× and then pressurized to 50 psi with carbon monoxide and was further stirred at 80° C. for 12 h. The reaction solution was filtered by filter paper, and the filtrate was concentrated under reduced pressure. The residue was purified by silica gel column chromatography, eluting with EA/PE (1:4) to afford methyl 4-amino-6-(1,1-difluoroethyl)-5-fluoro-pyridine-3-carboxylate (0.3 g) as a white solid. LCMS: (ESI, m/z):235 $[M+H]^+$ Step 8. Synthesis of 4-amino-6-(1,1-difluoroethyl)-5-fluoropyridine-3-carboxylic acid To a stirred solution of methyl 4-amino-6-(1,1-difluoroethyl)-5-fluoro-pyridine-3-carboxylate (0.3 g, 1 equiv., 1.28 mmol) in $H_2O$ (1 mL) and THF (3 mL) was added LiOH. 20 (64.5 mg, 1.2 equiv., 1.54 mmol), and the reaction solution was stirred at rt for 0.5 h. The p of reaction solution was adjusted to 7 by using hydrochloric acid (1 M) and concentrated under reduced pressure. The residue was purified by reversed phase chromatography: (CD01-Phenomenex luna C18150*25*10 um; flow rate: 50 mL/min; gradient: 34%-64% B over 10 min; mobile phase A: 0.05% aqueous $NH_4HCO_3$, mobile phase B: acetonitrile) to give 4-amino-6-(1,1-difluoroethyl)-5-fluoropyridine-3-carboxylic acid (270 mg) as a white solid. LCMS: (ESI, m/z):221 $[M+H]^+$ Step 9. Synthesis of (S or R)-2-(7-acryloyl-5-(4-amino-6-(1,1-difluoroethyl)-5-fluoronicotinoyl)-3,4,5,5a,6,7,8,9-octahydro-2H-1,2,5,7-tetraazabenzo[cd]azulen-2-yl)-5-cyclopropylphenyl Acetate To a stirred solution of 4-amino-6-(1,1-difluoroethyl)-5-fluoropyridine-3-carboxylic acid (130 mg, 1.2 equiv., 590 gmol) in DMF (3 mL) was added HATU (225 mg, 1.2 equiv., 590 μmol), DIEA (191 mg, 257 μL, 3 equiv., 1.48 mmol) and (Int. H-2) (0.2 g, equiv., 492 μmol). The mixture was stirred at rt for 1 h. The reaction solution was filtered, and t ie filtrate was purified by reversed phase flash chromatography: (Phenomenex Synergi C18 (150×25 mm, 10 um); flow rate: 50 mL/min; gradient: 30%-70% B over 15 min; mobile phase A: 0.1% FA in water, mobile phase B: acetonitrile) to give (S or R)-2-(7-acryloyl-5-(4-amino-6-(1,1-difluoroethyl)-5-fluoronicotinoyl)-3,4,5,5a,6,7,8,9-octahydro-2H-1,2,5,7-tetraazabenzo[d]azulen-2-yl)-5-cyclopropylphenyl acetate (82 mg) as a white solid. LCMS: (ESI, m/z): 09 $[M+H]^+$ Step 10. Synthesis of (R or S)-1-(5-(4-amino-6-(1,1-difluoroethyl)-5-fluoronicotinoyl)-2-(4-cyclopropyl-2-hydroxyphenyl)-2,3,4,5,5a,6,8,9-octahydro-7H-1,2,5,7-tetraazabenzo[cd]azulen-7-yl)prop-2-en-1-one To a stirred solution of (S or R)-2-(7-acryloyl-5-(4-amino-6-(1,1-difluoroethyl)-5-fluoronicotinoyl)-3,4,5,5a,6,7,8,9-octahydro-2H-1,2,5,7-tetraazabenzo[cd]azulen-2-yl)-5-cyclopropylphenyl acetate (82 mg, 1 equiv., 135 μmol) in MeOH (3 mL was added $K_2CO_3$ (37.2 mg, 2 equiv., 269 μmol), and the reaction solution was stirred at rt for 0.5 h. The reaction solution was filtered and the crude product was then purified by preparative HP C: (CD01-Phenomenex luna C18 150*25*10 um; flow rate: 15 mL/min; gradient: 34%-64% B over 10 min; mobile phase A: 0.05% aqueous FA, mobile phase B: acetonitrile) to give (R or S)-1-(5-(4-amino-6-(1,1-difluoroethyl)-5-fluoronicotinoyl)-2-(4-cyclopropyl-2-hydroxyphenyl)-2,3,4,5,5a,6,8,9-octahydro-7H-1,2,5,7-tetraazabenzo[cd]azulen-7-yl)prop-2-en-1-one (17.8 mg) as a white solid. LCMS: (ESI, m/z):567 $[M+H]^+$. $^1H$ NMR: (400 MHz, DMSO-$d_6$, ppm) δ=10.08-9.79 (m, 1H), 8.05-7.87 (m, 1H), 7.68-7.43 (m, 1H), 7.14 (d, J=8.4 Hz, 1H), 6.71-6.63 (m, 3H), 6.62-6.58 (m, 1H), 6.38-6.21 (m, 1H), 5.87-5.68 (m, 1H), 5.24-5.05 (m, 1H), 4.67 (br s, 1H), 4.57-4.40 (m, 1H), 3.78-3.59 (m, 1H), 3.40-3.34 (m, 1H), 3.19-3.03 (m, 1H), 2.96-2.74 (m, 4H), 2.44-2.35 (m, 1H), 2.00 (t, J=19.2 Hz, 3H), 1.92-1.84 (m, 1H), 1.01-0.89 (m, 2H), 0.70-0.57 (m, 2H)

Example A-13: Preparation of (R or S)-1-(5-(4-amino-5-fluoro-6-(trifluoromethyl)nicotinoyl)-2-(4-cyclopropyl-2-hydroxyphenyl)-2,3,4,5,5a,6,8,9-octahydro-7H-1,2,5,7-tetraazabenzo[cd]azulen-7-yl)prop-2-en-1-one

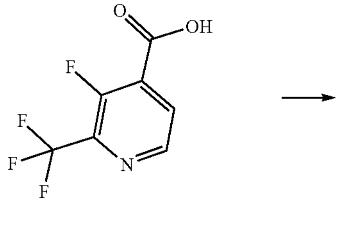

-continued

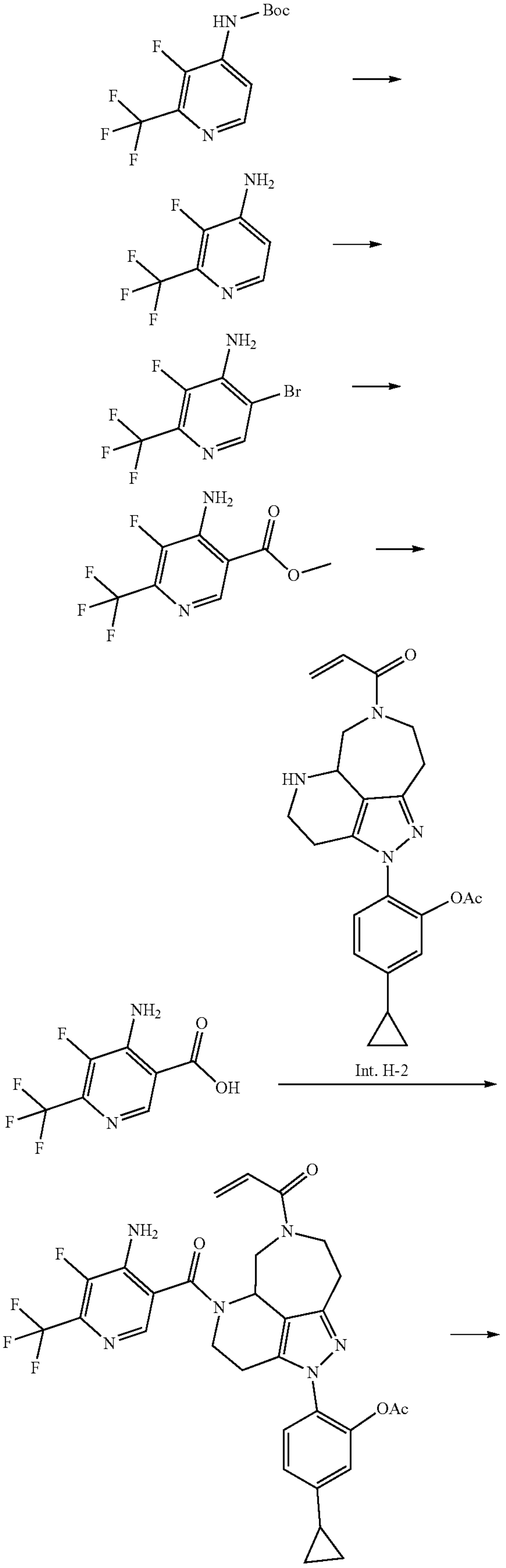

-continued

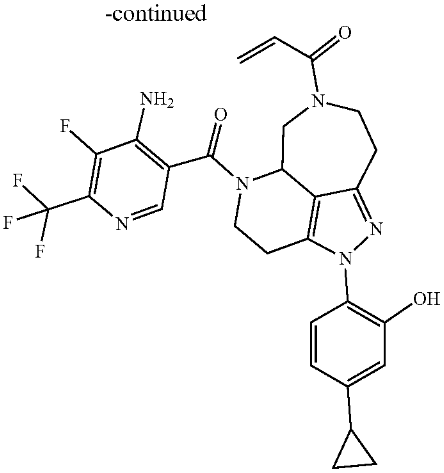

Step 1. Synthesis of Tert-Butyl (3-fluoro-2-(trifluoromethyl)pyridin-4-yl)carbamate To a solution of 3-fluoro-2-(trifluoromethyl)isonicotinic acid (4.50 g, 1 Equiv., 21.5 mmol) in toluene (90 mL) and tert-butanol (9 mL) were added TEA (4.36 g, 6.0 mL, 2 Equiv., 43.0 mmol) and diphenylphosphoryl azide (5.92 g, 4.64 mL, 1 Equiv., 21.5 mmol). The mixture was stirred at 110° C. for 12 hours. The mixture was then cooled to rt an diluted with water (100 mL) and EA (100 mL), and the aqueous layer was extracted with EA (×100 mL). The organic layers were combined and washed with saturated brine (3×100 mL), dried over anhydrous sodium sulfate and concentrated to give a residue. The residue was purified by flash column chromatography (18% EA in PE) to afford tert-butyl (3-fluoro-2-(trifluoromethyl)pyridin-4-yl)carbamate (4.7 g) as a colorless oil. LCMS: (ESI, m/z):281 $[M+H]^+$.

Step 2. Synthesis of 3-fluoro-2-(trifluoromethyl)pyridin-4-amine

A solution of tert-butyl (3-fluoro-2-(trifluoromethyl)pyridin-4 yl)carbamate (4.70 g, 1 Equiv., 16.8 mmol) in TFA (47 mL) and DCM (47 mL) was stirred at rt for 12 h. The solvent was then removed under reduced pressure. This resulted in 3-fluoro-2-(trifluoromethyl)pyridin-4-amine (4.5 g) as a crude yellow oil. The crude product was used in the next step directly without further purification. LCMS: (ESI, m/z):181 $[M+H]^+$ Step 3. Synthesis of 5-bromo-3-fluoro-2-(trifluoromethyl)pyridin-4-amine A solution of 3-fluoro-2-(trifluoromethyl)pyridin-4-amine (4.00 g, 1 Equiv., 22.2 mmol) in DMF (80 mL) was cooled to 0° C., and $Br_2$ (7.10 g, 2.29 mL, 2 Equiv., 44.4 mmol) was added dropwise under an atmosphere of nitrogen. The mixture was then warmed to rt and stirred for 2 h. The mixture was diluted with saturated sodium thiosulfate aqueous solution (100 mL) and EA (100 mL), and the aqueous layer was extracted with EA (2×100 mL). The combined organic layers were washed with saturated brine (2×50 mL), dried over anhydrous sodium sulfate and concentrated to give a residue. The residue was purified by flash column chromatography, eluting with EA/PE (1:5) to afford 5-bromo-3-fluoro-2-(trifluoromethyl)pyri in-4-amine (2.7 g) as a yellow oil. LCMS: (ESI, m/z):259 [M+H]+

Step 4. Synthesis of Methyl 4-Amino-5-fluoro-6-(trifluoromethyl)nicotinate

To a solution of 5-bromo-3-fluoro-2-(trifluoromethyl) pyridin-4 amine (1.00 g, 1 Equiv., 3.86 mmol) in MeOH (10 mL) were added $PdCl_2$(dppf) (315 mg, 0.1 Equiv., 0.386 mmol) and TEA (1.37 g, 1.88 mL, 3.5 Equiv., 13.5 mmol). The mixture was purged with nitrogen (×3) and then was pressurized 4 MPa with carbon monoxide at 80° C. for 12 hours. The reaction mixture was cooled to rt, filtered, and rinsed with EA (3×20 mL), then diluted with water (50 mL). The aqueous layer was extracted with EA (2×30 mL). The organic layers were combined and washed with saturated brine (3×30 mL), dried over anhydrous sodium sulfate and concentrated to give a residue. The crude product was purified by silica gel chromatography eluting with PE:EA (5:1) to give methyl 4-amino-5-fluoro-6-(trifluoromethyl) nicotinate (820 mg) as a yellow solid. LCMS: (ESI, m/z): 239 [M+H]+

Step 5. Synthesis of 4-amino-5-fluoro-6-(trifluoromethyl)nicotinic Acid

To a solution of methyl 4-amino-5-fluoro-6-(trifluoromethyl)nicotinate (750 mg, 1 Equiv., 3.15 mmol) in THF (3.75 mL) and $H_2O$ (3.75 mL) was added LiOH (151.2 mg, 2 Equiv., 6.3 mmol). The mixture was stirred at rt for 2 h. The mixture was then acidified to pH=3 with 1 M sulphuric acid, then diluted with EA (50 mL) and water (50 mL). The aqueous layer was extracted with EA (2×50 mL), and the combined organic layers were washed with saturated brine (50 mL), dried over anhydrous sodium sulfate, and concentrated to give a residue. The residue was purified by reverse phase chromatography (column: C18 column; Gradient: 45% MeCN in water with 0.2% formic acid) to afford 4-amino-5-fluoro-6-(trifluoromethyl)nicotinic acid (600 mg) as a white solid. LCMS: (ESI, m/z): 225 [M+H]+

Step 6. Synthesis of (R or S)-2-(7-acryloyl-5-(4-amino-5-fluoro-6-(trifluoromethyl)nicotinoyl)-3,4,5,5a,6,7,8,9-octahydro-2H-1,2,5,7-tetraazabenzo[cd]azulen-2-yl)-5-cyclopropylphenyl Acetate To a solution of Int. H-2 (200 mg, 1 Equiv., 492 umol) in DMF (10 mL) were added DIEA (637 mg, 857 μL, 10 Equiv., 4.93 mmol), HOBT (133 mg, 2 Equiv., 984 mol) EDC·HCl (189 mg, 2 Equiv., 984 μmol) and 4-amino-5-fluoro-6-(trifluoromethyl)nicotinic acid (110 mg, 1 Equiv., 492 μmol). The mixture was stirred at rt for 16 hours. The reaction was then quenched with water (50 mL), and the resulting mixture was extracted with EA (3×50 mL). The combined organic layers were washed with water(2×200 mL) and brine (2×200 mL), and dried over anhydrous sodium sulfate. After filtration, the filtrate was concentrated under reduced pressure. The crude product was purified by silica gel chromatography eluted with PE:EA=100% EA to give (R or S)-2-(7-acryloyl-5-(4-amino-5-fluoro-6-(trifluoromethyl)nicotinoyl)-3,4,5,5a,6,7,8,9-octahydro-2H-1,2,5,7-tetraazabenzo[cd]azulen-2-yl)-5-cyclopropylphenyl acetate (70 mg) as alight yellow solid. LCMS: (ESI, m/z): 613 [M+H]+

Step 7. Synthesis of (R or S)-1-(5-(4-amino-5-fluoro-6-(trifluoroethyl)nicotinoyl)-2-(4-cyclopropyl-2-hydroxyphenyl)-2,3,4,5,5a,6,8,9-octahydro-7H-1,2,5,7-tetraazabenzo[cd]azulen-7-yl)prop-2-en-1-one To a solution of (R or S)-2-(7-acryloyl-5-(4-amino-5-fluoro-6-(trifluoromethyl)nicotinoyl)-3,4,5,5a,6,7,8,9-octahydro-2H-1,2,5,7-tetraazabenzo[cd]azulen-2-yl)-5-cyclopropylphenyl acetate (70 mg, 1 Equiv., 0.11 mmol) in THF (1.4 mL) was added LiOH (8.2 mg, 3 Equiv., 0.34 mmol) in water (0.35 mL). The mixture was stirred at rt for 0.5 hour, after which the reaction was quenched with water (10 mL). The resulting mixture was extracted with EA (3×10 mL). The combined organic layers were washed with brine (2×20 mL), dried over anhydrous sodium sulfate, and filtered. After filtration, the filtrate was concentrated under reduced pressure. The crude product was purified by Prep-HPLC (Column: XSelect CSH Prep C18 OBD Column, 30*150 mm, 5 μm; Mobile Phase A: Water(0.1% FA), Mobile Phase B: ACN; Flow rate: 60 mL/min mL/min; Gradient: 35% B to 55% B in 9 min; Wave Length: 254 nm/220 nm nm; RT1(min): 7.88) to afford (R or S)-1-(5-(4-amino-5-fluoro-6-(trifluoromethyl)nicotinoyl)-2-(4-cyclopropyl-2-hydroxyphenyl)-2,3,4,5,5a,6,8,9-octahydro-7H-1,2,5,7-tetraazabenzo[cd]azulen-7-yl)prop-2-en-1-one (31 mg) as a white solid. LCMS: (ESI, m/z): 571 [M+H]+. $^1$H NMR (400 MHz, DMSO-$d_6$) δ 9.94 (br s, 1H), 8.09-7.93 (m, 1H), 7.60-7.41 (m, 1H), 7.14 (d, J=8.2 Hz, 1H), 6.93 (s, 2H), 6.72-6.67 (m, 1H), 6.64-6.57 (m, 1H), 6.30 (d, J=16.5 Hz, 1H), 5.85-5.66 (m, 1H), 5.24-5.06 (m, 1H), 4.74-4.53 (m, 1H), 4.52-4.13 (m, 1H), 3.77-3.59 (m, 1H), 3.40-3.34 (m, 1H), 3.23-3.01 (m, 1H), 2.98-2.68 (m, 4H), 2.44-2.31 in, 1H), 1.97-1.82 (m, 1H), 1.01-0.90 (m, 2H), 0.67-0.57 (m, 2H).

Example A-14: Preparation of (R or S)-1-(5-(4-amino-6-(1,1-difluoroethyl)nicotinoyl)-2-(4-cyclopropylphenyl)-2,3,4,5,5a,6,8,9-octahydro-7H-1,2,5,7-tetraazabenzo[cd]azulen-7-yl)prop-2-en-1-one

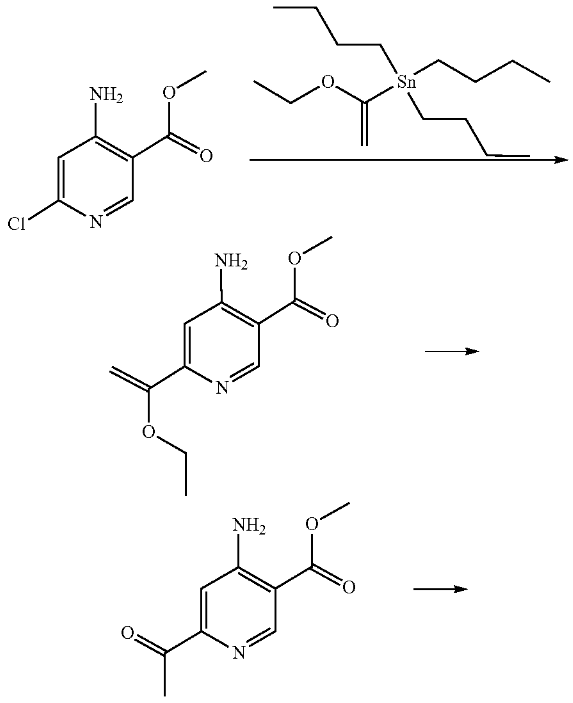

-continued

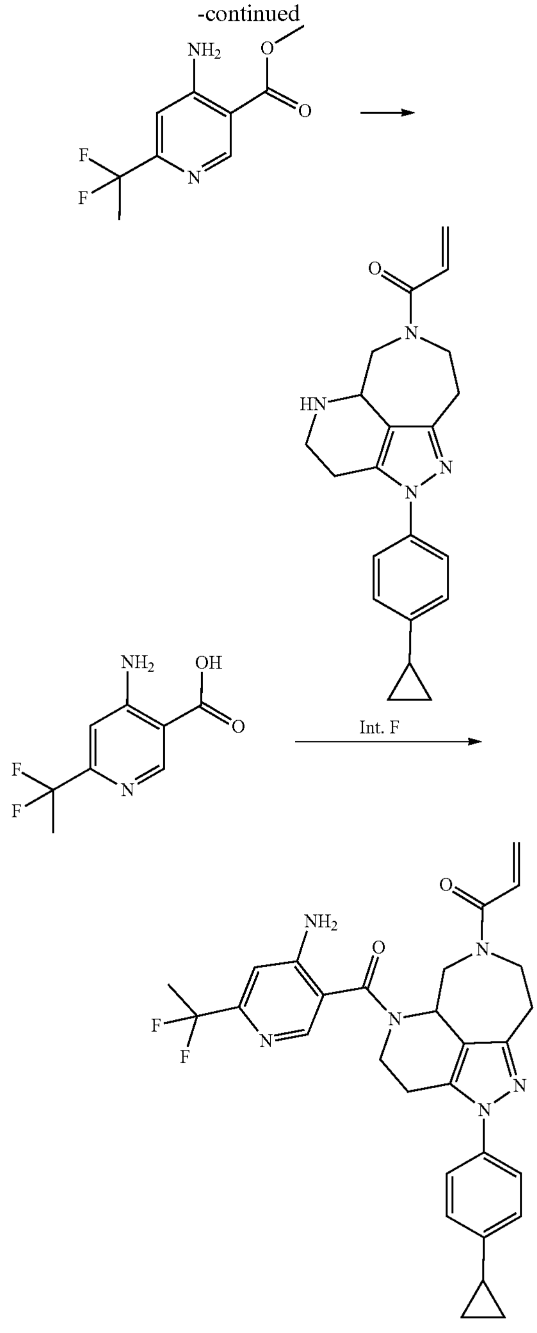

Step 1. Synthesis of Methyl 4-amino-6-(I-ethoxyvinyl)nicotinate

To a solution of methyl 4-amino-6-chloronicotinate (5 g, 1 Equiv., 0.03 mol) in 1,4-dioxane (50 mL) were added $Pd(PPh_3)_2Cl_2$ (6 g, 0.3 Equiv., 8 mmol) and tributyl(1-ethoxyvinyl)stannane (0.02 kg, 2 Equiv., 0.05 mol). The reaction mixture was then purged with nitrogen three times. The resulting mixture was stirred for 16 hours at 100° C. under a nitrogen atmosphere. The mixture was then diluted with a saturated solution of in water (100 mL) and EA (200 mL), and the aqueous layer was extracted with EA (2×200 mL). The combined organic layers were washed with saturated brine (2×200 mL), dried over anhydrous sodium sulfate and concentrated to afford methyl 4-amino-6-(1-ethoxyvinyl)nicotinate (4 g) s a crude yellow oil. The crude product was used in the next step directly without further purification. LCMS: (ESI, m/z): 223 $[M+H]^+$ Step 2. Synthesis of Methyl 6-acetyl-4-aminonicotinate A solution of methyl 4-amino-6-(1-ethoxyvinyl)nicotinate (4 g, 1 Equiv., 0.02 mol) in aqueous HCl (2 mol/L, 20 mL) and THF (40 mL) was stirred at 80° C. for 1 hour. The mixture was then adjusted to pH=7 with the addition of 1 M $Na_2CO_3$, then diluted with DCM (60 mL) and water (80 mL). The aqueous layer was extracted with DCM (2×100 mL), and the organic layers were combined and washed with saturated brine (20 mL), dried over anhydrous sodium sulfate and concentrated to give a residue. The residue was purified by flash column chromatography, eluting with EA/PE (30%) to afford methyl 6-acetyl-4-aminonicotinate (3 g) as a yellow solid. LCMS: (ESI, m/z): 195 $[M+H]^+$ Step 3. Synthesis of Methyl 4-amino-6-(1,1-difluoroethyl)nicotinate A solution of methyl 6-acetyl-4-aminonicotinate (500 mg, 1 Equiv., 2.57 mmol) was cooled to 0° C., and DAST (5 mL) was added dropwise to the above mixture. The mixture was then warmed to 80° C. and stirred for 1 h, after which the mixture was coo ed to rt and diluted with $NH_4HCO_3$ (20 mL) and EA (20 mL), and the aqueous layer was extracted with EA (2×20 mL). The combined organic layers were washed with saturated brine (2×20 mL), dried over anhydrous sodium sulfate and concentrated to give a residue. The residue was purified by flash column chromatography, eluting with EA/PE (1:3) to afford ethyl 4-amino-6-(1,1-difluoroethyl)nicotinate (150 mg) as a yellow solid. LCMS: (ESI, m/z): 217 $[M+H]^+$ Step 4. Synthesis of 4-amino-6-(1,1-difluoroethyl)nicotinic Acid To a solution of methyl 4-amino-6-(1,1-difluoroethyl) nicotinate (140 mg, 1 Equiv., 648 μmol) in THF (1 mL) and $H_2O$ (0.3 mL) was added LiOH (15.5 mg, 1 Equiv., 648 μmol). The mixture was stirred at rt for 5 hours, after which the mixture was acidified to pH=3 with the addition of 1 M Sulfuric acid, then diluted with EA (10 mL) and water (1 mL). The aqueous layer was extracted with EA (2×10 mL), and the organic layers were combined and washed with saturated brine (10 mL), dried over anhydrous sodium sulfate and the mixture was concentrated under reduced pressure. The crude product was purified by reversed-phase flash chromatography (column, C18; mobile phase, water (0.1% FA) in MeCN, 0% to 100% gradient in 30 min; detector, UV 254 nm) to afford 4-amino-6-(1,1-difluoroethyl)nicotinic acid (40 mg) as a white solid. LCMS: (ESI, m/z): 203 $[M+H]^+$ Step 5. Synthesis of (R or S)-1-(5-(4-amino-6-(1,1-difluoroethyl)nicotinoyl)-2-(4-cyclopropylphenyl)-2,3,4,5,5a,6,8,9-octahydro-7H-1,2,5,7-tetraazabenzo[cd]azulen-7-yl)prop-2-en-1-one To a solution of 4-amino-6-(1,1-difluoroethyl)nicotinic acid (50 mg, 1 Equiv., 0.25 mmol) and Int. F (86 mg, 1 equiv., 0.25 mmol) in DMF (1 mL) were added DIEA (0.16 g, 0.22 mL, 5 Equiv., 1.2 mmol) and HATU (0.19 g, 2 Equiv., 0.49 mmol). The mixture was stirred at rt for 5 h. The mixture was then diluted with water (20 mL) and EA (20 mL), and the aqueous layer was extracted with EA (2×20 mL). The organic layers were combined and washed with saturated brine (2×20 mL), dried over anhydrous sodium sulfate and concentrated to give a residue. The residue was purified by Prep-HPLC (Column: XBridge BEH C18 OBD Prep Column 130, 5 m, 30 mm*150 mm; Mobile Phase A: Water (17 mmol/L $NH_4HCO_3$), Mobile Phase B: ACN; Flow rate: 60 mL/min; Gradient: 39% B to 49% B in 7 min; Wave Length: UV 254 nm/220 nm) to afford (R or S)-1-(5-(4-amino-6-(1,1-difluoroethyl)nicotinoyl)-2-(4-cyclopropylphenyl)-2,3,4,5,5a,6,8,9-octahydro-7H-1,2,5,7-tetraazabenzo[cd]azulen-7-yl)prop-2-en-1-one (14.7 mg) as a white solid. LCMS: (ESI, m/z): 533 $[M+H]^+$. $^1H$ NMR: (400 MHz, DMSO-$d_6$, ppm) δ 8.19-8.10 (m, 1H), 7.61-7.44 (m, 1H), 7.39 (d, J=8.2 Hz, 2H), 7.22-7.14 (m, 3H), 6.9 (s, 1H), 6.62-6.13 (m, 3H), 5.91-5.68 (m, 1H), 5.24-5.05 (m, 1H), 4.76-4.59 (m, 1H), 4.54-4.14 (m, 1H), 3.79-3.57 (m, 1H), 3.23-3.05 (m, 2H), 3.01-2.74 (m, 3H), 2.74-2.58 (m, 1H), 2.02-1.86 (m, 4H), 1.01-0.92 (m, 2H), 0.75-0.63 (m, 2H).

Example A-15: Preparation of (S or R)-1-(2-(4-cyclopropylphenyl)-5-(2,4-diamino-5-fluoro-6-(trifluoromethyl)nicotinoyl)-2,3,4,5,5a,6,8,9-octahydro-7H-1,2,5,7-tetraazabenzo[cd]azulen-7-yl)prop-2-en-1-one

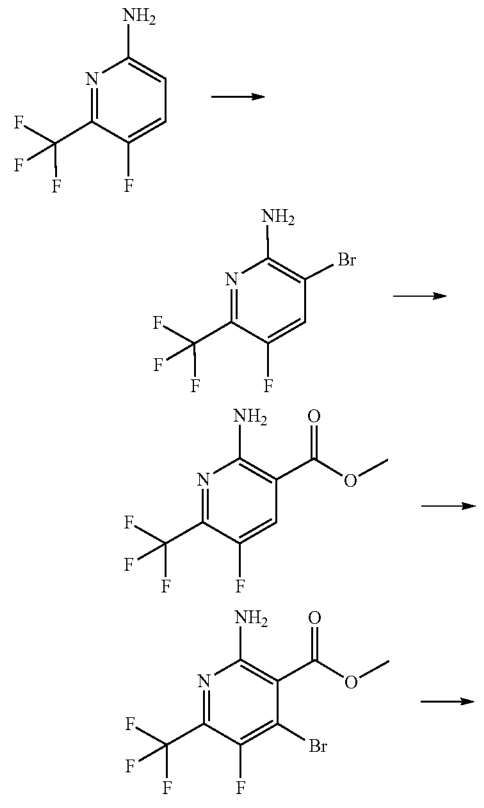

-continued

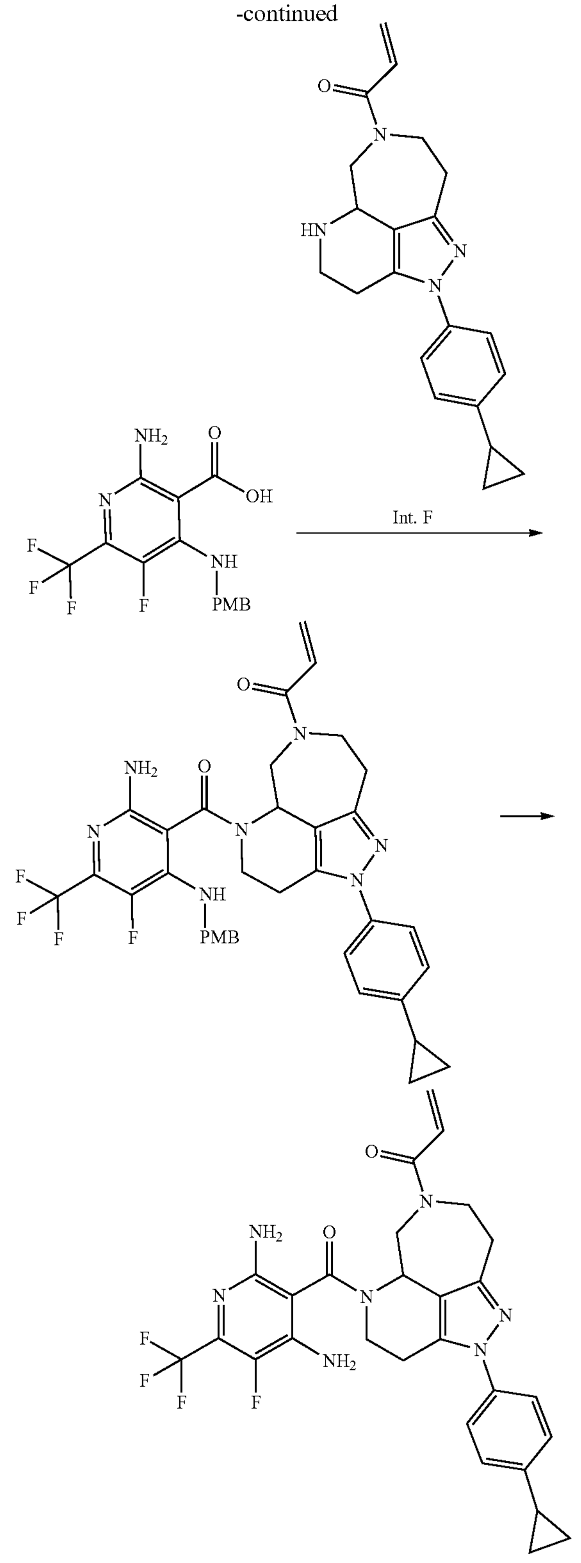

Step 1. Synthesis of 3-bromo-5-fluoro-6-(trifluoromethyl)pyridin-2-amine

To a solution of 5-fluoro-6-(trifluoromethyl)pyridin-2-amine (1.6 g, 1 Equiv., 8.9 mmol) in DMF (15 mL) was added NBS (1.7 g, 1.1 Equiv., 9.8 mmol). The resulting mixture was stirred for 2 h at rt under an atmosphere of nitrogen. The mixture was then filtered and rinsed with EA (3×20 mL), and the filtrate was diluted with water (20 mL). The aqueous layer was then extracted with EA (2×20 mL). The organic layers were combined and washed with saturated brine (3×20 mL), dried over anhydrous sodium sulfate and concentrated to give a residue. The crude product was purified by silica gel chromatography, eluting with PE:EA=2:1 to give 3-bromo-5-fluoro-6-(trifluoromethyl) pyridin-2-amine (2.1 g) as a yellow solid. LCMS: (ESI, m/z): 259 $[M+H]^+$ Step 2. Synthesis of Methyl 2-amino-5-fluoro-6-(trifluoromethyl)nicotinate To a solution of 3-bromo-5-fluoro-6-(trifluoromethyl) pyridin-2-amine (0.1 g, 1 Equiv., 0.4 mmol) in MeOH (2 mL) were added $PdCl_2$(dppf)-$CH_2Cl_2$ adduct (0.03 g, 0.1 Equiv., 0.04 mmol) and TEA (0.06 g, 1.5 Equiv., 0.6 mmol). The reaction system was then purged with CO gas (×3). The resulting mixture was stirred for 16 h at 100° C. under an atmosphere of CO (1 MPa). The reaction mixture was then cooled to rt, and the mixture was filtered and rinsed with EA (3×20 mL). The filtrate was then diluted with water (20 mL), and the aqueous layer was extracted with EA (2×20 mL). The organic layers were combined and washed with saturated brine (3×20 mL), dried over anhydrous sodium sulfate and concentrated to give a residue. The crude product was purified by silica gel chromatography, eluting with PE:EA=4:1 to give methyl 2-amino-5-fluoro-6-(trifluoromethyl)nicotinate (87 mg) as a yellow solid. LCMS: (ESI, m/z): 239 $[M+H]^+$ Step 3. Synthesis of Methyl 2-amino-4-bromo-5-fluoro-6-(trifluoromethyl)nicotinate To a solution of diisopropylamine (1.55 g, 2.2 Equiv., 15.3 mmol) in THF (30 mL) was added n-butyllithium (893 mg, 2 Equiv., 13.9 mmol) at −78° C. under a atmosphere of nitrogen. The mixture was stirred for 10 min, after which methyl 2-amino-5-fluoro-6-(trifluoromethyl)nicotinate (1.66 g, 1 Equiv., 6.97 mmol) in THF(10 mL) was added dropwise to the above mixture at −78° C. under a nitrogen atmosphere. The resulting solution was stirred for 30 min, after which 1,2-dibromo-1,1,2,2-tetrachloroethane (4.54 g, 2 Equiv., 13.9 mmol) in THF (10 mL) was added dropwise at −78° C. (under a nitrogen atmosphere) and the resulting solution was further stirred for 3 h. The mixture was then warmed to rt and quenched with the addition of 1N HCl (20 mL). The aqueous layer was extracted with DCM/MeOH:1 (3×20 mL), and the combined organic layers were washed with saturated brine (2×20 mL), dried over anhydrous sodium sulfate and concentrated to give a residue. The residue was purified by flash column chromatography, eluting with EA/PE (1:5) to afford methyl 2-amino-4-bromo-5-fluoro-6-(trifluoromethyl)nicotinate (766 mg) as a yellow solid. LCMS: (ESI, m/z): 317 $[M+H]^+$ Step 4. Synthesis of 2-amino-5-fluoro-4-((4-methoxybenzyl)amino)-6-(trifluoromethyl)nicotinic Acid To a solution of methyl 2-amino-4-bromo-5-fluoro-6-(trifluoromethyl)nicotinate (823 mg, 1 Equiv., 2.60 mmol) in toluene (10 mL) were added GPhos Pd G6 TES (245 mg, 0.1 Equiv., 260 μmol), sodium 2-methylpropan-2-olate (499 mg, 2 Equiv., 5.19 mmol), (4-methoxyphenyl)methanamine (427 mg, 1.2 Equiv., 3.12 mmol) and GPhos (139 mg, 0.1 Equiv., 260 μmol). The reaction was evacuated and purged with nitrogen (×3). The resulting mixture was then stirred for 3 h at 90° C. under an atmosphere of nitrogen. The reaction was then cooled to room temperature, and the mixture was acidified to pH=3 with 1 M Sulfuric acid, then diluted with EA (20 mL) and water (15 mL), and the aqueous layer was extracted with EA (2×20 mL). The organic layers were combined and washed with saturated brine (3×20 mL), dried over anhydrous sodium sulfate and concentrated to give a residue. The crude product was purified by silica gel chromatography, eluting with water (0.001M TFA): MeCN=3:1 to give 2-amino-5-fluoro-4-((4-methoxybenzyl)amino)-6-(trifluoromethyl)nicotinic acid (245 mg) as a yellow solid. LCMS: (ESI, m/z): 360 $[M+H]^+$ Step 5. Synthesis of (R or S)-1-(5-(2-amino-5-fluoro-4-((4-methoxybenzyl)amino)-6-(trifluoromethyl)nicotinoyl)-2-(4-cyclopropylphenyl)-2,3,4,5,5a,6,8,9-octahydro-7H-1,2,5,7-tetraazabenzo[cd]azulen-7-yl)prop-2-en-J-one To a solution of Int. F (40 mg, 1 Equiv., 0.11 mmol) in DMF (mL) were added HATU (87 mg, 2 Equiv., 0.23 mmol), 2-amino-5-fluoro-4-((4-ethoxybenzyl)amino)-6-(trifluoromethyl)nicotinic acid (62 mg, 1.5 Equiv., 0.17 mmol) and DIEA (0.10 g, 7 Equiv., 0.80 mmol). The mixture was stirred at rt for 2 h, after which the mixture was diluted with water (20 mL) and EA (20 mL), and the aqueous layer was extracted with EA (×20 mL). The organic layers were combined and washed with saturated brine (2×20 mL), dried over anhydrous sodium sulfate, and concentrated to give a residue. The residue was purified by flash column chromatography, eluting with EA/DCM (1:1) to afford (R or S)-1-(5-(2-amino-5-fluoro-4-((4-methoxybenzyl)amino)-6-(trifluoromethyl)nicotinoyl)-2-(4-cyclopropylphenyl)-2,3,4,5,5a,6,8,9-octahydro-7H-1,2,5,7-tetraazabenzo[cd]azulen-7-yl)prop-2-en-1-one (50 mg) as a yellow solid. LCMS: (ESI, m/z): 690 $[M+H]^+$ Step 6. Synthesis of (S or R)-1-(2-(4-cyclopropylphenyl)-5-(2,4-diamino-fluoro-6-(trifluoromethyl)nicotinoyl)-2,3,4,5,5a,6,8,9-octahydro-7H-1,2,5,7-tetraazabenzo[cd]azulen-7-yl)prop-2-en-1-one A solution of (R or S)-1-(5-(2-amino-5-fluoro-4-((4-ethoxybenzyl)amino)-6-(trifluoromethyl)nicotinoyl)-2-(4-cyclopropylphenyl)-2,3,4,5,5a,6,8,9-octahydro-7H-1,2,5,7-tetraazabenzo[cd]azulen-7-yl)prop-2-en-1-one (40 mg, 1 Equiv., 58 μmol) in TFA (2 mL) was stirred at 60° C. for 4 h. The mixture was then concentrated to give a residue, which was purified by Prep-HPLC (Column: XBridge Shield RP18 OBD Column 30*150 mm, 5 μm; Mobile Phase A: Water (10 mmol/L NH4HCO3), Mobile Phase B: ACN; Flow rate: 60 m/min mL/min; Gradient: 40% B to 34% B in 10 min; Wave Length: 254 nm/220 nm nm) to afford (R or S)-1-(2-(4-cyclopropylphenyl)-5-(2,4-diamino-5-fluoro-6-(trifluoromethyl)nicotinoyl)-2,3,4,5,5a,6,8,9-octahydro-7H-1,2,5,7-tetraazabenzo[cd]azulen-7-yl)prop-2-en-1-one (12.1 mg) as a white solid. LCMS: (ESI, m/z): 570 $[M+H]^+$. 1H NMR: (400 MHz, Chloroform-d, ppm) δ 7.34-7.28 (m, 2H), 7.18-7.10 (m, 2H), 6.69-6.26 (m, 1H), 5.94-5.68 (m, 1H), 5.47-5.17 (m, 1H), 5.02-4.87 (m, 1H), 4.83-4.69 (m, 1H), 4.67-4.48 (m, 1H), 4.48-4.28 (m, 1H), 4.24-3.83 (m, 1H), 3.46-2.88 (m, 4H); 2.81-2.64 (m, 2H), 2.00-1.87 (m, 1H), 1.34-1.17 (m, 3H), 1.07-0.96 (m, 2H), 0.92-0.79 (m, 1H), 0.76-0.65 (m, 2H).

Example A-16: Preparation of (R or S)-1-(2-(4-cyclopropylphenyl)-5-(2,4-diamino-6-(trifluoromethyl)nicotinoyl)-2,3,4,5,5a,6,8,9-octahydro-7H-1,2,5,7-tetraazabenzo[cd]azulen-7-yl)prop-2-en-1-one

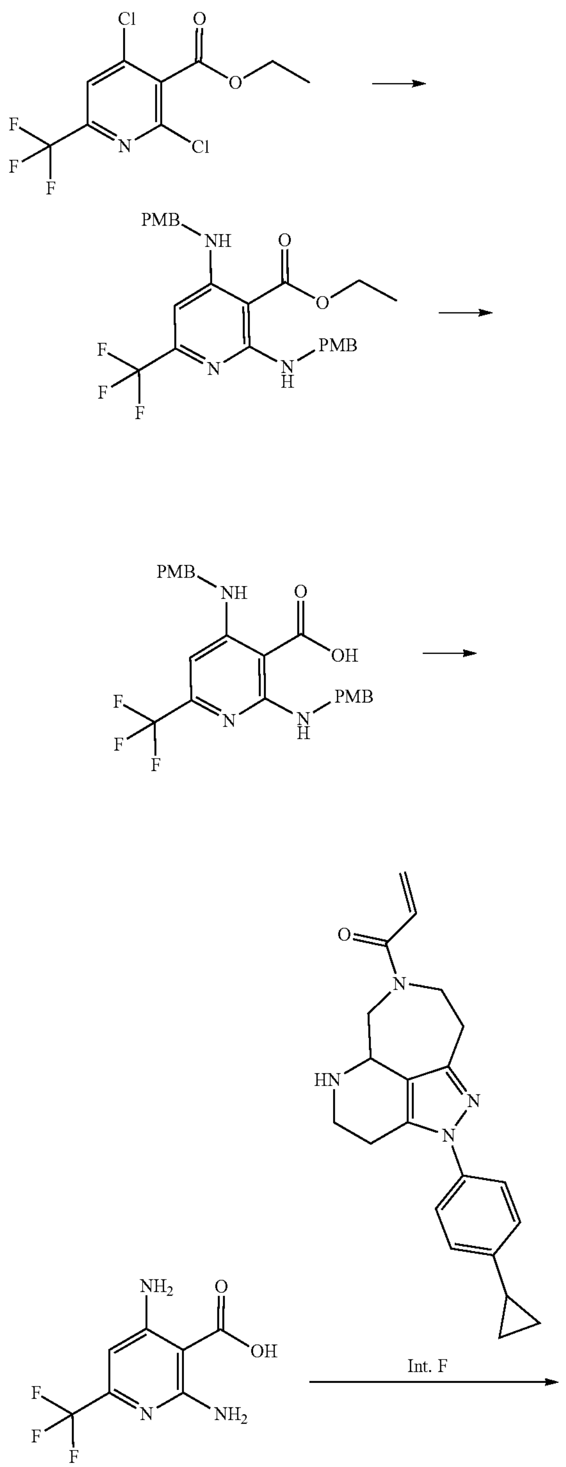

-continued

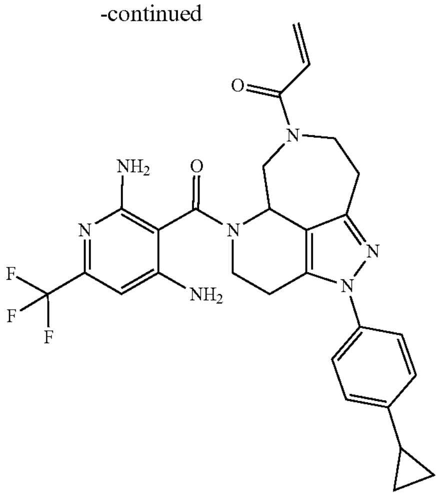

Step 1. Synthesis of Ethyl 2,4-bis((4-methoxybenzyl)amino)-6-(trifluoromethyl)nicotinate To a stirred solution of ethyl 2,4-dichloro-6-(trifluoromethyl)nicotinate (760 mg, 1 Equiv., 2.64 mmol) in DMF (19 mL) was added $K_2CO_3$ (1.09 g, 3 Equiv., 7.92 mmol) and 4-methoxybenzylamine (796 mg, 758 μL, 2.2, Equiv., 5.8 mmol) at 100° C. and the resulting mixture was stirred for 12 h. The reaction was then cooled to rt and quenched by the addition of water (30 mL), and the resulting mixture was extracted with EA (2×30 mL). The combined organic layers were washed with brine (2×30 mL) and dried over anhydrous $Na_2SO_4$. After filtration, the filtrate was concentrated under reduced pressure. The residue was purified by silica gel column chromatography, eluting with EA/PE (1:5) to afford ethyl 2,4-bis((4-methoxybenzyl)amino)-6-(trifluoromethyl)nicotinate (700 mg) as a white solid. LCMS: (ESI, m/2): 490 $[M+H]^+$ Step 2. Synthesis of 2,4-bis((4-methoxybenzyl)amino)-6-(trifluoromethyl nicotinic Acid To a stirred solution of ethyl 2,4-bis((4-ethoxybenzyl) amino)-6-(trifluoromethyl)nicotinate (600 mg, 1 Equiv., 1.23 mmol) in THF (6 mL) and water (3 mL) was added LiOH (88.1 mg, 3 Equiv., 3.68 mmol) at 60° C., and the resulting mixture was stirred for 12 hours. The reaction was then cooled to rt and quenched by the addition of water (20 mL) and the pH was adjusted to 4-5. The resulting mixture was extracted with EA (2×20 mL). The combined organic layers were washed with brine (2×20 mL) and dried over anhydrous $Na_2SO_4$. After filtration, the filtrate was concentrated under reduced pressure. The residue was purified by silica gel column chromatography, eluting with DCM/MeOH (10:1) to afford 2,4-bis((4-methoxybenzyl)amino)-6-(trifluoromethyl)nicotinic acid (400 mg) as a white solid. LCMS: (ESI, m/z): 462 $[M+H]^+$ Step 3. Synthesis of 2,4-diamino-6-(trifluoromethyl)nicotinic Acid A stirred solution of 2,4-bis((4-methoxybenzyl)amino)-6-(trifluoromethyl)nicotinic acid (390 mg, 1 Equiv., 845 μmol) in TFA (8 mL) was stirred for 1 h at 60° C. The reaction mixture was then concentrated under reduced pressure and the residue was purified by reversed-phase flash chromatography: (column, C18; mobile phase, MeCN in Water (TFA0.1%), 10% to 50% gradient in 10 min; detector, UV 254 nm) to afford 2,4-diamino-6-(trifluoromethyl)nicotinic acid (140 mg) as a white solid. LCMS: (ESI, m/z): 222 $[M+H]^+$ Step 4. Synthesis of (R or S)-1-(2-(4-cyclopropylphenyl)-5-(2,4-diamino-6-(trifluoromethyl)nicotinoyl)-2,3,4,5,5a,6,8,9-octahydro-7H-1,2,5,7-tetraazabenzo[cd]azulen-7-yl)prop-2-en-1-one To a stirred solution of 2,4-diamino-6-(trifluoromethyl) nicotinic acid (31.9 mg, 1 Equiv., 144 μmol) in DMF (2 mL) was added DIEA (74.6 mg, 4 Equiv., 577 μmol), HATU (110 mg, 2 Equiv., 288 gmol) and Int. F (50.3 mg, 1 Equiv., 144 mol) and the mixture was stirred at 40° C. for 12 h. The reaction was then cooled to rt and quenched by the addition of water (20 mL). The resulting mixture was extracted with EA (2×20 mL). The combined organic layers were washed with brine (2×20 mL) and dried over anhydrous $Na_2SO_4$. After filtration, the filtrate was concentrated under reduced pressure. The residue was purified by Prep-HPLC (Column: Sunfire C18 5 μm, 30 mm*150 mm; Mobile Phase A: Water (0.1% FA), Mobile Phase B: ACN; Flow rate: 60 mL/min; Gradient: 36% B to 51% B in 9 min; Wave Length: UV 254 nm/220 nm) to afford (R or S)-1-(2-(4-cyclopropylphenyl)-5-(2,4-diamino-6-(trifluoromethyl)nicotinoyl)-2,3,4,5,5a,6,8,9-octahydro-7H-1,2,5,7-tetraazabenzo[cd]azulen-7-yl) prop-2-en-1-one (13.7 mg) as a white solid. LCMS: (ESI, m/z): 552 $[M+H]^+$. $^1H$ NMR (400 MHz, Chloroform-d) δ 7.36-7.28 (m, 2H), 7.17-7.08 (m, 2H), 6.53-6.41 (m, 2H), 5.86-5.73 (m, 1H), 5.38-5.27 (m, 1H), 5.10-4.73 (m, 4H), 4.72-4.51 (m, 2H), 4.51-4.29 (m, 1H), 4.26-3.93 (m, 1H), 3.29-3.10 (m, 2H), 3.09-3.01 (m, 2H), 3.00-2.87 (m, 1H), 2.81-2.63 (m, 2H), 1.97-1.86 (m, 1H), 1.05-0.96 (m, 2H), 0.76-0.63 (m, 2H).

Example A-17: Preparation of (R or S)-1-(5-(4-amino-6-(methylthio)nicotinoyl)-2-(4-cyclopropyl-2-hydroxyphenyl)-2,3,4,5,5a,6,8,9-octahydro-7H-1,2,5,7-tetraazabenzo[cd]azulen-7-yl)prop-2-en-1-one

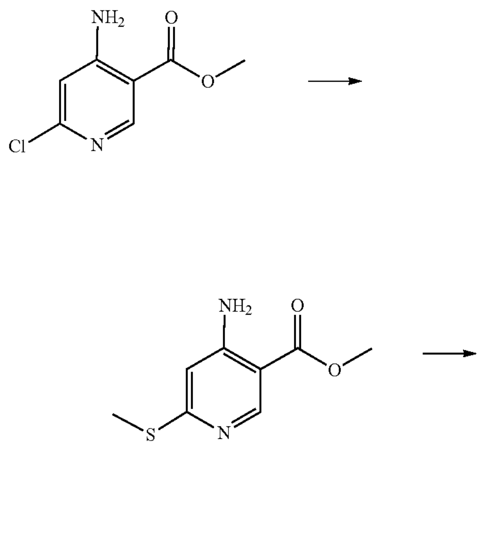

-continued

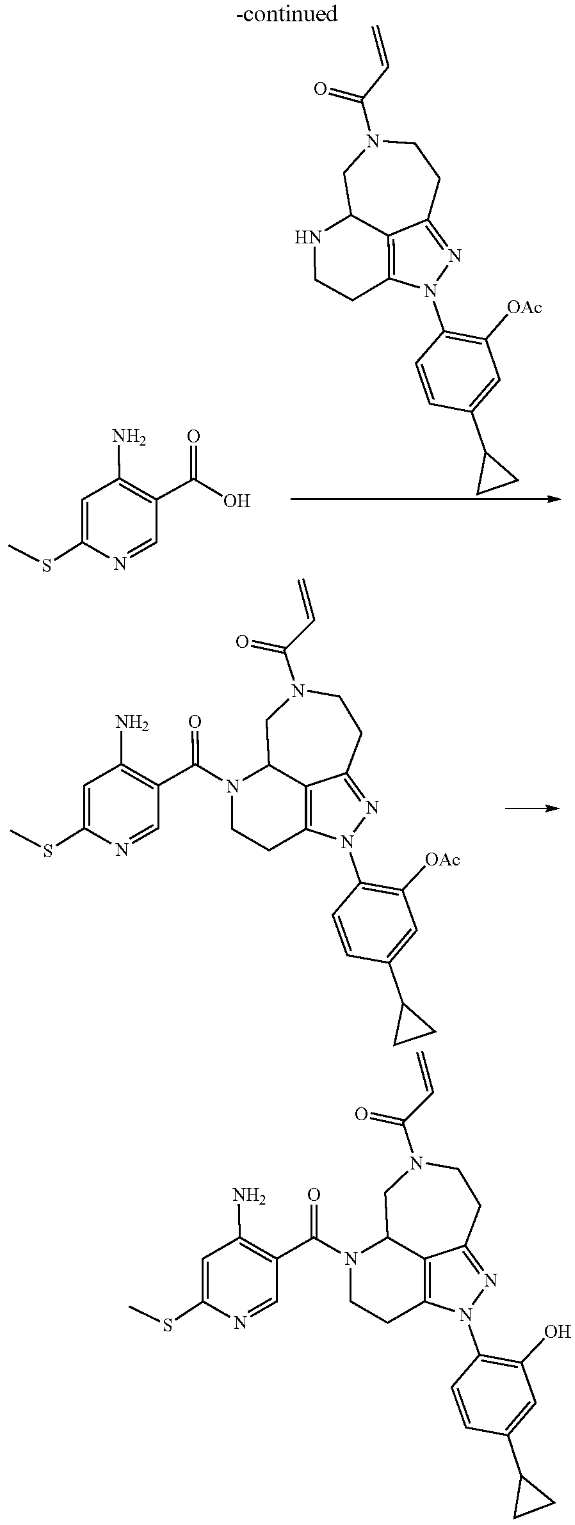

Step 1. Synthesis of Methyl 4-amino-6-(methylthio)nicotinate

To a solution of methyl 4-amino-6-chloronicotinate (1000 mg, 1 Equiv., 5.4 mmol) in 1,4-dioxane (10 mL) were added Xantphos (1.24 g, 0.4 Equiv., 2.14 mmol), methanethiol (1.03 g, 4 Equiv., 21.4 mmol), Bis-(triphenylphosphine)- palladium chloride (752 mg, 0.2 Equiv., 1.07 mmol) and DIEA (2.77 g, 3.73 mL, 4 Equiv., 21.4 mmol). The reaction was placed under an atmosphere of nitrogen and subjected to three backfilling cycles under high vacuum. The resulting mixture was stirred at 110° C. for 12 h under a nitrogen atmosphere, after which the reaction was cooled to rt, and the mixture was filtered and rinsed with EA (3×50 mL). The filtrate was then diluted with water (20 mL), and the aqueous layer was extracted with EA (3×50 mL). The combined organic layers were washed with saturated brine (3×50 mL), dried over anhydrous sodium sulfate and concentrated to give a residue. The crude product as purified by silica gel chromatography eluting with DCM: MeOH=10:1 to give methyl 4-amino-6-(methylthio)nicotinate (220 mg) as a white solid. LCMS: (ESI, m/z): 19) $[M+H]^+$ Step 2. Synthesis of 4-amino-6-(methylthio)nicotinic Acid To a solution of methyl 4-amino-6-(methylthio)nicotinate (200 mg, 1 Equiv., 1.01 mmol) in THF (2 mL) and water (1 mL) was added LiOH (48.3 mg, 2 Equiv., 2.02 mmol). The mixture was stirred at rt for 1 h. The mixture was then acidified to pH=5 with the addition of 1 M sulfuric acid (aqueous), and then diluted with EA (20 mL) and water (15 mL). The aqueous layer was extracted with EA (2×20 mL), and the organic layers were combined and washed with saturated brine (20 mL), dried over anhydrous sodium sulfate and concentrated to afford 4-amino-6-(methylthio) nicotinic acid (50 mg) as a crude yellow solid. The crude product was used in the next step directly without further purification. LCMS: (ESI, m/z): 185 $[M+H]^+$ Step 3. Synthesis of (R or S)-2-(7-acryloyl-5-(4-amino-6-(methylthio)nicotinoyl)-3,4,5,5a,6,7,8,9-octahydro-2H-1,2,5,7-tetraazabenzo[cd]azulen-2-yl)-5-cyclopropylphenyl Acetate A pre-dried reaction flask under nitrogen was changed with 4-amino-6-(methylthio)nicotinic acid (23 mg, 1 Equiv., 0.12 mmol), Int. H-2 (50 mg, 1 Equiv., 0.12 mmol), and HATU (51 mg, 1.1 Equiv., 0.14 mmol). DMA (1.5 mL) was added to dissolve the mixture, and the resulting mixture was stirred at rt. DIEA (64 mg, 86 μL, 4 Equiv., 0.49 mmol) was then added, and the mixture was heated to 40° C. and stirred for 5 h. The reaction mixture was then cooled to rt, quenched with water, and extracted with DCM (5 mL×3). The combined organic layers were then washed with saturated brine, dried over anhydrous $Na_2SO_4$, and concentrated under reduced pressure. The crude product was used in the next step directly without further purification. LCMS: (ESI, m/z): 573 $[M+H]^+$ Step 4. Synthesis of (R or S)-1-(5-(4-amino-6-(methylthio)nicotinoyl)-2-(4-cyclopropyl-2-hydroxyphenyl)-2,3,4,5,5a,6,8,9-octahydro-7H-1,2,5,7-tetraazabenzo[cd]azulen-7-yl)prop-2-en-1-one A flask was charged with (R or S)-2-(7-acryloyl-5-(4-amino-6-(methylthio)nicotinoyl)-3,4,5,5a,6,7,8,9-octahydro-2H-1,2,5,7-tetraazabenzo[cd]azulen-2-yl)-5-cyclopropylphenyl acetate (70.4 mg, 1 Equiv., 0.123 mmol), followed by THF (2 mL) and water (2 mL). Lithium hydroxide monohydrate (25.8 mg, 17.1 μL, 5 Equiv., 615 μmol) was thin added, and the mixture was stirred at rt for 1 hour. The mixture was then extracted with DCM (10 mL×3), and the combined organic layers were dried over anhydrous $Na_2SO_4$, and then concentrated under reduced pressure. After drying, the residue was dissolved in 2 mL of DMF and purified by Prep-HPLC (Column: YMC-Actus Triart C18 ExRS 30*150 mm, 5 m; Mobile Phase A: Water(10 mmol/L $NH_4HCO_3$), Mobile Phase B: ACN; Flow rate: 60 mL/min mL/min; Gradient: 31% B to 45% B in min; Wave Length: 254 nm/220 nm;) to provide (R or S)-1-(5-(4-amino-6-(methylthio)nicotinoyl)-2-(4-cyclopropyl-2-hydroxyphenyl)-2,3,4,5,5a,6,8,9-octahydro-7H-1,2,5,7-tetraazabenzo[cd]azulen-7-yl)prop-2-en-1-one (15.3 mg) as an off-white solid. LCMS: (ESI, m/z): 531 $[M+H]^+$. $^1H$ NMR: (400 MHz, Chloroform-d) δ 10.23-10.01 (m, 1H), 8.25-8.10 (m, 1H), 7.59-7.29 (m, 1H), 6.99-6.93 (m, 1H), 6.81-6.76 (m, 1H), 6.67-6.57 (m, 2H), 6.48-6.38 (m, OH), 5.87-5.76 (m, 1H), 5.61-5.06 (m, 3H), 4.99-0.91 (m, 1H), 4.56-4.15 (m, 3H), 3.32-2.90 (m, 5H), 2.90-2.67 (m, 2H), 2.58 (s, 3H), 1.92-0.81 (m, 1H), 1.03-0.94 (m, 2H), 0.75-0.67 (m, 2H).

TABLE A6

The compound of Example A-17-1 was made in an analogous fashion to Example A-17 except that ethyl 4-amino-6-chloro-5-fluoro-pyridine-3-carboxylate was used in place of methyl 4-amino-6-chloronicotinate.

| Example No. | Structure | Compound Name | LCMS $[M + H]^+$ | NMR |
| --- | --- | --- | --- | --- |
| A-17-1 | 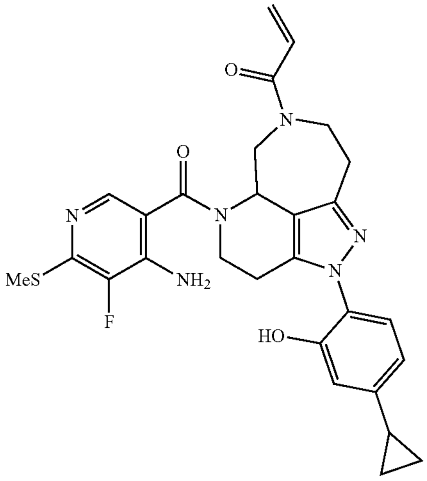 [SMILES: C=CC(=O)N1CCc2nn(-c3ccc(C4CC4)cc3O)c3c2C(C1)N(C(=O)c1cnc(SC)c(F)c1N)CC3] | (R or S)-1-(5-(4-amino-5-fluoro-6-(methylthio)nicotinoyl)-2-(4-cyclopropyl-2-hydroxyphenyl)-2,3,4,5,5a,6,8,9-octahydro-7H-1,2,5,7-tetraazabenzo[cd]azulen-7-yl)prop-2-en-1-one | 549 | $^1H$ NMR (400 MHz, Chloroform-d) δ 10.16 (br s, 1H), 8.03 (s, 1H), 7.47-7.42 (m, 1H), 6.98 (d, J = 8.4 Hz, 1H), 6.80 (d, J = 4.4 Hz, 1H), 6.65 (dd, J = 1.6, 8.0 Hz, 1H), 6.53 (d, J = 16.8 Hz, 1H), 5.86 (br d, J = 10.4 Hz, 1H), 5.38 (br d, J = 9.2 Hz, 1H), 5.17 (br s, 2H), 4.99 (br d, J = 14.0 Hz, 1H), 4.50-4.29 (m, 2H), 3.19-2.06 (m, 5H), 2.86-2.73 (m, 2H), 2.61 (s, 3H), 1.88-1.87 (m, 1H), 1.02-0.97 (m, 2H), 0.74-0.72 (m, 2H). |

Example A-18: Preparation of (R or S)-1-(5-(4-amino-5-methyl-6-(trifluoromethyl)nicotinoyl)-2-(4-cyclopropyl-2-hydroxyphenyl)-2,3,4,5,5a,6,8,9-octahydro-7H-1,2,5,7-tetraazabenzo[cd]azulen-7-yl)prop-2-en-1-one

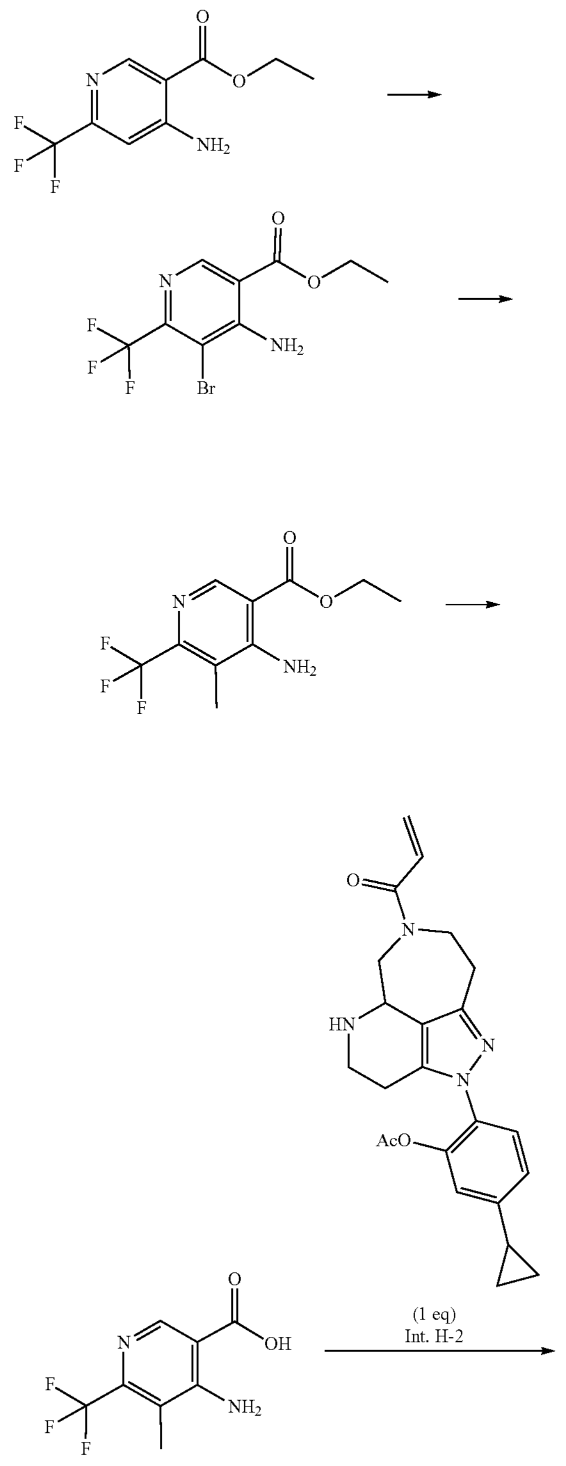

-continued

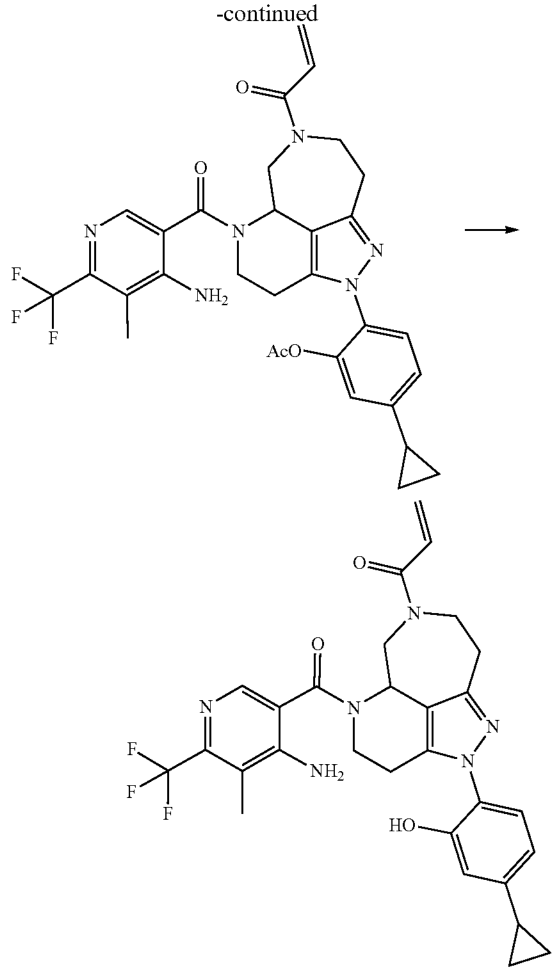

Step 1. Synthesis of Ethyl 4-amino-5-bromo-6-(trifluoromethyl)nicotinat

To a stirred solution of ethyl 4-amino-6-(trifluoromethyl)nicotinate (12.6 g, 1 Equiv., 53.8 mmol) in ACN (80 mL) was added NBS (14.4 g, 1.5 Equiv., 80.7 mmol) at 80° C. and the resulting mixture was stirred for 16 h. The reaction solution was then concentrated under reduced pressure. The residue was purified by silica gel column chromatography, eluting with EA/PE (1:3) to afford ethyl 4-amino-5-bromo-6-(trifluoromethyl)nicotinate (14.1 g) as a yellow solid. LCMS: (ESI, m/z): 313 $[M+H]^+$ Step 2. Synthesis of Ethyl 4-amino-5-methyl-6-(trifluoromethyl)nicotinate To a solution of ethyl 4-amino-5-bromo-6-(trifluoromethyl)nicotinate (300 mg, 1 Equiv., 958 μmol,) in 1,4-dioxane (4 mL) and water (0.8 mL) were added potassium phosphate, tribasic (610 mg, 238 μL, 3 Equiv., 2.87 mmol), methylboronic acid (86.0 mg, 1.5 Equiv., 1.44 mmol) and Pd(dppf)$Cl_2$ (78.3 mg, 0.1 Equiv., 95.8 μmol). The mixture was then stirred at 90° C. for 2 h, after which the mixture was cooled to rt and diluted with ice water (100 mL) and EA (100 mL). The aqueous layer was extracted with EA (2×100 mL), and the organic layers were combined and washed with saturated brine (3×100 mL), dried over anhydrous sodium sulfate and concentrated to give a residue. The residue was purified by flash column chromatography (120 g silica gel column, 25% EA in PE) to afford ethyl 4-amino-5-methyl-6-(trifluoromethyl)nicotinate (170 mg) as a yellow solid. LCMS: (ESI, m/z): 249 $[M+H]^+$ Step 3. Synthesis of 4-amino-5-methyl-6-(trifluoromethyl)nicotinic Acid To a solution of ethyl 4-amino-5-methyl-6-(trifluoromethyl)nicotinate (170 mg, 1 Equiv., 685 μmol) in THF (2 mL) and $H_2O$ (0.5 mL) was added LiOH (65.6 ng, 4 Equiv., 2.74 mmol). The mixture was stirred at rt for 2 hours, after which the mixture was acidified to pH=3 with the addition of 1 M sulfuric acid (aqueous), then diluted with EA (20 mL) and water (15 mL). The aqueous layer was extracted with EA (2×20 mL), and the organic layers were combined and washed with saturated brine (20 mL), dried over anhydrous sodium sulfate and concentrated to afford 4-amino-5-methyl-6-(trifluoromethyl)nicotinic acid (100 mg) as a white solid. LCMS: (ESI, m/z): 221 $[M+H]^+$ Step 4. Synthesis of (R or S)-2-(7-acryloyl-5-(4-amino-5-methyl-6-(trifluoromethyl)nicotinoyl)-3,4,5,5a,6,7,8,9-octahydro-2H-1, 2,5,7-tetraazabenzo[cd]azulen-2-yl)-5-cyclopropylphenyl Acetate To a solution of Int. H-2 (50 mg, 1 Equiv., 0.12 mmol) in DMA (0.5 mL) were added 4-amino-5-methyl-6-(trifluoromethyl)nicotinic acid (27 mg, 1 Equiv., 0.12 mmol), DIEA (79 mg, 0.11 mL, 5 Equiv., 0.62 mmol) and HATU (94 mg, 2 Equiv., 0.25 mmol). The mixture was stirred at rt for 1 h, after which the mixture was diluted with water (20 mL) and EA (20 mL), and the aqueous layer was extracted with EA (2×20 mL). The organic layers w re combined and washed with saturated brine (2×20 mL), dried over anhydrous sodium sulfate and concentrated to give (R or S)-2-(7-acryloyl-5-(4-amino-5-methyl-6-(trifluoromethyl)nicotinoyl)-3,4,5,5a,6,7,8,9-octahydro-2H-1,2,5,7-tetraazabenzo[cd]azulen-2-yl)-5-cyclopropylphenyl acetate (70 mg) which was used without further purification. LCMS: (ESI, m/z): 609 $[M+H]^+$ Step 5. Synthesis of (R or S)-1-(5-(4-amino-5-methyl-6-(trifluoromethyl)nicotinoyl)-2-(4-cyclopropyl-2-hydroxyphenyl)-2,3,4,5,5a,6,8,9-octahydro-7H-1,2,5,7-tetraazabenzo[cd]azulen-7-yl)prop-2-en-1-one To a solution of (R or S)-2-(7-acryloyl-5-(4-amino-5-methyl-6-(trifluoromethyl)nicotinoyl)-3,4,5,5a,6,7,8,9-octahydro-2H-1,2,5,7-tetraazabenzo[cd]azulen-2-yl)-5-cyclopropylphenyl acetate (50 mg, 1 Equiv., 82 gmol) in THF (0.5 mL) and $H_2O$ (0.1 mL) was added lithium hydroxide monohydrate (6.9 mg, 2 Equiv., 0.16 mmol). The mixture was stirred at rt for 1 h, after which the mixture was acidified to pH=3 with the addition of 1 M sulfuric acid (aqueous), then diluted with water (20 mL) and EA (20 mL), and the aqueous layer was extracted with EA (2×20 mL). The organic layers were combined and washed with saturated brine (2×20 mL), dried over anhydrous sodium sulfate and concentrated to give a residue. The residue was purified by Prep-HPLC (Column: XBridge Prep Phenyl OBD Column 19*250 mm, 5 μm; Mobile Phase A: Water (10 mmol/L $NH_4HCO_3$), Mobile Phase B: ACN; Flow rate: 60 mL/min mL/min; Gradient: 5% B to 5% B in 1 min, 5% B to 35% B in 2 min, 35% to 2% B in 10 min; Wave Length: 254 nm/220 nm) to afford (R or S)-1-(5-(4-amino-5-methyl-6-(trifluoromethyl)nicotinoyl)-2-(4-cyclopropyl-2-hydroxyphenyl)-2,3,4,5,5a,6,8,9-octahydro-7H-1,2,5,7-tetraazabenzo[cd]azulen-7-yl)prop-2-en-1-one (9.7 mg) as a white solid LCMS: (ESI, m/z): 567 $[M+H]^+$. $^1H$ NMR (400 MHz, Chloroform-d) δ 8.38-8.19 (m, 1H), 7.53-7.31 (m, 1H), 7.07-6.87 (m, 1H), 6.83-6.76 (m, 1H), 6.69-6.60 (m, 1H), 6.51 (d, J=16.4 Hz, 1H), 5.98-5.70 (m, 1H), 5.41 (s, 2H), 4.98 (d, J=13.4 Hz, 1H), 4.59-4.43 (m, 1H), 4.29-4.06 (m, 1H), 3.44-2.86 (m, 6H), 2.86-2.66 (m, 2H), 2.38-2.24 (m, 3H), 1.93-1.81 (m, 1H), 1.05-0.93 (m, 2H), 0.75-0.67 (m, 2H).

Example A-19: Preparation of (R or S)-1-(5-(4-amino-6-(trifluoromethyl)nicotinoyl)-2-(4-cyclopropyl-2-(hydroxymethyl)phenyl)-2,3,4,5,5a,6,8,9-octahydro-7H-1,2,5,7-tetraazabenzo[cd]azulen-7-yl)prop-2-en-1-one

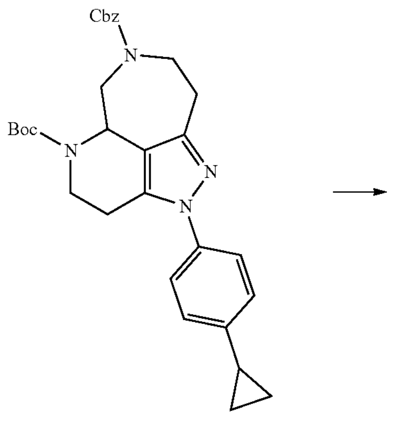

Int. E-3

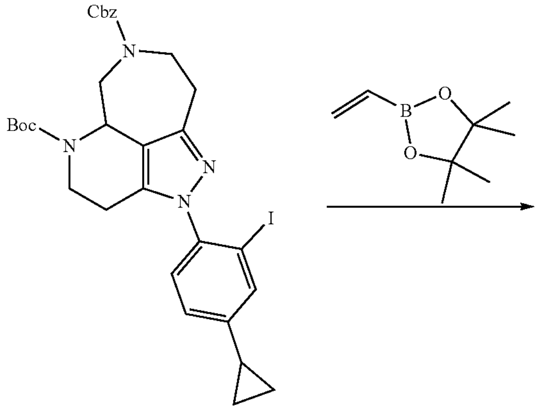

Int. QQ

-continued
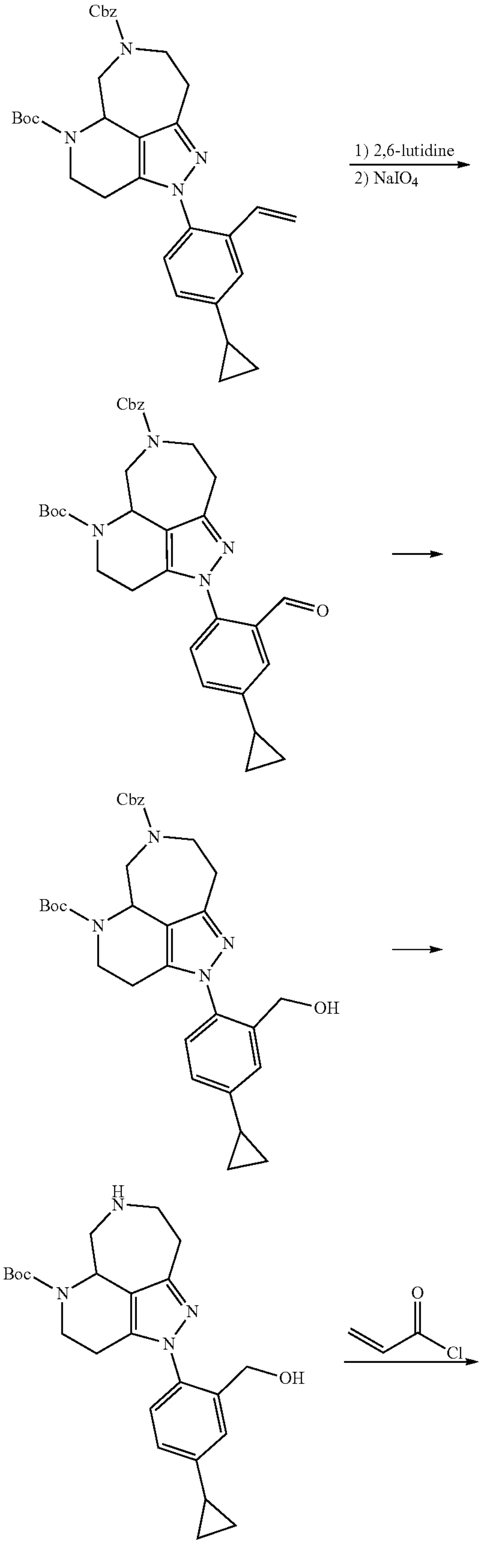
-continued
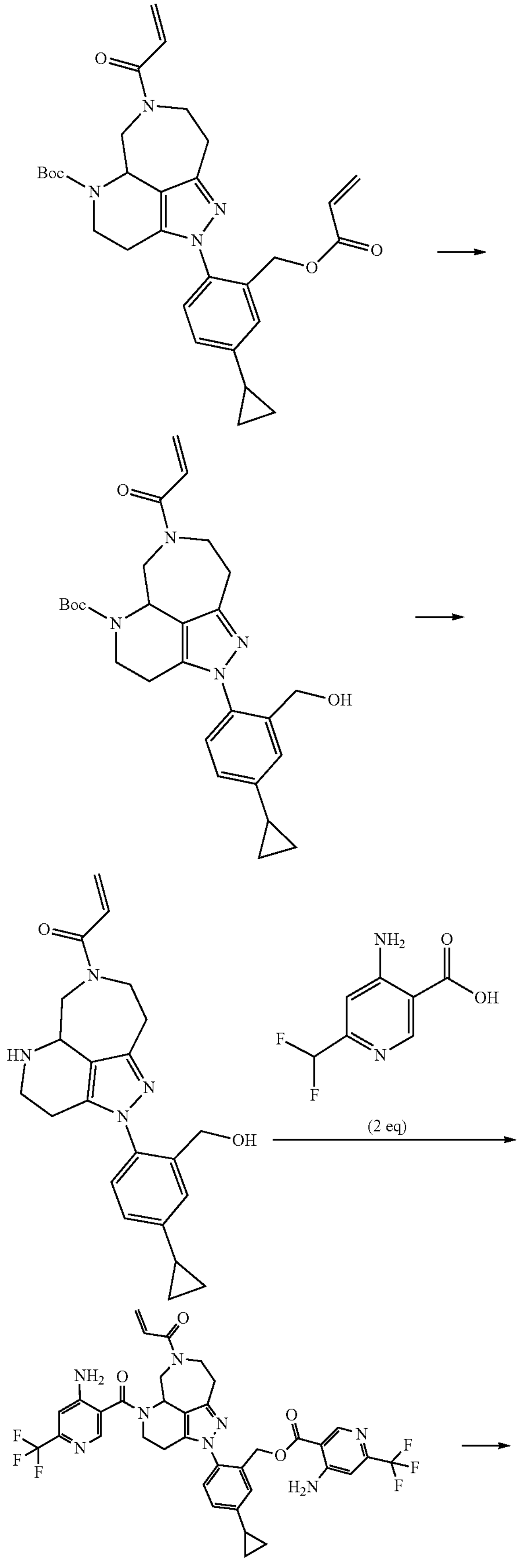

-continued

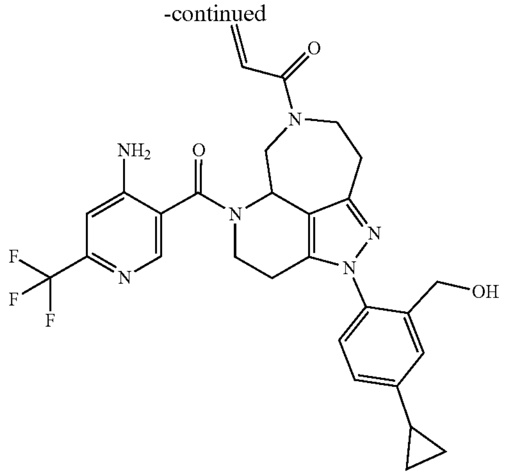

Step 1: Synthesis of 7-benzyl 5-(tert-butyl) (R or S)-2-(4-cyclopropyl-2-iodophenyl)-3,4,5a,6,8,9-hexahydro-2H-1,2,5,7-tetraazabenzo[cd]azulene-5,7-dicarboxylate (Int. QQ)

To a stirred solution of Int. E-3 (4 g, 1 equiv., 8 mmol) and 1,3-cyclopentadiene, 1,2,3,4,5-pentamethyl-, rhodium complex (1.8 g, 0.4 Equiv., 4 mmol) in DCE (80 mL) was added iodobenzenediacetate (4 g, 1.5 Equiv., 0.01 mol), sodium iodide (3 g, 0.9 mL, 3 Equiv., 0.02 mol) and TFA (2 g, 1 mL, 2 Equiv., 0.02 mol) at rt. The reaction was placed under a positive pressure of nitrogen and subjected to three evacuation cycles under hi h vacuum. The resulting mixture was stirred for 2 h at 40° C. The mixture was then allowed to cool to rt, and the reaction was quenched by the addition of water (200 mL) at rt. The resulting mixture was extracted with EA (2×200 mL), and the combined organic layers were washed with brine (2×200 mL), dried over anhydrous $Na_2SO_4$, and filtered. The filtrate was concentrated under reduced pressure. The residue was purified by silica gel column chromatography, eluting with EA:PE (1:5) to afford 7-benzyl 5-(tert-butyl) (R or S)-2-(4-cyclopropyl-2-iodophenyl)-3,4,5a,6,8,9-hexahydro-2H-1,2,5,7 -tetraazabenzo[cd]azulene-5,7-dicarboxylate (4 g) as a brown solid. LCMS: (ESI, m/z): 655 [M+H]

Step 2: Synthesis of 7-benzyl 5-(tert-butyl) (R or S)-2-(4-cyclopropyl-2-vinylphenyl)-3,4,5a,6,8,9-hexahydro-2H-1,2,5,7-tetraazabenzo[cd]azulene-5,7-dicarboxylate To a stirred solution of 4,4,5,5-tetramethyl-2-vinyl-1,3,2-dioxaborolane (0.7 g, 3 Equiv., 5 mmol) and Int. QQ (1 g, 1 Equiv., 2 mmol) in dioxane (10 ml) and water (2 mL) was added potassium phosphate, tribasic (1 g, 0.4 mL, 2.5 Equiv., 5 mmol) and Pd(dppf)$Cl_2$·DCM (0.1 g, 0.1 Equiv., 0.2 mmol) at rt. The mixture was placed under a positive pressure of nitrogen and the solution was subjected to three evacuation cycles under high vacuum. The resulting mixture was stirred for 2 h at 90° C. The mixture was then cooled to rt and was quenched by the addition of water (50 mL) at room temperature. The resulting mixture was extracted with EA (2×50 mL) and the combined organic layers were washed with brine (2×50 m), dried over anhydrous $Na_2SO_4$, and filtered. The filtrate was concentrated under reduced pressure, and the residue was purified by silica gel column chromatography, eluting with EA/PE (1:1) to afford 7-benzyl 5-(tert-butyl) (R or S)-2-(4-cyclopropyl-2-vinylphenyl)-3,4,5a,6,8,9-hexahydro-2H-1,2,5,7-tetraazabenzo[cd]azulene-5,7-dicarboxylate (700 mg) as a brown solid. LCMS: (ESI, m/z): 555 $[M+H]^+$ Step 3: Synthesis of 7-benzyl 5-(tert-butyl) (R or S)-2-(4-cyclopropyl-2-formylphenyl)-3,4,5a,6,8,9-hexahydro-2H-1,2,5,7-tetraazabenzo[cd]azulene-5,7-dicarboxylate To a stirred solution of 7-benzyl 5-(tert-butyl) (R or S)-2-(4-cyclopropyl-2-vinylphenyl)-3,4,5a,6,8,9-hexahydro-2H-1,2,5,7-tetraazabenzo[cd]azulene-5,7-dicarboxylate (700 mg, 1 Equiv., 1.26 mmol) and 2,6-dimethylpyridine (406 mg, 4 Equiv., 3.79 mmol) in THF (7 mL) and water (1 mL) was added potassium tetrahydroxydioxidoosmium (46.5 mg, 0.3 Equiv., 126 μmol) in portions at 0° C. under an atmosphere of air. The resulting mixture was stirred for 10 min at 0° C. To the above mixture was then added sodium periodate (1.08 g, 4 Equiv., 5.05 mmol) in portions over 30 min at 0° C., and the resulting mixture was stirred for additional 1 h at rt. The mixture was then concentrated under reduced pressure to afford 7-benzyl 5-(tert-butyl) (R or S)-2-(4-cyclopropyl-2-formylphenyl)-3,4,5a,6,8,9-hexahydro-2H-1,2,5,7-tetraazabenzo[cd]azulene-5,7-dicarboxylate (1.25 g) as a brown oil which was used in the next reaction without further purification. LCMS: (ESI, m/z): 557 $[M+H]^+$ Step 4: Synthesis of 7-benzyl 5-(tert-butyl) (R or S)-2-(4-cyclopropyl-2 (hydroxymethyl)phenyl)-3,4,5a,6,8,9-hexahydro-2H-1,2,5,7-tetraazabenzo[cd]azulene-5,7-dicarboxylate To a stirred solution of 7-benzyl 5-(tert-butyl) (R or S)-2-(4-cyclopropyl-2-formylphenyl)-3,4,5a,6,8,9-hexahydro-2H-1,2,5,7-tetraazabenzo[cd]azulene-5,7-dicarboxylate (1.25 g, 40% wt, 1 Equiv., 898 gmol) in THF (12 mL) and MeOH (2 mL) was added sodium tetrahydroborate (102 mg, 95.4 μL, 2 Equiv., 2.69 mmol) and the resulting mixture was stirred for 2 h at rt. The reaction was then quenched by the addition of water (20 mL) at rt. The resulting mixture was extracted with EA (2×20 mL), and the combined organic layers were washed with brine (2×20 mL), dried over anhydrous $Na_2SO_4$, and filtered. The filtrate was concentrated under reduced pressure, and the residue was purified by silica gel column chromatography, eluting with DCM:MEOH (5:1) to afford 7-benzyl 5-(tert-butyl) (R or S)-2-(4-cyclopropyl-2-(hydroxymethyl)phenyl)-3,4,5a,6,8,9-hexahydro-2H-1,2,5,7-tetraazabenzo[cd]azulene-5,7-dicarboxylate (250 mg) as a brown solid. LCMS: (ESI, m/z): 559 $[M+H]^+$ Step 5: Synthesis of Tert-Butyl (R or S)-2-(4-cyclopropyl-2 (hydroxymethyl)phenyl)-2,3,4,5a,6,7,8,9-octahydro-5H-1,2,5,7-tetraazabenzo[cd]azulene-5-carboxylate To a solution of 7-benzyl 5-(tert-butyl) (R or S)-2-(4-cyclopropyl-2-(hydroxymethyl)phenyl)-3,4,5a,6,8,9-hexahydro-2H-1,2,5,7-tetraazabenzo[cd]azulene-5,7-dicarboxylate (250 mg, 1 Equiv., 447 μmol) in 1,4-dioxane (3 mL) was added Pd/C (47.6 mg, 1 Equiv., 447 μmol) in a pressure tank. The mixture was purged with nitrogen three times and then was pressurized to 2 mpa with hydrogen gas at rt for 16 h. The mixture was then filtered and the filtrate was concentrated under reduced pressure. The crude product tert-butyl (R or S)-2-(4-cyclopropyl-2-(hydroxymethyl)phenyl)-2,3,4,5a,6,7,8,9-octahydro-5H-1,2,5,7-tetraazabenzo[cd]azulene-5-carboxylate (250 mg) was used in the next step directly without further purification. LCMS: (ESI, m/z): 425 $[M+H]^+$ Step 6: Synthesis of Tert-Butyl (R or S)-7-acryloyl-2-(2-((acryloyloxy)methyl)-4-cyclopropylphenyl)-2,3,4,5a,6,7,8,9-octahydro-5H-1,2,5,7-tetraazabenzo[cd]azulene-5-carboxylate To a stirred solution of tert-butyl (R or S)-2-(4-cyclopropyl-2-(hydroxymethyl)phenyl)-2,3,4,5a,6,7,8,9-octahydro-5H-1,2,5,7-tetraazabenzo[cd]azulene-5-carboxylate (200 mg, 1 Equiv., 471 gmol) in DCM (2 mL) was added TEA (143 mg, 197 μL, 3 Equiv., 1.41 mmol) and acryloyl chloride (60.2 mg, 3 Equiv., 35 mol) at rt and the resulting mixture as stirred for 2 h. The reaction was quenched by the addition of water (20 mL), and the resulting mixture was extracted with EA (2×20 mL). The combined organic layers were washed with brine (2×20 mL), dried over anhydrous $Na_2SO_4$, and filtered. The filtrate was concentrated under reduced pressure, and the residue was purified by silica gel column chromatography, eluting with EA:PE (1:5) to afford tert-butyl (R or S)-7-acryloyl-2-(2-((acryloyloxy)methyl)-4-cyclopropylphenyl)-2,3,4,5a,6,7,8,9-octahydro-5H-1,2,5,7-tetraazabenzo[cd]azulene-5-carboxylate (100 mg) as a white solid. LCMS: (ESI, m/z): 533 $[M+H]^+$ Step 7: Synthesis of Tert-Butyl (R or S)-7-acryloyl-2-(4-cyclopropyl-2-(hydroxymethyl)phenyl)-2,3,4,5a,6,7,8,9-octahydro-5H-1, 2,5,7-tetraazabenzo[cd]azulene-5-carboxylate To a stirred solution of tert-butyl (R or S)-7-acryloyl-2-(2-((acryloyloxy)methyl)-4-cyclopropylphenyl)-2,3,4,5a,6,7,8,9-octahydro-5H-1,2,5,7-tetraazabenzo[cd]azulene-5-carboxylate (90 mg, 1 Equiv., 0.17 mmol) in THF (1 mL) and water (0.2 mL) was added lithium hydroxide (20 mg, 5 Equiv., 0.84 mmol) and the resulting mixture was stirred for 1 h at rt. The reaction mixture was then filtered, and the filtrate was concentrated under reduced pressure to afford tert-butyl (R or S)-7-acryloyl-2-(4-cyclopropyl-2-(hydroxymethyl)phenyl)-2,3,4,5a,6,7,8,9-octahydro-5H-1,2,5,7-tetraazabenzo[cd]azulene-5-carboxylate (140 mg) as a white solid. LCMS: (ESI, m/z): 479 $[M+H]^+$ Step 8: Synthesis of (R or S)-1-(2-(4-cyclopropyl-2-(hydroxymethylphenyl)-2,3,4,5,5a,6,8,9-octahydro-7H-1,2,5,7-tetraazabenzo[cd]azulen-7-yl)prop-2-en-1-one A solution of tert-butyl (R or S)-7-acryloyl-2-(4-cyclopropyl-2-(hydroxymethyl)phenyl)-2,3,4,5a,6,7,8,9-octahydro-5H-1,2,5,7-tetraazabenzo[cd]azulene-5-carboxylate (120 mg, 20 wt %, 1 Equiv., 50.1 μmol) in DCM (2 mL) and TFA (0.4 mL) was stirred at rt for 1 h. The solvent was then removed under reduced pressure to afford (R or S)-1-(2-(4-cyclopropyl-2-(hydroxymethyl)phenyl)-2,3,4,5,5a,6,8,9-octahydro-7H-1,2,5,7-tetraazabenzo[cd]azulen-7-yl)prop-2-en-1-one (240 mg) as a crude yellow oil which was used in the next step directly without further purification. LCMS: (ESI, m/z): 379 $[M+H]^+$ Step 9: Synthesis of (R or S)-2-(7-acryloyl-5-(4-amino-6-(trifluoromethyl)nicotinoyl)-3,4,5,5a,6,7,8,9-octahydro-2H-1,2,5,7-tetraazabenzo[cd]azulen-2-yl)-5-cyclopropylbenzyl 4-amino-6-(trifluoromethyl)nicotinate To a solution of (R or S)-1-(2-(4-cyclopropyl-2-(hydroxymethyl)phenyl)-2,3,4,5,5a,6,8,9-octahydro-7H-1,2,5,7-tetraazabenzo[cd]azulen-7-yl)prop-2-en-1-one (240 mg, 20 wt %, 1 Equiv., 127 gmol) in DMA (1 mL) were added 4-amino-6-(trifluoromethyl)nicotinic acid (57.5 mg, 2 Equiv., 279 μmol), DIEA (82.0 mg, 5 Equiv., 634 μmol) and HATU (57.9 mg, 1.2 Equiv., 152 μmol). The mixture was stirred at rt for 1 h, after which the mixture was diluted with water (20 mL) and EA (20 mL), and the aqueous layer was extracted with EA (2×20 mL). The organic layers were combined and washed with saturated brine (2×20 mL) and filtered, and the filtrate was concentrated under reduced pressure. The residue was purified by silica gel column chromatography, eluting with DCM/MEOH (10:1) to afford (R or S)-2-(7-acryloyl-5-(4-amino-6-(trifluoromethyl)nicotinoyl)-3,4,5,5a,6,7,8,9-octahydro-2H-1,2,5,7-tetraazabenzo[cd]azulen-2-yl)-5-cyclopropylbenzyl 4-amino-6-(trifluoromethyl)nicotinate (20 mg) as a white solid.

Step 10: Synthesis of (R or S)-1-(S-(4-amino-6-(trifluoromethyl)nicotinoyl)-2-(4-cyclopropyl-2-(hydroxymethyl)phenyl)-2,3,4,5,5a,6,8,9-octahydro-7H-1,2,5,7-tetraazabenzo[cd]azulen-7-yl)prop-2-en-1-one To a stirred solution of (R or S)-2-(7-acryloyl-5-(4-amino-6-(trifluoromethyl)nicotinoyl)-3,4,5,5a,6,7,8,9-octahydro-2H-1,2,5,7-tetraazabenzo[cd]azulen-2-yl)-5-cyclopropylbenzyl 4-amino-6-(trifluoromethyl)nicotinate (30 mg, 50 wt %, 1 Equiv., 20 μmol) in THF (1 mL) and water (0.2 mL) was added LiOH (2.4 mg, 5 Equiv., 99 μmol) and the mixture was stirred at rt for 1 h. After filtration, the filtrate was concentrated under reduced pressure and the residue was purified by Prep-HPLC (Column: XSelect CSH Fluoro Phenyl 30*150 mm, 5 μm; Mobile Phase A: Water(0.1% FA), Mobile Phase B: MeOH; Flow rate: 60 mL/min mL/min; Gradient: 52% B to 69% B in 30 min) to afford (R or S)-1-(5-(4-amino-6-(trifluoromethyl)nicotinoyl)-2-(4-cyclopropyl-2-(hydroxymethyl)phenyl)-2,3,4,5,5a,6,8,9-octahydro-7H-1,2,5,7-tetraazabenzo[cd]azulen-7-yl)prop-2-en-1-one (2.3 mg) as a white solid LCMS: (ESI, m/z): 567 $[M+H]^+$. $^1H$ NMR (400 MHz, Chloroform-d) δ 8.38-8.29 (m, 1H), 7.54-7.30 (m, 1H), 7.22 (s, 1H), 7.13-6.97 (m, 3H), 6.57-6.37 (m, 1H), 5.93-5.71 (m, 1H), 5.49-5.27 (m, 2H), 5.09-4.91 (m, 1H), 4.57-4.46 (m, 1H), 4.46-4.35 (m, 1H), 4.34-4.25 (m, 1H), 4.24-4.06 (m, 1H), 3.36-3.16 (m, 2H), 3.15-2.83 (m, 4H), 2.82-2.68 (m, 1H), 2.67-2.51 (m, 1H), 1.26 (s, 1H), 1.09-0.99 (m, 2H), 0.91-0.81 (m, 1H), 0.78-0.71 (m, 2H).

Example A-20: Preparation of (R or S)-1-(5-(4-amino-6-(trifluoromethyl)nicotinoyl)-2-(4-cyclopropyl-2-(difluoromethoxy)phenyl)-2,3,4,5,5a,6,8,9-octahydro-7H-1,2,5,7-tetraazabenzo[cd]azulen-7-yl)prop-2-en-1-one

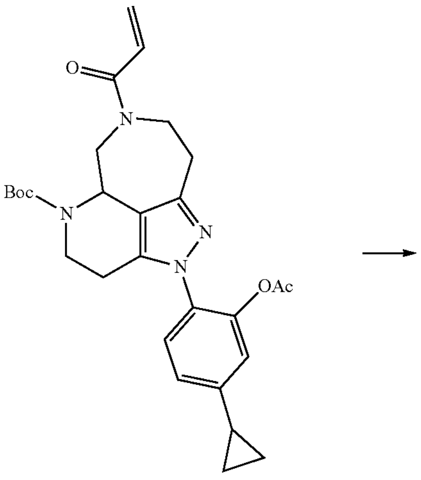

Int. E-4

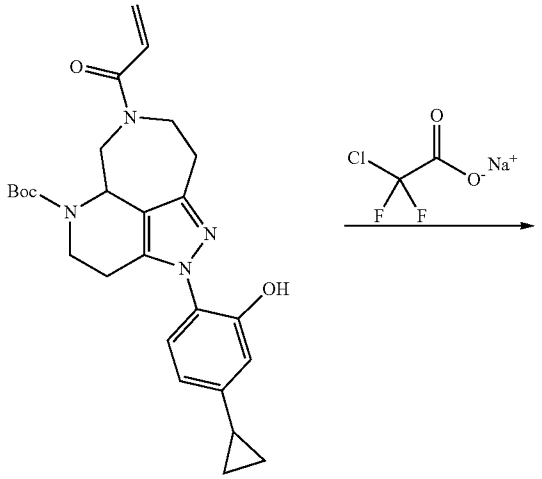

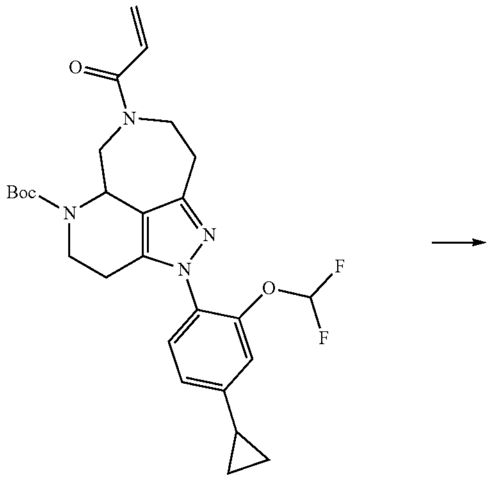

-continued

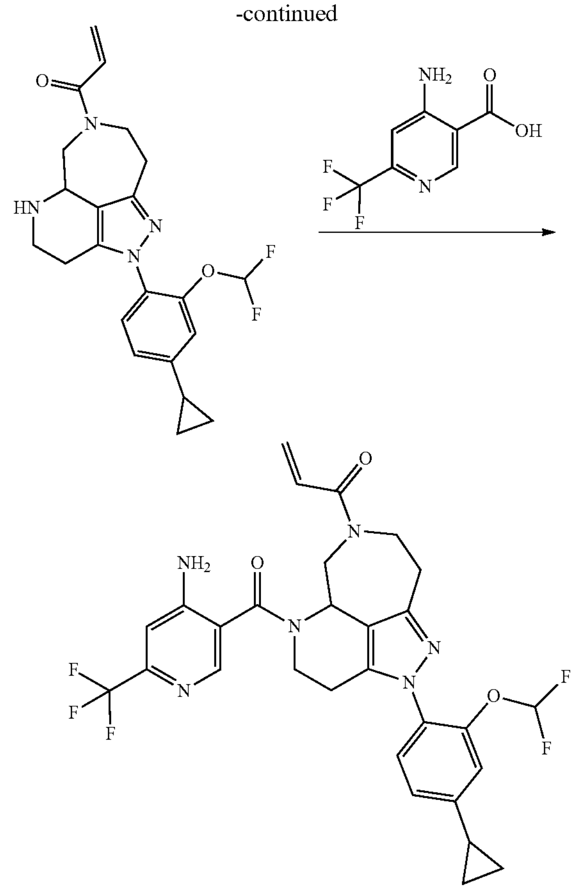

Step 1: Synthesis of Tert-Butyl (R or S)-7-acryloyl-2-(4-cyclopropyl-2-hydroxyphenyl)-2,3,4,5a,6,7,8,9-octahydro-5H-1,2,5,7-tetraazabenzo[cd]azulene-5-carboxylate To a solution of Int. E-4 (100 mg, 1 Equiv., 197 gmol) in TH (0.4 mL) and water (0.1 mL) was added LiOH (32.4 mg, 4 Equiv., 790 μmol). The mixture was stirred at rt for 1 h, after which the mixture was acidified to pH=3 with the addition of 1 M sulfuric acid. The mixture was then diluted with EA (20 mL) and water (15 mL), and the aqueous layer was extracted with EA (2×20 mL). The combined organic layers were washed with saturated brine (20 mL), dried over anhydrous sodium sulfate, and concentrated to afford tert-butyl (R or S)-7-acryloyl-2-(4-cyclopropyl-2-hydroxyphenyl)-2,3,4,5a,6,7,8,9-octahydro-5H-1,2,5,7-tetraazabenzo[cd]azulene-5-carboxylate (80 mg) as a yellow solid. The crude product was used in the next step directly without further purification. LCMS: (ESI, m/z): 465 $[M+H]^+$ Step 2: Synthesis of Tert-Butyl (R or S)-7-acryloyl-2-(4-cyclopropyl-2-(difluoromethoxy)phenyl)-2,3,4,5a,6,7,8,9-octahydro-5H-1,2,5,7-tetraazabenzo[cd]azulene-5-carboxylate To a solution of tert-butyl (R or S)-7-acryloyl-2-(4-cyclopropyl-2-hydroxyphenyl)-2,3,4,5a,6,7,8,9-octahydro-5H-1,2,5,7-tetraazabenzo[cd]azulene-5-carboxylate (150 mg, 1 Equiv., 323 μmol) in NMP (0.2 mL) was added sodium chloro(difluoro)acetate (148 mg, 3 Equiv., 969 gmol) and $Cs_2CO_3$ (210 mg, 2 Equiv., 646 gmol) The mixture was warmed to 100° C. and stirred for 24 h. The mixture was then cooled and diluted with ice water (100 mL) and EA (100 mL), and the aqueous layer was extracted with EA (2×100 mL). The combined organic layers were washed with saturated brine (3×100 mL), dried over anhydrous sodium sulfate, and concentrated to give a residue. The residue was purified by flash column chromatography (120 g silica gel column, 25% EA in PE) to afford tert-butyl (R or S)-7-acryloyl-2-(4-cyclopropyl-2-(difluoromethoxy)phenyl)-2,3,4,5a,6,7,8,9-octahydro-5H-1,2,5,7-tetraazabenzo[cd]azulene-5-carboxylate (30 mg) as a yellow solid. LCMS: (ESI, m/z): 515 $[M+H]^+$

Step 3: Synthesis of (R or S)-1-(2-(4-cyclopropyl-2-(difluoromethoxy)phenyl)-2,3,4,5,5a,6,8,9-octahydro-7H-1,2,5,7-tetraazabenzo[cd]azulen-7-yl)prop-2-en-1-one A solution of tert-butyl (R or S)-7-acryloyl-2-(4-cyclopropyl-2-(difluoromethoxy)phenyl)-2,3,4,5a,6,7,8,9-octahydro-5H-1,2,5,7-tetraazabenzo[cd]azulene-5-carboxylate (30 mg, 1 Equiv., 58 μmol) in DCM (0.6 mL) and TFA (0.2 mL) was stirred at rt for 1 h. The solvent was then removed under reduced pressure to afford (R or S)-1-(2-(4-cyclopropyl-2-(difluoromethoxy)phenyl)-2,3,4,5,5a,6,8,9-octahydro-7H-1,2,5,7-tetraazabenzo[cd]azulen-7-yl)prop-2-en-1-one (25 mg) as a crude yellow oil which was used in the next step directly without further purification. LCMS: (ESI, m/z): 415 $[M+H]^+$

Step 4: Synthesis of (R or S)-1-(5-(4-amino-6-(trifluoromethyl)nicotinoyl)-2-(4-cyclopropyl-2-(difluoromethoxy)phenyl)-2,3,4,5,5a,6,8,9-octahydro-7H-1,2,5,7-tetraazabenzo[cd]azulen-7-yl)prop-2-en-1-one To a solution of (R or S)-1-(2-(4-cyclopropyl-2-(difluoromethoxy)phenyl)-2,3,4,5,5a,6,8,9-octahydro-7H-1,2,5,7-tetraazabenzo[cd]azulen-7-yl)prop-2-en-1-one (30 mg, 1 Equiv., 72 gmol) in DMA (0.5 mL) were added 4-amino-6-(trifluoromethyl)nicotinic acid (17.9 mg, 1.2 Equiv., 86.9 μmol), DIEA (46.8 mg, 63.0 μL, 5 Equiv., 362 mol) and HATU (55.0 mg, 2 Equiv., 145 mol). The resulting mixture was stirred for 1 h at rt, after which the mixture was diluted with water (20 mL) and EA (20 mL). The aqueous layer was then extracted with EA (2×20 mL), and the combined organic layers were washed with saturated brine (2×20 mL), dried over anhydrous sodium sulfate and concentrated to give a residue. The residue was purified by Prep-HPLC (Column: XBridge Shield RP18 OBD Column 30*150 mm, 5 μm; Mobile Phase A: Water(10 mmol/L $NH_4HCO_3$), Mobile Phase B: ACN; Flow rate: 60 mL/min mL/min; Gradient: 39% B to 53% B in 10 min) to afford (R or S)-1-(5-(4-amino-6-(trifluoromethyl)nicotinoyl)-2-(4-cyclopropyl-2-(difluoromethoxy)phenyl)-2,3,4,5,5a,6,8,9-octahydro-7H-1,2,5,7-tetraazabenzo[cd]azulen-7-yl)prop-2-en-1-one (3.2 mg) as a white solid. LCMS: (ESI, m/z): 603 $[M+H]^+$. 1H NMR (400 MHz, Chloroform-d) δ 8.31 (s, 1H), 7.55-7.31 (m, 2H), 7.10-6.91 (m, 3H), 6.57-6.08 (m, 2H), 5.91-5.72 (m, 1H), 5.45-5.25 (m, 3H), 4.97 (d, J=13.4 Hz, 1H), 4.74-4.41 (m, 1H), 4.25-4.06 (m, 1H), 3.27-3.16 (m, 2H), 3.12-2.91 (m, 2H), 2.89-2.71 (m, 2H), 2.48 (d, J=15.8 Hz, 1H), 2.03-1.82 (m, 1H), 1.16-1.00 (m, 2H), 0.78-0.68 (m, 2H).

Example A-21: Preparation of (R or S)-1-(5-(4-amino-6-(trifluoromethyl)nicotinoyl)-2-(4-cyclopropyl-2-(trifluoromethyl)phenyl)-2,3,4,5,5a,6,8,9-octahydro-7-1,2,5,7-tetraazabenzo[cd]azulen-7-yl)prop-2-en-1-one

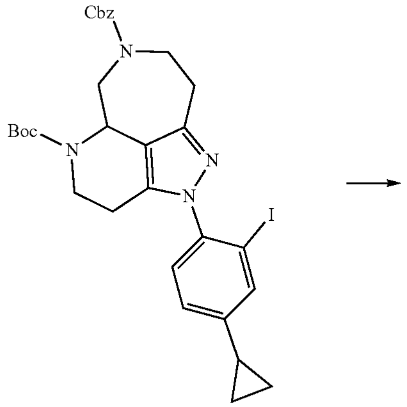

Int. QQ

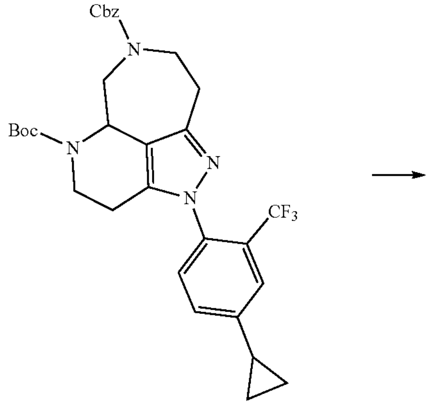

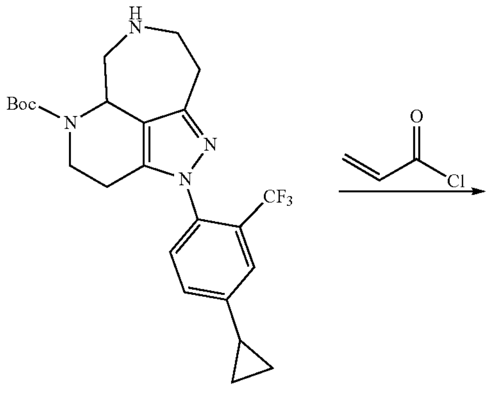

-continued

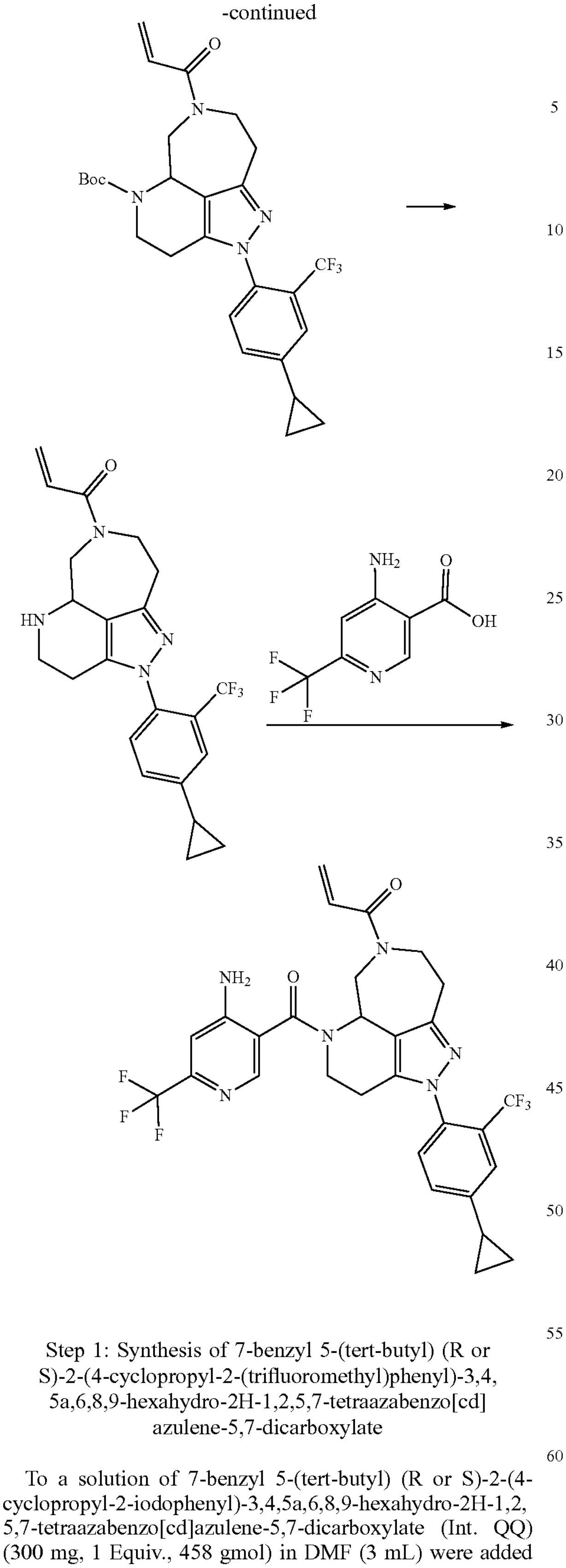

Step 1: Synthesis of 7-benzyl 5-(tert-butyl) (R or S)-2-(4-cyclopropyl-2-(trifluoromethyl)phenyl)-3,4,5a,6,8,9-hexahydro-2H-1,2,5,7-tetraazabenzo[cd]azulene-5,7-dicarboxylate To a solution of 7-benzyl 5-(tert-butyl) (R or S)-2-(4-cyclopropyl-2-iodophenyl)-3,4,5a,6,8,9-hexahydro-2H-1,2,5,7-tetraazabenzo[cd]azulene-5,7-dicarboxylate (Int. QQ) (300 mg, 1 Equiv., 458 gmol) in DMF (3 mL) were added methyl difluoro(fluorosulphonyl)acetate (616 mg, 407 μL, 7 Equiv., 3.21 mmol) and CuI (611 mg, 7 Equiv., 3.21 mmol). The resulting mixture was stirred for 6 h at 60° C., after which the mixture was diluted with ice water (50 mL) and EA (50 mL), and the aqueous layer was extracted with EA (2×100 mL). The combined organic layers were washed with saturated brine (3×50 mL), dried over anhydrous sodium sulfate and concentrated to give a residue. The residue was purified by flash column chromatography (40 g silica gel column, 30% EA in PE) to afford 7-benzyl 5-(tert-butyl) (R or S)-2-(4-cyclopropyl-2-(trifluoromethyl)phenyl)-3,4,5a,6,8,9-hexahydro-2H-1,2,5,7-tetraazabenzo[cd]azulene-5,7-dicarboxylate (120 mg) as a yellow solid. LCMS: (ESI, m/z): 597 [M+]

Step 2: Synthesis of Tert-Butyl (R or S)-2-(4-cyclopropyl-2-trifluoromethyl)phenyl)-2,3,4,5a,6,7,8,9-octahydro-5H-1,2,5,7-tetraazabenzo[cd]azulene-5-carboxylate To a solution of 7-benzyl 5-(tert-butyl) (R or S)-2-(4-cyclopropyl-2-(trifluoromethyl)phenyl)-3,4,5a,6,8,9-hexahydro-2H-1,2,5,7-tetraazabenzo[cd]azulene-5,7-dicarboxylate (80 mg, 1 Equiv., 0.13 mmol) in DCM (1 mL) were added Pd/C (40 mg, 2.8 Equiv., 0.38 mmol). The mixture was purged with nitrogen three times, and then was pressurized to 0.4 MPa with hydrogen at rt and the mixture was stirred for 4 h. The reaction mixture was then filtered, and the filtrate was concentrated under reduced pressure to afford tert-butyl (R or S)-2-(4-cyclopropyl-2-(trifluoromethyl)phenyl)-2,3,4,5a,6,7,8,9-octahydro-5H-1,2,5,7-tetraazabenzo[cd]azulene-5-carboxylate (80 mg) as a crude white solid which was used in the next step directly without further purification. LCMS: (ESI, m/z): 463 $[M+H]^+$ Step 3: Synthesis of Tert-Butyl (R or S)-7-acryloyl-2-(4-cyclopropyl-2-(trifluoromethyl)phenyl)-2,3,4,5a,6,7,8,9-octahydro-5H-1, 2,5,7-tetraazabenzo[cd]azulene-5-carboxylate To a solution of tert-butyl (R or S)-2-(4-cyclopropyl-2-(trifluoromethyl)phenyl)-2,3,4,5a,6,7,8,9-octahydro-5H-1,2,5,7-tetraazabenzo[cd]azulene-5-carboxylate (130 mg, 1 Equiv., 281 μmol) in DCM (1.3 mL) was added TEA (85.3 mg, 118 μL, 3 Equiv., 843 μmol). The mixture was then cooled to 0° C., and acryloyl chloride (25.4 mg, 1 Equiv., 281 μmol) was added dropwise to the above mixture at 0° C. under an atmosphere of nitrogen. The mixture was then stirred for 30 min, after which the mixture was diluted with ice water (20 mL) and EA (20 mL), and the aqueous layer was extracted with EA (2×20 mL). The combined organic layers wire washed with saturated brine (3×20 mL), dried over anhydrous sodium sulfate and concentrated to give a residue. The residue was purified by flash column chromatography (25 g silica gel column, 70% EA in PE) to afford tert-butyl (R or S)-7-acryloyl-2-(4-cyclopropyl-2-(trifluoromethylphenyl)-2,3,4,5a,6,7,8,9-octahydro-5H-1,2,5,7-tetraazabenzo[cd]azulene-5-carboxylate (110 mg) as a yellow solid. LCMS: (ESI, m/z): 517 $[M+H]^+$ Step 4: Synthesis of (R or S)-1-(2-(4-cyclopropyl-2-(trifluoromethyl)phenyl)-2,3,4,5,5a,6,8,9-octahydro-7H-1,2,5,7-tetraazabenzo[cd]azulen-7-yl)prop-2-en-1-one A solution of tert-butyl (R or S)-7-acryloyl-2-(4-cyclopropyl-2-(trifluoromethyl)phenyl)-2,3,4,5a,6,7,8,9-octahydro-5H-1,2,5,7-tetraazabenzo[cd]azulene-5-carboxylate (100 mg, 1 Equiv., 194 μmol) in DCM (3 mL) and TFA (1 mL) was stirred at rt for 1 h. The solvent was then removed under reduced pressure to afford (R or S)-1-(2-(4-cyclopropyl-2-trifluoromethyl)phenyl)-2,3,4,5,5a,6,8,9-octahydro-7H-1,2,5,7-tetraazabenzo[cd]azulen-7-yl)prop-2-en-1-one (100 mg) as a crude yellow oil which was used in the next step directly without further purification. LCMS: (ESI, m/z): 417 $[M+H]^+$ Step 5: Synthesis of (R or S)-1-(5-(4-amino-6-(trifluoromethyl)nicotinoyl)-2-(4-cyclopropyl-2-(trifluoromethyl)phenyl)-2,3,4,5,5a,6,8,9-octahydro-7H-1,2,5,7-tetraazabenzo[cd]azulen-7-yl)prop-2-en-1-one To a solution of (R or S)-1-(2-(4-cyclopropyl-2-(trifluoromethyl)phenyl)-2,3,4,5,5a,6,8,9-octahydro-7H-1,2,5,7-tetraazabenzo[cd]azulen-7-yl)prop-2-en-1-one (90 mg, 1 Equiv., 0.22 mmol) in DMA (1 mL) were added 4-amino-6-(trifluoromethyl)nicotinic acid (67 mg, 1.5 Equiv., 0.32 mmol), DIEA (0.17 g, 6 Equiv., 1.3 mmol) and HATU (0.12 g, 1.5 Equiv., 0.32 mmol). The mixture was stirred at rt for 3 h, after which the mixture was diluted with water (20 mL) and EA (20 mL), and the aqueous layer was extracted with EA (2×20 mL). The combined organic layers were washed with saturated brine (2×20 mL), dried over anhydrous sodium sulfate and concentrated to give a residue. The residue was purified by Prep-HPLC (Column: XBridge Prep Phenyl OBD Column 19*250 mm, 5 μm; Mobile Phase A: Water(10 mmol/L $NH_4HCO_3$), Mobile Phase B: ACN; Flow rate: 60 mL/min mL/min; Gradient: 5% B to 5% 3 in 1 min, 5% B to 33% B in 2 min, 33% to 50% B in 11 min) to afford (R or S)-1-(5-(4-amino-6-(trifluoromethyl)nicotinoyl)-2-(4-cyclopropyl-2-(trifluoromethyl)phenyl-2,3,4,5,5a,6,8,9-octahydro-7H-1,2,5,7-tetraazabenzo[cd]azulen-7-yl)prop-2-en-1-one (19.4 mg) as a white solid. LCMS: (ESI, m/z): 605 $[M+H]^+$. 1H NMR (400 MHz, Chloroform-d) δ 8.28 (s, 1H), 7.52-7.47 (m, 1H), 7.31 (dd, J=8.2, 2.0 Hz, 1H), 7.27 (s, 1H), 7.25 (s, 1H), 7.01 (s, 1H), 6.50 (d, J=16.4 Hz, 1H), 5.92-5.80 (m, 1H), 5.37-5.27 (m, 3H), 4.97 (d, J=13.1 Hz, H), 4.50 (d, J=13.4 Hz, 1H), 4.13-4.09 (m, 1H), 3.28-3.21 (m, 2H), 3.15-2.85 (m, 2H), 2.85-2.48 (m, 2H), 2.37 (d, J=15.6 Hz, 1H), 2.02-1.98 (m, 1H), 1.19-1.06 (m, 2H), 0.79-0.68 (m, 2H).

Example A-22: Preparation of 1-((5a(R or S),9(R or S))-5-(4-amino-6-(trifluoromethyl)nicotinoyl)-2-(4-cyclopropylphenyl)-9-hydroxy-2,3,4,5,5a,6,8,9-octahydro-7H-1,2,5,7-tetraazabenzo[cd]azulen-7-yl)prop-2-en-1-one

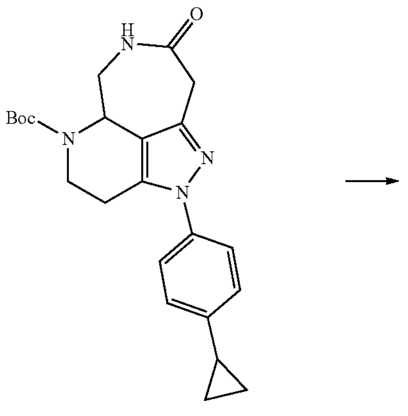

Int. E''

-continued

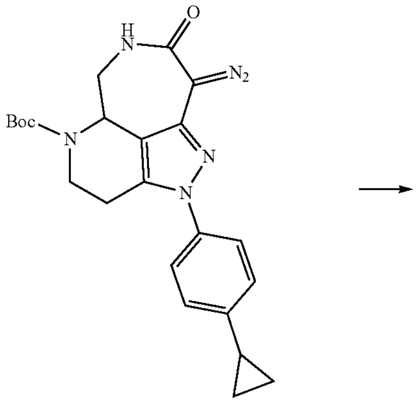

Int. E'''

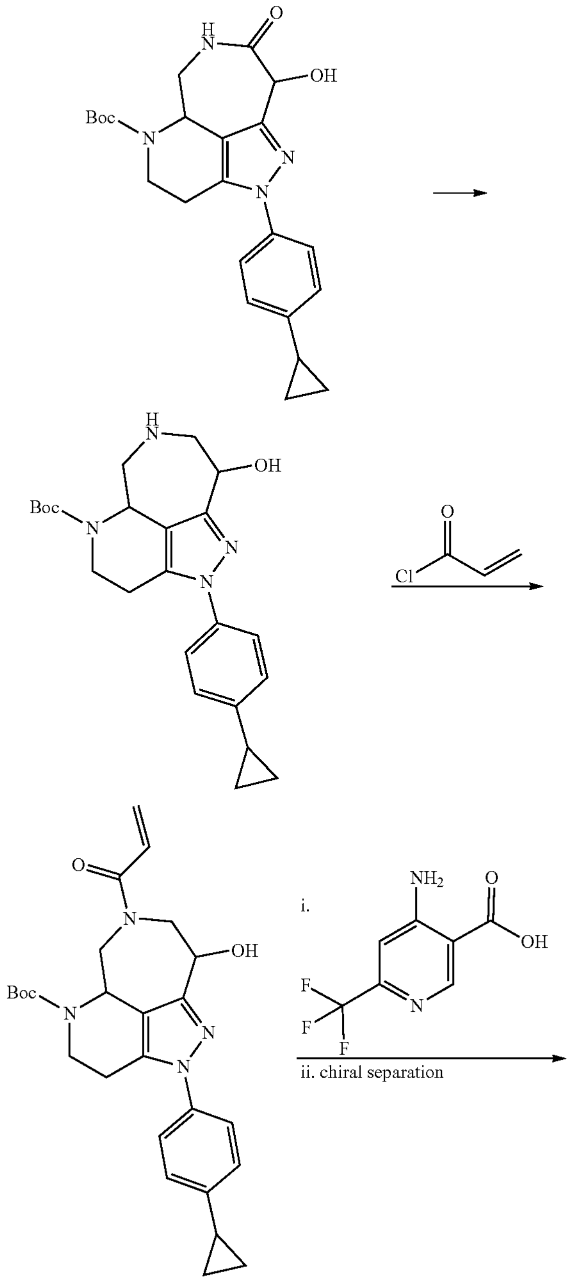

-continued

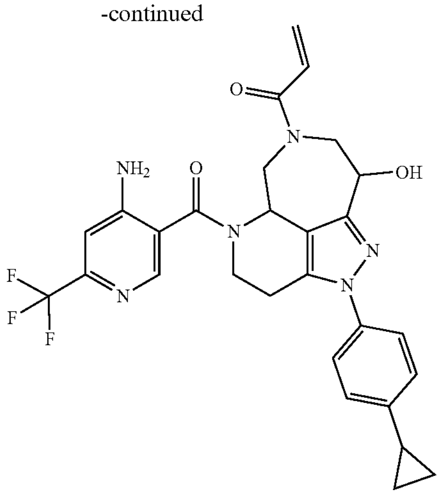

Step 1: Synthesis of Tert-Butyl 2-(4-cyclopropylphenyl)-9-diazo-8-oxo-2,3,4,5a,6,7,8,9-octahydro-5H-1,2,5,7-tetraazabenzo[cd]azulene-5-carboxylate. (Int. E''')

To a solution of Int. E'' (3 g, 1 Equiv., 7 mmol) in acetonitrile (60 mL) were added 1,8-diazabicyclo[5.4.0]undec-7-ene (2 g, 2 mL, 1.5 Equiv., 0.01 mol) and p-toluenesulfonyl azide (4 g, 5 mL, 3 Equiv., 0.02 mol). The mixture was stirred at rt for 12 h, and the resulting mixture was quenched with water (100 mL) and extracted with EA (2×100 mL). The combined organic layers were washed with brine (100 mL), dried over $Na_2SO_4$, filtered, and evaporated under reduced pressure. The residue was purified by silica gel column chromatography, eluting with DCM/EA (3:1) to afford tert-butyl 2-(4-cyclopropylphenyl)-9-diazo-8-oxo-2,3,4,5a,6,7,8,9-octahydro-5H-1,2,5,7-tetraazabenzo[cd]azulene-5-carboxylate (2.7 g) as a yellow solid. LCMS: (ESI, m/z): 435 $[M+H]^+$ Step 2: Synthesis of Tert-Butyl 2-(4-cyclopropylphenyl)-9-hydroxy-8-oxo-2,3,4,5a,6,7,8,9-octahydro-5H-1,2,5,7-tetraazabenzo [cd]azulene-5-carboxylate To a stirred solution of tert-butyl 2-(4-cyclopropylphenyl)-9-diazo-8-oxo-2,3,4,5a,6,7,8,9-octahydro-5H-1,2,5,7-tetraazabenzo[cd]azulene-5-carboxylate (450 mg, 1 Equiv., 1.04 mmol) in 1,2-dichloroethane (9 mL) and water (0.9 mL) was added rhodium(II)acetate dimer (45.8 mg, 0.1 Equiv., 104 mol). The resulting solution was placed un er a positive pressure of nitrogen and subjected to three evacuation cycles under high vacuum. The resulting mixture was stirred for 2 h at 80° C., after which it was quenched by the addition of water (20 mL) at rt. The resulting mixture was extracted with EA (2×30 mL). The combined organic layers were washed with water (2×50 mL) and brine (1×50 mL) and dried over anhydrous $Na_2SO_4$. After filtration, the filtrate was concentrated under reduced pressure. The residue was purified by silica gel column chromatography, eluting with EA/PE (1:2) to afford tert-butyl 2-(4-cyclopropylphenyl)-9-hydroxy-8-oxo-2,3,4,5a,6,7,8,9-octahydro-5H-1,2,5,7-tetraazabenzo [cd]azulene-5-carboxylate (420 mg) as a yellow solid. LCMS: (ESI, m/z): 425 $[M+H]^+$ Step 3: Synthesis of Tert-Butyl 2-(4-cyclopropylphenyl)-9-hydroxy-2,3,4,5a,6,7,8,9-octahydro-5H-1,2,5,7-tetraazabenzo[cd]azulene-5-carboxylate To a stirred solution of tert-butyl 2-(4-cyclopropylphenyl)-9-hydroxy-8-oxo-2,3,4,5a,6,7,8,9-octahydro-5H-1,2,5,7-tetraazabenzo[cd]azulene-5-carboxylate (570 mg, 1 Equiv., 1.34 mmol) in THF (11.4 mL) was added $BH_3$·THF (462 mg, 518 µL, 4 Equiv., 5.37 mmol) at 60° C. and the mixture was stirred for 2 h. The resulting solution was concentrated under reduced pressure, and the mixture was then diluted and stirred with MeOH (30 mL) for 0.5 h. the reaction mixture was concentrated under reduced pressure to afford tert-butyl 2-(4-cyclopropylphenyl)-9-hydroxy-2,3,4,5a,6,7,8,9-octahydro-5H-1,2,5,7-tetraazabenzo[cd]azulene-5-carboxylate (410 mg) as a crude white solid which was used in the next step without further purification. LCMS: (ESI, m/z): 411 $[M+H]^+$ Step 4: Synthesis of Tert-Butyl (5a(S or R),9(Sor R) and 5a(S or R),9(S or R))-7-acryloyl-2-(4-cyclopropylphenyl)-9-hydroxy-2,3,4,5a,6,7,8,9-octahydro-5H-1,2,5,7-tetraazabenzo[cd]azulene-5-carboxylate To a stirred solution of tert-butyl 2-(4-cyclopropylphenyl)-9-hydroxy-2,3,4,5a,6,7,8,9-octahydro-5H-1,2,5,7-tetraazabenzo[cd]azulene-5-carboxylate (320 mg, 1 Equiv., 779 gmol) in DCM (6.4 mL) was added acryloyl chloride (106 mg, 1.5 Equiv., 1.17 µmol) and TEA (237 mg, 3 Equiv., 2.34 mmol) and the reaction mixture was stirred at rt for 1 h. The reaction was then concentrated under reduced pressure, and the residue was purified by silica gel column chromatography, eluting with PE/EA (2:1) to afford of tert-butyl (5a(S or R),9(Sor R) and 5a(S or R),9(S or R))-7-acryloyl-2-(4-cyclopropylphenyl)-9-hydroxy-2,3,4,5a,6,7,8,9-octahydro-5H-1,2,5,7-tetraazabenzo[cd]azulene-5-carboxylate (100 mg) as a white solid as a single diastereomer. LCMS: (ESI, m/z): 465 $[M+H]^+$ Step 5: Synthesis of 1-((5a(R or S),9(R or S))-5-(4-amino-6-(trifluoromethyl)nicotinoyl)-2-(4-cyclopropylphenyl)-9-hydroxy-2,3,4,5,5a,6,8,9-octahydro-7H-1,2,5,7-tetraazabenzo[cd]azulen-7-yl)prop-2-en-1-one To a stirred solution of tert-butyl (5a(S or R),9(S or R) and 5a(S or R),9(S or R))-7-acryloyl-2-(4-cyclopropylphenyl)-9-hydroxy-2,3,4,5a,6,7,8,9-octahydro-5H-1,2,5,7-tetraazabenzo[cd]azulene-5-carboxylate (45 mg, 1 Equiv., 0.12 mmol) and 4-amino-6-(trifluoromethyl)nicotinic acid (25 mg, 1 Equiv., 0.12 mmol) in DMF (0.45 mL) were added HATU (61 mg, 1.3 Equiv., 0.16 mmol) and DIEA (96 mg, 0.13 mL, 6 Equiv., 0.74 mmol) and the mixture was stirred for 1 h at rt. The mixture was then diluted with water (10 mL) and EA (10 mL), and the aqueous layer was extracted with EA (2×10 mL). The combined organic layers were washed with saturated brine (2×20 mL), dried over anhydrous sodium sulfate and concentrated to give a residue. The residue was purified by Prep-HPLC with the following conditions Column: (Column: Xselect CSH Fluoro-Phenyl, 30 mm*150 mm; Mobile Phase A: Water (0.1% FA), Mobile Phase B: ACN; Flow rate: 60 mL/min; Gradient: 30% B to 46% B in 8 min; Wave Length: UV 254 nm/220 nm) to afford the racemic product (22.8 mg). The racemate was purified by Prep-Chiral-HPLC with the following conditions: (Column: CHIRALPAK-IC 2*25 cm, 5 µm; Mobile Phase A: HEX(0.1% DEA), Mobile Phase B: MeOH: DCM=1:1; Flow rate: 20 mL/min; Gradient: isocratic 50; Wave Length: UV 254/220 nm; RT1(min): 9; RT2(min): 15) to afford 1-((5a(R or S),9(R or S))-5-(4-amino-6-(trifluoromethyl)nicotinoyl)-2-(4-cyclopropylphenyl)-9-hydroxy-2,3,4,5,5a,6,8,9-octahydro-7H-1,2,5,7-tetraazabenzo[cd]azulen-7-yl)prop-2-en-1-one (8.7 mg) as a white solid as the second-eluting enantiomer. LCMS: (ESI, m/z): 553 [M+H]. $^1$H NMR: (400 MHz, Chloroform-d, ppm) (8.34 (s, 1H), 7.40-7.30 (m, 2H), 7.20-7.12 (m, 2H), 6.95-6.32 (m, 2H), 5.98-5.60 (m, 1H), 5.51-5.20 (m, 2H), 5.09-4.63 (m, 2H), 4.58-4.02 (m, 2H), 3.39-2.88 (m, 3H), 2.88-2.64 (m, 2H), 2.08-1.84 (m, 2H), 1.09-0.97 (m, 3H), 0.79-0.66 (m, 3H).

Example A-23: Preparation of 1-((5a(R or S),9(R or S))-7-acryloyl-2 (4-cyclopropylphenyl)-5-(4-(trifluoromethyl)benzoyl)-3,4,5,5a,6,7,8,9-octahydro-2H-1,2,5,7-tetraazabenzo[cd]azulen-9-yl)pyridin-2(1H)-one

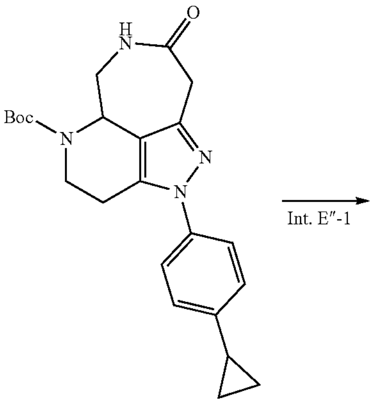

Int. E″

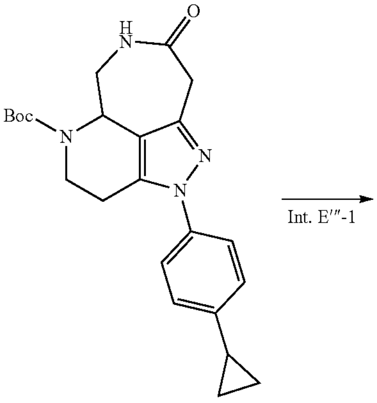

-continued

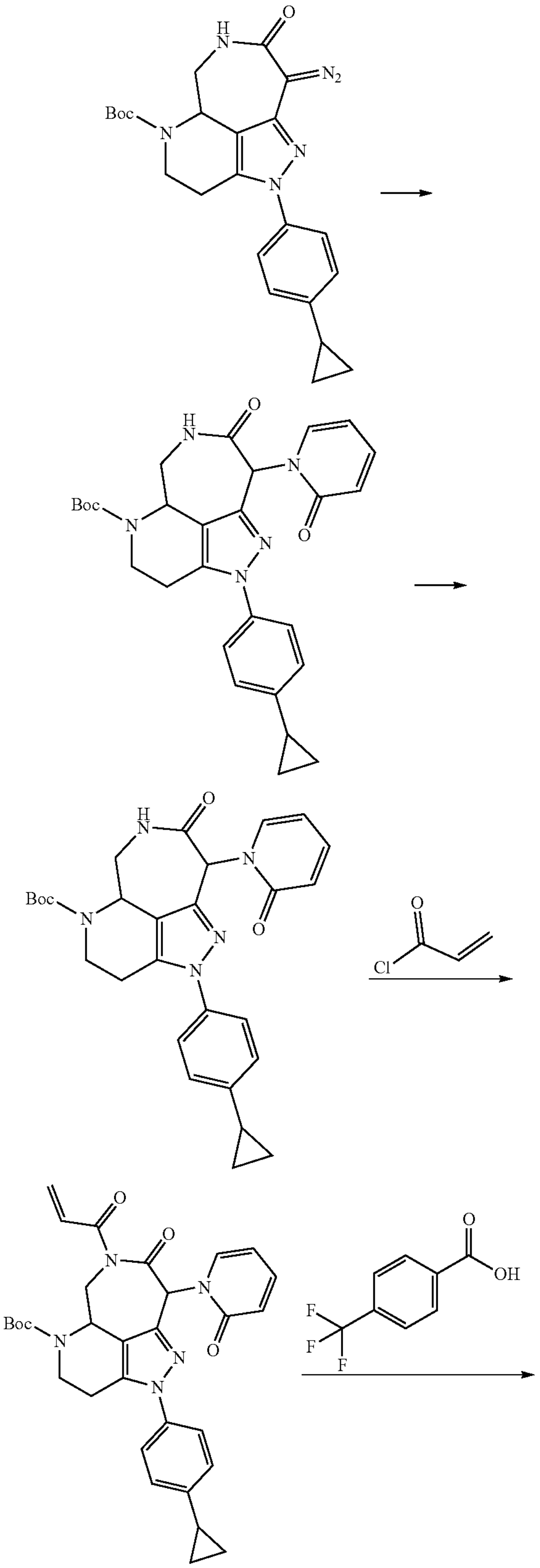

-continued

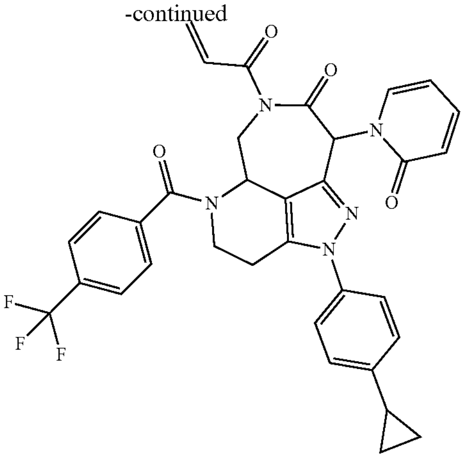

Step 1: Separation of Int. E" to Afford Int. E"-1

Racemic Int. E" was purified by Prep-Chiral-HPLC with the following conditions (Column: CHIRAL ART Cellulose-SC, 5*25 cm, 10 μm; Mobile Phase: $CO_2$, Mobile Phase B: EtOH; Flow rate: 200 mL/min; Gradient: isocratic 55% B; Column Temperature(° C.): 30; Back Pressure(bar): 100; Wave Length: 280 nm; RT1(min): 8; RT2(min): 11) to afford tert-butyl (R or S)-2-(4-cyclopropylphenyl)-8-oxo-2,3,4,5a,6,7,8,9-octahydro-5H-1,2,5,7-tetraazabenzo[cd]azulene-5-carboxylate (Int. E"-1) (20 g) as the second-eluting peak as a white solid.

Step 2: Synthesis of Tert-Butyl (R or S)-2-(4-cyclopropylphenyl)-9-diazo-8-oxo-2,3,4,5a,6,7,8,9-octahydro-5H-1,2,5,7-tetraazabenzo[cd]azulene-5-carboxylate (Int. E'"-1)

A solution of Int. E"-1 (6.8 g, 1 Equiv., 17 mmol) in MeCN (6 mL) was cooled to 0° C., then DBU (3.8 g, 3.7 mL, 1.5 Equiv., 25 mmol) and p-toluenesulfonyl azide (13 g, 15 mL, 75 wt %, 3 Equiv., 50 mmol) was added dropwise to the above mixture at 0° C. under a nitrogen atmosphere. The mixture was warmed to rt and was stirred for 2 h, after which the mixture was diluted with ice water (200 mL) and EA (200 mL), and the aqueous layer was extracted with EA (2×200 mL). The combined organic layers were washed with saturated brine (2×200 mL), dried over anhydrous sodium sulfate and concentrated to give a residue. The residue was purified by flash column chromatography, eluting with EA/DCM (1:1) to afford tert-butyl (R or S)-2-(4-cyclopropylphenyl)-9-diazo-8-oxo-2,3,4,5a,6,7,8,9-octahydro-5H-1,2,5,7-tetraazabenzo[cd]azulene-5-carboxylate (Int. E'"-1) (5.2 g) as a yellow solid. LCMS: (ESI, m/z): 435 $[M+H]^+$ Step 3: Synthesis of Tert-Butyl (5a(R or S),9(S or R))-2-(4-cyclopropylphenyl)-8-oxo-9-(2-oxopyridin-1(2H)-yl)-2,3,4,5a,6,7,8,9-octahydro-5H-1, 2,5,7-tetraazabenzo[cd]azulene-5-carboxylate To a solution of tert-butyl (R or S)-2-(4-cyclopropylphenyl)-9-diazo-8-oxo-2,3,4,5a,6,7,8,9-octahydro-5H-1,2,5,7-tetraazabenzo[cd]azulene-5-carboxylate (0.41 g, 1 Equiv., 0.95 mmol) in dry dioxane (4.1 mL) were added pyridin-2-ol (60 mg, 0.7 Equiv., 0.63 mmol) and triflic acid (9.5 mg, 5.6 μL, 0.1 Equiv., 63 μmol). The reaction system was purged and backfilled with nitrogen (3×), and the resulting mixture was stirred for 3 h at rt. The solvent was then removed under reduced pressure, and the residue was purified by flash column chromatography (80 g silica gel column, 25% EA in PE) to afford tert-butyl (5a(R or S),9(S or R))-2-(4-cyclopropylphenyl)-8-oxo-9-(2-oxopyridin-1(2H)-yl)-2,3,4,5a,6,7,8,9-octahydro-5H-1,2,5,7-tetraazabenzo[cd]azulene-5-carboxylate (100 mg) as a yellow solid. LCMS: (ESI, m/z): 502 $[M+H]^+$ Step 4: Synthesis of Tert-Butyl (5a(R or S),9(R or S))-2-(4-cyclopropylphenyl)-9-(2-oxopyridin-1(2H)-yl)-2,3,4,5a,6,7,8,9-octahydro-5H-1, 2,5,7-tetraazabenzo[cd]azulene-5-carboxylate To a solution of zinc chloride (68 mg, 32 μL, 5 Equiv., 0.50 ol) in THF (1.4 mL) was added $NaBH_4$ (19 mg, 5 Equiv., 0.50 mmol). The mixture was cooled to ° C., then tert-butyl (5a(R or S),9(S or R))-2-(4-cyclopropylphenyl)-8-oxo-9-(2-oxopyridin-1(2H)-yl)-2,3,4,5a,6,7,8,9-octahydro-5H-1,2,5,7-tetraazabenzo[cd]azulene-5-carboxylate (50 mg, Equiv., 0.10 mmol) was added dropwise to the above mixture at 0° C. under a nitrogen atmosphere. The mixture was warmed to rt and stirred for 2 h. The mixture was then diluted with ice water (20 mL) and EA (20 mL), and the aqueous layer was extracted with EA (2×20 mL). The combined organic layers were washed with saturated brine (2×20 mL), dried over anhydrous sodium sulfate, and concentrated to afford tert-butyl (5a(R or S),9(R or S))-2-(4-cyclopropylphenyl)-9-(2-oxopyridin-1(2H)-yl)-2,3,4,5a,6,7,8,9-octahydro-5H-1,2,5,7-tetraazabenzo[cd]azulene-5-carboxylate (50 mg) as a crude yellow oil which was used in the next step directly without further purification. LCMS: (ESI, m/z): 488 $[M+H]^+$ Step 5: Synthesis of Tert-Butyl (5a(R or S),9(R or S))-7-acryloyl-2-(4-cyclopropylphenyl)-9-(2-oxopyridin-1(2H)-yl)-2,3,4,5a,6,7,8,9-octahydro-5H-1,2,5,7-tetraazabenzo[cd]azulene-5-carboxylate To a solution of tert-butyl (5a(R or S),9(R or S))-2-(4-cyclopropylphenyl)-9-(2-oxopyridin-1(2H)-yl)-2,3,4,5a,6,7,8,9-octahydro-5H-1,2,5,7-tetraazabenzo[cd]azulene-5 -carboxylate (50 mg, 1 Equiv., 0.10 mmol) in DCM (1 mL) were added acryloyl chloride (14 mg, 12 μL, 1.5 Equiv., 0.15 mmol) and TEA (31 mg, 43 μL, 3 Equiv., 0.31 mmol). The mixture was stirred at rt for 1 h, after which the solvent was removed under reduced pressure. The residue was purified by flash column chromatography (4 g silica gel column, 25% EA in PE) to afford tert-butyl (5a(R or S),9(R or S))-7-acryloyl-2-(4-cyclopropylphenyl)-9-(2-oxopyridin-1(2H)-yl)-2,3,4,5a,6,7,8,9-octahydro-5H-1,2,5,7-tetraazabenzo [cd]azulene-5-carboxylate (10 mg) as a yellow oil. LCMS: (ESI, m/z): 542 $[M+H]^+$ Step 6: Synthesis of 1-((5a(R or S),9(R or S))-7-acryloyl-2-(4-cyclopropylphenyl)-3,4,5,5a,6,7,8,9-octahydro-2H-1,2,5,7-tetraazabenzo[cd]azulen-9-yl) pyridin-2(1H)-one The solution of tert-butyl (5a(R or S),9(R or S))-7-acryloyl-2-(4-cyclopropylphenyl)-9-(2-oxopyridin-1(2H)-yl)-2,3,4,5a,6,7,8,9-octahydro-5H-1,2,5,7-tetraazabenzo [cd]azulene-5-carboxylate (10 mg, 1 Equiv., 18 μmol) in DCM (1 mL) and TFA (0.3 mL) was stirred at rt for 1 h. The solvent was then removed under reduced pressure to afford 1-((5a(R or S),9(R or S))-7-acryloyl-2-(4-cyclopropylphenyl)-3,4,5,5a,6,7,8,9-octahydro-2H-1,2,5,7-tetraazabenzo [cd]azulen-9-yl)pyridin-2(1H)-one (10 mg) as a crude yellow oil which was used in the next step directly without further purification. LCMS: (ESI, m/z): 442 $[M+H]^+$ Step 7: Synthesis of 1-((5a(R or S),9(R or S))-7-acryloyl-2-(4-cyclopropylphenyl)-5-(4-(trifluoromethyl)benzoyl)-3,4,5,5a,6,7,8,9-octahydro-2H-1, 2,5, 7-tetraazabenzo[cd]azulen-9-yl)pyridin-2(1H)-one To a solution of 1-((5a(R or S),9(R or S))-7-acryloyl-2-(4-cyclopropylphenyl)-3,4,5,5a,6,7,8,9-octahydro-2H-1,2,5,7-tetraazabenzo[cd]azulen-9-yl)pyridin-2(1H)-one (10 mg, 1 Equiv., 23 μmol) in DMA (1 mL) were added HATU (13 mg, 1.5 Equiv., 34 μmol), 4-(trifluoromethyl)benzoic acid (6.5 mg, 1.5 Equiv., 34 μmol) and DIEA (18 mg, 5 Equiv., 0.14 mmol). The mixture was stirred at 40° C. for 12 h, after which the mixture was diluted with water (20 mL) and EA (20 mL), and the aqueous layer was extracted with EA (2×20 mL). The combined organic layers were washed with saturated brine (2×20 mL), dried over anhydrous sodium sulfate and concentrated to give a residue. The residue was purified by Prep-HPLC (Column: XBridge Shield RP18 OBD Column 19*250 mm, 10 μm; Mobile Phase A: Water (10 mmol/L $NH_4HCO_3$), Mobile Phase B: ACN; Flow rate: 60 mL/min mL/min; Gradient: 5% B to 5% B in 1 min, 5% B to 48% B in 2 min, 48% to 68% B in 12 min) to afford 1-((5a(R or S),9(R or S))-7-acryloyl-2-(4-cyclopropylphenyl)-5-(4-(trifluoromethyl)benzoyl)-3,4,5,5a,6,7,8,9-octahydro-2H-1,2,5,7 -tetraazabenzo[cd]azulen-9-yl)pyridin-2 (1H)-one (0.8 mg) as a white solid. LCMS: (ESI, m/z): 614 $[M+H]^+$. $^1H$ NMR (400 MHz, Chloroform-d) δ 8.30-8.14 (m, 1H), 7.80-7.73 (m, 3H), 7.65-7.63 (m, 1H), 7.62-7.56 (m, 1H), 7.38-7.33 (m, 1H), 7.15-7.04 (m, 3H), 7.04-6.87 (m, 1H), 6.59-6.47 (m, 2H), 6.43-6.25 (m, 1H), 5.97-5.80 (m, 1H), 5.66-5.36 (m, 1H), 5.17-5.00 (m, 1H), 4.69-4.45 (m, 1H), 4.34-4.15 (m, 1H), 4.04-3.85 (m, 1H), 3.32-2.87 (m, 3H), 2.78-2.61 (m, 1H), 2.37-1.61 (m, 2H), 1.04-0.92 (m, 2H), 0.76-0.60 (m, 2H).

Example A-24: Preparation of (R or S)-1-(5-(4-amino-6-(difluoromethoxy)nicotinoyl)-2-(4-cyclopropylphenyl)-2,3,4,5,5a,6,8,9-octahydro-7H-1,2,5,7-tetraazabenzo[cd]azulen-7-yl)prop-2-en-1-one

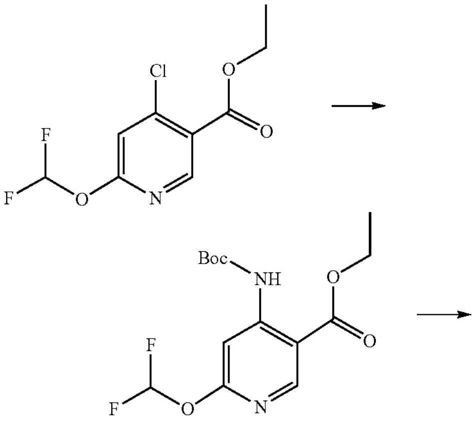

-continued

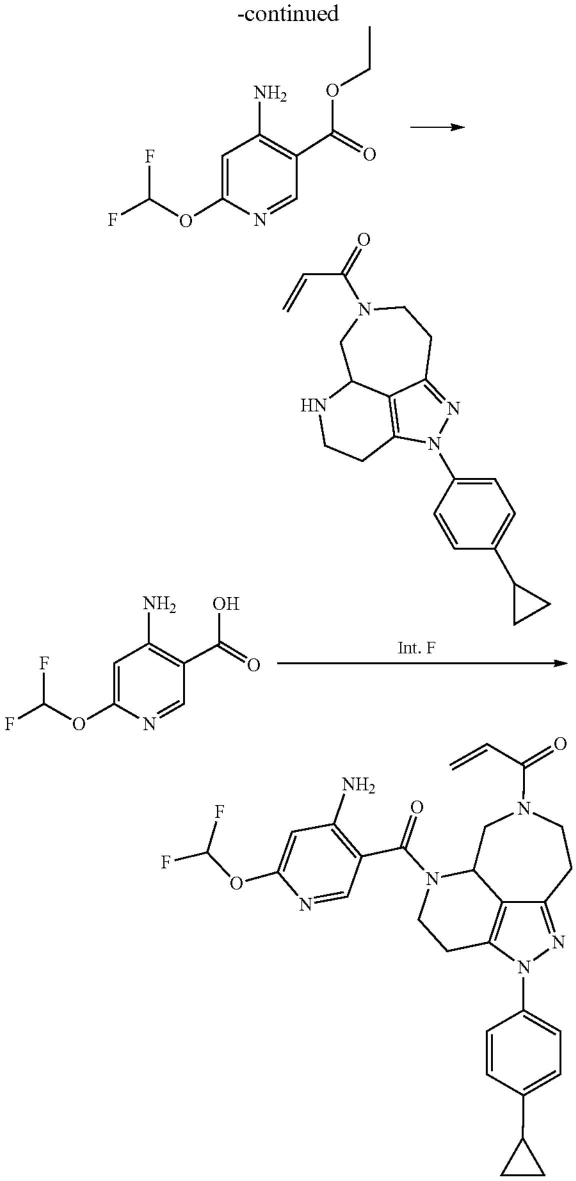

Step 1: Synthesis of Ethyl 4-((tert-butoxycarbonyl) amino)-6-(difluoromethoxy)nicotinate To a solution of ethyl 4-chloro-6-(difluoromethoxy)nicotinate (1.00 g, 1 Equiv., 3.97 mmol) in 1,4-dioxane (20 mL) were added $Cs_2CO_3$ (3.24 g, 2.5 Equiv., 9.94 mmol), tert-butyl carbamate (931 mg, 2 Equiv., 7.95 mmol) X-Phos (379 mg, 0.2 Equiv., 95 μmol) and $Pd(OAc)_2$ (89.2 mg, 0.1 Equiv., 397 mol). The reaction was purged and back-filled with nitrogen (3×) and the resulting mixture was stirred for 2 h at 100° C. under a nitrogen atmosphere. The mixture was then cooled to rt and diluted with water (100 mL) and EA (100 mL), a d the aqueous layer was extracted with EA (2×100 mL). The combined organic layers were washed with saturated brine (3×100 mL), dried over anhydrous sodium sulfate and concentrated to give a residue. The residue was purified by flash column chromatography (80 g silica gel column, eluting with 25% EA in PE) to afford ethyl 4-((tert-butoxycarbonyl)amino)-6-(difluoromethoxy)nicotinate (1.6 g) as a white solid. LCMS: (ESI, m/z): 333 $[M+H]^+$ Step 2: Synthesis of Ethyl 4-amino-6-(difluoromethoxy)nicotinate A solution of ethyl 4-((tert-butoxycarbonyl)amino)-6-(difluoroethoxy)nicotinate (1.4 g, 1 Equiv., 4.2 mmol) in DCM (14 mL) and TFA (7 mL) was stirred at rt for 2 h. The solvent was then removed under reduced pressure to afford ethyl 4-amino-6-(difluoromethoxy)nicotinate (1.4 g) as a crude yellow oil which was used in the next step directly without further purification. LCMS: (ESI, m/z): 233 $[M+H]^+$ Step 3: Synthesis of 4-amino-6-(difluoromethoxy)nicotinic Acid To a solution of ethyl 4-amino-6-(difluoromethoxy)nicotinate (1.20 g, 1 Equiv., 5.17 mmol) in THF (12 mL) and water (6 mL) was added LiOH (620.4 mg, 5 Equiv., 25.85 mmol). The mixture was stirred at rt for 12 h, after which it was acidified to pH=3 with the addition of 1 M sulphuric acid, and the solvent was removed under reduced pressure. Purification by reverse phase chromatography (column: C18 column; eluting with gradient: 45% MeCN in water with 0.5% formic acid) afforded 4-amino-6-(difluoromethoxy) nicotinic acid (560 mg) as a white solid. LCMS: (ESI, m/z): 205 $[M+H]^+$ Step 4: Synthesis of (R or S)-1-(5-(4-amino-6-(difluoromethoxy)nicotinoyl)-2-(4-cyclopropylphenyl)-2,3,4,5,5a,6,8,9-octahydro-7H-1,2,5,7-tetraazabenz [cd]azulen-7-yl)prop-2-en-1-one To a solution of Int. F (90.0 mg, 1 Equiv., 258.3 μmol) in DMF (0.9 mL) were added 4-amino-6-(difluoromethoxy) nicotinic acid (63.23 mg, 1.2 Equiv., 309.96 μmol), HATU (196 mg, 2 Equiv., 516.6 μmol) and DIEA (166.9 mg, 225 μL, 5 Equiv., 1.291 mmol). The mixture was stirred at rt for 2 h, after which the mixture was diluted with water (20 mL) and EA (20 mL), and the aqueous layer was extracted with EA (2×20 mL). The combined organic layers were washed with saturated brine (2×20 mL), dried over anhydrous sodium sulfate and concentrated to give a residue. The residue was purified by Prep-HPLC (Column: Xselect CSH™ Prep C18 5 μm 30*150 mm OBD; Mobile Phase A: Water (0.1% FA), Mobile Phase B: ACN; Flow rate: 60 mL/min; Gradient: 40% B to 60% B in 7 min; Wave Length: UV 254 nm/220 nm) to afford (R or S)-1-(5-(4-amino-6-(difluoromethoxy)nicotinoyl)-2-(4-cyclopropylphenyl)-2,3,4,5,5a,6,8,9-octahydro-7H-1,2,5,7-tetraazabenzo[cd]azulen-7-yl)prop-2-en-1-one (8.2 mg) as a white solid. LCMS: (ESI, m/z): 535 $[M+H]^+$. $^1H$ NMR (400 MHz, Chloroform-d) δ 7.90 (s, 1H), 7.42 (s, 1H), 7.36-7.29 (m, 2H), 7.17-7.11 (m, 2H), 6.53-6.45 (m, 1H), 6.19 (s, 1H), 5.87-5.80 (m, 1H), 5.41-5.12 (m, 3H), 5.01-4.93 (m, 1H), 4.55-4.43 (m, 1H), 4.31-4.14 (m, 1H), 3.31-3.11 (m, 2H), 3.11-3.03 (m, 2H), 3.03-2.99 (m, 1H), 2.82-2.70 (m, 2H), 2.03-1.88 (m, 1H), 1.57-1.24 (m, 1H), 1.06-0.95 (m, 2H), 0.79-0.66 (m, 2H).

Example A-25: Preparation of (R or S)-1-(5-(7-bromo-2-(difluoromethyl)-1H-benzo[d]imidazole-4-carbonyl)-2-(4-cyclopropyl-2-hydroxyphenyl)-2,3,4,5,5a,6,8,9-octahydro-7H-1,2,5,7-tetraazabenzo[cd] azulen-7-yl)prop-2-en-1-one

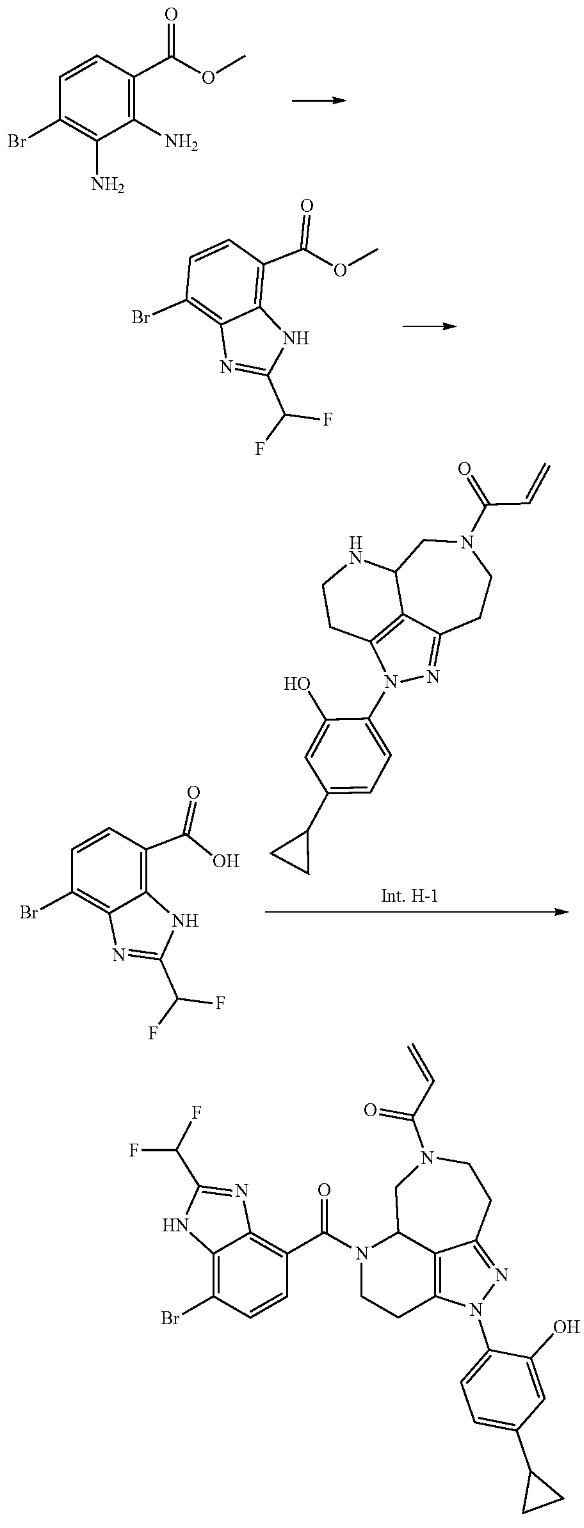

Step 1: Synthesis of Methyl 4-bromo-2-(difluoromethyl)-1H-benzo[d]imidazole-7-carboxylate A stirred solution of methyl 2,3-diamino-4-bromobenzoate (100 mg, 1 Equiv., 408 μmol) in difluoroacetic acid (2 mL) was stirred at 100° C. for 2 h. The reaction was quenched by the addition of water (3 mL) at rt and was adjusted to pH=7 by the addition of $NaHCO_3$(aq, sat.) The resulting mixture was extracted with EA (2×3 mL), and the combined organic layers were washed with brine (2×3 mL) and dried over anhydrous $Na_2SO_4$. After filtration, the filtrate was concentrated under reduced pressure. The residue was purified by silica gel column chromatography, eluting with EA/PE (1:1) to afford methyl 4-bromo-2-(difluoromethyl)-1H-benzo[d]imidazole-7-carboxylate (110 mg) as a white solid. LCMS: (ESI, m/z): 305 $[M+H]^+$ Step 2: Synthesis of 4-bromo-2-(difluoromethyl)-1H-benzo[d]imidazole-7-carboxylic Acid To a solution of methyl 4-bromo-2-(difluoromethyl)-1H-benzo[d]imidazole-7-carboxylate (100 mg, 1 Equiv., 328 μmol) in THF (2 mL) and water (0.4 mL) was added LiOH (39.3 mg, 5 Equiv., 1.64 mmol). The mixture was stirred at 60° C. for 2 h, after which the mixture was acidified to pH=3 with the addition of 1 M sulfuric acid. The mixture was then diluted with EA (2 mL) and water (2 mL), and the aqueous layer was extracted with EA(2×2 mL). The organic layers were combined and washed with saturated brine (2 mL), dried over anhydrous sodium sulfate and concentrated to afford 4-bromo-2-(difluoromethyl)-1H-benzo[d]imidazole-7-carboxylic acid (90 mg) as a crude white solid which was used in the next step directly without further purification. LCMS: (ESI, m/z): 291 $[M+H]^+$ Step 3: Synthesis of (R or S)-1-(5-(7-bromo-2-(difluoromethyl)-1H-benzo[d]imidazole-4-carbonyl)-2-(4-cyclopropyl-2-hydroxyphenyl)-2,3,4,5,5a,6,8,9-octahydro-7H-1,2,5,7-tetraazabenzo[cd]azulen-7-yl)prop-2-en-1-one Intermediate H-1 was prepared from Int. E" in an analogous manner to Example A-8 steps 2-8. To a solution of tert-butyl (R or S)-7-acryloyl-2-(4-cyclopropyl-2-hydroxyphenyl)-2,3,4,5a,6,7,8,9-octahydro-5H-1,2,5,7-tetraazabenzo[cd]azulene-5-carboxylate (Int. H-1) (70.0 mg, 1 Equiv., 150.7 mol) in DMF (1 mL) were added 7-bromo-2-(difluoromethyl)-1H-benzo[d]imidazole-4-carboxylic acid (131.6 mg, 3 Equiv., 452.0 μmol), DIEA (97.37 mg, 131 μL, 5 Equiv., 753.4 μmol) and HBTU (171.4 mg, 3 Equiv., 452.0 μmol). The mixture was stirred at rt for 1 h. The mixture was diluted with water (20 mL) and EA (20 mL), and the aqueous layer was extracted with EA (2×20 mL). The combined organic layers were washed with saturated brine (2×20 mL), dried over anhydrous sodium sulfate and concentrated to give a residue. The residue was then dissolved in THF (1 mL) and water (0.5 mL) and LiOH (5.26 mg, 2 Equiv., 220 μmol) was added. The resulting mixture was stirred at rt for 1 h. The mixture as then acidified to pH=3 with 1 M sulfuric acid, then diluted with EA (20 mL) and water (15 mL), and the aqueous layer was extracted with EA (2×20 mL). The combined organic layers were washed with saturated brine (2×20 mL), dried over anhydrous sodium sulfate and concentrated to give a residue. The residue was purified by Prep-HPLC (Column: XBridge BEH C18 OBD Prep Column 130, 5 m, 30 mm*150 mm; Mobile Phase A: Water (10 mmol/L $NH_4HCO_3$), Mobile Phase B: ACN; Flow rate: 60 mL/min; Gradient: 25% B to 55% B in 10 min; Wave Length: UV 254 nm/220 nm) to afford (R or S)-1-(5-(7-bromo-2-(difluoromethyl)-1H-benzo[d]imidazole-4-carbonyl)-2-(4-cyclopropyl-2-hydroxyphenyl)-2,3,4,5,5a,6,8,9-octahydro-7H-1,2,5,7-tetraazabenzo[cd]azulen-7-yl)prop-2-en-1-one (19.2 mg) as a white solid. LCMS: (ESI, m/z): 637 $[M+H]^+$. $^1$H NMR: (400 MHz, Chloroform-d) δ 10.30-9.70 (m, 1H), 7.69-7.53 (m, 1H), 7.51-0.32 (m, 1H), 7.25-7.05 (m, 11H), 7.04-6.74 (m, 2H), 6.71-6.39 (m, 3H), 5.90-5.70 (m, 1H), 5.59-5.33 (m, 1H), 5.07-4.82 (m, 1H), 4.72-4.15 (m, 2H), 3.47-3.02 (m, 3H), 2.98-2.81 (m, 2H), 2.81-2.51 (m, 3H), 1.85-1.75 (m, 1H), 1.05-0.84 (m, 2H), 0.79-0.57 (m, 2H).

TABLE A7

The compound of Example A-25-1 was prepared in an analogous manner to Example A-25 using the corresponding carboxylic acid.

| Example No. | Structure | Compound Name | LCMS $[M + H]^+$ | NMR |
|---|---|---|---|---|
| A-25-1 | 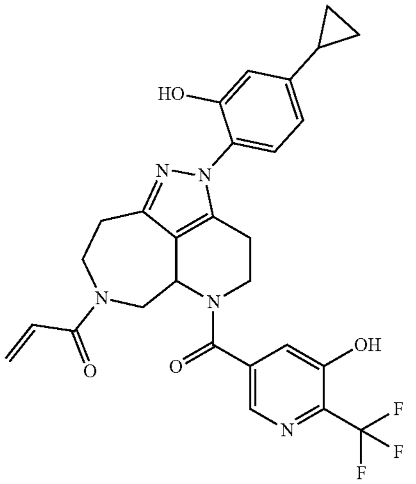 [SMILES: C=CC(=O)N1CCc2nn(-c3ccc(C4CC4)cc3O)c3c2C(C1)N(C(=O)c1cnc(C(F)(F)F)c(O)c1)CC3] | (R or S)-1-(2-(4-cyclopropyl-2-hydroxyphenyl)-5-(5-hydroxy-6-(trifluoromethyl) nicotinoyl)-2,3,4,5,5a,6,8,9-octahydro-7H-1,2,5,7-tetraazabenzo[cd]azulen-7-yl)prop-2-en-1-one | 554 | $^1$H NMR (400 MHz, DMSO-$d_6$) δ 11.49 (s, 1H), 9.94 (s, 1H), 8.36-8.13 (m, 1H), 7.57-7.37 (m, 2H), 7.15 (d, J = 8.1 Hz, 1H), 6.70 (br d, J = 1.9 Hz, 1H), 6.66-6.56 (m, 1H), 6.29 (d, J = 16.5 Hz, 1H), 5.80 (br d, J = 10.5 Hz, 1H), 5.15 (br d, J = 10.4 Hz, 1H), 4.80-4.58 (m, 1H), 4.36-4.16 (m, 1H), 3.74 (d, J = 12.8 Hz, 1H), 3.28-3.04 (m, 1H), 2.99-2.70 (m, 5H), 2.44-2.27 (m, 1H), 1.99-1.81 (m, 1H), 1.02-0.87 (m, 2H), 0.73-0.54 (m, 2H). |

Example A-26: Preparation of (R or S)-1-(5-(2-amino-5-fluoro-6-(trifluoromethyl)nicotinoyl)-2-(4-cyclopropyl-2-hydroxyphenyl)-2,3,45,5a,6,8,9-octahydro-7H-1,2,5,7-tetraazabenzo [cd]azulen-7-yl) prop-2-en-1-one

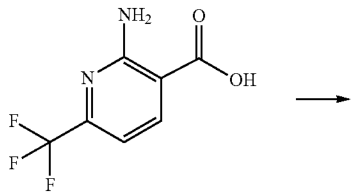

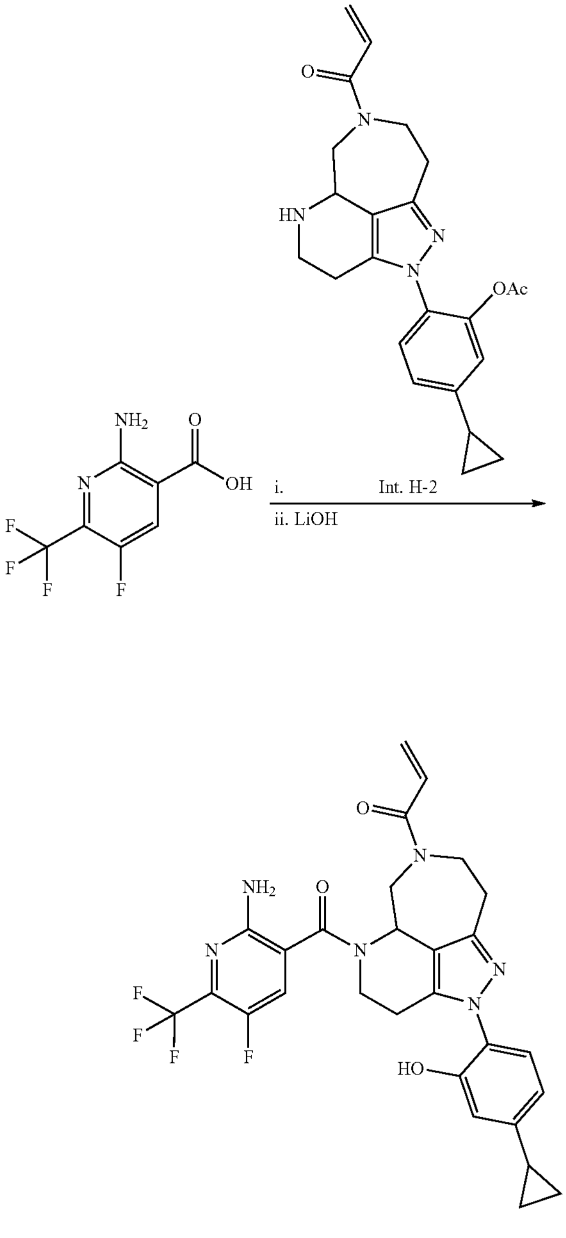

Step 1: Synthesis of 2-amino-5-fluoro-6-(trifluoromethyl) nicotinic Acid

To a solution of 2-amino-6-(trifluoromethyl) nicotinic acid (1 g, 1 Equiv., 5 mmol) in MeCN (10 mL) was added Selectfluor (3 g, 1.5 Equiv., 7 mmol). The mixture was stirred for 12 h at 50° C. under a nitrogen atmosphere. After the reaction mixture was cooled to rt, the mixture was concentrated under vacuum. The mixture was filtered and rinsed with EA (3×200 mL), and the aqueous layer was extracted with EA (2×200 mL). The combined organic layers were washed with saturated brine (3×200 mL), dried over anhydrous sodium sulfate and concentrated to give a residue. The residue was purified by reverse phase chromatography (column: C18 column; Gradient: MeCN in water with 0.1% formic acid, 10% to 100% gradient in 20 min; detector, UV 254 nm) to afford 2-amino-5-fluoro-6-(trifluoromethyl) nicotinic acid (210 mg) as a pale yellow solid. LCMS: (ESI, m/z): 225 $[M+H]^+$ Step 2: Synthesis of (R or S)-1-(5-(2-amino-5-fluoro-6-(trifluoromethyl)nicotinoyl)-2-(4-cyclopropyl-2-hydroxyphenyl)-2,3,4,5,5a,6,8,9-octahydro-7H-1,2,5,7-tetraazabenzo[cd]azulen-7-yl)prop-2-en-1-one To a stirred solution of Int. H-2 (45 mg, 1 Equiv., 0.11 mmol) in DMA (0.45 mL) was added 2-amino-5-fluoro-6-(trifluoromethyl) nicotinic acid (50 mg, 2 Equiv., 0.22 mmol), HATU (84 mg, 2 Equiv., 0.22 mmol) and DIEA (0.14 g, 0.19 mL, 10 Equiv., 1.1 mmol) at rt and the resulting mixture was stirred for 1 h. The reaction was then quenched by the addition of water (20 mL) at rt, and extracted with EA (2×20 mL). The combined organic layers were washed with brine (2×20 mL), dried over anhydrous $Na_2SO_4$, and filtered. The filtrate was concentrated under reduced pressure, and then redissolved in THF (1.1 mL) and water (0.55 mL). To the mixture was added LiOH (11 mg, 5 Equiv., 0.45 mmol) and the mixture was stirred for 1 h at rt. The reaction was then quenched by the addition of water (10 mL) at rt and the resulting mixture was extracted with EA (2×10 mL). The combined organic layers were washed with brine (2×10 mL), dried over anhydrous $Na_2SO_4$, and filtered. The filtrate was concentrated under reduced pressure and the residue was purified by reversed-phase flash chromatography (Column: XBridge Prep Shield RP18 Sum 19*10 mm; Mobile Phase A: Water($1_0$ mmol/L $NH_4HCO_3$), Mobile Phase B: ACN; Flow rate: 60 mL/min mL/min; Gradient: 5% B to 5% B in 1 min, 5% B to 35% B in 2 min, 35% to 53% B in 10 min; Wave Length: 254 nm/220 nm nm) to afford (R or S)-1-(5-(2-amino-5-fluoro-6-(trifluoromethyl)nicotinoyl)-2-(4-cyclopropyl-2-hydroxyphenyl)-2,3,4,5,5a,6,8,9-octahydro-7H-1,2,5,7-tetraazabenzo[cd]azulen-7-yl)prop-2-en-1-one (10.3 mg) as a white solid. LCMS: (ESI, m/z): 571 $[M+H]^+$. $^1H$ NMR: (400 MHz, Chloroform-d) δ 7.38-7.30 (m, 1H), 7.02-6.93 (m, 1H), 6.81 (d, J=2.0 Hz, 1H), 6.68-6.62 (m, 1H), 6.54-6.39 (m, 11H), 5.94-5.75 (m, 1H), 5.39 (s, 1H), 4.96 (d, J=13.2 Hz, 1H), 4.56-4.00 (m, 2H), 3.30-3.15 (m, 2H), 3.11-3.01 (m, 3H), 2.88-2.70 (m, 2H), 1.86 (m, 1H), 1.38-1.22 (m, 1H), 1.04-0.9 (m, 2H), 0.76-0.64 (m, 2H).

Example A-27: Preparation of (R or S)-1-(5-(4-amino-6-((trifluoromethyl)thio)nicotinoyl)-2-(4-cyclopropyl-2-hydroxyphenyl)-2,3,4,5,5a,6,8,9-octahydro-7H-1,5,7-tetraazabenzo[cd]azulen-7-yl)prop-2-en-1-one
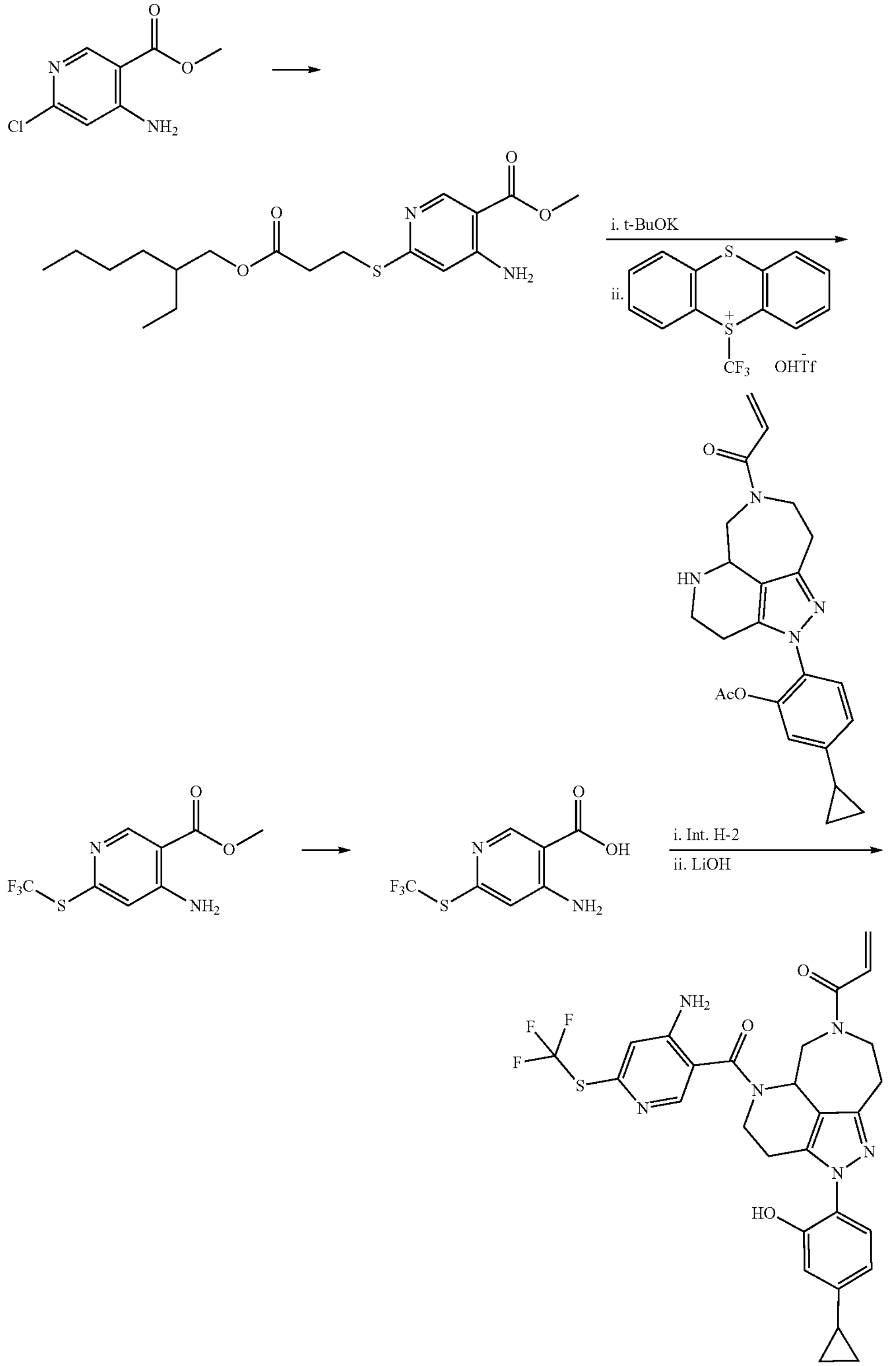

Step 1: Synthesis of Methyl 4-amino-6-((3-((2-ethylhexyl)oxy)-3-oxopropyl)thio)nicotinate To a solution of methyl 4-amino-6-chloronicotinate (200 mg, 1 Equiv., 1.07 mmol) in 1,4-dioxane (2 mL) were added $Pd_2(dba)_3$ (98.1 mg, 0.1 Equiv., 107 mol), 2-ethylhexyl 3-mercaptopropanoate (281 mg, 1.2 Equiv., 1.29 mmol), Xantphos (124 mg, 0.2 Equiv., 214 mol) and DIEA (277 mg, 373 μL, 2 Equiv., 2.14 mmol). The mixture was evacuated and backfilled with nitrogen (3×). The resulting mixture was stirred at 100° C. for 18 h, after which it was cooled to rt, filtered and rinsed with EA (3×20 mL), then diluted with water (20 mL). The aqueous layer was extracted with EA (2×20 mL), and the combined organic layers were washed with saturated brine (3×20 mL), dried over anhydrous sodium sulfate and concentrated to give a residue. The crude product was purified by silica gel chromatography eluting with PE:EA=10:1 to give methyl 4-amino-6-((3-((2-ethylhexyl)oxy)-3-oxopropyl)thio)nicotinate (250 mg) as a yellow oil. LCMS: (ESI, m/z): 369 $[M+H]^+$ Step 2: Synthesis of Methyl 4-amino-6-((trifluoromethyl)thio)nicotinate A solution of methyl 4-amino-6-((3-((2-ethylhexyl)oxy)-3-oxopropyl)thio)nicotinate (500 mg, 1 equiv., 1.36 mmol) in THF (15 mL) was cooled to 0° C., then 2-methylpropan-2-olate potassium (305 mg, 2 equiv., 2.71 mmol) was added at 0° C. under a nitrogen atmosphere. The resulting solution was stirred for 1 h at 0° C., then 5-(trifluoromethyl)-5H-thianthren-5-ium (774 mg, 2 equiv., 2.71 mmol) was added. The mixture was warmed to rt and stirred for 2 h, after which was filtered and rinsed with EA (3×20 mL), then diluted with water (20 mL). The aqueous layer was extracted with EA (2×20 mL), and the combined organic layers were washed with saturated brine (3×20 mL), dried over anhydrous sodium sulfate and concentrated to give a residue. The crude product was purified by silica gel chromatography, eluting with PE:EA=10:1 to give methyl 4-amino-6-((trifluoromethyl)thio)nicotinate (150 mg) as a white solid. LCMS: (ESI, m/z): 253 $[M+H]^+$ Step 3: Synthesis of 4-amino-6-((trifluoromethyl)thio)nicotinic Acid To a solution of methyl 4-amino-6-((trifluoromethyl)thio) nicotinate (130 mg, 1 equiv., 515 μmol) in THF (0.5 mL) and water (0.5 mL) was added LiOH (61.7 g, 5 equiv., 2.58 mmol). The mixture was stirred at rt for 2 h, after which the mixture was acidified to pH=3 with the addition of 1 M sulfuric acid, then diluted with EA (20 mL) and water (15 mL). The aqueous layer was extracted with EA (2×20 mL), and the combined organic layers were washed with saturated brine (20 mL), dried over anhydrous sodium sulfate and concentrated to afford 4-amino-6-((trifluoromethyl)thio) nicotinic acid as a yellow which was used in the next step directly without further purification. LCMS: (ESI, m/z): 239 $[M+H]^+$ Step 4: Synthesis of (R or S)-1-(5-(4-amino-6-((trifluoromethyl)thio)nicotinoyl)-2-(4-cyclopropyl-2-hydroxyphenyl)-2,3,4,5,5a,6,8,9-octahydro-7H-1,2,5,7-tetraazabenzo[cd]azulen-7-yl)prop-2-en-1-one To a solution of Int. H-2 (30 mg, 1 equiv., 74 gmol) in DMA (mL) were added HATU (28 mg, 1 equiv., 74 gmol), 4-amino-6-((trifluoromethyl)thio)nicotinic acid (18 mg, 1 equiv., 74 gmol) and DIEA (9.5 mg, 13 μL, 1 equiv., 74 gmol). The mixture was stirred at 40° C. for 2 h, after which it was cooled to rt and diluted with water (20 mL) and EA (20 mL). The aqueous layer was then extracted with EA (2×20 mL), and the combined organic layers were washed with saturated brine (2×20 mL), dried over anhydrous sodium sulfate and concentrated to give a residue. The residue was dissolved in THF (0.5 mL), and water (0.5 mL), MeOH (0.2 mL), and LiOH (1.1 mg, 3 equiv., 48 gmol) were added. The mixture was stirred at 40° C. for 1 h, after which it was diluted with water (20 mL) and EA (20 mL), and the aqueous layer was extracted with EA (2×20 mL). The combined organic layers were washed with saturated brine (2×20 mL), dried over anhydrous sodium sulfate and concentrated to give a residue. The residue was purified by Prep-HPLC (Column: XBridge Prep Phenyl OBD Column 19*250 mm, 5 μm; Mobile Phase A: Water(10 mmol/L $NH_4HCO_3$), Mobile Phase B: ACN; Flow rate: 60 mL/min mL/min; Gradient: 5% B to 5% B in 1 min, 5% B to 35% B in 2 min, 35% to 55% B in 10 min) to afford (R or S)-1-(5-(4-amino-6-((trifluoromethyl)thio)nicotinoyl)-2-(4-cyclopropyl-2-hydroxyphenyl)-2,3,4,5,5a,6,8,9-octahydro-7H-1,2,5,7-tetraazabenzo[cd]azulen-7-yl)prop-2-en-1-one (3.8 mg) as a white solid. LCMS: (ESI, m/z): 585 $[M+H]^+$. $^1H$ NMR (400 MHz, Chloroform-d) δ 10.11 (s, 1H), 8.40-8.10 (m, 1H), 7.50-7.30 (m, 1H), 7.10-6.85 (m, 2H), 6.79 (d, J=2.0 Hz, 1H), 6.64 (dd, J=8.3, 2.0 Hz, 1H), 6.51 (d, J=16.5 Hz, 1H), 6.00-5.65 (m, 1H), 5.53-5.16 (m, 2H), 4.97 (d, J=13.5 Hz, 1H), 4.47 (d, J=13.6 Hz, 1H), 4.30-4.10 (m, 1H), 3.27-2.96 (m, 5H), 2.89-2.69 (m, 2H), 1.92-1.82 (m, 1H), 1.38-1.26 (m, 1H), 1.04-0.92 (m, 2H), 0.75-0.65 (m, 2H).

Example A-28: Preparation of (R or S)-1-(5-(5-amino-7-bromo-1H-benzo[d]imidazole-4-carbonyl)-2-(4-cyclopropylphenyl)-2,3,4,5,5a,6,8,9-octahydro-7H-1,2,5,7-tetraazabenzo[cd]azulen-7-yl)prop-2-en-1-one

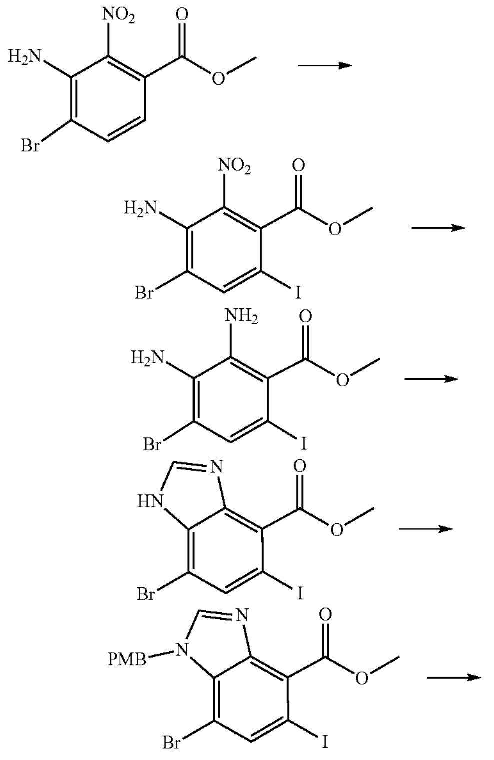

-continued

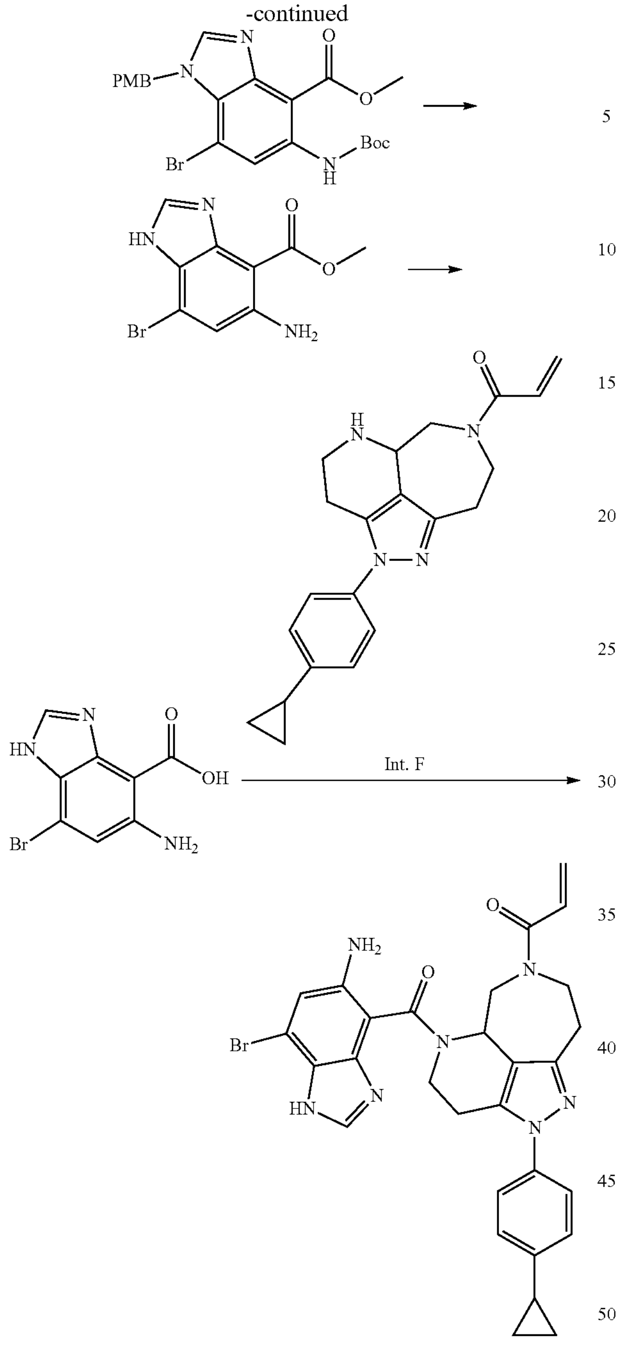

Step 1: Synthesis of Methyl 3-amino-4-bromo-6-iodo-2-nitrobenzoate

To a solution of methyl 3-amino-4-bromo-2-nitrobenzoate (5 g, 1 Equiv., 0.02 mol) in acetic acid (25 mL) was added NIS (5 g, 1.2 Equiv., 0.02 mol). The reaction was evacuated and back-filled with nitrogen (3×), and the resulting mixture was stirred for 4 h at 80° C. The mixture was cooled to rt, filtered and rinsed with EA (3×50 mL). The aqueous layer was extracted with EA (2×50 mL) and the combined organic layers were washed with saturated $Na_2S_2O_3$ (3×50 mL), dried over anhydrous sodium sulfate and concentrated to give a residue. The residue was purified by flash column chromatography, eluting with EA/PE (3:5) to afford methyl 3-amino-4-bromo-6-iodo-2-nitrobenzoate (3.2 g) as a brown solid.

Step 2: Synthesis of Methyl 2,3-diamino-4-bromo-6-iodobenzoate

To a solution of methyl 3-amino-4-bromo-6-iodo-2-nitrobenzoate (2.7 g, 1 Equiv., 6.7 mmol) in DMF (15 mL) was added hypodiboric acid (1.8 g, 3 Equiv., 20 mmol). The mixture was cooled to 0° C., then 4,4'-dipyridyl (0.53 g, 0.48 mL, 0.5 Equiv., 3.4 mmol) in DMF (27 mL) was added dropwise to the above mixture at 0° C. under a nitrogen atmosphere and stirred for 0.5 h. The mixture was then filtered and rinsed with EA (3×100 mL), and the aqueous layer was extracted with EA (2×100 mL). The combined organic layers were washed with saturated brine (3×100 mL), dried over anhydrous sodium sulfate and concentrated to give a residue. The residue was purified by flash column chromatography, eluting with EA/PE (4:5) to afford methyl 2,3-diamino-4-bromo-6-iodobenzoate (1.5 g) as a yellow solid.

Step 3: Synthesis of Methyl 7-bromo-5-iodo-1H-benzo[d]imidazole-4-carboxylate

A solution of methyl 2,3-diamino-4-bromo-6-iodobenzoate 1900 mg, 1 Equiv., 2.43 mmol) in formic acid (9 mL) and acetic anhydride (0.9 mL) was stirred for 4 h at 120° C. The mixture was then cooled to rt, filtered, and rinsed with EA (3×50 mL), and the aqueous layer was extracted with EA (2×50 mL). The combined organic layers were washed with saturated brine (3×50 mL), dried over anhydrous sodium sulfate and concentrated to give a residue. The residue was purified by flash column chromatography, eluting with EA/PE (4:5) to afford methyl 7-bromo-5-iodo-1H-benzo[d]imidazole-4-carboxylate (570 mg) as a yellow solid. LCMS: (ESI, m/z): 380 $[M+H]^+$ Step 4: Synthesis of Methyl 7-bromo-5-iodo-1-(4-methoxybenzyl)-1H-benzo[d]imidazole-4-carboxylate To a solution of methyl 7-bromo-5-iodo-1H-benzo[d]imidazole-4-carboxylate (550 mg, 1 Equiv., 1.44 mmol) in DMF (5.5 mL) and was added $K_2CO_3$ (399 mg, 2 Equiv., 2.89 mmol) and 1-chloromethyl-4-methoxy-benzene (181 mg, 157 μL, 0.8 Equiv., 1.15 mmol). The reaction system was evacuated and backfilled with nitrogen (3×), and the resulting mixture was stirred for 2 h at rt. The mixture was then filtered and rinsed with EA (3×100), and the aqueous layer was extracted with EA (2×100 mL). The combined organic layers we e washed with saturated brine (3×100 mL), dried over anhydrous sodium sulfate and concentrated to give a residue. The residue was purified by flash column chromatography, eluting with EA/PE (3:5) to afford methyl 7-bromo-5-iodo-1-(4-methoxybenzyl)-1H-benzo[d]imidazole-4-carboxylate (370 mg) as yellow oil. LCMS: (ESI, m/z): 501 $[M+H]^+$ Step 5: Synthesis of Methyl 7-bromo-5-((tert-butoxycarbonyl)amino)-1-(4-methoxybenzyl)-1H-benzo[d]imidazole-4-carboxylate To a solution of methyl 7-bromo-5-iodo-1-(4-methoxybenzyl)-1H-benzo[d]imidazole-4-carboxylate (360 mg, 1 Equiv., 718 μmol) in 1,4-dioxane (3.6 mL) was added tert-butyl carbamate (84.2 mg, 1 Equiv., 718 μmol), $Pd(OAc)_2$ (16.1 mg, 0.1 Equiv., 71.8 μmol), Xantphos (83.1 mg, 0.2 Equiv., 144 μmol) and $Cs_2CO_3$ (468 mg, 2 Equiv., 1.44 mmol). The reaction system was evacuated and backfilled with nitrogen (3×), and the resulting mixture was stirred for 4 h at 100° C. The reaction mixture was then cooled to rt, filtered and rinsed with EA (3×20 mL). The aqueous layer was extracted with EA (2×20 mL), and the combined organic layers were washed with saturated brine (3×20 mL), dried over anhydrous sodium sulfate and concentrated to give a residue. The residue was purified by flash column chromatography, eluting with EA/PE (2:5) to afford methyl 7-bromo-5-((tert-butoxycarbonyl)amino)-1-(4-methoxybenzyl)-1H-benzo[d]imidazole-4-carboxylate (135 mg) as a yellow solid. LCMS: (ESI, m/z): 490 $[M+H]^+$ Step 6: Synthesis of Methyl 5-amino-7-bromo-1H-benzo[d]imidazole-4-carboxylate To a solution of methyl 7-bromo-5-((tert-butoxycarbonyl) amino)-1-(4-methoxybenzyl)-1H-benzo[d]imidazole-4-carboxylate (125 mg, 1 Equiv., 255 μmol) in TFA (1.25 mL) was added p-toluenesulfonic acid monohydrate (48.5 mg, 39.1 μL, 1 Equiv., 255 μmol). The reaction system was evacuated and backfilled with nitrogen (3×), and the resulting mixture was stirred for 2 h at 60° C. After the reaction mixture was cooled to room temperature, the solvent was removed under reduced pressure to afford methyl 5-amino-7-bromo-1H-benzo[d]imidazole-4-carboxylate (55 mg) as a yellow oil which was used in the next step directly without further purification. LCMS: (ESI, m/z): 270 $[M+H]^+$ Step 7: Synthesis of 5-amino-7-bromo-1H-benzo[d]imidazole-4-carboxylic Acid To a solution of methyl 5-amino-7-bromo-1H-benzo[d]imidazole-4-carboxylate (50 mg, 1 Equiv., 0.19 mmol) in THF (2 mL) and water (1 mL), and was added LiOH (22 mg, 5 Equiv., 0.93 mmol). The resulting mixture was stirred for 2 h at 60° C. After the reaction mixture was cooled to rt, the mixture was filtered and rinsed with EA (3×10 mL), and the aqueous layer was extracted with EA (2×10 mL). The combined organic layers were wash d with saturated brine (3×10 mL) and dried over anhydrous sodium sulfate and concentrated to give a residue. The residue was purified by flash column chromatography, eluting with EA/PE (4:5) to afford 5-amino-7-bromo-1H-benzo[d]imidazole-4-carboxylic acid (16 mg) as a white solid. LCMS: (ESI, m/z): 256 $[M+H]^+$ Step 8: Synthesis of (R or S)-1-(5-(5-amino-7-bromo-1H-benzo[d]imidazole-4-carbonyl)-2-(4-cyclopropylphenyl)-2,3,4,5,5a,6,8,9-octahydro-7H-1,2,5,7-tetraazabenzo[cd]azulen-7-yl)prop-2-en-1-one To a stirred solution of 5-amino-7-bromo-1H-benzo[d]imidazole-4-carboxylic acid (12 mg, 1 Equiv., 47 mol) in DMF (0.12 mL) was added Int. F (20 mg, 1.2 Equiv., 56 mol), HATU (36 mg, 2 Equiv., 94 μmol) and DIEA (61 mg, 82 μL, 10 Equiv., 0.47 mmol). The reaction mixture was stirred at 60° C. for 2 h. The reaction was then cooled to rt and quenched by the addition of water (10 mL). The resulting mixture was extracted with EA (2×20 mL) and the combined organic layers were washed with brine (2×10 mL), dried over anhydrous $Na_2SO_4$, and filtered. The filtrate was concentrated under reduced pressure and the residue was purified by reversed-phase flash chromatography with the following conditions: Column=XBridge BEH C18 OBD Prep Column 130, 5 μm, 30 mm*150 mm; Mobile Phase A: Water(10 mmol/L $NH_4HCO_3$), Mobile Phase B: ACN; Flow rate: 60 ml/min mL/min; Gradient: 45% B to 70% B in 10 min; Wave Length: 254 nm/220 nm nm; to afford (R or S)-1-(5-(5-amino-7-bromo-1H-benzo[d]imidazole-4-carbonyl)-2-(4-cyclopropylphenyl)-2,3,4,5,5a,6,8,9-octahydro-7H-1,2,5,7-tetraazabenzo[cd]azulen-7-yl)prop-2-en-1-one (1.3 mg) as a white solid. LCMS: (ESI, m/z): 588 $[M+H]^+$. $^1H$ NMR: (400 MHz, Chloroform-d, ppm) δ 8.22-7.90 (m, 1H), 7.38-7.30 (m, 1H), 7.15-7.10 (m, 2H), 7.00-6.90 (m, 1H), 6.91-5.95 (m, 2H), 5.86-5.43 (m, 1H), 5.41-4.70 (m, 1H), 4.65-4.05 (m, 1H), 4.04-3.65 (m, 1H), 3.50-3.20 (m, 11H), 3.19-2.95 (m, 4H), 2.8 (s, 1H), 2.69-2.51 (m, 1H), 2.00-1.80 (m, 4H), 1.30 (s, 1H), 1.05-0.99 (m, 2H), 0.94-0.81 (m, 1H), 0.72-0.61 (m, 2H).

TABLE A8

The compound of Example A-29 was prepared in an analogous fashion to ExampleA-8, using the corresponding boronate ester in the first step, and the corresponding carboxylic acid to afford the racemic final compound of the example.

| Example No. | Structure and Name | LCMS (ESI, m/z) |
| --- | --- | --- |
| Example A-29 | 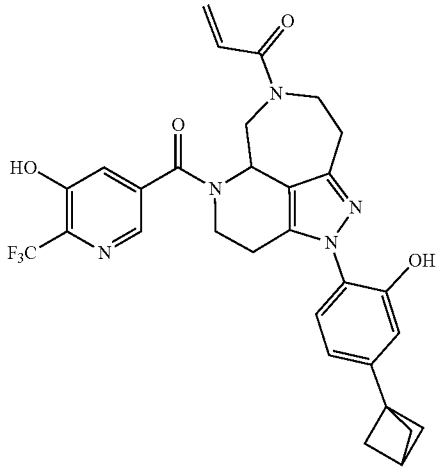 [SMILES: C=CC(=O)N1CCc2nn(-c3ccc(C45CC(C4)C5)cc3O)c3c2C(C1)N(C(=O)c1cnc(C(F)(F)F)c(O)c1)CC3] 1-(2-(4-(bicyclo[1.1.1]pentan-1-yl)-2-hydroxyphenyl)-5-(5-hydroxy-6- | 580 $[M + H]^+$ |

TABLE A8-continued

The compound of Example A-29 was prepared in an analogous fashion to ExampleA-8, using the corresponding boronate ester in the first step, and the corresponding carboxylic acid to afford the racemic final compound of the example.

| Example No. | Structure and Name | LCMS (ESI, m/z) |
|---|---|---|
| | (trifluoromethyl)nicotinoyl)-2,3,4,5,5a,6,8,9-octahydro-7H-1,2,5,7-tetraazabenzo[cd]azulen-7-yl)prop-2-en-1-one | |

Example A-30: Preparation of (R or S)-1-(5-(4-amino-5-fluoro-6-((trifluoromethyl)thio)nicotinoyl)-2-(4-cyclopropyl-2-hydroxyphenyl)-2,3,4,5,5a,6,8,9-octahydro-7H-1,2,5,7-tetraazabenzo[cd]azulen-7-yl)prop-2-en-1-one

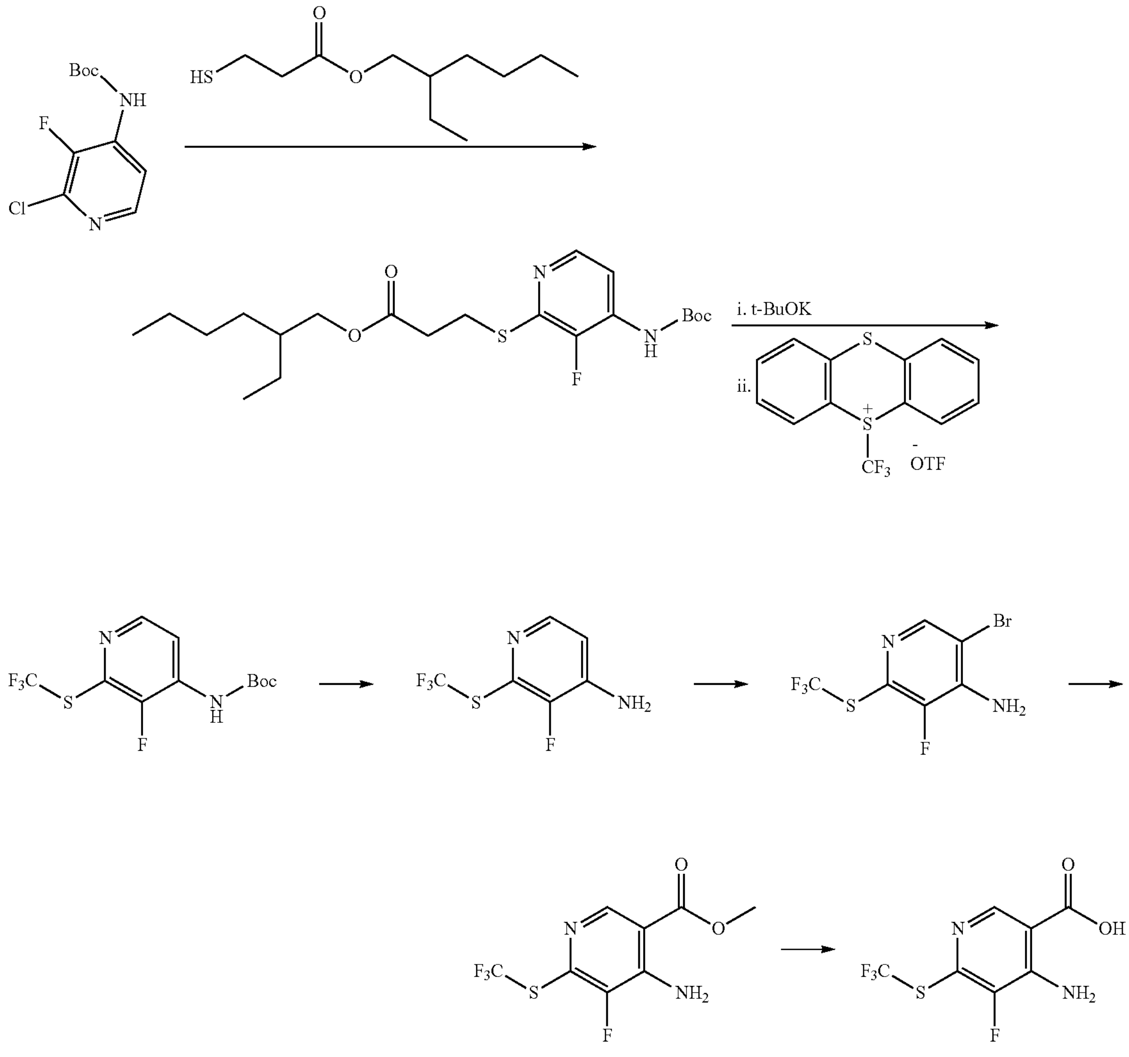

-continued

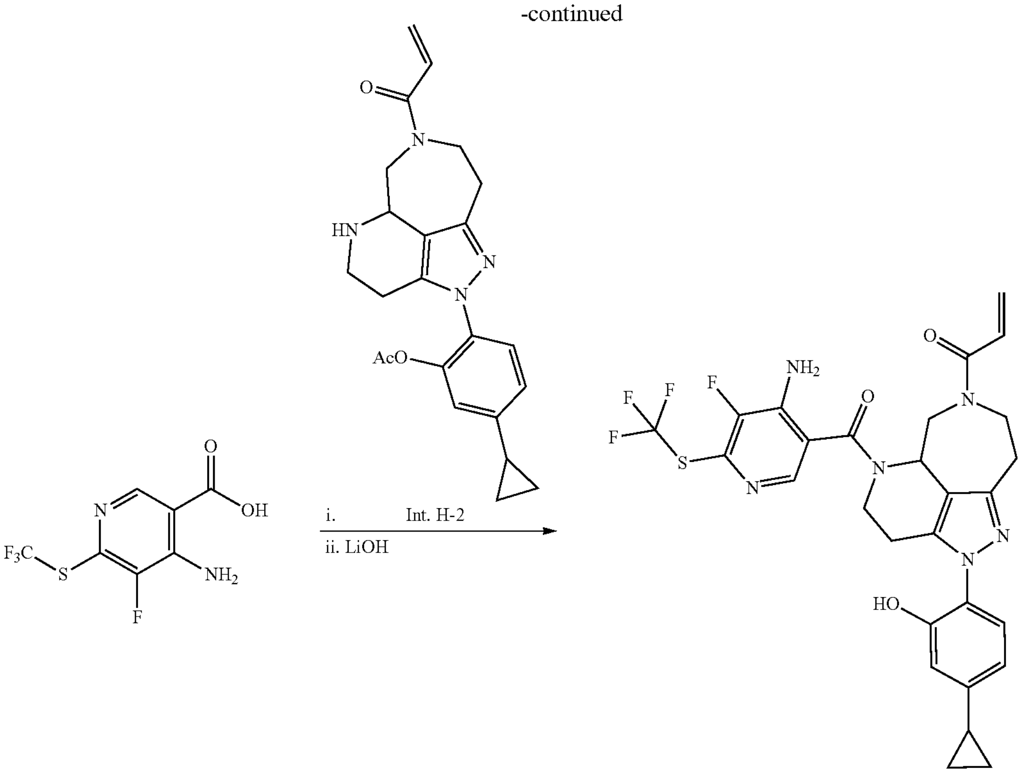

Step 1: Synthesis of 2-ethylhexyl 3-((4-((tert-butoxycarbonyl)amino)-3-fluoropyridin-2-yl)thio)propanoate To a stirred solution of tert-butyl (2-chloro-3-fluoropyridin-4-yl)carbamate (1.6 g, 1 equiv., 6.5 mmol), 2-ethylhexyl 3-sulfanylpropanoate (1.6 g, 1.6 mL 1.1 equiv., 7.1 mmol), $Pd_2(dba)_3$ (0.59 g, 0.1 equiv., 0.65 mmol), and xantphos (0.75 g, 0.2 equiv., 1.3 mmol) in 1,4-dioxane (20 mL) was added DIEA (1.7 g, 2.3 mL, 2 equiv., 13 mmol), and the resulting mixture was stirred at 95° C. for 2 h. The reaction was then quenched by the addition of water (20 mL) at rt, and the mixture was extracted with EA (2×20 mL). The combined organic layers were washed with brine (2×20 mL), dried over anhydrous $Na_2SO_4$, filtered, and the filtrate was concentrated under reduced pressure. The residue was purified by silica gel column chromatography, eluting with EA/PE (1:10) to afford 2-ethylhexyl 3-((4-((tert-butoxycarbonyl)amino)-3-fluoropyridin-2-yl)thio)propanoate (2.3 g) as a yellow solid. LCMS:(ESI, m/z): 429 $[M 1]^+$ Step 2: Synthesis of Tert-butyl (3-fluoro-2-((trifluoromethyl)thio)pyridin-4-yl)carbamate To a stirred solution of 2-ethylhexyl 3-((4-((tert-butoxycarbonyl amino)-3-fluoropyridin-2-yl)thio)propanoate (1 g, 1 equiv., 2 mmol) in THF (20 mL) was added t-BuOK (0.5 g, 0.5 mL, 2 equiv., 5 mmol) at −5° C. and the resulting mixture was stirred for 0.5 h. To this mixture was then added 5-(trifluoromethyl)-5H-thianthren-5-ium trifluoromethanesulfonate (2 g, 2 equiv., 5 mmol) at rt and the resulting mixture was stirred for 2 h, after which the reaction was quenched by the addition of water (20 mL) at rt, and was extracted with EA (2×20 mL). The combined organic layers were washed with brine (2×20 mL), dried over anhydrous $Na_2SO_4$ and filtered, and the filtrate was concentrated under reduced pressure. The residue was purified by silica gel column chromatography, eluting with EA/PE (1:5) to afford tert-butyl (3-fluoro-2-((trifluoromethyl)thio)pyridin-4-yl) carbamate (600 mg) as a yellow oil. LCMS:(ESI, m/z): 313 $[M+1]^+$ Step 3: Synthesis of 3-fluoro-2-((trifluoromethyl)thio)pyridin-4-amine To a stirred solution of tert-butyl (3-fluoro-2-((trifluoromethyl)thio)pyridin-4-yl)carbamate (415 mg, 1 equiv., 1.33 mmol) in DCM (3 mL) was added TFA (1 mL) at rt and the mixture was further stirred for 1 h, after which it was concentrated und er reduced pressure. The crude product was used in the next step directly without further purification. LCMS:(ESI, m/z): 213 $[M+1]^+$ Step 4: Synthesis of 5-bromo-3-fluoro-2-((trifluoromethyl)thio)pyridin-4-amine To a stirred solution of 3-fluoro-2-((trifluoromethyl)thio) pyridin-4-amine (800 mg, 1 equiv., 3.77 mmol, crude from the previous step) in DMF (10 mL) was added $Br_2$ (1.21 g, 389 μL, 2 equiv., 7.54 mmol) at 0° C. and the resulting mixture was stirred for 2 h. The reaction was then quenched at rt by the addition of water (20 mL), and the mixture was extracted with EA (2×20 mL). The combined organic layers were washed with brine (2×20 mL), dried over anhydrous $Na_2SO_4$, and filtered. The filtrate was concentrated under reduced pressure, and the residue was purified by silica gel column chromatography, eluting with EA/PE (1:4) to afford 5-bromo-3-fluoro-2-((trifluoromethyl)thio)pyridin-4-amine (500 mg) as a white solid. LCMS:(ESI, m/z): 291, 293 $[M+1]^+$ Step 5: Synthesis of Methyl 4-amino-5-fluoro-6-((trifluoromethyl)thio)nicotinate To a stirred solution of 5-bromo-3-fluoro-2-((trifluoromethyl)thio)pyridin-4-amine (410 mg, 1 equiv., 1.41 mmol) and TEA (713 mg, 982 μL, 5 equiv., 7.04 mmol) in MeOH (5 mL) was added $PdCl_2$(dppf)-$CH_2Cl_2$ adduct (230 mg, 0.2 equiv., 282 μmol). The resulting mixture was heated to 100° C. and stirred for 12 h under a CO atmosphere (40 atm). The reaction was then cooled to rt and quenched by the addition of water (20 mL). The resulting mixture was extracted with EA (2×20 mL) and the combined organic layers were washed with brine (2×20 mL), dried over anhydrous $Na_2SO_4$. After filtration, the filtrate was concentrated u der reduced pressure and the residue was purified by silica gel column chromatography, eluting with EA/PE (1:5) to afford methyl 4-amino-5-fluoro-6-((trifluoromethyl)thio)nicotinate (300 mg) as a yellow solid.

Step 6: Synthesis of 4-amino-5-fluoro-6-((trifluoromethyl)thio)nicotinic Acid

To a stirred solution of methyl 4-amino-5-fluoro-6-((trifluoromethyl)thio)nicotinate (280 mg, 1 equiv., 1.04 mmol) in THF (4 mL) and $H_2O$ (1 mL) was added LiOH (49.6 mg, 2 equiv., 2.07 mmol) at 60° C. and the mixture was stirred for 1 h. The residue was then purified by reversed-phase flash chromatography with the following conditions: Column-C18 silica gel; mobile phase, ACN in Water (0.1% FA), 10% to 50% gradient in 10 min; to afford 4-amino-5-fluoro-6-((trifluoromethyl)thio)nicotinic acid (150 mg) as a yellow solid. LCMS:(ESI, m/z): 257 $[M+1]^+$ Step 7: Synthesis of (R or S)-1-(5-(4-amino-5-fluoro-6-((trifluoromethyl)thio)nicotinoyl)-2-(4-cyclopropyl-2-hydroxyphenyl)-2,3,4,5,5a,6,8,9-octahydro-7H-1,2,5,7-tetraazabenzo[cd]azulen-7-yl)prop-2-en-1-one To a stirred solution of (R or S)-2-(7-acryloyl-3,4,5,5a,6,7,8,9-octahydro-2H-1,2,5,7-tetraazabenzo[cd]azulen-2-yl)-5-cyclopropylphenyl acetate Int. H-2 (75 mg, 1 equiv., 0.18 mmol), DIEA (0.12 g, 0.16 mL, 5 equiv., 0.92 mmol), and HATU (0.1 g, 2 equiv., 0.37 mmol) in DMA (2 mL) was added 4-amino-5-fluoro-6-((trifluoromethyl)thio)nicotinic acid (95 mg, 2 equiv., 0.37 mmol). The mixture was heated to 40° C. and stirred for 2 h. The residue was purified by reversed-phase flash chromatography with the following conditions: Column-C18 silica gel; mobile phase, ACN in water(0.1% FA), 10% to 50% gradient in 10 mii; to afford (R or S)-2-(7-acryloyl-5-(4-amino-5-fluoro-6-((trifluoromethyl)thio)nicotinoyl)-3,4,5,5a,6,7,8,9-octahydro-2H-1,2,5,7-tetraazabenzo[cd]azulen-2-yl)-5-cyclopropylphenyl acetate (20 mg). This residue was then dissolved in THF (0.4 mL) and water (0.1 mL) and LiOH (1.5 mg, 2 equiv., 62 μmol) was added. The resulting mixture was heated to 40° C. and stirred for 1 h. The residue was then purified by reversed-phase flash chromatography with the conditions: Column-C18 silica gel; mobile phase, MeOH in water(0.1% $NH_4HCO_3$), 10% to 90% gradient in 10 min; to afford (R or S)-1-(5-(4-amino-5-fluoro-6-((trifluoromethyl)thio)nicotinoyl)-2-(4-cyclopropyl-2-hydroxyphenyl)-2,3,4,5,5a,6,8,9-octahydro-7H-1,2,5,7-tetraazabenzo[cd]azulen-7-yl)prop-2-en-1-one (7 mg) as a white solid. LCMS:(ESI, m/z): 603 $[M+1]^+$. $^1H$ NMR (400 MHz, Chloroform-d) δ 10.09 (s, 1H), 8.14 (s, 1H), 7.50-7.30 (m, 1H), 7.06-6.88 (m, 1H), 6.79 (d, J=1.9 Hz, 1H), 6.64 (dd, J=8.3, 2.0 Hz, 1H), 6.52 (d, J=16.5 Hz, 1H), 5.90-5.80 (m, 1H), 5.65-5.18 (m, 3H), 4.97 (d, J=13.3 Hz, 1H), 4.48 (d, J=13.6 Hz, 1H), 4.30-4.20 (m, 1H), 3.45-2.92 (m, 5H), 2.92-2.63 (m, 2H), 1.90-1.80 (m, 1H), 1.08-0.94 (m, 2H), 0.75-0.65 (m, 2H).

Example A-31: Preparation of (R or S)-1-(5-(6-amino-4-bromo-1H-benzo[d]imidazole-7-carbonyl)-2-(4-cyclopropyl-2-hydroxyphenyl)-2,3,4,5,5a,6,8,9-octahydro-7H-1,2,5,7-tetraazabenzo[cd]azulen-7-yl)prop-2-en-1-one

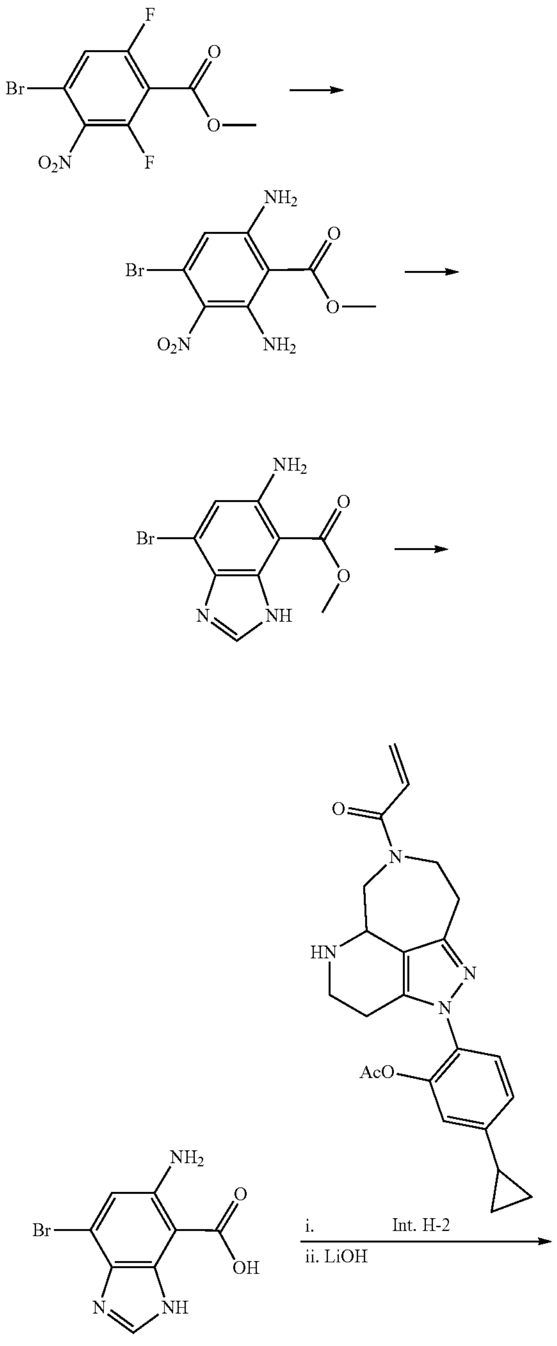

-continued

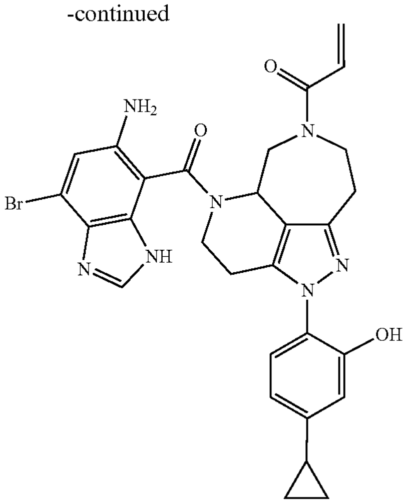

Step 1: Synthesis of methyl 2,6-diamino-4-bromo-3-nitrobenzoate

To a solution of methyl 4-bromo-2,6-difluoro-3-nitrobenzoate (5 g, 1 equiv., 0.02 mol) in dioxane (60 mL) was added $NH_3$ in MeOH (7N, 20 mL). The mixture was warmed to rt and stirred for 20 h, after which the mixture was diluted with saturated sodium bicarbonate solution (200 mL) and EA (200 mL), and the aqueous layer was extracted with EA (2×200 mL). The combined organic layers were washed with saturated brine (2×200 mL), dried over anhydrous sodium sulfate, and concentrated to give a residue. The residue was purified by flash column chromatography, eluting with EA/PE (1:5) to afford methyl 2,6-diamino-4-bromo-3-nitrobenzoate (3.4 g) as a white solid. LCMS:(ESI, m/z): 290 $[M+1]^+$ Step 2: Synthesis of Methyl 6-amino-4-bromo-1H-benzo[d]imidazole-7-carboxylate To a solution of methyl 2,6-diamino-4-bromo-3-nitrobenzoate (2 g, 1 equiv., 7 mmol) in MeOH (20 mL) and formic acid (20 mL) were added ammonium chloride (1 g, 1 mL, 4 equiv., 0.03 mol) and iron (0.8 g, 0.1 mL, 2 equiv., 0.01 mol). The mixture was stirred at 60° C. for 18 h, after which the mixture was cooled to rt and diluted with saturated sodium bicarbonate aqueous solution (200 mL) and EA (200 mL), and the aqueous layer was extracted with EA (2×200 mL). The combined organic layers were washed with saturated brine (2×200 mL), dried over anhydrous sodium sulfate and concentrated to give a residue. The residue was purified by flash column chromatography, eluting with EA/PE (1:1) to afford methyl 6-amino-4-bromo-1H-benzo[d]imidazole-7-carboxylate (1 g) as a brown solid. LCMS:(ESI, m/z): 270 $[M+1]^+$ Step 3: Synthesis of 6-amino-4-bromo-1H-benzo[d]imidazole-7-carboxylic Acid To a solution of methyl 6-amino-4-bromo-1H-benzo[d]imidazole-7-carboxylate (110 mg, 1 equiv., 407 μmol) in THF (1.2 mL) and $H_2O$ (0.3 mL) was added LiOH (19.5 mg, 2 equiv., 815 μmol), and the resulting mixture was stirred for 12 h at rt under a nitrogen atmosphere. The mixture was then acidified to pH=4 with the addition of 1 M sulfuric acid (aq.), then diluted with EA (20 mL) and water (15 mL), and the aqueous layer was extracted with EA (2×20 mL). The combined organic layers were washed with saturated brine (20 mL), dried over anhydrous sodium sulfate and concentrated to give a residue. The residue was purified by flash column chromatography, eluting with DCM/MEOH (10:1) to afford 6-amino-4-bromo-1H-benzo[ ]imidazole-7-carboxylic acid (20 mg) as a brown solid. LCMS:(ESI, m/z): 256 $[M+1]^+$ Step 4: Synthesis of (R or S)-1-(5-(6-amino-4-bromo-1H-benzo[d]imidazole-7-carbonyl)-2-(4-cyclopropyl-2-hydroxyphenyl)-2,3,4,5,5a,6,8,9-octahydro-7H-1,2,5,7-tetraazabenzo[cd]azulen-7-yl)prop-2-en-1-one A solution of (R or S)-2-(7-acryloyl-3,4,5,5a,6,7,8 9-octahydro-2H-1,2,5,7-tetraazabenzo[cd]azulen-2-yl)-5-cyclopropylphenyl acetate (40 mg, 1 equiv., 98 mol) in DMA (0.4 mL) were added DIEA (Int. H-2) (64 mg, 86 μL, 5 equiv., 0.49 mmol), 6-amino-4-bromo-1H-benzo[d]imidazole-7-carboxylic acid (25 mg, 1 equiv., 98 μmol) and HATU (56 mg, 1.5 equiv., 0.15 mmol). The mixture was stirred at rt for 48 h, then diluted with water (20 mL) and EA (20 mL), and the aqueous layer was extracted with EA (2×20 mL). The combined organic layers were washed with saturated brine (2×20 mL), dried over anhydrous sodium sulfate and concentrated to give a residue. The residue was purified by flash column chromatography, eluting with EA/DCM (10:1) to afford (R or S)-2-(7-acryloyl-5-(6-amino-4-bromo-1H-benzo[d]imidazole-7-carbonyl)-3,4,5,5a,6,7,8,9-octahydro-2H-1,2,5,7-tetraazabenzo[cd]azulen-2-yl)-5-cyclopropylphenyl acetate (15 mg) as a yellow solid.

To a solution of (R or S)-2-(7-acryloyl-5-(6-amino-4-bromo-1H-benzo[d]imidazole-7-carbonyl)-3,4,5,5a,6,7,8,9-octahydro-2H-1,2,5,7-tetraazabenzo[cd]azulen-2-yl)-5-cyclopropylphenyl acetate (15 mg, 1 equiv., 23 μmol) in THF (0.4 mL) and $H_2O$ (0.1 mL) was added LiOH (1.1 mg, 2 equiv., 47 mol). The mixture was stirred at rt for 20 h, after which the mixture was diluted with water (10 mL) and EA (10 mL), and the aqueous layer was extracted with EA (4×10 mL). The combined organic layers were washed with saturated brine (2×10 mL), dried over anhydrous sodium sulfate and concentrated to give a residue. The residue was purified by Prep-HPLC (Column: XSelect CSH Prep C18 OBD Column, 30*150 mm, 5 m; Mobile Phase A: Water(0.1% FA), Mobile Phase B: MeCN; Flow rate: 60 mL/min mL/min; Gradient: 19% B to 35% B in 9 min) to afford (R or S)-1-(5-(6-amino-4-bromo-1H-benzo[d]imidazole-7-carbonyl)-2-(4-cyclopropyl-2-hydroxyphenyl)-2,3,4,5,5a,6,8,9-octahydro-7H-1,2,5,7-tetraazabenzo[cd]azulen-7-yl)prop-2-en-1-one (1.4 mg) as a white solid. LCMS:(ESI, m/z): 602 $[M+1]^+$. $^1H$ NMR: δ 10.24 (s, 1H), 8.21-7.78 (m, 1H), 7.05-6.82 (m, 2H), 6.60 (d, J=8.2 Hz, 1H), 6.58-6.41 (m, 2H), 6.01-5.40 (m, 1H), 4.94 (s, 1H), 4.54 (s, 1H), 3.93 (s, 1H), 3.39-2.89 (m, 5H), 2.71-2.52 (m, 2H), 1.84 (s, 2H), 1.25-1.20 (m, 2H), 0.99-0.89 (m, 2H), 0.86-0.81 (m, 1H), 0.71-0.66 (m, 2H).

Example A-32: Preparation of (R or S)-1-(5-(4-amino-5-methoxy-6-(trifluoromethyl)nicotinoyl)-2-(4-cyclopropyl-2-hydroxyphenyl)-2,3,4,5,5a,6,8,9-octahydro-7H-1,2,5,7-tetraazabenzo[cd]azulen-7-yl) prop-2-en-1-one

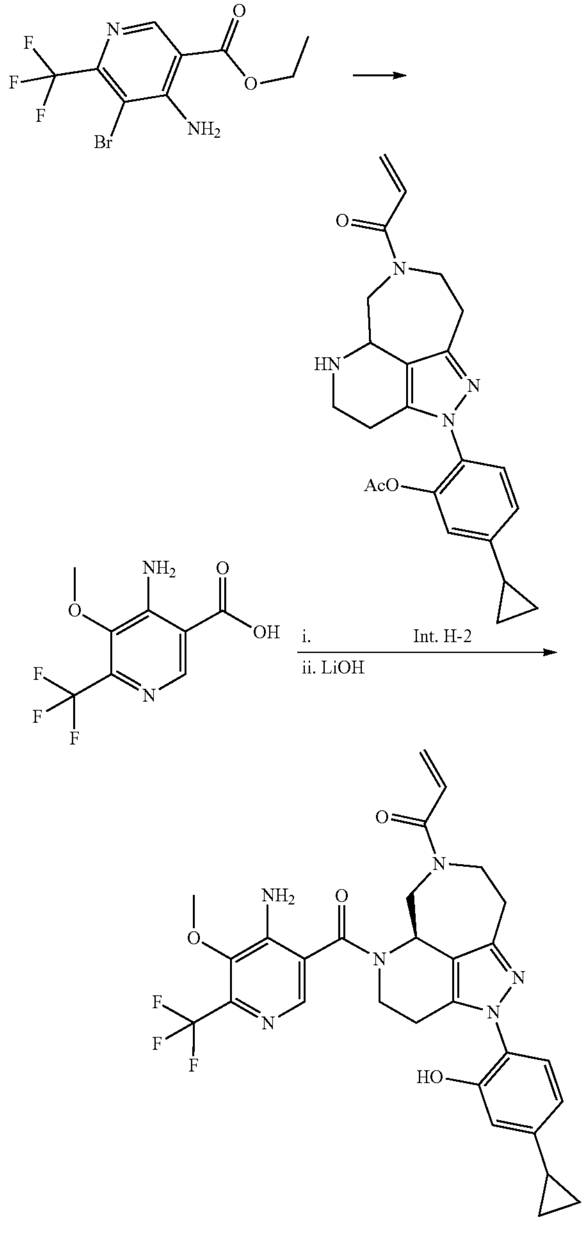

Step 1: Synthesis of 4-amino-5-methoxy-6-(trifluoromethyl)nicotinic Acid

To a stirred solution of ethyl 4-amino-5-bromo-6-(trifluoromethyl)nicotinate (200 mg, 1 equiv., 639 mol) and copper (40.6 mg, 4.54 μL, 1 equiv., 639 mol) in MeOH (3 mL) was added sodium methoxide (345 mg, 369 μL, 10 equiv., 6.39 mmol) and the resulting mixture was stirred at 100° C. for 12 h. The reaction was then quenched by the addition of water (20 mL) at rt. The resulting mixture was extracted with EA (2×20 mL) and the combined organic layers were washed with brine (2×20 mL), dried over anhydrous $Na_2SO_4$, and filtered. The filtrate was concentrated under reduced pressure and the residue was purified by silica gel column chromatography, eluting with EA/PE (1:5) to afford 4-amino-5-methoxy-6-(trifluoromethyl)nicotinic acid (30 mg) as a yellow solid. LCMS:(ESI, m/z): 237 $[M+1]^+$ Step 2: Synthesis of (R or S)-1-(5-(4-amino-5-methoxy-6-(trifluoromethyl)nicotinoyl)-2-(4-cyclopropyl-2-hydroxyphenyl)-2,3,4,5,5a,6,8,9-octahydro-7H-1,2,5,7-tetraazabenzo[cd]azulen-7-yl) prop-2-en-1-one To a stirred solution of (R or S)-2-(7-acryloyl-3,4,5,5a,6,7,8,9-octahydro-2H-1,2,5,7-tetraazabenzo[cd]azulen-2-yl)-5-cyclopropylphenyl acetate (Int. H-2) (75 mg, 1 equiv., 0.18 mmol,), 4-amino-5-methoxy-6-(trifluoromethyl)nicotinic acid (65 mg, 1.5 equiv., 0.28 mmol), and TEA (93 mg, 0.13 mL, 5 equiv., 0.92 mmol) in DMA (0.75 mL) was added HATU (0.11 g, 1.5 equiv., 0.28 mmol) and the resulting mixture was stirred at 40° C. for 1 h. The residue was purified by reversed-phase flash chromatography (column, C18 silica gel; mobile phase, ACN in Water(0.1% FA), 10% to 50% gradient in 10 min) to afford (R or S)-2-(-acryloyl-5-(4-amino-5-methoxy-6-(trifluoromethyl)nicotinoyl)-3,4,5,5a,6,7,8,9-octahydro-2H-1,2,5,7-tetraazabenzo[cd]azulen-2-yl)-5-cyclopropylphenyl acetate (30 mg) as a yellow solid.

To a stirred solution of (R or S)-2-(7-acryloyl-5-(4-amino-5-methoxy-6-(trifluoromethyl)nicotinoyl)-3,4,5,5a,6,7,8,9-octahydro-2H-1,2,5,7-tetraazabenzo[cd]azulen-2-yl)-5-cyclopropylphenyl acetate (25 mg, 1 equiv., 40 μmol) in THF (0.2 mL) and water (0.05 mL) was added LiOH (1.9 mg, 2 equiv., 80 μmol) and the mixture was stirred at 40° C. for 1 h. The mixture was purified by reversed-phase flash chromatography (column, C18 silica gel; mobile phase, MeCN in water (0.1% $NH_4HCO_3$), 10% to 50% gradient in 10 min) to afford (R or S)-1-(5-(4-amino-5-methoxy-6-(trifluoromethyl)nicotinoyl)-2-(4-cyclopropyl-2-hydroxyphenyl)-2,3,4,5,5a,6,8,9-octahydro-7H-1,2,5,7-tetraazabenzo[cd]azulen-7-yl)prop-2-en-1-one (12.0 mg) as an off-white solid. LCMS:(ESI, m/z): 583 $[M+1]^+$. $^1$H NMR (400 MHz, Chloroform-d) δ 10.09 (br s, 1H), 8.15 (s, 1H), 7.60-7.32 (m, 1H), 7.05-6.88 (m, 1H), 6.79 (d, J=1.9 Hz, 1H), 6.64 (dd, J=8.2, 2.0 Hz, 1H), 6.56-6.36 (m, 1H), 5.94-5.70 (m, 1H), 5.71-5.32 (m, 3H), 4.98 (d, J=13.3 Hz, 1H), 4.51 (d, J=13.6 Hz, 1H), 4.30-4.10 (m, 1H), 3.91 (s, 3H), 3.42-2.96 (m, 5H), 2.90-2.70 (m, 2H), 1.90-1.80 (m, 1H), 1.05-0.95 (m, 2H), 0.76-0.65 (m, 2H).

Example A-33: Preparation of (R or S)-1-(2-(4-cyclopropylphenyl)-5-(4-(methylamino)-6-(trifluoromethyl)nicotinoyl)-2,3,4,5,5a,6,8,9-octahydro-7H-1,2,5,7-tetraazabenzo[cd]azulen-7-yl)prop-2-en-1-one

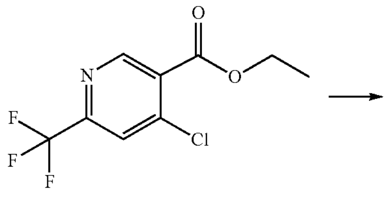

-continued

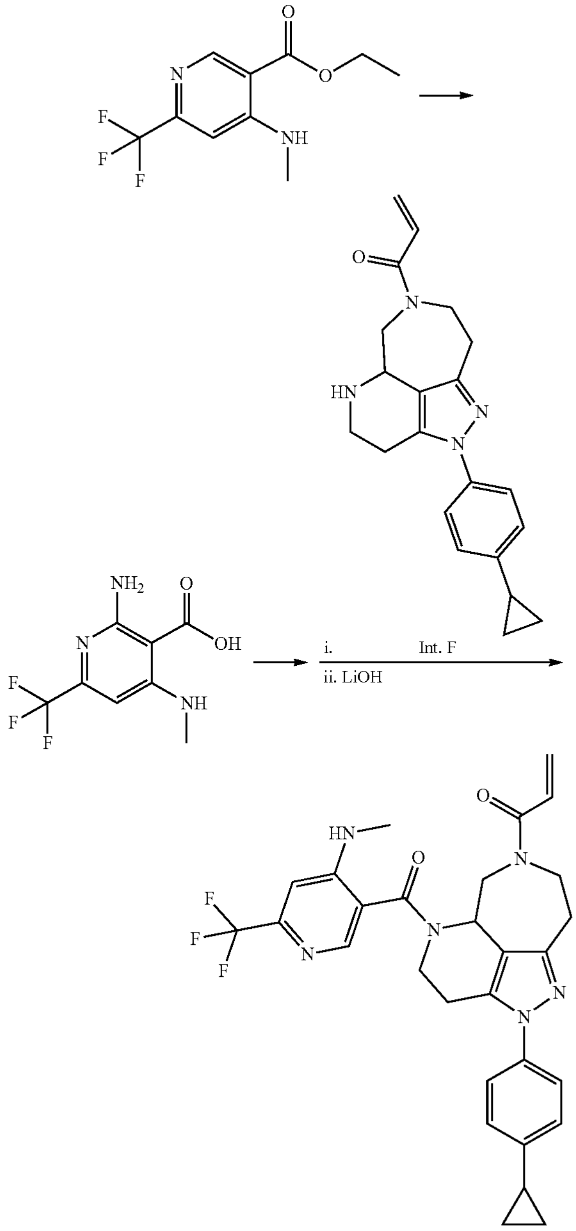

Step 1: Synthesis of Ethyl-4-(methylamino)-6-(trifluoromethyl)nicotinate

To a stirred solution of ethyl 4-chloro-6-(trifluoromethyl) nicotinate (1 g, 1 equiv., 4 mmol) in THF (10 mL) was added methylamine (0.2 g, 0.2 mL, 1.3 equiv., 5 mmol) and $K_2CO_3$ (1 g, 2.5 equiv., 0.01 mol) at rt and the mixture was stirred for 2 h. The reaction was then quenched by the addition of water (20 mL) at rt, and the resulting mixture was extracted with EA (2×20 mL). The combined organic layers were washed with brine (2×20 mL) and dried over anhydrous $Na_2SO_4$. After filtration, the filtrate was concentrated under reduced pressure. The residue was purified by silica gel column chromatography, eluting with EA/PE (2:5) to afford ethyl 4-(methylamino)-6-(trifluoromethyl)nicotinate (535 mg) as a white solid. LCMS:(ESI, m/z)249 $[M+1]^+$ Step 2: Synthesis of 4-(methylamino)-6-(trifluoromethyl)nicotinic Acid To a stirred solution of ethyl 4-(methylamino)-6-(trifluoromethyl)nicotinate (500 mg, 1 equiv., 2.01 mmol) in THF (4 mL) and $H_2O$ (2 mL) was added LiOH (241 mg, 5 equiv., 10.1 mmol) at rt and the reaction was stirred for 2 h. The reaction was then quenched by the addition of water (20 mL) at rt. The resulting mixture was extracted with EA (2×20 mL), and the combined organic layers were washed with brine (2×20 mL) and dried over a hydrous $Na_2SO_4$. After filtration, the filtrate was concentrated under reduced pressure to afford 4-(methylamino)-6 -(trifluoromethyl)nicotinic acid (300 mg) as a crude white solid which was used in the next step directly without further purification. LCMS:(ESI, m/z): 221 $[M+1]^+$ Step 3: Synthesis of (R or S)-1-(2-(4-cyclopropylphenyl)-5-(4-(methylamino)-6-(trifluoromethyl) nicotinoyl)-2,3,4,5,5a,6,8,9-octahydro-7H-1,2,5,7-tetr azabenzo[cd]azulen-7-yl)prop-2-en-1-one To a solution of (R or S)-1-(2-(4-cyclopropylphenyl)-2,3,4,5,5a,6,8,9-octahydro-7H-1,2,5,7-tetraazabenzo[cd]azulen-7-yl)prop-2-en-1-one (Int. F) (42.9 mg, 1 equiv., 123 μmol) in DMF (0.5 mL) were added DIEA (95.5 mg, 6 equiv., 739 μmol), 4-(methylamino)-6-(trifluoromethyl) nicotinic acid (32.5 mg, 1.2 equiv., 148 μmol) and HA TU (93.6 mg, 2 equiv., 246 μmol). The mixture was stirred at rt for 1 h, after which the mixture was filtered and purified directly by Prep-HPLC (Column:Xselect CSHTM Prep C18 5 μm 30*159 mm OBD; Mobile Phase A: Water (0.1% FA), Mobile Phase B: ACN; Flow rate: 60 mL/min; Gradient: 42% B to 56% B in 7 min) to afford (R or S)-1-(2-(4-cyclopropylphenyl)-5-(4-(methylamino)-6-(trifluoromethyl)nicotinoyl)-2,3,4,5,5a,6,8,9-octahydro-7H-1,2,5,7-tetraazabenzo[cd]azulen-7-yl)prop-2-en-1-one (11.7 mg) as a white solid. LCMS:(ESI, m/z): 551 $[M+1]^+$. $^1H$ NMR: (400 MHz, DMSO-$d_6$, ppm) δ 8.24-8.11 (m, 1H), 7.60-7.45 (m, 1H), 7.44-7.32 (m, 2H), 7.27-7.13 (m, 2H), 6.99 (s, 1H), 6.88-6.69 (m, 1H), 6.38-6.21 (m, 1H), 5.92-5.60 (m, 11H), 5.27-5.05 (m, 1H), 4.78-4.15 (m, 2H), 3.78-3.57 (m, 1H), 3.21-2.71 (m, 1H), 2.05-1.90 (m, 1H), 1.05-0.91 (m, 2H), 0.76-0.62 (m, 2H).

Example A-34: Preparation of (R or S)-1-(5-(3-amino-7-bromo-1H-indazole-4-carbonyl)-2-(4-cyclopropylphenyl)-2,3,4,5,5a,6,8,9-octahydro-7H-1,2,5,7-tetraazabenzo[cd]azulen-7-yl)prop-2-en-1-one

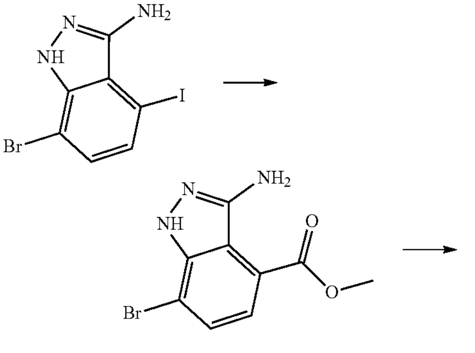

-continued

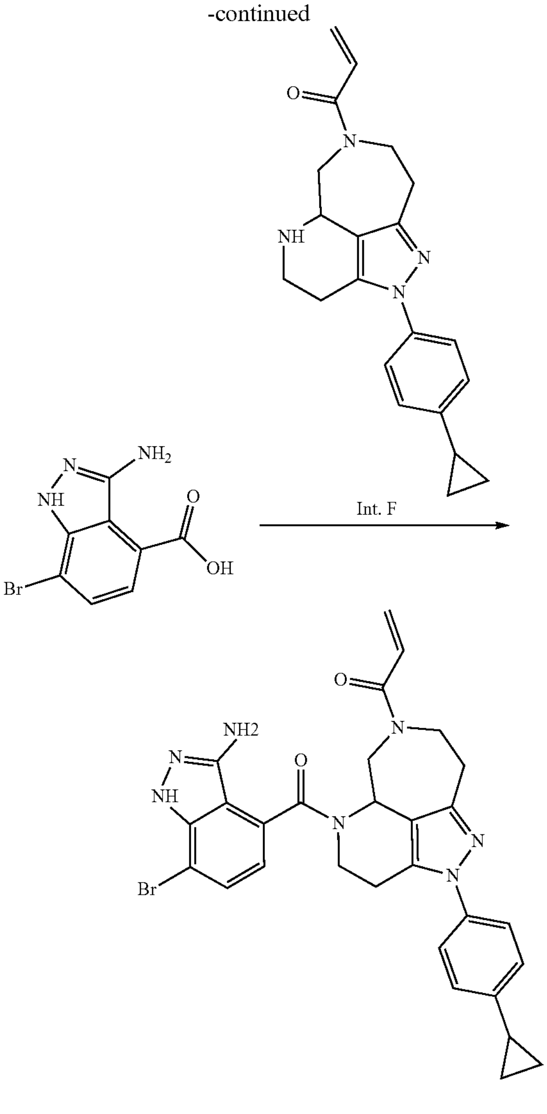

Step 1: Synthesis of Methyl 3-amino-7-bromo-1H-indazole-4-carboxylat

To a solution of 7-bromo-4-iodo-1H-indazol-3-amine (680 mg, 1 equiv., 2.01 mmol) in MeOH (13.6 ml) were added TEA (611 mg, 841 μL, 3 equiv., 6.04 mmol) and $PdCl_2$(dppf) (164 mg, 0.1 equiv., 201 μmol). The mixture was purged with carbon monoxide (×3) and then was pressurized to 2 MPa of carbon monoxide and heated to 60° C. for 12 h. The reaction mixture was cooled to rt and filtered, rinsed with EA (3×20 mL), then the diluted with water (20 mL). The aqueous layer was extracted with EA (2×20 mL) and the combined organic layers were washed with saturated brine (3×20 mL), dried over anhydrous sodium sulfate a d concentrated to give a residue. The crude product was purified by silica gel chromatography, eluting with PE:EA=10:1 to give methyl 3-amino-7-bromo-1H-indazole-4-carboxylate (440 g) as a yellow solid. LCMS: (ESI, m/z): 272 $[M+1]^+$ Step 2: Synthesis of 3-amino-7-bromo-1H-indazole-4-carboxylic Acid To a solution of methyl 3-amino-7-bromo-1H-indazole-4-carboxylate (400 mg, 1 equiv., 1.48 mmol) in THF (2 mL) and water (1 mL) was added LiOH (53.2 mg, 1.5 equiv., 2.22 mmol). The mixture was stirred at rt for 2 h, after which the mixture was aci ified to pH=3 with 1 M Sulfuric acid (aq.), then diluted with EA (20 mL) and water (15 mL) and the aqueous layer was extracted with EA (2×20 mL). The combined organic layers were washed with saturated brine (20 mL), dried over anhydrous sodium sulfate, filtered, and concentrated under reduced pressure. The residue was purified by reversed-phase flash chromatography (column-C18; mobile phase, (0.5% FA) water in ACN, 5% to 50% gradient in 15 min) to afford 3-amino-7-bromo-1H-indazole-4-carboxylic acid (110 mg) as a yellow solid. LCMS:(ESI, m/z): 256 $[M+1]^+$ Step 3: Synthesis of (R)-1-(5-(3-amino-7-bromo-1H-indazole-4-carbonyl)-2-(4-cyclopropylphenyl)-2,3,4,5,5a,6,8,9-octahydro-7H-1,2,5,7-tetraazabenzo[cd]azulen-7-yl)prop-2-en-1-one To a solution of (R or S)-1-(2-(4-cyclopropylphenyl)-2,3,4,5,5a,6,8,9-octahydro-7H-1,2,5,7-tetraazabenzo[cd]azulen-7-yl)prop-2-en-1-one (Int F) (50 mg, 1 equiv., 0.14 mmol) in DMF (1.5 mL) were added HBTU (82 mg, 1.5 equiv., 0.22 mmol), HAT (82 mg, 1.5 equiv., 0.22 mmol), DIEA (0.19 g, 0.25 mL, 10 equiv., 1.4 mmol), and 3-amino-7-bromo-1H-indazole-4-carboxylic acid (73 mg, 2 equiv., 0.29 mmol). The mixture was stirred at for 1 h, after which the mixture was diluted with water (20 mL) and EA (20 mL), and the aqueous layer was extracted with EA (2×20 mL). The combined organic layers were washed with saturated brine (2×20 mL), dried over anhydrous sodium sulfate and concentrated to give a residue. The residue was purified by Prep-HPLC (Column: Kinetex 5 μm EVO C18, 30 mm*150 mm; Mobile Phase A: Water (10 mmol/L $NH_4HCO_3$), Mobile Phase B: ACN; Flow rate: 60 mL/min; Gradient: 40% B to 57% B in 7 min) to afford (R or S)-1-(5-(3-amino-7-bromo-1H-indazole-4-carbonyl)-2-(4-cyclopropylphenyl)-2,3,4,5,5a,6,8,9-octahydro-7H-1,2,5,7-tetraazabenzo[cd]azulen-7-yl)prop-2-en-1-one (9.2 mg) as a yellow solid. LCMS:(ESI, m/z): 588 $[M+1]^+$. $^1$H MR: (400 MHz, DMSO-$d_6$, ppm) δ 12.31 (s, 1H), 7.59 (dd, J=7.7, 3.1 Hz, 1H), 7.50-7.33 (m, 1H), 7.26-7.12 (m, 2H), 7.04-6.98 (m, 1H), 6.39-6.21 (m, 1H), 5.80 (d, J=10.9 Hz, 1H), 5.31 (s, 1H), 5.10-4.60 (m, 2H), 4.38-4.24 (m, 1H), 3.88-3.73 (m, 1H), 3.01-2.76 (m, 1H), 2.00-1.94 (m, 1H), 0.99-0.95 (m, 2H), 0.72-0.66 (m, 2H) (some peaks obscured by solvent peak).

Example A-35: Preparation of (R or S)-1-(5-(4-amino-6-(trifluoromethyl)pyridazine-3-carbonyl)-2-(4-cyclopropyl-2-hydroxyphenyl)-2,3,4,5,5a,6,8,9-octahydro-7H-1,2,5,7-tetraazabenzo[cd]azulen-7-yl)prop-2-en-1-one

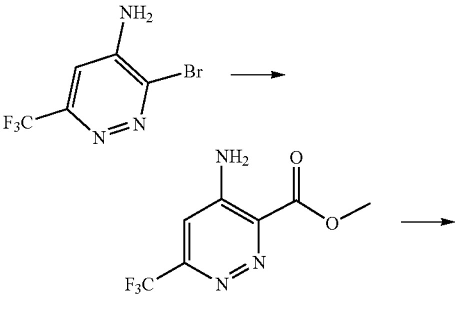

-continued

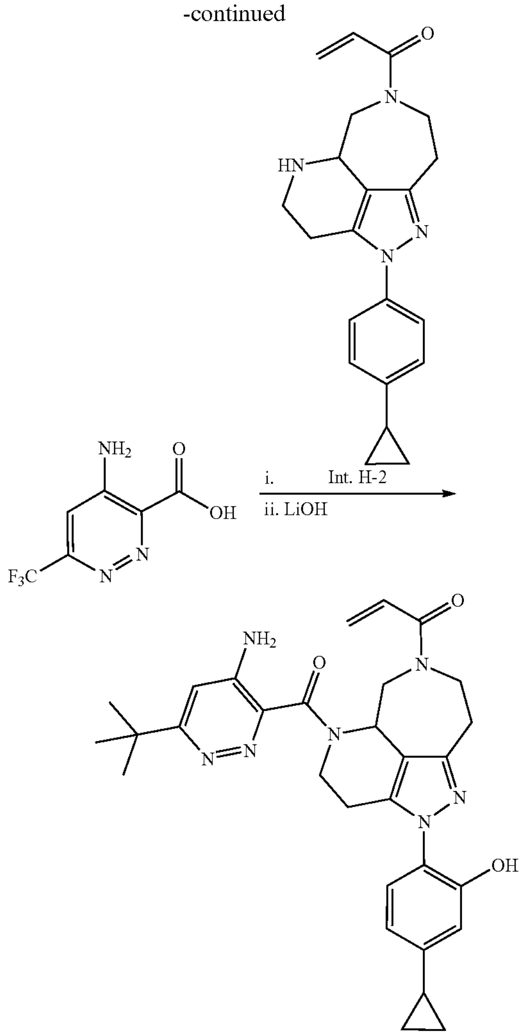

Step 1: Synthesis of Methyl 4-amino-6-(trifluoromethyl)pyridazine-3-carboxylate

To a solution of 3-bromo-6-(trifluoromethyl)pyridazin-4-amine (1.00 g, 1 equiv., 4.13 mmol) in MeOH (20 mL) were added Pd(dppf)$_2$ DCM complex (3.37 g, 1 equiv., 4.13 mmol) and TEA (418 mg, 576 μL, 1 equiv., 4.13 mmol). The mixture was purged with nitrogen (3×) and then was pressurized to 4.0 MPa with hydrogen and stirred at 80° C. for 12 h. The reaction mixture was cooled to rt and filtered, rinsed with EA (5×30 mL), filtered, and the filtrate was concentrated under reduced pressure to give a residue. The residue was purified by flash column chromatography (eluting with 25% EA in PE) to afford methyl 4-amino-6-(trifluoromethyl)pyridazine-3-carboxylate (560 mg) as a yellow solid. LCMS:(ESI, m/z): 222 $[M+1]^+$ Step 2: Synthesis of 4-amino-6-(trifluoromethyl)pyridazine-3-carboxylic Acid To a solution of methyl 4-amino-6-(trifluoromethyl) pyridazine-3-carboxylate (500 mg, 1 equiv., 2.26 mmol) in THF (5 mL) and $H_2O$ (2.5 mL) was added LiOH (108 mg, 2 equiv., 4.52 mmol). The mixture was stirred at rt for 4 h, after which the mixture was acidified to pH=3 with 1 M aqueous $H_2SO_4$. The mixture was diluted with EA (30 mL) and water (30 mL), and the aqueous layer was extracted with EA (2×30 mL). The combined organic layers were washed with saturated brine (20 mL), dried over anhydrous sodium sulfate and concentrated to give a residue. Purification by reverse phase chromatography (column: C18 column; Gradient: 35% MeCN in water with 0.2% formic acid) afforded 4-amino-6-(trifluoromethyl)pyridazine-3-carboxylic acid (150 mg) as a white solid. LCMS:(ESI, m/z): 208 $[M+1]^+$ Step 3: Synthesis of Afford (R or S)-1-(5-(4-amino-6-(trifluoromethyl)pyridazine-3-carbonyl)-2-(4-cyclopropyl-2-hydroxyphenyl)-2,3,4,5,5a,6,8,9-octahydro-7H-1,2,5,7 tetraazabenzo[cd]azulen-7-yl) prop-2-en-1-one To a solution of (R or S)-2-(7-acryloyl-3,4,5,5a,6,7,8,9-octahydro-2H-1,2,5,7-tetraazabenzo[cd]azulen-2-yl)-5-cyclopropylphenyl acetate (Int. H-2) (50 mg, 1 equiv., 0.12 mmol) in DMA (1 mL) were added DIEA (95 mg, 0.13 mL, 6 equiv., 0.74 mmol), HATU (70 mg, 1.5 equiv., 0.18 mmol) and 4-amino-6-(trifluoromethyl) pyridazine-3-carboxylic acid (25 mg, 1 equiv., 0.12 mmol). The mixture was stirred at rt for 30 min, after which the mixture was diluted with water (20 mL) and EA (20 mL), and the aqueous layer was extracted with EA (2×20 mL). The combined organic layers were washed with saturated brine (2×20 mL), dried over anhydrous sodium sulfate and concentrated to give a yellow oil which was used directly in the next step. The crude oil (50 mg, 1 equiv., 84 μmol) was re-dissolved in THF (0.4 mL) and water (0.1 mL) and LiOH (12 mg, 6 equiv., 0.50 mmol) was added. The mixture was stirred at rt for 30 min, after which the mixture was diluted with water (20 mL) and EA (20 mL), and the aqueous layer was extracted with EA (2×20 mL). The combined organic layers were washed with saturated brine (2× 20 mL), dried over anhydrous sodium sulfate and concentrated to give a residue. The residue was purified by Prep-HPLC (Column: XBridge Prep OBD C18 Column 30*150 mm, 5 μm; Mobile Phase A: Water(10 mmol/L $NH_4HCO_3$), Mobile Phase B: AC; Flow rate: 60 mL/min mL/min; Gradient: 30% B to 52% B in 8 min) to afford (R or S)-1-(5-(4-amino-6-(trifluoromethyl)pyridazine-3-carbonyl)-2-(4-cyclopropyl-2-hydroxyphenyl)-2,3,4,5,5a,6,8,9-octahydro-7H-1,2,5,7-tetraazabenzo[cd]azulen-7-yl)prop-2-en-1-one (4.2 mg) as a white solid. LCMS:(ESI, m/z): 554 $[M+1]^+$. $^1$H NMR: (400 MHz, Chloroform-d) δ 7.51-7.41 (m, 1H), 7.20-7.12 (m, 1H), 7.09-6.79 (m, 1H), 6.67-6.65 (m, 1H), 6.64-6.61 (m, 1H), 6.58-6.49 (m, 1H), 6.00 (s, 1H), 5.87 (d, J=10.4 Hz, 1H), 5.43-5.39 (m, 1H), 5.12-4.87 (m, 1H), 4.75-4.23 (m, 2H), 3.59-3.41 (m, 1H), 3.30-3.20 (m, 1H), 3.19-2.99 (m, 3H), 2.95-2.66 (m, 2H), 1.95-1.78 (m, 2H), 1.26 (s, 1H), 1.03-0.93 (m, 2H), 0.79-0.69 (m, 2H).

Example B-1: Preparation of Tert-Butyl 3-(hydroxymethyl)-1-(4-isopropylphenyl)-1,4,6,7-tetrahydro-5H-pyrazolo[4,3-c]pyridine-5-carboxylate (Int. J)

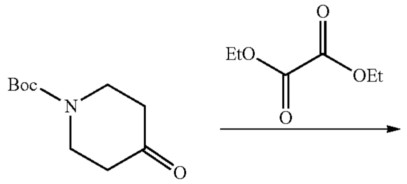

-continued

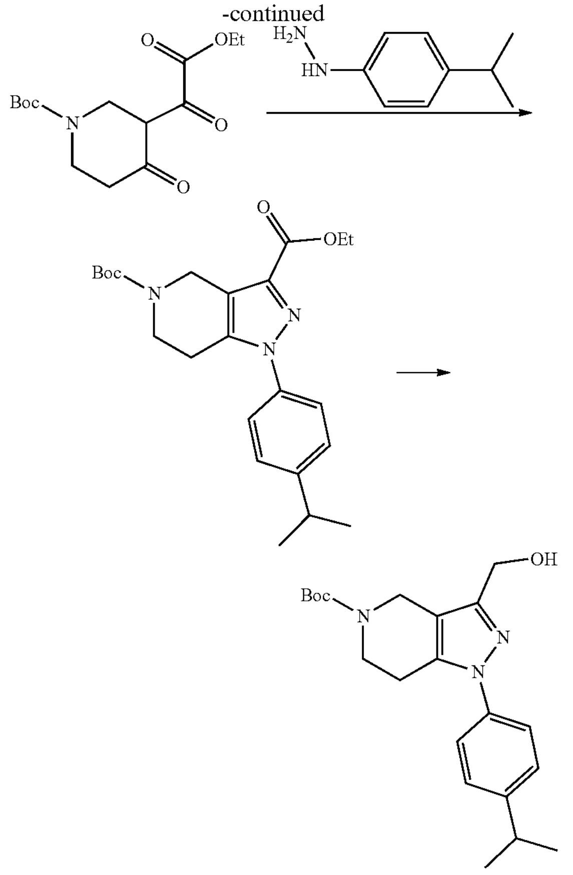

Int. J

Step 1: Synthesis of Tert-Butyl 3-(2-ethoxy-2-oxoacetyl)-4-oxopiperidine-1-carboxylate To a solution of tert-butyl 4-oxopiperidine-1-carboxylate (150, 753 mmol, 1.00 eq) in THF (1500 mL) was added LHMDS (1 M, 790 mL, 1.05 eq) dropwise over 30 min at 0° C. The mixture was stirred 30 min at 0° C. To the reaction liquid was added diethyl oxalate (116 g, 790 mmol, 108 mL, 1.05 eq) at 0° C. The mixture was stirred at 0° C. for 2 h after which the reaction mixture was quenched by addition AcOH (64.5 mL) at 0° C. The quenched reaction mixture was used into the next step directly without further workup. LCMS: m/z=322 (M+Na).$^+$ Step 2: Synthesis of 5-(tert-butyl) 3-ethyl 1-(4-isopropylphenyl)-1,4,6,7-tetrahydro-5H-pyrazolo[4,3-c]pyridine-3,5-dicarboxylate To the quenched reaction solution of tert-butyl 3-(2-ethoxy-2-oxoacetyl)-4-oxopiperidine-1-carboxylate (225 g, 748 mmol, 1.00 eq) in THF (1500 mL) was added (4-isopropylphenyl)hydrazine hydrochloride salt (147 g, 786 mmol, 1.05 eq). The mixture was stirred at 50° C. for 5 h, after which the reaction was quenched with water (200 mL), then the mixture was extracted with EtOAc (500 mL*2), the combined organics were w shed with $NaHCO_3$ (sat. aqueous, 500 mL*2), brine (500 mL*2), dried, concentrated under reduced pressure to yield a residue. The residue was purified by column chromatography ($SiO_2$, eluting with a gradient of petroleum ether/ethyl acetate=1/0 to 5/1) to afford 5-(tert-butyl) 3-ethyl 1-(4-isopropylphenyl)-1,4,6,7-tetrahydro-5H-pyrazolo[4,3-c]pyridine-3,5-dicarboxylate (220 g as a yellow oil. LCMS: m/z=414 $(M+H)^+$. $^1$H NMR: δ 7.56-7.49 (m, 2H), 7.43-7.38 (m, 2H), 4.57 (s, 2H), 4.37-4.25 (m, 2H), 3.62-3.55 (m, 2H), 3.02-2.93 (m, 1H), 2.83 (br t, J=5.3 Hz, 2H), 1.44 (s, 9H), 1.34-1.29 (m, 3H), 1.24 (d, J=6.9 Hz, 6H).

Step 3: Synthesis of Tert-Butyl 3-(hydroxymethyl)-1-(4-isopropylphenyl)-1,4,6,7-tetrahydro-5H-pyrazolo[4,3-c]pyridine-5-carboxylate (Int. J.)

To a solution of 5-(tert-butyl) 3-ethyl 1-(4-isopropylphenyl)-1,4,6,7-tetrahydro-5H-pyrazolo[4,3-c]pyridine-3,5-dicarboxylate (80.0 g, 193 mmol, 1.00 eq) in THF (750 mL) was added $LiAlH_4$ (2.5 M, 69.6 mL, 0.90 eq) dropwise at −20° C., then the reaction mixture was stirred at −20° C. for further 2 h, after which the reaction mixture was quenched by addition water (7.0 mL), NaOH (aq., 15.0%, 7.0 mL), water (20 mL) successively at −10° C., and then $Na_2SO_4$ (100 g) was added, the reaction mixture was stirred at room temperature for 30 min, filtered and the filtrate was concentrated under reduced pressure to give a residue. The residue was purified by column chromatography (SiO2, eluting with a gradient of PE/EtOAc=5/1 to 1/1) to afford tert-butyl 3-(hydroxymethyl)-1-(4-isopropylphenyl)-1,4,6,7-tetrahydro-5H-pyrazolo[4,3-c]pyridine-5-carboxylate (Int. J.) (41.0 g, 106 mmol, 54.8% yield, 96% purity) as a white solid. LCMS: m/z=372 $(M+H)^+$. $^1$H NMR: 400 MHz, DMSO-$d_6$. δ 7.45 (d, 2H), 7.35 (d, 2H), 5.10 (t, J=5.6 Hz, 1H), 4.48 (d, J=5.6 Hz, 2H), 4.44 (s, 2H), 3.57 (t, J=5.6 Hz, 2H), 2.94 (td, J=6.9, 13.8 Hz, 1H), 2.81 (br t, J=5.4 Hz, 2H), 1.44 (s, 9H), 1.23 (d, J=7.0 Hz, 6H)

Example B-2: Preparation of (S or R)-1-(5-(7-bromo-1H-benzo[d]imidazole-4-carbonyl)-2-(4-isopropylphenyl)-2,3,4,5,5a,6,8,9-octahydro-7H-1,2,5,7-tetraazabenzo[cd]azulen-7-yl)prop-2-en-1-one

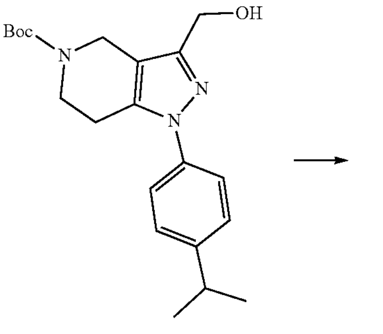

Int. J

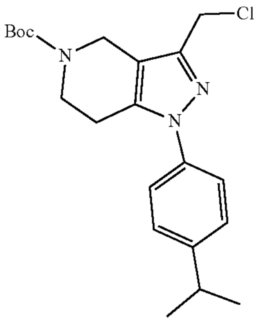

-continued
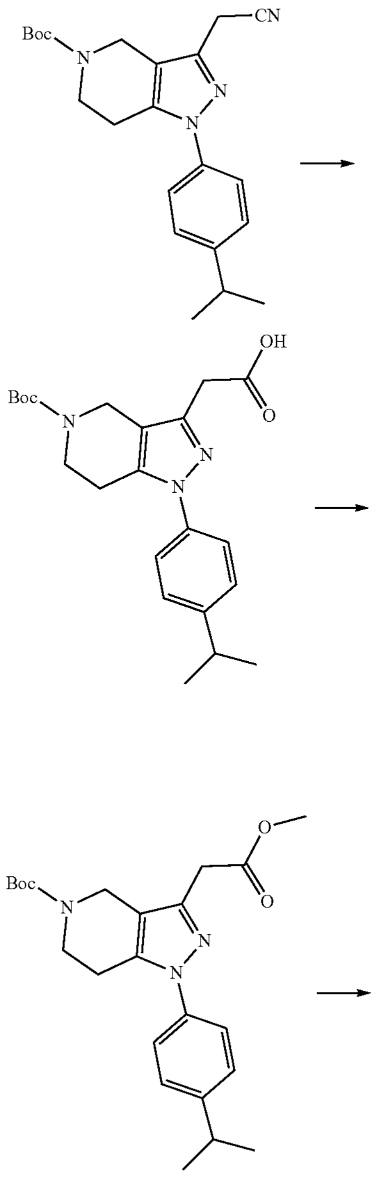
Int. K
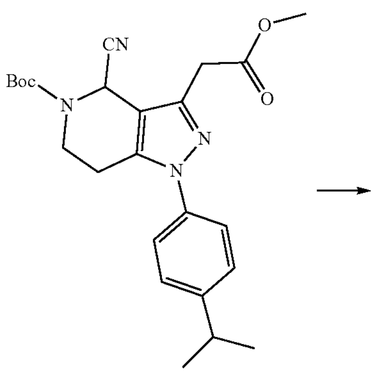
-continued
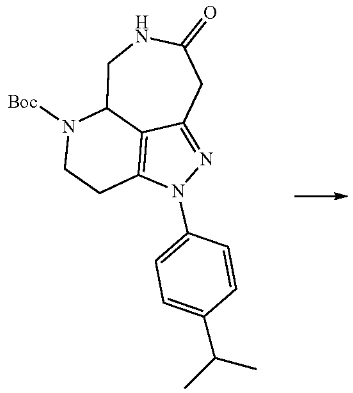
Int. L
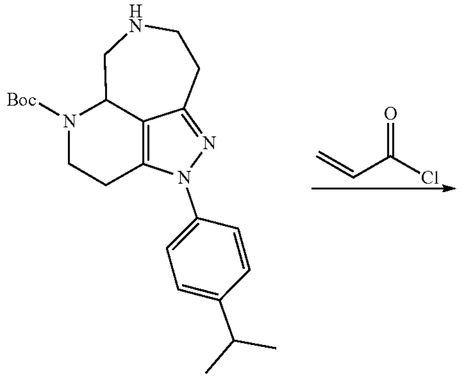
Int. M
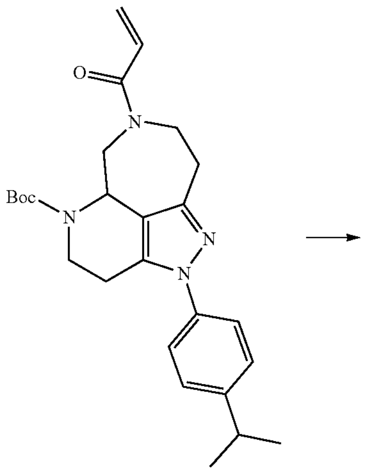

-continued

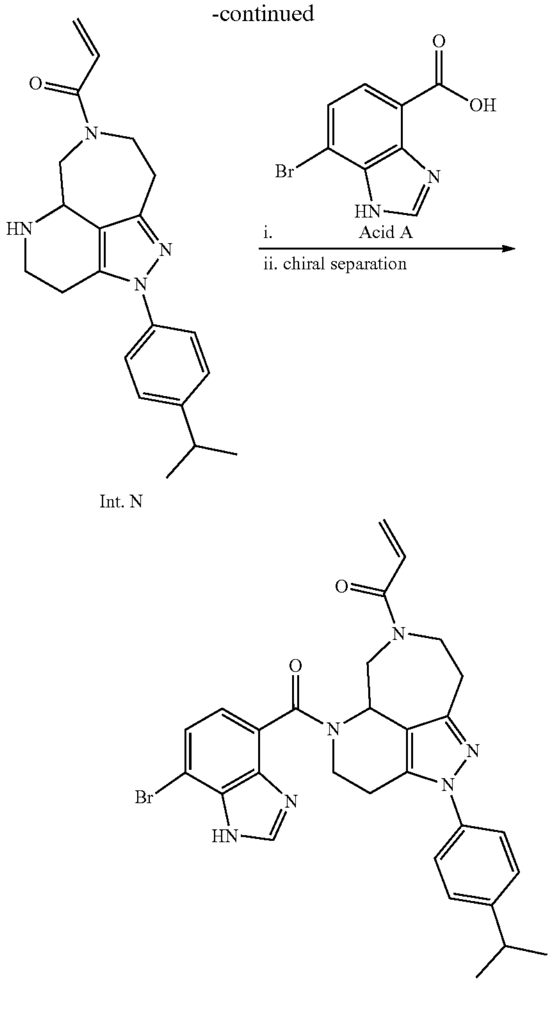

Int. N

Step 1: Synthesis of 1-(S-(7-bromo-1H-benzo[d] imidazole-4-carbonyl)-2-(4-(2,2-difluorocyclobutyl)-2-hydroxyphenyl)-2, 3,4,5,5a, 6,8,9-octahydro-7H-1,2, 5,7-tetraazabenzo[cd]azulen-7-yl)prop-2-en-1-one To a stirred solution of Int. J (10 g, 1 equiv., 27 mmol) in DCM (200 mL) was added thionyl chloride (4.5 g, 2.8 mL, 1.4 equiv., 38 mmol) at −10° C. and the resulting reaction mixture was stirred for 2 h. The reaction was then quenched by the addition of water (200 mL) at rt. The resulting mixture was extracted with DCM (2×50 mL). The combined organic layers were washed with brine (200 mL) and dried over anhydrous $Na_2SO_4$. After fil ration, the filtrate was concentrated under reduced pressure to afford tert-butyl 3-(chloromethyl)-1-(4-isopropylphenyl)-1,4,6,7-tetrahydro-5H-pyrazolo[4,3-c]pyridine-5-carboxylate (9.7 g) as a colorless oil, which was used directly without further purification. LCMS:(ESI, m/z):390 [M+1]

Step 2: Synthesis of Tert-Butyl 3-(cyanomethyl)-1-(4-isopropylphenyl)-1,4,6,7-tetrahydro-5H-pyrazolo [4,3-c]pyridine-5-carboxylate A mixture of tert-butyl 3-(chloromethyl)-1-(4-isopropylphenyl)-1,4,6,7-tetrahydro-5H-pyrazolo[4,3-c]pyridine-5-carboxylate (10 g, 1 equiv., 26 mmol), TBAF (13.3 g, 2 equiv., 51 mmol) and TMSCN (7.7 g, 3 equiv., 77 mmol) in MeCN (300 mL) was stirred for 15 h at room temperature. The mixture was then concentrated under reduced pressure. The residue was diluted with water (300 mL) and extracted with EtOAc (3×100 mL). The combined organic layers were washed with brine (300 mL) and dried over $Na_2SO_4$, filtered, and evaporated under reduced pressure. The residue was purified by silica gel column chromatography, eluting with PE/EtOAc (5:1) to afford tert-butyl 3-(cyanomethyl)-1-(4-isopropylphenyl)-1,4,6,7-tetrahydro-5H-pyrazolo[4,3-c]pyridine-5-carboxylate (9.2 g). LCMS:(ESI, m/z):381[M+1]

Step 3: Synthesis of 2-(5-(tert-butoxycarbonyl)-1-(4-isopropylphenyl)-4,5,6,7-tetrahydro-1H-pyrazolo [4,3-c]pyridin-3-yl)acetic Acid A solution of tert-butyl-3-(cyanomethyl)-1-(4-isopropylphenyl)-1,4,6,7-tetrahydro-5H-pyrazolo[4,3-c]pyridine-5-carboxylate (1.0 g, 1 equiv., 2.63 mmol) in 4M NaOH aqueous solution (40 mL) was stirred at 110° C. for 20 h. The reaction mixture was then cooled to rt, and the pH was adjusted to 5 with 1M hydrochloric acid aqueous solution. The mixture was extracted with DCM (2×50 mL), and the combined organic layers were washed with brine (2×200 mL) and dried over anhydrous $Na_2SO_4$. After filtration, the filtrate was concentrated under reduced pressure to afford 2-(5-(tert-butoxycarbonyl)-1-(4-isopropylphenyl)-4,5,6,7-tetrahydro-1H pyrazolo[4,3-c]pyridin-3-yl)acetic acid (0.82 g) as a light yellow solid. LCMS:(ESI, m/z):400 $[M+1]^+$ Step 4: Synthesis of Tert-Butyl 1-(4-isopropylphenyl)-3-(2-methoxy-2-oxoethyl)-1,4,6,7-tetrahydro-5H-pyrazolo[4,3-c]pyridine-5-carboxylate (Int. K)

A mixture of 2-(5-(tert-butoxycarbonyl)-1-(4-isopropylphenyl)-4,5,6,7-tetrahydro-1H-pyrazolo[4,3-c]pyridin-3-yl)acetic acid (1.05 g, 1 equiv., 2.63 mmol), iodomethane (1.12 g, 510 μL, 3 equiv., 7.89 mmol) and potassium carbonate (1.09 g, 462 μL, 3 equiv., 7.89 mmol) in DMF (20 mL) was stirred for 2 h at room temperature. The resulting mixture was quenched by water (50 mL) and extracted with EtOAc (2×30 mL). The combined organic layer were washed with brine (50 mL), dried over $Na_2SO_4$, filtered, and evaporated under reduced pressure to afford tert-butyl 1-(4-isopropylphenyl)-3-(2-methoxy-2-oxoethyl)-1,4,6,7-tetrahydro-5H-pyrazolo[4,3-c]pyridine-5-carboxylate (0.96 g), which was used in the next step without further purification. LCMS:(ESI, m/z):414 $[M+1]^+$ Step 5: Synthesis of Tert-Butyl (rac)-4-cyano-1-(4-isopropylphenyl)-3-(2-methoxy-2-oxoethyl)-1,4,6,7-tetrahydro-5H-pyrazolo[4,3-c]pyridine-5-carboxylate A mixture of Int. K (0.96 g, 1 equiv., 2.3 mmol), acetic acid (0.14 g, 0.13 mL, 1 equiv., 2.3 mmol), TMSCN (0.92 g, 1.2 mL, 4 equiv., 9.3 mmol) and $TEMPO^+BF_4^-$ (1.7 g, 2 mL, 3 equiv., 7.0 mmol) in MeCN (20 mL) was stirred for 2 h at room temperature. The mixture was concentrated under reduced pressure. The residue was diluted with sodium bicarbonate aqueous solution (40 mL) and extracted with EtOAc (2×20 mL). The combined organic layers were dried over $Na_2SO_4$, filtered, and evaporated under reduced pressure. The residue was purified by silica gel column chromatography, eluting with PE/EtOAc (4:1) to afford t rt-butyl (rac)-4-cyano-1-(4-isopropylphenyl)-3-(2-methoxy- 2-oxoethyl)-1,4,6,7-tetrahydro-5H-pyrazolo[4,3-c]pyridine-5-carboxylate (0.76 g) as a colorless oil. LCMS:(ESI, m/z): 439 [M+1]$^+$ Step 6: Synthesis of Tert-Butyl (rac)-2-(4-isopropylphenyl)-8-oxo-2,3,4,5a,6,7,8,9-octahydro-5H-1,2,5,7-tetraazabenzo[cd]azulene-5-carboxylate (Int. L)

To a solution of tert-butyl (rac)-4-cyano-1-(4-isopropylphenyl)-3-(2-methoxy-2-oxoethyl)-1,4,6,7-tetrahydro-5H-pyrazolo[4,3-c]pyridine-5-carboxylate (0.3 g, 1 equiv., 0.7 mmol) in MeOH (12 mL) was added Raney nickel (0.08 g, 0.01 mL, 50% wt, 1 equiv., 0.7 mmol) in a pressure tank. The mixture was purged with hydrogen×3 and then was pressurized to 3 MPa with hydrogen at 60° C. for 8 h. The reaction mixture was cooled to rt and filtered to remove insoluble solids. The filter cake was washed with MeOH (2×10 mL). The filtrate was concentrated under reduced pressure, and the residue was purified by reverse phase chromatography (column: C18 column; Gradient: MeCN in water with 0.05% $NaHCO_3$) to afford tert-butyl (rac)-2-(4-isopropylphenyl)-8-oxo-2,3,4,5a,6,7,8,9-octahydro-5H-1,2,5,7-tetraazabenzo[cd]azulene-5-carboxylate (Int. L) (0.22 g) as a white solid. LCMS:(ESI, m/z): 411 [M+1]$^+$ Step 7: Synthesis of Tert-Butyl 2-(4-isopropylphenyl)-2,3,4,5a,6,7,8,9-octahydro-5H-1, 2,5,7-tetraazabenzo[cd]azulene-5-carboxylate (Int. M)

To a solution of Int. L (450 mg, 1 equiv., 1.1 mmol) in THF (9 mL) was added borane-tetrahydrofuran complex solution (377 mg, 0.42 mL, 4 equiv., 4.38 mm 1). The resulting mixture was stirred for 15 h at 60° C., after which the reaction mixture was concentrated under reduced pressure and the mixture was stirred with MeOH (20 mL) for 0.5 h. the reaction mixture was then concentrated under reduced pressure, and the residue was purified by reverse phase chromatography (column: C18 column; Gradient: 60% MeCN in water with 0.05% $NaHCO_3$) to afford tert-butyl (rac)-2-(4-isopropylphenyl)-2,3,4,5a,6,7,8,9-octahydro-5H-1,2,5,7-tetraazabenzo[cd]azulene-5-carboxylate (Int. M) (320 mg) as a white solid. LCMS:(ESI, m/z):397 [M+1]$^+$ Step 8: Synthesis of Tert-Butyl (rac)-7-acryloyl-2-(4-isopropylphenyl)-2, 3,4,5a,6,7,8,9-octahydro-5H-1,2,5,7-tetraazabenzo[cd]azulene-5-carboxylate To a solution of Int. M (0.4 g, 1 equiv., 1 mmol) in DCM (8 mL) were added acryloylchloride (0.5 g, 0.4 mL, 5 equiv., 5 mmol) and TEA (1 g, 1 mL, 10 equiv., 0.01 mol). The mixture was stirred at room temperature for 2 h, after which the mixture was concentrated under reduced pressure. The residue was purified by silica gel column chromatography, eluting with DCM:MeOH (20:1) to afford tert-butyl (rac)-7-acryloyl-2-(4-isopropylphenyl)-2,3,4,5a,6,7,8,9-octahydro-5H-1,2,5,7-tetraazabenzo[cd]azulene-5-carboxylate (180 mg) as a white solid. LCMS:(ESI, m/z):451 [M+1]$^+$ Step 9: Synthesis of (rac)-1-(2-(4-isopropylphenyl)-2,3,4,5,5a,6,8,9-octahydro-7H-1,2,5,7-tetraazabenzo [cd]azulen-7-yl)prop-2-en-1-one (Int. N)

A solution of tert-butyl (rac)-7-acryloyl-2-(4-isopropylphenyl)-2,3,4,5a,6,7,8,9-octahydro-5H-1,2,5,7-tetraazabenzo[cd]azulene-5-carboxylate (160 m 1 equiv., 355 mol) in DCM (2.4 mL) and TFA (0.8 mL) was stirred at room temperature for 1 h. The solvent was then removed under reduced pressure to afford 1-(2-(4-isopropylphenyl)-2,3,4,5,5a,6,8,9-octahydro-7H-1,2,5,7-tetraazabenzo[cd]azulen-7-yl)prop-2-en-1-one (160 mg) as a crude yellow oil. The crude product (Int. N) was used in the next step directly without further purification. LCMS:(ESI, m/z): 351 [M+1]$^+$ Step 10: Synthesis of (S or R)-1-(5-(7-bromo-1H-benzo[d]imidazole-4-carbonyl)-2-(4-isopropylphenyl)-2,3,4,5,5a,6,8,9-octahydro-7H-1,2,5,7-tetraazabenzo[ed]azulen-7-yl)prop-2-en-1-one To a solution of Int. N (90 mg, 1 equiv., 0.26 mmol) in DMF (1.8 mL) were added 7-bromo-1H-benzo[d]imidazole-4-carboxylic acid (Acid A) (93 mg, 1.5 equiv., 0.39 mmol), DIEA (0.33 g, 0.44 mL, 10 equiv., 2.6 mmol), EDC hydrochloride (74 mg, 1.5 equiv., 0.39 mmol) and HOBT (69 mg, 71 μL, 2.0 equiv., 0.51 mmol). The mixture was stirred at room temperature for 2 h, after which the mixture was purified by Prep-HPLC (Column: YMC Triart C18 ExRs 5 m, 30 mm*150 mm; Mobile Phase A: water (10 mmol/L $NH_4HCO_3$), Mobile Phase B: MeCN; Flow rate: 60 mL/min; Gradient: 40% B to 60% B in 8 min; Wave Length: UV 254 nm/220 nm; retention time 1: 7.2 min) to afford (rac)-1-(5-(7-bromo-1H-benzo[d]imidazole-4-carbonyl)-2-(4-isopropylphenyl)-2,3,4,5,5a,6,8,9-octahydro-7H-1,2,5,7-tetraazabenzo[cd]azulen-7-yl)prop-2-en-1-one (15.6 mg) as a white solid. LCMS:(ESI, m/z): 573 [M+1]$^+$ Racemic 1-(5-(7-bromo-1H-benzo[d]imidazole-4-carbonyl)-2-(4-isopropylphenyl)-2,3,4,5,5a,6,8,9-octahydro-7H-1,2,5,7-tetraazabenzo[cd]azulen-7-yl)prop-2-en-1-one (15.6 mg, 27.0 μmol, 10.5%, 98.9% purity) was then purified by Prep-Chiral-HPLC (CHIRAL ART Cellulose-SB 3*25 cm, 5 μm; Mobile Phase A: HEX(0.1FA), Mobile Ph se B: EtOH: DCM=1:1; Flow rate: 40 mL/min; Gradient: isocratic 25; Wave Length: UV 254/20 nm; Sample Solvent: EtOH; Injection Volume: 0.75 mL; Number Of Runs: 2) to afford (S or R)-1-(5-(7-bromo-1H-benzo[d]imidazole-4-carbonyl)-2-(4-isopropylphenyl)-2,3,4,5,5a,6,8,9-octahydro-7H-1,2,5,7-tetraazabenzo[cd]azulen-7-yl)prop-2-en-1-one as the second-eluting peak (retention time 12.7 min, 6.6 mg, 11 μmol, 4.4%) as a white solid. LCMS:(ESI, m/z): 573 [M+1]$^+$. $^1$H NMR: (400 MHz, Chloroform-d, ppm) δ 12.58-10.48 (m, 1H), 8.60-7.94 (m, 1H), 7.56-7.35 (m, 2H), 7.34-7.15 (m, 4H), 6.78-6.31 (m, 1H), 5.89-5.69 (m, 1H), 5.57-5.22 (m, 1H), 4.95 (d, J=13.0 Hz, 1H), 4.68-4.17 (m, 2H), 3.38-2.55 (m, 8H), 1.34-1.19 (m, 6H). (some protons obscured by solvent peaks). Analytical Chiral HPLC: Column: CHIRAL ART Cellulose-SB; Column Size: 4.6*100 mm, 3 μm; Mobile Phase: Hex(0.1% FA):(EtOH:DCM=1:1)=65:35; Flow: 1.0 mL/min; Temperature: 25° C.; Retention time=2.8 min.

TABLE B1

The compounds of Examples B-2-1 through B-24 were prepared in an analogous manner to Example B-2 using the corresponding carboxylic acids. For Example B-2-1, the racemic final compound was separated using the following conditions: CHIRAL-HPLC with the following conditions: Column-CHIRALPAK-IC 2*25 cm, 5 μm; Mobile Phase A: HEX(0.1 % FA), Mobile Phase B: EtOH: DCM = 1:1; Flow rate: 20 mL/min; Gradient: isocratic 55; Wave Length: UV 254/220 nm; RT1(min): 4.3; RT2(min): 6.2 to afford the compound of the example as the second-eluting peak. For Example B-2-2, the racemic final compound was separated using the following conditions: CHIRALPAK IG-3 Column Size: 4.6*50 mm, 3 μm Mobile Phase: Hex (0.1% FA):(EtOH:DCM = 1:1)-75:25 Flow: 1.0 mL/min Temperature: rt to afford the compound of the example as the first-eluting peak. For Example B-2-3, the racemic final compound was separated using the following conditions: Column-CHIRALPAK-ID 3*25 cm, 5 μm; Mobile Phase A: HEX(0.1% FA), Mobile Phase B: EtOH:DCM = 1:1; Flow rate: 20 mL/min; Gradient: isocratic 30; Wave Length: UV 254/220 nm; RT1(min): 8.7; RT2(min): 15; to provide the compound of the example as the first-eluting peak. For Example B-2-4, the racemic final compound was separated using the following conditions: Column-CHIRALPAK IA, 2*25 cm, 5 μm; Mobile Phase A: Hex(0.1% FA)--HPLC, Mobile Phase B: EtOH:DCM = 1:1; Flow rate: 20 mL/min; Gradient: isocratic 25; Wave Length: UV 254/220 nm; RT1(min): 12; RT2(min): 16 to afford the compound of the example as the first-eluting peak.

| Example No. | Structure and Name | LCMS (ESI, m/z) | NMR |
|---|---|---|---|
| Example B-2-1 | 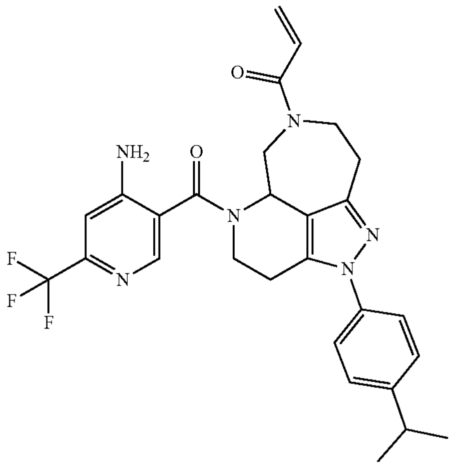 [SMILES: C=CC(=O)N1CCc2nn(-c3ccc(C(C)C)cc3)c3c2C(C1)N(C(=O)c1cnc(C(F)(F)F)cc1N)CC3] (R or S)-1-(5-(4-amino-6-(trifluoromethyl)nicotinoyl)-2-(4-isopropylphenyl)-2,3,4,5,5a,6,8,9-octahydro-7H-1,2,5,7-tetraazabenzo[cd]azulen-7-yl)prop-2-en-1-one | 539 $[M + H]^+$ | $^1H$ NMR (400 MHz, DMSO-$d_6$, ppm) δ 8.29-8.15 (m, 1H), 7.46-7.40 (m, 3H), 7.36 (d, J = 8.6 Hz, 2H), 7.10 (s, 1H), 6.74 (s, 2H), 6.30 (d, J = 16.5 Hz, 1H), 5.77 (dd, J = 24.9, 11.4 Hz, 1H), 5.16 (s, 1H), 4.68 (s, 1H),4.57-4.50 (m, 1H), 4.45 (d, J = 13.6 Hz, 1H), 3.68 (s, 1H), 3.01-2.89 (m, 2H) 2.94 (dt, J = 15.4, 7.7 Hz, 2H), 2.82 (d, J = 11.1 Hz, 2H), 2.71-2.60 (m, 1H), 1.22 (d, J = 7.0 Hz, 6H). |
| Example B-2-2 | 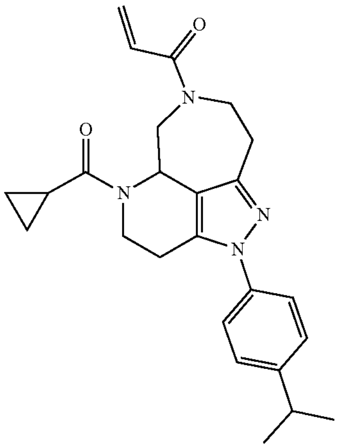 [SMILES: C=CC(=O)N1CCc2nn(-c3ccc(C(C)C)cc3)c3c2C(C1)N(C(=O)C1CC1)CC3] (R or S)-1-(5-(cyclopropanecarbonyl)-2-(4-isopropylphenyl)-2,3,4,5,5a,6,8,9-octahydro-7H- | 419 $[M + H]^+$ | $^1H$ NMR (400 MHz, Chloroform-d, ppm) δ 7.39-7.33 (m, 2H), 7.33-7.28 (m, 2H), 6.82-6.70 (m, 1H), 6.51-6.34 (m, 1H), 5.87-5.76 (m, 1H), 5.27-5.20 (m, 1H), 5.13-4.77 (m, 2H), 4.59-4.11 (m, 2H), 3.30-2.47 (m, 8H), 1.30-1.22 (m, 6H), 1.11-0.75 (m, 4H) |

TABLE B1-continued

The compounds of Examples B-2-1 through B-24 were prepared in an analogous manner to Example B-2 using the corresponding carboxylic acids. For Example B-2-1, the racemic final compound was separated using the following conditions: CHIRAL-HPLC with the following conditions: Column-CHIRALPAK-IC 2*25 cm, 5 μm; Mobile Phase A: HEX(0.1 % FA), Mobile Phase B: EtOH: DCM = 1:1; Flow rate: 20 mL/min; Gradient: isocratic 55; Wave Length: UV 254/220 nm; RT1(min): 4.3; RT2(min): 6.2 to afford the compound of the example as the second-eluting peak. For Example B-2-2, the racemic final compound was separated using the following conditions: CHIRALPAK IG-3 Column Size: 4.6*50 mm, 3 μm Mobile Phase: Hex (0.1% FA):(EtOH:DCM = 1:1)-75:25 Flow: 1.0 mL/min Temperature: rt to afford the compound of the example as the first-eluting peak. For Example B-2-3, the racemic final compound was separated using the following conditions: Column-CHIRALPAK-ID 3*25 cm, 5 μm; Mobile Phase A: HEX(0.1% FA), Mobile Phase B: EtOH:DCM = 1:1; Flow rate: 20 mL/min; Gradient: isocratic 30; Wave Length: UV 254/220 nm; RT1(min): 8.7; RT2(min): 15; to provide the compound of the example as the first-eluting peak. For Example B-2-4, the racemic final compound was separated using the following conditions: Column-CHIRALPAK IA, 2*25 cm, 5 μm; Mobile Phase A: Hex(0.1% FA)--HPLC, Mobile Phase B: EtOH:DCM = 1:1; Flow rate: 20 mL/min; Gradient: isocratic 25; Wave Length: UV 254/220 nm; RT1(min): 12; RT2(min): 16 to afford the compound of the example as the first-eluting peak.

| Example No. | Structure and Name | LCMS (ESI, m/z) | NMR |
|---|---|---|---|
| | 1,2,5,7-tetraazabenzo[cd]azulen-7-yl)prop-2-en-1-one | | |
| Example B-2-3 | 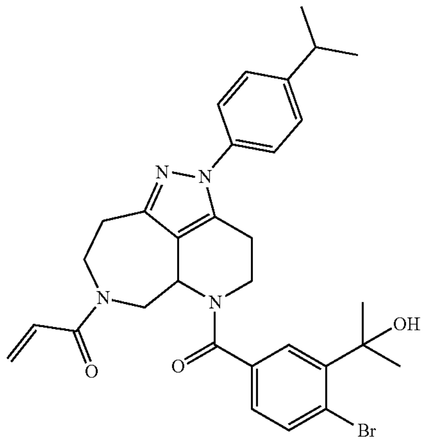 [SMILES: C=CC(=O)N1CCc2nn(-c3ccc(C(C)C)cc3)c3c2C(C1)N(C(=O)c1ccc(Br)c(C(C)(C)O)c1)CC3] (R or S)-1-(5-(4-bromo-3-(2-hydroxypropan-2-yl)benzoyl)-2-(4-isopropylphenyl)-2,3,4,5,5a,6,8,9-octahydro-7H-1,2,5,7-tetraazabenzo[cd]azulen-7-yl)prop-2-en-1-one | 591 $[M + H]^+$ | $^1H$ NMR (400 MHz, DMSO-d, ppm) 7.99-7.92 (m, 1H), 7.74-7.65 (m, 1H), 7.56-7.41 (m, 3H), 7.41-7.28 (m, 3H), 6.23 (dd, J = 35.6, 16.5 Hz, 1H), 5.77 (dd, J = 14.9, 7.9 Hz, 1H), 5.47 (s, 1H), 5.15 (d, J = 10.4 Hz, 1H), 4.68 (d, J = 11.1 Hz, 1H), 4.28 (d, J = 14.2 Hz, 1H), 3.78 (s, 1H), 3.42 (d, J = 12.8 Hz, 1H), 3.22-2.56 (m, 6H), 1.69-1.62 (m, 6H), 1.26-1.12 (m, 7H). |
| Example B-2-4 | 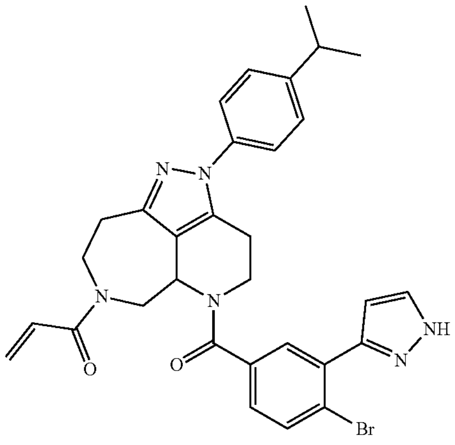 [SMILES: C=CC(=O)N1CCc2nn(-c3ccc(C(C)C)cc3)c3c2C(C1)N(C(=O)c1ccc(Br)c(-c2cc[nH]n2)c1)CC3] (S or R)-1-(5-(4-bromo-3-(1H-pyrazol-3-yl)benzoyl)-2-(4-isopropylphenyl)- | 599 $[M + H]^+$ | $^1H$ NMR (400 MHz, Chloroform-d, ppm) δ 7.98-7.64 (m, 3H), 7.49-7.26 (m, 6H), 6.89-6.41 (m, 2H), 5.98-5.75 (m, 1H), 5.35 (t, J = 4.7 Hz, 1H), 5.16-4.73 (m, 2H), 4.67-4.39 (m, 1H), 4.32-4.04 (m, 1H), 3.23-2.67 (m, 7H), 1.27 (d, J = 3.4 Hz, 6H). |

TABLE B1-continued

The compounds of Examples B-2-1 through B-24 were prepared in an analogous manner to Example B-2 using the corresponding carboxylic acids. For Example B-2-1, the racemic final compound was separated using the following conditions: CHIRAL-HPLC with the following conditions: Column-CHIRALPAK-IC 2*25 cm, 5 μm; Mobile Phase A: HEX(0.1 % FA), Mobile Phase B: EtOH: DCM = 1:1; Flow rate: 20 mL/min; Gradient: isocratic 55; Wave Length: UV 254/220 nm; RT1(min): 4.3; RT2(min): 6.2 to afford the compound of the example as the second-eluting peak. For Example B-2-2, the racemic final compound was separated using the following conditions: CHIRALPAK IG-3 Column Size: 4.6*50 mm, 3 μm Mobile Phase: Hex (0.1% FA):(EtOH:DCM = 1:1)-75:25 Flow: 1.0 mL/min Temperature: rt to afford the compound of the example as the first-eluting peak. For Example B-2-3, the racemic final compound was separated using the following conditions: Column-CHIRALPAK-ID 3*25 cm, 5 μm; Mobile Phase A: HEX(0.1% FA), Mobile Phase B: EtOH:DCM = 1:1; Flow rate: 20 mL/min; Gradient: isocratic 30; Wave Length: UV 254/220 nm; RT1(min): 8.7; RT2(min): 15; to provide the compound of the example as the first-eluting peak. For Example B-2-4, the racemic final compound was separated using the following conditions: Column-CHIRALPAK IA, 2*25 cm, 5 μm; Mobile Phase A: Hex(0.1% FA)--HPLC, Mobile Phase B: EtOH:DCM = 1:1; Flow rate: 20 mL/min; Gradient: isocratic 25; Wave Length: UV 254/220 nm; RT1(min): 12; RT2(min): 16 to afford the compound of the example as the first-eluting peak.

| Example No. | Structure and Name | LCMS (ESI, m/z) | NMR |
|---|---|---|---|
| | 2,3,4,5,5a,6,8,9-octahydro-7H-1,2,5,7-tetraazabenzo[cd]azulen-7-yl)prop-2-en-1-one | | |

Example B-3: Preparation of (S or R)-1-(5-(2-amino-7-bromo-1H-benzo[d]imidazole-4-carbonyl)-2-(4-isopropylphenyl)-2,3,4,5,5a,6,8,9-octahydro-7H-1,2,5,7-tetraazabenzo[cd]azulen-7-yl)prop-2-en-1-one

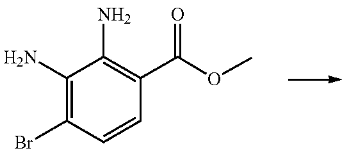

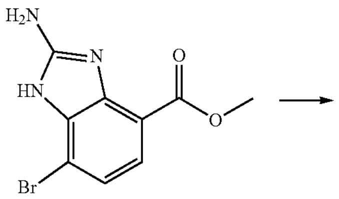

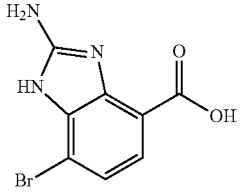

-continued

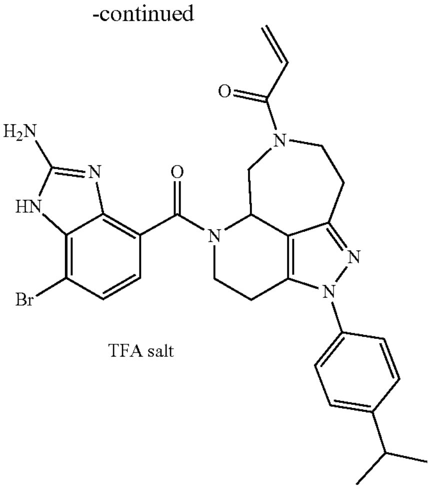

TFA salt

Step 1: Synthesis of Methyl 2-amino-7-bromo-1H-benzo[d]imidazole-4-carboxylate The solution of methyl 2,3-diamino-4-bromobenzoate (1 g, 1 equiv., 4 mmol) in MeOH (5 mL) and water (5 mL) was added cyanic bromide (0.6 g, 1.5 equiv., 6 mmol). The mixture was warmed to 60° C. and stirred for 12 h. The mixture was then diluted with water (20 mL) and EtOAc (20 mL), and the aqueous layer was extracted with EtOAc (2×20 mL). The combined organic layers were washed with saturated brine (2×20 mL), dried over anhydrous sodium sulfate and concentrated to afford methyl 2-amino-7-bromo-1H-benzo[d]imidazole-4-carboxylate (1.2 g) as a yellow solid. The crude product was used in the next step directly without further purification. LCMS:(ESI, m/z):270 $[M+1]^+$ $^1H$ NMR (400 MHz, DMSO-$d_6$) δ 11.08 (s, 1H), 7.32 (d, J=8.4 Hz, 1H), 7.21 (d, J=8.4 Hz, 1H), 6.56 (s, 2H), 3.90 (s, 3H).

Step 2: Synthesis of 2-amino-7-bromo-1H-benzo[d]imidazole-4-carboxylic Acid

To a solution of methyl 2-amino-7-bromo-1H-benzo[d]imidazole-4-carboxylate (1 g, 1 equiv., 4 mmol) in water (5 mL) and THF (15 mL) was added lithium hydroxide (0.2 g, 2 equiv., 7 mmol). The mixture was stirred at 50° C. for 12 h. The residue was then purified by flash column chromatography, eluting with MeOH/DCM (1:2) to afford 2-amino-7-bromo-1H-benzo[d]imidazole-4-carboxylic acid (382 mg) as a yellow solid. LCMS:(ESI, m/z):256 $[M+1]^+$. $^1H$ NMR: (400 MHz, DMSO-$d_6$) δ 11.88 (s, 1H), 7.19 (d, J=8.2 Hz, 2H), 6.85 (s, 3H).

Step 3: Synthesis of(rac)-1-(5-(2-amino-7-bromo-1H-benzo[d]imidazole-4-carbonyl)-2-(4-isopropylphenyl)-2,3,4,5,5a,6,8,9-octahydro-7H-1,2,5,7-tetraazabenzo[cd]azulen-7-yl)prop-2-en-1-one To a solution of (rac)-1-(2-(4-isopropylphenyl)-2,3,4,5,5a,6,8,9-octahydro-7H-1,2,5,7-tetraazabenzo[cd]azulen-7-yl)prop-2-en-1-one (Int. N) (200 mg, 1 equiv., 571 gmol) in DMF (2 mL) were added DIEA (221 mg, 3 equiv., 1.71 mmol), 2-amino-7-bromo-1H-benzo[d]imidazole-4-carboxylic acid (219 mg, 1.5 equiv., 856 μmol) and HBTU (433 mg, 2 equiv., 1.14 mmol). The mixture was stirred at room temperature for 1 h, after which the mixture was diluted with water (20 mL) and EtOAc (20 mL), and the aqueous layer was extracted with EtOAc (2×20 mL). The combined organic layers were washed with saturated brine (2×20 mL), dried over anhydrous sodium sulfate and concentrated to give a residue. The residue was purified by Prep-HPLC (Column: XBridge BEH C18 OBD Prep Column 130, 5 m, 30 mm*150 mm; Mobile Phase A: water (10 mmol/L $NH_4HCO_3$), Mobile Phase B: MeCN; Flow rate: 60 mL/min; Gradient: 31% B to 51% B in 10 min; Wave Length: UV 254 nm/220 nm; retention time 1: 9.5) to afford (rac)-1-(5-(2-amino-7-bromo-1H-benzo[d]imidazole-4-carbonyl)-2-(4-isopropylphenyl)-2,3,4,5,5a,6,8,9-octahydro-7H-1,2,5,7-tetraazabenzo[cd]azulen-7-yl)prop-2-en-1-one (17 mg) as a white solid. LCMS:(ESI, m/z):588 $[M+1]^+$ The (rac)-1-(5-(2-amino-7-bromo-1H-benzo[d]imidazole-4-carbonyl)-2-(4-isopropylphenyl)-2,3,4,5,5a,6,8,9-octahydro-7H-1,2,5,7-tetraazabenzo[cd]azulen-7-yl)prop-2-en-1-one (17 mg) was then purified by chiral prep-HPLC with the following conditions (Column: CHIRALPAK-IC 2*25 cm, 5 μm; Mobile Phase A: HEX(0.1% DEA), Mobile Phase B: IPA: DCM=1:1; Flow rate: 20 mL/min; Gradient: isocratic 30; Wave Length: UV 254/220 nm; Injection Volume: 2.5 mL; Number Of Runs: 1) to afford (S or R)-1-(5-(2-amino-7-bromo-1H-benzo[d]imidazole-4-carbonyl)-2-(4-isopropylphenyl)-2,3,4,5,5a,6,8,9-octahydro-7H-1,2,5,7-tetraazabenzo[cd]azulen-7-yl)prop-2-en-1-one as the second-eluting peak (7.4 mg, 12 μmol, 43%, 98.7% purity) as a white solid. LCMS:(ESI, m/z):588 $[M+1]^+$. $^1H$ NMR (400 MHz, Chloroform-d) δ 12.10 (brs, 1H), 8.70 (brs, 1H), 7.60-7.54 (m, 1H), 7.45-6.96 (m, 5H), 6.94-6.57 (m, 1H), 6.10-5.62 (m, 1H), 5.58-5.28 (m, 1H), 5.19-4.88 (m, 1H), 4.61-0.51 (m, 3H), 3.49-2.53 (m, 8H), 1.34-1.17 (m, 6H). Analytical Chiral HPLC: Column: CH(RAL ART Cellulose-SB 4.6*50 mm, 3 μm; Mobile Phase: Hex(0.1% TFA):(EtOH:DCM=1:1)=65:35; Flow rate: 1 mL/min; Temperature:25° C.; retention time=4.0 min.

Example B-4: Preparation of (S or R)-1-(5-(2-(azetidin-1-yl)-7-bromo-1H-benzo[d]imidazole-4-carbonyl)-2-(4-isopropylphenyl)-2,3,4,5,5a,6,8,9-octahydro-7H-1,2,5,7-tetraazabenzo[cd]azulen-7-yl)prop-2-en-1-one

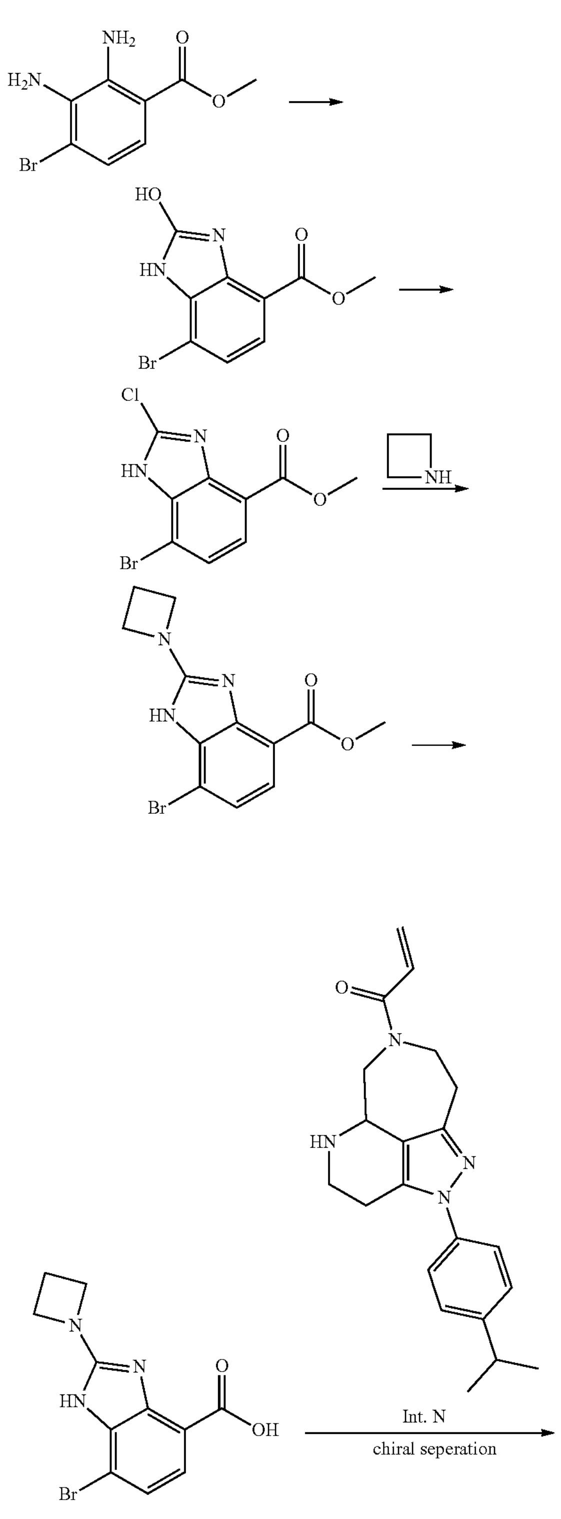

-continued

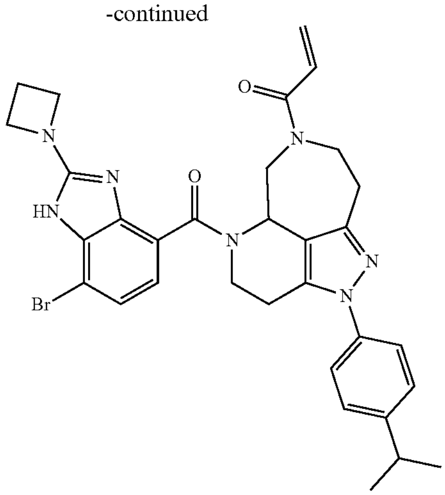

Step 1: Synthesis of Methyl 7-bromo-2-hydroxy-1H-benzo[d]imidazole-4-carboxylate To a solution of methyl 2,3-diamino-4-bromobenzoate (2 g, 1 equiv., 8 mmol) in dioxane (20 mL) were added DIEA (3 g, 3 equiv., 0.02 mol) and CDI (3 g, 2 equiv., 0.02 mol). The reaction was placed under a positive pressure of nitrogen and subjected to three backfilling cycles under high vacuum. The resulting mixture was stirred for 100° C. at 24 h under a nitrogen atmosphere. The reaction mixture was then cooled to RT, and the mixture was filtered and rinsed with EtOAc (3×20 mL), then diluted with water (20 mL). The aqueous layer was extracted with EtOAc (2×20 mL). The combined organic layers were washed with saturated brine (3×20 mL), dried over anhydrous sodium sulfate, filtered, and concentrated to give a residue. The crude product was purified by silica gel chromatography, eluting with PE: EtOAc=4:1 to give methyl 7-bromo-2-hydroxy-1H-benzo[d]imidazole-4-carboxylate (2.89 g) as a white solid. LCMS:(ESI, m/z): 271 [M+1]$^+$ Step 2: Synthesis of Methyl 7-bromo-2-chloro-1H-benzo[d]imidazole-4-carboxylate A solution of methyl 7-bromo-2-hydroxy-1H-benzo[d]imidazole-4-carboxylate (1.7 g, 1 equiv., 6.3 mmol) in phosphoryl trichloride (14 g, 15 equiv., 94 mmol) was stirred at 110° C. for 1.5 h. The mixture was then diluted with water (20 mL) and EtOAc (20 mL), and the aqueous layer was extracted with EtOAc (2×20 mL). The combined organic layers were washed with saturated brine (2×20 mL), dried over anhydrous sodium sulfate and concentrated to give a residue. The residue was purified by silica gel chromatography eluting with PE: EtOAc=3:1 to afford methyl 7-bromo-2-chloro-1H-benzo[d]imidazole-4-carboxylate (1.5 g) as a white solid. LCMS:(ESI, m/z):291 [M+1]$^+$ Step 3: Synthesis of Methyl 2-(azetidin-1-yl)-7-bromo-1H-benzo[d]imidazole-4-carboxylate To a solution of methyl 7-bromo-2-chloro-1H-benzo[d]imidazole-4-carboxylate (2.66 g, 1 equiv., 9.19 mmol) in DMF (39.9 mL) were added DIEA (5.94 g, 5 equiv., 45.9 mmol) and azetidine (787 mg, 1.5 equiv., 13.8 mmol). The mixture was stirred at 80° C. for 24 h. The mixture was diluted with water (20 mL) and EtOAc (20 mL), and the aqueous layer was extracted with EtOAc (2×20 mL). The combined organic layers were washed with saturated brine (2×20 mL), dried over anhydrous sodium sulfate and concentrated to give a residue. The residue was purified by silica gel chromatography eluting with PE: EtOAc=3:1) to afford methyl 2-(azetidin-1-yl)-7-bromo-1H-benzo[d]imidazole-4-carboxylate (0.5 g) as a white solid. LCMS:ESI, m/z):310 [M+1]$^+$ Step 4: Synthesis of (S or R)-1-(5-(2 509 zetidinein-1-yl)-7-bromo-1H-benzo[d]imidazole-4-carbonyl)-2-(4-isopropylphenyl)-2,3,4,5,5a,6,8,9-octahydro-7H-1,2,5,7-tetraazabenzo[cd]azulen-7-yl)prop-2-en-1-one To a solution of methyl 2-(azetidin-1-yl)-7-bromo-1H-benzo[d]imidazole-4-carboxylic acid (100 mg, 1 equiv., 338 gmol) in DMF (2 mL) were added HBTU (192 mg, 1.5 equiv., 507 μmol), (rac)-1-(2-(4-isopropylphenyl)-2,3,4,5,5a,6,8,9-octahydro-7H-1,2,5,7-tetraazabenzo[cd]azulen-7-yl)prop-2-en-1-one (Int. N) (118 mg, 1 equiv., 338 μmol) and DIEA (273 mg, 6.25 equiv., 2.11 mmol). The mixture was stirred at room temperature for 24 h. The mixture was diluted with water (20 mL) and EtOAc (20 mL), and the aqeuous layer was extracted with EtOAc (2×20 mL). The combined organic layers were washed with saturated brine (2×20 mL), dried over anhydrous sodium sulfate, filtered, and concentrated to give a residue. The residue was purified by Prep-HPLC (Column: YMC Triart C18 ExRs 5 m, 30 mm*150 mm; Mobile Phase A: water (10 mmol/L $NH_4HCO_3$), Mobile Phase B: MeCN; Flow rate: 60 mL/min; Gradient: 42% B to 58% B in 10 min; Wave Length: UV 254 nm/220 nm); to afford (rac)-1-(5-(2-(azetidin-1-yl)-7-bromo-1H-benzo[d]imidazole-4-carbonyl)-2-(4-isopropylphenyl)-2,3,4,5,5a,6,8,9-octahydro-7H-1,2,5,7-tetraazabenzo[cd]azulen-7-yl)prop-2-en-1-one (8.8 mg) as a white solid. LCMS:(ESI, m/z):628 [M+1]$^+$ The racemic 1-(5-(2-(azetidin-1-yl)-7-bromo-1H-benzo[d]imidazole-4-carbonyl)-2-(4-isopropylphenyl)-2,3,4,5,5a,6,8,9-octahydro-7H-1,2,5,7-tetraazabenzo[cd]azulen-7-yl)prop-2-en-1-one (8.8 mg) was then purified by chiral prep-HPLC (Column: CHIRAL ART Cellulose-SB 2*25 cm, 5 μm; Mobile Phase A: HEX(0.1% FA), Mobile Phase B: EtOH: DCM=1:1; Flow rate: 20 mL/min; Gradient: isocratic 25; Wave Length: UV 254/220 nm; retention time 1: 12.3; retention time 2: 20.6; Sample Solvent: EtOH; Injection Volume: 0.85 mL; Number Of Runs: 2) to afford (S or R)-1-(5-(2-(azetidin-1-yl)-7-bromo-1H-benzo[d]imidazole-4-carbonyl)-2-(4-isopropylphenyl)-2,3,4,5,5a,6,8,9-octahydro-7H-1,2,5,7-tetraazabenzo[cd]azulen-7-yl)prop-2-en-1-one (3.0 mg, 4.8 μmol, 34%, 99.6% purity) as the second-eluting peak is a white solid (retention time=20.6 min, 3.6 mg, 5.7 μmol, 41%, 99.7% purity). LCMS: (ESI, m/Z):628 [M+H]$^+$. $^1$H NMR: (400 MHz, Chloroform-d, ppm) δ 7.58-7.44 (m, 1H), 7.42-7.29 (m, 2H), 7.05-6.84 (m, 1H), 6.72-6.26 (m, 1H), 5.93-5.62 (m, 1H), 5.36 (s, 1H), 5.13-4.79 (m, 11H), 4.71-3.91 (m, 6H), 3.40-2.86 (m, 5H), 2.86-2.61 (m, 2H), 2.61-2.40 (m, 3H), 1.35-1.21 (m, 6H). (some protons are obscured by solvent/water peaks)

Example B-5: Preparation of (S or R)-(7-bromo-1H-imidazo[4,5-c]pyridine-4-carbonyl)-2-(4-isopropylphenyl)-2,3,4,5,5a,6,8,9-octahydro-7H-1,2,5,7-tetraazabenzo[cd]azulen-7-yl)prop-2-en-1-one

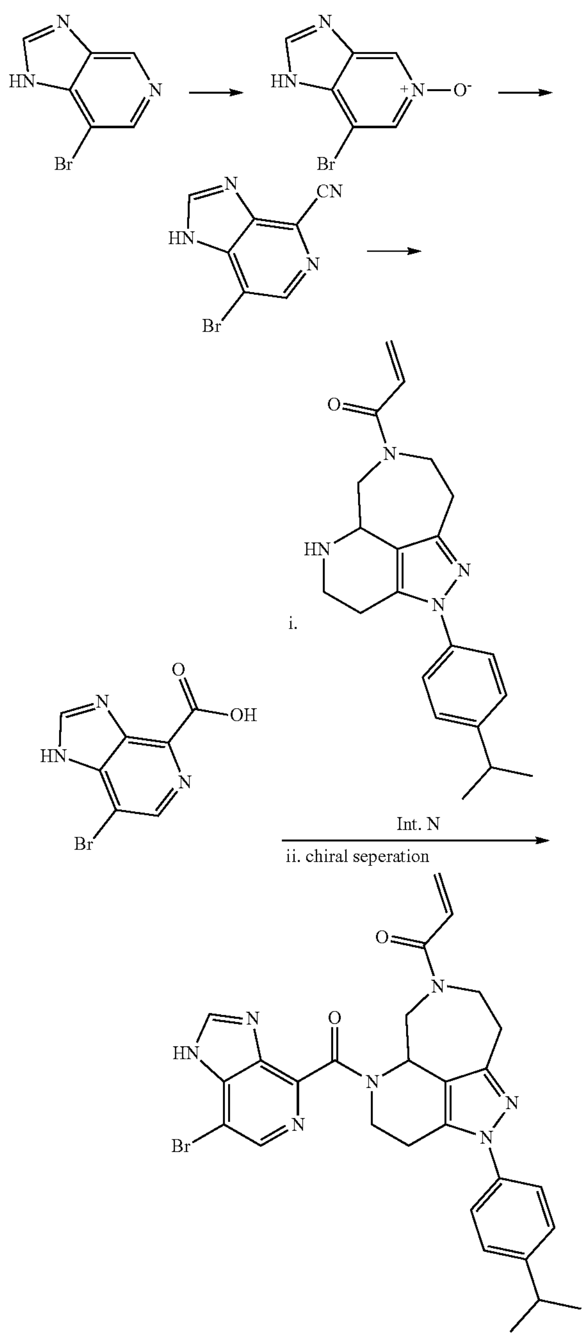

Step 1: Synthesis of 7-bromo-1H-imidazo[4,5-c]pyridine 5-oxide

To a solution of 7-bromo-1H-imidazo[4,5-c]pyridine (4.5 g, 1 equiv., 23 mmol) in DCM (90 mL) were added 3-chloroperoxybenzoic acid (7.8 g, 14 mL, 2 equiv., 45 mmol). The mixture was stirred at room temperature for 24 h, after which it was concentrated under reduced pressure at 0° C. to afford 7-bromo-1H-imidazo[4,5-c]pyridine 5-oxide as a yellow solid. The crude product was used in the next step directly without further purification. LCMS:(ESI, m/z): 214 $[M+1]^+$ Step 2: Synthesis of 7-bromo-1H-imidazo[4,5-c]pyridine-4-carbonitrile A solution of 7-bromo-1H-imidazo[4,5-c]pyridine 5-oxide (14 g, 30 wt %, 1 equiv., 20 mmol) in TMSCN (0.12 kg, 0.15 L, 60 equiv., 1.2 mol) was stirred for 2 h at 120° C. The mixture was then allowed to cool down to rt. The reaction was quenched by the addition of sodium bicarbonate solution (400 mL) at rt. The resulting mixture was extracted with DCM (2×100 mL). The combined organic layers were dried over anhydrous $Na_2SO_4$. After filtration, the filtrate was concentrated under reduced pressure. The residue was purified by reverse phase chromatography (column: C18 column; Gradient: 22% MeCN in water with 0.05% TFA) to afford 7-bromo-1H-imidazo[4,5-c]pyridine-4-carbonitrile (2 g) as a yellow solid. LCMS:(ESI, m/z): 223 $[M+1]^+$ Step 3: Synthesis of 7-bromo-1H-imidazo[4,5-c]pyridine-4-carboxylic Acid A mixture of 7-bromo-1H-imidazo[4,5-c]pyridine-4-carbonitrile (2 g, 1 equiv., 9 mmol) and sodium hydrate (9 g, 8 mL, 25 equiv., 0.2 mol) in MeOH (60 mL) and water (60 mL) was stirred for 8 h at 80° C. The reaction mixture was cooled down to rt, and the pH was adjusted to 3 with 1M hydrochloric acid solution. The mixture was extracted with DCM (2×50 mL) and dried over anhydrous $Na_2SO_4$. After filtration, the filtrate was concentrated under reduced pressure. The residue was purified by reverse phase chromatography (column: C18 column; Gradient: 20% MeCN in water with 0.05% TFA) to afford 7-bromo-1H-imidazo[4,5-c]pyridine-4-carboxylic acid (2 g) as a white solid. LCMS:(ESI, m/z): 242 $[M+1]^+$ Step 4: Synthesis of (S or R)-(7-bromo-1H-imidazo[4,5-c]pyridine-4-carbonyl)-2-(4-isopropylphenyl)-2,3,4,5,5a,6,8,9-octahydro-7H-1,2,5,7-tetraazabenzo[cd]azulen-7-yl)prop-2-en-1-one To a solution of Int. N (100 mg, 1 equiv., 285 μmol) in DMF (2 mL) were added 7-bromo-1H-imidazo[4,5-c]pyridine-4-carboxylic acid (82.9 mg, 1.2 equiv., 342 μmol), HATU (141 mg, 1.3 equiv., 371 μmol) and DIEA (221 mg, 296 μL, 6 equiv., 1.71 mmol) The mixture was stirred at room temperature for 2 h. The mixture was then purified by Prep-HPLC (Column: YMC Triart C18 ExRs 5 m, 30 mm*150 mm; Mobile Phase A: water (10 mmol/L $NH_4HCO_3$), Mobile Phase B: MeCN; Flow rate: 60 mL/min; Gradient: 37% B to 55% B in 8 min; Wave Length: UV 254 nm/221 nm; retention time: 7.4 min) to afford (rac)-1-(5-(7-bromo-1H-imidazo[4,5-c]pyridine- 4-carbonyl)-2-(4-isopropylphenyl)-2,3,4,5,5a,6,8,9-octahydro-7H-1,2,5,7-tetraazabenzo[cd]azulen-7-yl)prop-2-en-1-one (25.0 mg) as a white solid.

The racemic 1-(5-(7-bromo-1H-imidazo[4,5-c]pyridine-4-carbonyl)-2-(4-isopropylphenyl)-2,3,4,5,5a,6,8,9-octahydro-7H-1,2,5,7-tetraazabenzo[cd]azulen-7-yl)prop-2-en-1-one (25.0 mg, 44 μmol, 15.1%, 99.7% purity) was then purified by chiral prep-HPLC (Column: CHIRAL ART Cellulose-SC 2*25 cm, 5 μm; Mobile Phase A: HEX(0.1% FA), Mobile Phase B: EtOH: DCM=1:1; Flow rate: 20 mL/min; Gradient: isocratic 55; Wave Length: UV 254/220 nm; Sample Solvent: EtOH; Injection Volume: 1.9 mL; Number Of Runs: 2) to afford (S or R)-1-(5-(7-bromo-1H-imidazo[4,5-c]pyridine-4-carbonyl)-2-(4-isopropylphenyl)-2,3,4,5,5a,6,8,9-octahydro-7H-1,2,5,7-tetraazabenzo[cd]azulen-7-yl)prop-2-en-1-one as the second-eluting peak (retention time 11.3 min., 8.8 mg, 15 mol, 5.3%, 99.1% purity) as a white solid. LCMS: (ESI, m/z): 574 $[M+1]^+$. $^1$H NMR: (400 MHz, Chloroform-d, ppm) δ 8.60 (brs, 2H), 7.56-7.45 (m, 1H), 7.44-7.29 (m, 3H), 6.85-6.45 (m, 1H), 5.97-4.24 (m, 5H), 3.51-2.66 (m, 9H), 1.36-1.21 (m, 6H). Analytical chiral-HPLC: Column: CHIRALPAK IC-3; Column Size: 4.6*50 mm, 3 μm; Mobile Phase: Hex(0.1% FA):(EtOH:DCM=1:1)=45:55; Flow: 1.0 mL/in; Temperature: 25° C.; retention time=2.1.

Example B-6: Preparation of (S or R)-1-(2-(4-isopropylphenyl)-5-(1-(trifluoromethyl)-1H-indazole-5-carbonyl)-2,3,4,5,5a,6,8,9-octahydro-7H-1,2,5,7-tetraazabenzo[cd]azulen-7-yl)prop-2-en-1-one

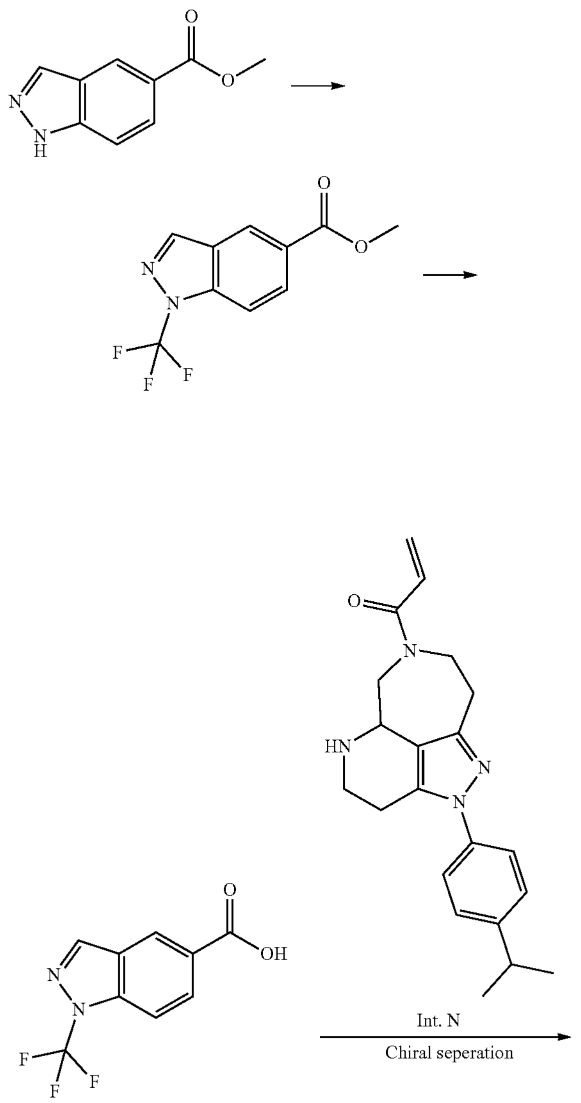

-continued

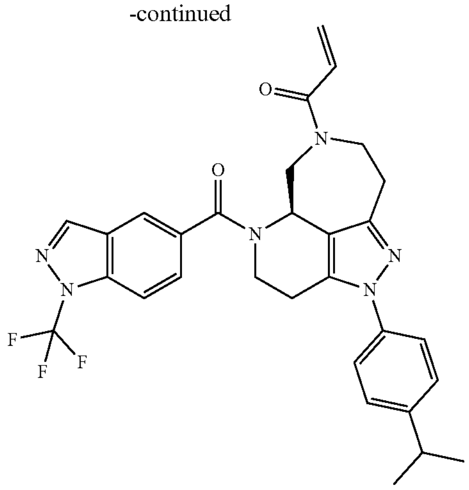

Step 1: Synthesis of Methyl 1-(trifluoromethyl)-1H-indazole-5-carboxylate

A solution of methyl 1H-indazole-5-carboxylate (2.00 g, 1 equiv., 11.4 mmol) in DCM (2 mL) was treated with lithium bis((trifluoromethyl)sulfonyl)amide (163 g, 0.05 equiv., 568 μmol) for 10 min at rt followed by the addition of 3,3-dimethyl-1-(trifluoromethyl)-1,3-dihydro-113-benzo[d][1,2]iodaoxole (5.62 g, 1.5 equiv., 17.0 mmol) and 1,1,1-trifluoro-N-((trifluoromethyl)sulfonyl)methanesulfonamide (958 mg, 0.3 equiv., 3.41 mmol) in portions at rt. The resulting mixture was stirred for additional 2 h at 35° C. The reaction was quenched with water at rt. The resulting mixture was extracted with DCM (3×30 mL). The combined organic layers were washed with brine (3×15 mL) and dried over anhydrous $Na_2SO_4$. After filtration, the filtrate was concentrated under reduced pressure. The residue was purified by silica gel column chromatography, eluting with PE:EtOAc (10:1) to afford methyl 1-(trifluoromethyl)-1H-indazole-5-carboxylate (205 mg) as an off-white solid. LCMS:(ESI, m/z): 245 $[M+H]^+$

Step 2: Synthesis of 1-(trifluoromethyl)-1H-indazole-5-carboxylic Acid

A solution of methyl 1-(trifluoromethyl)-1H-indazole-5-carboxylate (190 mg, 1 equiv., 778 μmol) and NaOH (40 mg, 1.3 equiv., 1.0 mmol) (1M in 1 mL water) in THF (2 mL) was stirred for 1 h at room temperature, after which the mixture was allowed to cool own to room temperature and the mixture was acidified to pH 4 with HCl (1M solution). The resulting mixture was extracted with EtOAc (3×10 mL), and the combined organic layers were washed with brine (3×5 mL) and dried over anhydrous $Na_2SO_4$. After filtration, the filtrate was concentrated under reduced pressure to afford the crude product 1-(trifluoromethyl)-1H-indazole-5-carboxylic acid (170 mg) which was used in the next step without further purification. LCMS:(ESI, m/z): 23 $[M+1]^+$. $^1$H NMR (400 MHz, $CDCl_3$) δ 8.66 (t, J=1.2 Hz, 1H), 8.58 (s, 1H), 8.04 (dd, J=1.6 Hz, 9.6 Hz, 1H), 7.84 (dt, J=10.4, 1H)

Step 3: Synthesis of (S or R)-1-(2-(4-isopropylphenyl)-5-(1-(trifluoromethyl)-1H-indazole-5-carbonyl)-2,3,4,5,5a,6,8,9-octahydro-7H-1,2,5,7-tetraazabenzo[cd]azulen-7-yl)prop-2-en-1-one A solution of 1-(trifluoromethyl)-1H-indazole-5-carboxylic acid (55.0 mg, 1 equiv., 239 μmol) in DMF (1 mL) was treated with EDC (57.4 mg, 1.5 equiv., 300 μmol), HOBT (45.9 mg, 1.5 equiv., 300 μmol) and N-ethyl-N-isopropyl-propan-2-amine (155 mg 3 equiv., 0.6 mmol) for 30 min at room temperature under a nitrogen atmosphere, followed by the addition of (rac)-1-(2-(4-isopropylphenyl)-2,3,4,5,5a,6,8,9-octahydro-7H-1,2,5,7-tetraazabenzo[cd]azulen-7-yl)prop-2-en-1-one (Int. N) (70.0 mg, 1.1 equiv., 200 μmol) in portions at room temperature. The resulting mixture was stirred for additional 30 min at room temperature. The resulting mixture was then filtered, and the filtrate was purified by reverse-phase flash chromatography with the following conditions: (Column: XBridge BEH C18 OBD Prep Column 130, 5 m, 0 mm*150 mm; Mobile Phase A: water (10 mmol/L $NH_4HCO_3$), Mobile Phase B: MeCN; Flow rate: 60 mL/min; Gradient: 40% B to 63% B in 10 min; Wave Length: UV 254 nm/220 nm) to afford (rac)-1-(2-(4-isopropylphenyl)-5-(1-(trifluoromethyl)-1H-indazole-5-carbonyl)-2,3,4,5,5a,6,8,9-octahydro-7H-1,2,5,7-tetraazabenzo[cd]azulen-7-yl)prop-2-en-1-one (15 mg) as a white solid. LCMS: (ESI, m/z): 563 $[M+H]^+$ The racemic 1-(2-(4-isopropylphenyl)-5-(1-(trifluoromethyl)-1H-indazole-5-carbonyl)-2,3,4,5,5a,6,8,9-octahydro-7H-1,2,5,7-tetraazabenzo[cd]azulen-7-yl)prop-2-en-1-one was purified by chiral prep-HPLC (Column: CHIRAL ART Cellulose-SB 3*25 cm, 5 m; Mobile Phase A: Hex(0.1% DEA)--HPLC, Mobile Phase B: EtOH: DCM=1:1; Flow rate: 40 mL/min; Gradient: isocratic 30; Wave Length: UV 254/220 nm) (S or R)-1-(2-(4-isopropylphenyl)-5-(1-(trifluoromethyl)-1H-indazole-5-carbonyl)-2,3,4,5,5a,6,8,9-octahydro-7H-1,2,5,7-tetraazabenzo[cd]azulen-7-yl)prop-2-en-1-one as the first-eluting peak (retention time=9.0 min; 0.8 mg, 1 μmol, 0.7%, 98.2% purity) as a white solid. LCMS: (ESI, m/z):563 $[M+H]^+$. $^1H$ NMR (400 MHz, $CDCl_3$) δ 8.43 (s, 1H), 7.88-7.77 (m, 2H), 7.39 (d, J=9.2 Hz, 1H), 7.30 (d, J=8.3 Hz, 2H), 7.23 (d, J=8.3 Hz, 2H), 6.60-6.30 (m, 1H), 5.98-5.61 (m, 1H), 5.42-5.24 (m, 1H), 5.04-4.79 (m, 1H), 4.60-4.34 (m, 1H), 4.18-3.90 (m, 1H), 3.24-2.82 (m, 7H), 2.81-2.52 (m, 2H), 1.19 (d, 6.9 Hz, 6H).

TABLE B2

The following examples were prepared in an analogous manner to Example B-6, using the corresponding carboxylic acids, and using these described chiral separation conditions: Example B-7: The compound was purified via chiral Prep-HPLC with the following conditions (Column: CHIRAL ART Cellulose-SC, 2 * 25 cm, 5 μm; Mobile Phase A: HEX(0.1% FA), Mobile Phase B: EtOH:DCM = 1:1; Flow rate: 20 mL/min; Gradient: isocratic 40; Wave Length: UV 254/220 nm; Injection Volume: 2.5 mL) to provide the compound of example B-6 as the second eluted peak, retention time 14.3 min. Example B-8: The compound was purified by chiral Prep-HPLC with the following conditions (Column: CHIRALPAK-IC 2 * 25 cm, 5 μm; Mobile Phase A: HEX(0.1% FA), Mobile Phase B: EtOH:DCM = 1:1; Flow rate: 20 mL/min; Gradient: isocratic 40; Wave Length: UV 254/220 nm; Sample Solvent: EtOH; Injection Volume: 2.5 mL) to provide the compound of Example B-7 as the second eluted peak, retention time 14.8 min.

| Example No. | Structure and Name | LCMS (ESI, m/z) | NMR |
|---|---|---|---|
| Example B-7 | 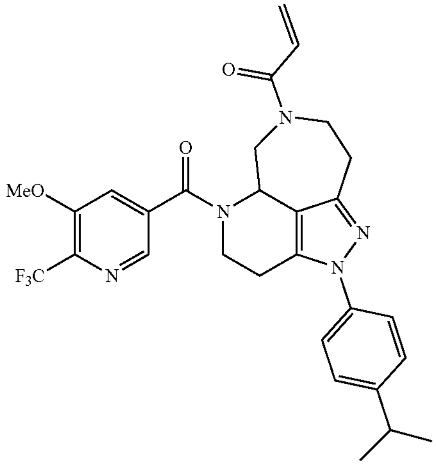 [SMILES: C=CC(=O)N1CCc2nn(-c3ccc(C(C)C)cc3)c3c2C(C1)N(C(=O)c1cnc(C(F)(F)F)c(OC)c1)CC3] (S or R)-1-(2-(4-isopropylphenyl)-5-(5-methoxy-6-(trifluoromethyl)nicotinoyl)-2,3,4,5,5a,6,8,9-octahydro-7H-1,2,5,7-tetraazabenzo[cd]azulen-7-yl)prop-2-en-1-one | 554 $[M + H]^+$ | $^1H$ NMR (400 MHz, Chloroform-d, ppm) δ 8.30 (s, 1H), 7.65-7.30 (m, 5H), 6.75-6.29 (m, 1H), 5.97-5.73 (m, 1H), 5.54-5.31 (m, 1H), 5.12-4.91 (m, 1H), 4.75-4.41 (m, 1H), 4.02 (s, 4H), 3.54-2.58 (m, 9H), 1.27 (d, J = 6.8 Hz, 6H). |

TABLE B2-continued

The following examples were prepared in an analogous manner to Example B-6, using the corresponding carboxylic acids, and using these described chiral separation conditions: Example B-7: The compound was purified via chiral Prep-HPLC with the following conditions (Column: CHIRAL ART Cellulose-SC, 2 * 25 cm, 5 μm; Mobile Phase A: HEX(0.1% FA), Mobile Phase B: EtOH:DCM = 1:1; Flow rate: 20 mL/min; Gradient: isocratic 40; Wave Length: UV 254/220 nm; Injection Volume: 2.5 mL) to provide the compound of example B-6 as the second eluted peak, retention time 14.3 min. Example B-8: The compound was purified by chiral Prep-HPLC with the following conditions (Column: CHIRALPAK-IC 2 * 25 cm, 5 μm; Mobile Phase A: HEX(0.1% FA), Mobile Phase B: EtOH:DCM = 1:1; Flow rate: 20 mL/min; Gradient: isocratic 40; Wave Length: UV 254/220 nm; Sample Solvent: EtOH; Injection Volume: 2.5 mL) to provide the compound of Example B-7 as the second eluted peak, retention time 14.8 min.

| Example No. | Structure and Name | LCMS (ESI, m/z) | NMR |
|---|---|---|---|
| Example B-8 | 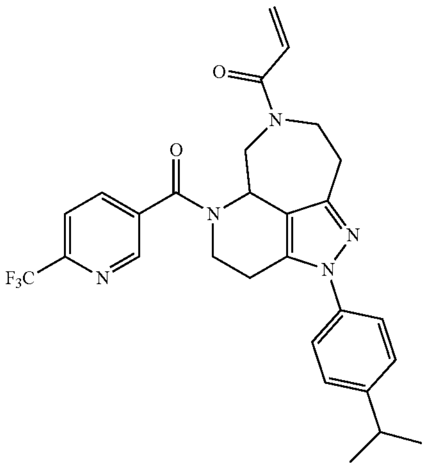 [SMILES: C=CC(=O)N1CCc2nn(-c3ccc(C(C)C)cc3)c3c2C(C1)N(C(=O)c1ccc(C(F)(F)F)nc1)CC3] (S or R)-1-(2-(4-isopropylphenyl)-5-(6-(trifluoromethyl)nicotinoyl)-2,3,4,5,5a,6,8,9-octahydro-7H-1,2,5,7-tetraazabenzo[cd]azulen-7-yl)prop-2-en-1-one | 524 $[M + 1]^+$ | $^1H$ NMR (400 MHz, Chloroform-d, ppm) δ 8.84 (s, 1H), 8.13-7.96 (m, 1H), 7.94-7.77 (m, 1H), 7.35 (d, J = 24.2 Hz, 4H), 6.76-6.20 (m, 1H), 6.00-5.66 (m, 1H), 5.56-5.33 (m, 1H), 5.10-4.89 (m, 1H), 4.76-4.45 (m, 1H), 4.29-3.79 (m, 1H), 3.48-2.59 (m, 8H), 1.36-1.17 (m, 6H). |

Example B-9: Preparation of (S or R)-1-(5-(5-hydroxy-6-(trifluoromethyl)nicotinoyl)-2-(4-isopropylphenyl)-2,3,4,5,5a,6,8,9-octahydro-7H-1,2,5,7-tetraazabenzo[cd]azulen-7-yl)prop-2-en-1-one

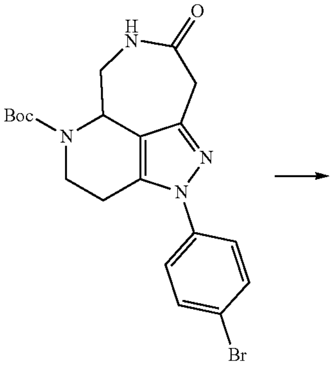

Int. E

-continued

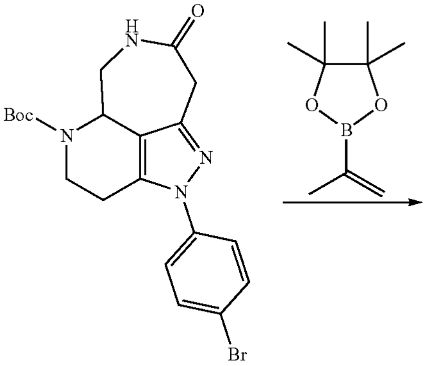

single enantiomer
Int. E'

-continued

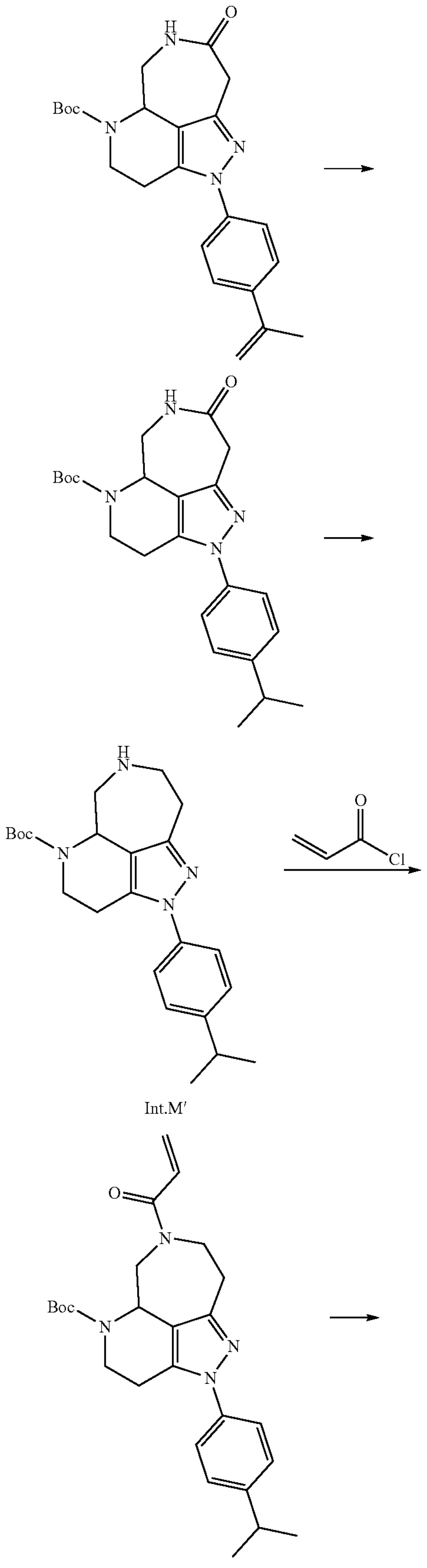

-continued

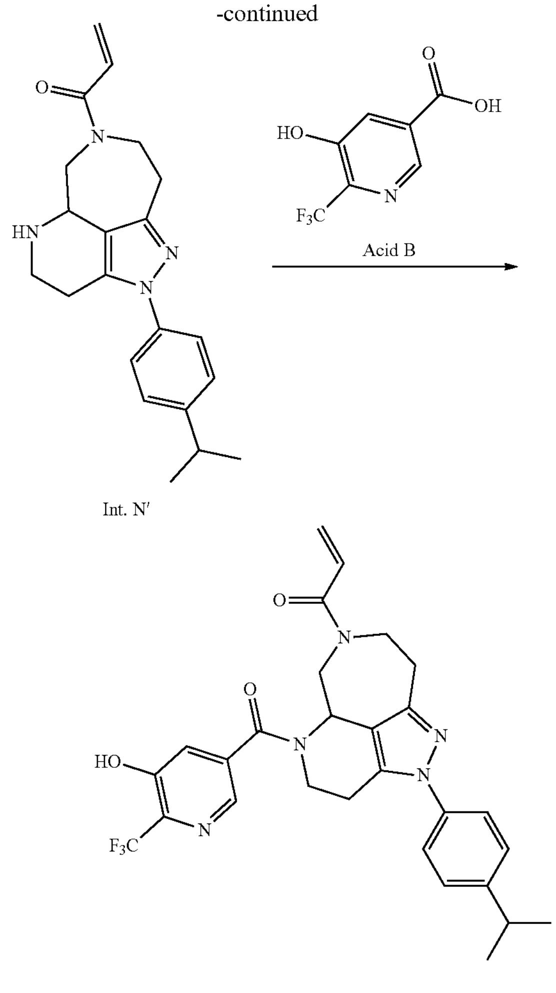

Step 1: Chiral Separation of Tert-Butyl (S or R)-2-(4-bromophenyl)-8-oxo-2,3,4,5a,6,7,8,9-octahydro-5H-1,2,5,7-tetraazabenzo[cd]azulene-5-carboxylate (Int. E')

The racemic compound, tert-butyl (rac)-2-(4-bromophenyl)-8-oxo-2,3,4,5a,6,7,8,9-octahydro-5H-1,2,5,7-tetraazabenzo[cd]azulene-5-carboxylate (5.00 g, equiv., 11.2 mmol) was separated into its constituent enantiomers by Chiral HPLC separation under the following conditions (Column: CHIRAL ART Cellulose-SC 2*25 cm, 5 m; Mobile Phase A: HEX (0.1% FA), Mobile Phase B: IPA: DCM=1:1; Flow rate: 20 mL/min; Gradient: isocratic 80; Wave Length: UV 254/220 nm; retention time 1(min): 5.2; retention time 2: 6.7 min; Sample Solvent: MeOH: DCM; Number Of Runs: 27) to afford tert-butyl (S or R)-2-(4-bromophenyl)-8-oxo-2,3,4,5a,6,7,8,9-octahydro-5H-1,2,5,7-tetraazabenzo[cd]azulene-5-carboxylate (Int. E') as the second eluting peak (retention time=6.7 min., 2.5 g) as a white solid. LCMS:(ESI, m/z): 449 $[M+1]^+$ Step 2: Synthesis of Tert-Butyl (S or R)-8-oxo-2-(4-(prop-1-en-2-yl) phenyl)-2,3,4,5a,6,7,8,9-octahydro-5H-1,2,5,7-tetraazabenzo[cd]azulene-5-carboxylate A mixture of Int. E' (2.50 g, 1 equiv., 5.59 mmol), $PdCl_2(dppf)$ (204 mg, 0.05 equiv., 279 gmol), 4,4,5,5- tetramethyl-2-(prop-1-en-2-yl)-1,3,2-dioxaborolane (1.41 g, 1.5 equiv., 8.38 mmol) and potassium phosphate, tribasic (2.37 g, 925 μL, 2 equiv., 11.2 mmol) in 1,4-dioxane (20 mL) and water (2 mL) The reaction mixture was stirred for 2 h at 80° C. under nitrogen atmosphere. The resulting mixture was diluted with water (30 mL) and extracted with EtOAc (3×20 mL). The combined organic layers were washed with brine (2×20 mL) and dried over anhydrous $Na_2SO_4$. After filtration, the filtrate was concentrated under reduced pressure. The residue was purified by silica gel column chromatography, eluting with PE/EtOAc (1:1) to afford tert-butyl (S or R)-8-oxo-2-(4-(prop-1-en-2-yl) phenyl)-2,3,4,5a,6,7,8,9-octahydro-5H-1,2,5,7-tetraazabenzo [cd]azulene-5-carboxylate (2.2 g) as a yellow solid. LCM: (ESI, m/z): 409 $[M+1]^+$ Step 3: Synthesis of Tert-Butyl (S or R)-2-(4-isopropylphenyl)-8-oxo-2, 3,4,5a,6,7,8,9-octahydro-5H-1,2,5,7-tetraazabenzo [cd]azulene-5-carboxylate A mixture of tert-butyl (S or R)-8-oxo-2-(4-(prop-1-en-2-yl)phenyl)-2,3,4,5a,6,7,8,9-octahydro-5H-1,2,5,7-tetraazabenzo[cd]azulene-5-carboxylate (2.10 g, 1 equiv., 5.14 mmol) and Pd/C (1.09 g, 10 wt %, 0.2 equiv., 1.03 mmol) in MeOH (40 mL) was stirred for 2 h at room temperature under $H_2$ atmosphere. The resulting mixture was filtered and the filter cake was washed with MeOH (50 mL). The filtrate was concentrated under reduced pressure. The crude product was used in the next step directly without further purification. This resulted in tert-butyl (S or R)-2-(4-isopropylphenyl)-8-oxo-2,3,4,5a,6,7,8,9-octahydro-5H-1,2,5,7-tetraazabenzo [cd]azulene-5-carboxylate (2.0 g) as a yellow solid. LCMS: (ESI, m/z): 411 $[M+1]^+$ Step 4: Synthesis of Tert-Butyl (S or R)-2-(4-isopropylphenyl)-2, 3,4,a,6,7,8,9-octahydro-5H-1,2,5,7-tetraazabenzo [cd]azulene-5-carboxylate (Int. M')

A mixture of tert-butyl (S or R)-2-(4-isopropylphenyl)-8-oxo-2,3,4,5a,6,7,8,9-octahydro-5H-1,2,5,7-tetraazabenzo [cd]azulene-5-carboxylate (2.00 g, 1 equiv., 4.87 mmol) and $BH_3$·THF (1.67 g, 19.5 mL, 1M solution, 4 equiv., 19.5 mmol) in THF (20 mL) was stirred for 2 h at 60° C. under a nitrogen atmosphere. The reaction was quenched by the addition of MeOH at 0° C. The resulting mixture was diluted with water (40 mL). The resulting mixture was extracted with EtOAc (3×40 mL). The combined organic layers were washed with brine (1×20 mL) and dried over anhydrous $Na_2SO_4$. After filtration, the filtrate was concentrated under reduced pressure. The residue was purified by silica gel column chromatography, eluting with PE/EtOAc (1:1) to afford tert-butyl (S or R)-2-(4-isopropylphenyl)-2,3,4,5a,6,7,8,9-octahydro-5H-1,2,5,7-tetraazabenzo [cd]azulene-5-carboxylate (Int. M') (1.4 g) as a yellow solid. LCMS: (ESI, m/z): 397 $[M+1]^+$ Step 5: Synthesis of Tert-Butyl (S or R)-7-acryloyl-2-(4-isopropylphenyl)-2,3,4,5a,6,7,8,9-octahydro-5H-1,2,5,7-tetraazabenzo[cd]azulene-5-carboxylate To a stirred mixture of Int. M' (600 mg, 1 equiv., 1.51 mmol) and TEA (919 mg, 1.27 mL, 6 equiv., 9.08 mmol) in DCM (15 mL) was added acryloyl chloride (205.4 mg, 1.5 equiv., 2.270 mmol) dropwise at 0° C. under air atmosphere. The resulting mixture was stirred for 1 h at room temperature under air atmosphere. The resulting mixture was concentrate under reduced pressure. The residue was purified by silica gel column chromatography, eluting with PE/EtOAc (1:1) to afford tert-butyl (S or R)-7-acryloyl-2-(4-isopropylphenyl)-2,3,4,5a,6,7,8,9-octahydro-5H-1,2,5,7-tetraazabenzo[cd]azulene-5-carboxylate (280 mg) as a white solid. LCMS: (ESI, m/z): 451 [M+1]

Step 6: Synthesis of (S or R)-1-(2-(4-isopropylphenyl)-2,3,4,5,5a,6,8,9-octahydro-7H-1,2,5,7-tetraazabenzo[cd]azulen-7-yl) prop-2-en-1-one (Int. N')

To a stirred mixture of tert-butyl (S or R)-7-acryloyl-2-(4-isopropylphenyl)-2,3,4,5a,6,7,8,9-octahydro-5H-1,2,5,7-tetraazabenzo[cd]azulene-5-carboxylate (230.0 mg, 1 equiv., 510.5 gmol) in DCM (5 mL) was added TFA (582.0 mg, 393.3 μL, 10 equiv., 5.105 mmol) dropwise at room temperature under air atmosphere. The resulting mixture was stirred for 2 h at room temperature under air atmosphere. The resulting mixture was concentrated under reduced pressure. The crude (S or R)-1-(2-(4-isopropylphenyl)-2,3,4,5,5a,6,8,9-octahydro-7H-1,2,5,7-tetraazabenzo [cd]azulen-7-yl) prop-2-en-1-one (Int. N') was used in the next step directly without further purification (260 mg) as a light yellow oil. LCMS: (ESI, m/z): 351 $[M+1]^+$ Step 7: (S or R)-1-(5-(5-hydroxy-6-(trifluoromethyl)nicotinoyl)-2-(4-isopropylphenyl)-2,3,4,5,5a,6,8,9-octahydro-7H-1,2,5,7-tetraazabenzo[cd]azulen-7-yl)prop-2-en-1-one A mixture of (S or R)-1-(2-(4-isopropylphenyl)-2,3,4,5,5a,6,8,9-octahydro-7H-1,2,5,7-tetraazabenzo [cd]azulen-7-yl)prop-2-en-1-one (Int. N') (150 mg, 1 equiv., 428 gmol), HATU (244.1 mg, 1.5 equiv., 642.0 mol), 5-hydroxy-6-(trifluoromethyl)nicotinic acid (88.6 mg, 1 equiv., 428 μmol) and DIEA (332 mg, 447 μL, 6 equiv., 2.57 mmol) in DMF (5 μL) was stirred for 2 h at room temperature under air atmosphere. The resulting mixture was diluted with water (10 mL), and then was extracted with EtOAc (3×20 mL). The combined organic layers were washed with brine (1×20 mL) and dried over anhydrous $Na_2SO_4$. After filtration, the filtrate was concentrated under reduced pressure. The crude product (200 mg) was purified by Prep-HPLC (Column: XBridge BEH C18 OBD Prep Column 130, 5 m, 30 mm*150 mm; Mobile Phase A: water (10 mmol/L $NH_4HCO_3$), Mobile Phase B: MeCN; Flow rate: 60 mL/min; Gradient: 20% B to 47% B in 8 min; Wave Length: UV 254 nm/221 nm; retention time 1(min): 7.2 in) to afford (S or R)-1-(5-(5-hydroxy-6-(trifluoromethyl)nicotinoyl)-2-(4-isopropylphenyl)-2,3,4,5,5a,6,8,9-octahydro-7H-1,2,5,7-tetraazabenzo[cd]azulen-7-yl)prop-2-en-1-one (55.8 mg, 10 μmol, 23.8%, 98.6% purity) as a white solid. LCMS: (ESI, m/z): 540 $[M+1]^+$. $^1H$ NMR:(400 MHz, Chloroform-d, ppm) δ 8.56-8.24 (m, 1H), 8.20-7.90 (m, 1H), 7.83-7.53 (m, 1H), 7.35 (brs, 1H), 7.33-7.26 (m, 2H), 7.17-6.96 (m, 1H), 6.83-6.55 (m, 1H), 6.52-6.36 (m, 1H), 5.96-5.60 (m, 1H), 5.31) 4.96 (m, 1H), 4.89 (brs, 1H), 4.73-64.14 (m, 2H), 3.95-3.53 (m, 1H), 3.29-2.4 (m, 7H), 1.43-0.79 (m, 6H).

TABLE B3

| The compounds of Examples B-9-1 and B-9-2 were prepared in an analogous manner to Example B-9 using the corresponding carboxylic acids. | | | |
|---|---|---|---|
| Example No. | Structure and Name | LCMS (ESI, m/z) | NMR |
| Example B-9-1 | 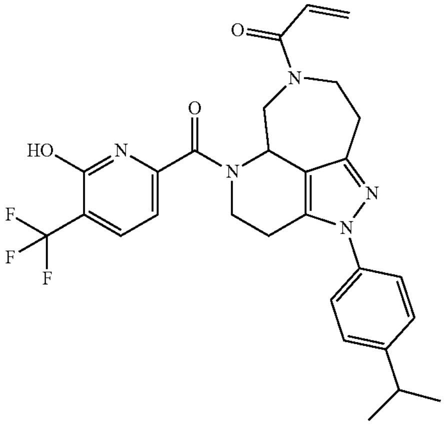 [SMILES: C=CC(=O)N1CCc2nn(-c3ccc(C(C)C)cc3)c3c2C(C1)N(C(=O)c1ccc(C(F)(F)F)c(O)n1)CC3] (R or S)-1-(5-(6-hydroxy-5-(trifluoromethyl)picolinoyl)-2-(4-isopropylphenyl)-2,3,4,5,5a,6,8,9-octahydro-7H-1,2,5,7-tetraazabenzo[cd]azulen-7-yl)prop-2-en-1-one | 540 $[M + H]^+$ | $^1H$ NMR (400 MHz, Chloroform-d, ppm) δ 11.12 (br s, 1H), 8.00-7.86 (m, 1H), 7.64-7.60 (m, 1H), 7.40-7.27 (m, 4H), 6.79-6.67 (m, 1H), 6.63-6.45 (m, 1H), 5.91 (dd, J = 10.2, 1.9 Hz, 1H), 5.87-5.73 (m, 1H), 5.38-5.28 (m, 1H), 5.04-4.81 (m, 1H), 4.50-4.29 (m, 1H), 3.39-2.64 (m, 6H), 2.62 (s, 1H), 1.31-1.23 (m, 6H). |
| Example B-9-2 | 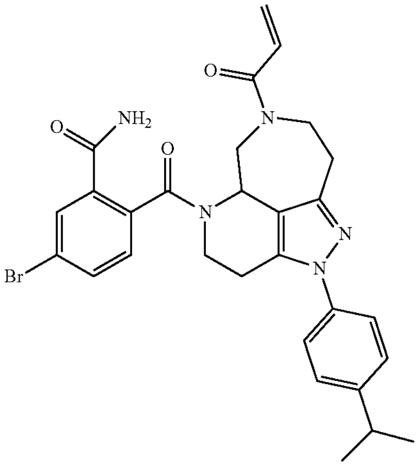 [SMILES: C=CC(=O)N1CCc2nn(-c3ccc(C(C)C)cc3)c3c2C(C1)N(C(=O)c1ccc(Br)cc1C(N)=O)CC3] (R or S)-2-(7-acryloyl-2-(4-isopropylphenyl)-3,4,5,5a,6,7,8,9-octahydro-2H-1,2,5,7-tetraazabenzo[cd]azulene-5-carbonyl)-5-bromobenzamide | 576 $[M + H]^+$ | $^1H$ NMR (400 MHz, Chloroform-d, ppm) δ 7.99-7.75 (m, 1H), 7.75-7.57 (m, 1H), 7.57-7.25 (m, 3H), 6.49 (d, J = 15.9 Hz, 1H), 5.95-4.20 (m, 6H), 3.76-2.48 (m, 9H), 1.25 (d, J = 6.7 Hz, 6H). |

TABLE B3-continued

| The compounds of Examples B-9-1 and B-9-2 were prepared in an analogous manner to Example B-9 using the corresponding carboxylic acids. | | | |
|---|---|---|---|
| Example No. | Structure and Name | LCMS (ESI, m/z) | NMR |
| Example B-9-3 | 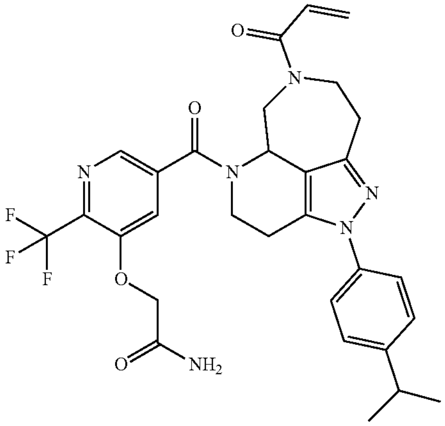 [SMILES: C=CC(=O)N1CCc2nn(-c3ccc(C(C)C)cc3)c3c2C(C1)N(C(=O)c1cnc(C(F)(F)F)c(OCC(N)=O)c1)CC3] (R or S)-2-((5-(7-acryloyl-2-(4-isopropylphenyl)-3,4,5,5a,6,7,8,9-octahydro-2H-1,2,5,7-tetraazabenzo[cd]azulene-5-carbonyl)-2-(trifluoromethyl)pyridin-3-yl)oxy)acetamide | 597 $[M + H]^+$ | $^1H$ NMR (400 MHz, Chloroform-d, ppm) δ 8.47-8.31 (m, 1H), 7.79-7.51 (m, 1H), 7.40-7.35 (m, 2H), 7.33-7.29 (m, 2H), 7.11-6.45 (m, 2H), 6.45-5.85 (m, 1H), 5.83-5.34 (m, 2H), 5.35-4.74 (m, 2H), 4.71-4.23 (m, 3H), 4.21-3.80 (m, 1H), 3.31-3.18 (m, 1H), 3.21-3.07 (m, 2H), 3.02-2.87 (m, 3H), 2.85-2.69 (m, 2H), 1.27 (dd, J = 6.9, 3.9 Hz, 6H). |
| Example B-9-4 | 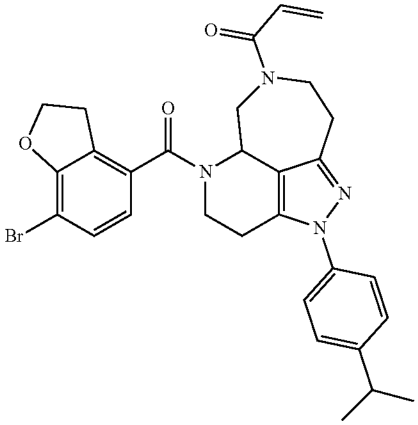 [SMILES: C=CC(=O)N1CCc2nn(-c3ccc(C(C)C)cc3)c3c2C(C1)N(C(=O)c1ccc(Br)c2c1CCO2)CC3] (R or S)-1-(5-(7-bromo-2,3-dihydrobenzofuran-4-carbonyl)-2-(4-isopropylphenyl)-2,3,4,5,5a,6,8,9-octahydro-7H-1,2,5,7-tetraazabenzo[cd]azulen-7-yl)prop-2-en-1-one | 577 $[M + H]^+$ | $^1H$ NMR (400 MHz, Chloroform-d, ppm) δ 7.52-7.28 (m, 5H), 6.74-6.68 (m, 1H), 6.52-6.43 (m, 1H), 5.94-5.64 (m, 1H), 5.52-5.28 (m, 1H), 4.97-4.90 (m, 1H), 4.79-4.68 (m, 2H), 4.48-4.35 (m, 1H), 4.08-3.90 (m, 1H), 3.52-1.98 (m, 9H), 1.27 (d, J = 6.9 Hz, 6H). |

Example B-10: Preparation of (S or R,E)-1-(5-(7-bromo-1H-benzo[d]imidazole-4-carbonyl)-2-(4-isopropylphenyl)-2,3,4,5,5a,6,8,9-octahydro-7H-1,2,5,7-tetraazabenzo[cd]azulen-7-yl)-4-(dimethylamino)but-2-en-1-one

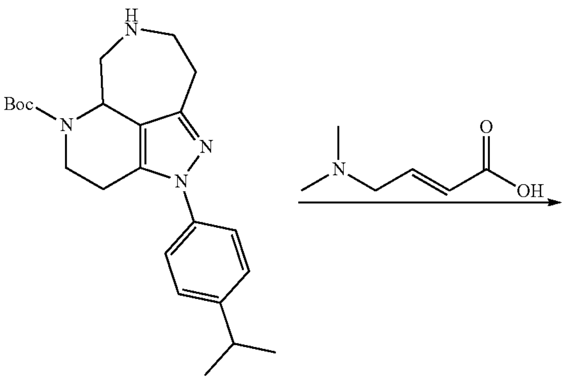

Int. M'

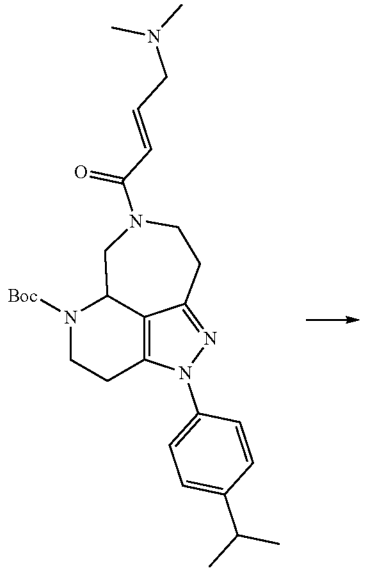

-continued

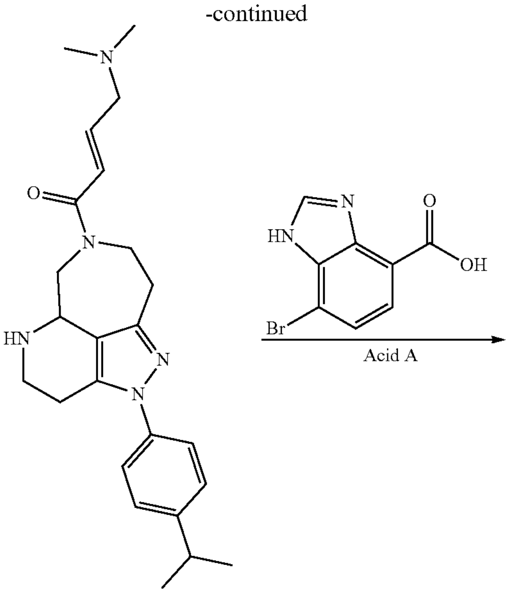

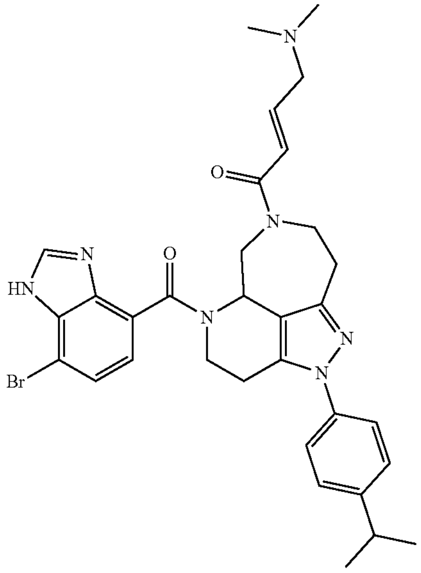 [SMILES: CC(C)c1ccc(-n2nc3c4c2CCN(C(=O)c2ccc(Br)c5[nH]cnc25)C4CN(C(=O)/C=C/CN(C)C)CC3)cc1]

Step 1: Synthesis of Tert-Butyl (S or R,E)-7-(4-(dimethylamino)but-2-enoyl)-2-(4-isopropylphenyl)-2,3,4,5a,6,7,8,9-octahydro-5H-1, 2,5,7-tetraazabenzo[cd]azulene-5-carboxylate To a solution of tert-butyl (S or R)-2-(4-isopropylphenyl)-2,3,4,5a,6,7,8,9-octahydro-5H-1,2,5,7-tetraazabenzo[cd]azulene-5-carboxylate (Int. M') (90 mg, 1 equiv., 0.23 mmol) in DCM (1.8 mL) were added (E)-4-(dimethylamino)but-2-enoic acid (29 mg, 1 equiv., 0.23 mmol), DIEA (88 mg, 0.12 mL, 3 equiv., 0.68 mmol), EDC·hydrochloride (87 mg, 2 equiv., 0.45 mmol) and HOBT (61 mg, 2 equiv., 0.45 mmol). The resulting mixture was stirred for 3 h at room temperature. The reaction was then quenched with water (10 mL). The aqueous layer was extracted with DCM (3×10 mL). The combined organic layers were washed with saturated brine (2×20 mL), dried over anhydrous sodium sulfate and concentrated to give a residue. The crude product was purified by silica gel chromatography eluting with DCM:MeOH=3:1 to give tert-butyl (S or R,E)-7-(4-(dimethylamino)but-2-enoyl)-2-(4-isopropylphenyl)-2,3,4,5a,6,7,8,9-octahydro-5H-1,2,5,7-tetraazabenzo[cd]azulene-5-carboxylate (70 mg) as a yellow solid. LCMS: (ESI, m/z): 508 [M+1]+

Step 2: Synthesis of (S or R,E)-4-(dimethylamino)-1-(2-(4-isopropylphenyl)-2,3,4,5,5a,6,8,9-octahydro-7H-1,2,5,7-tetraazabenzo[cd]azulen-7-yl)but-2-en-1-one The solution of tert-butyl (S or R,E)-7-(4-(dimethylamino)but-2-enoyl)-2-(4-isopropylphenyl)-2,3,4,5a,6,7,8,9-octahydro-5H-1,2,5,7-tetraazabenzo[cd]azulene-5-carboxylate (60 mg, 1 equiv., 0.12 mmol) in DCM (1.2 mL) and TFA (0.6 mL) was stirred at room temperature for 30 min. The reaction was monitored by LCMS. The solvent was removed under reduced pressure. This resulted in (S or R,E)-4-(dimethylamino)-1-(2-(4-isopropylphenyl)-2,3,4,5,5a,6,8,9-octahydro-7H-1,2,5,7-tetraazabenzo[cd]azulen-7-yl)but-2-en-1-one (60 mg) as a crude yellow oil. The crude product was used in the next step directly without further purification. LCMS: (ESI, m/z): 408 [M+1]+

Step 3: Synthesis of (S or R,E)-1-(5-(7-bromo-1H-benzo[d]imidazole-4-carbonyl)-2-(4-isopropylphenyl)-2,3,4,5,5a,6,8,9-octahydro-7H-1,2,5, 7-tetraazabenzo[cd]azulen-7-yl)-4-(dimethylamino)but-2-en-1-one To a solution of (S or R,E)-4-(dimethylamino)-1-(2-(4-isopropylphenyl)-2,3,4,5,5a,6,8,9-octahydro-7H-1,2,5,7-tetraazabenzo[cd]azulen-7-yl)but-2-en-1-one (60 mg, 1 equiv., 0.15 mmol) in DCM (1.2 mL) were added DIEA (57 mg, 77 μL, 3 equiv., 0.44 mmol), HBTU (0.11 g, 2 equiv., 0.29 mmol) and 7-bromo-1H-benzo[d]imidazole-4-carboxylic acid (35 g, 1 equiv., 0.15 mmol). The mixture was stirred at room temperature for 3 h. The reaction was t en quenched with water (10 mL). The resulting mixture was extracted with DCM (3×10 mL). The combined organic layers were washed with brine (2×20 mL) and dried over anhydrous $Na_2SO_4$. After filtration, the filtrate was concentrated under reduced pressure. The crude product was purified by flash chromatography (Column: Ultimate AQ-C18; Mobile Phase A: water (0.05% TFA), Mobile Phase B: MeCN; Flow rate: 100 mL/min; Gradient: 20% B to 48% B in 20 min; Wave Length: UV 254 nm/221 nm; retention time: 18 min) to afford (S or R,E)-1-(5-(7-bromo-1H-benzo[d]imidazole-4-carbonyl)-2-(4-isopropylphenyl)-2,3,4,5,5a,6,8,9-octahydro-7H-1,2,5,7-tetraazabenzo[cd]azulen-7-yl)-4-(dimethylamino)but-2-en-1-one (46.8 mg, 73.0 μmol, 50%, 98.4% purity) as a light yellow solid. LCMS: (ESI, m/z): 630 [M+H]+. $^1$H NMR: (400 MHz, Chloroform-d, ppm) δ 11.99 (s, 1H), 8.76 (s, 1H), 7.92 (d, J=15.1 Hz, 1H), 7.60 (d, J=7.9 Hz, 1H), 7.39 (d, J=8.3 Hz, 2H), 7.32 (d, J=8.2 Hz, 2H), 7.25 (s, 1H), 6.87 (ddd, J=15.1, 8.2, 4.9 Hz, 1H), 5.24 (dd, J=10.6, 2.7 Hz, 1H), 4.93 (dt, J=13.5, 3.3 Hz, 1H), 4.52 (dd, J=13.7, 2.9 Hz, 1H), 4.23 (d, J=9.5 Hz, 2H), 4.10 (dd, J=13.7, 8.2 Hz, 1H), 3.84 (dd, J=13.5, 4.9 Hz, 1H), 3.27-3.19 (m, 1H), 3.15 (t, J=11.3 Hz, 2H), 3.07 (q, J=3.8 Hz, 2H), 2.97 (s, 3H), 2.98 (s, 3H), 2.79 (dd, J=11.5, 8.2 Hz, 2H), 1.27 (d, J=6.9 Hz, 6H).

TABLE B4

The following examples were prepared in an analogous manner to Example B-10, using the corresponding acrylic acids (Example B-11) or acryloyl chlorides (Example B-12):

| Example No. | Structure and Name | LCMS (ESI, m/z) | NMR |
|---|---|---|---|
| Example B-11 | 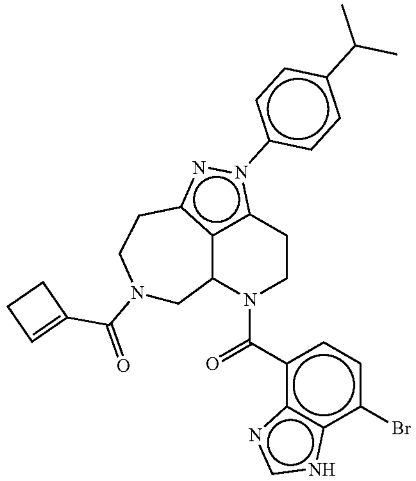 (S or R)-(7-bromo-1H-benzo[d]imidazol-4-yl)(7-(cyclobut-1-ene-1-carbonyl)-2-(4-isopropylphenyl)-2,3,4,5a,6,7,8,9-octahydro-5H-1,2,5,7-tetraazabenzo[cd]azulen-5-yl)methanone | 600 [M + 1]+ | $^1$H NMR (400 MHz, Chloroform-d, ppm) δ 8.28-8.11 (m, 1H), 7.64-7.48 (m, 1H), 7.42-7.19 (m, 5H), 6.96-6.48 (m, 1H), 5.83-5.43 (m, 1H), 5.05-3.82 (m, 3H), 3.47-2.60 (m, 10H), 2.51 (brs, 2H), 1.37-1.18 (m, 6H). |

TABLE B4-continued

| The following examples were prepared in an analogous manner to Example B-10, using the corresponding acrylic acids (Example B-11) or acryloyl chlorides (Example B-12): | | | |
|---|---|---|---|
| Example No. | Structure and Name | LCMS (ESI, m/z) | NMR |
| Example B-12 | 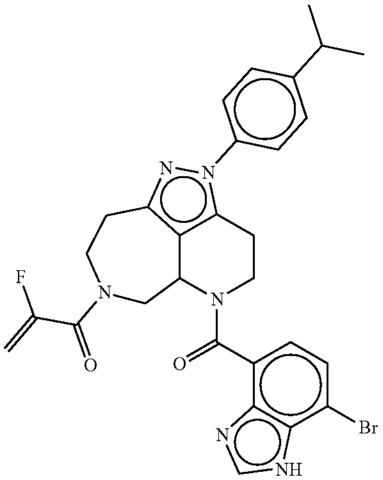 (S or R)-1-(5-(7-bromo-1H-benzo[d]imidazole-4-carbonyl)-2-(4-isopropylphenyl)-2,3,4,5,5a,6,8,9-octahydro-7H-1,2,5,7-tetraazabenzo[cd]azulen-7-yl)-2-fluoroprop-2-en-1-one | 591 [M + H]$^+$ | $^1$H NMR (400 MHz, Chloroform-d, ppm) δ 9.71-8.65 (m, 1H), 7.69-7.47 (m, 1H), 7.44-7.10 (m, 5H), 5.76-4.87 (m, 3H), 4.84-3.81 (m, 2H), 3.49-2.51 (m, 9H), 1.32-1.19 (m, 6H). |

Example B-13: Preparation of (S or R)-4-(7-acryloyl-2-(4-cyclopropylphenyl)-ID-81TR, 3,4,5,5a,6,7,8,9-octahydro-2H-1,2,5,7-tetraazabenzo [cd]azulene-5-ca bonyl)-1H-benzo[d]imidazole-7-carbonitrile

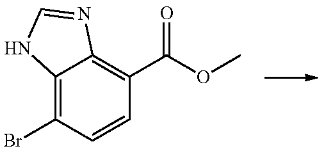

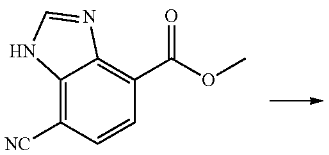

-continued

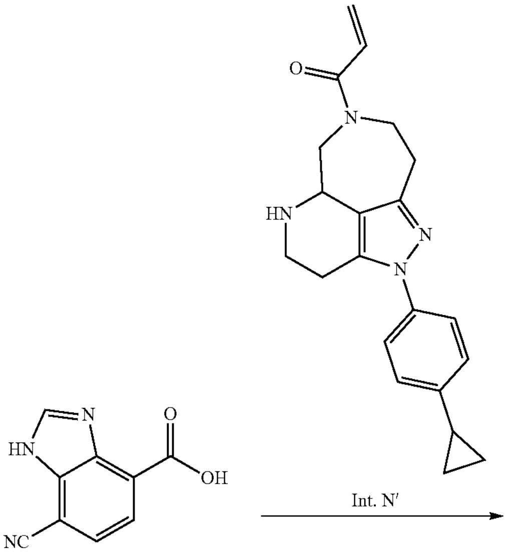

-continued

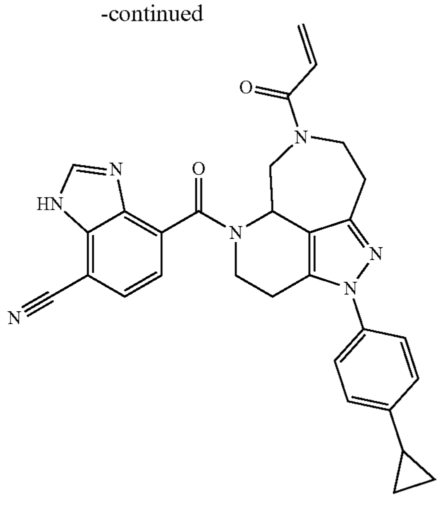

Step 1: Synthesis of Methyl 7-cyano-1H-benzo[d]imidazole-4-carboxylate

To a stirred solution of methyl 7-bromo-1H-benzo[d]imidazole-4-carboxylate (100 mg, 1 equiv., 392 mol) in DMF (2 mL) was added zinc (5.13 mg, 0.2 equiv., 78.4 μmol), Xphos (18.7 mg, 0.1 equiv., 39.2 mol), Xphos Pd G3 (33.2 mg, 0.1 equiv., 39.2 μmol) and $Zn(CN)_2$ (69.1 mg, 1.5 equiv., 588 μmol) at 100° C. and stirred for 4 h. The reaction was then quenched by the addition of water (20 mL) at rt. The resulting mixture was extracted with EtOAc (2×20 mL). The combined organic layers were washed with brine (2×20 mL) and dried over anhydrous $Na_2SO_4$. After filtration, the filtrate was concentrated under reduced pressure. The residue was purified by silica gel column chromatography, eluting with EtOAc/PE (1:5) to afford methyl 7-cyano-1H-benzo[d]imidazole-4-carboxylate (50 mg) as a white solid. LCMS:(ESI, m/z): 202 $[M+1]^+$ Step 2: Synthesis of 7-cyano-1H-benzo[d]imidazole-4-carboxylic Acid The solution of methyl 7-cyano-1H-benzo[d]imidazole-4-carboxylate (50 mg, 1 equiv., 0.25 mmol) in THF (0.75 mL) and water (0.25 mL) was added lithium hydroxide (12.0 mg, 2 equiv., 0.5 mmol) and was stirred at room temperature for 4 h, after which the solvent was removed under reduced pressure. This resulted in 7-cyano-1H-benzo[d]imidazole-4-carboxylic acid (60 mg) as a crude yellow solid, which was used without further purification. LCMS:(ESI, m/z): 188 $[M+1]^+$ Step 3: Synthesis of (S or R)-4-(7-acryloyl-2-(4-cyclopropylphenyl)-3,4,5,5a,6,7,8,9-octahydro-2H-1,2,5,7-tetraazabenzo[cd]azulene-5-carbonyl)-1H-benzo[d]imidazole-7-carbonitrile To a stirred solution of 7-cyano-1H-benzo[d]imidazole-4-carboxylic acid (30 mg, 1 equiv., 0.16 mmol) in DMF (0.6 mL) was added DIEA (0.12 g, 0.17 mL, 6 equiv., 0.96 mmol), HATU (91 mg, 1.5 equiv., 0.24 mmol) and (S or R)-1-(2-(4-cyclopropylphenyl)-2,3,4,5,5a,6,8,9-octahydro-7H-1,2,5,7-tetraazabenzo[cd]azulen-7-yl)prop-2-en-1-one (Int. N') (84 mg, 1.5 equiv., 0.24 mmol) at room temperature and stirred for 2 h, and after which the reaction was quenched by the addition of water (20 mL) at rt. The resulting mixture was extracted with EtOAc (2×20 mL). The combined organic layers were washed with brine (2×20 mL) and dried over anhydrous $Na_2SO_4$. After filtration, the filtrate was concentrated under reduced pressure. The residue was purified by reverse-phase flash chromatography (Column: Kinetex 5 m EVO C18, 30 mm*150 mm; Mobile Phase A: water (10 mmol/L $NH_4HCO_3$), Mobile Phase B: MeCN; Flow rate: 60 mL/min; Gradient: 20% B to 48% B in 10 min; Wave Length: UV 254 nm/221 nm; retention time: 8.8 min) to afford (S or R)-4-(7-acryloyl-2-(4-cyclopropylphenyl)-3,4,5, a,6,7,8,9-octahydro-2H-1,2,5,7-tetraazabenzo[cd]azulene-5-carbonyl)-1H-benzo[d]imidazole-7-carbonitrile (4.4 mg, 8.3 gmol, 5.2%, 97.4% purity) as a white solid. LCMS:(ESI, m/z): 518 $[M+1]^+$. $^1H$ NMR: (400 MHz, Chloroform-d, ppm) δ 11.52-10.51 (m, 1H), 8.54-8.15 (m, 1H), 7.68 (brs, 1H), 7.53-7.38 (m, 1H), 7.36-7.28 (m, 1H), 7.18-6.96 (m, 2H), 6.71-6.32 (m, 1H), 5.92-0.73 (m, 1H), 5.66-4.80 (m, 3H), 4.76-4.07 (m, 2H), 3.79-2.42 (m, 6H), 1.97-1.84 (m, 2H), 0.11-0.94 (m, 2H), 0.80-0.60 (m, 2H).

Example B-14: Preparation of (S or R)-1-(5-(4-bromo-3-((2,2,2-trifluoroethyl)amino)benzoyl)-2-(4-isopropylphenyl)-2,3,4,5,5a,6,8,9-octahydro-7H-1,2,5,7-tetraazabenzo[cd]azulen-7-yl)prop-2-en-1-one

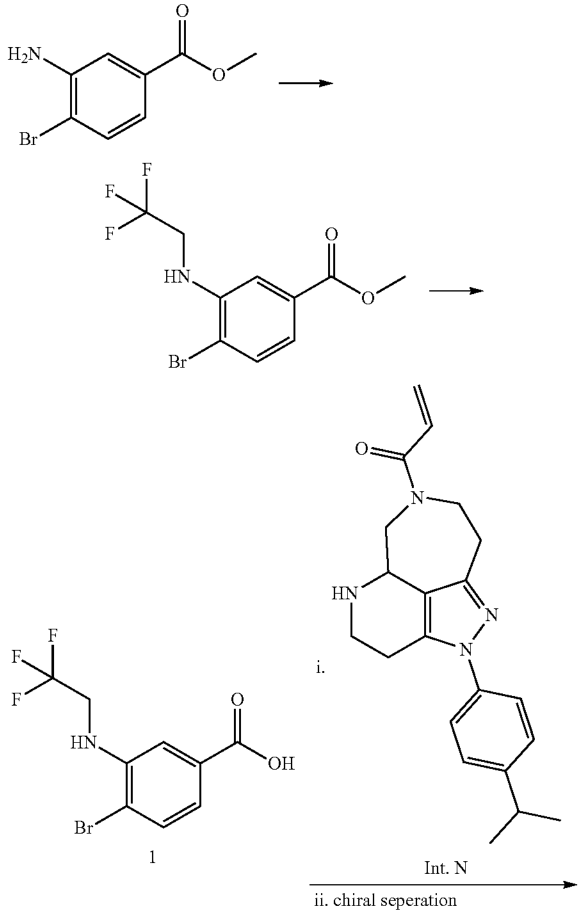

-continued

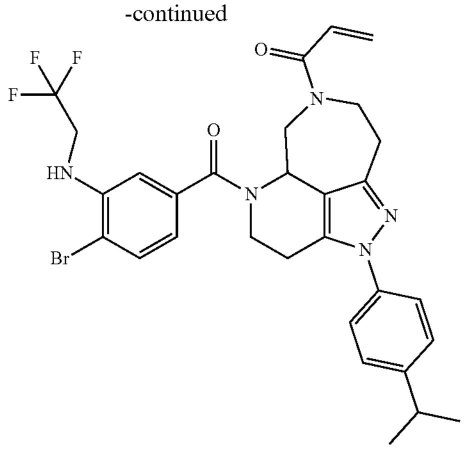

Step 1: Synthesis of Methyl 4-bromo-3-((2,2,2-trifluoroethyl)amino)benzoate

A solution of methyl 3-amino-4-bromobenzoate (10 g, 1 equiv. 43 mmol) in DCM (200 mL) was cooled to 0° C. and $NaBH_3CN$ (5.5 g, 2 equiv., 87 mmol) was added, followed by TFA (50 g, 33 mL, 10 equiv., 0.43 mol) slowly at 0° C. To this mixture was added drop-wise 2,2,2-trifluoroacetaldehyde (17 g, 12 mL, 4 equiv., 0.17 mol), and the mixture was then warmed to rt and stirred for 5 h. The mixture was then adjusted to PH=8 with the addition of saturated $NaHCO_3$(aq). The mixture was diluted with ice water (20 mL) and EA (20 mL), and the aqueous layer was extracted with EA (2×20 mL). The combined organic layers were washed with saturated brine (2×20 mL), dried over anhydrous sodium sulfate and concentrated to give a residue. The residue was purified by flash column chromatography, eluting with EA/E (1:5) to afford methyl 4-bromo-3-((2,2,2-trifluoroethyl)amino)benzoate (4.4 g) as a white solid. LCMS:(ESI, m/z): 314 $[M+1]^+$ Step 2: Synthesis of 4-bromo-3-((2,2,2-trifluoroethyl)amino)benzoic Acid To a solution of methyl 4-bromo-3-((2,2,2-trifluoroethyl)amino)benzoate (500 mg, 1 equiv., 1.6 mmol) in THF (10 mL) and water (5 mL) was added LiOH (115 mg, 3 equiv., 4.81 mmol). The mixture was stirred at 40° C. for 5 h, after which the solution was cooled to rt and acidified to pH=3 with the addition of aqueous 1 M Sulfuric acid, then diluted with EA (20 mL) and water (15 mL), and the aqueous layer was extracted with EA (2×20 mL). The combined organic layers were combined and washed with saturated brine (20 mL), dried over anhydrous sodium sulfate and concentrated to afford 4-bromo-3-((2,2,2-trifluoroethyl)amino)benzoic acid (440 mg) as a yellow solid which was used in the next step directly without further purification. LCMS:(ESI, m/z): 298 $[M+1]^+$ Step 3: Synthesis of (S or R)-1-(5-(4-bromo-3-((2,2,2-trifluoroethyl)amino)benzoyl)-2-(4-isopropylphenyl)-2,3,4,5,5a,6,8,9-octahydro-7H-1,2,5,7-tetraazabenzo[cd]azulen-7-yl)prop-2-en-1-one To a solution of 1-(2-(4-isopropylphenyl)-2,3,4,5,5a,6,8,9-octahydro-7H-1,2,5,7-tetraazabenzo[cd]azulen-7-yl)prop-2-en-1-one (80 mg, 1 equiv., 0.23 m ol) in DMF (1 mL) were added DIEA (0.15 g, 0.2 mL, 5 equiv., 1.1 mmol), 4-bromo-3-((2,2,2-trifluoroethyl)amino)benzoic acid (82 mg, 1.2 equiv., 0.27 mmol) and HBTU (0.13 g, 1.5 equiv., 0.34 mmol). The mixture was stirred at rt overnight. The mixture was diluted with water (20 mL) and EA (20 mL), and the aqueous layer was extracted with EA (2×20 mL). The combined organic layers were washed with saturated brine (2×20 mL), dried over anhydrous sodium sulfate and concentrated to give a residue. The residue was purified by Prep-HPLC to afford the racemic compound. The racemic compound was separated into constituent enantiomers by chiral HPLC (Column: CHIRALPAK-IA 2*25 cm, 5 μm; Mobile Phase A: HEX(0.1% FA), Mobile Phase B: EtOH: DCM=1:1; Flow rate: 20 mL/min; Gradient: isocratic 25; Wave Length: UV 254/220 nm; RT1(min): 7.4; RT2(min): 10.3) to afford (S or R)-1-(5-(4-bromo-3-((2,2,2-trifluoroethyl)amino)benzoyl)-2-(4-isopropylphenyl)-2,3,4,5,5a,6,8,9-octahydro-7H-1,2,5,7-tetraazabenzo[cd]azulen-7-yl)prop-2-en-1-one (13.5 mg) as the first-eluting peak as a white solid. LCMS:(ESI, m/z): 632 $[M+1]^+$. $^1H$ NMR: (400 MHz, Chloroform-d, ppm) δ 7.59--7.41 (m, 2H), 7.37 (d, =8.2 Hz, 2H), 7.31 (d, J=7.9 Hz, 2H), 6.81 (s, 1H), 6.73 (dd, J=8.0, 1.7 Hz, 1H), 6.56-6.35 (m, 1H), 5.95-5.71 (m, 1H), 5.39-5.27 (m, 1H), 5.01-4.94 (m, 1H), 4.90-4.82 (m, 1H), 4.68-4.36 (m, 1H), 4.17-3.79 (m, 3H), 3.25-2.58 (m, 7H), 1.27 (d, J=6.9 Hz, 6H).

Example B-15: Preparation of (R or S)-1-(5-(5-(azetidin-3-yloxy)-6-(trifluoromethyl)nicotinoyl)-2-(4-isopropylphenyl)-2,3,4,5,5a,6,8,9-octahydro-7H-1,2,5,7-tetraazabenzo[cd]azulen-7-yl)prop-2-en-1-one

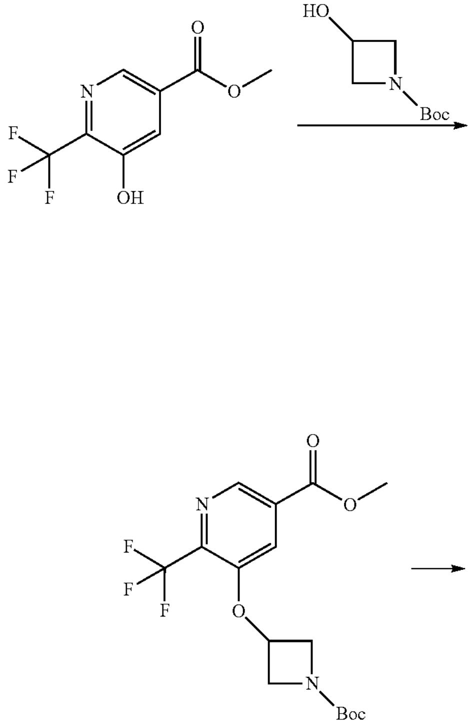

-continued

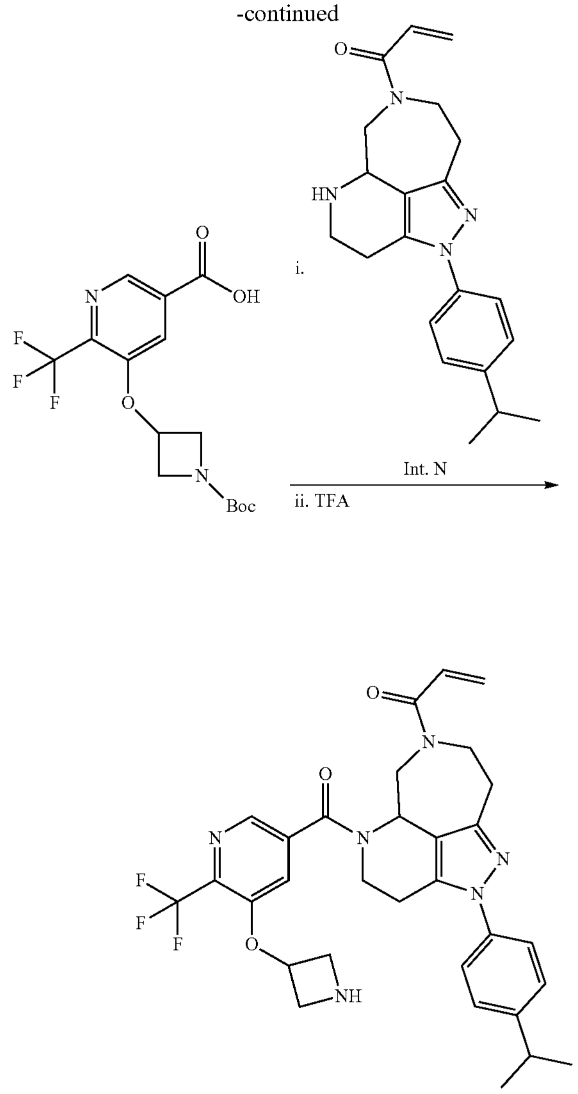

Step 1: Synthesis of Methyl 5-((1-(tert-butoxycarbonyl)azetidin-3-yl)oxy)-6-(trifluoromethyl)nicotinate To a solution of methyl 5-hydroxy-6-(trifluoromethyl) nicotinate (50 mg, 1 equiv., 0.23 mmol) in toluene (1 mL) were added tert-butyl 3-hydroxyazetidine-1-carboxylate (47 mg, 1.2 equiv., 0.27 mmol) $PPh_3$ (0.12 g, 2 equiv., 0.45 mmol) and DIAD (91 mg, 88 μL, 2 equiv., 0.45 mmol). The reaction was placed under a positive pressure of nitrogen and subjected to three backfilling cycles under vacuum. The resulting mixture was stirred for 2 h at 80° C., after which the reaction mixture was cooled to rt, and the mixture was filtered and rinsed with EA (3×20 mL), then diluted with water (20 mL). The aqueous layer was extracted with EA (2×20 mL), and the combined organic layers were washed with saturated brine (3×20 mL), dried over anhydrous sodium sulfate and concentrated to give a residue. The crude product was purified by silica gel chromatography, eluting with PE:EA=5:1 to give methyl 5-((1-(tert-butoxycarbonyl) azetidin-3-yl)oxy)-6-(trifluoromethyl)nicotinate (100 mg) as a colorless oil. LCMI:(ESI, m/z): 377 $[M+1]^+$ Step 2: Synthesis of 5-((1-(tert-butoxycarbonyl) azetidin-3-yl)oxy)-6-trifluoromethyl)nicotinic Acid To a solution of methyl 5-((1-(tert-butoxycarbonyl)azetidin-3-yl)oxy)-6-(trifluoromethyl)nicotinate (200 mg, 1 equiv., 531 μmol) in THF (2 mL) and $H_2O$ (1 mL) was added LiOH (63.6 mg, 5 equiv., 2.66 mmol). The mixture was stirred at 40° C. for 2 h, after which the mixture was acidified to pH=3 with the addition of 1 M sulfuric acid. The solvent was removed under reduced pressure and the residue was purified by reverse phase chromatography (column-C18; Gradient: MeCN in water with 60% formic acid) to afford 5-((1-(tert-butoxycarbonyl)azetidin-3-yl)oxy)-6-(trifluoromethyl)nicotinic acid (150 mg) as an off-white solid. LCMS:(ESI, m/z): 363 $[M+1]^+$ Step 3: Synthesis of (R or S)-1-(5-(5-(azetidin-3-yloxy)-6-(trifluoromethyl)nicotinoyl)-2-(4-isopropylphenyl)-2,3,4,5,5a,6,8,9-octahydro-7H-1,2,5,7-tetraazabenzo[(d]azulen-7-yl)prop-2-en-1-one To a solution of (R or S)-1-(2-(4-isopropylphenyl)-2,3,4,5,5a,6,8,9-octahydro-7H-1,2,5,7-tetraazabenzo[cd]azulen-7-yl)prop-2-en-1-one (Int. N') (50 mg, 1 equiv., 0.14 mmol) in DMF (1 mL) were added 5-((1-(tert-butoxycarbonyl) azetidin-3-yl)oxy)-6-(trifluoromethyl)nicotinic acid (78 mg, 1.5 equiv., 0.21 mmol), HATU (0.11 g, 2 equiv., 0.29 mmol) and DIEA (92 mg, 0.12 mL, 5 equiv., 0.71 mmol). The mixture was stirred at rt for 6 h, after which the mixture was diluted with water (30 mL) and EA (20 mL), and the aqueous layer was extracted with EA (2×100 mL). The combined organic layers were washed with saturated brine (3×20 mL), dried over anhydrous sodium sulfate and concentrated to give a residue. The residue was purified by flash column chromatography (eluting with 100% EA) to afford tert-butyl (R or S)-3-((5-(7-acryloyl-2-(4-isopropylphenyl)-3,4,5,5a,6,7,8,9-octahydro-2H-1,2,5,7-tetraazabenzo[d]azulene-5-carbonyl)-2-(trifluoromethyl)pyridin-3-yl)oxy)azetidine-1-carboxylate (60 mg) as a off-white solid.

A solution of tert-butyl (R or S)-3-((5-(7-acryloyl-2-(4-isopropylphenyl)-3,4,5,5a,6,7,8,9-octahydro-2H-1,2,5,7-tetraazabenzo[cd]azulene-5-carbonyl)-2-(trifluormethyl)pyridin-3-yl)oxy)azetidine-1-carboxylate (30 mg, 1 equiv., 43 μmol) in DCM (1 mL) and TFA (0.2 mL) was stirred at rt for 2 h. The solvent was removed under reduced pressure, and the residue was purified by Prep-HPLC (Column-Xselect CSH™ Prep C18 5 μm 30*150 mm OBD; Mobile Phase A: Water (0.1% FA), Mobile Phase B: ACN; Flow rate: 60 mL/min; Gradient: 15% B to 40%-B in 8 min) to afford (R or S)-1-(5-(5-(azetidin-3-yloxy)-6-(trifluormethyl)nicotinoyl)-2-(4-isopropylphenyl)-2,3,4,5,5a,6,8,9-octahydro-7H-1,2,5,7-tetraazabenzo[cd]azulen-7-yl)prop-2-en-1-one (10.3 mg) as a white solid. LCMS:(ESI, m/z): 595 $[M+1]^+$. $^1H$ NMR: (400 MHz, Chloroform-d, ppm) δ 7.59-7.41 (m, 2H), 7.37 (d, J=8.2 Hz, 2H), 7.3 (d, J=7.9 Hz, 2H), 6.81 (s, 1H), 6.73 (dd, J=8.0, 1.7 Hz, 1H), 6.56-6.35 (m, 1H), 5.95-5.71 (m, 1H), 5.39-5.27 (m, 1H), 5.01-4.94 (m, 1H), 4.90-4.82 (m, 1H), 4.68-4.36 (m, 1H), 4.17-3.79 (m, 3H), 3.25-2.58 (m, 7H), 1.27 (d, J=6.9 Hz, 6H).

Example C-1: Preparation of (S or R)-1-(2-(4-(bicyclo[1.1.1]pentan-1-yl)phenyl)-5-(7-(trifluoromethyl)-1H-indazole-4-carbonyl)-2,3,4,5,5a,6,8,9-octahydro-7H-1,2,5,7-tetraazabenzo[cd]azulen-7-yl)prop-2-en-1-one
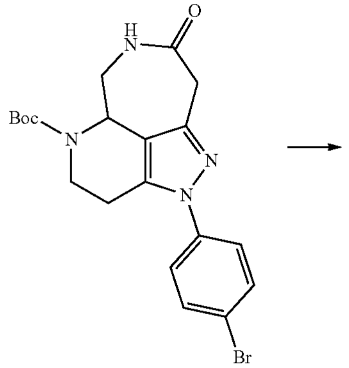
Int. E
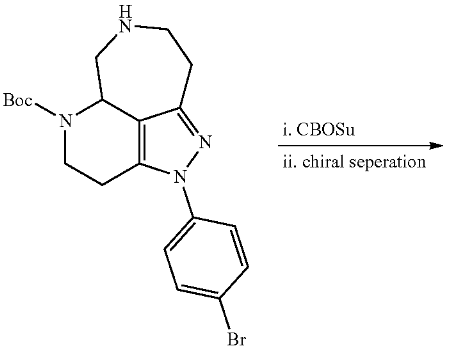
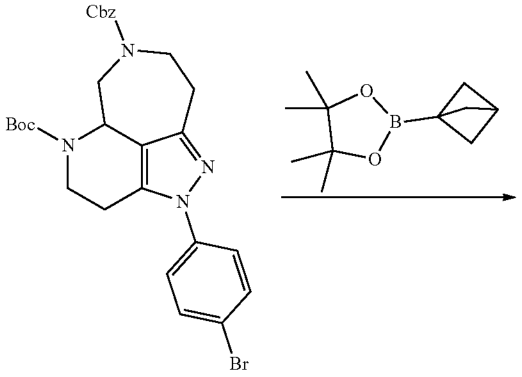
Int. O'
-continued
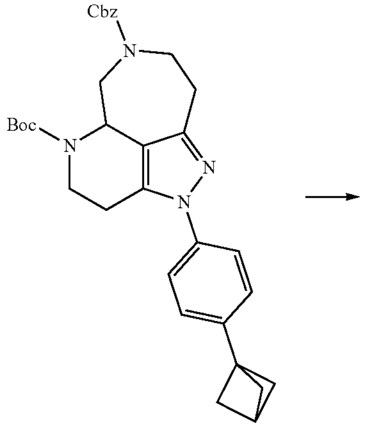
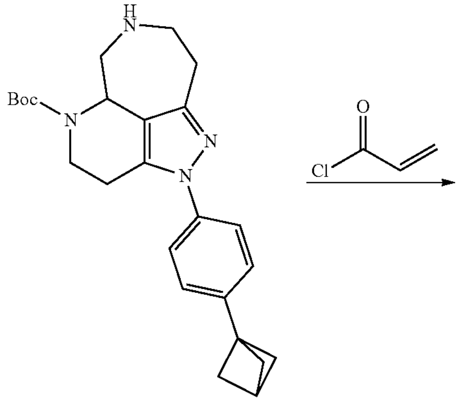
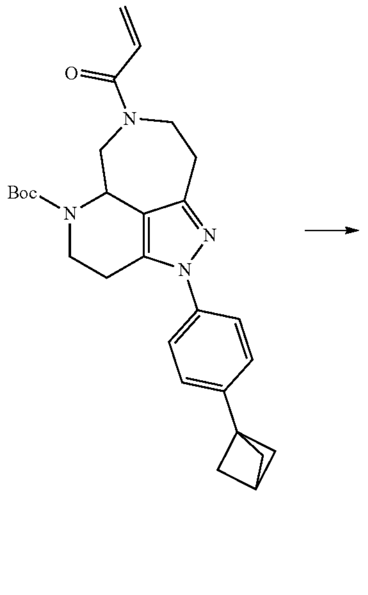

-continued

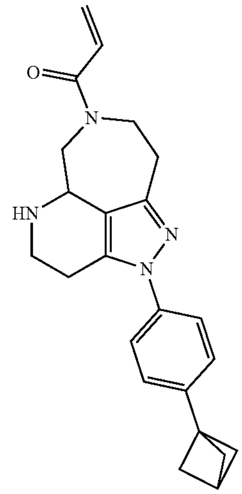

Int. G'

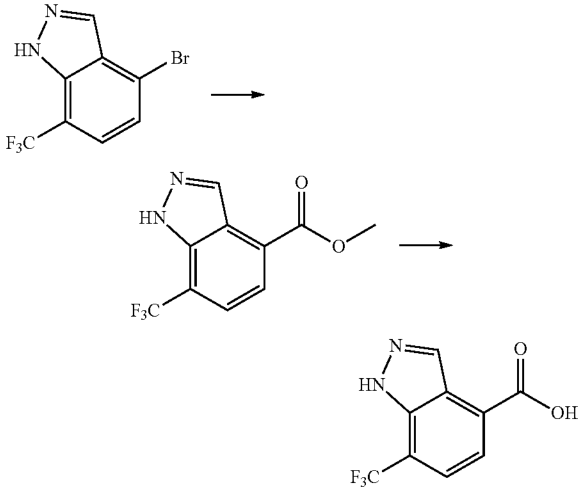

Acid C

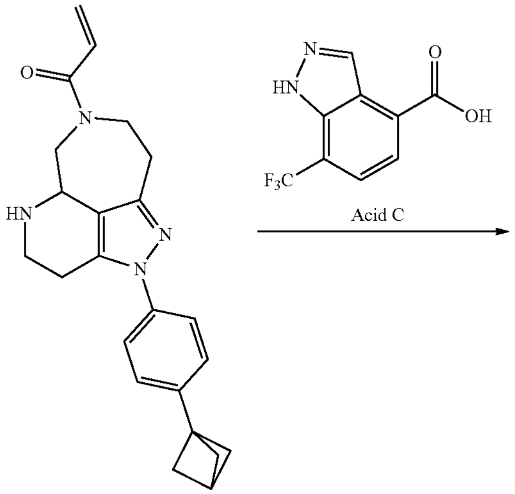

Int. G'

-continued

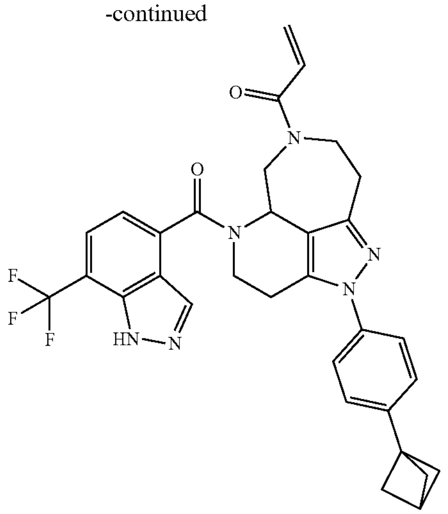

Step 1: Synthesis of Tert-Butyl 2-(4-bromophenyl)-2,3,4,5a,6,7,8,9-octahydro-5H-1,2,5,7-tetraazabenzo[cd]azulene-5-carboxylate To a solution of tert-butyl 2-(4-bromophenyl)-8-oxo-2,3,4,5a,6,7,8,9-octahydro-5H-1,2,5,7-tetraazabenzo[cd]azulene-5-carboxylate (Int. E) (9 g, 1 equiv., 0.02 mol) in THF (90 mL) was added $BH_3$·THF (7 g, 0.08 L, 1 molar, 4 equiv., 0.08 mol). The mixture was warmed to 60° C. and stirred for 1 h. The reaction was monitored by LCMS. The filtrate was concentrated under reduced pressure. The crude product was used in the next step directly without further purification. LCMS: (ESI, m/z):433 $[M+H]^+$ Step 2: Synthesis of 7-Benzyl 5-(tert-butyl) (S or R)-2-(4-bromophenyl)-3,4,5a,6,8,9-hexahydro-2H-1,2,5,7-tetraazabenzo[cd]azulene-5,7-dicarboxylate (Int. O')

To a solution of tert-butyl 2-(4-bromophenyl)-2,3,4,5a,6,7,8,9-octahydro-5H-1,2,5,7-tetraazabenzo[cd]azulene-5-carboxylate (9 g, 1 equiv., 0.02 mol) in D M (180 mL) was added TEA (6 g, 9 mL, 3 equiv., 0.06 mol), CBzOSu (0.02 kg, 3 equiv., 0.05 mol). The mixture was warmed to 40° C. and stirred for 16 h. The reaction was monitored by CMS. The mixture was diluted with ice water (200 mL) and EtOAc (200 mL), and the aqueous layer was extracted with EtOAc (2×200 mL). The combined organic layers were washed with saturated brine (2×200 mL), dried over anhydrous sodium sulfate and concentrated to give a residue. The residue was purified by flash column chromatography, eluting with EtOAc/PE (1:5) to afford 7-benzyl 5-(tert-butyl) 2-(4-bromophenyl)-3,4,5a,6,8,9-hexahydro-2H-1,2,5,7-tetraazabenzo[cd]azulene-5,7-dicarboxylate (7 g) as a white solid.

The racemic 7-benzyl 5-(tert-butyl) 2-(4-bromophenyl)-3,4,5a,6,8,9-hexahydro-2H-1,2,5,7-tetraazabenzo[cd]azulene-5,7-dicarboxylate (7 g, 1 equiv., 0.01 mol) was separated into constituent enantiomers by chiral HPLC separation under the condition (Column: CHIRAL ART Cellulose-SB 3*25 cm, 5 μm; Mobile Phase A: HEX(0.1% FA), Mobile phase B: EtOH: DCM=1:1; Flow rate: 40 mL/min; Gradient: isocratic 15; Wave Length: UV 254/220 nm) to afford 7-benzyl 5-(tert-butyl) (S or R)-2-(4-bromophenyl)-3,4,5a,6,8,9-hexahydro-2H-1,2,5,7-tetraazabenzo

[cd]azulene-5,7-dicarboxylate as the first eluting peak (retention time 8.4 min., 3.3 g) as a white solid. LCMS: (ESI, m/z): 567 $[M+H]^+$ Step 3: Synthesis of 7-benzyl 5-(tert-butyl) (S or R)-2-(4-(bicyclo[1.1.1]pentan-1-yl)phenyl)-3,4,5a,6,8,9-hexahydro-2H-1, 2,5,7-tetraazabenzo[cd]azulene-5,7-dicarboxylate 7-benzyl 5-(tert-butyl) (S or R)-2-(4-bromophenyl)-3,4,5a,6,8,9-hexahydro-2H-1,2,5,7-tetraazabenzo[cd]azulene-5,7-dicarboxylate (Int. O') (900 mg, 1 equiv., 1.59 mmol), $Ir[(dF(CF_3)ppy)_2dtbbpy]PF_6$ (356 mg, 0.2 equiv., 317 μmol), 2-(bicyclo[1.1.1]pentan-1-yl)-4,4,5,5-tetramethyl-1,3,2-dioxaborolane (462 mg, 1.5 equiv., 2.38 mmol), were added to a 8 mL glass vial equipped with a magnetic stir bar and dissolved in DMF (25 mL). morpholine (207 mg, 205 μL, 1.5 equiv., 2.38 mmol) was added. Ina second vial dtbbpy (85.1 g, 0.2 equiv., 317 mol) and $NiCl_2$*glyme (69.7 mg, 0.2 equiv., 317 μmol) were added and dissolved in 1 mL DMF. The mixture was sonicated for 30 seconds and heated afterwards to 100° (heat gun) until a clear green solution was obtained. Both mixtures were combined, and the resulting reaction mixture was irradiated with blue LEDs (445 nm at 220 mW) at room temperature for 3 h. After the reaction mixture was cooled to RT, the mixture was filtered and rinsed with EtOAc (3×20 mL), then diluted with water (20 mL). The aqueous layer was extracted with EtOAc (2×20 mL). The combined organic layers were washed with saturated brine (3×20 mL), dried over anhydrous sodium sulfate and concentrated to give a residue. The crude product was purified by silica gel chromatography eluting with PE: EtOAc=5:1 to give 7-benzyl 5-(tert-butyl) (S or R)-2-(4-(bicyclo[1.1.1]pentan-1-yl)phenyl)-3,4,5a,6,8,9-hexahydro-2H-1,2,5,7-tetraazabenzo[cd]azulene-5,7-dicarboxylate (150 mg) as a white solid. LCMS: (ESI, m/z):555 $[M+H]^+$ Step 4: Synthesis of Tert-Butyl (S or R)-2-(4-(bicyclo[1.1.1]pentan-1-yl)phenyl)-2,3,4,5a,6,7,8,9-octahydro-5H-1,2,5,7-tetraazabenzo[cd]azulene-5-carboxylate To a solution of 7-benzyl 5-(tert-butyl) (S or R)-2-(4-(bicyclo[1.1.1]pentan-1-yl)phenyl)-3,4,5a,6,8,9-hexahydro-2H-1,2,5,7-tetraazabenzo[cd]azulene-5,7-dicarboxylate (120 mg, 1 equiv., 216 μmol) in $NH_3$ in MeOH (2 mL) were added $Pd(OH)_2/C$ (60.8 mg, 50 wt %, 1 equiv., 216 mol) Pd/C (46.0 mg, 50 wt %, 1 equiv., 216 μmol). The mixture was purged with nitrogen for three times and then was pressurized 4.0 MPa with hydrogen at room temperature for 2 h. The reaction mixture was cooled to rt. The reaction was monitored by LCMS. The mixture was filtered and rinsed with EtOAc (5×50 mL), the filtrate was concentrated under vacuum to give a residue. This resulted in tert-butyl (S or R)-2-(4-(bicyclo[1.1.1]pentan-1-yl)phenyl)-2,3,4,5a,6,7,8,9-octahydro-5H-1,2,5,7-tetraazabenzo[cd]azulene-5-carboxylate (100 mg) as a crude white solid. The crude product was used in the next step directly without further purification. LCMS: (ESI, m/z): 421 $[M+H]^+$.

Step 5: Synthesis of Tert-Butyl (S or R)-7-acryloyl-2-(4-(bicyclo[1.1.1]pentan-1-yl)phenyl)-2,3,4,5a,6,7,8,9-octahydro-5H-1,2,5,7-tetraazabenzo[cd]azulene-5-carboxylate To a solution of tert-butyl (S or R)-2-(4-(bicyclo[1.1.1]pentan-1-yl)phenyl)-2,3,4,5a,6,7,8,9-octahydro-5H-1,2,5,7-tetraazabenzo[cd]azulene-5-carboxylate (95.0 mg, 1 equiv., 225.9 μmol) in DCM (2 mL) was added TEA (68.57 mg, 94.5 μL, 3 equiv., 677.7 mol). The mixture was cooled to 0° C., then acryloyl chloride (30.7 mg, 27.6 μL, 1.5 equiv., 339 μmol) was added dropwise to the above mixture at 0° C. under nitrogen atmosphere. The mixture was warmed to room temperature and stirred for 0.5 h. The reaction was monitored by LCMS. The mixture was diluted with ice water (20 mL) and EtOAc (20 mL), and the aqueous layer was extracted with EtOAc (2×20 mL). The combined organic layers were washed with saturated brine (2×20 mL), dried over anhydrous sodium sulfate and concentrated to give a residue. The residue was purified by flash column chromatography, eluting with EtOAc/PE (1:5) to afford tert-butyl (S or R)-7 -acryloyl-2-(4-(bicyclo[1.1.1]pentan-1-yl)phenyl)-2,3,4,5a,6,7,8,9-octahydro-5H-1,2,5,7-tetraazabenzo[cd]azulene-5-carboxylate (65 mg) as a light yellow solid. LCMS: (ESI, m/z):475 $[M+H]^+$ Step 6: Synthesis of (S or R)-1-(2-(4-(bicyclo[1.1.1]pentan-1-yl)phenyl)-2,3,4,5,5a,6,8,9-octahydro-7H-1,2,5,7-tetraazabenzo[cd]azulen-7-yl)prop-2-en-1-one (Int. G')

The solution of tert-butyl (S or R)-7-acryloyl-2-(4-(bicyclo[1.1.1]pentan-1-yl)phenyl)-2,3,4,5a,6,7,8,9-octahydro-5H-1,2,5,7-tetraazabenzo[cd]azulene-5-carboxylate (65 mg, 1 equiv., 0.14 mmol) in DCM (1.5 mL) and TFA (0.5 mL) was stirred at room temperature for 0.5 h. The solvent was then removed under reduced pressure, resulting in (S or R)-1-(2-(4-(bicyclo[1.1.1]pentan-1-yl)phenyl)-2,3,4,5,5a,6,8,9-octahydro-7H-1,2,5,7-tetraazabenzo[cd]azulen-7-yl)prop-2-en-1-one (Int. G') (65 mg) as a crude yellow oil. The crude product was used in the next step directly without further purification. LCMS: (ESI, m/z): 375 $[M+H]^+$ Step 7: Synthesis of Methyl 7-(trifluoromethyl)-1H-indazole-4-carboxylate To a solution of 4-bromo-7-(trifluoromethyl)-1H-indazole (1.0 g, 1 equiv., 3.8 mmol) in MeOH (10 mL) and DMF (5 mL) were added TEA (1.7 g, 2.4 mL, 4.5 Eq, 17 mmol) and $PdCl_2(dppf)$ (1.1 g, 0.4 equiv., 1.5 mmol). The mixture was purged with nitrogen×3 and then was pressurized 4.to 0 MPa with carbon monoxide at 70° C. for 24 hour. The reaction mixture was then cooled to rt. The mixture was then diluted with water (20 mL) and EA (0 mL), and the aqueous layer was extracted with EtOAc (2×20 mL). The combined organic layers were washed with saturated brine (2×20 mL), dried over anhydrous sodium sulfate and concentrated to give a residue. The residue was purified by flash column chromatography, eluted with EA/PE (1:5) to afford methyl 7-(trifluoromethyl)-1H-indazole-4-carboxylate (500 mg %) as a yellow solid. LCMS: (ESI, m/z): 245 $[M+H]^+$ Step 8: Synthesis of 7-(trifluoromethyl)-1H-indazole-4-carboxylic Acid (Acid C)

To a solution of methyl 7-(trifluoromethyl)-1H-indazole-4-carboxylate (200 mg, 1 equiv., 819 μmol) in THF (2 mL) and water (1 mL) was added LiOH (39.2 m, 2 Eq, 1.64 mmol). The mixture was stirred at room temperature for 1 h. The mixture was then acidified to pH=3 with 1M Sulfuric acid, then diluted with EtOAc (20 mL) and water (15 mL), and the aqueous layer was extracted with EtOAc (2×20 mL). The combined organic layers were washed with saturated brine (20 mL), dried over anhydrous sodium sulfate and concentrated to afford 7-(trifluoromethyl)-1H-indazole-4-carboxylic acid (Acid C) (200 mg) as a white solid. The crude product was used in the next step directly without further purification. LCMS: (ESI, m/z): 231 [M+H]$^+$ Step 9: Synthesis of (S or R)-1-(2-(4-(bicyclo[1.1.1]pentan-1-yl)phenyl). 5-(7-(trifluoromethyl)-1H-indazole-4-carbonyl)-2,3,4,5,5a,6,8,9-octahydro-7H-1,2,5, 7-tetraazabenzo[cd]azulen-7-yl)prop-2-en-1-one To a stirred solution of (S or R)-1-(2-(4-(bicyclo[1.1.1]pentan-1-yl)phenyl)-2,3,4,5,5a,6,8,9-octahydro-7H-1,2,5,7-tetraazabenzo[cd]azulen-7-yl)prop-2-en-1-one (30 mg, 1 equiv., 80 μmol) in DMF (0.5 mL) was added HBTU (76 mg, 2.5 equiv., 0.2 mmol), DIEA (0.10 g, 0.14 mL, 10 equiv., 0.8 mmol) and 7-(trifluoromethyl)-1H-indazole-1-carboxylic acid (46 mg, 2.5 equiv., 0.2 mmol) at room temperature and stirred for 30 min. The reaction was then quenched by the addition of water (4 mL) at rt. The resulting mixture was extracted with EtOAc (2×2 mL). The combined organic layers were washed with brine (2×2 mL) and dried over anhydrous $Na_2SO_4$. The residue was purified by reverse-phase flash chromatography (Column: Sunfire C18 5 m, 30 mm*150 mm; Mobile Phase A: water (0.1% FA), Mobile Phase B: MeCN; Flow rate: 60 mL/min; Gradient: 42% B to 68% B in 8 min; Wave Length: UV 254 nm/221 nm; retention time 1: 7.6 min) to afford (S or R)-1-(2-(4-(bicyclo[1.1.1]pentan-1-yl)phenyl)-5-(7-(trifluoromethyl)-1H-indazole-4-carbonyl)-2,3,4,5,5a,6,8,9-octahydro-7H-1,2,5,7-tetraazabenzo[cd]azulen-7-yl)prop-2-en-1-one (7.4 mg, 13 μmol, 16%, 99.7% purity) as a white solid. LCMS: (ESI, m/z): 587 [M+H]$^+$. $^1$H NMR: (400 MHz, Chloroform-d, ppm) δ 8.20 (s, 1H), 7.77 (d, J=7.2 Hz, 1H), 7.60-7.43 (m, 1H), 7.42-7.30 (m, 3H), 6.69-6.26 (m, 1H), 5.99-5.69 (m, 1H), 5.68-5.43 (m, 1H), 5.10-4.88 (m, 1H), 4.76-4.42 (m, 1H), 4.23-3.64 (m, 1H), 3.43-2.77 (m, 4H), 2.73-2.59 (m, 1H), 2.59-2.54 (m, 1H), 2.09 (s, 6H).

Example C-2: Preparation of (S or R)-1-(5-(7-bromo-1H-benzo[d]imidazole-4-carbonyl)-2-(2-hydroxy-4-isopropylphenyl)-2,3,4,5,5a,6,8,9-octahydro-7H-1,2,5,7-tetraazabenzo[cd]azulen-7-yl)prop-2-en-1-one

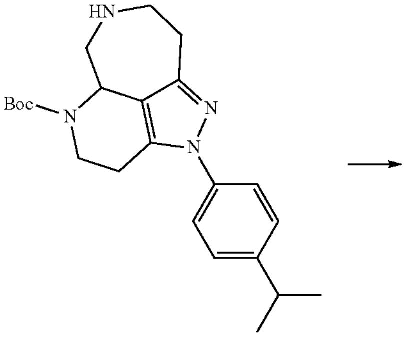

Int. M

-continued

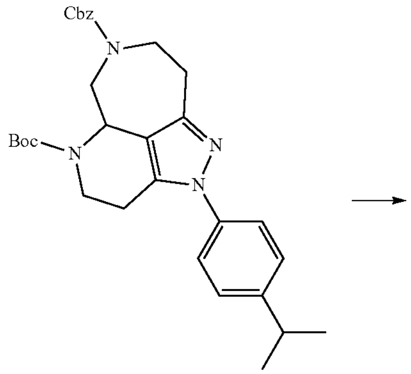

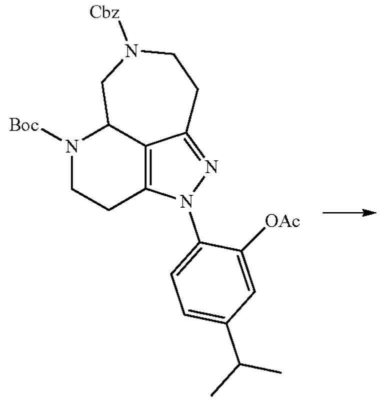

Int. P

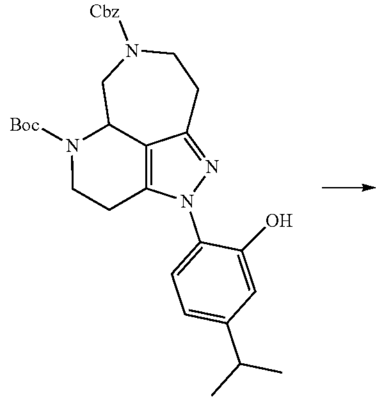

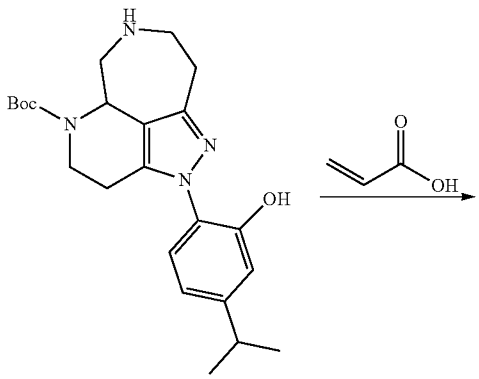

-continued

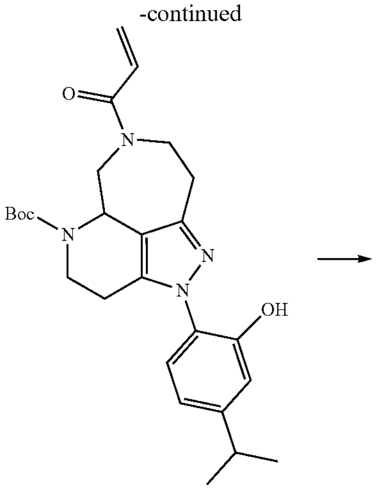

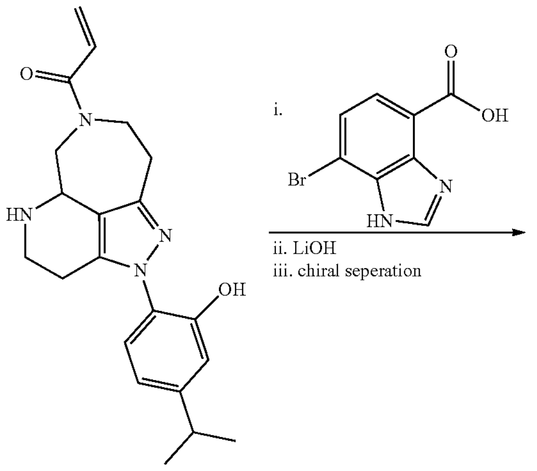

Int. Q

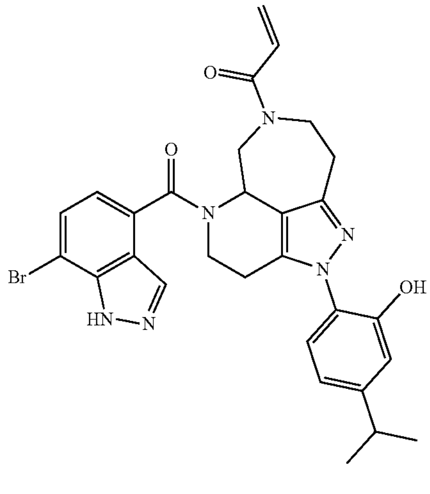 [SMILES: C=CC(=O)N1CCc2nn(-c3ccc(C(C)C)cc3O)c3c2C(C1)N(C(=O)c1ccc(Br)c2[nH]ncc12)CC3]

Step 1: Synthesis of 7-benzyl 5-(tert-butyl) 2-(4-isopropylphenyl)-3,4,5a,6,8,9-hexahydro-2H-1,2,5,7-tetraazabenzo[cd]azulene-5,7-dicarboxylate To a solution of tert-butyl 2-(4-isopropylphenyl)-2,3,4,5a,6,7,8,9-octahydro-5H-1,2,5,7-tetraazabenzo[cd]azulene-5-carboxylate (Int. M) (0.6 g, 1 equiv., 2 mmol) in DCM (12 mL) were added Triethylamine (1 g, 2 mL, 7.5 equiv., 0.01 mol) and CBzOSu (1 g, 3 equiv., 5 mmol). The mixture was stirred at 40° C. for 6 h. The mixture was then diluted with water (20 mL) and EtOAc (20 mL) and the aqueous layer was extracted with EtOAc (2×20 mL). The combined organic layers were washed with saturated brine (2×20 mL), dried over anhydrous sodium sulfate and concentrated to give a residue. The residue was purified by silica gel column chromatography, eluting with PE/EtOAc (3:1) to afford 7-benzyl 5-(tert-butyl) 2-(4-isopropylphenyl)-3,4,5a,6,8,9-hexahydro-2H-1,2,5,7-tetraazabenzo[cd]azulene-5,7-dicarboxylate (0.7 g) as a white solid. LCMS:(ESI, m/z): 531 $[M+1]^+$ Step 2: Synthesis of 7-benzyl 5-(tert-butyl) 2-(2-acetoxy-4-isopropylphenyl)-3,4,5a,6,8,9-hexahydro-2H-1,2,5,7-tetraazabenzo[cd]azulene-5,7-dicarboxylate (Int. P)

To a solution of 7-benzyl 5-(tert-butyl) 2-(4-isopropylphenyl)-3,4,5a,6,8,9-hexahydro-2H-1,2,5,7-tetraazabenzo[cd]azulene-5,7-dicarboxylate (0.68 g, 1 equiv., 1.3 mmol) in acetic acid (12 mL) and 1,4-dioxane (1.2 mL) were added (acetyloxy)(phenyl)-lamda3-iodanyl acetate (0.83 g, 2 equiv., 2.6 mmol) and palladium diacetate (29 mg, 0.1 equiv., 0.13 mmol). The mixture was stirred at 90° C. for 2 h. The reaction was monitored by LCMS, and upon completion it was concentrated under reduced pressure. The residue was purified by silica gel column chromatography, eluting with PE/EtOAc (3:1) to afford 7-benzyl 5-(tert-butyl) 2-(2-acetoxy-4-isopropylphenyl)-3,4,5a,6,8,9-hexahydro-2H-1,2,5,7-tetraazabenzo[cd]azulene-5,7-dicarboxylate (Int. P) (0.42 g) as a yellow solid. LCMS:(ESI, m/z): 589 $[M+1]^+$ Step 3: Synthesis of 7-benzyl 5-(tert-butyl) 2-(2-hydroxy-4-isopropylphenyl)-3,4,5a,6,8,9-hexahydro-2H-1,2,5,7-tetraazabenzo[cd]azulene-5,7-dicarboxylate To a solution of 7-benzyl 5-(tert-butyl) 2-(2-acetoxy-4-isopropylphenyl)-3,4,5a,6,8,9-hexahydro-2H-1,2,5,7-tetraazabenzo[cd]azulene-5,7-dicarboxylate (230 mg, 1 equiv., 391 μmol) in MeOH (4.6 mL) and water (0.46 mL) was added sodium hydrate (62.4 mg, 56.4 μL, 4 equiv., 1.56 mmol). The mixture was stirred at room temperature for 1 h. The reaction was monitored by LCMS. The mixture was neutralized to pH=7 with formic acid, then diluted with EtOAc (20 mL) and water (20 mL), and the aqueous layer was extracted with EtOAc (×10 mL). The organic layers were combined and washed with saturated brine (2×10 mL), dried over anhydrous sodium sulfate and concentrated to afford 7-benzyl 5-(tert-butyl) 2-(2-hydroxy-4-isopropylphenyl)-3,4,5a,6,8,9-hexahydro-2H-1,2,5,7-tetraazabenzo[cd]azulene-5,7-dicarboxylate (195 mg) as a yellow solid. The crude product was used in the next step directly without further purification. LCMS:(ESI, m/z): 547 $[M+1]^+$ Step 4: Synthesis of Tert-Butyl 2-(2-hydroxy-4-isopropylphenyl)-2,3,4,5a,6,7,8,9-octahydro-5H-1,2,5,7-tetraazabenzo[cd]azulene-5-carboxylate To a solution of 7-benzyl 5-(tert-butyl) 2-(2-hydroxy-4-isopropylphenyl)-3,4,5a,6,8,9-hexahydro-2H-1,2,5,7-tetraazabenzo[cd]azulene-5,7-dicarboxylate (200 mg, 1 equiv., 366 gmol) in MeOH (4 mL) was added Pearlman's catalyst (77.9 mg, 50% wt, 1 equiv., 366 μmol) in a pressure tank. The mixture was purged with hydrogen for three times and then was pressurized to 3 MPa with hydrogen at room temperature for 3 h. The reaction mixture was cooled to rt and filtered to remove insoluble solids. The filter cake was washed with MeOH (5 mL) two times. The filtrate was concentrated under reduced pressure to afforded tert-butyl 2-(2-hydroxy-4-isopropylphenyl)-2,3,4,5a,6,7,8,9-octahydro-5H-1,2,5,7-tetraazabenzo[cd]azulene-5-carboxylate (150 mg) as a white solid. LCMS:(ESI, m/z): 413 [M+1]$^+$ Step 5: Synthesis of Tert-Butyl 7-acryloyl-2-(2-hydroxy-4-isopropylphenyl)-2,3,4,5a,6,7,8,9 -octahydro-5H-1,2,5,7-tetraazabenzo[cd]azulene-5-carboxylate To a solution of tert-butyl 2-(2-hydroxy-4-isopropylphenyl)-2,3,4,5a,6,7,8,9-octahydro-5H-1,2,5,7-tetraazabenzo[cd]azulene-5-carboxylate (140 mg, 1 equiv., 339 μmol) in DMF (2.8 mL) were added acrylic acid (24.5 mg, 23.3 μL, 1 equiv., 339 μmol), DIE (274 mg, 367 μL, 6.25 equiv., 2.12 mmol) and propylphosphonic anhydride (162 mg, 151 μL, 1.5 equiv., 509 μmol). The mixture was stirred at room temperature for 2 h. The mixture was then quenched by water (5 mL) and extracted with EtOAc (2×3 mL). The combined organic layers were washed with brine (5 mL), dried over $Na_2SO_4$, filtered, and evaporated under reduced pressure. The residue was purified by silica gel column chromatography, eluting with PE/EtOAc (2:1) to afford tert-butyl 7-acryloyl-2-(2-hydroxy-4-isopropylphenyl)-2,3,4,5a,6,7,8,9-octahydro-5H-1,2,5,7-tetraazabenzo[cd]azulene-5-carboxylate (0.11 g) as a yellow solid. LCMS:(ESI, m/z):467 [M+1]$^+$ Step 6: Synthesis of 1-(2-(2-hydroxy-4-isopropylphenyl)-2,3,4,5,5a,6,8,9-octahydro-7H-1,2,5,7-tetraazabenzo[cd]azulen-7-yl)prop-2-en-1-one (Int. Q)

A solution of tert-butyl 7-acryloyl-2-(2-hydroxy-4-isopropylphenyl)-2,3,4,5a,6,7,8,9-octahydro-5H-1,2,5,7-tetraazabenzo[cd]azulene-5-carboxylate (0.16 g, 1 equiv., 0.34 mmol) in DCM (2.4 mL) and TFA (0.8 mL) was stirred at room temperature f r 1 h. The reaction was monitored by LCMS. The solvent was removed under reduced pressure. This resulted in 1-(2-(2-hydroxy-4-isopropylphenyl)-2,3,4,5,5a,6,8,9-octahydro-7H-1,2,5,7-tetraazabenzo[cd]azulen-7-yl)prop-2-en-1-one (Int. Q) (0.11 g) as a crude yellow oil. The crude product was used in the next step directly without further purification. LCMS:(ESI, m/z): 367 [M+1]$^+$ Step 7: Synthesis of (S or R)-1-(5-(7-bromo-1H-benzo[d]imidazole-4-carbonyl)-2-(2-hydroxy-4-isopropylphenyl)-2,3,4,5,5a,6, 8,9-octahydro-7H-1,2,5,7-tetraazabenzo[d]azulen-7-yl)prop-2-en-1-one To a solution of 1-(2-(2-hydroxy-4-isopropylphenyl)-2,3,4,5,5a,6,8,9-octahydro-7H-1,2,5,7-tetraazabenzo[cd]azulen-7-yl)prop-2-en-1-one (160 mg, 1 equiv., 437 μmol) in DMF (3.6 mL) were added 7-bromo-1H-benzo[d]imidazole-4-carboxylic acid (316 mg, 3 equiv., 1.31 mmol), EDC hydrochloride (335 mg, 4 equiv., 1.75 mmol), HOBT (236 mg, 240 μL, 4 equiv., 1.75 mmol) and DIEA (677 mg, 905 μL, 12 equiv., 5.24 mmol). The mixture was stirred at room temperature for 3 h. The reaction was monitored by LCMS. The resulting mixture was quenched by water (20 mL) and extracted with EtOAc (40 mL). The organic layers were washed with brine (3×20 mL), dried over $Na_2SO_4$, filtered, and evaporated under reduced pressure to afford 2-(7-acryloyl-5-(7 -bromo-1H-benzo[d]imidazole-4-carbonyl)-3,4,5,5a,6,7,8,9-octahydro-2H-1,2,5,7-tetraazabenzo[cd]azulen-2-yl)-5-isopropylphenyl 7-bromo-1H-benzo[d]imidazole-4-carboxylate (220 mg) as a yellow solid without further purification. LCMS:(ESI, m/z):811 [M+1]

To a solution of 2-(7-acryloyl-5-(7-bromo-1H-benzo[d]imidazole-4-carbonyl)-3,4,5,5a,6,7,8,9-octahydro-2H-1,2,5,7-tetraazabenzo[cd]azulen-2-yl)-5-isopropylphenyl 7-bromo-1H-benzo[d]imidazole-4-carboxylate (250 mg, 1 equiv., 308 μmol) in THF (5 mL) and water (2.5 mL) were added LiOH (36.8 mg, 22.6 μL, 5 equiv., 1.54 mmol. The mixture was stirred at room temperature for 1 h. The reaction was monitored by LCMS. The mixture was purified by Prep-HPLC (Column: XBridge BEH Shield RP18 5 μm, 30 mm*150 mm; Mobile Phase A: water (10 mmol/L $NH_4HCO_3$), Mobile Phase B: MeCN; Flow rate: 60 mL/min, Gradient: 32% B to 53% B in 10 min; Wave Length: UV 254 nm/220 nm; retention time 1: 8.1 min) to afford 1-(5-(7-bromo-1H-benzo[d]imidazole-4-carbonyl)-2-(2-hydroxy-4-isopropylphenyl)-2,3,4,5,5a,6,8,9-octahydro-7H-1,2,5,7-tetraazabenzo[cd]azulen-7-yl)prop-2-en-1-one (47 mg) as a white solid.

The racemic 1-(5-(7-bromo-1H-benzo[d]imidazole-4-carbonyl)-2-(2-hydroxy-4-isopropylphenyl)-2,3,4,5,5a,6,8,9-octahydro-7H-1,2,5,7-tetraazabenzo[cd]azulen-7-yl)prop-2-en-1-one (47 mg, 79.7 mol, 25.88%, 99.6% purity) was purified by Prep-Chiral-HPLC (Column: CHIRAL ART Cellulose-SB 2*25 cm, 5 μm; Mobile Phase A: HEX(0.1% FA), Mobile Phase B: EtOH: DCM=1:1; Flow rate: 20 mL/min; Gradient: isocratic 25; Wavelength: UV 254/220 nm; Sample Solvent: EtOH; Injection Volume: 0.7 mL; Number Of Runs: 3) to afford (S or R)-1-(5-(7-bromo-1H-benzo[d]imidazole-4-carbonyl)-2-(2-hydroxy-4-isopropylphenyl)-2,3,4,5,5a,6,8,9-octahydro-7H-1,2,5,7-tetraazabenzo[cd]azulen-7-yl)prop-2-en-1-one as the second-eluting peak (retention time 11.5 min., 16.0 mg, 27.0 μmol, 8.79%, 99.6% purity) as a white solid. LCMS:(ESI, m/z): 589 [M+1]$^+$. $^1H$ NMR: (400 MHz, Chloroform-d, ppm) δ 10.12 (brs, 1H), 8.44 (brs, 1H), 7.56 (d, J=7.9 Hz, 1H), 7.52-7.41 (m, 1H), 7.09-6.90 (m, 1H), 6.83-6.65 (m, 1H), 6.60-6.40 (m, 1H), 5.95-5.70 (m, 1H), 5.55-5.36 (m, 1H), 5.01-4.89 (m, 1H), 4.65-4.47 (m, 1H), 4.31-4.06 (m, 1H), 3.37-2.60 (m, 9H), 1.28-1.19 (m, 6H). Analytical chiral-HPLC: Column: CHIRAL ART Cellulose-SB; Column Size: 4.6*100 mm, 3 m; Mobile Phase: Hex(0.1% FA):(EtOH: DCM=1:1)=75:25; Flow: 1.0 mL/min; Temperature: 25° C.; retention time=4.4 min (second peak).

Example C-3: Preparation of (S or R)-1-(2-(2-hydroxy-4-isopropylphenyl)-5-(5-hydroxy-6 -(trifluoromethyl)nicotinoyl)-2,3,4,5,5a,6,8,9-octahydro-7H-1,2,5,7-tetraazabenzo[cd]azulen-7-yl)prop-2-en-1-one

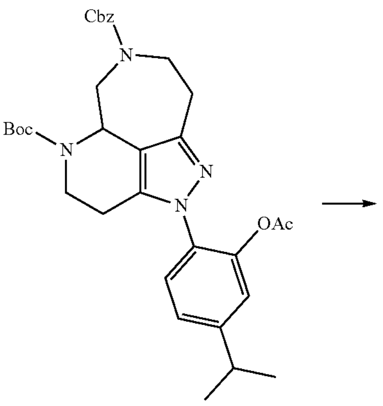

Int. P

-continued

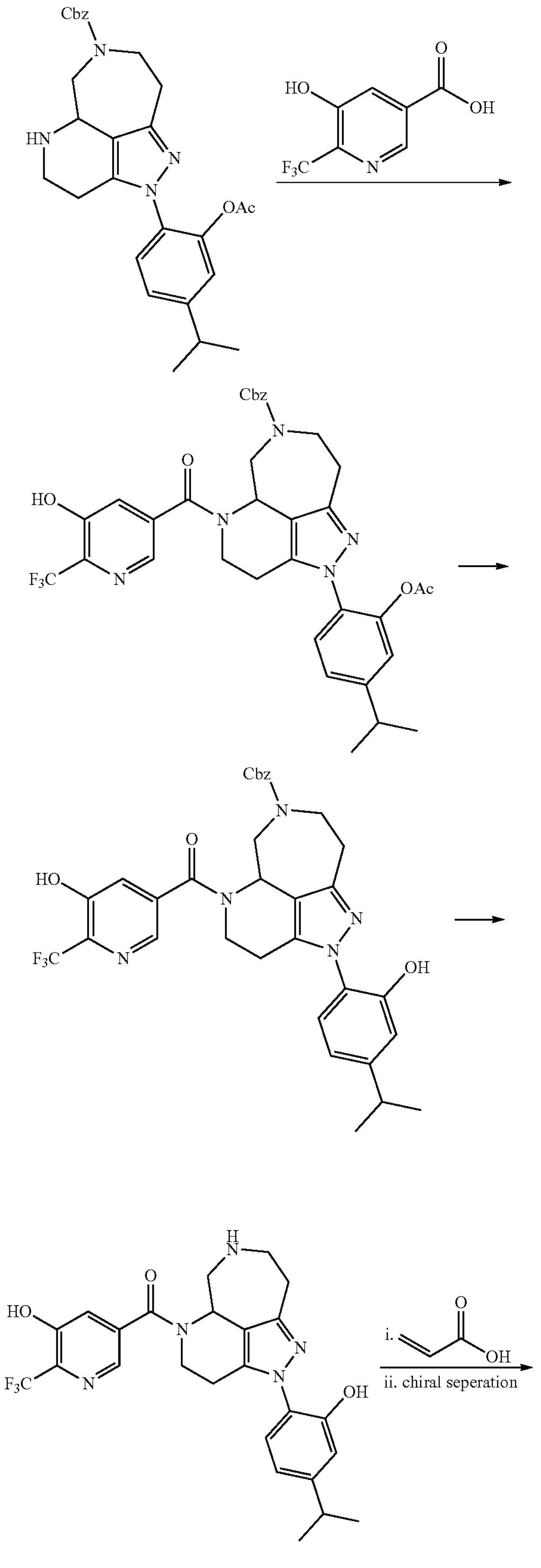

-continued

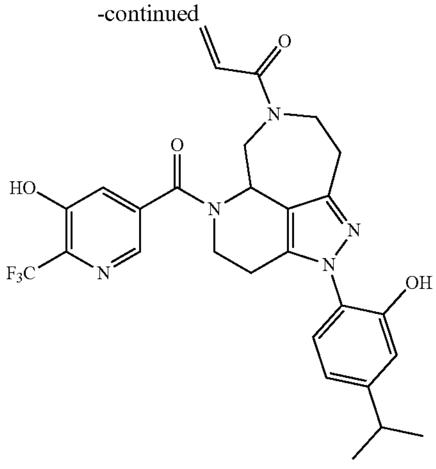

single enantiomer

Step 1: Synthesis of Benzyl 2-(2-acetoxy-4-isopropylphenyl)-2,3,4,5,5a,6,8,9-octahydro-7H-1,2,5,7-tetraazabenzo[cd]azulene-7-carboxylate The solution of 7-benzyl 5-(tert-butyl) 2-(2-acetoxy-4-isopropylphenyl)-3,4,5a,6,8,9-hexahydro-2H-1,2,5,7-tetraazabenzo[cd]azulene-5,7-dicarboxylate (Int. P) (340 mg, 1 equiv., 578 μmol) in DCM (5.1 mL) and TFA (1.7 mL) was stirred at room temperature for 1 h. The reaction was monitored by LCMS. The solvent was removed under reduced pressure. This resulted in benzyl 2-(2-acetoxy-4-isopropylphenyl)-2,3,4,5,5a,6,8,9-octahydro-7H-1,2,5,7-tetraazabenzo[cd]azulene-7-carboxylate (320 mg) as a crude yellow oil. The crude product was used in the next step directly without further purification. LCMS:(ESI, T/z):489 $[M+1]^+$ Step 2: Synthesis of Benzyl 2-(2-acetoxy-4-isopropylphenyl)-5-(5-hydroxy-6-(trifluoromethyl)nicotinoyl)-2,3,4,5,5a,6,8,9-octahydro-7H-1,2,5,7-tetraazabenzo[cd]azulene-7-carboxylate To a solution of benzyl 2-(2-acetoxy-4-isopropylphenyl)-2,3,4,5,5a,6,8,9-octahydro-7H-1,2,5,7-tetraazabenzo[cd]azulene-7-carboxylate (120 mg, 1 equiv., 246 μmol) in DMF (2.4 mL) were added 5-hydroxy-6-(trifluoromethyl)nicotinic acid (50.9 mg, 1 equiv., 246 μmol), HATU (121 mg, 1.3 equiv., 319 μmol) and DIEA (254 mg, 340 μL, 8 equiv., 1.96 mmol). The mixture was stirred at room temperature for 2 h. The reaction was monitored by LCMS. The mixture was purified by Prep-HPLC (Column: Kinetex 5 m EVO C18, 30 mm*150 mm; Mobile Phase A: water (10 mmol/L $NH_4HCO_3$), Mobile Phase B: MeCN; Flow rate: 60 mL/min; Gradient: 10% B to 41% B in 10 min; Wave Length: UV 254 nm/220 nm; retention time 1 retention time 1: 9.85) to afford benzyl 2-(2-acetoxy-4-isopropylphenyl)-5-(5-hydroxy-6-(trifluoromethyl)nicotinoyl)-2,3,4,5,5a,6,8,9-octahydro-7H-1,2,5,7-tetraazabenzo[cd]azulene-7-carboxylate (70 mg) as a white solid. LCMS:(ESI, m/z):678 $[M+1]^+$ Step 3: Synthesis of Benzyl 2-(2-hydroxy-4-isopropylphenyl)-5-(5-hydroxy-6-(trifluoromethyl)nicotinoyl)-2,3,4,5,5a,6,8,9-octahydro-7H-1,2,5,7-tetraazabenzo[cd]azulene-7-carboxylate To a solution of benzyl 2-(2-acetoxy-4-isopropylphenyl)-5-(5-hydroxy-6-(trifluoromethyl)nicotinoyl)-2,3,4,5,5a,6,8, 9-octahydro-7H-1,2,5,7-tetraazabenzo[cd]azulene-7-carboxylate (75 mg, 1 equiv., 0.11 mmol) in MeOH (1.5 mL) and water (0.15 mL) was added sodium hydroxide (18 mg, 4 equiv., 0.44 mmol). The mixture was stirred at room temperature for 1 h. The reaction was monitored by LCMS. The mixture was neutralized to pH=7 with formic acid, then diluted with EtOAc (5 mL) and water (5 mL), and the aqueous layer was extracted with EtOAc (2×5 mL). The organic layers were combined and washed with saturated brine (2×5 mL), dried over anhydrous sodium sulfate and concentrated to afford benzyl 2-(2-hydroxy-4-isopropylphenyl)-5-(5-hydroxy-6-(trifluoromethyl)nicotinoyl)-2,3,4,5,5a,6,8,9-octahydro-7H-1,2,5,7-tetraazabenzo[cd]azulene-7-carboxylate (62 mg) as a yellow solid. The crude product was used in the next step directly without further purification. LCMS:(ESI, m/z):636 $[M+1]^+$ Step 4: Synthesis of (2-(2-hydroxy-4-isopropylphenyl)-2,3,4,5a,6,7,819-octahydro-5H-1,2,5,7-tetraazabenzo[cd]azulen-5-yl)(5-hydroxy-6-(trifluoromethyl)pyridin-3-yl methanone To a solution of benzyl 2-(2-hydroxy-4-isopropylphenyl)-5-(5-hydroxy-6-(trifluoromethyl)nicotinoyl)-2,3,4,5,5a,6,8,9-octahydro-7H-1,2,5,7-tetraazabenzo[cd]azulene-7-carboxylate (220 mg, 1 equiv., 346 μmol) in MeOH (4.4 mL) was added palladium/C (92.1 mg, 20% wt, 0.5 equiv., 173 mol) in a pressure tank. The mixture was purged with hydrogen for three times and then was pressurized to 3 MPa with hydrogen at room temperature for 3 h. The reaction mixture was cooled to rt and filtered to remove insoluble solids. The filter cake was washed with MeOH (5 mL) two times. The filtrate was concentrated under reduced pressure to afforded (2-(2-hydroxy-4-isopropylphenyl)-2,3,4,5a,6,7,8,9-octahydro-5H-1,2,5,7-tetraazabenzo[cd]azulen-5-yl)(5-hydroxy-6-(trifluoromethyl)pyridin-3-yl)methanone (130 mg) as a yellow solid. LCMS:(ESI, m/z):502 $[M+1]^+$ Step 5: Synthesis of (S or R)-1-(2-(2-hydroxy-4-isopropylphenyl)-5-(S-hydroxy-6-(trifluoromethyl) nicotinoyl)-2,3,4,5,5a,6,8,9-octahydro-7H-1,2,5,7-tetraazabenzo[cd]azulen-7-yl)prop-2-en-1-one To a solution of (2-(2-hydroxy-4-isopropylphenyl)-2,3,4,5a,6,7,8,9-octahydro-5H-1,2,5,7-tetraazabenzo[cd]azulen-5-yl)(5-hydroxy-6-(trifluoromethyl)pyridin-3-yl)methanone (60 mg, 1 equiv., 0.12 mmol) in DMF (1.2 mL) were added acrylic acid (13 mg, 12 μL, 1.5 equiv., 0.18 mmol), DIEA (0.12 g, 0.17 mL, 8 equiv., 0.96 mmol) and T3P (0.11 g, 0.11 mL, 3 equiv., 0.36 mmol). The mixture was stirred at room temperature for 2 h, after which the mixture was purified by Prep-HPLC (Column: XBridge BEH Shield RP18 5 μm, 30 mm*10 mm; Mobile Phase A: water (10 mmol/L $NH_4HCO_3$), Mobile Phase B: MeCN; Flow rate: 60 L/min; Gradient: 22% B to 38% B in 10 min; Wave Length: UV 254 nm/220 nm; retention time 1 retention time 1: 8.12) to afford 1-(2-(2-hydroxy-4-isopropylphenyl)-5-(5-hydroxy-6-(trifluoromethyl)nicotinoyl)-2,3,4,5,5a,6,8,9-octahydro-7H-1,2,5,7-tetraazabenzo[cd]azulen-7-yl)prop-2-en-1-one (14.0 mg) as a white solid. LCMS:(ESI, m/z):556 $[M+1]^+$ The racemic 1-(2-(2-hydroxy-4-isopropylphenyl)-5-(5-hydroxy-6-(trifluoromethyl)nicotinoyl)-2,3,4,5,5a,6,8,9-octahydro-7H-1,2,5,7-tetraazabenzo[cd]azulen-7-yl)prop-2-en-1-one (14.0 mg, 25.2 μmol, 21.0%, 98.1% purity) was purified by Prep-Chiral-HPLC (Column: CHIRAL ART Cellulose-SB 2*25 cm, 5 μm; Mobile Phase A: MTBE(0.1% FA), Mobile Phase B: EtOH: DCM=1:1; Flow rate: 20 mL/min; Gradient: isocratic 15; Wave Length: UV 254/220 nm; Sample Solvent: EtOH: DCM; Injection Volume: 0.7 mL; Number Of Runs: 3) to afford (S or R)-1-(2-(2-hydroxy-4-isopropylphenyl)-5-(5-hydroxy-6-(trifluoromethyl)nicotinoyl)-2,3,4,5,5a,6,8,9-octahydro-7H-1,2,5,7-tetraazabenzo[cd]azulen-7-yl)prop-2-en-1-one as the first-eluting peak (retention time 6.1 min., 2.5 mg, 4.4 μmol, 3.7%, 98.1% purity) as a white solid. LCMS:(ESI, m/z): 556 $[M+1]^+$. $^1H$ NMR: (400 MHz, DMSO-$d_6$, ppm) δ 9.99 (s, 1H), 8.22 (s, 1H), 7.57-0.38 (m, 2H), 7.20 (d, J=8.1 Hz, 1H), 6.88 (s, 1H), 6.79 (d, J=8.2 Hz, 1H), 6.29 (d, J=16.5 Hz, H), 5.88-5.70 (m, 1H), 5.16 (d, J=10.4 Hz, 1H), 4.82-4.57 (m, 1H), 4.41-3.96 (m, 2H), 3.82-3.69 (m, 1H), 3.53-3.08 (m, 3H) (obscured by water), 2.95-2.75 (m, 4H), 2.47-2.30 (m, 1H), 1.20 (d, J=6.9 Hz, 6H).

Example C-4: Preparation of 1-(5-(4-bromo-3H-imidazo[4,5-c]pyridine-7-carbonyl)-2-(2-hydroxy-4-isopropylphenyl)-2,3,4,5,5a,6,8,9-octahydro-7H-1,2,5,7-tetraazabenzo[cd]azulen-7-yl)prop-2-en-1-one

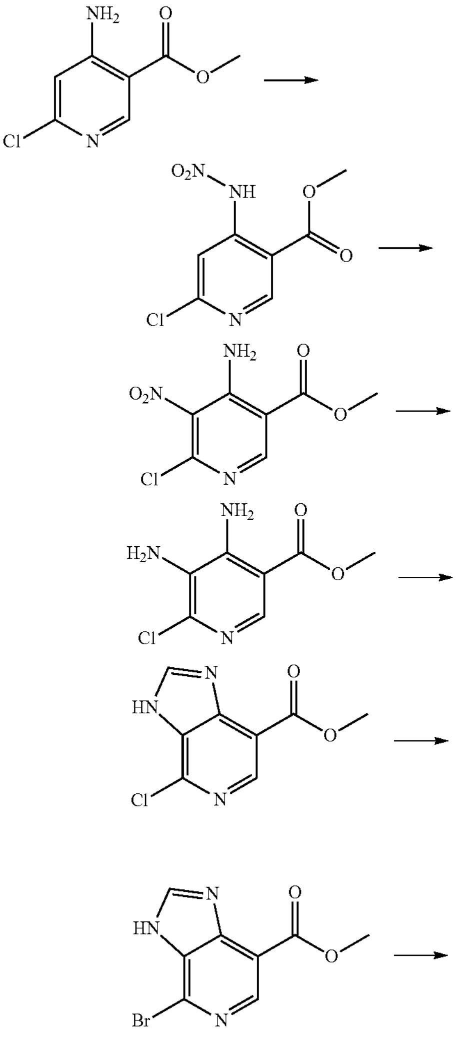

-continued

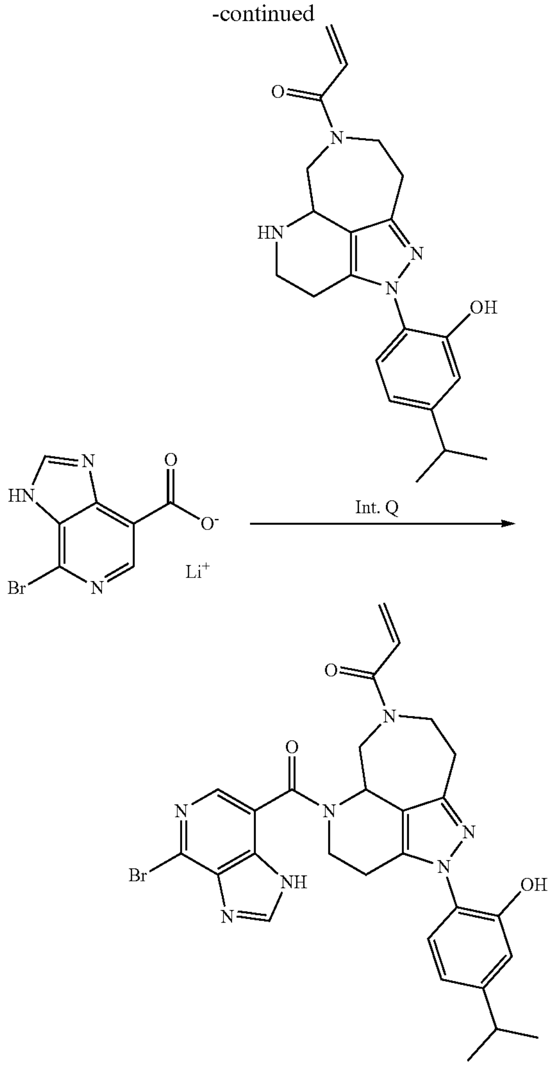

Step 1: Synthesis of Methyl 6-chloro-4-(nitroamino)pyridine-3-carboxylate

To a stirred solution of methyl 4-amino-6-chloropyridine-3-carboxylate (4.5 g, 24.116 mmol, 1 equiv) was added $HNO_3$ (7.60 g, 120.580 mmol, 5 equiv) and $H_2SO_4$ (40 mL, 120.580 mmol, 5 equiv). The reaction mixture was stirred at −30° C. for a period of 1 h. The reaction was quenched with water/ice at rt. The resulting mixture was extracted with EtOAc (1×200 mL). The combined organic layers were washed with water (2×100 mL), dried over anhydrous $Na_2SO_4$. After filtration, the filtrate was concentrated under reduced pressure to afford methyl 6-chloro-4-(nitroamino) pyridine-3-carboxylate (4 g) as a yellow solid. LCMS:(ESI, m/z):232 $[M+1]^+$ Step 2: Synthesis of Methyl 4-amino-6-chloro-5-nitropyridine-3-carboxylate A solution of methyl 6-chloro-4-(nitroamino)pyridine-3-carboxylate (4 g, 17 mmol, 1 equiv) in $H_2SO_4$ (40 mL, 86 mmol, 10 equiv) was stirred for 2 h at 60'C. The resulting mixture was extracted with EtOAc (2×80 mL). The combined organic layers were washed with water (1×40 mL), dried over anhydrous $Na_2SO_4$. After filtration, the filtrate was concentrated under reduced pressure to afford methyl 4-amino-6-chloro-5-nitropyridine-3-carboxylate (3 g) as a yellow solid. LCMS:(ESI, m/z):232 $[M+1]^+$ Step 3: Synthesis of Methyl 4-chloro-3H-imidazo [4,5-c]pyridine-7-carboxylate A solution of methyl 4,5-diamino-6-chloropyridine-3-carboxylate (2.5 g, 12.4 mmol, 1 equiv) and triethyl orthoformate (25 mL, 10 equiv) was stirred for 6 h at 80° C. under nitrogen atmosphere. The resulting mixture was extracted with EtOAc (2×50 mL). The combined organic layers were washed with water (1×25 mL), dried over anhydrous $Na_2SO_4$. After filtration, the filtrate was concentrated under reduced pressure. The residue was purified by silica gel column chromatography, eluting with DCM/MeOH (10:1) to afford methyl 1-chloro-3H-imidazo[4,5-c]pyridine-7-carboxylate (2 g) as a white solid. LCMS:(ESI, m/z):202 $[+1]^+$ Step 4: Synthesis of Methyl 4-chloro-3H-imidazo [4,5-c]pyridine-7-carboxylate A solution of methyl 4,5-diamino-6-chloropyridine-3-carboxyl e (2.5 g, 12.400 mmol, 1 equiv) and triethyl orthoformate (25 mL, 10 equiv) was stirred for 6 h at 80° C. under nitrogen atmosphere. The resulting mixture was extracted with EtOAc (2×50 mL). The combined organic layers were washed with water (1×25 mL), dried over anhydrous $Na_2SO_4$. After filtration, the filtrate was concentrated under reduced pressure. The residue was purified by silica gel column chromatography, eluting with DCM/MeOH (10:1) to afford methyl-chloro-3H-imidazo[4,5-c]pyridine-7-carboxylate (2 g) as a white solid. LCMS:(ESI, m/z):212 $[M+1]^+$ Step 5: Synthesis of Methyl 4-bromo-3H-imidazo [4,5-c]pyridine-7-carboxylate Into a 40 mL vial were added methyl 4-chloro-3H-imidazo[4,5-c]pyridine-7-carboxylate (1.4 g, 6.616 mmol, 1 equiv) and $POBr_3$ (9.48 g, 33.080 mmol, 5 equiv.) at 80° C. The reaction was quenched with water/Ice at rt. The resulting mixture was extracted with EtOAc (2×50 mL). The combined organic layers were washed with water (1×50 mL), dried over anhydrous $Na_2SO_4$. After filtration, the filtrate was concentrated under reduced pressure to afford methyl 4-bromo-3H-imidazo[4,5-c]pyridine-7-carboxylate (1.2 g) as a white solid. LCMS:(ESI, m/z):256 $[M+1]^+$ Step 6: Synthesis of 4-bromo-3H-imidazo[4,5-c] pyridine-7-carboxylic Acid A solution of methyl 4-bromo-3H-imidazo[4,5-c]pyridine-7-carboxylate (1.2 g, 4.686 mmol, 1 equiv) and LiOH (0.22 g, 9.372 mmol, 2 equiv) in THF (10 mL) water (2 mL) was stirred for 2 h at rt. The resulting mixture was concentrated under reduced pressure to afford 4-bromo-3H-imidazo [4,5-c]pyridine-7-carboxylic acid, lithium salt (1.1 g) as a white solid. LCMS:(ESI, m/z):242 $[M+1]^+$ Step 7: Synthesis of 1-(5-(4-bromo-3H-imidazo[4, 5-c]pyridine-7-carbonyl)-2-(2-hydroxy-4-isopropylphenyl)-2,3,4,5,5a,6,8,9-octahydro-7H-1,2,5, 7-tetraazabenzo[cd]azulen-7-yl)prop-2-en-1-one A solution of 1-(2-(2-hydroxy-4-isopropylphenyl)-2,3,4, 5,5a,6,8,9-octahydro-7H-1,2,5,7-tetraazabenzo[cd]azulen- 7-yl)prop-2-en-1-one (Int. Q) (200 mg, 1 equiv., 546 μmol), lithium 4-bromo-3H-imidazo[4,5-c]pyridine-7-carboxylate (135 mg, 1 equiv., 546 μmol), HBTU (414 mg, 2 equiv., 1.09 mmol), DIEA (353 mg, 475 μL, 5 equiv., 2.73 mmol) in DMF (5 mL) was stirred for 2 h at room temperature under nitrogen atmosphere. The crude product was purified by Prep-HPLC (Column: XBridge BEH Shield RP18 5 μm, 30 mm*150 mm; Mobile Phase A: water (10 mmol/L $NH_4HCO_3$), Mobile Phase B: MeCN; Flow rate: 60 mL/min; Gradient: 15% B to 50% B in 10 min; Wave Length: UV 254 nm/220 nm; retention time 1 retention time 1: 9.02) to afford 1-(5-(4-bromo-3H-imidazo[4,5-c]pyridine-7-carbonyl)-2-(2-hydroxy-4-isopropylphenyl)-2,3,4,5,5a,6,8,9-octahydro-7H-1,2,5,7-tetraazabenzo[cd]azulen-7-yl)prop-2-en-1-one (1.9 mg, 3.1 μmol, 0.57%, 96.5% purity) as white solid. LCMS:(ESI, m/z): 590 $[M+1]^+$. $^1H$ NMR: (400 MHz, Chloroform-d, ppm) δ 12.75 (brs, 1H), 10.32-9.63 (m, 1H), 8.47-8.26 (m, 1H), 8.26-8.08 (m, 1H), 7.09-6.93 (m, 2H), 6.93-6.79 (m, 1H), 6.75 (d, J=8.1 Hz, 1H), 6.56-6.33 (m, 1H), 5.97-5.66 (m, 1H), 5.65-5.34 (m, 1H), 5.15-4.82 (m, 1H), 4.48-4.19 (m, 2H), 3.68-2.53 (m, 7H), 1.35-1.06 (m, 6H), 0.95-0.74 (m, 1H).

Example C-5: Preparation of (S or R) 7-bromo-1H-benzo[d]imidazole-4-carbonyl)-2-(4-cyclobutyl-2-hydroxyphenyl)-2,3,4,5,5a,6,8,9-octahydro-7H-1,2,5,7-tetraazabenzo[cd]azulen-7-yl)prop-2-en-1-one

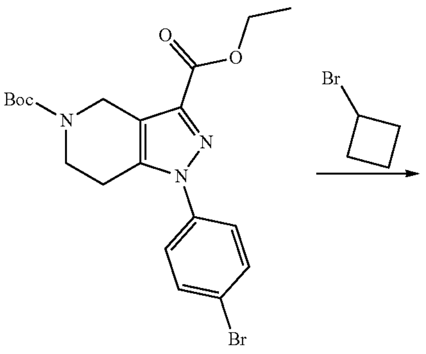

Int. D

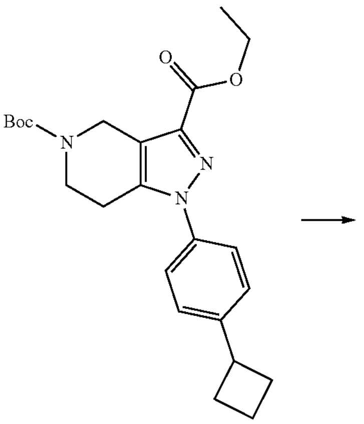

-continued

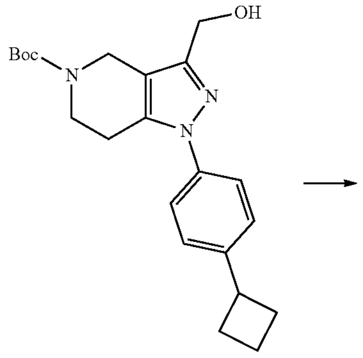

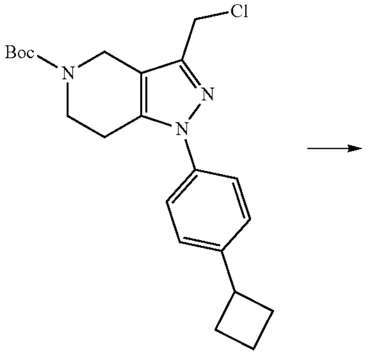

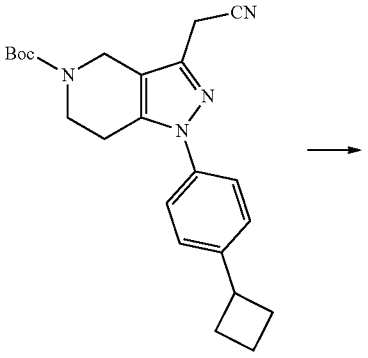

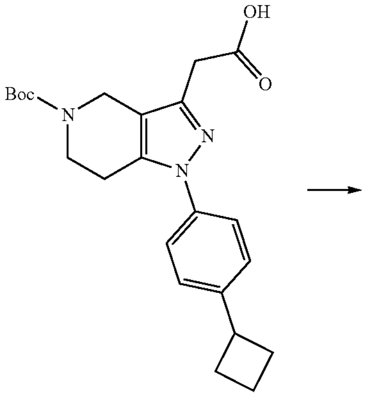

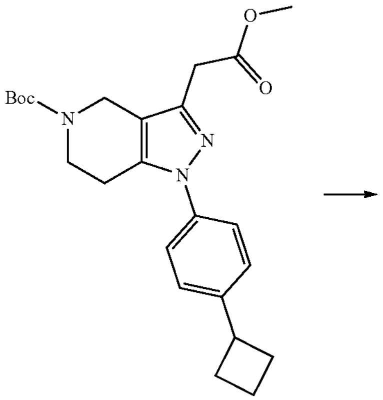
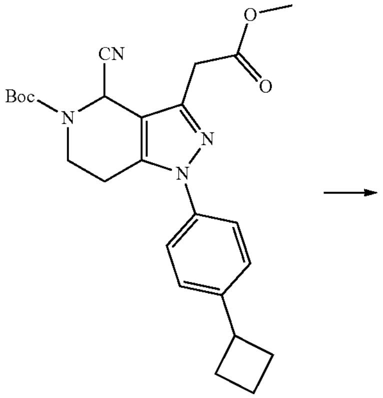
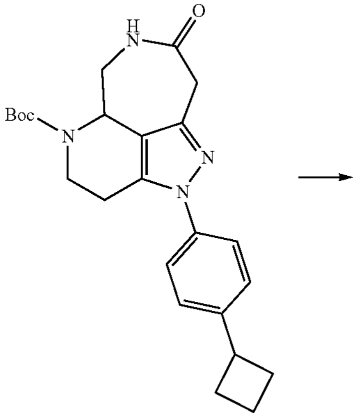
Int. R
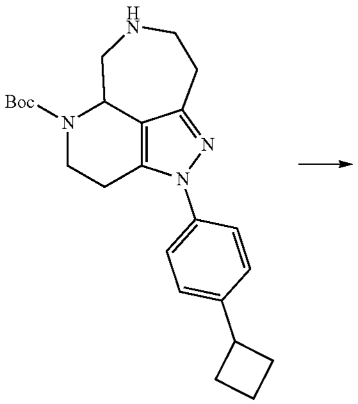
Int. S
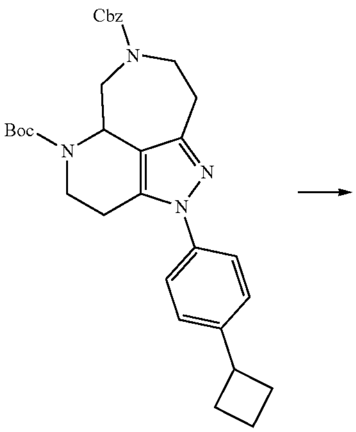
Int. S″
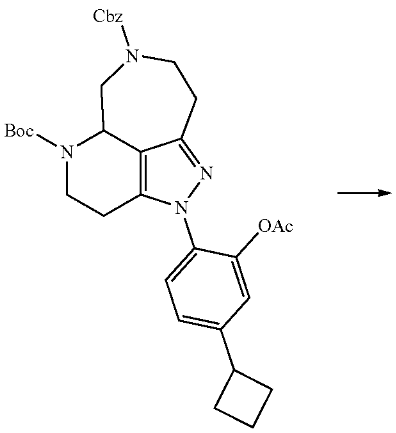
Int. S′
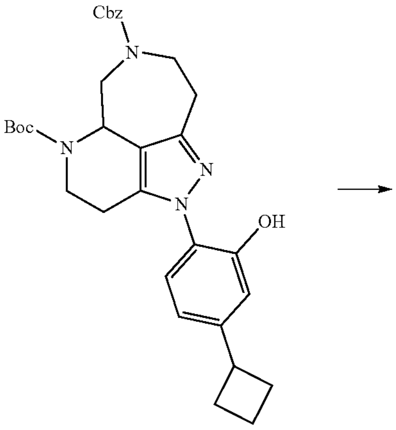

-continued

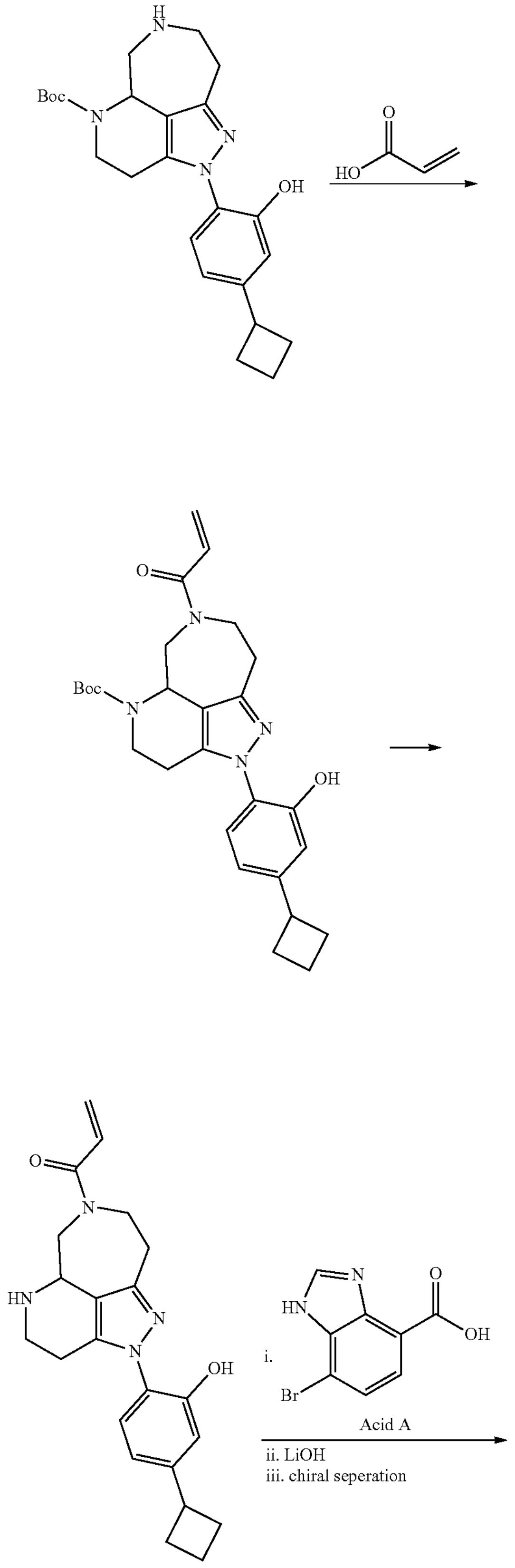

Int. T

-continued

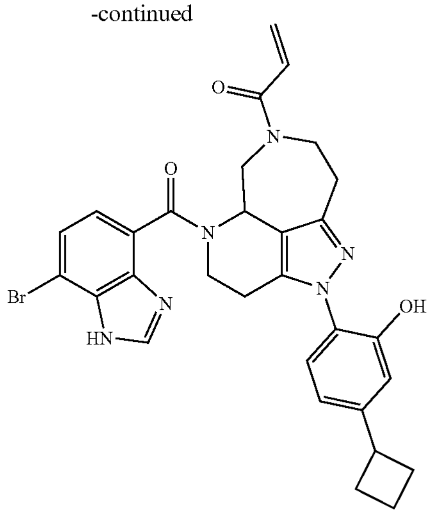

single enantiomer

Step 1: Synthesis of 5-(tert-butyl) 3-ethyl 1-(4-cyclobutylphenyl)-1,4,6,7-tetrahydro-5H-pyrazolo[4,3-c]pyridine-3,5-dicarboxylate To a stirred solution of 5-(tert-butyl) 3-ethyl 1-(4-bromophenyl)-1,4,6,7-tetrahydro-5H-pyrazolo[4,3-c]pyridine-3,5-dicarboxylate (Int. D) (53.5 g, 1 equiv., 119 mmol) in DMA (550 mL) were added picolinimidamide. HCl (5.62 g, 0.3 equiv., 35.6 mmol), bromocyclobutane (80.2 g, 5 equiv., 594 mmol), Nickel(II) dichloride (4.62 g, 1.3 mL, 0.3 equiv., 35.6 mmol). TBAI (43.9 g, 1 equiv., 119 mmol) and manganese (32.6 g, 4.52 mL, 5 equiv., 594 mmol). The resulting mixture was stirred for 16 h at 60° C. under nitrogen atmosphere. The reaction progress was monitored by LCMS. After completion of reaction, the reaction was quenched by the addition of water (500 mL) at rt. The resulting mixture was filtered and the filter cake was-washed with EtOAc (3×500 mL). The filtrate was concentrated under reduced pressure. The resulting mixture was extracted with EtOAc (2×500 mL). The combined organic layers were washed with 1:1 water/brine (2×1000 mL) and dried over anhydrous $Na_2SO_4$. After filtration, the filtrate was concentrated under reduced pressure. The residue was purified by silica gel column chromatography, eluting with EtOAc/PE (1:3) to afford 5-(tert-butyl) 3-ethyl 1-(4-cyclobutylphenyl)-1,4,6,7-tetrahydro-5H-pyrazolo[4,3-c]pyridine-3,5-dicarboxylate (23.1 g) as a yellow solid. LCMS:(ESI, m/z): 426 $[M+1]^+$ Step 2: Synthesis of Tert-Butyl 1-(4-cyclobutylphenyl)-3-(hydroxymethyl)-1,4,6,7-tetrahydro-5H-pyrazolo[4,3-c]pyridine-5-carboxylate To a stirred solution of 5-(tert-butyl) 3-ethyl 1-(4-cyclobutylphenyl)-1,4,6,7-tetrahydro-5H-pyrazolo[4,3-c]pyridine-3,5-dicarboxylate (33.1 g, 1 equiv., 77.8 mmol) in EtOH (330 mL) was added $NaBH_4$ (29.4 g, 10 equiv., 778 mmol) at room temperature and stirred for 48 h. The reaction progress was monitored by LCMS. After completion of reaction, the reaction was quenched by the addition of water (300 mL) at 0° C. The resulting mixture was extracted with EtOAc (2×300 mL). The combined organic layers were washed with water (2×500 mL) and brine (1×500 mL), dried over anhydrous $Na_2SO_4$. After filtration, the filtrate was concentrated under reduced pressure. The residue was purified by silica gel column chromatography, eluting with EtOAc/PE (1:1) to afford tert-butyl 1-(4-cyclobutylphenyl)-3-(hydroxymethyl)-1,4,6,7-tetrahydro-5H-pyrazolo[4,3-c]pyridine-5-carboxylate (27.8 g) as a white solid. LCMS:(ESI, m/z): 384 $[M+1]^+$ Step 3: Synthesis of Tert-Butyl 3-(chloromethyl)-1-(4-cyclobutylphenyl)-1,4,6,7-tetrahydro-5H-pyrazolo[4,3-c]pyridine-5-carboxylate To a solution of tert-butyl 1-(4-cyclobutylphenyl)-3-(hydroxymethyl)-1,4,6,7-tetrahydro-5H-pyrazolo[4,3-c]pyridine-5-carboxylate (27.80 g, 1 equiv., 72.49 mmol) in DCM (280 mL) was added $SOCl_2$ (11.2 g, 6.88 mL, 1.3 equiv., 94.2 mmol) dropwise at −10° C. under nitrogen atmosphere. The reaction mixture was stirred at −10° C. for 2 h. The reaction was quenched with saturated aqueous $NaHCO_3$ (280 mL). The resulting mixture was extracted with DCM (2×200 mL). The combined organic layers were washed with water (2×500 mL) and brine (1×500 mL), dried over anhydrous $Na_2SO_4$. After filtration, the filtrate was concentrated under reduced pressure. The residue was purified by silica gel column chromatography, eluting with EtOAc/PE (1:2) to afford tert-butyl 3-(chloromethyl)-1-(4-cyclobutylphenyl)-1,4,6,7-tetrahydro-5H-pyrazolo[4,3-c]pyridine-5-carboxylate (27.7 g) as a white solid. LCMS:(ESI, m/z): 402 $[M+1]^+$ Step 4: Synthesis of Tert-Butyl 3-(cyanomethyl)-1-(4-cyclobutylphenyl)-1,4,6,7-tetrahydro-5H-pyrazolo[4,3-c]pyridine-S-carboxylate To a stirred solution of tert-butyl 3-(chloromethyl)-1-(4-cyclobutylphenyl)-1,4,6,7-tetrahydro-5H-pyrazolo[4,3-c]pyridine-5-carboxylate (35.3 g, 1 equiv., 87.8 mmol) in MeCN (280 mL) was added TMSCN (26.1 g, 3 equiv., 263 mmol) and TBAF (45.9 g, 2 equiv., 176 mmol) at rt and reaction was stirred for 12 h. The reaction was then quenched by the addition of water (200 mL) at rt. The resulting mixture was extracted with EtOAc (2×200 mL). The combined organic layers were washed with brine (2×500 mL), dried over anhydrous $Na_2SO_4$, and filtered. After filtration, the filtrate was concentrated under reduced pressure. The residue was purified by silica gel column chromatography, eluting with EtOAc/PE (1:3) to afford tert-butyl 3-(cyanomethyl)-1-(4-cyclobutylphenyl)-1,4,6,7-tetrahydro-5H-pyrazolo[4,3-c]pyridine-5-carboxylate (32.5 g) as a white solid. LCMS:(ESI, m/z): 393 $[M+1]^+$ Step 5: Synthesis of 2-(5-(tert-butoxycarbonyl)-1-(4-cyclobutylphenyl)-4,5,6,7-tetrahydro-1H-pyrazolo[4,3-c]pyridin-3-yl)acetic Acid A solution of tert-butyl 3-(cyanomethyl)-1-(4-cyclobutylphenyl)-1,4,6,7-tetrahydro-5H-pyrazolo[4,3-c]pyridine-5-carboxylate (33 g, 1 equiv., 84 mmol) in EtOH (330 mL) was added NaOH (52.8 g, 16 equiv., 1.32 mol) in water (330 mL) and heated to 80° C. for 1 h. The reaction was then quenched by the addition of water (100 mL) at rt. The resulting mixture was extracted with EtOAc (2×300 mL). The combined organic layers were washed with water (2×500 mL) and brine (1×500 mL), dried over anhydrous $Na_2SO_4$. After filtration, the filtrate was concentrated under reduced pressure. The residue was purified by silica gel column chromatography, eluting with DCM/MeOH (10:1) to afford 2-(5-(tert-butoxycarbonyl)-1-(4-cyclobutylphenyl)-4,5,6,7-tetrahydro-1H-pyrazolo[4,3-c]pyridin-3-yl) acetic acid (33.8 g) as a yellow solid. LCMS:(ESI, m/z): 412 $[M+1]^+$ Step 6: Synthesis of Tert-Butyl 1-(4-cyclobutylphenyl)-3-(2-methoxy-2-oxoethyl)-1,4,6,7-tetrahydro-5H-pyrazolo[4,3-c]pyridine-5-carboxylate To a stirred solution of 2-(5-(tert-butoxycarbonyl)-1-(4-cyclobutylphenyl)-4,5,6,7-tetrahydro-1H-pyrazolo[4,3-c]pyridin-3-yl)acetic acid (28.2 g, 1 equiv., 68.5 mmol) and $Cs_2CO_3$ (44.7 g, 2 equiv., 137 mmol) in DMF (300 mL) was added $CH_3I$ (14.6 g, 1.5 equiv., 103 mmol) at rt and stirred for 2 h. After completion of reaction, the reaction was quenched by the addition of water (100 mL) at rt. The resulting mixture was extracted with EtOAc (2×300 mL). The combined organic layers were washed with 1:1 water/brine (3×500 mL) and brine (1×500 mL) and dried over anhydrous $Na_2SO_4$. The reaction was then filtered, and the filtrate was concentrated under reduced pressure. The residue was purified by silica gel column chromatography, eluting with EtOAc/PE (1:2) to afford tert-butyl 1-(4-cyclobutylphenyl)-3-(2-methoxy-2-oxoethyl)-1,4,6,7-tetrahydro-5H-pyrazolo[4,3-c]pyridine-5-carboxylate (26.1 g) as a yellow solid. LCMS:(ESI, m/z): 426 $[M+1]^+$ Step 7: Synthesis of Tert-Butyl 4-cyano-1-(4-cyclobutylphenyl)-3-(2-methoxy-2-oxoethyl)-1,4,6,7-tetrahydro-5H-pyrazolo[4,3-c]pyridine-5-carboxylate To a stirred solution of tert-butyl 1-(4-cyclobutylphenyl)-3 (2-methoxy-2-oxoethyl)-1,4,6,7-tetrahydro-5H-pyrazolo[4,3-c]pyridine-5-carboxylate (28.7 g, equiv., 67.4 mmol) in MeCN (300 mL) was added AcOH (12.2 g, 11.6 mL, 3 equiv., 202 mmol). TEMPO-BF4 (49.2 g, 3 equiv., 202 mmol). TMSCN (26.8 g, 33.8 mL, 4 equiv., 270 mmol) at r and stirred for 2 h. After completion of reaction, the reaction was quenched by the addition of brine (200 mL) at rt. The resulting mixture was extracted with EtOAc (2×200 mL). The combined organic layers were washed with brine (2×500 mL) and dried over anhydrous $Na_2SO_4$. After filtration, the filtrate was concentrated under reduced pressure. The residue was purified by silica gel column chromatography, eluting with EtOAc/PE (1:4) to afford tert-butyl 4-cyano-1-(4-cyclobutylphenyl)-3-(2-methoxy-2-oxoethyl)-1,4,6,7-tetrahydro-5H-pyrazolo[4,3-c]pyridine-5-carboxylate (24.3 g) as a yellow solid. LCMS:(ESI, m/z): 451 $[M+1]^+$ Step 8: Synthesis of Tert-Butyl 2-(4-cyclobutylphenyl)-8-oxo-2,3,4,5a,6,7,8,9-octahydro-5H-1,2,5,7-tetraazabenzo[cd]azulene-5-carboxylate (Int. R)

To a solution of tert-butyl 4-cyano-1-(4-cyclobutylphenyl)-3-(2-methoxy-2-oxoethyl)-1,4,6,7-tetrahydro-5H-pyrazolo[4,3-c]pyridine-5-carboxylate (22.0 g, 1 equiv., 48.8 mmol) in MeOH (1100 mL) was added Raney nickel (22.0 g, 2.99 mL, 50% Wt, 3.84 equiv., 187 mmol) in a pressure tank. The mixture was hydrogenated at 50° C. under 4000 kPa of hydrogen pressure for 24 h, filtered through a Celite pad and concentrated under reduced pressure. The residue was purified by silica gel column chromatography, eluting with DCM/MeOH (10/1) to afford tert-butyl 2-(4-cyclobutylphenyl)-8-oxo-2,3,4,5a,6,7,8,9-octahydro-5H-1,2,5, 7-tetraazabenzo[cd]azulene-5-carboxylate (Int. R) (18.0 g) as a white solid. LCMS:(ESI, m/z): 423 [M+1]$^+$ Step 9: Synthesis of Tert-Butyl 2-(4-cyclobutylphenyl)-2,3,4,5a,6,7,8,9-octahydro-5H-1, 2,5,7-tetraazabenzo [cd]azulene-5-carboxylate (Int. S)

To a stirred solution of tert-butyl 2-(4-cyclobutylphenyl)-8-oxo-2,3,4,5a,6,7,8,9-octahydro-5H-1,2,5,7-tetraazabenzo [cd]azulene-5-carboxylate (10 g, 1 equiv., 24 mmol) in THF (100 mL) was added $BH_3$·THF (8.1 g, 4 equiv., 95 mmol) at 60° C. and stirred for 1 h. The reaction progress was monitored by LCMS. After completion of reaction, the reaction was quenched by the addition of water (50 mL) at rt. The resulting mixture was extracted with EtOAc (2×100 mL). The combined organic layers were washed with brine (2×200 mL) and dried over anhydrous $Na_2SO_4$. After filtration, the filtrate was concentrated under reduced pressure to afford tert-butyl 2-(4-cyclobutylphenyl)-2,3,4,5a,6,7,8,9-octahydro-5H-1,2,5,7-tetraazabenzo [cd]azulene-5-carboxylate (Int. S) (10.5 g) as a white solid. The crude product was used in the next step directly without further purification. LCMS:(ESI, m/z): 409 [M+1]$^+$ Step 10: Synthesis of 7-Benzyl 5-(tert-butyl) 2-(4-cyclobutylphenyl)-3,4,5a,6,8,9-hexahydro-2H-1,2,5,7-tetraazabenzo[cd]azulene-5,7-dicarboxylate (Int. S")

To a stirred solution of tert-butyl 2-(4-cyclobutylphenyl)-2,3,4,5a,6,7,8,9-octahydro-5H-1,2,5,7-tetraazabenzo[cd] azulene-5-carboxylate (9.50 g, 1 equiv., 23.3 mol) in DCM (200 mL) was added TEA (11.8 g, 16.2 mL, 5 equiv., 116 mmol) and Cbz-OSu (17.4 g, 3 equiv., 69.8 mmol) at 40° C. and the reaction was stirred for 6 h. The reaction was then quenched by the addition of water (200 mL) at rt. The resulting mixture was extracted with DCM (2×200 mL). The combined organic layers were washed with water (2×300 mL) and brine (1×300 mL), and dried over anhydrous $Na_2SO_4$. After filtration, the filtrate was concentrated under reduced pressure. The residue was purified by silica gel column chromatography, eluting with EtOAc/PE (1:1) to afford 7-benzyl 5-(tert-butyl) 2-(4-cyclobutylphenyl)-3,4,5a,6,8,9-hexahydro-2H-1,2,5,7-tetraazabenzo[cd]azulene-5,7-dicarboxylate (9.53 g) as a white solid. LCMS:(ESI, m/z): 543 [M+1]$^+$ Step 11: Synthesis of 7-benzyl 5-(tert-butyl) 2-(2-acetoxy-4-cyclobutylphenyl)-3,4,5a,6,8,9-hexahydro-2H-1,2,5,7-tetraazabenzo[cd]azulene-5,7-dicarboxylate (Int. S')

To a stirred solution of 7-benzyl 5-(tert-butyl) 2-(4-cyclobutylphenyl)-3,4,5a,6,8,9-hexahydro-2H-1,2,5,7-tetraazabenzo[cd]azulene-5,7-dicarboxylate (9.53 g, 1 equiv., 17.6 mmol) in 1,4-dioxane (100 mL) and AcOH (20 mL) was added $Pd(OAc)_2$ (789 nig, 0.2 equiv., 3.51 mmol) and PIDA (11.3 g, 2 equiv., 35.1 mmol) at 90° C. and stirred for 3 h. The reaction progress was monitored by LCMS. After completion of reaction, the reaction mixture was quenched with saturated $NaHCO_3$ solution (200 mL) and extracted with EtOAc (2×200 mL). The combined organic layers were washed with brine (3×400 mL), dried over $Na_2SO_4$, filtered, and evaporated under reduced pressure to get the crude compound. The residue was purified by silica gel column chromatography, eluting with EtOAc/PE (1:1) to afford 7-benzyl 5-(tert-butyl) 2-(2-acetoxy-4-cyclobutylphenyl)-3,4,5a,6,8,9-hexahydro-2H-1,2,5,7-tetraazabenzo[cd]azulene-5,7-dicarboxylate (4.28 g) as a yellow solid. LCMS:(ESI, m/z): 601 [M+1]$^+$ Step 12: Synthesis of 7-Benzyl 5-(tert-butyl) 2-(4-cyclobutyl-2-hydroxyphenyl)-3,4,5a,6,8,9-hexahydro-2H-1,2,5,7-tetraazabenzo[cd]azulene-5,7-dicarboxylate To a stirred solution of 7-benzyl 5-(tert-butyl) 2-(2-acetoxy-4-cyclobutylphenyl)-3,4,5a,6,8,9-hexahydro-2H-1,2,5,7-tetraazabenzo[cd]azulene-5,7-dicarboxylate (4.28 g, 1 equiv., 7.12 mmol) in THF (40 mL) and water (10 mL) was added LiOH (341 mg, 2 equiv., 14.2 mmol) at room temperature and stirred for 1 h. The reaction progress was monitored by LCMS. After completion of reaction, the reaction was quenched by the addition of water (50 mL) at rt. The resulting mixture was extracted with EtOAc (2×50 mL). The combined organic layers were washed with water (2×100 mL) and brine (1×100 mL), dried over anhydrous $Na_2SO_4$. After filtration, the filtrate was concentrated under reduced pressure. The residue was purified by silica gel column chromatography, eluting with EtOAc/PE (1:2) to afford 7-benzyl 5-(tert-butyl) 2-(4-cyclobutyl-2-hydroxyphenyl)-3,4,5a,6,8,9-hexahydro-2H-1,2,5,7-tetraazabenzo [cd]azulene-5,7-dicarboxylate (3.05 g) as a white solid. LCMS:(ESI, m/z): 559 [M+1]$^+$ Step 13: Synthesis of Tert-Butyl 2-(4-cyclobutyl-2-hydroxyphenyl)-2,3,4, a,6,7,8,9-octahydro-5H-1,2,5,7-tetraazabenzo[cd]azulene-5-carboxylate To a solution of 7-benzyl 5-(tert-butyl) 2-(4-cyclobutyl-2-hydroxyphenyl)-3,4,5a,6,8,9-hexahydro-2H-1,2,5,7-tetraazabenzo[cd]azulene-5,7-dicarboxylate (3.0 g, 1 equiv., 5.4 mmol) in EtOH (60 mL) was added $Pd(OH)_2$ (1.5 g, 20 wt %, 0.40 equiv., 2.1 mmol) and Pd/C (1.5 g, 20% wt, 0.52 equiv., 2.8 mmol) in a pressure tank. The mixture was purged with nitrogen for three times and then was pressurized to 3000 kPa with hydrogen at 40° C. for 4 h. The reaction mixture was cooled to rt and filtered to remove insoluble solids. The filter cake was washed with EtOH (3×50 mL). The filtrate was concentrated under reduced pressure. The residue was purified by silica gel column chromatography, eluting with DCM/MeOH (10:1) to afford tert-butyl 2-(4-cyclobutyl-2-hydroxyphenyl)-2,3,4,5a,6,7,8,9-octahydro-5H-1,2,5,7-tetraazabenzo[cd]azulene-5-carboxylate (2.1 g) as a white solid. LCMS:(ESI, m/z): 425 $[M+1]^+$ Step 14: Synthesis of Tert-Butyl 7-acryloyl-2-(4-cyclobutyl-2-hydroxyphenyl)-2,3,4,5a,6,7,8,9-octahydro-5H-1,2,5,7-tetraazabenzo[cd]azulene-5-carboxylate To a stirred solution of tert-butyl 2-(4-cyclobutyl-2-hydroxyphenyl)-2,3,4,5a,6,7,8,9-octahydro-5H-1,2,5,7-tetraazabenzo[cd]azulene-5-carboxylate (2.10 g, 1 equiv., 4.95 mmol) in DMF (20 mL) was added DIEA (1.92 g, 2.58 mL, 3 equiv., 14.8 mmol), acrylic acid (356 mg, 1 equiv., 4.95 mmol) and T3P (4.72 g, 50% Wt, 1.5 equiv., 7.42 mmol) at room temperature and stirred for 1 h. The reaction progress was monitored by LCMS. After completion of reaction, the reaction was quenched by the addition of water (20 mL) at rt. The resulting mixture was extracted with EtOAc (2×20 mL). The combined organic layers were washed with 1:1 water/brine (4×40 mL) and brine (1×40 mL) and dried over anhydrous $Na_2SO_4$. After filtration, the filtrate was concentrated under reduced pressure. The residue was purified by silica gel column chromatography, eluting with EtOAc/PE (1:1) to afford tert-butyl 7-acryloyl-2-(4-cyclobutyl-2-hydroxyphenyl)-2,3,4,5a,6,7,8,9-octahydro-5H-1,2,5,7-tetraazabenzo[c]azulene-5-carboxylate (580 mg) as a white solid. LCMS:(ESI, m/z): 479 $[M+1]^+$ Step 15: Synthesis of 1-(2-(4-cyclobutyl-2-hydroxyphenyl)-2,3,4,5,5a,6,8,9-octahydro-7H-1,2,5,7-tetraazabenzo[cd]azulen-7-yl)prop-2-en-1-one (Int. T)

A solution of tert-butyl 7-acryloyl-2-(4-cyclobutyl-2-hydroxyphenyl)-2,3,4,5a,6,7,8,9-octahydro-5H-1,2,5,7-tetraazabenzo[cd]azulene-5-carboxylate (580 mg, 1 equiv., 1.21 mmol) in TFA (2 mL) and DCM (6 mL) was stirred for 1 h at room temperature u der nitrogen atmosphere. The resulting mixture was concentrated under reduced pressure. This resulted in 1-(2-(4-cyclobutyl-2-hydroxyphenyl)-2,3,4,5,5a,6,8,9-octahydro-7H-1,2,5,7-tetr azabenzo[cd]azulen-7-yl)prop-2-en-1-one (Int. T) (620 mg) as a yellow solid, which was used in the next step directly without further purification. LCMS:(ESI, m/z): 379 $[M+1]^+$ Step 16: Synthesis of (S or R) 7-bromo-1H-benzo[d]imidazole-4-carbonyl)-2-(4-cyclobutyl-2-hydroxyphenyl)-2,3,4,5,5a,6,8,9-octahydro-7H-1,2,5,7-tetraazabenzo[cd]azulen-7-yl)prop-2-en-1-one To a stirred solution of 1-(2-(4-cyclobutyl-2-hydroxyphenyl)-2,3,4,5,5a,6,8,9-octahydro-7H-1,2,5,7-tetraazabenzo[cd]azulen-7-yl)prop-2-en-1-one (180 mg, 1 equiv., 476 μmol) in DMF (4 mL) was added HBTU (902 mg, 5 equiv., 2.38 mmol) and 7-bromo-1H-benzo[d]imidazole-4-carboxylic acid (Acid A). After completion of reaction, the reaction was quenched by the addition of water (10 mL) at rt. The resulting mixture was extracted with EtOAc (2×10 mL). The combined organic layers were washed with 1:1 water/brine (4×20 mL) and brine (1×20 mL), dried over anhydrous $Na_2SO_4$. After filtration, the filtrate was concentrated under reduced pressure. The crude 2-(7-acryloyl-5-(7-bromo-1H-benzo[d]imidazole-4-carbonyl)-3,4,5,5a,6,7,8,9-octahydro-2H-1,2,5,7-tetraazabenzo[cd]azulen-2-yl)-5-cyclobutylphenyl 7-bromo-1H-benzo[d]imidazole-4-carboxylate (280 mg) was used in the next step directly without further purification. LCMS:(ESI, m/z): 825 $[M+1]^+$ The crude reaction product (260 mg, 1 equiv., 315 μmol) was then dissolved in THF (4 mL) and water (1 mL) was added LiOH (15.1 mg, 2 equiv., 631 μmol) at room temperature and stirred for 1 h. The reaction progress was monitored by LCMS. After completion of reaction, the reaction was quenched by the addition of water (10 mL) at rt. The resulting mixture was extracted with EtOAc (2×10 mL). The combined organic layers were washed with brine (2×20 mL) and dried over anhydrous $Na_2SO_4$. After filtration, the filtrate was concentrated under reduced pressure. The crude product was purified by Prep-HPLC (Column: YMC Triart C18 ExRs 5 m, 30 mm*150 mm; Mobile Phase A: water (10 mmol/L $NH_4HCO_3$), Mobile Phase B: MeCN; Flow rate: 60 mL/min; Gradient: 40% B to 61% B in 8 min; Wave Length: UV 254 nm 220 nm; retention time 1 retention time 1: 6.98) to afford 1-(5-(7-bromo-1H-benzo[d]imidazole-4-carbonyl)-2-(4-cyclobutyl-2-hydroxyphenyl)-2,3,4,5,5a,6,8,9-octahydro-7H-1,2,5,7-tetraazabenzo[cd]azulen-7-yl)prop-2-en-1-one (85 mg) as a white solid.

The racemic compound, 1-(5-(7-bromo-1H-benzo[d]imidazole-4-carbonyl)-2-(4-cyclobutyl-2-hydroxyphenyl)-2,3,4,5,5a,6,8,9-octahydro-7H-1,2,5,7-tetraazabenzo[cd]azulen-7-yl)prop-2-en-1-one (85 mg, 0.14 mmol) was separated into constituent enantiomers by chiral HPLC separation (Column: CHIRAL ART Cellulose-SB 3*25 cm, 5 μm; Mobile Phase A: HEX(0.1% FA), Mobile Phase B: EtOH: DCM=1:1; Flow rate: 40 mL/min; Gradient: isocratic 25; Wave Length: UV 254/220 nm; Sample Solvent: EtOH: DCM; Injection Volume: 1.0 mL; Number Of Runs: 4) to afford (S or R)-1-(5-(7-bromo-1H-benzo[d]imidazole-4-carbonyl)-2-(4-cyclobutyl-2-hydroxyphenyl)-2,3,4,5,5a,6,8,9-octahydro-7H-1,2,5,7-tetraazabenzo[d]azulen-7-yl)prop-2-en-1-one as the second eluting peak (retention time 15.5 min., 37.9 mg, 62.7 μmol, 44.5%, 99.5% purity) as a white solid. LCMS:(ESI, m/z): 601 $[M+1]^+$. $^1$H NMR: (400 MHz, Chloroform-d, ppm) δ 10.10 (brs, 1H), 8.29 (s, 1H), 7.54 (d, J=7.9 Hz, 2H), 7.23 (s, 1H), 6.96 (d, J=8.7 Hz, 1H), 6.88 (s, 1H), 6.69 (d, J=7.9 Hz, 1H), 6.59-6.40 (m, 1H), 5.83 (brs, 1H), 5.43 (brs, 1H), 5.07-4.90 (m, 1H), 4.54 (brs, 1H), 4.22 (brs, 1H), 3.59-3.38 (m, 1H), 3.27-0.85 (m, 5H), 2.82-2.59 (m, 2H), 2.42-2.28 (m, 2H), 2.17-1.72 (m, 4H). Analytical Chiral HPLC: Column: CHIRAL ART Cellulose-SB, 4.6*100 mm, 3 μm; Mobile Phase: Hex(0.1% FA):(EtOH: DCM=1:1)=75:25; Flow rate: 1 mL/min; Temperature:25° C.; retention time=5.4 min.

TABLE C1

The compound of Example C-6 was prepared in an analogous fashion to Example C-5, using 3-bromo-1H-indazole-6-carboxylic acid in place of Acid A in the final step. The racemic compound was separated into constituent enantiomers by chiral HPLC separation under the condition (Column: CHIRAL ART Cellulose-SB 3 * 25 cm, 5 μm; Mobile Phase A: HEX(0.1% FA), Mobile Phase B: EtOH:DCM = 1:1; Flow rate: 40 mL/min; Gradient: isocratic 35; Wave Length: UV 254/220 nm; retention time 1 retention time 1: 8; retention time 2: 13; Sample Solvent: EtOH: DCM; Injection Volume: 0.8 mL; Number Of Runs: 5) to afford (S or R)-1-(5-(3-bromo-1H-indazole-6-carbonyl)-2-(4-cyclobutyl-2-hydroxyphenyl)-2,3,4,5,5a,6,8,9-octahydro-7H-1,2,5,7-tetraazabenzo[cd]azulen-7-yl)prop-2-en-1-one as the first eluting peak (retention time 8 min., 37.3 mg, 60.5 μmol, 41.4%, 97.5% purity) as a white solid.

| Example No. | Structure and Name | LCMS (ESI, m/z) | NMR |
|---|---|---|---|
| Example C-6 | 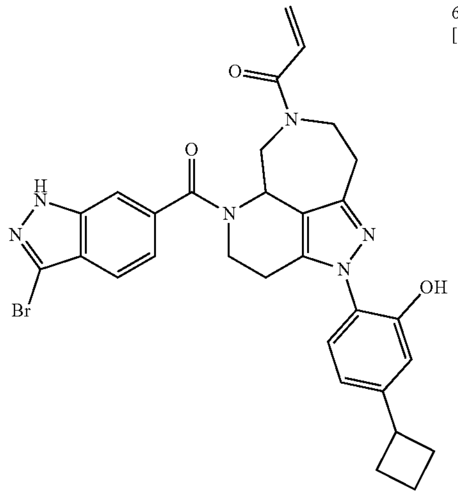 (S or R)-1-(5-(3-bromo-1H-indazole-6-carbonyl)-2-(4-cyclobutyl-2-hydroxyphenyl)-2,3,4,5,5a,6,8,9-octahydro-7H-1,2,5,7-tetraazabenzo[cd]azulen-7-yl)prop-2-en-1-one | 601, 603 $[M + H]^+$ | $^1H$ NMR (400 MHz, Chloroform-d, ppm) δ 11.13 (brs, 1H), 10.19 (brs, 1H), 7.81-7.38 (m, 2H), 7.36-7.19 (m, 1H), 7.07-6.90 (m, 2H), 6.81-6.25 (m, 2H), 5.85 (brs, 1H), 5.36 (s, 1H), 5.10-4.84 (m, 1H), 4.65-3.87 (m, 2H), 3.60-3.34 (m, 1H), 3.31-2.92 (m, 5H), 2.82-2.64 (m, 2H), 2.43-2.25 (m, 2H), 2.20-1.93 (m, 3H), 1.93-1.76 (m, 1H). |

TABLE C2

The compounds of Examples C-6-1 through C-6-9 were prepared in an analogous fashion to Example C-5, using the corresponding acids in place of Acid A in the final step. The racemic compounds were separated under the following conditions: Example C-6-1: Column: CHIRAL ART Cellulose-SB 3 * 25 cm, 5 μm; Mobile Phase A: HEX(0.1% FA), Mobile Phase B: EtOH:DCM = 1:1; Flow rate: 40 mL/min; Gradient: isocratic 25; Wave Length: UV 254/220 nm; RT1(min): 6.5; RT2(min): 13. The compound of the example is the second-eluting peak. Example C-6-2: CHIRAL ART Cellulose-SB, 3 * 25 cm, 5 μm; Mobile Phase A: Hex(0.1% FA)--HPLC, Mobile Phase B: EtOH:DCM = 1:1; Flow rate: 40 mL/min; Gradient: isocratic 20; Wave Length: UV 254/220 nm; RT1(min): 11; RT2(min): 14. The compound of the example is the second-eluting peak. Example C-6-3: CHIRALPAK-IE 2 * 25 cm, 5 μm; Mobile Phase A: HEX(0.1% FA), Mobile Phase B: EtOH:DCM = 1:1; Flow rate: 20 mL/min; Gradient: isocratic 40; Wave Length: UV 254/220 nm; RT1(min): 8; RT2(min): 11. The compound of the example is the first-eluting peak. Example C-6-4: CHIRALPAK-IE 2 * 25 cm, 5 μm; Mobile Phase A: HEX(0.1% FA), Mobile Phase B: ETOH:DCM = 1:1; Flow rate: 20 mL/min; Gradient: isocratic 40; Wave Length: 254/220 nm; RT1(min): 10; RT2(min): 13.5. The compound of the example is the first-eluting peak. For this example, the penultimate lithium, hydroxide step was not needed and was skipped, and HATU was employed in place of HBTU in the final amide-coupling step. Example C-6-5: CHIRALPAK-IA 2 * 25 cm, 5 μm; Mobile Phase A: HEX(0.1% FA), Mobile Phase B: MeOH:DCM = 1:1; Flow rate: 20 mL/min; Gradient: isocratic 30; Wave Length: UV 254/220 nm; RT1(min): 8; RT2(min): 12. The compound of the example is the second-eluting peak. For this example, EDC and HOBT were used in place of HBTU in the final amide coupling step. Example C-6-6: CHIRAL ART Cellulose-SC 2 * 25 cm, 5 μm; Mobile Phase A: HEX(0.1% FA), Mobile Phase B: EtOH:DCM = 1:1; Flow rate: 40 mL/min; Gradient: isocratic 40; Wave Length: UV 254/220 nm; RT1(min): 7.6; RT2(min): 12. The compound of the example is the second-eluting peak. For this example, EDC and HOBT were used in place of HBTU in the final amide coupling step. Example C-6-7: CHIRALPAK-ID 2 * 25 cm, 5 μm; Mobile Phase A: HEX(0.1% FA), Mobile Phase B: EtOH: DCM = 1:1; Flow rate: 20 mL/min; Gradient: isocratic 50; Wave Length: UV 254/220 nm; RT1(min): 5; RT2(min): 12. The compound of the example is the second-eluting peak. For this example, HATU was used in place of HBTU in the final amide coupling step. Example C-6-8: Example C-6-8 was prepared as the racemate. For this example, EDC and HOBT were used in place of HBTU in the final amide coupling step. Example C-6-9: Example C-6-9 was prepared as a racemate.

| Example No. | Structure and Name | LCMS (ESI, m/z) | NMR |
|---|---|---|---|
| C-6-1 | 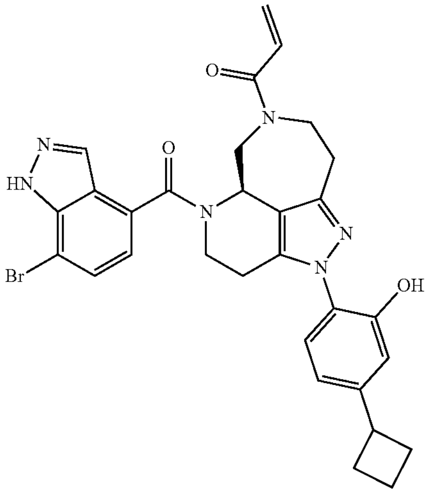 [SMILES: C=CC(=O)N1CCc2nn(-c3ccc(C4CCC4)cc3O)c3c2[C@H](C1)N(C(=O)c1ccc(Br)c2[nH]ncc12)CC3] (R or S)-1-(5-(7-bromo-1H-indazole-4-carbonyl)-2-(4-cyclobutyl-2-hydroxyphenyl)-2,3,4,5,5a,6,8,9-octahydro-7H-1,2,5,7-tetraazabenzo[cd]azulen-7-yl)prop-2-en-1-one | 601 $[M + H]^+$ | $^1H$ NMR (400 MHz, Chloroform-d, ppm) δ 8.19 (s, 1H), 7.67-7.41 (m, 2H), 7.15 (d, J = 7.5 Hz, 1H), 7.01-6.89 (m, 2H), 6.70 (d, J = 8.5 Hz, 1H), 6.48 (s, 1H), 5.84 (s, 1H), 5.52 (s, 1H), 4.98 (s, 1H), 4.55 (s, 1H), 3.97 (s, 1H), 3.48-2.74 (m, 8H), 2.34-1.84 (m, 6H). |

TABLE C2-continued

| | | | |
|---|---|---|---|
| C-6-2 | 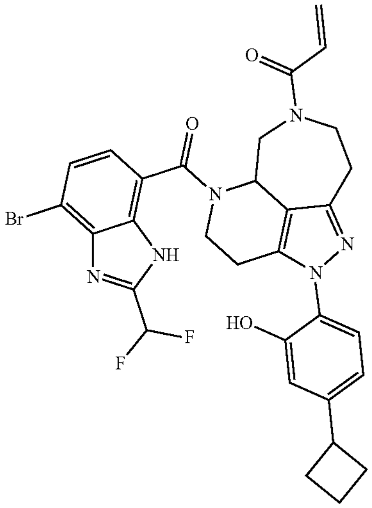 [SMILES: C=CC(=O)N1CCc2nn(-c3ccc(C4CCC4)cc3O)c3c2C(C1)N(C(=O)c1ccc(Br)c2nc(C(F)F)[nH]c12)CC3] (R or S)-1-(5-(4-bromo-2-(difluoromethyl)-1H-benzo[d]imidazole-7-carbonyl)-2-(4-cyclobutyl-2-hydroxyphenyl)-2,3,4,5,5a,6,8,9-octahydro-7H-1,2,5,7-tetraazabenzo[cd]azulen-7-yl)prop-2-en-1-one | 651 $[M + H]^+$ | $^1H$ NMR (400 MHz, Chloroform-d, ppm) δ 7.61 (s, 1H), 7.47 (s, 1H), 7.33 (s, 1H), 6.99-6.79 (m, 3H), 6.71 (d, J = 7.7 Hz, 1H), 6.51 (d, J = 16.7 Hz, 1H), 5.82 (d, J = 11.0 Hz, 1H), 5.48 (s, 1H), 4.97 (d, J = 12.3 Hz, 1H), 4.67-4.54 (m, 2H), 3.58-3.42 (m, 1H), 3.20-2.72 (m, 7H), 2.32 (d, J = 8.8 Hz, 2H), 2.10-1.98 (m, 4H), 1.85 (t, J = 9.2 Hz, 1H). |
| C-6-3 | 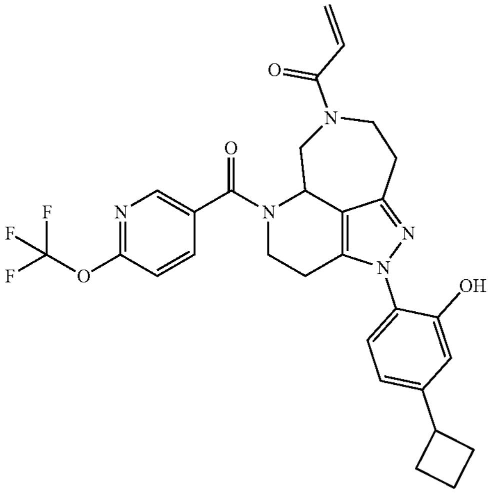 [SMILES: C=CC(=O)N1CCc2nn(-c3ccc(C4CCC4)cc3O)c3c2C(C1)N(C(=O)c1ccc(OC(F)(F)F)nc1)CC3] (R or S)-1-(2-(4-cyclobutyl-2-hydroxyphenyl)-5-(6-(trifluoromethoxy)nicotinoyl)-2,3,4,5,5a,6,8,9-octahydro-7H-1,2,5,7-tetraazabenzo[cd]azulen-7-yl)prop-2-en-1-one | 568 $[M + H]^+$ | $^1H$ NMR (400 MHz, Chloroform-d, ppm)δ 8.46 (d, J = 2.1 Hz, 1H), 7.96 (dd, J = 8.4, 2.3 Hz, 1H), 7.41 (s, 1H), 7.14 (d, J = 8.3 Hz, 1H), 7.05-6.89 (m, 2H), 6.79-6.69 (m, 1H), 6.51 (d, J = 16.4 Hz, 1H), 5.87 (d, J = 10.2 Hz, 1H), 5.39 (s, 1H), 4.98 (d, J = 12.8 Hz, 1H), 4.51 (d, J = 13.0 Hz, 1H), 4.04 (s, 1H), 3.52 (p, J = 8.6 Hz, 1H), 3.32-2.96 (m, 5H), 2.87-2.72 (m, 2H), 2.40-2.27 (m, 2H), 2.20-1.93 (m, 3H), 1.92-1.78 (m, 1H). |

TABLE C2-continued

| | | | |
|---|---|---|---|
| C-6-4 | 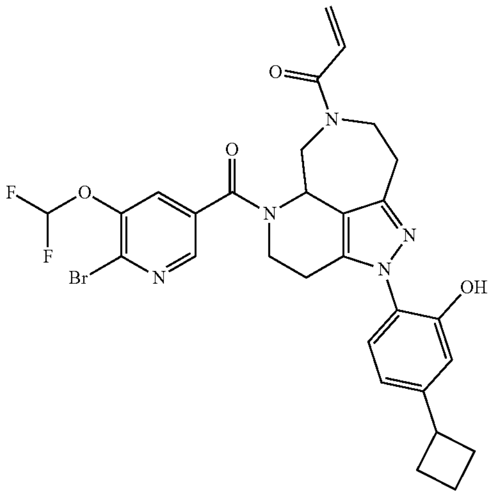 [SMILES: C=CC(=O)N1CCc2nn(-c3ccc(C4CCC4)cc3O)c3c2C(C1)N(C(=O)c1cnc(Br)c(OC(F)F)c1)CC3] (R or S)-1-(5-(6-bromo-5-(difluoromethoxy)nicotinoyl)-2-(4-cyclobutyl-2-hydroxyphenyl)-2,3,4,5,5a,6,8,9-octahydro-7H-1,2,5,7-tetraazabenzo[cd]azulen-7-yl)prop-2-en-1-one | 628 $[M + H]^+$ | $^1H$ NMR (400 MHz, Chloroform-d, ppm) δ 10.08 (s, 1H), 8.41-8.24 (m, 1H), 7.69 (s, 1H), 7.38 (s, 1H), 7.03-6.91 (m, 2H), 6.82-6.66 (m, 2H), 6.57-6.46 (m, 1H), 5.94-5.76 (m, 1H), 5.45-5.26 (m, 1H), 4.98 (d, J = 13.0 Hz, 1H), 4.49 (s, 1H), 4.26-3.95 (m, 1H), 3.58-3.44 (m, 1H), 3.20-3.06 (m, 5H), 2.87-2.74 (m, 2H), 2.35 (d, J = 8.6 Hz, 2H), 2.14 (t, J = 9.8 Hz, 2H), 2.02 (q, J = 9.7, 8.9 Hz, 1H), 1.86 (d, J = 10.0 Hz, 1H). |
| C-6-5 | 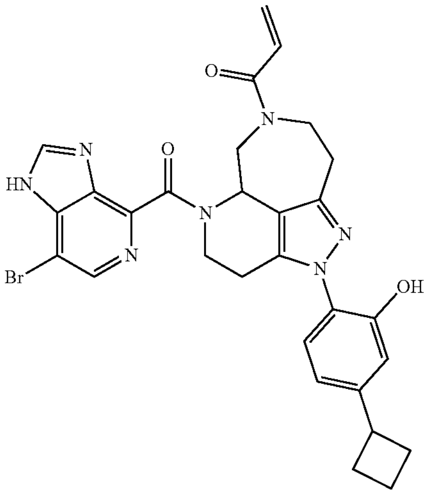 [SMILES: C=CC(=O)N1CCc2nn(-c3ccc(C4CCC4)cc3O)c3c2C(C1)N(C(=O)c1ncc(Br)c2[nH]cnc12)CC3] (R or S)-1-(5-(7-bromo-1H-imidazo[4,5-c]pyridine-4-carbonyl)-2-(4-cyclobutyl-2-hydroxyphenyl)-2,3,4,5,5a,6,8,9-octahydro-7H-1,2,5,7-tetraazabenzo[cd]azulen-7-yl)prop-2-en-1-one | 602 $[M + H]^+$ | |

TABLE C2-continued

| | | | |
|---|---|---|---|
| C-6-6 | 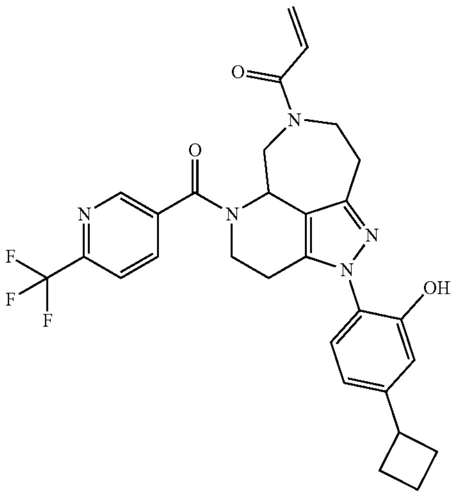 [SMILES: C=CC(=O)N1CCc2nn(-c3ccc(C4CCC4)cc3O)c3c2C(C1)N(C(=O)c1ccc(C(F)(F)F)nc1)CC3] (R or S)-1-(2-(4-cyclobutyl-2-hydroxyphenyl)-5-(6-(trifluoromethyl)nicotinoyl)-2,3,4,5,5a,6,8,9-octahydro-7H-1,2,5,7-tetraazabenzo[cd]azulen-7-yl)prop-2-en-1-one | 552 $[M + H]^+$ | $^1$H NMR (400 MHz, Chloroform-d, ppm) δ 10.08 (s, 1H), 8.84 (s, 1H), 8.16-7.68 (m, 2H), 7.41 (s, 1H), 6.98 (dd, J = 8.6, 5.0 Hz, 2H), 6.74 (d, J = 7.8 Hz, 1H), 6.62-6.42 (m, 1H), 5.98-5.63 (m, 1H), 5.43 (s, 1H), 5.17-4.80 (m, 1H), 4.78-4.46 (m, 1H), 4.30-3.85 (m, 1H), 3.61-3.42 (m, 1H), 3.22 (s, 2H), 3.15-2.94 (m, 3H), 2.93-2.64 (m, 2H), 2.55-2.23 (m, 2H), 2.22-2.06 (m, 2H), 2.06-1.93 (m, 1H), 1.92-1.77 (m, 1H). |
| C-6-7 | 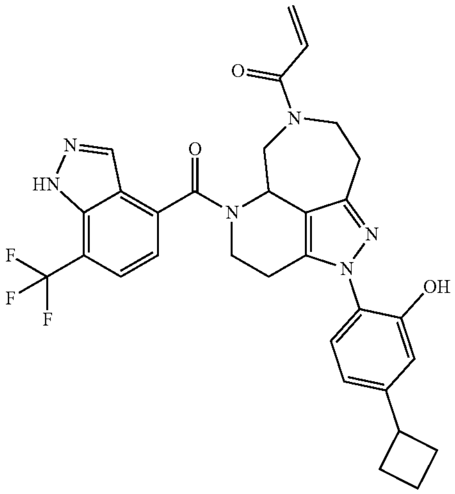 [SMILES: C=CC(=O)N1CCc2nn(-c3ccc(C4CCC4)cc3O)c3c2C(C1)N(C(=O)c1ccc(C(F)(F)F)c2[nH]ncc12)CC3] (R or S)-1-(2-(4-cyclobutyl-2-hydroxyphenyl)-5-(7-(trifluoromethyl)-1H-indazole-4-carbonyl)-2,3,4,5,5a,6,8,9-octahydro-7H-1,2,5,7-tetraazabenzo[cd]azulen-7-yl)prop-2-en-1-one | 591 $[M + H]^+$ | $^1$H NMR (400 MHz, Chloroform-d, ppm) δ 12.01 (s, 1H), 8.31 (s, 1H), 7.82 (d, J = 7.0 Hz, 1H), 7.50 (d, J = 20.5 Hz, 1H), 7.36 (d, J = 7.2 Hz, 1H), 6.98 (s, 2H), 6.74 (d, J = 7.0 Hz, 1H), 6.50 (d, J = 16.3 Hz, 1H), 5.82 (d, J = 51.8 Hz, 1H), 5.56 (s, 1H), 5.00 (s, 1H), 4.60 (s, 1H), 4.22-3.76(m, 1H), 3.60-3.41 (m, 1H), 3.30 (t, J = 12.1 Hz, 1H), 3.21-3.02 (m, 3H), 2.97 (s, 1H), 2.77 (t, J = 18.0 Hz, 2H), 2.38-2.29 (m, 2H), 2.16-2.08 (m, 2H), 2.07-1.98 (m, 1H), 1.91-1.81(m, 1H). |

TABLE C2-continued

| | | | |
|---|---|---|---|
| C-6-8 | 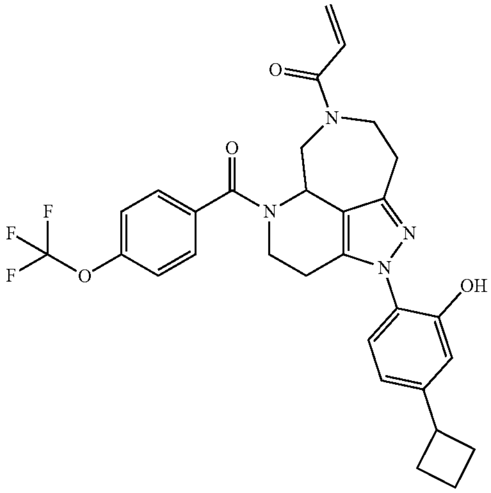 [SMILES: C=CC(=O)N1CCc2nn(-c3ccc(C4CCC4)cc3O)c3c2C(C1)N(C(=O)c1ccc(OC(F)(F)F)cc1)CC3] 1-(2-(4-cyclobutyl-2-hydroxyphenyl)-5-(4-(trifluoromethoxy)benzoyl)-2,3,4,5,5a,6,8,9-octahydro-7H-1,2,5,7-tetraazabenzo[cd]azulen-7-yl)prop-2-en-1-one | 567 [M + H]$^+$ | $^1$H NMR (400 MHz, Chloroform-d, ppm) δ 7.46 (d, J = 8.3 Hz, 2H), 7.27 (d, J = 8.1 Hz, 2H), 6.92 (dd, J = 5.0, 3.2 Hz, 2H), 6.65 (dd, J = 8.2, 1.9 Hz, 1H), 6.42 (d, J = 16.4 Hz, 1H), 5.79 (d, J = 10.1 Hz, 1H), 5.33 (d, J = 10.0 Hz, 1H), 4.91 (d, J = 13.0 Hz, 1H), 4.43 (s, 1H), 3.97 (s, 1H), 3.44 (t, J = 8.8 Hz, 1H), 3.12-2.96 (m, 5H), 2.72 (d, J = 15.3 Hz, 2H), 2.30-2.24 (m, 2H), 2.14-2.05 (m, 2H), 1.98-1.87 (m, 2H), 1.84-1.78 (m, 1H), 1.18 (s, 1H). |
| C-6-9 | 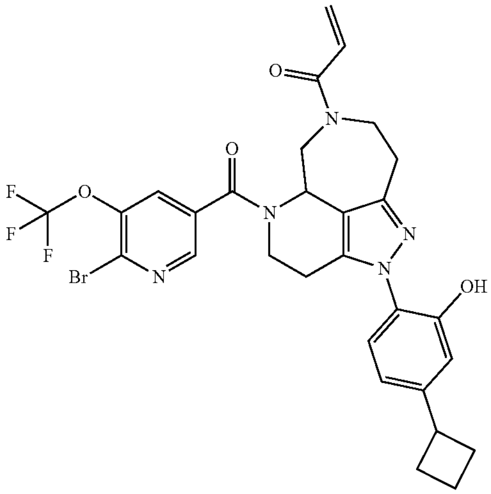 [SMILES: C=CC(=O)N1CCc2nn(-c3ccc(C4CCC4)cc3O)c3c2C(C1)N(C(=O)c1cnc(Br)c(OC(F)(F)F)c1)CC3] 1-(5-(6-bromo-5-(trifluoromethoxy)nicotinoyl)-2-(4-cyclobutyl-2-hydroxyphenyl)-2,3,4,5,5a,6,8,9-octahydro-7H-1,2,5,7-tetraazabenzo[cd]azulen-7-yl)prop-2-en-1-one | 646 [M + H]$^+$ | $^1$H NMR (400 MHz, Chloroform-d, ppm)δ 8.45 (d, J = 1.9 Hz, 1H), 7.84-7.72 (m, 1H), 7.37 (s, 1H), 7.03-6.94 (m, 2H), 6.75 (dd, J = 8.2, 1.9 Hz, 1H), 6.64-6.34 (m, 1H), 5.95-5.72 (m, 1H), 5.37 (s, 1H), 4.98 (d, J = 13.3 Hz, 1H), 4.51 (d, J = 13.7 Hz, 1H), 4.26-3.88 (m, 1H), 3.52 (p, J = 8.6 Hz, 1H), 3.30-2.98 (m, 5H), 2.89-2.72 (m, 2H), 2.35 (dtd, J = 10.2, 8.0, 2.3 Hz, 2H), 2.14 (p, J = 9.2 Hz, 2H), 2.07-1.95 (m, 1H), 1.87 (t, J = 9.4 Hz, 1H). |

Example C-7: Preparation of (R or S)-1-(2-(4-cyclobutyl-2-hydroxyphenyl)-5-(5-hydroxy-6-(trifluoromethyl)nicotinoyl)-2,3,4,5,5a,6,8,9-octahydro-7H-1,2,5,7-tetraazabenzo[cd]azulen-7-yl)prop-2-en-1-one

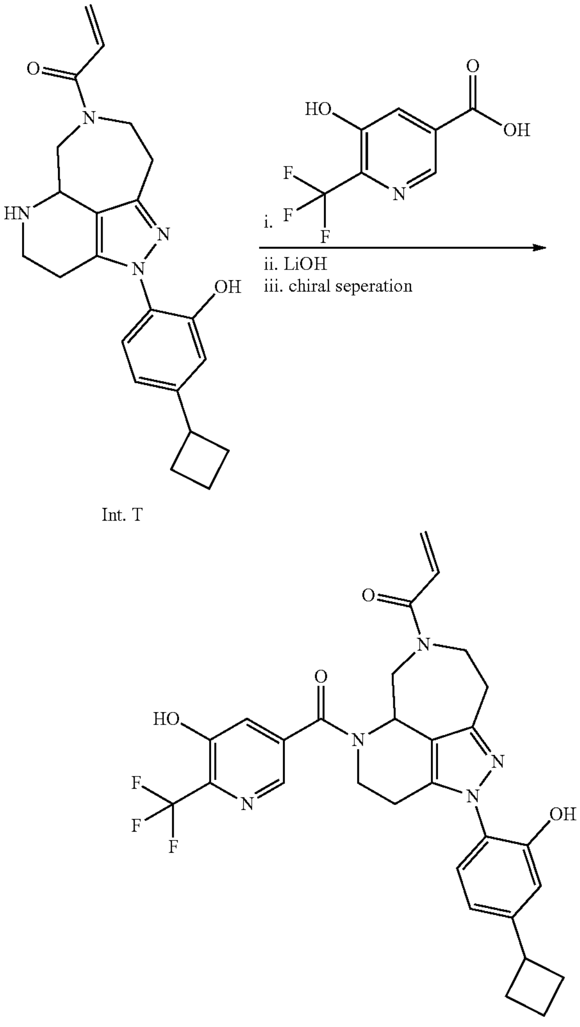

Int. T single enantiomer

To a solution of 1-(2-(4-cyclobutyl-2-hydroxyphenyl)-2,3,4,5,5a,6,8,9-octahydro-7H-1,2,5,7-tetraazabenzo[cd]azulen-7-yl)prop-2-en-1-one (Int. T) (180.0 mg, 1 equiv., 475.6 µmol) in DMF (3.6 mL) were added 5-hydroxy-6-(trifluoromethyl)nicotinic acid (197.0 mg, 2 equiv., 951.2 µmol), DIEA (184.4 mg, 249 µL, 3 equiv., 1.427 mmol), EDC·HCl (182.3 mg, 2 equiv., 951.2 gmol) and HOBT (128.5 mg, 2 equiv., 951.2 µmol). The mixture was stirred at room temperature for 16 h, after which the reaction was quenched with water (10 mL). The resulting mixture was extracted with EtOAc (3×10 mL). The combined organic layers were washed with semi-saturated brine (2×20 mL) and sat. brine (20 mL) and dried over anhydrous $Na_2SO_4$. After filtration, the filtrate was concentrated under reduced pressure. The crude product was purified by silica gel chromatography eluting with DCM: MeOH=4:1 to afford 2-(7-acryloyl-5-(5-hydroxy-6-(trifluoromethyl)nicotinoyl)-3,4,5,5a,6,7,8,9-octahydro-2H-1,2,5,7-tetraazabenzo[cd]azulen-2-yl)-5-cyclobutylphenyl 5-hydroxy-6-(trifluoromethyl)nicotinate (120 mg) as a light brown solid. LCMS: (ESI, m/z): 757 $[M+1]^+$ To a solution of 2-(7-acryloyl-5-(5-hydroxy-6-(trifluoromethyl)nicotinoyl)-3,4,5,5a,6,7,8,9-octahydro-2H-1,2,5,7-tetraazabenzo[cd]azulen-2-yl)-5-cyclobutylphenyl 5-hydroxy-6-(trifluoromethyl)nicotinate (120 mg, 1 equiv., 159 µmol) in THF (1.2 mL) were added LiOH (7.6 mg, 2 equiv., 317 µmol) in water (0.24 mL). The mixt re was stirred at room temperature for 30 min. The reaction was monitored by LCMS. The mixture was purified by Prep-HPLC (Column: Sunfire C18 5 m, 30 mm*150 mm; Mobile Phase A: water (0.1% FA), Mobile Phase B: MeCN; Flow rate: 60 mL/min; Gradient: 40% B to 62% B in 8 min; Wave Length: UV 254 nm/220 nm; retention time 1 retention time 1: 7.72) to afford 1-(2-(4-cyclobutyl-2-hydroxyphenyl)-5-(5-hydroxy-6-(trifluoromethyl)nicotinoyl)-2,3,4,5,5a,6,8,9-octahydro-7H-1,2,5,7-tetraazabenzo[cd]azulen-7-yl)prop-2-en-1-one (45 mg) as a white solid.

The racemic compound was separated into constituent enantiomers by chiral HPLC separation (Column: CHIRAL ART Cellulose-SB 3*25 cm, 5 µm; Mobile Phase A: Hexanes(0.1% FA), Mobile Phase B: EtOH: DCM=1:1; Flow rate: 20 m/min; Gradient: isocratic 25; Wave Length: UV 254/220 nm; retention time 1 retention time 1: 6.9; retention time 2: 11.0; Injection Volume: 1.83 mL; Number Of Runs: 3) to provide (S or R)-1-(2-(4-cyclobutyl-2-hydroxyphenyl)-5-(5-hydroxy-6-(trifluoromethyl) nicotinoyl)-2,3,4,5,5a,6,8,9-octahydro-7H-1,2,5,7-tetraazabenzo[cd] azulen-7-yl)prop-2-en-1-one as the first-eluting peak (retention time=6.9 min., 19.9 mg, 34.6 mol, 44%, 98.6% purity) as a white solid. LCMS:(ESI, m/z):568 [M+H]+. $^1H$ NMR: (400 MHz, Chloroform-d, ppm) δ 8.65 (brs, 1H), 8.51 (s, 1H), 8.37 (s, 1H), 7.18-6.90 (m, 2H), 6.88-6.62 (m, 2H), 6.49 (d, J=16.4 Hz, 1H), 5.93 (d, J 10.1 Hz, 1H), 5.17 (d, J=12.5 Hz, 1H), 4.90 (d, J=12.4 Hz, 1H), 4.69 (d, J=10.0 Hz, 1H), 434 (d, J=14.8 Hz, 1H), 3.66-3.45 (m, 1H), 3.33-2.58 (m, 7H), 2.41-2.25 (m, 2H), 2.25-1.95 (m, 3H), 1.95-1.80 (m, 1H). Analytical Chiral HPLC: Column: CHIRAL ART Cellulose-SB; Column Size: 4.6*100 mm, 3 µm; Mobile Phase: Hex(0.1% FA):(EtOH:DCM=1:1)=75:25; Flow: 1.0 mL/min; Temperature: 25° C.; retention time=2.5 min.

Example C-8: Preparation of (S or R)-1-(2-(4-cyclobutylphenyl)-5-(5-hydroxy-6-(trifluoromethyl) nicotinoyl)-2,3,4,5,5a,6,8,9-octahydro-7H-1,2,5,7-tetraazabenzo[cd]azulen-7-yl)prop-2-en-1-one

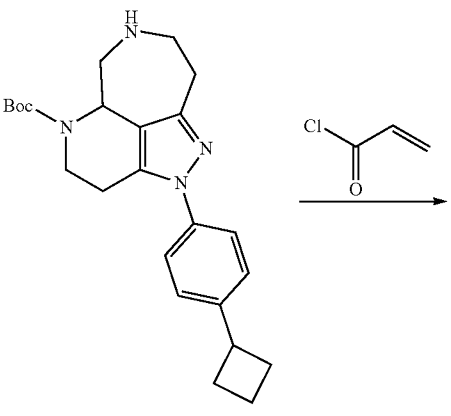
Int. S

-continued

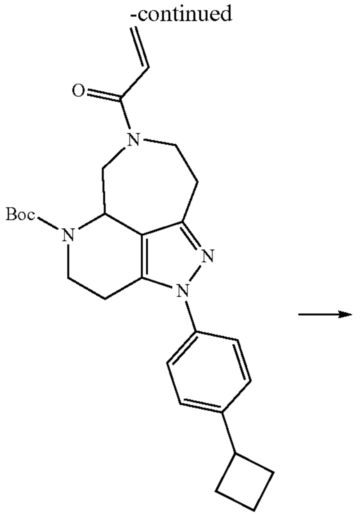

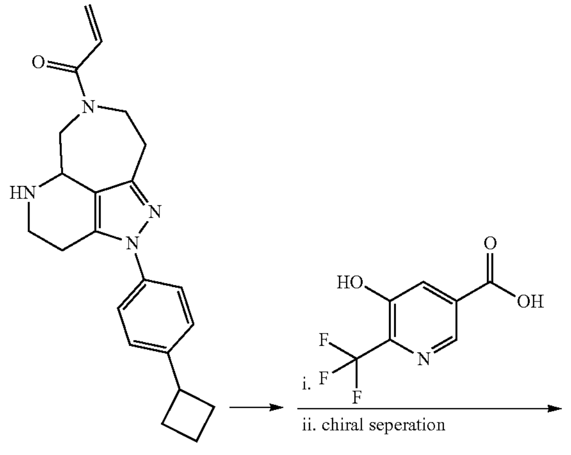

Int. U

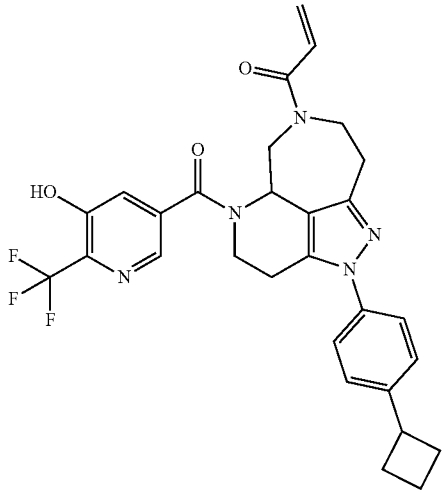

single enantiomer

Step 1: Synthesis of Tert-Butyl (R)-7-acryloyl-2-(4-cyclobutylphenyl)-2,3,4,5a,6,7,8,9-octahydro-5H-1,2,5,7-tetraazabenzo[cd]azulene-5-carboxylate To a stirred solution of tert-butyl 2-(4-cyclobutylphenyl)-2,3,4, a,6,7,8,9-octahydro-5H-1,2,5,7-tetraazabenzo[cd]azulene-5-carboxylate (Int. S) (300 mg, 1 equiv., 734 μmol) and TEA (223 mg, 307 μL, 3 equiv., 2.20 mmol) in DCM (3 mL) were added acryloyl chloride (99.69 mg, 1.5 equiv., 1.101 mmol) dropwise at 0° C. under nitrogen atmosphere. The resulting mixture was stirred for additional 1 h at room temperature. The reaction was monitored by LCMS. After completion of reaction, the reaction was quenched by the addition of water (10 mL) at rt. The resulting mixture was extracted with EtOAc (2×10 mL). The combined organic layers were washed with water (2×20 mL) and brine (1×20 mL) and dried over anhydrous $Na_2SO_4$. After filtration, the filtrate was concentrated under reduced pressure. The residue was purified by silica gel column chromatography, eluting with EtOAc/PE (3:2) to afford tert-butyl (R)-7-acryloyl-2-(4-cyclobutylphenyl)-2,3,4,5a,6,7,8,9-octahydro-5H-1,2,5,7-tetraazabenzo[d]azulene-5-carboxylate (210 mg) as a yellow solid. LCMS:(ESI, m/z): 463 $[M+1]^+$ Step 2: Synthesis of 1-(2-(4-cyclobutylphenyl)-2,3,4,5,5a,6,8,9-octahydro-7H-1,2,5,7 -tetraazabenzo[cd]azulen-7-yl)prop-2-en-1-one (Int. U)

A solution of tert-butyl 7-acryloyl-2-(4-cyclobutylphenyl)-2,3,4,5a,6,7,8,9-octahydro-5H-1,2,5,7-tetraazabenzo[cd]azulene-5-carboxylate (200 mg, 1 equiv., 632 μmol) in TFA (1 mL) and DCM (3 mL) was stirred for 1 h at room temperature under nitrogen atmosphere. The reaction was monitored by LCMS. 90% product could be observed in LCMS. The resulting mixture was concentrated under reduced pressure. The 1-(2-(4-cyclobutylphenyl)-2,3,4,5,5a,6,8,9-octahydro-7H-1,2,5,7-tetraazabenzo[cd]azulen-7-yl)prop-2-en-1-one (Int. U) (200 mg) resulting mixture was used in the next step directly without further purification. LCMS:(ESI, m/z): 363 $[M+1]^+$ Step 3: Synthesis of (S or R)-1-(2-(4-cyclobutylphenyl)-5-(5-hydroxy-6-(trifluoromethyl)nicotinoyl)-2,3,4,5,5a,6,8,9-octahydro-7H-1,2,5,7-tetraazabenzo[cd]azulen-7-yl)prop-2-en-1-one To a stirred solution of 1-(2-(4-cyclobutylphenyl)-2,3,4,5,5a,6,8,9-octahydro-7H-1,2,5,7-tetraazabenzo[cd]azulen-7-yl)prop-2-en-1-one (200.0 mg, 1 equiv., 551.8 mol) in DMF (2 mL) was added 5-hydroxy-6-(trifluoromethyl)nicotinic acid (114.3 mg, 1 equiv., 551.8 μmol), HBTU (313.9 mg, 1.5 equiv., 827.6 μmol), DIEA (213.9 mg, 288 μL, 3 equiv., 1.655 mmol) at room temperature and stirred for 1 h, after which the reaction was quenched b the addition of water (10 mL) at rt. The resulting mixture was extracted with EtOAc (2×10 mL). The combined organic layers were washed with brine (2×20 mL) and dried over anhydrous $Na_2SO_4$. After filtration, the filtrate was concentrated under reduced pressure. The crude product was purified by Prep-HPLC (Column: Kinetex 5 m EVO C18, 30 mm*150 mm; Mobile Phase A: water (10 mmol/L $NH_4HCO_3$), Mobile Phase B: MeCN; Flow rate: 60 mL/min; Gradient: 22% B to 40% B in 8 min; Wave Length: UV 254 nm/220 nm; retention time 1 retention time 1: 7.72) to afford 1-(2-(4-cyclobutylphenyl)-5-(5-hydroxy-6-(trifluoromethyl)nicotinoyl)-2,3,4,5,5a,6,8,9-octahydro-7H-1,2,5,7-tetraazabenzo[cd]azulen-7-yl)prop-2-en-1-one (100 mg) as a white solid.

The racemic compound, 1-(2-(4-cyclobutylphenyl)-5-(5-hydroxy-6-(trifluoromethyl)nicotinoyl)-2,3,4,5,5a,6,8,9-octahydro-7H-1,2,5,7-tetraazabenzo[cd]azulen-7-yl)prop-2-en-1-one (100 mg, 181 mol) was separated into constituent enantiomers by chiral HPLC separation (Column: CHIRAL ART Cellulose-SB 3*25 cm, μm; Mobile Phase A: HEX (0.1% FA), Mobile Phase B: EtOH: DCM=1:1; Flow rate: 40 mL/m n; Gradient: isocratic 25; Wave Length: UV 254/220 nm; Sample Solvent: EtOH: DCM; Injection Volume: 2.5 mL; Number Of Runs: 4) to afford (R)-1-(2-(4-cyclobutylphenyl)-5-(5-hydroxy-6-(trifluoromethyl)nicotinoyl)- 2,3,4,5,5a,6,8,9-octahydro-7H-1,2,5,7-tetraazabenzo [cd]azulen-7-yl)prop-2-en-1-one as the first-eluting peak (retention time 6.3 min., 26.1 mg, 47.1 μmol, 26.1%, 99.6% purity) as a white solid. LCMS:(ESI, m/z): 552 $[M+H]^+$. $^1H$ NMR: (400 MHz, Chloroform-d, ppm) δ 9.03-7.58 (m, 3H), 7.42-7.27 (m, 2H), 7.09 (brs, 1H), 6.82-6.61 (m, 1H), 6.47 (d, J=16.3 Hz, 1H), 5.98-5.66 (m, 1H), 5.29-5.03 (m, 1H), 4.98-4.77 (m, 1H), 4.85-4.18 (m, 2H), 3.93-1.15 (m, 13H). $^{19}F$ NMR: (376 MHz, DMSO) δ −64.91. Analytical Chiral HPLC: Column: CHIRAL ART Cellulose-SB, 4.6*100 mm, 3 μm; Mobile Phase: Hex(0.1% FA):(EtOH:DCM=1:1)=75:25; Flow rate: 1 mL/min; Temperature:25° C.; retention time 2.4 min.

TABLE C3

The compound of Example C-8-1 was prepared in an analogous manner to Example C-8, using the corresponding carboxylic acid. The racemic final compound was separated using the following conditions: Column: YMC Triart C18 ExRs 5 m, 30 mm * 150 mm; Mobile Phase A: Water (10 mmol/L $NH_4HCO_3$), Mobile Phase B: ACN; Flow rate: 60 mL/min; Gradient: 40% B to 68% B in 10 min; Wave Length: UV 254 nm/220 nm to provide the compound of the example as the second-eluting peak. The compound of Example C-8-2 was prepared in an analogous manner to Example C-8, using the corresponding acid and Int. S-1 in place of Int. S. The compound of Example C-8-3 was prepared in an analogous manner to Example C-8. The carboxylic acid for the compound of Example C-8-3 was prepared in an analogous fashion to Example A-34, starting by treating 6-bromo-2-fluoro-3-(trifluoromethyl)benzonitrile with hydrazine to form 4-bromo-7-(trifluoromethyl)-1H-indazol-3-amine, which was then used to prepare the analogous methyl carboxylate in a manner analogous to Example A-34 step 1. The racemic final compound was separated into its constitutive isomers using the following conditions: Column-CHIRALPAK-IC 2 * 25 cm, 5 μm; Mobile Phase A: HEX(0.1% FA), Mobile Phase B: EtOH:DCM = 1:1; Flow rate: 20 mL/min; Gradient: isocratic 50; Wave Length: UV 254/220 nm; RT1(min): 9.8; RT2(min): 12.6; to afford the compound of the example as the second-eluting peak. The compound of Example C-8-4 was prepared in an analogous fashion to Example C-8, using the carboxylic acid described in Example A-34. The racemic final compound was separated into its constitutive isomers using the following conditions: CHIRALPAK-IA 2 * 25 cm, 5 μm; Mobile Phase A: HEX(0.1% FA), Mobile Phase B: EtOH:DCM = 1:1; Flow rate: 18 mL/min; Gradient: isocratic 40; Wave Length: UV 254/220 nm; RT1(min): 27; RT2(min): 41 to provide the compound of the example as the first-eluting peak.

| Example No. | Structure and Name | LCMS (ESI, m/z) | NMR |
|---|---|---|---|
| C-8-1 | 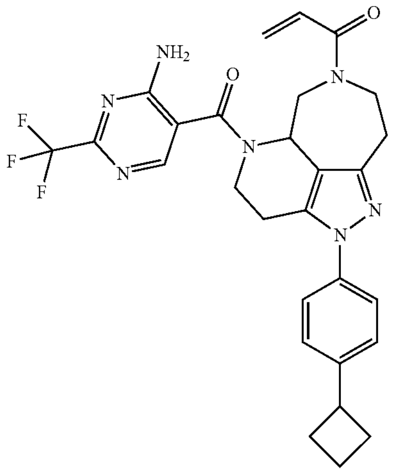 [SMILES: C=CC(=O)N1CCc2nn(-c3ccc(C4CCC4)cc3)c3c2C(C1)N(C(=O)c1cnc(C(F)(F)F)nc1N)CC3] (R or S)-1-(5-(4-amino-2-(trifluoromethyl)pyrimidine-5-carbonyl)-2-(4-cyclobutylphenyl)-2,3,4,5,5a,6,8,9-octahydro-7H-1,2,5,7-tetraazabenzo[cd]azulen-7-yl)prop-2-en-1-one | 552 $[M + H]^+$ | $^1H$ NMR (400 MHz, Chloroform-d, ppm) δ 8.36-8.42 (m, 1H), 7.46-7.31 (m, 2H), 7.26 (s, 2H), 6.72-5.75 (m, 4H), 5.37 (s, 1H), 4.98 (d, J = 11.5 Hz, 1H), 4.47 (s, 1H), 4.20 (d, J = 3.4 Hz, 1H), 3.59 (p, J = 8.6 Hz, 1H), 3.41-2.20 (m, 8H), 2.19-2.01 (m, 2H), 1.88 (q, J = 9.3 Hz, 3H), 1.28-0.90 (m, 1H). |

TABLE C3-continued

| | | | |
|---|---|---|---|
| C-8-2 | 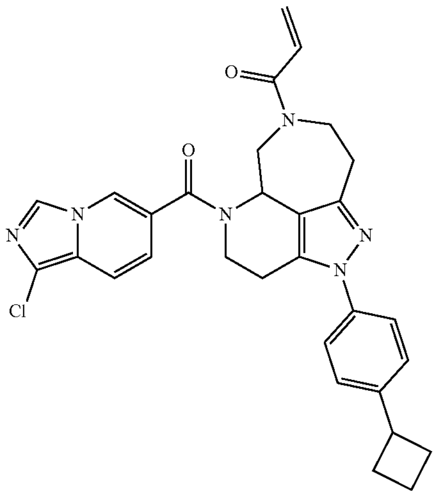 [SMILES: C=CC(=O)N1CCc2nn(-c3ccc(C4CCC4)cc3)c3c2C(C1)N(C(=O)c1ccc2c(Cl)ncn2c1)CC3]<br>(S or R)-1-(5-(1-chloroimidazo[1,5-a]pyridine-6-carbonyl)-2-(4-cyclobutylphenyl)-2,3,4,5,5a,6,8,9-octahydro-7H-1,2,5,7-tetraazabenzo[cd]azulen-7-yl)prop-2-en-1-one | 541 [M + H]+ | $^1$H NMR (400 MHz, CDCl3) δ 8.88-8.47 (m, 1H), 8.11 (d, J = 28.3 Hz, 2H), 7.52 (d, J = 9.3 Hz, 1H), 7.46-7.33 (m, 3H), 6.98 (d, J = 9.3 Hz, 1H), 6.78 (d, J = 9.3 Hz, 1H), 6.66 (dd, J = 16.5, 10.1 Hz, 1H), 6.49 (d, J = 16.3 Hz, 1H), 6.39 (d, J = 16.4 Hz, 1H), 5.78 (d, J = 10.2 Hz, 1H), 5.34 (s, 1H), 5.17-4.68 (m, 2H), 4.29 (dd, J = 83.1, 68.4 Hz, 1H), 3.58 (p, J = 8.6 Hz, 1H), 3.29-2.62 (m, 4H), 2.38 (q, J = 8.2 Hz, 2H), 2.24-1.83 (m, 4H), 0.86 (dt, J = 13.7, 6.5 Hz, 1H). |
| C-8-3 | 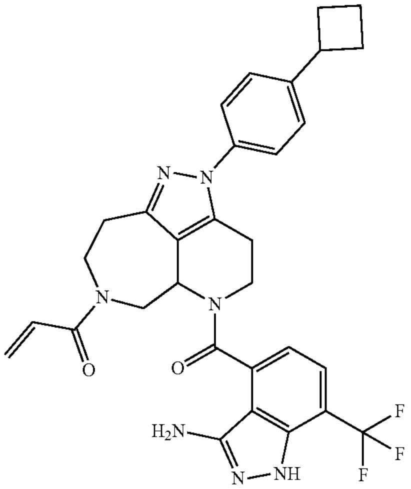 [SMILES: C=CC(=O)N1CCc2nn(-c3ccc(C4CCC4)cc3)c3c2C(C1)N(C(=O)c1ccc(C(F)(F)F)c2[nH]nc(N)c12)CC3]<br>(R or S)-1-(5-(3-amino-7-(trifluoromethyl)-1H-indazole-4-carbonyl)-2-(4-cyclobutylphenyl)-2,3,4,5,5a,6,8,9-octahydro-7H-1,2,5,7-tetraazabenzo[cd]azulen-7-yl)prop-2-en-1-one | 590 [M + H]+ | $^1$H NMR (400 MHz, Chloroform-d) δ 7.65 (s, 1H), 7.35 (s, 2H), 7.13-7.01 (m, 1H), 6.51 (d, J = 16.3 Hz, 1H), 5.93-5.35 (m, 2H), 4.99 (s, 1H),4.53 (s, 1H), 3.96 (s, 1H), 3.67-3.44 (m, 2H), 3.34-3.14 (m, 4H), 2.88-2.08 (m, 9H), 1.86 (s, 3H), 1.25 (s, 2H). |

TABLE C3-continued

| | | | |
|---|---|---|---|
| C-8-4 | 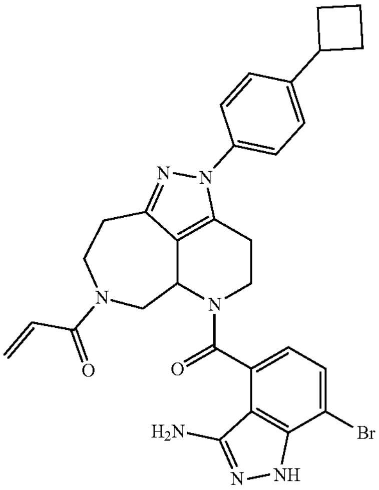 [SMILES: C=CC(=O)N1CCc2nn(-c3ccc(C4CCC4)cc3)c3c2C(C1)N(C(=O)c1ccc(Br)c2[nH]nc(N)c12)CC3] (R or S)-1-(5-(3-amino-7-bromo-1H-indazole-4-carbonyl)-2-(4-cyclobutylphenyl)-2,3,4,5,5a,6,8,9-octahydro-7H-1,2,5,7-tetraazabenzo[cd]azulen-7-yl)prop-2-en-1-one | 602 $[M + H]^+$ | $^1$H NMR (400 MHz, Chloroform-d, ppm) δ 7.65 (d, J = 7.6 Hz, 1H), 7.46-7.26 (m, 5H), 6.94 (d, J = 7.6 Hz, 1H), 6.70-6.41 (m, 1H), 5.91-5.74 (m, 1H), 5.62 (s, 1H), 5.01 (s, 1H), 4.53 (s, 1H), 4.16 (s, 1H), 3.69-3.55 (m, 1H), 3.38-2.68 (m, 5H), 2.45-2.35 (m, 2H), 2.23-1.95 (m, 6H), 1.90-1.75 (m, 2H), 1.25 (s, 1H). |

Example C-9: Preparation of 1-((5a(S or R),9(S or R))-5-(7-bromo-13-benzo[d]imidazole-4-carbonyl)-2-(4-cyclobutylphenyl)-9-methoxy-2,3,4,5,5a,6,8,9-octahydro-7H-1,2,5,7-tetraazabenzo[cd]azulen-7-yl) prop-2-en-1-one

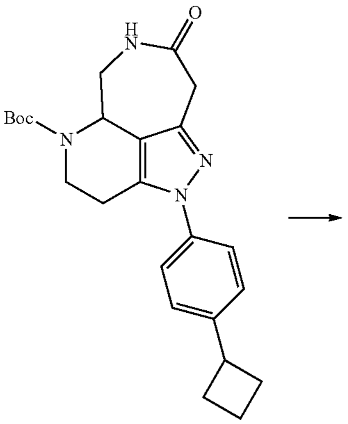

Int. R

-continued

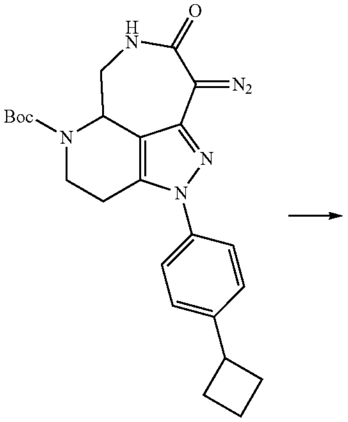

Int. V

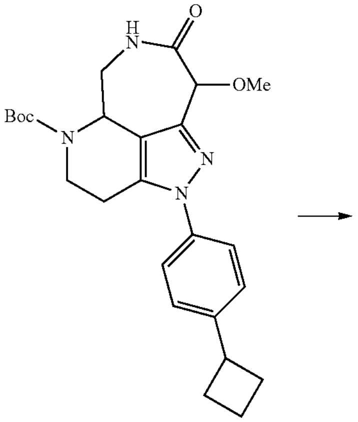

single diastereomer

-continued

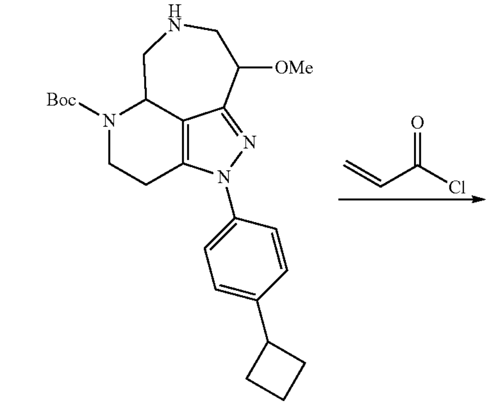

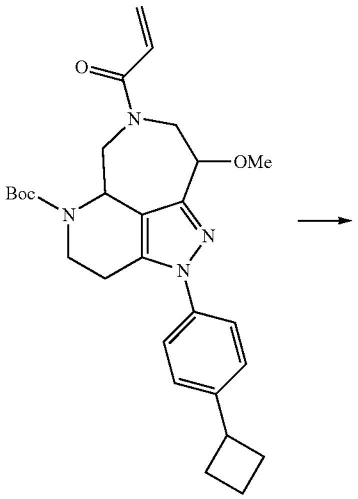

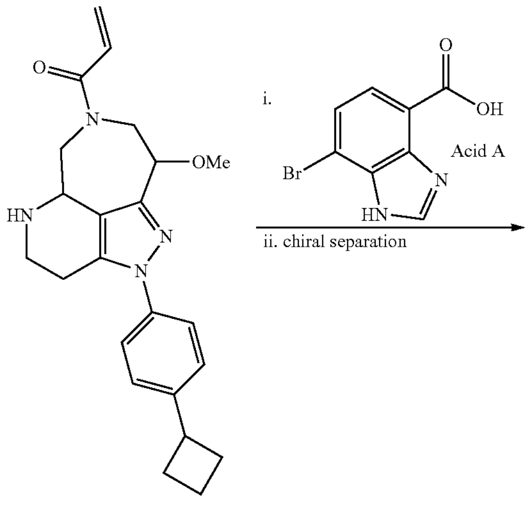

Int. W

-continued

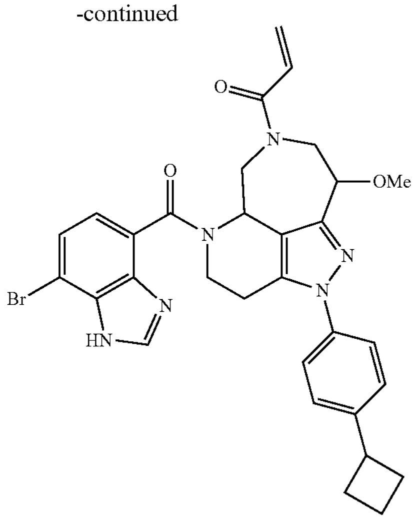

single enantiomer

Step 1: Synthesis of Tert-Butyl 2-(4-cyclobutylphenyl)-9-diazo-8-oxo-2,3,4,5a,6,7,8,9-octahydro-5H-1,2,5,7-tetraazabenzo[cd]azulene-5-carboxylate (Int. V)

To a stirred, ice cooled solution of the tert-butyl 2-(4-cyclobutylphenyl)-8-oxo-2,3,4,5a,6,7,8,9-octahydro-5H-1,2,5,7-tetraazabenzo[cd]azulene-5-carboxylate (Int. R) (7.8 g, 1 equiv., 18 mmol) and 4-methylbenzenesulfonyl azide (22 g, 50 wt %, 3 equiv., 55 mmol) in MeCN (160 mL) were added 2,3,4,6,7,8,9,10-octahydropyrimido[1,2-a]azepine (4.2 g, 1.5 equiv., 28 mmol) dropwise. The solution was stirred overnight while slowly warming up to rt. The reaction was monitored by LCMS. The mixture was concentrated under reduced pressure, and the residue was purified by silica gel chromatography (Gradient: 0-10% EtOAc in heptane) yielded tert-butyl 2-(4-cyclobutylphenyl)-9-diazo-8-oxo-2,3,4,5a,6,7,8,9-octahydro-5H-1,2,5,7-tetraazabenzo[cd]azulene-5-carboxylate (Int. V) (8 g) as a yellow solid LCMS: (ESI, m/z): 449 $[M+H]^+$ Step 2: Synthesis of Tert-Butyl (trans or cis)-2-(4-cyclobutylphenyl)-9-methoxy-8-oxo-2,3,4,5a,6,7,8,9-octahydro-5H-1,2,5,7-tetraazabenzo[cd]azulene-5-carboxylate A solution of tert-butyl 2-(4-cyclobutylphenyl)-9-diazo-8-oxo-2,3,4,5a,6,7,8,9-octahydro-5H-1,2,5,7-tetraazabenzo[cd]azulene-5-carboxylate (Int. V) (3.9 g, 1 equiv., 8.7 mmol) and MeOH (1.4 g, 1.8 mL, 5 equiv., 43 mmol) in DCE (40 mL) to the r action tube at rt. Fill the reaction system with 1 atm nitrogen. The reaction mixture was stirred at room temperature for 4 h under the irradiation of 1 W blue LED. The reaction was monitored by CMS. The mixture was diluted with $NaHCO_3$ in water (20 mL) and EtOAc (20 mL), and the aqueous layer was extracted with EtOAc (2×20 mL). The combined organic layers were washed with saturated brine (2×20 mL), dried over anhydrous sodium sulfate and concentrated to give a residue. The residue was purified-by flash column chromatography, eluting with EtOAc/PE (1:5) to afford tert-butyl (trans or cis)-2-(4-cyclobutylphenyl)-9-methoxy-8-oxo-2,3,4,5a,6,7,8,9-octahydro-5H-1,2,5,7-tetraazabenzo[cd]azulene-5-carboxylate (1150 mg) as a light yellow solid. LCMS: (ESI, m/z): 453 [M+H]$^+$ Step 3: Synthesis of Tert-Butyl (trans or cis)-2-(4-cyclobutylphenyl)-9-methoxy-2,3,4,5a,6,7,8,9-octahydro-5H-1,2,5,7-tetraazabenzo[cd]azulene-5-carboxylate To a solution of tert-butyl (trans or cis)-2-(4-cyclobutylphenyl)-9-methoxy-8-oxo-2,3,4,5a,6,7,8,9-octahydro-5H-1,2,5,7-tetraazabenzo[cd]azulene-5-carboxylate (1.10 g, 1 equiv., 2.43 mmol) in THF (10 mL) was added $BH_3$·THF (836 mg, 9.72 mL, 1 molar, 4 equiv., 9.72 mmol). The mixture was warmed to 60° C. and stirred for 1 h. The reaction was monitored by LCMS. The filtrate was concentrated under reduced pressure. The crude product tert-butyl (trans or cis)-2-(4-cyclobutylphenyl)-9-methoxy-2,3,4,5a,6,7,8,9-octahydro-5H-1,2,5,7-tetraazabenzo[cd]azulene-5-carboxylate was used in the next step directly without further purification. LCMS: (ESI, m/z): 439 [M+H]$^+$ Step 4: Synthesis of Tert-Butyl (trans or cis)-7-acryloyl-2-(4-cyclobutylphenyl)-9-methoxy-2,3,4,5a,6,7,8,9-octahydro-5H-1, 2,5,7-tetraazabenzo[cd]azulene-5-carboxylate To a solution of tert-butyl (trans or cis)-2-(4-cyclobutylphenyl)-9-methoxy-2,3,4,5a,6,7,8,9-octahydro-5H-1,2,5,7-tetraazabenzo[cd]azulene-5-carboxylate (1100 mg, 1 equiv., 2.51 mmol) in DCM (20 mL) was added TEA (761 mg, 1.05 mL, 3 equiv., 7.52 mmol). The mixture was cooled to 0° C., then acryloyl chloride (454.0 mg, 407.7 μL, 2 equiv., 5.016 mmol) was added dropwise to the above mixture at 0° C. under nitrogen atmosphere. The mixture was warmed to room temperature and stirred for 0.5 h. The reaction was monitored by LCMS. The mixture was diluted with ice water (20 mL) and EtOAc (20 mL), and the aqueous layer was extracted with EtOAc (2×20 mL). The combined organic layers were washed with saturated brine (2×20 mL), dried over anhydrous sodium sulfate and concentrated to give a residue. The residue was purified by flash column chromatography, eluting with EtOAc/PE (1:5) to afford tert-butyl (trans or cis)-7-acryloyl-2-(4-cyclobutylphenyl)-9-methoxy-2,3,4,5a,6,7,8,9-octahydro-5H-1,2,5,7-tetraazabenzo[cd]azulene-5-carboxylate (350 mg) as a light yellow solid. LCMS: (ESI, m/z): 493 [M+]$^+$ Step 5: Synthesis of 1-(Trans or Cis)-(2-(4-cyclobutylphenyl)-9-methoxy-2,3,4,5,5a,6,8,9-octahydro-7H-1,2,5,7-tetraazabenzo[cd]azulen-7-yl)prop-2-en-1-one (Int. W)

The solution of tert-butyl (trans or cis)-7-acryloyl-2-(4-cyclobutylphenyl)-9-methoxy-2,3,4,5a,6,7,8,9-octahydro-5H-1,2,5,7-tetraazabenzo[cd]azulene-5-carboxylate (375 mg, 1 equiv., 761 μmol) in DCM (5.25 mL) and TFA (1.75 mL) was stirred at room temperature for 0.5 h. The reaction was monitored by LCMS. The solvent was removed under reduced pressure. This resulted in 1-(trans or cis)-(2-(4-cyclobutylphenyl)-9-methoxy-2,3,4,5,5a,6,8,9-octahydro-7H-1,2,5,7-tetraazabenzo[cd]azulen-7-yl)prop-2-en-1-one (Int. W) (300 mg) as a crude yellow oil. The crude product was used in the next step directly without further purification. LCMS: (ESI, m/z): 493 [M+H]$^+$ Step 6: Synthesis of 1-((5a(R or S),9(R or S)-5-(7-bromo-1H-benzo[d]imidazole-4-carbonyl)-2-(4-cyclobutylphenyl)-9-methoxy-2,3,4,5,5a,6,8,9-octahydro-7H-1,2,5,7-tetraazabenzo[cd]azulen-7-yl)prop-2-en-1-one To a solution of 1-(trans or cis)-(2-(4-cyclobutylphenyl)-9--ethoxy-2,3,4,5,5a,6,8,9-octahydro-7H-1,2,5,7-tetraazabenzo[cd]azulen-7-yl)prop-2-en-1-one (Int. W) (300 mg, 1 equiv., 764 μmol) in DMF (6 mL) were added 7-bromo-1H-benzo[d]imidazole-4-carboxylic acid (276 mg, 1.5 equiv., 1.15 mmol), HBTU (580 mg, 2 equiv., 1.53 mmol) and DI A (988 mg, 1.33 mL, 10 equiv., 7.64 mmol). The mixture was stirred at room temperature for 0.5 h. The reaction was monitored by LCMS. The mixture was diluted with water (20 mL) and EtOAc (20 mL), and the aqueous layer was extracted with EtOAc (2×20 mL). The combined organic layers were washed with saturated brine (2×20 mL), dried over anhydrous sodium sulfate d concentrated to give a residue. The residue was purified by Prep-HPLC (Column: Ultimate μ AQ-C18; Mobile Phase A: water (0.1% FA), Mobile Phase B: MeCN; Flow rate: 100 mL/min; Gradient: 35% B to 65% B in 23 min; Wave Length: UV 254 nm/220 nm; retention time 1 retention time 1: 19) to afford 1-((trans or cis)-5-(7-bromo-1H-benzo[d]imidazole-4-carbonyl)-2-(4-cyclobutylphenyl)-9-methoxy- 2,3,4,5,5a,6,8,9-octahydro-7H-1,2,5,7-tetraazabenzo[cd]azulen-7-yl)prop-2-en-1-one (200 mg) as a white solid.

The racemic compound was separated into constituent enantiomers by chiral HPLC separation under the following conditions (Column: CHIRAL ART Cellulose-SC 2-25 cm, 5 μm; Mobile Phase A: HEX(0.1% FA), Mobile Phase B: MeOH: DCM=1:1; Flow rate: 20 mL/min; Gradient: isocratic 55; Wave Length: UV 254/220 nm; Sample Solvent: MeOH; Injection Volume: 0.9 mL; Number Of Runs: 2) to afford 1-((5a(S or R),9(S or R))-5-(7-bromo-1H-benzo[d]imidazole-4-carbonyl)-2-(4-cyclobutylphenyl)-9-methoxy-2,3,4,5,5a,6,8,9-octahydro-7H-1,2,5,7-tetraazabenzo[cd]azulen-7-yl)prop-2-en-1-one as the second eluting pea (retention time=9.8 min., 75.2 mg, 121 gmol, 37.3%, 99.3% purity) as a white solid. LCMS: (ESI, m/z): 615, 617 [M+H]$^+$. $^1$H NMR: (400 MHz, Chloroform-d, ppm) δ 8.41-8.11 (m, 1H), 7.56-7.38 (m, 1H), 7.37-7.27 (m, 2H), 7.25-7.14 (m, 3H), 6.86-6.29 (m, 1H), 5.81 (s, 1H), 5.39-5.23 (m, 1H), 5.07 (d, J=12.4 Hz, 1H), 4.61-4.45 (m, 2H), 4.12 (s, 1H), 3.78-3.60 (m, 4H), 3.60-3.45 (m, 1H), 3.27-3.02 (m, 2H), 3.02-2.53 (m, 2H), 2.43-2.25 (m, 3H), 2.22-1.76 (m, 3H).

Example C-10: Preparation of 1-((5aR,9R)-5-(7-bromo-1H-benzo[d]imidazole-4-carbonyl)-2-(4-cyclobutylphenyl)-9-fluoro-2,3,4,5,5a,6,8,9-octahydro-7H-1,2,5,7-tetraazabenzo[cd]azulen-7-yl)prop-2-en-1-one

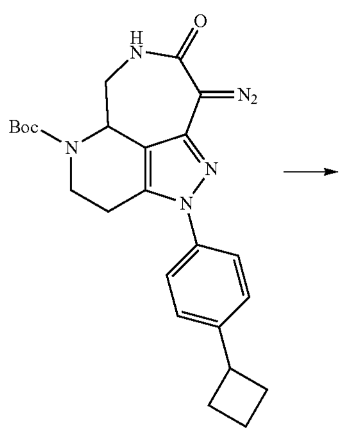

Int. V

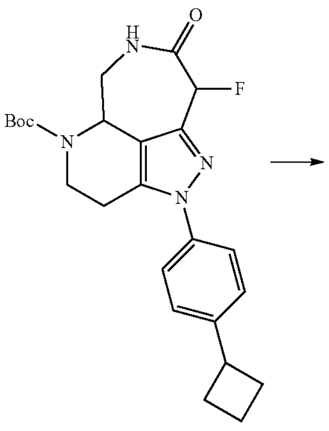

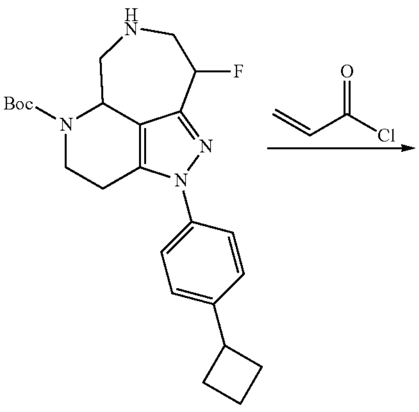

-continued

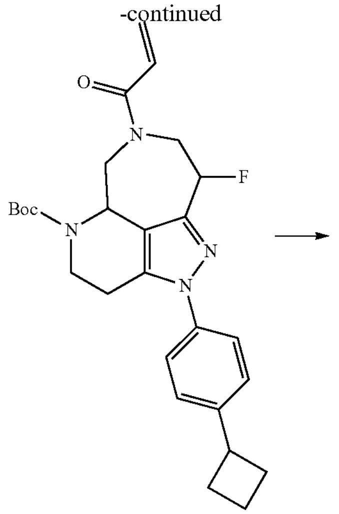

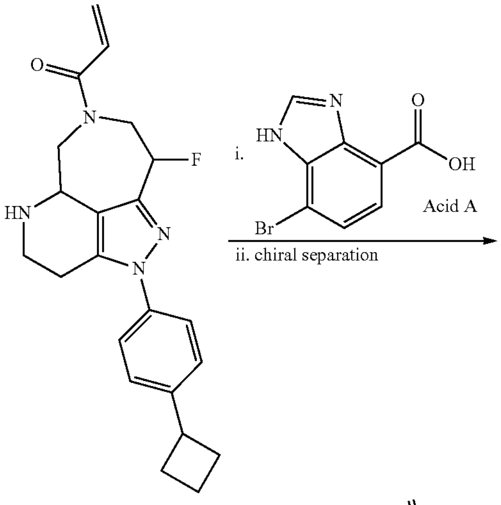

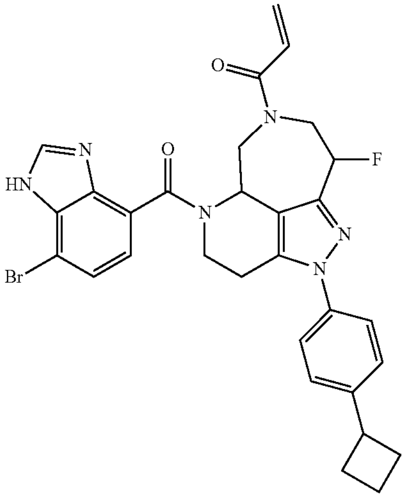

Step 1: Synthesis of Tert-Butyl (Trans or Cis)-2-(4-cyclobutylphenyl)-9-fluoro-8-oxo- 2,3,4,5a,6,7,8,9-octahydro-5H-1,2,5, 7-tetraazabenzo[cd]azulene-5-carboxylate A solution of tert-butyl 2-(4-cyclobutylphenyl)-9-diazo-8-oxo-2,3,4,5a,6,7,8,9-octahydro-5H-1,2,5,7-tetraazabenzo [cd]azulene-5-carboxylate (Int. V) (2 g, 1 equiv., 4 mmol)

and HF-pyridine (3 g, 70 wt %, 5.0 equiv., 0.02 mol) in DCE (20 mL) to the reaction tube at rt. Fill the reaction system with 1 atm nitrogen. The reaction mixture was stirred at room temperature for 4 h under the irradiation of 1 W blue LED. The reaction was monitored by CMS. The mixture was diluted with $NaHCO_3$ in water (20 mL) and EtOAc (20 mL), and the aqueous layer was extracted with EtOAc (2×20 mL). The combined organic layers were washed with saturated brine (2×20 mL), dried over anhydrous sodium sulfate and concentrated to give a residue. The residue was purified by flash column chromatography, eluting with EtOAc/PE (1:5) to afford tert-butyl (trans or cis)-2-(4-cyclobutylphenyl)-9-fluoro-8-oxo-2,3,4,5a,6,7,8,9-octahydro-5H-1,2,5,7-tetraazabenzo[cd]azulene-5-carboxylate (300 mg) as a light yellow solid. LCMS: (ESI, m/z):441 $[M+H]^+$ Step 2: Synthesis of Tert-Butyl (Cis or Trans)-2-(4-cyclobutylphenyl)-9-fluoro-2,3,4,5a,6,7,8,9-octahydro-5H-1,2,5,7-tetraazabenzo[cd]azulene-5-carboxylate To a solution of tert-butyl (trans or cis)-2-(4-cyclobutylphenyl)-9-fluoro-8-oxo-2,3,4,5a,6,7,8,9-octahydro-5H-1,2,5,7-tetraazabenzo[cd]azulene-5-carboxylate (450 mg, 1 equiv., 1.02 mmol) in THF (5 mL) was added $BH_3$·THF (351 mg, 4.09 mL, 1 molar, 4 equiv., 4.09 mmol). The mixture was warmed to 60° C. and stirred for 1 h. The reaction was monitored by LCMS. The filtrate was concentrated under reduced pressure. The crude tert-butyl (cis or trans)-2-(4-cyclobutylphenyl)-9-fluoro-2,3,4,5a,6,7,8,9-octahydro-5H-1,2,5,7-tetraazabenzo[cd]azulene-5-carboxylate was used in the next step directly without further purification. LCMS: (ESI, m/z): 427 $[M+H]^+$ Step 3: Synthesis of Tert-Butyl (Cis or Trans)-7-acryloyl-2-(4-cyclobutylphenyl)-9-fluoro-2,3,4,5a,6,7,8,9-octahydro-5H-1,2,5, 7-tetraazabenzo[cd]azulene-5-carboxylate To a solution of tert-butyl (cis or trans)-2-(4-cyclobutylphenyl)-9-fluoro-2,3,4,5a,6,7,8,9-octahydro-5H-1,2,5,7-tetraazabenzo[cd]azulene-5-carboxylate (450 mg, 1 equiv., 1.06 mmol) in DCM (10 mL) was added TEA (320 mg, 441 μL, 3 equiv., 3.17 mmol). The mixture was cooled to 0° C., then acryloyl chloride (191 mg, 171 μL, 2 equiv., 2.11 mmol) as added dropwise to the above mixture at 0° C. under nitrogen atmosphere. The mixture was wan ed to room temperature and stirred for 0.5 h. The reaction was monitored by LCMS. The mixture was diluted with ice water (20 mL) and EtOAc (20 mL), and the aqueous layer was extracted with EtOAc (2×20 mL). The combined organic layers were washed with saturated brine (2×20 mL), dried over anhydrous sodium sulfate and concentrated to give a residue. The residue was purified by flash column chromatography, eluting with EtOAc/PE (1:5) to afford tert-butyl (cis or trans)-7-acryloyl-2-(4-cyclobutylphenyl)-9-fluoro-2,3,4,5a,6,7,8,9-octahydro-5H-1,2,5,7-tetraazabenzo[cd]azulene-5-carboxylate (190 mg) as a light yellow solid. LCMS: (ESI, m/z): 481 $[M+H]^+$ Step 4: Synthesis of 1-(Cis or Trans)-(2-(4-cyclobutylphenyl)-9-fluoro-2, 3,4,5,5a,6,8,9-octahydro-7H-1,2,5,7-tetraazabenzo[cd]azulen-7-yl)prop-2-en-1-one The solution of tert-butyl (cis or trans)-7-acryloyl-2-(4-cyclobutylphenyl)-9-fluoro-2,3,4,5a,6,7,8,9-octahydro-5H-1,2,5,7-tetraazabenzo[cd]azulene-5-carboxylate (190 mg, 1 equiv., 395 μmol) in DCM (3 mL) and TFA (1 mL) was stirred at room temperature for 0.5 h. The reaction was monitored by LCMS. The solvent was removed under reduced pressure. This resulted in 1-(cis or trans)-(2-(4-cyclobutylphenyl)-9-fluoro-2,3,4,5,5a,6,8,9-octahydro-7H-1,2,5,7-tetraazabenzo[cd]azulen-7-yl)prop-2-en-1-one (150 mg) as a crude yellow oil. The crude product was used in the next step directly without further purification. LCMS: (ESI, m/z): 381 $[M+H]^+$ Step 5: Synthesis of 1-(Cis or Trans)-5-(7-bromo-1H-benzo[d]imidazole-4-carbonyl)-2-(4-cyclobutylphenyl)-9-fluoro-2,3,4,5,5a,6,8,9-octahydro-7H-1,2,5, 7-tetraazabenzo[cd]azulen-7-yl)prop-2-en-1-one To a solution of 1-(cis or trans)-(2-(4-cyclobutylphenyl)-9-fluoro-2,3,4,5,5a,6,8,9-octahydro-7H-1,2,5,7-tetraazabenzo[cd]azulen-7-yl)prop-2-en-1-one (150 mg, 1 equiv., 394 gmol) in DMF (3 mL) were added DIEA (510 mg, 687 μL, 10 equiv., 3.94 n-mol), HBTU (299 mg, 2 equiv., 788 gmol) and 7-bromo-1H-benzo[d]imidazole-4-carboxylic acid (114 mg, 1.2 equiv., 473 μmol). The mixture was stirred at room temperature for 0.5 h. The reaction was monitored by LCMS. The mixture was diluted with water (20 mL) and EtOAc (20 mL), and the aqueous layer was extracted with EtOAc (2×20 mL). The combined organic layers were washed with saturated brine (2×20 mL), dried over anhydrous sodium sulfate and concentrated to give a residue. The residue was purified by Prep-HPLC (Column: Sunfire C18 5 m, 30 mm*150 mm; Mobile Phase A: water (0.1% FA), Mobile Phase B: MeCN; Flow rate: 60 mL/min; Gradient: 42% B to 54% B in 10 min; Wave Length: UV 254 nm/220 nm; retention time 1: 9.3 min) to afford 1-(cis or trans)-5-(7-bromo-1H-benzo[d]imidazole-4-carbonyl)-2-(4-cyclobutylphenyl)-9-fluoro- 2,3,4,5,5a,6,8,9-octahydro-7H-1,2,5,7-tetraazabenzo[cd]azulen-7-yl)prop-2-en-1-one (48 mg) as a white solid.

The racemic compound was separated into constituent enantiomers by chiral HPLC separation under the following conditions (Column: CHIRALPAK-II 2*25 cm, 5 m; Mobile Phase A: HEX(0.1% FA), Mobile Phase B: MeOH: DCM=1: 1; Flow rate: 20 mL/min; Gradient: isocratic 45; Wave Length: UV 254/220 nm; retention time 1: 11.755; retention time 2: 13.28; Injection Volume: 1.0 mL; Number Of Runs: 5) to afford 1-((5a(S or R),9(S or R))-5-(7-bromo-1H-benzo[d]imidazole-4-carbonyl)-2-(4-cyclobutylphenyl)-9-fluoro-2,3,4,5,5a,6,8,9-octahydro-7H-1,2,5,7-tetraazabenzo[cd]azulen-7-yl)prop-2-en-1-one as the second eluted peak (retention time=13.3 min., 20.3 mg, 33.5 μmol, 42%, 99.6% purity) as a white solid. LCMS: (ESI, m/z):603, 605 $[M+H]^+$. $^1H$ NMR: (400 MHz, Chloroform-d, ppm) δ 8.49-8.03 (m, 1H), 7.62-7.43 (m, 1H), 7.42-7.29 (m, 2H), 7.31-7.16 (m, 3H), 6.94-6.27 (m, 1H), 6.04-5.54 (m, 2H), 5.45-5.21 (m, 1H), 5.21-4.96 (m, 1H), 4.73-3.67 (m, 2H), 3.67-3.46 (m, 1H), 3.36-2.87 (m, 3H), 2.84-2.54 (m, 1H), 2.51-2.28 (m, 2H), 2.24-1.96 (m, 3H), 1.94-1.79 (m, 1H).

Example C-11: Preparation of (S or R)-1-(5-(1-chloroimidazo[1,5-a]pyridine-6-carbonyl)-2-(4-cyclobutylphenyl)-2,3,4,5,5a,6,8,9-octahydro-7H-1,2,5,7-tetraazabenzo[cd]azulen-7-yl)prop-2-en-1-one
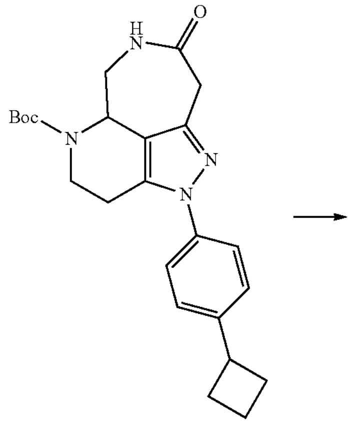
Int. R
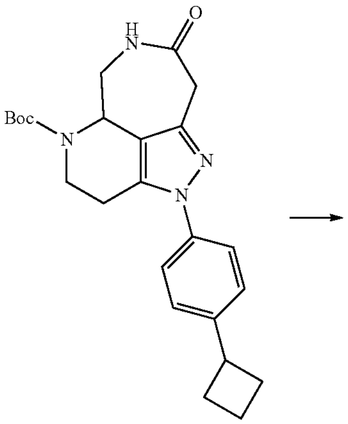
Int. R-1
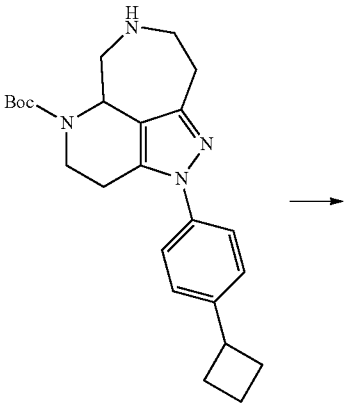
Int. S-1
-continued
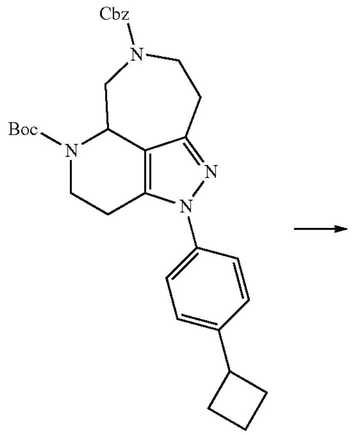
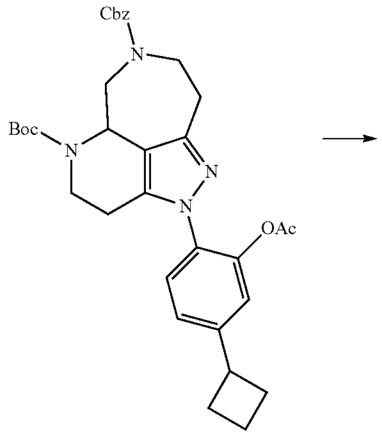
Int. S'-1
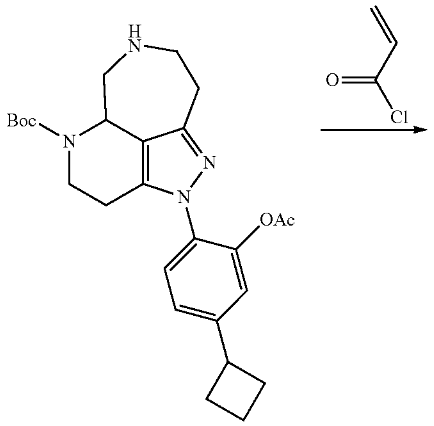

-continued

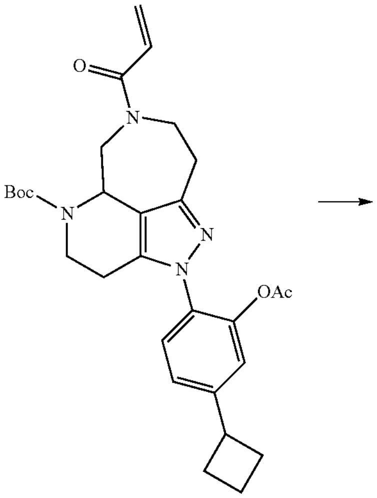

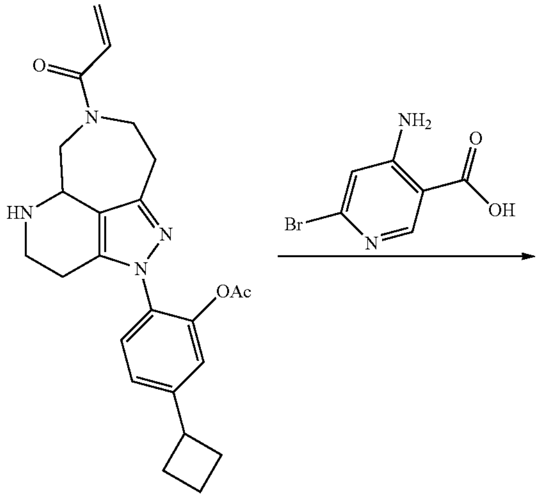

Int. Z-1

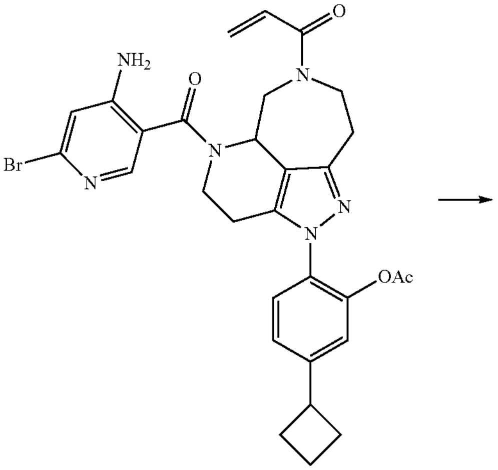

-continued

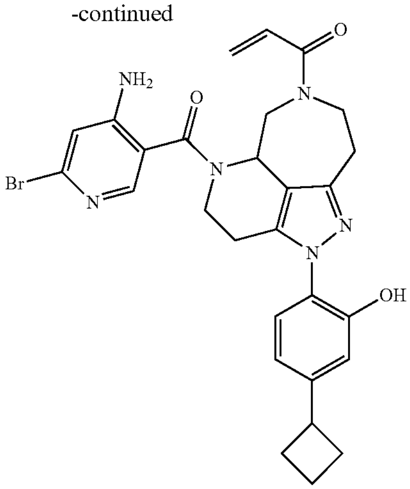

Step 1. Synthesis of Tert-Butyl (S or R)-2-(4-cyclobutylphenyl)-8-oxo-2, 3,4,5a,6,7,8,9-octahydro-5H-1,2,5,7-tetraazabenzo[cd]azulene-5-carboxylate (Int. R-1)

The racemic m t. R (145 g, 333 mmol) was separated by chiral SEC (column: DAICEL CHIRALPAK IC (250 mm 50 mm, 0 um); mobile phase: [C02 (Phase A)-MeOH (Phase B) (0.1% NH3·H2O)]; B %: 40%, isocratic elution mode) to provide Int. R-1 as the second-eluting peak (68.8 g) as an off-white solid. LCMS: (ESI, m/z): 423 $[M+1]^+$. $^1H$ NMR: (400 MHz, $CDCl_3$) δ ppm 7.34-7.40 (m, 2H) 7.28-7.33 (m, 2H) 6.23 (br s, 1H) 4.87 (br d, J=9.63 Hz, 1H) 4.40 (br d, J=11.01 Hz, 1H) 3.91-4.04 (m, 2H) 3.59 (quin, J=8.57 Hz, 2H) 3.43-3.53 (m, 1H) 2.84-2.95 (m, 1H) 2.67-2.78 (m, 2H) 2.38 (q, J=8.25 Hz, 2H) 2.09-2.23 (m, 2H) 1.98-2.09 (m, 1H) 1.82-1.93 (m, 1H) 1.53 (s, 9H). Analytical chiral SFC: Column-Chiralpak IK 50×4.6 mm I.D., 3 μm; mobile phase: [$CO_2$(Phase A)-MeOH (0.05% DEA) (Phase B)]; 40% B isocratic elution; Flow rate: 3 mL/min Int. R-1 is the second-eluting peak (RT(min)=1.8 min). (the undesired enantiomer is the first eluting peak; RT (min)=1.3 min).

Step 2: Synthesis of Tert-Butyl (S or R)-2-(4-cyclobutylphenyl)-2,3,4,5a,6,7,8,9-octahydro-5H-1,2,5,7-tetraazabenzo[cd]azulene-5-carboxylate (Int. S-1)

To a solution of Int. R-1 (16.00 g, 1 equiv., 37.87 mmol) in THF (160 mL) was added BH3·THF (13.02 g, 4 equiv., 151.5 mmol). The mixture was then heated and stirred at 60° C. for 1 h, after which the reaction mixture was cooled to −78° C. and quenched with MeOH (120 ml). The mixture was then warmed to rt and stirred for 1 h. The solvent was then removed under reduced pressure. To afford tert-butyl (S or R)-2-(4-cyclobutylphenyl)-2,3,4,5a,6,7,8,9-octahydro-5H-1,2,5,7-tetraazabenzo[cd]azulene-5-carboxylate (Int. S-1) (20 g) as a yellow solid which was used in the next step without further purification. LCMS:(ESI, m/z): 409 $[M+1]^+$ Step 3: Synthesis of 7-benzyl 5-(tert-butyl) (R or S)-2-(4-cyclobutylphenyl)-3,4,5a,6,8,9-hexahydro-2H-1,2,5,7-tetraazabenzo[cd]azulene-5,7-dicarboxylate To a solution of tert-butyl (R or S)-2-(4-cyclobutylphenyl)-2,3,4,5a,6,7,8,9-octahydro-5H-1,2,5,7-tetraazabenzo

[cd]azulene-5-carboxylate (19.4 g, 1 equiv., 47.5 mmol) in DCM (200 mL) were added Cbz-OSu (47.3 g, 4 equiv., 190 mmol) and TEA (33.64 g, 7 equiv., 332 mmol). The mixture was then stirred at 40° C. for 12 h. The mixture was then diluted with ice water (100 mL) and EA (200 mL), and the aqueous layer was extracted with EA (2×300 mL). The combined organic layers were washed with saturated brine (2×100 mL), dried over anhydrous sodium sulfate and concentrated to give a residue. The residue was purified by flash column chromatography, eluting with EA/PE (1:3) to afford a white solid. The residue was then purified by revered phase flash column chromatography, eluting with ACN/water (100%) to afford 7-benzyl 5-(tert-butyl) (R or S)-2-(4-cyclobutylphenyl)-3,4,5a,6,8,9-hexahydro-2H-1,2,5,7-tetraazabenzo[cd]azulene-5,7-dicarboxylate (17.3 g) as a white solid. LCMS:(ESI, m/z): 543 $[M+1]^+$ Step 4: Synthesis of 7-benzyl 5-(tert-butyl) (R or S)-2-(2-acetoxy-4-cyclobutylphenyl)-3,4,5a,6,8,9-hexahydro-2H-1,2,5,7-tetraazabenzo[cd]azulene-5,7-dicarboxylate To a solution of 7-benzyl 5-(tert-butyl) (R or S)-2-(4-cyclobutylphenyl)-3,4,5a,6,8,9-hexahydro-2H-1,2,5,7-tetraazabenzo[cd]azulene-5,7-dicarboxylate (16.0 g, 1 equiv., 29.5 mmol) in AcOH (240 mL) were added PIDA (19.0 g, 2 equiv., 59.0 mmol) and $Pd(OAc)_2$ (1.32 g, 0.2 equiv., 5.9 mmol). The reaction system with was then purged with $N_2$ replacement (×3). The resulting mixture was stirred for 3 hour at 90° C. under a $N_2$ atmosphere. The mixture was then diluted with ice water (100 mL), and subsequently acidified to pH=7-8 with saturated $Na_2CO_3$, then diluted with EA (500 mL) and water (200 mL), and the aqueous layer was extracted with EA (2×300 mL). The organic layers were combined and washed with saturated brine (200 mL), dried over anhydrous sodium sulfate and concentrated to give a residue. The residue was purified by flash column chromatography, eluting with EA/PE (1:1) to afford 7-ben yl 5-(tert-butyl) (R or S)-2-(2-acetoxy-4-cyclobutylphenyl)-3,4,5a,6,8,9-hexahydro-2H-1,2,5,7-tetraazabenzo[cd]azulene-5,7-dicarboxylate (9.3 g) as a yellow solid. LCMS:(ESI, m/z): 601 $[M+1]^+$ Step 5: Synthesis of Tert-Butyl (R or S)-2-(2-acetoxy-4-cyclobutylphenyl)-2,3,4,5a,6,7,8,9-octahydro-5H-1,2,5,7-tetraazabenzo[cd]azulene-5-carboxylate To a solution of 7-benzyl 5-(tert-butyl) (R or S)-2-(2-acetoxy-4-cyclobutylphenyl)-3,4,5a,6,8,9-hexahydro-2H-1,2,5,7-tetraazabenzo[cd]azulene-5,7-dicarboxylate (8.10 g, 1 equiv., 13.5 mmol) in 1,4-dioxane (81 mL) were added $Pd(OH)_2$ (4.05 g, 1.18 mL, 20% Wt, 0.428 equiv., 5.77 mmol) and Pd/C (4.05 g, 10% Wt, 0.282 equiv., 3.81 mmol). The mixture was purged with $N_2$ (×3) and then was pressurized to 4.0 MPa with hydrogen at rt and stirred for 2 h. The reaction mixture was then cooled to rt, and the mixture was, filtered and rinsed with DCM (5×400 mL). The filtrate was concentrated in vacuo to give tert-butyl (or S)-2-(2-acetoxy-4-cyclobutylphenyl)-2,3,4,5a,6,7,8,9-octahydro-5H-1,2,5,7-tetraazabenzo[d]azulene-5-carboxylate (6.4 g) as a brown solid which was used in the next step directly without further purification. LCMS:(ESI, m/z): 467 $[M+1]^+$ Step 6: Synthesis of Tert-Butyl (R or S)-2-(2-acetoxy-4-cyclobutylphenyl)-7-acryloyl-2,3,4,5a,6,7,8,9-octahydro-5H-1, 2,5,7-tetraazabenzo[cd]azulene-5-carboxylate To a solution of tert-butyl (R or S)-2-(2-acetoxy-4-cyclobutylphenyl)-2,3,4,5a,6,7,8,9-octahydro-5H-1,2,5,7-tetraazabenzo[cd]azulene-5-carboxylate (5.40 g, 1 equiv., 11.6 mmol) in DCM (40 mL) was added TEA (2.34 g, 3.23 mL, 2 equiv., 23.1 mmol). The mixture was cooled to 0° C., then acryloyl chloride (1.05 g, 1 equiv., 11.6 mmol) was added dropwise at 0° C. The mixture was then stirred for 1 h at 0° C., after which the mixture was diluted with ice water (100 mL) and EA (100 mL), and the aqueous layer was extracted with EA (2×100 mL). The combined organic layers were washed with saturated brine (2×50 mL), dried over anhydrous sodium sulfate and concentrated to give a residue. The residue was purified by flash column chromatography, eluting with EA/PE (1:1) to afford tert-butyl (R or S)-2-(2-acetoxy-4-cyclobutylphenyl)-7-acryloyl-2,3,4,5a,6,7,8,9-octahydro-5H-1,2,5,7-tetraazabenzo[cd]azulene-5-carboxylate (4.5 g) as a yellow solid. LCMS:(ESI, m/z): 521 $[M+1]^+$. 1H NMR (400 MHz, Chloroform-d) δ 7.24 (s, 1H), 7.17-7.12 (m, 1H), 7.06 (d, J=1.8 Hz, 1H), 6.76-6.08 (m, 2H), 5.89-5.69 (m, 1H), 4.92 (dd, J=10.6, 6.5 Hz, 1H), 4.39 (s, 1H), 4.25 (d, J=13.5 Hz, 1H), 3.59 (p, J=8.6 Hz, 1H), 3.29-2.90 (m, 3H), 2.82-2.54 (m, 3H), 2.51-2.28 (m, 3H), 2.22-2.12 (m, 2H), 2.10 (s, 3H), 2.07-1.98 (m, 2H), 1.92-1.83 (m, 1H), 1.58-1.55 (m, 9H).

Step 7: Synthesis of (R or S)-2-(7-acryloyl-3,4,5,5a,6,7,8,9-octahydro-2-1,2,5,7-tetraazabenzo[cd]azulen-2-yl)-5-cyclobutylphenyl acetate (Int. Z-1)

To a solution of tert-butyl (R or S)-2-(2-acetoxy-4-cyclobutylphenyl)-7-acryloyl-2,3,4,5a,6,7,8,9-octahydro-5H-1,2,5,7-tetraazabenzo[cd]azulene-5-carboxylate (500 mg, 1 equiv., 960 μmol) in DCM (5 mL) was added TFA (1 mL). The mixture was stirred for 2 hour at rt, after which the resulting mixture was concentrated under reduced pressure to afford (R or S)-2-(7-acryloyl-3,4,5,5a,6,7,8,9-octahydro-2H-1,2,5,7-tetraazabenzo[cd]azulen 2-yl)-5-cyclobutylphenyl acetate (Int. Z-1) (380 mg) as a yellow oil which as used in the next step directly without further purification. LCMS: (ESI, m/z): 421 $[M+1]^+$ Step 8: Synthesis of (R or S)-2-(7-acryloyl-S-(4-amino-6-bromonicotinoyl)-3,4,5,5a,6,7,8,9-octahydro-2H-1,2,5,7-tetraazabenzo[cd]azulen-2-yl)-5-cyclobutylphenyl acetate To a stirred solution of (R or S)-2-(7-acryloyl-3,4,5,5a,6,7,8,9-octahydro-2H-1,2,5,7-tetraazabenzo[cd]azulen-2-yl)-5-cyclobutylphenyl acetate (45 mg, 1 equiv., 0.11 mmol) in DMF (1 mL) was added 4-amino-6-bromonicotinic acid (28 mg, 1.2 equiv., 0.13 mmol), HATU (61 mg, 1.5 equiv., 0.16 mmol) and DIEA (41 mg, 56 μL, 3 equiv., 0.32 mmol) at rt and the resulting solution was stirred for 1 h. The resulting mixture was then extracted with EA (2×20 mL), and the combined organic layers were washed with brine (2×20 mL), dried over anhydrous $Na_2SO_4$, and filtered. The filtrate was concentrated under reduced pressure to afford (R or S)-2-(7-acryloyl-5-(4-amino-6-bromonicotinoyl)-3,4,5,5a,6,7,8,9-octahydro-2H-1,2,5,7-tetraazabenzo[cd]azulen-2-yl)-5-cyclobutylphenyl acetate (70 mg) as a brown oil which was use in the next step without further purification. LCMS: (ESI, m/z): 619 $[M+1]^+$ Step 9: Synthesis of (R or S)-1-(5-(4-amino-6-bromonicotinoyl)-2-(4-cyclobutyl-2-hydroxyphenyl)-2,3,4,5,5a,6,8,9-octahydro-7H-1,2,5,7-tetraazabenzo[cd]azulen-7-yl)prop-2-en-1-one To a stirred solution of (R or S)-2-(7-acryloyl-5-(4-amino-6-bromonicotinoyl)-3,4,5,5a,6,7,8,9-octahydro-2H-1,2,5,7- tetraazabenzo[cd]azulen-2-yl)-5-cyclobutylphenyl acetate (50 mg, 1 equiv, 81 μmol) in THF (1 mL) and $H_2O$ (1 mL) was added LiOH (5.8 mg, 3 equiv., 0.24 mmol) at rt. The mixture was then stirred for 1 h, after which the resulting mixture was extracted with EA (2×20 mL). The combined organic layers were washed with semi-saturated brine (5×10 mL) and dried over anhydrous $Na_2SO_4$. After filtration, the filtrate was concentrated under reduced pressure, and the residue was purified by reversed-phase flash chromatography with these conditions: (Column: Xselect CSH™ Prep C18 5 μm 30*150 mm OBD; Mobile Phase A: Water (0.1% FA), Mobile Phase B: ACN; Flow rate: 60 mL/min; Gradient: 25% B to 60% B in 10 min). This afforded (R or S)-1-(5-(4-amino-6-bromonicotinoyl)-2-(4-cyclobutyl-2-hydroxyphenyl)-2,3,4,5,5a,6,8,9-octahydro-7H-1,2,5,7-tetraazabenzo[c]azulen-7-yl)prop-2-en-1-one (3.1 mg) as a white solid. LCMS:(ESI, m/z): 579 $[M+1]^+$. $^1H$ NMR: (400 MHz, Chloroform-d, ppm) δ 10.07 (s, 1H), 7.96 (s, 1H), 7.33 (s, 1H), 6.92 (s, 2H), 6.81 (s, 1H), 6.67 (d, J=7.7 Hz, 1H), 6.44 (d, J=16.3 Hz, 1H), 5.79 (d, J=10.2 Hz, 1H), 5.52-5.01 (m, 3H), 4.90 (d, J=13.1 Hz, 1H), 4.40 (s, 1H), 4.15 (s, 1H), 3.45 (t, J=8.8 Hz, 1H), 3.18-2.95 (m, 5H), 2.82-2.63 (m, 2H), 2.32-2.22 (m, 2H), 2.09 (q, J=9.8 Hz, 2H), 1.96 (t, J=9.4 Hz, 1H), 1.80 (t, J=9.3 Hz, 1H).

TABLE C4

The compounds of Examples C-11-1 through C-11-11 were prepared in an analogous fashion to Example C-11, using the corresponding acids in place of Acid A in the final steps, with the following adjustments. Examples C-11-3 and C-11-11: In these examples, EDC and HOBT were used in the place of HATU. Examples C-11-7 and C-11-10: In these examples, HBTU was used in the place of HATU in the amide coupling step.

| Example No. | Structure and Name | LCMS (ESI, m/z) | NMR |
|---|---|---|---|
| C-11-1 | 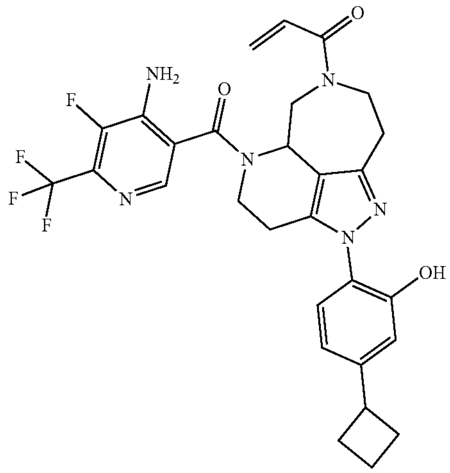 [SMILES: C=CC(=O)N1CCc2nn(-c3ccc(C4CCC4)cc3O)c3c2C(C1)N(C(=O)c1cnc(C(F)(F)F)c(F)c1N)CC3] (R or S)-1-(5-(4-amino-5-fluoro-6-(trifluoromethyl)nicotinoyl)-2-(4-cyclobutyl-2-hydroxyphenyl)-2,3,4,5,5a,6,8,9-octahydro-7H-1,2,5,7-tetraazabenzo[cd]azulen-7-yl)prop-2-en-1-one | 585 $[M + H]^+$ | $^1H$ NMR: (400 MHz, Chloroform-d, ppm) δ 10.08 (s, 1H), 8.17 (s, 1H), 7.37 (s, 1H), 7.03-6.92 (m, 2H), 6.80-6.70 (m, 1H), 6.58-6.42 (m, 1H), 5.93-5.76 (m, 1H), 5.60-5.35 (m, 3H), 4.97 (d, J = 13.4 Hz, 1H), 4.49 (d, J = 13.5 Hz, 1H), 4.29-4.11 (m, 1H), 3.52 (p, J = 8.6 Hz, 1H), 3.32-2.95 (m, 5H), 2.91-2.70 (m, 2H), 2.41-2.28 (m, 2H), 2.23-1.95 (m, 3H), 1.91-1.81 (m, 1H). |
| C-11-2 | 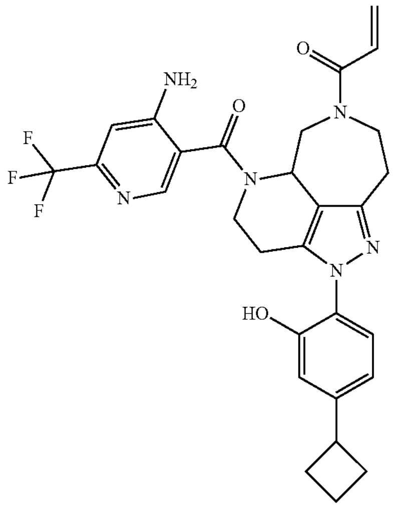 [SMILES: C=CC(=O)N1CCc2nn(-c3ccc(C4CCC4)cc3O)c3c2C(C1)N(C(=O)c1cnc(C(F)(F)F)cc1N)CC3] | 567 $[M + H]^+$ | $^1H$ NMR: (400 MHz, Chloroform-d, ppm) δ 10.01 (s, 1H), 8.19 (s, 1H), 7.51 (s, 1H), 7.20-6.29 (m, 7H), 5.79 (s, 1H), 5.16 (s, 1H), 4.67 (s, 1H), 4.43 (s, 1H), 3.66-2.77 (m, 8H), 2.45-2.17 (m, 3H), 2.13-1.88 (m, 3H), 1.80 (q, J = 9.2 Hz, 1H). |

TABLE C4-continued

The compounds of Examples C-11-1 through C-11-11 were prepared in an analogous fashion to Example C-11, using the corresponding acids in place of Acid A in the final steps, with the following adjustments. Examples C-11-3 and C-11-11: In these examples, EDC and HOBT were used in the place of HATU. Examples C-11-7 and C-11-10: In these examples, HBTU was used in the place of HATU in the amide coupling step.

| Example No. | Structure and Name | LCMS (ESI, m/z) | NMR |
|---|---|---|---|
| | (R or S)-1-(5-(4-amino-6-(trifluoromethyl)nicotinoyl)-2-(4-cyclobutyl-2-hydroxyphenyl)-2,3,4,5,5a,6,8,9-octahydro-7H-1,2,5,7-tetraazabenzo[cd]azulen-7-yl)prop-2-en-1-one | | |
| C-11-3 | 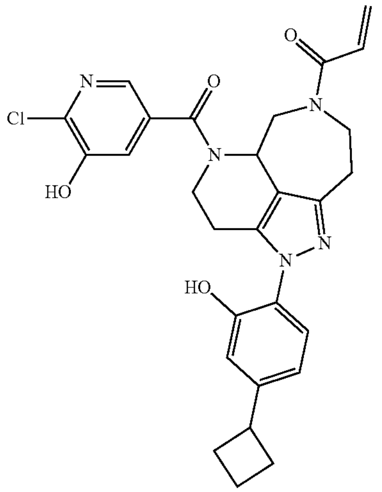 [SMILES: C=CC(=O)N1CCc2nn(-c3ccc(C4CCC4)cc3O)c3c2C(C1)N(C(=O)c1cnc(Cl)c(O)c1)CC3] (R or S)-1-(5-(6-chloro-5-hydroxynicotinoyl)-2-(4-cyclobutyl-2-hydroxyphenyl)-2,3,4,5,5a,6,8,9-octahydro-7H-1,2,5,7-tetraazabenzo[cd]azulen-7-yl)prop-2-en-1-one | 534 [M + H]$^+$ | $^1$H NMR (400 MHz, DMSO-$d_6$, ppm) δ 11.11-10.89 (m, 1H), 9.98 (s, 1H), 8.03-7.98 (m, 1H), 7.41 (t, J = 11.2 Hz, 2H), 7.21 (d, J = 8.1 Hz, 1H), 6.86 (s, 1H), 6.78-6.74 (m, 1H), 6.28 (d, J = 16.4 Hz, 1H), 5.78 (t, J = 9.6 Hz, 1H), 5.13 (s, 1H), 4.67 (s, 1H), 4.29 (d, J = 14.1 Hz, 1H),3.83-3.69 (m, 1H),3.61-3.52 (m, 1H), 3.28-3.09 (m, 2H);2.81 (d, J = 13.9 Hz, 3H), 2.49-2.38 (m, 1H), 2.35-2.23 (m, 2H), 2.01-1.92 (m, 3H), 1.80 (q, J = 10.4, 9.5 Hz, 1H), 1.17 (t, J = 7.3 Hz, 1H). |
| C-11-4 | 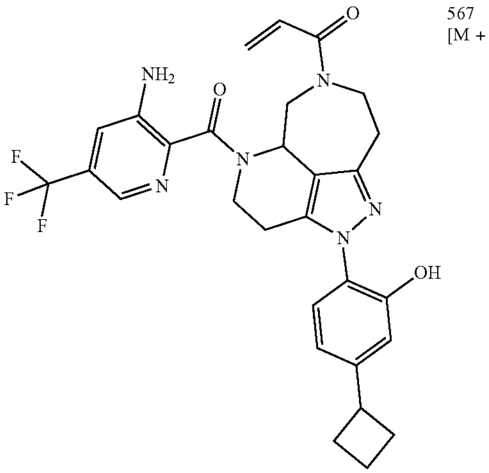 (R or S)-1-(5-(3-amino-5-(trifluoromethyl)picolinoyl)-2-(4-cyclobutyl-2-hydroxyphenyl)-2,3,4,5,5a,6,8,9-octahydro-7H-1,2,5,7-tetraazabenzo[cd]azulen-7-yl)prop-2-en-1-one | 567 [M + H]$^+$ | $^1$H NMR: (400 MHz, Chloroform-d, ppm) δ 10.54-9.40 (m, 1H), 8.24 (s, 1H),7.54-6.50 (m, 7H), 5.93-4.28 (m, 7H), 3.61-2.62 (m, 7H), 2.40-1.77 (m, 6H). |

TABLE C4-continued

The compounds of Examples C-11-1 through C-11-11 were prepared in an analogous fashion to Example C-11, using the corresponding acids in place of Acid A in the final steps, with the following adjustments. Examples C-11-3 and C-11-11: In these examples, EDC and HOBT were used in the place of HATU. Examples C-11-7 and C-11-10: In these examples, HBTU was used in the place of HATU in the amide coupling step.

| Example No. | Structure and Name | LCMS (ESI, m/z) | NMR |
|---|---|---|---|
| C-11-5 | 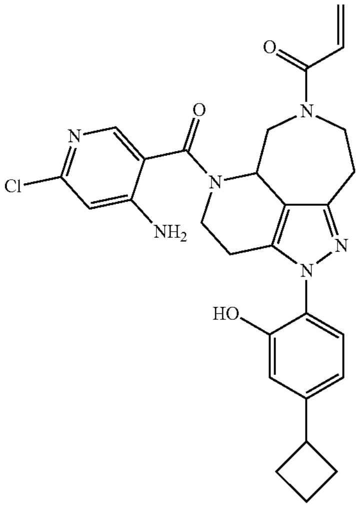 [SMILES: C=CC(=O)N1CCc2nn(-c3ccc(C4CCC4)cc3O)c3c2C(C1)N(C(=O)c1cnc(Cl)cc1N)CC3] (S or R)-1-(5-(4-amino-6-chloronicotinoyl)-2-(4-cyclobutyl-2-hydroxyphenyl)-2,3,4,5,5a,6,8,9-octahydro-7H-1,2,5,7-tetraazabenzo[cd]azulen-7-yl)prop-2-en-1-one | 533 [M + H]$^+$ | $^1$H NMR: (400 MHz, DMSO-$d_6$, ppm) δ 9.97 (s, 1H), 7.88 (s, 1H), 7.49 (s, 1H), 7.20 (d, J = 8.1 Hz, 1H), 6.85 (d, J = 1.9 Hz, 1H), 6.76 (dd, J = 8.2, 1.9 Hz, 1H), 6.67 (s, 1H), 6.51 (s, 2H), 6.28 (d, J = 16.4 Hz, 1H), 5.76 (d, J = 8.0 Hz, 1H), 5.13 (s, 1H), 4.66 (d, J = 8.4 Hz, 1H), 4.39 (s, 1H), 3.92-3.36 (m, 4H), 3.20-3.04 (m, 1H), 2.96-2.70 (m, 3H), 2.40 (d, J = 15.4 Hz, 1H), 2.34-2.18 (m, 2H), 2.16-1.86 (m, 3H), 1.86-1.74 (m, 1H). |
| C-11-6 | 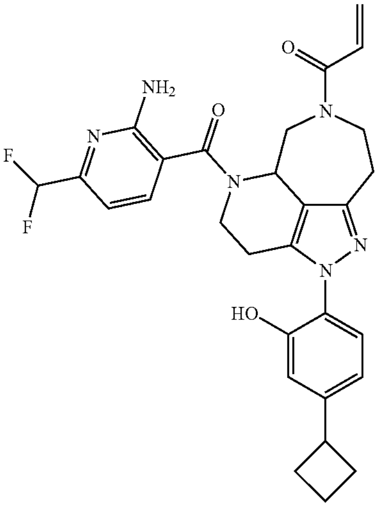 [SMILES: C=CC(=O)N1CCc2nn(-c3ccc(C4CCC4)cc3O)c3c2C(C1)N(C(=O)c1ccc(C(F)F)nc1N)CC3] (S or R)-1-(5-(2-amino-6-(difluoromethyl)nicotinoyl)-2-(4-cyclobutyl-2-hydroxyphenyl)-2,3,4,5,5a,6,8,9-octahydro-7H-1,2,5,7-tetraazabenzo[cd]azulen-7-yl)prop-2-en-1-one | 549 [M + H]$^+$ | $^1$H NMR: (400 MHz, Chloroform-d, ppm) δ 10.13 (s, 1H), 7.55 (d, J = 7.6 Hz, 1H), 7.39 (s, 1H), 7.06 (s, 1H), 6.99 (dd, J = 5.1, 3.1 Hz, 2H), 6.73 (dd, J = 8.2, 2.0 Hz, 1H), 6.63-6.30 (m, 2H), 5.97-5.71 (m, 1H), 5.40 (s, 1H), 5.29 (s, 2H), 5.05-4.71 (m 1H), 4.45 (s, 1H), 4.28-3.96 (m, 1H), 3.52 (p, J = 8.6 Hz, 1H), 3.33-2.98 (m, 5H), 2.87-2.68 (m, 2H), 2.34 (qt, J = 7.5, 2.4 Hz, 2H), 2.22-2.08 (m, 2H), 2.07-1.96 (m, 1H), 1.93-1.80 (m, 1H). |

TABLE C4-continued

The compounds of Examples C-11-1 through C-11-11 were prepared in an analogous fashion to Example C-11, using the corresponding acids in place of Acid A in the final steps, with the following adjustments. Examples C-11-3 and C-11-11: In these examples, EDC and HOBT were used in the place of HATU. Examples C-11-7 and C-11-10: In these examples, HBTU was used in the place of HATU in the amide coupling step.

| Example No. | Structure and Name | LCMS (ESI, m/z) | NMR |
|---|---|---|---|
| C-11-7 | 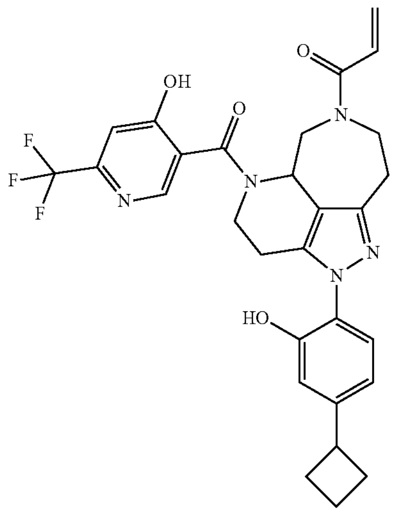 [SMILES: C=CC(=O)N1CCc2nn(-c3ccc(C4CCC4)cc3O)c3c2C(C1)N(C(=O)c1cnc(C(F)(F)F)cc1O)CC3] (S or R)-1-(2-(4-cyclobutyl-2-hydroxyphenyl)-5-(4-hydroxy-6-(trifluoromethyl)nicotinoyl)-2,3,4,5,5a,6,8,9-octahydro-7H-1,2,5,7-tetraazabenzo[cd]azulen-7-yl)prop-2-en-1-one | 568 $[M + H]^+$ | $^1H$ NMR: (400 MHz, DMSO-$d_6$, ppm) δ 12.16 (s, 1H), 9.98 (s, 1H), 8.55 (s, 1H), 7.45 (dd, J = 16.5, 10.5 Hz, 1H), 7.29 (s, 1H), 7.21 (d, J = 8.1 Hz, 1H), 6.84 (s, 1H), 6.76 (d, J = 8.3 Hz, 1H), 6.29 (dd, J = 16.6, 2.4 Hz, 1H), 5.83-5.73 (m, 1H), 5.18 (d, J = 10.2 Hz, 1H), 4.68 (d, J = 7.0 Hz, 1H), 4.28 (d, J = 13.3 Hz, 1H), 4.11 (s, 1H),3.20-3.13 (m, 3H)2.84 (t, J = 12.0 Hz, 3H), 2.35-2.24 (m, 3H), 2.07 (s, 1H), 2.07-1.90 (m, 3H), 1.81 (t, J = 8.9 Hz, 1H). |
| C-11-8 | 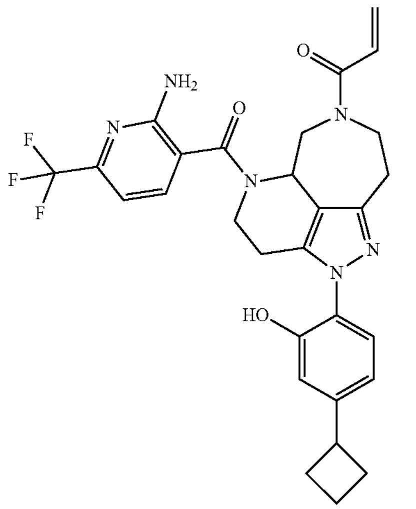 (R or S)-1-(5-(2-amino-6-(trifluoromethyl)nicotinoyl)-2-(4-cyclobutyl-2-hydroxyphenyl)-2,3,4,5,5a,6,8,9-octahydro-7H-1,2,5,7-tetraazabenzo[cd]azulen-7-yl)prop-2-en-1-one | 563 $[M + H]^+$ | $^1H$ NMR: (400 MHz, Chloroform-d, ppm) δ 10.12 (s, 1H), 7.51 (d, J = 7.4 Hz, 1H), 7.26 (s, 1H), 7.05 (d, J = 7.5 Hz, 1H), 7.02-6.94 (m, 2H), 6.78-6.70 (m, 1H), 6.56-6.43 (m, 1H), 5.96-5.68 (m, 1H), 5.49-5.15 (m, 2H), 4.96 (d, J = 13.1 Hz, 1H), 4.45 (s, 1H), 4.30-3.95 (m, 1H), 3.51 (p, J = 8.6 Hz, 1H), 3.27-2.92 (m, 5H), 2.88-2.65 (m, 2H), 2.41-2.26 (m, 2H), 2.21-2.07 (m, 2H), 2.06-1.90 (m, 4H), 1.89-1.79 (m, 2H). |

TABLE C4-continued

The compounds of Examples C-11-1 through C-11-11 were prepared in an analogous fashion to Example C-11, using the corresponding acids in place of Acid A in the final steps, with the following adjustments. Examples C-11-3 and C-11-11: In these examples, EDC and HOBT were used in the place of HATU. Examples C-11-7 and C-11-10: In these examples, HBTU was used in the place of HATU in the amide coupling step.

| Example No. | Structure and Name | LCMS (ESI, m/z) | NMR |
|---|---|---|---|
| C-11-9 | 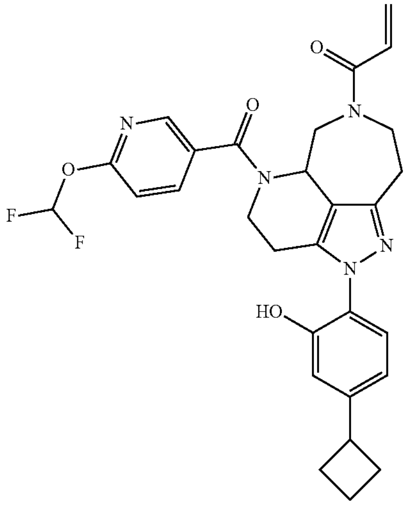 [SMILES: C=CC(=O)N1CCc2nn(-c3ccc(C4CCC4)cc3O)c3c2C(C1)N(C(=O)c1ccc(OC(F)F)nc1)CC3] (R or S)-1-(2-(4-cyclobutyl-2-hydroxyphenyl)-5-(6-(difluoromethoxy)nicotinoyl)-2,3,4,5,5a,6,8,9-octahydro-7H-1,2,5,7-tetraazabenzo[cd]azulen-7-yl)prop-2-en-1-one | 550 [M + H]+ | $^1$H NMR: (400 MHz, Chloroform-d, ppm) δ 8.50-8.28 (m, 1H), 8.14-7.82 (m, 1H), 7.73-7.31 (m, 2H), 7.09-6.91 (m, 3H), 6.81-6.59 (m, 1H), 6.59-6.34 (m, 1H), 5.93-5.72 (m, 1H), 5.38 (s, 1H), 4.98 (d, J = 12.6 Hz, 1H), 4.82-4.43 (m, 1H), 4.29-3.90 (m, 1H), 3.56-3.38 (m, 1H), 3.30-2.96 (m, 5H), 2.94-2.67 (m, 2H), 2.42-2.28 (m, 2H), 2.14 (p, J = 9.6 Hz, 2H), 2.08-1.96 (m, 1H), 1.91-1.81 (m, 1H). |
| C-11-10 | 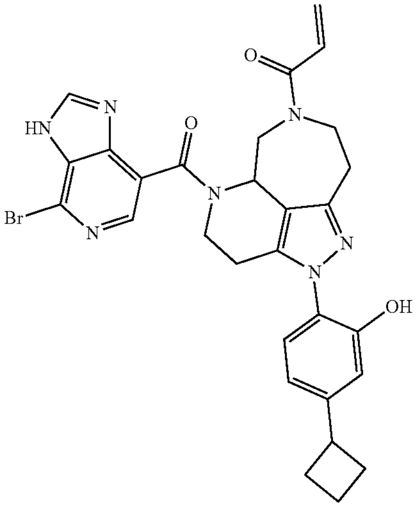 [SMILES: C=CC(=O)N1CCc2nn(-c3ccc(C4CCC4)cc3O)c3c2C(C1)N(C(=O)c1cnc(Br)c2[nH]cnc12)CC3] (R or S)-1-(5-(4-bromo-3H-imidazo[4,5-c]pyridine-7-carbonyl)-2-(4-cyclobutyl-2-hydroxyphenyl)-2,3,4,5,5a,6,8,9-octahydro-7H-1,2,5,7-tetraazabenzo[cd]azulen-7-yl)prop-2-en-1-one | 602 [M + H]+ | $^1$H NMR: (400 MHz, DMSO-$d_6$, ppm) δ 13.64 (s, 1H), 10.02 (s, 1H), 8.58 (s, 1H), 8.24 (s, 1H), 7.58-7.42 (m, 1H), 7.20 (d, J = 8.2 Hz, 1H), 6.84 (s, 1H), 6.75 (d, J = 8.0 Hz, 1H), 6.31 (d, J = 16.4 Hz, 1H), 5.80 (d, J = 10.3 Hz, 1H), 5.26 (d, J = 10.4 Hz, 1H), 4.69 (s, 1H), 4.43 (s, 1H), 3.89-3.67 (m, 1H), 3.51-3.45 (m, 2H), 3.18-3.13 (m, 2H),2.96-2.72 (m, 4H), 2.27 (d, J = 8.2 Hz, 2H), 2.07-1.96 (m, 3H), 1.79 (d, J = 9.3 Hz, 1H) |

TABLE C4-continued

The compounds of Examples C-11-1 through C-11-11 were prepared in an analogous fashion to Example C-11, using the corresponding acids in place of Acid A in the final steps, with the following adjustments. Examples C-11-3 and C-11-11: In these examples, EDC and HOBT were used in the place of HATU. Examples C-11-7 and C-11-10: In these examples, HBTU was used in the place of HATU in the amide coupling step.

| Example No. | Structure and Name | LCMS (ESI, m/z) | NMR |
|---|---|---|---|
| C-11-11 | 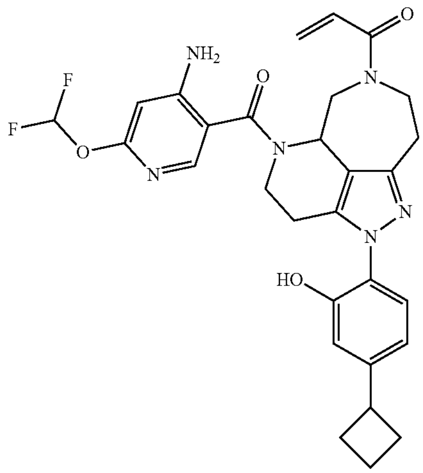 [SMILES: C=CC(=O)N1CCc2nn(-c3ccc(C4CCC4)cc3O)c3c2C(C1)N(C(=O)c1cnc(OC(F)F)cc1N)CC3] (R or S)-1-(5-(4-amino-6-(difluoromethoxy)nicotinoyl)-2-(4-cyclobutyl-2-hydroxyphenyl)-2,3,4,5,5a,6,8,9-octahydro-7H-1,2,5,7-tetraazabenzo[cd]azulen-7-yl)prop-2-en-1-one | 565 $[M+H]^+$ | $^1H$ NMR: (400 MHz, Chloroform-d, ppm) δ 10.16 (s, 1H), 7.92 (s, 1H), 7.52 (d, J = 7.6 Hz, 1H), 7.24 (s, 1H), 6.99 (dd, J = 5.1, 3.1 Hz, 2H), 6.74 (dd, J = 8.2, 1.9 Hz, 1H), 6.50 (d, J = 16.7 Hz, 1H), 6.20 (s, 1H), 5.91-5.75 (m, 1H), 5.37 (d, J = 10.4 Hz, 1H), 5.23 (s, 2H), 4.97 (d, J = 13.3 Hz, 1H), 4.64-4.13 (m, 2H), 3.52 (p, J = 8.7 Hz, 1H), 3.26-2.98 (m, 5H), 2.89-2.70 (m, 2H), 2.34 (tdt, J = 8.9, 7.7, 3.3 Hz, 2H), 2.22-1.95 (m, 3H), 1.92-1.81 (m, 1H). |
| C-11-12 | 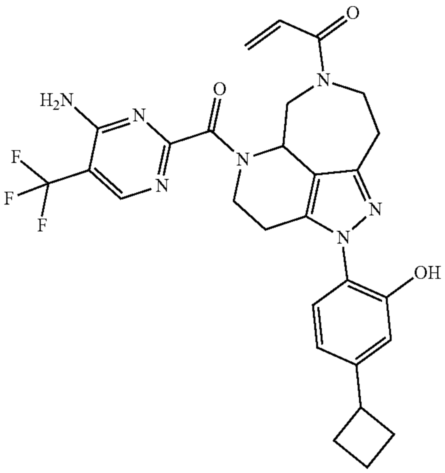 [SMILES: C=CC(=O)N1CCc2nn(-c3ccc(C4CCC4)cc3O)c3c2C(C1)N(C(=O)c1ncc(C(F)(F)F)c(N)n1)CC3] (R or S)-1-(5-(4-amino-5-(trifluoromethyl)pyrimidine-2-carbonyl)-2-(4-cyclobutyl-2-hydroxyphenyl)-2,3,4,5,5a,6,8,9-octahydro-7H-1,2,5,7-tetraazabenzo[cd]azulen-7-yl)prop-2-en-1-one | 568 $[M+H]^+$ | |

TABLE C5

| Example No. | Structure and Name | LCMS (ESI, m/z) | NMR |
|---|---|---|---|
| | The compounds of Examples C-12-1 and C-12-2 were prepared in an analogous fashion to Example C-5, from Intermediate S', except that the single-enantiomer Intermediate S'-1 from Example C-11 was used in place of Intermediate S' to provide the final compounds as single enantiomers. | | |
| C-12-1 | 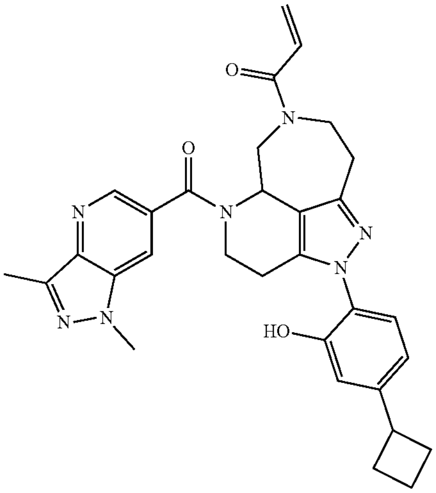 [SMILES: C=CC(=O)N1CCc2nn(-c3ccc(C4CCC4)cc3O)c3c2C(C1)N(C(=O)c1cnc2c(C)nn(C)c2c1)CC3] (R or S)-1-(2-(4-cyclobutyl-2-hydroxyphenyl)-5-(1,3-dimethyl-1H-pyrazolo[4,3-b]pyridine-6-carbonyl)-2,3,4,5,5a,6,8,9-octahydro-7H-1,2,5,7-tetraazabenzo[cd]azulen-7-yl)prop-2-en-1-one | 552 [M + H]$^+$ | $^1$H NMR: (400 MHz, DMSO-$d_6$, ppm) δ 10.02 (s, 1H), 8.57-8.31 (m, 2H), 7.51-6.28 (m, 5H), 5.81 (d, J = 9.9 Hz, 1H), 5.22 (s, 1H), 4.70 (s, 1H), 4.36-3.18 (m, 8H), 2.98-1.81 (m, 14H). |
| C-12-2 | 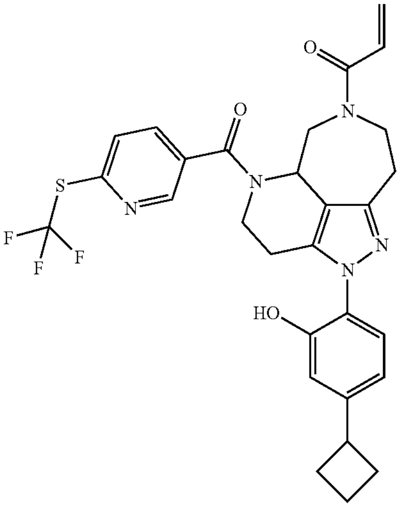 [SMILES: C=CC(=O)N1CCc2nn(-c3ccc(C4CCC4)cc3O)c3c2C(C1)N(C(=O)c1ccc(SC(F)(F)F)nc1)CC3] (R or S)-1-(2-(4-cyclobutyl-2-hydroxyphenyl)-5-(6-((trifluoromethyl)thio)nicotinoyl)-2,3,4,5,5a,6,8,9-octahydro-7H-1,2,5,7-tetraazabenzo[cd]azulen-7-yl)prop-2-en-1-one | 584 [M + H]$^+$ | $^1$H NMR: (400 MHz, Chloroform-d, ppm) δ 10.12 (s, 1H), 8.76-8.65 (m, 1H), 7.90-7.83 (m, 1H), 7.73-7.63 (m, 1H), 7.49-7.33 (m, 1H), 7.06-6.95 (m, 2H), 6.79-6.70 (m, 1H), 6.51 (d, J = 16.4 Hz, 1H), 5.94-5.73 (m, 1H), 5.43 5.37 (m, 1H), 5.03-4.68 (m, 1H), 4.58-4.17 (m, 1H), 4.03-3.96 (m, 1H), 3.58-3.45 (m, 1H), 3.33-2.93 (m, 5H), 2.92-2.67 (m, 2H), 2.41-2.27 (m, 2H), 2.21-1.77 (m, 4H). |

Example C-13: Preparation of (R or S)-1-(2-(4-cyclobutyl-2-hydroxyphenyl)-5-(7-(trifluoromethyl)-1H-pyrazolo[3,4-c]pyridine-4-carbonyl)-2,3,4,5,5a 6,8,9-octahydro-7H-1,2,5,7-tetraazabenzo[cd]azulen-7-yl)prop-2-en-1-one

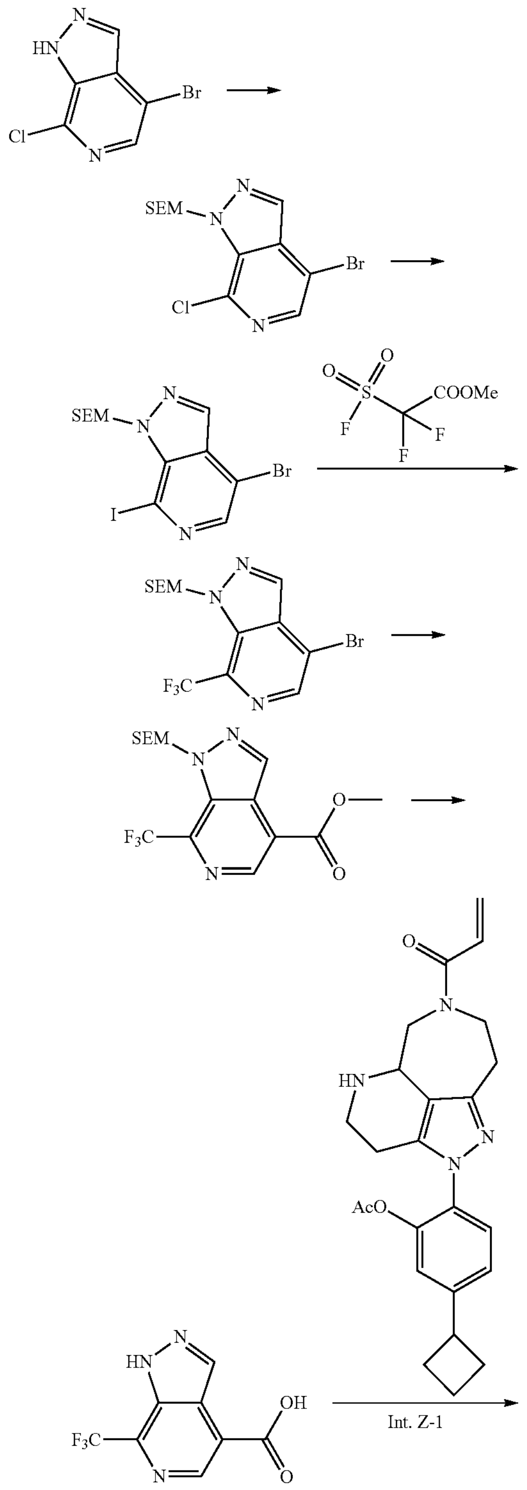

-continued

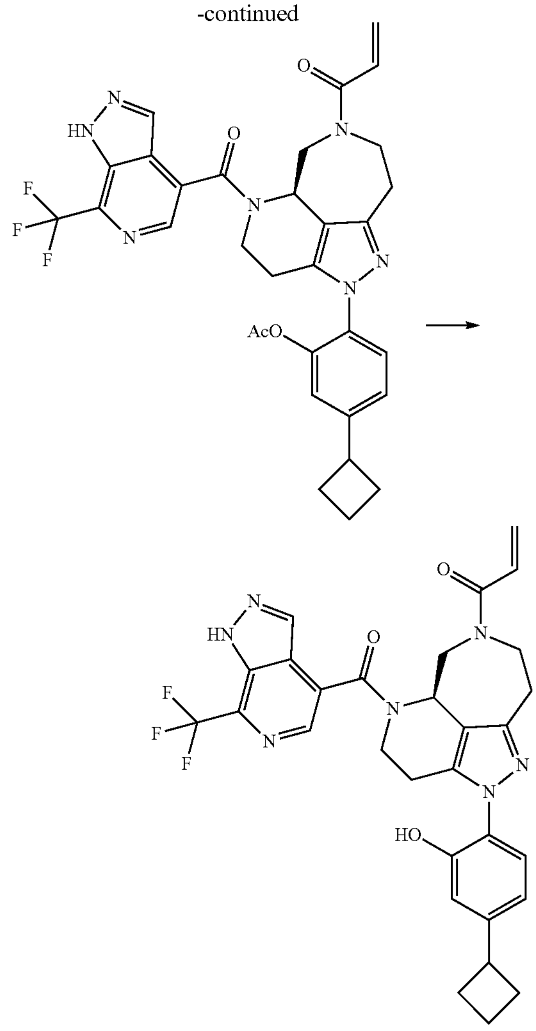

Step 1: Synthesis of 4-bromo-7-chloro-1-((2-(trimethylsilyl)ethoxy)methyl)-1H-pyrazolo[3,4-c]pyridine To a solution of 4-bromo-7-chloro-1H-pyrazolo[3,4-c] pyridine 4.5 g, 1.equiv., 19 mmol) in DMF (90 mL) were added NaH (0.56 g, 1.2 equiv., 23 mmol) at 0° C. and the resulting mixture was stirred for 30 min. To the mixture was then added SEM-Cl (3.9, 4.1 mL, 1.2 equiv., 23 mmol) and the mixture was further stirred at rt for 2 h. The reaction as then quenched by the addition of sat. $NH_4Cl$ (aq.) (100 mL), and the resulting mixture was extracted with EA (3×60 mL). The combined organic layers were washed with water (3×50 mL) and dried over anhydrous $Na_2SO_4$. After filtration, the filtrate was concentrated under reduced pressure. The residue was purified by silica gel column chromatography, eluting with PE/EA (1:1) to afford 4-bromo-7-chloro-1-((2-(trimethylsilyl)ethoxy)methyl)-1H-pyrazolo[3,4-c]pyridine (5.4 g) as a white solid. LCMS:(ESI, m/z): 362 $[M+1]^+$ Step 2: Synthesis of 4-bromo-7-iodo-J-((2-(trimethylsilyl)ethoxy)methyl)-1H-pyrazolo[3,4-c]pyridine To a solution of 4-bromo-7-chloro-1-((2-(trimethylsilyl) ethoxy) ethyl)-1H-pyrazolo[3,4-c]pyridine (5 g, 1 equiv., 0.01 mol) in MeCN (100 mL) were added iodotrimethylsilane solution (3 g, 2 mL, 1 equiv., 0.01 mol) and sodium iodide (6 g, 2 mL, 3 equiv. 0.04 mol). The reaction was then stirred for 3 h at rt. The reaction was quenched by the water (0 mL), and the resulting mixture was extracted with EA (3×60 mL). The combined organic layer were washed with water (3×30 mL) and dried over anhydrous $Na_2SO_4$. After filtration, the filtrate was concentrated under reduced pressure. The residue was purified by silica gel column chromatography, eluting with PE/EA (10:1) to afford 4-bromo-7-iodo-1-((2-(trimethylsilyl)ethoxy) ethyl)-1H-pyrazolo[3,4-c]pyridine (4.5 g) as a yellow solid. LCMS:(ESI, m/z): 454 $[M+1]^+$ Step 3: Synthesis of 4-bromo-7-(trifluoromethyl)-1-((2-(trimethylsilyl)ethoxy)methyl)-1H-pyrazolo[3,4-c]pyridine To a solution of 4-bromo-7-iodo-1-((2-(trimethylsilyl) ethoxy) ethyl)-1H-pyrazolo[3,4-c]pyridine (4 g, 1 equiv., 9 mmol) in DMF (24 mL) were added CuI (2 g, 1.2 equiv., 0.01 mol), methyl 2,2-difluoro-2-(fluorosulfonyl)acetate (8 g, 5 equiv., 0.04 mol) end HMPA (8 g, 8 mL, 5 equiv., 0.04 mol). The reaction was then stirred for 16 h at 60° C. The reaction was quenched by the addition of water (50 mL), and the resulting mixture was extracted with EA (3×50 mL). The combined organic layers were washed with brine (3×50 mL) and dried over anhydrous $Na_2SO_4$. After filtration, the filtrate was concentrated under reduced pressure. The residue was purified by silica gel column chromatography, eluting with PE/EA (3:1) to afford 4-bromo-7 -(trifluoromethyl)-1-((2-(trimethylsilyl)ethoxy)methyl)-1H-pyrazolo[3,4-c]pyridine (2.2 g) as a yellow oil. LCMS:(ESI, m/z): 396 $[M+1]^+$ Step 4: Synthesis of 7-(trifluoromethyl)-1-((2-(trimethylsilyl)ethoxy)methyl)-1H-pyrazolo[3,4-c]pyridine-4-carboxylate To a solution of 4-bromo-7-(trifluoromethyl)-1-((2-(trimethylsilyl)ethoxy)methyl)-1H-pyrazolo[3,4-c]pyridine (1.7 g, 1 equiv., 4.3 mmol) in MeOH (17 mL) were added $PdCl_2$(dppf) (0.31 g, 0.1 equiv., 0.43 mmol) and TEA (1.3 g, 1.8 mL, 3 equiv., 13 mmol). The resulting mixture was stirred for 3 hours at 100° C. under an atmosphere of CO. The reaction mixture was then quenched with water (10 mL). The aqueous layer was extracted with EA (3×20 mL). The organic layer was combined and washed with a half of saturated brine (3×20 mL) and saturated brine (20 mL), dried over anhydrous sodium sulfate and concentrated to give a residue which was purified by silica gel column chromatography, eluting with PE/EA (1:1) to give methyl 7-(trifluoromethyl)-1-((2-(trimethylsilyl)ethoxy)methyl)-1H-pyrazolo[3,4-c]pyridine-4-carboxylate (1.5 g) as a white solid. LCMS:(ESI, m/z): 376 $[M+1]^+$ Step 5: Synthesis of 7-(trifluoromethyl)-1H-pyrazolo[3,4-c]pyridine-4-carboxylic Acid To a solution of methyl 7-(trifluoromethyl)-1-((2-(trimethylsilyl)ethoxy)methyl)-1H-pyrazolo[3,4-c]pyridine-4-carboxylate (700 mg, 1 equiv., 1.86 mmol) in THF (7 mL) were added AcOH (560 mg, 534 μL, 5 equiv., 9.32 mmol) and HCl (6N) (7 mL). The resulting mixture was stirred for 16 hours at 90° C., after which the reaction was quenched with water (10 mL). The aqueous layer was extracted with EA (3×10 mL), and the organic layers were combined and washed with a half of saturated brine (3×20 mL) and saturated brine (20 mL), dried over anhydrous sodium sulfate and concentrated to give a residue. The crude product was purified by reversed-phase flash chromatography with the following conditions: column, C18; mobile phase, MeCN in Water (0.1% FA), 10% to 50% gradient in 10 min; detector, UV 254 nm to give 7-(trifluoromethyl)-1H-pyrazolo[3,4-c]pyridine-4-carboxylic acid (230 mg) as a white solid. LCMS:(ESI, m/z): 332 $[M+1]^+$ Step 6: Synthesis of (R or S)-2-(7-acryloyl-5-(7-(trifluoromethyl)-1H-pyrazolo[3,4-c]pyridine-4-carbonyl)-3,4,5,5a,6,7,8,9-octahydro-2H-1,2,5, 7-tetraazabenzo[cd]azulen-2-yl)-5-cyclobutylphenyl Acetate To a solution of Int. Z-1 (60 mg, 1 equiv., 0.14 mmol) in DM (1.2 mL) were added 7-(trifluoromethyl)-1H-pyrazolo [3,4-c]pyridine-4-carboxylic acid (36 mg 1.1 equiv., 0.16 mmol) DIEA (92 mg, 0.12 mL, 5 equiv., 0.71 mmol) and HATU (81 mg, 1.5 equiv., 0.21 mmol). The resulting mixture was stirred for 2 h at 20° C., after which the reaction was quenched with water (10 mL). The aqueous layer was extracted with EA (3×10 mL), and the organic layers were combined and washed with half saturated brine (3×20 mL) and saturated brine (20 mL), dried over anhydrous sodium sulfate and concentrated to give a residue. The c de product was purified by silica gel chromatography, eluting with DCM:MeOH=1:1 to give (R or S)-2-(7-acryloyl-5-(7-(trifluoromethyl)-1H-pyrazolo[3,4-c]pyridine-4-carbonyl)-3,4,5,5a,6,7,8,9-octahydro-2H-1,2,5,7-tetraazabenzo[cd]azulen-2-yl)-5-cyclobutylphenyl acetate (40 mg) as a white solid. LCMS:(ESI, m/z): 634 $[M+1]^+$ Step 7: Synthesis of (R or S)-1-(2-(4-cyclobutyl-2-hydroxyphenyl)-5-(7-(trifluoromethyl)-1H-pyrazolo [3,4-c]pyridine-4-carbonyl)-2,3,4,5,5a,6,8,9-octahydro-7H-1,2,5,7-tetraazabenzo[cd]azulen-7-yl) prop-2-en-1-one To a solution of (R or S)-2-(7-acryloyl-5-(7-(trifluoroethyl)-1H-pyrazolo[3,4-c]pyridine-4-carbonyl)-3,4,5,5a,6,7,8,9-octahydro-2H-1,2,5,7-tetraazabenzo[cd]azulen-2-yl)-5-cyclobutylphenyl acetate (60 mg, 1 equiv., 95 μmol) in THF (0.6 mL) were added LiOH (4.5 mg, 2 equiv., 0.19 mmol) and water (0.2 mL). The reaction was then stirred for 20 min at rt, after which the resulting mixture was extracted with EA (3×10 mL). The combined organic layers were washed with water (2×10 mL) and filtered, and the filtrate was concentrated under reduced pressure. The residue was purified by Prep-HPLC (Column: Xselect CSH™ Prep C18 5 μm 30*150 mm OBD; Mobile Phase A: Water (0.1% FA), Mobile Phase B: ACN; Flow rate: 60 mL/min; Gradient: 32% B to 62% B in 8 min; Wave Length: UV 254 nm/220 nm) to afford (R or S)-1-(2-(4-cyclobutyl-2-hydroxyphenyl)-5-(7-(trifluoromethyl)-1H-pyrazolo[3,4-c]pyridine-4-carbonyl)-2,3,4,5,5a,6,8,9-octahydro-7H-1,2,5,7-tetraazabenzo[cd]azulen-7-yl)prop-2-en-1-one (10.9 mg) as a white solid. LCMS:(ESI, m/z): 592 $[M+1]^+$. $^1H$ NMR: (400 MHz, Chloroform-d, ppm) δ 8.51 (s, 1H), 8.33 (s, 1H), 7.43 (s, 1H), 6.99 (s, 2H), 6.71 (s, 1H), 6.51 (s, 1H), 5.94-2.89 (m, 11H), 2.79 (s, 2H), 2.41-2.20 (m, 2H), 2.18-1.94 (m, 3H), 1.90-1.75 (m, 1H).

Example C-14: Preparation of (R or S)-1-(2-(4-cyclobutyl-2-hydroxyphenyl)-5-(7-hydroxybenzo[d]thiazole-5-carbonyl)-2,3,4,5,5a,6,8,9-octahydro-7H-1,2,5,7-tetraazabenzo[cd]azulen-7-yl)prop-2-en-1-one

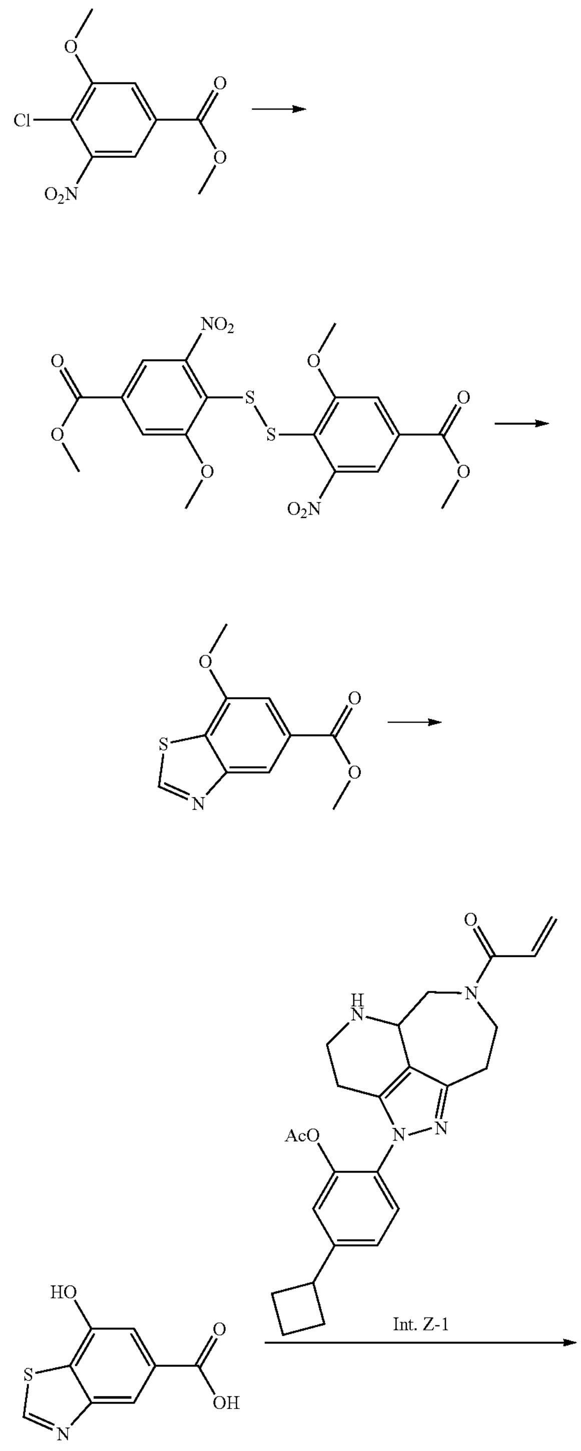

-continued

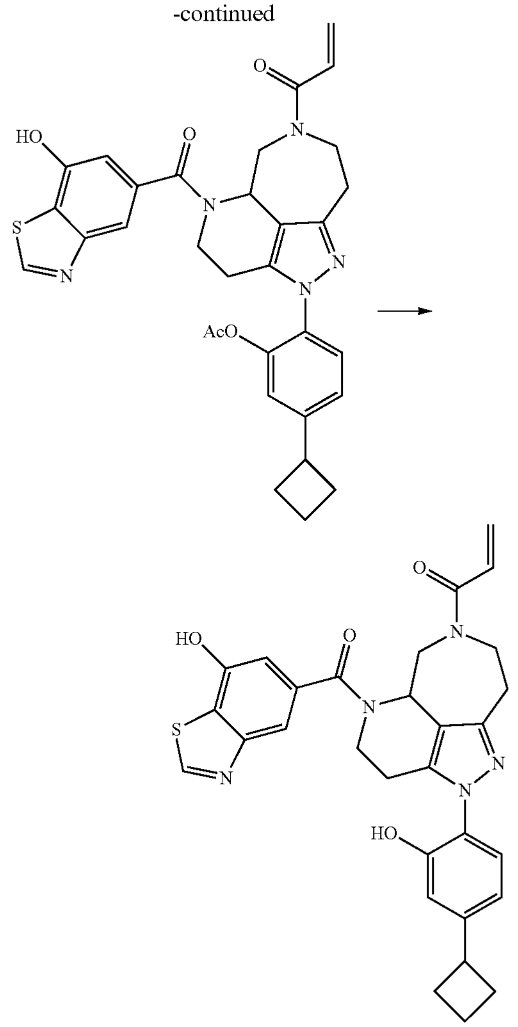

Step 1: Synthesis of Dimethyl 4,4'-disulfanediylbis(3-methoxy-5-nitrobenzoate)

To a solution of sodium sulfide nonahydrate (1.08 g, 753 μL, 1.1 equiv., 4.48 mmol) in MeOH (10 mL) and water (5 mL) was added sulfur (1.04 g, 1 equiv., 4.07 mmol). The mixture was warmed to 60° C. and stirred for 0.25 h. Then methyl 4-chloro-3-methoxy-5-nitrobenzoate (1.00 g, 1 equiv., 4.07 mmol) was added dropwise to the above mixture at rt under an atmosphere of nitrogen. The mixture was then heated and stirred at 60° C. for 0.5 h. The mixture was then cooled and filtered, and the filtrate was concentrated under vacuum to give a residue. The resulting dimethyl 4,4'-disulfanediylbis(3-methoxy-5-nitrobenzoate) (2 g) was used in the next step directly without further purification. LCMS: (ESI, m/z): 485 $[M+1]^+$ Step 2: Synthesis of Methyl 7-methoxybenzo[d]thiazole-5-carboxylate To a solution of dimethyl 4,4'-disulfanediylbis(3-methoxy-5-nitrobenzoate) (2 g, 1 equiv., 4 mmol) in EtOH (20 mL) was added tin (4 g, 0.5 mL, 8 equiv., 0.03 mol). The mixture was heated to 70° C. and stirred for 0.5 h under a nitrogen atmosphere. HCl (6 mL) was then added dropwise to the above mixture at 70° C. under a nitrogen atmosphere and stirred f r 0.5 h. The mixture was then filtered and the filtrate was concentrated under vacuum to give a residue. Formic acid (10 mL) and zinc (0.1 g, 0.5 equiv., 2 mmol) were then added to the mixture under a nitrogen atmosphere. The mixture was then heated to 100° C. and stirred for 1 h. The mixture was diluted with ice water (20 mL) and EA (20 mL), the aqueous layer was extracted with EA (2×20 mL). The combined organic layers were washed with saturated brine (2×20 L), dried over anhydrous sodium sulfate and concentrated to give a residue. The residue was purified by flash column chromatography, eluting with EA/PE (1:5) to afford methyl 7-methoxybenzo[d]thiazole-5-carboxylate (490 mg) as a light yellow solid. LCMS:(ESI, m/z): 238 [M 1]$^+$ Step 3: Synthesis of 7-hydroxybenzo[d]thiazole-5-carboxylic Acid To a solution of ethyl 7-methoxybenzo[d]thiazole-5-carboxylat (470 mg, 1 equiv., 1.98 mmol) was added HBr (5 mL). The mixture was then heated to 100° C. and stirred for 12 h, after which the mixture was diluted with ice water (10 mL) and EA (10 mL). The aqueous layer was then extracted with EA (2×10 mL). The combined organic layers were washed with saturated brine (2×10 mL), dried over anhydrous sodium sulfate and concentrated to give a residue. The residue was purified by reversed-phase flash chromatography with these conditions: (column, C18; mobile phase, water (0.1% FA) in MeCN, 10% to 50% gradient in 10 m n; detector, UV 254 nm) to afford 7-hydroxybenzo[d]thiazole-5-carboxylic acid (210 mg) as a brown solid. LCMS:(ESI, m/z): 196 [M+1]$^+$ Step 4: Synthesis of (R or S)-2-(7-acryloyl-5-(7-hydroxybenzo[d]thiazole-5-carbonyl)-3,4,5,5a,6,7,8,9-octahydro-2H-1,2,5, 7-tetraazabenzo[cd]azulen-2-yl)-5-cyclobutylphenyl Acetate To a solution of Int. Z-1 (70.0 mg, 1 equiv., 167 μmol) in DMF (1.4 mL) were added DIEA (215 mg, 290 μL, 10 equiv., 1.67 mmol), HATU (127 mg, 2 equiv., 333 μmol) and 7-hydroxybenzo[d]thiazole-5-carboxylic acid (65 mg, 2 equiv., 333 μmol). The mixture was stirred at rt for 1 h, after which the reaction was diluted with water (20 mL) and A (20 mL) The aqueous layer was then extracted with EA (2×20 mL), and the organic layers were combined and washed with saturated brine (2×20 mL), dried over anhydrous sodium sulfate a d concentrated to give a residue. The crude product was used in the next step directly without further purification. LCMS:(ESI, m/z): 598 [M+1]$^+$ Step 5: Synthesis of (R or S)-1-(2-(4-cyclobutyl-2-hydroxyphenyl)-5-(7-hydroxybenzo[d]thiazole-5-carbonyl)-2,3,4,5,5a,6,8,9-octahydro-7H-1,2,5, 7-tetraazabenzo[cd]azulen-7-yl)prop-2-en-J-one To a solution of (R or S)-2-(7-acryloyl-5-(7-hydroxybenzo[d]thiazole-5-carbonyl)-3,4,5,5a,6,7,8,9-octahydro-2H-1,2,5,7-tetraazabenzo[cd]azulen-2-yl)-5-cyclobutylphenyl acetate (50 mg, 1 equiv., 84 mol) in THF (0.8 mL) and water (0.4 mL) was added LiOH (4.0 mg, 2 equiv., 0.17 mmol). The mixture was stirred at rt for 1 h, after which the mixture was diluted with water (20 mL) and EA (20 mL), and the aqueous layer was extracted with EA (2×20 mL). The organic layers were combined and washed with saturated brine (2×20 L), dried over anhydrous sodium sulfate and concentrated to give a residue. The residue was purified by Prep-HPLC (Column: Sunfire C18 5 m, 30 mm*150 mm; Mobile Phase A: Water (0.1% FA), Mobile Phase B: ACN; Flow rate: 60 mL/min; Gradient: 33% B to 56% B in 10 min; Wave Length: UV 254 nm/220 nm) to afford (R or S)-1-(2-(4-cyclobutyl-2-hydroxyphenyl)-5-(7-hydroxybenzo[d]thiazole-5-carbonyl)-2,3,4,5,5a,6,8,9-octahydro-7H-1,2,5,7-tetraazabenzo[cd]azulen-7-yl)prop-2-en-1-one (3.1 mg) as a white solid. LCMS:(ESI, m/z): 556 [M+1]$^+$. $^1$H NMR: (400 MHz, Chloroform-d, ppm) δ 9.06-8.58 (m, 2H), 8.07-7.43 (m, 2H), 7.09-6.72 (m, 3H), 6.70 (d, J=7.6 Hz, 1H), 6.59 (s, 1H), 6.45 (d, J=16.4 Hz, 1H), 5.83 (d, J=10.0 Hz, 1H), 5.37-5.15 (m, 1H), 4.85 (s, 1H), 4.31-4.14 (m, 1H), 3.50-3.34 (m, 1H), 3.31-2.82 (m, 5H), 2.81-2.55 (m, 3H), 2.30-2.15 (m, 2H), 2.01-1.91 (m, 2H), 1.83-1.73 (m, 2H).

Example C-15: Preparation of (R and S)-1-(5-(2-amino-5-fluoro-6-(trifluoromethyl)nicotinoyl)-2-(4-cyclobutyl-2-hydroxyphenyl)-2,3,4,5,5a,6,8,9-octahydro-7H-1,2,5,7-tetraazabenzo[cd]azulen-7-yl) prop-2-en-1-one

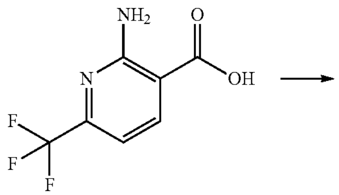

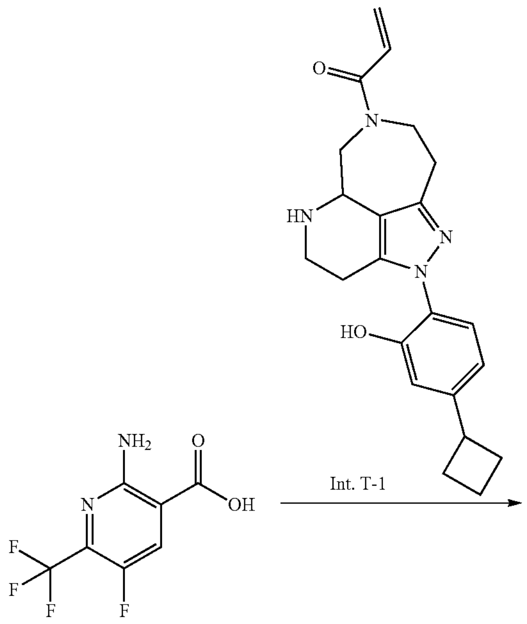

-continued

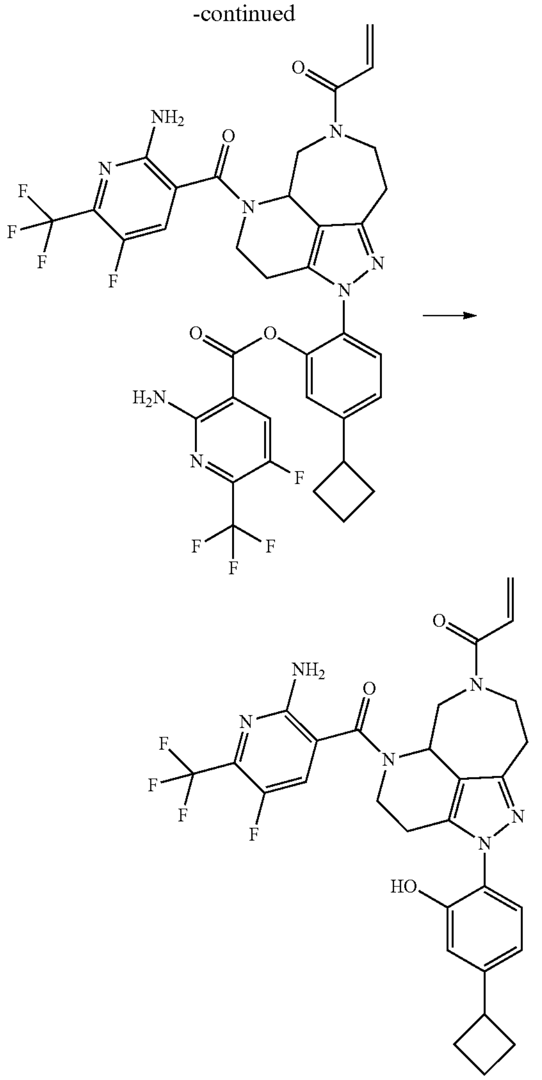

Step 1: Synthesis 2-amino-5-fluoro-6-(trifluoromethyl)nicotinic Acid

To a solution of 2-amino-6-(trifluoromethyl)nicotinic acid (500 g, 1 equiv., 2.43 mmol) in MeCN (5 mL) was added Selectfluor (1.20 g, 1.4 equiv., 3.4 mmol). The mixture was stirred at 50° C. for 18 hours, after which the mixture was diluted with ice water (20 mL) and EA (20 mL), and the aqueous layer was extracted with EA (2×20 mL). The combined organic layers were washed with saturated brine (2×20 mL), dried over anhydrous sodium sulfate and concentrated to give a residue. The residue was purified by reversed-phase flash chromatography with the conditions (column, C18; mobile phase, water (1% $NH_4HCO_3$) and ACN (20% B to 70% B in 10 min; detector, UV 254 nm) to afford 2-amino-5-fluoro-6-(trifluoromethyl)nicotinic acid (80 mg) as a white solid. LCMS:(ESI, m/z): 556 $[M+1]^+$ Step 2: (R or S)-2-(7-acryloyl-5-(2-amino-5-fluoro-6-(trifluoromethyl)nicotinoyl)-3,4,5,5a,6,7,8,9-octahydro-2H-1,2,5, 7-tetraazabenzo[cd]azulen-2-yl)-5-cyclobutylphenyl 2-amino-5-fluoro-6-(trifluoromethyl)nicotinate To a solution of (R or S)-1-(2-(4-cyclobutyl-2-hydroxyphenyl)-2,3,4,5,5a,6,8,9-octahydro-7H-1,2,5,7-tetraazabenzo[cd]azulen-7-yl)prop-2-en-1-one (Int. T-1, which was prepared in a matter analogous to Int. T in Example C-5, using Int. S'-1 in place of Int. S') (50.0 mg, 1 equiv., 132 μmol) in DMF (1 mL) were added DIEA (102.4 mg 138 μL, 6 equiv., 792.6 μmol), 2-amino-5-fluoro-6-(trifluoromethyl) nicotinic acid (59.21 mg, 2 equiv., 264 μmol) and HATU (151 mg, 3 equiv., 396 μmol). The mixture was stirred at rt for 1 h, after which the mixture was diluted with water (20 mL) and EA (20 mL), and the aqueous layer was extracted with EA (2×20 mL). The organic layers were combined and washed with saturate brine (2×20 mL), dried over anhydrous sodium sulfate and concentrated to afford (R or S)-2-(-acryloyl-5-(2-amino-5-fluoro-6-(trifluoromethyl)nicotinoyl)-3,4,5,5a,6,7,8,9-octahydro-2H-1,2,5,7-tetraazabenzo[cd]azulen-2-yl)-5-cyclobutylphenyl 2-amino-5-fluoro-6-(trifluoromethyl)nicotinate (80 mg) as a yellow solid. LCMS:(ESI, m/z): 791 $[M+1]^+$ Step 3: Synthesis of (R or S)-1-(5-(2-amino-5-fluoro-6-(trifluoromethyl)nicotinoyl)-2-(4-cyclobutyl-2-hydroxyphenyl)-2,3,4,5,5a,6,8,9-octahydro-7H-1,2,5, 7-tetraazabenzo[cd]azulen-7-yl) prop-2-en-1-one To a solution of (R or S)-2-(7-acryloyl-5-(2-amino-5-fluoro-6-(trifluoromethyl)nicotinoyl)-3,4,5,5a,6,7,8,9-octahydro-2H-1,2,5,7-tetraazabenzo[cd]azulen-2-yl)-5-cyclobutylphenyl 2-amino-5-fluoro-6-(trifluoromethyl) nicotinate (80 mg, 1 equiv., 0.1 mmol) in THF (0.8 mL) and water (0.4 mL) was added LiOH (4.8 mg, 2 equiv., 0.2 mmol). The mixture was stirred at rt for 1 h, after which the mixture was diluted with EA (20 mL) and water (15 mL), and the aqueous layer was extracted with EA (2×20 mL). The organic layers were combined and washed with saturated brine (20 mL), dried over anhydrous sodium sulfate and concentrated to give a residue. The residue was purified by Prep-HPLC with the conditions (Column: XBridge BEH C18 OBD Prep Column 130, 5 m, 30 mm*150 mm; Mobile Phase A: Water (17 mmol/L $NH_4HCO_3$), Mobile Phase B: ACN; Flow rate: 60 mL/min; Gradient: 48% B to 57% B in 10 min; Wave Length: UV 254 nm/220 nm) to afford (R or S-1-(5-(2-amino-5-fluoro-6-(trifluoromethyl)nicotinoyl)-2-(4-cyclobutyl-2-hydroxyphenyl)-2,3,4,5,5a,6,8,9-octahydro-7H-1,2,5,7-tetraazabenzo[cd]azulen-7-yl)prop-2-en-1-one (11.4 mg) as a yellow solid. LCMS:(ESI, m/z): 585 $[M+1]^+$. $^1H$ NMR: (400 MHz, Chloroform-d, ppm) δ 10.09 (s, 1H), 7.56-7.29 (m, 2H), 6.98 (d, J=8.0 Hz, 2H), 6.82-6.68 (m, 1H), 6.66-6.37 (m, 1H), 5.98-5.65 (m, 1H), 5.39 (s, 1H), 5.05-4.64 (m, 1H), 4.54-4.19 (m, 1H), 4.00 (s, 1H), 3.52 (p, J=8.7 Hz, 1H), 3.31-2.66 (m, 7H), 2.34 (dtd, J=10.0, 7.8, 2.4 Hz, 2H), 2.21-1.77 (m, 4H).

Example C-16: Preparation of (R or S)-1-(5-(7-bromo-2-(hydroxymethyl)-1H-benzo[d]imidazole-4-carbonyl)-2-(4-cyclobutyl-2-hydroxyphenyl)-2,3,4,5,5a,6,8,9-octahydro-7H-1,2,5,7-tetraazabenzo[cd]azulen-7-yl)prop-2-en-1-one

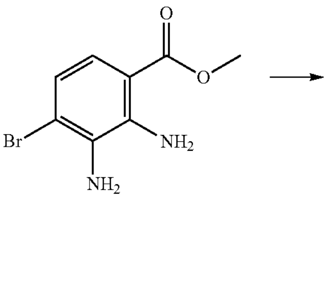

-continued

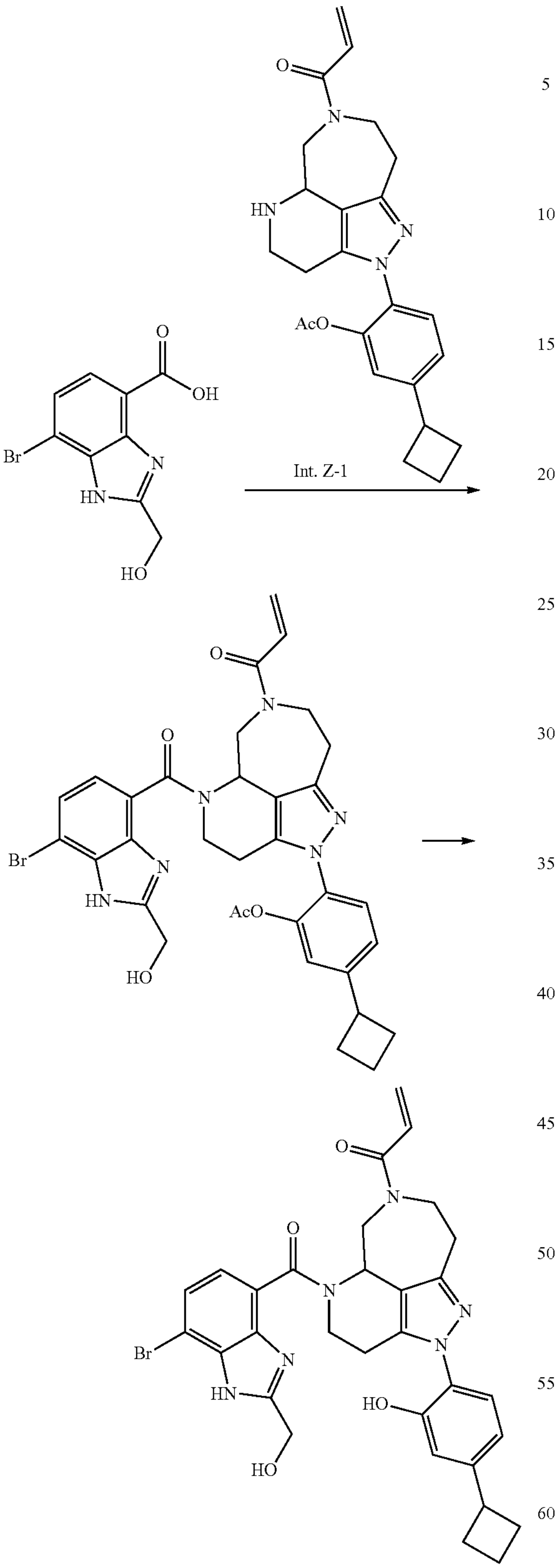

Step 1: Synthesis of 7-bromo-2-(hydroxymethyl)-1H-benzo[d]imidazole-4-carboxylic Acid To a solution of methyl 2,3-diamino-4-bromobenzoate (0.9 g, 1 equiv., 4 mmol) in water (10 mL) were added glycolic acid (0.8 g, 0.6 mL, 3 equiv., 0.01 mol) an hydrogen chloride (1 g, 1 mL, 10 equiv., 0.04 mol). The mixture was stirred at 120° C. for 4 h, after which the mixture was concentrated under reduced pressure. The residue was purified by reverse phase chromatography (column: C18 column; Gradient: 20% MeCN in water with 0.05% TFA) to afford 7-bromo-2-(hydroxymethyl)-1H-benzo[d]imidazole-4-carboxylic acid (0.4 g) as a yellow solid. LCMS:(ESI, m/z): 271 $[M+1]^+$ Step 2: Synthesis of (S or R)-2-(7-acryloyl-S-(7-bromo-2-(hydroxymethyl)-1H-benzo[d]imidazole-4-carbonyl)-3,4,5,5a,6,7,8,9-octahydro-2H-1,2,5,7-tetraazabenzo[cd]azulen-2-yl)-5-cyclobutylphenyl Acetate To a solution of Int. Z-1 (55 mg, 1 equiv., 0.13 mmol) in DMF (1 mL) were added 7-bromo-2-(hydroxymethyl)-1H-benzo[d]imidazole-4-carboxylic acid (39 mg, 1.1 equiv., 0.14 mmol), HATU (65 mg, 1.3 equiv., 0.17 mmol) and DIEA (0.14 g, 8 equiv, 1.0 mmol). The mixture was stirred at rt for 2 h, after which the mixture was diluted with water (10 mL) and EA (20 mL). The organic layer was washed with saturated brine (2×10 mL), dried over anhydrous sodium sulfate and concentrated to afford (R or S)-2-(7-acryloyl-5-(7-bromo-2-(hydroxymethyl)-1H-benzo[d]imidazole-4-carbonyl)-3,4,5,5a,6,7,8,9-octahydro-2H-1,2,5,7-tetraazabenzo[cd]azulen-2-yl)-5-cyclobutylphenyl acetate (50 mg) as a yellow solid which was used in the next step without further purification. LCMS:(ESI, m/z): 673 $[M+1]^+$ Step 3: (R or S)-1-(5-(7-bromo-2-(hydroxymethyl)-1H-benzo[d]imidazole-4-carbonyl)-2-(4-cyclobutyl-2-hydroxyphenyl)-2,3,4,5,5a,6,8,9-octahydro-7H-1,2,5,7-tetraazabenzo[cd]azulen-7-yl)prop-2-en-1-one To a solution of (R or S)-2-(7-acryloyl-5-(7-bromo-2-(hydroxymethyl)-1H-benzo[d]imidazole-4-carbonyl)-3,4,5,5a,6,7,8,9-octahydro-2H-1,2,5,7-tetraazabenzo[cd]azulen-2-yl)-5-cyclobutylphenyl acetate (50 mg, 1 equiv., 74 μmol) in THF (2 mL) and water (0.5 mL) was added LiOH (7.1 mg, 4.4 μL, 4 equiv., 0.3 mmol). The resulting mixture was stirred at rt for 2 h, after which the mixture was purified by reverse phase chromatography (Column: XBridge BEH Shield RP18 5 μm, 30 mm*150 mm; Mobile Phase A: Water (10 mmol/L $NH_4HCO_3$), Mobile Phase B: ACN; Flow rate: 60 mL/min; Gradient: 27% B to 53% B in 10 min; Wave Length: UV 254 nm/220 nm) to afford (R or S)-1-(5-(7-bromo-2-(hydroxymethyl)-1H-benzo[d]imidazole-4-carbonyl)-2-(4-cyclobutyl-2-hydroxyphenyl)-2,3,4,5,5a,6,8,9-octahydro-7H-1,2,5,7-tetraazabenzo[cd]azulen-7-yl)prop-2-en-1-one (7.9 mg) as a white solid. LCMS:(ESI, m/z): 631 $[M+1]^+$. $^1H$ NMR: (400 MHz, Chloroform-d, ppm) δ 10.10 (s, 1H), 7.45 (d, J=8.0 Hz, 2H), 7.14 (d, J=8.0 Hz, 1H), 7.01-6.83 (m, 2H), 6.66 (d, J=8.3 Hz, 1H), 6.59-6.41 (m, 1H), 5.85 (s, 1H), 5.43 (s, 1H), 5.04 (s, 2H), 4.94 (s, 3H), 4.54 (s, 1H), 4.19 (s, 1H), 3.51-3.42 (m, 1H), 3.20 (d, J= 12.4 Hz, 1H), 2.99 (s, 3H), 2.78-2.60 (m, 2H), 2.31 (d, J=8.6 Hz, H), 2.16-1.95 (m, 4H), 1.85 (s, 1H).

Example C-17: Preparation of (R or S,E)-1-(5-(4-amino-6-(trifluoroethyl)nicotinoyl)-2-(4-cyclobutyl-2-hydroxyphenyl)-2,3,4,5,5a,6,8,9-octahydro-7H-1,2,5,7-tetraazabenzo[cd]azulen-7-yl)-4-methoxybut-2-en-1-one
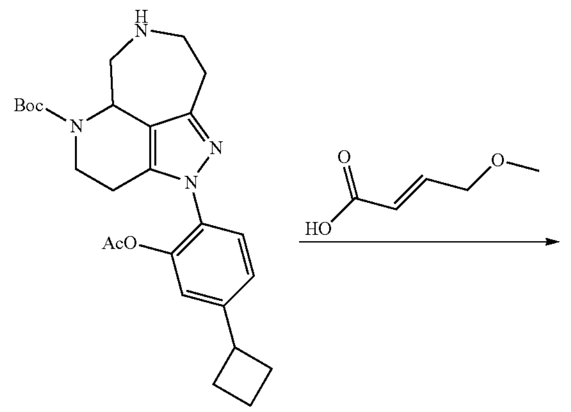
-continued
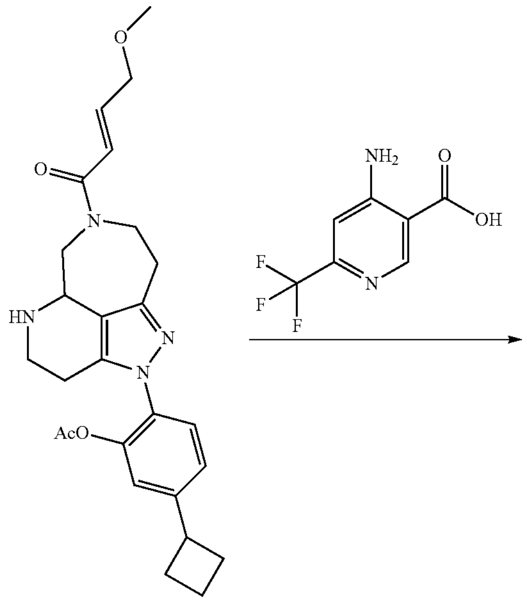
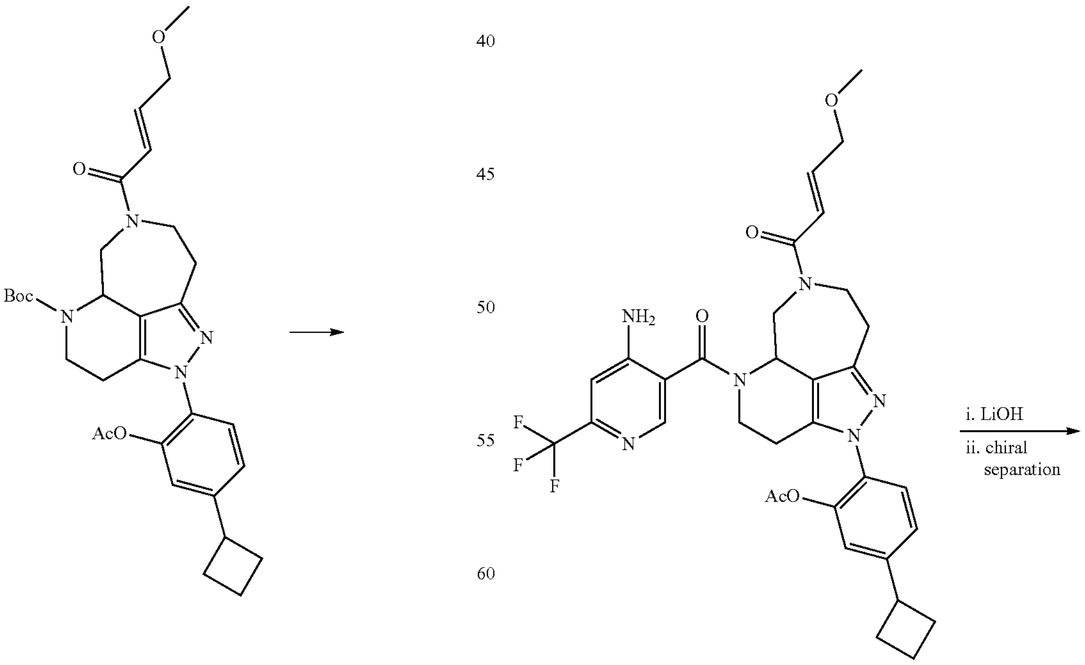

-continued

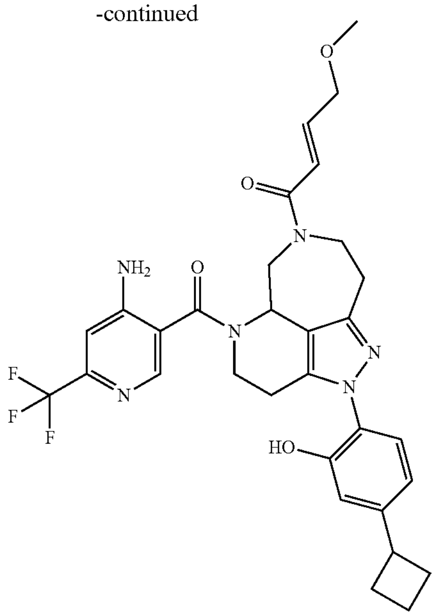

Step 1: Synthesis of(R and S)-tert-butyl (E)-2-(2-acetoxy-4-cyclobutylphenyl)-7-(4-methoxybut-2-enoyl)-2,3,4,5a,6,7,8,9-octahydro-5H-1,2,5,7-tetraazabenzo[cd]azulene-5-carboxylate To a stirred solution of (R and S)-tert-butyl 2-(2-acetoxy-4-cyclobutylphenyl)-2,3,4,5a,6,7,8,9-octahydro-5H-1,2,5,7-tetraazabenzo[cd]azulene-5-carboxylate (prepared in an analogous fashion to Example C-11 step, except Int. S' was used in place of Int. S'-1) (250 mg, 1 equiv., 536 μmol) in DMF (3 mL) was added (E)-4-methoxybut-2-enoic acid (187 mg, 3 equiv., 1.61 mmol) DIEA (693 mg, 933 μL, 10 equiv., 5.36 mmol) and HATU (611 mg, 3 equiv., 1.61 mmol) at rt and the resulting mixture was stirred for 1 h. The reaction was then quenched by the addition of water (20 mL), and the resulting mixture was extracted with EA (2×20 mL). The combined organic layers were washed with brine (2×20 mL) and dried over anhydrous $Na_2SO_4$. After filtration, the filtrate was concentrated under reduced pressure to afford (R and S)-tert-butyl (E)-2-(2-acetoxy-4-cyclobutylphenyl)-7-(4-methoxybut-2-enoyl)-2,3,4, 5a, 6,7,8, 9-octahydro-5H-1,2,5,7-tetraazabenzo[cd]azulene-5-carboxylate (230 mg) as a crude yellow solid. The crude product was used in the next step directly without further purification LCMS:(ESI, m/z): 565 $[M+1]^+$ Step 2: Synthesis of (R and S)-(E)-5-cyclobutyl-2-(7-(4-methoxybut-2-en yl)-3,4,5,5a,6,7,8,9-octahydro-2H-1,2,5, 7-tetraazabenzo[cd]azulen-2-yl) phenyl Acetate The solution of (R and S)-tert-butyl (E)-2-(2-acetoxy-4-cyclobutylphenyl)-7-(4-methoxybut-2-enoyl)-2,3,4,5a,6,7, 8,9-octahydro-5H-1,2,5,7-tetraazabenzo[cd]azulene-5-carboxylate (230 mg, 1 equiv., 407 μmol) in DCM (6 mL) and TFA (2 L) was stirred at rt for 1 h, after which the solvent was removed under reduced pressure to afford (R and S)-(E)-5-cyclobutyl-2-(7-(4-methoxybut-2-enoyl)-3,4,5,5a, 6,7,8,9-octahydro-2H-1,2,5,7-tetraazabenzo[cd]azulen-2-yl)phenyl acetate (180 mg) as a crude yellow solid. The crude product was used in the next step directly without further purification. LCMS:(ESI, m/z): 465 $[M+1]^+$ Step 3: Synthesis of (R and S)-(E)-2-(5-(4-amino-6-(trifluoromethyl)nicotinoyl)-7-(4-methoxybut-2-enoyl)-3,4,5,5a,6,7,8,9-octahydro-2H-1,2,5,7-tetraazabenzo[cd]azulen-2-yl)-5-cyclobutylphenyl acetate To a stirred solution of (R and S)-(E)-5-cyclobutyl-2-(7-(4-methoxybut-2-enoyl)-3,4,5,5a,6,7,8,9-octahydro-2H-1,2, 5,7-tetraazabenzo[cd]azulen-2-yl)phenyl acetate (180 mg, 1 equiv., 387 μmol) in DMF (3 mL) was added HATU (442 mg, 3 equiv. 1.16 mmol) 4-amino-6-(trifluoromethyl)nicotinic acid (240 mg, 3 equiv., 1.16 mmol) and DI A (501 mg, 675 μL, 10 equiv., 3.87 mmol) at rt. After stirring for 2 h, the reaction was quenched by the addition of water (20 mL) at rt. The resulting mixture was extracted with EA (2×20 mL), and the combined organic layers were washed with brine (2×20 mL) and dried over anhydrous $Na_2SO_4$. After filtration, the filtrate was concentrated under reduced pressure to afford (R ad S)-(E)-2-(5-(4-amino-6-(trifluoromethyl)nicotinoyl)-7-(4-methoxybut-2-enoyl)-3,4,5,5a,6,7,8,9-octahydro-2H-1,2,5,7-tetraazabenzo[cd]azulen-2-yl)-5-cyclobutylphenyl acetate (150 mg) as a crude light yellow solid. The crude product was used in the next step directly without further purification. LCMS:(ESI, m/z): 653 $[M+1]^+$ Step 4: Synthesis of (R and S)-(E)-1-(5-(4-amino-6-(trifluoromethyl)nicotinoyl)-2-(4-cyclobutyl-2-hydroxyphenyl)-2,3,4,5,5a,6,8,9-octahydro-7H-1,2,5, 7-tetraazabenzo[cd]azulen-7-yl)-4-methoxybut-2-en-1-one To a stirred solution of (R and S)-(E)-2-(5-(4-amino-6-(trifluormethyl)nicotinoyl)-7-(4-methoxybut-2-enoyl)-3,4, 5,5a,6,7,8,9-octahydro-2H-1,2,5,7-tetraazabenzo[cd]azulen-2-yl)-5 -cyclobutylphenyl acetate (150 mg, 1 equiv., 230 mol) in THF (4 mL) an water (2 mL) was added LiOH (27.5 mg, 5 equiv., 1.15 mmol) at rt and the resulting mixture was stirred for 2 h. The reaction was then diluted with water (20 mL) at rt. The resulting mixture was extracted with EA (2×20 mL) and the combined organic layers were washed with brine (2×20 mL) and dried over anhydrous $Na_2SO_4$. After filtration, the filtrate was concentrated under reduced pressure. The residue was purified by reversed-phase flash chromatography with the conditions (Column: Kinetex 5 m EVO C18, 30 mm*150 mm; Mobile Phase A: Water (10 mmol/L $NH_4HCO_3$), Mobile Phase B: ACN; Flow rate: 60 mL/min; Gradient: 35% B to 51% B in E min; Wave Length: UV 254 nm/220 nm; RT1(min): 7.65 to afford (E)-1-(5-(4-amino-6-(trifluoromethyl)nicotinoyl)-2-(4-cyclobutyl-2-hydroxyphenyl)-2,3,4,5,5a,6,8,9-octahydro-7H-1,2,5,7-tetraazabenzo[cd]azulen-7-yl)-4-methoxybut-2-en-1-one (40 mg, 66 mol, 29%) as a white solid. The racemic compound was separated by chiral HPLC separation under the following conditions: Column: CHIRALPAK-IE 2*25 cm, 5 μm; Mobile Phase A: HEX(0.1% FA), Mobile Phase B: EtOH: DCM=1:1; Flow rate: 20 mL/min; Gradient: isocratic 40; Wave Length: UV 220/254 nm to afford (S or R,E)-1-(5-(4-amino-6-(trifluoromethyl)nicotinoyl)-2-(4-cyclobutyl-2-hydroxyphenyl)-2,3,4,5,5a,6,8,9-octahydro-7H-1,2,5,7-tetraazabenzo[cd]azulen-7-yl)-4-methoxybut-2-en-1-one (5.5 mg) as the first-eluting enantiomer as a light brown solid. LCMS:(ESI, m/z): 611 $[M+1]^+$. $^1H$ NMR: (400 MHz, Chloroform-d, ppm) δ 10.15 (s, 1H), 7.55-6.28 (m, 1H), 7.18-0.88 (m, 4H), 6.83-6.71 (m, 1H), 5.44 (s, 2H), 4.97 (s, 1H), 4.52 (s, 1H), 4.31-4.04 (m, 3H), 3.58-3.44 (m, 4H), 3.28-2.75 (m, 4H), 2.35 (s, 2H), 2.21-2.08 (m, 2H), 2.02 (dt, J=10.2, 8.0 z, 1H), 1.92-1.79 (m, 2H), 1.35-1.18 (m, 2H).

Example C-18: Preparation of (R or S,Z)-1-(5-(4-amino-6-(trifluoromethyl)nicotinoyl)-2-(4-cyclobutylphenyl)-2,3,4,5,5a,6,8,9-octahydro-7H-1,2,5,7-tetraazabenzo[cd]azulen-7-yl)-3-chloroprop-2-en-1-one

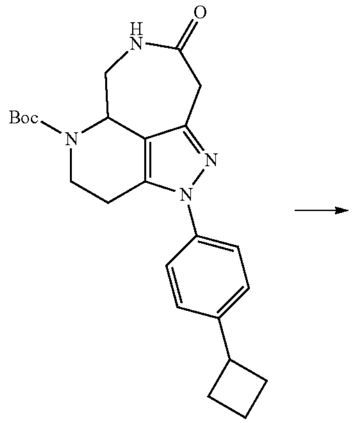

Int. R-1

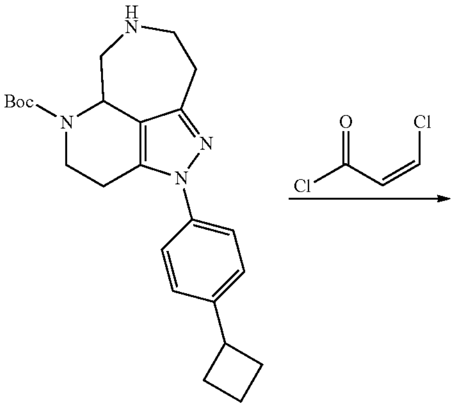

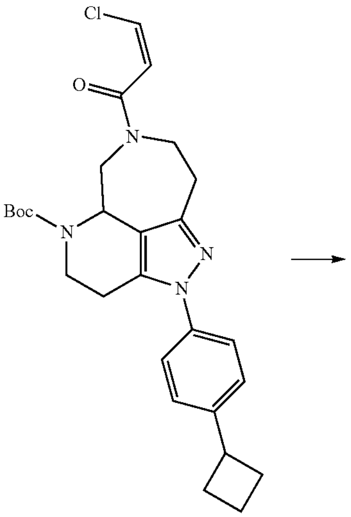

-continued

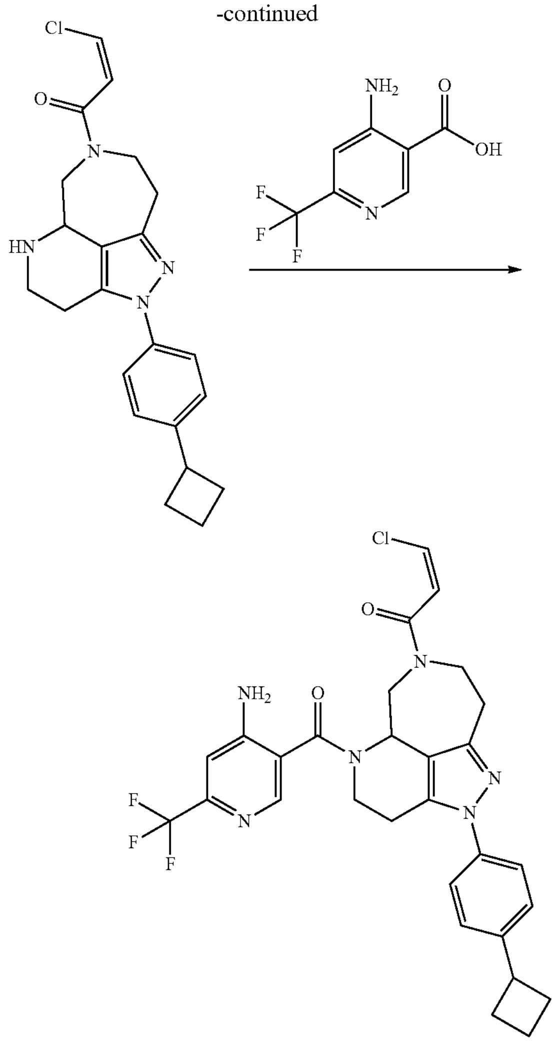

Step 1: Synthesis of Tert-Butyl (R or S)-2-(4-cyclobutylphenyl)-2,3,4,5a,6,7,8,9-octahydro-5H-1,2,5,7-tetraazabenzo[cd]azulene-5-carboxylate To a solution of Int. R-1 (500 mg, 1 equiv., 1.18 mm 1) in THF (5 mL) were added $BH_3$·THF (407 mg, 4 equiv., 4.73 mmol). The resulting mixture w s stirred for 1 h at 60° C., after which the reaction mixture was cooled to −78° C. and quenched with MeOH (50 ml). The resulting mixture was stirred at rt for 1 h. The solvent was then removed under reduced pressure to give tert-butyl (R or S)-2-(4-cyclobutylphenyl)-2,3,4,5a,6,7,8,9-octahydro-5H-1,2,5,7-tetraazabenzo[cd]azulene-5-carboxylate (520 mg) as a crude white solid. The crude product was used in the next step directly without further purification. LCMS:(ESI, T/z): 409 $[M+1]^+$ Step 2: Synthesis of Tert-Butyl (R or S,Z)-7-(3-chloroacryloyl)-2-(4-cyclobutylphenyl)-2,3,4,5a,6,7,8,9-octahydro-5H-1,2,5,7-tetraazabenzo[cd]azulene-5-carboxylate To a solution of tert-butyl (R or S)-2-(4-cyclobutylphenyl)-2,3,4,5a,6,7,8,9-octahydro-5H-1,2,5,7-tetraazabenzo[cd]azulene-5-carboxylate (300 mg, 1 equiv., 734 mol) in DCM (5 mL) was added DIEA (1.90 g, 2.56 mL, 20 equiv., 14.7 mmol). The resulting mixture was stirred for 30 min, after which (Z)-3-chloroacryloyl chloride (367 mg, 4 equiv., 2.94 mmol) was added slowly. The mixture was stirred at rt for 1 hour, after which it was diluted with water (20 mL) and DCM (20 mL), and the aqueous layer was extracted with DCM (2×20 mL). The organic layers were combined and washed with saturated brine (2×20 mL), dried over anhydrous sodium sulfate and concentrated to give a residue. The residue was purified by silica gel chromatography, eluting with PE:EA=10:1 to give tert-butyl (R or S,Z)-7-(3-chloroacryloyl)-2-(4-cyclobutylphenyl)- 2,3,4,5a,6,7,8,9-octahydro-5H-1,2,5,7-tetraazabenzo[cd]azulene-5-carboxylate (306 mg) as a yellow solid. LCMS:(ESI, m/z): 497 $[M+1]^+$ Step 3: Synthesis of (R or S,Z)-3-chloro-J-(2-(4-cyclobutylphenyl)-2,3,4,5,5a,6,8,9-octahydro-7H-1,2,5, 7-tetraazabenzo[cd]azulen-7-yl)prop-2-en-1-one A solution of tert-butyl (R or S,Z)-7-(3-chloroacryloyl)-2-(4-cyclobutylphenyl)-2,3,4,5a,6,7,8,9-octahydro-5H-1,2,5,7-tetraazabenzo[cd]azulene-5-carboxylate (306 mg, 1 equiv., 616 μmol) in DCM (3 mL) and TFA (9 mL) was stirred at rt for 1 h. The solvent was then removed under reduced pressure to afford (R or S,Z)-3-chloro-1 (2-(4-cyclobutylphenyl)-2,3,4,5,5a,6,8,9-octahydro-7H-1,2,5,7-tetraazabenzo[cd]azulen-7-yl)prop-2-en-1-one (536 mg, 1.35 mmol, 219%) as a crude yellow oil. The crude product was use in the next step directly without further purification. LCMS:(ESI, m/z): 397 $[M+1]^+$.

Step 4: Synthesis of (R or S,Z)-1-(5-(4-amino-6-(trifluoromethyl)nicotinyl)-2-(4-cyclobutylphenyl)-2,3,4,5,5a,6,8,9-octahydro-7H-1,2,5,7-tetraazabenzo [d]azulen-7-yl)-3-chloroprop-2-en-1-one To a solution of (R or S,Z)-3-chloro-1-(2-(4-cyclobutylphenyl)-2,3,4,5,5a,6,8,9-octahydro-7H-1,2,5,7-tetraazabenzo[cd]azulen-7-yl)prop-2-en-1-one (100 mg, 1 equiv., 252 μmol) in DMF (2 mL) were added DIEA (500 mg, 15.4 equiv., 0.87 mmol), 4-amino-6-(trifluoromethyl) nicotinic acid (77.9 mg, 1.5 equiv., 378 μmol) and 2-(3H-[1,2,3]triazolo[4,5-b]pyridin-3-yl)-1,1,3,3-tetramethylisouronium hexafluorophosphate(V) (192 mg, 2 equiv., 504 μmol). The mixture was stirred at rt for 1 h, after which the reaction was diluted with water (20 mL) and EA (20 mL), and the aqueous layer was extracted with EA (2×20 mL). The combined organic layers were washed with saturated brine (2×20 mL), dried over anhydrous sodium sulfate and concentrated to give a residue. The residue was purified by Prep-HPLC (Column: YMC-Actus Triart C18 ExRS 30*150 mm, 5 μm; Mobile Phase A: Water(10 mmol/L $NH_4HCO_3$), Mobile Phase B: ACN; Flow rate: 60 mL/min mL/min; Gradient: 46% B to 62% B in 10 min) to afford (R or S,Z)-1-(5-(4-amino-6-(trifluoromethyl)nicotinoyl)-2-(4-cyclobutylphenyl)-2,3,4,5,5a,6,8,9-octahydro-7H-1,2,5,7-tetraazabenzo[cd]azulen-7-yl)-3-chloroprop-2-en-1-one (9.5 mg) as a white solid. LCMS:(ESI, m/z): 585 $[M+1]^+$. $^1H$ NMR: (400 MHz, Chloroform-d, ppm) δ 8.34 (s, 1H), 7.35 (d, J=8.5 Hz, 2H), 7.29 (d, J=8.4 Hz, 2H), 7.05 (s, 1H), 6.61-0.55 (m, 1H), 6.52-6.46 (m, 1H), 5.50-5.28 (m, 2H), 5.00-4.84 (m, 1H), 4.32-3.93 (m, 2H), 3.58-3.45 (m, 1H), 3.29- 2.67 (m, 6H), 2.47-2.31 (m, 2H), 2.21-2.11 (m, 2H), 2.08-1.97 (m, 1H), 1.95-1.83 (m, 1H), 1.80-1.67 (m, 2H).

Example C-19: Preparation of (R or S)-1-(5-(4-amino-6-(trifluoroethyl)nicotinoyl)-2-(4-cyclobutyl-2-methylphenyl)-2,3,4,5,5a,6,8,9-octahydro-7H-1,2,5,7-tetraazabenzo[cd]azulen-7-yl)prop-2-en-1-one

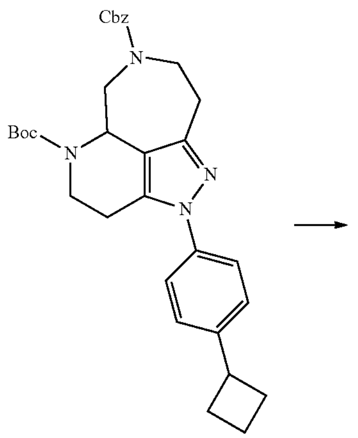

Int. S″

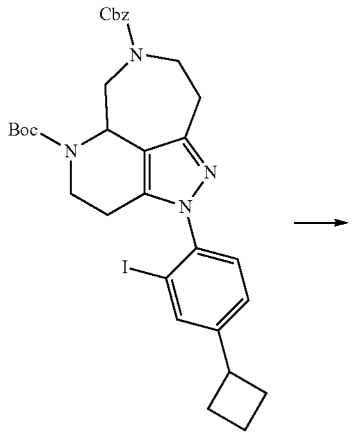

Int. RR

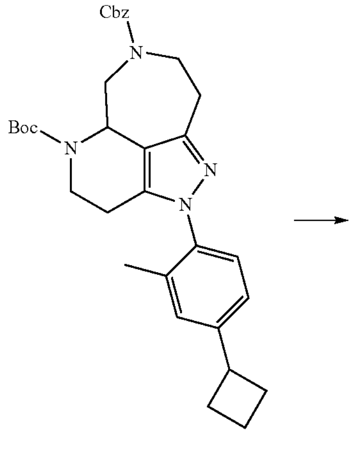

-continued

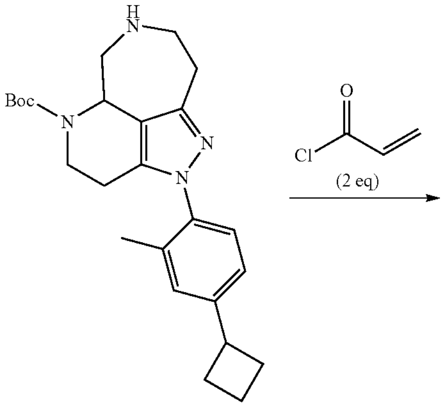

-continued

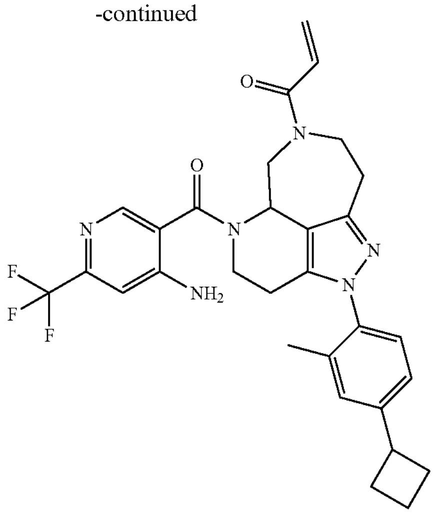

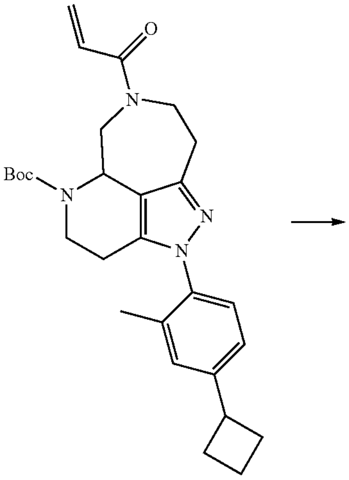

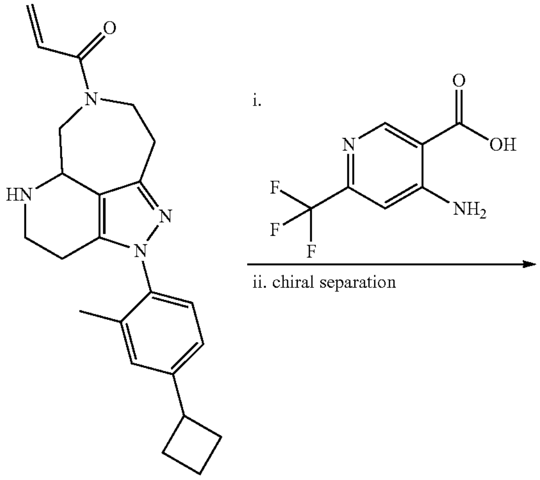

Step 1: Synthesis of 7-benzyl 5-(tert-butyl) 2-(4-cyclobutyl-2-iodophenyl)-3,4,5a,6,8,9-hexahydro-2H-1,2,5,7-tetraazabenzo[cd]azulene-5,7-dicarboxylate (Int RR)

To a solution of Int. S" (4 g, 1 Eq, 7 mmol) in DCE (40 mL) were added (diacetoxyiodo)benzene (4 g, 1.5 Eq, 0.01 mol), $[Cp^*RhCl_2]_2$ (0.9 g, 0.2 Eq, 1 mmol), NaI (3 g, 3 Eq, 0.02 mol) and TFA (2 g, 1 mL, 2 Eq, 0.01 mol). The reaction system was evacuated and purged with nitrogen (×3), and the resulting mixture was stirred for 12 h at 40° C. under an atmosphere of nitrogen. The mixture was then diluted with ice water (50 mL) and EA (50 mL), and the aqueous layer was extracted with EA (2×50 mL). The combined organic layers were washed with saturated brine (2×50 mL), dried over anhydrous sodium sulfate and concentrated to give a residue. The residue was purified by flash column chromatography, eluting with EA/PE (1:1) to afford 7-benzyl 5-(tert-butyl) 2-(4-cyclobutyl-2-iodophenyl)-3,4,5a,6,8,9-hexahydro-2H-1,2,5,7-tetraazabenzo[cd]azulene-5,7-dicarboxylate (3.8 g) as a yellow solid. LCMS:(ESI, m/z): 669 $[M+1]^+$.

Step 2: Synthesis of 7-benzyl 5-(tert-butyl) 2-(4-cyclobutyl-2-methylphenyl)-3,4,5a,6,8,9-hexahydro-2H-1,2,5,7-tetraazabenzo[cd]azulene-5, 7-dicarboxylate To a solution of 7-benzyl 5-(tert-butyl) 2-(4-cyclobutyl-2-iodophenyl)-3,4,5a,6,8,9-hexahydro-2H-1,2,5,7-tetraazabenzo[cd]azulene-5,7-dicarboxylate (1 g 1 Eq, 1 mmol) in 1,4-dioxane (10 mL) and $H_2O$ (1.0 mL) were added pd(pph3)cl2 (0.2 g, 0.1 Eq, 0.1 mmol), methylboronic acid (1 g, 10 Eq, 10 mmol) and potassium carbonate (0.5 g, 2.5 Eq, 4 mmol). The reaction system was evacuated and purged with nitrogen (×3), and the resulting mixture was stirred for 12 h at 80° C. under an atmosphere of nitrogen. After the reaction mixture was cooled to rt, the mixture was filtered and rinsed with EA (3×20 mL), then the diluted with water (20 mL). The aqueous layer was extracted with EA (2×20 mL), and the combined organic layers were washed with saturated brine (3×20 mL), dried over anhydrous sodium sulfate a d concentrated to give a residue. The crude product was purified by silica gel chromatography, eluting with PE:EA=1:1 to give 7-benzyl 5-(tert-butyl) 2-(4-cyclobutyl- 2-methylphenyl)-3,4,5a,6,8,9-hexahydro-2H-1,2,5,7-tetraazabenzo[cd]azulene-5,7-dicarboxylate (570 mg) as a white solid. LCMS:(ESI, m/z): 557 [M+1]+.

Step 3: Synthesis of Tert-Butyl 2-(4-cyclobutyl-2-methylphenyl)-2,3,4,5a,6,7,8,9-octahydro-5H-1,2,5,7-tetraazabenzo[cd]azulene-5-carboxylate To a solution of 7-benzyl 5-(tert-butyl) 2-(4-cyclobutyl-2-methylphenyl)-3,4,5a,6,8,9-hexahydro-2H-1,2,5,7-tetraazabenzo[cd]azulene-5,7-dicarboxylate (300 mg, 1 Eq, 539 μmol) in a solution of ammonia in dioxane (0.4 M, 15 mL) were added $Pd(OH)_2/C$ (150 mg, 20 wt %) and Pd/C (150 mg, 10 wt %). The mixture was purged with nitrogen (×3) and then was pressurized to 4.0 MPa with an atmosphere of hydrogen and the reaction mixture was stirred at 50° C. for 12 h. The reaction was then cooled to rt, the mixture was filtered and rinsed with EA (5×50 mL), and the filtrate was concentrated under reduced pressure to provide tert butyl 2-(4-cyclobutyl-2-methylphenyl)-2,3,4,5a,6,7,8,9-octahydro-5H-1,2,5,7-tetraazabenzo[cd]azulene-5-carboxylate (300 mg) as a crude yellow oil which was used in the next step directly without further purification. LCMS:(ESI, m/z): 423 [M+1]+.

Step 4: Synthesis of Tert-Butyl 7-acryloyl-2-(4-cyclobutyl-2-methylphenyl)-2,3,4,5a,6,7,8,9-octahydro-5H-1,2,5,7-tetraazabenzo[cd]azulene-5-carboxylate To a solution of tert-butyl 2-(4-cyclobutyl-2-methylphenyl)-2,3,4,5a,6,7,8,9-octahydro-5H-1,2,5,7-tetraazabenzo[cd]azulene-5-carboxylate (300 mg, 1 Eq, 71 μmol) in DCM (6 mL) was added TEA (216 mg, 3 Eq, 2.13 mmol). The mixture was cooled to 0° C., then acryloyl chloride (129 mg, 2 Eq, 1.42 mmol) was added dropwise to the above mixture. The mixture was warmed to rt and stirred for 2 h. The mixture was then diluted with ice water (10 mL) and DCM (10 mL), the aqueous layer was extracted with DCM (2×10 mL). The combined organic layers were washed with saturated brine (2×10 mL), dried over anhydrous sodium sulfate and concentrated to give a residue. The residue was purified by flash column chromatography, eluting with EA/PE (3:1) to afford tert-butyl 7-acryloyl-2-(4-cyclobutyl-2-methylphenyl)-2,3,4,5a,6,7,8,9-octahydro-5H-1,2,5,7-tetraazabenzo[cd]azulene-5-carboxylate (130 mg) as a white solid. LCMS:(ESI, m/z): 477 [M+1]+.

Step 5: Synthesis of 1-(2-(4-cyclobutyl-2-methylphenyl)-2,3,4,5,5a,6,8,9-octahydro-7H-1,2,5,7-tetraazabenzo[cd]azulen-7-yl)prop-2-en-1-one A solution of tert-butyl 7-acryloyl-2-(4-cyclobutyl-2-methy phenyl)-2,3,4,5a,6,7,8,9-octahydro-5H-1,2,5,7-tetraazabenzo[cd]azulene-5-carboxylate (130 mg, 1 Eq, 273 μmol) in DCM (1 mL) and TFA (0.3 mL) was stirred at rt for 2 h. The solvent was the removed under reduced pressure to afford 1-(2-(4-cyclobutyl-2-methylphenyl)-2,3,4,5,5a,6,8,9-octahydro-7H-1,2,5,7-tetraazabenzo[cd]azulen-7-yl)prop-2-en-1-one (130 mg) as a crude yell w oil which was used in the next step without further purification. LCMS:(ESI, m/z): 377 [M+1]+.

Step 6: Synthesis of (R or S)-1-(5-(4-amino-6-(trifluoromethyl)nicotinoyl)-2-(4-cyclobutyl-2-methylphenyl)-2,3,4,5,5a,6,8,9-octahydro-7H-1,2,5,7-tetraazabenzo[cd]azulen-7-yl)prop-2-en-1-one To a solution of 1-(2-(4-cyclobutyl-2-methylphenyl)-2,3,4,5,5a,6,8,9-octahydro-7H-1,2,5,7-tetraazabenzo[cd]azulen-7-yl)prop-2-en-1-one (80 mg, 1 Eq, 0.21 mmol) in DMF (1.6 mL) were added DIEA (135 mg, 185 μL, 5 Eq, 1 mmol), 4-amino-6-(trifluoroethyl)nicotinic acid (50 mg, 1.2 Eq, 0.25 mmol) and HATU (162 mg, 2 Eq, 0.42 mmol). The mixture was stirred at rt for 5 h, after which the mixture was diluted with water (5 mL) and EA (5 m L), and the aqueous layer was extracted with EA (2×5 mL). The combined organic layers were washed with saturated brine (2×5 mL), dried over anhydrous sodium sulfate and concentrated to give a residue. The residue was purified by Prep-HPLC (Column: Kinetex 5 n EVO C18, 30 mm*150 mm; Mobile Phase A: Water (10 mmol/L $NH_4HCO_3$), Mobile Phase B: ACN; Flow rate: 60 n L/min; Gradient: 35% B to 56% B in 8 min) to afford racemic 1-(5-(4-amino-6-(trifluoromethyl)nicotinoyl)-2-(4-cyclobutyl-2-methylphenyl)-2,3,4,5,5a,6,8,9-octahydro-7H-1,2,5,7-tetraazabenzo[cd]azulen-7-yl)prop-2-en-1-one (28 mg) as a white solid. The racemic compound was separated by Prep chiral-HPLC with the following conditions: Column: CHIRALPAK-IC 2*25c, 5 μm; Mobile Phase A: HEX(0.1% FA), Mobile Phase B: EtOH: DCM=1:1; Flow rate: 20 mL/min; Gradient: isocratic 50; Wave Length: UV 254/220 nm; RT1(min): 5.543; RT2(min): 9.663. This afforded (R or S)-1-(5-(4-amino-6-(trifluoromethyl)nicotinoyl)-2-(4-cyclobutyl-2-methylphenyl)-2,3,4,5,5a,6,8,9-octahydro-7H-1,2,5,7-tetraazabenzo[cd]azulen-7-yl)prop-2-en-1-one (12 mg) as a white solid as the second-eluting peak. LCMS:(ESI, m/z): 565 [M+1]+. $^1$H NMR: (400 MHz, DMSO-$d_6$, ppm) δ 8.19 (d, J=15.8 Hz, 1H), 7.51 (s, 1H), 7.23 (s, 1H), 7.16 (d, J=1.2 Hz, 2H), 7.07 (s, 1H), 6.77-6.59 (m, 2H), 6.41-6.08 (m, 1H), 5.88-5.64 (m, 1H), 5.27-4.98 (m, 1H), 4.76-4.57 (m, 1H), 4.55-4.31 (m, 1H), 3.78-3.45 (m, 2H), 3.00-2.63 (m, 4H), 2.41-1.65 (m, 12H).

Example C-20: Preparation of (R or S)-2-(7-acryloyl-5-(4-amino-6-(trifluoromethyl)nicotinoyl)-3,4,5,5a,6,7,8,9-octahydro-2H-1,2,5,7-tetraazabenzo[cd]azulen-2-yl)-5-cyclobutylbenzonitrile

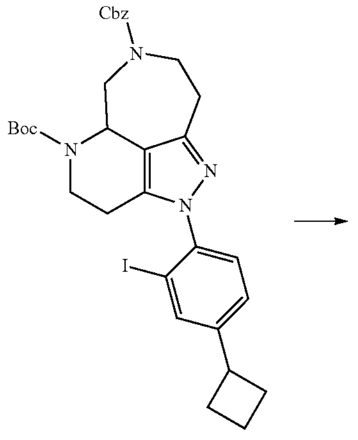

Int. RR

-continued

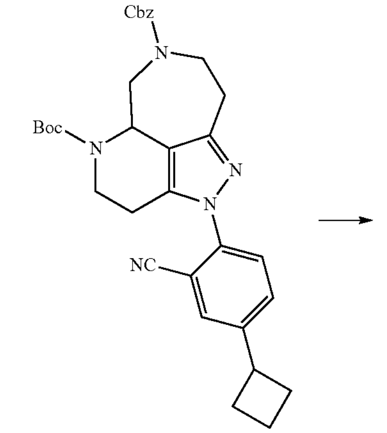

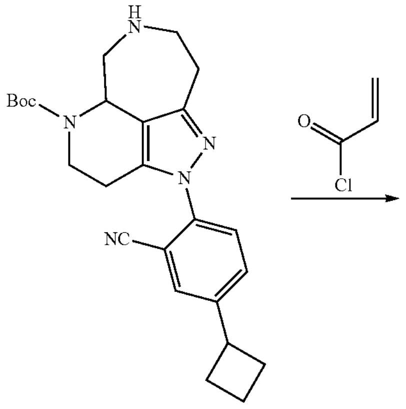

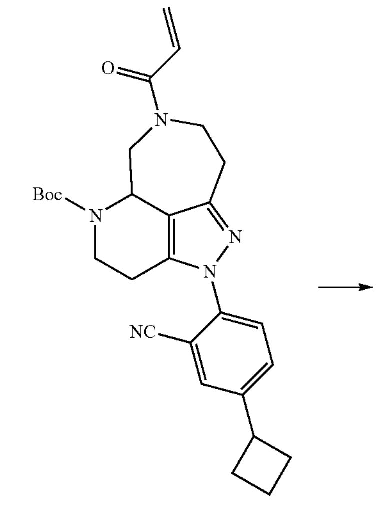

-continued

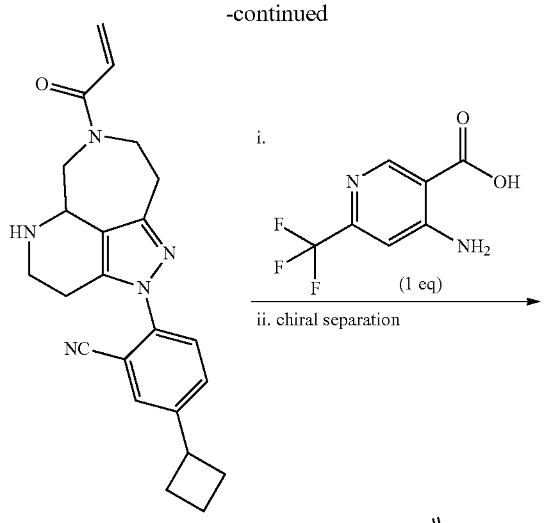

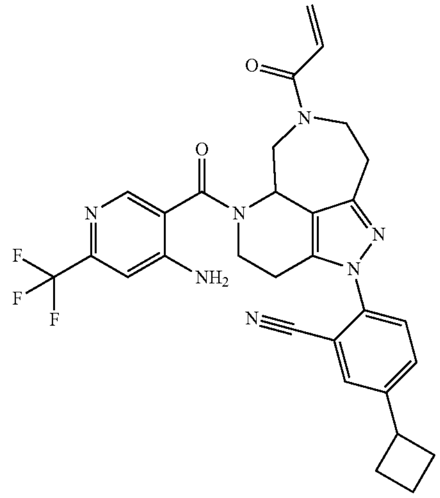

Step 1: Synthesis of 7-Benzyl 5-(tert-butyl) 2-(2-cyano-4-cyclobutylphenyl)-3,4,5a,6,8,9-hexahydro-2H-1,2,5,7-tetraazabenzo[cd]azulene-5,7-dicarboxylate To a stirred solution of 7-benzyl 5-(tert-butyl) 2-(4-cyclobutyl-2-iodophenyl)-3,4,5a,6,8,9-hexahydro-2H-1,2,5,7-tetraazabenzo[cd]azulene-5,7-dicarboxylate (300 mg, 1 Eq, 449 μmol) and copper (II) cyanide (207 mg, 4 Eq, 1.79 mmol) in DMF (3 mL) was added $Pd(PPh_3)_4$ (51.9 mg, 0.1 Eq, 44.9 μmol) at rt. The reaction mixture was placed un der a positive pressure of nitrogen and subjected to three back-filling cycles under high vacuum. The resulting mixture was stirred for 2 h at 80° C., after which the mixture was allowed to cool to rt and quenched by the addition of water (20 mL). The resulting mixture was extracted with EA (2×20 mL), and the combined organic layers were washed with brine (2×20 mL) and dried over anhydrous $Na_2SO_4$. After filtration, the filtrate was concentrated under reduced pressure. The residue was purified by silica gel column chromatography, eluting with EA/PE (1:5) to afford 7-benzyl 5-(tert-butyl) 2-(2-cyano-4-cyclobutylphenyl)-3,4,5a,6,8,9-hexahydro-2H-1,2,5,7-tetraaabenzo[cd]azulene-5,7-dicarboxylate (160 mg) as a yellow solid. LCMS:(ESI, m/z): 568 $[M+1]^+$.

Step 2: Synthesis of Tert-Butyl 2-(2-cyano-4-cyclobutylphenyl)-2,3,4,5a,6,7,8,9-octahydro-5H-1,2,5,7-tetraazabenzo[cd]azulene-5-carboxylate To a solution of 7-benzyl 5-(tert-butyl) 2-(2-cyano-4-cyclobutylphenyl)-3,4,5a,6,8,9-hexahydro-2H-1,2,5,7-tetraazabenzo[cd]azulene-5,7-dicarboxylate (250 mg, 1 Eq, 440 gmol) in 1,4-dioxane (5 mL) was added Pd/C (46.9 mg, 10 wt %) and $Pd(OH)_2/C$ (61.8 mg, 20 wt %) in a pressure tank. The mixture was purged with nitrogen (×3) and then was pressurized to 4 MPa with a hydrogen atmosphere and the mixture was stirred at rt for 12 h. The reaction mixture was then filtered, and filter cake was washed with EA (3×10 mL). The filtrate was concentrated under reduced pressure to afford tert-butyl 2-(2-cyano-4-cyclobutylphenyl)-2,3,4,5a,6,7,8,9-octahydro-5H-1,2,5,7-tetraazabenzo[cd]azulene-5-carboxylate (150 mg) as a crude yellow oil, which was used in the next step without further purification. LCMS:(ESI, m/z): 434 $[M+1]^+$.

Step 3: Synthesis of Tert-Butyl 2-(2-cyano-4-cyclobutylphenyl)-2,3,4,5a,6,7,8,9-octahydro-5H-1,2,5,7-tetraazabenzo[cd]azulene-5-carboxylate To a stirred solution of tert-butyl 2-(2-cyano-4-cyclobutylphenyl)-2,3,4,5a,6,7,8,9-octahydro-5H-1,2,5,7-tetraazabenzo[cd]azulene-5-carboxylate (150 mg, 1 Eq, 346 μmol) in DCM (2 mL) was added TEA (105 mg, 145 μL, 3 Eq, 1.04 mmol) and acryloyl chloride (37.6 mg, 1.2 Eq, 415 mol) at 0° C. The mixture reaction was then stirred for 30 min at rt, after which the reaction was quenched by the addition of water (20 mL) at rt. The resulting mixture was extracted with EA (2×20 mL), and the combined organic layers were washed with brine (2×20 mL) and dried over anhydrous $Na_2SO_4$. After filtration, the filtrate was concentrated under reduced pressure. The residue was purified by silica gel column chromatography, eluting with EA/PE (1:5) to afford tert-butyl 7-acryloyl-2-(2-cyano-4-cyclobutylphenyl)-2,3,4,5a,6,7,8,9-octahydro-5H-1,2,5,7-tetraazabenzo [cd]azulene-5-carboxylate (50 mg) as a yellow oil LCMS: (ESI, m/z): 488 $[M+1]^+$.

Step 4: Synthesis of 2-(7-acryloyl-3,4,5,5a,6,7,8,9-octahydro-2H-1,2,5,7-tetraazabenzo[cd]azulen-2-yl)-5-cyclobutylbenzonitrile To a stirred solution of tert-butyl 7-acryloyl-2-(2-cyano-4-cyclobutylphenyl)-2,3,4,5a,6,7,8,9-octahydro-5H-1,2,5,7-tetraazabenzo[cd]azulene-5-carboxylate (35 mg, 1 Eq, 72 μmol) in DCM (2 mL) was added TFA (1 mL) and the resulting mixture was stirred for 1 h at rt. The reaction mixture was then concentrated under reduced pressure to afford 2-(7-acryloyl-3,4,5,5a,6,7,8,9-octahydro-2H-1,2,5,7-tetraazabenzo[cd]azulen-2-yl)-5-cyclobutylbenzonitrile (50 mg) as a crude yellow oil which was used in next batch directly without further purification. LCMS:(ESI, m/z): 388 $[M+1]^+$.

Step 5: Synthesis of (R or S)-2-(7-acryloyl-5-(4-amino-6-(trifluoromethyl)nicotinoyl)-3,4,5,5a,6,7,8,9-octahydro-2H-1,2,5,7-tetraazabenzo[cd]azulen-2-yl)-5-cyclobutylbenzonitrile To a stirred solution of 2-(7-acryloyl-3,4,5,5a,6,7,8,9-octahydro-2H-1,2,5,7-tetraazabenzo[cd]azulen-2-yl)-5-cyclobutylbenzonitrile (50 mg, 1 Eq, 0.13 mmol) in DMF (2 mL) was added DIEA (67 mg, 4 Eq, 0.52 mmol),4-amino-6-(trifluoromethyl)nicotinic acid (27 mg, 1 Eq, 0.13 mmol) and HATU (98 mg, 2 Eq, 0.26 mmol) and the resulting mixture was stirred at rt for 2 h. The reaction was then quenched by the addition of water (20 mL) at rt, and the mixture was extracted with EA (2×20 mL). The combined organic layers were washed with brine (2×20 mL) and dried over anhydrous $Na_2SO_4$. After filtration, the filtrate was concentrated under reduced pressure. The residue was purified by chiral Column: CHIRALPAK-IC 2*25 cm, 5 μm; Mobile Phase A: hex (0.1% FA), Mobile Phase B: EtOH: DCM=1:1; Flow rate: 20 mL/min; Gradient: isocratic 50; Wave Length: UV 254/220 nm; RT1(min): 6.087; RT2(min: 8.073. This afforded (R or S)-2-(7-acryloyl-5-(4-amino-6-(trifluoromethyl)nicotinoyl)-3,4,5, a,6,7,8,9-octahydro-2H-1,2,5,7-tetraazabenzo[cd]azulen-2-yl)-5-cyclobutylbenzonitrile (2.8 mg) as the second-eluting peak as a white solid. LCMS:(ESI, m/z): 576 $[M+1]^+$. $^1$H NMR: (400 MHz, Chloroform-d, ppm) δ 8.33 (s, 1H), 7.59 (d, J=2.0 Hz, 2H), 7.49-7.30 (m, 2H), 7.02 (s, 1H), 6.51 (d, J=16.4 Hz, 1H), 5.86 (d, J=10.2 Hz, 1H), 5.38 (d, J=10.4 Hz, 3H), 4.98 (d, J=13.4 Hz, 1H), 4.49 (d, J=13.6 Hz, 1H), 4.19 (s, 1H), 3.62 (p, J=8.6 Hz, 1H), 3.24 (dd, J=13.5, 10.6 Hz, 2), 3.09 (dd, J=7.5, 3.7 Hz, 3H), 2.84-2.71 (m, 1H), 2.56 (d, J=15.6 Hz, 1H), 2.42 (dq, J=10.4, 4.5, 3.6 Hz, 2H), 2.24-2.04 (m, 3H), 1.93 (t, J=7.6 Hz, 1H).

Example C-21: Preparation of (S)-1-(5-(4-amino-6-(trifluoromethyl)nicotinoyl)-2-(2-chloro-4-cyclobutylphenyl)-2,3,4,5,5a,6,8,9-octahydro-7H-1,2,5,7-tetraazabenzo[cd]azulen-7-yl)prop-2-en-1-one

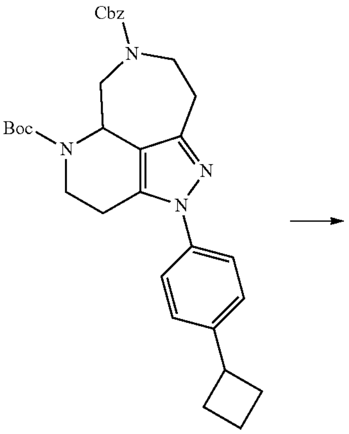

Int. S″

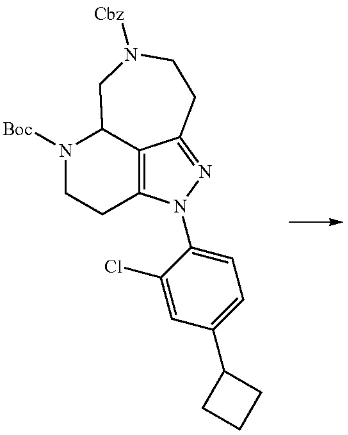

-continued

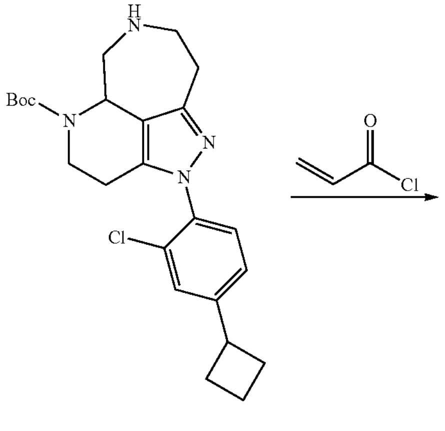

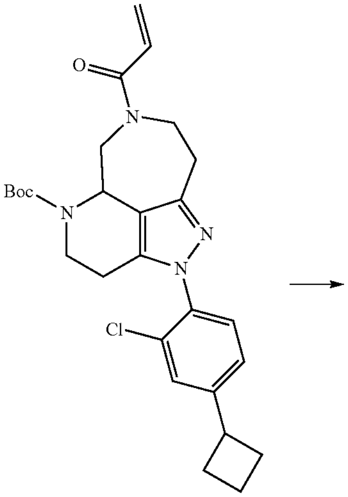

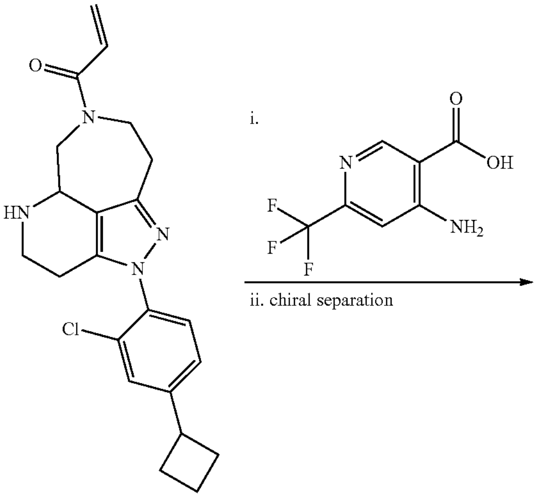

-continued

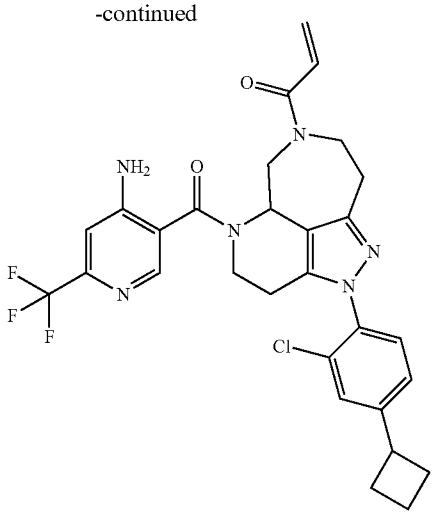

Step 1: Synthesis of 7-Benzyl 5-(tert-butyl) 2-(2-chloro-4-cyclobutylphenyl)-3,4,5a,6,8,9-hexahydro-2H-1,2,5,7-tetraazabenzo[cd]azulene-5,7-dicarboxylate To a solution of Int. S" (100 mg, 1 Eq, 184 gmol) in acetone (5 mL) were added (diacetoxyiodo)benzene (356 mg, 6 Eq, 1.11 mmol) $[Cp^*RhCl_2]_2$ (18.2 mg, 0.16 Eq, 29.5 μmol) sodium chloride (64.6 mg, 6 Eq, 1.11 mmol) and TFA (126 mg, 6 Eq, 1.11 mmol). The reaction mixture was placed under a positive pressure of nitrogen and subjected to three backfilling cycles under high vacuum. The resulting mixture was stirred for 24 h at 55° C., after which the reaction mixture was cooled to rt, and the mixture was filtered and rinsed with EA (3×20 mL), then diluted with water (20 mL). The aqueous layer was extracted with EA (2×20 mL), and the combined organic layers were washed with saturated brine (3×20 mL), dried over anhydrous sodium sulfate and concentrated to give a residue. The crude product was purified by silica gel chromatography, eluting with PE:EA=10:1 to give 7-benzyl 5-(tert-butyl) 2-(2-chloro-4-cyclobutylphenyl)-3,4,5a,6,8,9-hexahydro-2H-1,2,5,7-tetraazabenzo[cd]azulene-5,7-dicarboxylate (116 mg) as a yellow solid. LCMS:(ESI, m/z): 577 $[M+1]^+$.

Step 2: Synthesis of Tert-Butyl 2-(2-chloro-4-cyclobutylphenyl)-2,3,4,5a,6,7,8,9-octahydro-5H-1,2,5,7-tetraazabenzo[cd]azulene-5-carboxylate To a solution of 7-benzyl 5-(tert-butyl) 2-(2-chloro-4-cyclobutylphenyl)-3,4,5a,6,8,9-hexahydro-2H-1,2,5,7-tetraazabenzo[cd]azulene-5,7-dicarboxylate (205 mg, 1 Eq, 355 gmol) in DMA (1.5 mL) were added potassium phosphate (302 mg, 4 Eq, 1.42 mmol) and 2-mercaptoethan-1-ol (55.5 mg, 2 Eq, 710 gmol). The mixture was placed under a positive pressure of nitrogen and subjected to three backfilling cycles under high vacuum. The resulting mixture was stirred for 24 h at 75° C., after which it was cooled to room temperature and the mixture was filtered and rinsed with EA (3×20 mL), then the diluted with water (20 mL). The aqueous layer was extracted with EA (2×20 mL), and the combined organic layers were washed with saturated brine (3×20 mL), dried over anhydrous sodium sulfate and concentrated to give a residue. The crude product was purified by silica gel chromatography eluting with PE:EA=1:1 to give tert-butyl 2-(2-chloro-4-cyclobutylphenyl)-2,3,4,5a,6,7,8,9-octahydro-5H-1,2,5,7-tetraazabenzo[cd]azulene-5-carboxylate (132 mg) as a yellow solid. LCMS:(ESI, m/z): 443 $[M+1]^+$.

Step 3: Synthesis of Tert-Butyl 7-acryloyl-2-(2-chloro-4-cyclobutylphenyl-2,3,4,5a,6,7,8,9-octahydro-5H-1,2,5,7-tetraazabenzo[cd]azulene-5-carboxylate To a solution of tert-butyl 2-(2-chloro-4-cyclobutylphenyl)-2,3,4,5a,6,7,8,9-octahydro-5H-1,2,5,7-tetraazabenzo [cd]azulene-5-carboxylate (175 mg, 1 Eq, 395 mol) in DCM (3 mL) were added TEA (79.9 mg, 110 μL, 2 Eq, 790 gmol) and acryloyl chloride (39.3 mg, 1.1 Eq, 435 μmol). The resulting mixture was placed under an atmosphere of nitrogen and was stirred for 0.5 h at 0° C. The reaction mixture was then allowed to come to rt and the mixture was filtered and rinsed with EA (3×20 mL), then the diluted with water (20 mL). The aqueous layer was extracted with EA (2×20 mL), and the combined organic layers were washed with saturated brine (3×20 mL), dried over anhydrous sodium sulfate and concentrated to give a residue. The crude product was purified by silica gel chromatography, eluting with PE:EA=10:1 to give tert-butyl 7-acryloyl-2-(2-chloro-4-cyclobutylphenyl)-2,3,4,5a,6,7,8,9-octahydro-5H-1,2,5,7-tetraazabenzo[cd]azulene-5-carboxylate (147.5 mg) as a white solid. LCMS:(ESI, m/z): 497 $[M+1]^+$.

Step 4: Synthesis of 1-(2-(2-chloro-4-cyclobutylphenyl)-2,3,4,5,5a,6,8,9-octahydro-7H-1,2,5,7-tetraazabenzo[cd]azulen-7-yl)prop-2-en-1-one A solution of tert-butyl 7-acryloyl-2-(2-chloro-4-cyclobutylphenyl)-2,3,4,5a,6,7,8,9-octahydro-5H-1,2,5,7-tetraazabenzo[cd]azulene-5-carboxylate (137 mg, 1 Eq, 276 gmol) in TFA (1.5 mL) and DCM (0.5 mL) was stirred at rt for 0.5 h. The solvent was then removed under reduced pressure to afford 1-(2-(2-chloro-4-cyclobutylphenyl)-2,3,4,5,5a,6,8,9-octahydro-7H-1,2,5,7-tetraazabenzo[cd]azulen-7-yl)prop-2-en-1-one (200 mg) as a crude yellow oil which was used in the next reaction without further purification. LCMS:(ESI, m/z) 397 $[M+1]^+$.

Step 5: Synthesis of (R or S)-1-(5-(4-amino-6-(trifluoromethyl)nicotinoyl)-2-(2-chloro-4-cyclobutylphenyl)-2,3,4,5,5a,6,8,9-octahydro-7H-1,2,5,7-tetraazabenzo[cd]azulen-7-yl)prop-2-en-1-one To a solution of 1-(2-(2-chloro-4-cyclobutylphenyl)-2,3,4,5,5a,6,8,9-octahydro-7H-1,2,5,7-tetraazabenzo[cd]azulen-7-yl)prop-2-en-1-one (70 mg, 1 Eq, 0.18 mmol) in DMF (2 mL) were added HATU (0.13 g, 2 Eq, 0.35 mmol), 4-amino-6-(trifluoromethyl)nicotinic acid (55 mg, 1.5 Eq, 0.26 mmol) and DIEA (0.16 g, 7 Eq, 1.2 mmol). The mixture was stirred at rt for 2 h, after which the mixture was diluted with water (20 mL) and EA (20 mL), and the aqueous layer was extracted with EA (2×20 mL). The organic layer was combined and washed with saturated brine (2×20 mL), dried over anhydrous sodium sulfate and concentrated to give a residue. The residue was purified by Prep-HPLC (Column: XBridge BEH C18 OBD Prep Column 130, 5 m, 30 mm*150 mm; Mobile Phase A: Water (17 mmol/L $NH_4HCO_3$), Mobile Phase B: ACN; Flow rate: 60 mL/min; Gradient: 44% B to 60% B in 8 min) to afford racemic 1-(5-(4-amino-6-(trifluoromethyl)nicotinoyl)-2-(2-chloro-4-cyclobutylphenyl)-2,3,4,5,5a,6,8,9-octahydro-7H-1,2,5,7-tetraazabenzo[cd]azulen-7-yl)prop-2-en-1-one (21.3 mg). The racemic product was separated by Prep-chiral HPLC with the following conditions: Column: CHIRALPAK-IC 2*25 cm, 5 μm; Mobile Phase A: HEX(0.1% FA), Mobile Phase B: EtOH: DCM=1:1; Flow rate: 20 mL/min; Gradient: isocratic 50; Wave Length: UV 220/254 nm; RT1(min): 6.62; RT2(min): 11.59. This afforded (R or S)-1-(5-(4-amino-6-(trifluoromethyl)nicotinoyl)-2-(2-chloro-4-cyclobutylphenyl)-2,3,4,5,5a,6,8,9-octahydro-7H-1,2,5,7-tetraazabenzo[d]azulen-7-yl)prop-2-en-1-one (7.1 mg) as the second-eluting peak as a white solid. LCMS:(ESI, m/z): 585 $[M+1]^+$. $^1$H NMR: (400 MHz, Chloroform-d, ppm) δ 8.31 (s, 1H), 7.41-7.30 (m, 2H), 7.25-7.15 (m, 2H), 7.02 (s, 1H), 6.50 (d, J=16.5 Hz, 1H), 5.80 (m, 1H), 5.38 (s, 3H), 4.98 (d, J=13.4 Hz, 1H), 4.51 (d, J=13.8 Hz, 1H), 4.15 (s, 1H), 3.57 (m, 1H), 3.35-3.16 (m, 2H), 3.14-2.93 (m, 2H), 2.91-2.73 (m, 2H), 2.53-2.29 (m, 3H), 2.27-2.00 (m, 3H), 1.97-1.81 (m, 1H).

Example C-22: Preparation of 1-((5a(S or R),9(S or R))-5-(4-amino-6-(trifluoromethyl)nicotinoyl)-2-(4-cyclobutylphenyl)-9-cyclopropoxy-2,3,4,5,5a,6,8,9-octahydro-7H-1,2,5,7-tetraazabenzo[ed]azulen-7-yl) prop-2-en-1-one

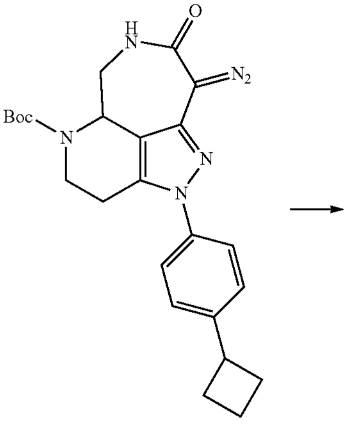

Int. V

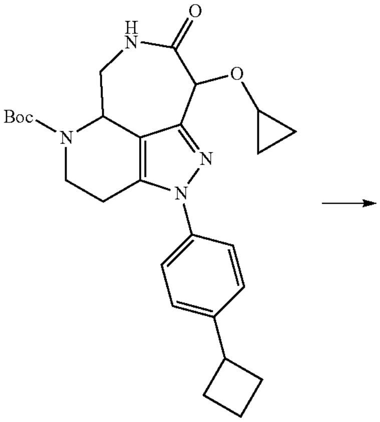

-continued

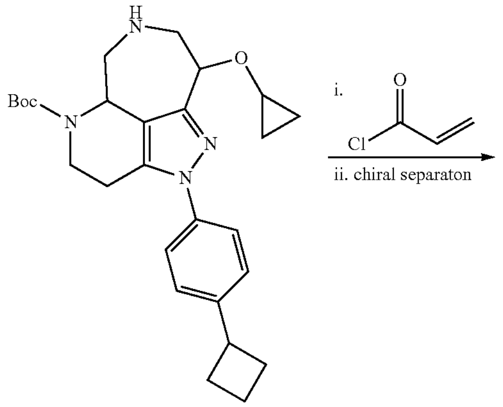

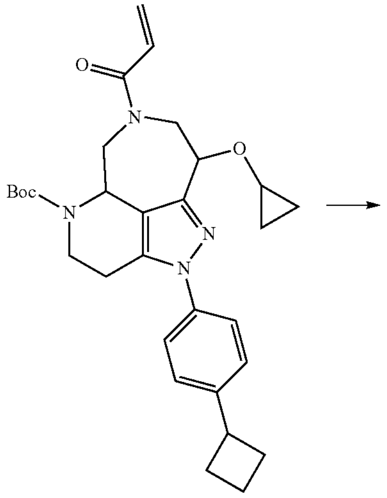

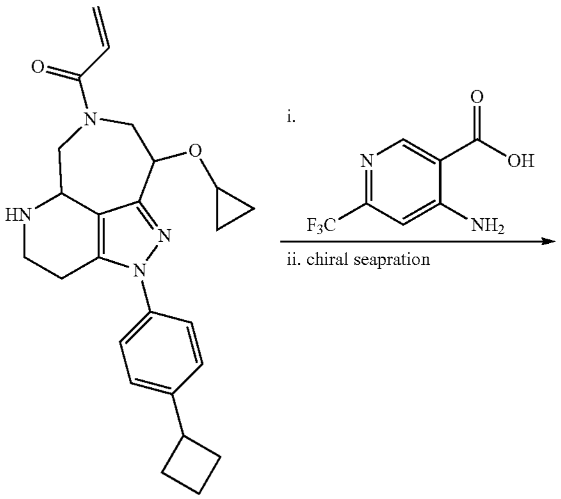

-continued

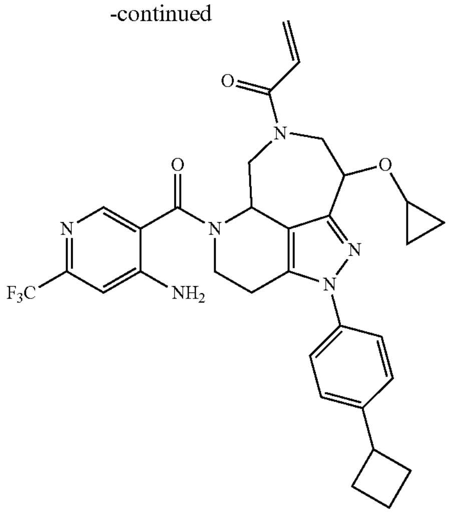

Step 1: Synthesis of Tert-Butyl 2-(4-cyclobutylphenyl)-9-cyclopropoxy-8-oxo-2,3,4,5a,6,7,8,9-octahydro-5H-1,2,5,7-tetraazabenzo[cd]azulene-5-carboxylate To a stirred solution of Int. V (3.75 g, 1 Eq, 8.36 mmol) in cyclopropanol (40 mL) was added rhodium(II) acetate (37.0 mg, 0.01 Eq, 83.6 mol). The solution w s placed under a positive pressure of nitrogen and subjected to three evacuation cycles under high vacuum. The resulting mixture was stirred for 2 h at 80° C., after which the reaction was quenched by the addition of water (100 mL) at rt. The resulting mixture was extracted with EA (2×100 mL) and the combined organic layers were washed with water (2×200 mL) and brine (1×200 mL) and dried over anhydrous $Na_2SO_4$. After filtration, the filtrate was concentrated under reduced pressure. The residue was purified by silica gel column chromatography, eluting with EA/PE (1:2) to afford tert-butyl 2-(4-cyclobutylphenyl)-9-cyclopropoxy-8-oxo-2,3,4,5a,6,7,8,9-octahydro-5H-1,2,5,7-tetraazabenzo[cd]azulene-5-carboxylate (1.92 g) as yellow solid. LCMS(ESI, m/z): 479 $[M+1]^+$.

Step 2: Synthesis of Tert-Butyl 2-(4-cyclobutylphenyl)-9-cyclopropoxy-2,3,4,5a,6,7,8,9-octahydro-5H-1,2,5,7-tetraazabenzo[cd]azulene-5-carboxylate Into an ice cold suspension of zinc chloride (1.3 g, 2.5 Eq, 9.4 mmol) in THF (36 mL) was added $NaBH_4$ (0.37 g, 2.6 Eq, 9.8 mmol) under a nitrogen atmosphere. After 1 h stirring at 0° C., the suspension was allowed to warm up to rt, and tert-butyl 2-(4-cyclobutylphenyl)-9-cyclopropoxy-8-oxo-2,3,4,5a,6,7,8,9-octahydro-5H-1,2,5,7-tetraazabenzo[cd]azulene-5-carboxylate (1.8 g, 1 Eq, 3.8 mmol) was then added in one portion into the resulting mixture and the mixture was stirred at 80° C. for 5 h. The reaction was then cooled to rt and water (20 mL) was added into the mixture. The residue was treated with 20% NaOH to adjust to pH=12 and the solution was extracted with EA (3×20 mL). After phase separation, the combined organic phases were dried over $Na_2SO_4$ and concentrated in vacuo to afford tert-butyl 2-(4-cyclobutylphenyl)-9-cyclopropoxy-2,3,4,5a,6,7,8,9-octahydro-5H-1,2,5,7-tetraazabenzo[cd]azulene-5-carboxylate (2.56 g) as a yellow solid which was used in the next step without further purification. LCMS:(ESI, m/z): 465 $[M+1]^+$.

Step 3: Synthesis of Tert-Butyl 7-acryloyl-2-(4-cyclobutylphenyl)-9-cyclopropoxy-2,3,4,5a,6,7,8,9-octahydro-5H-1, 2,5,7-tetraazabenzo[cd]azulene-5-carboxylate To a stirred solution of tert-butyl 2-(4-cyclobutylphenyl)-9-cyclopropoxy-2,3,4,5a,6,7,8,9-octahydro-5H-1,2,5,7-tetraazabenzo[cd]azulene-5-carboxylate (2.56 g, 1 Eq, 5.51 mmol) and TEA (2.79 g, 3.84 mL, 5 Eq, 27.5 mmol) in DCM (50 mL) was added acryloyl chloride (997 mg, 2 Eq, 11.0 mmol) dropwise at 0° C. under a nitrogen atmosphere. The resulting mixture was stirred for additional 1 h at rt, after which the reaction was quenched by the addition of water (50 mL) at rt. The resulting mixture was extracted with DCM (2×100 mL), and the combined organic layers were washed with water (2×200 mL) and brine (1×200 mL) and dried over anhydrous $Na_2SO_4$. After filtration, the filtrate was concentrated und r reduced pressure. The residue was purified by silica gel column chromatography, eluting with A/PE (1:2) to afford tert-butyl 7-acryloyl-2-(4-cyclobutylphenyl)-9-cyclopropoxy-2,3,4,5a,6,7,8,9-octahydro-5H-1,2,5,7-tetraazabenzo[cd]azulene-5-carboxylate (1.56 g) as a yellow solid. The racemic compound was separated into constituent enantiomers by Chiral HPLC separation under the condition (Column: CHIRALPAK-ID 3*25 cm, 5 μm; Mobile Phase A: HEX(0.1% FA), Mobile Phase B: EtOH: DCM=1:1; Flow rate: 40 mL/min; Gradient: isocratic 10; Wave Length: UV 254/220 nm; RT1(min): 15.75; RT2(min): 25.21; Sample Solvent: EtOH; Injection Volume: 0.9 mL; Number Of Runs: 11) to afford cis-tert-butyl (5a(S or R),9(S and R))-7-acryloyl-2-(4-cyclobutylphenyl)-9-cyclopropoxy-2,3,4,5a,6,7,8,9-octahydro-5H-1,2,5,7-tetraazabenzo[cd]azulene-5-carboxylate (236 mg, peak 1) and trans-tert-butyl (5a(R or S),9(S and R))-7-acryloyl-2-(4-cyclobutylphenyl)- 9-cyclopropoxy-2,3,4,5a,6,7,8,9-octahydro-5H-1,2,5,7-tetraazabenzo[cd]azulene-5-carboxylate (237 mg, peak 2) as yellow solids. LCMS:(ESI, m/z): 465 $[M+1]^+$ (peak 1), 465 $[M+1]^+$ (peak 2).

Step 4: Synthesis of 1-((5a(R or S),9(S and R))-2-(4-cyclobutylphenyl)-9 cyclopropoxy-2,3,4,5,5a,6,8,9-octahydro-7H-1,2,5, 7-tetraazabenzo[cd]azulen-7-yl)prop-2-en-1-one A solution of trans-tert-butyl (5a(R or S),9(S and R))-7-acryloyl-2-(4-cyclobutylphenyl)-9-cyclopropoxy-2,3,4,5a,6,7,8,9-octahydro-5H-1,2,5,7-tetraazabenzo[cd]azulene-5-carboxylate (237 mg, peak 2, 1 Eq, 251 mol) in DCM (2.1 mL) and TFA (0.7 mL) was stirred for 1 hour at 25° C. under nitrogen atmosphere. The reaction was monitored by LCMS. After completion of reaction, the resulting mixture was concentrated under vacuum to afford 1-((5a(R or S),9(S and R))-2-(4-cyclobutylphenyl)-9-cyclopropoxy-2,3,4,5,5a,6,8,9-octahydro-7H-1,2,5,7-tetraazabenzo[cd]azulen-7-yl)prop-2-en-1-one (150 mg) as a yellow solid which was used directly in the next step without further purification. LCMS: (ESI, m/z): 419 $[M+1]^+$.

Step 5: Synthesis of 1-((5a(R or S),9(S or R))-5-(4-amino-6-(trifluoromethyl)nicotinoyl)-2-(4-cyclobutylphenyl)-9-cyclopropoxy-2,3,4,5,5a,6,8,9-octahydro-7H-1,2,5,7-tetraazabenzo[cd]azulen-7-yl) prop-2-en-1-one A solution of 1-((5a(R or S),9(S and R))-2-(4-cyclobutylphenyl)-9-cyclopropoxy-2,3,4,5,5a,6,8,9-octahydro-7H-1,2,5,7-tetraazabenzo[cd]azulen-7-yl)prop-2-en-1-one (150 mg, 1 Eq, 358 mol), HATU (273 mg, 2 Eq, 717 mol), 4-amino-6-(trifluoromethyl)nicotinic acid (73.9 mg, 1 Eq, 358 μmol) and DIEA (232 mg, 312 μL, 5 Eq, 1.79 mmol) in DMF (3 mL) was stirred for 1 h at rt under a nitrogen atmosphere. The reaction was then quenched by the addition of water (20 mL) at rt, and the resulting mixture was extracted with EA (2×20 mL.). The combined organic layers were washed with water (2×20 mL) and brine (1×20 mL) and dried over anhydrous $Na_2SO_4$. After filtration, the filtrate was concentrated under reduced pressure. The crude product was purified by Prep-HPLC with the following conditions (Column: Xselect CSH™ Prep C18 5 μm 30*150 mm OBD; Mobile Phase A: Water (0.1% FA), Mobile Phase B: ACN; Flow rate: 60 mL/min; Gradient: 40% B to 68% B in 10 min; Wave Length: UV 254 nm/220 nm; RT1(min): 9.08) to afford 1-((5a(R or S),9(S and R))-5-(4-amino-6-(trifluoromethyl)nicotinoyl)-2-(4-cyclobutylphenyl)-9-cyclopropoxy-2,3,4,5,5a,6,8,9-octahydro-7H-1,2,5,7-tetraazabenzo[cd]azulen-7-yl)prop-2-en-1-one (50 mg) as a mixture of two diastereomers. The mixture was further purified by chiral HPLC separation under the condition: Column: LUX-Cellulose-4 250*21.2 mm, 5 μm; Mobile Phase A: HEX(0.1% FA), Mobile Phase B: EtOH; Flow rate: 20 mL/min; Gradient: isocratic 30; Wave Length: UV 254/220 nm; RT1(min): 9; RT2(min): 17) to afford 1-((5a(R or S),9(S or R))-5-(4-amino-6-(trifluoromethyl)nicotinoyl)-2-(4-cyclobutylphenyl)-9-cyclopropoxy-2,3,4,5,5a,6,8,9-octahydro-7H-1,2,5,7-tetraazabenzo[cd]azulen-7-yl)prop-2-en-1-one (21 mg) as the first-eluting isomer as a white solid. LCMS:(ESI, m/z): 607 $[M+1]^+$. $^1H$ NMR: (400 MHz, Chloroform-d, ppm) δ 8.34 (s, 1H), 7.45-7.39 (m, 2H), 7.26 (s, 2H), 7.03 (s, 1H), 6.58-6.36 (m, 1H), 5.91-5.73 (m, 1H), 5.33 (d, J=26.7 Hz, 2H), 5.03 (d, J=13.0 Hz, 1H), 4.86-4.70 (m, 1H), 4.60-4.34 (m, 1H), 4.25-3.95 (m, 2H), 3.64-3.51 (m, 1H), 3.31-2.93 (m, 3H), 2.90-2.65 (m, 2H), 2.44-2.30 (m, 2H), 2.25-1.77 (m, 4H), 1.34-1.16 (m, 2H), 0.90-0.81 (m, 2H), 0.73-0.53 (m, 2H).

TABLE C6

The compound of Example C-22-1 was made in analogous fashion to example C-22, using Int. E''' in place of Int. V. The first-eluting peak after step 1 (flash column chromatography eluting with EA/PE (2:5)) was carried on to afford the final compound as a racemate, which was separated using these conditions: LUX-Cellulose-4 250 * 21.2 mm, 5 μm; Mobile Phase A: HEX(0.1% FA), Mobile Phase B: EtOH; Flow rate: 20 mL/min; Gradient: isocratic 40; Wave Length: UV 254/220 nm; RT1 = 8 min; RT2 = 11 min) as the first-eluting peak.
[1547] The compound of Example C-22-2 was prepared in an analogous fashion to example C-22 using the corresponding amide. The final compound was separated into its pure enantiomer under the following conditions: CHIRAL ART Cellulose-SB, 3 * 25 cm, 5 μm; Mobile Phase A: Hex(0.1% FA)--HPLC, Mobile Phase B: EtOH:DCM = 1:1; Flow rate: 40 mL/min; Gradient: isocratic 25; Wave Length: UV 254/220 nm; RT1(min): 6; RT2(min): 11. The compound of example C-22-2 is the first-eluting peak.

| Example No. | Structure and Name | LCMS (ESI, m/z) | NMR |
|---|---|---|---|
| C-22-1 | 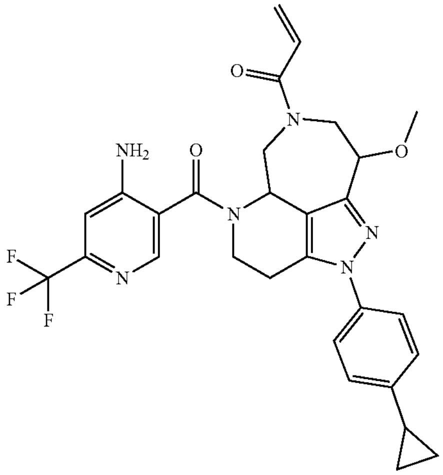 [SMILES: C=CC(=O)N1CC(OC)c2nn(-c3ccc(C4CC4)cc3)c3c2C(C1)N(C(=O)c1cnc(C(F)(F)F)cc1N)CC3] 1-((5a(R or S),9(R or S))-5-(4-amino-6-(trifluoromethyl)nicotinoyl)-2-(4-cyclopropylphenyl)-9-methoxy-2,3,4,5,5a,6,8,9-octahydro-7H-1,2,5,7-tetraazabenzo[cd]azulen-7-yl)prop-2-en-1-one | 567 [M + H]$^+$ | $^1$H NMR: (400 MHz, Chloroform-d, ppm) δ 8.32-8.18 (m, 1H), 7.44-7.37 (m, 4H), 7.24-7.15 (m, 2H), 7.10 (s, 1H), 6.80-6.63 (m, 2H), 6.37-6.10 (m, 1H), 5.91-5.69 (m, 1H), 5.17-5.03 (m, 1H), 4.72-4.64 (m, 1H), 4.53-4.18 (m, 2H), 3.72-3.54 (m, 3H), 3.17-3.11 (m, 3H), 2.94-2.82 (m, 1H), 2.65-2.57 (m, 1H), 2.03-1.92 (m, 1H), 1.04-0.92 (m, 2H), 0.74-0.64 (m, 2H). |
| C-22-2 | 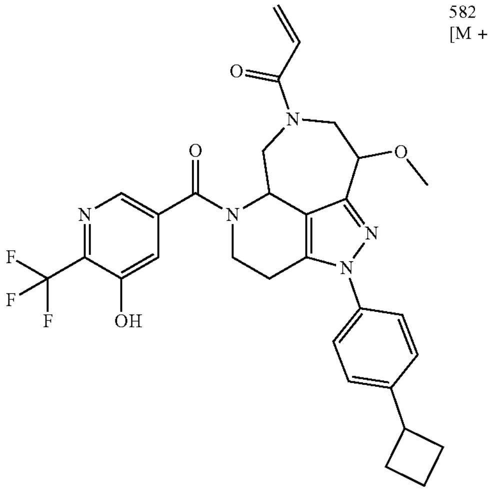 1-((5a(S or R),9(S or R))-2-(4-cyclobutylphenyl)-5-(5-hydroxy-6-(trifluoromethyl)nicotinoyl)-9-methoxy-2,3,4,5,5a,6,8,9-octahydro-7H-1,2,5,7-tetraazabenzo[cd]azulen-7-yl)prop-2-en-1-one | 582 [M + H]$^+$ | |

Example C-23: Preparation of (R or S)-1-(2-(4-cyclobutyl-2-hydroxyphenyl)-5-(8-(trifluoromethyl) quinazoline-5-carbonyl)-2,3,4,5,5a,6,8,9-octahydro 7H-1,2,5,7-tetraazabenzo[cd]azulen-7-yl)prop-2-en-1-one

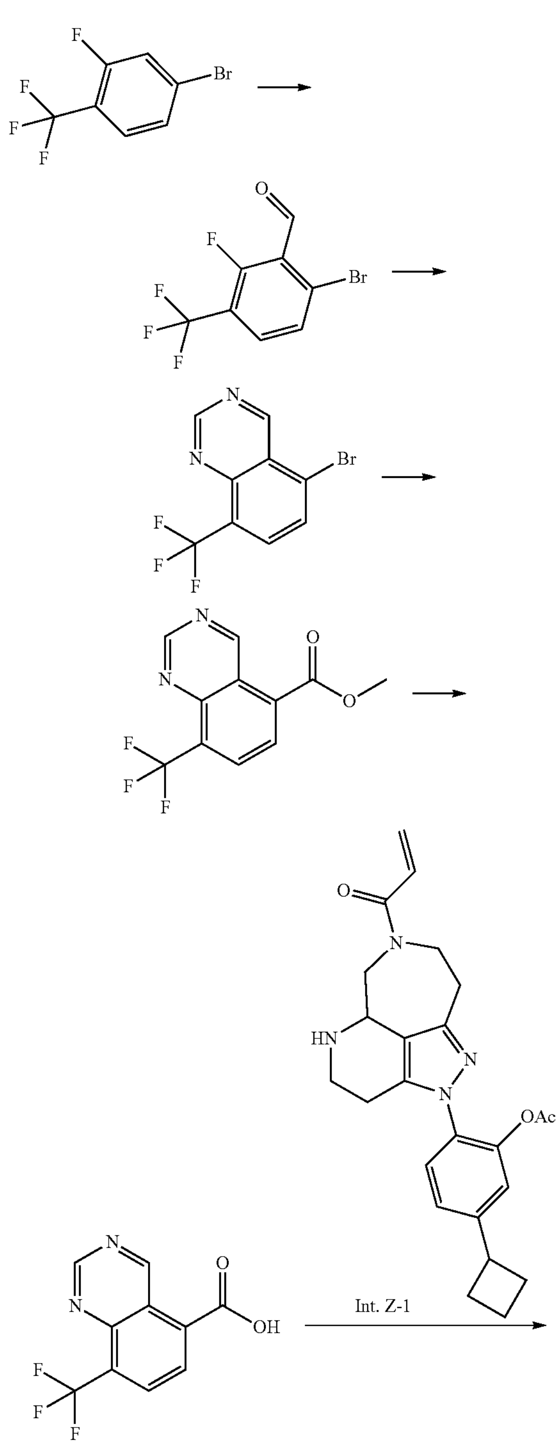

-continued

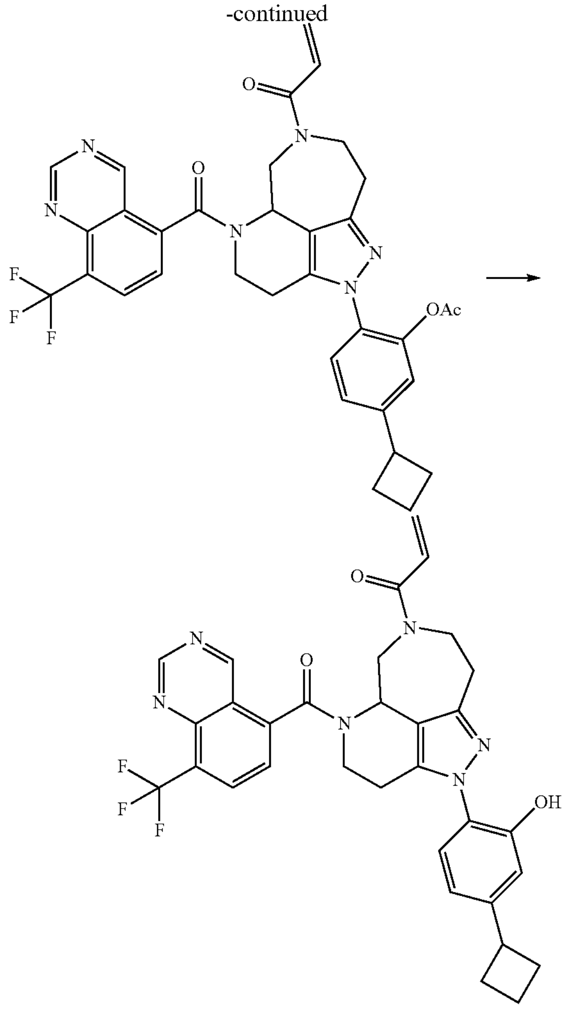

Step 1: Synthesis of 6-bromo-2-fluoro-3-(trifluoromethyl) benzaldehyde

To a solution of 2,2,6,6 tetramethyl piperidine (13 g, 15 mL, 1.1 Eq, 91 mmol) in THF (300 mL) was added dropwise n-butyllithium (2.5M in hexane, 8.1 mL, 1.1 Eq, 91 mmol) at −70° C. and the resulting solution was stirred for 30 min under an atmosphere of nitrogen. To the mixture was then added 4-bromo-2-fluoro-1-(trifluoromethyl) benzene (20 g, 1 Eq, 82 mmol) dropwise to the at −70° C. and the resulting mixture was stirred for 2 h, after which DMF (6.6 g, 7.0 mL, 1.1 Eq, 91 mmol) was added dropwise and the mixture was further stirred for 2 h under an atmosphere of nitrogen. The mixture was then diluted with ice water (300 mL) and EA (300 mL), and the aqueous layer was extracted with EA (2×2300 mL). The combined organic layers were washed with saturated brine (2×300 mL), dried over anhydrous sodium sulfate and concentrated to give a residue. The residue was purified by flash column chromatography, eluted with EA/PE (1:1) to afford 6-bromo-2-fluoro-3-(trifluoromethyl) benzaldehyde (18 g) as a white solid. LCMS: (ESI, m/z): 271 $[M+1]^+$.

Step 2: Synthesis of 5-bromo-8-(trifluoromethyl)quinazoline

To a solution of 6-bromo-2-fluoro-3-(trifluoromethyl) benzaldehyde (18 g, 1 Eq, 66 mmol) in MeCN (180 mL)

were added $K_2CO_3$ (32 g, 3.5 Eq, 0.23 mol) formamidine hydrochloride (8.0 g, 1.5 Eq, 0.10 mol) and molecular sieves (4 Å, 650 mg). The resulting mixture was stirred for 12 h at 80° C. under a nitrogen atmosphere. After the reaction mixture was cooled to rt, and the mixture was filtered and rinsed with EA (3×200 mL), then the filtrate was diluted with water (200 mL). The aqueous layer was extracted with EA (2×200 mL), and the organic layer was combined and washed with saturated brine (3×200 mL), dried over anhydrous sodium sulfate and concentrated to give a residue. The crude product was purified by silica gel chromatography eluted with PE:EA=2:1 to give 5-bromo-8-(trifluoromethyl) quinazoline 3 g) as a yellow oil. LCMS:(ESI, m/z): 277 $[M+1]^+$.

Step 3: Synthesis of Methyl 8-(trifluoromethyl) quinazoline-5-carboxylate

To a solution of 5-bromo-8-(trifluoromethyl)quinazoline (18 g, 1 Eq, 65 mmol) in MEOH (36 mL) were added TEA (20 g, 27 mL, 3 Eq, 0.19 mol) and $Pd(dppf)Cl_2$ (5.3 g, 0.1 Eq, 6.5 mmol). The mixture was purged with CO (×3) and then was pressurized 4.0 MPa with CO and stirred at 60° C. for 12 h. The mixture was then cooled to rt and was filtered and rinsed with EA (5×50 mL), then diluted with ice water (20 mL) and EA (20 mL), and the aqueous layer was extracted with EA (2×20 mL). The combined organic layers were washed with saturated brine (2×20 mL), dried over anhydrous sodium sulfate and concentrated to give a residue. The residue was purified by flash column chromatography, eluting with EA/PE (1:5) to afford methyl 8-(trifluoromethyl) quinazoline-5-carboxylate (3 g) as a yellow oil. LCMS:(ESI, m/z): 257 $[M+1]^+$.

Step 4: Synthesis of 8-(trifluoromethyl) quinazoline-5-carboxylic Acid

To a stirred solution of methyl 8-(trifluoromethyl) quinazoline-5-carboxylate (200 mg, 1 Eq, 781 mol) in THF (1.6 mL) and water (0.4 mL) was added LiOH (37.4 mg, 2 Eq, 1.56 mmol). The reaction mixture was then stirred for 1 h at rt, after which the reaction was quenched by the addition of water (20 mL) at rt. The resulting mixture was extracted with EA (2×20 mL), and the combined organic layers were washed with brine (2×20 mL), dried over anhydrous $Na_2SO_4$, and filtered. The filtrate was concentrated under reduced pressure, and the residue was purified by reversed-phase flash chromatography with the following conditions: column, C18 silica gel; mobile phase, ACN in water, 10% to 70% gradient in 10 min; detector, UV 254 nm, to afford 8-(trifluoromethyl) quinazoline-5-carboxylic acid (90 mg) as white solid LCMS:(ESI, m/z): 243 $[M+1]^+$.

Step 5: Synthesis of (R or S)-2-(7-acryloyl-5-(8-(trifluoromethyl) quinazoline-5-carbonyl)-3,4,5,5a,6,7,8,9-octahydro-2H-1, 2,5,7-tetraazabenzo[cd]azulen-2-yl)-5-cyclobutylphenyl acetate To a stirred solution of Int. Z-1 (45 mg, 1 Eq, 0.11 mmol) in DMF (0.5 mL) was added 8-(trifluoromethyl) quinazoline-5-carboxylic acid (39 mg, 1.5 Eq, 0.16 mmol), HATU (61 mg, 1.5 Eq, 0.16 mmol) and DIEA (55 mg, 4 Eq, 0.43 mmol) at rt and the resulting mixture was stirred for 1 h. The reaction was then quenched by the addition of water (20 mL), and the resulting mixture was extracted with EA (2×20 mL). The combined organic layers were washed with brine (2×20 mL), dried over anhydrous $Na_2SO_4$. After filtration, the filtrate was concentrated under reduced pressure to afford (R or S)-2-(7-acryloyl-5-(8-(trifluoromethyl) quinazoline-5-carbonyl)-3,4,5,5a,6,7,8,9-octahydro-2H-1,2,5,7-tetraazabenzo[cd]azulen-2-yl)-5-cyclobutylphenyl acetate (85 mg) as yellow solid which was used in the next step directly without further purification. LCMS:(ESI, m/z): 645 $[M+1]^+$.

Step 6: Synthesis of (R or S)-1-(2-(4-cyclobutyl-2-hydroxyphenyl)-5-(8-(trifluoromethyl)quinazoline-5-carbonyl)-2,3,4,5,5a,6,8,9-octahydro-7-1,2,5,7-tetraazabenzo[cd]azulen-7-yl)prop-2-en-1-one To a stirred solution of (R or S)-2-(7-acryloyl-5-(8-(trifluoromethyl) quinazoline-5-carbonyl)-3,4,5,5a,6,7,8,9-octahydro-2H-1,2,5,7-tetraazabenzo[cd]azulen-2-yl)-5-cyclobutylphenyl acetate (80 mg, 1 Eq, 0.12 mmol) in THF (0.4 mL) and water (0.1 mL) was added LiOH (5.9 mg, 3.7 μL, 2 Eq, 0.25 mmol) at rt and the resulting mixture was stirred for 1 h. The reaction was then quenched by the addition of water (30 mL) at rt and extracted with EA (2×30 mL). The combined organic layers were washed with brine (3×30 mL), dried over anhydrous $Na_2SO_4$ and filtered. The filtrate was concentrated under reduced pressure, and the residue was purified by reversed-phase flash chromatography with the following conditions: Column-XselectCSHTMPrep C18 5 μm 30*150 mm OBD; Mobile Phase A: Water(0.1% FA), Mobile Phase B: ACN; Flow rate: 60 ml/min mL/min; Gradient: 38% B to 56% in 10 min) to afford (R or S)-1-(2-(4-cyclobutyl-2-hydroxyphenyl)-5-(8-(trifluoromethyl)quinazoline-5-carbonyl)-2,3,4,5,5a,6,8,9-octahydro-7H-1,2,5,7-tetraazabenzo[cd]azulen-7-yl)prop-2-en-1-one (13.6 mg) as white solid. LCMS:(ESI, m/z): 603 $[M+1]^+$. $^1H$ NMR: (400 MHz, DMSO-d6)) δ 10.01 (s, 1H), 9.80-9.60 (m, 11H), 9.60-9.42 (m, 11H), 8.70-8.37 (m, 11H), 8.06-7.89 (m, 1H), 7.72-7.45 (m, 1H), 7.38-7.15 (m, 1H), 7.10-6.65 (m, 2H), 6.49-6.19 (m, 1H), 5.92-5.68 (m, 1H), 5.62-5.25 (m, 1H), 4.89-4.20 (m, 2H), 3.70-3.40 (m, 3H), 3.27-3.10 (m, 1H), 2.98-2.75 (m, 3H), 2.65-2.55 (m, 1H), 2.35-2.15 (m, 3H), 2.10-1.90 (m, 3H), 1.85-1.65 (m, 1H).

Example C-24: Preparation of (R or S)-1-(5-(2-amino-6-(1,1-difluorethyl)nicotinoyl)-2-(4-cyclobutyl-2-hydroxyphenyl)-2,3,4,5,5a,6,8,9-octahydro-7H-1,2,5,7-tetraazabenzo[cd]azulen-7-yl) prop-2-en-1-one

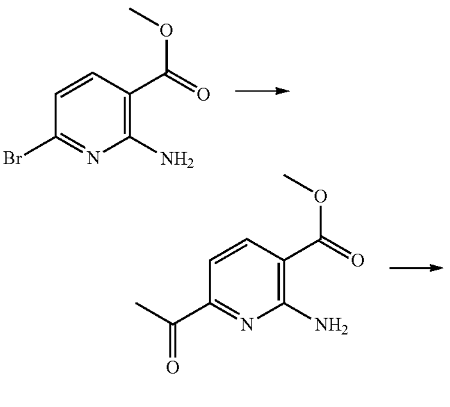

-continued

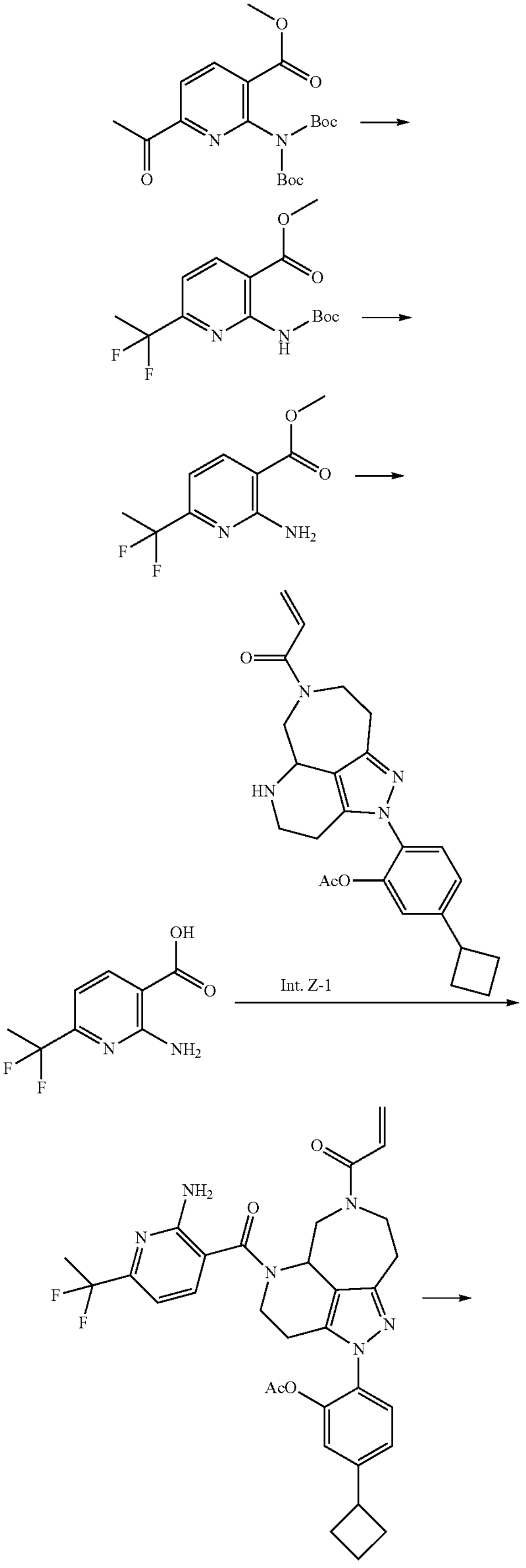

-continued

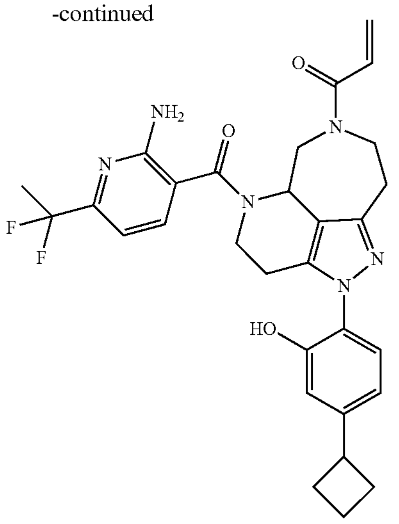

Step 1: Synthesis of Methyl 6-acetyl-2-aminonicotinate

To a solution of methyl 2-amino-6-bromonicotinate (2.00 g, Eq, 8.66 mmol) in 1,4-dioxane (20 mL) were added tributyl(1-ethoxyvinyl)stannane (6.25 g, 2 Eq, 17.3 mmol) and bis-(triphenylphosphino)-palladium chloride (1.22 g, 0.2 Eq, 1.73 mmol). The reaction mixture was placed under a positive pressure of nitrogen and was subjected to three backfilling cycles under high vacuum. The resulting mixture was stirred for 100° C. for 16 h under a nitrogen atmosphere, after which the reaction mixture was cooled to rt, and the mixture was filtered and rinsed with EA (3×20 mL). The filtrate was then diluted with water (20 mL). The aqueous layer was extracted with EA (2×20 mL). The organic layer was combined and washed with saturated brine (3×20 mL), dried over anhydrous sodium sulfate and concentrated to give a residue. To the residue was then added 4N HCl (10 mL) and THF (20 mL) and the resulting mixture was stirred at rt for 1 hour. The solvent was then removed under reduced pressure, and the residue was purified by flash column chromatography, eluting with EA/PE (1:5) to afford methyl 6-acetyl-2-aminonicotinate (860 mg) as a yellow solid. LCMS:(ESI, m/z): 195 $[M+1]^+$.

Step 2: Synthesis of Methyl 6-acetyl-2-(bis(tert-butoxycarbonyl)amino)nicotinate To a solution of methyl 6-acetyl-2-aminonicotinate (760 mg, 1 Eq, 3.91 mmol) in DCM (8 mL) were added DMAP (956 mg, 2 Eq, 7.83 mmol), $Boc_2O$ (2.56 g, 2.70 mL, 3 Eq, 11.7 mmol) and $Et_3N$ (1.98 g, 2.73 mL, 5 Eq, 19.6 mmol). The mixture was stirred at rt for 16 h, after which the mixture was diluted with water (20 mL) and EA (20 mL), the aqueous layer was extracted with EA (2×20 mL). The combined organic layers were washed with saturated brine (2×20 mL), dried over anhydrous sodium sulfate, and concentrated to give a residue. The residue was purified by flash column chromatography, eluting with EA/PE (1:5) to afford methyl 6-acetyl- 2-(bis(tert-butoxycarbonyl)amino)nicotinate (790 mg) as a yellow solid. LCMS:(ESI, m/z): 395 $[M+1]^+$.

Step 3: Synthesis of Methyl 2-((tert-butoxycarbonyl)amino)-6-(1,1-difluoroethyl)nicotinate A solution of methyl 6-acetyl-2-((tert-butoxycarbonyl) amino)nicotinate (600 mg, 1 Eq, 2.04 mmol) in DAST (6 mL) was stirred at 80° C. for 3 h. The mixture was then diluted with ice water (20 mL) and EA (20 mL), and the aqueous layer was extracted with EA (2×20 mL). The combined organic layers were washed with saturated brine (2×20 mL), dried over anhydrous sodium sulfate and concentrated to give a residue. The residue was purified by flash column chromatography, eluting with EA/PE (1:5) to afford methyl 2-((tert-butoxycarbonyl)amino)-6-(1,1-difluoroethyl)nicotinate (500 mg) as a yellow solid. LCMS:(ESI, m/z): 317 $[M+1]^+$.

Step 4: Synthesis of Methyl 2-amino-6-(1,1-difluoroethyl)nicotinate

A solution of methyl 2-((tert-butoxycarbonyl)amino)-6-(1,1-difluoroethyl)nicotinate (270 mg, 1 Eq, 854 μmol) in TFA (1.5 mL) and DCM (3 mL) was stirred at rt for 30 min. The solvent was then removed under reduced pressure to afford ethyl 2-amino-6-(1,1-difluoroethyl)nicotinate (250 mg) as a crude yellow oil which was use in the next step directly without further purification. LCMS:(ESI, m/z): 217 $[M+1]^+$.

Step 5: Synthesis of 2-amino-6-(1,1-difluoroethyl)nicotinic Acid

To a solution of methyl 2-amino-6-(1,1-difluoroethyl) nicotinate (230 mg, 1 Eq, 1.06 mmol) in THF (3 mL) and $H_2O$ (1.5 mL) was added LiOH (51.0 mg, 2 Eq, 2.13 mmol). The mixture was stirred at rt for 1 h, after which the mixture was acidified to H=3 with 1 M Sulfuric acid, then diluted with EA (20 mL) and water (15 mL), and the aqueous layer was extracted with EA (2×20 mL). The organic layers were combined and washed with saturated brine (20 mL), dried over anhydrous sodium sulfate and concentrated to give a residue. The residue was purified by reverse phase chromatography (column: C18 column; Gradient: MeCN in water with 0.2% formic acid) afforded 2-amino-6-(1,1-difluoroethyl)nicotinic acid (150 mg) as a yellow solid. LCMS:(ESI, m/z): 203 $[M+1]^+$.

Step 6: Synthesis of (R or S)-2-(7-acryloyl-5-(2-amino-6-(1,1-difluoroethyl)nicotinoyl)-3,4,5,5a,6,7,8,9-octahydro-2H-1, 2,5,7-tetraazabenzo[cd]azulen-2-yl)-5-cyclobutylphenyl acetate To a solution of 2-amino-6-(1,1-difluoroethyl)nicotinic acid (24 mg, 1 Eq, 0.12 mmol) in DMF (2 mL) were added HATU (68 mg, 1.5 Eq, 0.18 mmol), DIEA (92 mg, 0.12 mL, 6.0 Eq, 0.71 mmol) and Int. Z-1 (50 mg, 1 Eq, 0.12 mmol). The mixture was stirred at rt for 5 h. The mixture was then diluted with water (20 mL) and EA (20 mL), and the aqueous layer was extracted with EA (2×20 mL). The combined organic layers were washed with saturated brine (2×20 mL), dried over anhydrous sodium sulfate and concentrated to give a crude yellow product (50.0 mg) which was used in the next reaction without further purification. LCMS:(ESI, m/z): 605 $[M+1]^+$.

Step 7: Synthesis of (R or S)-1-(5-(2-amino-6-(1,1-difluoroethyl)nicotinoyl)-2-(4-cyclobutyl-2-hydroxyphenyl)-2,3,4,5,5a,6,8,9-octahydro-7H-1,2,5, 7-tetraazabenzo[cd]azulen-7-yl)prop-2-en-1-one To a solution of (R or S)-2-(7-acryloyl-5-(2-amino-6-(1, 1-difluoroethyl)nicotinoyl)-3,4,5,5a,6,7,8,9-octahydro-2H-1,2,5,7-tetraazabenzo[cd]azulen-2-yl)-5-cyclobutylphenyl acetate (50 mg, 1 Eq, 83 μmol) in THF (1.5 mL) and water (0.75 mL) was added LiOH (10.5 mg, 5.3 Eq, 438 mol). The mixture was stirred at rt for 5 h. The mixture was diluted with water (20 mL) and EA (20 mL), and the aqueous layer was extracted with EA (2×20 mL). The combined organic layers were washed with saturated brine (2×20 mL), dried over anhydrous sodium sulfate and concentrated to give a residue. The residue was purified by Prep-HPLC (Column: Sunfire C18 5 m, 30 mm*150 mm; Mobile Phase A: Water (0.1% FA), Mobile Phase B: ACN; Flow rate: 60 mL/min; Gradient: 48% B to 68% B in 8 min; Wave Length: UV 254 nm/220 nm; RT1(min): 6.33) to afford (R or S)-1-(5-(2-amino-6-(1,1-difluoroethyl)nicotinoyl)-2-(4-cyclobutyl-2-hydroxyphenyl)-2,3,4,5,5a,6,8,9-octahydro-7H-1,2,5,7-tetraazabenzo[ca]azulen-7-yl)prop-2-en-1-one (10.0 mg) as a white solid. LCMS:(ESI, m/z): 563 $[M+1]^+$. $^1H$ NMR: (400 MHz, Chloroform-d, ppm) δ 10.12 (s, 1H), 7.51 (d, J=7.4 Hz, 1H), 7.26 (s, 1H), 7.05 (d, J=7.5 Hz, 1H), 7.02-6.94 (m, 2H), 6.78-6.70 (m, 1H), 6.56-6.43 (m, 1H), 5.96-5.68 (m, 1H), 5.49-5.15 (m, 2H), 4.96 (d, J=13.1 Hz, 1H), 4.45 (s, 1H), 4.30-3.95 (m, 1H), 3.51 (p, J=8.6 Hz, 1H), 3.27-2.92 (m, 5H), 2.88-2.65 (m, 2H), 2.41-2.26 (m, 2H), 2.21-2.07 (m, 2H), 2.06-1.90 (m, 4H), 1.89-1.79 (m, 2H).

Example C-25: Preparation of 3-(((5a(R or S))-7-acryloyl-5-(4-amino-6-(trifluoromethyl)nicotinoyl)-2-(4-cyclobutylphenyl)-3,4,5,5a,6,7,8,9-octahydro-2H-1,2,5,7-tetraazabenzo[cd]azulen-9-yl)oxy) cyclobutane-1-carbonitrile

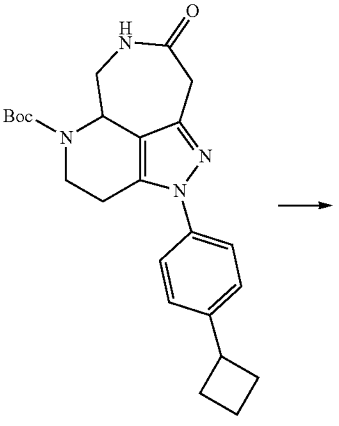

Int. R-1

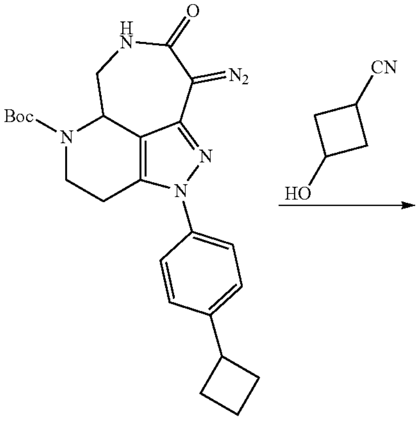

Int. R-1′

-continued

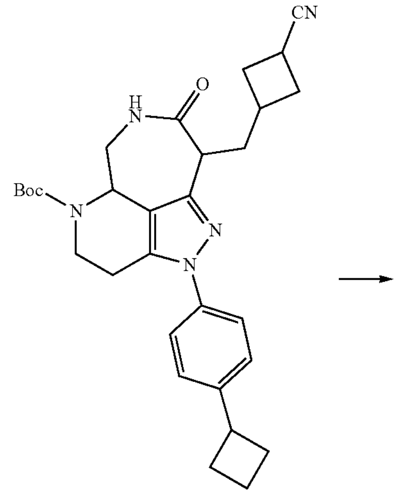

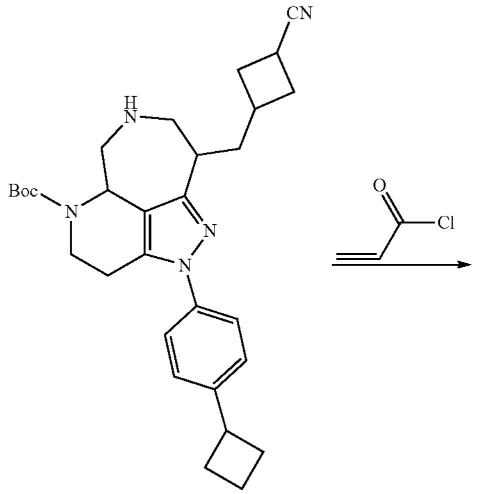

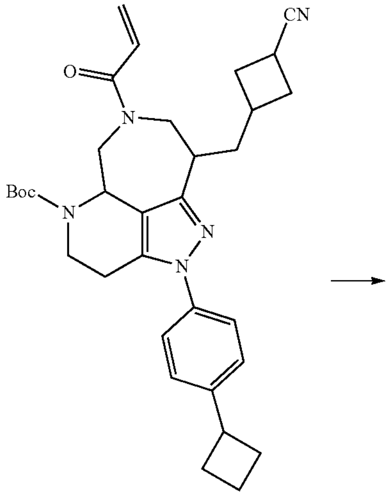

-continued

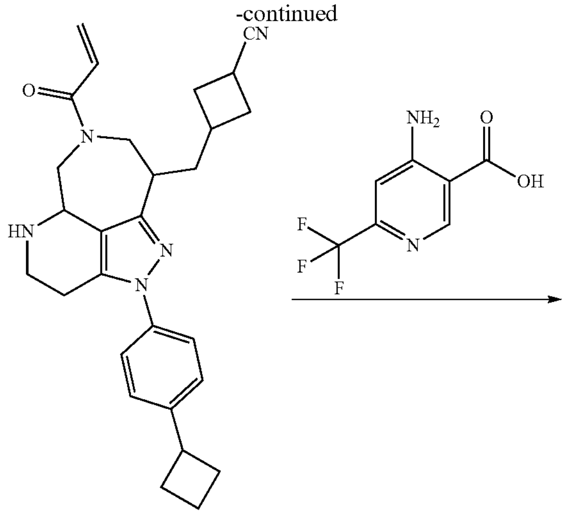

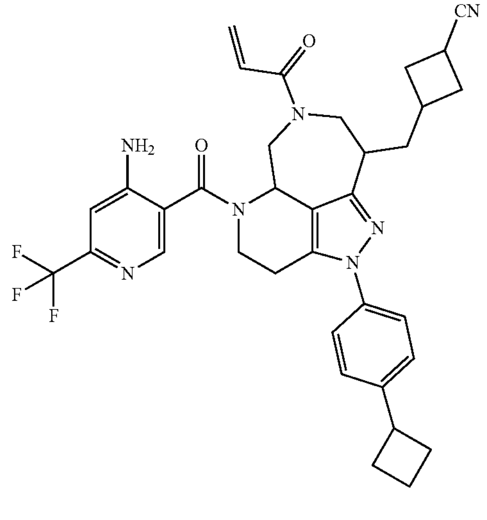 [SMILES: C=CC(=O)N1CC(CC2CC(C#N)C2)c2nn(-c3ccc(C4CCC4)cc3)c3c2C(C1)N(C(=O)c1cnc(C(F)(F)F)cc1N)CC3]

Step 1: Synthesis of Tert-Butyl (R or S)-2-(4-cyclobutylphenyl)-9-diazo-8-oxo-2,3,4,5a,6,7,8,9-octahydro-5H-1,2,5,7-tetraazabenzo[cd]azulene-5-carboxylate (Int. R-1')

To a solution of Int. R-1 (500 mg, 1 Eq, 1.18 mmol) in ACN (5 mL) was added DBU (270 mg, 268 μL, 1.5 Eq, 1.78 mmol). The mixture was cooled to 0° C., they p-toluenesulfonyl azide (700 mg, 808 μL, 3 Eq, 3.55 mmol) was added dropwise to the above mixture at 0° C. under a nitrogen atmosphere. The mixture was then allowed to come to rt where it was stirred for 2 h. The mixture was then diluted with ice water (20 mL) and EA (20 mL), and the aqueous layer was extracted with EA (2×20 mL). The combined organic layers were washed with saturated brine (2×20 mL), dried over anhydrous sodium sulfate and concentrated to give a residue. The residue was purified by flash column chromatography, eluting with EA/PE (1:5) to afford tert-butyl (R or S)-2-(4-cyclobutylphenyl)-9-diazo-8-oxo-2,3,4,5a,6,7,8,9-octahydro-5H-1,2,5,7-tetraazabenzo[cd]azulene-5-carboxylate (500 mg) as a yellow solid. LCMS:(ESI, m/z): 449 $[M+1]^+$.

Step 2: Synthesis of Tert-Butyl (5a(R or S))-9-(3-cyanocyclobutoxy)-2-(4-cyclobutylphenyl)-8-oxo-2,3,4,5a,6,7,8,9-octahydro-5H-1,2,5, 7-tetraazabenzo[cd]azulene-5-carboxylate To a solution of Int. R-1' (500 mg, 1 Eq, 1.11 mmol) in DCM (10 mL) under a nitrogen atmosphere was added 3-hydroxycyclobutane-1-carbonitrile (325 mg, 3 Eq, 3.34 mmol). The mixture was subjected to 450 nm wavelength light and was stirred for 1 h. The mixture was then diluted with ice water (20 mL) and EA (20 mL), the aqueous layer was extracted with EA (2×20 mL). The combined organic layer was washed with saturated brine (2×20 mL), dried over anhydrous sodium sulfate and concentrated to give a residue. The residue was purified by flash column chromatography, eluting with EA/PE (1:5) to afford tert-butyl (5a(R or S))-9-(3-cyanocyclobutoxy)-2-(4-cyclobutylphenyl)-8-oxo-2,3,4,5a,6,7,8,9-octahydro-5H-1,2,5,7-tetraazabenzo[cd]azulene-5-carboxylate (380 mg) as a yellow solid. LCMS: (ESI, m/z): 518 $[M+1]^+$.

Step 3: Synthesis of in Tert-Butyl (5a(R or S))-9-(3-cyanocyclobutoxy)-2-(4-cyclobutylphenyl)-2,3,4,5a,6,7,8,9-octahydro-5H-1,2,5, 7-tetraazabenzo[cd]azulene-5-carboxylate To a solution of tert-butyl (5a(R or S))-9-(3-cyanocyclobutoxy)-2-(4-cyclobutylphenyl)-8-oxo-2,3,4,5a,6,7,8,9-octahydro-5H-1,2,5,7-tetraazabenzo[cd]azulene-5-carboxylate (150 mg, 1 Eq, 290 μmol) in THF (3 mL). The mixture was cooled to 0° C., then $BH_3$·THF (99.6 mg, 4 Eq, 1.16 mmol) was added dropwise to the above mixture at 0° C. under a nitrogen atmosphere. The mixture was warmed to 60° C. and stirred for 2 h. The mixture was cooled to 0° C., then MeOH (30 mL) was added drop-wise and the mixture was further stirred for 10 min. The solvent was then removed under reduced pressure to afford tert-butyl (5a(R or S))-9-(3 cyanocyclobutoxy)-2-(4-cyclobutylphenyl)-2,3,4,5a,6,7,8,9-octahydro-5H-1,2,5,7-tetraazabenzo[cd]azulene-5-carboxylate (160 mg) as a crude white solid which was used in the next step directly without further purification. LCMS: (ESI, m/z): 504 $[M+1]^+$.

Step 4: Synthesis of Tert-Butyl (5a(R or S))-7-acryloyl-9-(3-cyanocyclobutoxy)-2-(4-cyclobutylphenyl)-2,3,4,5a,6,7,8,9-octahydro-5H-1,2,5, 7-tetraazabenzo[cd]azulene-5-carboxylate To a solution of tert-butyl (5a(R or S))-9-(3-cyanocyclobutoxy)-2-(4-cyclobutylphenyl)-2,3,4,5a,6,7,8,9-octahydro-5H-1,2,5,7-tetraazabenzo[cd]azulene-5-carboxylate (150 mg, 1 Eq, 298 mol) in DCM (3 mL) was added TEA (151 mg, 208 μL, 5 Eq, 1.49 mmol). The mixture was cooled to 0° C., then acryloylchloride (40.4 mg, 36.3 μL, 1.5 Eq, 447 mol) was added dropwise to the above mixture at 0° C. under a nitrogen atmosphere. The mixture was then warmed to rt and stirred for 2 h, after which the mixture was diluted with ice water (20 mL) and EA (20 mL), and the aqueous layer was extracted with EA (2×20 mL). The combined organic layers were washed with saturated brine (2×20 mL), dried over anhydrous sodium sulfate and concentrated to give a residue. The residue was purified by flash column chromatography, eluting with EA/PE (1:5) to afford tert-butyl (5a(R or S))-7-acryloyl-9-(3-cyanocyclobutoxy)-2-(4-cyclobutylphenyl)- 2,3,4,5a,6,7,8,9-octahydro-5H-1,2,5,7-tetraazabenzo[cd]azulene-5-carboxylate (60 mg) as a white solid. LCMS:(ESI, m/z): 558 $[M+1]^+$.

Step 5: Synthesis of 3-(((5a(R or S))-7-acryloyl-2-(4-cyclobutylphenyl)-3,4,5,5a,6,7,8,9-octahydro-2H-1,2,5,7-tetraazabenzo[cd]azulen-9-yl)oxy)cyclobutane-1-carbonitrile A solution of tert-butyl (5a(R or S))-7-acryloyl-9-(3 cyanocyclobutoxy)-2-(4-cyclobutylphenyl)-2,3,4,5a,6,7,8,9-octahydro-5H-1,2,5,7-tetraazabenzo[cd]azulene-5-carboxylate (55 mg, 1 Eq, 99 μmol) in TFA (0.5 mL) and DCM (1 mL) was stirred at rt for 0.5 h. The solvent was then removed under reduced pressure to afford 3-(((5a R or S))-7-acryloyl-2-(4-cyclobutylphenyl)-3,4,5,5a,6,7,8,9-octahydro-2H-1,2,5,7-tetraazabenzo[cd]azulen-9-yl)oxy)cyclobutane-1-carbonitrile (60 mg) as a crude yellow oil which was used in the next step directly without further purification. LCMS:(ESI, m/z): 458 $[M+1]^+$.

Step 6: Synthesis of 3-(((5a(R or S))-7-acryloyl-5-(4-amino-6-(trifluoromethyl)nicotinoyl)-2-(4-cyclobutylphenyl)-3,4,5,5a,6,7,8,9-octahydro-2H-1,2,5,7-tetraazabenzo[cd]azulen-9-yl)oxy)cyclobutane-1-carbonitrile To a solution of 3-(((5a(R or S))-7-acryloyl-2-(4-cyclobutylphenyl)-3,4,5,5a,6,7,8,9-octahydro-2H-1,2,5,7-tetraazabenzo[cd]azulen-9-yl)oxy)cyclobutane-1-carbonitrile (60 mg, 1 Eq, 0.13 mmol) in DMF (1 mL) were added 4-amino-6-(trifluoromethyl)nicotinic acid (32 mg, 1.2 Eq, 0.16 mmol), HATU (75 mg, 1.5 Eq, 0.20 mmol) and DIEA (85 mg, 0.11 mL, 5 Eq, 0.66 mmol). The mixture was stirred at rt for 1 h, after which the mixture was diluted with water (20 mL) and EA (20 mL), and the aqueous layer was extracted with EA (2×20 mL). The combined organic layers were washed with saturated brine (2×20 mL), dried over anhydrous sodium sulfate and concentrated to give a residue. The residue was purified by Prep-HPL (Column: YMC-Actus Triart C18 ExRS 30*150 mm, 5 μm; Mobile Phase A: Water(10 mmol/L $NH_4HCO_3$), Mobile Phase B: ACN; Flow rate: 60 mL/min mL/min; Gradient: 49% B to 64% B in 10 min) to afford 3-(((5a(R or S))-7-acryloyl-5-(4-amino-6-(trifluoromethyl)nicotinoyl)-2-(4-cyclobutylphenyl)-3,4,5,5a,6,7,8,9-octahydro-2H-1,2,5,7-tetraazabenzo[cd]azulen-9-yl)oxy cyclobutane-1-carbonitrile (5.2 mg) as a white solid. LCMS:(ESI, m/z): 646 [M+1]. $^1H$ NMR (400 MHz, Chloroform-d) δ 8.34 (s, 1H), 7.54-7.28 (m, 5H), 7.02 (s, 1H), 6.53 (d, J=16.5 Hz, 1H), 5.94-5.77 (m, 1H), 5.44 (s, 2H), 5.36-5.23 (m, 1H), 4.89 (d, J=12.8 Hz, 1H), 4.71-4.56 (m, 1H), 4.53-4.39 (m, 2H), 4.24-4.04 (m, 1H), 3.66-3.51 (m, 1H), 3.30-3.10 (m, 2H), 3.09-2.97 (m, 1H), 2.93-2.73 (m, 4H), 2.71-2.49 (m, 3H), 2.45-2.32 (m, 2H), 0.24-2.09 (m, 2H), 2.08-1.98 (m, 1H), 1.94-1.82 (m, 1H).

TABLE C7

The compounds of Examples C-25-1, C-25-2, C-25-3, C-25-4, C-25-7, and C-25-8 were prepared in an analogous manner to Example C-25, with Int. E"-1 in place of Int. R-1. The compounds of Examples C-25-5 and C-25-6, and C-25-9 was prepared in a manner analogous to Example C-25. For the compounds of Example C-25-8 and C-25-9, two isomers of the adduct were obtained after step 2. For the compound of Example C-25-8, these were separated at the final step via chiral separation using the following conditions: Column-(R, R)-WHELK-O1-Kromasil, 3 * 25 cm, 5 μm; Mobile Phase A: MtBE(0.1% FA)--HPLC, Mobile Phase B: ETOH; Flow rate: 40 mL/min; Gradient: isocratic 10; Wave Length: 217/262 nm; RT1(min): 7.7; RT2(min): 10 to afford the compound of the example as the first-eluting peak. For the compound of Example C-25-9, these were separated at step 2 by column chromatography, eluting with EA/PE (1:1). The second-eluting peak was carried on to the final compound as a single enantiomer.

| Example No. | Structure and Name | LCMS (ESI, m/z) | NMR |
|---|---|---|---|
| C-25-1 | 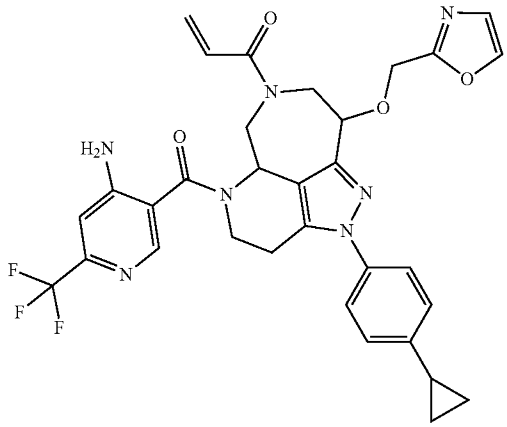 [SMILES: C=CC(=O)N1CC(OCc2ncco2)c2nn(-c3ccc(C4CC4)cc3)c3c2C(C1)N(C(=O)c1cnc(C(F)(F)F)cc1N)CC3] 1-((5aS or R,9S or R)-5-(4-amino-6-(trifluoromethyl)nicotinoyl)-2-(4-cyclopropylphenyl)-9-(oxazol-2-ylmethoxy)-2,3,4,5,5a,6,8,9-octahydro-7H-1,2,5,7-tetraazabenzo[cd]azulen-7-yl)prop-2-en-1-one | 632 $[M + H]^+$ | $^1H$ NMR (400 MHz, Chloroform-d) δ 8.33 (s, 1H), 7.72-7.65 (m, 1H), 7.44-7.31 (m, 2H), 7.20-6.72 (m, 4H), 6.60-6.25 (m, 1H), 5.98-4.71 (m, 7H), 4.59-3.58 (m, 2H), 3.42-2.67 (m, 5H), 1.98-1.87 (m, 1H), 1.09-0.94 (m, 2H), 0.81-0.61 (m, 2H) |
| C-25-2 | 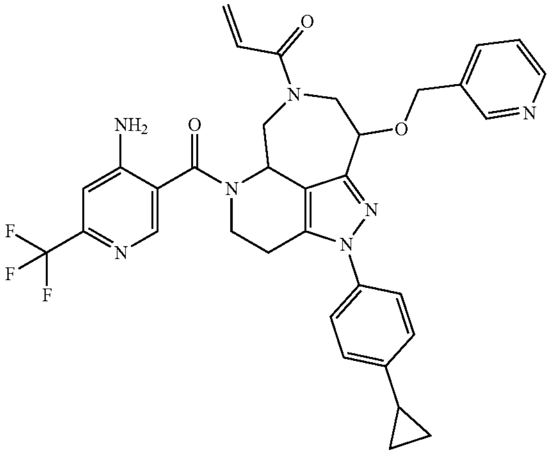 [SMILES: C=CC(=O)N1CC(OCc2cccnc2)c2nn(-c3ccc(C4CC4)cc3)c3c2C(C1)N(C(=O)c1cnc(C(F)(F)F)cc1N)CC3] 1-((5a(R or S),9(R or S)-5-(4-amino-6-(trifluoromethyl)nicotinoyl)-2-(4-cyclopropylphenyl)-9-(pyridin-3-ylmethoxy)-2,3,4,5,5a,6,8,9-octahydro-7H-1,2,5,7-tetraazabenzo[cd]azulen-7-yl)prop-2-en-1-one | 644 $[M + H]^+$ | $^1H$ NMR (400 MHz, Chloroform-d) δ 8.92 (s, 1H), 8.58 (d, J = 5.1 Hz, 1H), 8.34 (s, 1H), 8.16-7.91 (m, 1H), 7.57-7.51 (m, 1H),7.41-7.30 (m, 3H), 7.18-7.10 (m, 2H), 7.03-6.99 (m, 1H), 6.53 (d, J = 16.5 Hz, 1H), 5.99-5.81 (m, 1H), 5.49-5.20 (m, 4H), 5.05-4.98 (m, 2H), 4.82 (dd, J = 10.4, 3.3 Hz, 1H), 4.52-4.45 (m, 1H), 4.21-4.07 (m, 1H), 3.27-3.17 (m, 2H), 3.09-2.91 (m, 2H), 2.79-2.71 (m, 1H), 2.0-1.94 (m, 1H), 1.06-0.97 (m, 2H), 0.73-0.60 (m, 2H). |

TABLE C7-continued

The compounds of Examples C-25-1, C-25-2, C-25-3, C-25-4, C-25-7, and C-25-8 were prepared in an analogous manner to Example C-25, with Int. E"-1 in place of Int. R-1. The compounds of Examples C-25-5 and C-25-6, and C-25-9 was prepared in a manner analogous to Example C-25. For the compounds of Example C-25-8 and C-25-9, two isomers of the adduct were obtained after step 2. For the compound of Example C-25-8, these were separated at the final step via chiral separation using the following conditions: Column-(R, R)-WHELK-O1-Kromasil, 3 * 25 cm, 5 μm; Mobile Phase A: MtBE(0.1% FA)--HPLC, Mobile Phase B: ETOH; Flow rate: 40 mL/min; Gradient: isocratic 10; Wave Length: 217/262 nm; RT1(min): 7.7; RT2(min): 10 to afford the compound of the example as the first-eluting peak. For the compound of Example C-25-9, these were separated at step 2 by column chromatography, eluting with EA/PE (1:1). The second-eluting peak was carried on to the final compound as a single enantiomer.

| Example No. | Structure and Name | LCMS (ESI, m/z) | NMR |
|---|---|---|---|
| C-25-3 | 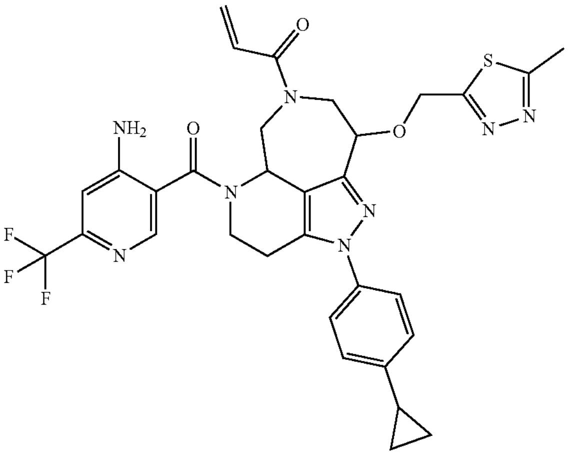 [SMILES: C=CC(=O)N1CC(OCc2nnc(C)s2)c2nn(-c3ccc(C4CC4)cc3)c3c2C(C1)N(C(=O)c1cnc(C(F)(F)F)cc1N)CC3] 1-((5a(R or S),9(S or R))-5-(4-amino-6-(trifluoromethyl)nicotinoyl)-2-(4-cyclopropylphenyl)-9-((5-methyl-1,3,4-thiadiazol-2-yl)methoxy)-2,3,4,5,5a,6,8,9-octahydro-7H-1,2,5,7-tetraazabenzo[cd]azulen-7-yl)prop-2-en-1-one | 665 $[M + H]^+$ | $^1H$ NMR (400 MHz, Chloroform-d) δ 8.34 (s, 1H), 7.36 (d, J = 8.1 Hz, 2H), 7.15 (d, J = 8.2 Hz, 2H), 7.09-6.99 (m, 1H), 6.62-6.31 (m, 1H), 5.96-5.80 (m, 1H), 5.65-5.52 (m, 1H), 5.40-5.25 (m, 4H), 5.11-4.81 (m, 2H), 4.59-4.10 (m, 2H), 3.20 (t, J = 12.3 Hz, 2H), 3.11-2.83 (m, 2H), 2.82-2.71 (m, 5H), 1.94 (s, 1H), 1.05-0.98 (m, 2H), 0.76-0.69 (m, 2H). |
| C-25-4 | 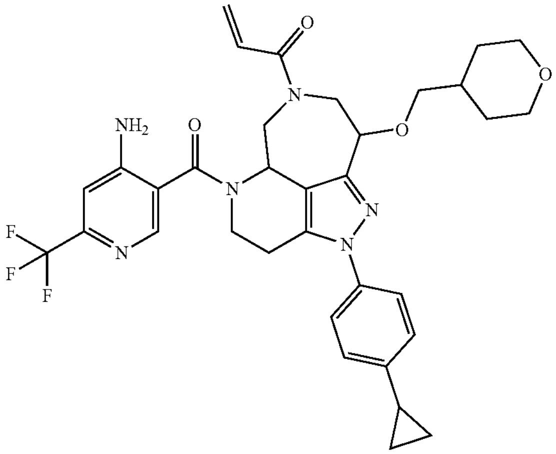 [SMILES: C=CC(=O)N1CC(OCC2CCOCC2)c2nn(-c3ccc(C4CC4)cc3)c3c2C(C1)N(C(=O)c1cnc(C(F)(F)F)cc1N)CC3] 1-((5a(R or S),9(S or R))-5-(4-amino-6-(trifluoromethyl)nicotinoyl)-2-(4-cyclopropylphenyl)-9-((tetrahydro-2H-pyran-4-yl)methoxy)-2,3,4,5,5a,6,8,9-octahydro-7H-1,2,5,7-tetraazabenzo[cd]azulen-7-yl)prop-2-en-1-one | 651 $[M + H]^+$ | $^1H$ NMR: (400 MHz, Chloroform-d) δ 8.33 (s, 1H), 7.42-7.35 (m, 2H), 7.18-7.10 (m, 2H), 7.03 (s, 1H), 6.58-6.37 (m, 1H), 5.93-5.74 (m, 1H), 5.44 (s, 2H), 5.34-4.96 (m, 2H), 4.65-4.60 (m, 1H), 4.46 (d, J = 13.9 Hz, 1H), 4.21-4.09 (m, 1H), 4.03-3.86 (m, 3H), 3.71-3.65 (m, 1H), 3.51-3.36 (m, 2H), 3.19-2.70 (m, 4H), 2.07-1.91 (m, 2H), 1.90-1.78 (m, 2H), 1.50-1.37 (m, 2H), 1.04-0.97 (m, 2H), 0.75-0.69 (m, 2H). |

TABLE C7-continued

The compounds of Examples C-25-1, C-25-2, C-25-3, C-25-4, C-25-7, and C-25-8 were prepared in an analogous manner to Example C-25, with Int. E"-1 in place of Int. R-1. The compounds of Examples C-25-5 and C-25-6, and C-25-9 was prepared in a manner analogous to Example C-25. For the compounds of Example C-25-8 and C-25-9, two isomers of the adduct were obtained after step 2. For the compound of Example C-25-8, these were separated at the final step via chiral separation using the following conditions: Column-(R, R)-WHELK-O1-Kromasil, 3 * 25 cm, 5 μm; Mobile Phase A: MtBE(0.1% FA)--HPLC, Mobile Phase B: ETOH; Flow rate: 40 mL/min; Gradient: isocratic 10; Wave Length: 217/262 nm; RT1(min): 7.7; RT2(min): 10 to afford the compound of the example as the first-eluting peak. For the compound of Example C-25-9, these were separated at step 2 by column chromatography, eluting with EA/PE (1:1). The second-eluting peak was carried on to the final compound as a single enantiomer.

| Example No. | Structure and Name | LCMS (ESI, m/z) | NMR |
|---|---|---|---|
| C-25-5 | 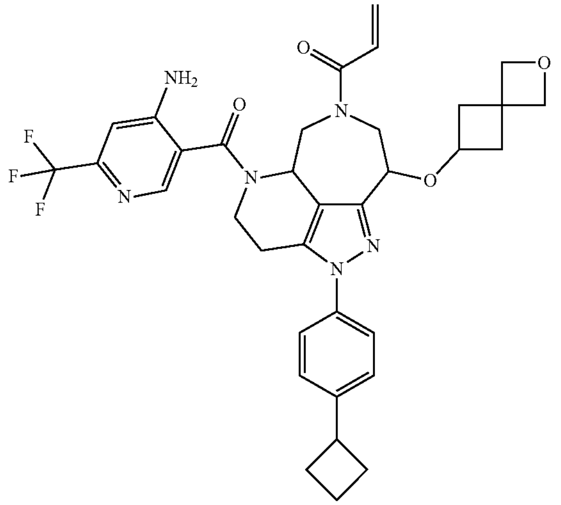 [SMILES: C=CC(=O)N1CC(OC2CC3(COC3)C2)c2nn(-c3ccc(C4CCC4)cc3)c3c2C(C1)N(C(=O)c1cnc(C(F)(F)F)cc1N)CC3] 1-((5a(R or S),9(S or R))-9-((2-oxaspiro[3.3]heptan-6-yl)oxy)-5-(4-amino-6-(trifluoromethyl)nicotinoyl)-2-(4-cyclobutylphenyl)-2,3,4,5,5a,6,8,9-octahydro-7H-benzo[cd]azulen-7-yl)prop-2-en-1-one | 663 $[M + H]^+$ | $^1$H NMR: (400 MHz, Chloroform-d) δ 8.22 (s, 1H), 7.44 (d, J = 8.3 Hz, 2H), 7.37 (d, J = 8.3 Hz, 2H), 7.09 (s, 1H), 6.82-6.61 (m, 2H), 6.41-6.25 (m, 1H), 5.89-5.70 (m, 1H), 5.21-4.97 (m, 1H), 4.61-4.52 (m, 4H), 4.50-4.35 (m, 2H), 4.35-4.23 (m, 1H), 3.77-3.49 (m, 3H), 3.22-3.06 (m, 2H), 2.94-2.82 (m, 1H), 2.71-2.54 (m, 3H), 2.38-2.09 (m, 5H), 2.08-1.89 (m, 2H), 1.88-1.77 (m, 1H), 1.58-1.43 (m, 2H). |
| C-25-6 | 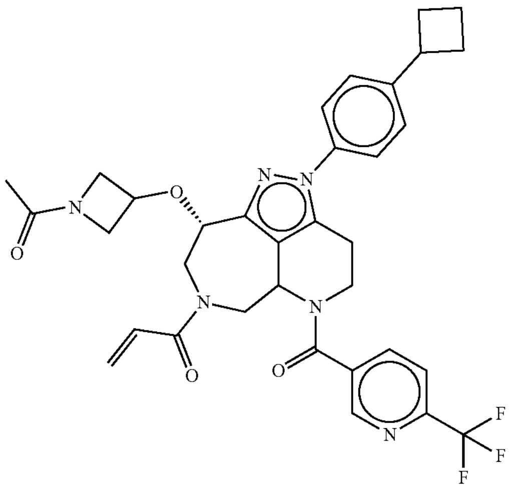 1-((5a(R or S),9(S or R))-9-((1-acetylazetidin-3-yl)oxy)-2-(4-cyclobutylphenyl)-5-(6-(trifluoromethyl)nicotinoyl)-2,3,4,5,5a,6,8,9-octahydro-7H-1,2,5,7-tetraazabenzo[cd]azulen-7-yl)prop-2-en-1-one | 649 $[M + H]^+$ | $^1$H NMR (400 MHz, Chloroform-d) δ 8.82 (s, 1H), 8.09-7.96 (m, 1H), 7.84 (d, J = 7.9 Hz, 1H), 7.42-7.29 (m, 4H), 6.61-6.29 (m, 1H), 5.99-5.73 (m, 1H), 5.48-5.21 (m, 1H), 5.01-4.64 (m, 3H), 4.63-3.78 (m, 7H), 3.69-3.46 (m, 1H), 3.34-3.14 (m, 2H), 3.09-2.82 (m, 2H), 2.80-2.65 (m, 1H), 2.47-2.32 (m, 2H), 2.27-1.99 (m, 4H), 1.92-1.75 (m, 3H). |

TABLE C7-continued

The compounds of Examples C-25-1, C-25-2, C-25-3, C-25-4, C-25-7, and C-25-8 were prepared in an analogous manner to Example C-25, with Int. E"-1 in place of Int. R-1. The compounds of Examples C-25-5 and C-25-6, and C-25-9 was prepared in a manner analogous to Example C-25. For the compounds of Example C-25-8 and C-25-9, two isomers of the adduct were obtained after step 2. For the compound of Example C-25-8, these were separated at the final step via chiral separation using the following conditions: Column-(R, R)-WHELK-O1-Kromasil, 3 * 25 cm, 5 μm; Mobile Phase A: MtBE(0.1% FA)--HPLC, Mobile Phase B: ETOH; Flow rate: 40 mL/min; Gradient: isocratic 10; Wave Length: 217/262 nm; RT1(min): 7.7; RT2(min): 10 to afford the compound of the example as the first-eluting peak. For the compound of Example C-25-9, these were separated at step 2 by column chromatography, eluting with EA/PE (1:1). The second-eluting peak was carried on to the final compound as a single enantiomer.

| Example No. | Structure and Name | LCMS (ESI, m/z) | NMR |
|---|---|---|---|
| C-25-7 | 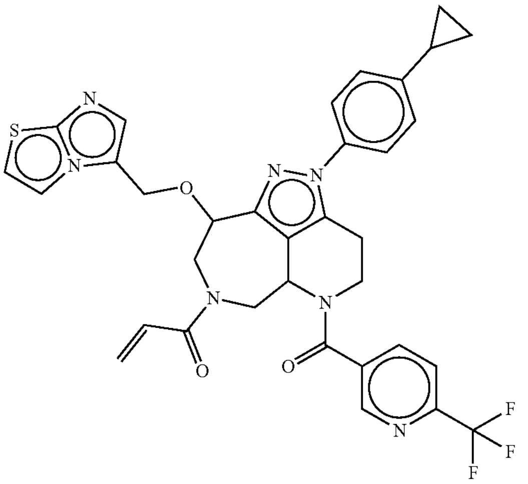 1-((5a(R or S), 9(R or S))-2-(4-cyclopropylphenyl)-9-(imidazo[2,1-b]thiazol-5-ylmethoxy)-5-(6-(trifluoromethyl)nicotinoyl)-2,3,4,5,5a,6,8,9-octahydro-7H-1,2,5,7-tetraazabenzo[cd]azulen-7-yl)prop-2-en-1-one | 647 $[M + H]^+$ | $^1$H NMR (400 MHz, Chloroform-d) δ 8.95-8.68 (m, 2H) 8.02 (d, J = 8.1 Hz, 1H), 7.84 (d, J = 8.0 Hz, 1H), 7.64-7.41 (m, 1H), 7.36-7.28 (m, 2H), 7.25-7.15 (m, 4H), 6.56 (d, J = 16.4 Hz, 1H), 5.94 (d, J = 10.4 Hz, 1H), 5.41-5.33 (m, 1H), 5.30 (d, J = 12.2 Hz, 1H), 5.12 (d, J = 12.1 Hz, 1H), 4.95 (d, J = 12.7 Hz, 1H), 4.85 (d, J = 10.1 Hz, 1H), 4.55 (d, J = 13.8 Hz, 1H), 4.00-3.83 (m, 1H), 3.34-3.10 (m, 2H), 3.06-2.90 (m, 2H), 2.77-2.64 (m, 1H), 2.04-1.91 (m, 1H), 1.13-1.00 (m, 2H), 0.80-0.71 (m, 2H)). |
| C-25-8 | 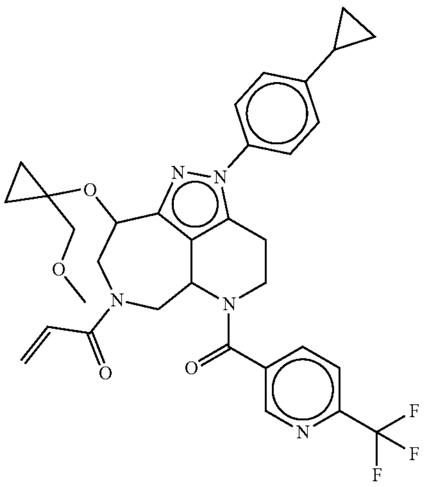 1-((5a(R or S),9(S or R))-2-(4-cyclopropylphenyl)-9-(1-(methoxymethyl)cyclopropoxy)-5-(6-(trifluoromethyl)nicotinoyl)-2,3,4,5,5a,6,8,9-octahydro-7H-1,2,5,7-tetraazabenzo[cd]azulen-7-yl)prop-2-en-1-one | 622 $[M + H]^+$ | $^1$H NMR (400 MHz, Chloroform-d) δ 8.82 (s, 1H), 8.00 (d, J = 7.8 Hz, 1H), 7.92-7.73 (m, 1H), 7.38-6.95 (m, 3H), 7.21-6.96 (m, 3H), 6.57-6.34 (m, 1H), 5.92-5.78 (m, 1H), 5.40-5.18 (m, 1H), 5.08-4.75 (m, 2H), 4.67-4.43 (m, 1H), 4.25-4.00 (m, 1H), 3.95-3.84 (m, 1H), 3.44-3.35(m, 3H), 3.26-3.13 (m, 2H), 3.01-2.72 (m, 3H), 1.97-1.92 (m, 1H), 1.11-0.87 (m, 4H), 0.82-0.50 (m, 4H). |

TABLE C7-continued

The compounds of Examples C-25-1, C-25-2, C-25-3, C-25-4, C-25-7, and C-25-8 were prepared in an analogous manner to Example C-25, with Int. E"-1 in place of Int. R-1. The compounds of Examples C-25-5 and C-25-6, and C-25-9 was prepared in a manner analogous to Example C-25. For the compounds of Example C-25-8 and C-25-9, two isomers of the adduct were obtained after step 2. For the compound of Example C-25-8, these were separated at the final step via chiral separation using the following conditions: Column-(R, R)-WHELK-O1-Kromasil, 3 * 25 cm, 5 μm; Mobile Phase A: MtBE(0.1% FA)--HPLC, Mobile Phase B: ETOH; Flow rate: 40 mL/min; Gradient: isocratic 10; Wave Length: 217/262 nm; RT1(min): 7.7; RT2(min): 10 to afford the compound of the example as the first-eluting peak. For the compound of Example C-25-9, these were separated at step 2 by column chromatography, eluting with EA/PE (1:1). The second-eluting peak was carried on to the final compound as a single enantiomer.

| Example No. | Structure and Name | LCMS (ESI, m/z) | NMR |
|---|---|---|---|
| C-25-9 | 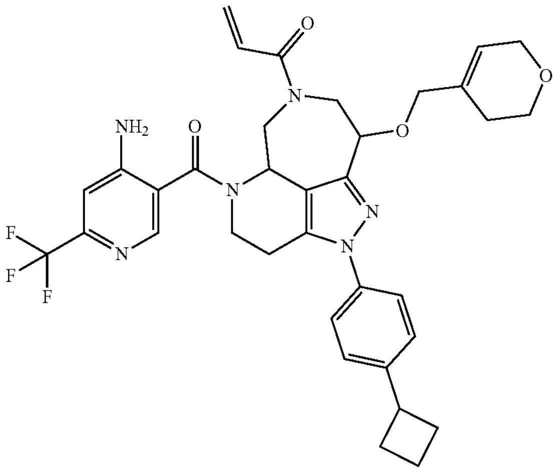 [SMILES: C=CC(=O)N1CC(OCC2=CCOCC2)c2nn(-c3ccc(C4CCC4)cc3)c3c2C(C1)N(C(=O)c1cnc(C(F)(F)F)cc1N)CC3] 1-((5a(R or S),9(R or S))-5-(4-amino-6-(trifluoromethyl)nicotinoyl)-2-(4-cyclobutylphenyl)-9-((3,6-dihydro-2H-pyran-4-yl)methoxy)-2,3,4,5,5a,6,8,9-octahydro-7H-1,2,5,7-tetraazabenzo[cd]azulen-7-yl)prop-2-en-1-one | 663 [M + H]$^+$ | $^1$H NMR (400 MHz, Chloroform-d) δ 8.33 (s, 1H), 7.42 (d, J = 8.0 Hz, 3H), 7.29 (d, J = 8.1 Hz, 2H), 7.04 (s, 1H), 6.51 (d, J = 16.3 Hz, 1H), 5.97-5.73 (m, 2H), 5.70-5.20 (m, 3H), 4.97 (d, J = 12.4 Hz, 1H), 4.70-4.60 (m, 1H), 4.47 (d, J = 12.4 Hz, 2H), 4.32 (d, J = 12.3 Hz, 1H), 4.27-4.01 (m, 3H), 3.90-3.80 (m, 2H), 3.58 (t, J = 8.8 Hz, 1H), 3.30-3.10 (m, 2H), 3.09-3.00 (m, 1H), 2.95-2.67 (m, 2H), 2.47-2.32 (m, 2H), 2.26 (s, 2H), 2.20-2.10 (m, 2H), 2.09-1.98 (m, 1H), 1.92-1.85 (m, 1H). |

Example C-26: Preparation of (R or S)-1-(5-(7-bromo-1H-benzo[d]imidazole-4-carbonyl)-2-(4-cyclobutylphenyl)-2,3,4,5,5a,6-hexahydro-1,2,5,7-tetraazaspiro[benzo[cd]azulene-9,1'-cyclopropan]-1(9a),2a-dien-7(8H)-yl)prop-2-en-1-one

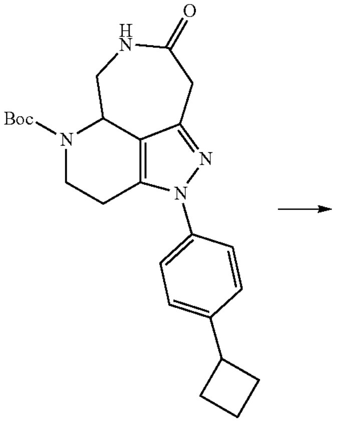

-continued

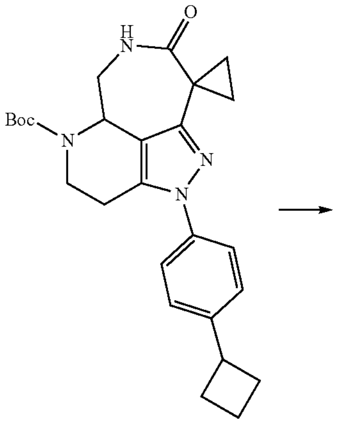

-continued

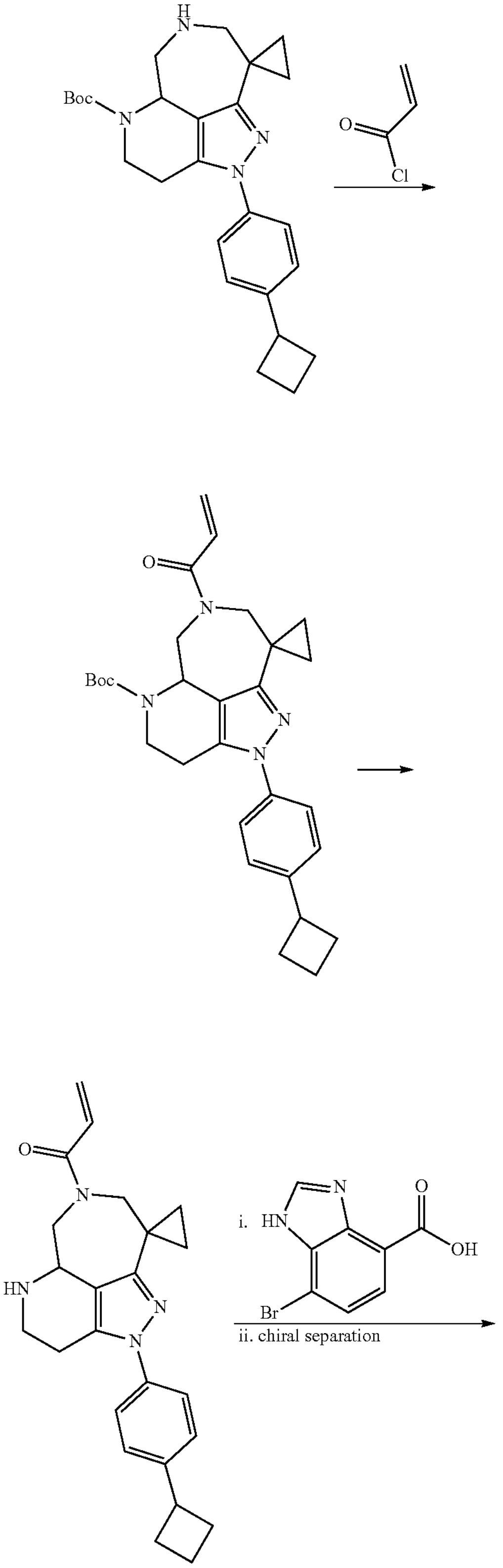

-continued

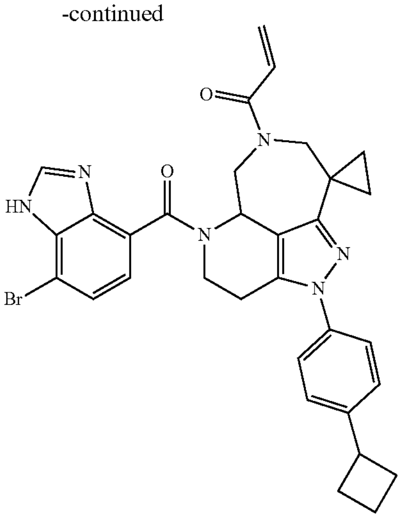

Step 1: Synthesis of Tert-Butyl 2-(4-cyclobutylphenyl)-8-oxo-3,4,5a,6,7,8 hexahydro-1, 2,5,7-tetraazaspiro[benzo[cd]azulene-9,1'-cyclopropan]-1(9a),2a-diene-5(2H)-carboxylate To a solution of 2-methylpropan-2-olate potassium (239 mg, 245 μL, 2 Eq, 2.13 mmol) in DMF (1 mL) was added trimethyl(oxo)sulfonium iodide (469 mg, 2 q, 2.13 mmol) under a nitrogen atmosphere. The mixture was stirred at 45° C. for 1 h, after which a solution of tert-butyl 2-(4-cyclobutylphenyl)-8-oxo-2,3,4,5a,6,7,8,9-octahydro-5H-1,2,5,7-tetraazabenzo[cd]azulene-5-carboxylate (Int. R) (450 mg, 1 Eq, 1.07 mmol), paraformaldehyde 1320 mg, 321 μL, 10 Eq, 10.7 mmol), and cesium carbonate (694 mg, 170 μL, 2 Eq, 2.13 mmol) in THF (1 mL) (pre-stirred at 40° C. for 1 h under a nitrogen atmosphere and then cooled to rt) was added dropwise at rt under a nitrogen atmosphere. The mixture was warmed to 40° C. and stirred for 1 h, after which the reaction was quenched by the addition of water (5 mL) at rt. The resulting mixture was extracted with EA (2×5 mL), and the combined organic layers were washed with brine (2×5 mL) and dried over anhydrous $Na_2SO_4$. After filtration, the filtrate was concentrated under reduced pressure. The residue was purified by silica gel column chromatography, eluting with EA/PE (1:1) to afford tert-butyl 2-(4-cyclobutylphenyl)-8-oxo-3,4,5a,6,7,8-hexahydro-1,2,5,7 -tetraazaspiro[benzo[cd]azulene-9,1'-cyclopropan]-1(9a),2a-diene-5(2H)-carboxylate (120 mg) as a white solid. LCMS:(ESI, m/z): 449 $[M+1]^+$.

Step 2: Synthesis of Tert-Butyl 2-(4-cyclobutylphenyl)-3,4,5a,6,7,8-hexahydro-1,2,5,7-tetraazaspiro[benzo[cd]azulene-9,1'-cyclopropan]-1(9a),2a-diene-5(2H)-carboxylate To a stirred solution of tert-butyl 2-(4-cyclobutylphenyl)-8-oxo-3,4,5a,6,7,8-hexahydro-1,2,5,7-tetraazaspiro[benzo[cd]azulene-9,1'-cyclopropan]-1(9a),2a-diene-5(2H)-carboxylate (110 mg, 1 Eq, 245 μmol) in THF (1 mL) was added $BH_3$·THF (1.23 mL, 1 molar solution, 5 Eq, 1.23 mmol) at 40° C., and the resulting mixture was further stirred for 2 hours. The reaction was then quenched by the addition of water (2 mL) at rt. The resulting mixture was extracted with EA (2×2 mL), and the combined organic layers were washed with brine (2×2 mL) and dried over anhydrous $Na_2SO_4$. After filtration, the filtrate was concentrated under reduced pressure to afford tert-butyl 2-(4-cyclobutylphenyl)-3,4,5a,6,7,8-hexahydro-1,2,5,7-tetraazaspiro[benzo[cd]azulene-9,1'-cyclopropan]-1(9a),2a-diene-5(2H)-carboxylate (120 mg) as a crude white solid which was used in the next reaction without further purification. LCMS:(ESI, m/z): 435 $[M+1]^+$.

Step 3: Synthesis of Tert-Butyl 7-acryloyl-2-(4-cyclobutylphenyl)-3,4,5a,6,7,8-hexahydro-1,2,5,7-tetraazaspiro[benzo[cd]azulene-9,1'-cyclopropan]-1(9a),2a-diene-5(2H)-carboxylate To a stirred solution of tert-butyl 2-(4-cyclobutylphenyl)-3,4,5a,6,7,8-hexahydro-1,2,5,7-tetraazaspiro[benzo[cd]azulene-9,1'-cyclopropan]-1(9a),2a-diene-5(2H)-carboxylate (100 mg, 1 Eq, 230 μmol) in DCM (1 mL) was added TEA (69.9 mg, 96.2 μL, 3 Eq, 690 μmol) and acryloyl chloride (31.2 mg, 1.5 Eq, 345 μmol) at rt and the resulting solution was stirred for 1 h. The reaction was then quenched by the addition of water (2 mL) at rt. The resulting mixture was extracted with EA (2×2 mL), and the combined organic layers were washed with brine (2×2 mL) and dried over anhydrous $Na_2SO_4$. After filtration, the filtrate was concentrated under reduced pressure and the residue was purified by silica gel column chromatography, eluting with EA/PE (1:3) to afford tert-butyl 7-acryloyl-2-(4-cyclobutylphenyl)-3,4,5a,6,7,8-hexahydro-1,2,5,7-tetraazaspiro[benzo[cd]azulene-9,1'-cyclopropan]-1(9a),2a-diene-5(2H)-carboxylate (60 mg) as a white solid. LCMS:(ESI, m/z): 489 $[M+1]^+$.

Step 4: Synthesis of 1-(2-(4-cyclobutylphenyl)-2,3,4,5,5a,6-hexahydro-1, 2,5,7-tetraazaspiro[benzo[cd]azulene-9,1'-cyclopropan]-1(9a),2a-dien-7(8H)-yl)prop-2-en-1-one A solution of tert-butyl 7-acryloyl-2-(4-cyclobutylphenyl)-3,4,5a,6,7,8-hexahydro-1,2,5,7-tetraazaspiro[benzo[cd]azulene-9,1'-cyclopropan]-1(9a),2a-dien-5(2H)-carboxylate (60 mg, 1 Eq, 0.12 mmol) in DCM (1 mL) and TFA (0.3 mL) was stirred at rt for 1 h, after which the solvent was removed under reduced pressure to afford 1-(2-(4-cyclobutylphenyl)-2,3,4,5,5a,6-hexahydro-1,2,5,7-tetraazaspiro[benzo[cd]azulene-9,1'-cyclopropan]-1(9a),2a-dien-7(8H)-yl)prop-2-en-1-one (70 mg) as a crude yellow oil which was used in the next step directly without further purification. LCMS:(ESI, m/z): 389 [M+1]+.

Step 5: Synthesis of (S or R)-1-(5-(7-bromo-1H-benzo[d]imidazole-4-ca bonyl)-2-(4-cyclobutylphenyl)-2,3,4,5,5a,6-hexahydro-1,2,5,7-tetraazaspiro[benzo[d]azulene-9,1'-cyclopropan]-1(9a),2a-dien-7(8H)-yl)prop-2-en-1-one To a stirred solution of 1-(2-(4-cyclobutylphenyl)-2,3,4,5,5a,6-hexahydro-1,2,5,7-tetraazaspiro[benzo[cd]azulene-9,1'-cyclopropan]-1(9a),2a-dien-7(8H)-yl)prop-2-en-1-one (65 mg, 1 Eq, 0.17 mmol) in DMF (1 mL) was added HBTU (95 mg, 1.5 Eq, 0.25 mmol), 7-bromo-1H-benzo[d]imidazole-4-carboxylic acid (48 mg, 1.2 Eq, 0.2 mmol) and DIEA (65 mg, 87 μL, 3 Eq, 0.5 mmol) at rt and the resulting reaction was stirred for 2 h. The reaction was then quenched by the addition of water (5 mL) at rt, and the resulting mixture was extracted with EA (2×3 mL). The combined organic layers were washed with brine (2×3 mL) and dried over anhydrous $Na_2SO_4$. After filtration, the filtrate was concentrated under reduced pressure. The residue was purified by reversed-phase flash chromatography under the following conditions: Column: Xselect CSH™ Prep C18 5 μm 30*150 mm OBD; Mobile Phase A: Water (0.05% TFA), Mobile Phase B: ACN; Flow rate: 60 mL/min; Gradient: 38% B to 60% B in 10 in; Wave Length: UV 254 nm/220) to afford racemic 1-(5-(7-bromo-1H-benzo[d]imidazole-4-carbonyl)-2-(4-cyclobutylphenyl)-2,3,4,5,5a,6-hexahydro-1,2,5,7-tetraazaspiro[benzo[cd]azulene-9,1'-cyclopropan]-1(9a),2a-dien-7(8H)-yl)prop-2-en-1-one (28 mg) as a white solid. The racemic compound (28 mg) was separated into constituent enantiomers by chiral HPLC separation under the following conditions (Column: CHIRAL ART Cellulose-SB, 3*25 cm, 5 m; Mobile Phase A: Hex(0.1% FA)--HPLC, Mobile Phase B: EtOH: DCM=1:1; Flow rate: 40 mL/min; Gradient: isocratic 20; Wave Length: UV 254/220 nm; RT1(min): 11; RT2(min): 14) to afford (S or R)-1-(5-(7-bromo-1H-benzo[d]imidazole-4-carbonyl)-2-(4-cyclobutylphenyl)-2,3,4,5,5a,6-hexahydro-1,2,5,7-tetraazaspiro[benzo[cd]azulene-9,1'-cyclopropan]-1(9a),2a-dien-7(8H)-yl)prop-2-en-1-one (9.5 mg) as the first-eluting isomer as a white solid. LCMS:(ESI, m/z): 611 $[M+1]^+$ $^1$H NMR: (400 MHz, Chloroform-d, ppm) δ 9.05-8.62 (m, 1H), 7.71-7.40 (m, 2H), 7.38-7.32 (m, 3H), 6.69-6.33 (d, 1H), 5.90-5.69 (m, 1H), 5.61-5.47 (m, 1H), 0.00-4.47 (m, 1H), 4.32 (d, J=13.9 Hz, 1H), 4.16-3.78 (m, 1H), 3.63-3.45 (m, 1H), 3.45-0.94 (m, 3H), 2.73-2.45 (m, 1H), 2.40-2.30 (m, 2H), 2.28-1.58 (m, 6H), 1.51-1.22 (m, 2H), 1.08-0.75 (m, 2H), 0.71-0.60 (m, 1H) (some peaks obscured by solvent).

TABLE C8

The compound of Example C-27 was prepared in an analogous fashion to Example A-22 from Int. V in place of Int. E'''. The diastereomeric mixture was separated after the third step to obtain tert-butyl-7-acryloyl-2-(4-cyclobutylphenyl)-9-hydroxy-2,3,4,5a,6,7,8,9-octahydro-5H-1,2,5,7-tetraazabenzo[cd]azulene-5-carboxylate as a single diastereomer as a racemic mixture, and the second peak was carried on to the final product using the corresponding carboxylic acid. The racemic final compound was separated using the following conditions: Column-CHIRALPAK-IC 2 * 25 cm, 5 μm; Mobile Phase A: HEX(0.1% FA), Mobile Phase B: EtOH: DCM = 1:1; Flow rate: 20 mL/min; Gradient: isocratic 65; Wave Length: UV 254/220 nm; RT1(min): 6.2; RT2(min): 9.0 to provide the compound of the example as the second-eluting peak.

| Example No. | Structure and Name | LCMS (ESI, m/z) | NMR |
|---|---|---|---|
| C-27 | 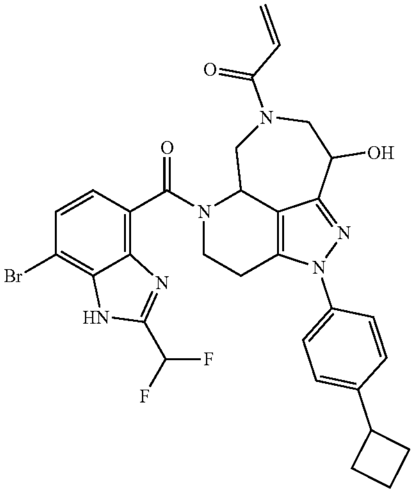 [SMILES: C=CC(=O)N1CC(O)c2nn(-c3ccc(C4CCC4)cc3)c3c2C(C1)N(C(=O)c1ccc(Br)c2[nH]c(C(F)F)nc12)CC3] 1-((5a(S or R),9(R or S))-5-(7-bromo-2-(difluoromethyl)-1H-benzo[d]imidazole-4-carbonyl)-2-(4-cyclobutylphenyl)-9-hydroxy-2,3,4,5,5a,6,8,9-octahydro-7H-1,2,5,7-tetraazabenzo[cd]azulen-7-yl)prop-2-en-1-one | 651 $[M + H]^+$ | $^1$H NMR(400 MHz, Chloroform-d, ppm) δ 13.27 (s, 1H), 7.55 (d, J = 6.6 Hz, 1H), 7.41 (s, 1H), 7.25-6.85 (m, 5H), 6.81-6.48 (m, 1H), 6.32-5.94 (m, 1H), 5.46-4.87 (m, 3H), 4.71-2.17 (m, 12H), 2.14-1.92 (m, 3H), 1.83 (d, J = 9.8 Hz, 1H). |

TABLE C9

The compounds of Examples C-28-C-30 were prepared in an analogous fashion to Example C-2 using the corresponding carboxylic acids, except that the acetate group was not removed immediately from intermediate P, and was instead removed in the saponification step after the carboxylic acid coupling in the corresponding Example C-2 step 7. The chiral final compounds of the examples were obtained using the following conditions: Example C-28: Column: XBridge BEH C18 OBD Prep Column 130, 5 μm, 30 mm * 150 mm; Mobile Phase A: Water (17 mmol/L $NH_4HCO_3$), Mobile Phase B: ACN; Flow rate: 60 mL/min; Gradient: 31% B to 59% B in 8 min to afford the compound of the example as the second-eluting peak. Example C-29: CHIRALPAK-IC 2 * 25 cm, 5 μm; Mobile Phase A: HEX(0.1% FA), Mobile Phase B: EtOH: DCM = 1:1; Flow rate: 20 mL/min; Gradient: isocratic 45; Wave Length: UV 220/254 nm; RT1(min): 5.8; RT2(min): 8.0 to provide the column of the example as the second-eluting peak. Example C-30: CHIRALPAK-IC 2 * 25 cm, 5 μm; Mobile Phase A: HEX(0.1% FA), Mobile Phase B: EtOH:DCM = 1:1; Flow rate: 20 mL/min; Gradient: isocratic 30; Wave Length: UV 254/220 nm; RT1(min): 11.5; RT2(min): 15.1 to provide the compound of the example as the second-eluting peak.

| Example No. | Structure and Name | LCMS (ESI, m/z) | NMR |
|---|---|---|---|
| C-28 | 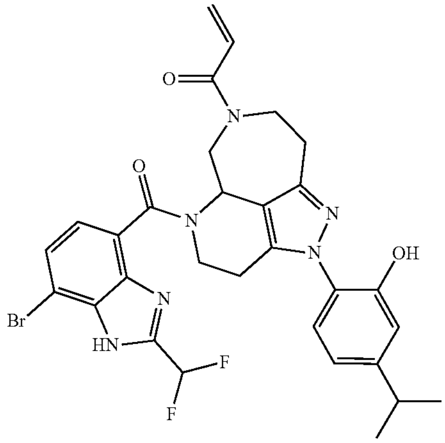 [SMILES: C=CC(=O)N1CCc2nn(-c3ccc(C(C)C)cc3O)c3c2C(C1)N(C(=O)c1ccc(Br)c2[nH]c(C(F)F)nc12)CC3] (R or S)-1-(5-(7-bromo-2-(difluoromethyl)-1H-benzo[d]imidazole-4-carbonyl)-2-(2-hydroxy-4-isopropylphenyl)-2,3,4,5,5a,6,8,9-octahydro-7H-1,2,5,7-tetraazabenzo[cd]azulen-7-yl)prop-2-en-1-one | 639 $[M + H]^+$ | $^1H$ NMR (400 MHz, Chloroform-d) δ 7.69-7.54 (m, 1H), 7.54-7.36 (m, 1H), 7.15-6.36 (m, 6H), 5.86-5.74 (m, 1H), 5.50-5.38 (m, 1H), 5.04-4.89 (m, 1H), 4.57-4.00 (m, 2H), 3.48-2.58 (m, 8H), 1.32-1.11 (m, 6H). |
| C-29 | 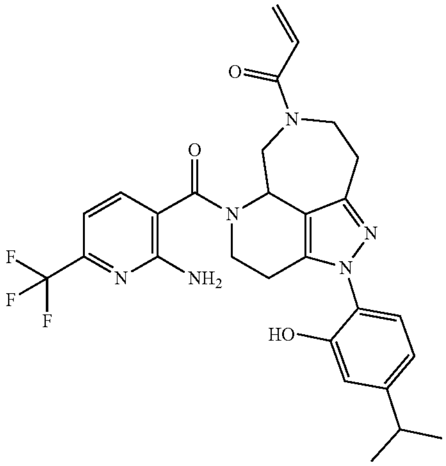 [SMILES: C=CC(=O)N1CCc2nn(-c3ccc(C(C)C)cc3O)c3c2C(C1)N(C(=O)c1ccc(C(F)(F)F)nc1N)CC3] (S or R)-1-(5-(2-amino-6-(trifluoromethyl)nicotinoyl)-2-(2-hydroxy-4-isopropylphenyl)-2,3,4,5,5a,6,8,9-octahydro-7H-1,2,5,7-tetraazabenzo[cd]azulen-7-yl)prop-2-en-1-one | 555 $[M + H]^+$ | $^1H$ NMR (400 MHz, Chloroform-d, ppm) δ 7.59-7.52 (m, 1H), 7.46-7.28 (m, 1H), 7.15-6.90 (m, 3H), 6.82-6.60 (m, 1H), 6.58-6.31 (m, 1H), 5.94-5.71 (m, 1H), 5.42 (s, 2H), 5.12-4.64 (m, 1H), 4.64-3.87 (m, 2H), 3.33-2.97 (m, 5H), 2.96-2.72 (m, 3H), 1.25 (d, J = 6.8 Hz, 6H). |

TABLE C9-continued

The compounds of Examples C-28-C-30 were prepared in an analogous fashion to Example C-2 using the corresponding carboxylic acids, except that the acetate group was not removed immediately from intermediate P, and was instead removed in the saponification step after the carboxylic acid coupling in the corresponding Example C-2 step 7. The chiral final compounds of the examples were obtained using the following conditions: Example C-28: Column: XBridge BEH C18 OBD Prep Column 130, 5 μm, 30 mm * 150 mm; Mobile Phase A: Water (17 mmol/L $NH_4HCO_3$), Mobile Phase B: ACN; Flow rate: 60 mL/min; Gradient: 31% B to 59% B in 8 min to afford the compound of the example as the second-eluting peak. Example C-29: CHIRALPAK-IC 2 * 25 cm, 5 μm; Mobile Phase A: HEX(0.1% FA), Mobile Phase B: EtOH: DCM = 1:1; Flow rate: 20 mL/min; Gradient: isocratic 45; Wave Length: UV 220/254 nm; RT1(min): 5.8; RT2(min): 8.0 to provide the column of the example as the second-eluting peak. Example C-30: CHIRALPAK-IC 2 * 25 cm, 5 μm; Mobile Phase A: HEX(0.1% FA), Mobile Phase B: EtOH:DCM = 1:1; Flow rate: 20 mL/min; Gradient: isocratic 30; Wave Length: UV 254/220 nm; RT1(min): 11.5; RT2(min): 15.1 to provide the compound of the example as the second-eluting peak.

| Example No. | Structure and Name | LCMS (ESI, m/z) | NMR |
|---|---|---|---|
| C-30 | 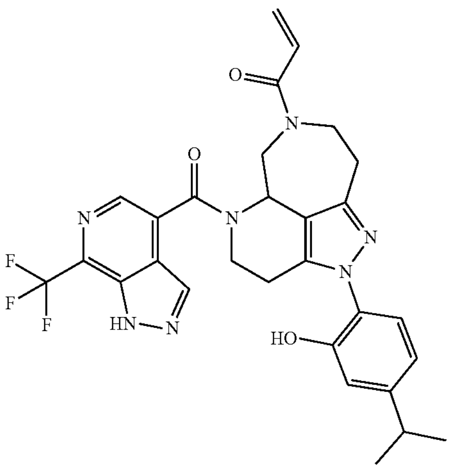 [SMILES: C=CC(=O)N1CCc2nn(-c3ccc(C(C)C)cc3O)c3c2C(C1)N(C(=O)c1cnc(C(F)(F)F)c2[nH]ncc12)CC3] (S or R)-1-(2-(2-hydroxy-4-isopropylphenyl)-5-(7-(trifluoromethyl)-1H-pyrazolo[3,4-c]pyridine-4-carbonyl)-2,3,4,5,5a,6,8,9-octahydro-7H-1,2,5,7-tetraazabenzo[cd]azulen-7-yl)prop-2-en-1-one | 580 $[M + H]^+$ | $^1H$ NMR (400 MHz, Chloroform-d, ppm) δ 11.34-11.30 (m, 1H), 10.10-10.03 (m, 1H), 8.52 (s, 1H), 8.34 (s, 1H), 7.56-7.37 (m, 1H)7.46 (s, 1H), 7.03-6.93 (m, 2H), 6.85-6.66 (m, 1H)6.75 (d, J = 7.9 Hz, 1H), 6.54 (d, J = 16.3 Hz, 1H), 6.00-5.51 (m, 2H), 5.12-4.86 (m, 1H), 4.70-4.54 (m, 1H), 4.27-3.81 (m, 1H)5.97-3.86 (m, 5H), 3.45-2.63 (m, 8H), 1.24 (d, J = 6.8 Hz, 6H). |

Example C-31: Preparation of (R or S)-1-(5-(7-bromo-2-(difluoromethoxy)-11H-benzo[d]imidazole-4-carbonyl)-2-(4-cyclobutyl-2- hydroxyphenyl)-2,3,4,5,5a,6,8,9-octahydro-7H-1,2,5,7-tetraazabenzo [cd]azulen-7-yl)prop-2-en-1-one

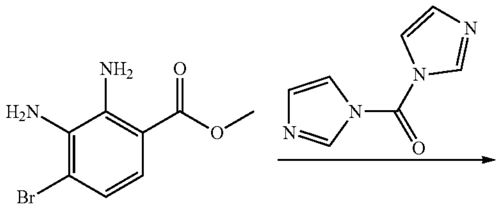

-continued

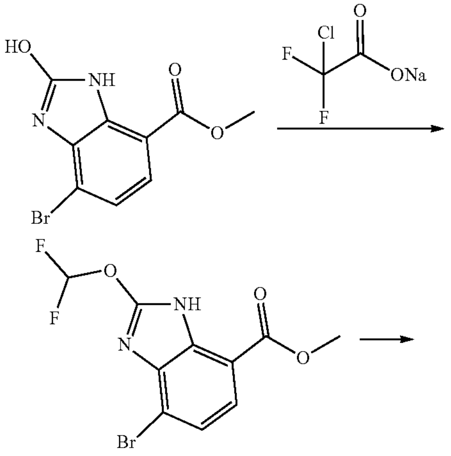

-continued

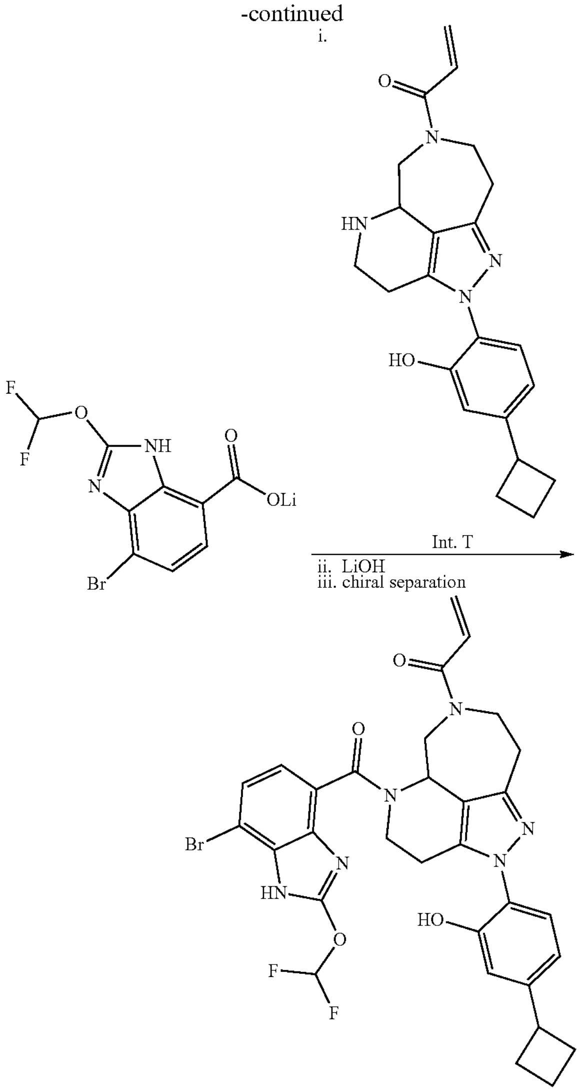

Step 1: Synthesis of Methyl 7-bromo-2-hydroxy-3H-1,3-benzodiazole-4-carboxylate

A solution of methyl 2,3-diamino-4-bromobenzoate (2 g, 8.2 mmol, 1 equiv), carbonyldiimidazole (2.65 g, 16.3 mmol, 2 equiv) and DIEA (3.16 g, 24.5 mmol, 3 equiv) in dioxane (20 mL) was stirred for 16 h at 100° C. under air. The residue was purified by trituration with MBTE (12 mL) and DCM (12 mL) to provide methyl 7-bromo-2-hydroxy-3H-1,3-benzodiazole-4-carboxylate (2 g) as a yellow solid which was used in the next step directly without further purification. LCMS:(ESI, m/z): 271 [M+1]+.

Step 2: Synthesis of Methyl 7-bromo-2-(difluoromethoxy)-3H-1,3-benzodiazole-4-carboxylate A solution of methyl 7-bromo-2-hydroxy-3H-1,3-benzodiazole-4-carboxylate (400 mg, 1.5 mmol, 1 equiv), sodium 2-chloro-2,2-difluoroacetate (787 mg, 5.17 mmol, 3.5 equiv) and $Cs_2CO_3$ (1683 mg, 5.17 mmol, 3.5 equiv) in DMF (1 mL) was stirred for 1 h at 80° C. under air. The resulting mixture was extracted with EtOAc (3×10 mL) and the combined organic layers were washed with brine (3×7 mL), dried over anhydrous $Na_2SO_4$, and filtered. After filtration, the filtrate was concentrated under reduced pressure and the residue was purified by silica gel column chromatography, eluting with PE/EA (5:1) to afford methyl 7-bromo-2-(difluoromethoxy)-3H-1,3-benzodiazole-4-carboxylate (100 mg) as a yellow solid. LCMS:(ESI, m/z): 321 $[M+1]^+$.

Step 3: Synthesis of 7-bromo-2-(difluoromethoxy)-3H-1,3-benzodiazole-4-carboxylic acid A solution of methyl 7-bromo-2-(difluoromethoxy)-3H-1,3-benzodiazole-4-carboxylate (100 mg, 0.31 mmol, 1 equiv) and LiOH (29.8 mg, 1.24 mmol, 4 equiv) in THF (0.5 mL) and $H_2O$ (0.06 mL) was stirred for 2 h at 50° C. under air. The resulting mixture was concentrated under reduced pressure to afford 7-bromo-2-(difluoromethoxy)-3H-1,3-benzodiazole-4-carboxylic acid (100 mg) as a yellow solid which was used in the next step directly without further purification.

Step 4: Synthesis of (R or S)-1-(5-(7-bromo-2-(difluoromethoxy)-1H-benzo[d]imidazole-4-carbonyl)-2-(4-cyclobutyl-2-hydroxyphenyl)-2,3,4,5,5a,6,8,9-octahydro-7H-1,2,5,7-tetraazabenzo[cd]azulen-7-yl)prop-2-en-1-one To a solution of 1-(2-(4-cyclobutyl-2-hydroxyphenyl)-2,3,4,5,5a,6,8,9-octahydro-7H-1,2,5,7-tetraazabenzo[cd]azulen-7-yl)prop-2-en-1-one (Int. T) (40 mg, 1 equiv., 0.11 mmol) in DMF (0.5 mL) were added 7-bromo-2-(difluoromethoxy)-1H-benzo[d]imidazole-4-carboxylic acid (49 mg, 1.5 equiv., 0.16 mmol), HATU (60 mg, 1.5 equiv., 0.16 mmol) and DIEA (68 mg, 5 equiv., 0.53 mmol). The mixture was stirred at rt for 4 h, after which it was diluted with water (5 mL) and EA (5 mL), and the aqueous layer was extracted with EA (2×5 mL). The combined organic layers were washed with saturated brine (2×5 mL), dried over anhydrous sodium sulfate and concentrated to afford 2-(7-acryloyl-5-(7-bromo-2-(difluoromethoxy)-1H-benzo[d]imidazole-4-carbonyl)-3,4,5,5a,6,7,8,9-octahydro-2H-1,2,5,7-tetraazabenzo[cd]azulen-2-yl)-5-cyclobutylphenyl 7-bromo-2-(difluoromethoxy)-1H-benzo[d]imidazole-4-carboxylate (45 mg) as a white solid which was used in the next step without further purification.

The white solid (40 mg, 1 equiv., 42 μmol) was dissolved in THF (0.8 mL) and $H_2O$ (0.2 mL) and LiOH was added (3.0 mg, 3 equiv., 0.14 mmol). The mixture was stirred at rt for 4 h, after which the mixture was acidified to pH=3 with the addition of 1 M Sulfuric acid (aq.), then it was diluted with EA (5 mL) and water (5 mL), and the aqueous layer was extracted with EA (2×5 mL). The combined organic layers were washed with saturated brine (5 mL), dried over anhydrous sodium sulfate and concentrated to give a residue. The residue was purified by flash column chromatography, eluting with EA/PE (1:1) to afford racemic 1-(5-(7-bromo-2-(difluoromethoxy)-1H-benzo[d]imidazole-4-carbonyl)-2-(4-cyclobutyl-2-hydroxyphenyl)-2,3,4,5,5a,6,8,9-octahydro-7H-1,2,5,7-tetraazabenzo[cd]azulen-7-yl)prop-2-en-1-one (8 mg) as a white solid. The racemic mixture was purified by Prep chiral-HPLC with the following conditions: Column-CHIRALPAK IC-3 4.6*50 mm, 3 m; Mobile Phase A: HEX(0.1% FA), Mobile Phase B: EtOH: DCM=1:1; Flow rate: 1 mL/min; Gradient: isocratic 30; Wave Length: UV 254/220 nm; RT1(min): 1.5; RT2(min): 2.3 to afford (R or S)-1-(5-(7-bromo-2-(difluoromethoxy)-1H-benzo[d]imidazole-4-carbonyl)-2-(4-cyclobutyl-2-hydroxyphenyl)-2,3,4,5,5a,6,8,9-octahydro- 7H-1,2,5,7-tetraazabenzo[cd]azulen-7-yl)prop-2-en-1-one (1.9 mg) as the second-eluting peak as a white solid. LCMS:(ESI, m/z): 667 [M+1]+. $^{1}$H NMR: (400 MHz, Chloroform-d, ppm):δ 7.61-7.34 (m, 1H), 7.08-6.81 (m, 2H), 6.81-6.37 (m, 1H), 5.85 (s, 1H), 0.44 (s, 1H), 4.97 (s, 1H), 4.49 (s, 1H), 3.58-2.63 (m, 8H), 2.60-1.81 (m, 5H), 0.91-0.70 (m, 1H), 0.08--0.13 (m, 5H) (some peaks obscured by solvent).

Example C-32: Preparation of (R or S)-1-(2-(4-cyclobutyl-2-hydroxyphenyl)-5-(5-(methylthio)-6-(trifluoromethyl)nicotinoyl)-2,3,4,5,5a,6,8,9-octahydro-7H-1,2,5,7-tetraazabenzo[cd]azulen-7-yl)prop-2-en-1-one

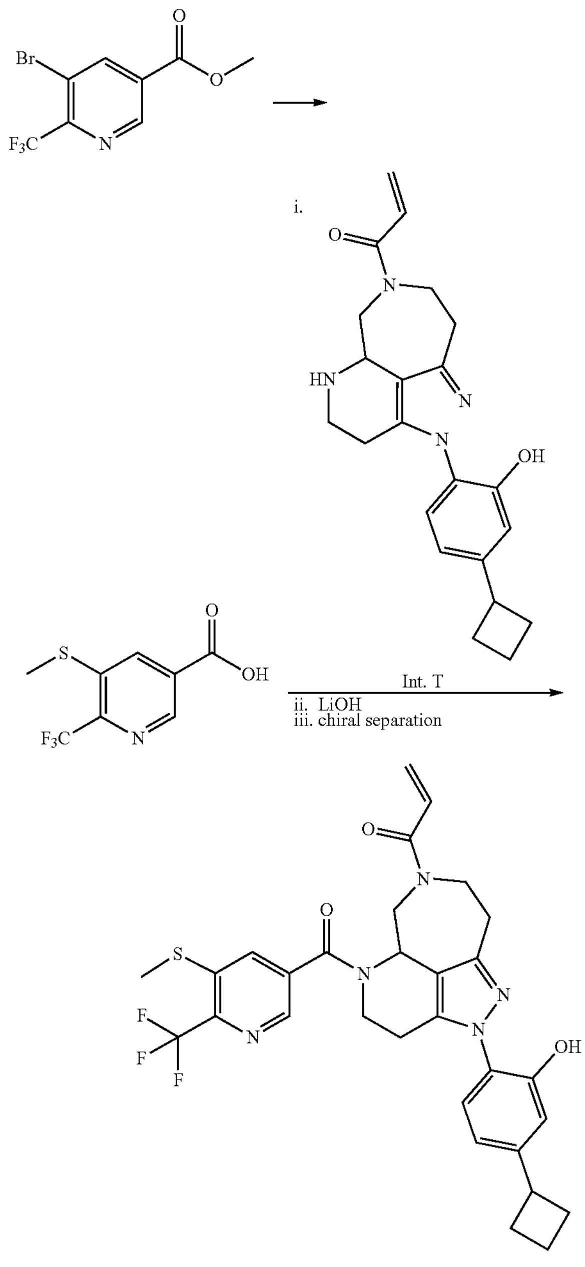

Step 1: Synthesis of 5-(methylthio)-6-(trifluoromethyl)nicotinic Acid

To a stirred solution of methyl 5-bromo-6-(trifluoromethyl)nicotinate (3 g, 1 equiv., 0.01 mol) in DMF (60 mL) was added sodium methanethiolate (1 g, 2 equiv., 0.02 mol) and the reaction was stirred at 100° C. for 2 h. The reaction mixture was then cooled to rt and formic acid was added to adjust the pH to 6. The resulting mixture was extracted with EA (2×2 0 mL) and the combined organic layers were washed with brine (2×200 mL) and dried over anhydrous $Na_2SO_4$. After filtration, the filtrate was concentrated under reduced pressure to afford 5-(methylthio)-6-(trifluoromethyl)nicotinic acid (1.2 g) as a crude white solid which was used in the next step directly without further purification. LCMS:(ESI, m/z): 238 [M+1]+.

Step 2: Synthesis of (R or S)-1-(2-(4-cyclobutyl-2-hydroxyphenyl)-5-(5-(methylthio)-6-(trifluoromethyl)nicotinoyl)-2,3,4,5,5a,6,8,9-octahydro-7H-1,2,5,7-tetraazabenzo[cd]azulen-7-yl)prop-2-en-1-one To a stirred solution of 5-(methylthio)-6-(trifluoromethyl) nicotinic acid (100 mg, 2 equiv., 422 μmol) in DMF (2 mL) was added HBTU (240 mg, 3 equiv., 632 μmol), 1-(2-(4-cyclobutyl-2-hydroxyphenyl)-2,3,4,5,5a,6,8,9-octahydro-7H-1,2,5,7-tetraazabenzo[cd]azulen-7-yl)prop-2-en-1-one (Int. T) (39.9 mg, 0.5 equiv., 105 gmol), and DIEA (163 mg, 220 μL, 6 equiv., 1.26 mmol) at rt and the mixture was stirred for 2 h. The reaction was then quenched by the addition of water (20 mL) at rt, and the resulting mixture was extracted with EA (2×20 mL). The combined organic layers were washed with brine (2×20 mL) and dried over anhydrous $Na_2SO_4$. After filtration, the filtrate was concentrated under reduced pressure and the product (200 mg) was used directly in the next step. The solid was re-dissolved in THF (3 mL) and $H_2O$ (1 mL) and LiOH (15.15 mg, 3 equiv., 632 μmol) was added. The mixture was stirred for 2 h at rt, after which the solvent was removed under reduced pressure. The residue was purified by reversed-phase flash chromatography (Column: XBridge BEH C18 OBD Prep Column 130, 5 μm, 30 mm*150 mm; Mobile Phase A: Water (10 mmol/L NH4HCO3), Mobile Phase B: AC; Flow rate: 60 mL/min; Gradient: 42% B to 72% B in 10 min) to afford racemic 1-(2-(4-cyclobutyl-2-hydroxyphenyl)-5-(5-(methylthio)-6-(trifluoromethyl)nicotinoyl)-2,3,4,5,5a,6,8,9-octahydro-7H-1,2,5,7-tetraazabenzo[cd]azulen-7-yl)prop-2-en-1-one (15 mg) as a white solid. The racemate was separated into its constitutive enantiomers by Prep-chiral HPLC with the following conditions: Column-CHIRAL ART Cellulose-SB, 3*25 cm, 5 μm; Mobile Phase: Hex(0.1% FA)—HPLC, Mobile Phase B: EtOH:DCM=1:1; Flow rate: 40 mL/min; Gradient: isocratic 25; Wave Length: UV 254/220 nm; RT1(min): 9.8; RT2(min): 14; to afford (R or S)-1-(2-(4-cyclobutyl-2-hydroxyphenyl)-5-(5-(methylthio)-6-(trifluoromethyl)nicotinoyl)-2,3,4,5,5a,6,8,9-octahydro-7H-1,2,5,7-tetraazabenzo[cd]azulen-7-yl)prop-2-en-1-one (3.8 mg) as the second-eluting isomer as a white solid. LCMS:(ESI, m/z): 598 $[M+1]^+$. $^{1}$H NMR: (400 MHz, Chloroform-d, ppm) δ 10.07 (s, 1H), 8.46 (d, J=1.7 Hz, 1H), 7.89-7.77 (m, 1H), 7.47-7.36 (m, 1H), 7.04-6.92 (m, 2H), 6.74 (dd, J=8.2, 1.9 Hz, 1H), 6.52 (d, J=16.4 Hz, 1H), 5.89 (d, J=10.4 Hz, H), 5.41 (d, J=10.6 Hz, 1H), 5.00 (d, J=13.3 Hz, 1H), 4.54 (d, J=13.5 Hz, 1H), 4.25-3.85 (m, 1H), 3.52 (p, J=8.7 Hz, 1H), 3.33-2.93 (m, 5H), 2.93-2.69 (m, 2H), 2.60 (s, 2H), 2.35 (dtd, J=10.1, 7.8, 2.5 Hz, 2H), 2.21-1.71 (m, 4H).

Example C-33: Preparation of (R or S)-1-(5-(4-bromo-2-(2-hydroxyethyl)-1H-benzo[d]imidazole-7-carbonyl)-2-(4-cyclobutyl-2-hydroxyphenyl)-2,3,4,5,5a,6,8,9-octahydro-7H-1,2,5,7-tetraazabenzo[cd]azulen-7-yl)prop-2-en-1-one

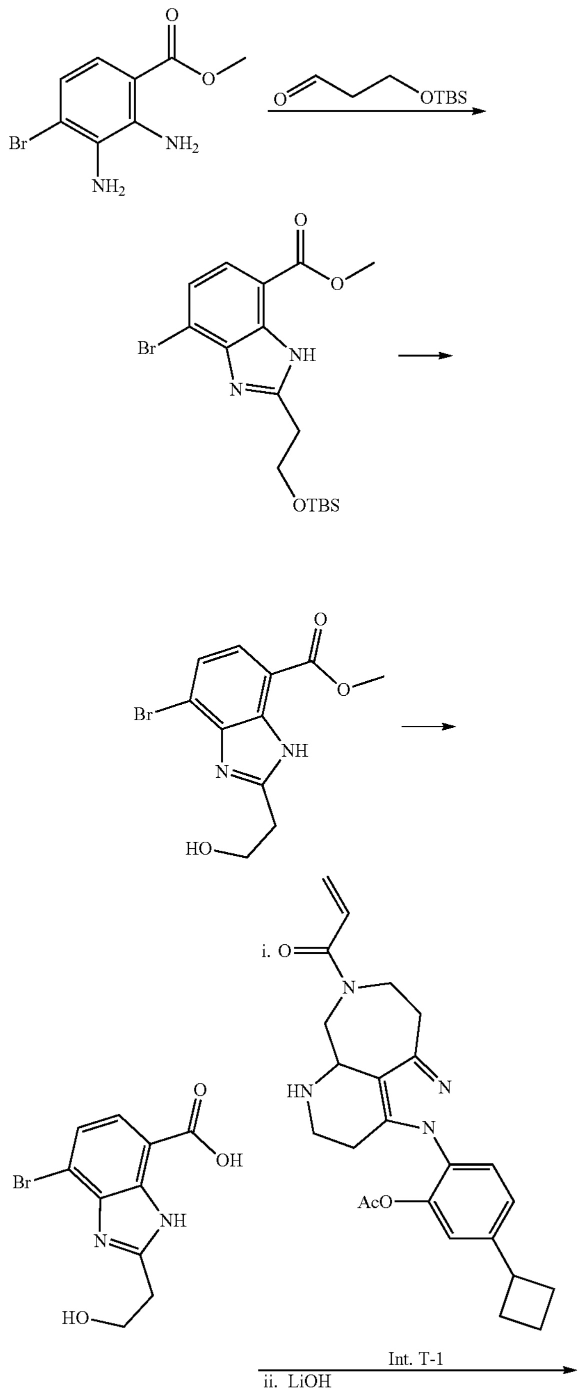

-continued

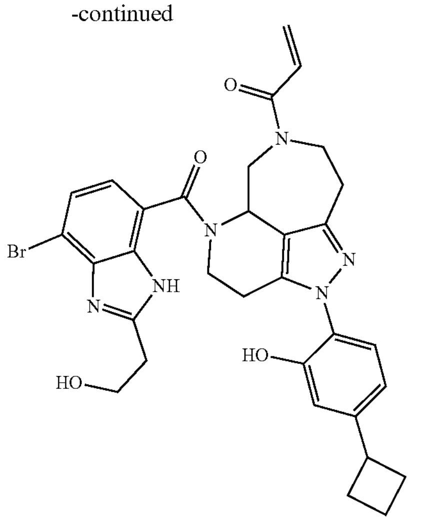

Step 1: Synthesis of Methyl 4-bromo-2-(2-((tert-butyldimethylsilyl)oxy)ethyl)-JH-benzo[d]imidazole-7-carboxylate To a solution of methyl 2,3-diamino-4-bromobenzoate (2 g, 1 equiv., 8 mmol) in IPA (50 mL) were added Pd—C (9 g, 10% wt) and 3-((tert-butyldimethylsilyl)oxy) propanal (2 g, 1.2 equiv., 0.01 mol). The resulting mixture was stirred then at 60° C. for 1 h under a $H_2$ atmosphere. The mixture was then cooled and filtered, and rinsed with EA (5×50 mL). The filtrate was concentrated under vacuum to give a residue, which was purified by silica gel chromatography eluted with PE:EA=3:1 to give methyl 4-bromo-2-(2-((tert-butyldimethylsilyl)oxy)ethyl)-1H-benzo[d]imidazole-7-carboxylate (1 g) as a white solid. LCMS:(ESI, m/z): 413 $[M+1]^+$.

Step 2: Synthesis of Methyl 4-bromo-2-(2-hydroxyethyl)-1H-benzo[d]imidazole-7-carboxylate To a solution of methyl 4-bromo-2-(2-((tert-butyldimethylsilyl)oxy)ethyl)-1H-benzo[d]imidazole-7-carboxylate (900 mg, 1 equiv., 2.18 mmol) in THF 18 mL) was added TBAF (569 mg, 1 equiv., 2.18 mmol). The mixture was stirred at rt for 2 h, after which the mixture was diluted with water (20 mL) and EA (20 mL). The aqueous layer was extracted with EA (2×20 mL), and the combined organic layers were washed with saturated brine (2×20 mL), dried over anhydrous sodium sulfate and concentrated to give a residue. The crude product was purified by silica gel chromatography, eluting with PE:EA=2:1 to give to afford methyl 4-bromo-2-(2-hydroxyethyl)-1H-benzo[d]imidazole-7-carboxylate (350 mg) as a white solid. LCMS:(ESI, m/z): 299 $[M+1]^+$.

Step 3: Synthesis of 4-bromo-2-(2-hydroxyethyl)-1H-benzo[d]imidazole-7-carboxylic Acid To a solution of methyl 4-bromo-2-(2-hydroxyethyl)-1H-benzo[d]imidazole-7-carboxylate (300 mg, 1 equiv., 1.00 mmol) in THF (3 mL) and water (3 mL) was added lithium hydroxide (72.1 mg, 3 equiv., 3.01 mmol). The mixture was then stirred at 40° C. for 2 h, after which the mixture was cooled to rt and acidified to pH=3 with 1 M sulfuric acid (aq). The precipitated solids were collected by filtration and washed with water (2×3 mL) to afford 4-bromo-2-(2-hydroxyethyl)-1H-benzo[d]imidazole-7-carboxylic acid (164 mg) as a yellow solid which was used without further purification. LCMS:(ESI, m/z): 285 $[M+1]^+$.

Step 4: Synthesis of (R or S)-7-(5-(4-bromo-2-(2-hydroxyethyl)-1H-benz[d]imidazole-7-carbonyl)-2-(4-cyclobutyl-2-hydroxyphenyl)-2,3,4,5,5a,6,8,9-octahydro 7H-1,2,5,7-tetraazabenzo[cd]azulen-7-yl) prop-2-en-1-one To a solution of (R or S)-2-(7-acryloyl-3,4,5,5a,6,7,8,9-octahydro-2H-1,2,5,7-tetraazabenzo[cd]azulen-2-yl)-5-cyclobutylphenyl acetate (Int. T-1) (90 mg, 1 equiv., 0.21 mmol) in DMF (0.9 mL) were added DIPEA (83 mg, 3 equiv., 0.64 mmol), 4-bromo-2-(2-hydroxyethyl)-1H-benzo [d]imidazole-7-carboxylic acid (61 mg, 1 equiv., 0.21 mmol) and HATU (0.16 g, 2 equiv., 0.43 mmol). The mixture was stirred at rt for 1 h, after which the mixture was diluted with water (2 mL) and EA (2 mL), and the aqueous layer was extracted with EA (2×2 mL). The combined organic layers were washed with saturated brine (2×2 mL), dried over anhydrous sodium sulfate and concentrated to give a residue. The residue was purified by flash column chromatography, eluting with EA/PE (1:3) to afford (R or S)-2-(7-acryloyl-5-(4-bromo-2-(2-hydroxyethyl)-1H-benzo[d] imidazole-7-carbonyl)-3,4,5,5a,6,7,8,9-octahydro-2H-1,2,5,7-tetraazabenzo[cd]azulen-2-yl)-5-cyclobutylphenyl acetate (100 mg) as a white solid. To a solution of (R or S)-2-(7-acryloyl-5-(4-bromo-2-(2-hydroxyethyl)-1H-benzo[d]imidazole-7-carbonyl)-3,4,5,5a,6,7,8,9-octahydro-2H-1,2,5,7-tetraazabenzo[cd]azulen-2-yl)-5-cyclobutylphenyl acetate (90 mg, 1 equiv., 0.13 mmol) in THF (4 mL) and water (1 mL) was added LiOH (6.2 mg, 2 equiv., 0.26 mmol). The mixture was stirred at rt for 1 h, after which the mixture was diluted with water (5 mL) and EA (5 mL), and the aqueous layer was extracted with EA (2×5 mL). The combined organic layers were washed with saturated brine (2×10 mL), dried over anhydrous sodium sulfate and concentrated to give a residue. The residue was purified by Prep-HP IC (Column: Sunfire C18 5 μm, 30 mm*150 mm; Mobile Phase A: Water (0.1% FA), Mobile Phase B: ACN; Flow rate: 60 mL/min; Gradient: 35% B to 57% B in 7 min.) to afford (R or S)-1-(5-(4-bromo-2-(2-hydroxyethyl)-1H-benzo[d]imidazole-7-carbonyl)-2-(4-cyclobutyl-2-hydroxyphenyl)- 2,3,4,5,5a,6,8,9-octahydro-7H-1,2,5,7-tetraazabenzo[cd]azulen-7-yl)prop-2-en-1-one (18 mg) as a white solid. LCMS: (ESI, m/z): 645 $[M+1]^+$. $^1$H NMR: (400 MHz, Chloroform-d, ppm) δ 10.11 (s, 1H), 7.56-7.35 (m, 2H), 7.23-7.17 (m, 1H), 7.08-6.84 (m, 2H), 6.84-6.25 (m, 2H), 5.97-5.73 (m, 1H), 5.54-5.33 (m, 1H), 5.05-4.43 (m, 2H), 4.40-3.96 (m, 2H), 3.57-3.43 (m, 1H), 3.43-2.91 (m, 7H), 2.91-2.58 (m, 1H), 2.36-2.20 (m, 2H), 2.17-1.94 (m, 2H), 0.88-0.78 (m, 1H).

Example C-34: Preparation of (R or S)-1-(2-(4-cyclobutyl-2-hydroxyphenyl)-5-(7-(trifluoromethyl)-1H-imidazo[4,5-c]pyridine-4-carbonyl)-2,3,4,5,5a,6,8,9-octahydro-7H-1,2,5,7-tetraazabenzo[cd]azulen-7-yl)prop-2-en-1-one

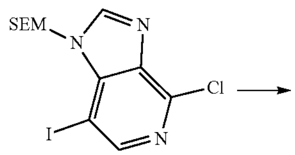

-continued

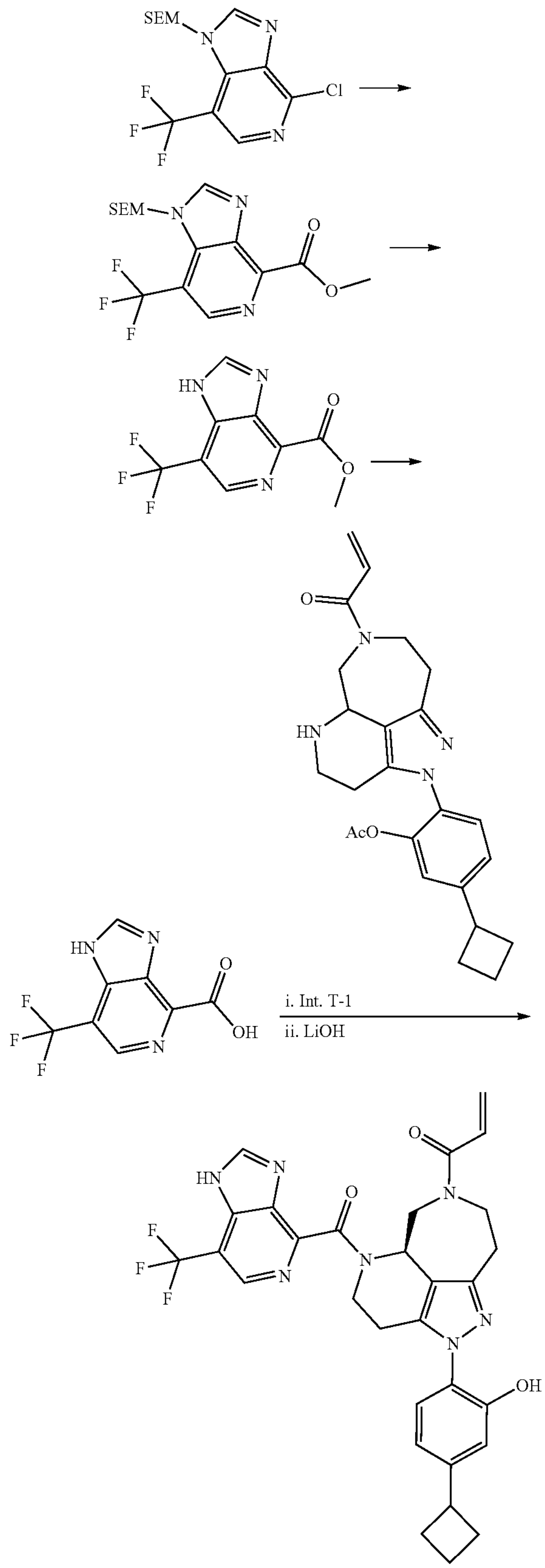

Step 1: Synthesis of 4-chloro-7-(trifluoromethyl)-1-((2-(trimethylsilyl) ethoxy) methyl)-1H-imidazo[4,5-c]pyridine A mixture of 4-chloro-7-iodo-1-((2-(trimethylsilyl) ethoxy) methyl)-1H-imidazo[4,5-c]pyridine (2.0 g, 1 equiv., 4.9 mmol). trifluoromethyltrimethylsilane (3.7 g, 3.66 mL, 5 equiv., 24.4 mmol), potassium fluoride (567 mg, 229 μL, 2 equiv., 9.76 mmol) and CuI (930 mg, 1 equiv., 4.88 mmol) in DMF (40 mL) was stirred for 12 h at 100° C. under an air atmosphere. The resulting mixture was cooled to rt an diluted with water (40 mL), and the resulting mixture was extracted with EtOAc (3x40 mL). The combined organic layers were washed with brine (1x40 mL) and dried over anhydrous $Na_2SO_4$. After filtration, the filtrate was concentrated under reduced pressure. The residue was purified by silica gel column chromatography, eluting with PE/EA (1:1) to afford 4-chloro-7-(trifluoromethyl)-1-((2-(trimethylsilyl) ethoxy) methyl)-1H-imidazo[4,5-c]pyridine (520 mg) as a yellow oil. LCMS:(ESI, m/z): 352 $[M+1]^+$.

Step 2: Synthesis of Methyl 7-(trifluoromethyl)-1-((2-(trimethylsilyl) ethoxy) methyl)-1H-imidazo[4,5-c]pyridine-4-carboxylate A mixture of 4-chloro-7-(trifluoromethyl)-1-((2-(trimethylsilyl) ethoxy) methyl)-1H-imidazo[4,5-c]pyridine (680 mg, 1 equiv., 1.93 mmol). TEA (1.17 g, 1.62 mL, 6 equiv., 11.6 mmol) and $PdCl_2$(dppf) (141 mg, 0.1 equiv., 193 mol) in MeOH (10 mL) was stirred for 4 h at 100° C. under a CO atmosphere. The resulting mixture was then cooled to rt and concentrated under reduced pressure. The residue was purified by silica gel column chromatography, eluting with PE/EA (1:1) to afford methyl 7-(trifluoromethyl)-1-((2-(trimethylsilyl) ethoxy) methyl)-1H-imidazo[4,5-c]pyridine-4-carboxylate (350 mg) as a yellow oil. LCMS:(ESI, m/z): 376 $[M+1]^+$.

Step 3: Synthesis of Methyl 7-(trifluoromethyl)-1H-imidazo[4,5-c]pyridine-4-carboxylate A mixture of methyl 7-(trifluoromethyl)-1-((2-(trimethylsilyl) ethoxy) methyl)-1H-imidazo[4,5-c]pyridine-4-carboxylate (290 mg, 1 equiv., 772 μmol) in DCE (5 mL) and TFA (5 mL) was stirred for 2 h at rt under an air atmosphere. The resulting mixture was then concentrated under reduced pressure to provide methyl 7-(trifluoromethyl)-1H-imidazo[4,5-c]pyridine-4-carboxylate (210 mg) as a crude yellow oil which was used in the next step directly without further purification. LCMS:(ESI, m/z): 246 $[M+1]^+$.

Step 4: Synthesis of 7-(trifluoromethyl)-1H-imidazo[4,5-c]pyridine-4-carboxylic Acid To a stirred mixture of methyl 7-(trifluoromethyl)-1H-imidazo[4,5-c]pyridine-4-carboxylate (190 mg, 1 equiv., 775 μmol) in MeOH (4 mL) was added LiOH (37 mg, 2 equiv., 1.56 mmol) rt under an air atmosphere. The resulting mixture was stirred for 2 h at rt under an air atmosphere. The mixture acidified to pH=5 with HCl (1M, aq.). The resulting mixture was extracted with EtOAc (3x20 mL) and the combined organic layers were washed with brine (1x40 mL) and dried over anhydrous $Na_2SO_4$. After filtration, the filtrate was concentrated under reduced pressure and the residue was purified by reversed-phase flash chromatography with the following conditions: column, C18; mobile phase, MeCN in Water (0.1% FA), 10% to 50% gradient in 10 min; to provide 7-(trifluoromethyl)-1H-imidazo[4,5-c]pyridine-4-carboxylic acid (140 mg) as a white solid. LCMS:(ESI, m/z): 232 $[M+1]^+$.

Step 5:Synthesis of (R or S)-1-(2-(4-cyclobutyl-2-hydroxyphenyl)-5-(7-(trifluoromethyl)-1H-imidazo[4,5-c]pyridine-4-carbonyl)-2,3,4,5,5a,6,8,9-octahydro-7H-1,2,5,7-tetraazabenzo[cd]azulen-7-yl) prop-2-en-1-one A mixture of 7-(trifluoromethyl)-1H-imidazo[4,5-c]pyridine-4-carboxylic acid (50.0 mg, 1 equiv., 216 μmol), DIEA (168 mg, 226 μL, 6 equiv., 1.23 mmol), HATU (123.4 mg, 1.5 equiv., 324.5 μmol) and (R or S)-2-(7-acryloyl-3,4,5,5a,6,7,8,9-octahydro-2H-1,2,5,7-tetraazabenzo[cd]azulen-2-yl)-5-cyclobutylphenyl acetate (Int. T-1) (109 mg, 1.2 equiv., 260 μmol) in DMF (2 mL) was stirred for 2 h at rt, after which it was diluted with water (20 mL) and was extracted with EtOAc (3x20 mL). The combined organic layers were washed with brine (1x20 mL) and dried over anhydrous $Na_2SO_4$. After filtration, the filtrate was concentrated under reduced pressure and purified by silica gel column chromatography, eluting with PE/EA (1:1) to afford (R or S)-2-(7-acryloyl-5-(7-(trifluoromethyl)-1H-imidazo[4,5-c]pyridine-4-carbonyl)-3,4,5,5a,6,7,8,9-octahydro-2H-1,2,5,7-tetraazabenzo[cd]azulen-2-yl)-5-cyclobutylphenyl acetate (26.0 mg) as a yellow solid. This solid was re-dissolved in THF (2 mL) and LiOH (6.05 mg, 4 equiv., 253 mol) was added at rt under an air atmosphere. The resulting mixture was stirred for 2 h, after which it was diluted with water (10 mL) and extracted with EtOAc (3x10 mL) and the combined organic layers were washed with brine (1x20 mL) and dried over anhydrous $Na_2SO_4$. After filtration, the filtrate was concentrated under reduced pressure and purified by Prep-HPLC with the following conditions (Column: Sunfire C18 5 m, 30 mm*150 mm; Mobile Ph se A: Water (0.1% FA), Mobile Phase B: ACN; Flow rate: 60 mL/min; Gradient: 35% B to 59% B in 10 min) to afford (R or S)-1-(2-(4-cyclobutyl-2-hydroxyphenyl)-5-(7-(trifluoromethyl)-1H-imidazo[4,5-c]pyridine-4-carbonyl)-2,3,4,5,5a,6,8,9-octahydro-7H-1,2,5,7-tetraazabenzo[cd]azulen-7-yl) prop-2-en-1-one (10.4 mg) as a white solid. LCMS:(ESI, m/z): 592 $[M+1]^+$. $^1$H NMR: (400 MHz, Chloroform-d, ppm) δ 8.72 (s, 1H), 8.61 (s, 1H), 7.45 (dd, J=16.3, 10.3 Hz, 1H), 7.18-6.87 (m, 1H), 6.80-6.75 (m, 1H), 6.69-6.39 (m, 2H), 6.01-4.79 (m, 4H), 4.58-4.29 (m, 1H), 3.66-2.52 (m, 8H), 2.43-2.23 (m, 2H), 2.23-1.69 (m, 4H).

Example C-35: Preparation of (R or S)-1-(2-(4-cyclobutylphenyl)-5-(1-methyl-3-(trifluoromethyl)-1H-pyrazolo[4,3-b]pyridine-6-carbonyl)-2,3,4,5,5a,6,8,9-octahydro-7H-1,2,5,7-tetraazabenzo[cd]azulen-7-yl)prop-2-en-1-one

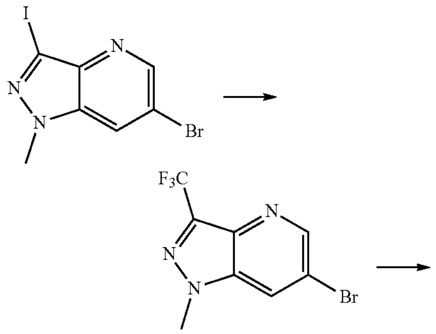

-continued

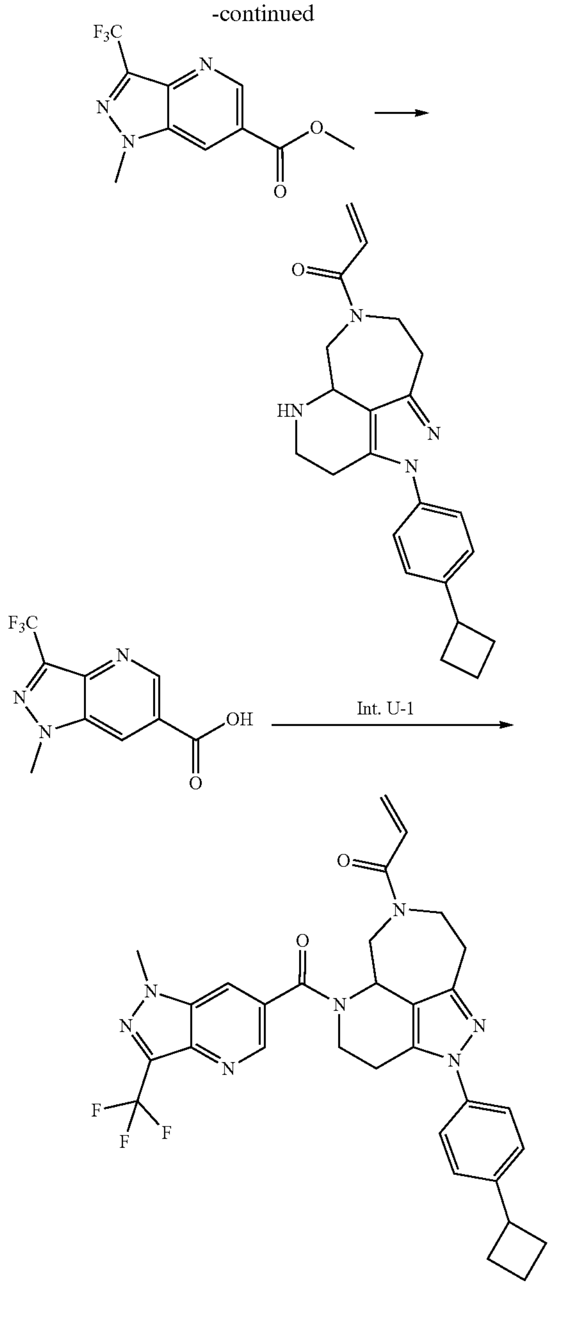

Step 1: Synthesis of 6-bromo-3-methyl-3-(trifluoromethyl)-1H-pyrazolo[4,3-b]pyridine To a solution of 6-bromo-3-iodo-1-methyl-1H-pyrazolo [4,3-b]pyridine (3 g, 1 equiv., 9 mmol) in DMF (150 mL) were added methyl difluoro(fluorosulphonyl)acetate (3 g, 2 mL, 2 equiv., 0.02 mol) and $Cu(OAc)_2$ (0.8 g, 0.5 equiv., 4 mmol). The resulting mixture was placed under a positive pressure of nitrogen and subjected to three backfilling cycles under vacuum. The resulting mixture was stirred for 12 h at 110° C. under a nitrogen atmosphere. The reaction mixture was then cooled to rt, filtered, and rinsed with EA (3×200 mL). The combined filtrate was diluted with water (200 mL) and the aqueous layer was extracted with EA (2×200 mL). The combined organic layers were washed with saturated brine (3×200 mL), dried over anhydrous sodium sulfate and concentrated to give a residue. The crude product was purified by silica gel chromatography, eluting with PE:EA=5:1 to give 6-bromo-1-methyl-3-(trifluoromethyl)-1H-pyrazolo[4,3-b]pyridine (700 mg) as white solid. LCMS:(ESI, m/z): 281 $[M+1]^+$.

Step 2: Synthesis of Methyl 1-methyl-3-(trifluoromethyl)-JH-pyrazolo[4,3-b]pyridine-6-carboxylate To a solution of 6-bromo-1-methyl-3-(trifluoromethyl)-1H-pyrazolo[4,3-b]pyridine (600 mg, 1 equiv., 2.14 mmol) in MeOH (12 mL) were added TEA (650 mg, 896 μL, 3 equiv., 6.43 mmol) and $Pd(dppf)Cl_2$ (175 mg, 0.1 equiv., 214 mol). The mixture was purged with nitrogen (×3) and then was pressurized to 4.0 MPa with CO at 100° C. for 12 h. The reaction mixture was then cooled to rt, filtered, and rinsed with EA (3×50 mL). The combined filtrate was concentrated under vacuum to give methyl 1-methyl-3-(trifluoromethyl)-1H-pyrazolo[4,3-b]pyridine-6-carboxylate (650 mg) as crude white solid which was used in the next step directly without further purification. LCMS:(ESI, m/z): 260 $[M+1]^+$.

Step 3: Synthesis of 1-methyl-3-(trifluoromethyl)-1H-pyrazolo[4,3-b]pyridine-6-carboxylic Acid To a solution of methyl 1-methyl-3-(trifluoromethyl)-1H-pyrazolo[4,3-b]pyridine-6-carboxylate (650 mg, 1 equiv., 2.51 mmol) in THF (7 mL) and $H_2O$ (2 nL) was added LiOH (180 mg, 3 equiv., 7.52 mmol). The mixture was stirred at rt for 4 h. The mixture was then acidified to pH=3 with 1 M Sulfuric acid, diluted with EA (20 mL) and water (15 m L), and the aqueous layer was extracted with EA (2×20 mL). The combined organic layers were washed with saturated brine (20 mL), and dried over anhydrous sodium sulfate. The crude product was purified by reversed-phase flash chromatography with the following conditions: column, C18; mobile phase, water (0.1% FA) in MeCN, 0% to 100% gradient in 30 min and concentrated to afford 1-methyl-3-(trifluoromethyl)-1H-pyrazolo[4,3-b]pyridine-6-carboxylic acid (500 mg) as a white solid. LCMS:(ESI, m/z): 246 $[M+1]^+$.

Step 4: Synthesis of (R or S)-1-(2-(4-cyclobutylphenyl)-S-(1-methyl-3-(trifluoromethyl)-1H-pyrazolo[4,3-b]pyridine-6-carbonyl)-2,3,4,5,5a,6,8,9-octahydro-7H-1,2,5,7-tetraazabenzo[cd]azulen-7-yl)prop-2-en-1-one To a solution of (R or S)-1-(2-(4-cyclobutylphenyl)-2,3,4,5,5a,6,8,9-octahydro-7H-1,2,5,7-tetraazabenzo [cd]azulen-7-yl)prop-2-en-1-one (prepared from Int. U by chiral separation) (50 mg, 1 equiv., 0.14 mmol) in DMF (1 mL) were added HATU (0.10 g, 2 equiv., 0.28 mmol), 1-methyl-3-(trifluoromethyl)-1H-pyrazolo[4,3-b]pyridine-6-carboxylic acid (34 mg, 1 equiv., 0.14 mmol) and DIEA (89 mg, 0.12 mL, 5 equiv., 0.69 mmol). The mixture was stirred at rt for 5 h, then diluted with water (5 mL) and EA (5 mL), and the aqueous layer as extracted with EA (2×10 mL). The combined organic layers were washed with saturated brine (2×10 mL), dried over anhydrous sodium sulfate and concentrated to give a residue. The residue was purified by Prep-HPLC (Column: YMC Triart C18 ExRs 5 μm, 30 mm*150 mm; Mobile Phase A: Water (10 mmol/L $NH_4HCO_3$), Mobile Phase B: ACN; Flow rate: 60 mL/min; Gradient: 53% B to 74% B in 7 min) to afford (R or S)-1-(2-(4-cyclobutylphenyl)-5-(1-methyl-3-(trifluoromethyl)-1H-pyrazolo[4,3-b]pyridine-6-carbonyl)-2,3,4,5,5a, 6,8,9-octahydro-7H-1,2,5,7-tetraazabenzo[cd]azulen-7-yl)prop-2-en-1-one (5 mg) as a white solid. LCMS:(ESI, m/z): 590 [M+1]$^+$. $^1$H NMR: (400 MHz, Chloroform-d, ppm) δ 8.80 (s, 1H), 8.45-8.09 (m, 1H), 7.77-7.26 (m, 5H), 6.72-6.37 (m, 1H), 6.37-5.26 (m, 2H), 5.12-4.52 (m, 2H), 4.23 (s, 3H), 4.49-3.84 (m, 1H), 3.64-3.51 (m, 1H), 3.38-1.76 (m, 12H).
Example D-1: Preparation of 1-(2-(6-(bicyclo[1.1.1]pentan-1-yl)pyridin-3-yl)-5-(7-bromo-1H-benzo[d]imidazole-4-carbonyl)-2,3,4,5,5a,6,8,9-octahydro-7H-1,2,5,7-tetraazabenzo[cd]azulen-7-yl)prop-2-en-1-one
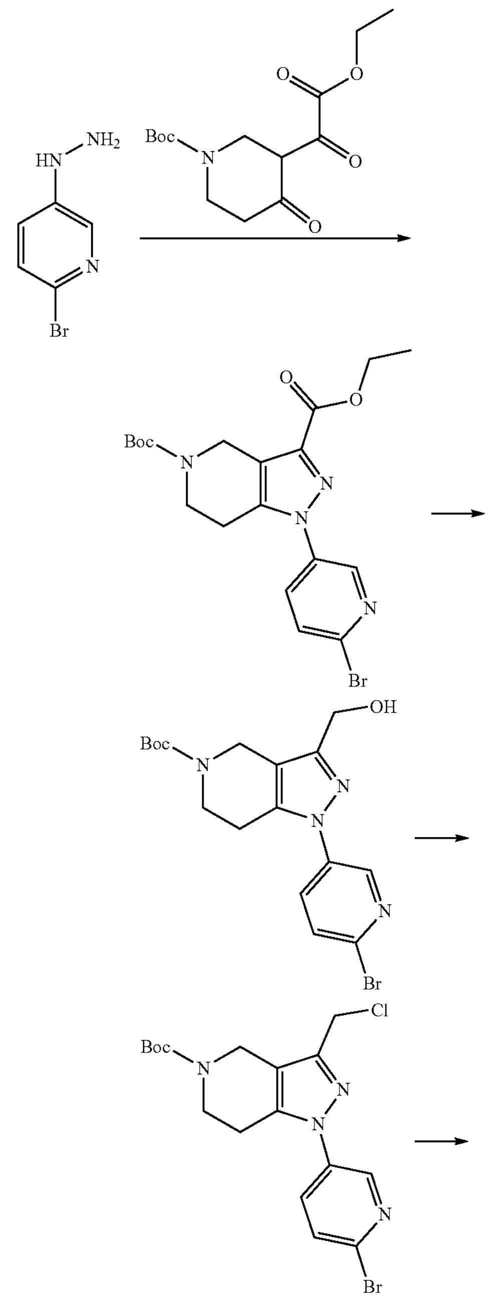
-continued
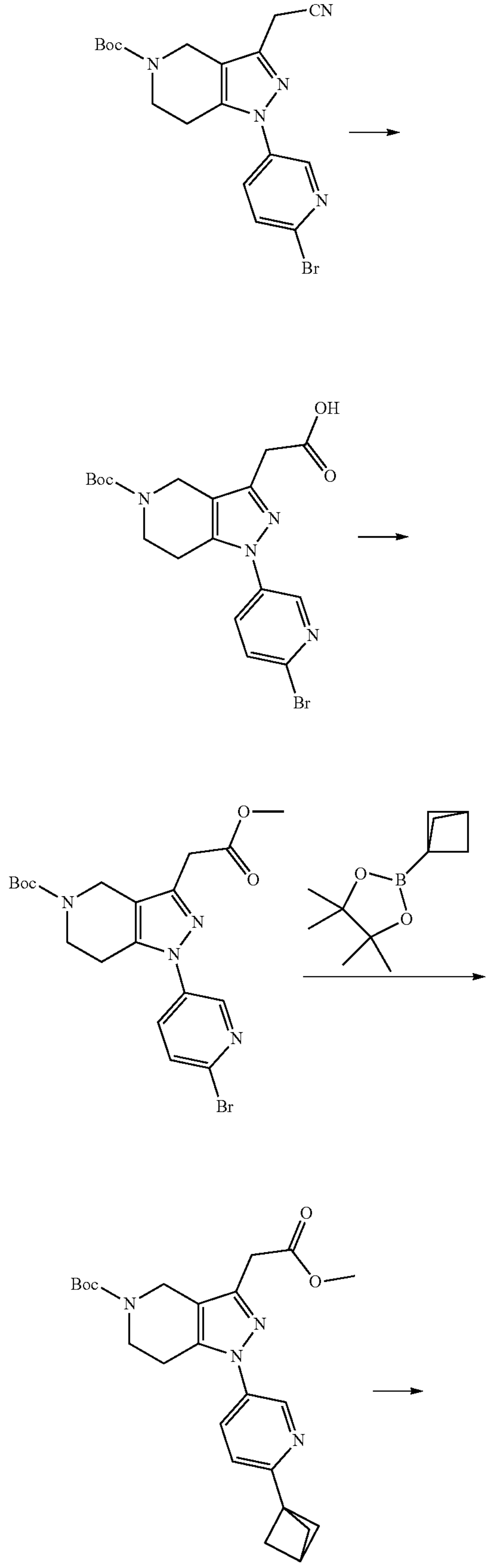

-continued

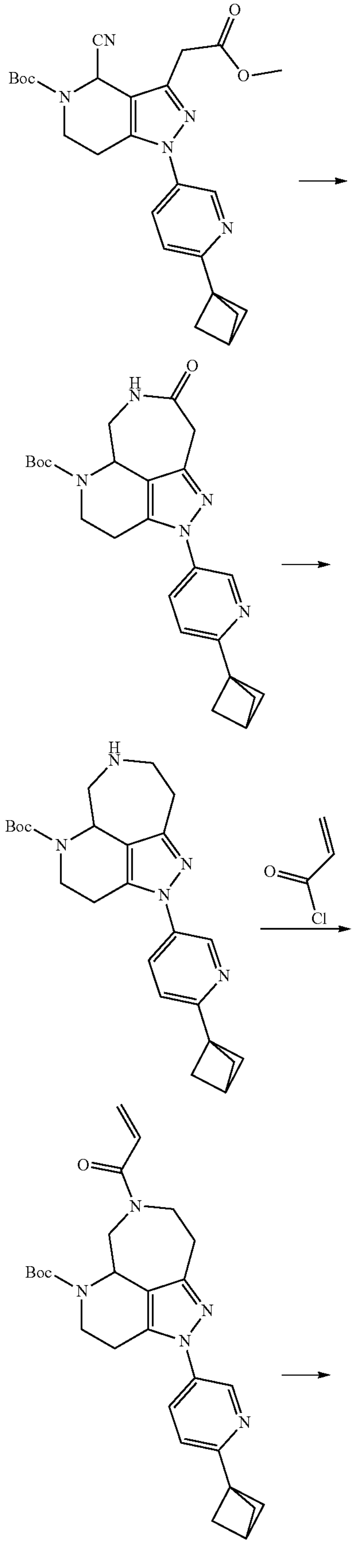

-continued

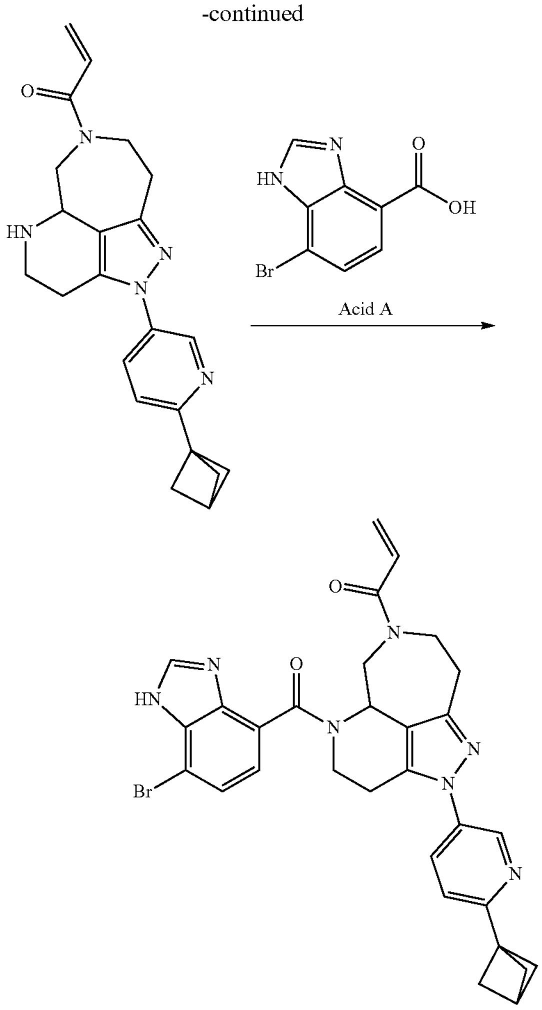

Step 1: Synthesis of 5-(tert-butyl) 3-ethyl 1-(6-bromopyridin-3-yl-1,4,6,7-tetrahydro-5H-pyrazolo[4,3-c]pyridine-3,5-dicarboxylate To a stirred solution of 2-bromo-5-hydrazineylpyridine (23 g, 1 equiv., 0.12 mol) in EtOH (200 mL) was added tert-butyl 3-(2-ethoxy-2-oxoacetyl)-4-oxopiperidine-1-carboxylate (40 g, 1.1 equiv., 0.13 mol) at room temperature and stirred overnight. The reaction was quenched by the addition of water (200 mL) at rt. The resulting mixture was extracted with EtOAc (2×200 mL). The combined organic layers were washed with brine (2×200 mL) and dried over anhydrous $Na_2SO_4$. After filtration, the filtrate was concentrated under reduced pressure. The residue was purified by silica gel column chromatography, eluting with EtOAc/PE (1:8) to afford 5-(tert-butyl) 3-ethyl 1-(6-bromopyridin-3-yl)-1,4,6,7-tetrahydro-5H-pyrazolo[4,3-c]pyridine-3,5-dicarboxylate (22 g) as a white solid. LCMS: (ESI, m/z): 451 $[M+H]^+$.

Step 2: Synthesis of Tert-Butyl 1-(6-bromopyridin-3-yl)-3-(hydroxymethyl)-1,4,6,7-tetrahydro-5H-pyrazolo[4,3-c]pyridine-5-carboxylate To a stirred solution of 5-(tert-butyl) 3-ethyl 1-(6-bromopyridin 3-yl)-1,4,6,7-tetrahydro-5H-pyrazolo[4,3-c]pyridine-3,5-dicarboxylate (21.8 g, 1 equiv., 48.3 mmol) in EtOH (200 mL) was added $LiBH_4$ (3.16 g, 3 equiv., 145 mmol) at room temperature, and the mixture was stirred overnight. The reaction was then quenched by the addition of water (200 mL) at rt. The resulting mixture was extracted with EtOAc (2×200 mL). The combined organic layers were washed with brine (2×200 mL) and dried over anhydrous $Na_2SO_4$. After filtration, the filtrate was concentrated under reduced pressure. The residue was purified by silica gel column chromatography, eluting with EtOAc/PE (1:1) to afford tert-butyl 1-(6-bromopyridin-3-yl)-3-(hydroxymethyl)-1,4,6,7-tetrahydro-5H-pyrazolo[4,3-c]pyridine-5-carboxylate (19.8 g) as a white solid. LCMS: (ESI, m/z): 409 $[M+H]^+$.

Step 3: Synthesis of Tert-Butyl 1-(6-bromopyridin-3-yl)-3-(chloromethyl)-1,4,6,7-tetrahydro-5H-pyrazolo[4,3-c]pyridine-5-carboxylate To a solution of tert-butyl 1-(6-bromopyridin-3-yl)-3-(hydroxymethyl)-1,4,6,7-tetrahydro-5H-pyrazolo[4,3-c] pyridine-5-carboxylate (17.8 g, 1 equiv., 43.5 mmol) in DCM (200 mL). The mixture was cooled to 0° C., then $SOCl_2$ (7.24 g, 4.44 mL, 1 equiv., 60.9 mmol) was added dropwise to the above mixture at 0° C. under nitrogen atmosphere. The mixture was warmed to room temperature and stirred for 2 h. The reaction was monitored by LCMS. The mixture was diluted with ice $NH_4HCO_3$ (500 mL), and the aqueous layer was extracted with DCM (2×400 mL). The combined organic layers were washed with saturated brine (2×200 mL), dried over anhydrous $Na_2SO_4$ and concentrated to give a residue. The residue was purified by silica gel flash column chromatography, eluting with EtOAc/PE (1:3) to afford tert-butyl 1-(6-bromopyridin-3-yl)-3-(chloromethyl)-1,4,6,7-tetrahydro-5H-pyrazolo[4,3-c]pyridine-5-carboxylate (17.6 g) as a light yellow oil. LCMS: (ESI, m/z): 427 $[M+H]^+$.

Step 4: Synthesis of Tert-Butyl 1-(6-bromopyridin-3-yl)-3-(cyanomethyl)-1,4,6,7-tetrahydro-5H-pyrazolo[4,3-c]pyridine-5-carboxylate To a stirred solution of tert-butyl 1-(6-bromopyridin-3-yl)-3-(chloromethyl)-1,4,6,7-tetrahydro-5H-pyrazolo[4,3-c] pyridine-5-carboxylate (16 g, 1 equiv., 37 mol) in MeCN (200 mL) was added trimethylsilyl cyanide (11 g, 15 mL, 3 equiv., 0.11 mol) and TBAF (20 g, 2 equiv., 75 mmol). The reaction mixture was stirred at room temperature for 5 h. The reaction was quenched by the addition of water (400 mL) at rt. The resulting mixture was extracted with EtOAc (2×200 mL). The combined organic layers were washed with brine (2×200 mL) and dried over anhydrous $Na_2SO_4$. After filtration, the filtrate was concentrated under reduced pressure. The residue was purified by silica gel column chromatography, eluting with EtOAc/PE (1:3) to afford tert-butyl 1-(6-bromopyridin-3-yl)-3-(cyanomethyl)-1,4,6,7-tetrahydro-5H-pyrazolo[4,3-c]pyridine-5-carboxylate (12 g) as a brown solid. LCMS: (ESI, m/z): 418 $[M+H]^+$.

Step 5: Synthesis of 2-(1-(6-bromopyridin-3-yl)-5-(tert-butoxycarbonyl)-4,5,6,7-tetrahydro-1H-pyrazolo[4,3-c]pyridin-3-yl)acetic Acid To a stirred solution of tert-butyl 1-(6-bromopyridin-3-yl)-3-(cyanomethyl)-1,4,6,7-tetrahydro-5H-pyrazolo[4,3-c] pyridine-5-carboxylate (5 g, 1 equiv., 0.01 mol) in water (25 mL) and MeOH (25 mL) was added NaOH (5 g, 10 equiv., 0.1 mol). The reaction mixture was stirred at 80° C. for 4 h. The reaction was quenched by the addition of water (100 mL) at rt and the pH of the reaction mixture was adjusted to 3-5 with 1 M HCl (aq.). The resulting mixture was extracted with EtOAc (2×100 mL). The combined organic layers were washed with brine (2×200 mL), dried over anhydrous $Na_2SO_4$. The solvent was removed under reduced pressure. This resulted in 2-(1-(6-bromopyridin-3-yl)-5-(tert-butoxycarbonyl)-4,5,6,7-tetrahydro-1H-pyrazolo[4,3-c]pyridin-3-yl)acetic acid (1.2 g) as a crude yellow oil. The crude product was used in the next step directly without further purification. LCMS: (ESI, m/z): 438 $[M+H]^+$.

Step 6: Synthesis of Tert-Butyl 1-(6-bromopyridin-3-yl)-3-(2-methoxy-2-oxoethyl)-1,4,6,7-tetrahydro-5H-pyrazolo[4,3-c]pyridine-5-carboxylate To a stirred solution of 2-(1-(6-bromopyridin-3-yl)-5-(tert-butoxycarbonyl)-4,5,6,7-tetrahydro-1H-pyrazolo[4,3-c]pyridin-3-yl)acetic acid (1.2 g, 1 equiv., 2.7 mmol) in DMF (10 mL) was added $Cs_2CO_3$ (2.7 g, 3 equiv., 8.2 mmol) and methyl iodide (0.58 g 0.27 mL, 1.5 equiv., 4.1 mmol) at room temperature and stirred for 1 h. The reaction was quenched by the addition of water (20 mL) at rt. The resulting mixture was extracted with EtOAc (2×20 mL). The combined organic layers were washed with brine (2×20 mL) and dried over anhydrous $Na_2SO_4$. After filtration, the filtrate was concentrated under reduced pressure. The residue was purified by silica gel column chromatography, eluting with EtOAc/PE (1:3) to afford tert-butyl 1-(6-bromopyridin-3-yl)-3-(2-methoxy-2-oxoethyl)-1,4,6,7-tetrahydro-5H-pyrazolo[4,3-c]pyridine-5-carboxylate (1.1 g) as a white solid. LCMS: (ESI, m/z): 452 $[M+H]^+$.

Step 7: Synthesis of Tert-Butyl 1-(6-(bicyclo[1.1.1] pentan-1-yl)pyridin-3-yl)-3-(2-methoxy-2-oxoethyl)-1,4,6,7-tetrahydro-5H-pyrazolo[4,3-c]pyridine-5-carboxylate To a stirred solution of tert-butyl 1-(6-bromopyridin-3-yl)-3-(2-methoxy-2-oxoethyl)-1,4,6,7-tetrahydro-5H-pyrazolo[4,3-c]pyridine-5-carboxylate (1 g, 1 equiv., 2 mmol) and morpholine (0.3 g, 0.3 mL, 1.5 equiv., 3 mmol) in DMF (210 mL) was added 2-{bicyclo[1.1.1]pentan-1-yl}-4,4,5,5-tetramethyl-1,3,2-dioxaborolane (0.6 g, 1.5 equiv., 3 mmol), nickel, [4,4'-bis(1,1-dimethylethyl)-2,2'-bipyridine-κN1, κN1']dibromo-, (SP-4-2)-(0.05 g, 0.05 equiv., 0.1 mmol) and (4,4'-di-t-butyl-2,2'-bipyridine)bis[3,5-difluoro-2-(5-trifluoromethyl-2-pyridinyl-kN)phenyl-kC]iridium(III) hexafluorophosphate (0.1 g, 0.05 equiv., 0.1 mmol). The reaction mixture was placed under a positive pressure of nitrogen and subjected to three evacuation/refill cycles using high vacuum. The resulting mixture was stirred at room temperature for 2 h under LED 450 nm. The reaction was quenched by the addition of water (20 mL) at rt. The resulting mixture was extracted with EtOAc (2×20 mL). The combined organic layers were washed with brine (2×20 mL) and dried over anhydrous $Na_2SO_4$. After filtration, the filtrate was concentrated under reduced pressure. The residue was purified by silica gel column chromatography, eluting with EtOAc/PE (1:2) to afford tert-butyl 1-(6-(bicyclo[1.1.1]pentan-1-yl)pyridin-3-yl)-3-(2-methoxy-2-oxoethyl)-1,4,6,7-tetrahydro-5H-pyrazolo[4,3-c]pyridine-5-carboxylate (174 mg) as a light yellow solid. LCMS: (ESI, m/z): 439 $[M+H]^+$.

Step 8: Synthesis of Tert-Butyl 1-(6-(bicyclo[1.1.1]pentan-1-yl)pyridin-3-yl)-4-cyano-3-(2-methoxy-2-oxoethyl)-1,4,6,7-tetrahydro-5H-pyrazolo[4,3-c]pyridine-5-carboxylate To a stirred solution of tert-butyl 1-(6-(bicyclo[1.1.1]pentan-1-yl)pyridin-3-yl)-3-(2-methoxy-2-oxoethyl)-1,4,6,7-tetrahydro-5H-pyrazolo[4,3-c]pyridine-5-carboxylate (120 mg, 1 equiv., 274 μmol) in MeCN (1 mL) was added trimethylsilyl cyanide (4.3 mg, 71 μL, 2 equiv., 547 μmol). TEMPO+$BF_4$- (126 mg, 2 equiv., 547 mol) and AcOH (33 mg, 31 μL, 2 equiv., 547 μmol) at room temperature and stirred for 2 h. The reaction was quenched by the addition of water (2 mL) at rt. The resulting mixture was extracted with EtOAc (2×2 mL). The combined organic layers were washed with brine (2×2 mL) and dried over anhydrous $Na_2SO_4$. After filtration, the filtrate was concentrated under reduced pressure. The residue was purified by silica gel column chromatography, eluting with EtOAc/PE (1:3) to afford tert-butyl 1-(6-(bicyclo[1.1.1]pentan-1-yl)pyridin-3-yl)-4-cyano-3-(2-methoxy-2-oxoethyl)-1,4,6,7-tetrahydro-5H-pyrazolo[4,3-c]pyridine-5-carboxylate (60 mg) as a light yellow oil. LCMS: (ESI, m/z): 464 $[M+H]^+$.

Step 9: Synthesis of Tert-Butyl 2-(6-(bicyclo[1.1.1]pentan-1-yl)pyridin-3-yl)-8-oxo-2,3,4,5a,6,7,8,9-octahydro-5H-1,2,5,7-tetraazabenzo[cd]azulene-5-carboxylate To a solution of tert-butyl 1-(6-(bicyclo[1.1.1]pentan-1-yl)pyridin-3-yl)-4-cyano-3-(2-methoxy-2-oxoethyl)-1,4,6,7-tetrahydro-5H-pyrazolo[4,3-c]pyridine-5-carboxylate (60 mg, 1 equiv., 0.13 mmol) in MeOH (1 mL) were added Raney nickel (6.9 mg, 50 wt). The mixture was purged with nitrogen for three times and then was pressurized 4.0 MPa with hydrogen at 40° C. for 7 h. The reaction mixture was cooled to rt. The reaction was monitored by LCMS. The mixture was filtered and rinsed with EtOAc (5×50 mL), the filtrate was concentrated under vacuum to give a residue. This resulted in tert-butyl 2-(6-(bicyclo[1.1.1]pentan-1-yl)pyridin-3-yl)-8-oxo-2,3,4,5a,6,7,8,9-octahydro-5H-1,2,5,7-tetraazabenzo[cd]azulene-5-carboxylate (30 mg) as a crude white solid. The crude product was used in the next step directly without further purification. LCMS: (ESI, m/z): 436 $[M+H]^+$.

Step 10: Tert-Butyl 2-(6-(bicyclo[1.1.1]pentan-1-yl)pyridin-3-yl)-2,3,4,3a,6,7,8,9-octahydro-5H-1,2,5,7-tetraazabenzo[cd]azulene-5-carboxylate To a solution of tert-butyl 2-(6-(bicyclo[1.1.1]pentan-1-yl)pyridin-3-yl)-8-oxo-2,3,4,5a,6,7,8,9-octahydro-5H-1,2,5,7-tetraazabenzo[cd]azulene-5-carboxylate (60 mg, 1 equiv., 0.14 mmol) in THF (0.5 mL) were added $BH_3$·THF (36 mg, 0.41 mL, 1 M, 3 equiv., 0.41 mmol). The mixture was stirred at 60° C. for 16 h. The mixture was filtered with MeOH (0.5 mL) and rinsed with EtOAc (2×2 mL), the filtrate was concentrated under vacuum to give a residue. This resulted in tert-butyl 2-(6-(bicyclo[1.1.1]pentan-1-yl)pyridin-3-yl)-2,3,4,5a,6,7,8,9-octahydro-5H-1,2,5,7-tetraazabenzo[cd]azulene-5-carboxylate (60 mg) as a crude white solid. The crude product was used in the next step directly without further purification. LCMS: (ESI, m/z): 422 $[M+H]^+$.

Step 11: Synthesis of Tert-Butyl 7-acryloyl-2-(6-(bicyclo[1.1.1]pentan-1-yl)pyridin-3-yl)-2,3,4,5a,6,7,8,9-octahydro-5H-1,2,5,7-tetraazabenzo[cd]azulene-5-carboxylate To a stirred solution of tert-butyl 2-(6-(bicyclo[1.1.1]pentan-1-yl)pyridin-3-yl)-2,3,4,5a,6,7,8,9-octahydro-5H-1,2,5,7-tetraazabenzo[cd]azulene-5-carboxylate (55 mg, 1 equiv., 0.13 mmol) in DCM (0.5 mL) was added acryloyl chloride (18 mg, 16 μL, 1.5 equiv., 0.2 mmol) and TEA (40 mg, 55 μL, 3 equiv., 0.39 mmol) at room temperature and stirred for 1 h. The reaction was quenched by the addition of water (2 mL) at rt. The resulting mixture was extracted with DCM (2×2 mL). The combined organic layers were washed with brine (2×2 mL) and dried over anhydrous $Na_2SO_4$. After filtration, the filtrate was concentrated under reduced pressure. The residue was purified by silica gel column chromatography, eluting with EtOAc/PE (1:1) to afford tert-butyl 7-acryloyl-2-(6-(bicyclo[1.1.1]pentan-1-yl)pyridin-3-yl)-2,3,4,5a,6,7,8,9-octahydro-5H-1,2,5,7-tetraazabenzo[cd]azulene-5-carboxylate (20 mg) as a light yellow oil. LCMS: (ESI, m/z): 475 $[M+H]^+$.

Step 12: Synthesis of 1-(2-(6-(bicyclo[1.1.1]pentan-1-yl)pyridin-3-yl)-2,3,4,5,5a,6,8,9-octahydro-7H-1,2,5,7-tetraazabenzo[cd]azulen-7-yl)prop-2-en-1-one The solution of tert-butyl 7-acryloyl-2-(6-(bicyclo[1.1.1]pentan-1-yl)pyridin-3-yl)-2,3,4,5a,6,7,8,9-octahydro-5H-1,2,5,7-tetraazabenzo[cd]azulene-5-carboxylate (15 mg, 1 equiv., 32 μmol) in DCM (0.5 mL) and TFA (0.1 mL) was stirred at room temperature for 1 h. The solvent was removed under reduced pressure. This resulted in 1-(2-(6-(bicyclo[1.1.1]pentan-1-yl)pyridin-3-yl)-2,3,4,5,5a,6,8,9-octahydro-7H-1,2,5,7-tetraazabenzo[cd]azulen-7-yl)prop-2-en-1-one (15 mg) as a crude light yellow oil. The crude material was used in the next step directly without further purification. LCMS: (ESI, m/z): 375 $[M+H]^+$.

Step 13: 1-(2-(6-(bicyclo[1.1.1]pentan-1-yl)pyridin-3-yl)-5-(7-bromo-1H-benzo[d]imidazole-4-carbonyl)-2,3,4,5,5a,6,8,9-octahydro-7H-1,2,5,7-tetraazabenzo[cd]azulen-7-yl)prop-2-en-1-one To a stirred solution of 1-(2-(6-(bicyclo[1.1.1]pentan-1-yl)pyridin-3-yl)-2,3,4,5,5a,6,8,9-octahydro-7H-1,2,5,7-tetraazabenzo[cd]azulen-7-yl)prop-2-en-1-one (20 mg, 1 equiv., 53 μmol) in DMF (0.5 mL) was added HBTU (30 mg, 1.5 equiv., 80 μmol), DIEA (21 mg, 28 μL, 3 equiv., 0.16 mmol) and 7-bromo-1H-benzo[d]imidazole-4-carboxylic acid (13 g, 1 equiv., 53 μmol) at room temperature and stirred for 2 h. The reaction was quenched by the addition of water (2 mL) at rt. The resulting mixture was extracted with EtOAc (2×2 mL). The combined organic layers were washed with brine (2×2 mL), dried over anhydrous $Na_2SO_4$. The residue was purified by reverse-phase flash chromatography with the conditions (Column: XBridge BEH C18 OBD Prep Column 130, 5 m, 30 mm*150 mm; Mobile Phase A: water (10 mmol/L $NH_4HCO_3$), Mobile Phase B: MeCN; Flow rate: 60 mL/min; Gradient: 26% B to 46% B in 8 min; Wave Length: UV 254 nm/221 nm; retention time 1: 7.65) to afford 1-(2-(6-(bicyclo[1.1.1]pentan-1-yl)pyridin-3-yl)-5-(7-bromo-1H-benzo[d]imidazole-4-carbonyl)-2,3,4,5,5a,6,8,9-octahydro-7H-1,2,5,7-tetraazabenzo[cd]azulen-7-yl)prop-2-en-1-one (1 mg, 2 μmol, 3% yield) as a white solid. LCMS: (ESI, m/z): 598 $[M+H]^+$. $^1H$ NMR: (400 MHz, Chloroform-d, ppm) δ 8.71-8.47 (m, 1H), 8.32-7.96 (m, 1H), 7.92-7.69 (m, 1H), 7.67-7.43 (m, 2H), 6.87-6.32 (m, 1H), 5.96-5.67 (m, 1H), 5.64-5.28 (m, 1H), 5.09-4.84 (m, 1H), 4.75-3.51 (m, 2H), 3.44-2.93 (m, 5H), 2.87-2.45 (m, 3H), 2.36-2.04 (m, 6H).

TABLE D1

The compound of Example D-2, (S or R)-1-(2-(4-(bicyclo[1.1.1]pentan-1-yl)-2-fluorophenyl)-5-(7-bromo-1H-benzo[d]imidazole-4-carbonyl)-2,3,4,5,5a,6,8,9-octahydro-7H-1,2,5,7-tetraazabenzo[cd]azulen-7-yl)prop-2-en-1-one, was prepared in an analogous manner to Example D-1, starting from (4-bromo-2-fluorophenyl)hydrazine in place of 2-bromo-5-hydrazineylpyridine, with the following exception to step 7. For Example D-2 step 7, a solution of nickel chloride, dimethoxyethane adduct (42 mg, 0.05 equiv., 0.19 mmol) and 4,4'-di-tert-butyl-2,2'-bipyridine (52 mg, 0.05 equiv., 0.19 mmol) in DMF (18 mL) were stirred at 100° C. for 5 min until a clear green solution was obtained. The reaction was cooled to room temperature to provide the catalyst solution. This solution was aliquoted into 18 × 8 mL sample bottles, followed by the addition of a solution of tert-butyl 1-(4-bromo-2-fluorophenyl)-3-(2-methoxy-2-oxoethyl)-1,4,6,7-tetrahydro-5H-pyrazolo[4,3-c]pyridine-5-carboxylate (1.8 g, 1 equiv., 3.8 mmol), (4,4'-di-t-butyl-2,2'-bipyridine)bis[3,5-difluoro-2-(5-trifluoromethyl-2-pyridinyl-kN)phenyl-kC]iridium(III) hexafluorophosphate (0.22 g, 0.05 equiv., 0.19 mmol), morpholine (0.50 g, 1.5 equiv., 5.8 mmol), 2-(bicyclo[1.1.1]pentan-1-yl)-4,4,5,5-tetramethyl-1,3,2-dioxaborolane (0.90 g, 1.2 equiv., 4.6 mmol) in DMF (18 mL, 1 ml to each bottle). The reactions were purged with nitrogen replacement three times. The resulting mixture was irradiated with blue LED for 3 h. The reactions were combined and quenched with water (20 mL). The aqueous layer was extracted with EtOAc (3 × 20 mL). The combined organic layers were washed with half saturated brine (3 × 30 mL) and then saturated brine (30 mL), dried over anhydrous $Na_2SO_4$ and concentrated to give a residue. The crude product was purified by silica gel chromatography eluting with PE:EtOAc = 8:1 to give tert-butyl 1-(4-(bicyclo[1.1.1]pentan-1-yl)-2-fluorophenyl)-3-(2-methoxy-2-oxoethyl)-1,4,6,7-tetrahydro-5H-pyrazolo[4,3-c]pyridine-5-carboxylate (660 mg) as a white solid. LCMS: (ESI, m/z): 456 $[M + H]^+$. Upon obtaining racemic (S or R)-1-(2-(4-(bicyclo[1.1.1]pentan-1-yl)-2-fluorophenyl)-5-(7-bromo-1H-benzo[d]imidazole-4-carbonyl)-2,3,4,5,5a,6,8,9-octahydro-7H-1,2,5,7-tetraazabenzo[cd]azulen-7-yl)prop-2-en-1-one, the compound was separated into its enantiomers by Prep chiral-HPLC with the following conditions: Column: CHIRAL ART Cellulose-SB 2 * 25 cm, 5 μm; Mobile Phase A: HEX (0.1% FA), Mobile Phase B: EtOH:DCM = 1:1; Flow rate: 20 mL/min; Gradient: isocratic 30% A; Wave Length: UV 254/220 nm; Sample Solvent: EtOH; Injection Volume: 1.0 mL; Number Of Runs: 2 to afford (S or R)-1-(2-(4-(bicyclo[1.1.1]pentan-1-yl)-2-fluorophenyl)-5-(7-bromo-1H-benzo[d]imidazole-4-carbonyl)-2,3,4,5,5a,6,8,9-octahydro-7H-1,2,5,7-tetraazabenzo[cd]azulen-7-yl)prop-2-en-1-one as the second-eluting peak (retention time 10.5 min).

| Example No. | Structure and Name | LCMS (ESI, m/z) | NMR |
|---|---|---|---|
| D-2 | 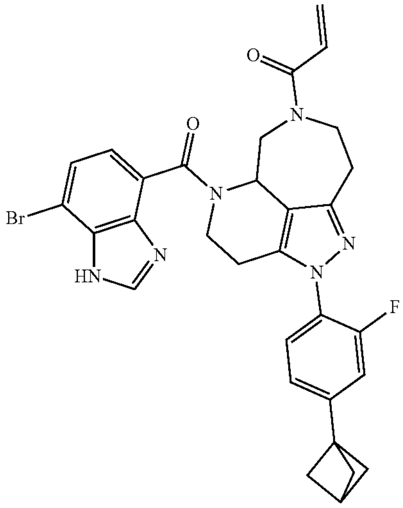 [SMILES: C=CC(=O)N1CCc2nn(-c3ccc(C45CC(C4)C5)cc3F)c3c2C(C1)N(C(=O)c1ccc(Br)c2[nH]cnc12)CC3] (S or R)-1-(2-(4-(bicyclo[1.1.1]pentan-1-yl)-2-fluorophenyl)-5-(7-bromo-1H-benzo[d]imidazole-4-carbonyl)-2,3,4,5,5a,6,8,9-octahydro-7H-1,2,5,7-tetraazabenzo[cd]azulen-7-yl)prop-2-en-1-one | 615, 617 ($^{81}Br$) $[M + H]^+$ | $^1H$ NMR (400 MHz, Chloroform-d, ppm) δ 10.34-9.53 (m, 1H), 7.78-7.61 (m, 1H), 7.59-7.36 (m, 2H), 7.17-6.87 (m, 3H), 6.84-6.28 (m, 1H), 5.91-5.56 (m, 1H), 5.53-5.31 (m, 1H), 4.95-4.71 (m, 1H), 4.41-3.80 (m, 1H), 3.61-2.70 (m, 7H), 2.57 (d, J = 5.1 Hz, 1H), 2.55-2.31 (m, 1H), 2.19-1.99 (m, 6H). (some protons obscured by solvent) |

TABLE D2

The compound of Example D-3 was prepared in an analogous fashion to Example D-2, starting from 4-bromo-3-fluoroaniline. The racemic compound of the example was separated under the following conditions: Column-CHIRAL ART Cellulose-SB, 3 * 25 cm, 5 μm; Mobile Phase A: Hex(0.1% FA)--HPLC, Mobile Phase B: EtOH:DCM = 1:1; Flow rate: 40 mL/min; Gradient: isocratic 20; Wave Length: UV 254/220 nm; RT1(min): 16.2; RT2(min): 19 to provide the compound of the example as the second-eluting peak. The compound of Example D-4 was prepared in an analogous fashion to Example D-3, using the corresponding carboxylic acid. The racemic compound of the example was separated by the following conditions: Column-CHIRAL ART Cellulose-SB 3 * 25 cm, 5 μm; Mobile Phase A: HEX(0.1% FA), Mobile Phase B: EtOH: DCM = 1:1; Flow rate: 40 mL/min; Gradient: isocratic 25; Wave Length: UV 254/220 nm; RT1(min): 6.5; RT2(min): 13 to afford the compound of the example as the first-eluting peak.

| Example No. | Structure and Name | LCMS (ESI, m/z) | NMR |
|---|---|---|---|
| D-3 | 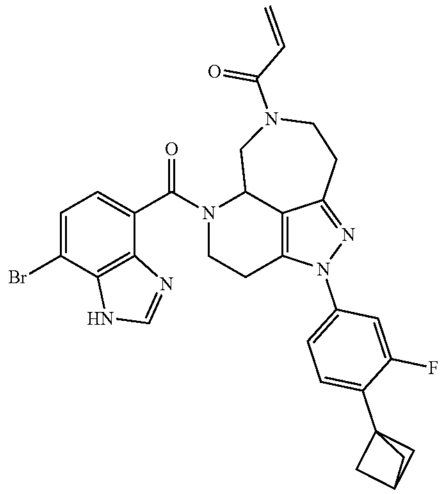 [SMILES: C=CC(=O)N1CCc2nn(-c3ccc(C45CC(C4)C5)c(F)c3)c3c2C(C1)N(C(=O)c1ccc(Br)c2[nH]cnc12)CC3] (R or S)-1-(2-(4-(bicyclo[1.1.1]pentan-1-yl)-3-fluorophenyl)-5-(7-bromo-1H-benzo[d]imidazole-4-carbonyl)-2,3,4,5,5a,6,8,9-octahydro-7H-1,2,5,7-tetraazabenzo[cd]azulen-7-yl)prop-2-en-1-one | 615 $[M + H]^+$ | $^1H$ NMR (400 MHz, Chloroform-d) δ 8.30-8.11 (m, 1H), 7.58-7.37 (m, 2H), 7.19-7.04 (m, 3H), 6.75-6.32 (m, 1H), 5.87-5.72 (m, 1H), 5.56-5.17 (m, 1H), 5.08-4.76 (m, 1H), 4.63-4.04 (m, 1H), 3.37-2.85 (m, 5H), 2.85-2.49 (m, 3H), 2.27-2.07 (m, 6H), 1.37-1.09 (m, 1H). |
| D-4 | 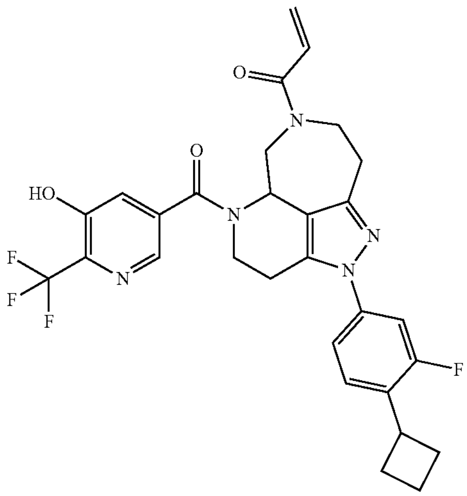 [SMILES: C=CC(=O)N1CCc2nn(-c3ccc(C4CCC4)c(F)c3)c3c2C(C1)N(C(=O)c1cnc(C(F)(F)F)c(O)c1)CC3] (R or S)-1-(2-(4-cyclobutyl-3-fluorophenyl)-5-(5-hydroxy-6-(trifluoromethyl)nicotinoyl)-2,3,4,5,5a,6,8,9-octahydro-7H-1,2,5,7-tetraazabenzo[cd]azulen-7-yl)prop-2-en-1-one | 570 $[M + H]^+$ | $^1H$ NMR (400 MHz, CDCl3) δ 8.77-8.16 (m, 2H), 7.35-6.96 (m, 1H), 6.82-6.60 (m, 1H), 6.60-6.37 (m, 1H), 6.03-5.66 (m, 1H), 5.34-4.78 (m, 2H), 4.74-4.21 (m, 2H), 3.94-3.54 (m, 2H), 3.23-2.45 (m, 6H), 2.44-1.37 (m, 9H). |

Example E-1: Preparation of 1-((5aR,9S)-5-(7-bromo-1H-benzo[d]imidazole-4-carbonyl)-2-(2-hydroxy-4-isopropylphenyl)-9-methyl-2,3,4,5,5a,6,8,9-octahydro-7H-1,2,5,7-tetraazabenzo[cd]azulen-7-yl)prop-2-en-1-one
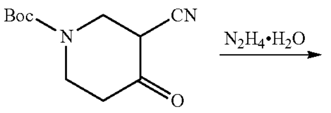
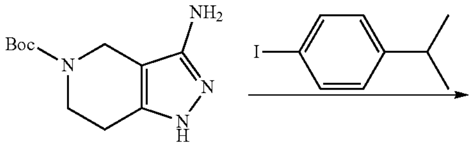
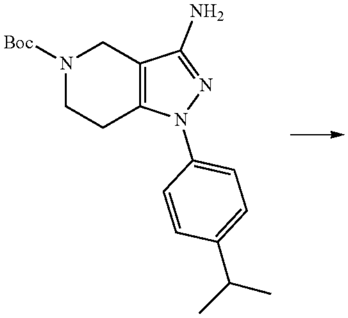
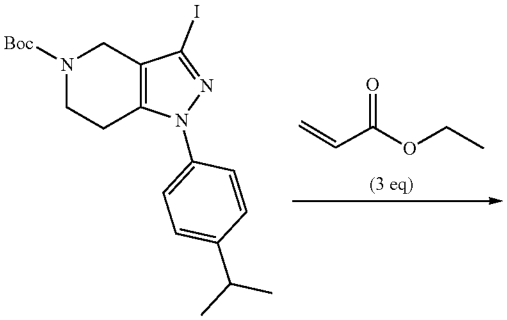
Int. JJ
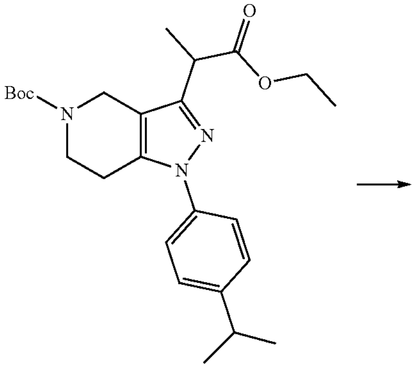
-continued
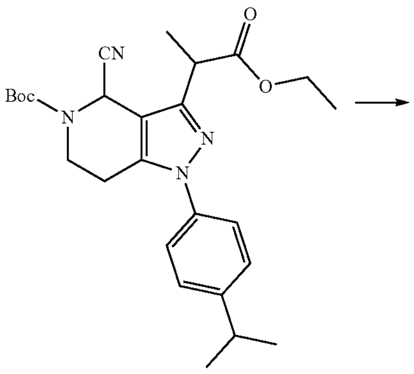
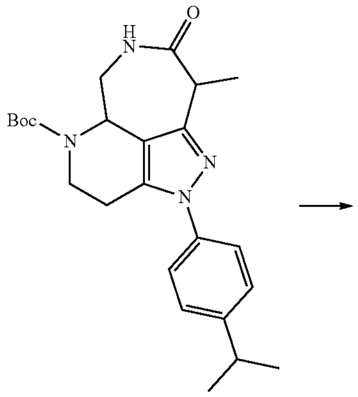
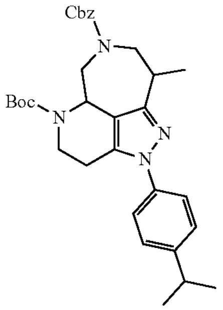
and
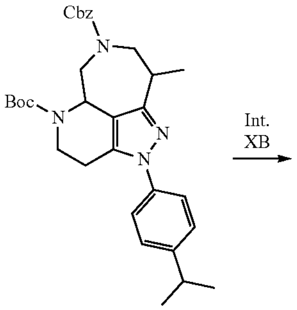
Int. XA
single diastereomer
cis or trans
Int. XB
single diastereomer
cis or trans
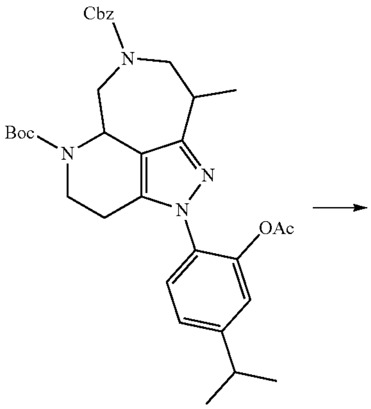
cis or trans -continued

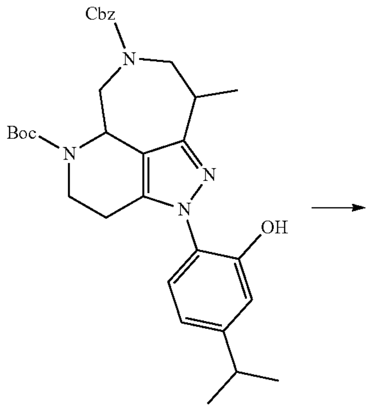

cis or trans

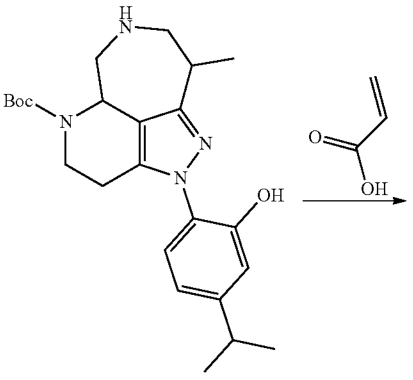

cis or trans

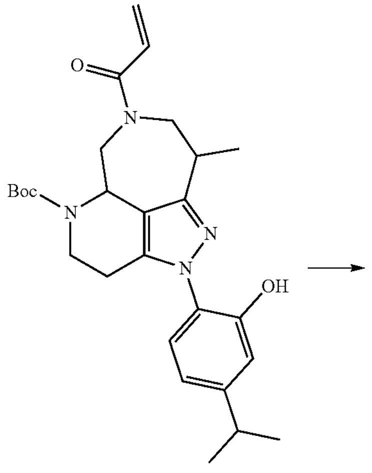

cis or trans

-continued

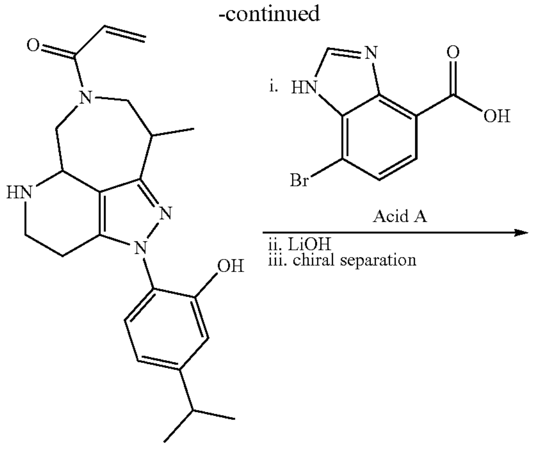

cis or trans

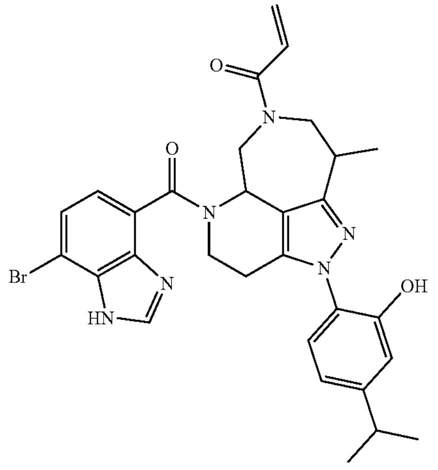

single enantiomer

Step 1: Synthesis of Tert-Butyl 3-amino-1,4,6,7-tetrahydro-5H-pyrazolo[4,3-c]pyridine-5-carboxylate To a solution of tert-butyl 3-cyano-4-oxopiperidine-1-carboxylate (200 g, 892 mmol, 1.00 eq) in EtOH (2000 mL) was added $N_2H_4 \cdot H_2O$ (113 g, 1.91 mol, 109 m, 85% purity, 2.14 eq) at room temperature. The mixture was stirred at 80° C. for 2 h. The mixture as allowed to cool down to rt and then concentrated under reduced pressure.

The crude product was triturated with PE (1.0 L) at room temperature for 0.5 h, then filtered and the cake was washed with PE (200 mL×3), the cake was collected and dried to yield tert-butyl 3-amino-1,4,6,7-tetrahydro-5H-pyrazolo[4,3-c]pyridine-5-carboxylate (200 g) was obtained as a white solid. LCMS:(ESI, m/z):=239 $[M+H])^+$.

Step 2: Synthesis of Tert-Butyl 3-amino-1-(4-isopropylphenyl)-1,4,6,7-tetrahydro-5H-pyrazolo[4,3-c]pyridine-5-carboxylate To a stirred solution of tert-butyl 3-amino-1,4,6,7-tetrahydro-5H-pyrazolo[4,3-c]pyridine-5-carboxylate (120 g, 504 mmol, 1.00 eq) and 1-iodo-4-isopropylbenzene (173 g, 705 mmol, 1.40 eq) in DMF (1.0 L) was added $Cs_2CO_3$ (196 g, 604 mmol, 1.20 eq) and $CUBr_2$ (11.3 g, 50.6 mmol, 2.37 mL, 0.10 eq) under nitrogen atmosphere at room temperature. Then the resulting mixture was stirred for additional 12 h at 120° C. The reaction was quenched with water (1.0 L) and extracted with EtOAc (2×1.0 L), and the combined organic layers were washed with water (500 mL), which was followed by brine (500 mL). The organic layer was dried over $Na_2SO_4$, filtered, and concentrated under reduced pressure to give a residue. The crude product was purified by silica gel chromatography (PE:EtOAc=10:1 to PE:EtOAc=2:1) to yield tert-butyl 3-amino-1-(4-isopropylphenyl)-1,4,6,7-tetrahydro-5H-pyrazolo[4,3-c]pyridine-5-carboxylate as a yellow solid (67.5 g). LCMS:(ESI, m/z): =357 [M+H]$^+$. $^1$H NMR: 400 MHz, DMSO $d_6$. δ 7.35 (d, J=8.4 Hz, 2H), 7.26 (d, J=8.4 Hz, 2H), 4.96 (brs, 2H), 4.22 (s, 2H), 3.63-3.48 (m, 2H), 2.93 -2.84 (m, 1H), 2.80-2.70 (m, 2H), 1.45 (s, 9H), 1.21 (d, J=6.8 Hz, 6H).

Step 3: Synthesis of Tert-Butyl 3-iodo-1-(4-isopropylphenyl)-4H,6H,7H-pyrazolo[4,3-c]pyridine-5-carboxylate (Int. JJ)

A solution of tert-butyl-3-amino-1-(4-isopropylphenyl)-4H,6H,7H-pyrazolo[4,3-c]pyridine-5-carboxylate (1 g, 2.8 mmol, 1 equiv) in $CH_3CN$ (30 mL) was stirred at rt for 10 min followed by the addition of CuI (801 mg, 4.2 mmol, 1.5 equiv). The mixture was heated to 50° C. and t-$BuNO_2$ (0.5 mL, 4.2 mmol, 1.5 equiv) was added dropwise and The resulting mixture was stirred at 50° C. for 30 min. The mixture was allowed to cool down to rt and quenched with water. The resulting mixture was extracted with EtOAc (15 mL×3). The combined organic layers were washed with sat. aqueous NaCl (20 mL), dried over anhydrous $Na_2SO_4$. After filtration, the filtrate was concentrated under reduced pressure. The residue was purified by silica gel column chromatography, eluting with EtOAc/PE (10%) to afford tert-butyl 3-iodo-1-(4-isopropylphenyl)-4H,6H,7H-pyrazolo[4,3-c]pyridine-5-carboxylate (400 mg) as a light yellow solid. LCMS:(ESI, m/z): 468 [M+H]$^+$.

Step 4: Synthesis of Tert-Butyl 3-(1-ethoxy-1-oxopropan-2-yl)-1-(4-isopropylphenyl)-1,4,6,7-tetrahydro-5H-pyrazolo[4,3-c]pyridine-5-carboxylate To a stirred solution of tert-butyl 3-iodo-1-(4-isopropylphenyl)-1,4,6,7-tetrahydro-5H-pyrazolo[4,3-c]pyridine-5-carboxylate (100 g, 1 equiv., 214 mmol) in dioxane (2 L) was added potassium phosphate, tribasic (90.8 g, 35.4 mL, 2 equiv., 428 mmol, tetramethylammonium formate (38.2 g, 37.5 mL, 1.5 equiv., 321 mmol), tris(4-fluorophenyl)phosphane (13.5 g, 0.2 equiv., 42.8 mmol), ethyl acrylate (64.3 g, 3 equiv., 642 mmol) and bis(dibenzylideneacetone)dipalladium (4.83 g, 0.025 equiv., 5.35 mmol). The resulting reaction mixture was stirred at 90° C. for 12 h. The reaction was quenched by the addition of water (2000 mL) at rt. The resulting mixture was extracted with EtOAc (2×1000 mL). The combined organic layers were washed with brine (3×500 mL) and dried over anhydrous $Na_2SO_4$. After filtration, the filtrate was concentrated under reduced pressure. The residue was purified by silica gel column chromatography, eluting with EtOAc/PE (1:4) to afford tert-butyl 3-(1-ethoxy-1-oxopropan-2-yl)-1-(4-isopropylphenyl)-1,4,6,7-tetrahydro-5H-pyrazolo[4,3-c]pyridine-5-carboxylate (74 g) as a yellow solid. LCMS: (ESI, m/z):442 [M+H]$^+$.

Step 5: Synthesis of Tert-Butyl 4-cyano-3-(1-ethoxy-1-oxopropan-2-yl)-1-(4-isopropylphenyl)-1,4,6,7-tetrahydro-5H-pyrazolo[4,3-c]pyridine-5-carboxylate To a stirred solution of tert-butyl 3-(1-ethoxy-1-oxopropan-2-yl)-1-(4-isopropylphenyl)-1,4,6,7-tetrahydro-5H-pyrazolo[4,3-c]pyridine-5-carboxylate (74 g, 1 equiv., 0.17 mol) in MeCN (1.5 L) was added AcOH (30 g, 29 mL, 3 equiv., 0.5 mol), TMSCN (67 g, 4 equiv., 0.67 mol) and $TEMPO^+BF_4$ (78 g, 3 equiv., 0.51 mol). And the resulting reaction mixture was stirred at room temperature for 1 h. The reaction was quenched by the addition of water (2 L) at rt. The resulting mixture was extracted with EtOAc (2×1 L). The combined organic layers were washed with brine (3×1 L) and dried over anhydrous $Na_2SO_4$. After filtration, the filtrate was concentrated under reduced pressure. The residue was purified by silica gel column chromatography, eluting with EtOAc/PE (1:4) to afford tert-butyl 4-cyano-3-(1-ethoxy-1-oxopropan-2-yl)-1-(4 -isopropylphenyl)-1,4,6,7-tetrahydro-5H-pyrazolo[4,3-c]pyridine-5-carboxylate (70 g) as a yellow solid. LCMS: (ESI, m/z): 467 [M+H]$^+$.

Step 6: Synthesis of Tert-Butyl 2-(4-isopropylphenyl)-9-methyl-8-oxo-2,3,4,5a,6,7,8,9-octahydro-5H-1,2,5,7-tetraazabenzo[cd]azulene-5-carboxylate To a solution of tert-butyl 4-cyano-3-(1-ethoxy 1-oxopropan-2-yl)-1-(4-isopropylphenyl)-1,4,6,7-tetrahydro-5H-pyrazolo[4,3-c]pyridine-5-carboxylate (23.3 g, 1 equiv., 49.9 mmol) in $NH_3$ in MeOH (7M, 466 mL) was added Rainey nickel (23.3 g, 7.95 equiv., 397 mmol) in a pressure tank. The mixture was purged with nitrogen for three times and then was pressurized to 4 MPa with hydrogen at 60° C. for 12 h. The reaction mixture was cooled to rt and use a magnet to pull the Rainey nickel out. The reaction solution was concentrated under reduced pressure. The reaction was repeated three times. The crude product (tert-butyl 2-(4-isopropylphenyl)-9-methyl-8-oxo-2,3,4,5a,6,7,8,9-octahydro-5H-1,2,5,7-tetraazabenzo[cd]azulene-5-carboxylate (58.8 g) was used in the next step directly without further purification. LCMS: (ESI, m/z):425 [M+H]$^+$.

Step 7: Synthesis of Tert-Butyl 2-(4-isopropylphenyl)-9-methyl-2,3,4,5a,6,7,8,9-octahydro-5H-1,2,5,7-tetraazabenzo[cd]azulene-5-carboxylate To a stirred solution of tert-butyl 2-(4-isopropylphenyl)-9-methyl-8-oxo-2,3,4,5a,6,7,8,9-octahydro-5H-1,2,5,7-tetraazabenzo[cd]azulene-5-carboxylate (58.8 g, 1 equiv., 138 mmol) THF (588 mL) was added $BH_3$ in THF (1M, 588 mL) and the resulting reaction mixture was stirred at 60° C. for 12 h. After completion of reaction, the reaction mixture was concentrated under reduced pressure. The crude product (tert-butyl 2-(4-isopropylphenyl)-9-methyl-2,3,4,5a,6,7,8,9-octahydro-5H-1,2,5,7-tetraazabenzo[cd]azulene-5-carboxylate (52 g) was used in the next step directly without further purification. LCMS: (ESI, m/z): 411 [M+H]$^+$.

Step 8: Synthesis of 7-benzyl 5-(tert-butyl) (cis or trans)-2-(4-isopropylphenyl)-9-methyl-3,4,5a,6,8,9-hexahydro-2H-1,2,5,7-tetraazabenzo[cd]azulene-5,7-dicarboxylate To a stirred solution of tert-butyl 2-(4-isopropylphenyl)-9-methyl-2,3,4,5a,6,7,8,9-octahydro-5H-1,2,5,7-tetraazabenzo[cd]azulene-5-carboxylate (48 g, 1 equiv., 0.12 mol) in DCM (960 mL) was added TEA (59 g, 81 mL, 5 equiv., 0.58 mol) and Cbz-OSu (87 g, 3 equiv., 0.35 mol). The resulting reaction mixture was stirred at 40° C. for 12 h. The r action was quenched by the addition of water (500 mL) at rt. The resulting mixture was extracted with EtOAc (2×1000 mL). The combined organic layers were washed with brine (3×500 mL) and dried over anhydrous $Na_2SO_4$. After filtration, the filtrate was concentrated under reduced pressure. The residue was purified by silica gel column chromatography, eluting with EtOAc/PE (1:3) to afford 7-benzyl 5-(tert-butyl) (cis or trans)-2-(4-isopropylphenyl)-9-methyl-3,4,5a,6,8,9-hexahydro-2H-1,2,5,7-tetraazabenzo[cd]azulene-5,7-dicarboxylate (Int. XA) (8 g) as a yellow oil and 7-benzyl 5-(tert-butyl) (cis or trans)-2-(4-isopropylphenyl)-9-methyl-3,4,5a,6,8,9-hexahydro-2H-1,2,5,7-tetraazabenzo[cd]azulene-5,7-dicarboxylate (Int. XB) (22 g) as a yellow oil. LCMS XA: (ESI, m/z):545 $[M+H]^+$; LCMS XB: (ESI, m/z):545 $[M+H]^+$.

Step 9: Synthesis of 7-benzyl 5-(tert-butyl) (cis or trans)-2-(2-acetoxy-4-isopropylphenyl)-9-methyl-3,4,5a,6,8,9-hexahydro-2H-1,2,5,7-tetraazabenzo[cd]azulene-5,7-dicarboxylate To a stirred solution of 7-benzyl 5-(tert-butyl) (cis or trans)-2-(4-isopropylphenyl)-9-methyl-3,4,5a,6,8,9-hexahydro-2H-1,2,5,7-tetraazabenzo[cd]azulene-5,7 dicarboxylate (Int. XB) (9 g, 1 equiv., 0.02 mol) in AcOH (180 mL) and MeCN (18 mL) was added PIDA (6 g, 1.2 equiv., 0.024 mol) and $Pd(OAc)_2$ (0.4 g, 0.1 equiv., 0.002 mol). The resulting mixture was stirred at 90° C. for 3 h. The reaction was quenched by the addition of water (200 mL) at rt. The resulting mixture was extracted with EtOAc (2×200 mL). The combined organic layers ere washed with brine (2×200 mL) and dried over anhydrous $Na_2SO_4$. After filtration, the filtrate was concentrated under reduced pressure. The residue was purified by silica gel column chromatography, eluting with EtOAc/PE (1:2) to afford 7-benzyl 5-(tert-butyl) (cis or trans)-2-(2-acetoxy-4-isopropylphenyl)-9-methyl-3,4,5a,6,8,9-hexahydro-2H-1,2,5,7-tetraazabenzo[cd]azulene-5,7-dicarboxylate (3.2 g) as a yellow oil. LCMS: (ESI, m/z): 603 $[M+H]^+$.

Step 9: Synthesis of 7-benzyl 5-(tert-butyl) (cis or trans)-2-(2-hydroxy-4-isopropylphenyl)-9-methyl-3,4,5a,6,8,9-hexahydro-2H-1,2,5,7-tetraazabenzo[cd]azulene-5,7-dicarboxylate To a stirred solution of 7-benzyl 5-(tert-butyl) (cis oi trans)-2-(2-acetoxy-4-isopropylphenyl)-9-methyl-3,4,5a,6,8,9-hexahydro-2H-1,2,5,7-tetraazabenzo[cd]azulene-5,7-dicarboxylate (3.2 g, 1 equiv., 5.3 mmol) in THF (48 mL) and water (16 mL) was added LiOH (0.38 g, 3 equiv., 16 mmol). The reaction mixture was stirred at room temperature for 3 h. The reaction was quenched by the addition of water (200 mL) at rt. The resulting mixture was extracted with EtOAc (2×200 mL). The combined organic layers were washed with brine (2×200 mL) and dried over anhydrous $Na_2SO_4$. After filtration, the filtrate was concentrate under reduced pressure. The residue was purified by silica gel column chromatography, eluting with EtOAc/PE (1:2) to afford 7-benzyl 5-(tert-butyl) (cis or trans)-2-(2-hydroxy-4-isopropylphenyl)-9-methyl- 3,4,5a,6,8,9-hexahydro-2H-1,2,5,7-tetraazabenzo[cd]azulene-5,7-dicarboxylate (2.5 g) as a white solid. LCMS: (ESI, m/z): 561 $[M+H]^+$.

Step 10: Synthesis of Tert-Butyl (cis or trans)-2-(2-hydroxy-4-isopropylphenyl)-9-methyl-2,3,4,5a,6,7,8,9-octahydro-5H-1,2,5,7-tetraazabenzo[cd]azulene-5-carboxylate To a solution of 7-benzyl 5-(tert-butyl) (cis or trans)-2-(2-hydroxy-4-isopropylphenyl)-9-methyl-3,4,5a,6,8,9-hexahydro-2H-1,2,5,7-tetraazabenzo[cd]azulene-5,7-dicarboxylate (3.1 g, 1 equiv., 5.5 mmol) in $NH_3$ in MeOH (7M, 62 mL) was added $Pd(OH)_2$/(0.47 g, 0.61 equiv., 3.3 mmol) and Pd/C (0.94 g, 1.6 equiv., 8.8 mmol) in a pressure tank. The mixture was purged with nitrogen for three times and then was pressurized to 4 MPa with hydrogen at room temperature for 3 h. The reaction mixture was filtered to remove insoluble solids. The fil er cake was washed with MeOH (200 mL) two times. The filtrate was concentrated under reduced pressure. The crude product tert-butyl (cis or trans)-2-(2-hydroxy-4-isopropylphenyl)-9-methyl-2,3,4,5a,6,7,8,9-octahydro-5H-1,2,5,7-tetraazabenzo[cd]azulene-5-carboxylate (2.1 g) was used in the next step directly without further purification. LCMS: (ESI, m/z): 427 $[M+H]^+$.

Step 11: Synthesis of Tert-Butyl (cis or trans)-7-acryloyl-2-(2-hydroxy-4-isopropylphenyl)-9-methyl-2,3,4,5a,6,7,8,9-octahydro-5H-1,2,5,7-tetraazabenzo[cd]azulene 5-carboxylate To a stirred solution of tert-butyl (cis or trans)-2-(2-hydroxy-4-isopropylphenyl)-9-methyl-2,3,4,5a,6,7,8,9-octahydro-5H-1,2,5,7-tetraazabenzo[cd]azulene 5-carboxylate (2 g, 1 equiv., 5 mmol) in DMF (40 mL) was added T3P (4 g, 2 equiv., 0.01 mol), acrylic acid (0.5 g, 1.5 equiv., 7 mmol) and DIEA (4 g, 5 mL, 6 equiv., 0.03 mol). The reaction mixture was stirred at room temperature for 2 h. The reaction was quenched by the addition of water (200 mL) at rt. The resulting mixture was extracted with EtOAc (2×200 mL). The combined organic layers were washed with brine (2×200 mL) and dried over anhydrous $Na_2SO_4$. After filtration, the filtrate was concentrated under reduced pressure. The residue was purified by silica gel column chromatography, eluting with EtOAc/PE (1:3) to afford tert-butyl (cis or trans)-7-acryloyl-2-(2-hydroxy-4-isopropylphenyl)-9-methyl-2,3,4,5a,6,7,8,9-octahydro-5H-1,2,5,7-tetraazabenzo[cd]azulene-5-carboxylate (950 mg) as a yellow solid. CMS: (ESI, m/z): 481 $[M+H]^+$.

Step 12: Synthesis of 1-((cis or trans)-2-(2-hydroxy-4-isopropylphenyl)-9-methyl-2,3,4,5,5a,6,8,9-octahydro-7H-1,2,5,7-tetraazabenzo[cd]azulen-7-yl) prop-2-en-1-one The solution of tert-butyl (cis or trans)-7-acryloyl-2-(2-hydroxy-4-isopropylphenyl)-9-methyl-2,3,4,5a,6,7,8,9-octahydro-5H-1,2,5,7-tetraazabenzo[cd]azulene 5-carboxylate (950 mg, 1 equiv., 2.0 mmol) in TFA (4.75 mL) and DCM (14 mL) was stirred at room temperature for 1 h. The solvent was removed under reduced pressure. This resulted in 1-((5aR,9S)-2-(2-hydroxy-4-isopropylphenyl)-9-methyl-2,3,4,5,5a,6,8,9-octahydro-7H-1,2,5,7-tetraazabenzo[cd]azulen-7-yl)prop-2-en-1-one (1.3 g) as a crude yellow solid. The crude product as used in the next step directly without further purification. LCMS: (ESI, m/z): 381 $[M+H]^+$.

Step 13: Synthesis of 1-((5a(R or S),9(S or R))-5-(7-bromo-1H-benzo[d]imidazole-4-carbonyl)-2-(2-hydroxy-4-isopropylphenyl)-9-methyl-2,3,4,5,5a,6,8,9-octahydro-7H-1,2,5,7-tetraazabenzo[cd]azulen-7-yl)prop-2-en-1-one To a stirred solution of 1-((cis or trans)-2-(2-hydroxy-4-isopropylphenyl)-9-methyl-2,3,4,5,5a,6,8,9-octahydro-7H-1,2,5,7-tetraazabenzo[cd]azulen-7-yl)prop-2-en-1-one (1.2 g, 1 equiv., 3.2 mmol) in DMF (24 mL) was added HBTU (3.6 g, 3 equiv., 0.5 mmol), 7-bromo-1H-benzo[d]imidazole-4-carboxylic acid (1.5 g, 2 equiv., 6.3 mmol) and DIEA(2.4 g, 3.3 mL, 6 equiv., 19 mmol). The resulting reaction mixture was stirred at room temperature for 2 h. The reaction was quenched by the addition of water (20 mL) at rt. The resulting mixture was extracted with EtOAc (2×20 mL). The combined organic layers were washed with brine (2×20 mL) and dried over anhydrous $Na_2SO_4$. After filtration, the filtrate was concentrated under reduced pressure. The residue was then dissolved in THF (18 mL) and water (6 mL), followed by the addition of LiOH (0.23 g, 3 equiv., 9.5 mmol). The reaction mixture was stirred at room temperature for 1 h. The residue was purified by reverse-phase flash chromatography with t e conditions (Column: XBridge BEH Shield RP18 5 m, 30 mm*150 mm; Mobile Phase A: water (10 mmol/$LNH_4HCO_3$), Mobile Phase B: MeCN; Flow rate: 60 mL/min; Gradient: 32% B to 58% in 8 min; Wave Length: UV 254 nm/220 nm; retention time 1: 7.25) to afford 1-((cis or trans)-5-(7-bromo-1H-benzo[d]imidazole-4-carbonyl)-2-(2-hydroxy-4-isopropylphenyl)-9-methyl-2,3,4,5,5a,6,8,9-octahydro-7H-1,2,5,7-tetraazabenzo[cd]azulen-7-yl)prop-2-en-1-one (600 mg) as a white solid.

The racemic compound was then separated by preparative chiral PLC with the condition (Column: CHIRALPAK-IG 2*25 cm, 5 μm; Mobile Phase A: HEX(0.1% FA), Mobile Phase B: EtOH:DCM=1:1; Flow rate: 20 mL/min; Gradient: isocratic 30; Wavelength: UV 254/220 nm; Sample Solvent: EtOH:DCM; Injection Volume: 0.95 mL; Number Of Runs: 4) to obtain 1-((5a(R or S),9(S or R))-5-(7-bromo-1H-benzo[d]imidazole-4-carbonyl)-2-(2-hydroxy-4 -isopropylphenyl)-9-methyl-2,3,4,5,5a,6,8,9-octahydro-7H-1,2,5,7-tetraazabenzo[cd]azulen-7-yl)prop-2-en-1-one as the first-eluting peak (retention time 8.6 min., 253.2 mg, 408 μmol, 97.2% purity) as a white solid. LCMS:(ESI, m/z): 603, 605 $(Br)^{81}$ $[M+1]^4$. $^1H$ NMR: (400 MHz, Chloroform-d, ppm) δ 10.16 (s, 1H), 8.59-7.97 (m, 1H), 7.66-7.41 (m, 1H), 7.39-7.27 (m, 1H), 6.99 (s, 2H), 6.81-6.66 (m, 1H), 6.59-6.34 (m, 1H), 5.93-5.69 (m, 1H), 5.64-5.49 (m, 1H), 5.07-4.92 (m, 1H), 4.68-4.45 (m, 1H), 4.32-3.53 (m, 2H), 3.47-3.31 (m, 1H), 3.31-3.05 (m, 3H), 3.05-2.62 (m, 3H), 1.56-1.05 (m, 9H). Analytical Chiral HPLC: CHIRAL ART Cellulose-SB; Column Size: 4.6*50 mm, 3 μm; Mobile Phase: Hex(0.1% FA):(EtOH:DCM=1:1)=70:30; Flow: 1.0 mL/min; Temperature: 25° C.; retention time=2.0 min.

TABLE E1

The compound of Example E-2 was prepared in an analogous manner to Example E-1, using Int. XA in place of Int. XB. 1-((cis or trans)-5-(7-bromo-1H-benzo[d]imidazole-4-carbonyl)-2-(2-hydroxy-4-isopropylphenyl)-9-methyl-2,3,4,5,5a,6,8,9-octahydro-7H-1,2,5,7-tetraazabenzo[cd]azulen-7-yl)prop-2-en-1-one (50 mg) was purified by Prep-chiral HPLC with the following conditions (Column: CHIRAL ART Cellulose-SB 2 * 25 cm, 5 μm; Mobile Phase A: HEX(0.1% FA), Mobile Phase B: EtOH:DCM = 1:1; Flow rate: 20 mL/min; Gradient: isocratic 25; Wave Length: UV 254/220 nm; Injection Volume: 0.8 mL; Number Of Runs: 5) to afford 1-((5a(R or S)S,9(R or S))-5-(7-bromo-1H-benzo[d]imidazole-4-carbonyl)-2-(4-isopropylphenyl)-9-methyl-2,3,4,5,5a,6,8,9-octahydro-7H-1,2,5,7-tetraazabenzo[cd]azulen-7-yl)prop-2-en-1-one as the second-eluting peak (retention time = 8.5 min., 23.6 mg, 40.0 μmol, 99.5% purity) as a white solid.

| Example No. | Structure and Name | LCMS (ESI, m/z) | NMR |
|---|---|---|---|
| E-2 | 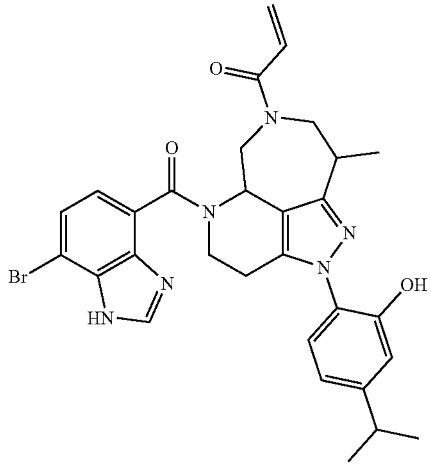 [SMILES: C=CC(=O)N1CC(C)c2nn(-c3ccc(C(C)C)cc3O)c3c2C(C1)N(C(=O)c1ccc(Br)c2[nH]cnc12)CC3] 1-((5a(R or S),9(S or R))-5-(7-bromo-1H-benzo[d]imidazole-4-carbonyl)-2-(2-hydroxy-4-isopropylphenyl)-9-methyl-2,3,4,5,5a,6,8,9-octahydro-7H-1,2,5,7-tetraazabenzo[cd]azulen-7-yl)prop-2-en-1-one | 603, 605 $(Br)^{81}$ $[M + H]^+$ | $^1H$ NMR (400 MHz, Chloroform-d, ppm) δ 10.33 (s, 1H), 8.45-8.05 (m, 1H), 7.68-7.37 (m, 1H), 7.14-6.89 (m, 3H), 6.74 (d, J = 7.4 Hz, 1H), 6.61-6.36 (m, 1H), 5.97-5.68 (m, 1H), 5.58-5.35 (m, 1H), 4.85-4.66 (m, 1H), 4.66-4.43 (m, 1H), 4.41-3.90 (m, 1H), 3.27-3.04 (m, 5H), 2.95-2.70 (m, 2H), 2.66-2.48 (m, 1H), 1.53-1.33 (m, 3H), 1.23 (d, J = 6.9 Hz, 6H). |

Example E-3: Preparation of 1-((5a(S or R),9(S or R))-5-(7-bromo-1-benzo[d]imidazole-4-carbonyl)-2-(4-isopropylphenyl)-9-methyl-2,3,4,5,5a,6,8,9-octahydro 7H-1,2,5,7-tetraazabenzo[cd]azulen-7-yl) prop-2-en-1-one
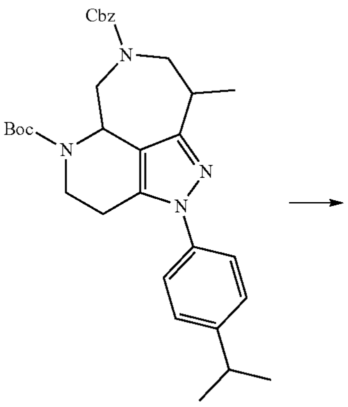
Int. X
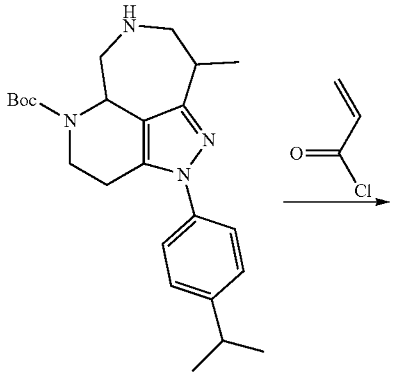
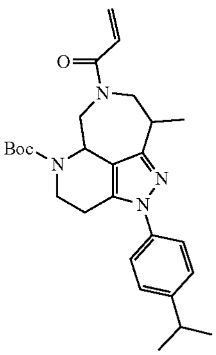
and
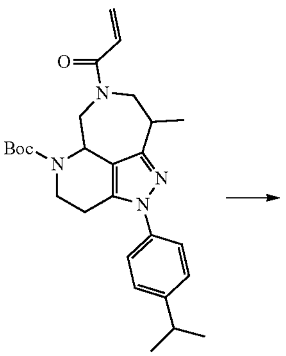
Int. YA
cis or trans
Int. YB
cis or trans
-continued
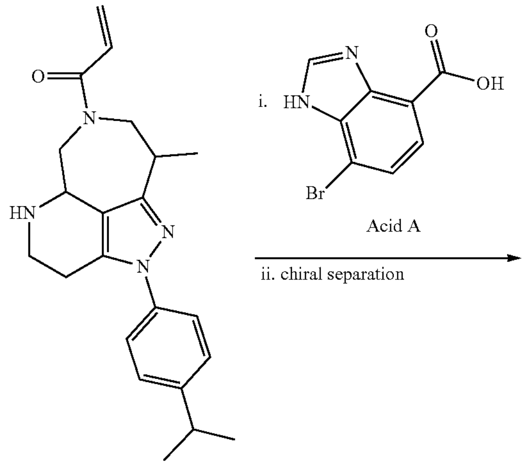
cis or trans
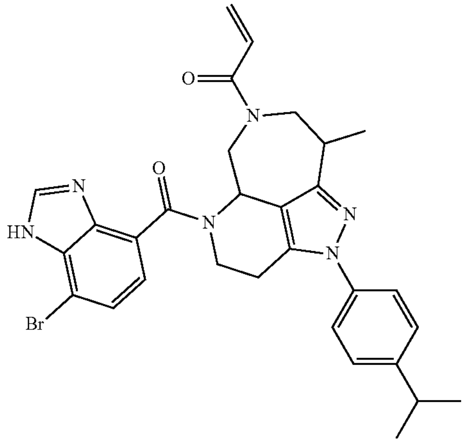
single enantiomer Step 1: Synthesis of Tert-Butyl 2-(4-isopropylphenyl)-9-methyl-2,3,4,5a, 6,7,8,9-octahydro-5H-1,2,5,7-tetraazabenzo[cd]azulene-5-carboxylate To a solution of 7-benzyl 5-(tert-butyl) 2-(4-isopropylphenyl)-9-methyl-3,4,5a,6,8,9-hexahydro-2H-1,2,5,7-tetraazabenzo[cd]azulene-5,7-dicarboxylate as a mixture of diastereomers (Int. X, as a mixture of Int. XA and Int. XB) (800 mg, 1 equiv., 1.47 mmol) in EtOH (16 mL) was added Pd/C (400 mg, 10% wt %) and $Pd(OH)_2/C$ (100 mg, 20 wt % in a pressure tank. The mixture was purged with nitrogen for three times and then was pressurize to 4 Mpa with hydrogen at room temperature for 12 h. The reaction mixture was filtered to remove insoluble solids. The filter cake was washed with EtOH (30 mL) two times. The filtrate was concentrated under reduced pressure. The crude product was used in the next step directly without further purification. LCMS: (ESI, m/z): 411 $[M+H]^+$.

Step 2: Synthesis of Tert-Butyl (cis or trans)-7-acryloyl-2-(4-isopropylphenyl)-9-methyl-2,3,4,5a,6,7,8,9-octahydro-5H-1,2,5,7-tetraazabenzo[cd]azulene-5-carboxylate (Int. YA and YB)

To a solution of tert-butyl 2-(4-isopropylphenyl)-9-methyl-2,3,4,5a,6,7,8,9-octahydro-5H-1,2,5,7-tetraazabenzo[cd]azulene-5-carboxylate (500 mg, 1 equiv., 1.2 mmol) in DCM (10 mL) was added TEA (370 mg, 510 μL, 3 equiv., 3.65 mmol). The mixture was cooled to 0° C., then acryloyl chloride (165 mg, 1.5 equiv., 1.83 mmol) was added slowly. The mixture was warmed to room temperature and stirred for 1 h. The mixture was diluted with ice water (20 mL) and EtOAc (20 mL), and the aqueous layer was extracted with EtOAc (2×20 mL). The combined organic layers were washed with saturated brine (2×20 mL), dried over anhydrous $Na_2SO_4$ and concentrated to give a residue. The residue was purified by silica gel flash column chromatography, eluting with EtOAc/PE (1:5) to afford tert-butyl (cis or trans)-7-acryloyl-2-(4-isopropylphenyl)-9-methyl-2,3,4,5a,6,7,8,9-octahydro-5H-1,2,5,7-tetraazabenzo[cd]azulene-5-carboxylate (Int. YA) (130 mg) as the first-eluting peak and tert-butyl (cis or trans)-7-acryloyl-2-(4-isopropylphenyl)-9-methyl-2,3,4,5a,6,7,8,9-octahydro-5H-1,2,5,7-tetraazabenzo[cd]azulene-5-carboxylate as the second-eluting peak (Int. YB) (300 mg) as colorless oils. LCMS YA: (ESI, m/z): 465 $[M+H]^+$; LCMS YB: (ESI, m/z): 465 $[M+H]^+$.

Step 3: Synthesis of 1-((cis or trans)-2-(4-isopropylphenyl)-9-methyl-2,3,4,5,5a,6,8,9-octahydro-7H-1,2,5,7-tetraazabenzo[cd]azulen-7-yl)prop-2-en-1-one A solution of tert-butyl (cis or trans)-7-acryloyl-2-(4-isopropylphenyl)-9-methyl-2,3,4,5a,6,7,8,9-octahydro-5H-1,2,5,7-tetraazabenzo[cd]azulene-5-carboxylate (Int. YB) (290 mg, 1 equiv., 624 μmol) in TFA (1.5 mL) and DCM (4.5 mL) was stirred at room temperature for 2 h. The solvent was removed under reduced pressure to provide 1-((cis or trans)-2-(4 -isopropylphenyl)-9-methyl-2,3,4,5,5a,6,8,9-octahydro-7H-1,2,5,7-tetraazabenzo[cd]azulen-7-yl)prop-2-en-1-one (350 mg) as a crude yellow oil. The crude product as used in the next step directly without further purification. LCMS: (ESI, m/z): 365 $[M+H]^+$.

Step 4: Synthesis of 1-((5a(S or R),9(S or R))-5-(7-bromo-JH-benzo[d]imidazole-4-carbonyl)-2-(4-isopropylphenyl)-9-methyl-2,3,4,5,5a,6,8,9-octahydro-7H-1,2,5,7-tetraazabenzo[cd]azulen-7-yl)prop-2-en-1-one To a stirred solution of 1-((cis or trans)-2-(4-isopropylphenyl)-9-methyl-2,3,4,5,5a,6,8,9-octahydro-7H-1,2,5,7-tetraazabenzo[cd]azulen-7-yl)prop-2-en-1-one (320 mg, 1 equiv., 880 μmol) in DMF (6.4 mL) was added HOBT (178 mg, 1.5 equiv., 1.32 mmol), 7-bromo-1H-benzo[d]imidazole-4-carboxylic acid (317 mg, 1.5 equiv., 1.32 mmol), EDCI (252 mg, 1.5 equiv., 1.32 mmol) and DIEA (681 mg, 918 μL, 6 equiv., 5.27 mmol). The resulting reaction mixture was stirred at room temperature for 2 h. The reaction was quenched by the addition of water (20 mL) at rt. The resulting mixture was extracted with EtOAc (2×20 mL). The combined organic layers were washed with brine (2×20 mL), dried over anhydrous $Na_2SO_4$. After filtration, the filtrate was concentrated under reduced pressure. The residue was purified by reverse-phase flash chromatography with the conditions (Column: XBridge BEH Shield RP18 5 m, 30 mm*150 mm; Mobile Phase A: water (10 mmol/L $NH_4HCO_3$), Mobile Phase B: MeCN; Flow rate: 60 mL/min; Gradient: 30% B to 65% B in 10 min; Wave Length: UV 254 nm/220n; retention time 1: 8.32) to afford 1-((cis or trans)-5-(7-bromo-1H-benzo[d]imidazole-4-carbonyl)-2-(4-isopropylphenyl)-9-methyl-2,3,4,5,5a,6,8,9-octahydro-7H-1,2,5,7-tetraazabenzo[cd]azulen-7-yl)prop-2-en-1-one (130 mg) as a white solid.

The racemic compound was purified by Prep-chiral HPLC with the following conditions (Column: CHIRAL ART Cellulose-SB 2*25 cm, 5 μm; Mobile Phase A HEX(0.1% FA), Mobile Phase B: EtOH:DCM=1:1; Flow rate: 40 mL/min; Gradient: isocratic 20; Wave Length: UV 254/220 nm; Injection Volume: 1.0 mL; Number Of Runs: 8) to afford 1 ((5a(S or R),9(R or S))-5-(7-bromo-1H-benzo[d]imidazole-4-carbonyl)-2-(4-isopropylphenyl)-9 methyl-2,3,4,5,5a,6,8,9-octahydro-7H-1,2,5,7-tetraazabenzo[cd]azulen-7-yl)prop-2-en-1-one as the second-eluting peak (retention time=15.5 min., 58.2 mg, 98.2 gmol, 99.1% purity) as a white solid. LCMS: (ESI, m/z): 587 $[M+H]^+$. 1H NMR (400 MHz, $CDCl_3$) δ 8.16 (brs, 1H), 7.57-7.37 (m, 1H), 7.31-7.25 (m, 2H), 7.24-7.15 (m, 3H), 6.71-6.24 (m, 1H), 5.84-5.60 (m, 1H), 5.57-5.38 (m, 1H), 5.03- 4.89 (m, 1H), 4.62-4.29 (m, 1H), 4.26-3.50 (m, 2H), 3.37-3.24 (m, 1H), 3.22-2.94 (m, 2H), 2.93-2.78 (m, 2H), 2.56 (d, J=15.2 Hz, H), 1.33-1.03 (m, 9H).

TABLE E2

The compound of Example E-4 was prepared in an analogous fashion to Example E-4, using Int. YA in place of Int. YB in step 3. The racemic 1-((cis or trans)-5-(7-bromo-1H-benzo[d]imidazole-4-carbonyl)-2-(4-isopropylphenyl)-9-methyl-2,3,4,5,5a,6,8,9-octahydro-7H-1,2,5,7-tetraazabenzo[cd]azulen-7-yl)prop-2-en-1-one (50 mg) was purified by Prep-chiral HPLC with the following conditions (Column: CHIRAL ART Cellulose-SB 2 * 25 cm, 5 μm; Mobile Phase A: HEX(0.1% FA), Mobile Phase B: EtOH:DCM = 1:1; Flow rate: 20 mL/min; Gradient: isocratic 25; Wave Length: UV 254/220 nm) to afford 1-((5a(R or S),9(R or S))-5-(7-bromo-1H-benzo[d]imidazole-4-carbonyl)-2-(4-isopropylphenyl)-9-methyl-2,3,4,5,5a,6,8,9-octahydro-7H-1,2,5,7-tetraazabenzo[cd]azulen-7-yl)prop-2-en-1-one as the second-eluting peak (retention time = 8.5 min) as a white solid.

| Example No. | Structure and Name | LCMS (ESI, m/z) | NMR |
|---|---|---|---|
| E-4 | 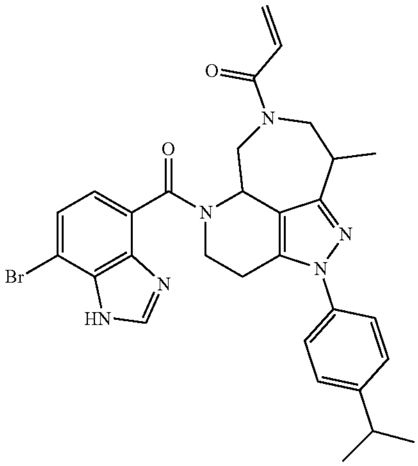 [SMILES: C=CC(=O)N1CC(C)c2nn(-c3ccc(C(C)C)cc3)c3c2C(C1)N(C(=O)c1ccc(Br)c2[nH]cnc12)CC3] 1-((5a(R or S),9(R or S))-5-(7-bromo-1H-benzo[d]imidazole-4-carbonyl)-2-(4-isopropylphenyl)-9-methyl-2,3,4,5,5a,6,8,9-octahydro-7H-1,2,5,7-tetraazabenzo[cd]azulen-7-yl)prop-2-en-1-one | 587, 589 $(Br)^{81}$ $[M + H]^+$ | $^1H$ NMR (400 MHz, Chloroform-d, ppm) δ 8.31-8.17 (m, 1H), 7.51 (d, J = 8.0 Hz, 1H), 7.41-7.29 (m, 2H), 7.28-7.19 (m, 4H), 6.69-6.26 (m, 1H), 5.88-5.64 (m, 1H), 5.45-5.26 (m, 1H), 4.86-4.66 (m, 1H), 4.63-4.40 (m, 1H), 4.33-3.90 (m, 1H), 3.30-2.83 (m, 4H), 2.71-2.49 (m, 2H), 1.54-1.32 (m, 3H), 1.31-1.20 (m, 6H). |

TABLE E3

The compounds of Examples E-5 and E-6 were prepared in an analogous fashion to Example E-1, using 1-iodo-4-cycopropylbenzene in place of 1-iodo-4-isopropylbenzene. The compound of Example E-5 was prepared from the first-eluting peak after step 7, and was separated by chiral HPLC (Chiral-HPLC(Column: CHIRALPAK-ID 3 * 25 cm, 5 μm; Mobile Phase A: HEX(0.1% FA), Mobile Phase B: IPA:DCM = 1:1; Flow rate: 40 mL/min; Gradient: isocratic 25) in the final step to provide the final compound as the first-eluting peak. The compound of Example E-6 was prepared from the second-eluting peak after step 7, and was separated by chiral HPLC (Column: CHIRALPAKIC3; Mobile Phase A: Hex(0.1% FA): (EtOH:DCM = 1:1) = 75:25; Flow rate: 1.0 mL/min mL/min; Gradient: isocratic) in the final step to provide the final compound as the second-eluting peak. The compound of Example E-7 was made in an analogous fashion to Example E-5, using the corresponding carboxylic acid. The final racemic mixture was separated by chiral HPLC (Column: CHIRALPAK-ID 3 * 25 cm, 5 μm; Mobile Phase A: HEX(0.1% FA), Mobile Phase B: ETOH:DCM = 1:1; Flow rate: 40 mL/min; Gradient: isocratic 30) to provide the compound of Example E-7 as the first-eluting peak.

| Example No. | Structure and Name | LCMS (ESI, m/z) | NMR |
|---|---|---|---|
| E-5 | 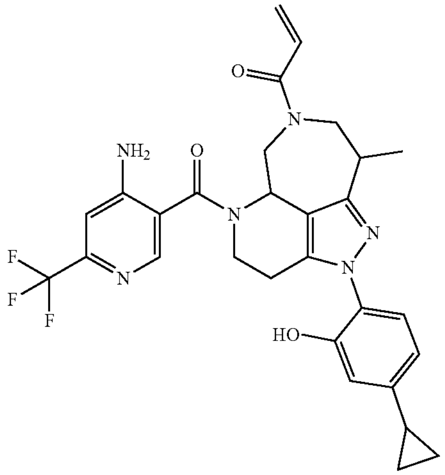 [SMILES: C=CC(=O)N1CC(C)c2nn(-c3ccc(C4CC4)cc3O)c3c2C(C1)N(C(=O)c1cnc(C(F)(F)F)cc1N)CC3] 1-((5a(R or S),9(S or R))-5-(4-amino-6-(trifluoromethyl)nicotinoyl)-2-(4-cyclopropyl-2-hydroxyphenyl)-9-methyl-2,3,4,5,5a,6,8,9-octahydro-7H-1,2,5,7-tetraazabenzo[cd]azulen-7-yl)prop-2-en-1-one | 567 $[M+H]^+$ | $^1H$ NMR (400 MHz, Chloroform-d, ppm) δ 8.37 (s, 1H), 7.45-7.30 (m, 1H), 7.06-6.98 (m, 1H), 6.93 (d, J = 8.3 Hz, 1H), 6.79 (s, 1H), 6.65 (d, J = 8.3 Hz, 1H), 6.52-6.44 (m, 1H), 5.93-5.68 (m, 1H), 5.59-5.30 (m, 3H), 5.05-4.86 (m, 1H), 4.55-4.10 (m, 2H), 3.46-2.74 (m, 6H), 1.93-1.80 (m, 1H), 1.36-1.22 (m, 3H), 1.05-0.93 (m, 2H), 0.77-0.66 (m, 2H). |
| E-6 | 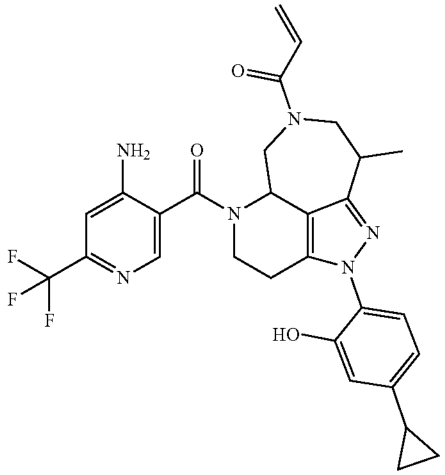 [SMILES: C=CC(=O)N1CC(C)c2nn(-c3ccc(C4CC4)cc3O)c3c2C(C1)N(C(=O)c1cnc(C(F)(F)F)cc1N)CC3] 1-((5a(R or S),9(S or R))-5-(4-amino-6-(trifluoromethyl)nicotinoyl)-2-(4-cyclopropyl-2-hydroxyphenyl)-9-methyl-2,3,4,5,5a,6,8,9-octahydro-7H- | 567 $[M+H]^+$ | $^1H$ NMR (400 MHz, Chloroform-d, ppm) δ 8.36 (s, 1H), 7.45-7.28 (m, 1H), 7.04-6.90 (m, 2H), 6.79 (s, 1H), 6.71-6.45 (m, 2H), 5.90-5.79 (m, 1H), 5.50-5.24 (m, 3H), 4.76 (d, J = 13.0 Hz, 1H), 4.47 (s, 2H), 3.33-2.45 (m, 6H), 1.97-1.81 (m, 1H), 1.30-1.19 (m, 3H), 1.02-0.94 (m, 2H), 0.74-0.69 (m, 2H). |

TABLE E3-continued

The compounds of Examples E-5 and E-6 were prepared in an analogous fashion to Example E-1, using 1-iodo-4-cycopropylbenzene in place of 1-iodo-4-isopropylbenzene. The compound of Example E-5 was prepared from the first-eluting peak after step 7, and was separated by chiral HPLC (Chiral-HPLC(Column: CHIRALPAK-ID 3 * 25 cm, 5 μm; Mobile Phase A: HEX(0.1% FA), Mobile Phase B: IPA:DCM = 1:1; Flow rate: 40 mL/min; Gradient: isocratic 25) in the final step to provide the final compound as the first-eluting peak. The compound of Example E-6 was prepared from the second-eluting peak after step 7, and was separated by chiral HPLC (Column: CHIRALPAKIC3; Mobile Phase A: Hex(0.1% FA): (EtOH:DCM = 1:1) = 75:25; Flow rate: 1.0 mL/min mL/min; Gradient: isocratic) in the final step to provide the final compound as the second-eluting peak. The compound of Example E-7 was made in an analogous fashion to Example E-5, using the corresponding carboxylic acid. The final racemic mixture was separated by chiral HPLC (Column: CHIRALPAK-ID 3 * 25 cm, 5 μm; Mobile Phase A: HEX(0.1% FA), Mobile Phase B: ETOH:DCM = 1:1; Flow rate: 40 mL/min; Gradient: isocratic 30) to provide the compound of Example E-7 as the first-eluting peak.

| Example No. | Structure and Name | LCMS (ESI, m/z) | NMR |
|---|---|---|---|
| | 1,2,5,7-tetraazabenzo[cd]azulen-7-yl)prop-2-en-1-one | | |
| E-7 | 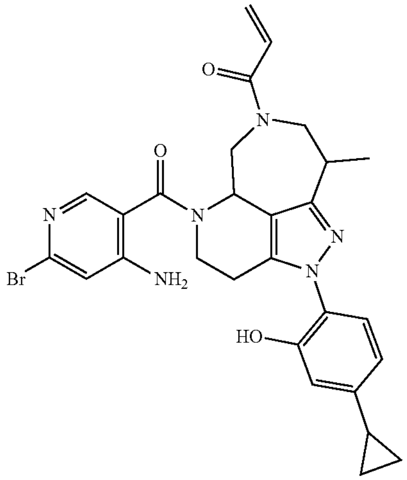 [SMILES: C=CC(=O)N1CC(C)c2nn(-c3ccc(C4CC4)cc3O)c3c2C(C1)N(C(=O)c1cnc(Br)cc1N)CC3] 1-((5a(R or S),9(R or S))-5-(4-amino-6-bromonicotinoyl)-2-(4-cyclopropyl-2-hydroxyphenyl)-9-methyl-2,3,4,5,5a,6,8,9-octahydro-7H-1,2,5,7-tetraazabenzo[cd]azulen-7-yl)prop-2-en-1-one | 577 $[M + H]^+$ | $^1$H NMR (400 MHz, Chloroform-d, ppm) δ 8.18-7.96 (m, 1H), 7.04-6.86 (m, 2H), 6.79 (s, 1H), 6.71-6.61 (m, 1H), 6.53-6.40 (m, 1H), 5.91-5.70 (m, 2H), 5.55-5.43 (m, 1H), 5.41-4.87 (m, 2H), 4.54-4.35 (m, 1H), 4.29-3.50 (m, 1H), 3.45-3.29 (m, 1H), 3.26-3.01 (m, 3H), 3.01-2.73 (m, 2H), 1.91-1.83 (m, 1H), 1.34-1.23 (m, 3H), 1.03-0.94 (m, 2H), 0.75-0.66 (m, 2H). |

Example E-8: Preparation of 1-((5a(S or R),6(R or S))-5-(4-amino-6-(trifluoromethyl)nicotinoyl)-2-(4-isopropylphenyl)-6-methyl-2,3,4,5, a,6,8,9-octahydro-7H-1,2,5,7-tetraazabenzo[cd]azulen-7-yl)prop-2-en-1-one

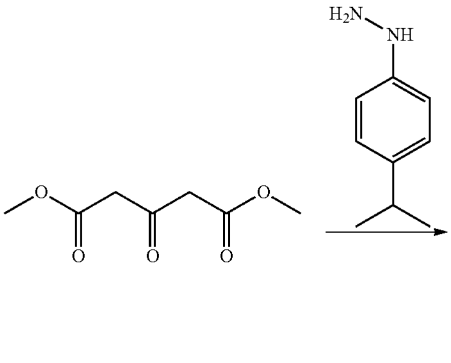

-continued

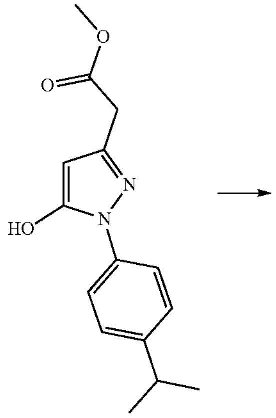

-continued
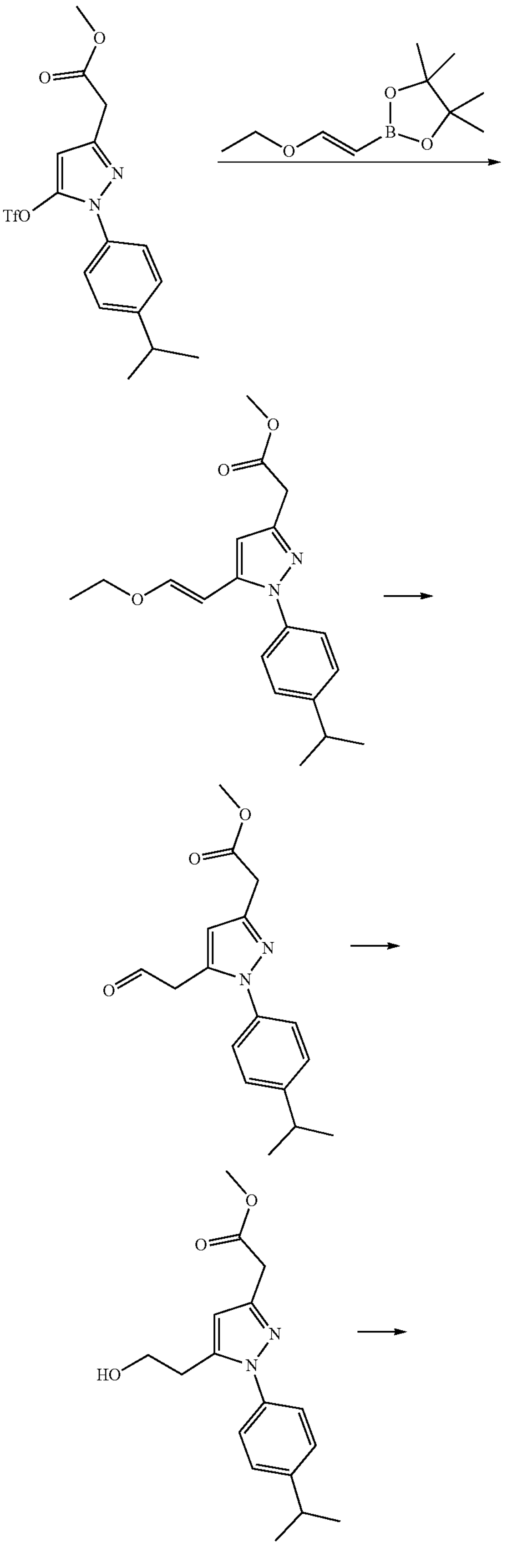
-continued
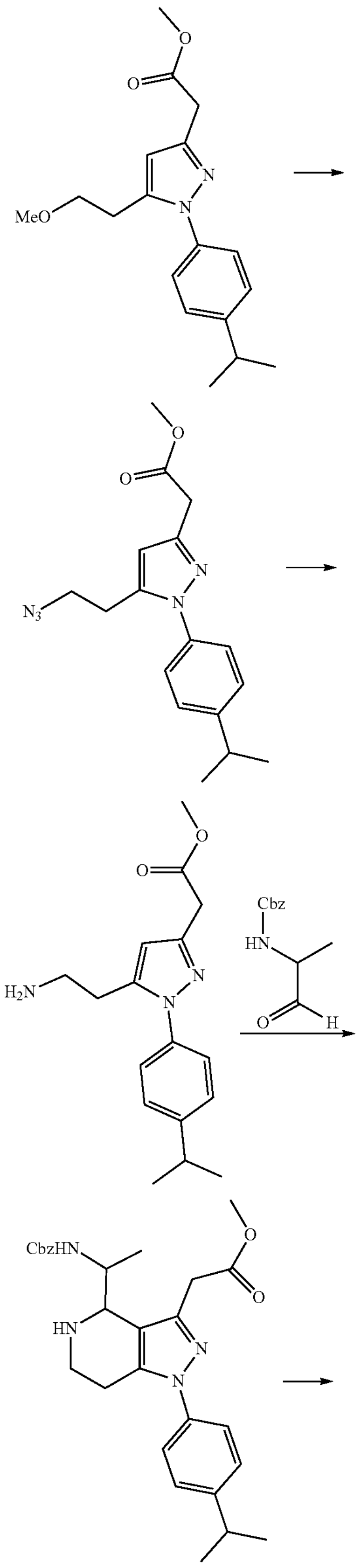

-continued

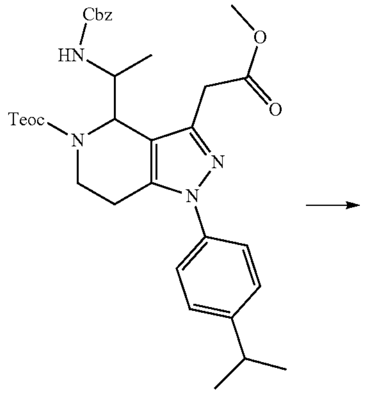

Int. E-A

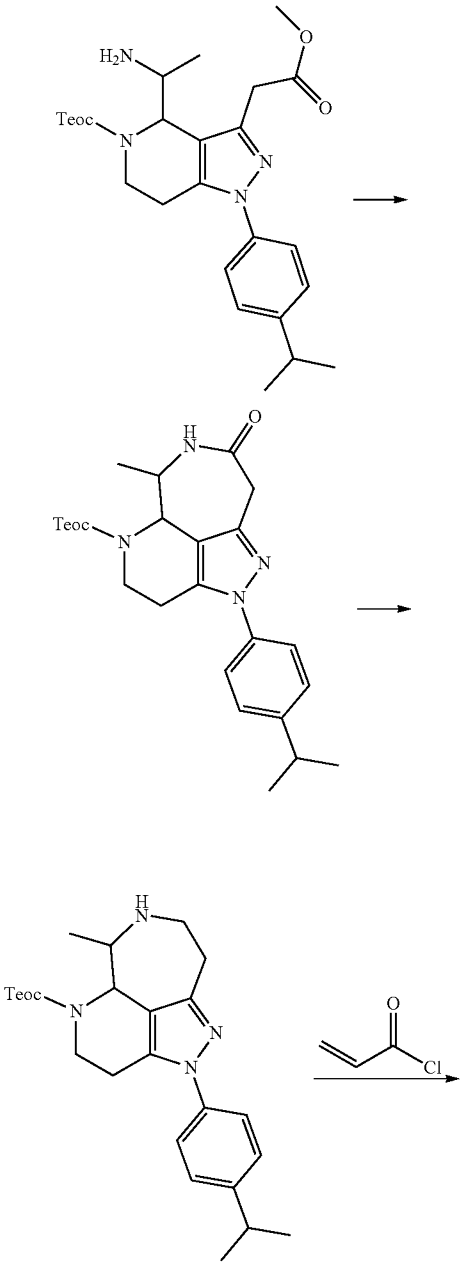

-continued

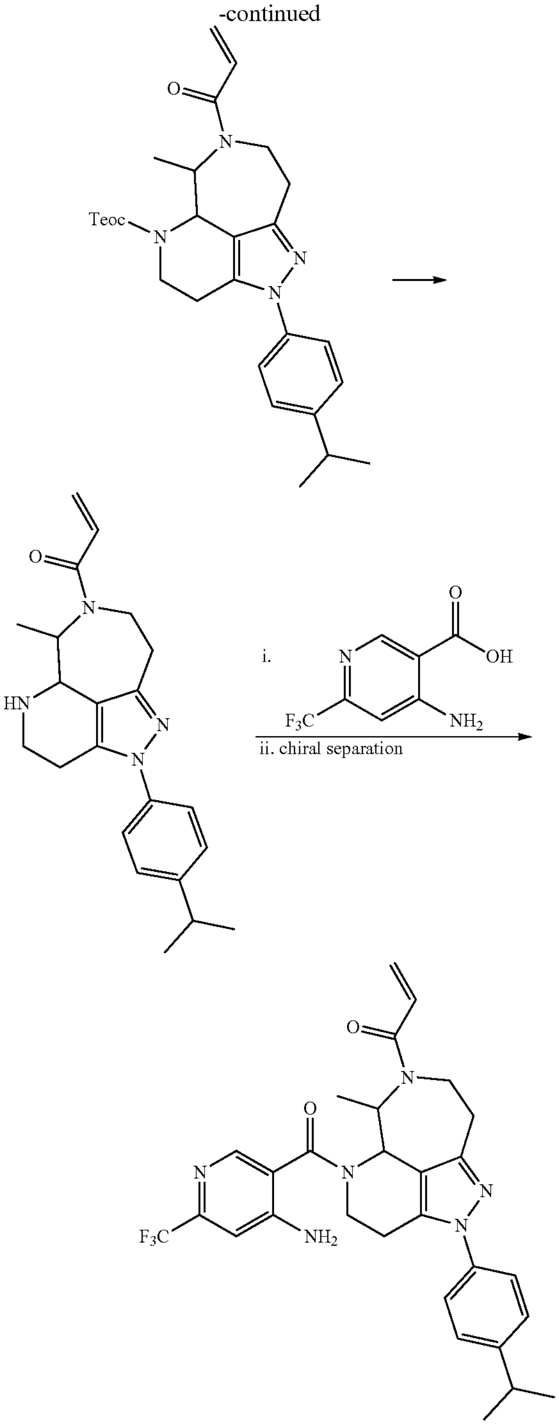

Step 1: Synthesis of Methyl 2-(5-hydroxy-1-(4-isopropylphenyl)-1H-pyrazol-3-yl)acetate To a solution of dimethyl 3-oxopentanedioate (48 g, 1 q, 0.28 mol) and (4-isopropylphenyl)hydrazine (41 g, 1 Eq, 0.28 mol) in toluene (500 mL) as added DIEA (43 g, 58 mL, 1.2 Eq, 0.33 mol). The mixture was then stirred at 120° C. for 12 h after which the solution was cooled and the solvent was removed under reduced pressure. Purification by silica gel chromatography, eluting with 35% EtOAc in PE, afforded methyl 2-(5-hydroxy-1-(4-isopropylphenyl)-1H-pyrazol-3-yl)acetate (60 g) as a pink solid. LCMS: (ESI, m/z): 275 $[M+H]^+$.

Step 2: Synthesis of Methyl 2-(1-(4-isopropylphenyl)-5-(((trifluoromethylsulfonyl)oxy)-1H-pyrazol-3-yl)acetate To a solution of methyl 2-(5-hydroxy-1-(4-isopropylphenyl)-1 pyrazol-3-yl)acetate (60 g, 1 Eq, 0.22 mol) in THF (600 mL) was added TEA (27 g, 37 mL, 1.2 Eq, 0.26 mol). The mixture was cooled to 0° C., then phenyl triflimide (86 g, 1.1 Eq, 0.24 mol) in THF (200 mL) was added slowly at 0° C. under a nitrogen atmosphere. The mixture was warmed to rt and stirred for 12 h, after which the reaction was quenched by the addition of water (200 m L). The resulting mixture was extracted with EA (3×200 mL) and the combined organic layers were washed with brine (500 mL) and dried over anhydrous $Na_2SO_4$. After filtration, the filtrate was concentrated under reduced pressure. The residue was purified by silica gel column chromatography, eluting with EA/PE (5:95) to afford methyl 2-(1-(4-isopropylphenyl)-5-(((trifluoromethyl)sulfonyl)oxy)-1H-pyrazol-3-yl)acetate (70 g) as a yellow oil. LCMS: (ESI, m/z): 407 $[M+H]^+$.

Step 3: Synthesis of Methyl (E)-2-(5-(2-ethoxyvinyl)-1-(4-isopropylphenyl)-JH-pyrazol-3-yl)acetate To a stirred solution of methyl 2-(1-(4-isopropylphenyl)-5-(((trifluoromethyl)sulfonyl)oxy)-1H-pyrazol-3-yl)acetate (900 mg, 1 Eq, 2.21 mmol) and (E)-2-(2-ethoxyvinyl)-4,4,5,5-tetramethyl-1,3,2-dioxaborolane (570 mg, 1.3 q, 2.88 mmol) in 1,4-dioxane (20 mL) was added potassium phosphate, tribasic (1.18 g, 458 μL, 2.5 Eq, 5.54 mmol), $H_2O$ (4 mL) and 1,1'-bis(di-t-butylphosphino)ferrocene palladium dichloride (72.2 mg, 0.05 Eq, 111 mol). The reaction vessel was evacuated and backfilled with nitrogen (3×) and stirred for 12 h at 80° C. The reaction was then cooled to rt and quenched by the addition of water (50 mL), and the resulting mixture was extracted with EA (3×50 mL). The combined organic layers were washed with brine (50 mL) and dried over anhydrous $Na_2SO_4$. After filtration, the filtrate was concentrated under reduced pressure. The residue was purified by silica gel column chromatography, eluting with EA/PE (5:95) to afford methyl (E)-2-(5-(2-ethoxyvinyl)-1-(4-isopropylphenyl)-1H-pyrazol-3-yl)acetate (600 mg) as a brown oil. LCMS: (ESI, m/z): 329 $[M+H]^+$.

Step 4: Synthesis of Methyl 2-(I-(4-isopropylphenyl)-5-(2-oxoethyl)-1H-pyrazol-3-yl)acetate A solution of methyl (E)-2-(5-(2-ethoxyvinyl)-1-(4-isopropylphenyl)-1H-pyrazol-3-yl)acetate (5 g, 1 Eq, 0.02 mol) in DCM (20 mL) and TFA (10 mL) was stirred at rt for 48 h. The solvent was then removed under reduced pressure to afford methyl 2-(1-(-isopropylphenyl)-5-(2-oxoethyl)-1H-pyrazol-3-yl)acetate (4.5 g) as a crude brown oil which was used in the next step directly without further purification. LCMS: (ESI, m/z): 301 $[M+H]^+$.

Step 5: Synthesis of Methyl 2-(5-(2-hydroxyethyl)-1-(4-isopropylphenyl)-H-pyrazol-3-yl)acetate To a solution of methyl 2-(1-(4-isopropylphenyl)-5-(2-oxoethyl)-1H-pyrazol-3-yl)acetate (4.5 g, 1 Eq, 15 mmol) in THF (100 mL) was added Pd/C (2.2 g, 10% wt, 0.14 Eq, 2.1 mmol). The mixture was purged with nitrogen (3×) and then was flushed with hydrogen gas. The mixture was stirred for 12 hours at rt under an atmosphere of hydrogen, after which the mixture was filtered and washed with THF (50 mL×2). The combined filtrate was concentrated under reduced pressure to afford methyl 2-(5-(2-hydroxyethyl)-1-(4-isopropylphenyl)-1H-pyrazol-3-yl)acetate (4.5 g) as a crude light brown oil which was used in the next step directly without further purification. LCMS: (ESI, m/z): 303 $[M+H]^+$.

Step 6: Synthesis of Methyl 2-(1-(4-isopropylphenyl)-5-(2-((methylsulfonyl)oxy)ethyl)-1H-pyrazol-3-yl)acetate To a stirred solution of methyl 2-(5-(2-hydroxyethyl)-1-(4-isopropylphenyl)-1H-pyrazol-3-yl)acetate (10.5 g, 1 Eq, 34.7 mmol) in DCM (200 mL) was added TEA (10.5 g, 14.5 mL, 3 Eq, 104 mmol). The mixture was cooled to 0° C., then methanesulfonyl chloride (5.97 g, 4.03 mL, 1.5 Eq, 52.1 mmol) was added slowly at 0° C. under a nitrogen atmosphere. The mixture was warmed to rt and stirred for 1 hour, after which the reaction was quenched by the addition of water (20 mL). The resulting mixture was extracted with EA (2×20 mL), and the combined organic layers were washed with brine (2×20 mL) and dried over anhydrous $Na_2SO_4$. After filtration, the filtrate was concentrated under reduced pressure. The residue was purified by silica gel column chromatography, eluting with EA/PE (1:5) to afford methyl 2-(1-(4-isopropylphenyl)-5-(2-((methylsulfonyl)oxy)ethyl)-1H-pyrazol-3-yl)acetate (10 g) as a yellow oil. LCMS: (ESI, m/z): 381 $[M+H]^+$.

Step 7: Synthesis of Methyl 2-(5-(2-azidoethyl)-1-(4-isopropylphenyl)-1-pyrazol-3-yl)acetate To a solution of methyl 2-(1-(4-isopropylphenyl)-5-(2-((methy sulfonyl)oxy)ethyl)-1H-pyrazol-3-yl)acetate (8.5 g, 1 Eq, 22 mmol) in THF (30 mL) were added TBAF (12 g, 2 Eq, 45 mmol) and TMS-N3 (5.1 g, 5.9 mL, 2 Eq, 45 mmol) slowly at 0° C. under a nitrogen atmosphere. The mixture was warmed to 60° C. and stirred for 12 h. The reaction was then cooled to rt and quenched by the addition of water (50 mL). The resulting mixture was extracted with DCM (3×100 mL) and the combined organic layers were washed with brine (1×100 mL) and dried over anhydrous $Na_2SO_4$. After filtration, the filtrate was concentrated under reduced pressure. The residue was purified by silica gel column chromatography, eluting with EA/PE (35/65) to afford methyl 2-(5-(2-azidoethyl)-1-(4-isopropylphenyl)-1H-pyrazol-3-yl) acetate (4 g) as a yellow oil. LCMS: (ESI, m/z): 328 $[M+H]^+$.

Step 8: Synthesis of Methyl 2-(5-(2-aminoethyl)-1-(4-isopropylphenyl)-1H-pyrazol-3-yl)acetate To a solution of methyl 2-(5-(2-azidoethyl)-1-(4-isopropylphenyl)-1H-pyrazol-3-yl)acetate (4 g, 1 Eq, 0.01 mol) in THF (80 mL) were added Pd/C (1.2 g, 10 wt %, 0.09 Eq, 1.1 mmol). The mixture was purged with nitrogen (3×) and then was flushed with hydrogen. The mixture was stirred for 1 h at rt under an atmosphere of hydrogen, after which the mixture was filtered and washed with THF (50 mL×2), and the filtrate was concentrated under reduced pressure to give a residue. The residue was purified by reverse phase chromatography (column: C18 column; Gradient: MeCN in water with 0.5% TFA) to afford methyl 2-(5-(2-aminoethyl)-1-(4-isopropylphenyl)-1H-pyrazol-3-yl)acetate (3.5 g) as a yellow oil as the trifluoroacetate salt. LCMS: (ESI, m/z): 302 $[M+H]^+$.

Step 9: Synthesis of Methyl 2-(4-(1-(((benzyloxy)carbonyl)amino)ethyl)-1-(4-isopropylphenyl)-4,5,6,7-tetrahydro-1H-pyrazolo[4,3-c]pyridin-3-yl)acetate To a solution of methyl 2-(5-(2-aminoethyl)-1-(4-isopropylphenyl)-1H-pyrazol-3-yl)acetate trifluoroacetate salt (3.3 g, 1 Eq, 11 mmol) in DCE (66 mL) were added benzyl (1-oxopropan-2-yl)carbamate (1.6 g, 0.7 Eq, 7.7 mmol) and TFA (2.5 g, 1.7 mL, 2 Eq, 22 mmol). The mixture was stirred at 60° C. for 12 h, after which the reaction was cooled to rt and quenched by the addition of water (200 mL). The resulting mixture was extracted with DCM (3×200 mL) and the combined organic layers were washed with brine (300 mL) a d dried over anhydrous $Na_2SO_4$. After filtration, the filtrate was concentrated under reduced pressure. The residue was purified by silica gel column chromatography, eluting with EA/PE (85:15) to afford methyl 2-(4-(1-(((benzyloxy)carbonyl)amino)ethyl)-1-(4-isopropylphenyl)-4,5,6,7-tetrahydro-1H-pyrazolo[4,3-c]pyridin-3-yl)acetate (2 g) as light brown oil. LCMS: (ESI, m/z): 491 $[M+H]^+$.

Step 10: Synthesis of 2-(trimethylsilyl)ethyl 4-(1-(((benzyloxy)carbonyl)amino)ethyl)-1-(4-isopropylphenyl)-3-(2-methoxy-2-oxoethyl)-1,4,6,7-tetrahydro-5H-pyrazolo[4,3-c]pyridine-S-carboxylate To a solution of methyl 2-(4-(1-(((benzyloxy)carbonyl)amino)ethyl)-1-(4-isopropylphenyl)-4,5,6,7-tetrahydro-1H-pyrazolo[4,3-c]pyridin-3-yl)acetate (2 g, 1 Eq, 4 mmol) in 1,4-dioxane (20 mL) and $H_2O$ (20 mL) were added TEA (1 g, 2 mL, 3 Eq, 0.01 mol) and 2,5-dioxopyrrolidin-1-yl [2-(trimethylsilyl)ethyl]carbonate (2 g, 1.5 Eq, 6 ol). The mixture was stirred at rt for 2 h, after which the reaction was quenched by the addition of water (100 mL). The resulting mixture was extracted with DCM (3×100 mL) and the combined organic layers were washed with brine (200 mL) and dried over anhydrous $Na_2SO_4$. After filtration, the filtrate was concentrated under reduced pressure. The residue was purified by silica gel column chromatography, eluting with EA/PE (35:65) to afford 2-(trimethylsilyl)ethyl 4-(1 -(((benzyloxy)carbonyl)amino)ethyl)-1-(4-isopropylphenyl)-3-(2-methoxy-2-oxoethyl)-1,4,6,7-tetrahydro-5H-pyrazolo[4,3-c]pyridine-5-carboxylate (1.8 g) as a white oil. LCMS: (ESI, m/z): 635 $[M+H]^+$.

Step 11: Synthesis of 2-(trimethylsilyl)ethyl 4-(1-aminoethyl)-1-(4-isopropylphenyl)-3-(2-methoxy-2-oxoethyl)-1,4,6,7-tetrahydro-5H-pyrazolo[4,3-c]pyridine-5-carboxylate To a solution of 2-(trimethylsilyl)ethyl 4-(1-(((benzyloxy)carbonyl)amino)ethyl)-1-(4-isopropylphenyl)-3-(2-methoxy-2-oxoethyl)-1,4,6,7-tetrahydro-5H-pyrazolo[4,3-c]pyridine-5-carboxylate (1.8 g, 1 Eq, 2.8 mmol) in $NH_3$ in dioxane (0.4 M, 60 mL) were added Pd/C (600 mg, 10 wt %, 0.20 Eq, 564 μmol) and $Pd(OH)_2/C$ (400 mg, 20 wt %, 0.20 Eq, 570 mol). The mixture was purged with nitrogen (3×) and then was pressurized 4.0 MPa with an atmosphere of hydrogen and stirred at 40° C. for 12 h. The reaction mixture was cooled to room temperature and filtered to remove insoluble solids. The filter cake was washed with dioxane (20 mL×2) and the combined filtrate was concentrated under reduced pressure to afford 2-(trimethylsilyl)ethyl 4-(1-aminoethyl)-1-(4-isopropylphenyl)-3-(2-methoxy-2-oxoethyl)-1,4,6,7-tetrahydro-5H-pyrazolo[4,3-c]pyridine-5-carboxylate (1.5 g) as a crude oil which w s used in the next step directly without further purification. LCMS: (ESI, m/z): 501 $[M+H]^+$.

Step 12: Synthesis of 2-(trimethylsilyl)ethyl 2-(4-isopropylphenyl)-6-methyl-8-oxo-2,3,4,5a,6,7,8,9-octahydro-5H-1,2,5,7-tetraazabenzo[cd]azulene-5-carboxylate To a solution of 2-(trimethylsilyl)ethyl 4-(1-aminoethyl)-1-(4-isopropylphenyl)-3-(2-methoxy-2-oxoethyl)-1,4,6,7-tetrahydro-5H-pyrazolo[4,3-c]pyridine-5-carboxylate (1.3 g, 1 Eq, 2.6 mmol) in THF (25 mL) was added LiOH (0.31 g, 5 Eq, 13 mmol). The mixture was stirred at rt for 12 h. The reaction mixture was filtered to remove insoluble solids and the filter cake was washed with THF (20 mL×2). The filtrate was concentrated under reduced pressure. The residue was purified by silica gel column chromatography, eluting with EA/PE (75:25) to afford 2-(trimethylsilyl)ethyl 2-(4-isopropylphenyl)-6-methyl-8-oxo-2,3,4,5a,6,7,8,9-octahydro-5H-1,2,5,7-tetraazabenzo[cd]azulene-5-carboxylate (380 mg) as white solid. LCMS: (ESI, m/z): 469 $[M+H]^+$.

Step 13: Synthesis of 2-(trimethylsilyl)ethyl 2-(4-isopropylphenyl)-6 methyl-2,3,4,5a,6,7,8,9-octahydro-5H-1,2,5,7-tetraazabenzo[cd]azulene-5-carboxylate A solution of 2-(trimethylsilyl)ethyl 2-(4-isopropylphenyl)-6-methyl-8-oxo-2,3,4,5a,6,7,8,9-octahydro-5H-1,2,5, 7-tetraazabenzo[cd]azulene-5-carboxylate (330 mg, 1 Eq, 704 μmol) in THF (4 mL) was cooled to 0° C., then $BH_3$·THF (0.3 g, 4 mL, 1 molar, 6 Eq, 4 mmol) was added slowly at under a nitrogen atmosphere. The mixture was then warmed to 60° C. and stirred for 2 h. The reaction was then cooled to 0° C. and quenched by t e addition of MeOH (20 mL). The mixture was warmed to rt and stirred for 2 hours, after which the solvent was removed under reduced pressure to afford 2-(trimethylsilyl)ethyl 2-(4-isopropylphenyl)-6-methyl-2,3,4,5a,6,7,8,9-octahydro-5H-1,2,5,7-tetraazabenzo[cd]azulene-5-carboxylate (350 mg) as a crude oil which was used in the next step directly without further purification. LCMS: (ESI, m/z): 455 $[M+H]^+$.

Step 14: Synthesis of 2-(trimethylsilyl)ethyl 7-acryloyl-2-(4-isopropylphenyl)-6-methyl-2,3,4,5a,6,7,8,9-octahydro-5H-1,2,5,7-tetraazabenzo[cd]azulene-5-carboxylate To a solution of 2-(trimethylsilyl)ethyl 2-(4-isopropylphenyl)-6-methyl-2,3,4,5a,6,7,8,9-octahydro-5H-1,2,5,7-tetraazabenzo[cd]azulene-5-carboxylate (300 mg, 1 Eq, 660 gmol) in DCM (10 mL) was added TEA (401 mg, 552 μL, 6 Eq, 3.96 mmol). The mixture was cooled to 0° C., then acryloyl chloride (119 mg, 2 Eq, 1.32 mmol) was added slowly at 0° C. under a nitrogen atmosphere. The mixture was warmed to rt and stirred for 2 h, after which the reaction was quenched by the addition of water (20 mL). The resulting mixture was extracted with DCM (2×30 mL) and the combined organic layers were washed with brine (30 mL) and dried over anhydrous $Na_2SO_4$. After filtration, the filtrate was concentrated under reduced pressure. The residue was purified by silica gel column chromatography, eluting with EA/PE (42/58) to afford 2-(trimethylsilyl)ethyl 7-acryloyl-2-(4-isopropylphenyl)-6-methyl-2,3,4,5a,6,7,8,9-octahydro-5H-1,2,5,7-tetraazabenzo[cd]azulene-5-carboxylate (200 mg) as yellow oil. LCMS: (ESI, m/z): 509 $[M+H]^+$.

Step 15: Synthesis of 1-(2-(4-isopropylphenyl)-6-methyl-2,3,4,5,5a,6,8,9-octahydro-7H-1,2,5,7-tetraazabenzo[cd]azulen-7-yl)prop-2-en-1-one A solution of 2-(trimethylsilyl)ethyl 7-acryloyl-2-(4-isopropylphenyl)-6-methyl-2,3,4,5a,6,7,8,9-octahydro-5H-1,2,5,7-tetraazabenzo[cd]azulene-5-carboxylate (100 mg, 1 Eq, 197 μmol) in DCM (2 mL) and TFA (1 mL) was stirred at rt for 2 h. The solvent was then removed under reduced pressure to afford 1-(2-(4-isopropylphenyl)-6-methyl-2,3,4,5,5a,6,8,9-octahydro-7H-1,2,5,7-tetraazabenzo[cd]azulen-7-yl)prop-2-en-1-one (80 mg) as a crude yellow oil which was used in the next step directly without further purification. LCMS: (ESI, m/z): 365 $[M+H]^+$.

Step 16: Synthesis of 1-((5a(S or R),6(S or R))-5-(4-amino-6-(trifluoromethyl)nicotinoyl)-2-(4-isopropylphenyl)-6-methyl-2,3,4,5,5a,6,8,9-octahydro-7H-1,2,5,7-tetraazabenzo[cd]azulen-7-yl)prop-2-en-1-one To a solution of 1-(2-(4-isopropylphenyl)-6-methyl-2,3,4,5,5a,6,8,9-octahydro-7H-1,2,5,7-tetraazabenzo[cd]azulen-7-yl)prop-2-en-1-one (80 mg, 1 Eq, 0.22 mmol) in DMF (3 mL) were added 4-amino-6-(trifluoromethyl)nicotinic acid (59 mg, 1.3 Eq, 0.29 mmol), HATU (0.13 g, 1.5 Eq, 0.33 mmol) and DIEA (0.14 g, 0.19 mL, 5 Eq, 1.1 mmol). The mixture was stirred at rt for 6 h, after which the mixture was diluted with water (20 mL) and EA (20 mL), and the aqueous layer was extracted with EA (3×20 mL). The combined organic layers were washed with half saturated brine (2×20 mL), then saturated brine (1×20 mL), dried over anhydrous sodium sulfate, filtered, and concentrated to give a residue. Purification by silica gel chromatography (EA/PE=55:45) afforded the racemic product mixture as a residue. The residue was purified by Prep-HPLC (Column: Sunfire C18 5 μm, 30 mm*150 mm; Mobile Phase A: Water (0.1% FA), Mobile Phase B: ACN; Flow rate: 60 mL/min; Gradient: 39% B to 59% B in 10 min; Wave Length: UV 254 nm/220 nm) to afford 1-(5-(4-amino-6-(trifluoromethyl)nicotinoyl)-2-(4-isopropylphenyl)-6-methyl-2,3,4,5,5a,6,8,9-octahydro-7H-1,2,5,7-tetraazabenzo[cd]azulen-7-yl)prop-2-en-1-one in two peaks as racemic mixture of single diastereomers. The second-eluting peak (7 mg) was carried on to the compound of the example and was separated into its constituent enantiomers by Chiral-HPLC (Column: CHIRALPAK-IC 2*25 cm, 5 μm; Mobile Phase A: HEX(0.1% FA), Mobile Phase B: EtOH:DCM=1; 1; Flow rate: 20 mL/min; Gradient: isocratic 50; Wave Length: UV 254/220 nm; RT1(min): 4.8; RT2(min): 7.89) to afford 1-((5a(S or R),6(R or S))-5-(4-amino-6-(trifluoromethyl)nicotinoyl)-2-(4-isopropylphenyl)-6-methyl-2,3,4,5,5a,6,8,9-octahydro-7H-1,2,5,7-tetraazabenzo[cd]azulen-7-yl)prop-2-en-1-one (2.4 mg) as the second-eluting peak as a white solid. LCMS: (ESI, m/z): 553 $[M+H]^+$. $^1H$ NMR: (400 MHz, Chloroform-d, ppm) δ 8.30 (s, 1H), 7.52-7.13 (m, 5H), 7.03 (s, 1H), 6.55-6.31 (m, 1H), 6.00-5.07 (m, 4H), 5.05-3.68 (m, 3H), 3.47-2.55 (m, 7H), 1.40-0.87 (m, 9H).

TABLE E4

The compound of Example E-9 was prepared in an analogous fashion to Example E-8, expect that Int. E-A was first subjected to analogous conditions to Example A-8 step 4. The resulting compound was carried on through the analogous steps in Example E-8, expect that DBU was used in place of LiOH in the analogous step to Example E-8 step 12. Following the final amide-coupling step, analogous to Example E-8 step 16, an additional step of stirring the amide coupling product with LiOH in THF was added as in Example A-8 step 10 to afford the racemic compound of the example as a mixture of diastereomers. The mixture was purified by Prep-HPLC, eluting with condition of Column: Xselect CSH C18 OBD Column 30*150 mm 5 μm, n; Mobile Phase A: Water(0.1% FA), Mobile Phase B: ACN; Flow rate: 60 mL/min mL/min; Gradient: 29% B to 48% B in 9 min to afford 1-(5-(4-amino-6-(trifluoromethyl)nicotinoyl)-2-(4-cyclopropyl-2-hydroxyphenyl)-6-methyl-2,3,4,5,5a,6,8,9-octahydro-7H-1,2,5,7-tetraazabenzo[cd]azulen-7-yl)prop-2-en-1-one (14 mg) as the second-eluting peak as a racemic mixture. The racemic mixture was purified by Chiral HPLC, eluting with these conditions: Column: CHIRALPAK ID, 3*25 cm, 5 μm; Mobile Phase A: MtBE(0.1% FA)—HPLC, Mobile Phase B: ETOH; Flow rate: 40 mL/min; Gradient: isocratic 10; Wave Length: 254/206 nm; RT1(min): 7.7; RT2(min): 16) to afford 1-((5a(R or S),6(R or S))-5-(4-amino-6-(trifluoromethyl)nicotinoyl)-2-(4-cyclopropyl-2-hydroxyphenyl)-6-methyl-2,3,4,5,5a,6,8,9-octahydro-7H-1,2,5,7-tetraazabenzo[cd]azulen-7-yl)prop-2-en-1-one (3.4 mg) as the second-eluting peak.

| Example No. | Structure and Name | LCMS (ESI, m/z) | NMR |
|---|---|---|---|
| E-9 | 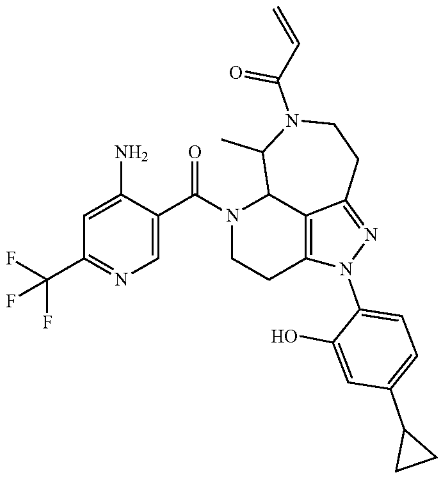 [SMILES: C=CC(=O)N1CCc2nn(-c3ccc(C4CC4)cc3O)c3c2C(C1C)N(C(=O)c1cnc(C(F)(F)F)cc1N)CC3] 1-((5a(R or S),6(R or S))-5-(4-amino-6-(trifluoromethyl)nicotinoyl)-2-(4-cyclopropyl-2-hydroxyphenyl)-6-methyl-2,3,4,5,5a,6,8,9-octahydro-7H-1,2,5,7-tetraazabenzo[cd]azulen-7-yl)prop-2-en-1-one | 567 $[M + H]^+$ | $^1H$ NMR (400 MHz, Chloroform-d, ppm) δ 8.32 (s, 1H), 7.51-7.33 (m, 1H), 7.02 (d, J = 17.7 Hz, 1H), 6.93 (d, J = 8.3 Hz, 1H), 6.80 (d, J = 2.1 Hz, 1H), 6.63 (d, J = 8.6 Hz, 1H), 6.55-6.32 (m, 1H), 5.97-5.73 (m, 1H), 5.73-5.51 (m, 1H), 5.32 (s, 2H), 4.93 (s, 1H), 4.72 (s, 1H), 4.33-4.11 (m, 1H), 3.42-3.21 (m, 1H), 3.03 (s, 4H), 2.92-2.83 (m, 1H), 1.92-1.87 (m, 1H), 1.27 (d, J = 8.7 Hz, 3H), 1.02-0.96 (m, 2H), 0.72-0.68 (m, 2H). |

TABLE E5

The compound of Examples E-10 and E-11 were prepared in an analogous fashion to Example E-1, except that the cyclobutane group was introduced through Int. CC. The diastereomers were separated at the analogous intermediates to Int. XA and XB, and the first peak was carried on to the racemic compound of Example E-10, which was separated into its constituent enantiomers by these conditions: Column-CHIRALPAK-IA 2*25 cm, 5 μm; Mobile Phase A: HEX(0.1% FA), Mobile Phase B: EtOH; Flow rate: 20 mL/min; Gradient: isocratic 20; Wave Length: UV 254/220 nm; RT1(min): 7.6; RT2(min): 12.0 to provide the compound of the example as the second-eluting peak. The second peak was carried on to the racemic compound of Example E-11, which was separated into its constituent enantiomers by these conditions: Column-CHIRALPAK-IE 2*25 cm, 5 μm; Mobile Phase A: HEX(0.1% FA), Mobile Phase B: EtOH: DCM = 1:1; Flow rate: 20 mL/min; Gradient: isocratic 25; Wave Length: UV 254/220 nm; RT1(min): 18; RT2(min): 24; to provide the compound of the example as the first-eluting peak.

| Example No. | Structure and Name | LCMS (ESI, m/z) | NMR |
|---|---|---|---|
| E-10 | 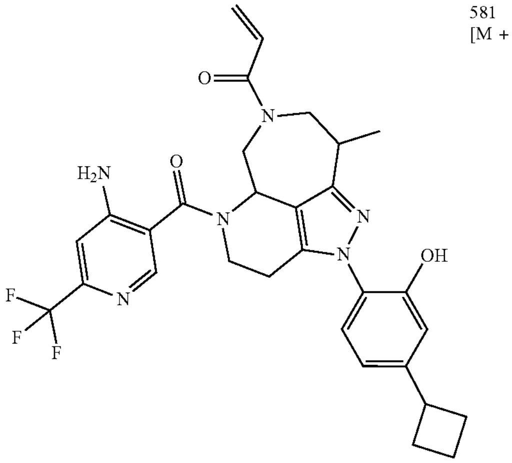 1-((5a(R or S),9(R or S))-5-(4-amino-6-(trifluoromethyl)nicotinoyl)-2-(4-cyclobutyl-2-hydroxyphenyl)-9-methyl-2,3,4,5,5a,6,8,9-octahydro-7H-1,2,5,7-tetraazabenzo[cd]azulen-7-yl)prop-2-en-1-one | 581 $[M + H]^+$ | $^1$H NMR (400 MHz, Chloroform-d, ppm) δ 10.31 (s, 1H), 8.36 (s, 1H), 7.51 - 7.29 (m, 1H), 7.10 - 6.86 (m, 3H), 6.74 (dd, J = 8.3, 1.9 Hz, 1H), 6.60 - 6.34 (m, 1H), 5.96 - 5.71 (m, 1H), 5.38 (s, 3H), 4.76 (d, J = 13.1 Hz, 1H), 4.60 - 4.39 (m, 1H), 4.28 - 3.95 (m, 1H), 3.59 - 3.46 (m, 1H), 3.35 - 2.71 (m, 5H), 2.62 - 2.51 (m, 1H), 2.45 - 2.27 (m, 2H), 2.27 - 1.79 (m, 4H), 1.47 (d, J = 6.9 Hz, 3H). |
| E-11 | 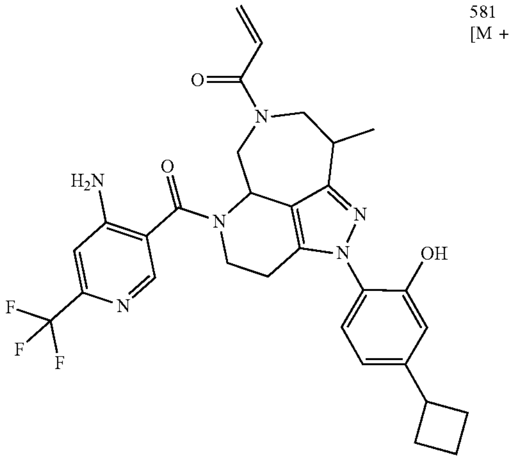 1-((5a(R or S),9(R or S))-5-(4-amino-6-(trifluoromethyl)nicotinoyl)-2-(4-cyclobutyl-2-hydroxyphenyl)-9-methyl-2,3,4,5,5a,6,8,9-octahydro-7H-1,2,5,7-tetraazabenzo[cd]azulen-7-yl)prop-2-en-1-one | 581 $[M + H]^+$ | $^1$H NMR (400 MHz, Chloroform-d, ppm) δ 10.14 (br s, 1H), 8.37 (s, 1H), 7.48 - 7.33 (m, 1H), 7.14 - 6.91 (m, 3H), 6.84 - 6.62 (m, 2H), 6.48 (d, J = 8.4 Hz, 1H), 5.98 - 5.69 (m, 1H), 5.62-5.28 (m, 3H), 4.99 (s, 1H), 4.62-4.08 (m, 2H), 4.02 - 3.62 (m, 1H), 3.58-2.70 (m, 6H), 2.45-2.28 (m, 2H), 2.22 - 1.95 (m, 3H), 1.93 - 1.81 (m, 1H), 1.39 - 1.17 (m, 3H). |

Example F-0: Preparation of 4-bromo-3-(methoxymethoxy)benzoic Acid (Acid D)

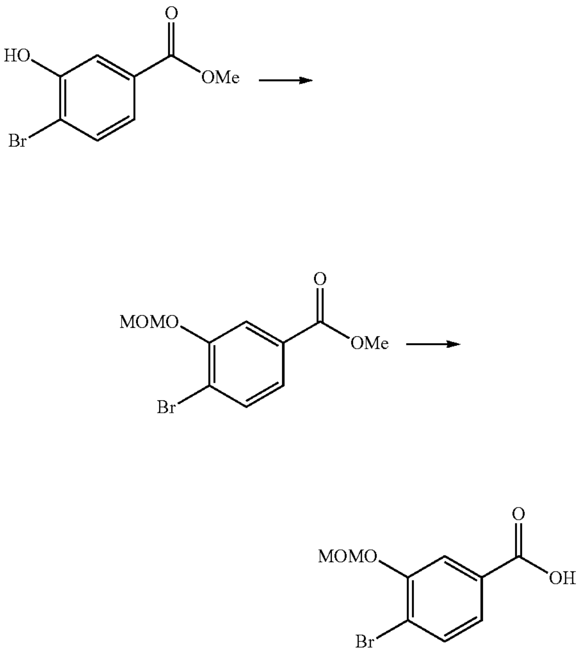

Acid D

Step 1: Synthesis of Methyl 4-bromo-3-(methoxymethoxy)benzoate

To a stirred solution of methyl 4-bromo-3-hydroxybenzoate (1, 4.3 mmol, 1 equiv) and $Cs_2CO_3$ (4231 mg, 12.98 mmol, 3 equiv) in MeCN (20 mL) was added bromo (methoxy)methane (811 mg, 6.49 mmol, 1.5 equiv) dropwise at 10° C. under a nitrogen atmosphere, after which the reaction mixture was stirred at rt overnight. The resulting mixture was filtered and the filter cake was washed with acetonitrile (2×30 mL). The filtrate was concentrated under reduced pressure. The residue was purified by silica gel column chromatography, eluting with PE/EtOAc (10:1) to afford methyl 4-bromo-3-(methoxymethoxy)benzoate (1.12 g) as a yellow oil.

Step 2: Synthesis of 4-bromo-3-(methoxymethoxy)benzoic Acid (Acid D)

A solution of methyl 4-bromo-3-(methoxymethoxy)benzoate (1.2 g, 4.07 mmol, 1 equiv) and LiOH (146 mg, 6.11 mmol, 1.5 equiv) in THF (10 mL) and water (5 mL) was stirred for 1 h at rt under a nitrogen atmosphere. The mixture was then acidified to pH 5 with 1N $H_2SO_4$ aqueous solution. The resulting mixture was extracted with EtOAc (2×10 mL)m and the combined organic layers were washed with brine (1×20 mL), dried over anhydrous $MgSO_4$. After filtration, the filtrate was concentrated under reduced pressure. This resulted in 4-bromo-3-(methoxymethoxy)benzoic acid (0.88 g) as a white solid, which was used in subsequent reactions without further purification. LCMS:(ESI, m/z): 261 $[M+H]^+$.

Example F-1: Preparation of (S AND R)-1-(6-(4-bromo-3-hydroxybenzoyl)-1-(4-isopropyl-2-methylphenyl)-1,5,5a,6,7,8-hexahydropyrazolo[3,4,5-de][1,7]naphthyridin-4(3H)-yl)prop-2-en-1-one

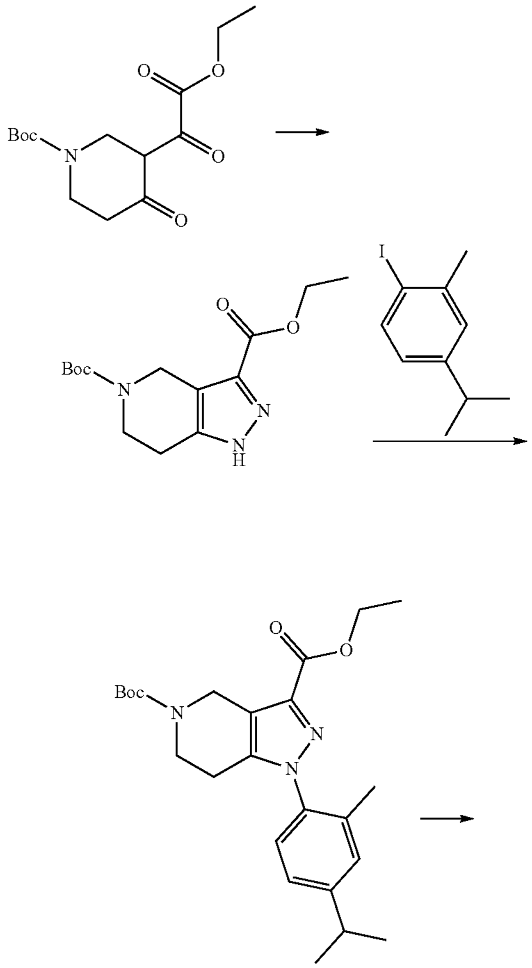

Int. AA

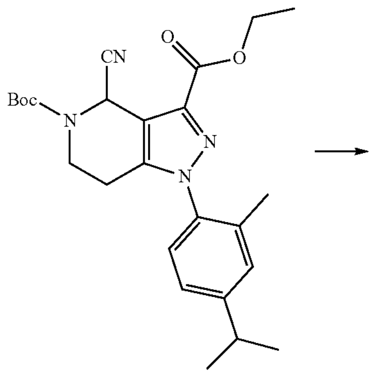

-continued

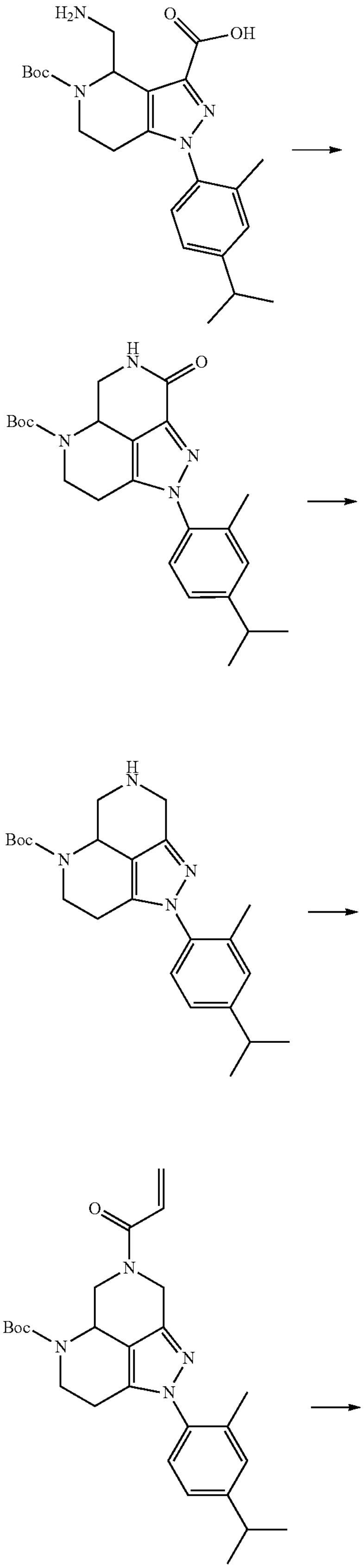

-continued

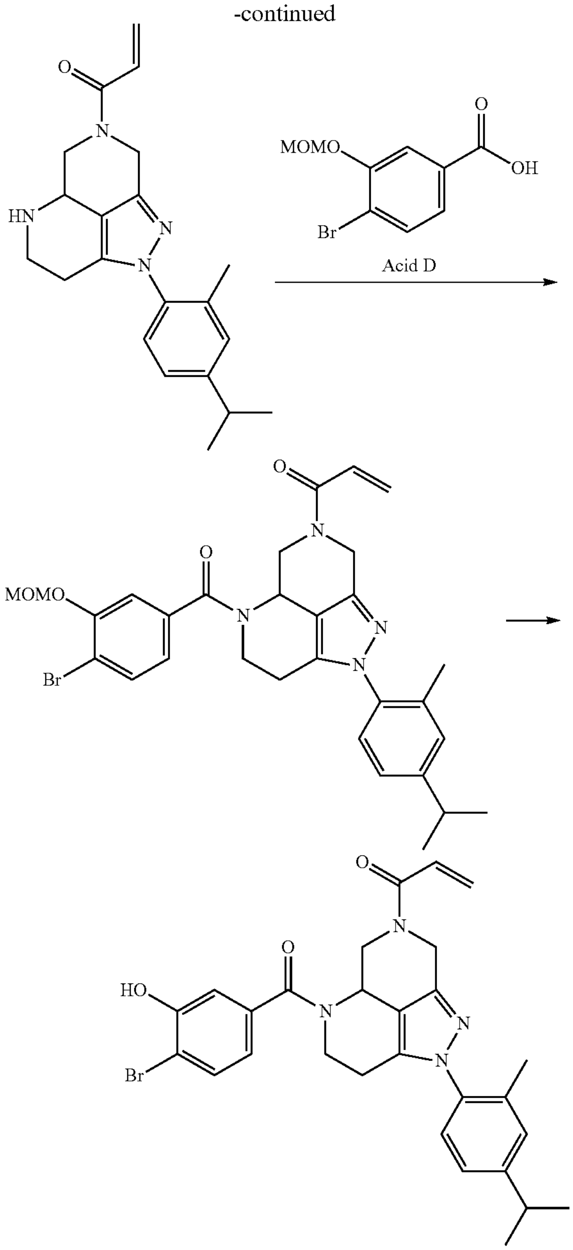

Step 1: Synthesis of 5-(tert-butyl) 3-ethyl 1,4,6,7-tetrahydro-5H-pyrazolo[4,3-c]pyridine-3,5-dicarboxylate To a stirred solution of tert-butyl 3-(2-ethoxy-2-oxoacetyl)-4-oxopiperidine-1-carboxylate (15 g, 51 mmol, 1 equiv) in EtOH (20 mL) was added hydrazine (1.63 g, 51.1 mmol, 1 equiv) dropwise at rt under nitrogen atmosphere. The resulting mixture was stirred for 2 h at rt under nitrogen atmosphere, and then was concentrated under reduced pressure. The residue was then purified by silica gel column chromatography, eluting with DCM:MeOH (12:1) to afford 5-(tert-butyl) 3-ethyl 1,4,6,7-tetrahydro-5H-pyrazolo[4,3-c]pyridine-3,5-dicarboxylate (13 g) as a yellow solid.

Step 2: Synthesis of 5-(tert-butyl) 3-ethyl 1-(4-isopropyl-2-methylphenyl)-1,4,6,7-tetrahydro-5H-pyrazolo[4,3-c]pyridine-3,5-dicarboxylate Into a 500 mL 3-necked round-bottom flask were added 5-(tert-butyl) 3-ethyl 1,4,6,7-tetrahydro-5H-pyrazolo[4,3-c] pyridine-3,5-dicarboxylate (5 g, 17 mmol, 1 equiv), 1-iodo-4-isopropyl-2-methylbenzene (6.61 g, 25.4 mmol, 1.5 equiv), $K_2CO_3$ (7.02 g, 50.8 mmol, 3 equiv), CuI (0.32 g, 1.69 mmol, 0.1 equiv), N-(anthracen-9-yl)-N'-[(pyridin-2-yl)methyl]ethanediamide (0.60 g, 1.69 mmol, 0.1 equiv) and DMF (100 mL). The resulting mixture was stirred for 3 h at 140° C. under an argon atmosphere, after which the mixture was allowed to cool to rt. The reaction was then quenched by the addition of water (100 mL). The resulting mixture was extracted with EtOAc (3×100 mL), and the combined organic layers were washed with a half saturated brine solution (2×200 mL) and brine (200 mL), after which it was dried over anhydrous $Na_2SO_4$. The mixture was then filtered, and the filtrate was concentrated under reduced pressure. The residue was purified by silica gel column chromatography, eluting with PE/EtOAc (5:1) to afford 5-(tert-butyl) 3-ethyl 1,4,6,7-tetrahydro-5H-pyrazolo[4,3-c] pyridine-3,5-dicarboxylate (1.5 g) as a brown solid.

Step 3: Synthesis of (rac)-5-(tert-butyl) 3-ethyl 4-cyano-1-(4-isopropyl-2-methylphenyl)-1,4,6,7-tetrahydro-5H-pyrazolo[4,3-c]pyridine-3,5-dicarboxylate To a stirred solution of 5-(tert-butyl) 3-ethyl 1,4,6,7-tetrahydro-5H-pyrazolo[4,3-c]pyridine-3,5-dicarboxylate (300 mg, 0.70 mmol, 1 equiv) and AcOH (168.6 mg, 2.81 mmol, 4 equiv) in MeCN (3 mL) were added TMSCN (278.45 mg, 2.808 mmol, 4 equiv) and TEMPO+BF4- (509.42 mg, 2.106 mmol, 3 equiv) in portions at rt. The resulting mixture was stirred for additional 2 h at rt. The reaction was quenched by the addition of brine (1 mL) at rt. The resulting mixture was extracted with EtOAc (2×2 mL). The combined organic layers were washed with brine (2×1 mL), and dried over anhydrous sodium sulfate. After filtration, the filtrate was concentrated under reduced pressure. The residue was purified by silica gel column chromatography, eluting with PE/EtOAc to afford (rac)-5-(tert-butyl) 3-ethyl 4-cyano-1-(4-isopropyl-2-methylphenyl)-1,4,6,7-tetrahydro-5H-pyrazolo[4,3-c]pyridine-3,5-dicarboxylate (240 mg) as a white solid.

Step 4: Synthesis of (rac)-4-(aminomethyl)-5-(tert-butoxycarbonyl)-1-(4-isopropyl-2-methylphenyl)-4,5,6,7-tetrahydro-JH-pyrazolo[4,3-c]pyridine-3-carboxylic Acid To a solution of (rac)-5-tert-butyl 3-ethyl 4-cyano-1-(4-isopropyl-2-methylphenyl)-4H,6H,7H-pyrazolo[4,3-c]pyridine-3,5-dicarboxylate (1.5 g, 3.3 mmol, 1 equiv) in $NH_3$(g) in MeOH (20 mL) was added Raney Ni (1.50 g, 17.5 mmol, 5.28 equiv) in a pressure tank. The tank was then charged with 30 psi of hydrogen pressure at 50° C. for 2 h, after which it was cooled and filtered through a Celite pad and concentrated under reduced pressure. The crude product was used in the next step directly without further purification. LCMS:(ESI, m/z)(ESI, m/z): 457 $[M+1]^+$.

A solution of (rac)-5-(tert-butyl) 3-methyl 4-(amino ethyl)-1-(4-isopropyl-2-methylphenyl)-1,4,6,7-tetrahydro-5H-pyrazolo[4,3-c]pyridine-3,5-dicarboxylate (1.2 g, 2.6 mmol, 1 equiv, crude from the previous step) and LiOH (0.13 g, 5.256 mmol, 2 equiv) in THF (12 mL) and water (6 mL) was stirred for 2 h at rt. The resulting mixture was concentrated under reduced pressure. The crude (rac)-4-(aminomethyl)-5-(tert-butoxycarbonyl)-1-(4-isopropyl-2-methylphenyl)-4,5,6,7-tetrahydro-1H-pyrazolo[4,3-c]pyridine-3-carboxylic acid was used in the next step directly without further purification. LCMS:(ESI, m/z)(ESI, m/z): 429 $[M+1]^+$.

Step 5: Synthesis of (rac)-tert-butyl 1-(4-isopropyl-2-methylphenyl)-3-oxo-3,4,5,5a,7,8-hexahydropyrazolo[3,4,5-de][1,7]naphthyridine-6(1H)-carboxylate To a stirred solution of (rac)-4-(aminomethyl)-5-(tert-butoxycarbonyl)-1-(4-isopropyl-2-methylphenyl)-4,5,6,7-tetrahydro-1H-pyrazolo[4,3-c]pyridine-3-carboxylic acid (1 g, 2.190 mmol, 1 equiv, used crude from the previous step) and DIEA (0.71 g, 5.475 mmol, 2.5 equiv) in DMF (10 mL) were added HATU (1.25 g, 3.285 mmol, 1.5 equiv). The resulting mixture was stirred for 1 h at rt. The reaction was then quenched by the addition of water (2 mL) at rt. The resulting mixture was extracted with EtOAc (2×10 mL). The combined organic layers ere washed with brine (2×2 mL), dried over anhydrous sodium sulfate, and filtered. After filtration, the filtrate was concentrated under reduced pressure, and the residue was purified by reverse-phase flash chromatography (column, C18; mobile phase, MeCN in water (10 mmol/L $NH_4HCO_3$), 40% to 70% gradient in 10 min; detector, UV 254 nm) to provide (rac)-tert-butyl 1-(4-isopropyl-2-methylphenyl)-3-oxo-3,4,5,5a,7,8-hexahydro-pyrazolo[3,4,5-de][1,7]naphthyridine-6(1H)-carboxylate (100 mg) as a white solid. LCMS:(ESI, m/z)(ESI, m/z): 41 $[M+1]^+$.

Step 6: Synthesis of (rac)-tert-butyl 1-(4-isopropyl-2-methylphenyl)-3,4,5,5a,7,8-hexahydropyrazolo[3,4,5-de][1,7]naphthyridine-6(1H)-carboxylate A solution of (rac)-tert-butyl 1-(4-isopropyl-2-methylphenyl)-3-oxo-3,4,5,5a,7,8-hexahydropyrazolo[3,4,5-de][1,7] naphthyridine-6(1H)-carboxylate (100 mg, 0.24 mmol, 1 equiv) and $BH_3$-THF (41.9 mg, 0.488 mmol, 2 equiv) in THF (1 mL) was stirred for 2 h at 60° C. The mixture was allowed to cool down to RT, after which it was quenched by the addition of ice water (1 mL) at rt. The resulting mixture was extracted with EtOAc (2×1 mL). The combined organic layers were washed with brine (2×1 mL), dried over anhydrous sodium sulfate, and filtered. The filtrate was concentrate under reduced pressure, and the resulting residue was purified by reverse-phase flash chromatography with the following conditions: column, C18; mobile phase, MeCN in water (10 mmol/L $NH_4HCO_3$), 30% to 70% gradient in 10 min; detector, UV 254 nm. This resulted in (rac)-tert-butyl 1-(4-isopropyl-2-methylphenyl)-3,4,5,5a,7,8-hexahydropyrazolo[3,4,5-de][1,7]naphthyridine-6(1H)-carboxylate (50 mg) as a yellow oil. LCMS (ESI, m/z): 397 $[M+1]^+$.

Step 7: Synthesis of (rac)-tert-butyl 4-acryloyl-1-(4-isopropyl-2-methylphenyl)-3,4,5,5a,7,8-hexahydro-pyrazolo[3,4,5-de][1,7]naphthyridine-6(1H)-carboxylate To a stirred solution of (rac)-tert-butyl 1-(4-isopropyl-2-methylphenyl)-3,4,5,5a,7,8-hexahydropyrazolo[3,4,5-de][1,7]naphthyridine-6(1H)-carboxylate (50 mg, 0.13 mmol, 1 equiv) and TEA (31.9 mg, 0.315 mmol, 2.5 equiv) in DCM (1 mL) was added acryloyl chloride (11.4 mg, 0.126 mmol, 1 equiv) dropwise at 0° C. The resulting mixture was then allowed to warm to rt and was stirred for 1 h. The reaction was then quenched by the addition of water (1 mL), and the resulting mixture was extracted with DCM (2×1 mL). The combined organic layers were washed with brine (2×1 mL), dried over anhydrous sodium sulfate, and filtered. After filtration, the filtrate was concentrated under reduced pressure, providing (rac)-tert-butyl 4-acryloyl-1-(4-isopropyl-2-methylphenyl)-3,4,5,5a,7,8-hexahydropyrazolo[3,4,5-de][1,7]naphthyridine-6(1H)-carboxylate (20 mg) as a colorless oil. LCMS:(ESI, m/z): 451 $[M+1]^+$.

Step 8: Synthesis of (rac)-1-(1-(4-isopropyl-2-methylphenyl)-1,5,5a,6,7,8-hexahydropyrazolo[3,4,5-de][1,7]naphthyridin-4(3H)-yl)prop-2-en-1-one A solution of tert-butyl 2-(4-isopropyl-2-methylphenyl)-6-(prop-2-enoyl)-2,3,6,9-tetraazatricyclo[6.3.1.0^{4,12}]dodeca-1(12),3-diene-9-carboxylate (20 mg, 0.044 mmol, 1 equiv) and TFA (0.1 mL) in DCM (0.2 mL) was stirred for 30 min at rt. The resulting mixture was concentrated under reduced pressure. The crude product was used in the next step directly without further purification. LCMS:(ESI, m/z): 351 $[M+1]^+$.

Step 9: Synthesis of (rac)-1-(6-(4-bromo-3-(methoxymethoxy)benzoyl)-1-(4-isopropyl-2-methylphenyl)-1,5,5a,6,7,8-hexahydropyrazolo[3,4,5-de][1,7]naphthyridin-4(3H)-yl)prop-2-en-1-one To a stirred solution of (rac)-1-(1-(4-isopropyl-2-methylphenyl)-1,5,5a,6,7,8-hexahydropyrazolo[3,4,5-de][1,7]naphthyridin-4(3H)-yl)prop-2-en-1-one (20 mg, 0.057 mmol, 1 equiv, used crude from the previous step) and 4-bromo-3-(methoxymethoxy)benzoic acid (14.9 mg, 0.057 mmol, 1 equiv) in DMF (0.5 mL) were added DIEA (18.4 mg, 0.143 mmol, 2.5 equiv), EDCI (16.41 mg, 0.086 mmol, 1.5 equiv) and HOBT (11.6 mg, 0.086 mmol, 1.5 equiv). The resulting mixture was stirred for additional 1 h at rt. The reaction was quenched by the addition of water (0.5 mL), and the resulting mixture was extracted with EtOAc (1×1 mL). The combined organic layers were washed with brine (2×0.5 mL), dried over anhydrous sodium sulfate, and filtered. After filtration, the filtrate was concentrated under reduced pressure, and the residue was purified by reverse-phase flash chromatography with the following conditions: column, C18; mobile phase, MeCN in water (10 μmol/L $NH_4HCO_3$), 60% to 90% gradient in 10 min; detector, UV 254 nm. This resulted in (rac)-1-(6-(4-bromo-3-(methoxymethoxy)benzoyl)-1-(4-isopropyl-2-methylphenyl)-1,5,5a,6,7,8-hexahydropyrazolo[3,4,5-de][1,7]naphthyridin-4(3H)-yl)prop-2-en-1-one (20 mg) as a white solid. LCMS:(ESI, m/z): 593 $[M+1]^+$.

Step 10: Synthesis of (SAND R)-1-(6-(4-bromo-3-hydroxybenzoyl)-1-(4-isopropyl-2-methylphenyl)-1,5,5a,6,7,8-hexahydropyrazolo[3,4,5-de][1,7]naphthyridin-4(3H)-yl)prop-2-en-1-one A solution of (rac)-1-(6-(4-bromo-3-(methoxymethoxy)benzoyl)-1-(4-isopropyl-2-methylphenyl)-1,5,5a,6,7,8-hexahydropyrazolo[3,4,5-de][1,7]naphthyridin-4(3H)-yl)prop-2-en-1-one (20 mg, 0.034 mmol, 1 equiv) and TFA (0.1 mL) in DCM (0.2 mL) was stirred for 30 min at rt. The resulting mixture was concentrated under reduced pressure. The crude product was purified by Prep-HPLC with the following conditions: Column, XBridge Prep OBD C18 Column, 30*150 mm, 5 m; mobile phase, water (10 mmol/L $NH_4HCO_3$) and MeCN (34% MeCN up to 65% in 8 min); Detector, UV 220 nm. The collected solution was concentrated under vacuum to remove $CH_3CN$ and the resulting solution was dried by lyophilization. This resulted in (S AND R)-1-(6-(4-bromo-3-hydroxybenzoyl)-1-(4-isopropyl-2-methylphenyl)-1,5,5a,6,7,8-hexahydropyrazolo[3,4,5-de][1,7]naphthyridin-4(3H)-yl)prop-2-en-1-one (4.9 mg, 26.31%) as a white solid. LCMS:(ESI, m/z): 551 $[M+1]^+$. $^1H$ NMR: (400 MHz, Chloroform-d) δ 7.55 (d, J=8.1 Hz, 1H), 7.22-7.10 (m, 4H), 6.91 (dd, J=8.1, 2.0 Hz, 1H), 6.38 (d, J=16.6 Hz, 1H), 6.00 (s, 1H), 5.78 (d, J=10.1 Hz, 1H), 5.63 (d, J=17.3 Hz, 1H), 5.03 (brs, 2H), 4.17 (d, J=17.2 Hz, 1H), 3.96 (brs, 1H), 3.18 (brs, 1H), 2.98-2.81 (m, 2H), 2.73 (dd, J=13.8, 9.1 Hz, 1H), 2.65-2.46 (m, 1H), 2.15 (s, 3H), 1.26 (d, J=6.9 Hz, 6H).

Example F-2: Preparation of (S or R)-1-(5-(4-bromo-3-hydroxybenzoyl)-2-(4-isopropyl-2-methylphenyl)-2,4,5,5a,6,8,9,11-octahydro-10-oxa-1,2,5,7-tetraazacyclonona[cd]inden-7(3H)-yl)prop-2-en-1-one

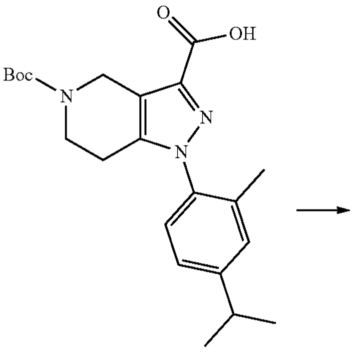

Int. AA

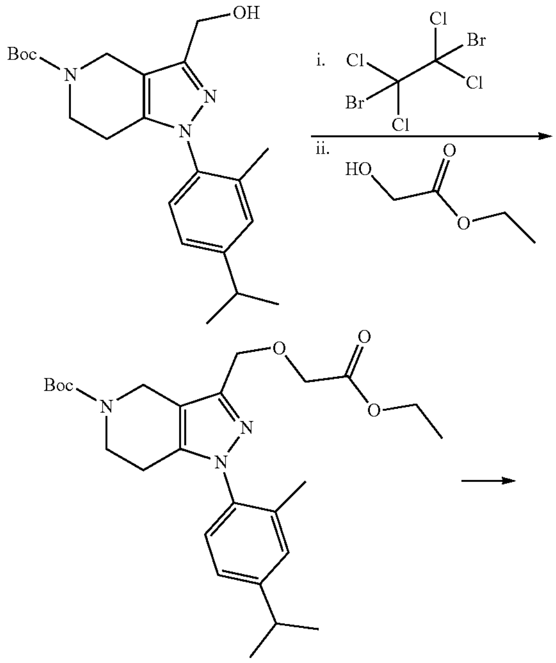

-continued

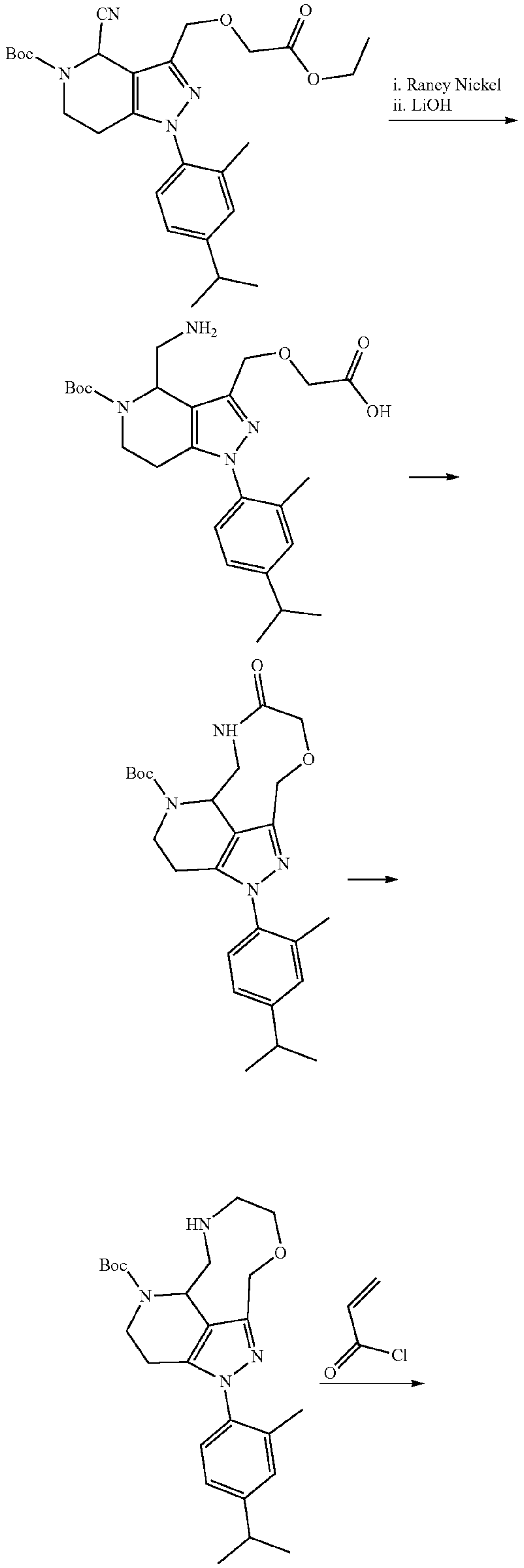

-continued

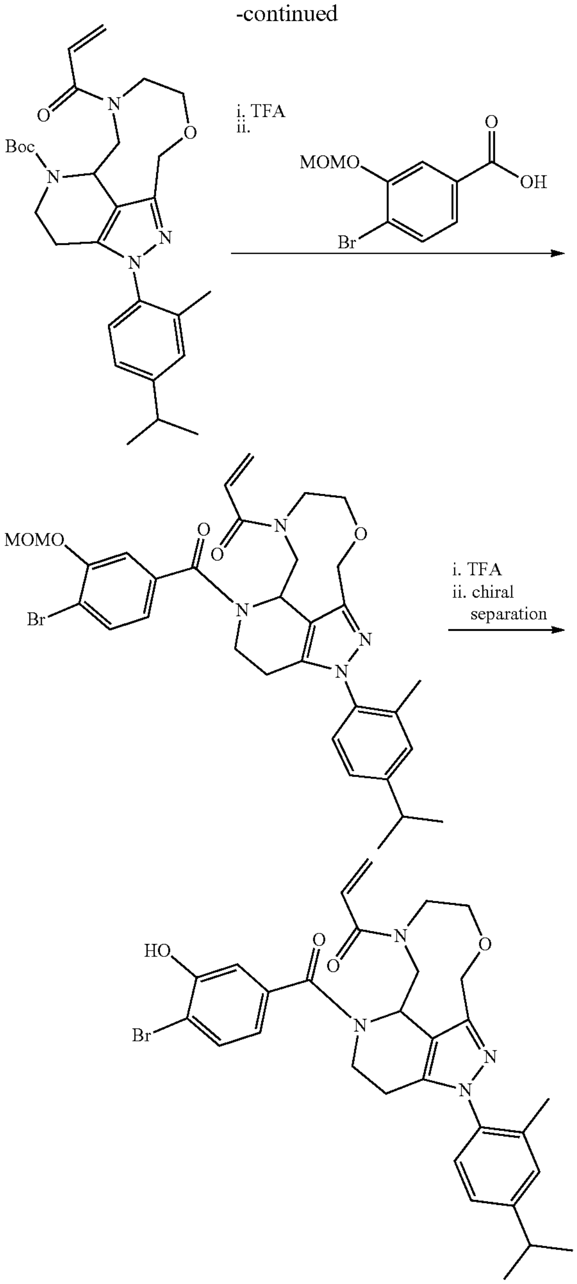

Step 1: Synthesis of 5-(tert-butoxycarbonyl)-1-(4-isopropyl-2-methylphenyl)-4,5,6,7-tetrahydro-1H-pyrazolo[4,3-c]pyridine-3-carboxylic Acid To a stirred mixture of 5-(tert-butoxycarbonyl)-1-(4-isopropyl-1-methylphenyl)-4,5,6,7-tetrahydro-1H-pyrazolo[4,3-c]pyridine-3-carboxylic acid (Int. AA) (4.5 g, 10.5 mmol, 1 equiv) in THF (40 mL) and MeOH (5 mL) was added $NaBH_4$ (0.80 g, 21.1 mmol, 2 equiv) in portions at 0° C. under a nitrogen atmosphere. The resulting mixture was further stirred for 1 h, after which it was quenched by the addition of water (50 mL) at rt. The resulting mixture was extracted with EtOAc (2×20 mL), and the combined organic layers were washed with brine (1×100 mL) and dried over anhydrous sodium sulfate. The mixture was then filtered, and the filtrate was concentrated under reduced pressure.

The residue was purified by silica gel column chromatography, eluting with PE/EtOAc (1:1) to afford tert-butyl 3-(hydroxymethyl)-1-(4-isopropyl-2-methylphenyl)-1,4,6,7-tetrahydro-5H-pyrazolo[4,3-c]pyridine-5-carboxylate (3.8 g) as a white solid.

Step 2: Synthesis of Tert-Butyl 3-(bromomethyl)-1-(4-isopropyl-2-methylphenyl)-1,4,6,7-tetrahydro-5H-pyrazolo[4,3-c]pyridine-5-carboxylate A solution of tert-butyl 3-(hydroxymethyl)-1-(4-isopropyl-2-methylphenyl)-1,4,6,7-tetrahydro-5H-pyrazolo[4,3-c]pyridine-5-carboxylate (2.9 g, 7.5 mmol 1 equiv), $PPh_3$ (4.34 g, 16.551 mmol, 2.2 equiv) and 1,2-dibromo-1,1,2,2-tetrachloroethane (5.39 g, 16.6 mmol, 2.2 equiv) in DCM (29 mL) was stirred for 20 min at rt under a nitrogen atmosphere. The mixture was then quenched with water (100 mL), after which it was extracted with EtOAc (1×100 mL). The combined organic layers were washed with brine (1×100 mL), dried over anhydrous $Na_2SO_4$. The mixture was the filtered, and the filtrate was concentrated under reduced pressure. The residue was purified by silica gel column chromatography, eluting with EtOAc/PE (1/1) to afford tert-butyl 3-(bromomethyl)-1-(4-isopropyl-2-methylphenyl)-1,4,6,7-tetrahydro-5H-pyrazolo[4,3-c]pyridine-5-carboxylate (2.5 g) as a yellow solid. LCMS:(ESI, m/z): 448[M+1]$^+$.

Step 3: Synthesis of Tert-Butyl 3-((2-ethoxy-2-oxoethoxy)methyl)-1-(4-isopropyl-2-methylphenyl)-1,4,6,7-tetrahydro-5H-pyrazolo[4,3-c]pyridine-5-carboxylate To a stirred solution of ethyl 2-hydroxyacetate (0.61 g, 5.9 mmol, 1.2 equiv) in THF (44 mL) was added NaH (0.14 g, 5.9 mmol, 1.2 equiv) in portions at 0° C. under a nitrogen atmosphere. The resulting mixture was further stirred for 30 min at 0° C., after which tert-butyl 3-(bromomethyl)-1-(4-isopropyl-2-methylphenyl)-1,4,6,7-tetrahydro-5H-pyrazolo [4,3-c]pyridine-5-carboxylate (2.2 g, 4.9 mmol, 1 equiv) was added in portions at 0° C. The resulting mixture was stirred for additional 1 h at rt. The reaction was then quenched with water at RT, and the resulting mixture was extracted with EtOAc (1×100 mL). The combined organic layers were washed with brine (1×100 mL) and dried over anhydrous $Na_2SO_4$. The mixture was then filtered, and the filtrate was concentrated under reduced pressure. The residue was purified by silica gel column chromatography, eluting with EtOAc/PE (1/1) to afford tert-butyl 3-((2-ethoxy-2-oxoethoxy)methyl)-1-(4-isopropyl-2-methylphenyl)-1,4,6,7-tetrahydro-5H-pyrazolo[4,3-c]pyridine-5-carboxylate (1.9 g) as a yellow solid. LCMS:(ESI, m/z): 472[M+1]$^+$.

Step 4: Synthesis of (rac)-tert-butyl 4-cyano-3-((2-ethoxy-2-oxoethoxy) ethyl)-1-(4-isopropyl-2-methylphenyl)-1,4,6,7-tetrahydro-5H-pyrazolo[4,3-c]pyridine-5-carboxylate A solution of tert-butyl 3-((2-ethoxy-2-oxoethoxy) methyl)-1-(4-isopropyl-2-methylphenyl)-1,4,6,7-tetrahydro-5H-pyrazolo[4,3-c]pyridine-5-carboxylate (1.9 g, 4.0 mmol, 1 equiv), AcOH (0.48 g, 8.1 mmol, 2 equiv). TMSCN (1.60 g, 16.1 mmol, 4 equiv) and TEMPO (tetrafluoroborate salt, 2.92 g, 12.1 mmol, 3 equiv) in MeCN (38 mL) was stirred for overnight at rt under a nitrogen atmosphere. The reaction was quenched by the addition of water (200 mL) at RT, and the resulting mixture was extracted with EtOAc (2×200 mL). The combined organic layers were washed with brine (1×200 mL) and dried over anhydrous $Na_2SO_4$. The resulting mixture was then filtered, and the filtrate was concentrated under reduced pressure. The residue was purified by silica gel column chromatography, eluting with EtOAc/PE (1/1) to afford (rac)-tert-butyl 4-cyano-3-((2-ethoxy-2-oxoethoxy)methyl)-1-(4-isopropyl-1-methylphenyl)-1,4,6,7-tetrahydro-5H-pyrazolo[4,3-c]pyridine-5-carboxylate (1.6 g) as a yellow solid. LCMS:(ESI, m/z): 497[M+1]$^+$.

Step 5: Synthesis of (rac)-tert-butyl 4-(aminomethyl)-3-((2-ethoxy-2-oxoethoxy)methyl)-1-(4-isopropyl-2-methylphenyl)-1,4,6,7-tetrahydro-5H-pyrazolo[4,3-c]pyridine-5-carboxylate To a solution of (rac)-tert-butyl 4-cyano-3-((2-ethoxy-2-oxoethoxy)methyl)-1-(4-isopropyl-2-methylphenyl)-1,4,6,7-tetrahydro-5H-pyrazolo[4,3-c]pyridine-5-carboxylate (1.3 g, 2.6 mmol, 1 equiv) in MeOH (39 mL) was added Raney nickel (130 mg, 0.15 mmol, 0.06 equiv, 10%) in a pressure tank. The mixture was stirred at rt under 3 MPa of hydrogen pressure for 3 h, after which the reaction was filtered through a Celite pad and concentrated under reduced pressure. The crude product (1.4 g) was used in the next step directly without further purification. LCMS:(ESI, m/z): 501[M+1]$^+$.

Step 6: Synthesis of (rac)-2-((4-(aminomethyl)-5-(tert-butoxycarbonyl)-1-(4-isopropyl-2-methylphenyl)-4,5,6,7-tetrahydro-JH-pyrazolo[4,3-c]pyridin-3-yl)methoxy)acetic Acid A solution of (rac)-tert-butyl 4-(aminomethyl)-3-((2-ethoxy-2-oxoethoxy)methyl)-1-(4-isopropyl-2-methylphenyl)-1,4,6,7-tetrahydro-5H-pyrazolo[4,3-c]pyridine-5-carboxylate (600 mg, 1.2 mmol, 1 equiv) and LiOH (57.4 mg, 2.40 mmol, 2 equiv) in EtOH (6 mL) and water (3 mL) was stirred for overnight at rt under a nitrogen atmosphere. The resulting mixture was then concentrated under vacuum. The crude product (700 mg) was used in the next step directly without further purification. LCMS:(ESI, m/z): 473[M+1]$^+$.

Step 7: Synthesis of (rac)-tert-butyl 2-(4-isopropyl-2-methylphenyl)-8-oxo-2,3,5a,6,7,8,9,11-octahydro-10-oxa-1,2,5,7-tetraazacyclonona[cd]indene-5(4H)-carboxylate A solution of (rac)-2-((4-(aminomethyl)-5-(tert-butoxycarbonyl)-1-(4-isopropyl-2-methylphenyl)-4,5,6,7-tetrahydro-1H-pyrazolo[4,3-c]pyridin-3-yl)methoxy)acetic acid (400 mg, 0.85 mmol, 1 equiv), HATU (643.67 mg, 1.692 mmol, 2 equiv) and DIE (656.37 mg, 5.076 mmol, 6 equiv) in DCM (200 mL) was stirred for 2 h at rt under a nitrogen atmosphere. The resulting mixture was concentrated under reduced pressure, and the residue was dissolved in water (100 mL). The resulting mixture was extracted with EtOAc (1×100 mL), and the combined organic layers were washed with brine (1×100 mL) and dried over anhydrous $Na_2SO_4$. The mixture was then filtered, and the filtrate was concentrated under reduced pressure. The residue was purified by silica gel column chromatography, eluting with EtOAc/PE (1/1) to afford (rac)-tert-butyl 2-(4-isopropyl-2-methylphenyl)-8-oxo-2,3,5a,6,7,8,9,11-octahydro-10-oxa-1,2,5,7-tetraazacyclonona[cd]indene-5(4H)-carboxylate (100 mg) as a yellow solid. LCMS:(ESI, m/z): 455[M+1]$^+$.

Step 8: Synthesis of (rac)-tert-butyl 2-(4-isopropyl-2-methylphenyl)-2,3,3a,6,7,8,9,11-octahydro-10-oxa-1,2,5,7-tetraazacyclonona[cd]indene-5(4H)-carboxylate A solution of (rac)-tert-butyl 2-(4-isopropyl-2-methylphenyl)-8-oxo-2,3,5a,6,7,8,9,11-octahydro-10-oxa-1,2,5,7-tetraazacyclonona[cd]indene-5(4H)-carboxylate (130 mg, 0.29 mmol, 1 equiv) and $BH_3$·THF (98.31 mg, 1.144 mmol, 4 equiv) in THF (2.6 mL) was stirred for 2 h at 60° C. under nitrogen atmosphere. The reaction was then quenched by the addition of MeOH (10 mL) at rt. The resulting mixture was extracted with EtOAc (1×100 mL), and the combined organic layers were washed with brine (1×100 mL) and dried over anhydrous $Na_2SO_4$. The mixture was then filtered, and the filtrate was concentrated under reduced pressure. The crude product (150 mg) was used in the next step directly without further purification. LCMS:(ESI, m/z): 441 $[M+1]^+$.

Step 9: Synthesis of (rac)-tert-butyl 7-acryloyl-2-(4-isopropyl-2-methylphenyl)-2,3,5a,6,7,8,9,11-octahydro-10-oxa-1,2,5,7-tetraazacyclonona[cd]indene-5(4H)-carboxylate To a stirred solution of (rac)-tert-butyl 2-(4-isopropyl-2-methylphenyl)-2,3,5a,6,7,8,9,11-octahydro-10-oxa-1,2,5,7-tetraazacyclonona[cd]indene-5(4H)-carboxylate (120 mg, 0.27 mmol, 1 equiv) and TEA (137.8 mg, 1.360 mmol, 5 equiv) in DCM (2.4 mL) was added acryloyl chloride (49.3 mg, 0.544 mmol, 2 equiv) dropwise at 0° C. under a. T nitrogen atmosphere. The resulting mixture was stirred for overnight at RT, after which the reaction was quenched by the addition of water (20 mL) at rt. The resulting mixture was extracted with EtOAc (1×30 mL), and the combined organic layers were washed with brine (1×20 mL), dried over anhydrous $Na_2SO_4$, and filtered. The filtrate was concentrated under reduced pressure, and the residue was further purified by silica gel column chromatography, eluting with EtOAc/PE (1/1) to afford (rac)-tert-butyl 7-acryloyl-2-(4-isopropyl-2-methylphenyl)-2,3,5a,6,7,8,9,11-octahydro-10-oxa-1,2,5,7 -tetraazacyclonona[cd]indene-5(4H)-carboxylate (46 mg) as a yellow solid. LCMS:(ESI, m/z): 495$[M+1]^+$.

Step 10: Synthesis of (rac)-1-(2-(4-isopropyl-2-methylphenyl)-2,4,5,5a,6,8,9,11-octahydro-10-oxa-1,2,5,7-tetraazacyclonona[cd]inden-7(3H)-yl)prop-2-en-1-one To a stirred solution of tert-butyl 3-(4-isopropyl-2-methylphenyl)-10-(prop-2-enoyl)-13-oxa-2,3,7,10-tetraazatricyclo[6.6.1.0^(4,15]pentadeca-1,4(15)-diene-7-carboxylate (40 mg, 0.081 mmol, 1 equiv) in DCM (0.8 mL) was added TFA (0.4 mL) dropwise at rt under a nitrogen atmosphere. The resulting mixture was stirred for 1 h at RT, after which the resulting mixture was concentrated under vacuum. The crude product was used in the next step directly without further purification. LCMS:(ESI, m/z): 395$[M+1]^+$.

Step 11: Synthesis of (rac)-1-(5-(4-bromo-3-(methoxymethoxy)benzoyl)-2-(4-isopropyl-2-methylphenyl)-2,4,5,5a,6,8,9,11-octahydro-10-oxa-1,2,5,7-tetraazacyclonona[cd]inden-7(3H)-yl)prop-2-en-1-one A solution of (rac)-1-(2-(4-isopropyl-2-methylphenyl)-2,4,5, a,6,8,9,11-octahydro-10-oxa-1,2,5,7-tetraazacyclonona[cd]inden-7(3H)-yl)prop-2-en-1-one (43 g, 0.11 mmol, 1 equiv), 4-bromo-3-(methoxymethoxy) benzoic acid (34.2 mg, 0.131 mmol, 1.2 equiv), DIEA (70.4 mg, 0.545 mmol, 5 equiv), EDCI (31.3 mg, 0.164 mmol, 1.5 equiv) and HOBT (22.1 mg, 0.164 mmol, 1.5 equiv) in DMF (0.86 mL) was stirred for 2 h at rt under a nitrogen atmosphere. The reaction was then quenched by the addition of water (20 mL) at rt. The resulting mixture was extracted with EtOAc (1×20 mL), and the combined organic layers were washed with brine (1×20 mL) and dried over anhydrous $Na_2SO_4$. The mixture was then filtered, and the filtrate was concentrated under reduced pressure. The residue was purified by silica gel column chromatography, eluting with EtOAc/PE (1/1) to afford (rac)-1-(5-(4-bromo-3-(methoxymethoxy)benzoyl)-2-(4-isopropyl-2-methylphenyl)-2,4,5,5a,6,8,9,11-octahydro-10-oxa-1,2,5,7-tetraazacyclonona[cd]inden-7(3H)-yl)prop one-2-en-1-one (45 mg) as a yellow solid. LCMS: (ESI, m/z): 637$[M+1]^+$.

Step 12: Synthesis of (S or R)-1-(5-(4-bromo-3-hydroxybenzoyl)-2-(4-isopropyl-2-methylphenyl)-2,4,5,5a,6,8,9,11-octahydro-10-oxa-1,2,5,7-tetraazacyclonona[cd]inden 7(3H)-yl)prop-2-en-1-one To a stirred solution of (rac)-1-(5-(4-bromo-3-(methoxymethoxy)benzoyl)-2-(4-isopropyl-2-methylphenyl)-2,4,5,5a,6,8,9,11-octahydro-10-oxa-1,2,5,7-tetraazacyclonona[cd]inden-7(3H)-yl)prop-2-en-1-one (46 mg, 0.072 mmol, 1 equiv) in DCM (0.92 mL) was added TFA (0.46 mL) dropwise at rt under a nitrogen atmosphere. The resulting mixture was then stirred for 30 min, and the resulting mixture was concentrated under vacuum. The crude product was purified by Prep-HPLC with the following conditions (Column: XBridge Shield RP18 OBD Column, 30*150 mm, 5 m; Mobile Phase A: water (10 mmol/L $NH_4HCO_3$), Mobile Phase B: MeCN; Flow rate: 60 mL/min; Gradient: 32% B to 60% in 8 min; Wave Length: UV 220 nm) to afford (rac)-1-(5-(4-bromo-3-hydroxybenzoyl)-2-(4-iso propyl-2-methylphenyl)-2,4,5,5a,6,8,9,11-octahydro-10-oxa-1,2,5,7-tetraazacyclonona[ed]inden-7(3H)-yl)prop-2-en-1-one (20 mg). The racemic product was then separated into its enantiomers via Prep-CHIRAL-HPLC with the following conditions (Column: CHIRALPAK IA, 2*25 cm, 20 μm; Mobile Phase A: Hex(0.1% FA)—HPLC, Mobile Phase B: EtOH:DCM=1:1-HPLC: Flow rate: 20 mL/min; Gradient: 25% B to 25% B in 18 min; Wave Length: UV 254/220 nm; Sample Solvent: EtOH—HPLC; Injection Volume: 0.5 mL; Number Of Runs: 2) to afford (S or R)-1-(5-(4-bromo-3-hydroxybenzoyl)-2-(4-isopropyl-2-methylphenyl)-2,4,5,5a,6,8,9,11-octahydro-10-oxa-1,2,5,7-tetraazacyclonona[cd]inden-7(3H)-yl)prop-2-en-1-one as the second-eluting peak (retention time: 14.8 min., 8.2 mg, 19.1%) as a white solid. LCMS:(ESI, m/z): 593.1$[M+]^+$. $^1$H NMR: (400 MHz, Chloroform-d) δ 7.55-7.46 (m, 1H), 7.18-7.02 (m, 4H), 6.97-6.80 (m, 1H), 6.55-6.26 (m, 1H), 6.23-6.05 (m, 2H), 5.75-5.37 (m, 1H), 5.35-4.94 (m, 1H), 4.91-4.49 (m, 1H), 4.49-3.70 (m, 5H), 3.70-2.97 (m, 3H), 2.97-2.64 (m, 1H), 2.64-2.08 (m, 2H), 2.02 (s, 3H), 1.24 (d, J=7.0 Hz, 6H).

Example F-3: Preparation of (S AND R)-1-(5-(4-bromo-3-hydroxybenzoyl)-2-(4-isopropylphenyl)-4,5,5a,6,8,9-hexahydro-1,5,7,9a-tetraazabenzo[cd]azulen-7(3H)-yl)prop-2-en-1-one
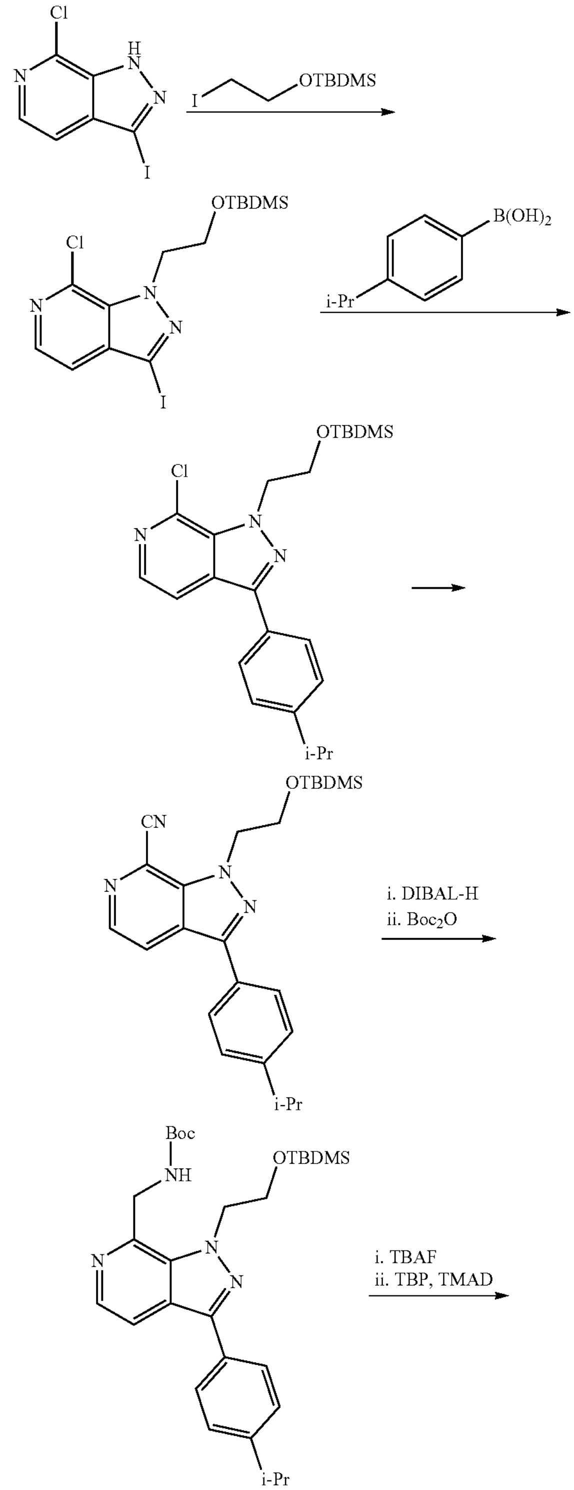
-continued
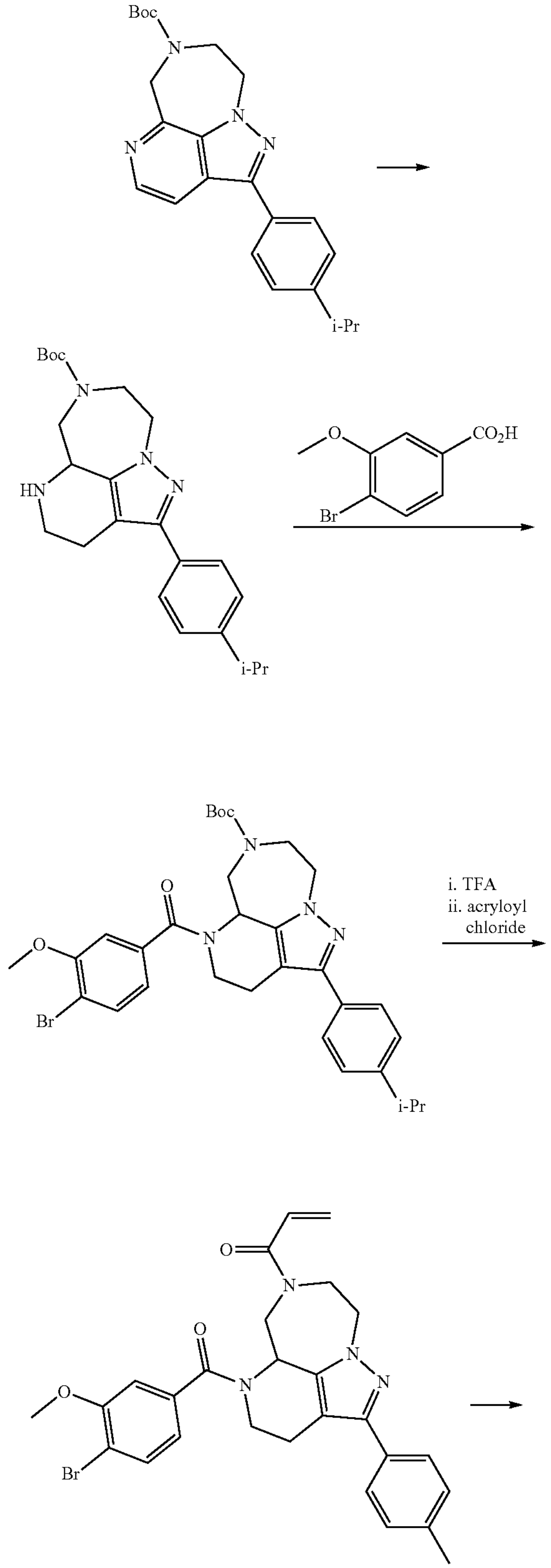

-continued

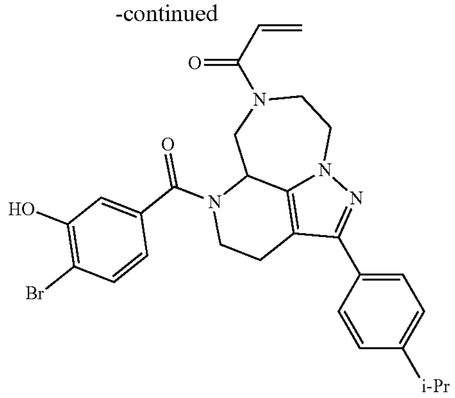

Step 1: Synthesis of 1-(2-((tert-butyldimethylsilyl) oxy)ethyl)-7-chloro-3-iodo-1H-pyrazolo[3,4-c]pyridine To a solution of 7-chloro-3-iodo-1H-pyrazolo[3,4-c]pyridine (2.73 g, 9.77 mmol) in DMF (32.6 mL) was added sodium hydride (430 mg, 10.7 mmol, 60% in mineral oil) in portions at 0° C. The mixture was allowed to slowly warm up to rt over 15 min, and tert-butyl(2-iodoethoxy)dimethylsilane (2.62 mL, 10.7 mmol) was added in portions at 0° C. The resulting mixture was then allowed to reach rt and stirred for 16 h. The reaction was then quenched at 0° C. with a sat. aqueous solution of NH4Cl and extracted with EtOAc. The combined organic layers were washed with water and brine, dried over anhydrous Na2SO4, filtered off, and concentrated under reduced pressure. The crude product was purified on silica gel chromatography (eluting with 0-10% ethyl acetate in hexane) to give 1-(2-((tert-butyldimethylsilyl)oxy)ethyl)-7-chloro-3-iodo-1H-pyrazolo[3,4-c] pyridine (2.31 g) as a solid. LCMS:(ESI, m/z): 438 $[M+1]^+$.

Step 2: Synthesis of 1-(2-((tert-butyldimethylsilyl) oxy)ethyl)-7-chloro-3 (4-isopropylphenyl)-JH-pyrazolo[3,4-c]pyridine A mixture of 1-(2-((tert-butyldimethylsilyl)oxy)ethyl)-7-chloro 3-iodo-1H-pyrazolo[3,4-c]pyridine (2.30 g, 5.25 mmol), 4-isopropylphenylboronic acid (1.07 g, 6.30 mmol) and potassium carbonate (1.45 g, 10.5 mmol) were suspended in dioxane (43.8 mL) and water (8.76 mL). The mixture was purged with argon before addition of 1,1'-bis (diphenylphosphino)ferrocene dichloropalladium (II) (192 mg, 263 umol). The mixture was then heated at 80° C. for 8 h. Upon completion, the reaction mixture was cooled to rt and diluted with EtOAc and washed with water, brine, and dried over sodium sulfate. Solvents were removed and the residue was purified by normal phase chromatography on 220 g silica (eluting with a gradient of EtOAc:Hexane, 0 to 15%) to give 1-(2-((tert-butyldimethylsilyl)oxy)ethyl)-7-chloro-3 (4-isopropylphenyl)-1H-pyrazolo[3,4-c]pyridine (1.75 g) as a light-yellow solid. LCMS:(ESI, m/s): 430 $[M+1]^+$. $^1$H NMR ($CHCl_3$-d, 400 MHz): δ 8.07 (1H, d, J=5.6 Hz), 7.82-7.78 (3H, m), 7.3 (2H, d, J=8.0 Hz), 4.99 (2H, t, J=5.8 Hz), 4.08 (2H, t, J=5.8 Hz), 3.01-2.94 (1H, m), 1.31 (6H d, J=6.9 Hz), 0.72 (9H, s), −0.17 (6H, s).

Step 3: Synthesis of 1-(2-((tert-butyldimethylsilyl) oxy)ethyl)-3 (4-isopropylphenyl)-1H-pyrazolo[3,4-c]pyridine-7-carbonitrile A mixture of 1-(2-((tert-butyldimethylsilyl)oxy)ethyl)-7-chloro-3-(4-isopropylphenyl)-1H-pyrazolo[3,4-c]pyridine (1.72 g, 4.00 mmol), zinc cyanide (352 mg, 3.00 mmol), zinc (26.7 mg, 400 umol), tris(dibenzylideneacetone)-dipalladium(0) (183 mg, 20 umol), DPPF (229 mg, 400 umol), and anhydrous N,N-Dimethylacetamide (16.0 mL) were placed into a pressure-capped glass reactor (10 mL) filled with argon. The mixture was stirred at 130° C. for 1 h. Upon completion, the reaction mixture was cooled to rt and diluted with EtOAc and washed with water, brine, and dried over sodium sulfate. Solvents were removed and the residue was purified by normal phase chromatography on 220 g silica (eluting with a gradient of EtOAc:Hexane, 0 to 10%) to give 1-(2-((tert-butyldimethylsilyl)oxy)ethyl)-3-(4-isopropylphenyl)-1H-pyrazolo[3,4-c]pyridine-7-carbonitrile (1.51 g) as a light-yellow solid. LCMS:(ESI, m/z): 421 $[M+1]^+$. $^1$H NMR (CHCl3-d, 400 MHz): δ 8.44 (1H, d, J=5.4 Hz), 8.09 (1H, d, J=5.4 Hz), 7.84-7.8 (2H, m), 7.42-7.40 (2H, m), 4.98 (2H, t, J=5.1 Hz), 4.09 (2H, t, J=5.1 Hz), 3.03-2.96 (1H, m), 1.31 (6H, d, J=6.9 Hz), 0.63 (9H, s), −0.22 (6H, s).

Step 4: Synthesis of (1-(2-((tert-butyldimethylsilyl) oxy)ethyl)-3-(4-isopropylphenyl)-1H-pyrazolo[3,4-c]pyridin-7-yl)methanamine 1-(2-((tert-butyldimethylsilyl)oxy)ethyl)-3-(4-isopropylphenyl) 1H-pyrazolo[3,4-c]pyridine-7-carbonitrile (1.51 g, 3.59 mmol) was dissolved in anhydrous DCM (23.9 mL) and cooled to −78° C. and diisobutylaluminum hydride (10.8 mL, 10.8 mmol) was added in small portions. After 1 h, the reaction mixture was allowed to warm to rt a d a saturated solution of ammonium chloride (5 mL) and saturated solution of sodium potassium tartrate (10 mL) were added. This solution was stirred until organic and water layers separated. The water layer was removed and extracted with DCM. The organic layer was dried over $Na_2SO_4$ and concentrated under reduced pressure to give crude (1-(2-((tert-butyldimethylsilyl)oxy)ethyl)-3-(4-isopropylphenyl)-1H-pyrazolo[3,4-c] pyridin-7-yl)methanamine (1.37 g which was used in the next step without further purification. LCMS:(ESI, m/z): 425 $[M+1]^+$.

Step 5: Synthesis of Tert-Butyl ((1-(2-((tert-butyldimethylsilyl)oxy)ethyl)-3-(4-isopropylphenyl)-1H-pyrazolo[3,4-c]pyridin-7-yl)methyl)carbamate A solution of (1-(2-((tert-butyldimethylsilyl)oxy)ethyl)-3-(4-isopropylphenyl)-1H-pyrazolo[3,4-c]pyridin-7-yl)methanamine (1.37 g, 3.23 mmol), di-tert-butyldicarbonate (1.42 g, 6.45 mmol) and TEA (904 uL, 6.45 mmol) in anhydrous DCM (32.3 mL) was stirred at rt for 16 h. The solvent was removed by rotary evaporation and the residue was purified by flash chromatography on silica gel (eluting with a gradient of 0 to 40% EtOAc in hexanes) to afford tert-butyl ((1-(2-((tert-butyldimethylsilyl)oxy)ethyl)-3-(4-isopropylphenyl)-1H-pyrazolo[3,4-c]pyridin-7-yl)methyl)carbamate (630 mg) as an off-white solid. LCMS:(ESI, m/z): 525 $[M+1]^+$. $^1$H NMR ($CHCl_3$-d, 400 MHz): δ 8.22 (1H, d, J=5.7 Hz), 7.82 (2H, d, =8.1 Hz), 7.76 (1H, d, J=5.7 Hz), 7.38 (2H, d, J=8.1 Hz), 6.48 (1H, s), 5.05 (2H, d, J=4.1 Hz), 4.75 (2H, t, J=4.9 Hz), 4.03 (2H, t, J=4.8 Hz), 3.02-2.95 (1H, m), 1.51 (9H, s), 1.31 (6H, d, J=6.9 Hz), 0.58 (9H, s), −0.34 (6H, s).

Step 6:Synthesis of Tert-butyl ((1-(2-hydroxyethyl)-3-(4-isopropylphenyl)-1H-pyrazolo[3,4-c]pyridin-7-yl)methyl)carbamate To a solution of tert-butyl ((1-(2-((tert-butyldimethylsilyl) oxy)ethyl)-3-(4-isopropylphenyl)-1H-pyrazolo[3,4-c]pyridin-7-yl)methyl)carbamate (300 mg, 572 umol) in THF (1.91 mL) at 0° C. was added tetrabutylammonium fluoride solution (686 uL, 686 umol) and the mixture was stirred at rt for 1 h. The mixture was quenched with water a d subsequently extracted with EtOAc. The combined organic layers were dried over $Na_2SO_4$ and concentrated. The residue was purified on a 12 g silica gel cartridge (eluting with a gradient of Hexanes/EtOAc from 0 to 100%). Appropriate fractions were combined and concentrated to afford tert-butyl ((1-(2-hydroxyethyl)-3-(4-isopropylphenyl)-1H-pyrazolo[3,4-c]pyridin-7-yl)methyl)carbamate (222 mg) as a light orange solid. LCMS:(ESI, m/z): 411 [M+1]$^+$. $^1$H NMR ($CH_3OH$-d4, 400 MHz): δ 8.19 (1H, d, J=5.7 Hz), 7.90-7.84 (3H, m), 7.40 (2H, d, J=8.1 Hz), 4.96 (2H, s), 4.78 (2H, t, J=5.3 Hz), 4.03 (2H, t, J=5.3 Hz), 3.01-2.96 (1H, m), 1.47 (9H, s), 1.31 (611, d, J=6.9 Hz).

Step 7: Synthesis of Tert-Butyl 2-(4-isopropylphenyl)-8,9-dihydro-1,5,7,9a-tetraazabenzo[cd]azulene-7(6H)-carboxylate An oven-dried vial equipped with a magnetic stir bar was char ed with tert-butyl ((1-(2-hydroxyethyl)-3-(4-isopropylphenyl)-1H-pyrazolo[3,4-c]pyridin-7-yl)methyl)carbamate (320 mg, 780 umol) and tributylphosphine (393 uL, 1.56 mmol) in toluene (14.3 mL). 1,1'-azobis(N,N-dimethylformamide) (274 mg, 1.56 mmol) were added slowly at 0° C. Within a few minutes solution went from yellow/orange to colorless with white solid precipitate. Removed the ice bath and left stirring at rt for 2 days. The solvent was then evaporated, and water was added and the residue was extracted with EtOAc. The organic layer was washed with brine, dried over $Na_2SO_4$, and the solvent was removed to afford the crude product. The residue as purified by silica-gel chromatography (eluting with a gradient of 0-100% EtOAc in Hexanes) to afford tert-butyl 2-(4-isopropylphenyl)-8,9-dihydro-1,5,7,9a-tetraazabenzo[cd]azulene-7(6H)-carboxylate (214 mg) as a white solid. LCMS:(ESI, m/z): 393 [M+H]$^+$.

Step 8: Synthesis of (rac)-tert-butyl 2-(4-isopropylphenyl)-4,5,5a,6,8,9-hexahydro-1,5,7,9a-tetraazabenzo[cd]azulene-7(3H)-carboxylate To a solution of tert-butyl 2-(4-isopropylphenyl)-8,9-dihydro-1,5,7,9a-tetraazabenzo[cd]azulene-7(6H)-carboxylate (214 mg, 545 umol) in Me H (10.0 mL) was added platinum (IV) oxide (43.0 mg, 189 umol). The reaction mixture was stirred under a pressure of 15 bar of $H_2$ gas overnight. Upon completion, the reaction mixture was filtered through Celite, and the solvents were removed to provide (rac)-tert-butyl 2-(4-isopropylphenyl)-4,5,5a,6,8,9-hexahydro-1,5,7,9a-tetraazabenzo[cd]azulene-7(3H)-carboxylate (195 mg) as a white solid. LCMS:(ESI, m/z): 397 [M+H]$^+$.

Step 9: Synthesis of (rac)-tert-butyl 5-(4-bromo-3-methoxybenzoyl)-2-(4 isopropylphenyl)-4,5,5a,6,8,9-hexahydro-1,5,7,9a-tetraazabenzo[cd]azulene-7(3H)-carboxylate A solution of (rac)-tert-butyl 2-(4-isopropylphenyl)-4,5,5a,6,8,9-hexahydro-1,5,7,9a-tetraazabenzo[cd]azulene-7(3H)-carboxylate (80.0 mg, 202 umol), 4-bromo-3-methoxybenzoic acid (57.1 mg, 242 umol), and DIPEA (105 uL, 605 umol) in anhydrous DMF (4.04 mL) was treated with HATU (117 mg, 303 umol) in one portion. The reaction mix e was stirred at rt for 1 h. The solvent was then removed in vacuo and the residue was taken up in EtOAc (25 mL). The organic solution was washed with water (15 mL), dried over $Na_2SO_4$, and in vacuo. The residue was purified by flash chromatography on 24 g silica gel (eluting with a gradient of 0 to 100% EtOAc in Hexanes) to afford (rac)-tert-butyl 5-(4-bromo-1-methoxybenzoyl)-2-(4-isopropylphenyl)-4,5,5a,6,8,9-hexahydro-1,5,7,9a-tetraazabenzo[cd]azulene-7(3H)-carboxylate (101 mg) as a white-off solid. LCMS:(ESI, m/z): 609 [M+H]$^+$.

Step 10: Synthesis of (rac)-(4-bromo-3-methoxyphenyl)(2-(4-isopropylphenyl)-3,5a,6,7,8,9-hexahydro-1,5,7,9a-tetraazabenzo[cd]azulen-5(4H)-yl)methanone The (rac)-tert-butyl 5-(4-bromo-3-methoxybenzoyl)-2-(4-isopropylphenyl)-4,5,5a,6,8,9-hexahydro-1,5,7,9a-tetraazabenzo[cd]azulene-7(3H)-carboxylate (101 mg, 166 umol) was dissolved in 1,4-dioxane (1.66 mL) and HCl (4.0 M in 1,4-dioxane, 1.66 mL, 6.63 mmol) was added under an argon atmosphere. The reaction mixture was stirred at for 1 h. The solvent was removed in vacuo to afford crude (rac)-(4-bromo-3-methoxyphenyl)(2-(4-isopropylphenyl)-3,5a,6,7,8,9-hexahydro-1,5,7,9a-tetraazabenzo[cd]azulen-5(4H)-yl)methanone (84.0 mg) as a light-yellow solid. LCMS:(ESI, m/z): 509 [M+H]$^+$.

Step 11: Synthesis of (rac)-1-(5-(4-bromo-3-methoxybenzoyl)-2-(4-isopropylphenyl)-4,5,5a,6,8,9-hexahydro-1,5,7,9a-tetraazabenzo[cd]azulen-7(3H)-yl)prop-2-en-1-one To an ice-cooled solution of (rac)-(4-bromo-3-methoxyphenyl)(2-(4-isopropylphenyl)-3,5a,6,7,8,9-hexahydro-1,5,7,9a-tetraazabenzo[ed]azulen-5(4H)-yl)methanone (84.0 mg, 165 umol) and DIPEA (144 uL, 824 umol) in DCM (2.36 mL) at 0° C. was added acryloyl chloride (16.1 uL, 198 umol), and the resulting mixture was stirred at 0° C. for 30 min. 2 mL MeOH was added to the reaction mixture and was stirred for 5 min. The volatiles was removed under reduced pressure and the material was purified by reverse phase chromatography (C18, 30 g), using a gradient of 10-100% acetonitrile in water (0.1% formic acid) to afford (rac)-1-(5-(4-bromo-3-methoxybenzoyl)-2-(4-isopropylphenyl)-4,5,5a,6,8,9-hexahydro-1,5,7,9-tetraazabenzo[cd]azulen-7(3H)-yl)prop-2-en-1-one (78.0 mg) as a white solid. LCMS:(ESI, m/z): 563 [M+H]$^+$.

Step 12: Synthesis of (SAND R)-1-(5-(4-bromo-3-hydroxybenzoyl)-2-(4-isopropylphenyl)-4,5,5a,6,8,9-hexahydro-1,5,7,9a-tetraazabenzo[cd]azulen-7(3H)-yl)prop-2-en-1-one Boron tribromide (692 uL, 692 umol) was added to an ice-cooled solution of (rac)-1-(5-(4-bromo-3-methoxybenzoyl)-2-(4-isopropylphenyl)-4,5,5a,6,8,9-hexahydro-1,5,7,9a-tetraazabenzo[cd]azulen-7(3H)-yl)prop-2-en-1-one (78.0 mg, 138 umol) in DCM (692 uL), and the resulting mixture was stirred at 0° C. for 20 min, then allowed to warn to rt and stirred for 2 h. Saturated aqueous $NaHCO_3$ was added to the reaction mixture, followed by EtOAc (50 mL). The organic layer was separated and washed with saturated aqueous $NaHCO_3$ (3×20 mL). The organic layer was then dried over $Na_2SO_4$, filtered, and concentrated in vacuo. The crude product was purified by chromatography on a silica gel column (eluting with a gradient of 0-10% MeOH in DCM)

to yield the crude product, which was purified again by prep-HP C to give (S AND R)-1-(5-(4-bromo-3-hydroxybenzoyl)-2-(4-isopropylphenyl)-4,5,5a,6,8,9-hexahydro-1,5,7,9a-tetraazabenzo[cd]azulen-7(3H)-yl)prop-2-en-1-one (7.0 mg, 7%) as a white solid. LCMS:(ESI, m/z): 549 $[M+H]^+$. $^1$H NMR (DMSO-d6, 400 MHz, 70° C.): δ 10.38-10.22 (1H, m), 7.62-7.55 (4H, m), 7.27 (2H, d, J=8.1 Hz), 7.04 (1H, d, J=1.9 Hz), 6.88 (1H, d, J=8.1, 1.9 Hz), 6.20 (1H, d, J=16.4 Hz), 5.74 (1H, d, J=10.6 Hz), 5.40 (1H, t, J=9.5 Hz), 4.83-4.63 (1H, m), 4.51 (1H, dd, J=14.6, 4.1 Hz), 4.37-4.18 (2H, m), 3.97-3.84 (1H, m), 3.60-3.43 (1H, m), 3.20-3.15 (1H, m), 2.98-2.81 (3H, m), 2.66-2.62 (1H, m), 1.22 (6H, d, J=6.9 Hz).

Example F-4: Preparation of (S or R)-1-(5-(7-bromo-1H-benzo[d]imidazole-4-carbonyl)-2-(4-isopropylphenyl)-4,5,5a,6,8,9-hexahydro-1,2a,5,7-tetraazabenzo[dd]azulen-7(3H)-yl)prop-2-en-1-one

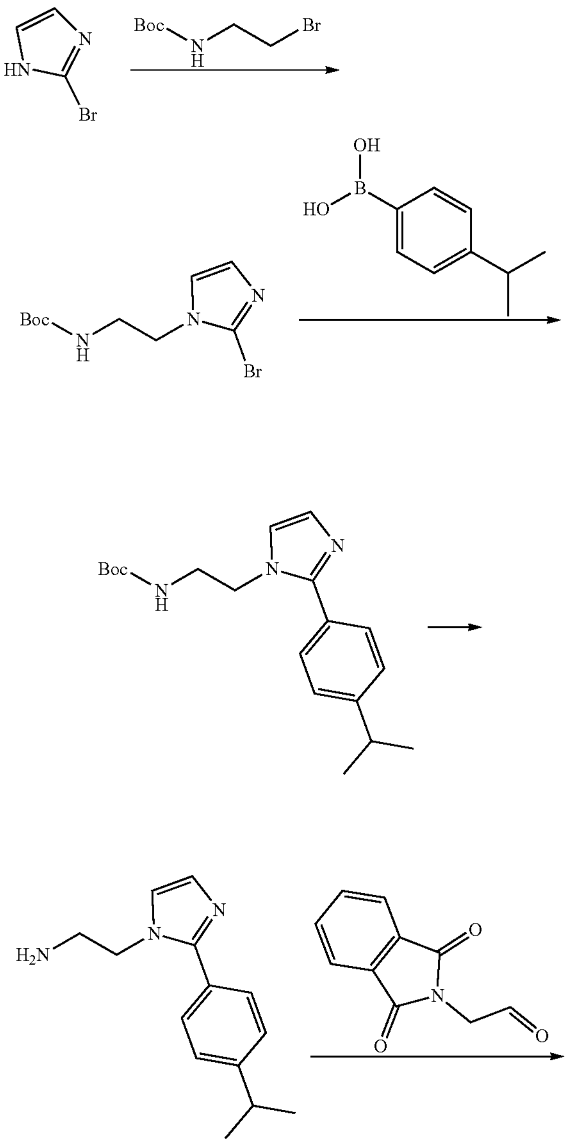

-continued

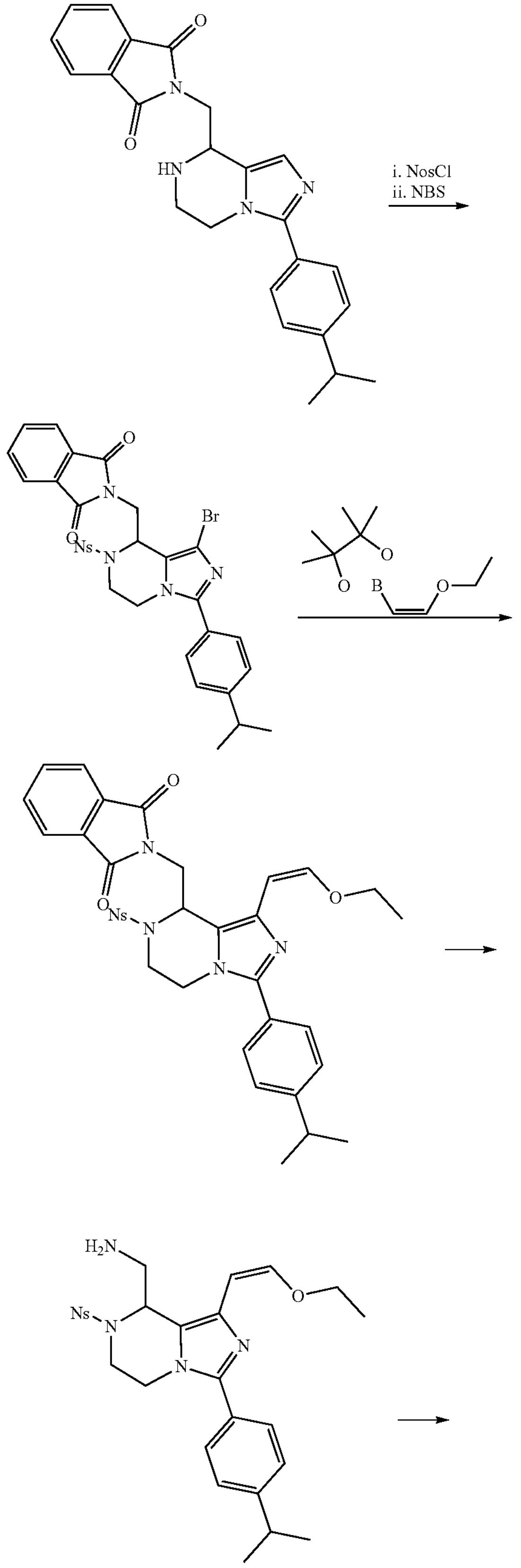

-continued

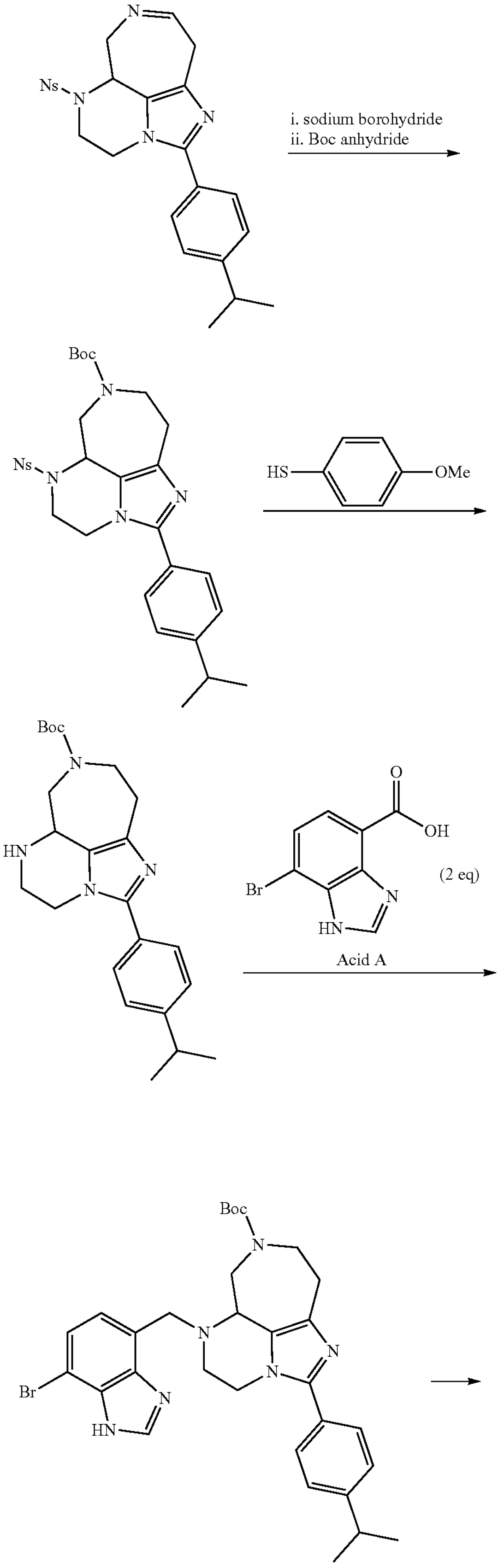

-continued

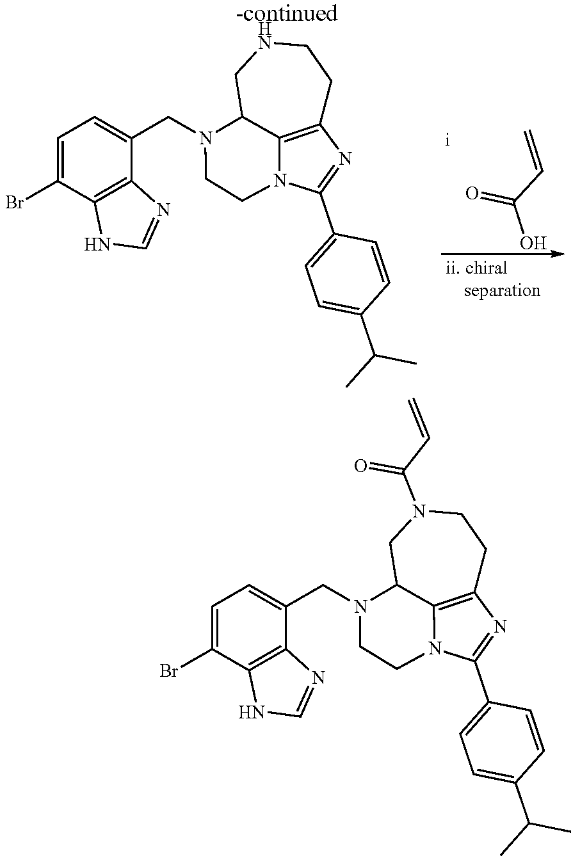

Step 1: Synthesis of Tert-Butyl (2-(2-bromo-1H-imidazol-1-yl)ethyl)carbamate

To a solution of 2-bromo-1H-imidazole (28 g, 1 equiv., 0.9 mol)) and potassium carbonate (190 g, 46 mL, 3 equiv., 0.57 mol) in acetonitrile (400 mL) was added tert-butyl (2-bromoethyl)carbamate (51 g, 1.2 equiv., 0.23 mol) at 80° C. The result ng mixture was refluxed for 16 h. The resulting mixture was cooled to rt and filtered. The filtrate was concentrated under reduced pressure and the crude product was recrystallized from diether to give tert-butyl (2-(2-bromo-1H-imi-dazol-1-yl)ethyl)carbamate (35 g) as a white solid. LCMS:(ESI, m/z): 290[M+H]$^+$.

Step 2: Synthesis of Tert-Butyl (2-(2-(4-isopropylphenyl)-1H-imidazol-1-yl)ethyl)carbamate The reaction was carried out by using a 500 mL three-necked flask. A solution of tert-butyl (2-(2-bromo-1H-imi-dazol-1-yl)ethyl)carbamate (40 g, 1 equiv., 0.14 mol), (4-isopropylphenyl)boronic acid (27 g, 1.2 equiv., 0.17 mol). tetrakis(triphenylphosphine)palladium(0) (8.0 g, 0.05 equiv., 6.9 mmol) and potassium carbonate (95 g, 40 mL, 5 equiv., 0.69 mol) in 1,4-dioxane (200 mL) and water (50.0 mL). The reaction mixture was stirred at 100° C. and monitored by LCMS. After completion the solvent was removed under reduced pressure, and EtOAc (100 mL) and water (50 mL) were added, and the mixture was filtered. The layers were separated, and the aqueous layer was extracted with EtOAc (80 mL). The combined organic layers were dried ($Na_2SO_4$) and filtered, and the solvent was removed. The residue was purified by column chromatography on silica gel to afford the desired product tert-butyl (2-(2-(4-isopropylphenyl)-1H-imidazol-1-yl)ethyl)carbamate (40 g). LCMS:(ESI, m/z): 330[M+H]$^+$.

Step 3: Synthesis of 2-(2-(4-isopropylphenyl)-1H-imidazol-1-yl)ethan-1-amine

A solution of tert-butyl (2-(2-(4-isopropylphenyl)-1H-imidazol 1-yl)ethyl)carbamate (40 g, 1 equiv., 0.12 mol) in a mixture of TFA (50 mL) and DCM (150 mL), which was stirred for 1 h at room temperature. The resulting mixture was concentrated in vacuo. The mixture was then redissolved in DCM(100 mL) and washed with sat. $NaHCO_3$ solution 50 mL), and the organic layer was dried over $Na_2SO_4$ and concentrated in vacuo. The crude product (60 g) was used in the next step directly without further purification. LCMS:(ESI, m/z): 230[+H]$^+$.

Step 4: Synthesis of (rac)-2-((3-(4-isopropylphenyl)-5,6,7,8-tetrahydroimidazo[1,5-a]pyrazin-8-yl)methyl)isoindoline-1,3-dione This reaction was performed 30 times in parallel. A mixture of 2-(2-(4-isopropylphenyl)-1H-imidazol-1-yl)ethan-1-amine (2.00 g, 1 equiv., 8.72 mmol), TFA (0.9 g, 0.1 equiv., 0.87 mmol) and 2-(1,3-dioxoisoindolin-2-yl)acetaldehyde (1.650 g, 1 equiv., 8.721 ol) in Ethanol (10 mL) was sealed and placed in a microwave reactor an stirred for 10 min (Biotage® Initiator+) (110° C.; 3-5 bars). All 30 reaction mixtures were collected and concentrated under vacuum, and the obtained crude product was recrystallized in DCM, the precipitate was redissolved in DCM (300 mL) and washed with sat. $NaHCO_3$ (200 mL). The organic layer was dried over $Na_2SO_4$ and concentrated under reduced pressure to give the product (rac)-2-((3-(4-isopropylphenyl)-5,6,7,8-tetrahydroimidazo[1,5-a]pyrazin-8-yl)methyl)isoindoline-1,3-dione (24.7 g) as a white solid. LCMS:(ESI, m/z): 401[M+H]$^+$.

Step 5: Synthesis of (rac)-2-((3-(4-isopropylphenyl)-7-((4-nitrophenyl)sulfonyl)-5,6,7,8-tetrahydroimidazo[1,5-a]pyrazin-8-yl)methyl)isoindoline-1,3-dione To a solution of freshly washed (rac)-2-((3-(4-isopropylphenyl)-5,6,7,8-tetrahydroimidazo[1,5-a]pyrazin-8-yl)methyl)isoindoline-1,3-dione (15.5 g, 1 equiv., 38.7 mmol) and TEA (11.7 g, 16.2 mL, 3 equiv., 116 mmol) in DCM (300 mL) was treated with 4-nitrobenzene- 1-sulfonyl chloride (43 g, 5 equiv., 194 mmol) at room temperature. The resulting mixture was stirred for 30 min. Excess 4-nitrobenzene-1-sulfonyl chloride was then added until the full consumption of the reactant. The mixture was then diluted with DCM (200 mL) and washed with water (2×300 mL). The collected organic layer was dried over $Na_2SO_4$ and filtered, and the solution was concentrated under reduced pressure. The crude product was purified by column chromatography ($SiO_2$, eluting with a gradient of MeOH in DCM from 9:1 to 4:1) and recrystallization from DCM/PE to give the product (rac)-2-((3-(4-isopropylphenyl)-7-((4-nitrophenyl)sulfonyl)-5,6,7,8-tetrahydroimidazo[1,5-a]pyrazin-8-yl)methyl)isoindoline-1,3-dione (18 g) as a light yellow solid. LCMS:(ESI, m/z): 586[M+H]$^+$.

Step 6: Synthesis of (rac)-2-((1-bromo-3-(4-isopropylphenyl)-7-((4-nitrophenyl)sulfonyl)-5,6,7,8-tetrahydroimidazo[1,5-a]pyrazin-8-yl)methyl)isoindoline-1,3-dione A solution of (rac)-2-((3-(4-isopropylphenyl)-7-((4-nitrophenyl)sulfonyl)-5,6,7,8-tetrahydroimidazo[1,5-a]pyrazin-8-yl)methyl)isoindoline-1,3-dione (18 g, 1 equiv., 30.74 mmol) in THF (500 mL) was added N-Bromosuccinimide (6.567 g, 1.2 equiv., 6.89 mmol), the mixture was stirred for 30 min at room temperature. LCMS tracked the full consumption of the reactant. The mixture was concentrated and redissolved in DCM(400 mL) and washed with water (2×200 mL). The collected organic layer was dried over $Na_2SO_4$. The solution was concentrated under reduced pressure. The crude product was purified by column chromatography ($SiO_2$, PE/EtOAc=4-2/1) to give (rac)-2-((1-bromo-3-(4-isopropylphenyl)-7-((4-nitrophenyl)sulfonyl)-5,6,7,8-tetrahydroimidazo[1,5-a]pyrazin-8-yl)methyl)isoindoline-1,3-dione (15.5 g). LCMS:(ESI, m/z): 664/666 [M+H]$^+$.

Step 7: (rac)-(Z)-2-((1-(2-ethoxyvinyl)-3-(4-isopropylphenyl)-7-((4-nitrophenyl)sulfonyl)-5,6,7,8-tetrahydroimidazo[1,5-a]pyrazin-8-yl)methyl)isoindoline-1,3-dione To a mixture of (rac)-2-((1-bromo-3-(4-isopropylphenyl)-7-((4-nitrophenyl)sulfonyl)-5,6,7,8-tetrahydroimidazo[1,5-a]pyrazin-8-yl)methyl)isoindoline-1,3-dione (9500 mg, 1 equiv., 14.3 mmol), (Z)-2-(2-ethoxyvinyl)-4,4,5,5-tetramethyl-1,3,2-dioxaborolane (5.63 g, 2 equiv., 28.6 mmol) and XPhos Pd G2 (1.13 g, 0.1 equiv., 1.43 mmol) in 1,4-dioxane (20 mL) was added sodium carbonate (4.55 g, 3 equiv., 42.9 mmol) in water (5.0 mL). The resulting mixture was stirred at 60° C. under nitrogen for 1 h. The mixture was then diluted was EtOAc (100 mL) and washed with water (50 mL). The collected organic layers were dried over $Na_2SO_4$, and concentrated under reduced pressure. The residue was purified by column chromatography (silica gel, eluting with a gradient of EtOAc in PE 20-50%) to give (rac)-(Z)-2-((1-(2-ethoxyvinyl)-3-(4-isopropylphenyl)-7-((4-nitrophenyl)sulfonyl)-5,6,7,8-tetrahydroimidazo[1,5-a]pyrazin-8-yl)methyl)isoindoline-1,3-dione (6.8 g) as a yellow solid. LCMS:(ESI, m/z): 656[M+H]$^+$.

Step 8: (rac)-(Z)-2-((1-(2-ethoxyvinyl)-3-(4-isopropylphenyl)-7-((4-nitrophenyl)sulfonyl)-5,6,7,8-tetrahydroimidazo[1,5-a]pyrazin-8-yl)methyl)isoindoline-1,3-dione A solution of (rac)-(Z)-2-((1-(2-ethoxyvinyl)-3-(4-isopropylphenyl)-7-((4-nitrophenyl)sulfonyl)-5,6,7,8-tetrahydroimidazo [1,5-a]pyrazin-8-yl)methyl)isoindoline-1,3-dione (6.8 g, 1 equiv., 10 mmol) in 30% methylamine in EtOH (70 mL) as stirred at 60° C. for 1 h. The resulting mixture was then concentrated in vacuo. The crude product (6.8 g crude) was used in the next step directly without further purification. LCMS:(ESI, m/z): 26[M+H]$^+$.

Step 9: Synthesis of (rac)-2-(4-isopropylphenyl)-5-((4-nitrophenyl)sulfonyl)-3,4,5,5a,6,9-hexahydro-1,2a,5,7-tetraazabenzo[cd]azulene The crude (rac)-(Z)-(1-(2-ethoxyvinyl)-3-(4-isopropylphenyl)-7-((4-nitrophenyl)sulfonyl)-5,6,7,8-tetrahydroimidazo[1,5-a]pyrazin-8-yl)methanamine (6.8 g, 1 equiv., 13 mmol) was dissolved in the mixture of THE (270 mL) and 1M HCl (270 mL). The resulting mixture was stirred at 60° C. for 2 h. The mixture was then diluted with Et Ac (40 mL) and washed with sat. $NaHCO_3$ (30 mL). The collected organic layer was dried over $Na_2SO_4$. The solution was concentrated under reduced pressure. The crude was purified by column chromatography (silica gel, eluting with a solution of PE/EtOAc=1/9) to give (rac)-2-(4-isopropylphenyl)-5-((4-nitrophenyl)sulfonyl)-3,4,5,5a,6,9-hexahydro-1,2a,5,7-tetraazabenzo[cd]azulene (900 mg). LCMS:(ESI, m/z): 480[M+H]$^+$.

Step 10: Synthesis of (rac)-2-(4-isopropylphenyl)-5-((4-nitrophenyl)sulfonyl)-3,4,5,5a,6,7,8,9-octahydro-1,2a,5,7-tetraazabenzo[cd]azulene To the (rac)-2-(4-isopropylphenyl)-5-((4-nitrophenyl)sulfonyl)-3,4,5,5a,6,9-hexahydro-1,2a,5,7-tetraazabenzo[cd]azulene (900 mg, 1 equiv., 1.88 mmol) in DCM (40 mL) and methanol (40 mL) was added sodium cyanoborohydride (1.18 g, 1.11 mL, 10 equiv., 18.8 mmol). The resulting mixture was stirred at room temperature overnight. The mix re was concentrated and redissolved in EtOAc (70 mL) and washed with water (2×30 mL). The collected organic layer was dried over $Na_2SO_4$. The solution was filtered, and the filtrate was concentrated under reduced pressure. The crude (970 mg) was used for the next step directly. LCMS:(ESI, m/z): 482[M+H]$^+$.

Step 11: Synthesis of (rac)-tert-butyl 2-(4-isopropylphenyl)-5-((4-nitrophenyl)sulfonyl)- 4,5,5a,6,8,9-hexahydro-1,2a,5,7-tetraazabenzo[cd]azule-ne-7(3H)-carboxylate To a suspended mixture of (rac)-2-(4-isopropylphenyl)-5-(4-nitrophenyl)sulfonyl)-3,4,5,5a,6,7,8,9-octahydro-1,2a,5,7-tetraazabenzo[cd]azulene (970 mg, equiv., 2.01 mmol) and TEA (611 mg, 842 μL, 3 equiv., 6.04 mmol) in DCM (40 mL) was added di-tert-butyl dicarbonate (528 mg, 539 μL, 1.2 equiv., 2.42 mmol) and a catalytic amount of MAP. The reaction was monitored by LCMS, and upon completion the mixture was concentrate and purified by column chromatography (silica gel, eluting with a gradient of PE:EtOAc=1:1-1:9) to afford (rac)-tert-butyl 2-(4-isopropylphenyl)-5-((4-nitrophenyl)sulfonyl)-4,5,5a,6,8,9-hexahydro-1,2a,5,7-tetraazabenzo[cd]azule-ne-7(3H)-carboxylate (721 mg) as a yellow solid. LCMS:(ESI, m/z): 582[M+H]$^+$.

Step 12: Synthesis of (rac)-tert-butyl 2-(4-isopropylphenyl)-4,5,5a,6,8,9-hexahydro-1,2a,5,7-tetraazabenzo[cd]azulene-7(3H)-carboxylate To a solution of (rac)-tert-butyl 2-(4-isopropylphenyl)-5-((4-nitrophenyl)sulfonyl)-4,5,5a,6,8,9-hexahydro-1,2a,5,7-tetraazabenzo[cd]azulene-7(3H)-carboxylate (621 mg, 1 equiv., 1.07 mmol) in $CH_3CN$ (50 mL) at room temperature was added cesium carbonate (3.48 g, 854 μL, 10 equiv., 10.7 mmol) and 4-methoxy-benzenethiol (748 mg, 656 μL, 5 equiv., 5.34 mmol). The mixture was stirred at room temperature for 1 h. The solvent was removed in vacuo and the residue was dissolved in DCM and extracted with 1 N aqueous HCl (80 mL), and the aqueous phase was adjusted to pH=12 with NaOH. Then the aqueous phase was extracted with EtOAc (60 mL), and the collected organic layer was dried over $Na_2SO_4$. The solution was then concentrated under reduced pressure. The crude (rac)-tert-butyl 2-(4-isopropylphenyl-4,5,5a,6,8,9-hexahydro-1,2a,5,7-tetraazabenzo[cd]azulene-7(3H)-carboxylate (327 mg) was use for the next step directly. LCMS:(ESI, m/z): 397[M+H]$^+$.

Step 13: Synthesis of (rac)-tert-butyl 5-(7-bromo-1H-benzo[d]imidazole 4-carbonyl)-2-(4-isopropylphenyl)-4,5,5a,6,8,9-hexahydro-1,2a,5,7-tetraazabenzo[cd]azulene-7(3H)-carboxylate To a solution of (rac)-tert-butyl 2-(4-isopropylphenyl)-4,5,5a,6,8,9-hexahydro-1,2a,5,7-tetraazabenzo[cd]azulene-7(3H)-carboxylate (200 mg, 1 equiv., 504 μmol) in DMF (1 mL) were added 7-bromo-1H-benzo[d]imidazole-4-carboxylic acid (243 mg, 2 equiv., 1.01 mmol), HATU (288 mg, 1.5 equiv., 757 mol) and DIPEA (196 mg, 261 μL, 3 equiv., 0.51 mmol). The mixture was stirred at room temperature for 16 h, after which the mixture was poured into water and extracted with EtOAc (40 mL×2). The organic layers were combined, dried over anhydrous sodium sulfate and concentrated in vacuo. The residue was purified by reverse-phase chromatography (Column: XBridge BEH Shield RP18 5 m, 30 mm*150 mm; Mobile Phase A: water (10 mmol/L $NH_4HCO_3$), Mobile Phase B: MeCN; Flow rate: 60 L/min; Gradient: 38% B to 57% B in 10 min; Wave Length: UV 254 nm/220 nm; retention time: 8.92) to afford (rac)-tert-butyl 5-(7-bromo-1H-benzo[d]imidazole-4-carbonyl)-2-(4-isopropylphenyl)-4,5,5a,6,8,9-hexahydro-1,2a,5,7-tetraazabenzo[cd]azulene-7(3H)-carboxylate (233 mg) as a white solid. LCMS:(ESI, m/z): 619/621 [M+H]$^+$.

Step 14: Synthesis of (rac)-tert-butyl 5-(7-bromo-JH-benzo[d]imidazole-4-carbonyl)-2-(4-isopropylphenyl)-4,5,5a,6,8,9-hexahydro-1,2a,5,7-tetraazabenzo[cd]azulene-7(3H)-carboxylate The solution of (rac)-tert-butyl 5-(7-bromo-1H-benzo[d]imidazole-4-carbonyl)-2-(4-isopropylphenyl)-4,5,5a,6,8,9-hexahydro-1,2a,5,7-tetraazabenzo[cd]azulene-7(3H)-carboxylate (240 mg, 1 equiv., 387 μmol) in DCM (10 mL) and TFA (3 mL) was stirred at room temperature for 1 h. The solvent was then removed in vacuo. The resulting (rac)-(7-bromo-1H-benzo[d]imidazol-4-yl)(2-(4-isopropylphenyl)-3,4,6,7,8,9-hexahydro-1,2a,5,7-tetraazabenzo[cd]azulen-5(5aH)-yl)methanone (425 mg) was obtained s a white solid, and the crude product was used in the next step directly without further purification. LCMS: (ESI, m/z): 619/621 [M+H]$^+$.

Step 15: Synthesis of Synthesis of (S or R)-1-(5-(7-bromo-JH-benzo[d]imidazole-4-carbonyl)-2-(4-isopropylphenyl)-4,5,5a,6,8,9-hexahydro-1,2a,5,7-tetraazabenzo[cd]azulen-7(3H)-yl)prop-2-en-1-one To a solution of (rac)-(7-bromo-1H-benzo[d]imidazol-4-yl)(2-(4-isopropylphenyl)-3,4,6,7,8,9-hexahydro-1,2a,5,7-tetraazabenzo[cd]azulen-5(5aH)-yl)methanone (100 mg, 1 equiv., 193 μmol) in DMF (2 mL) were added acrylic acid (20.8 mg, 19.8 μL, 1.5 equiv., 289 μmol), propylphosphonic anhydride (123 mg, 114 μL, 2 equiv., 385 μmol) and DIEA (249 mg, 335 μL, 10 equiv., 1.93 mmol). The mixture was stirred at room temperature or 16 h, after which the mixture was filtered and purified by reverse-phase chromatography (Column: Kinetex 5 m EVO C18, 30 mm*150 mm; Mobile Phase A: water (10 mmol/L $NH_4HCO_3$), Mobile Phase B: MeCN; Flow rate: 60 mL/min; Gradient: 22% B to 51% B in 8 min; Wave Length: UV 254 nm/220 nm; retention time: 7.48) to afford (rac)-1-(5-(7-bromo-1H-benzo[d]imidazole-4-carbonyl)-2-(4-isopropylphenyl)-4,5,5a,6,8,9-hexahydro-1,2a,5,7-tetraazabenzo[cd]azulen-7(3H)-yl)prop-2-en-1-one (30 mg) as a white solid.

The racemic compound was separated into constituent enantiomers by chiral HPLC separation under the following conditions (Column: CHIRAL ART Cel ulose-SB 2*25 cm, 5 μm; Mobile Phase A: HEX(0.1% FA), Mobile Phase B: EtOH:DCM=1:1 Flow rate: 20 mL/min; Gradient: isocratic 25; Wave Length: UV 254/220 nm; 16.85; Sample Solvent: EtOH:DCM; Injection Volume: 0.25 mL; Number Of Runs: 10) to afford the (R or S)-1-(5-(7-bromo-1H-benzo[d]imidazole-4-carbonyl)-2-(4-isopropylphenyl)-4,5,5a,6,8,9-hexahydro-1,2a,5,7-tetraazabenzo[cd]azulen-7(3H)-yl) prop-2-en-1-one as the second-eluting enantiomer (retention time=16.9 min, 10.1 mg, 17.4 mol, 33%, 98.93% purity) as a white foam. LCMS:(ESI, m/z): 573.3/575.3$[M+H]^+$. $^1H$ NMR: (400 MHz, DMSO-$d_6$, ppm) δ 13.09 (bis, 1H), 8.44 (s, 1H), 7.67-7.46 (m, 3H), 7.42-7.22 (m, 4H), 6.53-6.17 (m, 1H), 6.00-5.76 (m, 1H), 5.66-5.40 (m, 1H), 4.71-4.62 (m, 1H), 4.55-4.10 (m, 2H), 4.02-3.71 (m, 2H), 3.65-3.48 (m, 2H), 3.02-2.77 (m, 3H), 1.21 (d, J=6.9 Hz, 6H).

Example F-5: Preparation of (S or R)-1-(2-(4-cyclobutylphenyl)-5-(5 hydroxy-6-(trifluoromethyl) nicotinoyl)-4,5,5a,6,8,9-hexahydro-1,2a,5,7-tetraazabenzo[cd]azulen-7(3H)-yl)prop-2-en-1-one

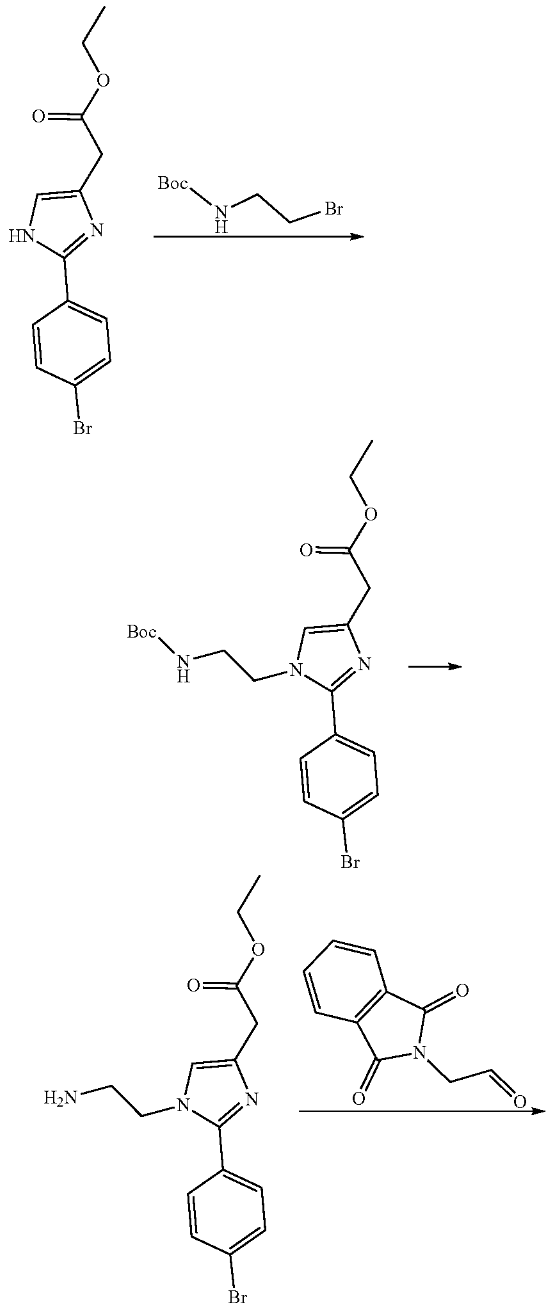

-continued

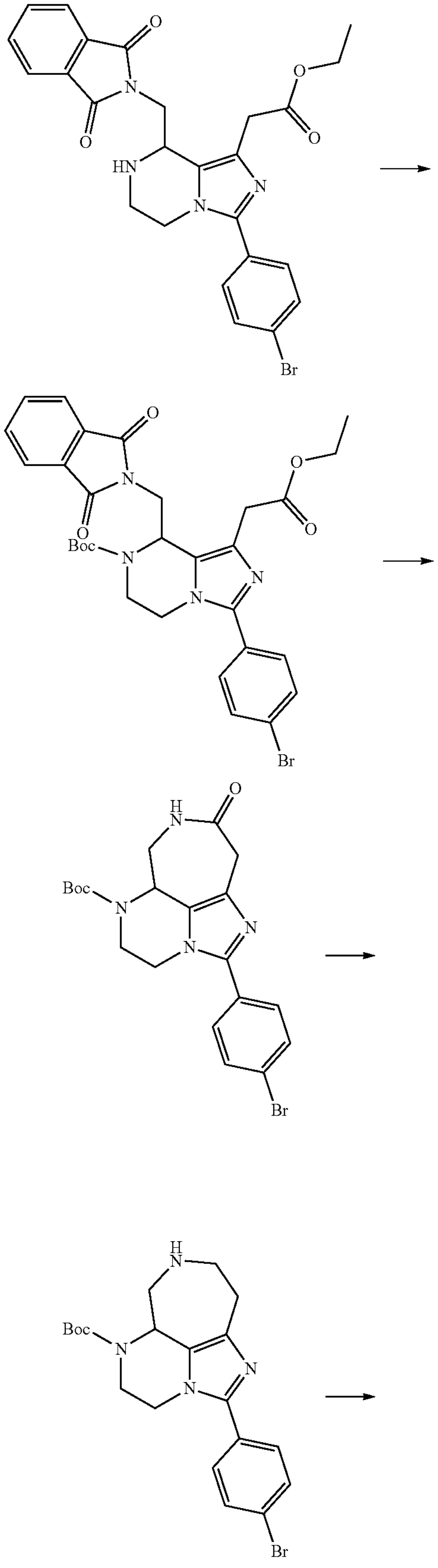

-continued

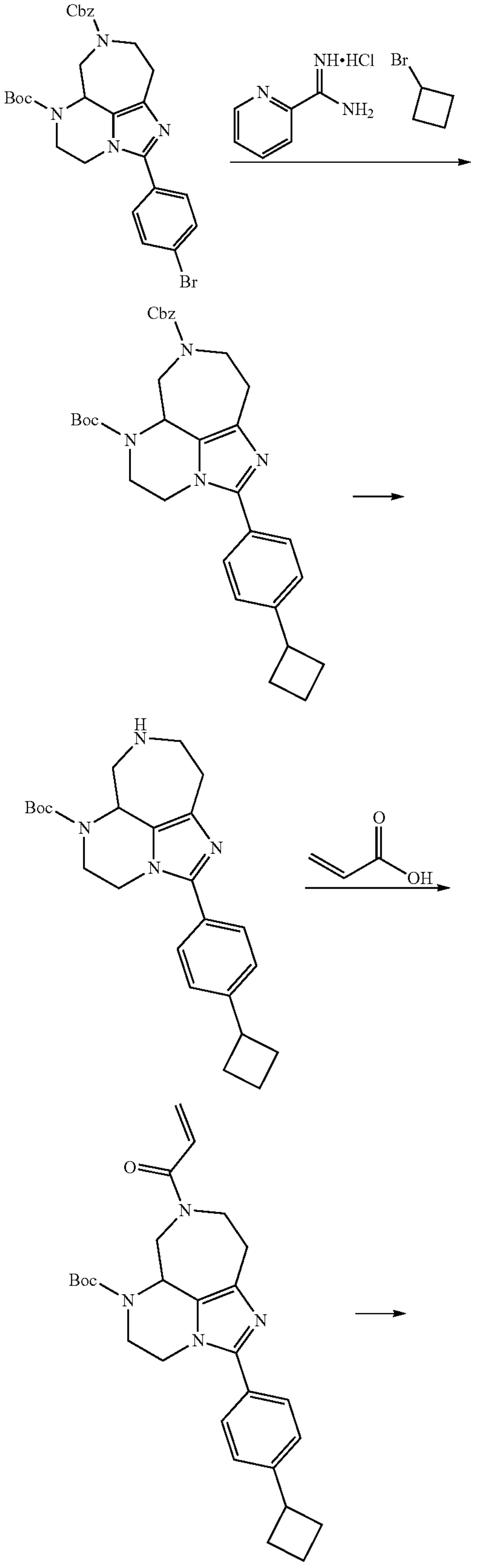

-continued

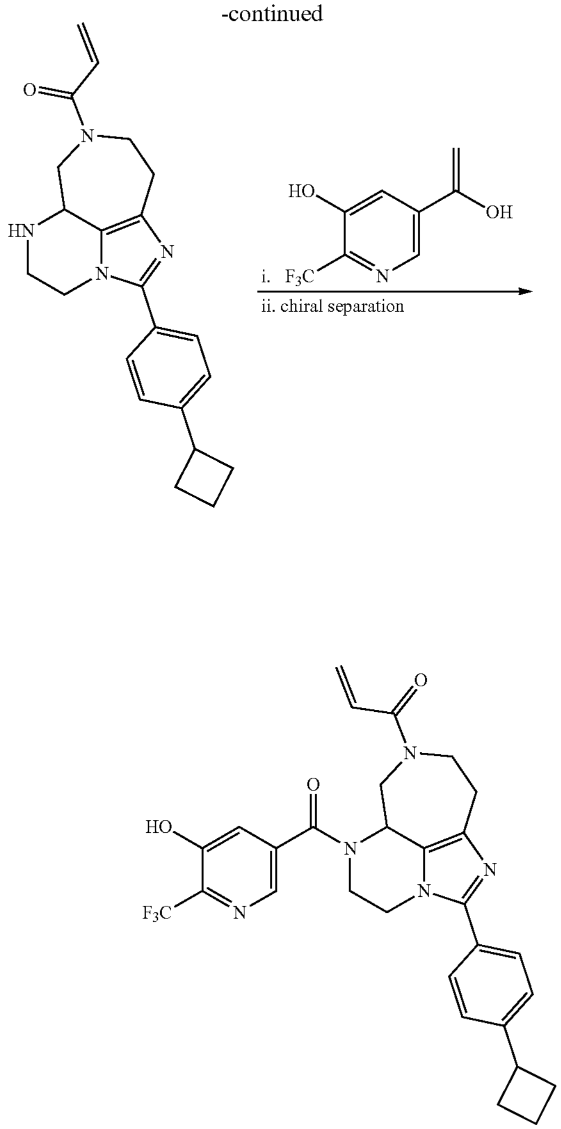

Step 1: Synthesis of Ethyl 2-(2-(4-bromophenyl)-1-(2-((tert-butoxycarbonyl)amino)ethyl)-1H-imidazol-4-yl)acetate To a solution of ethyl 2-(2-(4-bromophenyl)-1H-imidazol-4-yl)acetate (5 g, 1 equiv., 0.02 mol) in DMF (50 mL) were added $Cs_2CO_3$ (10 g, 2 equiv., 31 mmol) and tert-butyl (2-bromoethyl)carbamate (7 g, 2 equiv., 0.03 mol). The resulting mixture was stirred for 12 h at 80° C. under a $N_2$ atmosphere, after which it was cooled to rt and filtered. The filter was rinsed with EA (3×50 mL), and the combined filtrate was diluted with water (10 mL). The aqueous layer was extracted with EA (2×50 mL) and the combined organic layers were washed with saturated brine (3×80 mL), dried over anhydrous sodium sulfate and concentrated to give a residue. The crude product was purified by silica gel chromatography eluting with PE:EA=3:1 to give ethyl 2-(2-(4-bromophenyl)-1-(2-((tert-butoxycarbonyl)amino)ethyl)-1H-imidazol-4-yl)acetate (4 g) as a white solid. LCMS:(ESI, m/z): 452 $[M+1]^+$.

Step 2: Synthesis of Ethyl 2-(1-(2-aminoethyl)-2-(4-bromophenyl)-1H-imidazol-4-yl)acetate The solution of ethyl 2-(2-(4-bromophenyl)-1-(2-((tert-butoxycarbonyl)amino)ethyl)-1H-imidazol-4-yl)acetate (4 g, 1 equiv., 9 mmol) in TFA (10 mL) and DCM (40 mL) was stirred at rt for 4 h, after which the solvent was removed under reduced pressure to afford 2-(1-(2-aminoethyl)-2-(4-bromophenyl)-1H-imidazol-4-yl)acetate (6.5 g) as a crude yellow oil which was used in the next step directly without further purification. LCMS:(ESI, m/z): 352 $[M+1]^+$.

Step 3: Synthesis of Ethyl 2-(3-(4-bromophenyl)-8-((1,3-dioxoisoindolin-2-yl)methyl)-5,6,7,8-tetrahydroimidazo[1,5-a]pyrazin-1-yl)acetate A mixture of TFA (0.21 g, 0.1 Eq, 1.8 mmol), ethyl 2-(1-(2-aminoethyl)-2-(4-bromophenyl)-1H-imidazol-4-yl) acetate (6.5 g, 1 Eq, 18 mmol) and 2-(1,3-dioxoisoindolin-2-yl)acetaldehyde (7.0 g, 2 Eq, 37 mmol) in EtOH (130 mL) was sealed and put in the microwave reactor (Biotage® Initiator+) (140° C.; 3-5 bars; 0.5 h). The mixture was then collected and concentrated under vacuum, then diluted with DCM(20 mL) and adjusted the pH to 8 with TEA. Then the mixture was concentrated reduced pressure and the residue was purified by flash column chromatography, eluting with EA/PE(0.1% TEA) (1:2) to afford ethyl 2-(3-(4-bromophenyl)-8-((1,3-dioxoisoindolin-2-yl)methyl)-5,6,7,8-tetrahydroimidazo[1,5-a]pyrazin-1-yl)acetate (2 g) as a white solid. LCMS:(ESI, m/z): 523 $[M+1]^+$.

Step 4: Synthesis of Afford Tert-Butyl 3-(4-bromophenyl)-8-((1,3-dioxoisoindolin-2-yl)methyl)-1-(2-ethoxy-2-oxoethyl)-5,6-dihydroimidazo[1,5-a]pyrazine-7(8H)-carboxylate To a solution of ethyl 2-(3-(4-bromophenyl)-8-((1,3-dioxoisoindolin-2-yl)methyl)-5,6,7,8-tetrahydroimidazo[1,5-a]pyrazin-1-yl)acetate (2 g, 1 Eq, 4 mmcl) in DCM (20 mL) was added DMAP (0.2 g, 0.5 Eq, 2 mmol) and TEA (1 g, 3 Eq, 0.01 mol). The mixture was cooled to 0° C., then di-tert-butyl dicarbonate (1 g, 1.5 Eq, 6 mmol) was added dropwise to the above mixture at 0° C. The mixture was warmed to rt and stirred for 24 h. after which the mixture was diluted with ice water (20 mL) and EA (20 mL), and the aqueous layer was extracted with EA (2×20 mL). The combined organic layers were washed with saturated brine (2×20 mL), dried over anhydrous sodium sulfate and concentrated to give a residue. The residue was purified by flash column chromatography, eluting with EA/PE (1:1) to afford tert-butyl 3-4-bromophenyl)-8-((1,3-dioxoisoindolin-2-yl) methyl)-1-(2-ethoxy-2-oxoethyl)-5,6-dihydroimidazo[1,5-a]pyrazine-7(8H)-carboxylate (1.2 g) as a white solid. LCMS:(ESI, m/z): 623 $[M+1]^+$.

Step 5: Synthesis of Tert-Butyl 2-(4-bromophenyl)-8-oxo-3,4,6,7,8,9-hexahydro-1,2a,5,7-tetraazabenzo[cd]azulene-5(5aH)-carboxylate A solution of tert-butyl 3-(4-bromophenyl)-8-((1,3-dioxoisoindolin-2-yl)methyl)-1-(2-ethoxy-2-oxoethyl)-5,6-dihydroimidazo[1,5-a]pyrazine-7(8H)-carboxylate (1.1 g, 1 Eq, 1.8 mmol) and $MeNH_2$ (1.4 g, 20 Eq, 35 mmol) in EtOH (22 mL) was stirred at 80° C. for 20 h. The reaction mixture was then cooled to rt and concentrated under reduced pressure to provide a residue, which was purified by flash column chromatography, eluting with EA/PE (1:2) to afford tert-butyl 2-(4-bromophenyl)-8-oxo-3,4,6,7,8,9-hexahydro-1,2a,5,7-tetraazabenzo[cd]azulene-5(5aH)-carboxylate (0.9 g) as a white solid. LCMS:(ESI, m/z): 447 $[M 1]^+$.

Step 6: Synthesis of Tert-Butyl 2-(4-bromophenyl)-3,4,6,7,8,9-hexahydro-1,2a,5,7-tetraazabenzo[cd]azulene-5(5aH)-carboxylate A solution of tert-butyl 2-(4-bromophenyl)-8-oxo-3,4,6,7,8,9-hexahydro-1,2a,5,7-tetraazabenzo[cd]azulene-5(5aH)-carboxylate (960 mg, 1 Eq, 2.15 mmol) in THF (10 mL) was cooled to 0° C., then $BH_3$·THF (10.7 mL, 1 M, 5 Eq, 10.7 mmol) was added dropwise to the above mixture. The mixture was then heated to 60° C. and stirred for 2 h, after which the mixture was cooled to 0° C. and quenched by the addition of MeOH. The mixture was then directly concentrated under reduced pressure to afford tert-butyl 2-(4-bromophenyl)-3,4,6,7,8,9-hexahydro-1,2a,5,7-tetraazabenzo[cd]azulene-5(5aH)-carboxylate (980 mg) as a crude yellow oil which was used in the next step directly without further purification. LCMS:(ESI, m/z): 433 $[M+1]^+$.

Step 7: Synthesis of Benzyl 5-(tert-butyl) 2-(4-bromophenyl)-3,4,5a,6,8,9-hexahydro-1,2a,5,7-tetraazabenzo[cd]azulene-5,7-dicarboxylate To a solution of tert-butyl 2-(4-bromophenyl)-3,4,6,7,8,9-hexahydro-1,2a,5,7 -tetraazabenzo[cd]azulene-5(5aH)-carboxylate (880 mg, 1 Eq, 2.03 mmol) in DCM (9 mL) were added TEA (2.05 g, 2.83 mL, 10 Eq, 20.3 mmol) and Cbz-OSu (1.52 g, 3 Eq, 6.09 mmol). The resulting mixture was stirred for 16 h at 40° C., after which the mixture was cooled to rt, filtered, and rinsed with DCM (3×10 mL). The filtrate was diluted with water (50 mL) and the aqueous layer was extracted with DCM (2×20 mL). The combined organic layers were washed with saturated brine (2×50 mL), dried over anhydrous sodium sulfate and concentrated to give a residue. The crude product was purified by silica gel chromatography, eluting with PE:EA=1:1 to give 7-benzyl 5-(tert-butyl) 2-(4-bromophenyl)-3,4,5a,6,8,9-hexahydro-1,2a,5,7-tetraazabenzo[cd]azulene-5,7-dicarboxylate (450 mg) as a white solid. LCMS:(ESI, m/z): 567 $[M+1]^+$.

Step 8: Synthesis of 7-benzyl 5-(tert-butyl) 2-(4-cyclobutylphenyl)-3,4,5a,6,8,9-hexahydro-1,2a,5,7-tetraazabenzo[cd]azulene-5,7-dicarboxylate To a solution of 7-benzyl 5-(tert-butyl) 2-(4-bromophenyl)-3,4,5a,6,8,9-hexahydro-1,2a,5,7-tetraazabenzo[cd]azulene-5,7-dicarboxylate (420 mg, 1 Eq, 740 mol) in DMA (5 mL) were added bromocyclobutane (500 mg, 5 Eq, 3.7 mmol), picolinimidamide (89.7 mg, 1 Eq, 740 gmol), tetra-butylammonium iodide (273 mg, 1 Eq, 740 μmol), nickel(II) chloride (95.9 mg, 1 Eq, 740 μmol) and manganese (122 mg, 3 Eq, 2.22 mmol). The reaction system was flushed with nitrogen (×3) and the resulting mixture was stirred for 16 h at 60° C. The reaction mixture was then cooled to rt, and the mixture was filtered and rinsed with EA (3×10 mL), then the diluted with water (10 mL). The aqueous layer was extracted with EA (2×10 mL) and the combined organic layers were washed with saturated brine (3×10 mL), dried over anhydrous sodium sulfate and concentrated to give a residue. The crude product was purified by silica gel chromatography, eluting with PE:EA=2:1 to give 7-benzyl 5-(tert-butyl) 2-(4-cyclobutylphenyl)-3,4,5a,6,8,9-hexahydro-1,2a,5,7-tetraazabenzo[cd]azulene-5,7-dicarboxylate (205 g) as a white solid. LCMS:(ESI, m/z): 543 $[M+1]^+$.

Step 9: Synthesis of Tert-Butyl 2-(4-cyclobutylphenyl)-3,4,6,7,8,9-hexahydro-1,2a,5,7-tetraazabenzo[cd]azulene-5(5aH)-carboxylate To a solution of 7-benzyl 5-(tert-butyl) 2-(4-cyclobutylphenyl)-3,4,5a,6,8,9-hexahydro-1,2a,5,7-tetraazabenzo[cd]azulene-5,7-dicarboxylate (185 mg, 1 Eq, 341 mol) in a solution of $NH_3$ in 1,4-dioxane (0.4 mol, 2 mL) were added $Pd(OH)_2/C$ (93 mg, 2(% wt) and Pd/C (93 mg, 10% wt). The mixture was pressurized 3.0 MPa with hydrogen at 50° C. or 4 h. The mixture was then filtered and rinsed with EA (5×5 mL), and the filtrate was concentrated under reduced pressure to afford tert-butyl 2-(4-cyclobutylphenyl)-3,4,6,7,8,9-hexahydro-1,2a,5,7-tetraazabenzo[cd]azulene-5 (5aH)-carboxylate (200 mg) as a crude white solid which was used in the next step directly without further purification. LCMS:(ESI, m/z): 409 $[M+1]^+$.

Step 10: Synthesis of Tert-Butyl 7-acryloyl-2-(4-cyclobutylphenyl)-3,4,6,7,8,9-hexahydro-1,2a,5,7-tetraazabenzo[cd]azulene-5(5aH)-carboxylate To a solution of tert-butyl 2-(4-cyclobutylphenyl)-3,4,6,7,8,9-hexahydro-1,2a,5,7-tetraazabenzo[cd]azulene-5 (5aH)-carboxylate (180 mg, 1 Eq, 441 μmol) in DCM (2 mL) was added TEA (134 mg, 184 μL, 3 Eq, 1.32 mmol). The mixture was cooled to 0° C., then acrylic acid (63.5 mg, 2 Eq, 881 mol) was added dropwise to the above mixture. The mixture was warmed to rt and stirred for 2 h, after which the mixture was diluted with ice water (20 mL) and DCM (10 mL), and the aqueous layer was extracted with DCM (2×10 mL). The combined organic layers were washed with saturated brine (2×10 mL), dried over anhydrous sodium sulfate and concentrated to give a residue. The residue was purified by flash column chromatography, eluting with EA/PE (1:1) to afford tert-butyl 7-acryloyl-2-(4-cyclobutylphenyl)-3,4,6,7,8,9-hexahydro-1,2a,5,7-tetraazabenzo[cd]azulene-5(5aH)-carboxylate (95 mg) as a white solid. LCMS:(ESI, m/z): 463 $[M+1]^+$.

Step 11: Synthesis of 1-(2-(4-cyclobutylphenyl)-4,5,5a,6,8,9-hexahydro-,2a,5,7-tetraazabenzo[cd]azulen-7(3H)-yl) prop-2-en-1-one A solution of tert-butyl 7-acryloyl-2-(4-cyclobutylphenyl)-3,4,6,7,8,9-hexahydro-1,2a,5,7-tetraazabenzo[cd]azulene-5(5aH)-carboxylate (85 mg, 1 Eq, 0.18 mmol) in DCM (0.8 mL) and TFA (0.2 mL) was stirred at rt for 2 h. The solvent was then removed under reduced pressure to afford 1-(2-(4-cyclobutylphenyl)-4,5,5a,6,8,9-hexahydro-1,2a,5,7-tetraazabenzo[cd]azulen-7(3H)-yl)prop-2-en-1-one (120 mg) as a crude yellow oil. The crude product was used in the next step directly without further purification. LCMS:(ESI, m/z): 363 $[M+1]^+$.

Step 12: Synthesis of —(R or S)-1-(2-(4-cyclobutylphenyl)-S-(5-hydroxy-(trifluoromethyl)nicotinoyl)-4,5,5a,6,8,9-hexahydro-1,2a,5,7-tetraazabenzo[cd]azulen-7(3H)-yl) prop-2-en-1-one To a solution of 1-(2-(4-cyclobutylphenyl)-4,5,5a,6,8,9-hexahydro-1,2a,5,7-tetraazabenzo[cd]azulen-7(3H)-yl) prop-2-en-1-one (110 mg, 1 Eq, 303 μmol) in DMF (1.1 mL) were added HATU (173 mg, 1.5 Eq, 455 gmol), 5-hydroxy-6-(trifluoromethyl)nicotinic acid (62.9 mg, 1 Eq, 303 μmol) and DIEA (196 mg, 264 μL, 5 Eq, 1.52 mmol). The mixture was stirred at rt for 5 h, after which the mixture was diluted with water (5 mL) and EA (5 mL), and the aqueous layer was extracted with EA (2×5 mL). The combined organic layers were washed with saturated brine (2×5 mL), dried over anhydrous sodium sulfate, and concentrated under reduced pressure to give a residue. The residue was purified by Prep-HPLC (Column: YMC Triart C18 ExRs 5 m, 30 mm*150 mm; Mobile Phase A: Water (10 mmol/L NH4HCO3), Mobile Phase B: ACN; Flow rate: 60 mL/min; Gradient: 20% B to 40% B in 10 min) to afford racemic 1-(2-(4-cyclobutylphenyl)-5-(5-hydroxy-6-(trifluoromethyl)nicotinoyl)-4,5,5a,6,8,9-hexahydro-1,2a,5,7-tetraazabenzo[cd]azulen-7(3H)-yl)prop-2-en-1-one (35 mg) as a white solid. The racemate was separated into its constitutive enantiomers by chiral HPLC: Column-CHIRAL ART Cellulose-SB, 3*25 cm, 5 μm; Mobile Phase A: Hex(0.1% FA)—HPLC, Mobile Phase B: EtOH:DCM=1:1; Flow rate: 20 mL/min; Gradient: isocratic 40; Wave Length: UV 254/220 nm; RT1(min): 2.1; RT2(min): 7.2; to afford (R or S)-1-(2-(4-cyclobutylphenyl)-5-(5-hydroxy-6-(trifluoromethyl)nicotinoyl)-4,5,5a,6,8,9-hexahydro-1,2a,5,7-tetraazabenzo[cd]azulen-7(3H)-yl)prop-2-en-1-one (12.9 mg) as the second-eluting peak as a white solid. LCMS:(ESI, m/z): 552 $[M+1]^+$. $^1H$ NMR: (400 MHz, Chloroform-d, ppm): δ 8.55 (s, 1H), 8.43 (s, 1H), 8.26 (s, 1H), 7.98 (s, 1H), 7.80-7.52 (m, 1H), 7.30 (s, 2H), 6.88-6.42 (m, 2H), 6.01-5.9 (m, 1H), 5.31-4.78 (m, 3H), 4.62-3.89 (m, 3H), 3.72-2.68 (m, 6H), 2.37 (s, 2H), 2.16-1.95 (m, 4H).

TABLE F1

The compounds of Examples F-6 and F-7 were prepared in an analogous manner to Example F-5 using the corresponding carboxylic acids in Step 12. The racemic final compound of Example F-6 was separated into its constituent enantiomers using the following conditions: Column: CHIRALPAK-IC 2*25 cm, 5 μm; Mobile Phase A: HEX(0.1% FA), Mobile Phase B: EtOH; Flow rate: 20 mL/min; Gradient: isocratic 65; Wave Length: UV 254/220 nm; RT1(min): 5.9; RT2(min): 9.4; to afford the compound of the example as the second-eluting peak. The racemic final compound of Example F-7 was separated into its constituent enantiomers using the following conditions: Column: CHIRALPAK-IC 2*25 cm, 5 μm; Mobile Phase A: HEX(0.1% FA), Mobile Phase B: EtOH: DCM = 1:1; Flow rate: 20 mL/min; Gradient: isocratic 60; Wave Length: UV 254/220 nm; RT1(min): 5.0; RT2(min): 6.9; to afford the compound of the example as the second-eluting peak.

| Example No. | Structure and Name | LCMS (ESI, m/z) | NMR |
|---|---|---|---|
| F-6 | 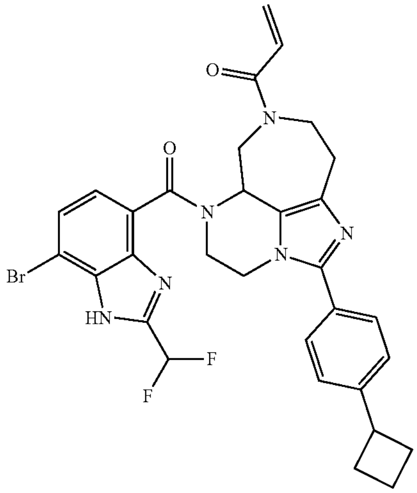 [SMILES: C=CC(=O)N1CCc2nc(-c3ccc(C4CCC4)cc3)n3c2C(C1)N(C(=O)c1ccc(Br)c2[nH]c(C(F)F)nc12)CC3] (R or S)-1-(5-(7-bromo-2-(difluoromethyl)-1H-benzo[d]imidazole-4-carbonyl)-2-(4-cyclobutylphenyl)-4,5,5a,6,8,9-hexahydro-1,2a,5,7-tetraazabenzo[cd]azulen-7(3H)-yl)prop-2-en-1-one | 635 [M + H]$^+$ | $^1$H NMR (400 MHz, Chloroform-d, ppm) δ 7.74 - 7.36 (m, 4H), 7.17 - 6.77 (m, 1H), 6.77 - 6.37 (m, 1H), 6.18 - 5.55 (m, 2H), 4.96 - 2.91 (m, 9H), 2.80 (s, 1H), 2.38 - 2.32 (m, 2H), 2.22 - 1.94 (m, 3H), 1.94 - 1.79 (m, 1H), 1.25 (s, 1H). |
| F-7 | 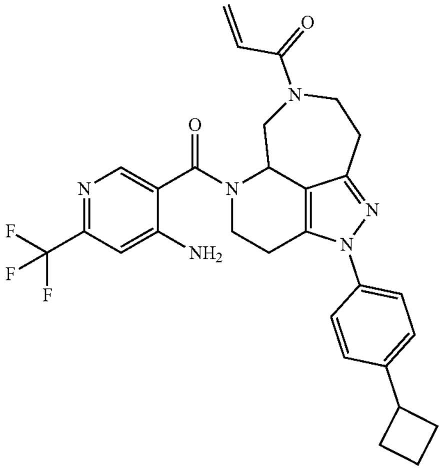 [SMILES: C=CC(=O)N1CCc2nn(-c3ccc(C4CCC4)cc3)c3c2C(C1)N(C(=O)c1cnc(C(F)(F)F)cc1N)CC3] (R or S)-1-(5-(4-amino-6-(trifluoromethyl)nicotinoyl)-2-(4-cyclobutylphenyl)-4,5,5a,6,8,9-hexahydro-1,2a,5,7-tetraazabenzo[cd]azulen-7(3H)-yl)prop-2-en-1-one | 551 [M + H]$^+$ | $^1$H NMR (400 MHz, Chloroform-d, ppm) δ 8.59 - 7.99 (m, 1H), 7.83 - 7.48 (m, 2H), 7.35 - 7.30 (m, 2H), 7.12 - 6.89 (m, 1H), 6.81 - 6.09 (m, 1H), 6.09 - 5.09 (m, 4H), 4.97 - 3.75 (m, 5H), 3.75 - 2.48 (m, 4H), 2.48 - 1.96 (m, 6H), 0.98 - 0.73 (m, 1H) (some peaks obscured by solvent). |

Example K-1: Preparation of Tert-Butyl 3-amino-1-(4-bromophenyl)-1,4,6,7-tetrahydro-5H-pyrazolo[4,3-c]pyridine-5-carboxylate (Int. CC)

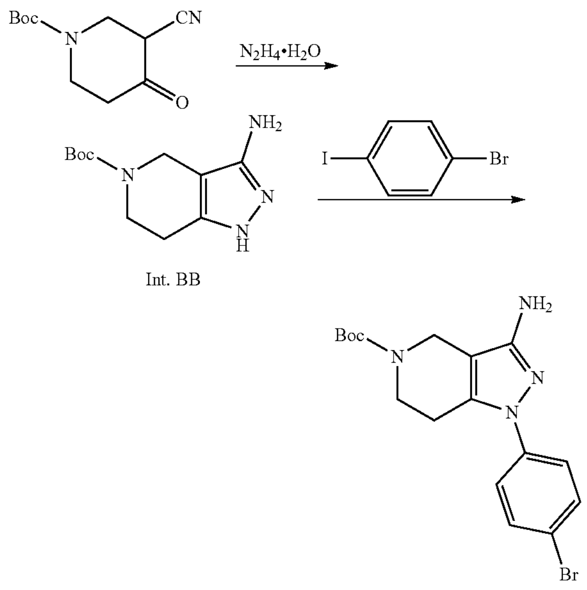

Int. BB

Int. CC

Step 1: Synthesis of Tert-Butyl 3-amino-1,4,6,7-tetrahydro-5H-pyrazolo[4,3-c]pyridine-5-carboxylate (Int. BB)

This reaction was launched in three parallel batches.

To a solution of tert-butyl 3-cyano-4-oxopiperidine-1-carboxylate (300 g, 1.34 mol, 1.0 eq) in EtOH (1.5 L) was added N2H4-water (157 g, 2.68 mol, 152 mL, 2.0 eq) at room temperature. The mixture was stirred at 80° C. for 2 h. The mixture was combined an allowed to cool down to rt and then concentrated under reduced pressure to provide tert-butyl 3-amino-1,4,6,7-tetrahydro-5H-pyrazolo[4,3-c]pyridine-5-carboxylate (900 g) as a yellow solid. LCMS: (ESI, m/z):=239 $(M+H)^+$. $^1H$ NMR: (400 MHz, DMSO-d6) δ 4.58 (brs, 2H), 4.16 (s, 2H), 3.58-3.51 (m, 2H), 2.54-2.48 (m, 2H), 1.45 (s, 9H). The crude product was used in the next step without further purification.

Step 2: Synthesis of tert-butyl 3-amino-1-(4-bromophenyl)-1,4,6,7-tetr hydro-5H-pyrazolo[4,3-c]pyridine-5-carboxylate (Int. CC)

This reaction was launched in two parallel batches.

To a solution of tert-butyl 3-amino-1,4,6,7-tetrahydro-5H-pyrazolo[4,3-c]pyridine-5-carboxylate (200 g, 839 mmol, 1.0 eq) and 1-bromo-4-iodobenzene (332 g, 1.18 mol, 1.4 eq) in DMF (1000 mL) was added $CuBr_2$ (37.4 g, 167 mmol, 7.86 mL, 0.2 eq) and $Cs_2CO_3$ (328 g, 1.01 mol, 1.2 eq) at room temperature. The mixture was stirred at 120° C. for 2 h. The reaction mixture was combined and filtered, and then diluted with water (500 mL) and extracted with EtOAc (1.0 L×2). The combined organic layers were washed with saturated brine (500 mL), dried over $Na_2SO_4$, filtered, and concentrated under reduced pressure to give a residue. The residue was purified by column chromatography ($SiO_2$, PE:EtOAc=10:1 to 1:1) to provide tert-butyl 3-amino-1-(4-bromophenyl)-1,4,6,7-tetrahydro-5H-pyrazolo[4,3-c]pyridine-5-carboxylate (116 g, 17.5% yield) as a yellow solid. LCMS: m/z=393, 395 ($^{81}Br$). $^1H$ NMR: (400 MHz, DMSO-$d_6$) δ 7.80-7.56 (m, 2H), 7.50-7.20 (m, 2H), 5.11 (brs, 2H), 4.21 (s, 2H), 3.63-3.46 (m, 2H), 2.87- 2.71 (m, 2H), 1.44 (s, 9H).

Example K-2: Preparation of Tert-Butyl 2-(4-bromophenyl)-8-oxo-2,3,4,5a,6,7,8,9-octahydro-5H-10-oxa-1,2,5,7-tetraazacycloocta[cd]indene-5-carboxylate (Int. FF)

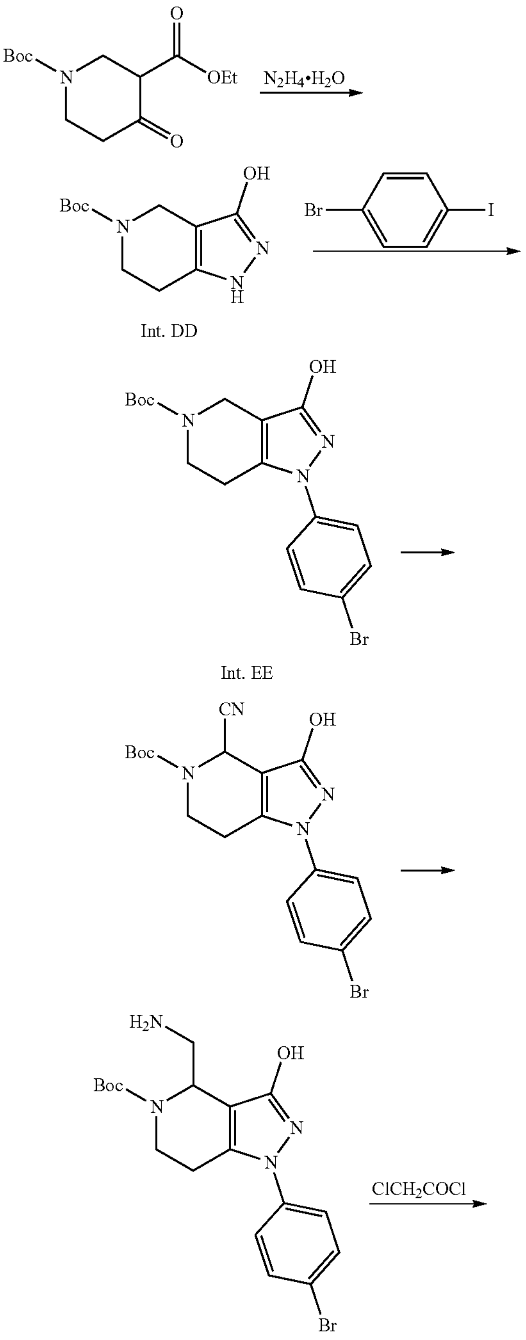

Int. DD

Int. EE

-continued

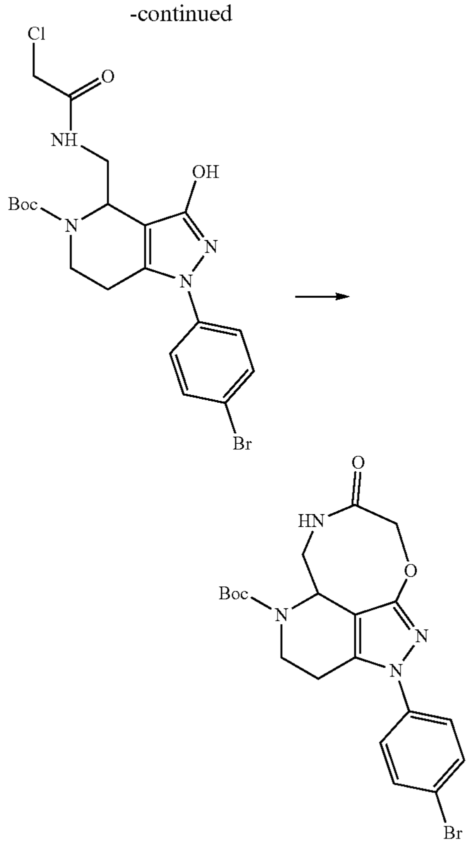

Int. FF

Step 1: Synthesis of Tert-Butyl 3-hydroxy-1,4,6,7-tetrahydro-5H-pyrazolo[4,3-c]pyridine-5-carboxylate (Int. DD)

This reaction was launched with two parallel batches.

To a solution of 1-(tert-butyl) 3-ethyl 4-oxopiperidine-1,3-dicarboxylate (500 g, 1.84 mol, 1.0 eq) in EtOH (2.5 L) was added hydrazine hydrate (239 g, 4.07 mol, 232 mL, 2.2 eq) at room temperature. The mixture was stirred at 30° C. for 0.5 h. The mixture was allowed to cool down to RT, combined and then concentrated under reduced pressure. The crude product tert-butyl 3-hydroxy-1,4,6,7-tetrahydro-5H-pyrazolo[4,3-c]pyridine-5-carboxylate (10 g) was obtained as a white solid and used directly into the next step. LCMS: m/z=240 $(M+H)^+$. $^1$H NMR: (400 MHz, DMSO-d6) δ 8.10 (brs, 2H), 4.13 (s, 2H), 3.52 (t, J=6.0 Hz, 2H), 2.55-2.49 (m, 2H), 1.40 (s, 9H).

Step 2: Synthesis of Tert-Butyl 1-(4-bromophenyl)-3-hydroxy-1,4,6,7-tetrahydro-5H-pyrazolo[4,3-c]pyridine-5-carboxylate (Int. EE)

This reaction was launched with four parallel batches.

To a solution of tert-butyl 3-hydroxy-1,4,6,7-tetrahydro-5H-pyrazolo[4,3-c]pyridine-5-carboxylate (130 g, 543 mmol, 1.0 eq) and 1-bromo-4-iodobenzene (184 g, 652 mmol, 1.2 eq) in DMF (1.0 L) was added $CuBr_2$ (24.3 g, 108 mmol, 5.09 mL, 0.2 eq) and $Cs_2CO_3$ (354 g, 1.09 mol, 2.0 eq) at room temperature. The mixture was stirred at 120° C. for 2 h under a nitrogen atmosphere. The reaction mixtures were cooled to rt and combined, and quenched by the addition of water (10 L) at rt. The reaction mixture was filtered, the cake was washed with EtOAc (200 mL×2), then the cake was collected and further triturated with EtOAc (2.0 L). The crude product was obtained by collecting the cake and dried. Tert-butyl 1-(4-bromophenyl)-3-hydroxy-1,4,6,7-tetrahydro-5H-pyrazolo[4,3-c]pyridine-5-carboxylate (280 g) was obtained as a brown solid and used directly in the next step, LCMS: m/z=394, 396 ($^{81}$Br) $[M+H]^+$.

Step 3: Synthesis of Tert-Butyl (rac)-1-(4-bromophenyl)-4-cyano-3-hydroxy-1,4,6,7-tetrahydro-5H-pyrazolo[4,3-c]pyridine-5-carboxylate To a solution of tert-butyl 1-(4-bromophenyl)-3-hydroxy-1,4,6,7-tetrahydro-5H-pyrazolo[4,3-c]pyridine-5-carboxylate (293 g, 743 mmol, 1.0 eq) in MeCN (2.95 L) was added AcOH (44.5 g, 742 mmol, 42.5 mL, 0.1 eq) and $TEMPO^+ BF_4^-$ (527 g, 3.35 mol, 4.5 eq), then TMSCN (294 g, 2.97 mol, 371 mL, 4.0 eq) was added dropwise at 0° C. Then the mixture was stirred at room temperature for 2 h. The reaction mixture was filtered, the cake was obtained as the first crop of the product. The mother liquor was then concentrated under reduced pressure to give a residue, which was triturated with MeOH (1.0 L) at room temperature to yield the second crop of product. Both crops were combined to provide tert-butyl (rac)-1-(4-bromophenyl)-4-cyano-3-hydroxy-1,4,6,7-tetrahydro-5H-pyrazolo[4,3-c]pyridine-5-carboxylate (208 g) as a yellow solid, which was used directly in the next step. LCMS: m/z=419, 421 ($^{81}$Br) $[M+H]^+$. $^1$H NMR: (400 MHz, $CDCl_3$) δ 7.64 (d, J=8.4 Hz, 2H), 7.26 (d, J=7.6 Hz, 2H), 6.15-5.74 (m, 1H), 4.66-4.31 (m, 1H), 3.30-3.06 (m, 1H), 2.96-2.83 (m, 1H), 2.72-2.58 (m, 1H), 1.54 (s, 9H).

Step 4: Synthesis of Tert-Butyl (rac)-4-(aminomethyl)-1-(4-bromophenyl)-3-hydroxy-1,4,6,7-tetrahydro-5H-pyrazolo[4,3-c]pyridine-5-carboxylate This reaction was launched with two parallel batches.

To a solution of tert-butyl 1-(4-bromophenyl)-4-cyano-3-hydroxy-1,4,6,7-tetrahydro-5H-pyrazolo[4,3-c]pyridine-5-carboxylate (106 g, 254 mmol, 1.0 eq) and cobalt chloride hexahydrate (72.5 g, 304 mmol, 1.2 eq) in MeOH (1.0 L) was added $NaBH_4$ (104 g, 2.75 mol, 11 eq) portion-wise at room temperature. The mixture was then stirred at room temperature for 3 h. The reaction mixture was quenched by addition of water (1.5 L) at a temperature of −5 to 5° C., then HCl (1N, 3.0 L) was added to adjust the pH to 6, and extracted with EtOAc (2.0 L×5). The combined organic layers were washed with saturated brine (3.0 L), dried over $Na_2SO_4$, filtered, and concentrated under reduced pressure to give a residue. The crude product was triturated with EtOAc (500 mL) at 20° C. for 0.5 h. The product tert-butyl (rac)-4-(aminomethyl)-1-(4-bromophenyl)-3-hydroxy-1,4,6,7-tetrahydro-5H-pyrazolo[4,3-c]pyridine-5-carboxylate (278 g) was obtained as a yellow solid and used directly in the next step. LCMS: m/z=423, 425 ($^{81}$Br) $[M+H]^+$.

Step 5: Synthesis of Tert-Butyl (rac)-1-(4-bromophenyl)-4-((2-chloroacetamido)methyl)-3-hydroxy-1,4,6,7-tetrahydro-5H-pyrazolo[4,3-c]pyridine-S-carboxylate To a solution of tert-butyl (rac)-4-(aminomethyl)-1-(4-bromophenyl)-3-hydroxy-1,4,6,7-tetrahydro-5H-pyrazolo[4,3-c]pyridine-5-carboxylate (73.0 g, 172 mmol, 1.0 eq) in THF (730 mL) and water (360 mL) was added $NaHCO_3$ (50.7 g, 603 mmol, 3.5 eq) at room temperature. To the reaction mixture was then added 2-chloroacetyl chloride (11.6 g, 103 mmol, 8.24 mL, 0.6 eq) at 0° C. The mixture was then allowed to warm and was stirred at room temperature for 2 h. The reaction mixture was then diluted with water (700 mL) and extracted with EtOAc (500 mL×2). The combined organic layers were washed with NaOH (2N, 350 mL) and saturated brine (400 mL), dried over $Na_2SO_4$, filtered, and concentrated under reduced pressure to give tert-butyl 1-(4-bromophenyl)-4-((2-chloroacetamido)methyl)-3-hydroxy-1,4,6,7-tetrahydro-5H-pyrazolo[4,3-c]pyridine-5-carboxylate (30.0 g) as a yellow solid. The crude product was used directly in the next step. LCMS: m/z=499, 501 ($^{81}$Br) $[M+H]^+$.

Step 6: Synthesis of Tert-Butyl (rac)-2-(4-bromophenyl)-8-oxo-2,3,4,$5^{a}$,6,7,8,9-octahydro-5H-10-oxa-1,2,5,7-tetraazacycloocta[cd]indene-S-carboxylate (Int. FF)

To a solution of tert-butyl (rac)-1-(4-bromophenyl)-4-((2-chloroacetamido)methyl)-3-hydroxy-1,4,6,7-tetrahydro-5H-pyrazolo[4,3-c]pyridine-5-carboxylate ($^{2}$0.0 g, 84.0 mmol, 1.0 eq) in DMF (1.7 L) was added $K_2CO_3$ (13.9 g, 100 mmol, 1.2 eq) and KI (2.79 g, 16.8 mmol, 0.2 eq). The mixture was stirred at 60° C. for 12 h. The reaction mixture was the diluted with water (1.0 L) and extracted with EtOAc (3.5 L×2). The combined organic layers were washed with saturated brine (500 mL), dried over $Na_2SO_4$, filtered, and concentrated under reduced pressure to give a residue. The crude product was triturated with PE:EtOAc=1:1 (30.0 KL) at 20° C. for 30 min and filtered to provide tert-butyl (rac)-2-(4-bromophenyl)-8-oxo-2,3,4, a,6,7,8,9-octahydro-5H- 10-oxa-1,2,5,7-tetraazacycloocta[cd]indene-5-carboxylate (12.8 g, 27.6 mmol, 33% yield) as a white solid. LCMS: m/z=463, 465 ($^{81}$Br) $[M+H]^+$. $^{1}$H NMR: (400 MHz, $CDCl_3$) δ 7.58 (d, J=8.6 Hz, 2H), 7.34 (d, J=8.6 Hz, 2H), 5.99 (brs, 1H), 5.02 (brs, 1H), 4.90-4.78 (m, 1H), 4.69 (br d, J=14.6 Hz, 1H), 4.41 (brs, 1H), 4.24-4.06 (m, 1H), 3.78-3.63 (m, 1H), 3.00-2.94 (m, 2H), 2.75-2.60 (m, 1H), 1.53 (s, 9H).

Example K-3: Preparation of 1-(5-(7-bromo-1H-benzo[d]imidazole-4-carbonyl)-2-(4-cyclobutyl-2-hydroxyphenyl)-2,3,4,5,5a,6,8,9-octahydro-7H-10-oxa-1,2,5,7-tetraazacycloocta[cd]inden-7-yl)prop-2-en-1-one

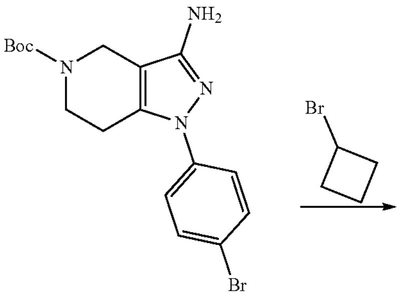

Int. CC

-continued

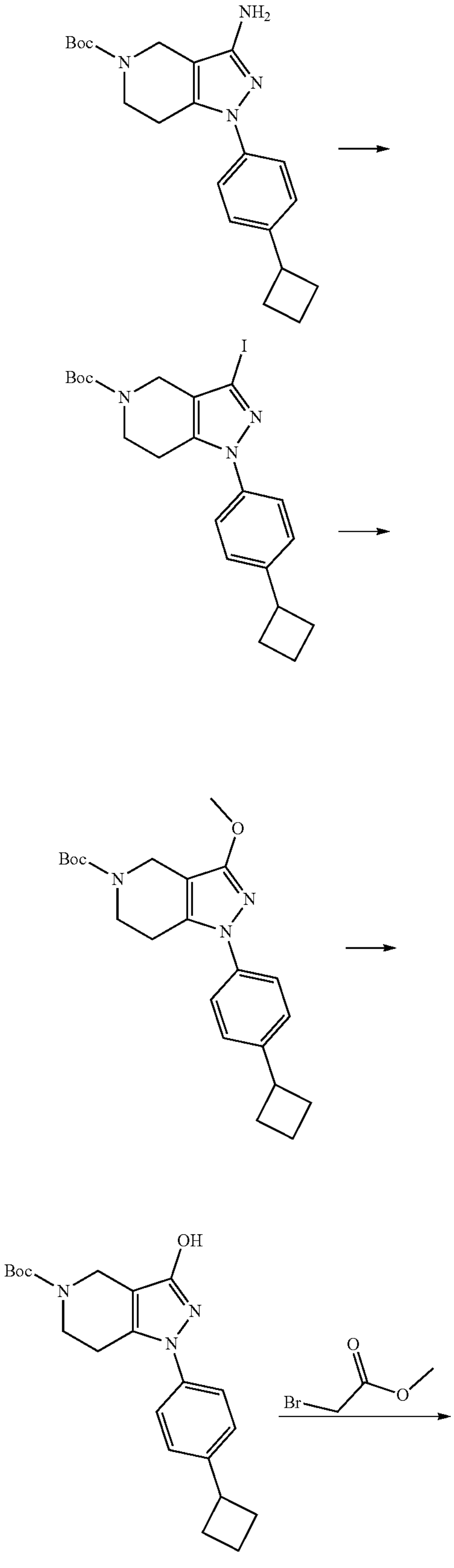

-continued
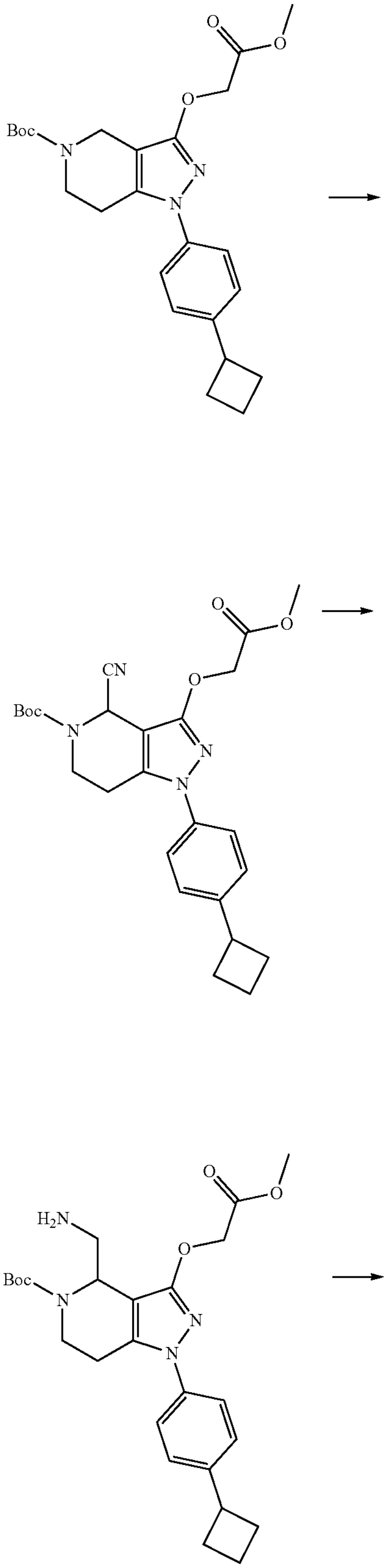
-continued
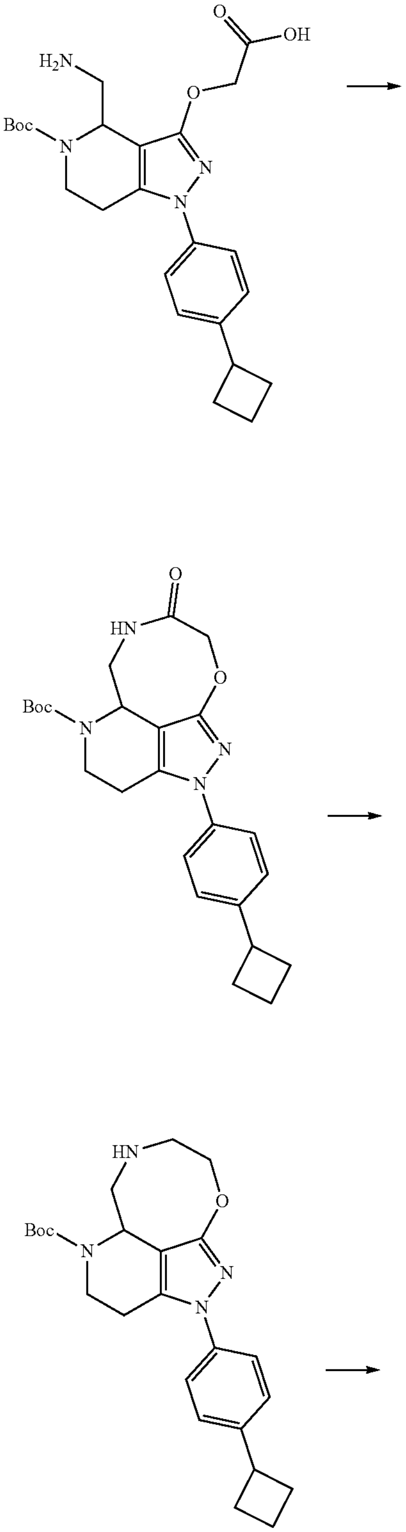
Int. GG

-continued
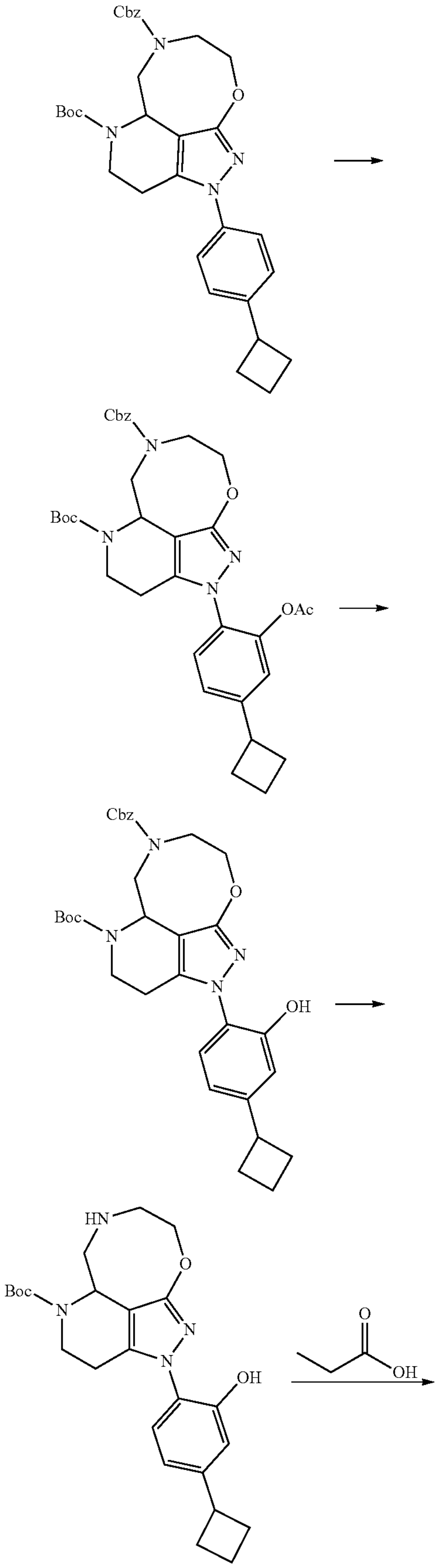
-continued
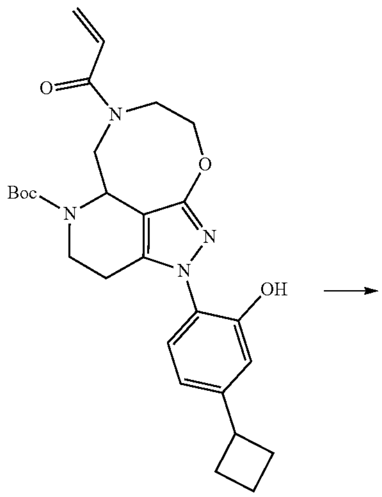
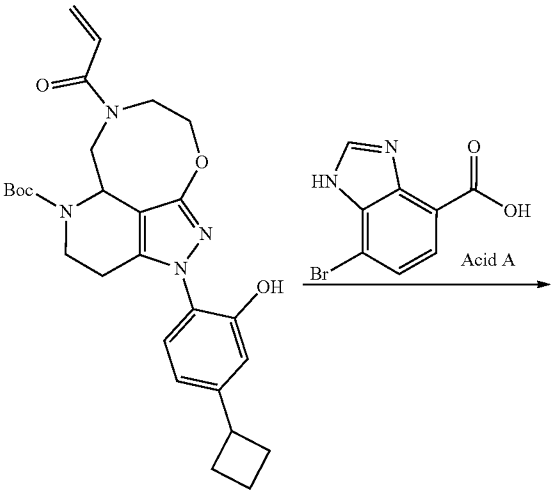
Int. HH
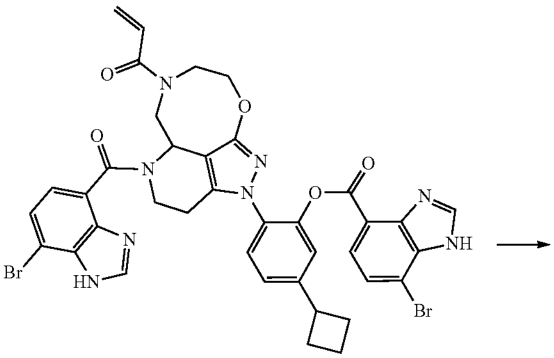

-continued

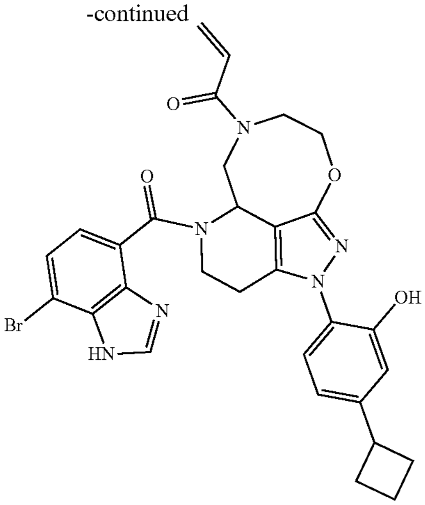

Step 1: Synthesis of Tert-Butyl 3-amino-1-(4-cyclobutylphenyl)-1,4,6,7-tetrahydro-5H-pyrazolo[4,3-c]pyridine-5-carboxylate To a stirred solution of tert-butyl 3-amino-1-(4-bromophenyl)-1,4,6,7-tetrahydro-5H-pyrazolo[4,3-c]pyridine-5-carboxylate (Int. CC) (20.0 g, 1 eq, 51 mmol) in DMA (400 mL) were added picolinimidamide hydrochloride (2.40 g, 0.3 eq, 15 mmol), bromo-cyclobutane (34.3 g, 24.5 mL, 5 eq, 254 mmol), tetra-n-butylammonium iodide (18.8 g, 1 eq, 51 mmol), nickel dichloride (2.0 g, 0.3 eq, 15 mmol) and manganese (14 g, 5 eq, 254 mmol). The resulting mixture was stirred overnight at 60° C. under a nitrogen atmosphere. The mixture was then allowed to rt and filtered. The mixture was diluted with water (0.5 L) and EtOAc (0.5 L), and the aqueous layer was extracted with EtOAc (2×0.5 L). The combined organic layers were washed with saturated brine (2×0.5 L) and dried over anhydrous $Na_2SO_4$. After filtration, the filtrate was concentrated under reduced pressure. The residue was purified by silica gel column chromatograph, eluting with EtOAc/PE (1:1) to afford tert-butyl 3-amino-1-(4-cyclobutylphenyl)-1,4,6,7-tetrahydro-5H-pyrazolo[4,3-c]pyridine-5-carboxylate (10 g) as a brown oil. LCMS: (ESI, m/z): $[M+]^+$ $^1H$ NMR: (400 MHz, DMSO-$d_6$) δ 7.38-7.33 (m, 2H), 7.27-7.22 (m, 2H), 4.97 (s, 2H), 4.22 (s, 2H), 3.57-3.46 (m, 3H), 2.76 (t, J=5.6 Hz, 2H), 2.28 (qt, J=7.8, 2.4 Hz, 2H), 2.15-2.06(m, 1H), 2.10-1.99 (m, 1H), 2.02-1.90 (m, 1H), 1.87-1.75 (m, 1H), 1.44 (s, 9H).

Step 2: Synthesis of Tert-Butyl 1-(4-cyclobutylphenyl)-3-iodo-1,4,6,7-tetr hydro-5H-pyrazolo[4,3-c] pyridine-S-carboxylate A solution of iodine (17 g, 1.2 eq, 65 mmol) in DCM (50 mL) was cooled to 0° C., then isoamyl nitrite (13 g, 15 mL, 2 eq, 0.11 mol) was added, after which tert-butyl 3-amino-1-(4-cyclobutylphenyl)-1,4,6,7-tetrahydro-5H-pyrazolo[4,3-c]pyridine-5-carboxylate (20 g, 1 eq, 54 mmol) in DCM (150 mL) was added dropwise to the above mixture at 0° C. under a nitrogen atmosphere. The resulting reaction mixture was warmed to room temperature and stirred for 2 h. The reaction was then quenched by the addition of $Na_2S_2O_3$ saturated solution (100 mL) at rt. The resulting mixture was extracted with DCM (2×100 mL). The combined organic layers were washed with saturated brine (2×100 mL) and dried over anhydrous $Na_2SO_4$. After filtration, the filtrate was concentrated under reduced pressure. The residue was purified by silica gel column chromatography, eluting with EtOAc/PE (1:5) to afford tert-butyl 1-(4-cyclobutylphenyl)-3-iodo-1,4,6,7-tetrahydro-5H-pyrazolo[4,3-c]pyridine-5-carboxylate (16 g) as a yellow solid. LCMS:(ESI, m/z): 480 $[M+H]^+$.$^1H$ NMR: (400 MHz, DMSO-$d_6$) δ 7.50-7.42 (m, 2H), 7.39-7.32 (m, 2H), 4.20 (s, 2H), 3.64-3.51 (m, 3H), 2.80 (t, J=5.7 Hz, 2H), 2.31 (dtd, J=10.5, 8.0, 2.4 Hz, 2H), 2.19-2.04 (m, 2H), 2.08-1.91 (m, 1H), 1.89-1.77 (m, 1H), 1.44 (s, 9H).

Step 3: Synthesis of Tert-Butyl 1-(4-cyclobutylphenyl)-3-methoxy-1,4,6,7-tetrahydro-5H-pyrazolo[4,3-c]pyridine-5-carboxylate To a solution of tert-butyl 1-(4-cyclobutylphenyl)-3-iodo-1,4,6,7-tetrahydro-5H-pyrazolo[4,3-c]pyridine-5-carboxylate (16.0 g, 1 eq, 33.4 mmol) in MeOH (160 mL) was added cuprous iodide (1.27 g, 0.2 eq, 6.68 mmol), 3,4,7,8-tetramethyl-1,10-phenanthroline (2.37 g, 0.3 eq, 10.0 mmol) and cesium carbonate (21.8 g, 5.34 mL, 2 eq, 66.8 mmol). The mixture was stirred at 80° C. for 16 h. The mixture was diluted with water (200 mL) and EtOAc (200 mL), and the aqueous layer was extracted with EtOAc (2×200 mL). The combined organic layers were washed with saturated brine (2×100 mL), dried over anhydrous sodium sulfate and concentrated to give a residue. The residue was purified by silica gel column chromatography, eluting with EtOAc/PE (1:5) to afford tert-butyl 1-(4-cyclobutylphenyl)-3-methoxy-1,4,6,7-tetrahydro-5H-pyrazolo[4,3-c]pyridine-5-carboxylate (8.4 g) as a yellow oil. LCMS: (ESI, m/z)(ESI, m/z): 384 $[M+H]^+$. $^1H$ NMR: (400 MHz, DMSO-$d_6$) δ 7.46-7.39 (m, 2H), 7.30 (d, J=8.1 z, 2H), 4.23 (s, 2H), 3.87 (s, 3H), 3.62-3.49 (m, 3H), 2.79 (t, J=5.4 Hz, 2H), 2.30 (qd, J=7.8, 3.5 Hz, 2H), 2.14-2.02 (m, 2H), 2.02-1.92 (m, 1H), 1.88-1.77 (m, 1H), 1.43 (s, 9H).

Step 4: Synthesis of Tert-Butyl 1-(4-cyclobutylphenyl)-3-hydroxyl-1,4,6,7-tetrahydro-5H-pyrazolo[4,3-c]pyridine-5-carboxylate To a stirred solution of tert-butyl 1-(4-cyclobutylphenyl)-3-methoxy-1,4,6,7-tetrahydro-5H-pyrazolo[4,3-c]pyridine-5-carboxylate (4.40 g, 1 eq, 11.5 mmol) in THE (44 mL) was added L-selectride, 1M in THE (21.8 g, 115 mL, 1 M, 10 eq, 115 mmol), and the resulting mixture was stirred for 6 h at 80° C. The reaction was then quenched by the addition of ice water (100 mL) at 0° C. The resulting mixture was extracted with EtOAc (2×100 mL). The combined organic layers were washed with saturated brine (2×50 mL) and dried over anhydrous $Na_2SO_4$. After filtration, the filtrate was concentrated under reduced pressure. The residue was purified by silica gel column chromatography, eluting with EtOAc/PE (1:5) to afford tert-butyl-(4-cyclobutylphenyl)-3-hydroxy-1,4,6,7-tetrahydro-5H-pyrazolo[4,3-c]pyridine-5-carboxylate (3.5 g) as a white solid. LCMS (ESI, m/z)(ESI, m/z): 370 $[M+H]^+$. $^1H$ NMR (400 MHz, DMSO-$d_6$) δ 10.19 (s, 1H), 7.42-7.33 (m, 2H), 7.28 (d, J=8.2 Hz, 2H), 4.23 (s, 2H), 3.58-3.48 (m, 3H), 2.78 (t, J=5.7 Hz, 2H), 2.29 (qt, J=7.8, 2.4 Hz, 2H), 2.09 (pd, J=9.3, 8.5, 1.8 Hz, 2H), 2.05-1.91 (m, 1H), 1.87-1.75 (m, 1H), 1.44 (s, 9H).

Step 5: Synthesis of Tert-Butyl 1-(4-cyclobutylphenyl)-3-(2-methoxy-2-oxoethoxy)-1,4,6,7-tetrahydro-5H-pyrazolo[4,3-c]pyridine-5-carboxylate To a solution of tert-butyl 1-(4-cyclobutylphenyl)-3-hydroxy-1,4,6,7-tetrahydro-5H-pyrazolo[4,3-c]pyridine-5-carboxylate (3.5 g, 1 eq, 9.5 mmol) in DMA (35 mL) was added methyl 2-bromoacetate (1.7 g, 1.1 mL, 1.2 eq, 11 mmol) and $Cs_2CO_3$ (6.2 g, 2 eq, 19 mmol). The mixture was stirred at room temperature for 2 h. The reaction was then quenched by the addition of water (50 mL) at rt. The resulting mixture was extracted with EtOAc (2×100 mL). The combined organic layers were washed with saturated brine (2×50 mL) and dried over anhydrous $Na_2SO_4$. After filtration, the filtrate was concentrated under reduced pressure. The residue was purified by silica gel column chromatography, eluting with EtOAc/PE (1:10) to afford tert-butyl 1-(4-cyclobutylphenyl)-3-(2-methoxy-2-oxoethoxy)-1,4,6,7-tetrahydro-5H-pyrazolo[4,3-c]pyridine-5-carboxylate (3.3 g) as a yellow oil. LCMS (ESI, m/z)(ESI, m/z): 442 $[M+H]^+$. 1H NMR: (400 MHz, DMSO-$d_6$) δ 7.41-7.34 (m, 2H), 7.34-7.27 (m, 2H), 4.86 (s, 2H), 4.28 (s, 2H), 3.69 (s, 3H), 3.61-3.47 (m, 3H), 2.80 (t, J=5.6 Hz, 2H), 2.29 (qt, J=7.7, 2.4 Hz, 2H), 2.17-2.00 (m, 2H), 2.03-1.91 (m, 1H), 1.88-1.76 (m, 1H), 1.44 (s, 9H).

Step 6: Synthesis of Tert-Butyl (rac)-4-cyano-1-(4-cyclobutylphenyl)-3-(2-methoxy-2-oxoethoxy)-1,4,6,7-tetrahydro-5H-pyrazolo[4,3-c]pyridine-5-carboxylate To a solution of tert-butyl 1-(4-cyclobutylphenyl)-3-(2-methoxy-2-oxoethoxy)-1,4,6,7-tetrahydro-5H-pyrazolo[4,3-c]pyridine-5-carboxylate (3.30 g, 1 eq, 7.47 mmol) in MeCN (33 mL) was added TMSCN (1.48 g, 2 eq, 14.9 mmol), AcOH (898 mg, 856, 2 eq, 14.9 mmol) and $TEMPO^+ BF_4^-$ (3.64 g, 2 eq, 14.9 mmol). The mixture was stirred at room temperature for 1 h. The mixture was then diluted with water (20 mL) and EtOAc (50 mL), and the aqueous layer was extracted with EtOAc (2×50 mL). The combined organic layers were w shed with saturated brine (2×50 mL), dried over anhydrous sodium sulfate and concentrated to give a residue. The residue was purified by silica gel column chromatography, eluting with EtOAc/PE (1:5) to afford tert-butyl (rac)-4-cyano-1-(4-cyclobutylphenyl)-3-(2-methoxy-2-oxoethoxy)-1,4,6,7-tetrahydro-5H-pyrazolo[4,3-c]pyridine-5-carboxylate (2.7 g) as a white solid. LCMS (ESI, m/z)(ESI, m/z): 467 $[M+H]^+$. $^1H$ NMR: (400 MHz, DMSO-$d_6$) δ 7.41 (d, J=8.5 Hz, 2H), 7.34 (d, J=8.5 Hz, 2H), 5.91 (s, 1H), 4.94 (d, J=2.7 Hz, 2H), 4.30 (brs, 1H), 3.69 (s, 3H), 3.56 (p, J=8.6 Hz, 1H), 3.13-2.96 (m, 2H), 2.74 (d, J=13.0 Hz, 1H), 2.30 (qt, J=7.7, 2.4 Hz, 2H), 2.10 (tt, J=8.9, 1.9 Hz, 2H), 1.98-1.89 (m, 1H), 1.88-1.76 (m, 1H), 1.49 (s, 9H).

Step 7: Synthesis of Tert-Butyl (rac)-4-(aminomethyl)-1-(4-cyclobutylphenyl)-3-(2-methoxy-2-oxoethoxy)-1,4,6,7-tetrahydro-5H-pyrazolo[4,3-c]pyridine-S-carboxylate To a solution of tert-butyl 4-cyano-1-(4-cyclobutylphenyl)-3-(2-methoxy-2-oxoethoxy)-1,4,6,7-tetrahydro-5H-pyrazolo[4,3-c]pyridine-5-carboxylate (2.7 g, 1 eq, 5.8 mmol) in MeOH (270 mL) was added Raney nickel (2.7 g, 50% wt, 4 eq, 23 mmol). The mixture was purged with nitrogen three times and then was pressurized under 4.0 MPa hydrogen at 50° C. for 5 h. The reaction mixture was then cooled to rt, and the mixture was filtered and rinsed with MeOH (3×50 mL), the filtrate was concentrated under vacuum to give a residue. The residue was purified by reverse-phase flash chromatography (column, C18; mobile phase, Mobile Phase A: water (10 mmol/L $NH_4HCO_3$), Mobile Phase B: MeCN; 10% to 100% gradient in 20 min; detector, UV 254 nm) to afford tert-butyl (rac)-4-(aminomethyl)-1-(4-cyclobutylphenyl)-3-(2-methoxy-2-oxoethoxy)-1,4,6,7-tetrahydro-5H-pyrazolo[4,3-c]pyridine-5-carboxylate (1.4 g) as a white solid. LCMS (ESI, m/z)(ESI, m/z): 471 $[M+H]^+$ Step 8: Synthesis of (rac)-2-((4-(aminomethyl)-5-(tert-butoxycarbonyl)-1-(4-cyclobutylphenyl)-4,5,6,7-tetrahydro-JH-pyrazolo[4,3-c]pyridin-3-yl)oxy)acetic acid A mixture of tert-butyl (rac)-4-(aminomethyl)-1-(4-cyclobutylphenyl)-3-(2-methoxy-2-oxoethoxy)-1,4,6,7-tetrahydro-5H-pyrazolo[4,3-c]pyridine-5-carboxylate (1.50 g, 1 eq, 3.19 mmol) and LiOH (153 mg, 2 eq, 6.38 mmol) in water (7.5 mL) and TH (15 mL) was stirred for 1 h at room temperature. The resulting mixture was concentrated under reduced pressure. The crude product (rac)-2-((4-(aminomethyl)-5-(tert-butoxycarbonyl-1-(4-cyclobutylphenyl)-4,5,6,7-tetrahydro-1H-pyrazolo[4,3-c]pyridin-3-yl)oxy)acetic acid (1.5 g was used in the next step directly without further purification. LCMS (ESI, m/z): 457 $[M+H]^+$ Step 9: Synthesis of Tert-Butyl (rac)-2-(4-cyclobutylphenyl)-8-oxo-2,3,4,3a,6,7,8,9-octahydro-5H-10-oxa-1,2,5,7-tetraazacycloocta[cd]indene-5-carboxylate To a stirred solution of (rac)-2-((4-(aminomethyl)-5-(tert-butoxycarbonyl)-1-(4-cyclobutylphenyl)-4,5,6,7-tetrahydro-1H-pyrazolo[4,3-c]pyridin-3-yl)oxy)acetic acid (1.5 g, 1 eq, 3.3 mmol) in DMF (150 mL) was added DIEA (1.3 g, 1.7 mL, 3 eq, 9.9 mmol) and HATU (1.9 g, 1.5 eq, 4.9 mmol). The resulting mixture was stirred for 1 h at rt. The reaction was then quenched by the addition of water (100 mL) at rt. The resulting mixture was extracted with EtOAc (2×100 mL). The combined organic layers were washed with saturated brine (2×50 mL) and dried over anhydrous $Na_2SO_4$. After filtration, the filtrate was concentrated under reduced pressure. The residue was purified by silica gel column chromatography, eluting with EtOAc/PE (5:1) to afford tert-butyl (rac)-2-(4-cyclobutylphenyl)-8-oxo-2,3,4,5a,6,7,8,9-octahydro-5H-10-oxa-1,2,5,7-tetraazacycloocta[cd]indene-5-carboxylate (300 mg) as a yellow oil. LCMS (ESI, m/z): 439 [M+H]. $^1H$ NMR (400 MHz, DMSO-$d_6$) δ 8.15-8.00 (m, 1H), 7.48-7.40 (m, 2H), 7.37-7.30 (m, 2H), 4.97 (s, 1H), 4.70 (d, J=13.2 Hz, 11H), 4.41 (d, J=13.3 Hz, 1), 4.24 (s, 1H), 3.71 (s, 1H), 3.60-3.45 (m, 2H), 3.00-2.91 (m, 1H), 2.81-2.70 (m, 1H), 2.64 (d, J=15.5 Hz, 1H), 2.29 (tt, J=7.7, 2.4 Hz, 2H), 2.16-2.05 (m, 2H), 2.01-1.93 (m, 1H), 1.88-1.76 (m, 1H), 1.47 (s, 9H).

Step 10: Synthesis of Tert-Butyl (rac)-2-(4-cyclobutylphenyl)-2,3,4,5a,6,7,8,9-octahydro-5H-10-oxa-1,2,5,7-tetraazacycloocta[cd]indene-5-carboxylate (Int. GG)

A solution of tert-butyl (rac)-2-(4-cyclobutylphenyl)-8-oxo-2,3,4,5a,6,7,8,9-octahydro-5H-10-oxa-1,2,5,7-tetraazacycloocta[cd]indene-5-carboxylate (310 mg, 1 eq, 707 μmol) and $BH_3$·THF (243 mg, 2.83 mL, 1 M, 4 eq, 2.83 mmol) was stirred at 60° C. for 1 h. The solvent was removed under reduced pressure to provide tert-butyl (rac)-2-(4-cyclobutylphenyl)-2,3,4,5a,6,7,8,9-octahydro-5H-10-oxa-1,2,5,7-tetraazacycloocta[cd]indene-5-carboxylate (Int.

G) (300 mg) as a yellow oil. The crude product was used in the next step directly without further purification. LCMS (ESI, m/z): 425 [M+H]+.

Step 11: Synthesis of (rac)-7-benzyl 5-(tert-butyl) 2-(4-cyclobutylphenyl)-3,4,5a,6,8,9-hexahydro-2H-10-oxa-1,2,5,7-tetraazacycloocta[cd]indene-5,7-dicarboxylate To a solution of tert-butyl (rac)-2-(4-cyclobutylphenyl)-2,3,4,5a,6,7,8,9-octahydro-5H-10-oxa-1,2,5,7-tetraazacycloocta[cd]indene-5-carboxylate (Int. GG) (300 mg, 1 eq, 707 μmol) in DCM (3 mL) was added N-(benzyloxycarbonyloxy)succinimide (528 mg, 3 eq, 2.12 mmol) and TEA (358 mg, 492 μL, 5 eq, 3.53 mmol). The mixture was stirred at room temperature for 16 h. The reaction was then quenched by the addition of water (10 mL) at rt. The resulting mixture was extracted with DCM (2×10 mL). The combined organic layers were washed with saturated brine (2×5 mL) and dried over anhydrous $Na_2SO_4$. After filtration, the filtrate was concentrated under reduced pressure. The residue was purified by silica gel column chromatography, eluting with EtOAc/PE (1:5) to afford (rac)-7-benzyl 5-(tert-butyl) 2-(4-cyclobutylphenyl)-3,4,5a,6,8,9-hexahydro-2H-10-oxa-1,2,5,7-tetraazacycloocta[cd]indene-5,7-dicarboxylate (220 mg) as a yellow oil. LCMS (ESI, m/z): 559 [M+H]. 1H NMR: (400 MHz, DMSO-$d_6$) δ 7.50-7.40 (m, 3H), 7.40-7.30 (m, 4H), 7.30-7.10 (m, 2H), 5.40-5.20 (m, 1H), 5.17-4.86 (m, 2H), 4.53-4.31 (m, 1H), 4.32-4.09 (m, 1H), 4.14-3.88 (m, 2H), 3.85-3.60 (m, 1H), 3.56 (q, J=8.8 Hz, 2H), 3.50-3.40 (m, 1H), 3.20-2.83 (m, 2H), 2.72-2.50 (m, 1H), 2.23-2.10 (m, 2H), 2.18-2.01 (m, 2H), 2.01-1.91 (m, 1H), 1.89-1.75 (m, 1H), 1.54-1.12 (m, 9H).

Step 12: Synthesis of (rac)-7-benzyl 5-(tert-butyl) 2-(2-acetoxy-4-cyclobutylphenyl)-3,4,5a,6,8,9-hexahydro-2H-10-oxa-1,2,5,7-tetraazacycloocta[cd]indene-5,7-dicarboxylate To a solution of (rac)-7-benzyl 5-(tert-butyl) 2-(4-cyclobutylphenyl)-3,4,5a,6,8,9-hexahydro-2H-10-oxa-1,2,5,7-tetraazacycloocta[cd]indene-5,7-dicarboxylate (200 mg, 1 eq, 358 μmol) in MeCN (0.2 mL) and AcOH (2 mL) was added (diacetoxyiodo)benzene (231 mg, 2 eq, 716 μmol) and palladium diacetate (8.0 mg, 0.1 eq, 36 μmol). The mixture was stirred at 90° C. for 2 h. The mixture was then diluted with $NaHCO_3$(aq) (10 mL) and EtOAc (10 mL), and the aqueous layer was extracted with EtOAc (2×10 mL). The combined organic layers were washed with saturated brine (2×5 mL), dried over anhydrous sodium sulfate and concentrated to give a residue. The residue was purified by Prep-HPLC (Column: YMC Triart C18 ExRs 5 m, 30 mm*150 mm; Mobile Phase A: water (10 mmol/L $NH_4HCO_3$), Mobile Phase B: MeCN; Flow rate: 60 mL/min; Gradient: 68% B to 86% B in 8 min; Wave Length: UV 254 nm/220 nm; retention time 1: 7.4 min) to afford (rac)-7-benzyl 5-(tert-butyl) 2-(2-acetoxy-4-cyclobutylphenyl)-3,4,5a,6,8,9-hexahydro-2H-10-oxa-1,2,5,7-tetraazacycloocta[cd]indene-5,7-dicarboxylate (100 mg) as a white solid. LCMS (ESI, m/z): 617 [M+H]+.

Step 13: Synthesis of 7-benzyl 5-(tert-butyl) 2-(4-cyclobutyl-2-hydroxyphenyl)-3,4,5a,6,8,9-hexahydro-2H-10-oxa-1,2,5,7-tetraazacycloocta[cd]indene-5,7-dicarboxylate A mixture of (rac)-7-benzyl 5-(tert-butyl) 2-(2-acetoxy-4-cyclobutylphenyl)-3,4,5a,6,8,9-hexahydro-2H-10-oxa-1,2,5,7-tetraazacycloocta[cd]indene-5,7-dicarboxylate (100 mg, 1 eq, 162 μmol) and NaOH (13 mg, 2 eq, 324 μmol) in MeOH (1 mL) and water (0.5 mL) was stirred at room temperature for 1 h. The solvent was then removed under reduced pressure. This resulted in (rac)-7-benzyl 5-(tert-butyl) 2-(4-cyclobutyl-2-hydroxyphenyl)-3,4,5a,6,8,9-hexahydro-2H-10-oxa-1,2,5,7-tetraazacycloocta[cd]indene-5,7-dicarboxylate (100 mg) as yellow solid. The crude product was used in the next step directly without further purification. LCMS (ESI, m/z): 575 [M+H]+.

Step 14: Synthesis of Tert-Butyl (rac)-2-(4-cyclobutyl-2-hydroxyphenyl)-2,3,4,5a,6,7,8,9-octahydro-5H-10-oxa-1,2,5,7-tetraazacycloocta[cd]indene-5-carboxylate To a solution of (rac)-7-benzyl 5-(tert-butyl) 2-(4-cyclobutyl-2-hydroxyphenyl)-3,4,5a,6,8,9-hexahydro-2H-10-oxa-1,2,5,7-tetraazacycloocta[cd]indene-7-dicarboxylate (100 mg, 1 eq, 174 mol) in EtOH (1 mL) were added $Pd(OH)_2/C$ (Pearlman's catalyst)(50 mg, 10% wt, 0.27 eq, 47 mol) and palladium dihydroxide (50 mg, 20% wt, 0.41 eq, 71 μmol). The mixture was purged with nitrogen three times, and then was pressurized under 3.0 MPa hydrogen at room temperature and stirred for 2 h. The mixture was filtered and rinsed with EtOH (5×5 mL), and the filtrate was concentrated under vacuum to give a residue. This resulted in tert-butyl (rac)-2-(4-cyclobutyl-2-hydroxyphenyl)-2,3,4,5a,6,7,8,9-octahydro-5H-10-oxa-1,2,5,7-tetraazacycloocta[cd]indene-5-carboxylate (100 mg) as a white solid. The crude product was used in the next step directly without further purification. LCMS (ESI, m/z): 441 [M+H]+.

Step 15: Synthesis of Tert-Butyl (rac)-7-acryloyl-2-(4-cyclobutyl-2-hydroxyphenyl)-2,3,4,5a,6,7,8,9-octahydro-5H-10-oxa-1,2,5,7-tetraazacycloocta[cd]indene-5-carboxylate To a solution of tert-butyl (rac)-2-(4-cyclobutyl-2-hydroxyphenyl)-2,3,4,5a,6,7,8,9-octahydro-5H-10-oxa-1,2,5,7-tetraazacycloocta[cd]indene-5-carboxylate (100 mg, 1 eq, 227 μmol) in DCM (1 mL) were added DIEA (88 mg, 120 μL, 3 eq, 681 μmol), acrylic acid (20 mg, 19 μL, 1.2 eq, 270 μmol) and propylphosphonic anhydride (217 mg, 200 μL, 50% wt, 1.5 eq, 340 μmol). The mixture was stirred at room temperature for 2 h. The mixture was then diluted with water (5 mL) and EtOAc (5 mL), and the aqueous layer was extracted with EtOAc (2×10 mL). The combined organic layers were washed with saturated brine (2×5 mL), dried over anhydrous sodium sulfate and concentrated to give a residue. The crude product was purified by silica gel chromatography eluting with PE:EtOAc=5:1 to give tert-butyl (rac)-7-acryloyl-2-(4-cyclobutyl-2-hydroxyphenyl)-2,3,4,5a,6,7,8,9-octahydro-5H-10-oxa-1,2,5,7-tetraazacycloocta[cd]indene-5-carboxylate (20 mg) as a white solid. LCMS (ESI, m/z): 495 [M+H]+.

Step 16: Synthesis of (rac)-1-(2-(4-cyclobutyl-2-hydroxyphenyl)-2,3,4,5a,6,8,9-octahydro-7H-10-oxa-1,2,5,7-tetraazacycloocta[cd]inden-7-yl)prop-2-en-1-one (Int. HH)

A solution of tert-butyl (rac)-7-acryloyl-2-(4-cyclobutyl-2-hydroxyphenyl)-2,3,4,5a,6,7,8,9-octahydro-5H-10-oxa-1,2,5,7-tetraazacycloocta[cd]indene-5-carboxylate (15 mg, 1 eq, 30 gmol) in TFA (0.5 mL) and DCM (0.5 mL) was stirred at room temperature for 30 min. The solvent was then removed under reduced pressure to provide (rac)-1-(2-(4-cyclobutyl-2-hydroxyphenyl)-2,3,4,5,5a,6,8,9-octahydro-7H-10-oxa-1,2,5,7-tetraazacyclooct[cd]inden-7-yl)prop-2-en-1-one (Int. HH) (20 mg) as a yellow oil. The crude product was used in the next step directly without further purification. LCMS (ESI, m/z): 395 $[M+H]^+$.

Step 17: Synthesis of (rac)-2-(7-acryloyl-5-(7-bromo-1H-benzo[d]imidazole-4-carbonyl)-3,4,5,5a,6,7,8,9-octahydro-2H-10-oxa-1,2,5,7-tetraazacycloocta[cd]inden-2-yl)-5-cyclobutylphenyl 7-bromo-1H-benzo[d]imidazole-4-carboxylate To a solution of (rac)-1-(2-(4-cyclobutyl-2-hydroxyphenyl)-2,3,4,5,5a,6,8,9-octahydro-7H-10-oxa-1,2,5,7-tetraazacycloocta[cd]inden-7-yl)prop-2-en-1-one (15 mg, 1 eq, 38 gmol) in DMF (0.5 mL) were added HBTU (22 mg, 1.5 eq, 57 mol), 7-bromo 1H-benzo[d]imidazole-4-carboxylic acid (18 mg, 2 eq, 76 μmol) and DIEA (12 mg, 17 μL, 2.5 eq, 95 gmol). The mixture was stirred at room temperature for 1 h. The mixture was then dilute with water (10 mL) and EtOAc (10 mL), and the aqueous layer was extracted with EtOAc (2×10 mL). The combined organic layers were washed with saturated brine (2×5 mL), dried over anhydrous sodium sulfate and concentrated to provide (rac)-2-(7-acryloyl-5-(7-bromo-1H-benzo[d]imidazole-4-carbonyl)-3,4,5,5a,6,7,8,9-octahydro-2H-10-oxa-1,2,5,7-tetraazacycloocta[cd]inden-2-yl)-5-cyclobutylphenyl 7-bromo-1H-benzo[d]imidazole-4-carboxylate (40 mg) as a crude brown solid. The crude product was used in the next step directly without further purification. LCMS (ESI, m/z): 839 $[M+H]^+$.

Step 18: Synthesis of (rac)-1-(5-(7-bromo-H-benzo[d]imidazole-4-carbonyl)-2-(4-cyclobutyl-2-hydroxyphenyl)-2,3,4,5,5a,6,8,9-octahydro-7H-10-oxa-1,2,5,7-tetraazacycloocta[cd]inden-7-yl)prop-2-en-1-one To a solution of (rac)-2-(7-acryloyl-5-(7-bromo-1H-benzo[d]imidazole-4-carbonyl)-3,4,5,5a,6,7,8,9-octahydro-2H-10-oxa-1,2,5,7-tetraazacycloocta[cd]inden-2-yl)-5-cyclobutylphenyl 7-bromo-1H-benzo[d]imidazole-4-carboxylate (15 mg, 1 eq, 18 μmol) in THF (0.5 mL) and water (0.2 mL) was added LiOH (0.9 mg, 2 eq, 36 mol), the resulting reaction mixture was stirred at room temperature for 1 h. The mixture was diluted with water (5 mL) and EtOAc (5 mL), and the aqueous layer was extracted with EtOAc (2×10 mL). The combined organic layers were washed with saturated brine (2×10 mL), dried over anhydrous sodium sulfate and concentrated to give a residue. The residue was purified by reversed phase Prep-HPLC (Column: XBridge BEH Shield RP18 5 m, 30 mm*150 mm; Mobile Phase A: water (10 mmol/L $NH_4HCO_3$), Mobile Phase B: MeCN; Flow rate: 60 mL/min; Gradient: 30% B to 50% B in 10 min; Wave Length: UV 254 nm/220 nm; retention time 1: 8.6 (min)) to afford (AND R)-1-(5-(7-bromo-1H-benzo[d]imidazole-4-carbonyl)-2-(4-cyclobutyl-2-hydroxyphenyl)-2,3,4,5,5a,6,8,9-octahydro-7H-10-oxa-1,2,5,7-tetraazacycloocta[cd]inden-7-yl)prop-2-en-1-one (3.0 mg, 4.8 μmol, 27% yield) as a white solid. LCMS (ESI, m/z): 617, 619 ($^{81}Br$) $[M+1]^+$. $^1H$ NMR (400 MHz, Chloroform-d) δ 11.60-11.10 (m, 1H), 9.50-9.23 (m, 1H), 8.30-8.02 (m, 1H), 7.60-7.41 (m, 1H), 7.40-7.15 (m, 1H), 7.09-6.81 (m, 2H), 6.78-6.65 (m, 1H), 6.59-6.28 (m, 1H), 6.38-6.01 (m, 1H), 5.89-5.61 (m, 1H), 5.02-4.59 (m, 1H), 4.58-4.29 (m, 2H), 4.27-3.96 (m, 2H), 3.73-3.40 (m, 3H), 3.98-2.99 (m, 2H), 2.80-2.50 (m, 1H), 2.40-2.20 (m, 2H), 2.20-1.90 (m, 3H), 1.90-1.80 (m, 2H).

Example K-4: Preparation of (R or S)-1-(5-(3-bromo-1H-indazole-6-carbonyl)-2-(4-cyclobutyl-2-hydroxyphenyl)-2,3,4,5,5a,6,8,9-octahydro-7H-10-oxa-1,2,5,7-tetraazacycloocta[cd]inden-7-yl)prop-2-en-1-one

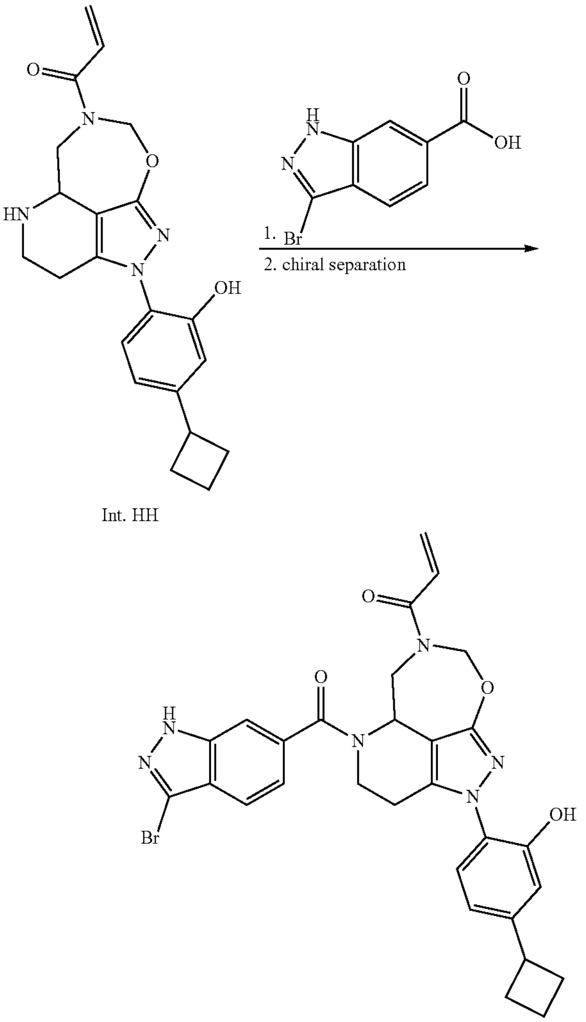

To a solution of 1-(2-(4-cyclobutyl-2-hydroxyphenyl)-2,3,4,5,5,6,8,9-octahydro-7H-10-oxa-1,2,5,7-tetraazacycloocta[cd]inden-7-yl)prop-2-en-1-one (Int. HH)(50 mg, 1 eq, 127 gmol) in DMF (0.5 mL) were added HBTU (144 mg, 3 eq, 380 mol), DIEA (98 mg, 132 μL, 6 eq, 761 mol) and 3-bromo-1H-indazole-6-carboxylic acid (61 mg, 2 eq, 254 μmol). The mixture was stirred at 40° C. for 2 h. The mixture was then diluted with water (20 mL) and EtOAc (20 mL), and the aqueous layer was extracted with EtOAc (2×20 mL). The combined organic layers were washed with saturated brine (2×20 mL), dried over anhydrous sodium sulfate and concentrated to give a residue. The residue was purified by reverse phase Prep-HPLC (Column: YMC Triart C18 ExRs 5 m, 30 mm*150 mm; Mobile Phase A: water (10 mmol/L $NH_4HCO_3$), Mobile Phase B: MeCN; Flow rate: 60 mL/min; Gradient: 38% B to 64% B in 8 min; Wave Length:

UV 254 nm/220 nm; retention time 1: 7.7 min) to afford (rac)-1-(5-(3-bromo-1H-indazole-6-carbonyl)-2-(4-cyclobutyl-2-hydroxyphenyl)-2,3,4,5,5a,6,8,9-octahydro-7H-10-oxa-1,2,5,7-tetraazacycloocta[cd]inden-7-yl)prop-2-en-1-one (13 mg, 17 mol, 14% yield) as a white solid. The racemic product (13 mg) was further separated into its constitutive enantiomers by chiral Prep-HPLC with the following conditions (Column: CHIRAL ART Cellulose-SB 3*25 cm, 5 m; Mobile Phase A: HEX(0.1% FA), Mobile Phase B: EtOH:DCM=1:1; Flow rate: 40 mL/min; Gradient: isocratic 50; Wave Length: UV 254/220 nm; retention time peak 1: 5.7 min; retention time peak 2: 7.7 min; Sample Solvent: EtOH; Injection Volume: 2.0 ml; Number Of Runs: 1) to afford (R or S)-1-(5-(3-bromo-1H-indazole-6-carbonyl)-2-(4-cyclobutyl-2-hydroxyphenyl)-2,3,4,5,5a,6,8,9-octahydro-7H-10-oxa-1,2,5,7-tetraazacycloocta[cd]inden-7-yl)prop-2-en-1-one as the first-eluting peak (retention time: 5.7 min, 3.9 mg, 6.2 mol, 5% yield) as a white solid. LCMS: (ESI, m/z): 617, 619 $(^{81}Br)$ $[M+H]^+$. $^1H$ NMR: (400 MHz, Chloroform-d) δ 11.31 (brs, 1H), 9.63-9.00 (m, 1H), 7.78-7.56 (m, 2H), 7.07 (d, J=7.8 Hz, 1H), 6.97-6.80 (m, 2H), 6.79-6.43 (m, 2H), 6.26-6.08 (m, 1H), 5.89-5.54 (m, 1H), 5.14-4.73 (m, 1H), 4.66-4.27 (m, 2H), 4.25-4.01 (m, 1H), 3.98-3.67 (m, 2H), 3.53-3.41 (m, 1H), 3.40-3.15 (m, 1H), 3.12-2.91 (m, 1H), 2.85-2.62 (m, 1H), 2.62-2.39 (m, 1H), 2.38-2.15 (m, 2H), 2.14-1.97 (m, 3H), 1.90-1.77 (m, 2H).

Example K-5: Preparation of 1-(5-(7-bromo-1H-benzo[d]imidazole-4-carbonyl)-2-(4-cyclobutylphenyl)-2,3,4,5,5a,6,8,9-octahydro-7H-10-oxa-1,2,5,7-tetraazacycloocta[cd]inden-7-yl)prop-2-en-1-one

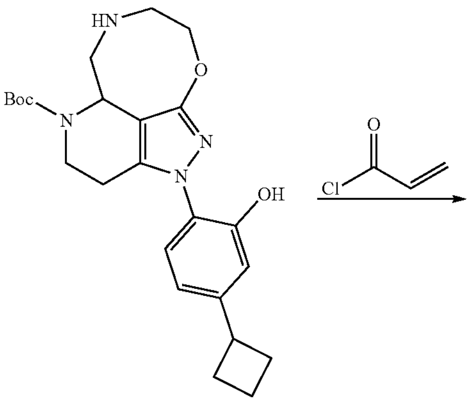

Int. GG

-continued

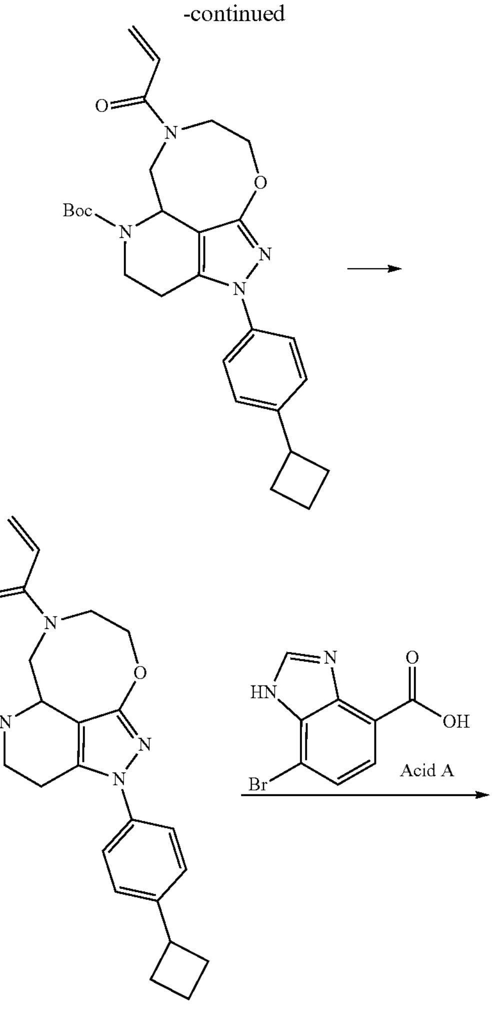

Int. II

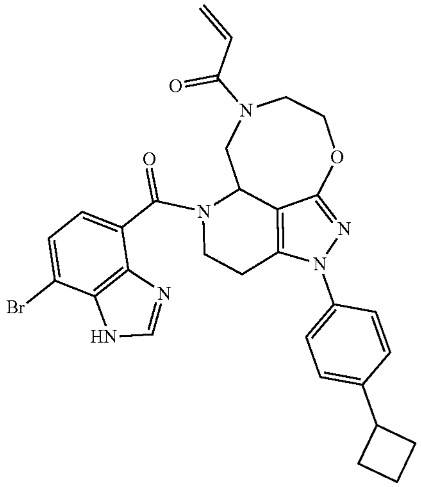

Step 1: Synthesis of Tert-Butyl (rac)-7-acryloyl-2-(4-cyclobutylphenyl)-2,3,4,5a,6,7,8,9-octahydro-5H-10-oxa-1,2,5,7-tetraazacycloocta[cd]indene-S-carboxylate To a solution of tert-butyl (rac)-2-(4-cyclobutylphenyl)-2,3,4, a,6,7,8,9-octahydro-5H-10-oxa-1,2,5,7-tetraazacyclooctal[cd]indene-5-carboxylate (Int. GG) (50 mg, 1 eq, 0.12 mmol) in DCM (0.5 mL) was added TEA (36 mg, 49 μL, 3 eq, 0.35 mmol). The mixture was cooled to 0° C., after which acryloyl chloride (11 mg, 1 eq, 0.12 mmol) was added dropwise to the above mixture. The mixture was warmed to room temperature and stirred for 0.5 h. The mixture was then diluted with ice water (2 mL) and EtOAc (2 mL), and the aqueous layer was extracted with EtOAc (2×2 mL). The combined organic layers were washed with saturated brine (2×2 mL), dried over anhydrous sodium sulfate and concentrated to give a residue. The residue was purified by flash column chromatography, eluting with EtOAc/PE (1:2) to afford tert-butyl (rac)-7-acryloyl-2-(4 -cyclobutylphenyl)-2,3,4,5a,6,7,8,9-octahydro-5H-10-oxa-1,2,5,7-tetraazacyclooctal[cd]indene-5-carboxylate (20 mg) as a white solid. LCMS (ESI, m/z): 479 $[M+H]^+$.

Step 2: Synthesis of (rac)-1-(2-(4-cyclobutylphenyl)-2,3,4,5,5a,6,8,9-octahydro-7H-10-oxa-1,2,5,7-tetraazacycloocta[cd]inden-7-yl)prop-2-en-1-one A solution of tert-butyl (rac)-7-acryloyl-2-(4-cyclobutylphenyl)-2,3,4,5a,6,7,8,9-octahydro-5H-10-oxa-1,2,5,7-tetraazacycloocta[cd]indene-5-carboxylate (20 mg, 1 eq, 42 mol), TFA (0.1 mL) in DCM (0.2 mL) was stirred at room temperature for 30 min. The solvent was then removed under reduced pressure, resulting in (rac)-1-(2-(4-cyclobutylphenyl)-2,3,4,5,5a,6,8,9-octahydro-7H-10-oxa-1,2,5,7-tetraazacycloocta[cd]inden-7-yl)prop-2-en-1-one (20 mg) as a crude yellow oil. The crude product was used in the next step directly without further purification. LCMS (ESI, m/z): 379 $[M+H]^+$.

Step 3: Synthesis of (S AND R)-1-(5-(7-bromo-JH-benzo[d]imidazole-4-carbonyl)-2-(4-cyclobutylphenyl)-2,3,4,5,5a,6,8,9-octahydro-7H-10-oxa-1,2,5,7-tetraazacycloocta[cd]inden-7-yl)prop-2-en-1-one (Int. H)

To a solution of (rac)-1-(2-(4-cyclobutylphenyl)-2,3,4,5,5a,6,8,9-octahydro-7H-10-oxa-1,2,5,7-tetraazacycloocta [cd]inden-7-yl)prop-2-en-1-one (20 mg, 1 eq, 53 μmol) in DMF (0.2 mL) was added DIEA (20 mg, 28 μL, 3 eq, 0.16 mmol), 7-bromo-1H-benzo[d]imidazole-4-carboxylic acid (13 mg, 1 eq, 53 mol) and HBTU (30 mg, 1.5 eq, 79 mol). The mixture was stirred at room temperature for 1 h. The mixture was then diluted with water (2 mL) and EtOAc (2 mL), and the aqueous layer was extracted with EtOAc (2×2 mL). The combined organic layers were washed with saturated brine (2×2 mL), dried over anhydrous sodium sulfate aid concentrated to give a residue. The residue was purified by reverse phase Prep-HPLC (Column: XBridge BEH C18 OBD Prep Column 130, 5 m, 30 mm*150 mm; Mobile Phase A: water (10 mmol/L $NH_4HCO_3$), Mobile Phase B: MeCN; Flow rate: 60 mL/min; Gradient: 33% B to 57% B in min; Wave Length: UV 254 nm/220 nm; retention time 1: 7.4 min) to afford (S AND R)-1-(5-(7-bromo-1H-benzo[d]imidazole-4-carbonyl)-2-(4-cyclobutylphenyl)-2,3,4,5,5a,6,8,9-octahydro-7H-10-oxa-1,2,5,7-tetraazacycloocta[cd]inden-7-yl)prop-2-en-1-one (2.9 mg, 4.8 μmol, 9% yield) as a white solid. LCMS (ESI, m/z): 603, 605 ($^{81}Br$) $[M+H]^+$. H NMR (400 MH, Chloroform-d) δ 11.61 (brs, 1H), 8.35-8.07 (m, 1H), 7.54 (dd, J=12.4, 7.3 Hz, 1H), 7.37 (d, J=7.7 Hz, 1H), 7.30 (d, J=8.8 Hz, 2H), 7.27-7.25 (m, 1H), 7.25-7.10 (m, 2H), 6.71-6.40 (m, 1H), 6.31-5.96 (m, 1H), 5.85-5.62 (m, 1H), 5.37-4.85 (m, 1H), 4.70-4.34 (m, 2H), 4.30-3.79 (m, 3H), 3.56 (dt, J=18.8, 9.5 Hz, 2H), 3.38-3.02 (m, 2H), 2.94-2.52 (m, 1H), 2.46-2.27 (m, 2H), 2.26-2.02 (m, 3H), 1.86 (d, J=9.4 Hz, 1H).

Example K-6: Preparation of (R or S)-1-(5-(7-bromo-1H-indazole-4-carbonyl)-2-(4-cyclobutylphenyl)-2,3,4,5,5a,6,8,9-octahydro-7H-10-oxa-1,2,5,7-tetraazacycloocta[cd]inden-7-yl)prop-2-en-1-one

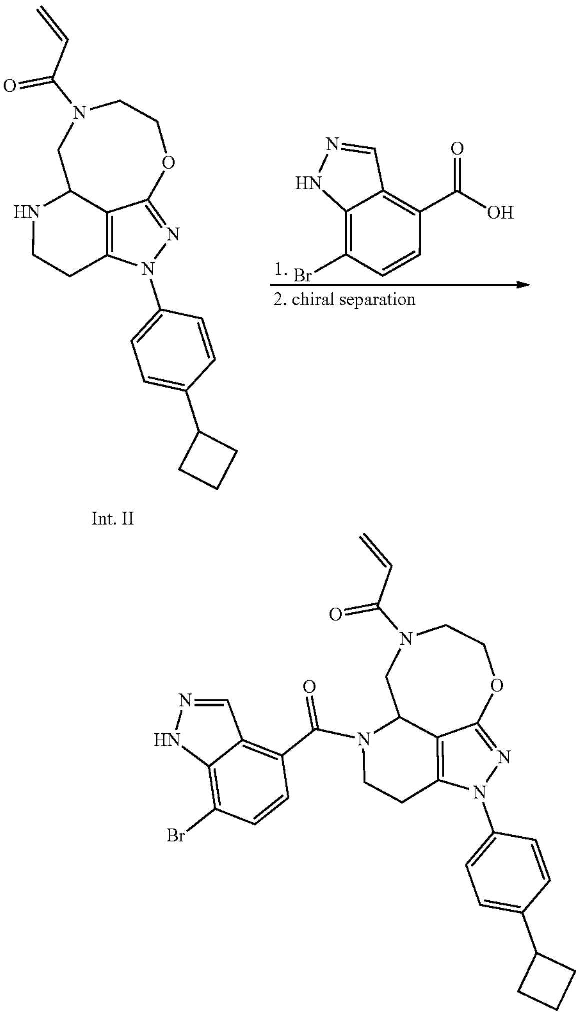

Int. II

To a solution of (rac)-1-(2-(4-cyclobutylphenyl)-2,3,4,5,5a,6,8,9-octahydro-7H-10-oxa-1,2,5,7-tetraazacycloocta [cd]inden-7-yl)prop-2-en-1-one (Int. II) (65 mg, 1 eq, 0.17 mmol) in DMF (0.5 mL) was added 7-bromo-1H-indazole-4-carboxylic acid (83 mg, 2 eq, 0.34 mmol), EDCI (66 mg, 2 eq, 0.34 mmol), HOBT (46 mg, 2 eq, 0.34 mmol) and DIEA (0.11 g, 0.15 mL, 5 eq, 0.86 mmol). The mixture was stirred at room temperature for 6 h. The mixture was diluted with water (20 mL) and EtOAc (20 mL), and the aqueous layer was extracted with EtOAc (2×20 mL). The organic layers were combined and washed with saturated brine (2×20 mL), dried over anhydrous sodium sulfate and concentrated to give a residue. The residue was purified by reversed phase Prep-HPLC (Column: XBridge BEH C18 OBD Prep Column 130, 5 m, 30 mm*150 mm; Mobile Phase A: water (10 mmol/L $NH_4HCO_3$), Mobile Phase B:

MeCN; Flow rate: 60 mL/min; Gradient: 37% B to 57% B in 8 min; Wave Length: UV 254 nm/221 nm; retention time: 7.6 min) to afford (rac)-1-(5-(7-bromo-1H-indazole-4-carbonyl)-2-(4-cyclobutylphenyl)-2,3,4,5,5a,6,8,9-octahydro-7H-10-oxa-1,2,5,7-tetraazacycloocta[cd]inden-7-yl)prop-2-en-1-one (20 mg) as a white solid. The racemic mixture was separated by preparative chiral-HPLC (Column: CHIRALPAK-IE 2*25 cm, 5 μm; Mobile Phase A: HEX(0.1% FA), Mobile Phase B: ETOH:DCM=1:1; Flow rate: 20 mL/min; Gradient: isocratic 55; Wave Length: 254/220 nm; retention time 1: 10.8 min; retention time peak 2: 14.8 min; Injection Volume: 3.0 mL; Number Of Runs: 1). The fractions containing the first-eluting peak of product were combined and lyophilized to afford (R or S)-1-(5-(7-bromo-1H-indazole-4-carbonyl)-2-(4-cyclobutylphenyl)-2,3,4,5,5a,6,8,9-octahydro-7H-10-oxa-1,2,5,7-tetraazacycloocta[cd]inden-7-yl)prop-2-en-1-one as the first-eluting peak (retention time 10.8 min, 3.7 mg, 6.1 mol, 4% yield) as a white solid. LCMS: (ESI, m/z): 601, 603 ($^{81}$Br) $[M+H]^+$. $^1$H NMR: (400 MHz, Chloroform-d) δ 8.30-8.10 (m, 1H), 7.62 (s, 1H), 7.46-7.25 (m, 2H), 7.25-7.00 (m, 2H), 6.77-6.38 (m, 1H), 6.38-6.00 (m, 1H), 5.92-5.20 (m, 2H), 4.89 (s, 1H), 4.69-4.28 (m, 2H), 4.27-3.88 (m, 2H), 3.75 (s, 1H), 3.74-3.36 (m, 2H), 3.35-3.02 (m, 2H), 3.02-2.81 (m, 1H), 2.80-2.40 (m, 2H), 2.23-1.99 (m, 2H), 1.98-1.80 (m, 3H). Analytical CHIRAL-HPLC: CHIRALPAK IE-3; Column Size: 4.6*100 mm, 3 μm; Mobile Phase: Hex (0.1% FA):(EtOH:DCM=1:1)=50:50; Flow: 0.0 mL/min; Temperature: 25° C.; T=3.5 min.

Example K-7: Preparation of (R or S)-1-(2-(4-(bicyclo[1.1.1]pentan-1-yl)phenyl)-5-(7-bromo-1H-benzo[d]imidazole-4-carbonyl)-2,3,4,5,5a,6,8,9-octahydro-7H-10-oxa-1,2,5,7-tetraazacycloocta[cd]inden-7-yl)prop-2-en-1-one

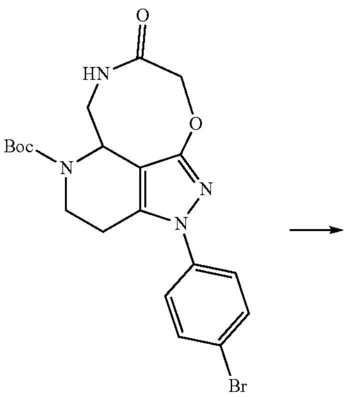

Int. FF

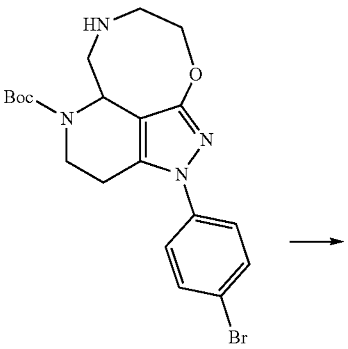

-continued

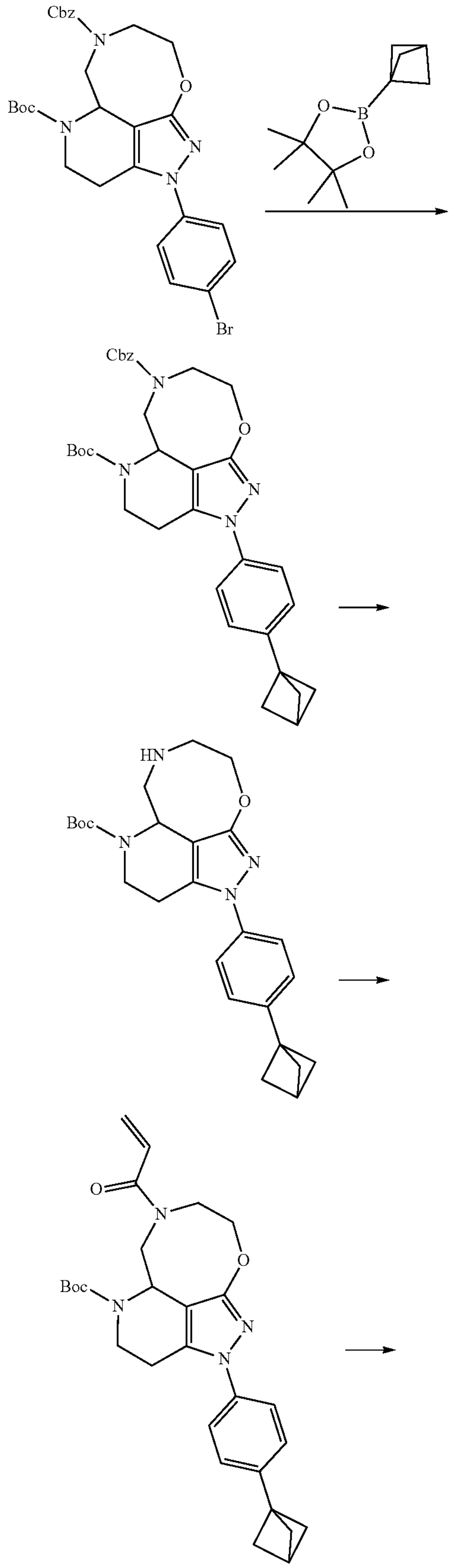

-continued

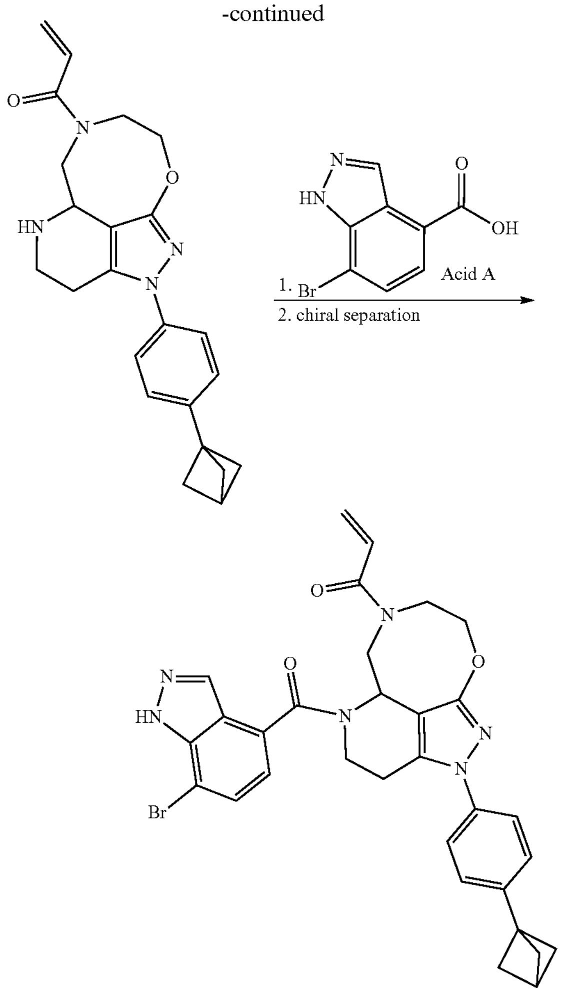

Step 1: Synthesis of Tert-Butyl (rac)-2-(4-bromophenyl)-2,3,4,5a,6,7,8,9-octahydro-5H-10-oxa-1,2,5,7-tetraazacycloocta[cd]indene-5-carboxylate The solution of tert-butyl (rac)-2-(4-bromophenyl)-8-oxo-2,3,4,5a,6,7,8,9-octahydro-5H-10-oxa-1,2,5,7-tetraazacycloocta[cd]indene-5-carboxylate (Int. FF) (10 g, 1 eq, 22 mmol) in THF (100 mL) and $BH_3$·THF (7.4 g, 86 mL, 1 M, 4 eq, 86 mmol) was stirred at room temperature for 16 h. The reaction was quenched by the addition of MeOH (50 mL) at 0° C. The solvent was removed under reduced pressure. This resulted in tert-butyl (ac)-2-(4-bromophenyl)-2,3,4,5a,6,7,8,9-octahydro-5H-10-oxa-1,2,5,7-tetraazacycloocta[cd]indene-5-carboxylate (11 g) as a yellow solid. The crude product was used in the next step directly without further purification. LCMS: (ESI, m/z): 449, 451 ($^{81}$Br) $[M+H]^+$.

Step 2: Synthesis of (rac)-7-benzyl 5-(tert-butyl) 2-(4-bromophenyl)-3,4,5a,6,8,9-hexahydro-2H-10-oxa-1,2,5,7-tetraazacycloocta[cd]indene-5,7-dicarboxylate To a solution of tert-butyl (rac)-2-(4-bromophenyl)-2,3,4,5a,6,7,8,9-octahydro-5H-10-oxa-1,2,5,7-tetraazacycloocta[cd]indene-5-carboxylate (16 g, 1 eq, 35.61 mmol) in DCM (160 mL) was added TEA (18.0 g, 24.8 mL, 5 eq, 178 mmol) and N-(benzyloxycarbonyloxy)succinimide (26.6 g, 3 eq, 107 mmol). The mixture was stirred at 40° C. for 2 h. The mixture was diluted with ice water (200 mL) and DCM (200 mL), and the aqueous layer was extracted with DCM (2×200 mL). The combined organic layers were washed with saturated brine (2×100 mL), dried over anhydrous sodium sulfate and concentrated to give a residue. The residue was purified by flash column chromatography, eluting with EtOAc/PE (1:5) to afford (rac)-7-benzyl 5-(tert-butyl) 2-(4-bromophenyl)-3,4,5a,6,8,9-hexahydro-2H-10-oxa-1,2,5,7-tetraazacycloocta[cd]indene-5,7-dicarboxylate (14 g) as a yellow oil. LCMS: (ESI, m/z): 583, 585 ($^{81}$Br) $[M+H]^+$. $^1$H NMR (400 MHz, DMSO-d6) δ 7.69-7.63 (m, 2H), 7.49-7.42 (m, 2H), 7.42-7.17 (m, 5H), 5.50-4.85 (m, 3H), 4.52-3.34 (m, 8H), 3.10-2.88 (m, 2H), 1.60-1.23 (m, 9H).

Step 3: Synthesis of (rac)-7-benzyl 5-(tert-butyl) 2-(4-(bicyclo[1.1.1]pentan-1-yl)phenyl)-3,4,5a,6,8,9-hexahydro-2H-10-oxa-1,2,5,7-tetraazacycloocta[cd] indene-5,7-dicarboxylate A mixture of (rac)-7-benzyl 5-(tert-butyl) 2-(4-bromophenyl)-3,4,5a,6,8,9-hexahydro-2H-10-oxa-1,2,5,7-tetraazacycloocta[cd]indene-5,7-dicarboxylate (500 ng, 1 eq, 860 μmol), 2-(bicyclo[1.1.1]pentan-1-yl)-4,4,5,5-tetramethyl-1,3,2-dioxaborolane (20 mg, 1.2 eq, 1.03 mmol) and Ir[(dF $(CF_3)ppy)_2dtbbpy]PF_6$ (48.1 mg, 0.05 eq, 42.8 μmol) was divided and added to five 8 mL glass vials each equipped with a magnetic stir bar. Then DMF (2.5 TL) and morpholine (112 mg, 111 μL, 1.5 eq, 1.29 mmol) were added. In a second vial, $NiCl_2$-glyme (9.41 mg, 0.05 eq, 42.8 μmol) and dtbbpy (11.5 mg, 0.05 eq, 42.8 mol) were added and dissolved in DMF (1 mL). The mixture was sonicated for 30 sec and heated afterwards to 100° C. with a heat gun until a clear green solution was obtained. This mixture was combined with the first mixture and the resulting reaction mixtures were irradiated with blue LEDs (445 nm at 220 mW) at room temperature for 3 h. After the reaction mixture was cooled to RT, the mixtures were filtered, combined, and rinsed with EtOAc (3×20 mL), then diluted with water (20 mL). The aqueous layer was extracted with EtOAc (2×20 mL). The combined organic layers were washed with saturated brine (3×20 mL), dried over anhydrous sodium sulfate and concentrated to give a residue. The crude product was purified by silica gel chromatography eluting with PE:EtOAc=5:1 to give (rac)-7-benzyl 5-(tert-butyl) 2-(4-(bicyclo[1.1.1]pentan-1-yl)phenyl)-3,4,5a,6,8,9-hexahydro-2H-10-oxa-1,2,5,7-tetraazacycloocta[cd]indene-5,7-dicarboxylate (220 mg) as a white solid. LCMS (ESI, m/z): 571 $[M+H]^+$.

Step 4: Synthesis of Tert-Butyl (rac)-2-(4-(bicyclo[1.1.1]pentan-1-yl)phenyl)-2,3,4,5a,6,7,8,9-octahydro-5H-10-oxa-1,2,5,7-tetraazacycloocta[cd]indene-5-carboxylate To a solution of (rac)-7-benzyl 5-(tert-butyl) 2-(4-(bicyclo[1.1.1]pentan-1-yl)phenyl)-3,4,5a,6,8,9-hexahydro-2H-10-oxa-1,2,5,7-tetraazacycloocta[cd]indene-5,7-dicarboxylate (220 mg, 1 eq, 385 gmol) in EtOH (4.4 mL) was added Pd/C (110 mg, 10 wt %, 104 μmol, 0.27 eq) and $Pd(OH)_2/C$ (110 mg, 20 wt %, 157 gmol, 0.4 eq) in a pressure tank. The mixture was purged with nitrogen three times, and then was pressurized to 4 MPa with hydrogen at room temperature for 3 h. The reaction mixture was then filtered to remove insoluble solids. The filter cake was washed with EtOH (50 mL)x2, and the filtrate was concentrated under reduced pressure. The crude product tert-butyl (rac)-2-(4-(bicyclo

[1.1.1]pentan-1-yl)phenyl)-2,3,4, a,6,7,8,9-octahydro-5H-10-oxa-1,2,5,7-tetraazacycloocta[cd]indene-5-carboxylate (140 mg) was used in the next step directly without further purification. LCMS (ESI, m/z): 437 $[M+H]^+$.

Step 5: Synthesis of Tert-Butyl (rac)-7-acryloyl-2-(4-(bicyclo[1.1.1]pentan-1-yl)phenyl)-2,3,4,5a,6,7,8,9-octahydro-5H-10-oxa-1,2,5,7-tetraazacycloocta[cd]indene-5-carboxylate To a solution of tert-butyl (rac)-2-(4-(bicyclo[1.1.1]pentan-1-yl)phenyl)-2,3,4,5a,6,7,8,9-octahydro-5H-10-oxa-1,2,5,7-tetraazacycloocta[cd]indene-5-carboxylat (140 mg, 1 eq, 321 gmol) in DCM (2.8 mL) was added TEA (97.4 mg, 134 µL, 3 eq, 962 µmol). The mixture was cooled to 0° C., then acryloyl chloride (43.5 mg, 1.5 eq, 481 µmol) was added slowly. The mixture was warmed to room temperature and stirred for 1 h. The mixture was then diluted with ice water (20 mL) and EtOAc (20 mL), and the aqueous layer was extracted with EtOAc (2×20 mL). The combined organic layers were washed with saturated brine (2×20 mL), dried over anhydrous sodium sulfate and concentrated to give a residue. The residue was purified by flash column chromatography, eluting with EtOAc/PE (1:5) to afford tert-butyl (rac)-7-acryloyl-2-(4-(bicyclo[1.1.1]pentan-1-yl)phenyl)-2,3,4,5a,6,7,8,9-octahydro-5H-10-oxa-1,2,5,7-tetraazacycloocta[cd]indene-5-carboxylate (70 mg) as a yellow oil. LCMS (ESI, m/z): 491 $[M+H]^+$.

Step 6: Synthesis of (rac)-1-(2-(4-(bicyclo[1.1.1]pentan-1-yl)phenyl)-2,3,4,5,5a,6,8,9-octahydro-7H-10-oxa-1,2,5,7-tetraazacycloocta[cd]inden-7-yl)prop-2-en-1-one The solution of tert-butyl (rac)-7-acryloyl-2-(4-(bicyclo[1.1.1]pentan-1-yl)phenyl)-2,3,4,5a,6,7,8,9-octahydro-5H-10-oxa-1,2,5,7-tetraazacycloocta[cd]indene-5-carboxylate (70 mg, 1 eq, 0.14 mmol) in TFA (0.35 mL) and DCM (1.05 mL) was stirred at room temperature for 1 h. The solvent was removed under reduced pressure. This resulted in (rac)-1-(2-(4-(bicyclo[1.1.1]pentan-1-yl)phenyl)-2,3,4,5,5a,6,8,9-octahydro-7H-10-oxa-1,2,5,7-tetraazacycloocta[cd]inden-7-yl)prop-2-en-1-one (100 mg) as a crude yellow oil. The crude product was used in the next step directly without further purification LCMS (ESI, m/z): 391 $[M+H]^+$.

Step 7: Synthesis of (R or S)-1-(2-(4-(bicyclo[1.1.1]pentan-1-yl)phenyl)-5-(7-bromo-JH-benzo[d]imidazole-4-carbonyl)-2,3,4,5,5a,6,8,9-octahydro-7H-10-oxa-,2,5,7-tetraazacycloocta[cd]inden-7-yl)prop-2-en-1-one To a stirred solution of (rac)-1-(2-(4-(bicyclo[1.1.1]pentan-1-yl)phenyl)-2,3,4,5,5a,6,8,9-octahydro-7H-10-oxa-1,2,5,7-tetraazacycloocta[cd]inden-7-yl)prop-2-en-1-one (80 mg, 1 eq, 0.2 mmol) in DMF (1.6 mL) was added HOBT (42 mg, 1.5 eq, 0.21 mmol), 7-bromo-1H-benzo[d]imidazole-4-carboxylic acid (74 mg, 1.5 eq, 0.31 mmol), EDCI (59 mg, 1.5 eq, 0.31 mmol) and DIEA (0.16 g, 0.21 mL, 6 eq, 1.2 mmol) at room temperature and stirred for 2 h. The reaction was quenched by the addition of water (20 mL) at rt. The resulting mixture was extracted with EtOAc (2×20 mL). The combined organic layers were washed with saturated brine (2×20 mL) and dried over anhydrous $Na_2SO_4$. After filtration, the filtrate was concentrated under reduced pressure. The residue was purified by reversed phase flash chromatography with the conditions (Column: XBridge BEH Shield RP18 5 m, 30 mm*150 mm; Mobile Phase A: water (10 mmol/L $NH_4HCO_3$), Mobile Phase B: MeCN; Flow rate: 60 mL/min; Gradient: 30% B to 60% B in 10 min; Wave Length: UV 254 nm/221 nm; retention time 1: 8.9 min) to afford (rac)-1-(2-(4-(bicyclo[1.1.1]pentan-1-yl)phenyl)-5-(7-bromo-1H-benzo[d]imidazole-4-carbonyl)-2,3,4,5,5a,6,8,9-octahydro-7H-10-oxa-1,2,5,7-tetraazacycloocta[cd]inden-7-yl)prop-2-en-1-one (35 mg, 56 gmol, 28% yield over 2 steps) as a white solid. LCMS (ESI, m/z): 613, 615 ($^{81}$Br) $[M+H]^+$.

The racemic material (35 mg) was purified by Prep-chiral HPLC with the following conditions (Column: CHIRALART Cellulose-SB 3*25 cm, 5 µm; Mobile Phase A: HEX (0.1% FA), Mobile Phase B: EtOH:DCM=1:1; Flow rate: 40 mL/min; Gradient: isocratic 30; Wave Length: UV 254/220 nm; Sample Solvent: EtOH; Number Of Runs: 2) to afford (R or S)-1-(2-(4-(bicyclo[1.1.1]pentan-1-yl)phenyl)-5-(7-bromo-1H-benzo[d]imidazole-4-carbonyl)-2,3,4,5,5a,6,8,9-octahydro-7H-10-oxa-1,2,5,7-tetraazacycloocta[cd]inden-7-yl)prop-2-en-1-one as the first-eluting peak (10.1 mg, 16.4 mol, 8% yield) as a white solid. LCMS: (ESI, m/z): 613, 615 ($^{81}$Br) $[M+H]^+$. $^1$H NMR (400 MHz, Chloroform-d) δ 8.29 (s, 1H), 7.53 (d, J=7.6 Hz, 1H), 7.36 (d, J=8.1 Hz, 1H), 7.28 (d, J=6.8 Hz, 2H), 7.21 (d, J=8.3 Hz, 2H), 6.65-6.40 (m, 1H), 6.31-6.03 (m, 1H), 5.87-5.69 (m, 1H), 5.60-4.80 (m, 1H), 4.62-4.12 (m, 3H), 4.10-3.81 (m, 2H), 3.70-3.40 (m, 1H), 3.37-2.95 (m, 3H), 2.73 (d, J=9.9 Hz, H), 2.70-2.55 (m, 1H), 2.09 (d, J=8.9 Hz, 6H). Analytical chiral HPLC: Column: CHIRAL ART Cellulose-SB 4.6*50 mm, 3 m; Mobile Phase: Hex(0.1% TFA):(EtOH:DCM=1:1)=65:35; Flow rate: 1 mL/min; Temperature: 25° C.; retention time=3.9 min.

Example K-8: Preparation of (R or S)-1-(5-(7-bromo-1H-benzo[d]imidazole-4-carbonyl)-2-(2-hydroxy-4-isopropylphenyl)-2,3,4,5,5a,6,8,9-octahydro-7H-10-oxa-1,2,5,7-tetraazacycloocta[ed]inden-7-yl)prop-2-en-1-one

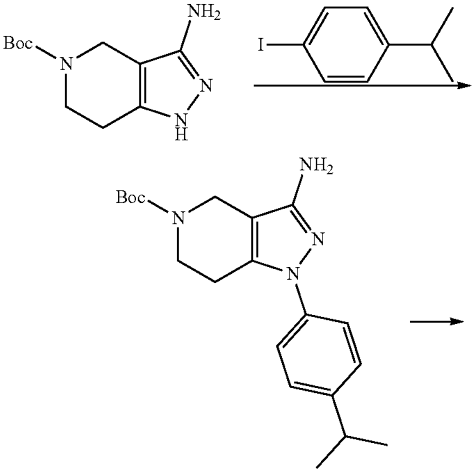

Int. PP

-continued
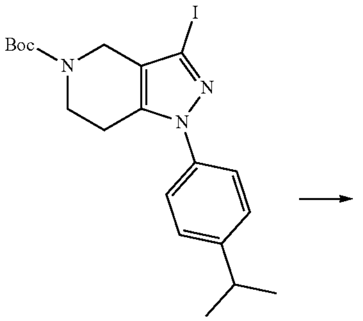
Int. JJ
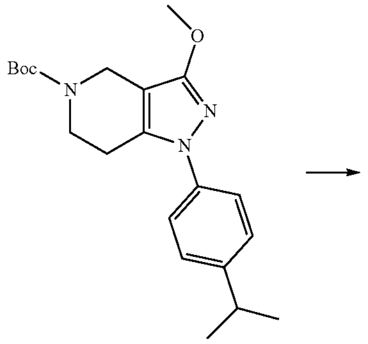
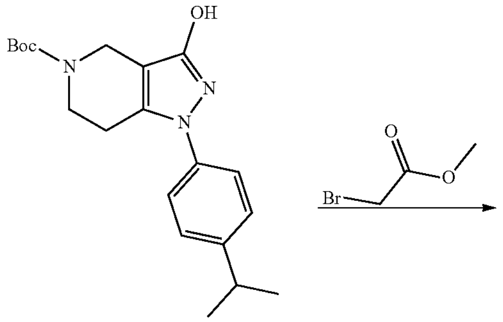
Int. KK
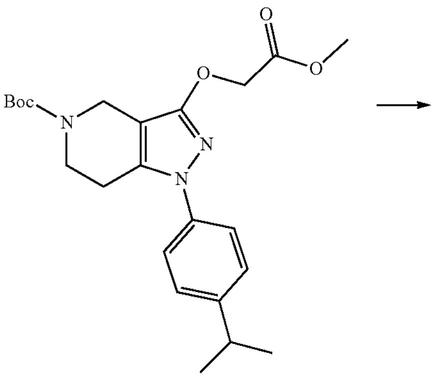
-continued
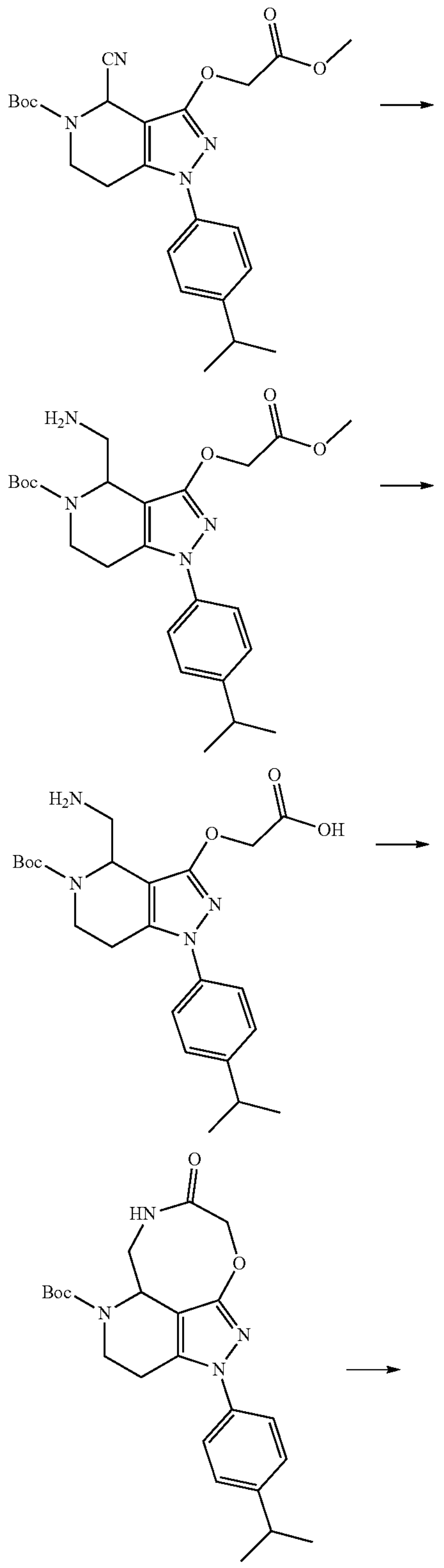

-continued
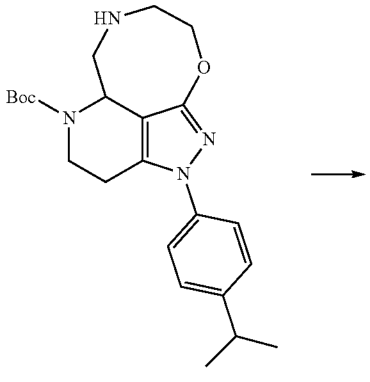
Int. LL
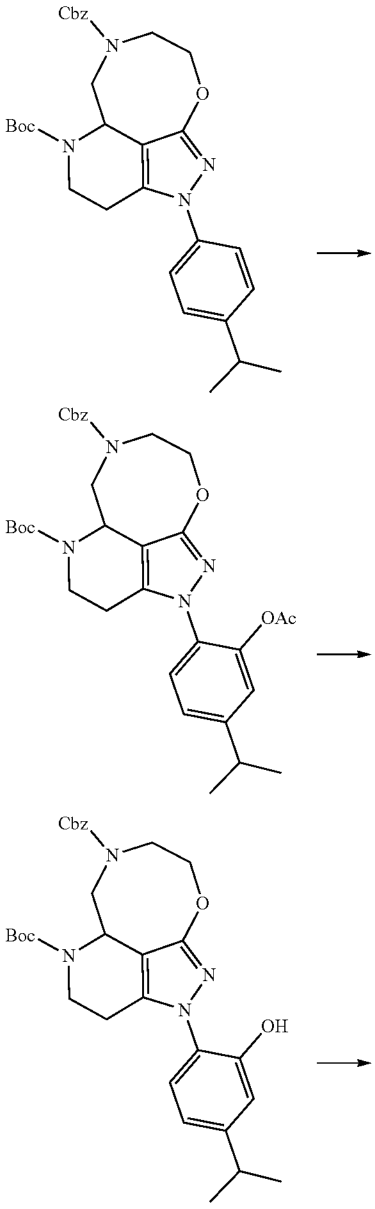
-continued
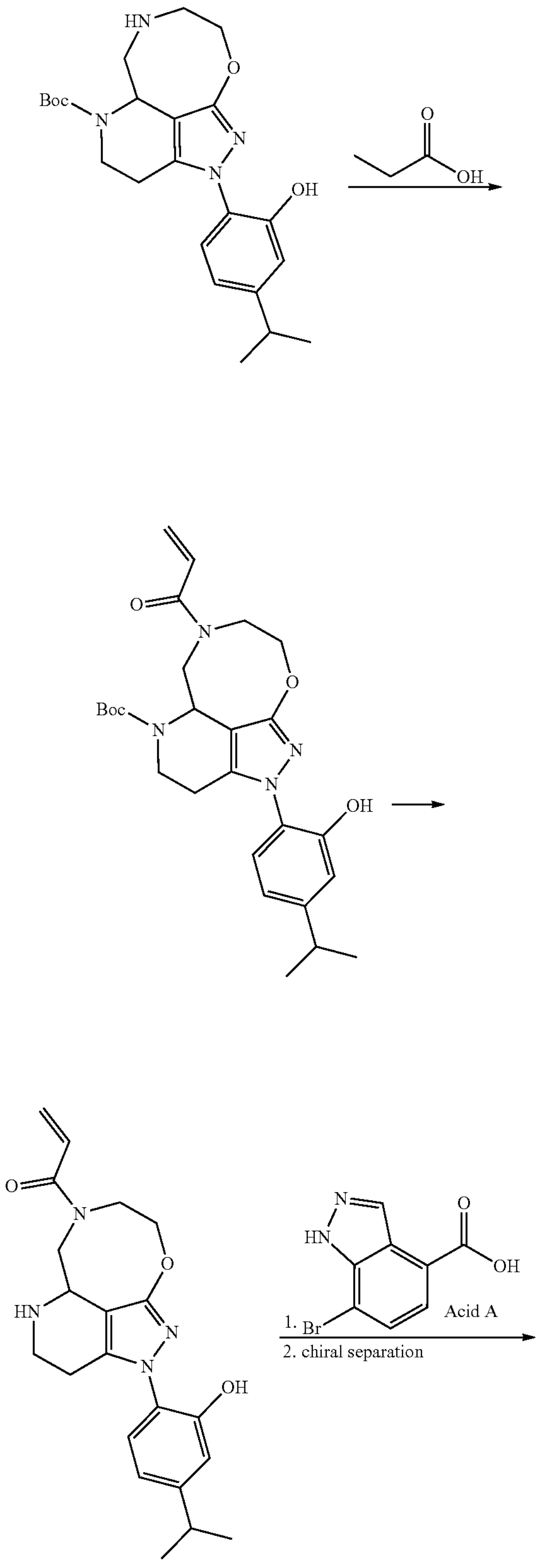
Int. MM

-continued

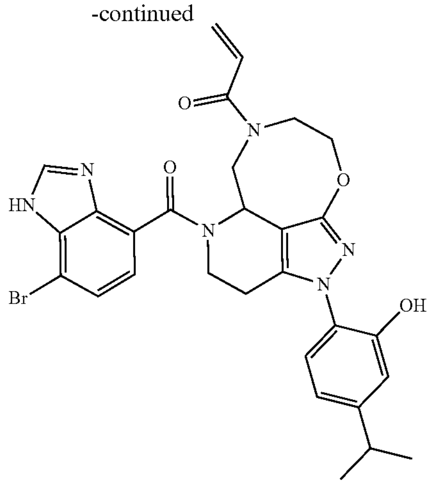

Step 1: Synthesis of Tert-Butyl 3-amino-1-(4-isopropylphenyl)-1,4,6,7-tetrahydro-5H-pyrazolo[ 4,3-c]pyridine-5-carboxylate (Int. PP)

To a solution of tert-butyl 3-amino-1,4,6,7-tetrahydro-5H-pyrazolo[4,3-c]pyridine-5-carboxylate (300 g, 1.26 mol, 1.0 eq) and 1-iodo-4-isopropylbenzene (433 g, 1.76 mol, 1.4 eq) in DMF (1.50 L) was added $CuBr_2$ (56.2 g, 251 mmol, 0.2 eq) and $Cs_2CO_3$ (492 g, 1.51 mol, 1.20 eq) at room temperature. The mixture was stirred at 120° C. for 2 h. The reaction mixture was then filtered, and then diluted with water (500 mL) and extracted with EtOAc (2×1.0 L). The combined organic layers were washed with brine (500 mL), dried over $Na_2SO_4$, filtered, and concentrated under reduced pressure to give a residue. The residue was purified by column chromatography ($SiO_2$, petroleum ether:ethyl acetate=10:1 to 1:1) to provide tert-butyl 3-amino-1-(4-isopropylphenyl)-1,4,6,7-tetrahydro-5H-pyrazolo[4,3-c] pyridine-5-carboxylate (110 g) as a white solid. LCMS: (ESI, m/z): 357 $[M+H]^+$. $^1$H NMR (400 MHz, Chloroform-d) δ 7.31 (d, J=8.2 Hz, 2H), 7.25 (d, J=8.4 Hz, 2H), 4.34 (s, 2H), 3.65 (s, 2H), 2.93 (h, J=6. Hz, 1H), 2.79 (t, J=5.6 Hz, 2H), 1.50 (s, 9H), 1.26 (d, J=6.9 Hz, 6H).

Step 2: Synthesis of Tert-Butyl 3-iodo-1-(4-isopropylphenyl)-1,4,6,7-tetrahydro-5H-pyrazolo[4,3-c] pyridine-S-carboxylate To a stirred mixture of $I_2$ (25.63 g, 1.2 eq, 101 mmol) in DCM (200 mL) was added isoamyl nitrite (19.7 g, 22.5 mL, 2 eq, 168 mmol) dropwise at 0° C. under air atmosphere. To the above mixture was added tert-butyl 3-amino-1-(4-isopropylphenyl)-1,4,6,7-tetrahydro-5H-pyrazolo[4,3-c]pyridine-5-carboxylate (30.0 g, 1 eq, 84.2 mmol) in DCM dropwise at rt. The resulting mixture was stirred for additional 1 h at rt, after which the reaction mixture was slowly poured in 50% $Na_2O_3S_2$ aqueous solution (50 mL). The resulting mixture was extracted with EtOAc. The combined organic layers were washed with saturated brine, dried over anhydrous $Na_2SO_4$, and filtered. After filtration, the filtrate was concentrated under reduced pressure. The residue was purified by silica gel column chromatography, eluting with EtOAc/PE (2:1) to afford tert-butyl 3-iodo-1-(4-isopropylphenyl)-1,4,6,7-tetrahydro-5H-pyrazolo[4,3-c]pyridine-5-carboxylate (20.5 g) as a white solid. LCMS: (ESI, m/z): 468 $[M+H]^+$. $^1$H NMR (400 MHz, DMSO-d) δ 7.36-7.34 (m, 2H), 7.33-7.30 (m, 2H), 4.31 (s, 2H), 3.71 (s, 2H), 2.98-2.91 (m, 1H), 2.80-2.75 (m, 2H), 1.51 (s, 9H), 1.26 (d, J=8 Hz, 6H).

Step 3: Synthesis of Tert-Butyl 1-(4-isopropylphenyl)-3-methoxy-1,4,6,7-tetrahydro-5H-pyrazolo[4,3-c]pyridine-5-carboxylate A mixture of tert-butyl 3-iodo-1-(4-isopropylphenyl)-1,4,6,7-tetrahydro-5H-pyrazolo[4,3-c]pyridine-5-carboxylate (5.0 g, 1 eq, 11 mmol), 3,4,7,8-tetramethyl-1,10-diazaphenanthrene (0.76 g, 0.3 eq, 3.2 mmol), CuI (0.41 g, 0.2 eq, 2.1 mmol) and $Cs_2CO_3$ (7.0 g, 2 eq, 21 mmol) in MeOH (100 mL) was stirred for 8 h at 80° C. under a nitrogen atmosphere. The resulting mixture was extracted with EtOAc (2×100 mL). The combined organic layers were washed with saturated brine (100 mL) and dried over anhydrous $Na_2SO_4$. After filtration, the filtrate was concentrated under reduced pressure. The residue was purified by silica gel column chromatography, eluting with EtOAc in PE (10%) to afford tert-butyl 1-(4-isopropylphenyl)-3-methoxy-1,4,6,7-tetrahydro-5H-pyrazolo[4,3-c]pyridine-5-carboxylate (2.2 g) as a yellow solid. LCMS (ESI, m/z): 372 $[M+H]^+$. $^1$H NMR (400 MHz, DMSO-$d_6$) δ 7.43-7.39 (m, 2H), 7.34-7.30 (m, 2H), 4.24 (s, 2H), 3.87 (s, 3H), 3.55 (t, J=5.6 Hz, 2H), 2.92 (p J=6.9 Hz, 1H), 2.80 (t, J=5.6 Hz, 2H), 1.43 (s, 9H), 1.22 (d, J=6.9 Hz, 6H).

Step 4: Synthesis of Tert-Butyl 3-hydroxy-1-(4-isopropylphenyl)-1,4,6,7-tetrahydro-5H-pyrazolo[4,3-c]pyridine-5-carboxylate A solution of tert-butyl 1-(4-isopropylphenyl)-3-methoxy-1,4,6,7-tetrahydro-5H-pyrazolo[4,3-c]pyridine-5-carboxylate (2.2 g, 1 eq, 5.9 mmol) and lithium tri-sec-butylhydroborate (23 g, 89 mL, 1 M THF solution, 15 eq, 89 mmol) was stirred for 3 h at 80° C. under a nitrogen atmosphere. The mixture was diluted with water (100 mL) and EtOAc (100 mL), and the aqueous layer was extracted with EtOAc (100 mL). The combined organic layers were washed with saturated brine (100 mL), dried over anhydrous sodium sulfate and concentrated to give a residue. The residue was purified by silica gel column chromatography, eluting with EtOAc/PE (1/1) to afford tert-butyl 3-hydroxy-1-(4-isopropylphenyl)-1,4,6,7-tetrahydro-5H-pyrazolo[4,3-c]pyridine-5-carboxylate (1.6 g) as a yellow solid. LCMS (ESI, m/z): 358 $[M+H]^+$.

Step 5: Synthesis of Tert-Butyl 1-(4-isopropylphenyl)-3-(2-methoxy-2-oxoethoxy)-1,4,6,7-tetrahydro-5H-pyrazolo[4,3-c]pyridine-5-carboxylate To a solution of tert-butyl 3-hydroxy-1-(4-isopropylphenyl)-1,4,6,7-tetrahydro-5H-pyrazolo[4,3-c]pyridine-5-carboxylate (1.6 g, 1 eq, 4.5 mmol) in DMA (32 mL) were added $Cs_2CO_3$ (2.9 g, 2 eq, 9.0 mmol) and methyl 2-bromoacetate (1.0 g, 1.5 eq, 6.7 mmol). The mixture was stirred at room temperature for 2 h. The mixture was diluted with water (20 mL) and EtOAc (20 mL), and the aqueous layer was extracted with EtOAc (2×20 mL. The combined organic layers were washed with saturated brine (2×20 mL), dried over anhydrous sodium sulfate and concentrated to give a residue. The residue was purified by silica gel column chromatography, eluting with EtOAc/PE (1/1) to afford tert-butyl 1-(4-isopropylphenyl)-3-(2-methoxy-2-oxoethoxy)-1,4,6,7-tetrahydro-5H-pyrazolo[4,3-c]pyridine-5-carboxylat e (1.8 g) as a yellow solid. LCMS (ESI, m/z): 430

[M+H]+. $^1H$ NMR (400 MHz, DMSO-$d_6$) δ 7.40-7.34 (m, 2H), 7.34-7.30 (m, 2H), 4.86 (s, 2H), 4.28 (s, 2H), 3.69 (s, 3H), 3.57 (t, J=5.6 Hz, 2H), 2.92 (p, J=6.9 Hz, 1H), 2.80 (t, J=5.7 Hz, 2H), 1.44 (s, 9H), 1.21 (d, J=6.9 Hz, 6H).

Step 6: Synthesis of Tert-Butyl (rac)-4-cyano-1-(4-isopropylphenyl)-3-(2-methoxy-2-oxoethoxy)-1,4,6,7-tetrahydro-5H-pyrazolo[4,3-c]pyridine-5-carboxylate To a solution of tert-butyl 1-(4-isopropylphenyl)-3-(2-methoxy-2-oxoethoxy)-1,4,6,7-tetrahydro-5H-pyrazolo[4,3-c]pyridine-5-carboxylate (1.80 g, 1 eq, 4.2 mol) in MeCN (18 mL) was added acetic acid (503 mg, 480 μL, 2 eq, 8.38 mmol), trimethylsilyl nitrile (832 mg, 1.1 mL, 2 eq, 8.38 mmol) and TEMPO$^+BF_4^-$ (2.04 g, 2 eq, 8.38 mmol). The rea tion flask was evacuated and back-filled with nitrogen. This process was repeated×3. The resulting mixture was stirred for 1 h at room temperature under a nitrogen atmosphere. The mixture was filtered and rinsed with EtOAc (3×20 mL), then diluted with water (20 mL). The aqueous layer was extracted with EtOAc (2×20 mL). The combined organic layers were combined organic layers were washed with saturated brine (3×20 mL), dried over anhydrous sodium sulfate and concentrated to give a residue. The crude product was purified by silica gel chromatography eluting with PE:EtOAc=10:1 to give tert-butyl (rac)-4-cyano-1-(4-isopropylphenyl)-3-(2-methoxy-2-oxoethoxy)-1,4,6,7-tetrahydro-5H-pyrazolo[4,3-c]pyridine-5-carboxylate (1.7 g) as a yellow solid. LCMS (ESI, m/z): 455 [M+H]+.

Step 7: Synthesis of Tert-Butyl 4-(aminomethyl)-1-(4-isopropylphenyl)-3-(2-methoxy-2-oxoethoxy)-1,4,6,7-tetrahydro-5H-pyrazolo[4,3-c]pyridine-5-carboxylate To a solution of tert-butyl (rac)-4-cyano-1-(4-isopropylphenyl)-3-(2-methoxy-2-oxoethoxy)-1,4,6,7-tetrahydro-5H-pyrazolo[4,3-c]pyridine-5-carboxylate (1.8 g, 1 eq, 4.0 mmol) in MeOH (54 mL) were added Raney nickel (900 mg, 50 wt %, 1.9 eq, 0.67 mmol). The mixture was purged with nitrogen×3 and then was pressurized 4.0 MPa with hydrogen at 60° cand was stirred overnight. The reaction mixture was then cooled to rt, filtered, and rinsed with EtOAc (5×50 mL). The filtrate was concentrated under reduced pressure to give tert-butyl (rac)-4-(aminomethyl)-1-(4-isopropylphenyl)-3-(2-methoxy-2-oxoethoxy)-1,4,6,7-tetrahydro-5H-pyrazolo[4,3-c]pyridine-5-carboxylate (1.7 g) as a crude yellow solid. The crude product was used in the next step directly without further purification. LCMS (ESI, m/z): 459 [M+H]+.

Step 8: Synthesis of 2-((4-(aminomethyl)-S-(tert-butoxycarbonyl)-1-(4-isopropylphenyl)-4,5,6,7-tetrahydro-JH-pyrazolo[4,3-c]pyridin-3-yl)oxy)acetic Acid To a solution of tert-butyl (rac)-4-(aminomethyl)-1-(4-isopropylphenyl)-3-(2-methoxy-2-oxoethoxy)-1,4,6,7-tetrahydro-5H-pyrazolo[4,3-c]pyridine-5-carboxylate (1.6 g, 1 eq, 3.5 mmol) in MeOH (32 mL) and water (16 mL) was added LiOH (0.13 g, 1.5 eq, 5.2 mmol). The mixture was stirred at room temperature overnight. The mixture was then acidified to pH=3 with 1 M sulfuric acid, then diluted with EtOAc (20 mL) and water (15 mL). T, a d the aqueous layer was extracted with EtOAc (2×20 mL), and the combined organic layers were washed with saturated brine (20 mL), dried over anhydrous sodium sulfate and concentrated to afford (rac)-2-((4-(aminomethyl)-5-(tert-butoxycarbonyl)-1-(4-isopropylphenyl)-4,5,6,7-tetrahydro-1H-pyrazolo[4,3-c]pyridin-3-yl)oxy)acetic acid (1.7 g) as a yellow solid. The crude product was used in the next step directly without further purification. LCMS (ESI, m/z): 45 [M+H]+.

Step 9: Synthesis of Tert-Butyl 2-(4-isopropylphenyl)-8-oxo-2,3,4,5a,6,7,8,9-octahydro-5H-10-oxa-1,2,5,7-tetraazacycloocta[cd]indene-5-carboxylate To a solution of (rac)-2-((4-(aminomethyl)-5-(tert-butoxycarbonyl)-1-(4-isopropylphenyl)-4,5,6,7-tetrahydro-1H-pyrazolo[4,3-c]pyridin-3-yl)oxy)acetic acid (200 mg, 1 eq, 450 μmol) in DMF (4 mL) was added HATU (222 mg, 1.3 eq, 585 μmol) and DIEA (174 mg, 235 μL, 3 eq, 1.35 mmol). The mixture was stirred at room temperature for 2 h. The mixture was then diluted with water (20 mL) and EtOAc (20 mL), and the aqueous layer was extracted with EtOAc (2×20 mL). The combined organic layers were washed with sat rated brine (2×20 mL), dried over anhydrous sodium sulfate and concentrated to give a residue. The residue was purified by silica gel column chromatography, eluting with EtOAc in PE (70%) to afford tert-butyl (rac)-2-(4-isopropylphenyl)-8-oxo-2,3,4,5a,6,7,8,9-octahydro-5H-10-oxa-1,2,5,7-tetraazacycloocta[cd]indene-5-carboxylate (60 mg) as a yellow solid. LCMS (ESI, m/z): 427 [M+H]+.

Step 10: Synthesis of Tert-Butyl (rac)-2-(4-isopropylphenyl)-2,3,4,5a,6,7,8,9-octahydro-5H-10-oxa-1,2,5,7-tetraazacycloocta[cd]indene-5-carboxylate To a solution of tert-butyl (rac)-2-(4-isopropylphenyl)-8-oxo-2,3,4,5a,6,7,8,9-octahydro-5H-10-oxa-1,2,5,7-tetraazacycloocta[cd]indene-5-carboxylate (360 mg, 1 eq, 844 μmol) in THF (7.2 mL) was added $BH_3$·THF (290 mg, 3.38 mL, 1 M, 4 eq, 3.38 mmol). The mixture was stirred at 60° C. for 2 h, after which the reaction was quenched with MeOH t room temperature. The resulting mixture was concentrated under vacuum. The crude product (300 mg) was used in the next step directly without further purification. LCMS (ESI, m/z): 413 [M+H]+.

Step 11: Synthesis of (rac)-7-benzyl 5-(tert-butyl) 2-(4-isopropylphenyl)-3,4,5a,6,8,9-hexahydro-2H-10-oxa-1,2,5,7-tetraazacycloocta[cd]indene-5,7-dicarboxylate To a solution of tert-butyl (rac)-2-(4-isopropylphenyl)-2,3,4,5a,6,7,8,9-octahydro-5H-10-oxa-1,2,5,7-tetraazacycloocta[cd]indene-5-carboxylate (300 mg, 1 eq, 727 μmol) in DCM (6 mL) were added TEA (221 mg, 304 μL, 3 eq, 2.18 mmol) and N-(benzyloxycarbonyloxy)succinimide (217 mg, 1.2 eq, 873 mol). The mixture was stirred at room temperature overnight. The mixture was diluted with water (20 mL) and EtOAc (20 mL), and the aqueous layer was extracted with EtOAc (2×20 mL). The combined organic layers were washed with saturated brine (2×20 mL), dried over anhydrous sodium sulfate and concentrated to give a residue. The residue was purified by silica gel column chromatography, eluting with EtOAc/PE (1/1) to afford (rac)-7-benzyl 5-(tert-butyl) 2-(4-isopropylphenyl)-3,4,5a,6,8,9-hexahydro-2H-10-oxa-1,2,5,7-tetraazacycloocta[cd]indene-5,7-dicarboxylate (210 mg) as a yellow solid. LCMS (ESI, m/z): 547 [M+H]+.

Step 12: Synthesis of 7-benzyl 5-(tert-butyl) 2-(2-acetoxy-4-isopropylphenyl)-3,4,5a,6,8,9-hexahydro-2H-10-oxa-1,2,5,7-tetraazacycloocta[cd]indene-5,7-dicarboxylate To a solution of (rac)-7-benzyl 5-(tert-butyl) 2-(4-isopropylphenyl)-3,4,5a,6,8,9-hexahydro-2H-10-oxa-1,2,5,7-tetraazacycloocta[cd]indene-5,7-dicarboxylate (410 mg, 1 eq, 750 μmol) in AcOH (8.2 mL) and MeCN (0.82 mL) were added PIDA (483 mg, 2 eq, 1.5 mmol) and $Pd(OAc)_2$ (16.8 mg, 0.1 eq, 75.0 μmol). The flask was placed under a positive pressure of nitrogen and subjected to three back-filling cycles under high vacuum. The resulting mixture was stirred for 1 h at 90° C. under a nitrogen atmosphere. After the reaction mixture was cooled to rt, the mixture was filtered and rinsed with EtOAc (3×200 mL), then diluted with water (200 mL). The aqueous layer was extracted with EtOAc (2×200 mL). The combined organic layers were washed with saturated brine (3×200 mL), dried over anhydrous sodium sulfate and concentrated to give a residue. The crude product was purified by silica gel chromatography eluting with PE:EtOAc=10:1 to give (rac)-7-benzyl 5-(tert-butyl) 2-(2-acetoxy-4-isopropylphenyl)-3,4,5a,6,8,9 -hexahydro-2H-10-oxa-1,2,5,7-tetraazacycloocta[cd]indene-5,7-dicarboxylate (300 mg) as a yellow solid. LCMS (ESI, m/z): 605 $[M+H]^+$.

Step 13: Synthesis of (rac)-7-benzyl 5-(tert-butyl) 2-(2-hydroxy-4-isopropylphenyl)-3,4,5a,6,8,9-hexahydro-2H-10-oxa-1,2,5,7-tetraazacycloocta[cd]indene-5,7-dicarboxylate To a solution of (rac)-7-benzyl 5-(tert-butyl) 2-(2-acetoxy-4-isopropylphenyl)-3,4,5a,6,8,9-hexahydro-2H-10-oxa-1,2,5,7-tetraazacycloocta[cd]indene 5,7-dicarboxylate (220 mg, 1 eq, 364 μmol) in MeOH (4.4 mL) and water (2.2 mL) was added NaOH (29 mg, 2 eq, 730 μmol). The mixture was stirred at room temperature for 1 h. The mixture was then acidified to pH=6 with 1 M sulfuric acid, then diluted with EtOAc (20 mL) and water (15 mL), and the aqueous layer was extracted with EtOAc (2×20 mL). The organic layers were combined and washed with saturated brine (20 mL), dried over anhydrous sodium sulfate and concentrated to afford (rac)-7-benzyl 5-(tert-butyl) 2-(2-hydroxy-4-isopropylphenyl)-3,4,5a,6,8,9-hexahydro-2H-10-oxa-1,2,5,7-tetraazacycloocta[cd]indene-5,7-dicarboxylate (230 mg) as a yellow solid. The crude product was used in the next step directly without further purification. LCMS (ESI, m/z): 563 $[M+H]^+$.

Step 14: Synthesis of Tert-Butyl (rac)-2-(2-hydroxy-4-isopropylphenyl)-2,3,4,5a,6,7,8,9-octahydro-5H-10-oxa-1,2,5,7-tetraazacycloocta[cd]indene-5-carboxylate To a solution of (rac)-7-benzyl 5-(tert-butyl) 2-(2-hydroxy-4-isopropylphenyl)-3,4,5a,6,8,9-hexahydro-2H-10-oxa-1,2,5,7-tetraazacycloocta[cd]indene-5,7-dicarboxylate (230 mg, 1 eq, 409 mol) in EtOH (4.6 mL) were added $Pd(OH)_2/C$ (115 mg, 10 wt %, 0.20 eq, 82 mol) and Pd/C (115 mg, 10 wt %, 0.26 eq, 108 μmol). The mixture was purged with nitrogen×3 times and then was pressurized to 3.0 MPa with hydrogen at room temperature for 3 h. The mixture was filtered and rinsed with EtOH (5×50 mL), and the filtrate was concentrated under vacuum to give a residue. The residue was purified by silica gel column chromatography, eluting with MeOH in DCM (10%) to afford tert-butyl (rac)-2-(2-hydroxy-4-isopropylphenyl)-2,3,4,5a,6,7,8,9-octahydro-5H-10-oxa-1,2,5,7-tetraazacycloocta[cd]indene-5-carboxylate (80 mg) as a yellow solid. LCMS (ESI, m/z): 445 $[M+H]^+$.

Step 15: Synthesis of Tert-Butyl (rac)-7-acryloyl-2-(2-hydroxy-4-isopropylphenyl)-2,3,4,5a,6,7,8,9-octahydro-5H-10-oxa-1,2,5,7-tetraazacycloocta[cd]indene-5-carboxylate To a solution of tert-butyl (rac)-2-(2-hydroxy-4-isopropylphenyl)-2,3,4,5a,6,7,8,9-octahydro-5H-10-oxa-1,2,5,7-tetraazacycloocta[cd]indene-5-carboxylate (80 mg, 1 eq, 0.19 mmol) in DCM (1.6 mL) were added propylphosphonic anhydride (89 mg, 83 μL, 1.5 eq, 0.28 mmol), acrylic acid (16 mg, 1.2 eq, 0.22 mmol) and DIEA (0.12 g, 0.16 mL, 5 eq, 0.93 mmol). The mixture was stirred at room temperature for 2 h. The mixture was diluted with water (20 mL) and EtOAc (20 mL), and the aqueous layer was extracted with EtOAc (2×20 ML). The combined organic layers were washed with saturated brine (2×20 mL), dried over anhydrous sodium sulfate and concentrated to give a residue. The residue was purified by silica gel column chromatography, eluting with EtOAc/PE (1/1) to afford tert-butyl (rac)-7-acryloyl-2-(2-hydroxy-4-isopropylphenyl)-2,3,4,5a,6,7,8,9-octahydro-5H-10-oxa-1,2,5,7-tetraazacycloocta[cd]indene-5-carboxylate (53 mg) as a yellow solid. LCMS (ESI, m/z): 483 $[M+H]^+$.

Step 16: Synthesis of (rac)-1-(2-(2-hydroxy-4-isopropylphenyl)-2,3,4,5,5a,6,8,9-octahydro-7H-10-oxa-1,2,5,7-tetraazacycloocta[cd]inden-7-yl)prop-2-en-1-one A solution of tert-butyl 7-acryloyl-2-(2-hydroxy-4-isopropylphenyl)-2,3,4,5a,6,7,8,9-octahydro-5H-10-oxa-1,2,5,7-tetraazacycloocta[cd]indene-5-carboxylate (53 mg, 1 eq, 0.11 mmol) in DCM (1 mL) and TFA (0.3 mL) was stirred at room temperature for 1 h. The solvent was removed under reduced pressure. This resulted in (rac)-1-(2-(2-hydroxy-4-isopropylphenyl)-2,3,4,5,5a,6,8,9-octahydro-7H-10-oxa-1,2,5,7-tetraazacycloocta[cd]inden-7-yl)prop-2-en-1-one (60 mg) as a crude yellow oil. The crude product was used in the next step directly without further purification.

Step 17: Synthesis of (R or S)-1-(5-(7-bromo-1H-benzo[d]imidazole-4-carbonyl)-2-(2-hydroxy-4-isopropylphenyl)-2,3,4,5,5a,6,8,9-octahydro-7H-10-oxa-1,2,5,7-tetraazacycloocta[cd]inden-7-yl)prop-2-en-1-one To a solution of (rac)-1-(2-(2-hydroxy-4-isopropylphenyl)-2,3,4,5,5a,6,8,9-octahydro-7H-10-oxa-1,2,5,7-tetraazacycloocta[cd]inden-7-yl)prop-2-en-1-one (40 mg, 1 eq, 0.1 mmol) in DMF (0.8 mL) were added 7-bromo-1H-benzo[d]imidazole-4-carboxylic acid (25 mg, 1 eq, 0.1 mmol), HBTU (48 mg, 1.2 eq, 0.13 mmol) and DIEA (0.11 g, 0.15 mL, 8 eq, 0.84 mmol). The mixture was stirred at room temperature for 2 h. The mixture was diluted with water (20 mL) and EtOAc (20 mL), and the aqueous layer was extracted with EtOAc (2×20 mL). The combined organic layers were washed with saturated brine (2×20 mL), dried over anhydrous sodium sulfate and concentrated to give a residue. The residue was purified by reverse-phase Prep-HPLC (Column: Sunfire C18 5 m, 30 mm*150 mm; Mobile Phase A: water (0.1% FA), Mobile Phase B: MeCN; Flow rate: 60 mL/min; Gradient: 20% B to 55% B in 10 min; Wave Length: UV 254 nm/220 nm; retention time 1: 9.1 min) to afford (rac)-1-(5-(7-bromo-1H-benzo[d]imidazole-4-carbonyl)-2-(2-hydroxy-4-isopropylphenyl)-2,3,4,5,5a,6,8,9-octahydro-7H-10-oxa-1,2,5,7-tetraazacycloocta[cd]inden-7-yl)prop-2-en-1-one (9 mg). The racemic residue was purified by chiral Prep-HPLC (Column: CHIRAL ART Cellulose-SB 2*25 cm, 5 μm; Mobile Phase A: HEX(0.1% FA), Mobile Phase B: EtOH:DCM=1:1; Flow rate: 20 mL/min; Gradient: isocratic 35; Wave Length: UV 254/220 nm; retention time 1: 6.5; retention time 2: 12.4; Sample Solvent: EtOH; Injection Volume: 0.5 mL; Number Of Runs: 2) to afford (R or S)-1-(5-(7-bromo-1H-benzo[d]

imidazole-4-carbonyl)-2-(2-hydroxy-4-isopropylphenyl)-2,3,4,5,5a,6,8,9-octahydro-7H-10-oxa-1,2,5,7-tetraazacycloocta[cd]inden-7-yl)prop-2-en-1-one as the first-eluting peak (retention time=6.5 min, 2.5 mg, 4.1 μmol, 4% yield) as a white solid LCMS (ESI, m/z): 605, 607 ($^{81}$Br) [M+H]$^+$. $^1$H NMR: (400 MHz, Chloroform-d) δ 9.38 (brs, 1H), 8.36-8.17 (m, 1H), 7.52 (s, 1H), 7.35-7.28 (m, 1H), 7.27-7.19 (m, 1H), 7.07-6.94 (m, 1H), 6.94-6.83 (m, 1H), 6.79-6.67 (m, 1H), 6.64-6.45 (m, 1H), 6.25-6.05 (m, 1H), 5.89-5.57 (m, 1H), 4.89-4.52 (m, 1H), 4.50-4.11 (m, 3H), 4.07-3.85 (m, 1H), 3.85-3.26 (m, 2H), 3.24-2.93 (m, 2H), 2.90-2.77 (m, 1H), 2.73-2.58 (m, 1H), 1.22 (d, J=6.7 Hz, 6H). Analytical chiral HPLC: Column: CHIRAL ART Cellulose-SB; Column Size: 4.6*100 mm, 3 m; Mobile Phase: Hex (0.1% FA):(EtOH: DCM=1:1)=65:35; Flow: 1.0 mL/min; Temperature: 25° C.; rt=2.5 min.

Example K-9: Preparation of (R or S)-1-(2-(2-hydroxy-4-isopropylphenyl)-5-(5-hydroxy-6-(trifluoromethyl)nicotinoyl)-2,3,4,5,5a,6,8,9-octahydro-7H-10-oxa-1,2,5,7-tetraazacycloocta[cd]inden-7-yl) prop-2-en-1-one

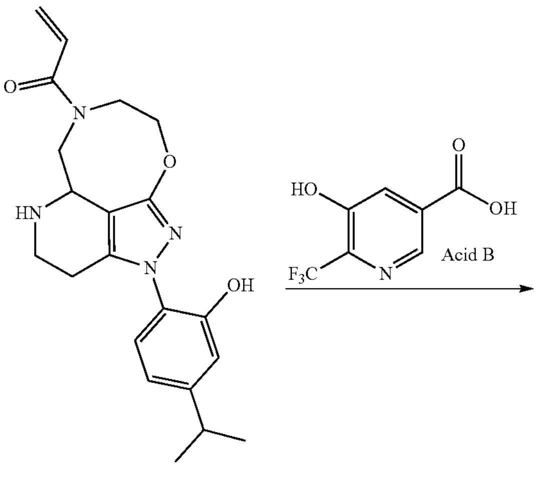

Int. MM

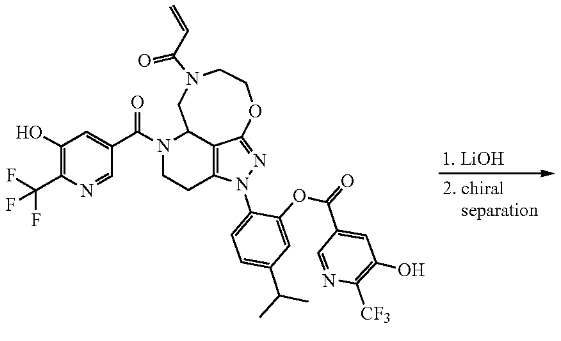

-continued

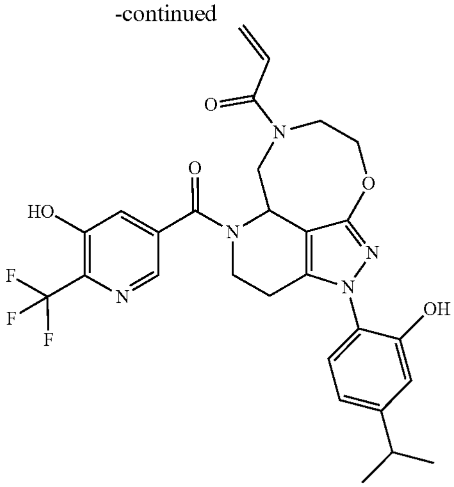

Step 1: Synthesis of (rac)-2-(7-acryloyl-5-(5-hydroxy-6-(trifluoromethyl)nicotinoyl)-3,4,5,5a,6,7,8,9-octahydro-2H-10-oxa-1,2,5,7-tetraazacycloocta[cd]inden-2-yl)-5-isopropylphenyl 5-hydroxy-6-(trifluoromethyl)nicotinate To a solution of (rac)-1-(2-(2-hydroxy-4-isopropylphenyl)-2,3,4,5,5a,6,8,9-octahydro-7H-10-oxa-1,2,5,7-tetraazacycloocta[cd]inden-7-yl)prop-2-en-1-one (Int. MM) (60 mg, 1 eq, 0.16 mmol) in DMF (1.2 mL) were added 5-hydroxy-6-(trifluoromethyl)nicotinic acid (65 mg, 2 eq, 0.31 mmol), HATU (78 mg, 1.3 eq, 0.2 mmol) and DIEA (0.16 g, 0.22 mL, 8 eq, 1.3 mmol). The mixture was stirred at room temperature for 2 h. The mixture was d luted with water (20 mL) and EtOAc (20 mL), and the aqueous layer was extracted with EtOAc (2×20 mL). The combined organic layers were washed with saturated brine (2×20 mL), dried over anhydrous sodium sulfate and concentrated to afford (rac)-2-(7-acryloyl-5-(5-hydroxy-6-(trifluoromethyl)nicotinoyl)-3,4,5,5a,6,7,8,9-octahydro-2H-10-oxa-1,2,5,7-tetraazacycloocta[cd]inden-2-yl)-5-isopropylphenyl 5-hydroxy-6-(trifluoromethyl)nicotinate (80 mg) as a crude yellow solid which was used in the next reaction without further purification. LCMS (ESI, m/z): 763 [M+H]$^+$.

Step 2: Synthesis of (R or S)-1-(2-(2-hydroxy-4-isopropylphenyl)-5-(5-hydroxy-6-(trifluoromethyl)nicotinoyl)-2,3,4,5,5a,6,8,9-octahydro-7H-10-oxa-1,2,5,7-tetraazacycloocta[cd]inden-7-yl)prop-2-en-1-one To a solution of (rac)-2-(7-acryloyl-5-(5-hydroxy-6-(trifluoromethyl)nicotinoyl)-3,4,5,5a,6,7,8,9-octahydro-2H-10-oxa-1,2,5,7-tetraazacycloocta[cd]inden-2-yl)-5-isopropylphenyl 5-hydroxy-6-(trifluoromethyl)nicotinate (80 mg, 1 eq, 105 μmol) in THF (1.6 mL) and water (0.8 mL) was added LiOH (5.0 mg, 2 eq, 0.21 mmol). The mixture was stirred at room temperature for 2 h. The mixture was then acidified to pH 5 with 1M HCl. The resulting mixture was extracted with EtOAc (100 mL). The combined organic layers were washed with saturated brine (100 mL) and dried over anhydrous $Na_2SO_4$. After filtration, the filtrate was concentrated under reduced pressure. The crude product was purified by reversed phase Prep-HPLC with the following conditions (Column: XselectCSHTMPrep C18 5 μm 19*150 mm OBD; Mobile Phase A: water (0.1% FA), Mobile Phase B: MeCN; Flow rate: 60 mL/min; Gradient: 35% B to 60% B in 8 min; Wave Length: UV 254 nm/220 nm; retention time: 6.9 min) to afford (rac)-1-(2-(2-hydroxy-4-isopropylphenyl)-5-(5-hydroxy-6-(trifluoromethyl)nicotinoyl)-2,3,4,5a,6,8,9-octahydro-7H-10-oxa-1,2,5,7-tetraazacycloocta[cd]inden-7-yl)prop-2-en-1-one (14.5 μg, 25.3 μmol, 41% yield over 2 steps) as a white solid. The crude product (12 mg) was purified by chiral Prep-HPLC with the following conditions (Column: CHIRAL ART Cellulose-SB 2*25 cm, 5 μm; Mobile Phase A: HEX (0.1% FA), Mobile Phase B: IPA; Flow rate: 20 mL/min; Gradient: isocratic 50; Wave Length: UV 254/220 nm; retention time 1: 4.3; retention time 2: 11.0; Injection Volume: 2.2 mL; Number Of Runs: 3) to afford (R or S)-1-(2-(2-hydroxy-4-isopropylphenyl)-5-(5-hydroxy-6-(trifluoromethyl)nicotinoyl)-2,3,4,5,5a,6,8,9-octahydro-7H-10-oxa-1,2,5,7 -tetraazacycloocta[cd]inden-7-yl)prop-2-en-1-one as the first-eluting peak (retention time=4.3 min, 4.1 mg, 7.1 gmol, 7% yield) as a white solid. LCMS (ESI, m/z): 573 $[M H]^+$. $^1$H NMR: (400 MHz, DMSO-$d_6$) δ 11.85 (brs, 1H), 10.00-9.84 (m, 1H), 8.24-8.13 (m, 1H) 7.45 (s, 1H), 7.19-7.01 (m, 2H), 6.92-6.82 (m, 1H), 6.81-6.73 (m, 1H), 6.32-5.88 (m, 1H), 5.87-5.62 (m, 1H), 5.38-4.70 (m, 1H), 4.65-4.54 (m, 1H), 4.22-4.08 (m, 1H), 4.02-3.80 (m, 2H), 3.79-3.61 (m, 2H), 3.57-3.40 (m, 1H), 3.28-3.19 (m, 1H), 2.93-2.82 (m, 1H), 2.1-2.69 (m, 1H), 2.55-2.28 (m, 1H), 1.19 (d, J=6.8 Hz, 6H). Analytical chiral HPLC: Column: CHIRAL ART Cellulose-SB; Column Size: 4.6*100 mm, 3 μm; Mobile Phase: Hex(0.1% FA):IPA=50:50 Flow: 1.0 mL/min; Temperature: 25° C.; retention time=1.9 min

Example K-10: Preparation of (R or S)-1-(5-(7-bromo-1H-benzo[d]imidazole-4-carbonyl)-2-(4-isopropylphenyl)-2,3,4,5,5a,6,8,9-octahydro-7H-10-oxa-1,2,5,7-tetraazacycloocta[cd]inden-7-yl)prop-2-en-1-one

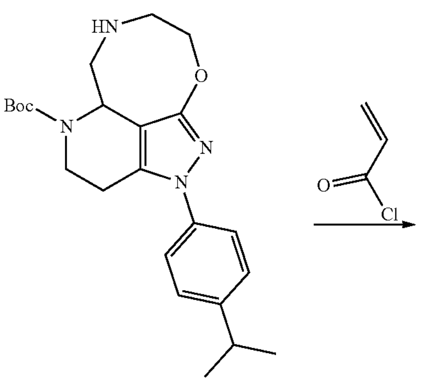

Int. LL

-continued

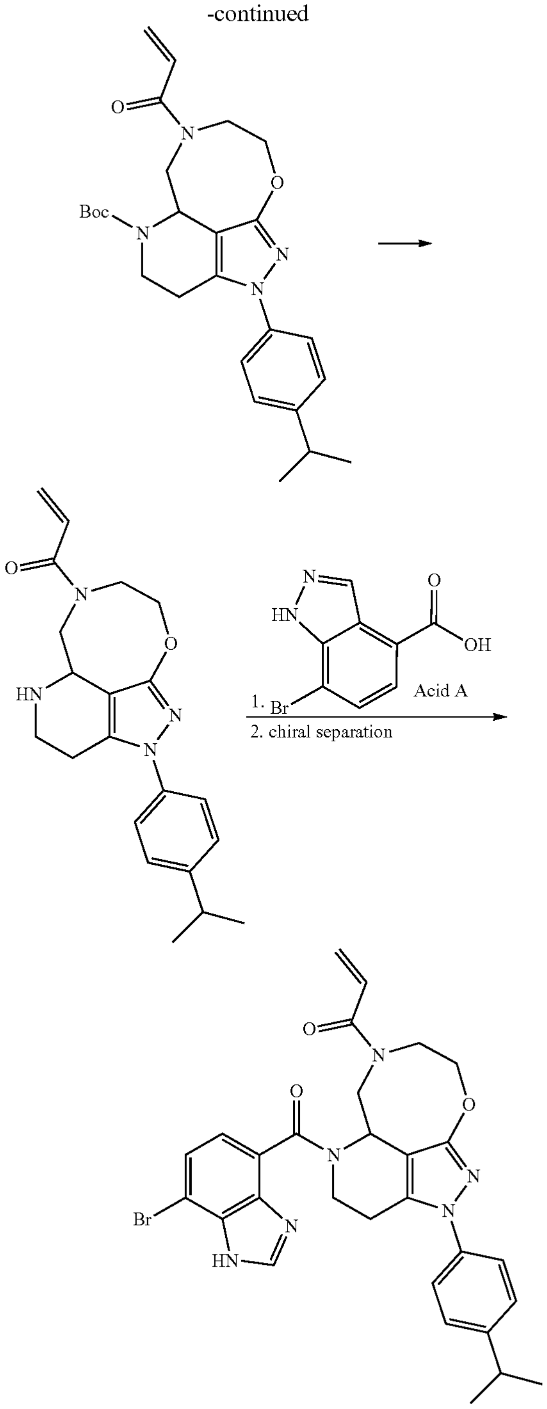

Step 1: Synthesis of Tert-Butyl (rac)-7-acryloyl-2-(4-isopropylphenyl)-2,3,4,5a,6,7,8,9-octahydro-5H-10-oxa-1,2,5,7-tetraazacycloocta [cd]indene-5-carboxylate To a solution of tert-butyl (rac)-2-(4-isopropylphenyl)-2,3,4,5a,6,7,8,9-octahydro-5H-10-oxa-1,2,5,7-tetraazacyclooocta[cd]indene-5-carboxylate (Int. LL) (240 mg, 1 eq, 582 gmol) in DCM (4.8 mL) was added TEA (471 mg, 649 μL, 8 eq, 4.65 mmol). The mixture was cooled to 0° C., then acryloyl chloride (105 mg, 2 eq, 1.16 mmol) was added dropwise to the above mixture at 0° C. under a nitrogen atmosphere. The mixture was warmed to room temperature and stirred for 2 h. The mixture was then diluted with ice water (20 mL) and EtOAc (20 mL), and the aqueous layer was extracted with EtOAc (2×20 mL). The combined organic layers were washed with saturated brine (2×20 mL), dried over anhydrous sodium sulfate and concentrated to give a residue. The residue was purified by flash column chromatography, eluting with EtOAc/PE (1:5) to afford tert-butyl (rac)-7-acryloyl-2-(4-isopropylphenyl)-2,3,4,5a,6,7,8,9-octahydro-5H-10-oxa-1,2,5,7 -tetraazacycloocta [cd] indene-5-carboxylate (105 mg) as a yellow solid. LCMS (ESI, m/z): 468 $[M+H]^+$.

Step 2: Synthesis of (rac)-1-(2-(4-isopropylphenyl)-2,3,4,5,5a,6,8,9-octahydro-7H-10-oxa-1,2,5,7-tetraazacycloocta[cd]inden-7-yl)prop-2-en-1-one A solution of tert-butyl (rac)-7-acryloyl-2-(4-isopropylphenyl)-2,3,4,5a,6,7,8,9-octahydro-5H-10-oxa-1,2,5,7-tetraazacycloocta[cd]indene-5-carboxylat (105 mg, 1 eq, 225 gmol) in DCM (1.5 mL) and TFA (0.5 mL) was stirred at room temperature for 1 h, after which the solvent was removed under reduced pressure. This resulted in (rac)-1-(2-(4-isopropylphenyl)-2,3,4,5,5a,6,8,9-octahydro-7H-10-oxa-1,2,5,7-tetraazacycloocta[cd]inden-7-yl)prop-2-en-1-one (120 mg) as a crude yellow oil. The crude product was used in the next step directly without further purification. LCMS (ESI, m/z): 367 $[M+H]^+$.

Step 3: Synthesis of (R or S)-1-(S-(7-bromo-1H-benzo[d]imidazole-4-carbonyl)-2-(4-isopropylphenyl)-2,3,4,5,5a,6,8,9-octahydro-7H-10-oxa-1,2,5,7-tetraazacycloocta[cd]inden-7-yl)prop-2-en-1-one To a solution of (rac)-1-(2-(4-isopropylphenyl)-2,3,4,5,5a,6,8,9-octahydro-7H-10-oxa-1,2,5,7-tetraazacycloocta [cd]inden-7-yl)prop-2-en-1-one (40 mg, 1 eq, 0.11 mmol) in DMF (0.8 mL) was added 7-bromo-1H-benzo[d]imidazole-4-carboxylic acid (39 mg, 1.5 eq, 0.16 mmol), DIEA (0.11 g, 0.15 mL, 8 eq, 0.87 mmol) and HBTU (54 mg, 1.3 eq, 0.14 mmol). The mixture was stirred at room temperature for 2 h. The mixture was then diluted with water (20 mL) and EtOAc (20 mL), and the aqueous layer was extracted with EtOAc (2×20 mL). The combined organic layers were washed with saturated brine (2×20 mL), dried over anhydrous sodium sulfate and concentrated to give a residue. The residue was purified by Prep-HPLC (Column: Xselect CSH™ Prep C18 5 μm 19*150 mm OBD; Mobile Phase A: water (0.1% FA), Mobile Phase B: MeCN; Flow rate: 60 mL/min; Gradient: 30% B to 55% B in 10 in; Wave Length: UV 254 nm/220 nm; retention time 1: 8.5 min) to afford (rac)-1-(5-(7-bromo-1H-benzo[d]imidazole-4-carbonyl)-2-(4-isopropylphenyl)-2,3,4,5,5a,6,8,9-octahydro-7H-10-oxa-1,2,5,7-tetraazacycloocta[cd]inden-7-yl)prop-2-en-1-one (13 mg). The product (3 mg) was separated into its constitutive enantiomers by chiral prep-chiral HPLC with the following conditions (Column: CHIRAL ART Cellulose-SB 2*25 cm, 5 μm; Mobile Phase A: HEX(0.1% FA), Mobile Phase B: EtOH:DCM=1:1; Flow rate: 20 mL/min; Gradient: isocratic 35; Wavelength: UV 254/220 nm; retention time 1: 6.5; retention time 2: 12.4; Sample Solvent: EtOH; Injection Volume: 0.5 mL; Number Of Runs: 2) to afford (R or S)-1-(5-(7-bromo-1H-benzo[d]imidazole-4-carbonyl)-2-(4-isopropylphenyl)-2,3,4,5,5a,6,8,9-octahydro-7H-10-oxa-1,2,5,7-tetraazacycloocta[cd]inden-7-yl)prop-2-en-1-one as the first-eluting peak (5.2 mg, 8.8 μmol, 8% yield as a white solid. LCMS: (ESI, m/z): 589 $[M+H]^+$. $^1$H NMR: (400 MHz, Chloroform-d) δ 8.28 (s, 1H), 7.53 (d, J=7.1 Hz, 1H), 7.42-7.33 (m, 1H), 7.33-7.28 (m, 2H), 7.28-7.22 (m, 2H), 6.63-6.41 (m, 1H), 6.27-6.00 (m, 1H), 5.84-5.67 (m, 1H), 5.55-4.76 (m, 1H), 4.61-4.37 (m, 1H), 4.32-4.11 (m, 2H), 4.08-3.97 (m, 1H), 3.96-3.75 (m, 1H), 3.62-3.47 (m, 1H), 3.45-3.18 (m, 1H), 3.10 (s, 2H), 2.99-2.63 (m, 3H), 1.26 (t, J=7.6 Hz, 6H). Analytical chiral HPLC: Column: CHIRAL ART Cellulose-SB; Column Size: 4.6*100 mm, 3 μm; Mobile Phase: Hex(0.1% FA):(EtOH:DCM=1:1)=70:30; Flow: 1.0 mL/min; Temperature: 25° C.; retention time=3.7 min.

Example K-11: Preparation of (R or S)-1-(5-(5-hydroxy-6-(trifluoromethyl)nicotinoyl)-2-(4-isopropylphenyl)-2,3,4,5,5a,6,8,9-octahydro-7H-10-oxa-1,2,5,7-tetraazacycloocta[cd]inden-7-yl)prop-2-en-1-one

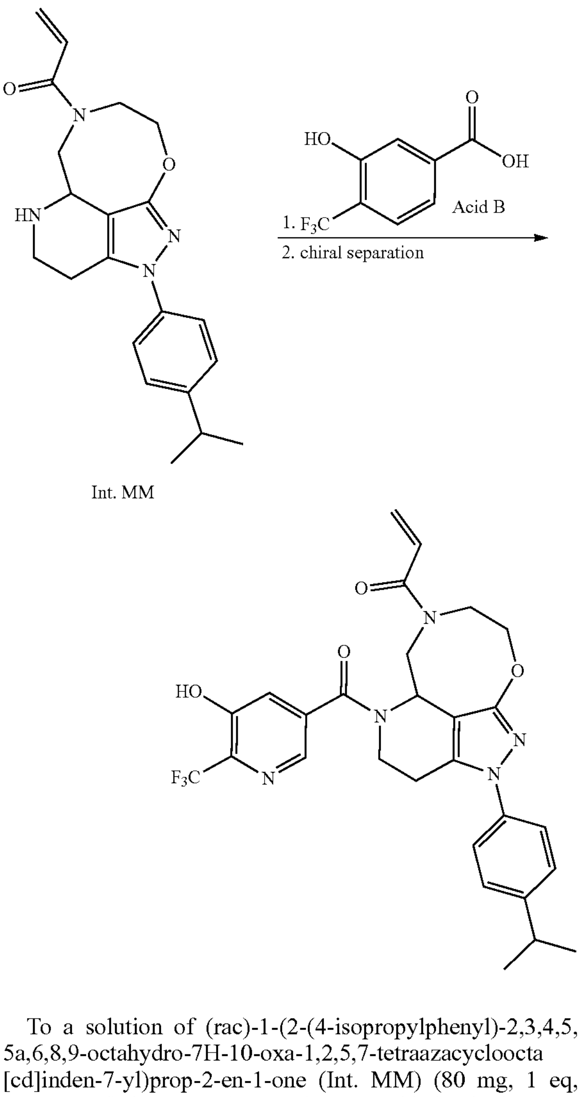

To a solution of (rac)-1-(2-(4-isopropylphenyl)-2,3,4,5,5a,6,8,9-octahydro-7H-10-oxa-1,2,5,7-tetraazacycloocta [cd]inden-7-yl)prop-2-en-1-one (Int. MM) (80 mg, 1 eq, 0.22 mmol) in DMF (1.6 mL) were added 5-hydroxy-6-(trifluoromethyl)nicotinic acid (45 mg, 1 eq, 0.22 mmol), HATU (0.11 g, 1.3 eq, 0.28 mmol) and DIEA (0.23 g, 0.3 mL, 8 eq, 1.7 mmol). The mixture was stirred at room temperature for 2 h. The mixture was then diluted with water (20 mL) and EtOAc (20 mL), and the aqueous layer was extracted with EtOAc (2×20 mL). The combined organic layers were washed with saturated brine (2×20 mL), dried over anhydrous sodium sulfate, and concentrated to give a residue. The residue was purified by Prep-HPLC (Column: Sunfire C18 5 m, 30 mm*150 mm; Mobile Phase A: water (0.1% FA), Mobile Phase B: MeCN; Flow rate: 60 mL/min; Gradient: 30% B to 65% B in 10 min; Wave Length: UV 254 nm/220 nm; retention time 1: 9.1 min) to afford (rac)-1-(5-(5-hydroxy-6-(trifluoromethyl)nicotinoyl)-2-(4-isopropylphenyl)-2,3,4,5,5a,6,8,9-octahydro-7H-10-oxa-1,2,5,7-tetraazacycloocta[cd]inden-7-yl)prop-2-en-1-one (22 mg, 40 μmol, 18% yield). The product (22 mg) was further separated into its constitutive enantiomers by chiral prep-HPLC with the following conditions (Column: CHIRAL ART Cellulose-SB, 2*25 cm, 5 μm; Mobile Phase A: Hex(0.1% FA)—HPLC Mobile Phase B: EtOH:DCM=1:1; Flow rate: 20 mL/min; Gradient: isocratic 40; Wave Length: UV 254/220 nm; retention time 1: 3.327; retention time 2: 6.463; Injection Volume: 2.0 mL; Number Of Runs: 22) to afford (R or S)-1-(5-(5-hydroxy-6-(trifluoromethyl)nicotinoyl)-2-(4-isopropylphenyl)-2,3,4,5,5a,6,8,9-octahydro-7H-10-oxa-1,2,5,7-tetraazacycloocta[cd]inden-7-yl)prop-2-en-1-one as the first-eluting peak (retention time=3.3 min, 7.8 mg, 14 μmol, 6% yield) as a white solid. LCMS: (ESI, m/z): 556 [M+H]. $^1$H NMR: (400 MHz, Chloroform-d) δ 8.54-8.05 (m, 2H), 7.81-7.44 (m, 1H), 7.37-7.29 (m, 1H), 7.17 (s, 1H), 6.52 (s, 2H), 6.31-5.65 (m, 2H), 5.61-5.23 (m, 1H), 5.02-4.69 (m, 2H), 4.57-1.55 (m, 10H), 1.19-0.99 (m, 6H). Analytical chiral HPLC: Column: CHIRAL ART Cellulose-SB; Column Size: 4.6*100 mm 3 μm; Mobile Phase: Hex (0.1% FA):(EtOH:DCM=1:1)=60:40; Flow: 1.0 mL/min; Temperature: 25° C.; RT=1.6 min.

Example K-12: Preparation of (S AND R)-1-(5-(4-bromo-1-hydroxybenzoyl)-2-(4-isopropylphenyl)-2,3,4,5,5a,6,8,9-octahydro-7H-10-oxa-1,2,5,7-tetraazacycloocta[cd]inden-7-yl)prop-2-en-1-one

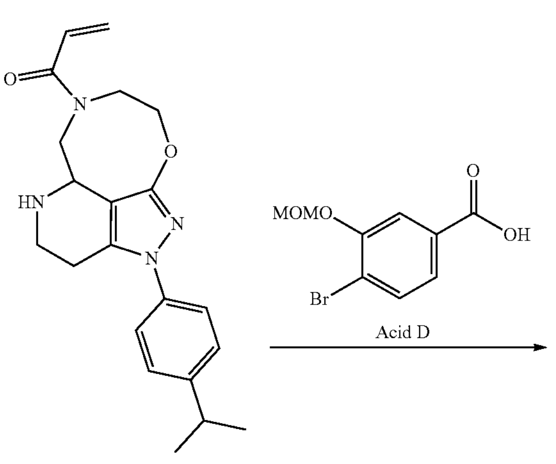
Int. MM

Acid D

-continued

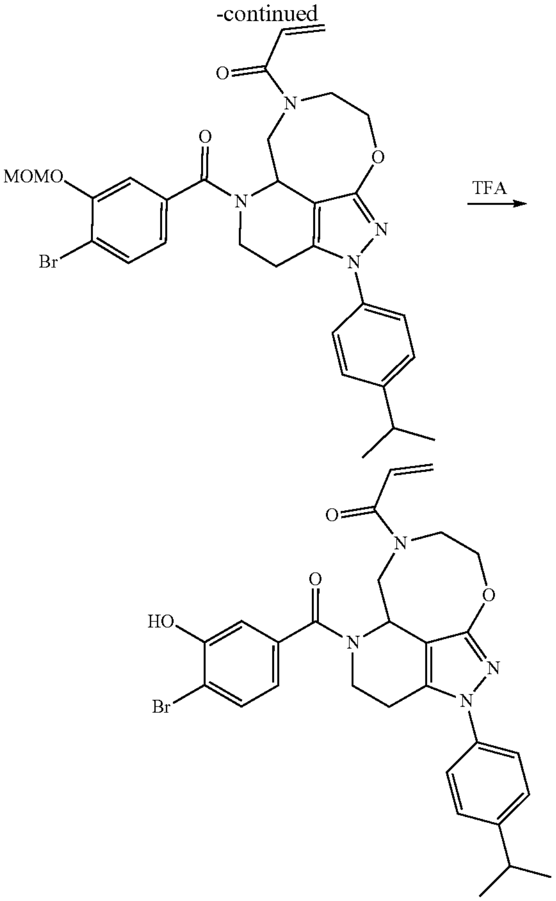

Step 1: Synthesis of (rac)-1-(5-(4-bromo-3-(methoxymethoxy)benzoyl)-2-(4-isopropylphenyl)-2,3,4,5,5a,6,8,9-octahydro-7H-10-oxa-1,2,5,7-tetraazacycloocta[cd]inden-7-yl)prop-2-en-1-one To a stirred solution of (rac)-1-(2-(4-isopropylphenyl)-2,3,4,5,5a,6,8,9-octahydro-7H-10-oxa-1,2,5,7-tetraazacycloocta[cd]inden-7-yl)prop-2-en-1-one (Int. MM) (8 mg, 0.022 mmol, 1 equiv) and 4-bromo-3-(methoxymethoxy) benzoic acid (Acid D) (5.7 mg, 0.022 mmol, 1 equiv) in DMF (0.3 mL) were added DIEA (11 uL, 0.066 mmol, 3.00 equiv) HOBt (4.4 mg, 0.033 mmol, 1.5 equiv) and EDC (6.3 mg, 0.033 mmol, 1.5 equiv) in portions at rt under an air atmosphere. The resulting mixture was stirred for 2 h at rt. The reaction was then quenched with water at rt, and the resulting mixture was extracted with EtOAc (3×2 mL). The combined organic layers were washed with saturated brine (2×1 mL), dried over anhydrous $Na_2SO_4$, and filtered. After filtration, the filtrate was concentrated under reduced pressure. The resulting (rac)-1-(5-(4-bromo-3-(methoxymethoxy)benzoyl)-2-(4-isopropylphenyl)-2,3,4,5,5a,6,8,9-octahydro-7H-10-oxa-1,2,5,7-tetraazacycloocta[cd]inden-7-yl)prop-2-en-1-one mixture was used in the next step directly without further purification. LCMS:(ESI, m/z): 609 [M+1]$^+$.

Step 2: Synthesis of (S AND R)-1-(5-(4-bromo-3-hydroxybenzoyl)-2-(4-isopropylphenyl)-2,3,4,5,5a,6,8,9-octahydro-7H-10-oxa-1,2,5,7-tetraazacycloocta[cd]inden-7-yl)prop-2-en-1-one A solution of (rac)-1-(5-(4-bromo-3-(methoxymethoxy)benzoyl)-2-(4-isopropylphenyl)-2,3,4,5,5a,6,8,9-octahydro- 7H-10-oxa-1,2,5,7-tetraazacycloocta[cd]inden-7-yl)prop-2-en-1-one (10 mg, 0.016 mmol, 1 equiv) in TFA (0.5 mL) and DCM (1.5 mL) was stirred for 30 min at rt under air atmosphere. The resulting mixture was concentrated under reduced pressure. The crude product was purified by Prep-HPLC with the following conditions: Column, Xselect CSH C18 OBD 30*150 mm 5 um; mobile phase, water (0.05% FA) and MeCN (40%/MeCN up to 65% in 10 min); Detector, UV 254 nm to afford (S AND R)-1-(5-(4-bromo-3-hydroxybenzoyl)-2-(4-isopropylphenyl)-2,3,4,5,5a,6,8,9-octahydro-7H-10-oxa-1,2,5,7-tetraazacycloocta[cd]inden-7-yl)prop-2-en-1-one (0.3 mg, 3% yield) as an off-white solid. LCMS:(ESI, m/z): 565 $[M+1]^+$. $^1H$ NMR: (400 MHz, Chloroform-d) δ 7.79-7.54 (m, 1H), 7.53-7.30 (m, 2H), 7.30-6.98 (m, 4H), 6.97-6.67 (m, 1H), 6.51-6.20 (m, 1H), 6.13-5.79 (m, 1H), 5.75-5.39 (m, 1H), 5.14-4.79 (m, 11H), 4.78-4.27 (m, 2H), 4.23-3.75 (m, 2H), 3.63 (s, 11H), 3.51-3.25 (m, 11H), 3.23-2.46 (m, 4H), 1.26 (s, 6H).

Example K-13: Preparation of (R or S)-1-(5-(7-bromo-1H-benzo[d]imidazole-4-carbonyl)-2-(4-cyclopropylphenyl)-2,3,4,5,5a,6,8,9-octahydro-7H-10-oxa-1,2,5,7-tetraazacycloocta[cd]inden-7-yl)prop-2-en-1-one

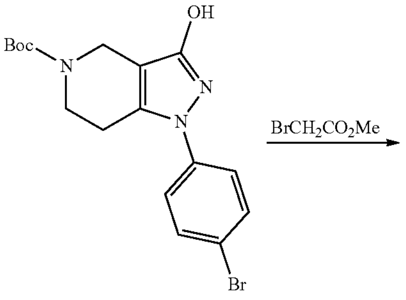

Int. EE

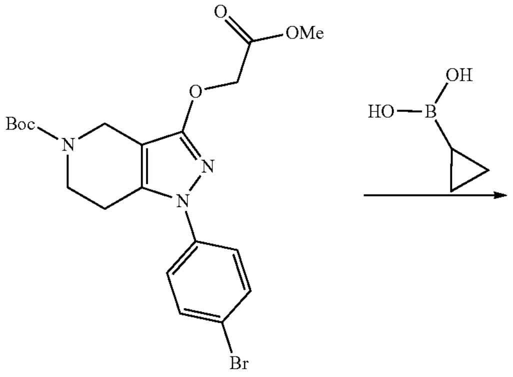

-continued

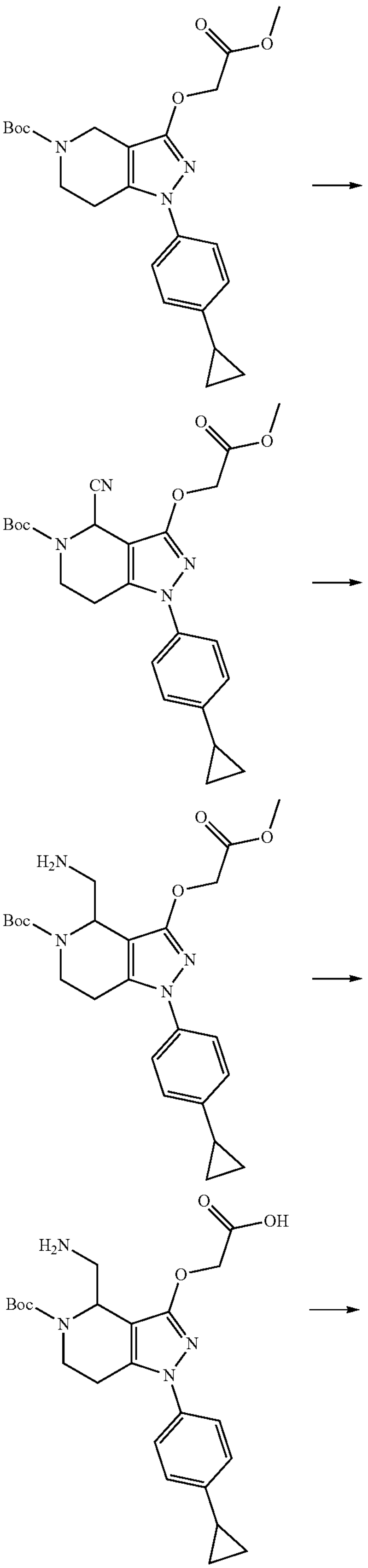

-continued

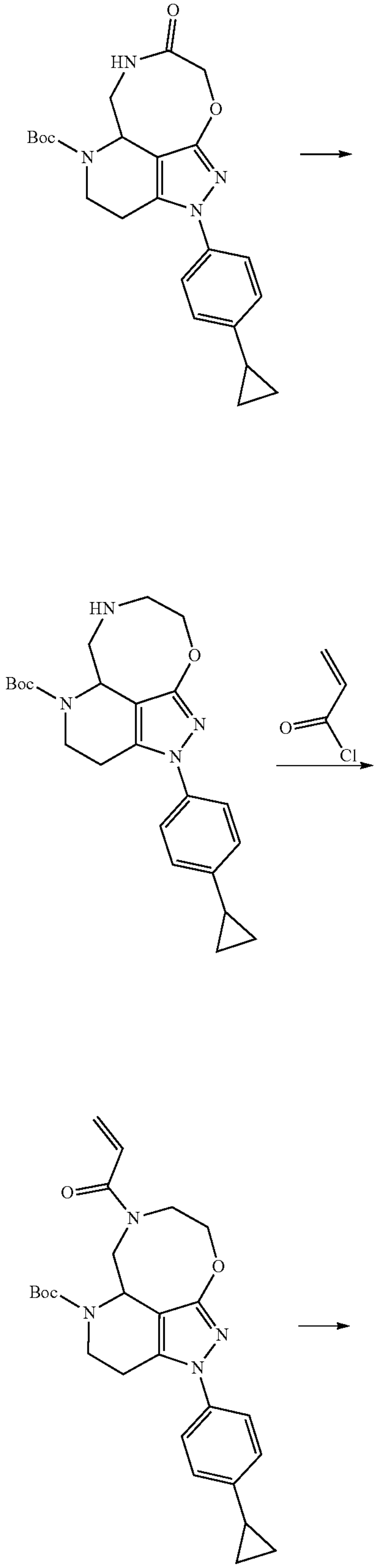

-continued

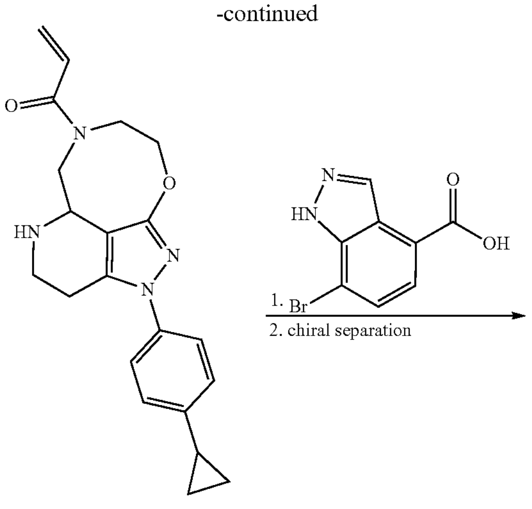

Int. NN

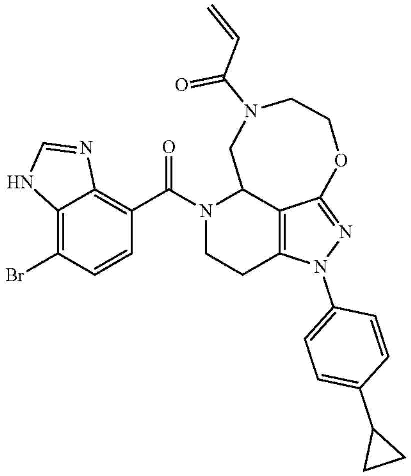

Step 1: Synthesis of Tert-Butyl 1-(4-bromophenyl)-3-(2-methoxy-2-oxoethoxy)-1,4,6,7-tetrahydro-5H-pyrazolo[4,3-c]pyridine-5-carboxylate This reaction was launched with two parallel batches.

To a solution of tert-butyl 1-(4-bromophenyl)-3-hydroxy-1,4,6,7-tetrahydro-5H-pyrazolo[4,3-c]pyridine-5-carboxylate (Int. EE) (400 g, 1.0 mol) and methyl 2-bromoacetate (186 g, 1.22 mol, 115 mL, 1.20 eq) in DMA (3.50 L) was added $Cs_2CO_3$ (66 g, 2.03 mol, 2.00 eq) at room temperature. The mixture was stirred at room temperature for 2 h. The reaction mixture was then filtered, and the filtrate was diluted with water (5.00 L) and extracted with MTBE (5.00 L×2). The combined organic layers were washed with saturated brine (500 KL), dried over $Na_2SO_4$, filtered, and concentrated under reduced pressure to give a residue. The residue was triturated with petroleum ether:ethyl acetate=5:1 (650 mL) at room temperature for 24 h to provide tert-butyl (rac)-1-(4-bromophenyl)-3-(2-methoxy-2-oxoethoxy)-1,4,6,7-tetrahydro-5H-pyrazolo[4,3-c]pyridine-5-carboxylate (423 g) as a yellow solid.

One third of the crude material (140 g) was purified by prep-HPLC (TFA condition, I.D.200 mm×H450 mm) to give tert-butyl 1-(4-bromophenyl)-3-(2-methoxy-2-oxoethoxy)-1,4,6,7-tetrahydro-5H-pyrazolo[4,3-c]pyridine-5-carboxylate (83.0 g, 175 mmol) as a yellow solid. LCMS: m/z=466

$(M+H)^+$, m/z=468 ($^{81}Br$). $^1H$ NMR: (400 MHz, $CDCl_3$) δ 7.52 (d, J=8.8 Hz, 2H), 7.28 (d, J=8.4 Hz, 2H), 4.86 (s, 2H), 4.42 (s, 2H), 3.80 (s, 3H), 3.72-3.62 (m, 2H), 2.85-2.75 (m, 2H), 1.50 (s, 9H).

Step 2: Synthesis of Tert-Butyl 1-(4-cyclopropylphenyl)-3-(2-methoxy-2-oxoethoxy)-1,4,6,7-tetrahydro-5H-pyrazolo[4,3-c]pyridine-S-carboxylate To a solution of tert-butyl 1-(4-bromophenyl)-3-(2-methoxy-2-oxoethoxy)-1,4,6,7-tetrahydro-5H-pyrazolo[4,3-c]pyridine-5-carboxylate (9.0 g, 1 eq, 19.3 ol) in toluene (180 mL) and water (45 mL) were added tricyclohexylphosphine (1.08 g, 0.2 eq, 3.86 mmol), cyclopropylboronic acid (3.32 g, 2 eq, 38.6 mmol), potassium phosphate (12.3 g, 3 eq, 57.9 mmol) and diacetoxypalladium (433 mg, 0.1 eq, 1.93 mmol). The solution was placed under a positive pressure of nitrogen and subjected to three backfilling cycles under high vacuum. The resulting mixture was stirred for 2 h at 100° C. under a nitrogen atmosphere. After the reaction mixture was cooled to rt, the mixture was filtered and rinsed with EtOAc (3×200 mL), then diluted with water (200 mL). The aqueous layer was extracted with EtOAc (2×200 mL), and the combined organic layers were washed with saturated brine (3×200 mL), dried over anhydrous sodium sulfate, and concentrated to give a residue. The residue was purified by silica gel chromatography eluting with PE:EtOAc=5:1 to give tert-butyl 1-(4-cyclopropylphenyl)-3-(2-methoxy-2-oxoethoxy)-1,4,6,7-tetrahydro-5H-pyrazolo[4,3-c]pyridine-5-carboxylate (8.3 g) as a yellow solid. LCMS: (ESI, m/z): 428 $[M+H]^+$. $^1H$ NMR: (400 MHz, DMSO-d6) δ 7.36-7.28 (m, 2H), 7.18-7.10 (m, 2H), 4.87 (d, J=10.7 Hz, 2H), 4.28 (s, 2H), 3.69 (d, J=3.0 Hz, 3H), 3.57 (t, J=5.4 Hz, 2H), 2.88-2.75 (m, 2H), 1.95 (tt, J=8.4, 5.0 Hz, 1H), 1.44 (s, 9H), 1.01-0.90 (m, 2H) 0.72-0.64 (m, 2H).

Step 3: Synthesis of Tert-Butyl (rac)-4-cyano-1-(4-cyclopropylphenyl)-3-(2-methoxy-2-oxoethoxy)-1,4,6,7-tetrahydro-5H-pyrazolo[4,3-c]pyridine-5-carboxylate To a solution of tert-butyl 1-(4-cyclopropylphenyl)-3-(2-methoxy-2-oxoethoxy)-1,4,6,7-tetrahydro-5H-pyrazolo[4,3-c]pyridine-5-carboxylate (7.5 g, 1 eq, 18 mmol) in MeCN (75 mL) were added AcOH (2.1 g, 2.0 mL, 2 eq, 35 mmol), TMSCN (3.5 g, 4.4 mL, 2 eq, 35 mmol), and $TEMPO^+BF_4-$ (8.5 g, 2 eq, 35 mmol). The mixture was stirred at room temperature for 1 h. The mixture was then diluted with water (20 mL) and EtOAc (20 mL), and the aqueous layer was extracted with EtOAc (2×20 mL). The combined organic layers were washed with saturated brine (2×20 mL), dried over anhydrous sodium sulfate, and concentrated to give a residue. The residue was purified by silica gel column chromatography, eluting with EtOAc in PE (23%) to afford tert-butyl (rac)-4-cyano-1-(4-cyclopropylphenyl)-3-(2-methoxy-2-oxoethoxy)-1,4,6,7-tetrahydro-5H-pyrazolo[4,3-c]pyridine-5-carboxylate (6.7 g) as a yellow solid. LCMS: (ESI, m/z): 453 $[M+H]^+$.

Step 4: Synthesis of Tert-Butyl (rac)-4-(aminomethyl)-1-(4-cyclopropylphenyl)-3-(2-methoxy-2-oxoethoxy)-1,4,6,7-tetrahydro-5H-pyrazolo[4,3-c]pyridine-5-carboxylate To a solution of tert-butyl (rac)-4-cyano-1-(4-cyclopropylphenyl)-3-(2-methoxy-2-oxoethoxy)-1,4,6,7-tetrahydro-5H-pyrazolo[4,3-c]pyridine-5-carboxylate (6 g, 1 eq, 0.01 mol) in MeOH (180 mL) were added Raney nickel (3 g, 0.4 mL, 50% wt, 2 eq, 0.03 mol). The mixture was purged with nitrogen×3 and then was pressurized with 4.0 MPa hydrogen and heated at 60° C. for 18 h. The reaction mixture was then cooled to rt. The mixture was filtered and rinsed with EtOAc (5×50 mL), and the filtrate was concentrated under vacuum to give a residue. This resulted in tert-butyl (rac)-4-(aminomethyl)-1-(4-cyclopropylphenyl)-3-(2-methoxy-2-oxoethoxy)-1,4,6,7-tetrahydro-5H-pyrazolo[4,3-c]pyridine-5-carboxylate (3 g) as a crude yellow solid. The crude product was used in the next step directly without further purification. LCMS: (ESI, m/z):457.20 $[M+H]^+$.

Step 5: Synthesis of (rac)-2-((4-(aminomethyl)-5-(tert-butoxycarbonyl)-1-(4-cyclopropylphenyl)-4,5,6,7-tetrahydro-JH-pyrazolo[4,3-c]pyridine-3-yl)oxy) acetic acid To a solution of tert-butyl (rac)-4-(aminomethyl)-1-(4-cyclopropylphenyl)-3-(2-methoxy-2-oxoethoxy)-1,4,6,7-tetrahydro-5H-pyrazolo[4,3-c]pyridine-5-carboxylate (3 g, 1 eq, 7 mmol) in MeOH (60 mL) and water (30 mL) was added LiOH (0.2 g, 1.5 eq, 0.01 mol). The mixture was stirred at room temperature for 18 h. The mixture was then acidified to pH 3 with 1 M sulfuric acid, then diluted with EtOAc (20 mL) and water (15 mL), and the aqeuous layer was extracted with EtOAc (2×200 mL). The organic layers were combined and washed with saturated brine (20 mL), dried over anhydrous sodium sulfate, and concentrated to afford (rac)-2-((4-(aminomethyl)-5-(tert-butoxycarbonyl)-1-(4-cyclopropylphenyl)-4,5,6,7-tetrahydro-1H-pyrazolo[4,3-c]pyridin-3-yl)oxy)acetic acid (3 g) as a yellow solid. The crude product was used in the next step directly without further purification. LCMS: (ESI, m/z): 444 $[M+H]^+$.

Step 6: Synthesis of Tert-Butyl (rac)-2-(4-cyclopropylphenyl)-8-oxo-2,3,4,5a,6,7,8,9-octahydro-5H-10-oxa-1,2,5,7-tetraazacycloocta[cd]indene-5-carboxylate To a solution of (rac)-2-((4-(aminomethyl)-5-(tert-butoxycarbonyl)-1-(4-cyclopropylphenyl)-4,5,6,7-tetrahydro-1H-pyrazolo[4,3-c]pyridin-3-yl)oxy)acetic acid (3 g, 1 eq, 7 mmol) in DMF (300 mL) were added DIEA (4 g, 6 mL, 5 eq, 0.03 mol) and COMU (2 g, 1.5 eq, 0.01 mol). The mixture was stirred at room temperature for 1 h then diluted with water (20 mL) and EtOAc (20 mL). The aqueous layer was extracted with EtOAc (2×20 mL) and the organic layer was combined, washed with saturated brine (2×20 mL), dried over anhydrous sodium sulfate, and concentrated to give a residue. The residue was purified by flash chromatography to afford tert-butyl (rac)-2-(4-cyclopropylphenyl)-8-oxo-2,3,4,5a,6,7,8,9-octahydro-5H-10-oxa-1,2,5,7-tetraazacycloocta[cd]indene-5-carboxylate (800 mg) as a white solid. LCMS: (ESI, m/z): 425 $[M+H]^+$.

Step. 7: Synthesis of Tert-Butyl (rac)-2-(4-cyclopropylphenyl)-2,3,4,5a,6,7,8,9-octahydro-5H-10-oxa-1,2,5,7-tetraazacycloocta[cd]indene-5-carboxylate To a solution of tert-butyl (rac)-2-(4-cyclopropylphenyl)-8-oxo-2,3,4,5a,6,7,8,9-octahydro-5H-10-oxa-1,2,5,7-tetraazacycloocta[cd]indene-5-carboxylate (800 mg, 1 eq, 1.88 mmol) in THF (16 mL) was added $BH_3$-THF (648 mg, 4 eq, 7.54 mmol). The mixture was stirred at 60° C. for 2 h and quenched with MeOH at room temperature then concentrated under vacuum. The crude product tert-butyl (rac)-2-

(4-cyclopropylphenyl)-2,3,4,5a,6,7,8,9-octahydro-5H-10-oxa-1,2,5,7-tetraazacycloocta[cd]indene-5-carboxylate (800 mg) was us d in the next step directly without further purification. LCMS: (ESI, m/z): 411 $[M+H]^+$.

Step 8: Synthesis of Tert-Butyl (rac)-7-acryloyl-2-(4-cyclopropylphenyl)-2,3,4,5a,6,7,8,9-octahydro-5H-10-oxa-1,2,5,7-tetraazacycloocta [cd]indene-5-carboxylate To a solution of tert-butyl (rac)-2-(4-cyclopropylphenyl)-2,3,4,5a,6,7,8,9-octahydro-5H-10-oxa-1,2,5,7-tetraazacycloocta[cd]indene-5-carboxylate (290 mg, 1 eg, 706 gmol) in DCM (5.8 mL) was added TEA (357 mg, 492 μL, 5 eq, 3.53 mmol). The mixture was cooled to 0° C., then acryloyl chloride (128 mg, 2 eq, 1.41 mmol) was added dropwise to the above mixture at 0° C. under a nitrogen atmosphere. The mixture was warmed to room temperature and stirred for 2 h then diluted with ice water (20 mL) and EtOAc (20 mL). The aqueous layer was extracted with EtOAc (2×20 mL) and the combined organic layers were washed with saturated brine (2×20 mL), dried over anhydrous sodium sulfate, and concentrated to give a residue. The residue was purified by flash column chromatography, with EtOAc/PE (1:5) to afford tert-butyl (rac)-7-acryloyl-2-(4-cyclopropylphenyl)-2,3,4,5a,6,7,8,9-octahydro-5H-10-oxa 1,2,5,7-tetraazacycloocta [cd]indene-5-carboxylate (100 mg) as a white solid. LCMS: (ESI, m/z):466 $[M+H]^+$.

Step 9: Synthesis of (rac)-1-(2-(4-cyclopropylphenyl)-2,3,4,5,5a,6,8,9-octahydro-7H-10-oxa- 1,2,5,7-tetraazacycloocta[cd]inden-7-yl)prop-2-en-1-one A solution of tert-butyl 7-acryloyl-2-(4-cyclopropylphenyl)-2,3,4,5a,6,7,8,9-octahydro-5H-10-oxa-1,2,5,7-tetraazacycloocta[cd]indene-5-carboxylate (100 mg, 1 eq, 215 gmol) in DCM (2 mL) and TFA (1 mL) was stirred at room temperature for 2 h. The solvent was then removed under reduced pressure to provide (rac)-1-(2-(4-cyclopropylphenyl)-2,3,4,5,5a,6,8,9-octahydro-7H-10-oxa-1,2,5,7-tetraazacycloocta[cd]inden-7-yl)prop-2-en-1-one (110 mg) as a crude yellow oil. The crude product was used in the next step directly without further purification. LCMS: (ESI, m/z): 365 $[M+H]^+$.

Step 10: Synthesis of (R or S)-1-(5-(7-bromo-JH-benzo[d]imidazole-4-carbonyl)-2-(4-cyclopropylphenyl)-2,3,4,5,5a,6,8,9-octahydro-7H-10-oxa-1,2,5,7-tetraazacycloocta[cd]inden-7-yl)prop-2-en-1-one To a solution of (rac)-1-(2-(4-cyclopropylphenyl)-2,3,4,5,5a,6,8,9-octahydro-7H-10-oxa-1,2,5,7-tetraazacycloocta [cd]inden-7-yl)prop-2-en-1-one (110 mg, 1 eq, 302 μmol) in DMF (2.2 mL) were added HBTU (149 mg, 1.3 eq, 392 μmol), 7-bromo-1H-benzo[d]imidazole-4-carboxylic acid (Acid A) (109 mg, 1.5 eq, 453 μmol) and DIEA (312 mg, 421 μL, 8 eq, 2.41 mmol). The mixture was stirred at room temperature for 2 h. The mixture was then diluted with water (20 mL) and EtOAc (20 mL), and the aqueous layer was extracted with EtOAc (2×20 mL). The combined organic layers were washed with saturated brine (2×20 mL), dried over anhydrous sodium sulfate, and concentrated to give a residue. The residue was purified by Prep-HPLC (Column: XBridge BEH Shield RP18 5 m, 30 mm*150 mm; Mobile Phase A: water (10 mol/L $NH_4HCO_3$), Mobile Phase B: MeCN; Flow rate: 60 mL/min; Gradient: 32% B to 50% B in 10 min; Wave Length: UV 254 nm/220 nm; retention time 1: 7.7 min) to afford (rac)-1-(5-(7-bromo-1H-benzo[d]imidazole-4-carbonyl)-2-(4-cyclopropylphenyl)-2,3,4,5,5a,6,8,9-octahydro-7H-10-oxa-1,2,5,7-tetraazacycloocta[cd]inden-7-yl)prop-2-en-1-one (65 mg). This product was further separated into its constitutive enantiomers by chiral prep-HPLC (Column: CHIRAL ART Cellulose-SB 3*25 cm, 5 μm; Mobile Phase A: HEX(0.1% FA), Mobile Phase B: EtOH:DCM=1:1; Flow rate: 40 mL/min; Gradient: isocratic 35; Wave Length: UV 254/220 nm; retention time 1: 10.5; retention time 2: 14.8; Sample Solvent: MeOH; Injection Volume: 3.0 mL; Number Of R ns: 3) to afford (R or S)-1-(5-(7-bromo-1H-benzo[d]imidazole-4-carbonyl)-2-(4-cyclopropylphenyl)-2,3,4,5,5a,6,8,9-octahydro-7H-10-oxa-1,2,5,7-tetraazacycloocta[cd]inden-7-yl)prop-2-en-1-one as the first-eluting peak (retention time=10.5 min, 19.8 mg, 33.4 μmol, 11% yield) as a white solid. LCMS: (ESI, m/z): 587, 589 $[M+H]^+$. $^1$H NMR: (400 MHz, Chloroform-d, ppm) δ 8.23 (d, J=16.2 Hz, 1H), 7.50 (d, J=7.7 Hz, 1H), 7.31 (d, J=8.0 Hz, 1H), 7.25-7.15 (m, 2H), 7.09 (dd, J=19.7, 8.0 Hz, 2H), 6.62-6.38 (m, 1H), 6.29-5.96 (m, 1H), 5.84-5.64 (m, 1H), 5.54-4.75 (m, 1H), 4.60-2.54 (m, 10H), 1.97-1.84 (m, 1H), 1.06-0.94 (m, 2H), 0.75-0.63 (m, 2H). Analytical chiral HPLC: Column: CHIRAL ART Cellulose-SB; Column Size: 4.6*100 mm, 3 μm; Mobile Phase: Hex (0.1% FA):(EtOH:DCM=1:1)=65:35; Flow: 1.0 mL/min; Temperature: 25° C.; retention time=3.1 min.

Example K-14: Preparation of (R or S)-1-(2-(4-cyclopropylphenyl-5-(7-(trifluoromethyl)-1H-indazole-4-carbonyl)-2,3,4,5,5a,6,8,9-octahydro-7H-10-oxa-1,2,5,7-tetraazacycloocta[cd]inden-7-yl)prop-2-en-1-one

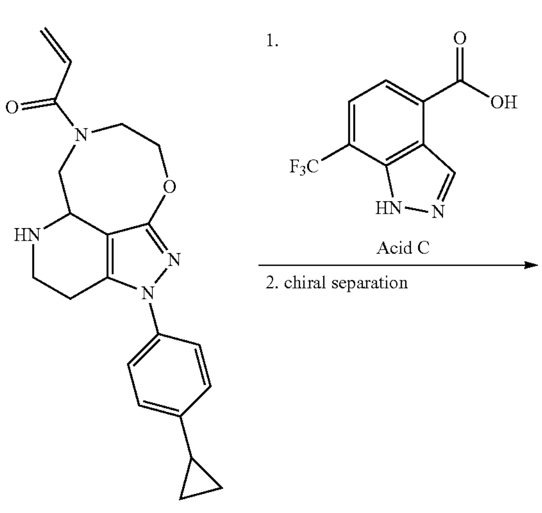

Int. NN

-continued

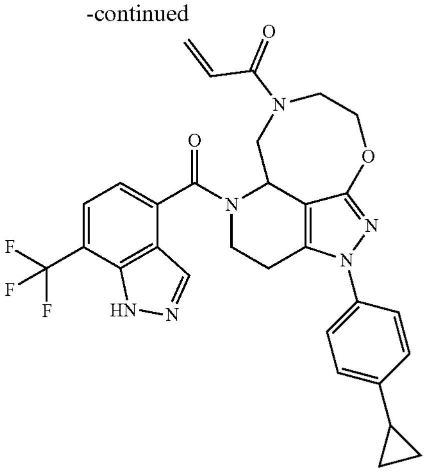

To a solution of (rac)-1-(2-(4-cyclopropylphenyl)-2,3,4,5,5a,6,8,9-octahydro-7H-10-oxa-1,2,5,7-tetraazacycloocta[cd]inden-7-yl)prop-2-en-1-one (Int. NN) (109 mg, 1 eq, 274 gmol) in DMF (1 mL) were added 7-(trifluoromethyl)-1H-indazole-4-carboxylic acid (Acid C) (94.7 mg, 1.5 eq, 412 gmol), HBTU (156 mg, 1.5 eq, 412 gmol) and DIEA (106 mg, 143 μL, 3 eq, 823 gmol). The mixture was stirred at room temperature for 1 h. The mixture was then diluted with water (20 mL) and EtOAc (20 mL), and the aqueous layer was extracted with EtOAc (2×20 mL). The combined organic layers were washed with saturated brine (2×20), dried over anhydrous sodium sulfate, and concentrated to give a residue. The residue was purified by Prep-HPLC (Column: Sunfire C18 5 m, 30 mm*150 mm; Mobile Phase A: water 0.1% FA), Mobile Phase B: MeCN; Flow rate: 60 mL/min; Gradient: 35% B to 55% B in 10 min; Wave Length: UV 254 nm/221 nm; retention time 1: 8.9 min) to afford (rac)-1-(2-(4-cyclopropylphenyl)-5-(7-(trifluoromethyl)-1H-indazole-4-carbonyl)-2,3,4,5,5a,6,8,9-octahydro-7H-10-oxa-1,2,5,7 -tetraazacycloocta[cd]inden-7-yl)prop-2-en-1-one (15 mg) as a white solid. LCMS: (ESI, m/z):577 $[M+H]^+$. The product (15 mg) was further separated into its constitutive enantiomers by chiral prep-HPLC with the following conditions (Column: CHIRALPAK IE, 2*25 cm, 5 μm; Mobile Phase A: Hex(0.1% FA)—HPLC, Mobile Phase B: EtOH:DCM=1:1 Flow rate: 20 mL/min; Gradient: isocratic 50%; Wave Length: UV 254/220 nm; retention time 1: 10.8; retention time 2: 13.8; Number Of Runs: 2) to afford (R or S)-1-(2-(4-cyclopropylphenyl)-5-(7-(trifluoromethyl)-1H-indazole-4-carbonyl)-2,3,4,5,5a,6,8,9-octahydro-7H-10-oxa-1,2,5,7 tetraazacycloocta[cd]inden-7-yl) prop-2-en-1-one as the first-eluting peak (retention time=10.8 min, 5.0 mg, 8.6 μmol; 3% yield) as a white solid. LCMS: (ESI, m/z): 577 $[M+H]^+$.$^1H$ NMR: (400 MHz, Chloroform-d, ppm) δ 8.25 (d, J=17.8 Hz, 1H), 7.76 (d, J=6.3 Hz, 1H), 7.40-7.29 (s, 2H), 7.22 (d, J=7.4 Hz, 1H), 7.16-7.02 (m, 2H), 6.78-6.43 (m, 1H), 0.40-5.63 (m, 2H), 5.26-4.78 (m, 1H), 4.72-2.50 (m, 10H), 1.99-1.84 (m, 1H), 1.06-0.92 (m, 2H), 0.69 (d, J=12.7 Hz, 2H).

Example K-15: Preparation of (S or R,E)-1-(5-(7-bromo-1H-benzo[ ]imidazole-4-carbonyl)-2-(4-cyclobutylphenyl)-2,3,4,5,$5^a$,6,8,9-octahydro-7H-10-oxa-1,2,5,7-tetraazacycloocta[cd]inden-7-yl)-4-(dimethylamino but-2-en-1-one

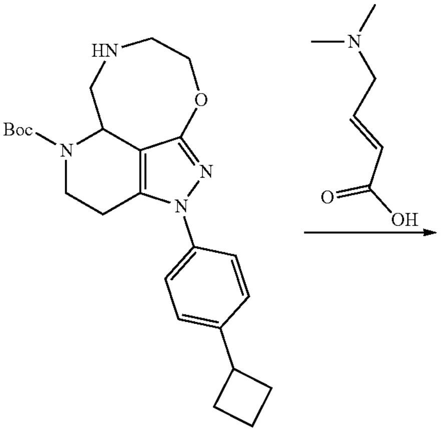

Int. GG

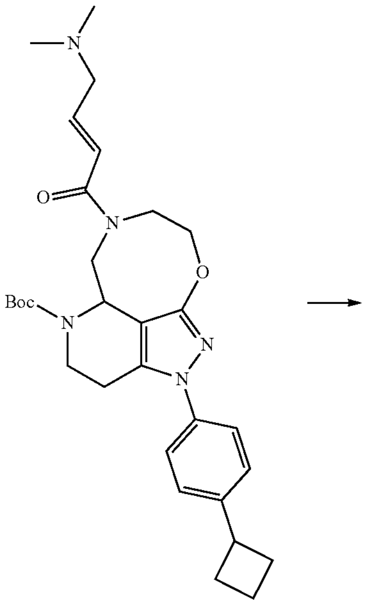

-continued

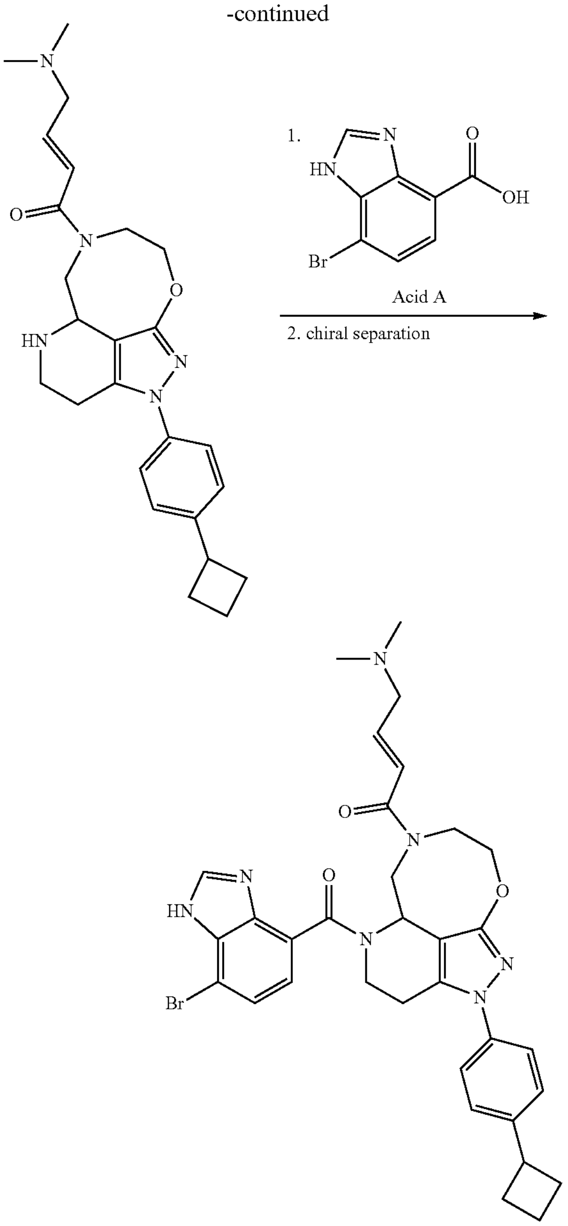

Step 1: Synthesis of Tert-Butyl €-2-(4-cyclobutylphenyl)-7-(4-(dim ethylamino)but-2-enoyl)-2,3,4,5a,6,7,8,9-octahydro-5H-10-oxa-1,2,5,7-tetraazacycloocta[cd]indene-5-carboxylate To a solution of tert-butyl (rac)-2-(4-cyclobutylphenyl)-2,3,4, a,6,7,8,9-octahydro-5H-10-oxa-1,2,5,7-tetraazacycloocta[cd]indene-5-carboxylate (Int. GG) (190 mg, 1 eq, 236 gmol) in DCM (0.5 mL) were added (E)-4-(dimethylamino)but-2-enoic acid (6$0.8 mg, 2 eq, 471 µmol), HATU (89.6 mg, 2 eq, 236 gmol) and DIEA (152 mg, 205 µL, 5 eq, 1.18 mmol). The mixture was stirred at room temperature for 2 h. The mixture was then diluted with ice water (30 mL) and EtOAc (30 mL), and the aqueous layer was extracted with EtOAc (2×30 mL). The combined organic layers were washed with saturated brine (2×30 mL), dried over anhydrous sodium sulfate, and concentrated to give a residue. The residue was purified by flash column chromatography (75% EtOAc in PE) to afford tert-butyl (rac,E)-2-(4-cyclobutylphenyl)-7-(4-(dimethylamino)but-2-enoyl)-2,3,4,5a,6,7,8,9-octahydro-5H-10-oxa-1,2,5,7-tetraazacycloocta[d]indene-5-carboxylate (70 mg) as a white solid. LCMS: (ESI, m/z):536 [M+H]$^+$.

Step 2: Synthesis of (E)-1-(2-(4-cyclobutylphenyl)-2,3,4,5,5a,6,8,9-octahydro-7H-10-oxa-1,2,5,7-tetraazacycloocta[cd]inden-7-yl)-4-(dimethylamino)but-2-en-1-one A solution of tert-butyl (rac,E)-2-(4-cyclobutylphenyl)-7-4-(dimethylamino)but-2-enoyl)-2,3,4,5a,6,7,8,9-octahydro-5H-10-oxa-1,2,5,7-tetraazacycloocta[d]indene-5-carboxylate (60 mg, 1 eq, 0.11 mmol) in DCM (3 mL) and TFA (1 mL) was stirred t room temperature for 2 h. The solvent was removed under reduced pressure. This resulted in (E)-1-(2-(4-cyclobutylphenyl)-2,3,4,5,5a,6,8,9-octahydro-7H-10-oxa-1,2,5,7-tetraazacycloocta[cd]inden-7-yl)-4-(dimethylamino)but-2-en-1-one (65 mg) as a crude yellow oil. The crude product was used in the next step directly without further purification. LCMS: (ESI, m/z) 436 [M+H]$^+$.

Step 3: Synthesis of (S or R,E)-1-(5-(7-bromo-1H-benzo[d]imidazole-4-carbonyl)-2-(4-cyclobutylphenyl)-2,3,4,5,5$^a$,6,8,9-octahydro-7H-10-oxa-1,2,5,7-tetraazacycloocta[cd]inden-7-yl)-4-(dimethylamino)but-2-en-1-one To a solution of (rac,E)-1-(2-(4-cyclobutylphenyl)-2,3,4,5,5,6,8,9-octahydro-7H-10-oxa-1,2,5,7-tetraazacycloocta[cd]inden-7-yl)-4-(dimethylamino)but-2-en-1-one (65 mg, 1 eq, 0.15 mmol) in DMF (1 mL) were added 7-bromo-1H-benzo[d]imidazol-4-carboxylic acid (Acid A) (72 mg, 2 eq, 0.3 mmol), HBTU (0.11 g, 2 eq, 0.3 mmol) and DIE (96 mg, 0.13 mL, 5 eq, 0.75 mmol). The mixture was stirred at room temperature for 6 h. The mixture was then diluted with water (20 mL) and EtOAc (20 mL), and the aqueous layer was extracted with EtOAc (2×20 mL). The combined organic layers were washed with saturated brine (2×20 mL), dried over anhydrous sodium sulfate, and concentrated to give a residue. The residue was purified by Prep-HPLC (Column: XBridge BEH Shield RP18 5 m, 30 mm*150 mm; Mobile Phase A: water (10 mmol/L $NH_4HCO_3$), Mobile Phase B: MeCN; Flow rate: 60 mL/min; Gradient: 30% B to 60% B in 8 min; Wave Length: UV 254 nm/221 nm; retention time 1: 6.6 min) to afford (rac,E)-1-(5-(7-bromo-1H-benzo[d]imidazole-4-carbonyl)-2-(4-cyclobutylphenyl)-2,3,4,5,5a,6,8,9-octahydro-7H-10-oxa-1,2,5,7-tetraazacycloocta[cd]inden-7-yl)-4-(dimethylamino)but-2-en-1-one (12 mg) as a white solid. The racemic mixture was further separated into its constitutive enantiomers by chiral prep-HPLC (Column: CHIRALPAK-IA 2*25 cm, 5 µm; Mobile Phase A: HEX (0.1% TFA), Mobile Phase B: EtOH:DCM=1:1; Flow rate: 20 mL/min; Gradient: isocratic 25; Wave Length: UV 254/220 nm; retention time 1: 20.5; retention time 2: 28.3; Number Of Runs: 1) to afforded ((S or R,E)-1-(5-(7-bromo-1H-benzo[d]imidazole-4-carbonyl)-2-(4-cyclobutylphenyl)-2,3,4,5,5a,6,8,9-octahydro-7H-10-oxa-1,2,5,7-tetraazacycloocta[cd]inden-7-yl)-4-(dimethylamino)but-2-en-1-one as the first-eluting peak (retention time=20.5 min, 2.8 mg, 3.6 µmol, 2% yield) as a white solid. LCMS: (ESI, m/z): 658, 660 [M+H]$^+$. $^1$H NMR: (400 MHz, Chloroform-d) δ 8.52 (s, 1H), 7.66 (d, J=9.6 Hz, 1H), 7.53 (d, J=7.8 Hz, 1H), 7.43-7.29 (m, 2H), 7.18 (d, J=8.9 Hz, 2H), 7.20-6.89 (m, 1H), 6.88 (s, 1H), 5.39 (d, J=10.1 Hz, 1H), 4.84-4.70 (m, 1H), 4.45 (d, J=12.5 Hz, 1H), 4.24 (d, J=18.0 Hz, 1H), 4.15 d, J=12.7 Hz, 3H), 3.77 (d, J=13.3 Hz, 11H), 3.63-3.53 (m, 1H), 3.30 (d, J=13.2 Hz, 11H), 3.34-3.18 (m, 1H) 3.13 (s, 11H), 3.02 (s, 3H), 2.97-2.83 (m, 3H), 2.83-2.48 (m, 1H), 2.38 (d, J=10.3 Hz, 2H), 2.21-2.11 (m, 3H), 2.12-1.89 (m, 2H), 1.88 (d, J=9.4 Hz, 1H). Analytical chiral HP C: CHIRALPAK IA-3; Column Size: 4.6*100 mm, 3 μm; Mobile Phase: Hex(0.1% TFA):(MeO:DCM=1:1)=75:25; Flow: 1.0 mL/min; Temperature: 25° C.; retention time=3.7 min.

Example K-16a and K-16b: Preparation of 1-(($5^a$(S or R),9(R or S))-5-(7-bromo-1H-benzo[d]imidazole-4-carbonyl)-2-(4-isopropylphenyl)-9-methyl-2,3,4,5,5a,6,8,9-octahydro-7H-10-oxa-1,2,5,7-tetraazacycloocta[cd]inden-7-yl)prop-2-en-1-one (K-16a) and 1-((5a(R or S),9(S or R))-5-(7-bromo-1H-benzo[d]imidazole-4-carbonyl)-2-(4-isopropylphenyl)-9-methyl-2,3,4,5,5a,6,8,9-octahydro-7H-10-oxa-1,2,5,7-tetraazacycloocta[cd]inden-7-yl)prop-2-en-1-one (K-16b)

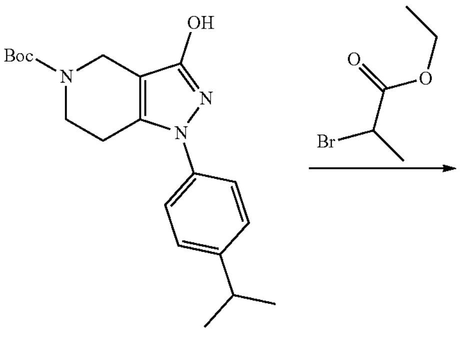

Int. KK

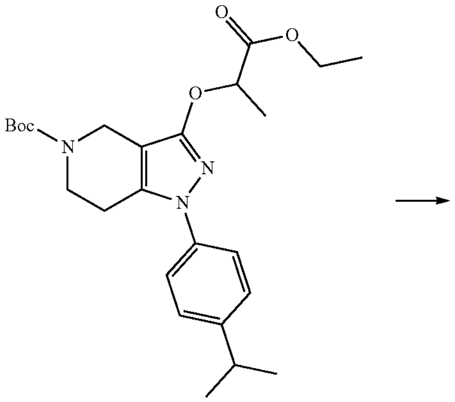

-continued

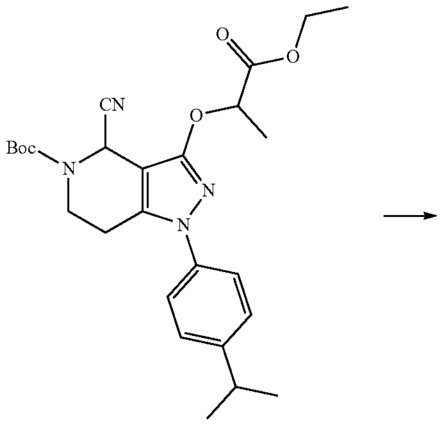

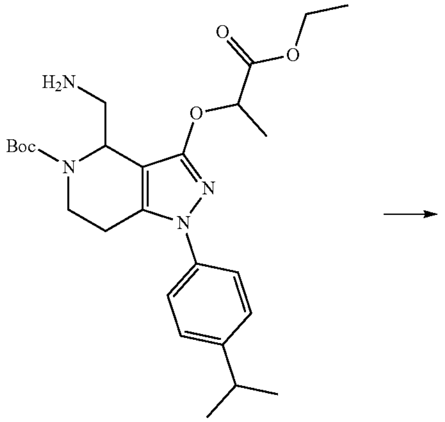

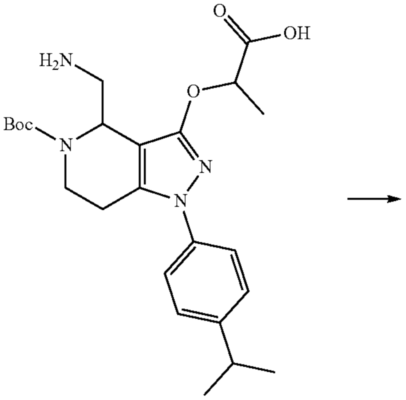

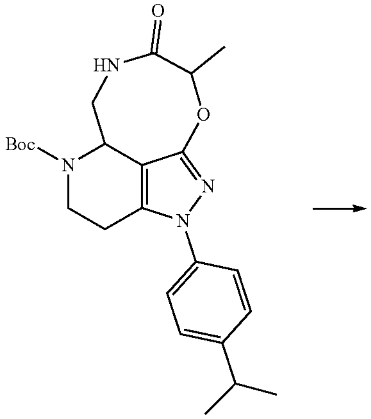

-continued

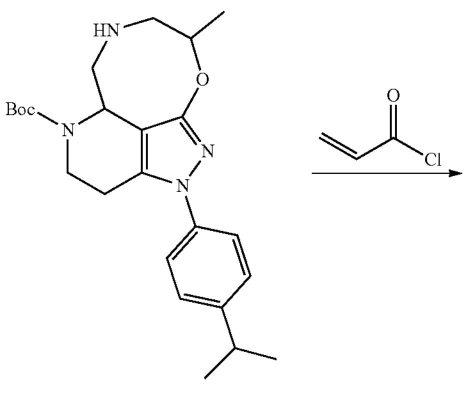

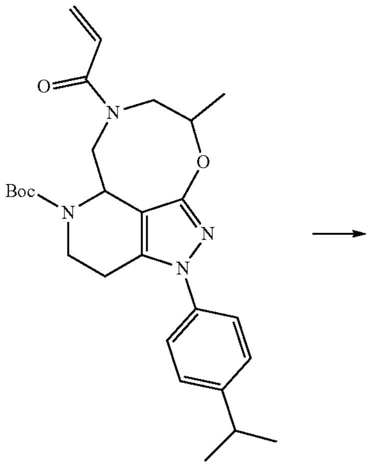

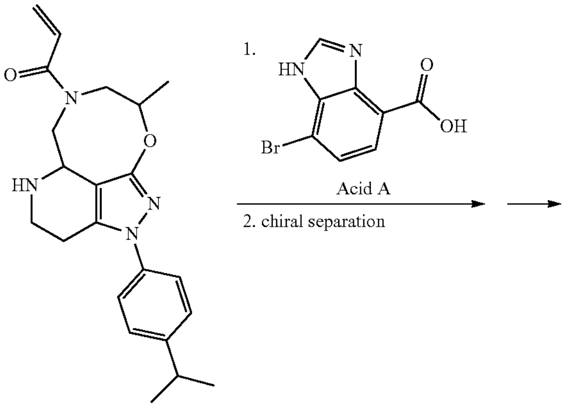

-continued

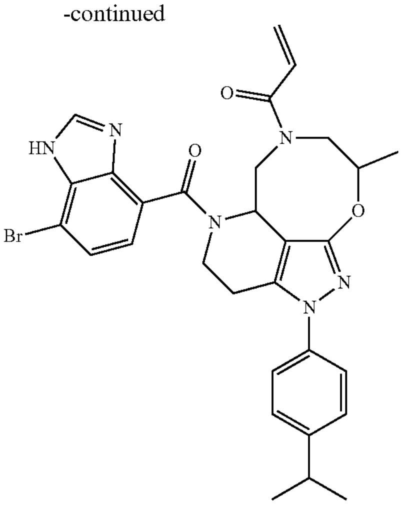

K-16a

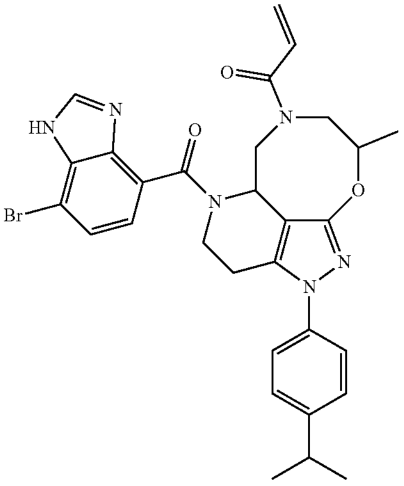

K-16b

Step 1: Synthesis of Tert-Butyl (rac)-3-((1-ethoxy-1-oxopropan-2-yl)oxy) J-(4-isopropylphenyl)-1,4,6,7-tetrahydro-5H-pyrazolo[4,3-c]pyridine-5-carboxylate To a solution of tert-butyl 3-hydroxy-1-(4-isopropylphenyl)-1,4,6,7-tetrahydro-5H-pyrazolo[4,3-c]pyridine-5-carboxylate (Jnt. KK) (9.00 g, 1 eq, 25.2 mmol) in DMF (90 mL) were added $Cs_2CO_3$ (16.4 g, 2 eq, 50.4 mmol) and ethyl 2-bromopropanoate (6.84 g, 1.5 eq, 37.8 mmol). The mixture was stirred at 60° C. for 2 h. The mixture was diluted with water (20 mL) and EtOAc (20 mL), and the aqueous layer was extracted with EtOAc (2×20 mL). The combined organic layers were washed with saturated brine (2×20 mL), dried over anhydrous sodium sulfate, and concentrated to give a residue. The residue was purified by flash column chromatography, EtOAc:PE (1:5) to afford tert-butyl (rac)-3-((1-ethoxy-1-oxopropan-2-yl)oxy)-1-(4-isopropylphenyl)-1,4,6,7-tetrahydro-5H-pyrazolo[4,3-c]pyridine-5-carboxylate (6.50 g) as a yellow solid. LCMS: (ESI, m/z):458 $[M+H]^+$.

Step 2: Synthesis of Tert-Butyl (rac)-4-cyano-3-((1-ethoxy-1-oxopropan-2-yl)oxy)-1-(4-isopropylphenyl)-1,4,6,7-tetrahydro-5H-pyrazolo[4,3-c]pyridine-5-carboxylate To a solution of tert-butyl 3-((1-ethoxy-1-oxopropan-2-yl)oxy)-1-(4-isopropylphenyl)-1,4,6,7-tetrahydro-5H-pyrazolo[4,3-c]pyridine-5-carboxylate (5.50 g, 1 eq, 12.0 mmol) in MeCN (10 mL) were added AcOH (1.44 g, 1.38 mL, 2 eq, 24.0 mmol) TMSCN (2.39 g, 2 eq, 24.0 mmol) and $TEMPO^+BF_4^-$ (5.85 g, 2 eq, 24.0 mmol). The mixture was stirred at room temperature for 2 h. The mixture was then diluted with water (20 mL) and EtOAc (20 mL), and the aqueous layer was extracted with EtOAc (2×20 mL). The combined organic layers were washed with saturated brine (2×20 mL), dried over anhydrous sodium sulfate, and concentrated to give a residue. The residue was purified by flash column chromatography, EtOAc:PE (1:5) to afford tert-butyl (rac)-4-cyano-3-((1-ethoxy-1-oxopropan-2-yl)oxy)-1-(4-isopropylphenyl)-1,4,6,7-tetrahydro-5H-pyrazolo[4,3-c] pyridine-5-carboxylate (5.45 g) as a yellow solid. LCMS (ESI, m/z): 483 $[M+H]^+$.

Step 3: Synthesis of Tert-Butyl (rac)-4-(aminomethyl)-3-((I-ethoxy-1-oxopropan-2-yl)oxy)-1-(4-isopropylphenyl)-1,4,6,7-tetrahydro-5H-pyrazolo[4,3-c]pyridine-5-carboxylate To a solution of tert-butyl (rac)-4-cyano-3-((1-ethoxy-1-oxopropan-2-yl)oxy)-1-(4-isopropylphenyl)-1,4,6,7-tetrahydro-5H-pyrazolo[4,3-c]pyridine-5-carboxylate (5.45 g, 1 eq, 11.3 mmol) in MeOH (60 mL) were added Raney nickel (2.65 g, 50 wt %). The mixture was purged with nitrogen×3 and was then pressurized with 4.0 MPa hydrogen at 60° C. for 6 h. The reaction mixture was cooled to rt, filtered, and rinsed with DCM (5×50 mL). The filtrate was then concentrated under reduced pressure to give afford tert-butyl (rac, 4-(aminomethyl)-3-((1-ethoxy-1-oxopropan-2-yl)oxy)-1-(4-isopropylphenyl)-1,4,6,7-tetrahydro-5H-pyrazolo[4,3-c] pyridine-5-carboxylate (5.31 g) as a crude white oil. The crude product was used in the next step directly without further purification. LCMS: (ESI, m/z): 487 $[M+H]^+$.

Step 4: Synthesis of (rac)-2-((4-(aminomethyl)-5-(tert-butoxycarbonyl)-1-(4-isopropylphenyl)-4,5,6,7-tetrahydro-JH-pyrazolo[4,3-c]pyridine-3-yl)oxy) propanoic Acid To a solution of tert-butyl (rac)-4-(aminomethyl)-3-((1-ethoxy-1-oxopropan-2-yl)oxy)-1-(4-isopropylphenyl)-1,4,6,7-tetrahydro-5H-pyrazolo[4,3-c]pyridine-5-carboxylate (5.31 g, 1 eq, 10.9 mmol) in THE (50 mL) and water (25 mL) was added LiOH (523 ng, 2 eq, 21.8 mmol). The mixture was stirred at room temperature for 1 h. The mixture was then acidified to pH=3 with 1 M sulfuric acid, then diluted with EtOAc (20 mL) and water (15 mL), and the aqueous layer was extracted with EtOAc (2×20 mL). The combined organic layers were washed with saturated brine (20 mL), dried over anhydrous sodium sulfate and concentrated to afford (rac)-2-((4-(aminomethyl)-5-(tert-butoxycarbonyl)-1-(4-isopropylphenyl)-4,5,6,7-tetrahydro-1H-pyrazolo[4,3-c]pyridin-3-yl)oxy)propanoic acid (5.30 g) as a yellow solid. The crude product was used in the next step directly without further purification. LCMS: (ESI, m/z): 459 $[M+H]^+$.

Step 5: Synthesis of Tert-Butyl (rac, cis AND trans)-2-(4-isopropylphenyl)-9-methyl-8-oxo-2,3,4,5a,6,7,8,9-octahydro-5H-10-oxa-1,2,5,7-tetraazacyclooctа[cd]indene-5-carboxylate To a solution of (rac)-2-((4-(aminomethyl)-5-(tert-butoxycarbonyl)-1-(4-isopropylphenyl)-4,5,6,7-tetrahydro-1H-pyrazolo[4,3-c]756 yridine-3-yl)oxy)propanoic acid (5.30 g, 1 eq, 11.6 mmol) in DMF (200 mL) were added DIEA (2.99 g, 4.03 mL, 2 eq, 23.1 mmol) and COMU (7.42 g, 1.5 eq, 17.3 mmol). The mixture was stirred at room temperature for 1 h. The mixture was then diluted with water (20 mL) and EtOAc (20 mL), and the aqueous layer was extracted with EtOAc (2×20 mL). The combined organic layers were washed with saturated brine (2×20 mL), dried over anhydrous sodium sulfate, and concentrated to give a residue. The residue was purified by flash column chromatography, eluting with EtOAc:PE (1:5) to afford tert-butyl (rac, cis AND trans)-2-(4-isopropylphenyl)-9-methyl-8-oxo-2,3,4,5a,6,7,8,9-octahydro-5H-10-oxa-1,2,5,7-tetraazacycloocta[cd]indene-5-carboxylate (810 mg) as a white solid. LCMS: (ESI, m/z): 441 $[M+H]^+$.

Step 6: Synthesis of Tert-Butyl (rac, cis AND trans)-2-(4-isopropylphenyl)-9-methyl-2,3,4,5a,6,7,8,9-octahydro-5H-10-oxa-1,2,5,7-tetraazacycloocta [cd]indene-5-carboxylate To a solution of tert-butyl (rac, cis AND trans)-2-(4-isopropylphenyl)-9-methyl-8-oxo-2,3,4,5a,6,7,8,9-octahydro-5H-10-oxa-1,2,5,7-tetraazacycloocta[cd]indene-5-carboxylate (810 mg, 1 eq, 1.84 mmol) in THF (9 mL) was added $BH_3$-THF (0.35 mL, 4 Eq, 7.35 mmol, 1 mol/L). The mixture was stirred at 60° C. for 1 h. The solvent was then removed under reduced pressure to provide tert-butyl (rac, cis AND trans)-2-(4-isopropylphenyl)-9-methyl-2,3,4,5a,6,7,8,9-octahydro-5H-10-oxa-1,2,5,7-tetraazacycloocta[cd] indene-5-carboxylate (260 mg) as a crude white solid. The crude product was used in the next step directly without further purification. LCMS: (ESI, m/z): 427 $[M+H]^+$.

Step 7: Synthesis of Tert-Butyl (rac, Cis AND Trans)-7-acryloyl-2-(4-isopropylphenyl)-9-methyl-2,3,4,5a,6,7,8,9-octahydro-5H-10-oxa-1,2,5,7-tetraazacycloocta[cd]indene-5-carboxylate To a solution of tert-butyl (rac, cis AND trans)-2-(4-isopropylphenyl)-9-methyl-2,3,4,5a,6,7,8,9-octahydro-5H-10-oxa-1,2,5,7-tetraazacycloocta[cd]indene-5-carboxylate (260 mg, 1 eq, 610 μmol) in DCM (3 mL) were added TEA (247 mg, 340 μL, 4 eq, 2.44 mmol) and acryloyl chloride (166 mg, 3 eq, 1.83 mmol). The mixture was stirred a room temperature for 30 min. The mixture was then diluted with water (20 mL) and EtOAc (20 mL), and the aqueous layer was extracted with EtOAc (2×20 mL). The combined organic layers were washed with saturated brine (2×20 mL), dried over anhydrous sodium sulfate, and concentrated to give a residue. The residue was purified by flash column chromatography, eluting with EtOAc:PE (1:5) to afford tert-butyl (rac, cis AND trans)-7-acryloyl-2-(4-isopropylphenyl)-9-methyl-2,3,4,5a,6,7,8,9-octahydro-5H-10-oxa-1,2,5,7-tetraazacycloocta[cd]indene-5-carboxylate (180 mg) as a yellow solid. LCMS: (ESI, m/z): 481 $[M+H]^+$.

Step 8: Synthesis of (rac, Cis AND Trans)-1-(2-(4-isopropylphenyl)-9-methyl-2,3,4,5,5a,6,8,9-octahydro-7H-10-oxa-1,2,5,7-tetraazacycloocta[cd]inden-7-yl)prop-2-en-1-one A solution of tert-butyl 7-acryloyl-2-(4-isopropylphenyl)-9-methyl-2,3,4,5a,6,7,8,9-octahydro-5H-10-oxa-1,2,5,7-tetraazacycloocta[cd]indene-5-carboxylat (180 mg, 1 eq, 375 μmol) in DCM (1 mL) and TFA (0.5 mL) was stirred at room temperature for 30 min. The solvent was then removed under reduced pressure to provide (rac, cis AND trans)-1-(2-(4-isopropylphenyl)-9-methyl-2,3,4,5,5a,6,8,9-octahydro-7H-10-oxa-1,2,5,7-tetraazacycloocta[cd]inden-7-yl) prop-2-en-1-one (160 mg) as a crude yellow oil. The crude product was used in the next step directly without further purification. LCMS: (ESI, m/z): 381 $[M+H]^+$.

Step 9: Synthesis of 1-((5a (R or S),9(R or S))-5-(7-bromo-JH-benzo[d]imidazole-4-carbonyl)-2-(4-isopropylphenyl)-9-methyl-2,3,4,5,5a,6,8,9-octahydro-7H-10-oxa-1,2,5,7-tetraazacycloocta[cd] inden-7-yl)prop-2-en-1-one and 1-(($5^a$(S or S_),9(S or RJ-5-(7-bromo-1H-benzo[d]imidazole-4-carbonyl)-2-(4-isopropylphenyl)-9-methyl-2,3,4, 5, $5^a$,6, 8,9-octahydro-7H-10-oxa-1,2,5,7-tetraazacycloocta [cd]inden-7-yl)prop-2-en-1-one To a solution of (rac, cis AND trans)-1-(2-(4-isopropylphenyl)-9-methyl-2,3,4,5,5a,6,8,9-octahydro-7H-10-oxa-1, 2,5,7-tetraazacycloocta[cd]inden-7-yl)prop-2-en-1-one (80 mg, 1 eq, 0.21 mmol) in DMF (1 mL) were added DIEA (82 mg, 0.11 mL, 3 eq, 0.63 μmol), HBTU (0.12 g, 1.5 eq, 0.32 mmol) and 7-bromo-1H-benzo[d]imidazole-4-carboxylic acid (Acid A) (76 mg, 1.5 eq, 0.32 mmol). The mixture was stirred at room temperature for 1 h. The mixture was then diluted with water (20 mL) and EtOAc (20 mL), and the aqueous layer was extracted with EtOAc (2×20 mL). The combined organic layers were washed with saturated brine (2×20 mL), dried over anhydrous sodium sulfate, and concentrated to give a residue. The residue was purified by prep-HPLC (Column: XBridge BEH Shield RP18 5 m, 30 mm*150 mm; Mobile Phase A: water (10 mmol/L $NH_4HCO_3$), Mobile Phase B: MeCN; Flow rate: 60 mL/min; Gradient: 35% B to 52% B in 10 min; Wave Length: UV 254 nm/220 nm; retention time 1: 8.8 min) to afford (rac, cis AND trans)-1-(5-(7-bromo-1H-benzo[d]imidazole-4-carbonyl)-2-(4-isopropylphenyl)-9-methyl-2,3,4, 5,5a,6,8,9-octahydro-7H-10-oxa-1,2,5,7-tetraazacycloocta [cd]inden-7-yl)prop-2-en-1-one (30 mg) as a white solid.

The product (30 mg), a mixture of four enantiomers, was separated into its constitutive enantiomers by Chiral Prep-HPLC with the following conditions (Column: CHIRALPAK-IE 2*25 cm, 5 μm; Mobile Phase A: HEX(0.1% FA), Mobile Phase B: EtOH:DCM=1:1; Flow rate: 20 mL/min; Gradient: isocratic 50; Wave Length: UV 254/220 nm; retention time 1: 9.8; retention time 2: 12.2; Injection Volume: 0.53 mL; Number Of Runs: 6) 1-((5a(S or R),9(R or S))-5-(7-bromo-1H-benzo[d]imidazole-4-carbonyl)-2-(4-isopropylphenyl)-9-me yl-2,3,4,5,5a,6,8,9-octahydro-7H-10-oxa-1,2,5,7-tetraazacycloocta[cd]inden-7-yl)prop-2-en-1-one as the second-eluting peak (retention time=12.2 min, 3.7 mg, 6.1 mol, 3% yield) as a white solid. LCMS: (ESI, m/z): 603, 605 $[M+H]^+$. $^1$H NMR: (400 MHz, Chloroform-d) δ 8.42 (s, 1H), 7.57 (s, 1H), 7.39-7.30 (m, 21H), 7.23-7.14 (m, 2H), 6.43 (s, 2H), 5.92 (s, 1H), 5.79 (s, 11H), 4.68 (s, 1H), 4.26 (s, 1H), 4.04 (d, J=14.8 Hz, 1H), 3.83 (s, 1H), 3.68 (s, 1H), 3.52-3.37 (m, 1H), 3.34-3.21 (m, 1H), 3.12 (s, 1H), 2.98-2.86 (m, 2H), 2.85-2.54 (m, 2H), 1.53 (d, J=5.2 Hz, 3H), 1.24 (d, J=6.7 Hz, 6H).

From the first chiral purification, the third peak was isolated a a mixture. This mixture was further purified by Chiral Prep-HPLC with the following conditions (Column: CHIRAL ART Cellulose-SC 2*25 cm, 5 μm; Mobile Phase A: HEX(0.1% FA), Mobile Phase B: EtOH:DCM=1:1; Flow rate: 20 mL/min; Gradient: isocratic 60; Wave Length: UV 254/20 nm; retention time 1: 8.8; retention time 2: 12.5; Injection Volume: 0.75 mL; Number Of Run: 2) to afford 1-((5a(R or S),9(S or R))-5-(7-bromo-1H-benzo[d]imidazole-4-carbonyl)-2-(4-isopropylphenyl)-9-methyl-2,3,4,5, 5a,6,8,9-octahydro-7H-10-oxa-1,2,5,7-tetraazacycloocta [cd]inden-7-yl)prop-2-en-1-one as the second-eluting peak in this purification (retention time=12.5 mi, 2.7 mg, 4.5 μmol, 2% yield) as a white solid.

LCMS: (ESI, m/z): 603, 605 $[M+H]^+$. $^1$H NMR:(400 MHz, Chloroform d) δ 8.25 (s, 1H), 7.54 (s, 1H), 7.37 (d, J=8.1 Hz, 1H), 7.29 (d, J=9.7 Hz, 2H), 7.23 (d, J=8.8 Hz, 2H), 6.75-6.36 (m, 1H), 6.26-6.06 (m, 1H), 5.85-5.41 (m, 1H), 5.12-4.68 (m, 1H), 4.41 (s, 1H), 4.14 (s, 1H), 4.07-3.69 (m, 2H), 3.68-3.42 (m, 1H), 3.39-3.00 (m, 2H), 2.93 (dp, J=13.6, 6.8 Hz, 1H), 2.83-2.61 (m, 2H), 1.51-1.30 (m, 3H), 1.25 (t, J=7.1 Hz, 6H).

Example K-17a: Preparation of 1-((5aR,9R)-5-(7-bromo-1-benzo[d]imidazole-4-carbonyl)-9-fluoro-2-(4-isopropylphenyl)-2,3,4,5,5a,6,8,9-octahydro 7H-10-oxa-1,2,5,7-tetraazacycloocta[cd]inden-7-yl) prop-2-en-1-one (K-17a)

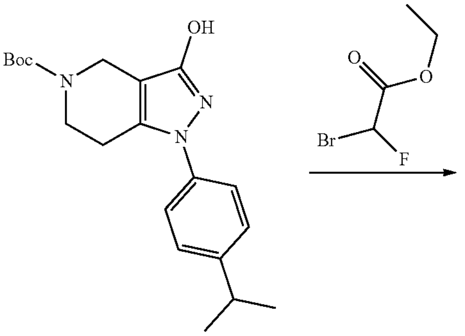

Int. KK

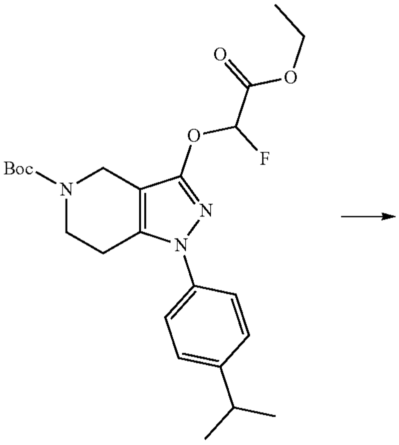

-continued
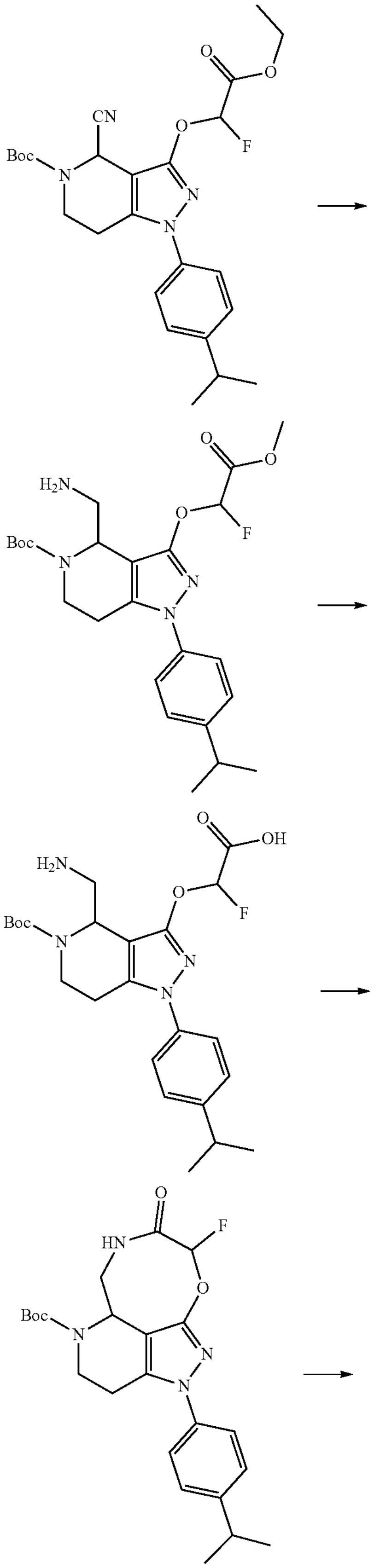
-continued
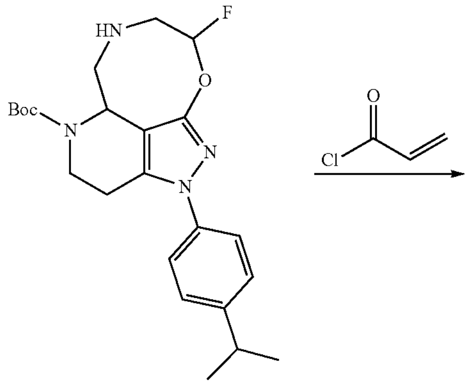
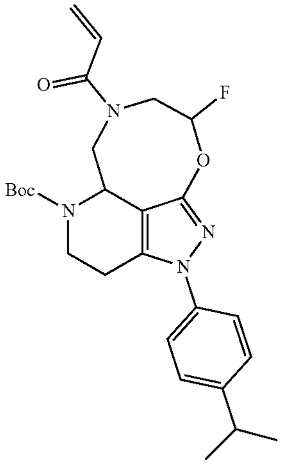
Int. OOA
cis OR trans
+
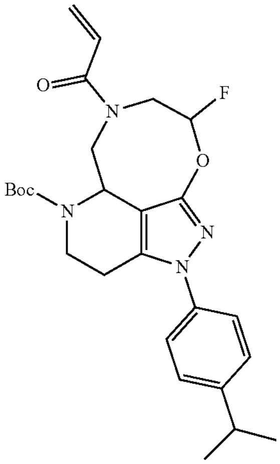
Int. OOB
cis OR trans -continued

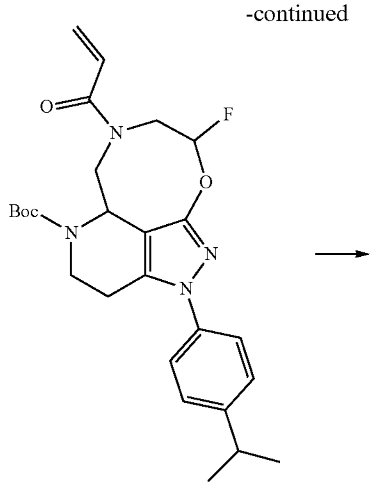

Int. OOA

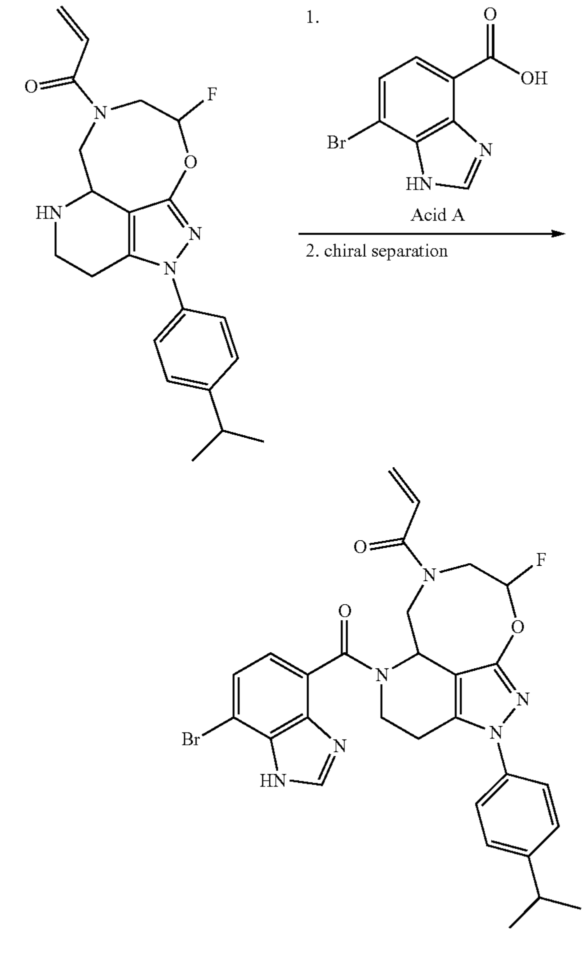

Step 1: Synthesis of Tert-Butyl (rac)-3-(2-ethoxy-1-fluoro-2-oxoethoxy)-1-(4-isopropylphenyl)-1,4,6,7-tetrahydro-5H-pyrazolo[4,3-c]pyridine-5-carboxylate To a solution of tert-butyl 3-hydroxy-1-(4-isopropylphenyl)-1,4,6,7-tetrahydro-5H-pyrazolo[4,3-c]pyridine-5-carboxylate (Int. KK) (8 g, 1 eq, 0.02 mol) in DMA (90 mL) were added ethyl 2-bromo-2-fluoroacetate (6 g, 1.5 eq, 0.03 mol) and $Cs_2CO_3$ (0.01 kg, 2 eq, 0.04 mol). The mixture was stirred at room temperature for 8 h. The reaction was quenched by the addition of ice water (150 mL) at rt. The resulting mixture was extracted with EtOAc (2×20 mL). The combined organic layers were washed with semi-saturated NaCl (2×100 mL) and sat.NaCl (100 mL), and dried over anhydrous $Na_2SO_4$. After filtration, the filtrate was concentrated under reduced pressure. The residue was purified by silica gel column chromatography, eluting with EtOAc:PE (18:82) to afford tert-butyl (rac)-3-(2-ethoxy-1-fluoro-2-oxoethoxy)-1-(4-isopropylphenyl)-1,4,6,7-tetrahydro-5H-pyrazolo[4,3-c]pyridine-5-carboxylate (6.5 g) as a yellow oil. LCMS: (ESI, m/z): 462 $[M+H]^+$.

Step 2: Synthesis of Tert-Butyl (rac)-4-cyano-3-(2-ethoxy-1-fluoro-2-oxoethoxy)-1-(4-isopropylphenyl)-1,4,6,7-tetrahydro-5H-pyrazolo[4,3-c]pyridine-5-carboxylate To a stirred solution of tert-butyl (rac)-3-(2-ethoxy-1-fluoro-2-oxoethoxy)-1-(4-isopropylphenyl)-1,4,6,7-tetrahydro-5H-pyrazolo[4,3-c]pyridine-5-carboxylate (6.5 g, 1 eq, 14 mmol) in MeCN (200 mL) was added TMS-CN (2.8 g, 3.5 mL, 2 eq, 28 mmol), AcOH (1.7 g, 1.6 mL, 2 eq, 28 mmol) and $TEMPO^+BF_4^-$ (10 g, 3 eq, 42 mmol) at room temperature and the resulting mixture was stirred for 6 h under a nitrogen atmosphere. The reaction progress was monitored by LCMS. After completion, the reaction was quenched by the addition of half-saturated $NaHCO_3$ (100 mL) at rt. The resulting mixture was extracted with EtOAc (2×200 mL). The combined organic layers were washed with brine (200 mL), and dried over anhydrous $Na_2SO_4$. After filtration, the filtrate was concentrated under reduced pressure. The residue was purified by silica gel column chromatography, eluting with EtOAc:PE (15:85) to afford t rt-butyl (rac)-4-cyano-3-(2-ethoxy-1-fluoro-2-oxoethoxy)-1-(4-isopropylphenyl)-1,4,6,7-tetrahydro-5H-pyrazolo[4,3-c]pyridine-5-carboxylate (6 g, 0.01 mol, 90% yield) as a light yellow oil. LCMS: (ESI, m/z): 487 $[M+H]^+$.

Step 3: Synthesis of Tert-Butyl (rac)-4-(aminomethyl)-3-(1-fluoro-2-methoxy-2-oxoethoxy)-1-(4-isopropylphenyl)-1,4,6,7-tetrahydro-5H-pyrazolo[4,3-c]pyridine-5-carboxylate To a solution of tert-butyl (rac)-4-cyano-3-(2-ethoxy-1-fluoro-2-oxoethoxy)-1-(4-isopropylphenyl)-1,4,6,7-tetrahydro-5H-pyrazolo[4,3-c]pyridine-5-carboxylate (5 g, 1 eq, 0.01 mol) in MeOH (200 mL) was added Raney nickel (3 g, 50 wt %). The mixture was purged with nitrogenx3 times and then pressurized with 3.0 MPa hydrogen at 60° C. for 8 h. The reaction mixture was then cooled to rt, filtered through a Celite pad, and concentrated under reduced pressure. This resulted in tert-butyl (rac)-4-(aminomethyl)-3-(1-fluoro-2-methoxy-2-oxoethoxy)-1-(4-isopropylphenyl)-1,4,6,7-tetrahydro-5H-pyrazolo[4,3-c]pyridine-5-carboxylate (5 g) as a crude white solid. The crude product was used in the next step directly without further purification. LCMS: (ESI, m/z): 477 $[M+H]^+$.

Step 4: Synthesis of (rac)-2-((4-(aminomethyl)-5-(tert-butoxycarbonyl)-1-(4-isopropylphenyl)-4,5,6,7-tetrahydro-JH-pyrazolo[4,3-c]pyridine-3-yl)oxy)-2-fluoroacetic acid To a solution of tert-butyl (rac)-4-cyano-3-(2-ethoxy-1-fluoro-2-oxoethoxy)-1-(4-isopropylphenyl)-1,4,6,7-tetrahydro-5H-pyrazolo[4,3-c]pyridine-5-carboxylate (5 g, 1 eq, 0.01 mol) in THF (20 mL) was added LiOH (0.7 g, 3 eq, 0.03 mol)/water (10 mL). The mixture was stirred at 50° C. for 16 h. Purification by reverse phase chromatography (column: C18 column; Gradient: MeCN in water with 0.5% TFA) afforded (rac)-2-((4-(aminomethyl)-5-(tert-butoxycarbonyl)- 1-(4-isopropylphenyl)-4,5,6,7-tetrahydro-1H-pyrazolo [4,3-c]pyridin-3-yl)oxy)-2-fluoroacetic acid (3 g) as a light pink solid. LCMS: (ESI, m/z): 463 [+H]$^+$.

Step 5: Synthesis of Tert-Butyl (rac,cis AND trans)-9-fluoro-2-(f-isopropylphenyl)-8-oxo-2,3,4,5a,6,7,8,9-octahydro-5H-10-oxa-1,2,5,7-tetraazacycloocta [cd]indene-5-carboxylate To a solution of (rac)-2-((4-(aminomethyl)-5-(tert-butoxycarbonyl)-1-(4-isopropylphenyl)-4,5,6,7-tetrahydro-1H-pyrazolo[4,3-c]pyridin-3-yl)oxy)-2-fluoroacetic acid (3 g, 1 eq, 6 mmol) in DMF (250 mL) were added DIEA (4 g, 6 mL, 5 eq, 0.03 mol) and HATU (3 g, 1.2 eq, 8 mmol). The mixture was stirred at room temperature for 2 h. The reaction mixture was quenched with water (20 mL) and extracted with EtOAc (3×50 mL). The combined organic layers were washed with half saturated brine (2×100 mL) and saturated brine (1×100 mL), dried over $Na_2SO_4$, filtered, and evaporated under reduced pressure to a residue. The residue was purified by silica gel chromatography (Gradient: PE:EA=7:3) afforded tert-butyl (rac, cis AND trans)-9-fluoro-2-(4-isopropylphenyl)-8-oxo-2,3,4,5a,6,7,8,9-octahydro-5H-10-oxa-1,2,5,7-tetraazacycloocta[cd]indene-5-carboxylate (450 mg) as colorless semi-solid. LCMS: (ESI, m/z): 445 [M+H]$^+$.

Step 6: Synthesis of Tert-Butyl (rac,cis AND trans)-9-fluoro-2-(4-isopropylphenyl)-2,3,4,5a,6,7,8,9-octahydro-5H-10-oxa-1,2,5,7-tetraazacycloocta[cd]indene-5-carboxylate A solution of tert-butyl (rac,cis AND trans)-9-fluoro-2-(4-isopropylphenyl)-8-oxo-2,3,4,5a,6,7,8,9-octahydro-5H-10-oxa-1,2,5,7-tetraazacycloocta[cd]indene-5-carboxylate (460 mg, 1 eq, 1.03 mmol) in THF (4 mL) was cooled to 0° C., then $BH_3$-THF (0.3 g, 4 mL, 1 M, 4 eq, 4 mmol) was added slowly at 0° C. The mixture was warmed to 60° C. and stirred for 1 h. After completion of the reaction, MeOH (10 mL) was added at 0° C. The so vent was removed under reduced pressure to provide tert-butyl (rac,cis AND trans)-9-fluoro-2-(4-isopropylphenyl)-2,3,4,5a,6,7,8,9-octahydro-5H-10-oxa-1,2,5,7-tetraazacycloocta[cd]indene-5-carboxylate (400 mg) as a white solid. The crude product was used in the next step directly without further purification. LCMS: (ESI, m/z): 431[M+H]$^+$.

Step 7: Synthesis Tert-Butyl (rac,cis or trans)-7-acryloyl-9-fluoro-2-(4-isopropylphenyl)-2,3,4,5a,6,7,8,9-octahydro-5H-10-oxa-1,2,5,7-tetraazacycloocta [cd]indene-5-carboxylate (Int. OOA) and Tert-Butyl (rac,trans or cis)-7-acryloyl-9-fluoro-2-(4-isopropylphenyl)-2,3,4,5a,6,7,8,9-octahydro-5H-10-oxa-1,2,5,7-tetraazacycloocta[cd]indene-5-carboxylate (Int. OOB)

To a stirred solution of tert-butyl (rac,cis AND trans)-9-fluoro-2-(4-isopropylphenyl)-2,3,4,5a,6,7,8,9-octahydro-5H-10-oxa-1,2,5,7-tetraazacycloocta[cd]indene-5-carboxylate (350 mg, 1 eq, 813 gmol) in DCM (7 mL) was added TEA (247 mg, 340 µL, 3 eq, 2.44 mmol). The mixture was cooled to 0° C., then acryloyl chloride (147 mg, 2 eq, 1.63 mmol) was added slowly at 0° C. The mixture was warmed to room temperature and stirred for h. After completion of reaction, the reaction was quenched by the addition of ice water (20 mL). The resulting mixture was extracted with DCM (3×20 mL). The combined organic layers were washed with saturated brine (2×20 mL), dried over anhydrous $Na_2SO_4$, and filtered. The filtrate was concentrated under reduced pressure. The resulting residue was purified by silica gel column chromatography. Tert-butyl (rac,cis or trans)-7-acryloyl-9-fluoro-2-(4-isopropylphenyl)-2,3,4, a,6,7,8,9-octahydro-5H-10-oxa-1,2,5,7-tetraazacycloocta[cd]indene-5-carboxylate (Int. OOA) eluted as the first peak; eluting with PE/EtOAc (66/34) as a light yellow solid (90 mg). LCMS: (ESI, m/z): 485 [M+H]$^+$. Tert-butyl (rac,trans or cis)-7-acryloyl-9-fluoro-2-(4-isopropylphenyl)-2,3,4,5a,6,7,8,9-octahydro-5H-10-oxa-1,2,5,7-tetraazacycloocta[cd]indene-5-carboxylate (Int. OOB) was then eluted as the second peak, eluting with PE/EtOAc (57/43) as a light yellow solid (150 mg, 310 µmol, 38% yield over 2 steps). LCMS: (ESI, m/z): 485 [M+H]$^+$.

Step 8: Synthesis of (rac,cis or trans)-1-(9-fluoro-2-(4-isopropylphenyl)-2,3,4,5,5a,6,8,9-octahydro-7H-10-oxa-1,2,5,7-tetraazacycloocta[cd]inden-7-yl) prop-2-en-1-one A solution of tert-butyl (rac,cis or trans)-7-acryloyl-9-fluoro-2-(4-isopropylphenyl)-2,3,4,5a,6,7,8,9-octahydro-5H-10-oxa-1,2,5,7-tetraazacycloocta[cd]indene-5-carboxylate (Int. OOA), (80 mg, 1 eq, 0.17 mmol) in DCM (2 mL) and TFA (0.5 mL) was stirred at room temperature for 2 h. The solvent was removed under reduced pressure to afford (rac,cis or trans)-1-(9-fluoro-2-(4-isopropylphenyl)-2,3,4,5,5a,6,8,9-octahydro-7H-10-oxa-1,2,5,7-tetraazacycloocta [cd]inden-7-yl)prop-2-en-1-one (80 mg) as a crude light yellow oil. The crude product was used in the next step directly without further purification. LCMS: (ESI, m/z): 385 [M+H]$^+$.

Step 9: Synthesis of 1-((5a(R or S),9(R or S))-5-(7-bromo-JH-benzo[d]imidazole-4-carbonyl)-9-fluoro-2-(4-isopropylphenyl)-2,3,4,5,5a,6,8,9-octahydro-7H-10-oxa-1,2,5,7-tetraazacycloocta[cd]inden-7-yl) prop-2-en-1-one To a solution of (rac,cis or trans)-1-(9-fluoro-2-(4-isopropylphenyl)-2,3,4,5,5a,6,8,9-octahydro-7H-10-oxa-1,2,5,7-tetraazacycloocta[cd]inden-7-yl)prop-2-en-1-one (80 mg, 1 eq, 0.21 mmol) in DMF (2 mL) was added 7-bromo-1H-benzo[d]imidazole-4-carboxylic acid (Acid A) (60 mg, 1.2 eq, 0.25 mmol), HATU (95 mg, 1.2 eq, 0.25 mmol) and DIEA (0.13 g, 0.18 mL, 5 eq, 1.0 mmol). The mixture was stirred at room temperature for 2 h. The mixture was then purified by Prep-HPLC(Column: XBridge BEH Shield RP18 5 m, 30 mm*150 mm; Mobile Phase A: water (0.1% FA), Mobile Phase B: MeCN; Flow rate: 60 mL/min; Gradient: 35% B to 60% B in 10 min; Wave Length: UV 254 nm/220 nm; retention time retention time 1: 9.5 min) to afford (rac,cis or trans)1-(5-(7-bromo-1H-benzo[d]imidazole-4-carbonyl)-9-fluoro-2-(4-isopropylphenyl)-2,3,4,5,5a,6,8,9-octahydro-7H-10-oxa-1,2,5,7-tetraazacycloocta[cd]inden-7-yl)prop-2-en-1-one (40 mg) as light yellow solid. The racemic mixture was separated by chiral-separation (Column: CHIRALPAK-IG 3*25 cm, 5 µm; Mobile Phase A: HEX(0.1% FA), Mobile Phase B: EtOH:DCM=1:1; Flow rate: 40 mL/min; Gradient: isocratic 50; Wave Length: UV 254/220 nm; retention time 1: 5.7; retention time 2: 17.5;

Sample Solvent: EtOH; Injection Volume: 2.25 mL; Number Of Runs: 2) to provide 1-((5a(R or S),9(R or S))-5-(7-bromo-1H-benzo[d]imidazole-4-carbonyl)-9-fluoro-2-(4-isopropylphenyl)-2,3,4,5,5a,6,8,9-octahydro-7H-10-oxa-1,2,5,7-tetraazacycloocta[cd]inden-7-yl)prop-2-en-1-one assigned as the first-eluting peak (retention time=5.7 min, 11.3 mg, 18.5 mol, 9% yield) as a white solid. LCMS: (ESI, m/z): 607, 609 $[M+H]^+$. $^1$H NMR: (400 MHz, Chloroform-d) δ 8.26 (s, 1H), 7.55-7.50 (m, 1H), 7.42-7.36 (m, 2H), 7.33-7.29 (m, 2H), 7.29-7.27 (m, 1H), 6.73-6.16 (m, 2H), 5.88 (s, 1H), 5.47 (s, 1H), 4.51-4.46 (m, 2H), 4.18-3.24 (m, 3H), 3.23-2.77 (m, 5H), 1.26 (d, J=6.9 Hz, 6H).

The compound of Example K-17b was prepared in a manner analogous to Example K-17a, steps 8-9, using Int. OOB in place of Int. OOA. The racemic (rac,trans or cis)-1-(5-(7-bromo-1H-benzo[d]imidazole-4-carbonyl)-9-fluoro-2-(4-isopropylphenyl)-2,3,4,5,5a,6,8,9-octahydro-7H-10-oxa-1,2,5,7-tetraazacycloocta[cd]inden-7-yl)prop-2-en-1-one was separated by chiral-separation (Column: CHIRALPAK-IG 3*25 cm, 5 μm; Mobile Phase A: HEX (0.1% FA), Mobile Phase B: EtOH:DCM=1:1; Flow rate: 40 mL/min; Gradient: isocratic 40; Wave Length: UV 254/220 nm; retention time 1: 16.7; retention time 2: 23.6; Samp e Solvent: EtOH:DCM; Injection Volume: 2.0 mL; Number Of Runs: 3) to provide 1-((5a(R or R),9(S or R))-5-(7-bromo-1H-benzo[d]imidazole-4-carbonyl)-9-fluoro-2-(4-isopropylphenyl)-2,3,4,5,5a,6,8,9-octahydro-7H-10-oxa-1,2,5,7-tetraazacycloocta[cd]inden-7-yl)prop-2-en-1-one as the first-eluting peak (retention time=16.7 min).

Example K-18: Preparation of Synthesis of (R or S)-1-(5-(7-bromo-1H-benzo[d]imidazole-4-carbonyl)-2-(4-isopropylphenyl)-10-methyl-2,4,5,5a,6,8,9,10-octahydro-1,2,5,7,10-pentaazacycloocta[cd]inden-7(3H)-yl)prop-2-en-1-one

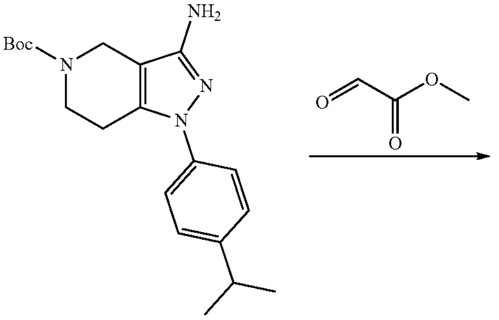

Int. PP

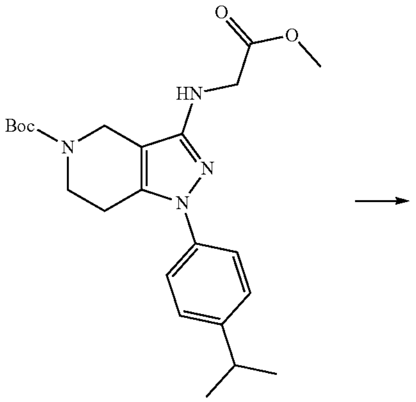

| Example No. | Structure and Name | LCMS (ESI, m/z) | NMR |
|---|---|---|---|
| K-17b | 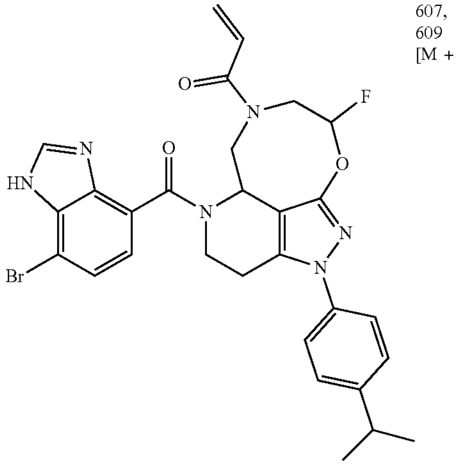 1-((5a(R or S),9(S or R))-5-(7-bromo-1H-benzo[d]imidazole-4-carbonyl)-9-fluoro-2-(4-isopropylphenyl)-2,3,4,5,5a,6,8,9-octahydro-7H-10-oxa-1,2,5,7-tetraazacycloocta[cd]inden-7-yl)prop-2-en-1-one | 607, 609 $[M + H]^+$ | $^1$H NMR (400 MHz, Chloroform-d, ppm) δ 8.57 (s, 1H), 8.04- 7.31 (m, 3H), 7.27 - 6.88 (m, 1H), 6.53 (s, 1H), 6.25 (s, 1H),6.08 - 5.05 (m, 3H), 4.96 - 3.22 (m, 7H), 2.93-2.62 (m, 4H), 1.43 - 1.10 (m, 6H). |

-continued

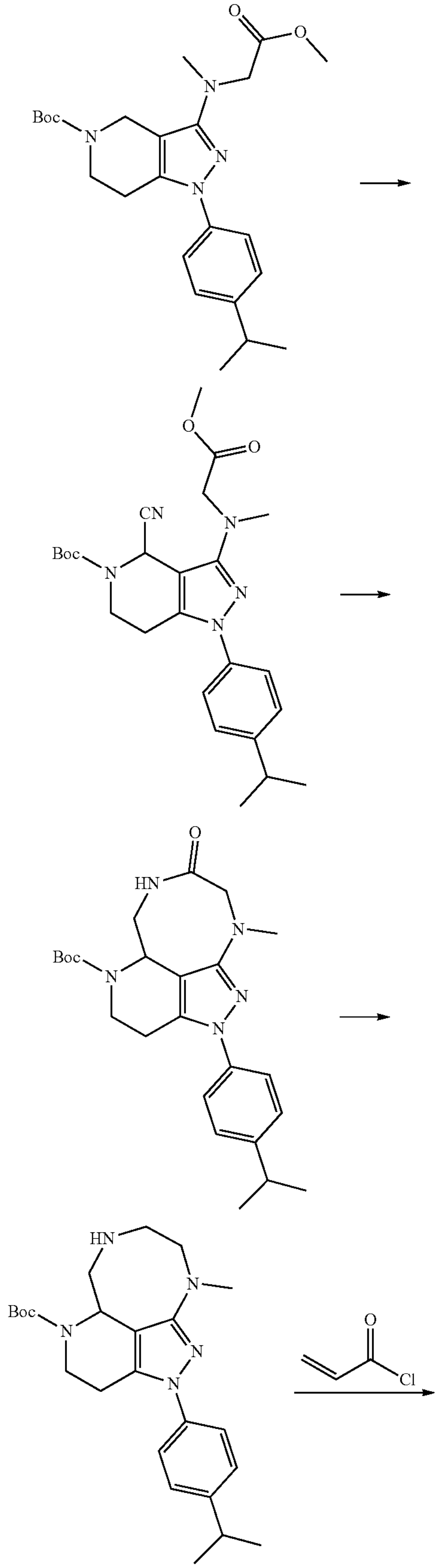

-continued

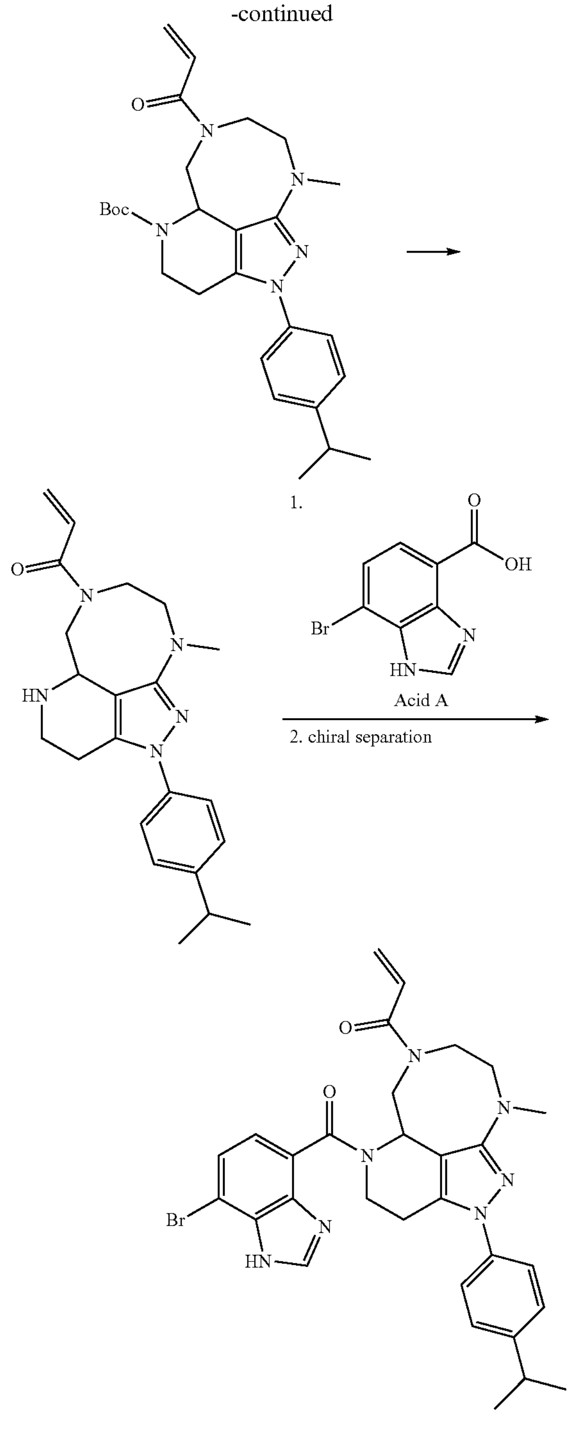

Step 1: Synthesis of Tert-Butyl 1-(4-isopropylphenyl)-3-[(2-methoxy-2-oxoethyl)amino]-4H,6H,7H-pyrazolo[4,3-c]pyridine-5-carboxylate A solution of tert-butyl 3-amino-1-(4-isopropylphenyl)-4H,6H,7H-pyrazolo[4,3-c]pyridine-5-carboxylate (Int. PP) (2 g, 6 mmol, 1 equiv) in EtOH (20 mL) was treated with methyl 2-oxoacetate (885 uL, 11.2 mmol, 2 equiv.) at 50° C. for 2 h then cooled to rt when $NaCNBH_3$ (705.16 mg, 11.222 mmol, 2 equiv) and AcOH (33.69 mg, 0.561 mmol, 0.1 equiv) were added in portions at rt under nitrogen atmosphere. The reaction was then stirred for 2 h, after which the reaction was quenched with water at rt and the resulting mixture was extracted with EtOAc (3×10 mL). The combined organic layers were washed with brine (2×20 mL) and dried over anhydrous $Na_2SO_4$. After filtration, the filtrate was concentrated und r reduced pressure. The residue was purified by silica gel column chromatography, eluting with PE:EA (5:1) to afford tert-butyl 1-(4-isopropylphenyl)-3-[(2-methoxy-2-oxoethyl)amino]-4H,6H,7H-pyrazolo[4,3-c]pyridine-5-carboxylate (900 mg) as a yellow oil. LCMS: (ESI, m/z): 429[M+H]$^+$.

Step 2: Synthesis of Tert-Butyl 1-(4-isopropylphenyl)-3-[(2-methoxy-2-oxoethyl)(methyl)amino]-4H,6H,7H-pyrazolo[4,3-c]pyridine-5-carboxylate A solution of tert-butyl 1-(4-isopropylphenyl)-3-[(2-me oxy-2-oxoethyl)amino]-4H,6H,7H-pyrazolo[4,3-c]pyridine-5-carboxylate (1 g, 2 mmol, 1 equiv) in MeOH (20 mL) was treated with formaldehyde (140.1 mg, 4.668 mmol, 2 equiv.) for 1 at rt under a nitrogen atmosphere. Pd/C (1 g, 10% wt %) was then added at rt, and the resulting mixture was stirred overnight at rt under a hydrogen balloon. The resulting mixture was filtered through Celite, and the filter cake was washed with MeOH (3×5 mL). The filtrate was concentrated under reduced pressure to provide a residue that was purified by silica gel column chromatography, PE:EA (5:1) to afford tert-butyl 1-(4-isopropylphenyl)-3-[(2-methoxy-2-oxoethyl)(ethyl)amino]-4H,6H,7H-pyrazolo[4,3-c]pyridine-5-carboxylate (616 mg) as a yellow oil. LCMS (ESI, m/z): 443 [M+H]$^+$.

Step 3: Synthesis of Tert-Butyl (rac)-4-cyano-1-(4-isopropylphenyl)-3-[(2-methoxy-2-oxoethyl)(methyl)amino]-4H,6H,7H-pyrazolo[4,3-c]pyridine-5-carboxylate A solution of tert-butyl 1-(4-isopropylphenyl)-3-[(2-methoxy-2-oxoethyl)(methyl)amino]-4H,6H,7H-pyrazolo[4,3-c]pyridine-5-carboxylate (410 mg, 0.93 mmol, 1 equiv) in DCM (10 mL) was treated with DDQ (420.6 mg, 1.852 mmol, 2 equiv) for 30 min at rt under a nitrogen atmosphere, followed by the addition of TMSCN (231.8 uL, 1.852 mmol, 2 equiv) dropwise at rt. The resulting mixture was stirred for 2 h at rt under a nitrogen atmosphere. The reaction was then quenched with water then the resulting mixture was filtered and the filter cake was washed with DCM (3×5 mL). The filtrate was concentrated under reduced pressure and the resulting mixture was extracted with EtOAc (3×5 mL). The combined organic layers were washed with saturated brine (2×10 mL), and dried over anhydrous $Na_2SO_4$. After filtration, the filtrate was concentrated under reduced pressure and purified by silica gel column chromatography, eluting with PE:EA (4:1) to afford tert-butyl (rac)-4-cyano-1-(4-isopropylphenyl)-3-[(2-methoxy-2-oxoethyl)(methyl)amino]-4H,6H,7H-pyrazolo[4,3-c]pyridine-5-carboxylate (290 mg) as a light yellow solid. LCMS(ESI, m/z): 468[M+H]$^+$.

Step 4: Synthesis of Tert-Butyl 2-(4-isopropylphenyl)-10-methyl-8-oxo-3,4,5a,6,7,8,9,10-octahydro-1,2,5,7,10-pentaazacycloocta[cd]indene-5(2H)-carboxylate To a solution of tert-butyl (rac)-4-cyano-1-(4-isopropylphenyl)-3-((2-methoxy-2-oxoethyl)(methyl)amino)-1,4,6,7-tetrahydro-5H-pyrazolo[4,3-c]pyridine-5-carboxylate (1.26 g, 1 equiv, 2.69 mmol) in $NH_3$/MeOH(30 mL, 7 mol/L) was added Raney Ni (1.26 g, 50% wt %) in a pressure tank. The mixture was purged with nitrogen×3 times and then pressurized to 4 MPa with hydrogen and heated to 50° C. for 2 h. The reaction mixture was then co led to rt and filtered. The filter cake was washed with MeOH (20 mL) two times. The filtrate was concentrated under reduced pressure and purified by silica gel column chromatography, eluting with EtOAc/PE (1:5) to afford tert-butyl 2-(4-isopropylphenyl)-10-methyl-8-oxo-3,4,5a,6,7,8,9,10-octahydro-1,2,5,7,10-pentaazacycloocta[cd]indene-5(2H)-carboxylate (920 mg) as a light yellow solid. LCMS:(ESI, m/z): 440[M+H]$^+$.

Step 5: Synthesis of Tert-Butyl (rac)-2-(4-isopropylphenyl)-10-methyl-3,4,5a,6,7,8,9,10-octahydro-1,2,5,7,10-pentaazacycloocta[cd]indene-5(2H)-carboxylate A solution of tert-butyl (rac)-2-(4-isopropylphenyl)-10-methyl-8-oxo-3,4,5a,6,7,8,9,10-octahydro-1,2,5,7,10-pentaazacycloocta[cd]indene-5(2H)-carboxylate 140 mg, 1 equiv, 319 mol) and $BH_3$-THF (54.7 mg, 2 equiv, 637 mol) in THF (2 mL) was stirred for 2 h at 60° C. The reaction was then quenched with water at rt. The resulting mixture was extracted with EtOAc (3×5 mL), and the combined organic layers were washed with brine (2×10 mL) and dried over anhydrous $Na_2SO_4$. After filtration, the filtrate was concentrated under reduced pressure and purified by reverse-phase flash chromatography with the following conditions: column, C18; mobile phase, water (0.05% $NH_4HCO_3$) in MeCN, 10% to 50% gradient: in 10 min; detector, UV 254 nm to provide tert-butyl (rac)-2-(4-isopropylphenyl)-10-methyl-3,4,5a,6,7,8,9,10-octahydro-1,2,5,7,10-pentaazacycloocta[cd]indene-5(2H)-carboxylate (44 mg) as a light yellow oil. LCMS:(ESI, m/z): 426[M+H]$^+$.

Step 6: Synthesis of Tert-Butyl (rac)-7-acryloyl-2-(4-isopropylphenyl)-10-methyl-3,4,5a,6,7,8,9,10-octahydro-1,2,5,7,10-pentaazacycloocta[cd]indene-5H)-carboxylate A solution of tert-butyl 2-(4-isopropylphenyl)-10-methyl-3,4,5a,6,7,8,9,10-octahydro-1,2,5,7,10-pentaazacycloocta[cd]indene-5(2H)-carboxylate (150 mg, 1 equiv, 352 µmol), TEA (107 mg, 3 equiv, 1.06 mmol), and acryloyl chloride (63.8 mg, 2 equiv, 705 µmol) in DCM (3 mL) was stirred for 1 h at room temperature. The resulting mixture was extracted with EtOAc (3×5 mL). The combined organic layers were washed with brine (2×10 m L), dried over anhydrous $Na_2SO_4$, and filtered. The filtrate was concentrated under reduced pressure, and the residue was purified by silica gel column chromatography, eluting with PE:EA (1:1) to afford tert-butyl (rac)-7-acryloyl-2-(4-isopropylphenyl)-10-methyl-3,4,5a,6,7,8,9,10-octahydro-1,2,5,7,10-pentaazacycloocta[cd]indene-5(2H)-carboxylate (69 mg) as a yellow solid. LCMS:(ESI, m/z): 480[M+H]$^+$.

Step 7: Synthesis of (rac)-1-(2-(4-isopropylphenyl)-10-methyl-2,4,5,5a,6,8,9,10-octahydro-1,2,5,7,10-pentaazacycloocta[cd]inden-7(3H)-yl)prop-2-en-1-one To a stirred solution of tert-butyl (rac)-7-acryloyl-2-(4-isopropylphenyl)-10-methyl-3,4,5a,6,7,8,9,10-octahydro-1,2,5,7,10-pentaazacycloocta[cd]indene-5(2H)-carboxylate (50 mg, 1 equiv, 0.1 mmol) in DCM (0.9 mL) was added TFA (0.3 mL) at room temperature and the reaction was stirred for 0.5 h. After 80% conversion was observed by LCMS, the solvent was removed under reduced pressure. This resulted in (rac)-1-(2-(4-isopropylphenyl)-10-methyl-2,4,5,5a,6,8,9,10-octahydro-1,2,5,7,10-pentaazacycloocta[cd]inden-7(3H)-yl)prop-2-en-1-one (50 mg) as a crude yellow oil. The crude product was used in the next step directly without further purification. LCMS:(ESI, m/z): 380 [M+H]$^+$.

Step 8: Synthesis of (R or S)-1-(5-(7-bromo-JH-benzo[d]imidazole-4-ca bonyl)-2-(4-isopropylphenyl)-10-methyl-2,4,5,5a,6,8,9,10-octahydro-1,2,5,7,10-pentaazacycloocta[cd]inden-7(3H)-yl)prop-2-en-1-one To a stirred solution of (rac)-1-(2-(4-isopropylphenyl)-10-methyl-2,4,5,5a,6,8,9,10-octahydro-1,2,5,7,10-pentaazacycloocta[cd]inden-7(3H)-yl)prop-2-en-1-one (40 mg, 1 equiv, 0.11 mmol) in DMF (0.5 mL) was added HOBT(28 mg, 29 µL, 2 equiv, 0.21 mmol) EDC (30 mg, 1.5 equiv, 0.16 mmol), DIEA (0.14 g, 0.18 mL, 10 equiv, 1.1 nmol), and 7-bromo-1H-benzo[d]imidazole-4-carboxylic acid (Acid A) (25 mg, 1 equiv, 0.11 mmol) at rt. The reaction was stirred for 2 h, and the resulting mixture was filtered and the filtrate was concentrated under reduced pressure. The crude product was purified by Prep-HPLC with the following conditions: (Column: CHIRAL ART Cellulose-SB 2*25 cm, 5 µm; Mobile Phase A: HEX(0.1FA), Mobile Phase B: EtOH: DCM=1:1; Flow rate: 20 mL/min; Gradient: isocratic 30; Wave Length: UV 254/220 nm retention time 1 retention time 2; Sample Solvent: EtOH; Injection Volume: 0.75 mL; Number Of Runs: 2) to afford (rac)-1-(5-(7-bromo-1H-benzo[d]imidazole-4-carbonyl)-2-(4-isopropylphenyl)-10-methyl-2,4,5,5a,6,8,9,10-octahydro-1,2,5,7,10-pentaazacycloocta[cd]inden-7(3H)-yl)prop-2-en-1-one (20 mg) as a white solid. The racemic compound was then separated into its constitutive enantiomers by chiral HPLC separation: (Column: HIRAL ART Cellulose-SB, 2*25 cm, 5 µm; Mobile Phase A: Hex(0.1% FA-), Mobile Phase B: EtOH: DCM=1:1-HPLC; Flow rate: 20 mL/min; Gradient: 30% B to 30% B in 14 min; Wave Length: UV 254/220 nm; retention time 1: 8.8; retention time 2: 11.5; Sample Solvent: MeOH; Injection Volume: 2 mL; Number Of Runs: 2) to afford (R or S)-1-(5-(7-bromo-1H-benzo[d]imidazole-4-carbonyl)-2-(4-isopropylphenyl)-10-methyl-2,4,5,5a,6,8,9,10-octahydro-1,2,5,7,10-pentaazacycloocta[cd]inden-7(3H)-yl) prop-2-en-1-one as the first-eluting peak (retention time=8.8 min, 3.2 mg, 5.3 µmol, 5% yield) as a white solid. LCMS: (ESI, m/z): 602, 604[M+H]$^+$. $^1$H NMR: 00 MHz, Chloroform-d) δ 8.24 (d, J=19.8 Hz, 1H), 7.52 (d, J=7.8 Hz, 1H), 7.28 (s, 1H), 7.26-7.20 (m, 3H), 6.55 (dd, J=16.8, 10.7 Hz, 11H), 6.19 (s, 1H), 6.02 (d, J=16.9 Hz, 1H), 5.63 (d, J=10.0 Hz, 1H), 4.44 (brs, 1H), 4.12 (brs, 2H), 3.93 (brs, 1H), 3.81-3.63 (m, 2H), 3.35 (d, J=13.2 Hz, 2H), 3.2-2.93 (m, 6H), 2.88 (d, J=6.8 Hz, 1H), 1.24 (t, J=7.1 Hz, 6H).

TABLE K1

The compound of Example K-19 was prepared in an analogous fashion to Example C-19, except that the CBz protected version of Int. GG (Example K-3) was used in place of Int. S". The final racemic compound was separated into its constituent enantiomers by chiral HPLC: Column-CHIRAL ART Cellulose-SB, 3*25 cm, 5 µm; Mobile Phase A: Hex(0.1% FA)—HPLC, Mobile Phase B: EtOH: DCM = 1:1; Flow rate: 40 mL/min; Gradient: isocratic 35; Wave Length: UV 254/220 nm; RT1(min): 7.5; RT2(min): 10.2; to provide the compound of the example as the first-eluting peak. The compound of Example K-20 was prepared in a manner analogous to Examples K-2 and K-3, using 6-chloro-3-isopropyl-2-methoxypyridine in place of 1-bromo-4-iodobenzene in Example K-2. The methyl group was removed from the pyridine using sodiumethanethiolate after the analogous step 11 in Example K-3. The final racemic compound was separated into its constituent enantiomers by chiral HPLC: Column-CHIRALPAK IA, 2*25 cm, 5 µm; Mobile Phase A: Hex(0.1% FA)—HPLC, Mobile Phase B: EtOH: DCM = 1:1; Flow rate: 20 mL/min; Gradient: isocratic 30; Wave Length: UV 254/220 nm; RT1(min): 7.6; RT2(min): 13.3; to afford the compound of the example as the first-eluting enantiomer.

| Example No. | Structure and Name | LCMS (ESI, m/z) | NMR |
|---|---|---|---|
| K-19 | 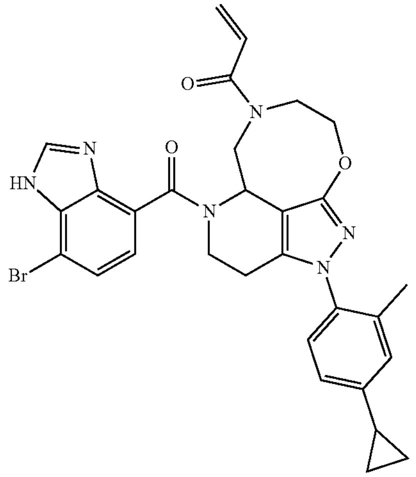 [SMILES: C=CC(=O)N1CCOc2nn(-c3ccc(C4CC4)cc3C)c3c2C(C1)N(C(=O)c1ccc(Br)c2[nH]cnc12)CC3] (S or R)-1-(5-(7-bromo-1H-benzo[d]imidazole-4-carbonyl)-2-(4-cyclopropyl-2-methylphenyl)- | 601 [M + H]$^+$ | $^1$H NMR (400 MHz, Chloroform-d, ppm) δ 8.43 (d, J = 17.2 Hz, 1H), 7.59 – 7.48 (m, 1H), 7.24 – 7.18 (m, 1H), 7.12 (d, J = 8.0 Hz, 1H), 7.06 – 6.99 (m, 1H), 6.97 – 6.85 (m, 1H), 6.65 – 6.40 (m, 1H), 6.27 – 6.04 (m, 1H), 5.85 – 5.66 (m, 1H), 5.59 – 4.77 (m, 1H), 4.61 –3.84 (m, 5H), 3.66 – 3.33 (m, 2H), 3.21 – 3.07 (m, 1H), 2.84 – 2.58 (m, 1H), 2.47 – 2.23 (m, 1H), 2.12 – 1.98 (m, 3H), 1.94 – 1.83 (m, 1H), 1.05 – 0.93 (m, 2H), 0.74 – 0.65 (m, 2H). |

TABLE K1-continued

| | | | |
|---|---|---|---|
| | 2,3,4,5,5a,6,8,9-octahydro-7H-10-oxa-1,2,5,7-tetraazacycloocta[cd]inden-7-yl)prop-2-en-1-one | | |
| K-20 | 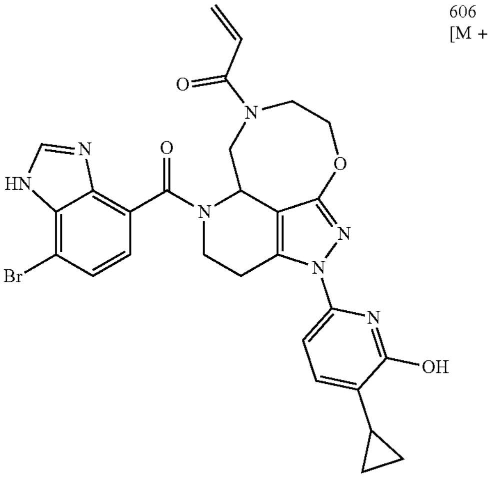 (S or R)-1-(5-(7-bromo-1H-benzo[d]imidazole-4-carbonyl)-2-(6-hydroxy-5-isopropylpyridin-2-yl)-2,3,4,5,5a,6,8,9-octahydro-7/-10-oxa-1,2,5,7-tetraazacycloocta[cd]inden-7-yl)prop-2-en-1-one | 606 [M + H]+ | $^1$H NMR (400 MHz, DMSO-$d_6$, ppm) δ 8.40 (d, J = 7.6 Hz, 1H), 7.69 - 7.47 (m, 2H), 7.39 - 6.74 (m, 3H), 6.42 - 5.91 (m, 1H), 5.91 - 5.54 (m, 1H), 5.51 - 5.03 (m, 1H), 5.03 - 4.03 (m, 3H), 4.02 - 3.86 (m, 1H), 3.84 - 3.41 (m, 3H), 3.03 (p, J = 7.2 Hz, 2H), 1.24 - 1.07 (m, 6H) (some protons obscured by solvent). |

Example L-1: Preparation of (R or S)-1-(5-(4-amino-6-(trifluoromethyl)nicotinoyl)-2-(4-cyclopropyl-3-fluoro-2-hydroxyphenyl)-2,3,4,5,5a,6,8,9-octahydro-7-1,2,5,7-tetraazabenzo [cd]azulen-7-yl)prop-2-en-1-one

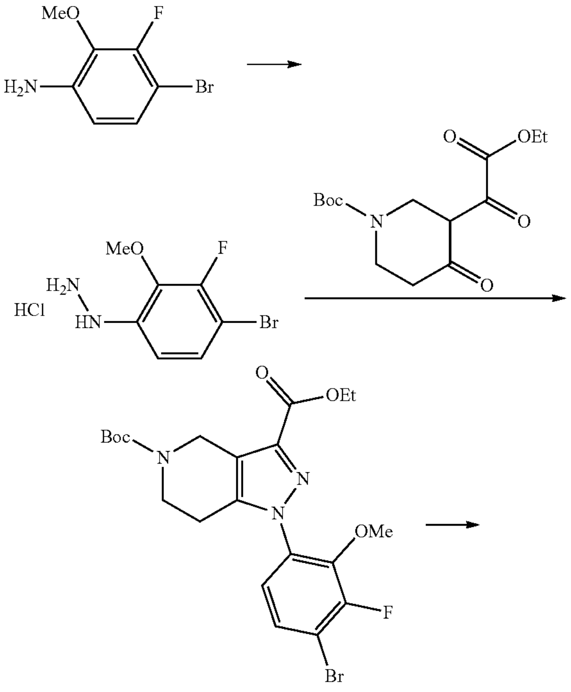

-continued

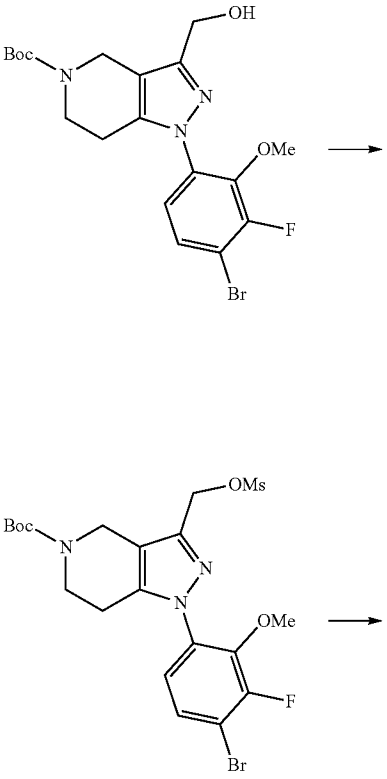

-continued
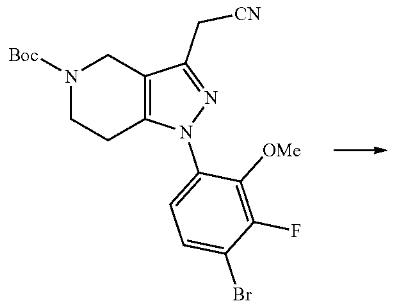
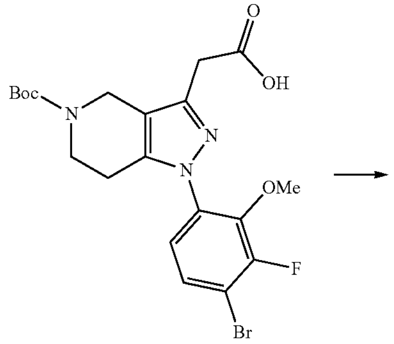
Int. L-A
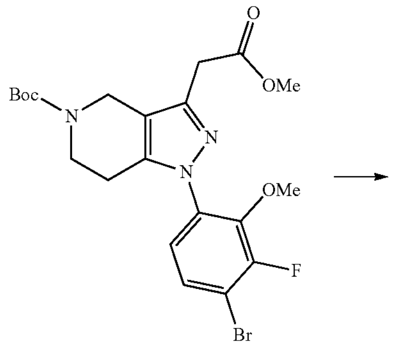
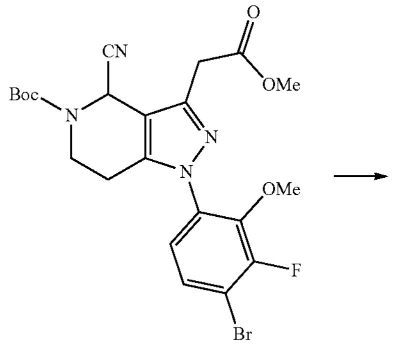
-continued
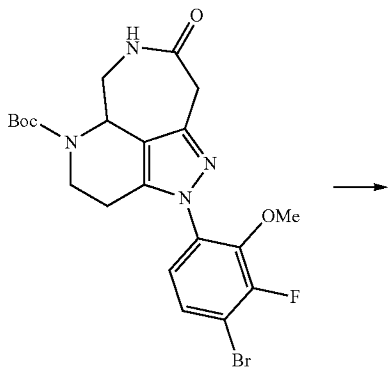
Int. L-B
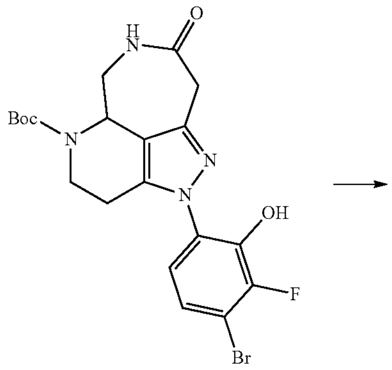
Int. L-C
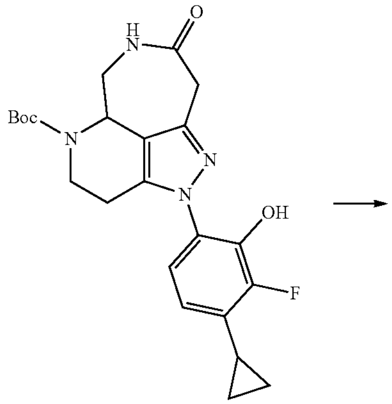
Int. L-E
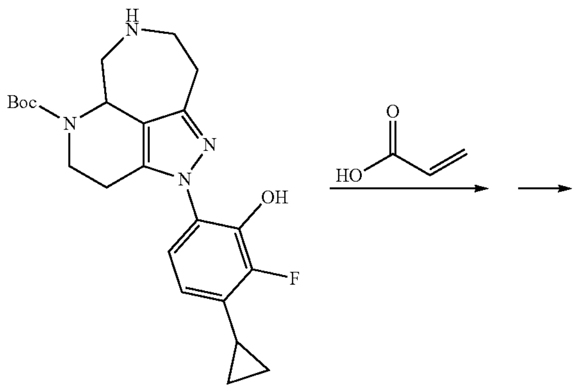

-continued

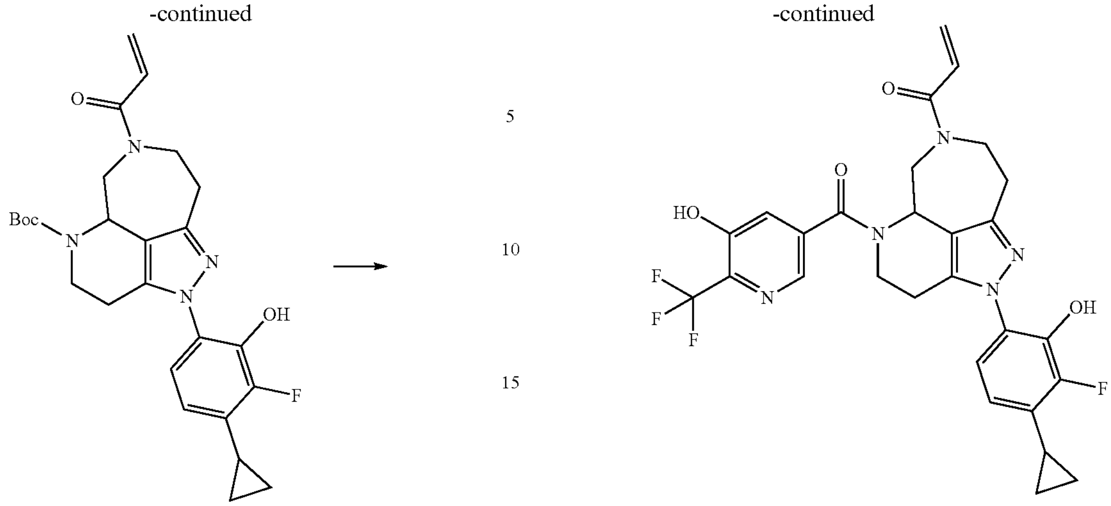

-continued

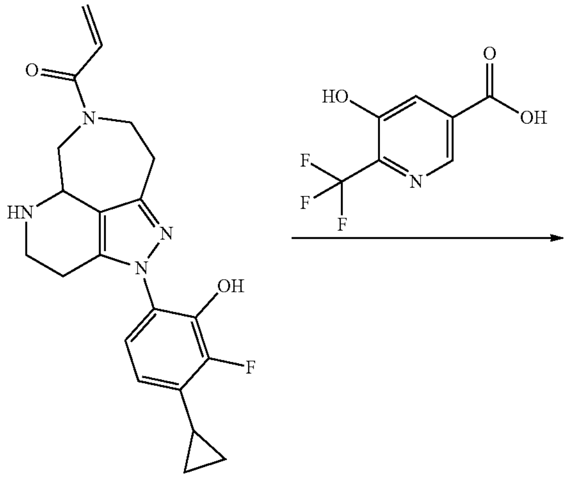

Int. L-D

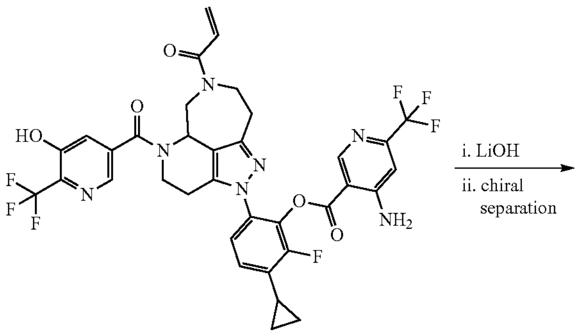

Step 1: Synthesis of (4-bromo-3-fluoro-2-methoxyphenyl)hydrazine Hydochloride

To a solution of 4-bromo-3-fluoro-2-methoxyaniline in water 600 mL) was added HCl (12 M, 454 mL, 12.0 eq) at 5° C. in 3 portions, and then $NaNO_2$ (32.9 g, 477 mmol, 1.05 eq) in $H_2O$ (300 mL) was added dropwise at 0° C. After addition, the mixture was stirred at this temperature for 1 h, after which $SnCl_2 \cdot 2H_2O$ (215 g, 954 mmol, 2.10 eq) in HCl (12 M, 227 mL, 6.00 eq) was added dropwise at −5~0° C. Additional water (800 mL) as added to dissolve the solid formed, and the resulting mixture was stirred at 0° C. for 1 h. The reaction mixture was filtered at 0° C., and the filter cake was collected. The filter cake was diluted with 10.0 L water, and extracted with 20 L EtOAc (10 L×2). The combined organic layers were dried over $Na_2SO_4$, filtered and concentrated under reduced pressure to give a residue. The crude product (1.2 kg) was used into the next step directly without further purification. LCMS: (ESI, m/z): 235 $[M+H]^+$.

Step 2: Synthesis of S-(tert-butyl) 3-ethyl 1-(4-bromo-3-fluoro-2-methoxyphenyl)-1,4,6,7-tetrahydro-5H-pyrazolo[4,3-c]pyridine-3,5-dicarboxylate To a solution of tert-butyl 3-(2-ethoxy-2-oxoacetyl)-4-oxopiperidine-1-carboxylate (1.50 kg, 5.01 mol, 1.00 eq) in THF (17.0 L) was added (4-bromo-3-fluoro-2-methoxyphenyl) hydrazine (1.20 kg, 4.42 mol, 0.882 equiv., HCl salt) at −5~0° C. The mixture was stirred at rt for 16 h. The reaction mixture was then diluted with 16.0 L DCM and filtered. The filtrate was collected and concentrated under reduced pressure to give a residue. The residue was purified by column chromatography ($SiO_2$, Petroleum ether/Ethyl acetate=3/1) to afford 5-(tert-butyl) 3-ethyl 1-(4-bromo-3-fluoro-2-methoxyphenyl)-1,4,6,7-tetrahydro-5H-pyrazolo [4,3-c]pyridine-3,5-dicarboxylate (1.30 kg) as a red oil. LCMS: (ESI, m/z): 500 $[M+H]^+$.

Step 3: Synthesis of Tert-Butyl 1-(4-bromo-3-fluoro-2-methoxyphenyl)-3-(hydroxymethyl)-1,4,6,7-tetrahydro-5H-pyrazolo[4,3-c]pyridine-5-carboxylate This reaction was performed in four parallel batches. To a solution of 5-(tert-butyl) 3-ethyl 1-(4-bromo-3-fluoro-2- methoxyphenyl)-1,4,6,7-tetrahydro-5H-pyrazolo[4,3-c]pyridine-3,5-dicarboxylate (250 g, 501 mmol, 1.00 eq) in THF (1.25 L), was added DIBAL-H (1 M, 1.66 L, 3.30 eq) drop-wise into the reaction at −5~0° C. under an atmosphere f nitrogen. The mixture was stirred at 20° C. for 0.5 h. The four parallel reaction mixtures were then quenched by the addition of a saturated solution of potassium sodium tartrate (20.0 L) at 0° C., warmed to rt, and then extracted with EtOAc (10.0 L×2). The combined organic layers were washed with brine (10.0 L), dried over $Na_2SO_4$, filtered and concentrated under reduced pressure to give a residue. The residue was purified by column chromatography ($SiO_2$, Petroleum ether/Ethyl acetate=1/1) to afford tert-butyl 1-(4-bromo-3-fluoro-2-methoxyphenyl)-3-hydroxymethyl)-1,4,6,7-tetrahydro-5H-pyrazolo[4,3-c]pyridine-5-carboxylate (350 g) as a brown oil. LCMS: (ESI, m/z): 456 $[M+H]^+$.

Step 4: Synthesis of Tert-Butyl 1-(4-bromo-3-fluoro-2-methoxyphenyl)-3-(((methylsulfonyl)oxy)methyl)-1,4,6,7-tetrahydro-5H-pyrazolo[4,3-c]pyridine-5-carboxylate To a solution of tert-butyl 1-(4-bromo-3-fluoro-2-methoxyphenyl)-3-(hydroxymethyl)-1,4,6,7-tetrahydro-5H-pyrazolo[4,3-c]pyridine-5-carboxylate (350 g, 767 mmol, 1.00 eq) in THF (1.80 L) was added TEA (194 g, 1.92 mol, 266 mL, 2.50 eq) at rt and M 20 (200 g, 1.15 mol, 1.50 eq) in THF (1.00 L) was added dropwise at 0° C. for 1 h. The mixture was stirred at rt for 0.5 h, after which the reaction mixture was quenched by addition of water (10.0 L) at 0° C., warmed to rt, and then diluted with 4 L EtOAc and extracted with 4 L EtOAc (2.00 L*2). The combined organic layers were washed with brine (5 L), and the combined organic layers were dried over $Na_2SO_4$, filtered and concentrated under reduced pressure to afford tert-butyl 1-(4-bromo-3-fluoro-2-methoxyphenyl)-3-(((methylsulfonyl)oxy)methyl)-1,4,6,7-tetrahydro-3H-pyrazolo[4,3-c]pyridine-5-carboxylate (410 g) as a brown oil which was used into the next step directly without further purification. LCMS: (ESI, m/z): 534 $[M+H]^+$.

Step 5: Synthesis of Tert-Butyl 1-(4-bromo-3-fluoro-2-methoxyphenyl)-3-(cyanomethyl)-1,4,6,7-tetrahydro-5H-pyrazolo[4,3-c]pyridine-5-carboxylate To the solution of tert-butyl 1-(4-bromo-3-fluoro-2-methoxyphenyl)-3-(((methylsulfonyl)oxy)methyl)-1,4,6,7-tetrahydro-5H-pyrazolo[4,3-c]pyridine-5-carboxylate (410 g, 767 mmol, 1.00 eq) in THF (2.00 L) was added TMSCN (114 g, 1.15 mol, 143 mL, 1.50 eq) at rt, and TBAF (1 M, 1.15 L, 1.50 eq) was added at 0° C. The mix re was stirred at rt for 3 h, after which the reaction mixture was quenched by addition water (9 L) at 0° C., warmed to rt, and then diluted with 4 L EtOAc and extracted with 4 L EtOAc (2 L*2). The combined organic layers were washed with brine (2.00 L), dried over $Na_2SO_4$, filtered and concentrated under reduced pressure to afford tert-butyl 1-(4-bromo-3-fluoro-2-methoxyphenyl)-3-(cyanomethyl)-1,4,6,7-tetrahydro-5H-pyrazolo[4,3-c]pyridine-5-carboxylate (360 g) as a black-brown oil which was used into the next step directly without further purification. LCMS: (ESI, m/z): 467 $[M+H]^+$.

Step 6: Synthesis of 2-(1-(4-bromo-3-fluoro-2-methoxyphenyl)-5-(tert-butoxycarbonyl)-4,5,6,7-tetrahydro-1H-pyrazolo[4,3-c]pyridin-3-yl)acetic Acid (Int. L-A)

To the solution of tert-butyl 1-(4-bromo-3-fluoro-2-methoxyphenyl)-3-(cyanomethyl)-1,4,6,7-tetrahydro-5H-pyrazolo[4,3-c]pyridine-5-carboxylate (360 g, 773 mmol, 1.00 eq) in 1,4-dioxane (1.80 L) was added NaOH (4 M, 3.60 L, 18.6 eq) at rt. The mixture was stirred at 110° C. for 24 h, after which the reaction mixture was quenched by addition water (9 L) at 0° C., warmed to rt, and then diluted with 2 L EtOAc and extracted with 2 L EtOAc (1 L*2). The combined organic layers were washed with brine (3 L), dried over $Na_2SO_4$, filtered and concentrated under reduced pressure to afford 2-(1-(4-bromo-3-fluoro-2-methoxyphenyl)-5-(tert-butoxycarbonyl)-4,5,6,7-tetrahydro-1H-pyrazolo[4,3-c]pyridin-3-yl)acetic acid (368 g) a, a black-brown oil which was used into the next step directly without further purification. LCMS: (ESI, m/z): 484 $[M+H]^+$.

Step 7: Synthesis of Tert-Butyl 1-(4-bromo-3-fluoro-2-methoxyphenyl)-3-(2-methoxy-2-oxoethyl)-1,4,6,7-tetrahydro-5H-pyrazolo[4,3-c]pyridine-5-carboxylate To a solution of 2-(1-(4-bromo-3-fluoro-2-methoxyphenyl)-5-(tert-butoxycarbonyl)-4,5,6,7-tetrahydro-1H-pyrazolo[4,3-c]pyridin-3-yl)acetic acid (368 g, 759 mmol, 1.00 eq) in DMF (3.70 L) was added $K_2CO_3$ (210 g, 1.52 mol, 2.00 eq). Then $CH_3I$ (215 g, 1.52 mol, 94.6 mL, 2.00 eq) was added dropwise at 0~10° C. The resulting mixture was stirred at rt for 2 h, after which the reaction mixture was quenched by addition $H_2O$ (10 L) at 0° C., warmed to rt, and then diluted with 4 L EtOAc and extracted with 4 L EtOAc (2 L×2). The combined organic layers were washed with brine (8 L), dried over $Na_2SO_4$, filtered and concentrated under reduced pressure to afford tert-butyl 1-(4-bromo-3-fluoro-2-methoxyphenyl)-3-(2-methoxy-2-oxoethyl)-1,4,6,7-tetrahydro-5H-pyrazolo[4,3-c]pyridine-5-carboxylate (376 g) as a black-brown oil which was used into the next step directly without further purification. LCMS: (ESI, m/2): 500 $[M+H]^+$.

Step 8: Synthesis of Tert-Butyl 1-(4-bromo-3-fluoro-2-methoxyphenyl)-4-cyano-3-(2-methoxy-2-oxoethyl)-1,4,6,7-tetrahydro-5H-pyrazolo[4,3-c]pyridine-5-carboxylate To a solution of $CoCl_2 \cdot 6H_2O$ (53.7 g, 225 mmol, 1.01 eq) in MeOH (600 mL) was added dropwise tert-butyl 1-(4-bromo-3-fluoro-2-methoxyphenyl)-3-(2-methoxy-2-oxoethyl)-1,4,6,7-tetrahydro-5H-pyrazolo[4,3-c]pyridine-5-carboxylate (117 g, 223 mmol, 1.00 eq) in MeOH (1.30 L) at −15~0° C., and then $NaBH_4$ (42.6 g, 1.13 mol, 5.04 eq) was added in portions at −20° C. The resulting mixture was stirred at −20° C. for 2 h, after which the reaction mixture was quenched at 0~10° C. with 6 L $H_2O$. After the addition, the resulting mixture was allowed to warm to rt, filtered and the filtrate was extracted with 4 L EtOAc (2 L×2). The combined organic layers were washed with 2 L $NaHCO_3$(aq, sat.), and 2 L brine, dried over $Na_2SO_4$, filtered and concentrated under reduced pressure to give a residue. The crude product was purified by reversed-phase HPLC (column: Phenomenex luna c18 250 mm*100 mm*10 um; mobile phase: [water (TFA)-ACN]; gradient: 38%-68% B over 23 min) to afford tert-butyl 1-(4-bromo-3-fluoro-2-methoxyphenyl)-4-cyano-3-(2-methoxy-2-oxoethyl)-1,4,6,7-tetrahydro-5H-pyrazolo[4,3-c]pyridine-5-carboxylate (30.0 g) as an off-white solid. LCMS: (ESI, m/z): 529 $[M+H]^+$.

Step 9: Synthesis of Tert-Butyl 2-(4-bromo-3-fluoro-2-methoxyphenyl)-8-oxo-2,3,4,5a,6,7,8,9-octahydro-5H-1,2,5,7-tetraazabenzo[cd]azulene-5-carboxylate (Int. L-B)

To a solution of tert-butyl 1-(4-bromo-3-fluoro-2-methoxyphenyl)-4-cyano-3-(2-methoxy-2-oxoethyl)-1,4,6, 7-tetrahydro-5H-pyrazolo[4,3-c]pyridine-5-carboxylate (30.0 g, 56.8 mmol, 1.00 eq) in MeOH (1.50 L) was added $Na_2CO_3$ (18.0 g, 170 mmol, 3.00 eq). The mixture was stirred at 60° C. for 3 h, after which the reaction mixture was filtered and the filtrate was diluted with 500 mL $H_2O$ and extracted with 300 mL EtOAc (150 mL×2). The combined organic layers were washed with 100 mL brine, dried over $Na_2SO_4$, filtered and concentrated under reduced pressure to give a residue. The crude product was purified by revers d-phase HPLC (column: Phenomenex luna C18 (250*70 mm, 10 um); mobile phase: [water(T A)-ACN]; gradient: 34%-64% B over 5 min) to afford tert-butyl 2-(4-bromo-3-fluoro-2-methoxyphenyl)-8-oxo-2,3,4,5a,6,7,8,9-octahydro-5H-1,2,5,7-tetraazabenzo[cd]azulene-5-carboxylate (19.5 g) was as a yellow solid. LCMS: (ESI, m/z): 495 $[M+H]^+$.

Step 10: Synthesis of Tert-Butyl 2-(4-bromo-3-fluoro-2-hydroxyphenyl)-8-oxo-2,3,4,5a,6,7,8,9-octahydro-5H-1,2,5,7-tetraazabenzo[cd]azulene-5-carboxylate (Int. L-C)

To a solution of tert-butyl 2-(4-bromo-3-fluoro-2-methoxyphenyl)-8-oxo-2,3,4,5a,6,7,8,9-octahydro-5H-1,2,5,7-tetraazabenzo[cd]azulene-5-carboxylate (1.05 g, 1 equiv., 2.12 mmol) in DCE at 0° C. (10 mL) was added $BBr_3$ (2.66 g, 10.6 mL, 1 molar, 5 equiv., 10.6 mmol). The mixture was stirred at 0° C. for 2 h, after which the mixture was poured into a solution of TEA (4.29 g, 5.91 mL, 20 equiv., 42.4 mmol) in MeOH (20 mL). Then $Boc_2O$ (1.39 g, 1.46 mL, 3 equiv., 6.36 mmol) was added and the mixture was stirred at 20° C. for 2 h, after which the reaction mixture was concentrated to afford a residue. The residue was purified by flash column chromatography, eluting with MeOH/DCM (1:10) to afford tert-butyl 2-(4-bromo-3-fluoro-2-hydroxyphenyl)-8-oxo-2,3,4,5a,6,7,8,9-octahydro-5H-1,2,5,7-tetraazabenzo[cd]azulene-5-carboxylate (750 mg) as a colorless oil. LCMS: (ESI, m/z): 481 $[M+H]^+$.

Step 11: Synthesis of Tert-Butyl 2-(4-cyclopropyl-3-fluoro-2-hydroxyphenyl)-8-oxo-2,3,4,5a,6,7,8,9-octahydro-5H-1,2,5,7-tetraazabenzo[cd]azulene-5-carboxylate (Int. L-E)

To a solution of tert-butyl 2-(4-bromo-3-fluoro-2-hydroxyphenyl)-8-oxo-2,3,4,5a,6,7,8,9-octahydro-5H-1,2,5,7-tetraazabenzo[cd]azulene-5-carboxylate (710 mg, 1 equiv., 1.48 mmol) in 1,4-dioxane (10 mL) were added $K_3PO_4$ (939 mg, 3 equiv., 4.43 mmol), cyclopropylboronic acid (380 mg, 3 equiv., 4.43 mmol) and $Pd(dppf)Cl_2 \cdot DCM$ (120 mg, 0.1 equiv., 148 mol). The reaction system was evacuated and backfilled with nitrogen (×3). The resulting mixture was stirred for 4 h at 90° C. under a nitrogen atmosphere. The mixture was then diluted with ice water (20 mL) and EA (20 mL), and the aqueous layer was extracted with EA (2×20 mL). The combined organic layers were washed with saturated brine (2×20 mL), dried over anhydrous sodium sulfate and concentrated to give a residue. The residue was purified by flash column chromatography, eluting with EA/PE (1:5) to afford tert-butyl 2-(4-cyclopropyl-3-fluoro-2-hydroxyphenyl)-8-oxo-2,3,4,5a,6,7,8,9-octahydro-5H-1,2,5,7-tetraazabenzo[cd]azulene-5-carboxylate (630 mg) as a yellow solid. LCMS: (ESI, m/z): 443 $[M+H]^+$.

Step 12: Synthesis of Tert-Butyl 2-(4-cyclopropyl-3-fluoro-2-hydroxyphenyl)-2,3,4,5a,6,7,8,9-octahydro-5H-1,2,5,7-tetraazabenzo[cd]azulene-5-carboxylate To a solution of tert-butyl 2-(4-cyclopropyl-3-fluoro-2-hydroxyphenyl)-8-oxo-2,3,4,5a,6,7,8,9-octahydro-5H-1,2,5,7-tetraazabenzo[cd]azulene-5-carboxylate (600 mg, 1 equiv., 1.36 mmol) in toluene (10 mL) was added nickel chloride (59.6 mg, 0.2 equiv., 271 μmol) and phenylsilane (587 mg, 672 μL, 4 equiv., 5.42 mmol). The mixture was heated to 110° C. and stirred for 2 h. The mixture was then diluted with ice water (10 mL) and DCM (10 mL), and the aqueous layer was extracted with DCM (2×10 mL). The combined organic layers were washed with saturated brine (2×10 mL), dried over anhydrous sodium sulfate and concentrated to give a residue. The residue was purified by reverse phase chromatography (column: C18 column; Gradient: MeCN in water with 0.2% $NH_4HCO_3$) to afford tert-butyl 2-(4-cyclopropyl-3-fluoro-2-hydroxyphenyl)-2,3,4,5a,6,7,8,9-octahydro-5H-1,2,5,7-tetraazabenzo[cd]azulene-5-carboxylate (507 mg) as a dark green oil. LCMS: (ESI, m/z): 429 $[M+H]^+$.

Step 13: Synthesis of Afford Tert-Butyl 7-acryloyl-2-(4-cyclopropyl-3-fluoro-2-hydroxyphenyl)-2,3,4,5a,6,7,8,9-octahydro-5H-1,2,5,7-tetraazabenzo[cd]azulene-5-carboxylate To a solution of tert-butyl 2-(4-cyclopropyl-3-fluoro-2-hydroxyphenyl)-2,3,4,5a,6,7,8,9-octahydro-5H-1,2,5,7-tetraazabenzo[cd]azulene-5-carboxylate (490 mg, 1 equiv., 1.14 mmol) in DMF (5 mL) was added DIEA (443 mg, 598 μL, 3 equiv., 3.43 mmol), acrylic acid (98.9 mg, 94.1 μL, 1.2 equiv., 1.37 mmol) and propylphosphonic anhydride (546 mg, 505 μL, 1.5 equiv., 1.72 mmol). The mixture was stirred for 2 h at 20° C. The mixture was then diluted with water (20 mL) and EA (20 mL), and the aqueous layer was extracted with EA (2×20 mL). The combined organic layers were washed with saturated brine (20 mL), dried over anhydrous sodium sulfate and concentrated to give a residue. The residue was purified by silica gel chromatography (Gradient: 0-20% MeOH in DCM) to afford tert-butyl 7-acryloyl-2-(4-cyclopropyl-3-fluoro-2-hydroxyphenyl)-2,3,4,5a,6,7,8,9-octahydro-5H-1,2,5,7-tetraazabenzo[cd]azulene-5-carboxylate (150 mg) as a colorless oil. LCMS: (ESI, m/z): 483 $[M+H]^+$.

Step 14: Synthesis of 1-(2-(4-cyclopropyl-3-fluoro-2-hydroxyphenyl)-2,3,4,5,5a,6,8,9-octahydro-7H-1,2,5,7-tetraazabenzo[cd]azulen-7-yl)prop-2-en-1-one (Int. L-D)

A solution of tert-butyl 7-acryloyl-2-(4-cyclopropyl-3-fluoro-2-hydroxyphenyl)-2,3,4,5a,6,7,8,9-octahydro-5H-1,2,5,7-tetraazabenzo[cd]azulene-5-carboxylate (110 mg, 1 equiv., 228 μmol) in TFA (0.5 mL) and DCM (1.5 mL) was stirred at 20° C. for h. The solvent was then removed under reduced pressure to afford 1-(2-(4-cyclopropyl-3-fluoro-2-hydroxyphenyl)-2,3,4,5,5a,6,8,9-octahydro-7H-1,2,5,7-tetraazabenzo[cd]azulen-7-yl)prop-2-en-1-one (87.2 mg) as a crude yellow oil which was used in the next step directly without fu her purification. LCMS: (ESI, m/z): 383 $[M+H]^+$.

Step 15: (R or S)-1-(2-(4-cyclopropyl-3-fluoro-2-hydroxyphenyl)-5-(5-hydroxy-6-(trifluoromethyl)nicotinoyl)-2,3,4,5,5a,6,8,9-octahydro-7H-1,2,5,7-tetraazabenzo[cd]azulen-7-yl)prop-2-en-1-one To a solution of 1-(2-(4-cyclopropyl-3-fluoro-2-hydroxyphenyl)-2,3,4,5,5a,6,8,9-octahydro-7H-1,2,5,7-tetraazabenzo[cd]azulen-7-yl)prop-2-en-1-one (87.2 mg, 1 equiv., 228 μmol) in DMF (1 mL) were added 5-hydroxy-6-(trifluoromethyl)nicotinic acid (118 mg, 2.5 equiv., 570 μmol), DIEA (177 mg, 238 μL, 6 equiv., 1.37 mmol) and HBTU (216 mg, 2.5 equiv., 570 μmol). The resulting mixture was stirred at 20° C. for 1 h, after which the mixture was diluted with water (5 mL) and EA (5 mL), and the aqueous layer was extracted with EA (2×25 mL). The combined organic layers were washed with saturated brine (5 mL), dried over anhydrous sodium sulfate and concentrated to give a residue. The residue was purified by Prep-HPLC (Column: Sunfire C18 5 m, 30 mm*150 mm; Mobile Phase A: Water (0.05% FA), Mobile Phase B: ACN; Flow rate: 60 mL/min; Gradient: 35% B to 55% B in 10 min) to afford the racemic final compound (8 mg, 6%) as a white solid. The mixture was purified by Prep-CHIRAL-HPLC (Column: CHIRAL ART Cellulose-SB, 3*25 cm, 5 μm; Mobile Phase A: Hex(0.1%

FA)—HPLC, Mobile Phase B: IPA:DCM=1:1; Flow rate: 40 mL/min; Gradient: isocratic 35; Wave Length: UV 254/220 nm; RT1(min): 6.6; RT2(min): 10.0) to afford (R or S)-1-(2-(4-cyclopropyl-3-fluoro-2-hydroxyphenyl)-5-(5-hydroxy-6-(trifluoromethyl)nicotinoyl)-2,3,4,5,5a,6,8,9-octahydro-7H-1,2,5,7-tetraazabenzo[cd]azulen-7-yl)prop-2-en-1-one (3.0 mg) as the first-eluting peak as a white solid. LCMS: (ESI, m/z): 572 $[M+H]^+$. $^1H$ NMR: (400 MHz, Chloroform-d, ppm) δ 8.66 (s, 1H), 8.50 (s, 1H), 8.42-8.22 (m, 1H), 6.88-6.60 (m, 2H), 6.60-6.30 (m, 2H), 6.04-5.79 (m, 1H), 5.18 (d, J=12.7 Hz, 1H), 4.90 (d, J=12.7 Hz, 1H), 4.71-4.64 (m, 1H), 4.35 (d, J=14.8 Hz, 1H), 3.27-2.62 (m, 7H), 2.15-2.08 (m, 1H), 1.03 (d, J=8.0 Hz, 2H), 0.75 (s, 2H).

TABLE L1

The compound of Example L-1-1 was prepared from Int. L-D using the corresponding acid. The final racemic compound was purified by the following conditions: CHIRAL ART Cellulose-SB, 2*25 cm, 5 μm; Mobile Phase A: MtBE(0.1% FA)—HPLC, Mobile Phase B: EtOH; Flow rate: 20 mL/min; Gradient: isocratic 10; Wave Length: 220/254 nm; RT1(min): 5.5; RT2(min): 8.5 and the compound of the example is the second-eluting peak. The compound of Example L-1-2 was prepared from Int. L-D in a manner analogous to Example L-1, using the corresponding acid. The final racemic compound was purified by the following conditions: Column: CHIRAL ART Cellulose-SC, 3*25 cm, 5 μm; Mobile Phase A: MtBE(0.1% FA)—HPLC, Mobile Phase B: ETOH; Flow rate: 40 mL/min; Gradient: isocratic 10; Wave Length: 210/252 nm; RT1(min): 7.6; RT2(min): 17 to provide the compound of the example as the second-eluting peak. The compound of Example L-1-3 was prepared from Int. L-D in a manner analogous to Example L-1, using the corresponding acid. The final racemic compound was purified by the following conditions: REGIS (R,R) WHELK-O1 (250 mm × 25 mm, 10 um); mobile phase: [$CO_2$-ACN/EtOH(0.1% $NH_3H_2O$)]; B%: 50%, isocratic elution mode. Flow rate: 100 mL/min; Gradient: isocratic 50; Wave Length: UV 254/220 nm; Sample Solvent: EtOH + ACN(DEA), and the compound of the example is the second-eluting peak (retention time = 1.6 min). The compounds of Examples L-1-4 and L-1-5 were prepared in an analogous fashion to Example L-1, except that Int. L-C was protected on the phenol with a TIPS group using standard conditions (TIPSCl, TEA in DCM at rt). The TIPS group was removed following the amide-coupling step using the corresponding carboxylic acid employing standard deprotection conditions (KF in DMF at rt). The final racemic compound of L-1-4 was separated by the following conditions: DAICEL CHIRALPAK IC (250 mm*30 mm, 10 um); mobile phase: [CO2—ACN/MeOH(0.1% $NH_3$ in $H_2O$)]; B%: 52%, isocratic elution mode to provide the compound of the example as the second-eluting peak. The final compound of L-1-5 was purified by the following conditions: DAICEL CHIRALPAK IC (250 mm*30 mm,10 um); mobile phase: [CO2—ACN/MeOH(0.1% $NH_3$ in $H_2O$)]; B%: 65%, isocratic elution mode to provide the final compound as the second-eluting peak. The compound of Example L-1-6 was prepared in an analogous fashion to Example L-1, using the carboxylic acid described in Example L-3. The final racemic compound was separated using the following conditions: DAICEL CHIRALPAK IK (250 mm × 30 mm, 10 μm); mobile phase: [CO2—ACN/i-PrOH(0.1% $NH_3$ in water)]; B%: 45%, isocratic elution mode. Flow rate: 120 mL/min; Gradient: isocratic 45; to provide the compound of the example as the second-eluting peak (retention time = 1.1 min).

| Example No. | Structure and Name | LCMS (ESI, m/z) | NMR |
|---|---|---|---|
| L-1-1 | 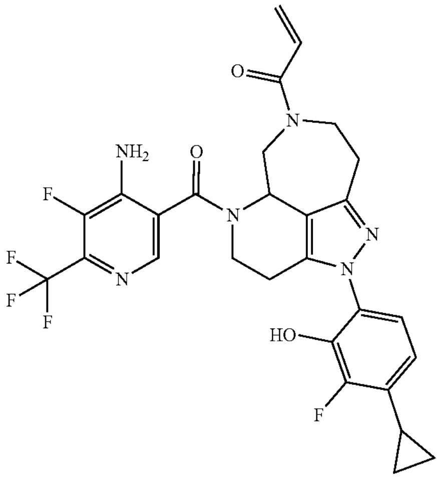 [SMILES: C=CC(=O)N1CCc2nn(-c3ccc(C4CC4)c(F)c3O)c3c2C(C1)N(C(=O)c1cnc(C(F)(F)F)c(F)c1N)CC3] (R or S)-1-(5-(4-amino-5-fluoro-6-(trifluoromethyl)nicotinoyl)-2-(4-cyclopropyl-3-fluoro-2- | 589 $[M + H]^+$ | $^1H$ NMR (400 MHz, Chloroform-d, ppm) δ 8.17 (s, 1H), 7.55 - 7.30 (m, 1H), 6.84 - 6.72 (m, 1H), 6.84 - 6.72 (m, 1H), 6.45 - 6.35 (m, 1H), 5.96 - 5.75 (m, 1H), 5.61 - 5.29 (m, 3H), 4.99 (d, J = 13.4 Hz, 1H), 4.64 - 4.43 (m, 1H), 4.32 - 4.06 (m, 1H), 3.40 - 3.18 (m, 2H), 3.15 - 3.01 (m, 3H), 2.88 - 2.72 (m, 2H), 2.20 - 2.07 (m, 1H), 1.42 - 1.25 (m, 1H), 1.10 - 0.99 (m, 2H), 0.79 - 0.67 (m, 2H). |

TABLE L1-continued

| | | | |
|---|---|---|---|
| | hydroxyphenyl)-2,3,4,5,5a,6,8,9-octahydro-7H-1,2,5,7-tetraazabenzo[cd]azulen-7-yl)prop-2-en-1-one | | |
| L-1-2 | 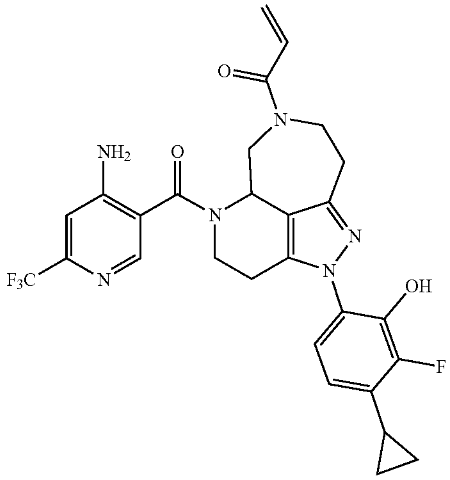 [SMILES: C=CC(=O)N1CCc2nn(-c3ccc(C4CC4)c(F)c3O)c3c2C(C1)N(C(=O)c1cnc(C(F)(F)F)cc1N)CC3] (R or S)-1-(5-(4-amino-6-(trifluoromethyl)nicotinoyl)-2-(4-cyclopropyl-3-fluoro-2-hydroxyphenyl)-2,3,4,5,5a,6,8,9-octahydro-7H-1,2,5,7-tetraazabenzo[cd]azulen-7-yl)prop-2-en-1-one | 571 $[M + H]^+$ | $^1H$ NMR (400 MHz, Chloroform-d) δ 10.24 (s, 1H), 8.35 (s, 1H), 7.40 (s, 1H), 7.04 (s, 1H), 6.76 (d, J = 8.7 Hz, 1H), 6.59 - 6.31 (m, 2H), 5.95 - 5.76 (m, 1H), 5.71 - 5.20 (m, 3H), 5.02 - 4.94 (m, 1H), 4.59 - 4.42 (m, 1H), 4.33 - 4.13 (m, 1H), 3.46 - 2.66 (m, 7H), 2.18 - 2.07 (m, 1H), 1.07 - 0.99 (m, 2H), 0.78 - 0.71 (m, 2H). |
| L-1-3 | 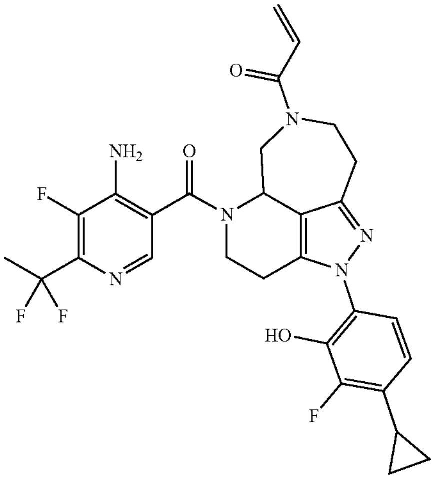 [SMILES: C=CC(=O)N1CCc2nn(-c3ccc(C4CC4)c(F)c3O)c3c2C(C1)N(C(=O)c1cnc(C(C)(F)F)c(F)c1N)CC3] (R or S)-1-(5-(4-amino-6-(1,1-difluoroethyl)-5-fluoronicotinoyl)-2-(4-cyclopropyl-3-fluoro-2-hydroxyphenyl)-2,3,4,5,5a,6,8,9-octahydro-7H-1,2,5,7-tetraazabenzo[cd]azulen-7-yl)prop-2-en-1-one | 585 $[M + H]^+$ | $^1H$ NMR (400 MHz, DMSO-$d_6$, ppm) δ = 10.49 - 10.05 (m, 1H), 8.17 - 8.09 (m, 1H), 7.49 - 7.32 (m, 1H), 6.85 - 6.71 (m, 1H), 6.61 - 6.46 (m, 1H), 6.45 - 6.35 (m, 1H), 5.95 - 5.75 (m, 1H), 5.49 - 5.29 (m, 3H), 5.07 - 4.93 (m, 1H), 4.60 - 4.40 (m, 1H), 4.36 - 4.13 (m, 1H), 3.30 - 2.99 (m, 5H), 2.92 - 2.68 (m, 2H), 2.20 - 2.12 (m, 1H), 2.06 (t, J = 18.8 Hz, 3H), 1.10 - 0.99 (m, 2H), 0.81 - 0.70 (m, 2H). |

TABLE L1-continued

| | | | |
|---|---|---|---|
| L-1-4 | 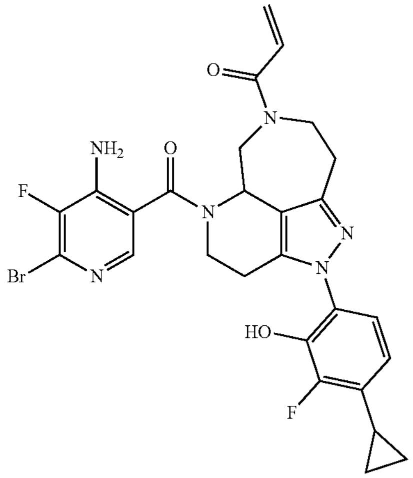 [SMILES: C=CC(=O)N1CCc2nn(-c3ccc(C4CC4)c(F)c3O)c3c2C(C1)N(C(=O)c1cnc(Br)c(F)c1N)CC3]<br>(S or R) 1-(5-(4-amino-6-bromo-5-fluoronicotinoyl)-2-(4-cyclopropyl-3-fluoro-2-hydroxyphenyl)-2,3,4,5,5a,6,8,9-octahydro-7H-1,2,5,7-tetraazabenzo[cd]azulen-7-yl)prop-2-en-1-one | 601 [M + H]+ | $^1$H NMR (400 MHz, DMSO-$d_6$, ppm) δ = 10.37 - 9.89 (m, 1H), 7.88 - 7.72 (m, 1H), 7.61 - 7.40 (m, 1H), 7.01 (d, J = 8.4 Hz, 1H), 6.73 (s, 2H), 6.49 (t, J = 8.0 Hz, 1H), 6.36 - 6.19 (m, 1H), 5.90 - 5.63 (m, 1H), 5.29 - 5.00 (m, 1H), 4.73 - 4.59 (m, 1H), 4.52 - 4.25 (m, 1H), 3.71 (br s, 1H), 3.31 - 3.26 (m, 1H), 3.10 (br d, J = 9.6 Hz, 1H), 2.93 - 2.72 (m, 4H), 2.40 (br d, J = 15.2 Hz, 1H), 2.12 - 1.99 (m, 1H), 1.01 - 0.96 (m, 2H), 0.76 - 0.71 (m, 2H). |
| L-1-5 | 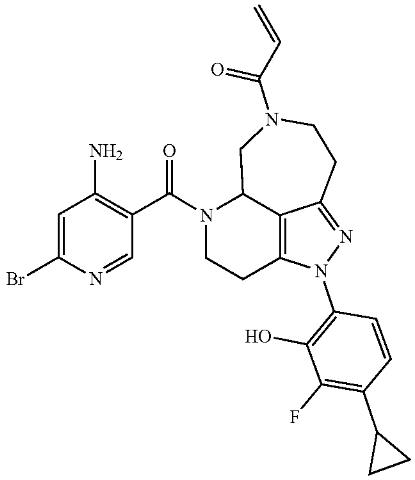 [SMILES: C=CC(=O)N1CCc2nn(-c3ccc(C4CC4)c(F)c3O)c3c2C(C1)N(C(=O)c1cnc(Br)cc1N)CC3]<br>(R or S) 1-(5-(4-amino-6-bromonicotinoyl)-2-(4-cyclopropyl-3-fluoro-2-hydroxyphenyl)-2,3,4,5,5a,6,8,9-octahydro-7H-1,2,5,7-tetraazabenzo[cd]azulen-7-yl)prop-2-en-1-one | 583 [M + H]+ | $^1$H NMR (400 MHz, DMSO-$d_6$, ppm) δ 10.18 (s, 1H), 7.85 (s, 1H), 7.63 - 7.36 (m, 1H), 7.04 - 6.98 (m, 1H), 6.82 (s, 1H), 6.56 - 6.45 (m, 3H), 6.35 - 6.22 (m, 1H), 5.84 - 5.71 (m, 1H), 5.20 - 5.02 (m, 1H), 4.70 - 4.57 (m, 1H), 4.46 - 4.27 (m, 1H), 3.80 - 3.60 (m, 1H), 3.33 - 3.28 (m, 1H), 3.10 - 3.05 (m, 1H), 2.87 - 2.77 (m, 3H), 2.49 - 2.35 (m, 2H), 2.09 - 2.02 (m, 1H), 1.02 - 0.96 (m, 2H), 0.78 - 0.68 (m, 2H). |

TABLE L1-continued
| | | | |
|---|---|---|---|
| L-1-6 | 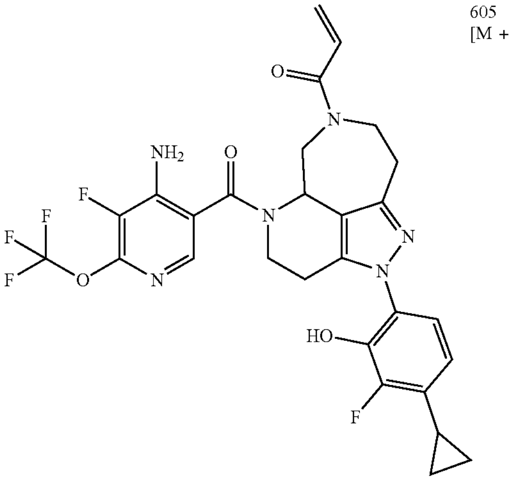<br>(S or R)- 1-(5-(4-amino-5-fluoro-6-(trifluoromethoxy)nicotinoyl)-2-(4-cyclopropyl-3-fluoro-2-hydroxyphenyl)-2,3,4,5,5a,6,8,9-octahydro-7H-1,2,5,7-tetraazabenzo[cd]azulen-7-yl)prop-2-en-1-one | 605 [M + H]+ | (400 MHz, Chloroform, ppm) δ = 10.59 – 9.87 (m, 1H), 7.90 – 7.82 (m, 1H), 7.48 – 7.34 (m, 1H), 6.77 (br d, J = 8.8 Hz, 1H), 6.52 (br d, J = 16.8 Hz, 1H), 6.46 – 6.36 (m, 1H), 5.93 – 5.76 (m, 1H), 5.55 – 5.27 (m, 3H), 5.06 – 4.91 (m, 1H), 4.59 – 4.41 (m, 1H), 4.37 – 4.19 (m, 1H), 3.31 – 3.00 (m, 5H), 2.90 – 2.68 (m, 2H), 2.20 – 2.09 (m, 1H), 1.06 – 1.00 (m, 2H), 0.80 – 0.72 (m, 2H). |

TABLE L2

The compounds of Examples L-1-7, L-1-8, and L-1-9 were prepared in an analogous fashion to Example L-1 coupling the corresponding groups to Int. L-C and using the appropriate carboxylic acids. Compound L-1-9 was prepared as the racemate. The compound of Example L-1-7 was separated into its constitutive enantiomers by the following conditions: Column – CHIRALPAK-IC 2*25cm, 5 μm; Mobile Phase A: HEX (0.1% FA), Mobile Phase B: EtOH: DCM = 1:1; Flow rate: 20 mL/min; Gradient: isocratic 40; Wave Length: UV 254/220 nm; RT1(min): 7.6; RT2(min): 9.2 to afford the compound of the example as the second-eluting peak. The compound of Example L-1-8 was separated into its constitutive enantiomers by the following conditions: Column-CHIRAL ART Cellulose-SB 3*25 cm, 5 μm; Mobile Phase A: HEX(0.1% FA), Mobile Phase B: EtOH: DCM = 1:1; Flow rate: 40 mL/min; Gradient: isocratic 25; Wave Length: UV 254/220 nm; RT1(min): 7.2; RT2(min): 12.0 to afford the compound of the example as the first-eluting peak. The compound of Example L-1-10 was prepared in an analogous manner to Example L-1, except that the isopropenyl group was coupled at Int. L-A. The group was then reduced to the isopropyl group, and the subsequent steps proceeded in an analogous manner to Example L-1, using the corresponding carboxylic acid. The final compound was separated into its constitutive enantiomers by the following conditions: Column-CHIRAL ART Cellulose-SB 3*25 cm, 5 μm; Mobile Phase A: HEX(0.1% FA), Mobile Phase B: EtOH: DCM = 1: 1; Flow rate: 40 mL/min; Gradient: isocratic 20; Wave Length: UV 254/220 nm; RT1(min): 9.8; RT2(min): 23 to provide the compound of the example as the first-eluting peak. The compound of Example L-1-11 was prepared in an analogous fashion to Example L-1 beginning from the 4-bromo-2-methoxyaniline in place of 4-bromo-3-fluoro-2-methoxyaniline. In this case the chiral separation to constitutive enantiomers was performed at the des-F version of Int. L-E. (column: DAICEL CHIRALPAK AS (250 mm*30 mm, 10 um); mobile phase: [CO2—MeOH(0.1% $NH_3H_2O$)]; B%: 40%, isocratic elution mode). The first-eluting peak was carried on to the compound of the example.

| Example No. | Structure and Name | LCMS (ESI, m/z) | NMR |
|---|---|---|---|
| L-1-7 | 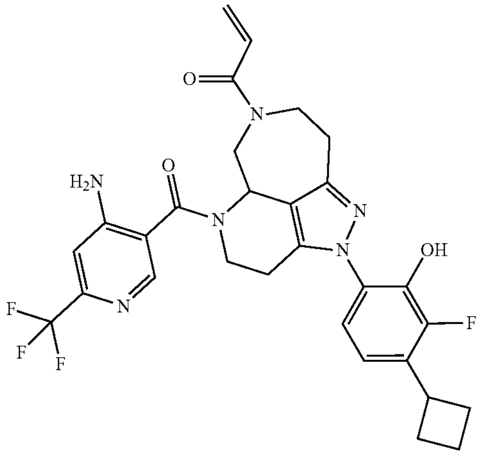 [SMILES: C=CC(=O)N1CCc2nn(-c3ccc(C4CCC4)c(F)c3O)c3c2C(C1)N(C(=O)c1cnc(C(F)(F)F)cc1N)CC3] (R or S)-1-(5-(4-amino-6-(trifluoromethyl)nicotinoyl)-2-(4-cyclobutyl-3-fluoro-2-hydroxyphenyl)-2,3,4,5,5a,6,8,9-octahydro-7H-1,2,5,7-tetraazabenzo[cd]azulen-7-yl)prop-2-en-1-one | 585 $[M + H]^+$ | $^1H$ NMR (400 MHz, Chloroform-d, ppm) δ 10.20 (s, 1H), 8.38 – 8.20 (m, 1H), 7.40 (s, 1H), 7.05 (s, 1H), 6.84 – 6.75 (m, 2H), 6.59 – 6.35 (m, 1H), 5.92 – 5.76 (m, 1H), 5.68 – 5.30 (m, 3H), 5.03 – 4.82 (m, 1H), 4.80 – 4.42 (m, 1H), 4.34 – 4.18 (m, 1H), 3.82 – 3.69 (m, 1H), 3.30 – 3.00 (m, 5H), 2.88 – 2.70 (m, 2H), 2.44 – 2.32 (m, 2H), 2.25 – 2.00 (m, 3H), 1.94 – 1.83 (m, 1H). |

TABLE L2-continued

| | | | |
|---|---|---|---|
| L-1-8 | 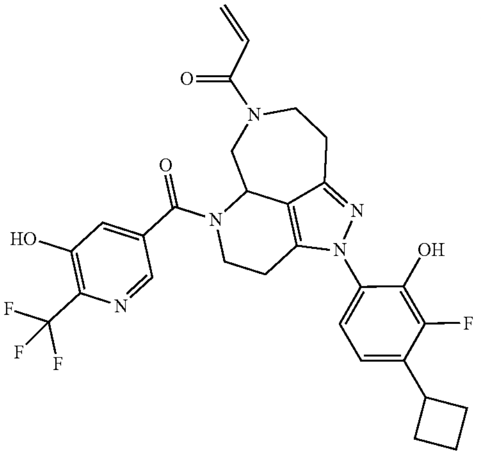 [SMILES: C=CC(=O)N1CCc2nn(-c3ccc(C4CCC4)c(F)c3O)c3c2C(C1)N(C(=O)c1cnc(C(F)(F)F)c(O)c1)CC3] (S or R)-1-(2-(4-cyclobutyl-3-fluoro-2-hydroxyphenyl)-5-(5-hydroxy-6-(trifluoromethyl)nicotinoyl)-2,3,4,5,5a,6,8,9-octahydro-7H-1,2,5,7-tetraazabenzo[cd]azulen-7-yl)prop-2-en-1-one | 586 $[M + H]^+$ | $^1$H NMR(400 MHz, Chloroform-d, ppm) δ 10.16 (s, 1H), 8.76 - 8.44 (m, 1H), 8.39 - 8.17 (m, 1H), 7.67 - 7.29 (m, 1H), 6.91 - 6.60 (m, 2H), 6.56 - 6.38 (m, 1H), 5.97 - 5.76 (m, 1H), 5.37 - 5.08 (m, 1H), 5.00 - 4.81 (m, 1H), 4.73 - 4.42 (m, 1H), 4.40 - 4.26 (m, 1H), 3.96 - 3.67 (m, 2H), 3.28 - 2.68 (m, 7H), 2.43 - 1.82 (m, 5H), 1.31 - 1.19 (m, 1H). |
| L-1-9 | 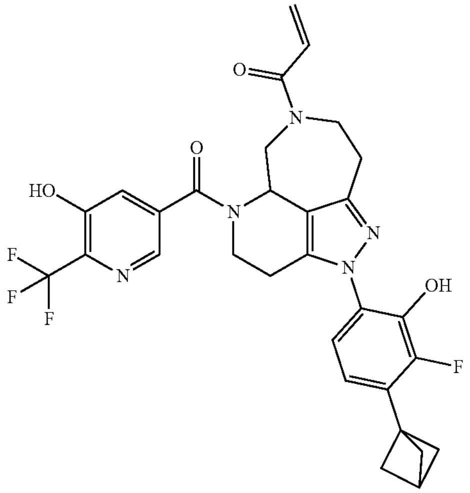 [SMILES: C=CC(=O)N1CCc2nn(-c3ccc(C45CC(C4)C5)c(F)c3O)c3c2C(C1)N(C(=O)c1cnc(C(F)(F)F)c(O)c1)CC3] (R and S)-1-(2-(4-(bicyclo[1.1.1]pentan-1-yl)-3-fluoro-2-hydroxyphenyl)-5-(5-hydroxy-6-(trifluoromethyl)nicotinoyl)-2,3,4,5,5a,6,8,9-octahydro-7H-1,2,5,7-tetraazabenzo[cd]azulen-7-yl)prop-2-en-1-one | 598 $[M + H]^+$ | $^1$H NMR (400 MHz, Chloroform-d, ppm) δ 10.21 (s, 1H), 8.65 (s, 1H), 8.50 (s, 1H), 8.42 - 8.24 (m, 1H), 6.88 - 6.41 (m, 3H), 6.00 - 5.78 (m, 1H), 5.22 - 5.14 (m, 1H), 4.90 (d, J = 12.8 Hz, 1H), 4.72 - 4.65 (m, 1H), 4.41 - 4.27 (m, 1H), 3.32 - 2.99 (m, 4H), 2.99 - 2.65 (m, 3H), 2.65 - 2.54 (m, 1H), 2.23 - 2.12 (m, 6H). |

TABLE L2-continued

| | | | |
|---|---|---|---|
| L-1-10 | 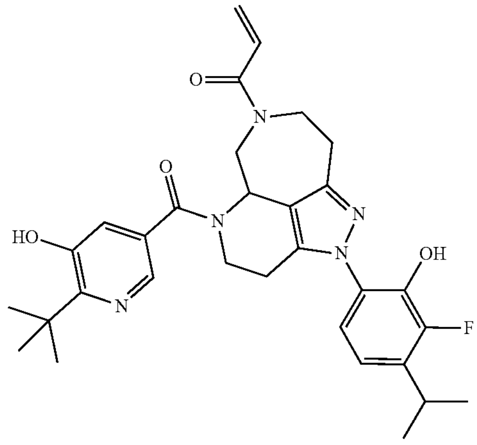<br>(S or R)-1-(2-(3-fluoro-2-hydroxy-4-isopropylphenyl)-5-(5-hydroxy-6-(trifluoromethyl)nicotinoyl)-2,3,4,5,5a,6,8,9-octahydro-7H-1,2,5,7-tetraazabenzo[cd]azulen-7-yl)prop-2-en-1-one | 574 $[M + H]^+$ | $^1H$ NMR (400 MHz, Chloroform-d, ppm) δ 10.90-9.01 (m, 1H), 8.60 – 8.35 (m, 1H), 8.32-7.28 (m, 1H), 6.97 – 6.57 (m, 3H), 6.50 (d, J = 16.5 Hz, 1H), 6.04 – 5.78 (m, 1H), 5.43 – 5.05 (m, 1H), 4.91 (d, J = 13.6 Hz, 1H), 4.69 (d, J = 10.3 Hz, 1H), 4.35 (d, J = 15.1 Hz, 1H), 3.28 – 3.04 (m, 5H), 2.91-2.70 (m, 3H), 1.26 (t, J = 8.6 Hz, 6H). |
| L-1-11 | 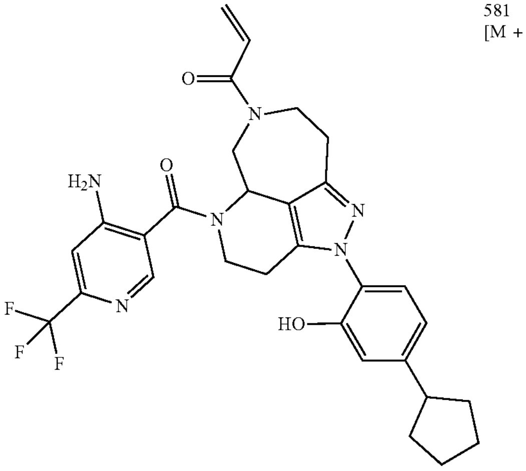<br>(R or S)-1-(5-(4-amino-6-(trifluoromethyl)nicotinoyl)-2-(4-cyclopentyl-2-hydroxyphenyl)-2,3,4,5,5a,6,8,9-octahydro-7H-1,2,5,7-tetraazabenzo[cd]azulen-7-yl)prop-2-en-1-one | 581 $[M + H]^+$ | $^1H$ NMR (400 MHz, DMSO-$d_6$, ppm) δ 9.97 (br s, 1H), 8.18 (s, 1H), 7.66 – 7.38 (m, 1H), 7.18 ( d, J = 7.6 Hz, 1H), 7.08 (s, 1H), 6.87 (s, 1H), 6.78 ( d, J = 8.4 Hz, 1H), 6.75 – 6.57 (m, 2H), 6.38 – 6.22 (m, 1H), 5.93 – 5.64 (m, 1H), 5.28 – 4.94 (m, 1H), 4.76 – 4.58 (m, 1H), 4.51 – 4.27 (m, 1H), 3.77 – 3.60 (m, 1H), 3.57 – 3.41 (m, 1H), 3.18 – 3.10 (m, 1H), 2.96 – 2.79 (m, 5H), 2.41 (d, J = 16 Hz, 1H), 2.05 – 1.98 (m, 2H), 1.79 – 1.72 (m, 2H), 1.68 – 1.61 (m, 2H), 1.55 – 1.46 (m, 2H). |

Example L-2: Preparation of (R or S)-1-(5-(4-amino-6-(trifluoromethyl)nicotinoyl)-2-(4-cyclopropyl-5-fluoro-2-hydroxyphenyl)-4,5,5a,6,8,9-hexahydro-2H-1,2,5,7-tetraazabenzo[cd]azulen-7(3H)-yl) prop-2-en-1-one
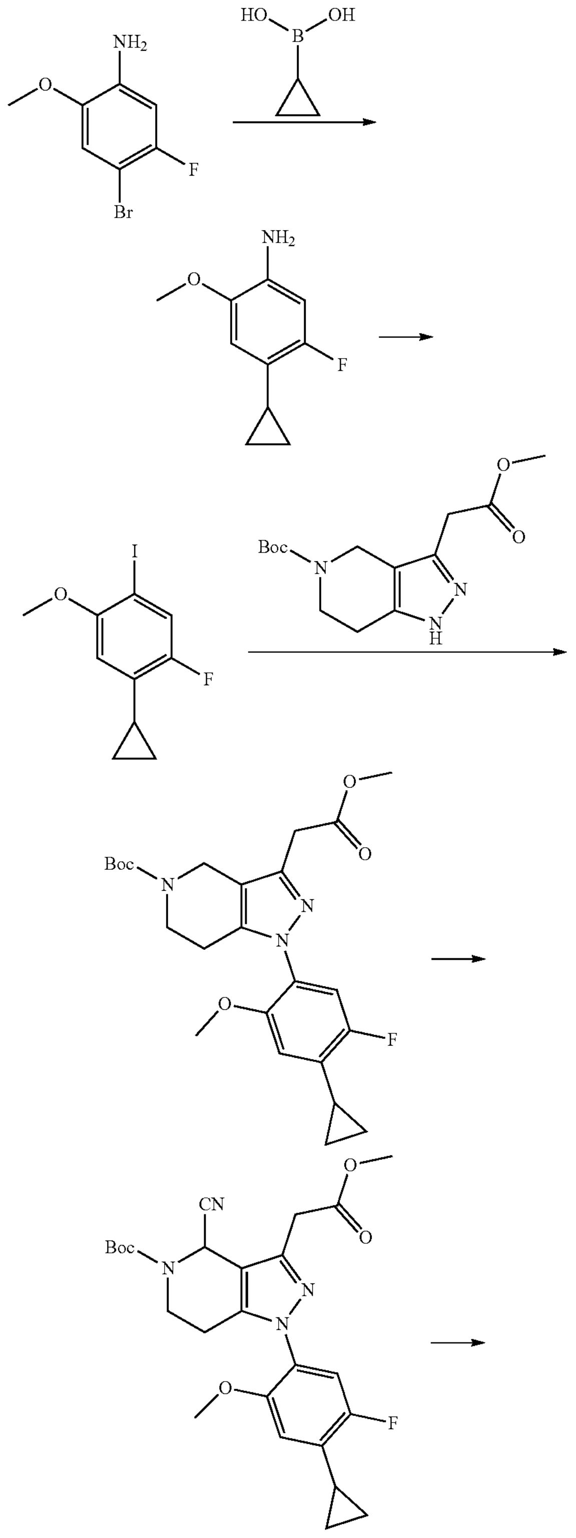
-continued
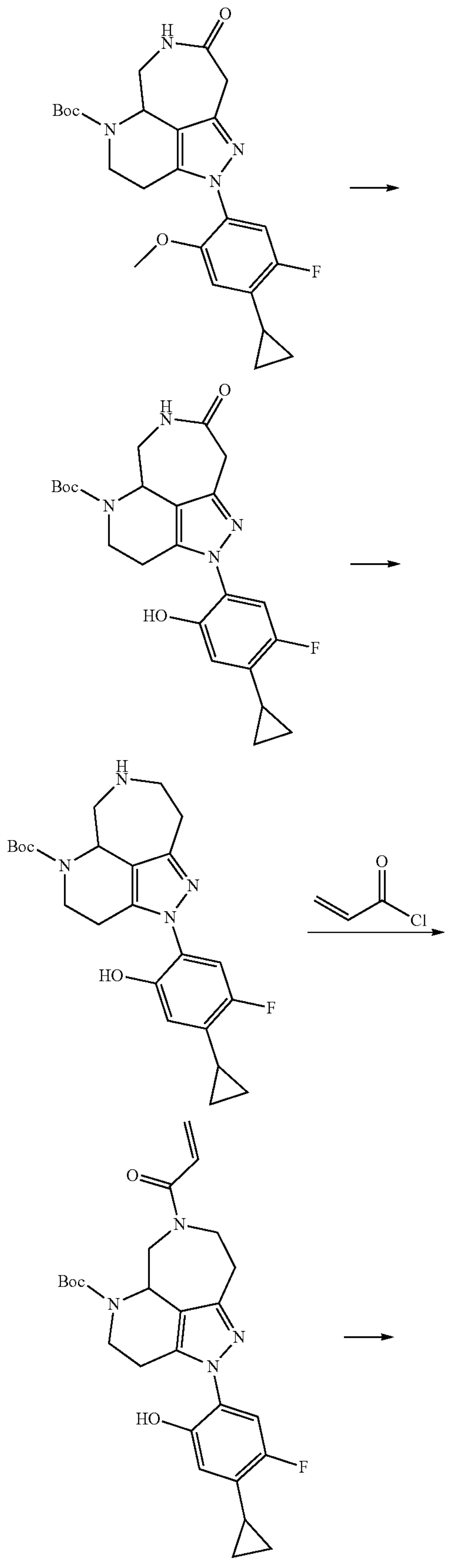

-continued

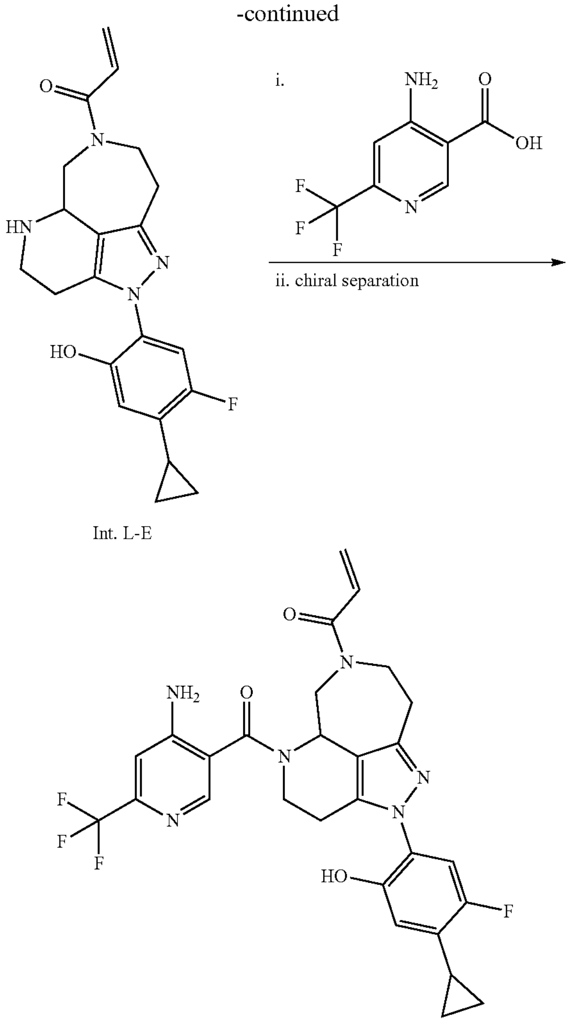

Int. L-E

Step 1: Synthesis of 4-cyclopropyl-5-fluoro-2-methoxy-aniline

To a stirred solution of 4-bromo-5-fluoro-2-methoxy-aniline (1 g, 1 equiv., 45.5 mmol) and cyclopropylboronic acid (11.7 g, 3 equiv., 136 mmol) in dioxane (160 mL) and 1120 (16 mL) was added Pd(dppf)$Cl_2$ (4.99 g, 0.15 equiv., 6.82 mmol) and $K_3PO_4$ (28.9 g, 3 equiv., 136 mmol), the reaction solution was stirred at 100° C. for 1 h under an atmosphere of nitrogen. The reaction solution was concentrated and the crude product was purified by silica gel column chromatography, eluting with EtOAc/PE (1:4) to afford 4-cyclopropyl-5-fluoro-2-methoxy-aniline (6 g) as a yellow oil. LCMS: (ESI, m/z):182 $[M+H]^+$.

Step 2: Synthesis of 1-cyclopropyl-2-fluoro-4-iodo-5-methoxybenzene

To a stirred solution of 4-cyclopropyl-5-fluoro-2-methoxy-aniline (6 g, 1 equiv., 33.11 mmol) in HCl (48 mL) (6 mol·$L^{-1}$ in $H_2O$) was added $NaNO_2$ (3.43 g, 1.5 equiv., 49.67 mmol) at 0° C., the reaction solution was stirred at 0° C. for 0.5 h, then the mixture was added KI (27.5 g, 5 equiv., 166 mmol) in 1120 (30 mL) and stirred at 25° C. for 0.5 h. The mixture was poured into water (100 mL), the pH of mixture was adjusted to 7 by using saturated aqueous sodium bicarbonate, the resulting mixture was extracted with EtOAc (3×70 mL). The combined organic layers were washed with brine (2×50 mL) and dried over anhydrous $Na_2SO_4$. After filtration, the filtrate was concentrated under reduced pressure. The residue was purified by silica gel column chromatography, eluting with EtOAc/PE (1:9) to afford 1-cyclopropyl-2-fluoro-4-iodo-5-methoxybenzene (6.6 g) as a brown oil.

Step 3: Synthesis of Tert-Butyl 3-(4-cyclopropyl-S-fluoro-2-methoxyphenyl)-11-oxo-2,3,7,10-tetrazatricyclo[6.4.1.$0^{4,13}$]trideca-1, 4(13)-diene-7-carboxylate To a stirred solution of tert-butyl 11-oxo-2,3,7,10-tetrazatricyclo[6.4.1.04,13]trideca-1,4(13)-diene-7-carboxylate (0.7 g, 1 equiv., 2.39 mmol) and 1-cyclopropyl-2-fluoro-4-iodo-5-methoxybenzene (1.40 g, 2 equiv., 4.79 mmol) in dioxane (15 L) was added N1-(2-methylnaphthalen-1-yl)-N2-(pyridin-2-ylmethyl)oxalamide (765 mg, 1 equiv., 2.39 mmol), CuI (228 mg, 0.5 equiv., 1.20 mmol) and $Cs_2CO_3$ (2.34 g, 3 equiv., 7.18 ol), the reaction solution was stirred at 100° C. for 12 h under an atmosphere of nitrogen. The reaction solution was filtered by filter paper and the filtrate was concentrated under reduced pressure. The residue was purified by reversed phase flash: (Phenomenex Gemini C18 (150×25 mm, 10 um); flow rate: 50 mL/min; gradient: 65%-85% B over 10 min; mobile phase A: 0.05% FA, mobile phase B: acetonitrile). The obtained solution was lyophilized to give tert-butyl 3-(4-cyclopropyl-5-fluoro-2-methoxy-phenyl)-11-oxo-2,3,7,10-tetrazatricyclo[6.4.1.$0^{4,}$ 13]trideca-1,4(13)-diene-7-carboxylate (0.3 g) as a white solid. LCMS: (ESI, m/z):457 $[M+H]^+$.

Step 4: Tert-Butyl 3-(4-cyclopropyl-5-fluoro-2-hydroxy-phenyl)-11-oxo-2,3,7,10-tetrazatricyclo [6.4.1.$0^{4,13}$]trideca-1, 4(13)-diene-7-carboxylate To a stirred solution of tert-butyl 3-(4-cyclopropyl-5-fluoro-2-ethoxy-phenyl)-11-oxo-2,3,7,10-tetrazatricyclo [6.4.1.$0^{4,13}$]trideca-1,4(13)-diene-7-carboxylate 0.3 g, 1 equiv., 657.16 μmol) in DCM (7 mL) was added $BCl_3$ (1 M, 2.63 mL, 4 equiv.) at 0° under an atmosphere of nitrogen, the mixture was stirred at 25° C. for 1 h. The mixture was quenched with $H_2O$ (2 mL), the mixture was stirred at 0° C. for 1 h. The mixture was adjusted pH=6-7 by $Na_2CO_3$ (780 mg, 11.2 equiv., 7.36 mmol) in $H_2O$ (2 mL) at 0° C., and then added $Boc_2O$ (287 g, 2 equiv., 1.31 mmol) at 0° C. The mixture was stirred at 25° C. for 12 hrs. The reaction mixture was diluted with water (5 mL) and extracted with DCM/MeOH=10/1, 30 mL×3).The combined organic layers were washed with brine (3×40 mL), dried over anhydrous $Na_2SO_4$, then the obtained solution was filtered and concentrated under reduced pressure to give tert-butyl 3-(-cyclopropyl-5-fluoro-2-hydroxy-phenyl)-11-oxo-2,3,7,10-tetrazatricyclo[6.4.1.$0^{4,13}$]trideca-1,4(3)-diene-7-carboxylate (290 mg) as a yellow oil. LCMS: (ESI, m/z):443 $[M+H]^+$.

Step 5: Tert-Butyl 3-(2-tert-butoxycarbonyloxy-4-cyclopropyl-5-fluoro phenyl)-11-oxo-2,3,7,10-tetrazatricyclo[6.4.1.$0^{4,13}$]trideca-1, 4(13)-diene-7-carboxylate To a stirred solution of tert-butyl 3-(4-cyclopropyl-5-fluoro-2-hydroxy-phenyl)-11-oxo-2,3,7,10-tetrazatricyclo [6.4.1.$0^{4,13}$]trideca-1,4(13)-diene-7-carboxylate (90 mg, 1 equiv., 655.39 μmol) in MeCN (4 mL) was added $Boc_2O$ (172 mg, 1.2 equiv., 786.4 μmol) and $Na_2CO_3$ (139 mg, 2 equiv., 1.31 mmol), the reaction solution was stirred at 80° C. for 0.5 h. The mixture was purified by silica gel column chromatography, eluting with EtOAc/PE (4:1) to afford tert-butyl 3-(2-tert-butoxycarbonyloxy-4-cyclopropyl-5-fluoro-phenyl)-11-oxo-2,3,7,10-tetrazatricyclo[6.4.1.$0^{4,13}$]trideca-1,4(13)-diene-7-carboxylate (210 mg) as a light yellow solid. LCMS: (ESI, m/z):543 $[M+H]^+$.

Step 6: Tert-Butyl 3-(2-tert-butoxycarbonyloxy-4-cyclopropyl-5-fluoro-phenyl)-2,3,7,10-tetrazatricyclo[6.4.1.$0^{4,13}$]trideca-1, 4(13)-diene-7-carboxylate To a stirred solution of tert-butyl 3-(2-tert-butoxycarbonyloxy-4-cyclopropyl-5-fluoro-phenyl)-11-oxo-2,3,7,10-tetrazatricyclo[6.4.1.$0^{4,13}$]trideca-1,4(13)-diene-7-carboxylate (210 mg, 1 equiv., 387.03 gmol) in THF (5 mL) was added $BH_3$·THF (1 M, 1.55 mL, 4 equiv.) at 0° C. under an atmosphere of nitrogen. Then the reaction mixture was stirred at 60° C. under nitrogen atmosphere for 1 h. The reaction solution was drop wised added MeOH (5 ml) at 25° C., and then the mixture was stirred at 60° C. for 12 h, then the mixture was concentrated under reduced pressure to give tert-butyl 3-(2-tert-butoxycarbonyloxy-4-cyclopropyl-5-fluoro-phenyl)-2,3,7,10-tetrazatricyclo[6.4.1.$0^{4,13}$]trideca-1,4(13)-diene-7-carboxylate (200 mg) was obtained as a yellow gum. LCMS: (ESI, m/z):529 $[M+H]^+$.

Step 7: Tert-Butyl 3-(2-tert-butoxycarbonyloxy-4-cyclopropyl-5-fluoro-phenyl)-10-prop-2-enoyl-2,3,7,10-tetrazatricyclo[6.4.1.$0^{4,13}$]trideca-1, 4(13)-diene-7-carboxylate To a stirred solution of tert-butyl 3-(2-tert-butoxycarbonyloxy-4-cyclopropyl-5-fluoro-phenyl)-2,3,7,10-tetrazatricyclo[6.4.1.$0^{4,13}$]trideca-1,4(13)-diene-7-carboxylate (0.2 g, 1 equiv., 378.35 μmol) and TEA (76.6 mg, 2 equiv., 757 μmol, 105.32 μL) in DCM (3 mL) was added prop-2-enoyl chloride (34.24 mg, 1 equiv., 378.35 μmol, 30.74 μL) at 0° C. under an atmosphere of nitrogen, the reaction solution was stirred at 0° C. for 1 h. The mixture was added water (20 mL). The resulting mixture was transferred to a separating funnel, and the aqueous layer mixture was extracted with DCM (20 mL×3). The combined organic layers were washed with brine (2×10 mL) and dried over anhydrous $Na_2SO_4$. After filtration, the filtrate was concentrated under reduced pressure to give tert-butyl 3-(2-tert-butoxycarbonyloxy-4-cyclopropyl-1-fluoro-phenyl)-10-prop-2-enoyl-2,3,7,10-tetrazatricyclo[6.4.1.$0^{4,13}$]trideca-1,4(13)-diene-7-carboxylate (220 mg) as a yellow solid. LCMS: (ESI, m/z):583 $[M+H]^+$.

Step 8: 1-[3-(4-cyclopropyl-5-fluoro-2 hydroxyphenyl)-2,3,7,10-tetrazatricyclo[6.4.1.$0^{4,13}$]trideca-1,4 (13)-dien-10-yl]prop-2-en-1-one (Int. L-E)

To a stirred solution of tert-butyl 3-(2-tert-butoxycarbonyloxy-4-cyclopropyl-5-fluoro-phenyl)-10-prop-2-enoyl-2,3,7,10-tetrazatricyclo[6.4.1.$0^{4,13}$]trideca-1,4(13)-diene-7-carboxylate (220 mg, 1 equiv., 378 μmol) in DCM (3 mL) was added TFA (1.54 g 13.46 mmol, 1 mL), the reaction solution was stirred at 25° C. for 0.5 h. The mixture was quenched by slow addition of saturated aqueous sodium bicarbonate (15 mL). The resulting mixture was transferred to a separating funnel, and the aqueous layer mixture was extracted with DCM (10 mL×3). The combined organic layers were washed with brine (2×10 mL) and dried over anhydrous $Na_2SO_4$. After filtration, the filtrate was concentrated under reduced pressure. The crude product was purified by reversed phase flash: (Phenomenex Gemini C18 (150×25 mm, 10 um); flow rate: 50 mL/min; gradient: 40%-60% B over 10 min; mobile phase A: 0.05% $NH_4HCO_3$, mobile phase B: acetonitrile). The obtained solution was lyophilized to give 1-[3-(4-cyclopropyl-5-fluoro-2-hydroxyphenyl)-2,3,7,10-tetrazatricyclo[6.4.1.04, 13]trideca-1,4(13)-dien-10-yl]prop-2-en-1-one (50 mg) as a white solid. LCMS: (ESI, m/z):383 $[M+H]^+$.

Step 9: Synthesis of (S or R)-1-[7-[4-amino-6-(trifluoromethyl)pyridine-3-carbonyl]-3-(4-cyclopropyl-S-fluoro-2-hydroxy-phenyl)-2,3,7,10-tetrazatricyclo [6.4.1.$0^{4,13}$]trideca-1, 4(13)-dien-10-yl]prop-2-en-1-one To a stirred solution of 1-[3-(4-cyclopropyl-5-fluoro-2-hydroxy-phenyl)-2,3,7,10-tetrazatricyclo[6.4.1.$0^{4,13}$]trideca-1,4(13)-dien-10-yl]prop-2-en-1-one (4 mg, 1 equiv., 105 μmol) and 4-amino-6-(trifluoromethyl)pyridine-3-carboxylic acid (int. C)(28.0 mg, 1.3 equiv., 136 μmol) in DCE (4 mL) was added CMPI (32.1 mg, 1.2 equiv., 125.51 μmol), the reaction solution was stirred at 60° C. for 12 h. The reaction solution was concentrated to remove DCE. The crude product was purified by silica gel column chromatography, eluting with EtOAc/PE (1:0) to afford 1-[7-[4-amino-6-(trifluoromethyl)pyridine-3-carbonyl]-3-(4-cyclopropyl-5-fluoro-2-hydroxy-phenyl)-2,3,7,10-tetrazatricyclo [6.4.1.$0^{4,13}$]trideca-1,4(13)-dien-10-yl]prop-2-en 1-one (38 mg) as a white solid. The racemic 1-[7-[4-amino-6-(trifluoromethyl)pyridine-3-carbonyl]-3-(4-cyclopropyl-5 -fluoro-2-hydroxy-phenyl)-2,3,7,10-tetrazatricyclo[6.4.1.$0^{4,13}$]trideca-1,4(13)-dien-10-yl]prop-2-en-1-one (38 mg) was purified by SFC (column: DAICEL CHIRALPAK IK(250 mm*30 mm, 10 um); mobile phase: [$CO_2$-i-PrOH(0.1% $NH_3H_2O$)]; %:43%, isocratic elution mode; RT1(min): 2.1; RT2(min): 2.4) to give (S or R) 1-[7-[4-amino-6-trifluoromethyl)pyridine-3-carbonyl]-3-(4-cyclopropyl-5-fluoro-2-hydroxy-phenyl)-2,3,7,10-tetrazatricyclo[6.4.1.$0^{4,13}$]trideca-1,4(13)-dien-10-yl]prop-2-en-1-one (5.69 mg, retention time 2.4 min) as the second-eluting peak as an off-white solid. LCMS: (ESI, m/z): 571 $[M+H]^+$. $^1H$ NMR: (400 MHz, DMSO-$d_6$) δ=10.03-9.85 (m, 1H), 8.24-8.13 (m, 1H), 7.59-7.43 (m, 1H), 7.13-7.04 (m, 2H), 6.72 (br s, 2H), 6.53 (d, J=7.2 Hz, 1H), 6.29 (br d, J=5.2 Hz, 1H), 5.88-5.70 (m, 1H), 5.25-5.10 (m, 11H), 4.67 (br d, J=6.0 Hz, 1H), 4.53-4.35 (m, 1H), 3.66 (br dd, $J_1$=1.2, $J_2$=8.8 Hz, 1H), 3.37 (br s, 1H), 3.12 (br t, J=10.4 Hz, 1H), 2.91-2.75 (m, 4H), 2.42 (br d, J=15.2 Hz, 1H), 2.06-1.95 (m, 1H), 1.03-0.96 (m, 2H), 0.72-0.61 (m, 2H).

TABLE L3

The compound of Example L-2-1 was prepared in an analogous fashion to Example L-2 using the carboxylic acid described in Example A-12. The racemic final compound was separated using the following conditions: column: (s,s) WHELK-01 (250 mm*30 mm, 10 um);mobile phase: [CO2—ACN/i-PrOH(0.1% $NH_3$ in water)]; B%: 60%, isocratic elution mode to provide the compound of the example as the second-eluting peak.

| Example No. | Structure and Name | LCMS (ESI, m/z) $[M + 1]^+$ | NMR |
|---|---|---|---|
| L-2-1 | 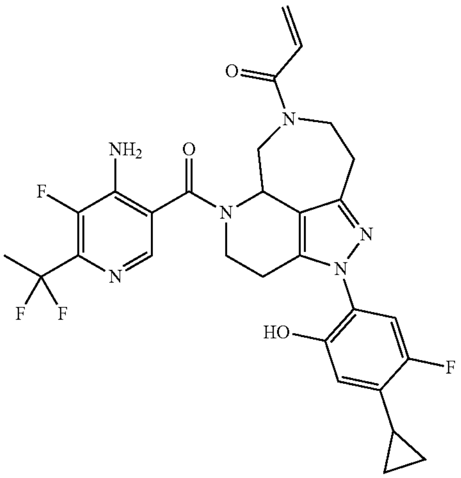 [SMILES: C=CC(=O)N1CCc2nn(-c3cc(F)c(C4CC4)cc3O)c3c2C(C1)N(C(=O)c1cnc(C(C)(F)F)c(F)c1N)CC3] (S or R) 1-[7-[4-amino-6-(1,1-difluoroethyl)-5-fluoro-pyridine-3-carbonyl]-3-(4-cyclopropyl-5-fluoro-2-hydroxy-phenyl)-2,3,7,10-tetrazatricyclo[6.4.1.04,13]trideca-1,4(13)-dien-10-yl]prop-2-en-1-one | 585 $[M + H]^+$ | $^1H$ NMR (400 MHz, DMSO-$d_6$, ppm) δ 9.98 - 9.93 (m, 1H), 7.98 - 7.92 (m, 1H), 7.62 - 7.40 (m, 1H), 7.08 (d, J = 10.4 Hz, 1H), 6.70 - 6.61 (m, 2H), 6.57 - 6.51 (m, 1H), 6.36 - 6.25 (m, 1H), 5.83 - 5.71 (m, 1H), 5.20 - 5.08 (m, 1H), 4.72 - 4.62 (m, 1H), 4.53 - 4.41 (m, 1H), 3.76 - 3.62 (m, 1H), 3.16 - 3.09 (m, 1H), 2.91 - 2.78 (m, 4H), 2.42 (br d, J = 14.4 Hz, 1H), 2.05 - 1.94 (m, 5H), 1.00 (dd, $J_1$ = 2.0Hz , $J_2$ = 8.4 Hz, 2H), 0.70 - 0.66 (m, 2H). |

Example L-3: Preparation of (R or S)-1-(5-(4-amino-5-fluoro-6-(trifluoromethoxy)nicotinoyl)-2-(4-cyclopropyl-5-fluoro-2-hydroxyphenyl)-2,3,4,5,5a,6,8,9-octahydro-7H-1,2,5,7-tetraazabenzo[cd]azulen-7-yl)prop-2-en-1-one

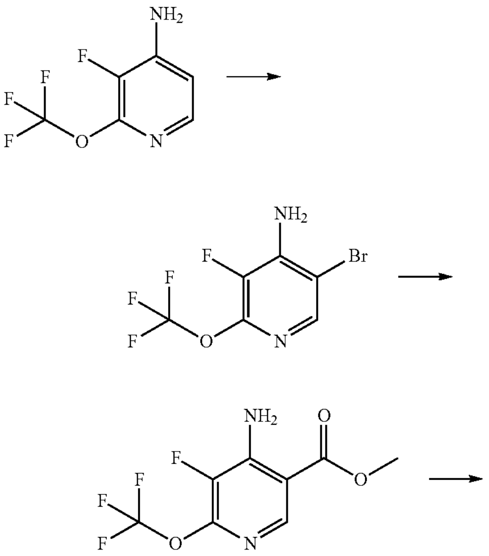

-continued

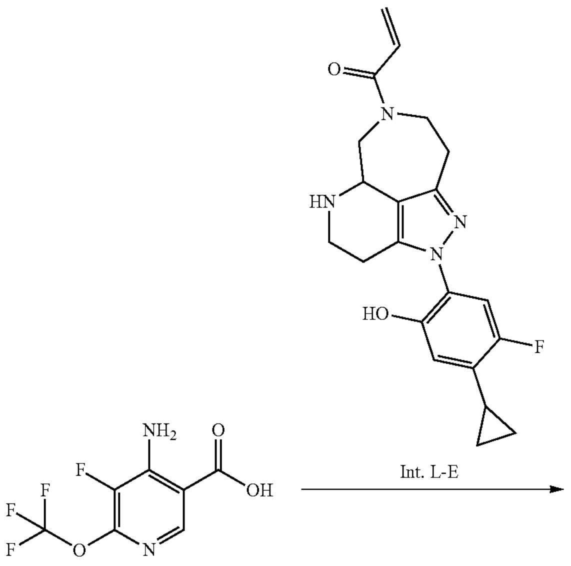

-continued

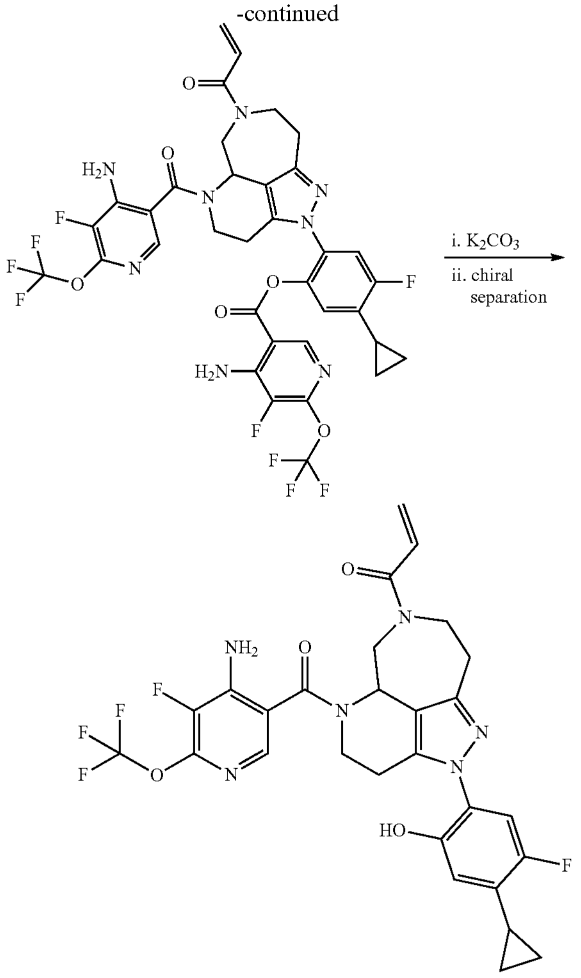

Step 1: Synthesis of 5-bromo-3-fluoro-2-(trifluoromethoxy)pyridin-4-amine

To a solution of 3-fluoro-2-(trifluoromethoxy)pyridin-4-amine (1.6 g, 8.16 mmol, 1 eq) in THF (15 mL) was added NBS (1.9 g, 10.6 mmol, 1.3 eq) and the mixture was stirred at 45° C. for 2 h. The reaction solution was quenched with saturated sodium thiosulfate aqueous solution (50 mL) and then extracted with EA (3×50 mL). The combined organic layers were washed with brine (2×50 mL), dried over anhydrous sodium sulfate, filtered and the filtrate was concentrated under reduced pressure. The crude product was purified by column ($SiO_2$, Petroleum ether:Ethyl acetate=1:0 to 3:1) to afford 5-bromo-3-fluoro-2-(trifluoromethoxy)pyridin-4-amine (1.4 g) as a white solid. LCMS: (ESI, m/z): 275 $[M+H]^+$.

Step 2: Synthesis of Methyl 4-amino-5-fluoro-6-(trifluoromethoxy)pyridine-3-carboxylate To a solution of 5-bromo-3-fluoro-2-(trifluoromethoxy) pyridin-4-amine (2.73 g, 9.93 mmol, 1 eq) in MeOH (20 mL) was added $Pd(dppf)Cl_2$ (726.39 mg, 992.73 mol, 0.1 eq) and TEA (3.01 g, 29.78 mmol, 4.15 mL, 3 eq) and the mixture was stirred at 8° C. for 12 h under a CO atmosphere (50 psi). The mixture was filtered through a bed of C elite and the filtrate was concentrated under reduced pressure. The residue was purified by column ($SiO_2$, Petroleum ether: Ethyl acetate=1:0 to 3:1) to afford methyl 4-amino-5-fluoro-6-(trifluoromethoxy)pyridine-3-carboxylate (2.16 g) as a white solid. LCMS: (ESI, m/z): 255 $[M+H]^+$.

Step 3: Synthesis of 4-amino-5-fluoro-6-(trifluoromethoxy)pyridine-3-carboxylic Acid To a solution of methyl 4-amino-5-fluoro-6-(trifluoromethoxy)pyridine-3-carboxylate (2.16 g, 8.50 mmol, 1 eq) in THF (20 mL) and $H_2O$ (10 mL) was added $LiOH{\cdot}H_2O$ (534.99 mg, 12.75 mmol, 1.5 eq) and the mixture was stirred at rt for 1.5 h. The mixture was concentrated under reduced pressure, after which a 1M HCl solution was added to adjust pH=5. A white precipitate formed. Then the mixture was filtered and the filter cake was collected and dried to afford 4-amino-5-fluoro-6-(trifluoromethoxy)pyridine-3-carboxylic acid (1.92 g, 0.92 mmol, 93.13% yield, 99.25% purity) as a white solid. LCMS: (ESI, m/z): 241 $[M+H]^+$.

Step 4: Synthesis of [2-[7-[4-amino-S-fluoro-6-(trifluoromethoxy)pyridine-3-carbonyl]-10-prop-2-enoyl-2,3,7,10-tetrazatricyclo[6.4.1.$0^{4,13}$]trideca-1,4 (13)-dien-3-yl]-5 cyclopropyl-4-fluoro-phenyl]4-amino-5-fluoro-6-(trifluoromethoxy)pyridine-3-carboxylate To a solution of Int. L-E (45 mg, 118 μmol, 1 equiv), 4-amino-5-fluoro-6-(trifluoromethoxy)pyridine-3-carboxylic acid (85 mg, 353 μmol, 3 equiv) and DIEA (45.6 mg, 353 μmol, 61.5 μL, 3 equiv) in DMF (3 mL) was added HATU (89.5 mg, 235 mol, 2 equiv). The mixture was stirred at rt for 2.5 h, after which the mixture was diluted w h water (5 mL), and then extracted with EA (2×5 mL). The combined organic layers were washed with brine (2×10 mL), dried over anhydrous sodium sulfate, filtered and concentrated under vacuum. The residue was purified by silica gel column chromatography, eluting with EtOAc/PE (2:1) to afford [2-[7-[4-amino-5-fluoro-6-(trifluoromethoxy)pyridine-3-carbonyl]-10-prop-2-en yl-2,3,7,10-tetrazatricyclo [6.4.1.04,13]trideca-1,4(13)-dien-3-yl]-5-cyclopropyl-4-fluoro-phenyl]4-amino-5-fluoro-6-(trifluoromethoxy) pyridine-3-carboxylate (62 mg, 75.00 μmol, 44.27% yield) as a colorless oil. LCMS: (ESI, m/z): 827 $[M+H]^+$.

Step 5: Synthesis of (R or S)-1-[7-[4-amino-5-fluoro-6-(trifluoromethoxy)pyridine-3-carbonyl]-3-(4-cyclopropyl-5-fluoro-2-hydroxy-phenyl)-2,3,7,10-tetrazatricyclo[6.4.1.04,13]trideca-1,4(13)-dien-10-yl]prop-2-en-1-one To a solution of [2-[7-[4-amino-5-fluoro-6-(trifluoromethoxy)pyridine-3-carbonyl]-10-prop-2-enoyl-2,3,7,10-tetrazatricyclo[6.4.1.04,13]trideca-1,4(13)-dien-3-yl]-5-cyclopropyl-4-fluoro-phenyl]4-amino-5-fluoro-6-(trifluoromethoxy)pyridine-3-carboxylate (62 mg, 75 gmol, 1 equiv) in MeOH (1 mL) was added $K_2CO_3$ (20.7 mg, 150 μmol, 2 equiv. The mixture was stirred at rt for 0.3 h. The mixture was then filtered, and the filtrate was purified by preparative HPLC: (Phenomenex luna C18 150*25 mm*10 um; flow rate: 25 mL/min; gradient: 40-60% B over 10 min; mobile phase A:0.1% aqueous ammonium bicarbonate, mobile phase B: acetonitrile) to afford racemic 1-[7-[4-amino-5-fluoro-6-(trifluoromethoxy)pyridine-3-carbonyl]-3-(4-cyclopropyl-5-fluoro-2-hydroxy-phenyl)-2,3,7,10-tetrazatricyclo[6.4.1.04,13]trideca-1,4(13)-dien-10-yl]prop-2-en-1-one (40 mg). The racemic product was purified by SFC separation:(column: DAICEL CHIRALPAK IK(250 mm*30 mm, 10 um); mobile phase: [CO2-i-PrOH(0.1% NH3H2O)]; B %:42%, isocratic elution mode) to afford (S or R) 1-[7-[4-amino-5-fluoro-6-(trifluoromethoxy)pyridine-3-carbonyl]-3-(4-cyclopropyl-5-fluoro-2-hydroxy-phenyl)-2,3,7,10-tetrazatricyclo[6.4.1.04,13]trideca-1,4(13)-dien-10-yl]prop-2-en-1-one as the second-eluting peak (16 mg) as an off-white solid. LCMS: (ESI, m/z):605 $[M+H]^+$. $^1H$ NMR: (400 MHz, DMSO-$d_6$, ppm) δ 9.98-9.91 (m, 1H), 7.77-7.70 (m, 1H), 7.58-7.42 (m, 1H), 7.07 (d, J=10.4 Hz, 1H), 6.86 (s, 2H), 6.54 (d, J=7.2 Hz, 1H), 6.37-6.22 (m, 1H), 5.83-5.69 (m, 1H), 5.17-5.07 (m, 1H), 4.73-4.59 (m, 1H), 4.56-4.38 (m, 1H), 3.80-3.61 (m, 1H), 3.16-3.04 (m, 1H), 2.92-2.75 (m, 4H), 2.45-2.37 (m, 2H), 2.04-1.98 (m, 1H), 1.03-0.97 (m, 2H), 0.70-0.64 (m, 2H).

Example L-4: Preparation of (R or S)-1-(2-(2-amino-4-cyclobutyl-3-fluorophenyl)-5-(5-hydroxy-6-(trifluoromethyl)nicotinoyl)-2,3,4,5,5a,6,8,9-octahydro-7-1,2,5,7-tetraazabenzo[cd]azulen-7-yl)prop-2-en-1-one

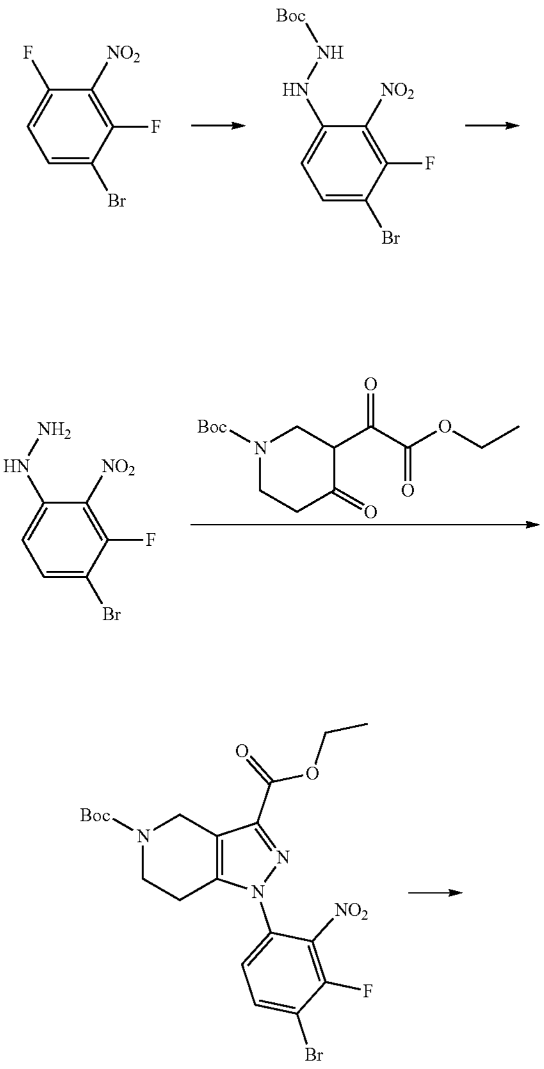

-continued

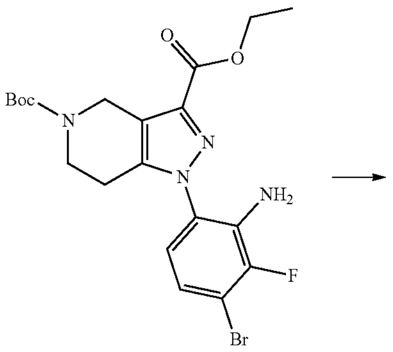

Int. L-G

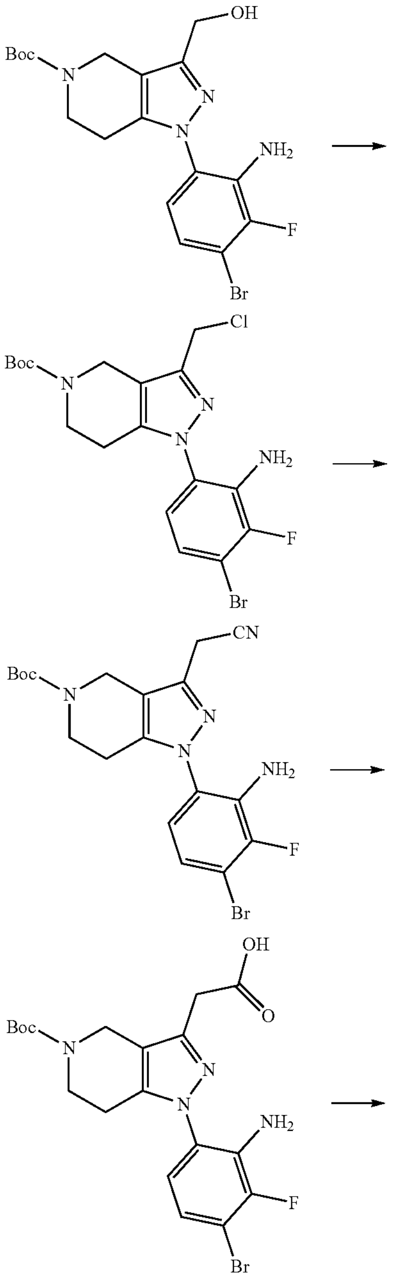

-continued
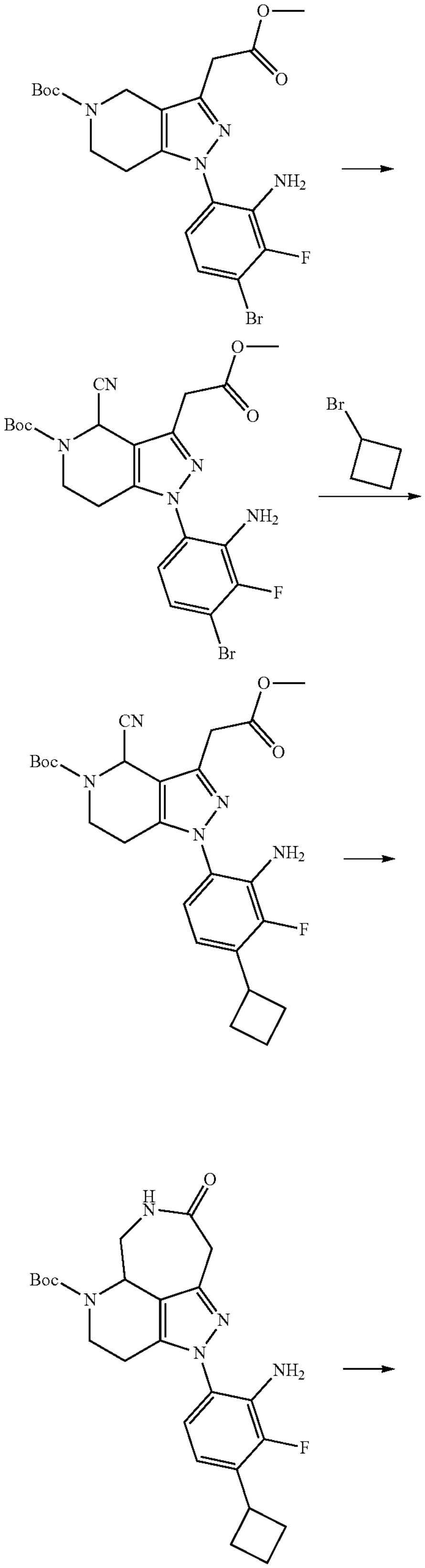
-continued
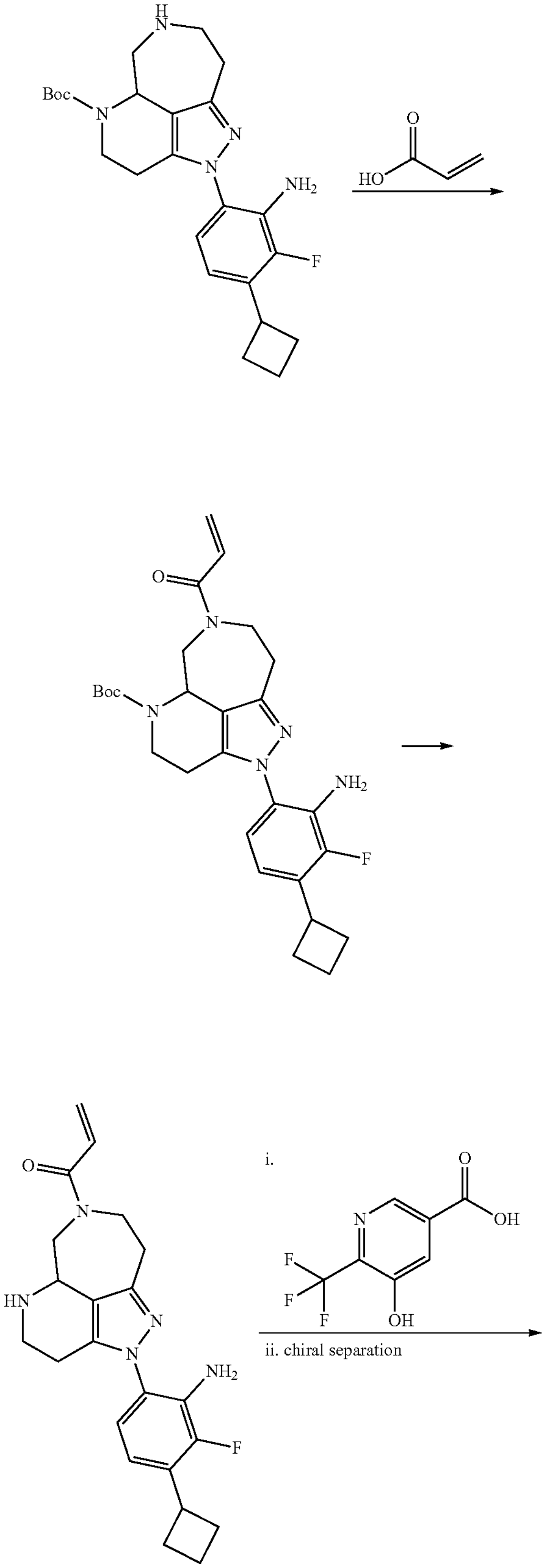

-continued

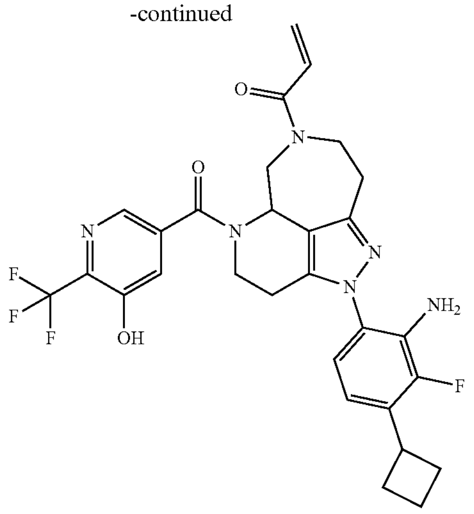

Step 1: Synthesis of Tert-Butyl 2-(4-bromo-3-fluoro-2-nitrophenyl)hydrazine-1-carboxylate To a solution of 1-bromo-2,4-difluoro-3-nitrobenzene (40 g, 1 equiv., 0.17 mol) in DMSO (400 mL) was added tert-butyl hydrazinecarboxylate (24 g, 1.1 equiv., 118 mol) drop-wise, and the mixture stirred at rt for 20 h. The mixture was then diluted with water (1000 mL), extracted with EA (300 mL×2), and concentrated under reduced pressure to afford a residue. The residue was purified by silica gel column chromatography, eluting with EA/PE (1:10) to afford tert-butyl 2-(4-bromo-3-fluoro-2-nitrophenyl)hydrazine-1-carboxylate (30 g) as yellow solid. LCMS: (ESI, m/z): 350 $[M+H]^+$.

Step 2: Synthesis of (4-bromo-3-fluoro-2-nitrophenyl)hydrazine (Hydrochloride Salt)

To a solution of tert-butyl 2-(4-bromo-3-fluoro-2-nitrophenyl)hydrazine-1-carboxylate (30 g, 1 equiv., 86 mmol) in 1,4-dioxane (300 mL) was added HCl (3.1 g, 1 equiv., 86 mmol), and the mixture stirred overnight at rt. The reaction was then concentrated under reduced pressure to afford (4-bromo-3-fluoro-2-nitrophenyl)hydrazine (25 g) as the hydrochloride salt as a yellow solid which was used in the next step directly without further purification. LCMS: (ESI, m/z): 250 $[M+H]^+$.

Step 3: Synthesis of S-(tert-butyl) 3-ethyl 1-(4-bromo-3-fluoro-2-nitrophenyl)-1,4,6,7-tetrahydro-5H-pyrazolo[4,3-c]pyridine-3,5-dicarboxylate To a solution of (4-bromo-3-fluoro-2-nitrophenyl) hydrazine hydrochloride salt (24 g, 1 equiv., 84 mmol, crude from previous step) in EtOH (480 mL) was added tert-butyl 3-(2-ethoxy-2-oxoacetyl)-4-oxopiperidine-1-carboxylate (32 g, 85 wt %, 1.1 equiv., 92 mmol), and the mixture stirred at rt for 2 h. The mixture was then diluted with water (1000 mL), extracted with EA (500 mL×2), and combined organic layers were washed with brine (100 mL×3), dried over anhydrous $Na_2SO_4$, and concentrated under reduced pressure. The residue was purified by silica gel column chromatography, eluting with PE:EA(4:1) to afford 5-(tert-butyl) 3-ethyl 1-(4-bromo-3-fluoro-2-nitrophenyl)-1,4,6,7-tetrahydro-5H-pyrazolo[4,3-c]pyridine-3,5-dicarboxylate (19 g) as a yellow solid. LCMS: (ESI, m/z): 513 $[M+H]^+$.

Step 4: Synthesis of Afford 5-(tert-butyl) 3-ethyl 1-(2-amino-4-bromo-3-fluorophenyl)-1,4,6,7-tetrahydro-5H-pyrazolo[4,3-c]pyridine-3,5-dicarboxylate (Int. L-G)

To a solution of 5-(tert-butyl) 3-ethyl 1-(4-bromo-3-fluoro-2-nitrophenyl)-1,4,6,7-tetrahydro-5H-pyrazolo[4,3-c]pyridine-3,5-dicarboxylate (19 g, 1 equiv., 37 mmol) in DMF (300 mL) was added hypodiboric acid (10 g, 3 equiv., 0.11 mol), the mixture was cooled to 0° C. To this mixture was added 4,4'-bipyridine (2.9 g, 0.5 equiv., 19 mmol) dropwise at 0° C., and the mixture was then allowed to come to rt an stirred for 20 min. The mixture was then diluted EA (500 mL) and water (1000 mL), and was extracted with EA (300 mL). The combined organic layers were washed with brine (100 mL×3), dried over anhydrous $Na_2SO_4$, filtered, and the filtrate was concentrated under reduced pressure. The residue was purified by silica gel column chromatography, eluting with EA/PE (1:4) to afford 5-(tert-butyl) 3-ethyl 1-(2-amino-4-bromo-3-fluorophenyl)-1,4,6,7-tetrahydro-5H-pyrazolo[4,3-c]pyridine-3,5-dicarboxylate (Int. L-G) (17 g) as a yellow oil. LCMS: (ESI, m/z): 483 $[M+H]^+$.

Step 5: Synthesis of Tert-Butyl 1-(2-amino-4-bromo-3-fluorophenyl)-3-(hydroxymethyl)-1,4,6,7-tetrahydro-5H-pyrazolo[4,3-c]pyridine-5-carboxylate To a solution of 5-(tert-butyl) 3-ethyl 1-(2-amino-4-bromo-3-fluorophenyl)-1,4,6,7-tetrahydro-5H-pyrazolo[4,3-c]pyridine-3,5-dicarboxylate (15 g, 1 equiv., 31 mmol) in THE (150 mL) was added $LiBH_4$ (1.0 g, 23 mL, 2 molar, 1.5 equiv., 47 mmol), and the mixture stirred at 60° C. for 3 h. The mixture was then cooled to rt, diluted with water (400 mL), extracted with EA (150 mL×2), and organic layer were washed with brine (200 mL), dried anhydrous $Na_2SO_4$, and concentrated under reduced pressure to afford tert-butyl 1-(2-amino-4-bromo-3-fluorophenyl)-3-(hydroxymethyl)-1,4,6,7-tetrahydro-5H-pyrazolo[4,3-c]pyridine-5-carboxylate (12 g) as a yellow solid which was used in the next step directly without further purification. LCMS: (ESI, m/z): 441 $[M+H]^+$.

Step 6: Synthesis of Tert-Butyl 1-(2-amino-4-bromo-3-fluorophenyl) 3-(chloromethyl)-1,4,6,7-tetrahydro-5H-pyrazolo[4,3-c]pyridine-5-carboxylate To a stirred solution of tert-butyl 1-(2-amino-4-bromo-3-fluorophenyl)-3-(hydroxymethyl)-1,4,6,7-tetrahydro-5H-pyrazolo[4,3-c]pyridine-5-carboxylate (12 g, 1 equiv., 27 mmol) in DCM (120 mL) at 0° C. was added $SOCl_2$ (3.4 g, 2.1 mL, 1.05 equiv., 29 mmol) dropwise, and the mixture stirred at 0° C. for 1 h. The mixture was then adjusted to pH=8 with the addition of $NaHCO_3$(sat., aq) (300 mL) at 0° C. and extracted with EA (100 mL×2). The combined organic layers were washed with brine (200 mL) and concentrated under reduced pressure to afford tert-butyl 1-(2-amino-4-bromo-3-fluorophenyl)-3-(chloromethyl)-1,4,6,7-tetrahydro-5H-pyrazolo[4,3-c]pyridine-5-carboxylate (10 g) as a yellow solid. The crude was the crude product was used in the next step directly without further purification. LCMS: (ESI, m/z): 459 $[M+H]^+$.

Step 7: Synthesis of Tert-Butyl 1-(2-amino-4-bromo-3-fluorophenyl)-3-(cyanomethyl)-1,4,6,7-tetrahydro-5H-pyrazolo[4,3-c]pyridine-5-carboxylate To a solution of tert-butyl 1-(2-amino-4-bromo-3-fluorophenyl)-3-(chloromethyl)-1,4,6,7-tetrahydro-5H-pyrazolo [4,3-c]pyridine-5-carboxylate (10 g, 1 equiv., 22 mmol) in MeCN (100 mL) was added TMS-CN (6.5 g, 65 mL, 1 molar, 3 equiv., 65 mmol) and TBAF (11 g, 2 equiv., 44 mmol), and the mixture stirred at rt for 16 h. The mixture was then diluted with water (300 mL), extracted with EA (100 mL×2), and the combined organic layers were washed with brine (50 mL×3) and concentrated under reduced pressure. The residue was purified by silica gel column chromatography, eluting with PE:EA (4:1) to afford tert-but 11-(2-amino-4-bromo-3-fluorophenyl)-3-(cyanomethyl)-1,4,6,7-tetrahydro-5H-pyrazolo[4,3-c]pyridine-5-carboxylate (7 g) as a white solid. LCMS: (ESI, m/z): 448 $[M+H]^+$.

Step 8: Synthesis of 2-(1-(2-amino-4-bromo-3-fluorophenyl)-5-(tert-butoxycarbonyl)-4,5,6,7-tetrahydro-JH-pyrazolo[4,3-c]pyridin-3-yl)acetic Acid To a solution of tert-butyl 1-(2-amino-4-bromo-3-fluorophenyl) 3-(cyanomethyl)-1,4,6,7-tetrahydro-5H-pyrazolo[4,3-c]pyridine-5-carboxylate (7 g, 1 equiv., 0.02 mol) in MeOH (70 mL) was added NaOH (11 g, 70 mL, 4 molar, 0.28 mol), and the resulting mixture was stirred at 80° C. for 3 h. The mixture was then cooled to 0° C., acidified to pH=5 with HCl (1 mol/L, 100 mL), extracted with EA(50 mL×2), and the combined organic layers were washed with brine (100 mL) and concentrated under reduced pressure to afford 2-(1-(2-amino-4-bromo-3-fluorophenyl)-5-(tert-butoxycarbonyl)-4,5,6,7-tetrahydro-1H-pyrazolo[4,3-c]pyridin-3-yl) acetic acid (7 g, 0.01 mol, 80%, 88% Purity) as a yellow solid, the crude was the crude product was used in the next step directly without further purification. LCMS: (ESI, m/z): 469 $[M+1]^+$.

Step 9: Synthesis of Tert-Butyl 1-(2-amino-4-bromo-3-fluorophenyl)-3-(2-methoxy-2-oxoethyl)-1,4,6,7-tetrahydro-5H-pyrazolo[4,3-c]pyridine-5-carboxylate To a solution of 2-(1-(2-amino-4-bromo-3-fluorophenyl)-5-(tert-butoxycarbonyl)-4,5,6,7-tetrahydro-1H-pyrazolo[4,3-c]pyridin-3-yl)acetic acid (7 g, 1 equiv., 0.01 mol) in DMF (70 mL) was added $K_2CO_3$ (4 g, 2 equiv., 0.03 mol) and $CH_3I$ (2 g, 1.1 equiv., 0.02 mol). The mixture was stirred at rt for 1 h. The mixture was then diluted with water (150 mL), extracted with EA (50 mL×2), and the combined organic layers were washed with brine (100 mL) and concentrated under reduced pressure. The residue was purified by silica gel column chromatography, eluting with PE:EA(3:1) to afford tert-butyl 1-(2-amino-4-bromo-3-fluorophenyl)-3-(2-methoxy-2-oxoethyl)-1,4,6,7-tetrahydro-5H-pyrazolo[4,3-c]pyridine-5-carboxylate (5 g) as a yellow solid. LCMS: (ESI, m/z): 483 $[M+H]^+$.

Step 10: Synthesis of Tert-Butyl 1-(2-amino-4-bromo-3-fluorophenyl)-4-cyano-3-(2-methoxy-2-oxoethyl)-1,4,6,7-tetrahydro-5H-pyrazolo[4,3-c]pyridine-5-carboxylate To a solution of tert-butyl 1-(2-amino-4-bromo-3-fluorophenyl)-3-(2-methoxy-2-oxoethyl)-1,4,6,7-tetrahydro-5H-pyrazolo[4,3-c]pyridine-5-carboxylate (2 g, 1 equiv., 4 mmol) in MeCN (20 mL) was added TEMPO, BF4 (2 g, 2 equiv., 8 mmol) and AcOH (0.5 g, 0.5 mL, 2 equiv., 8 mmol), and the mixture was purged with nitrogen bubbling for 2 min. The mixture was then cooled with stirring at 0° C., after which TMS-CN (1 g, 2 mL, 3 equiv., 0.01 mol) was added dropwise. The mixture was allowed to come to rt and was stirred overnight, after which the mixture was diluted with water (50 mL), extracted with EA (20 mL×2), and the combined organic layers were washed with brine (40 mL), and dried anhydrous $Na_2SO_4$. After filtration the filtrate was concentrated under reduced pressure and the residue was purified by silica gel column chromatography, eluting with PE:EA(4:1) to afford tert-butyl 1-(2-amino-4-bromo-3-fluorophenyl)-4-cyano-3-(2-methoxy-2-oxoethyl)-1,4,6,7-tetrahydro-5H-pyrazolo[4,3-c]pyridine-5-carboxylate (1.2 g) as a white solid. LCMS: (ESI, m/z): 508 $[M+H]^+$.

Step 11: Synthesis of Tert-Butyl 1-(2-amino-4-cyclobutyl-3-fluorophenyl)-4-cyano-3-(2-methoxy-2-oxoethyl)-1,4,6,7-tetrahydro-5H-pyrazolo[4,3-c]pyridine-5-carboxylate To a solution of tert-butyl 1-(2-amino-4-bromo-3-fluorophenyl)-4-cyano-3-(2-methoxy-2-oxoethyl)-1,4,6,7-tetrahydro-5H-pyrazolo[4,3-c]pyridine-5-carboxylate (1.2 g, 1 equiv., 2.4 mmol) in DMA (120 mL) was added picolinimidamide, HCl (0.37 g, 1 equiv., 2.4 mmol), bromocyclobutane (1.6 g, 5 equiv., 12 mmol), $NiCl_2$ (92 mg, 0.3 equiv., 0.71 mmol), TBAI (0.87 g, 1 equiv., 2.4 mmol) and Mn (0.39 g, 3 equiv., 7.1 mmol). The resulting mixture was purged with nitrogen for 2 min, after which the mixture was heated to 80° C. and stirred for 3 h. The mixture was cooled to rt, filtered to remove insoluble solids, diluted with water (50 mL), and extracted with EA(20 mL×2). The combined organic layers were washed with brine(40 mL), dried over anhydrous $Na_2SO_4$, filtered, and concentrated under reduced pressure. The residue was purified by silica gel column chromatography, eluting with EA/PE (1:4) to afford tert-butyl 1-(2-amino-4-cyclobutyl-3-fluorophenyl)-4-cyano-3-(2-methoxy-2-oxoethyl)-1,4,6,7-tetrahydro-5H-pyrazolo[4,3-c]pyridine-5-carboxylate as a yellow solid. LCMS: (ESI, m/z): 484 $[M+H]^+$.

Step 12: Synthesis of Tert-Butyl 2-(2-amino-4-cyclobutyl-3-fluorophenyl)-8-oxo-2,3,4,5a,6,7,8,9-octahydro-5H-1,2,5,7-tetraazabenzo[cd]azulene-5-carboxylate To a solution of tert-butyl 1-(2-amino-4-cyclobutyl-3-fluorophenyl)-4-cyano-3-(2-methoxy-2-oxoethyl)-1,4,6,7-tetrahydro-5H-pyrazolo[4,3-c]pyridine-5-carboxylate (300 mg, 1 equiv., 620 μmol) in MeOH (8 mL) was added Raney nickel (300 mg, 50% Wt). The mixture was purged with nitrogen (×3) and then was pressurized 4.0 MPa with hydrogen. The resulting mixture was stirred at 60° C. for 6 h. The reaction mixture was then cooled to rt and the mixture was filtered and rinsed with EA (5×10 mL). The combined filtrate was concentrated under vacuum to give a residue. The residue was purified by reversed-phase flash chromatography with these conditions: Column-C18; mobile phase, Water (1% $NH_4HCO_3$) and ACN (gradient of 20% B to 70% B in 10 min to afford tert-butyl 2-(2-amino-4-cyclobutyl-3-fluorophenyl)-8-oxo-2,3,4,5a,6,7,8,9-octahydro-5H-1,2,5,7-tetraazabenzo[cd]azulene-5-carboxylate (230 mg) as a white solid. LCMS: (ESI, m/z): 456 $[M+H]^+$.

Step 13: Synthesis of Tert-Butyl 2-(2-amino-4-cyclobutyl-3-fluorophenyl)-2,3,4,5a,6,7,8,9-octahydro-5H-1,2,5,7-tetraazabenzo[cd]azulene-5-carboxylate To a solution of tert-butyl 2-(2-amino-4-cyclobutyl-3-fluorophenyl)-8-oxo-2,3,4,5a,6,7,8,9-octahydro-5H-1,2,5,7-tetraazabenzo[cd]azulene-5-carboxylate (200 mg, 1 equiv., 439 μmol) in THF (4 mL) was added $BH_3$·THF (151 mg, 1.76 mL, 1 molar, 4 equiv., 1.76 mmol). The mixture was stirred at 60° C. for 1 h, after which the reaction mixture was quenched with MeOH and concentrated to afford tert-butyl 2-(2-amino-4-cyclobutyl-3-fluorophenyl)-2,3,4,5a,6,7,8,9-octahydro-5H-1,2,5,7-tetraazabenzo[cd]azulene-5-carboxylate (200 mg) as a yellow solid which was used in the next step directly without further purification.

Step 14: Synthesis of Tert-Butyl 7-acryloyl-2-(2-amino-4-cyclobutyl-3-fluorophenyl)-2,3,4,5a,6,7,8,9-octahydro-5H-1,2,5,7-tetraazabenzo[cd]azulene-5-carboxylate To a solution of tert-butyl 2-(2-amino-4-cyclobutyl-3-fluorophenyl)-2,3,4,5a,6,7,8,9-octahydro-5H-1,2,5,7-tetraazabenzo[cd]azulene-5-carboxylate (100 mg, 1 equiv., 226 gmol) in DMF (1 mL) were added acrylic acid (16.3 mg, 15.5 μL, 1 equiv., 226 μmol), T3P (216 mg, 200 μL, 50% wt, 1.5 equiv., 340 μmol) and DIEA (87.8 mg, 118 μL, 3 equiv., 679 μmol). The mixture was stirred at rt for 1 h, after which the mixture was diluted with water 120 mL) and EA (20 mL), and the aqueous layer was extracted with EA (2×20 mL). The combined organic layers were washed with saturated brine (2×20 mL), dried over anhydrous sodium sulfate and concentrated to give a residue. The residue was purified by reversed-phase flash chromatography with these conditions: Column: C18; mobile phase, $NH_4HCO_3$ in water with a gradient of MeCN 30% to 80% in 10 min; detector, UV 254 nm; to afford tert-butyl 7-acryloyl-2-2-amino-4-cyclobutyl-3-fluorophenyl)-2,3,4,5a,6,7,8,9-octahydro-5H-1,2,5,7-tetraazabenzo[cd]azulene-5-carboxylate (30 mg) as a white solid. LCMS: (ESI, m/z): 496 $[M+H]^+$.

Step 15: Synthesis of 1-(2-(2-amino-4-cyclobutyl-3-fluorophenyl)-2,3,4,5,a,6,8,9-octahydro-7H-1,2,5,7-tetraazabenzo[cd]azulen-7-yl)prop-2-en-1-one The solution of tert-butyl 7-acryloyl-2-(2-amino-4-cyclobutyl-3-fluorophenyl)-2,3,4,5a,6,7,8,9-octahydro-5H-1,2,5,7-tetraazabenzo[cd]azulene-5-carboxylate (30 mg, 1 equiv., 61 μmol) in TFA (0.15 mL) and DCM (0.3 mL) was stirred at rt for 30 min. The solvent was removed under reduced pressure to afford 1-(2-(2-amino-4-cyclobutyl-3-fluorophenyl)-2,3,4,5,5a,6,8,9-octahydro-7H-1,2,5,7-tetraazabenzo[cd]azulen-7-yl)prop-2-en-1-one (30 mg) as a crude yellow oil which was used in the next step directly without further purification. LCMS: (ESI, m/z): 396 $[M+H]^+$.

Step 16: Synthesis of (R or S)-1-(2-(2-amino-4-cyclobutyl-3-fluorphenyl)-5-(5-hydroxy-6-(trifluoromethyl)nicotinoyl)-2,3,4,5,5a,6,8,9-octahydro-7H-1,2,5,7-tetraazabenzo[cd]azulen-7-yl)prop-2-en-1-one To a solution of 1-(2-(2-amino-4-cyclobutyl-3-fluorophenyl)-2,3,4,5,5a,6,8,9-octahydro-7H-1,2,5,7-tetraazabenzo[cd]azulen-7-yl)prop-2-en-1-one (25 mg, 1 equiv., 63 μmol) in DMF (1 mL) were added HATU (36 mg, 1.5 equiv., 95 μmol), 5-hydroxy-6-(trifluoromethyl)nicotinic acid (10 mg, 0.8 equiv., 51 μmol) and DIEA (25 mg, 33 μL, 3 equiv., 0.19 mmol). The mixture was stirred at rt for 1 h, after which the mixture was diluted with water (20 TL) and EA (20 mL), and the aqueous layer was extracted with EA (2×20 mL). The combined organic layers were washed with saturated brine (2×20 mL), dried over anhydrous sodium sulfate and concentrated to give a residue. The residue was purified by Prep-HPLC (Column: XBridge BEH Shield RP18 5 m, 30 mm*150 mm; Mobile Phase A: Water (10 mmol/L $NH_4HCO_3$), Mobile Phase B: ACN; Flow rate: 60 mL/min; Gradient: 25% B to 45% B in 10 min; Wave Length: UV 254 nm/220 nm) to afford racemic 1-(2-(2-amino-4-cyclobutyl-3-fluorophenyl)-5-(5-hydroxy-6-(trifluoromethyl)nicotinoyl)-2,3,4,5,5a,6,8,9-octahydro-7H-1,2,5,7-tetraazabenzo[cd]azulen-7-yl)prop-2-en-1-one (6 mg). The racemic compound was purified by Chiral Prep-HPLC with the following conditions: (Column: CHIRAL ART Cellulose-SC, 2*25 cm 5 μm; Mobile Phase A: Hex(0.1% FA)—HPLC, Mobile Phase B: EtOH:DCM=1:1; Flow rate: 20 mL/min; Gradient: isocratic 35; Wave Length: UV 254/220 nm; RT1(min): 6.6; RT2(min): 10) to afford (R or S)-1-(2-(2-amino-4-cyclobutyl-3-fluorophenyl)-5-(5-hydroxy-6-(trifluoromethyl)nicotinoyl)-2,3,4,5,5a,6,8,9-octahydro-7H-1,2,5,7-tetraazabenzo[cd]azulen-7-yl)prop-2-en-1-one (1 mg) as the second-eluting peak as a white solid. LCMS: (ESI, m/z): 585 $[M+H]^+$. $^1$H NMR: (400 MHz, Chloroform-d, ppm) δ 8.66-7.80 (m, 2H), 7.69-7.33 (m, 1H), 6.82-6.43 (m, 4H), 6.06-5.72 (m, 1H), 5.34-5.04 (m, 1H), 4.90 (s, 1H), 4.75-4.20 (m, 4H), 3.84-3.66 (m, 1H), 3.20-2.67 (m, 6H), 2.45-2.02 (m, 6H).

Example L-5: Preparation of (R or S)-1-(5-(4-amino-6-(trifluoromethyl)nicotinoyl)-2-(2-hydroxy-4-((trifluoromethyl)thio)phenyl)-2,3,4,5,5a,6,8,9-octahydro-7H-1,2,5,7-tetraazabenzo[cd]azulen-7-yl)prop-2-en-1-one

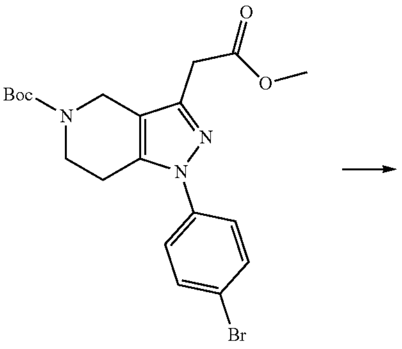

Int. D

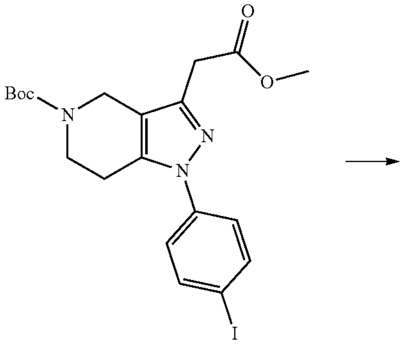

-continued
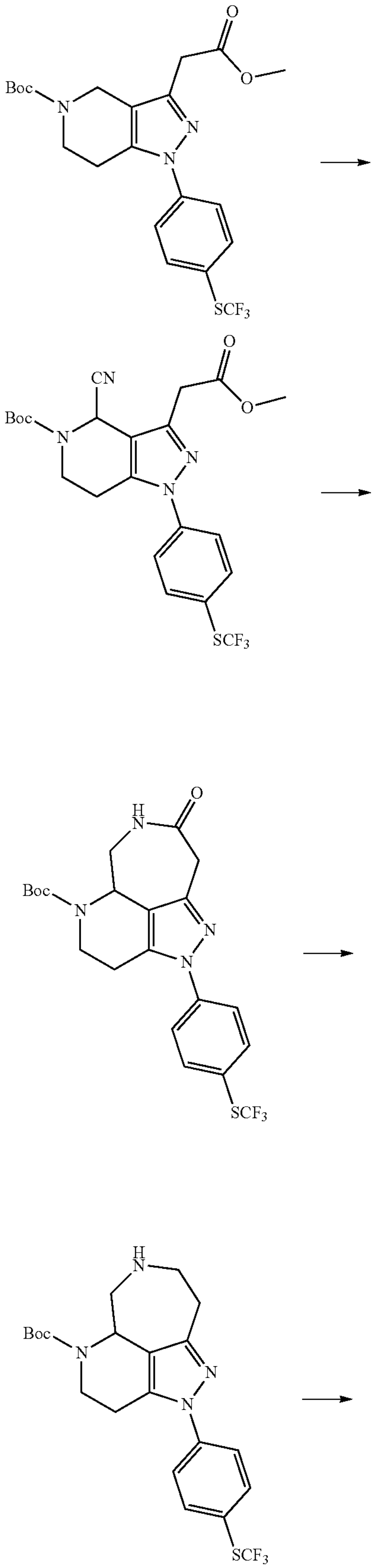
-continued
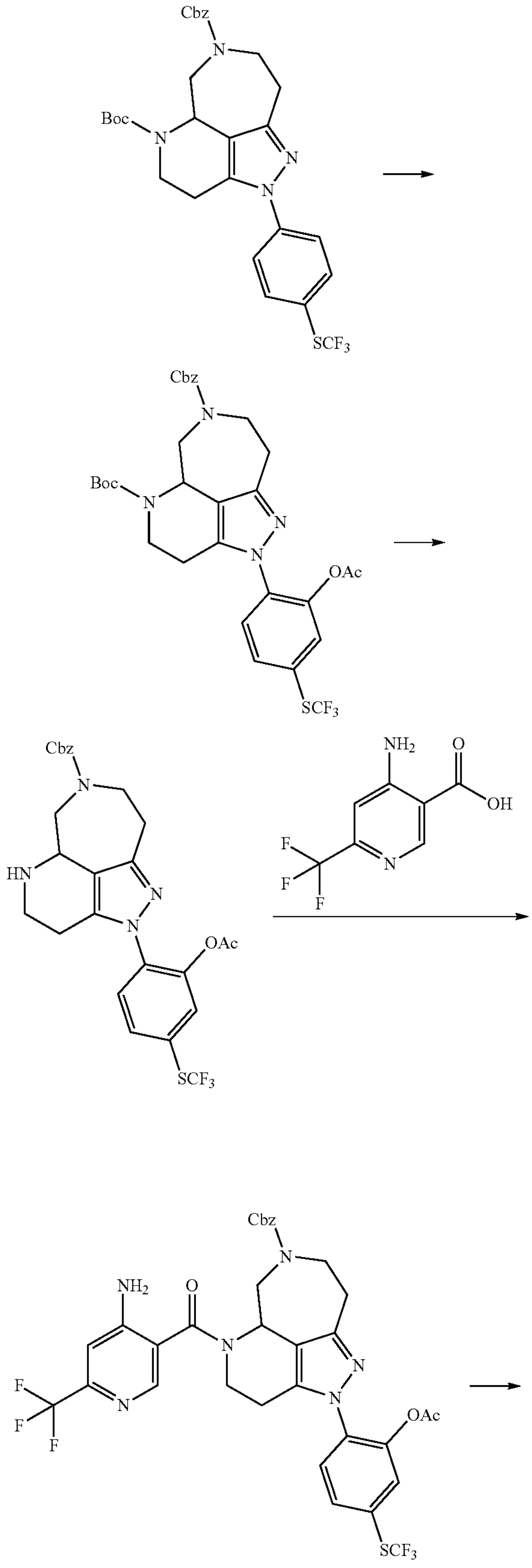

-continued

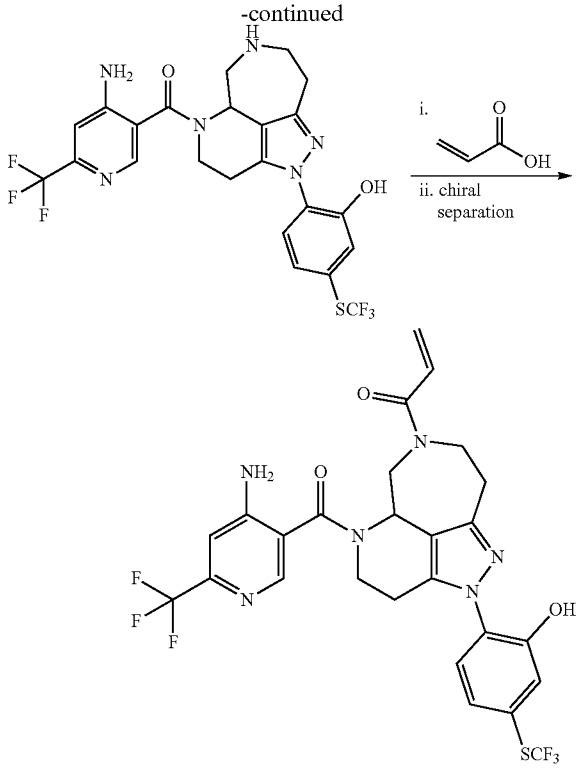

Step 1: Synthesis of Tert-Butyl 1-(4-iodophenyl)-3-(2-methoxy-2-oxoethyl)-1,4,6,7-tetrahydro-5H-pyrazolo[4,3-c]pyridine-5-carboxylate To a solution of tert-butyl 1-(4-bromophenyl)-3-(2-methoxy-2-oxoethyl)-1,4,6,7-tetrahydro-5H-pyrazolo[4,3-c]pyridine-5-carboxylate (10 g, 1 equiv., 22 mmol) in 1,4-dioxane (200 mL) were added NaI (10 g, 3 equiv., 67 mmol), DMEDA (1.4 g, 0.7 equiv., 16 mmol), and CuI (1.7 g, 0.4 equiv., 8.9 mmol). The reaction vessel was placed under a positive pressure of nitrogen and subjected to three back-filling cycles under high vacuum. The resulting mixture was stirred for 24 h at 100° C. under a nitrogen atmosphere, after which it was cooled to rt. The reaction was quenched with water (500 mL) and the aqueous layer was extracted with EA (2×200 mL). The combined organic layers were washed with saturated brine (2×500 mL), dried over anhydrous sodium sulfate and concentrated to give a residue. The crude product was purified by silica gel chromatography, eluting with PE:EA=4:1 to give tert-butyl 1-(4-iodophenyl)-3-(2-methoxy-2-oxoethyl)-1,4,6,7-tetrahydro-5H-pyrazolo[4,3-c]pyridine-5-carboxylate (9.5 g) as a light yellow solid. LCMS: (ESI, m/z): 498 $[M+H]^+$.

Step 2: Synthesis of Tert-Butyl 3-(2-methoxy-2-oxoethyl)-1-(4-((trifluoromethyl)thio)phenyl)-1,4,6,7-tetrahydro-5H-pyrazolo[4,3-c]pyridine-5-carboxylate Into four 30 mL vials were added a split solution of tert-butyl 1-(4-iodophenyl)-3-(2-methoxy-2-oxoethyl)-1,4,6,7-tetrahydro-5H-pyrazolo[4,3-c]pyridine-5-carboxylate (4 g, 1 equiv., 8 mmol), 2,2'-bipyridine (2 g, 2 mL, 1.5 equiv., 0.01 mol), and $CuSCF_3$ (2 g, 1.5 equiv., 0.01 mol) in MeCN (40 mL). The four reaction mixtures were evacuated and backfilled with argon (×3) and were then irradiated with microwave radiation for 4 hours at 140° C. The reaction mixtures were quenched with water (100 mL) and combined. The combined aqueous layers was extracted with EA (2×100 mL), and the combined organic layers were washed with saturated brine (2×200 mL), dried over anhydrous sodium sulfate and concentrated to give a residue. The crude product was purified by silica gel chromatography eluting with PE:EA=3:1 to give tert-butyl 3-(2-methoxy-2-oxoethyl)-1-(4-((trifluoromethyl)thio)phenyl)-1,4,6,7-tetrahydro-5H-pyrazolo[4,3-c]pyridine-5-carboxylate (2.8 g) as a white solid. LCMS: (ESI, m/z): 472 $[M+H]^+$.

Step 3: Synthesis of Tert-Butyl 4-cyano-3-(2-methoxy-2-oxoethyl)-1-(4-((trifluoromethyl)thio)phenyl)-1,4,6,7-tetrahydro-5H-pyrazolo[4,3-c]pyridine-S-carboxylate To a solution of tert-butyl 3-(2-methoxy-2-oxoethyl)-1-(4-((tri oromethyl)thio)phenyl)-1,4,6,7-tetrahydro-5H-pyrazolo[4,3-c]pyridine-5-carboxylate (2.8 g, 1 equiv., 5.9 mmol) in MeCN (28 mL) were added AcOH (0.71 g, 0.68 mL, 2 equiv., 12 mmol), $TEMPO{\cdot}BF_4$ (4.3 g, 3 equiv., 18 mmol), and TMSCN (1.8 g, 2.2 mL, 3 equiv., 18 mol). The resulting mixture was stirred for 2 h at rt under a nitrogen atmosphere. The reaction was quenched with a half of saturated solution of $NaHCO_3$ (200 mL), and the aqueous layer was extracted with EA (3×200 mL). The combined organic layers were washed with saturated brine (2×500 mL), dried over anhydrous sodium sulfate and concentrated to give a residue. The crude product was purified by silica gel chromatography, eluting with PE:EA=3:1 to give tert-butyl 4-cyano-3-(2-methoxy-2-oxoethyl)-1-(4-((trifluoromethyl)thio)phenyl)-1,4,6,7-tetrahydro-5H-pyrazolo[4,3-c]pyridine-5-carboxylate (2.6 g) as a light yellow solid. LCMS: (ESI, m/z): 497 $[M+H]^+$.

Step 4: Synthesis of Tert-Butyl 8-oxo-2-(4-((trifluoromethyl)thio)phenyl)-2,3,4,5a,6,7,8,9-octahydro-5H-1,2,5,7-tetraazabenzo[cd]azulene-5-carboxylate A 300 mL pressure tank reactor was charged with tert-butyl 4-cyano-3-(2-methoxy-2-oxoethyl)-1-(4-((trifluoromethyl)thio)phenyl)-1,4,6,7-tetrahydro-5H-pyrazolo[4,3-c]pyridine-5-carboxylate (2.6 g, 1 equiv., 5.2 mmol) in MeOH (52 mL) and $NH_3$ in MeOH (7 moL/L, 5.2 mL)) and Raney Ni (2.6 g, 50 wt %, 4.2 equiv., 22 mmol) were added. The resulting mixture was stirred for 16 h at 50° C. under a 4 MPa hydrogen atmosphere. The mixture was then cooled to rt and filtered, and the filter cake was washed with DCM (3×200 mL). T e combined filtrate was concentrated under reduced pressure and the residue was purified by silica gel chromatography, eluting with 100% EA to give tert-butyl 8-oxo-2-(4-((trifluoromethyl)thio)phenyl)-2,3,4,5a,6,7,8,9-octahydro-5H-1,2,5,7-tetraazabenzo[cd]azulene-5-carboxylate (1.5 g) as a white solid.

Step 5: Tert-Butyl 2-(4-((trifluoromethyl)thio)phenyl)-2,3,4,5a,6,7,8,9-octahydro-5H-1,2,5,7-tetraazabenzo[cd]azulene-5-carboxylate To a solution of tert-butyl 8-oxo-2-(4-((trifluoromethyl)thio)phenyl)-2,3,4,5a,6,7,8,9-octahydro-5H-1,2,5,7-tetraazabenzo[cd]azulene-5-carboxylate (1.5 g, 1 equiv., 3.2 mmol) in THF (15 mL) was added $BH_3{\cdot}THF$ (1.1 g, 4 equiv., 13 mmol) at 0° C. The mixture was stirred for 2 hours at 60° C., after which the reaction mixture was cooled to 0° C. and quenched with MeOH (50 mL). The resulting mixture was concentrated under vacuum to afford tert-butyl 2-(4-((trifluoromethyl)thio)phenyl)-2,3,4,5a,6,7,8,9-octahydro-5H-1,2,5,7-tetraazabenzo[cd]azulene-5-carboxylate (1.65 g, 3.63 mmol) as a crude solid which was used in the next step directly without further purification. LCMS: (ESI, m/z): 455 $[M+H]^+$.

Step 6: Synthesis of 7-benzyl 5-(tert-butyl) 2-(4-((trifluoromethyl)thio)phenyl)-3,4,5a,6,8,9-hexahydro-2H-1,2,5,7-tetraazabenzo[cd]azulene-5,7-dicarboxylate To a solution of tert-butyl 2-(4-((trifluoromethyl)thio)phenyl)-2,3,4,5a,6,7,8,9-octahydro-5H-1,2,5,7-tetraazabenzo[cd]azulene-5-carboxylate (1.5 g, 1 equiv., 3.3 mmol) in DCM (30 mL) were added TEA (3.3 g, 4.6 mL, 10 equiv., 33 mmol) and Cbz-Osu (4.1 g, 5 equiv., 17 mmol). The resulting mixture was stirred for 16 hours at 40° C., after which the reaction was cooled to rt and quenched with water (100 mL). The aqueous layer was extracted with DCM (2×50 mL) and the combined organic layers were washed with saturated brine (200 mL), dried over anhydrous sodium sulfate, filtered, and concentrated to give a residue. The crude product was purified by silica gel chromatography, eluting with PE:EA=4:1 to give 7-benzyl 5-(tert-butyl) 2-(4-((trifluoromethyl)thio)phenyl)-3,4,5a,6,8,9-hexahydro-2H-1,2,5,7-tetraaabenzo[cd]azulene-5,7-dicarboxylate (1.3 g) as a white solid. LCMS: (ESI, m/z): 589 $[M+H]^+$.

Step 7: Synthesis of 7-benzyl 5-(tert-butyl) 2-(2-acetoxy-4-((trifluoromethyl)thio)phenyl)-3,4,5a,6,8,9-hexahydro-2H-1,2,5,7-tetraazabenzo[cd]azulene-5,7-dicarboxylate To a solution of 7-benzyl 5-(tert-butyl) 2-(4-((trifluoromethyl)thio)phenyl)-3,4,5a,6,8,9-hexahydro-2H-1,2,5,7-tetraazabenzo[cd]azulene-5,7-dicarboxylate (1.1 g, 1 equiv., 1.9 mmol) in AcOH (5.5 mL) and MeCN (5.5 mL) were added $Pd(OAc)_2$ ($^{63}$ mg, 0.15 equiv., 0.28 mmol) and PIDA (0.90 g, 1.5 equiv., 2.8 mmol). The reaction vessel was placed under a positive pressure of nitrogen and subjected to three backfilling cycles under high vacuum. The resulting mixture was stirred for 2 hours at 90° C. under a nitrogen atmosphere, after which the reaction was cooled to rt and quenched with sat. $NaHCO_3$ (50 mL). The aqueous layer was extracted with EA (2×20 mL) and the combined organic layers were washed with saturated brine (3×20 mL), dried over anhydrous sodium sulfate, filtered and concentrated to give a residue. The crude product was purified by silica gel chromatography, eluting with PE:EA=3:1 to give 7-benzyl 5-(tert-butyl) 2-(2-acetoxy-4-((trifluoromethyl)thio)phenyl)-3,4,5a,6,8,9-hexahydro-2H-1,2,5,7-tetraazabenzo[cd]azulene-5,7-dicarboxylate (200 mg) as a yellow solid. LCMS: (ESI, m/z): 647 $[M+H]^+$.

Step 8: Synthesis of Benzyl 2-(2-acetoxy-4-((trifluoromethyl)thio)phenyl)-2,3,4,5,5a,6,8,9-octahydro-7H-1,2,5,7-tetraazabenzo[cd]azulene-7-carboxylate A solution of 7-benzyl 5-(tert-butyl) 2-(2-acetoxy-4-((trifluoromethyl)thio)phenyl)-3,4,5a,6,8,9-hexahydro-2H-1,2,5,7-tetraazabenzo[cd]azulene-5,7-dicarboxylate (170 mg, 1 equiv., 263 μmol) in DCM (3 mL) and TFA (1 mL) was stirred at rt or 0.5 h, after which the solvent was removed under reduced pressure to afford benzyl 2-(2-acetoxy-4-((trifluoromethyl)thio)phenyl)-2,3,4,5,5a,6,8,9-octahydro-7H-1,2,5,7-tetraazabenzo[cd]azulene-7-carboxylate (200 mg, crude) as a crude yellow oil which was used in the next step directly without further purification. LCMS: (ESI, m/z): 547 $[M+H]^+$.

Step 9: Synthesis Benzyl 2-(2-acetoxy-4-((trifluoromethyl)thio)phenyl)-5-(4-amino-6-(trifluoromethyl)nicotinoyl)-2,3,4,5,5a,6,8,9-octahydro-7H-1,2,5,7-tetraazabenzo[cd]azulene-7-carboxylate To a solution of benzyl 2-(2-acetoxy-4-((trifluoromethyl)thio)phenyl)-2,3,4,5,5a,6,8,9-octahydro-7H-1,2,5,7-tetraazabenzo[cd]azulene-7-carboxylate (200 mg, 1 equiv., 366 μmol) in DMA (4 mL) were added CMPI (187 mg, 2 equiv., 732 μmol) DIEA (236 mg, 319 μL, 5 equiv., 1.83 mmol) and 4-amino-6-(trifluoromethyl)nicotinic acid (151 mg, 2 equiv., 732 μmol). The mixture was stirred at rt for 1 h, after which the reaction was quenched with water (20 mL). The resulting mixture was extracted with EA (3×20 mL) and the combined organic layers were washed with brine (2×50 mL), dried over anhydrous $Na_2SO_4$, and filtered. The filtrate was concentrated under reduced pressure and the residue was purified by silica gel chromatography, eluting with PE:EA=1:20 to give benzyl 2-(2-acetoxy-4-((trifluoroethyl)thio)phenyl)-5-(4-amino-6-(trifluoromethyl)nicotinoyl)-2,3,4,5,5a,6,8,9-octahydro-7H-1,2,5,7-tetraazabenzo[cd]azulene-7-carboxylate (130 mg) as a yellow solid. LCMS: (ESI, m/z): 735 $[M+H]^+$.

Step 10: Synthesis of (4-amino-6-(trifluoromethyl)pyridin-3-yl)(2-(2-hydroxy-4-((trifluoromethyl)thio)phenyl)-2,3,4,5a,6,7,8,9-octahydro-5H-1,2,5,7-tetraazabenzo[cd]azulen-5-yl)methanone To a solution of benzyl 2-(2-acetoxy-4-((trifluoromethyl)thio)phenyl)-5-(4-amino-6-(trifluoromethyl)nicotinoyl)-2,3,4,5,5a,6,8,9-octahydro-7H-1,2,5,7-tetraazabenzo[cd]azulene-7-carboxylate (120 mg, 1 equiv., 163 mol) was added HBr (1.2 mL) at 0° C. The mixture was then heated and stirred at 40° C. for 0.5 h, after which the reaction was cooled and quenched with sat. $NaHCO_3$ (20 mL) at 0° C. The resulting mixture was extracted with EA (3×10 mL) and the combined organic layers were washed with brine (2×20 mL), dried over anhydrous $Na_2SO_4$, filtered and concentrated under reduced pressure. The residue was purified by reversed-phase flash chromatography with the following conditions: column, C18 silica gel; mobile phase, Water (0.1% $NH_4HCO_3$) in ACN, 10% to 95% gradient in 20 min; detector, UV 254 nm to afford (4-amino-6-(trifluoromethyl)pyridin-3-yl)(2-(2-hydroxy-4-((trifluoromethyl)thio)phenyl)-2,3,4,5a,6,7,8,9-octahydro-5H-1,2,5,7-tetraazabenzo[cd]azulen-5-yl)methanone (30 mg) as a light yellow solid. LCMS: (ESI, m/z): 559 $[M+H]^+$.

Step 11: Synthesis of (R or S)-1-(5-(4-amino-6-(trifluoromethyl)nicotinoyl)-2-(2-hydroxy-4-((trifluoromethyl)thio)phenyl)-2,3,4,5,5a,6,8,9-octahydro-7H-1,2,5,7-tetraazabenzo[cd]azulen-7-yl)prop-2-en-1-one To a solution of (4-amino-6-(trifluoromethyl)pyridin-3-yl)(2-(2-hydroxy-4-((trifluoromethyl)thio)phenyl)-2,3,4,5a,6,7,8,9-octahydro-5H-1,2,5,7-tetraazabenzo[cd]azulen-5-yl)methanone (28 mg, 1 equiv., 50 μmol) in DMA (0.56 mL) were added T3P (32 mg, 2 equiv., 0.10 mmol), DIEA (19 mg, 26 μL, 3 equiv., 0.15 mmol) and acrylic acid (4.3 mg, 1.2 equiv., 60 gmol). The mixture was stirred at rt for 3 h, after which the reaction was quenched with water (10 mL). The resulting mixture was extracted with EA (3×10 mL). The combined organic layers were washed with brine (2×20 mL), dried over anhydrous $Na_2SO_4$, and filtered. The filtrate was concentrated under reduced pressure and the residue was purified by Prep-HPLC (Column: YMC-Actus Triart C18 ExRS 30*250 mm, 5 μm; Mobile Phase A: Water(10 mmol/L $NH_4HCO_3$), Mobile Phase B: ACN; Flow rate: 60 mL/min mL/min; Gradient: 5% B to 5% B in 1 min, 5% B to 40% B in 2 min, 40% to 60% B in 11 min) to afford racemic 1-(5-(4-amino-6-(trifluoromethyl)nicotinoyl)-2-(2-hydroxy-4-((trifluoromethyl)thio)phenyl)-2,3,4,5,5a,6,8,9-octahydro-7H-1,2,5,7-tetraazabenzo[cd]azulen-7-yl)prop-2-en-1-one (10 mg). The racemic compound was separated by the following conditions: (Column: CHIRALPAK IA, 3*25 cm, 5 μm; Mobile Phase A: Hex(0.1% FA)—HPLC, Mobile Phase B: EtOH; Flow rate: 40 mL/min; Gradient: isocratic 20; Wave Length: 202/220 nm; RT1(min): 9.5; RT2(min): 14) to afford (R or S)-1-(5-(4-amino-6-(trifluoromethyl) nicotinoyl)-2-(2-hydroxy-4-((trifluoromethyl)thio)phenyl)-2,3,4,5,5a,6,8,9-octahydro-7H-1,2,5,7-tetraazabenzo[cd] azulen-7-yl)prop-2-en-1-one as the second-eluting peak. LCMS: (ESI, m/z): 613 [M+H]. $^1H$ NMR (400 MHz, Chloroform-d) δ 10.74 (s, 1H), 8.36 (s, 1H), 7.44-7.25 (m, 1H), 7.22-7.16 (m, 1H), 7.14-7.08 (m, 1H), 7.05 (s, 1H), 6.98-6.75 (m, 1H), 6.68-6.48 (m, 1H), 6.00-5.80 (m, 1H), 5.39 (s, 3H), 0.05 (d, J=13.4 Hz, 1H), 4.65-4.63 (m, 1H), 4.50-4.10 (m, 1H), 3.29-3.05 (m, 5H), 3.05-2.85 (m, 1H), 2.83-2.68 (m, 1H).

Example L-6: Preparation of (R or S)-1-(5-(4-amino-6-(trifluoromethyl)nicotinoyl)-2-benzyl-2,3,4,5,5a,6,8,9-octahydro-7H-1,2,5,7-tetraazabenzo[cd] azulen-7-yl)prop-2-en-1-one

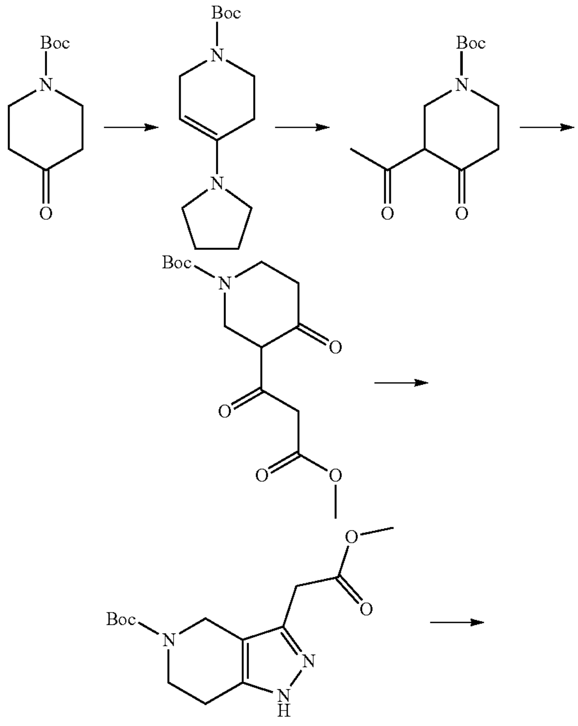

Int. L-B

-continued

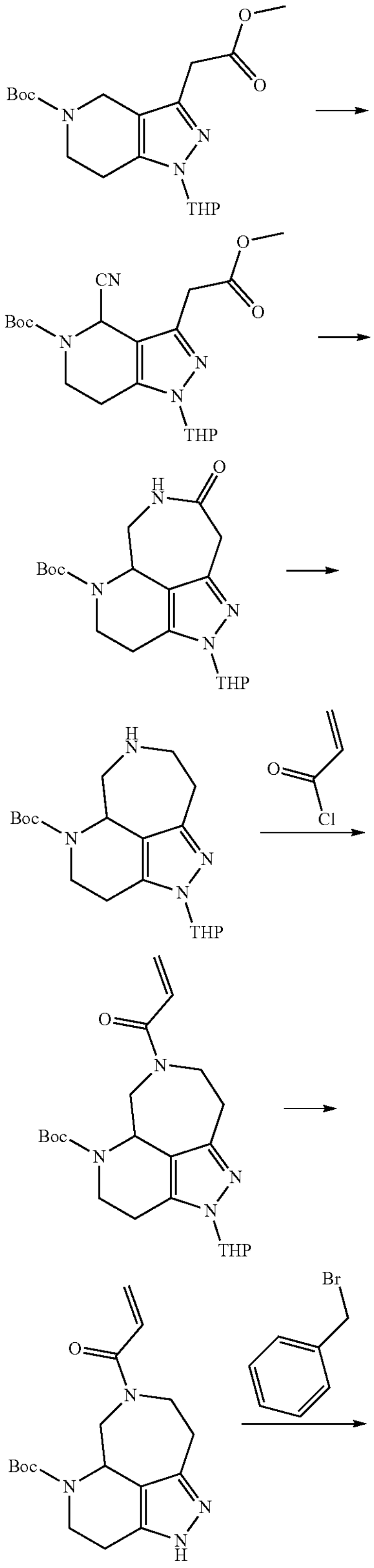

-continued

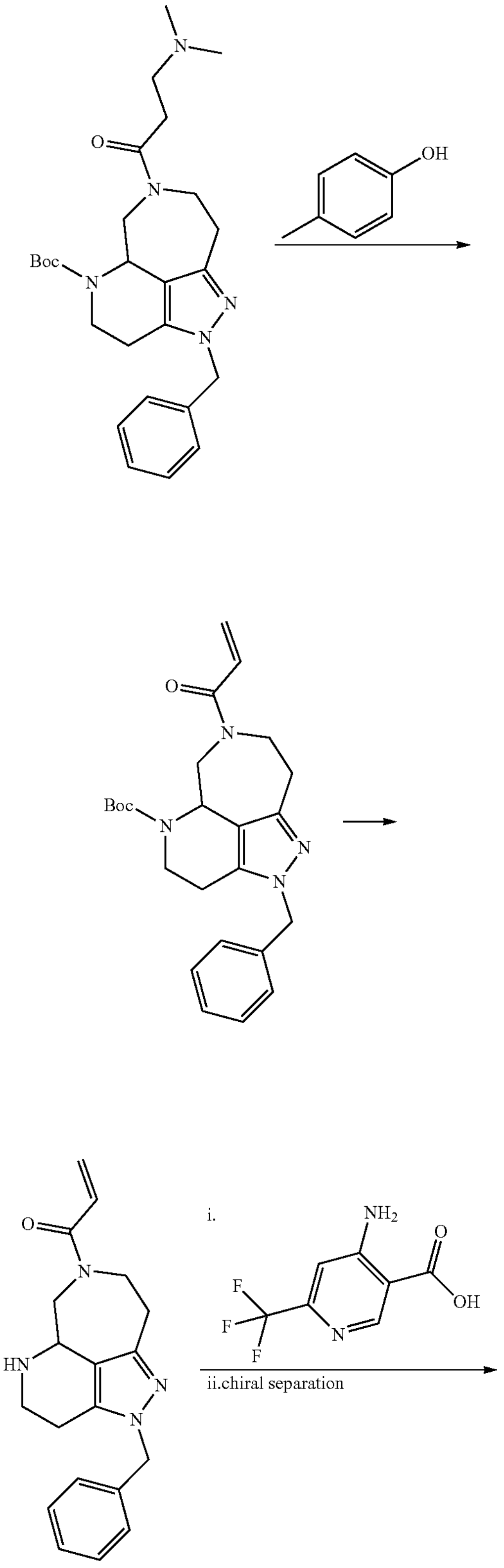

-continued

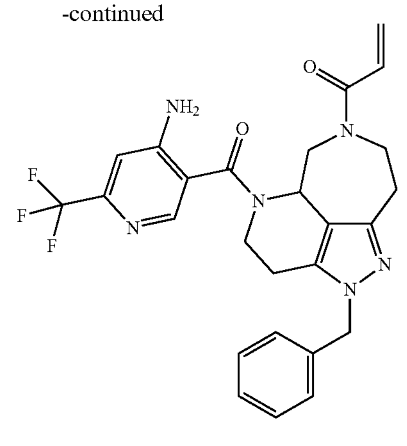

Step 1: Preparation of Tert-Butyl 4-(pyrrolidin-1-yl)-3,6-dihydropyridine-1(2H)-carboxylate To a stirred solution of tert-butyl 4-oxopiperidine-1-carboxylate (100 g, 1 equiv., 502 mmol) in Toluene (1 L) was added pyrrolidine (78.5 g, 91.5 mL, 2.2 equiv., 1.10 mol) and p-toluenesulfonic acid (259 mg, 233 μL, 0.003 equiv., 1.51 mmol) at 120° C. and the reaction was stirred for 12 h. The reaction was then concentrated under reduced pressure to afford tert-butyl 4-(pyrrolidin-1-yl)-3,6-dihydropyridine-1(2H)-carboxylate (120 g) as a yellow oil which was used directly in the next reaction.

Step 2: Synthesis of Tert-Butyl 3-acetyl-4-oxopiperidine-1-carboxylate

To a stirred solution of tert-butyl 4-(pyrrolidin-1-yl)-3,6-dihydropyridine-1(2H)-carboxylate (120 g, 1 equiv., 476 mmol) in dioxane (250 mL) was added $Ac_2O$ (107 g, 98.7 mL, 2.2 equiv., 1.05 mol) and the resulting mixture was stirred for 48 hour art. The reaction was then quenched by the addition of water (100 mL) at rt followed by stirring at 120° C. for 1 h. The resulting mixture was cooled to rt and extracted with EA (3×200 mL). The combined organic layers were washed with brine (2×100 mL), dried over anhydrous $Na_2SO_4$, and filtered. After filtration, the filtrate was concentrated under reduced pressure. The residue was purified by silica gel column chromatography, eluting with EA/PE (1:7) to afford tert-butyl 3-acetyl-4-oxopiperidine-1-carboxylate (56 g) as a light yellow oil. LCMS: (ESI, m/z): 198 $[M-CH_3CO]^+$.

Step 3: Synthesis of Tert-Butyl 3-(3-methoxy-3-oxopropanoyl)-4-oxopiperidine-1-carboxylate To a solution of tert-butyl 3-acetyl-4-oxopiperidine-1-carboxylate (45 g, 1 equiv., 0.19 mol) in THF (900 mL) was added lithium bis(trimethylsilyl)amide (94 g, 24 mL, 3 equiv., 0.56 mol) at −78° C. The mixture was stirred for 1 h, after which dimethyl carbonate (18 g, 1.1 equiv., 0.21 mol) was added. The mixture was warmed to −10° C. and stirred for 1 h, after which the mixture was diluted with saturated ammonium chloride (1000 mL) and EA (1000 mL), and the aqueous layer was extracted with EA (2×2000 mL). The combined organic layers were washed with saturated brine (2×2000 mL), dried over anhydrous sodium sulfate and concentrated to give a residue. The residue was purified by flash column chromatography, eluting with EA/PE (1:5) to afford tert-butyl 3-(3-methoxy-3-oxopropanoyl)-4-oxopiperidine-1-carboxylate (21.7 g) as a yellow solid. LCMS: (ESI, m/z): 300 [M+H]$^+$.

Step 4: Synthesis of Tert-Butyl 3-(2-methoxy-2-oxoethyl)-1,4,6,7-tetrahydro-5H-pyrazolo[4,3-c] pyridine-5-carboxylate To a solution of hydrazine hydrate (4.6 g, 80 wt %, 1.1 equiv., 73 mmol) in EtOH (4 mL) was added tert-butyl 3-(3-methoxy-3-oxopropanoyl)-4-oxopiperidine-1-carboxylate (20 g, 1 equiv., 67 mmol) at 0° C. The mixture was warmed to rt and stirred for 1 h, after which the mixture was diluted with ice water (20 mL) and EA (20 mL), and the aqueous layer was extracted with EA (2×20 mL). The combined organic layers were washed with saturated brine (2×20 mL), dried over anhydrous sodium sulfate and concentrated to give a residue. The residue was purified by flash column chromatography, eluting with EA/PE (2:1) to afford tert-butyl 3-(2-methoxy-2-oxoethyl)-1,4,6,7-tetrahydro-5H-pyrazolo[4,3-c]pyridine-5-carboxylate (19 g) as a white solid. LCMS: (ESI, m/z): 296 [M+H]$^+$.

Step 5: Synthesis of Tert-Butyl 3-(2-methoxy-2-oxoethyl)-1-(tetrahydro-2H-pyran-2-yl)-1,4,6,7-tetrahydro-5H-pyrazolo[4,3-c]pyridine-5-carboxylate To a solution of tert-butyl 3-(2-methoxy-2-oxoethyl)-1,4,6,7-tetrahydro-5H-pyrazolo[4,3-c]pyridine-5-carboxylate (18 g, 1 equiv., 61 mmol) in DCM (360 mL) was added TFA (0.69 g, 0.47 mL, 0.01 equiv., 6.1 mmol) and DHP (31 g, 33 mL, 3 equiv., 0.3.7 mol). The mixture was warmed to 40° C. and stirred for 12 h, after which the mixture was diluted with ice water (400 mL) and EA (400 mL), and the aqueous layer was extracted with EA (2×400 mL). The combined organic layers were washed with saturated brine (2×400 mL), dried over anhydrous sodium sulfate and concentrated to give a residue. The residue was purified by flash column chromatography, eluting with EA/PE (1:5) to afford tert-butyl 3-(2-methoxy-2-oxoethyl)-1-(tetrahydro-2H-pyran-2-yl)-1,4,6,7-tetrahydro-5H-pyrazolo[4,3-c]pyridine-5-carboxylate (20.5 g) as a light yellow solid.

Step 6: Synthesis of Tert-Butyl 4-cyano-3-(2-methoxy-2-oxoethyl)-1-(tetrahydro-2H-pyran-2-yl)-1,4,6,7-tetrahydro-5H-pyrazolo[4,3-c]pyridine-5-carboxylate To a solution of tert-butyl 3-(2-methoxy-2-oxoethyl)-1-(tetrahydro-2H-pyran-2-yl)-1,4,6,7-tetrahydro-5H-pyrazolo [4,3-c]pyridine-5-carboxylate (20.5 g, 1 equiv., 54.0 mmol) in MeCN (20 mL) was added AcOH (9.73 g, 9.28 mL, 3 equiv., 162 mmol), TEMPO (33.8 g, 4 equiv., 216 mmol) and TMS CN (21.4 g, 27.0 mL, 4 equiv., 216 mmol). The mixture was stirred for 2 h at rt, after which the mixture was diluted with ice water (40 mL) and EA (40 mL), and the aqueous layer was extracted with EA (2×40 mL). The combined organic layers were washed with saturated brine (2×40 mL), dried over anhydrous sodium sulfate and concentrated to give a residue. The residue was purified by flash column chromatography, eluting with EA/PE (1:5) to afford tert-butyl 4-cyano-3-(2-methoxy-2-oxoethyl)-1-(tetrahydro-2H-pyran-2-yl)-1,4,6,7-tetrahydro-5H-pyrazolo[4,3-c]pyridine-5-carboxylate. LCMS: (ESI, m/z): 405 [M+H]$^+$.

Step 7: Synthesis of Tert-Butyl 8-oxo-2-(tetrahydro-2H-pyran-2-yl)-2,3,4,5a,6,7,8,9-octahydro-5H-1,2,5,7-tetraazabenzo[cd]azulene-5-carboxylate To a solution of tert-butyl 4-cyano-3-(2-methoxy-2-oxoethyl)-1-(tetrahydro-2H-pyran-2-yl)-1,4,6,7-tetrahydro-5H-pyrazolo[4,3-c]pyridine-5-carboxylate (12 g, 1 equiv., 30 mmol) in MeOH (240 mL) and $NH_3$ in MeOH (7 moL/L, 48 mL) were added Raney nickel (12 g, 50 wt %, 3.4 equiv., 0.10 mol). The mixture was purged with nitrogen (×3) and then was pressurized to 4.0 MPa with hydrogen at 60° C. for 12 h. The reaction mixture was then cooled to rt, and the mixture was filtered and rinsed with EA (5×50 mL). The combined filtrates were concentrated under vacuum to give a residue. The residue was purification by reverse phase chromatography (column: C18 column; Gradient: MeCN in water with 0.1% formic acid) afforded tert-butyl 8-oxo-2-(tetrahydro-2H-pyran-2-yl)-2,3,4,5a,6,7,8,9-octahydro-5H-1,2,5,7-tetraazabenzo[cd]azulene-5-carboxylate (5 g) as a yellow solid. LCMS: (ESI, m/z): 377 [M+H]$^+$.

Step 8: Synthesis of Tert-Butyl 2-(tetrahydro-2H-pyran-2-yl)-2,3,4,5a,6,7,8,9-octahydro-5H-1,2,5,7-tetraazabenzo[cd]azulene-5-carboxylate To a solution of tert-butyl 8-oxo-2-(tetrahydro-2H-pyran-2-yl)-2,3,4,5a,6,7,8,9-octahydro-5H-1,2,5,7-tetraazabenzo [cd]azulene-5-carboxylate (490 mg 1 equiv., 1.30 mmol) in THF (5 mL) was added $BH_3$·THF (447 mg, 5.21 mL, 1 molar, 4 equiv., 5.21 mmol). The mixture was warmed to 60° C. and stirred for 1 h, after which the mixture was diluted with ice water (20 mL) and EA (20 mL), and the aqueous layer was extracted with EA (2×20 mL). The combined organic layers were washed with saturated brine (2×20 mL), dried over anhydrous sodium sulfate and concentrated to give a residue. The residue was purified by flash column chromatography, eluting with EA/PE (1:5) to afford tert-butyl 2-(tetrahydro-2H-pyran-2-yl)-2,3,4,5a,6,7,8,9-octahydro-5H-1,2,5,7-tetraazabenzo[cd]azulene-5-carboxylate (220 mg) as a yellow solid. LCMS: (ESI, m/z): 363 [M+H]$^+$.

Step 9: Synthesis of Tert-Butyl 7-acryloyl-2-(tetrahydro-2H-pyran-2-yl)-2,3,4,5a,6,7,8,9-octahydro-5H-1,2,5,7-tetraazabenzo[cd]azulene-5-carboxylate To a stirred solution of tert-butyl 2-(tetrahydro-2H-pyran-2-yl)-2,3,4,5a,6,7,8,9-octahydro-5H-1,2,5,7-tetraazabenzo [cd]azulene-5-carboxylate (200 mg 1 equiv., 552 mol) in DCM (2 mL) was added TEA (168 mg, 231 μL, 3 equiv., 1.66 mmol) and acryloyl chloride (75 mg, 1.5 equiv., 830 μmol) at rt and stirred for 1 h. The reaction was then quenched by the addition of water (10 mL) at rt. The resulting mixture was extracted with EA (2×5 mL) and the combined organic layers were washed with brine (2×20 mL), dried over anhydrous $Na_2SO_4$, and filtered. The filtrate was concentrated under reduced pressure and the residue vas purified by silica gel column chromatography, eluting with EA/PE (1:1) to afford tert-butyl 7-acryloyl-2-(tetrahydro-2H-pyran-2-yl)-2,3,4,5a,6,7,8,9-octahydro-5H-1,2,5,7-tetraazabenzo[cd]azulene-5-carboxylate (105 mg) as a light yellow solid. LCMS: (ESI, m/z): 417 [M+H]$^+$.

Step 10: Synthesis of Tert-Butyl 7-acryloyl-2,3,4,5a,6,7,8,9-octahydro-5H-1,2,5,7-tetraazabenzo[cd]azulene-5-carboxylate To a solution of tert-butyl 7-acryloyl-2-(tetrahydro-2H-pyran-2-yl)-2,3,4,5a,6,7,8,9-octahydro-5H-1,2,5,7-tetraazabenzo[cd]azulene-5-carboxylate (430 mg 1 equiv., 1.03 mmol) in MeOH (4.3 mL) was added p-toluenesulfonic acid monohydrate (589 mg, 475 μL, 3 Eq, 3.10 mmol). The mixture was stirred for 1 h at rt. The reaction was directly purified by reversed-phase flash chromatography with the following conditions: column, C18 silica gel; mobile phase, $NH_4HCO_3$ in ACN, 3% to 40% gradient in 20 min; detector, UV 254 nm to afford tert-butyl 7-acryloyl-2,3,4,5a,6,7,8,9-octahydro-5H-1,2,5,7-tetraazabenzo[cd]azulene-5-carboxylate (180 mg) as off-white solid. LCMS: (ESI, m/z): 333 [M+H]$^+$.

Step 11: Synthesis of Tert-Butyl 2-benzyl-7-(3-(dimethylamino)propanoyl)-2,3,4,5a,6,7,8,9-octahydro-5H-1,2,5,7-tetraazabenzo[cd]azulene-5-carboxylate To a stirred solution of tert-butyl 7-acryloyl-2,3,4,5a,6,7,8,9-octahydro-5H-1,2,5,7-tetraazabenzo[cd]azulene-5-carboxylate (155 mg, 1 equiv., 466 gmol) in DMF (4 mL) were added sodium hydride (28.0 mg, 60 wt %, 1.5 equiv., 699 μmol) in portions at 0° C. The resulting mixture was stirred for 1 h at 0° C. To the above mixture was added (bromomethyl)benzene (87.7 mg, 1.1 equiv., 513 gmol) in portions over 0.5 h at 0° C. The resulting mixture was stirred for additional 1 h at rt, after which the reaction was quenched with water (5 mL) at 0° C. Additional water (10 mL) was added and the resulting mixture was extracted with EA (3×10 mL). The combined organic layers were washed with brine (3×10 mL), dried over anhydrous sodium sulfate, and filtered. After filtration, the filtrate was concentrated under reduced pressure to afford crude product (160 mg) which was used in the next step without further purification. LCMS: (ESI, m/z): 468 [M+H]$^+$.

Step 12: Synthesis of Tert-Butyl 7-acryloyl-2-benzyl-2,3,4,5a,6,7,8,9-octahydro-5H-1,2,5,7-tetraazabenzo[cd]azulene-5-carboxylate A solution of tert-butyl 2-benzyl-7-(3-(dimethylamino)propanoyl)-2,3,4,5a,6,7,8,9-octahydro-5H-1,2,5,7-tetraazabenzo[cd]azulene-5-carboxylate (145 mg, 1 equiv., 310 gmol) and acetic anhydride (34.8 mg, 1.1 equiv., 341 gmol) in toluene (3 mL) was stirred for 1 h at 80° C. under a nitrogen atmosphere. To the above resulting mixture was added p-cresol (671 μg, 0.02 equiv., 6.20 μmol) and triethylamine (31.4 mg, 1 equiv., 310 μmol). The resulting mixture was stirred for additional 1 h at 110° C. mixture was then cooled to rt and concentrated under reduced pressure. The residue was purified by silica gel column chromatography, eluting with [PE/EA](1/1) to afford tert-butyl 7-acryloyl-2-benzyl-2,3,4,5a,6,7,8,9-octahydro-5H-1,2,5,7-tetraazabenzo[cd]azulene-5-carboxylate (60 mg) as a colorless oil. LCMS: (ESI, m/z): 423 [M+H]$^+$.

Step 13: Synthesis of 1-(2-benzyl-2,3,4,5,5a,6,6,9-octahydro-7H-1,2,5,7-tetraazabenzo[cd]azulen-7-yl)prop-2-en-1-one A solution of tert-butyl 7-acryloyl-2-benzyl-2,3,4,5a,6,7,8,9-octahydro-5H-1,2,5,7-tetraazabenzo[cd]azulene-5-carboxylate (50 mg, 1 equiv., 0.12 mmol) and TFA (13 mg, 0.5 mL, 1 equiv., 0.12 mmol) in DCM (1.5 mL) was stirred for 1 h at rt. The resulting mixture was concentrated under reduced pressure to afford the crude product (40 mg) which was used in the next step directly without further purification. LCMS: (ESI, m/z): 323 [+H]$^+$.

Step 14: Synthesis of (S)-1-(5-(4-amino-6-(trifluoromethyl)nicotinoyl)-2-benzyl-2,3,4,5,5a,6,8,9-octahydro-7H-1,2,5,7-tetraazabenzo[cd]azulen-7-yl)prop-2-en-1-one A solution of 1-(2-benzyl-2,3,4,5,5a,6,8,9-octahydro-7H-1,2,5,7-tetraazabenzo[cd]azulen-7-yl)prop-2-en-1-one (45 mg, 1 equiv., 0.14 mmol), 4-amino-6-(trifluoromethyl)nicotinic acid (29 mg, 1.2 equiv., 0.14 mmol), DIEA (54 mg, 73 μL, 6 equiv., 0.42 mmol and HATU (64 mg, 1.2 equiv., 0.17 mmol) in DMA (4 mL) was stirred for 1 h at rt under a nitrogen atmosphere. The reaction mixture was then quenched with saturated water (10 mL) and extracted with EA (2×10 mL). The combined organic layers were washed with brine (10 mL), dried over sodium sulfate, filtered, and evaporated under reduced pressure. The crude product (50 g) was purified by Prep-HPLC with the following conditions (Column: CHIRAL ART Cellulose-SB, 3*25 cm, 5 μm; Mobile Phase A: MtBE(0.1% FA)—HPLC, Mobile Phase B: ETOH; Flow rate: 40 mL/min; Gradient: isocratic 10; Wave Length: 208/240 nm) to afford racemic 1-(5-(4-amino-6-(trifluoromethyl)nicotinoyl)-2-benzyl-2,3,4,5,5a,6,8,9-octahydro-7H-1,5,7-tetraazabenzo[cd]azulen-7-yl)prop-2-en-1-one (20 mg). The racemic compound was purified by Prep-Chiral HPLC with the following conditions (Column: CHIRAL ART Cellulose-SB, 3*25 cm, 5 μm; Mobile Phase A: MtBE(0.1% FA)—HPLC, Mobile Phase B: ETOH; Flow rate: 40 mL/min; Gradient: isocratic 10; Wave Length: 208/240 nm; RT1(mii): 7.7; RT2(min): 9.5) to afford (R or S)-1-(5-(4-amino-6-(trifluoromethyl)nicotinoyl)-2-benzyl-2,3,4,5,5a,6,8,9-octahydro-7H-1,2,5,7-tetraazabenzo[cd]azulen-7-yl)prop-2-en-1-one (4.6 mg) as a white solid. LCMS: (ESI, m/z): 511 [M+H]$^+$. $^1$H NMR (400 MHz, Chloroform-d) δ 8.31-7.94 (m, 1H), 7.46-7.27 (m, 3H), 7.17-7.10 (m, 2H), 7.00 (s, 1H), 6.76-6.32 (m, 1H), 5.89-5.64 (m, 1H), 5.45-5.05 (m, 5H), 5.05-4.82 (m, 1H), 4.67-3.92 (m, 2H), 3.32-2.38 (i, 7H).

Example L-7: Preparation of (R or S)-1-(5-(4-amino-6-(trifluoromethyl)nicotinoyl)-2-(3-cyclopentylbicyclo[1.1.1]pentan-1-yl)-2,3,4,5,5a,6,8,9-octahydro-7H-1,2,5,7-tetraazabenzo[cd]azulen-7-yl)prop-2-en-1-one

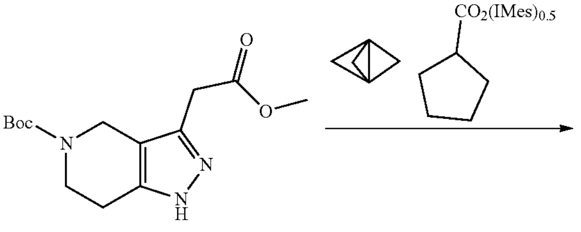

Int. L-B

-continued

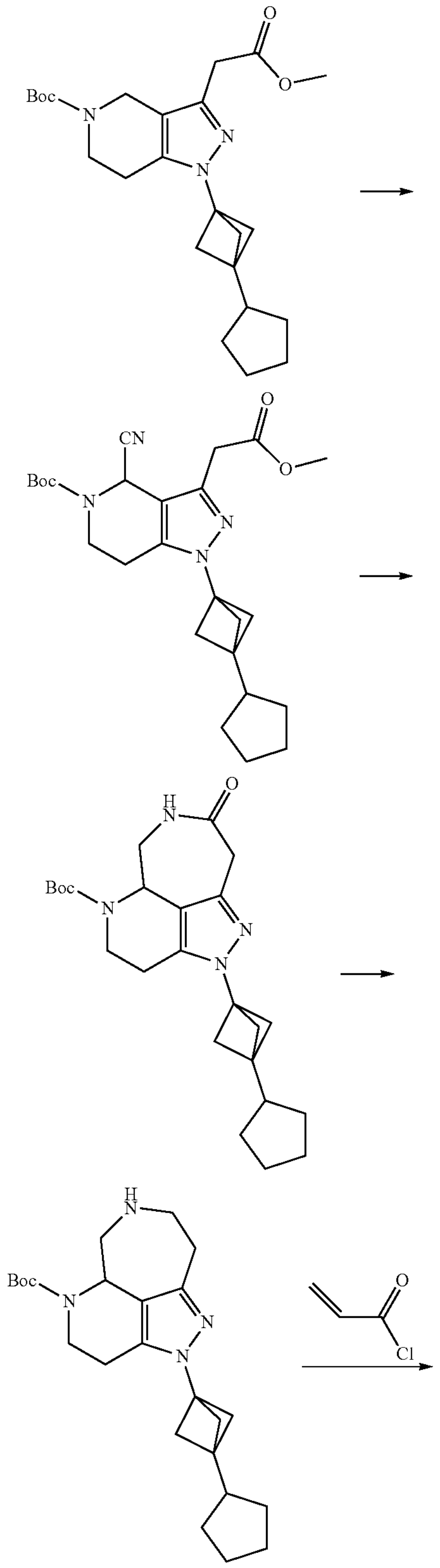

-continued

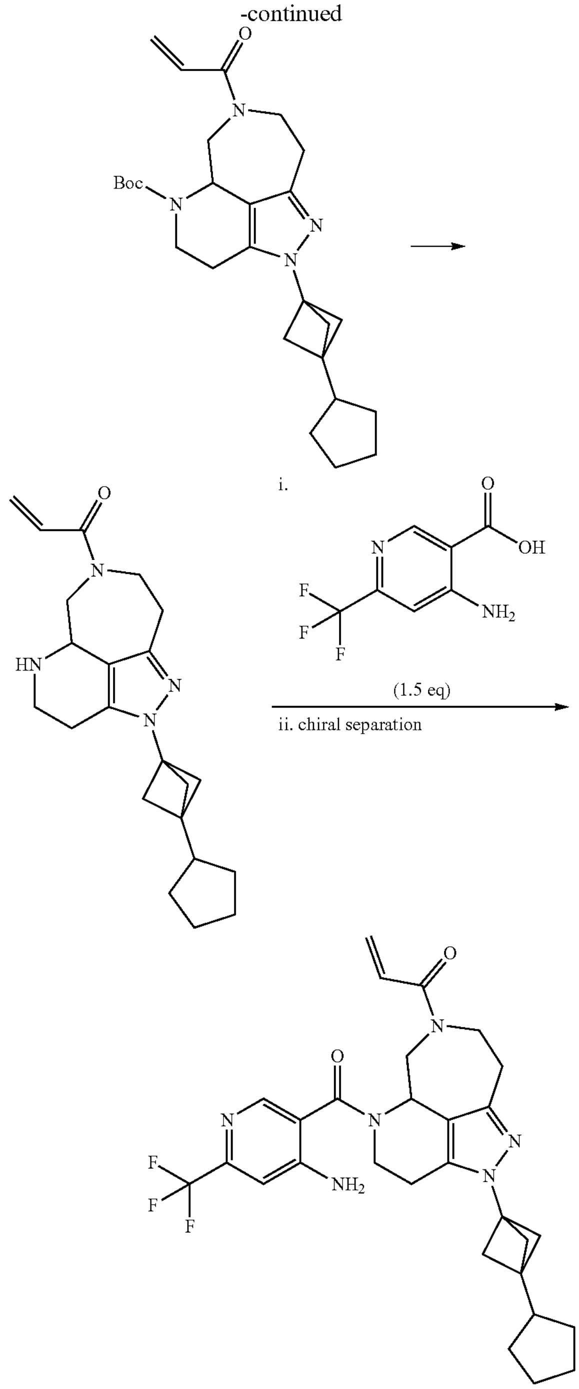

Step 1: Synthesis of Tert-Butyl 1-(3-cyclopentylbicyclo[1.1.1]pentan-1-yl)-3-(2-methoxy-2-oxoethyl)-1,4,6,7-tetrahydro-5H-pyrazolo[4,3-c]pyridine-5-carboxylate To a solution of tert-butyl 3-(2-methoxy-2-oxoethyl)-1,4,6,7-tetrahydro-5H-pyrazolo[4,3-c]pyridine-5-carboxylate (1.5 g, 1 equiv., 5.1 mmol), mesityl-l3-iodanediyl dicyclopentanecarboxylate (6.0 g, 2.5 equiv., 13 mmol), 2-(tert-butyl)-1,1,3,3-tetramethylguanidine (2.6 g, 3 equiv., 15 mmol), copper (II) acetylacetonate (0.80 g, 0.6 equiv., 3.0 mmol) in 1,4-dioxane (150 mL) were added tricyclo

[1.1.1.01,3]pentane (0.50 g, 9.9 mL, 0.77 molar, 1.5 equiv., 7.6 mmol) and tris[2-(2-pyridyl)phenyl]iridium (67 mg, 0.02 equiv., 0.10 mmol). The reaction system was evacuated and backfilled with nitrogen (×3). The resulting mixture was stirred for 4 h at rt under blue LED lights. The reaction was conducted in 15 parallel reactions. The reaction was quenched by the addition of water (20 mL) at rt. The resulting mixture was extracted with EA (3×50 mL). The combined organic layers were washed with brine (50 mL), dried over anhydrous sodium sulfate, and filtered. The filtrate was concentrated under reduced pressure and the residue was purified by silica gel chromatography (Gradient: 0-100% EtOAc in PE) to afford tert-butyl 1-(3-cyclopentyl-bicyclo[1.1.1]pentan-1-yl)-3-(2-methoxy-2-oxoethyl)-1,4,6,7-tetrahydro-5H-pyrazolo[4,3-c]pyridine-5-carboxylate (1 g) as a green solid. LCMS: (ESI, m/z): 430 [M+H]$^+$.

Step 2: Synthesis of Tert-Butyl 4-cyano-1-(3-cyclopentylbicyclo[1.1.1]pentan-1-yl)-3-(2-methoxy-2-oxoethyl)-1,4,6,7-tetrahydro-5H-pyrazolo[4,3-c]pyridine-5-carboxylate A solution of tert-butyl 1-(3-cyclopentylbicyclo[1.1.1]pentan-1-yl)-3-(2-methoxy-2-oxoethyl)-1,4,6,7-tetrahydro-5H-pyrazolo[4,3-c]pyridine-5-carboxylate (900 ng, 1 equiv., 2.10 mmol) in MeCN (30 mL) was cooled to 0° C., and then TMS-CN (520 m, 655 μL, 2.5 equiv., 5.24 mmol), AcOH (315 mg, 300 μL, 2.5 equiv., 5.24 mmol) and TEMPO$^+$BF$_4^-$ (1.02 g, 2 equiv., 4.19 mmol) was added slowly at 0° C. The mixture was warmed to rt and stirred for 12 h, after which the reaction was quenched by the addition of half saturated sodium carbonate (50 mL). The resulting mixture was extracted with EA (3×100 mL) and the combined organic layers were washed with brine (200 mL), dried over anhydrous sodium sulfate, and filtered. The filtrate was concentrated under reduced pressure and the residue was purified by silica gel column chromatography, eluting with EA/PE (35:65) to afford tert-butyl 4-cyano-1-(3-cyclopentylbicyclo[1.1.1]pentan-1-yl)-3-(2-methoxy-2-oxoethyl)-1,4,6,7-tetrahydro-5H-pyrazolo[4,3-c]pyridine-5-carboxylate (600 mg) as a yellow semi-solid. LCMS: (ESI, m/z): 455 [M+H]$^+$.

Step 3: Synthesis of Tert-Butyl 2-(3-cyclopentylbicyclo[1.1.1]pentan-1-yl)-8-oxo-2,3,4,5a,6,7,8,9-octahydro-5H-1,2,5,7-tetraazabenzo[cd]azulene-5-carboxylate To a solution of tert-butyl 4-cyano-1-(3-cyclopentylbicyclo[1.1.1]pentan-1-yl)-3-(2-methoxy-2-oxoethyl)-1,4,6,7-tetrahydro-5H-pyrazolo[4,3-c]pyridine-5-carboxylate (550 mg, 1 equiv., 1.21 mmol) in MeOH (15 mL) were added in ammonia in methanol (0.09 g, 0.75 mL, 7 molar, 0.6 equiv., 0.7 mmol) and Raney nickel (550 mg, 50 wt %). The mixture was purged with nitrogen (×3) and then was pressurized 4.0 MPa with hydrogen and stir ed at 50° C. for 12 h. The reaction mixture was cooled to rt and filtered and rinsed with MeOH $20 mL). The filtrate was concentrated under vacuum to give a residue which was purified by silica gel chromatography, eluting with EA/PE (85:15) to afford tert-butyl 2-(3-cyclopentylbicyclo[1.1.1]pentan-1-yl)-8-oxo-2,3,4,5a,6,7,8,9-octahydro-5H-1,2,5,7-tetraazabenzo[cd]azulene-5-carboxylate (300 mg) as a white solid. LCMS: (ESI, m/z): 427 [M+H]$^+$.

Step 4: Synthesis of Tert-Butyl 2-(3-cyclopentylbicyclo[1.1.1]pentan-1-yl)-2,3,4,5a,6,7,8,9-octahydro-5H-1,2,5,7-tetraazabenzo[cd]azulene-5-carboxylate A solution of tert-butyl 2-(3-cyclopentylbicyclo[0.1.1]pentan-1-yl)-8-oxo-2,3,4,5a,6,7,8,9-octahydro-5H-1,2,5,7-tetraazabenzo[cd]azulene-5-carboxylate (280 mg, 1 equiv., 656 μmol) in THF (9 mL) was cooled to 0° C., then $BH_3$·THF (226 mg, 2.63 mL, 1 molar, 4 equiv., 2.63 mmol) was added slowly at 0° C. under a nitrogen atmosphere. The mixture was warmed to 60° C. and stirred for 2 h, and the reaction mixture was quenched with MeOH (5 mL) at 0° C. The solvent was removed under reduced pressure to provide tert-butyl 2-(3-cyclopentylbicyclo[1.1.1]pentan-1-yl)-2,3,4,5a,6,7,8,9-octahydro-5H-1,2,5,7-tetraazabenzo[cd]azulene-5-carboxylate (280 mg) as a crude colorless oil which was used in the next step directly without further purification. LCMS: (ESI, m/z): 413 [M+H]$^+$.

Step 5: Synthesis of Tert-Butyl 7-acryloyl-2-(3-cyclopentylbicyclo[1.1.1]pentan-1-yl)-2,3,4,5a,6,7,8,9-octahydro-5H-1,2,5,7-tetraazabenzo[cd]azulene-5-carboxylate A solution of tert-butyl 2-(3-cyclopentylbicyclo[1.1.1]pentan-1-yl)-2,3,4,5a,6,7,8,9-octahydro-5H-1,2,5,7-tetraazabenzo[cd]azulene-5-carboxylate (280 mg, 1 equiv., 679 μmol) in DCM (6 mL) was cooled to 0° C., and then TEA (343 mg, 473 μL, 5 equiv., 3.39 mmol) was added, and acryloyl chloride (123 mg, 2 equiv., 1.36 mmol) was added slowly under a nitrogen atmosphere. The mixture was warmed to rt and stirred for 2 h. The mixture was quenched with ice water (20 mL), and the aqueous layer was extracted with DCM (3×20 mL). The combined organic layers were washed with saturated brine (2×20 mL), dried over anhydrous sodium sulfate and concentrated to give a residue. The residue was purified by flash column chromatography, eluting with EA/PE (7:3) to afford tert-butyl 7-acryloyl-2-(3-cyclopentylbicyclo[1.1.1]pentan-1-yl)-2,3,4,5a,6,7,8,9-octahydro-5H-1,2,5,7-tetraazabenzo[cd]azulene-5-carboxylate (90 mg) as a light yellow oil. LCMS: (ESI, m/z): 467 [M+H]$^+$.

Step 6: Synthesis of 1-(2-(3-cyclopentylbicyclo[1.1.1]pentan-1-yl)-2,3,4,5,5a,6,8,9-octahydro-7H-1,2,5,7-tetraazabenzo[cd]azulen-7-yl)prop-2-en-1-one A solution of tert-butyl 7-acryloyl-2-(3-cyclopentylbicyclo[1.1.1]pentan-1-yl)-2,3,4,5a,6,7,8,9-octahydro-5H-1,2,5,7-tetraazabenzo[cd]azulene-5-carboxylate (80 mg, 1 equiv., 0.17 mmol) in DCM (2 mL) and TFA (0.5 mL) was stirred at rt for 4 h. The solvent was then removed under reduced pressure to afford 1-(2-(3-cyclopentylbicyclo[1.1.1]pentan-1-yl)-2,3,4,5,5a,6,8,9-octahydro-7H-1,2,5,7-tetraazabenzo[cd]azulen-7-yl)prop-2-en-1-one (90 mg) as a crude yellow oil which was used in the next step directly without further purification. LCMS: (ESI, m/z): 367 [M+H]$^+$.

Step 7: Synthesis of 1-(5-(4-amino-6-(trifluoromethyl)nicotinoyl)-2-(3-cyclopentylbicyclo[1.1.1]pentan-1-yl)-2,3,4,5,5a,6,8,9-octahydro-7H-1,2,5,7-tetraazabenzo[cd]azulen-7-yl)prop-2-en-1-one To a solution of 1-(2-(3-cyclopentylbicyclo[1.1.1]pentan-1-yl)-2,3,4,5,5a,6,8,9-octahydro-7H-1,2,5,7-tetraazabenzo[cd]azulen-7-yl)prop-2-en-1-one (0 mg, 1 equiv., 0.22 mmol) in THF (3 mL) were added DIEA (0.14 g, 0.19 mL, 5 equiv., 1.1 mmol), EDCI (63 mg, 1.5 equiv., 0.33 mmol), HOBt (50 mg, 1.5 equiv., 0.33 mmol) and 4-amino-6-(trifluoromethyl)nicotinic acid (67 mg, 1.5 equiv., 0.33 mmol). The mixture was stirred at rt for 12 h, after which the reaction was quenched by the addition of water (20 mL) at rt. The resulting mixture was extracted with EA (3×20 mL), and the combined organic layers were washed with brine (50 mL), dried over anhydrous sodium sulfate, and filtered. After filtration, the filtrate was concentrated under reduced pressure. The residue was purified by silica gel column chromatography, eluting with MeOH/DCM (1:9) to afford 1-(5-(4-amino-6-(trifluoromethyl)nicotinoyl)-2-(3-cyclopentylbicyclo[1.1.1]pentan-1-yl)-2,3,4,5,5a,6,8,9-octahydro-7H-1,2,5,7-tetraazabenzo[cd]azulen-7-yl)prop-2-en-1-one (80 mg). The product was further purified by HPLC (Column: XBridge Prep Phenyl OBD Column 19*250 mm, 5 μm; Mobile Phase A: Water(10 mmol/L $NH_4HCO_3$), Mobile Phase B: ACN; Flow rate: 60 mL/min mL/min; Gradient: 5% B to 5% B in 1 min, 5% B to 37% B in 2 min, 37% to 57% B in 10 min) to the racemic final compound. The racemic compound was separated b chiral-HPLC separation (Column: CHIRALPAK ID, 3*25 cm, 5 μm; Mobile Phase A: MtBE(0.1% FA)—HPLC, Mobile Phase B: ETOH; Flow rate: 40 mL/min; Gradient: isocratic 5; Wave Length: 250/208 nm; RT1(min): 12.1; RT2(min): 17.9) to afford (S or R)-1-(5-(4-amino-6-(trifluoromethyl)nicotinoyl)- 2-(3-cyclopentylbicyclo[1.1.1]pentan-1-yl)-2,3,4,5,5a,6,8,9-octahydro-7H-1,2,5,7-tetraazabenzo[cd]azulen-7-yl)prop-2-en-1-one (17.9 mg) as the first-eluting peak as a white solid. LCMS: (ESI, m/z): 555 $[M+H]^+$. $^1H$ NMR (400 MHz, Chloroform-d) δ 8.31 (s, 1H), 7.45-7.30 (m, 1H), 7.05-7.00 (m, 1H), 6.73-6.36 (m, 1H), 5.89-5.69 (m, 1H), 5.54-5.15 (m, 3H), 5.03-4.69 (m, 1H), 4.52-4.02 (m, 2H), 3.34-2.47 (m, 7H), 2.17-2.05 (m, 7H), 1.34-1.07 (m, 3H) (some peaks obscured by solvent peak).

TABLE L4

The compound of Example L-8 was prepared in an analogous fashion to Example L-4, except that the isopropyl group was added after the formation of Int. L-G, coupling first with isopropenyl boronic acid pinacol ester under standard Suzuki coupling conditions and then hydrogenation with Pd/C. The remaining steps of Example L-4 were performed in an analogous fashion to afford the racemic final compound. The compound of Example L-9 was prepared in an analogous fashion to Example L-4, except that 2-chloro-6-(trifluoromethyl)pyridin-3-amine was used in place of 1-bromo-2,4-difluoro-3-nitrobenzene, and Boc-$NH_2$ was added into the 2-chloropyridine after the analogous step 3. The rest of the steps proceeded in an analogous fashion, with the aniline protected with a second Boc group after the analogous step 9, and all Boc groups removed simultaneously in the analogous step 15. The racemic final compound was separated into its constitutive enantiomers using the following conditions: Column-CHIRALPAK-IC, 2*25 cm, 5 μm; Mobile Phase A: Hex(0.1% FA)—HPLC, Mobile Phase B: EtOH: DCM = 1:1; Flow rate: 20 mL/min; Gradient: isocratic 55; Wave Length: UV 254/220 nm; RT1(min): 5.0; RT2(min): 6.7; to afford the compound of the example as the second-eluting peak. The compound of Example L-9-1 was prepared in an analogous fashion to Example L-4, using (4-bromo-3,5-difluoro-2-methoxyphenyl)hydrazine (prepared from 4-bromo-3,5-difluoro-2-methoxyaniline by treating with sodium nitrite, followed by tin chloride). The methoxy phenol was deprotected after the analogous step 12 of Example L-4 via treatment with BBr3, and was subsequently protected with a Boc group. The Boc group was removed during the analogous step 15 of Example L-4. The racemic final compound was separated into its constitutive enantiomers using the following conditions: Column-CHIRALPAK-IK, 3*25 mm, 5 um; Mobile Phase A: MtBE(0.1% FA)—HPLC, Mobile Phase B: ETOH; Flow rate: 40 mL/min; Gradient: isocratic 10; Wave Length: 254/210 nm; RT1(min): 4.8; RT2(min): 9.1; to afford the compound of the example as the second-eluting peak. The compound of Example L-9-2 was prepared in an analogous fashion to Example L-9-2 using (4-bromo-3-methoxyphenyl)hydrazine. In this case, the phenol was not protected by a Boc group and was carried as the free phenol through the rest of the analogous synthetic route. The final racemic compound was separated into its constitutive enantiomers using the following conditions: Column-CHIRAL ART Cellulose-SB, 2*25 cm, 5 μm; Mobile Phase A: Hex(0.1% FA)-HPLC, Mobile Phase B: ETOH: DCM = 1:1; Flow rate: 20 mL/min; Gradient: isocratic 25; Wave Length: 254/220 nm; RT1(min): 6.3; RT2(min): 9.2; to provide the compound of the example as the first-eluting peak.

| Example No. | Structure and Name | LCMS (ESI, m/z) | NMR |
|---|---|---|---|
| L-8 | 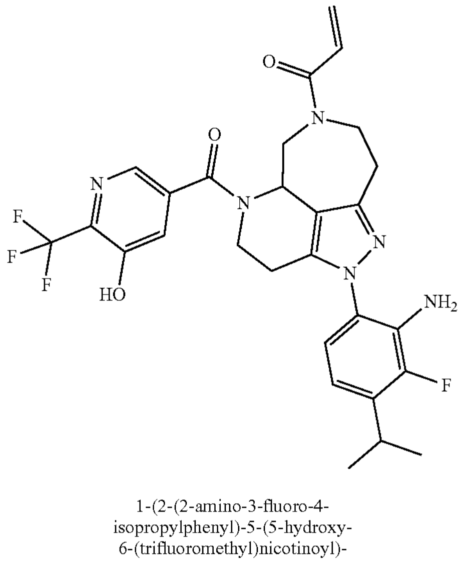 1-(2-(2-amino-3-fluoro-4-isopropylphenyl)-5-(5-hydroxy-6-(trifluoromethyl)nicotinoyl)- | 573 $[M + H]^+$ | $^1H$ NMR (400 MHz, Chloroform-d, ppm) δ 8.50 (s, 1H), 8.37 (s, 1H), 7.25 (d, J = 5.3 Hz, 2H), 6.93-6.35 (m, 4H), 5.91 (s, 1H), 5.18 (s, 1H), 4.88 (s, 1H), 4.66 (s, 1H), 4.32 (s, 1H), 3.33-2.84 (m, 6H), 2.57 (s, 3H), 1.26 (s, 6H). |

TABLE L4-continued

| | | | |
|---|---|---|---|
| | 2,3,4,5,5a,6,8,9-octahydro-7H-1,2,5,7-tetraazabenzo[cd]azulen-7-yl)prop-2-en-1-one | | |
| L-9 | 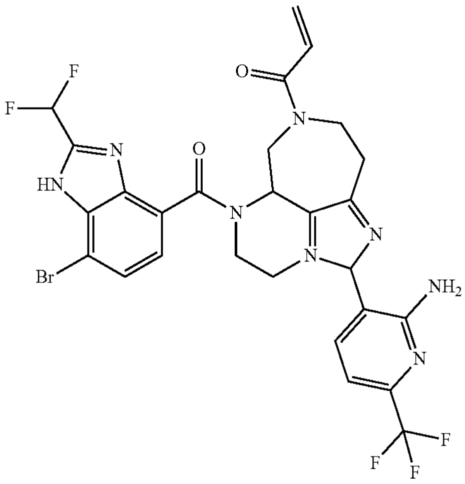 (R or S)-1-(2-(2-amino-6-(trifluoromethyl)pyridin-3-yl)-5-(7-bromo-2-(difluoromethyl)-1H-benzo[d]imidazole-4-carbonyl)-2,3,4,5,5a,6,8,9-octahydro-7H-1,2,5,7-tetraazabenzo[cd]azulen-7-yl)prop-2-en-1-one | 665 [M + 1]+ | $^1$H NMR (400 MHz, Chloroform-d, ppm) δ 12.59 (s, 1H), 7.67 – 7.32 (m, 3H), 7.25 (s, 1H), 7.11 – 6.62 (m, 2H), 6.55 – 6.37 (m, 1H), 5.98 – 5.34 (m, 4H), 5.05 – 4.82 (m, 1H), 4.69 – 4.44 (m, 1H), 4.29 – 3.76 (m, 1H), 3.42 – 2.62 (m, 6H), 2.61 – 2.37 (m, 1H). |
| L-9-1 | 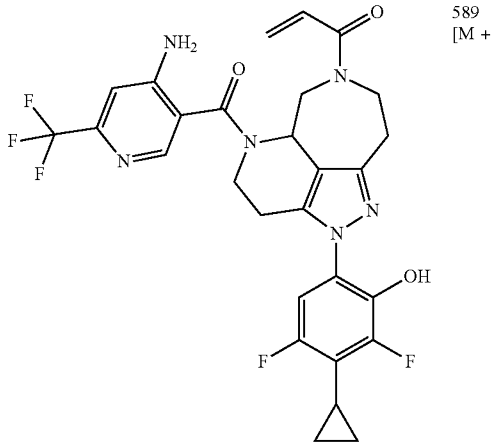 (R or S)-1-(5-(4-amino-6-(trifluoromethyl)nicotinoyl)-2-(4-cyclopropyl-3,5-difluoro-2-hydroxyphenyl)-2,3,4,5,5a,6,8,9-octahydro-7H-1,2,5,7-tetraazabenzo[cd]azulen-7-yl)prop-2-en-1-one | 589 [M + 1]+ | |

TABLE L4-continued

| | | | |
|---|---|---|---|
| L-9-2 | 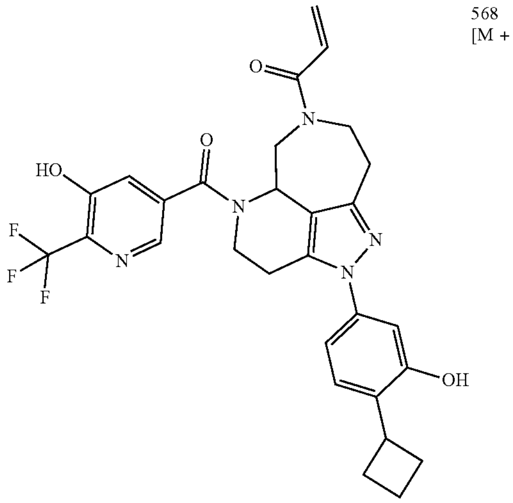<br>(S or R)-1-(2-(4-cyclobutyl-3-hydroxyphenyl)-5-(5-hydroxy-6-(trifluoromethyl)nicotinoyl)-2,3,4,5,5a,6,8,9-octahydro-7H-1,2,5,7-tetraazabenzo[cd]azulen-7-yl)prop-2-en-1-one | 568 [M + 1]$^+$ | $^1$H NMR (400 MHz, DMSO-$d_6$, ppm) δ 9.63 (brs, 1H), 8.27 (brs, 1H), 7.61 - 7.34 (m, 2H), 7.26 - 7.15 (m, 1H), 7.04 - 6.96 (m, 1H), 6.94 - 6.80 (m, 1H), 6.34 - 6.21 (m, 1H), 5.86 - 5.67 (m, 1H), 5.23 - 5.07 (m, 1H), 4.76 - 4.58 (m, 1H), 4.39 - 4.13 (m, 1H), 3.83 - 3.56 (m, 2H), 3.25 - 3.00 (m, 1H), 2.97 - 2.72 (m, 3H), 2.72 - 2.58 (m, 1H), 2.37 - 1.87 (m, 6H), 1.85 - 1.70 (m, 1H). |

TABLE L5

The compound of Example L-10 was prepared in an analogous fashion to Example L-1, except that step 10 was not performed, and intermediate L-B was taken on to the cyclopropylboronic acid coupling in step 11 and on to the final compound, using the corresponding carboxylic acid, of the example as a racemic mixture. The racemic compound was separated using the following conditions: Column-CHIRAL ART Cellulose-SB 3*25 cm, 5 μm; Mobile Phase A: HEX(0.1% FA), Mobile Phase B: ETOH: DCM = 1:1; Flow rate: 40 mL/min; Gradient: isocratic 20; Wave Length: 254/220 nm; RT1(min): 7.8; RT2(min): 11.7 to afford the compound of the example as the first-eluting peak.

| Example No. | Structure and Name | LCMS (ESI, m/z) | NMR |
|---|---|---|---|
| L-10 | 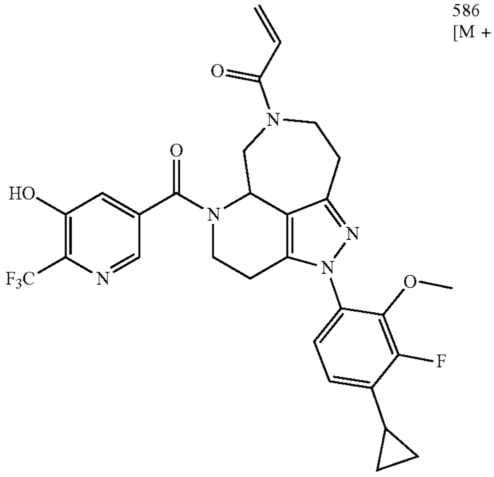<br>(R or S)-1-(2-(4-cyclopropyl-3-fluoro-2-methoxyphenyl)-5-(5-hydroxy-6-(trifluoromethyl)nicotinoyl)-2,3,4,5,5a,6,8,9-octahydro-7H-1,2,5,7-tetraazabenzo[cd]azulen-7-yl)prop-2-en-1-one | 586 [M + H]$^+$ | $^1$H NMR (400 MHz, $CDCl_3$) δ 8.73 (br s, 1H), 8.61 - 8.13 (m, 1H), 7.62 - 7.35 (m, 1H), 7.18 - 6.97 (m, 1H), 6.81 - 6.29 (m, 3H), 5.98 - 5.77 (m, 1H), 5.51 - 5.05 (m, 1H), 5.05 - 4.80 (m, 1H), 4.80 - 4.43 (m, 1H), 4.43 - 4.20 (m, 1H), 3.79 - 3.62 (m, 3H), 3.35 - 2.69 (m, 6H), 2.52 - 2.25 (m, 1H), 2.17 - 2.09 (m, 1H), 1.10 - 1.01 (m, 2H), 0.78 - 0.72 (m, 2H). |

Example L-11: Preparation of 1-((5a(S or R),9(S or R))-5-(4-amino-6-(trifluoromethyl)nicotinoyl)-9-cyclopropoxy-2-(4-cyclopropyl-2-hydroxyphenyl)-2,3,4,5,5a,6,8,9-octahydro-7H-1,2,5,7-tetraazabenzo[cd]azulen-7-yl)prop-2-en-1-one
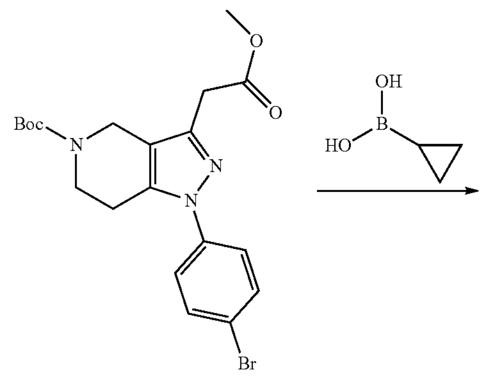
Int. D
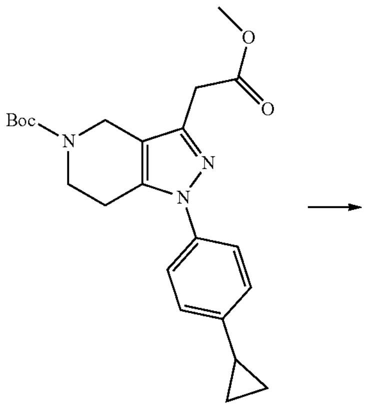
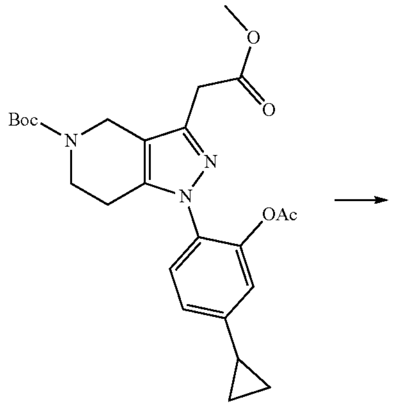
-continued
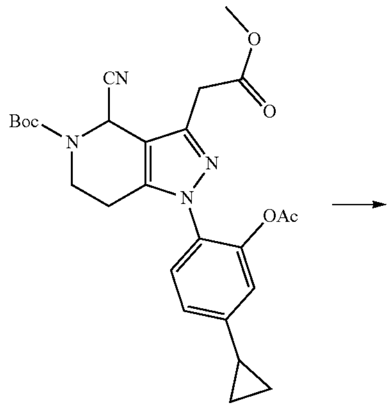
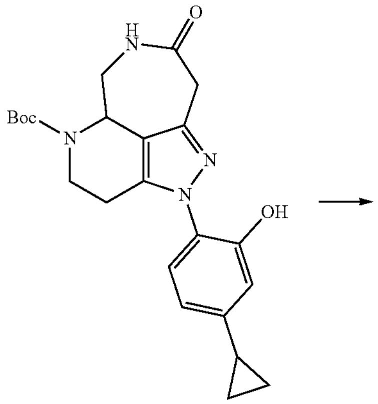
Int. L-F
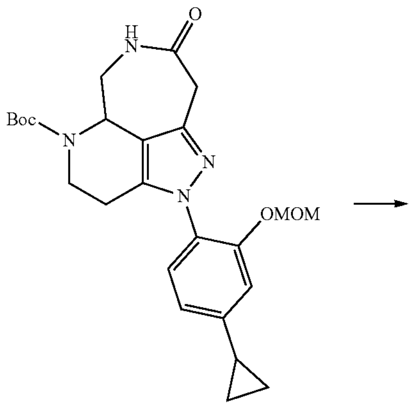
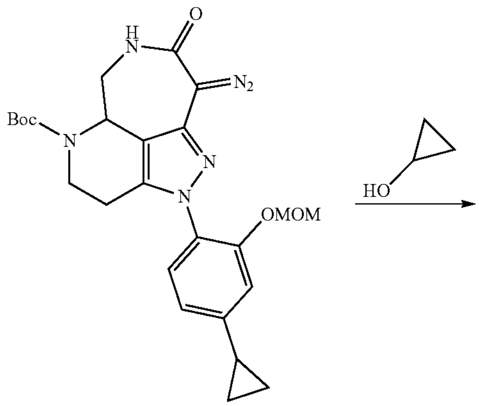

-continued

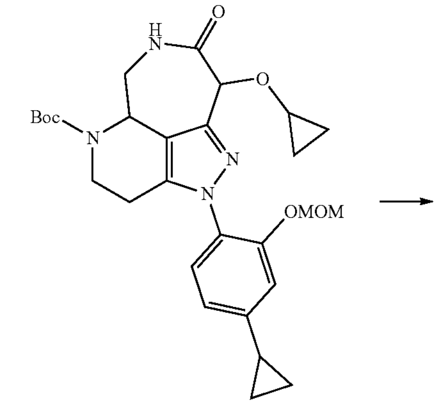

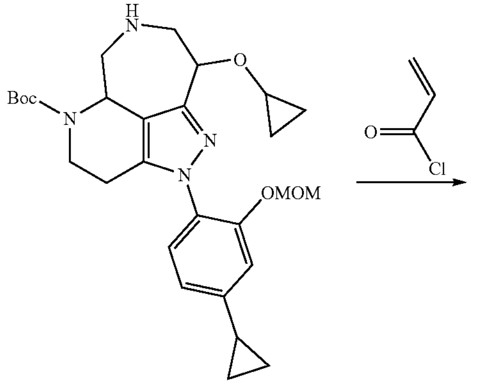

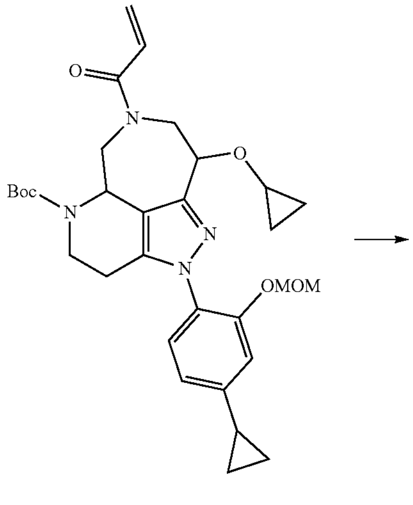

-continued

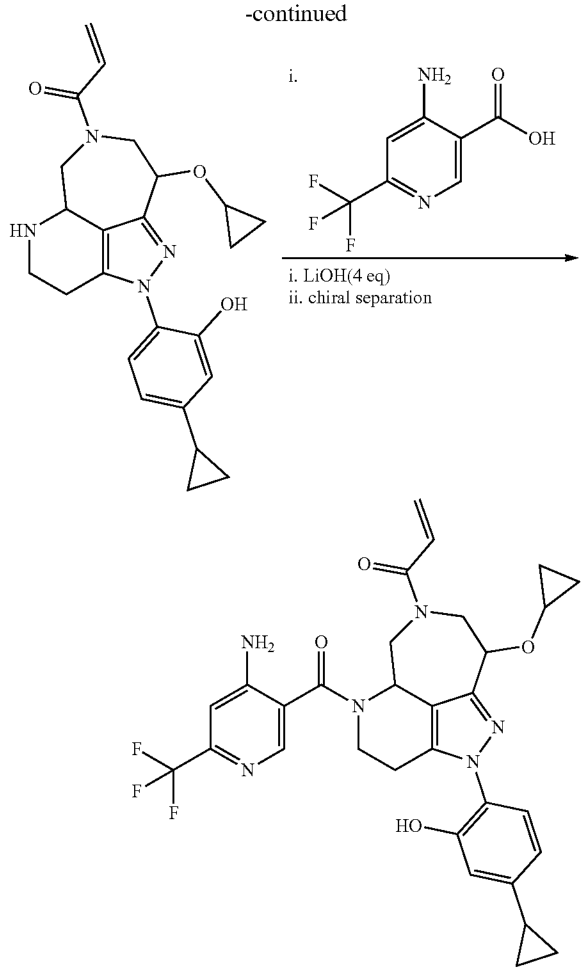

Step 1: Synthesis of Tert-Butyl 1-(4-cyclopropylphenyl)-3-(2-methoxy-2-oxoethyl)-1,4,6,7-tetrahydro-5H-pyrazolo[4,3-c]pyridine-5-carboxylate A solution of tert-butyl 1-(4-bromophenyl)-3-(2-methoxy-2-oxoethyl)-1,4,6,7-tetrahydro-5H-pyrazolo[4,3-c]pyridine-5-carboxylate (Int. D) (44 g, 1 equiv., 98 mmol), silver (I) oxide (23 g, 3.2 mL, 1 equiv., 98 mmol), cyclopropylboronic acid (16.8 g, 2 equiv., 196 mmol), $Cs_2CO_3$ (64 g, 2 equiv., 0.20 mol) and $PdCl_2$(dppf)-DCM adduct (8.0 g, 0.1 equiv., 9.8 mmol) in toluene (500 mL) was stirred for 2 h at 80° C. under a nitrogen atmosphere. The resulting mixture was then cooled to rt and filtered, and the filter cake was washed with EA (3×500 mL). The combined filtrate was concentrated under reduced pressure and purified by silica gel column chromatography, eluting with EA/PE (1:2) to afford tert-butyl 1-(4-cyclopropylphenyl)-3-(2-methoxy-2-oxoethyl)-1,4,6,7-tetrahydro-5H-pyrazolo[4,3-c]pyridine-5-carboxylate (40 g) as a white solid. LCMS:(ESI, m/z): 412 $[M+1]^+$.

Step 2: Synthesis of Tert-Butyl 1-(2-acetoxy-4-cyclopropylphenyl)-3-(2-methoxy-2-oxoethyl)-1,4,6,7-tetrahydro-5H-pyrazolo[4,3-c]pyridine-5-carboxylate A solution of tert-butyl 1-(4-cyclopropylphenyl)-3-(2-met oxy-2-oxoethyl)-1,4,6,7-tetrahydro-5H-pyrazolo[4,3-c]

pyridine-5-carboxylate (26 g, 1 equiv., 63 mmol), $Pd(OAc)_2$ (4.2 g, 0.3 equiv., 18.9 mmol), and PIDA (41 g, 2 equiv., 0.13 mol) in acetic acid (300 mL) was stirred for 2 h at 90° C. under a nitrogen atmosphere. The reaction was quenched by the addition of water (200 mL) at rt and the resulting mixture was extracted with EA (2×200 mL). The combined organic layers were washed with water (2×400 mL) and brine (1×400 mL), dried over anhydrous $Na_2SO_4$, and filtered. The filtrate was concentrated under reduced pre sure and the residue was purified by silica gel column chromatography, eluting with EA/PE (1:2) to afford tert-butyl 1-(2-acetoxy-4-cyclopropylphenyl)-3-(2-methoxy-2-oxoethyl)-1,4,6,7-tetrahydro-5H-pyrazolo[4,3-c]pyridine-5-carboxylate (9 g) as a yellow oil. LCMS:(ESI, m/z): 470 $[M+1]^+$.

Step 3: Synthesis of Tert-Butyl 1-(2-acetoxy-4-cyclopropylphenyl)-4-cyano-3-(2-methoxy-2-oxoethyl)-1,4,6,7-tetrahydro-5H-pyrazolo[4,3-c]pyridine-5-carboxylate A solution of tert-butyl 1-(2-acetoxy-4-cyclopropylphenyl)-3-(2-methoxy-2-oxoethyl)-1,4,6,7-tetrahydro-5H-pyrazolo[4,3-c]pyridine-5-carboxylate (2 g, 1 equiv., 4 mmol), TEMPO, BF4 (3 g, 3 equiv., 0.01 mol), TMS-CN (1 g, 2 mL, 4 equiv., 0.01 mol) and AcOH (1 g, 1 mL, 4 equiv., 0.02 mol) in MeCN was stirred for 2 h at rt. The mixture was then concentrated under reduced pressure and the residue was purified by silica gel column chromatography, eluting with [PE/EA](2/1) to afford tert-butyl 1-(2-acetoxy-4-cyclopropylphenyl)-4-cyano-3-(2-methoxy-2-oxoethyl)-1,4,6,7-tetrahydro-5H-pyrazolo[4,3-c]pyridine-5-carboxylate (1.5 g) as a yellow oil. LCMS:(ESI, m/z): 495 $[M+1]^+$.

Step 4: Synthesis of Tert-Butyl 2-(4-cyclopropyl-2-hydroxyphenyl)-8-oxo-2,3,4,5a,6,7,8,9-octahydro-5H-1,2,5,7-tetraazabenzo[cd]azulene-5-carboxylate (Int. L To a solution of tert-butyl 1-(2-acetoxy-4-cyclopropylphenyl)-4-cyano-3-(2-methoxy-2-oxoethyl)-1,4,6,7-tetrahydro-5H-pyrazolo[4,3-c]pyridine-5-carboxylate (8.7 g, 1 equiv., 18 mmol) in $NH_3$ in MeOH (9 mL) and MeOH (180 mL) was added nickel (10 g 1.2 mL, 10 equiv., 0.18 mol) in a pressure vessel. The mixture was purged with nitrogen (×3) and then was pressurized to 4 Mpa with hydrogen and stirred at 60° C. for 16 h. The reaction mixture was cooled to rt, filtered to remove insoluble solids and the filter cake was washed with MeOH (3×200 mL). The filtrate was concentrated under reduced pressure and the residue was purified by silica gel column chromatography, eluting with DCM/MeOH (10:1) to afford tert-butyl 2-(4-cyclopropyl-2-hydroxyphenyl)-8-oxo-2,3,4,5a,6,7,8,9-octahydro-5H-1,2,5,7-tetraazabenzo[cd]azulene-5-carboxylate (Int. L-F) (4.7 g) as a white solid. LCMS:(ESI, m/z): 425 $[M+1]^+$.

Step 5: Synthesis of Tert-Butyl 2-(4-cyclopropyl-2-(methoxymethoxy)phenyl)-8-oxo-2,3,4,5a,6,7,8,9-octahydro-5H-1,2,5,7-tetraazabenzo[cd]azulene-5-carboxylate To a solution of tert-butyl 2-(4-cyclopropyl-2-hydroxyphenyl)-8-oxo-2,3,4,5a,6,7,8,9-octahydro-5H-1,2,5,7-tetraazabenzo[cd]azulene-5-carboxylate (500 mg, 1 equiv., 1.18 mmol) in DCM (10 mL) was added DIEA (609 mg, 821 μL, 4 equiv., 4.71 mmol). The mixture was cooled to 0° C., and then bromomethyl methyl ether (221 mg, 144 μL, 1.5 equiv, 1.77 mmol) was added slowly at 0° C. under a nitrogen atmosphere. The mixture was then warmed to 30° C. and stirred for 12 h, after which it was diluted with ice water (100 mL) and EA (100 mL), and the aqueous layer was extracted with EA (2×100 mL). The combined organic layer was washed with saturated brine (2×100 mL), dried over anhydrous sodium sulfate and concentrated to give a residue. The residue was purified by flash column chromatography, eluting with EA/PE (1:1) to afford tert-butyl 2-(4-cyclopropyl-2-(methoxymethoxy)phenyl)-8-oxo-2,3,4,5a,6,7,8,9-octahydro-5H-1,2,5,7-tetraazabenzo[cd]azulene-5-carboxylate (440 mg) as a white solid. LCMS:(ESI, m/z): 469 $[M+1]^+$.

Step 6: Synthesis of Tert-Butyl 2-(4-cyclopropyl-2-(methoxymethoxy)phenyl)-9-diazo-8-oxo-2,3,4,5a,6,7,8,9-octahydro-5H-1,2,5,7-tetraazabenzo[cd]azulene-5-carboxylate To a solution of tert-butyl 2-(4-cyclopropyl-2-(methoxymethoxy)phenyl)-8-oxo-2,3,4,5a,6,7,8,9-octahydro-5H-1,2,5,7-tetraazabenzo[cd]azulene-5-carboxylate (2.35 g, 1 equiv., 5.02 mmol) in MeCN (5 mL) was added DBU (1.15 g, 1.13 mL, 1.5 equiv., 7.52 mmol). The mixture was cooled to 0° C., then 4-methylbenzenesulfonyl azide (2.97 g, 3 equiv., 15.0 mmol) was added dropwise to the above mixture at 0° C. under a nitrogen atmosphere. The mixture was warmed to rt and stirred for 2 h, after which it was filtered and rinsed with MeCN (3×5 mL). The filtrate was concentrated under vacuum to give a residue which was purified by flash column chromatography, eluting with EA/PE (1:1) to afford tert-butyl 2-(4-cyclopropyl-2-(methoxymethoxy)phenyl)-9-diazo-8-oxo-2,3,4,5a,6,7,8,9-octahydro-5E-1,2,5,7-tetraazabenzo[cd]azulene-5-carboxylate (1.6 g) as a yellow solid. LCMS:(ESI, m/z): 495 $[M+1]^+$.

Step 7: Synthesis of Tert-Butyl 9-cyclopropoxy-2-(4-cyclopropyl-2-(methoxymethoxy)phenyl)-8-oxo-2,3,4,5a,6,7,8,9-octahydro-5H-1,2,5,7-tetraazabenzo[cd]azulene-5-carboxylate A solution of tert-butyl 2-(4-cyclopropyl-2-(methoxymethoxy)phenyl)-9-diazo-8-oxo-2,3,4,5a,6,7,8,9-octahydro-5H-1,2,5,7-tetraazabenzo[cd]azulene-5-carboxylate (700 mg, 1 equiv., 1.42 mmol), cyclopropanol (247 mg, 3 equiv., 4.26 mmol) in DCM (15 L) was stirred for 1 h at rt under a nitrogen atmosphere. The reaction was then quenched by the addition of water (50 mL), and the resulting mixture was extracted with EA (2×50 mL). The combined organic layers were washed with water (2×50 mL) and brine (1×50 mL), dried over anhydrous $Na_2SO_4$, and filtered. The filtrate was concentrated under reduced pressure and the residue was purified by silica gel column chromatography, eluting with EA/PE (1:2) to afford tert-butyl 9-cyclopropoxy-2-(4-cyclopropyl-2-(methoxymethoxy)phenyl)-8-oxo-2,3,4,5a,6,7,8,9-octahydro-5H-1,2,5,7-tetraazabenzo[cd]azulene-5-carboxylate (160 mg) as a white solid. LCMS:(ESI, m/z): 525 $[M+1]^+$.

Step 8: Synthesis of Tert-Butyl 9-cyclopropoxy-2-(4-cyclopropyl-2-(methoxymethoxy)phenyl)-2,3,4,5a,6,7,8,9-octahydro-5H-1,2,5,7-tetraazabenzo[cd]azulene-5-carboxylate A solution of tert-butyl 9-cyclopropoxy-2-(4-cyclopropyl-2-(methoxymethoxy)phenyl)-8-oxo-2,3,4,5a,6,7,8,9-octahydro-5H-1,2,5,7-tetraazabenzo[cd]azulene-5-carboxylate (50 mg, 1 equiv., 95 μmol), zinc chloride (32 mg, 15 μL, 2.5 equiv., 0.24 mmol) and $NaBH_4$ (9.0 mg, 2.5 equiv., 0.24 mmol) in THF (0.5 mL) was stirred for 1 h at 60° C. under a nitrogen atmosphere. The resulting mixture was concentrated under reduced pressure to afford tert-butyl 9-cyclopropoxy-2-(4-cyclopropyl-2-(methoxymethoxy)phenyl)-2,3,4,5a,6,7,8,9-octahydro 5H-1,2,5,7-tetraazabenzo[cd]azulene-5-carboxylate (50 mg) as a yellow oil. LCMS:(ESI, m/z): 511 $[M+1]^+$.

Step 9: Synthesis of Tert-Butyl 7-acryloyl-9-cyclopropoxy-2-(4-cyclopropyl-2-(methoxymethoxy)phenyl)-2,3,4,5a,6,7,8,9-octahydro-5H-1,2,5,7-tetraazabenzo[cd]azulene-5-carboxylate To a stirred solution of tert-butyl 9-cyclopropoxy-2-(4-cyclopropyl-2-(methoxymethoxy)phenyl)-8-oxo-2,3,4,5a,6,7,8,9-octahydro-5H-1,2,5,7-tetraazabenzo[cd]azulene-5-carboxylate (180 mg, 1 equiv., 343 μmol) and TEA (104 mg, 143 μL, 3 equiv., 1.03 mmol) in DCM (5 mL) was added acryloyl chloride (46.6 mg, 1.5 equiv., 515 μmol) dropwise at 0° C. under a nitrogen atmosphere. The resulting mixture w s stirred for additional 1 h at rt, after which the reaction was quenched by the addition of water (20 mL) at rt. The resulting mixture was extracted with DCM (2×20 mL) and the combined organic layers were washed with water (2×20 mL) and brine (1×20 mL), dried over anhydrous $Na_2SO_4$ and filtered. The filtrate was concentrated under reduced pressure and the residue was purified by silica gel column chromatography, eluting with EA/PE (2:1) to afford tert-butyl 7-acryl yl-9-cyclopropoxy-2-(4-cyclopropyl-2-(methoxymethoxy)phenyl)-2,3,4,5a,6,7,8,9-octahydro-5H-1,2,5,7-tetraazabenzo[cd]azulene-5-carboxylate (65 mg) as a white solid. LCMS:(ESI, m/z): 565 $[M+1]^+$.

Step 10: Synthesis of 1-(9-cyclopropoxy-2-(4-cyclopropyl-2-hydroxyphenyl)-2,3,4,5,5a,6,8,9-octahydro-7H-1,2,5,7-tetraazabenzo[cd]azulen-7-yl)prop-2-en-1-one A solution of tert-butyl 7-acryloyl-9-cyclopropoxy-2-(4-cyclopropyl-2-(methoxymethoxy)phenyl)-2,3,4,5a,6,7,8,9-octahydro-5H-1,2,5,7-tetraazabenzo[cd]azulene-5 -carboxylate (55 mg, 1 equiv., 97 mol) in DCM (1.2 mL) and TFA (0.6 g, 0.4 mL, 5 mmol) was stirred for 1 h at rt under a nitrogen atmosphere. The resulting mixture was then concentrated under reduced pressure to afford 1-(9-cyclopropoxy-2-(4-cyclopropyl-2-hydroxyphenyl)-2,3,4,5,5a,6,8,9-octahydro-7H-1,2,5,7-tetraazabenzo[cd]azulen-7-yl)prop-2-en-1-one (60 mg) as a yellow oil which was used in the next step directly without further purification. LCMS:(ESI, m/z): 421 $[M+1]^+$.

Step 11: Synthesis of 1-((5a(S or R),9(S or R))-5-(4-amino-6-(trifluoromethyl)nicotinoyl)-9-cyclopropoxy-2-(4-cyclopropyl-2-hydroxyphenyl)-2,3,4,5,5a,6,8,9-octahydro-7H-1,2,5,7-tetraazabenzo[cd]azulen-7-yl)prop-2-en-1-one A solution of 1-(9-cyclopropoxy-2-(4-cyclopropyl-2-hydroxyphenyl)-2,3,4,5,5a,6,8,9-octahydro-7H-1,2,5,7-tetraazabenzo[cd]azulen-7-yl)prop-2-en-1-one (50 mg, 1 equiv., 0.12 mmol), HATU (90 mg, 2 equiv., 0.24 mmol), 4-amino-6-(trifluoromethyl)nicotinic acid (49 mg, 2 equiv., 0.24 mmol) and DIEA (46 mg, 62 μL, 3 equiv., 0.36 mmol) in DMA (2 mL) was stirred for 1 h at rt under a nitrogen atmosphere. The reaction was quenched by the addition of water (20 mL) at rt and the mixture was extracted with EA (2×20 mL). The combined organic layers were washed with water (2×30 mL) and brine (1×20 mL), dried over anhydrous $Na_2SO_4$, and filtered. The filtrate was concentrated under reduced pressure to afford 2-(7-acryloyl-5-(4-amino-6-(trifluoromethyl)nicotinoyl)-9-cyclopropoxy-3,4,5,5a,6,7,8,9-octahydro-2H-1,2,5,7-tetraazabenzo[cd]azulen-2-yl)-5-cyclopropylphenyl 4-amino-6-(trifluoromethyl)nicotinate (80 mg) which was used in the next step directly without further purification.

A solution of 2-(7-acryloyl-5-(4-amino-6-(trifluoromethyl)nicotinoyl)-9-cyclopropoxy-3,4,5,5a,6,7,8,9-octahydro-2H-1,2,5,7-tetraazabenzo[cd]azulen-2-yl)-5-cyclopropylphenyl 4-amino-6-(trifluoromethyl)nicotinate (70 mg, 1 equiv., 88 μmol), LiOH (8.4 mg, 4 equiv., 0.35 mmol) in THF (2 mL) and water (2 mL) was stirred for 1 h at 40° C. under nitrogen atmosphere. The reaction was cooled to rt and quenched with water, then acidified to pH=3 with 1M (aq.) $H_2SO_4$. The resulting mixture was extracted with EA (2×10 mL) and the combined organic layers were washed with water (2×10 mL) and brine (1×10 mL), dried over anhydrous $Na_2SO_4$ and filtered. The filtrate was concentrated under reduced pressure to prov de a residue which was purified by reversed-phase flash chromatography with the conditions (column, C18 silica gel; mobile phase, water (0.1% FA) in MeCN, 10% to 100% gradient in 15 min) to afford the racemic product (11 mg) as a white solid. The racemate was separated into its constitutive enantiomers using the following conditions: Column-CHIRALPAK ID, 3*25 cm, 5 μm; Mobile Phase A: MtBE(0.1% FA)—HPLC, Mobile Phase B: ETOH; Flow rate: 40 mL/m n; Gradient: isocratic 10; Wave Length: 208/254 nm; RT1(min): 5.1; RT2(min): 8.3; to afford 1-(5a(S or R),9(S or R))-5-(4-amino-6-(trifluoromethyl)nicotinoyl)-9-cyclopropoxy-2-(4-cyclopropyl-2-hydroxyphenyl)-2,3,4,5,5a,6,8,9-octahydro-7H-1,2,5,7-tetraazabenzo[cd]azulen-7-yl)prop-2-en-1-one (3.1 mg) as the first eluting peak. LCMS:(ESI, m/z): 609 $[M+1]^+$. $^1H$ NMR (400 MI z, DMSO-d6) δ 10.06 (s, 1H), 8.24-8.06 (m, 1H), 7.59-7.34 (m, 1H), 7.19-7.01 (m, 2H), 6.77-6.58 (m, 3H), 6.45-6.02 (m, 1H), 5.93-5.53 (m, 1H), 5.26-4.99 (m, 1H), 4.72-4.23 (m, 1H), 4.07-3.54 (m, 1H), 3.20-2.69 (m, 3H), 2.46-2.36 (m, 1H), 2.01-1.81 (m, 1H), 1.36-0.73 (m, 2H), 0.71-0.35 (m, 6H).

TABLE L6

Example L-11-1 was prepared in an analogous fashion to Example L-11 using the corresponding alcohol and carboxylic acid. The final compound was separated into its constituent isomers by chiral HPLC: Column-CHIRALPAK ID, 3*25 cm, 5 μm; Mobile Phase A: MtBE(0.1% FA)—HPLC, Mobile Phase B: ETOH; Flow rate: 40 mL/min; Gradient: isocratic 10; Wave Length: 254/206 nm; RT1(min): 4.7; RT2(min): 8.0; to the provide the compound of the example as the first-eluting peak. Example L-11-2 was prepared in an analogous fashion to Example L-11 using the corresponding cyclobutyl intermediates described herein and the corresponding alcohol and carboxylic acid. The final racemic compound was separated into its constituent isomers by chiral HPLC: column-CHIRAL ART Cellulose-SB 3*25 cm, 5 μm; Mobile Phase A: HEX(0.1% FA), Mobile Phase B: EtOH: DCM = 1:1; Flow rate: 40 mL/min; Gradient: isocratic 25; Wave Length: UV 254/220 nm; RT1(min): 6.8; RT2(min): 12.5; to provide the compound of the example as the first-eluting peak.

| Example No. | Structure and Name | LCMS (ESI, m/z) | $^1$H NMR |
|---|---|---|---|
| L-11-1 | 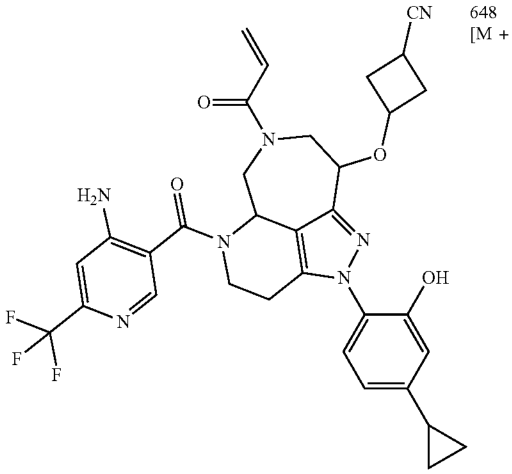 3-(((5a(S or R),9(S or R))-7-acryloyl-5-(4-amino-6-(trifluoromethyl)nicotinoyl)-2-(4-cyclopropyl-2-hydroxyphenyl)-3,4,5,5a,6,7,8,9-octahydro-2H-1,2,5,7-tetraazabenzo[cd]azulen-9-yl)oxy)cyclobutane-1-carbonitrile | 648 $[M + H]^+$ | $^1$H NMR (400 MHz, Chloroform-d) δ 8.35 (s, 1H), 7.46 - 7.31 (m, 1H), 7.06 - 7.02 (m, 1H), 6.99 - 6.90 (m, 1H), 6.83 - 6.78 (m, 1H), 6.71 - 6.61 (m, 1H), 6.59 - 6.47 (m, 1H), 5.96 - 5.79 (m, 1H), 5.50 - 5.17 (m, 3H), 4.97 - 4.71 (m, 1H), 4.71 - 3.96 (m, 4H), 3.33 - 2.95 (m, 3H), 2.95 - 2.40 (m, 6H), 1.94 - 1.83 (m, 1H), 1.05 - 0.95 (m, 2H), 0.76 - 0.68 (m, 2H). |
| L-11-2 | 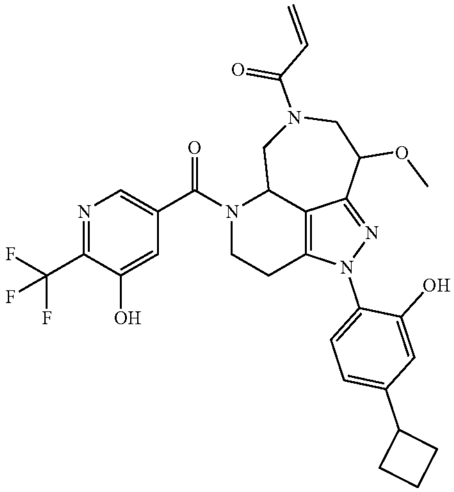 [SMILES: C=CC(=O)N1CC(OC)c2nn(-c3ccc(C4CCC4)cc3O)c3c2C(C1)N(C(=O)c1cnc(C(F)(F)F)c(O)c1)CC3] 1-((5a(R or S),9(R or S))-2-(4-cyclobutyl-2-hydroxyphenyl)-5-(5-hydroxy-6-(trifluoromethyl)nicotinoyl)-9-methoxy-2,3,4,5,5a,6,8,9-octahydro-7H-1,2,5,7-tetraazabenzo[cd]azulen-7-yl)prop-2-en-1-one | 598 $[M + H]^+$ | $^1$H NMR (400 MHz, DMSO-$d_6$, ppm) δ 10.10 (s, 1H), 8.17 (s, 1H), 7.47 - 7.35 (m, 2H), 7.22 (d, J = 8.1 Hz, 1H), 6.87 (s, 1H), 6.78 (d, J = 8.2 Hz, 1H), 6.34 - 6.26 (m, 1H), 5.88 - 5.67 (m, 1H), 5.12 (d, 1H), 4.68 (d, J = 12.2 Hz, 1H), 4.46 - 4.39 (m, 1H), 4.26 (d, J = 13.6 Hz, 1H), 3.74 (d, J = 13.5 Hz, 1H), 3.59 (s, 3H), 3.54 - 3.43 (m, 1H), 3.21 - 3.11 (m, 1H), 2.96 - 2.72 (m, 2H), 2.45 - 1.69 (m, 8H). |

Example L-12: Preparation of ((R or S),E)-(4-amino-6-(trifluoromethyl)pyridin-3-yl)(2-(4-cyclopropyl-2-hydroxyphenyl)-7-(3-(methylsulfonyl)allyl)-3,4,6,7,8,9-hexahydro-2H-1,2,5,7-tetraazabenzo[cd]azulen-5(5aH)-yl)methanone
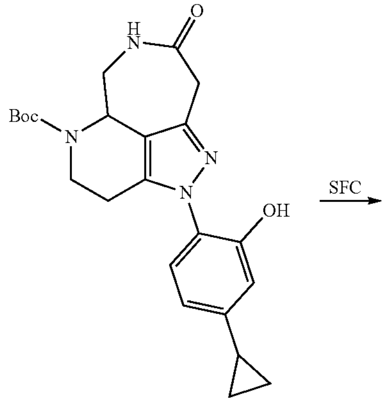
Int. L-F
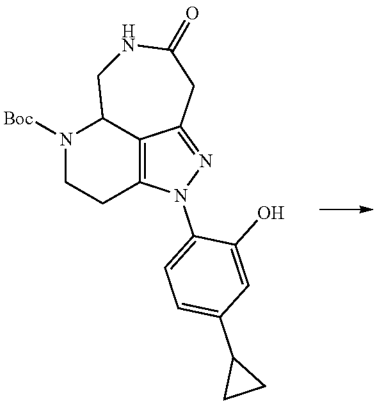
Int. L-F-1
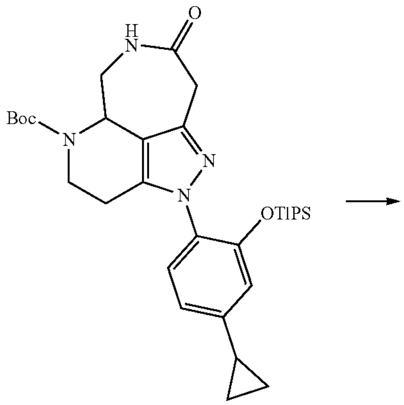
-continued
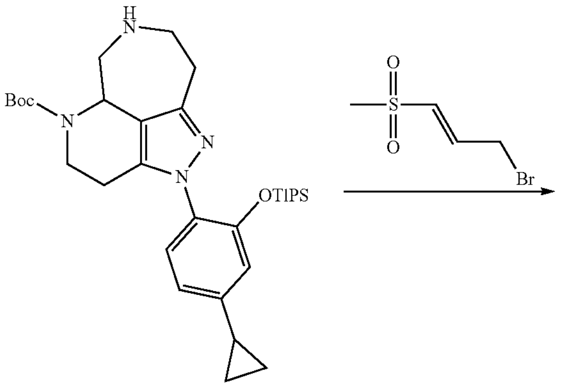
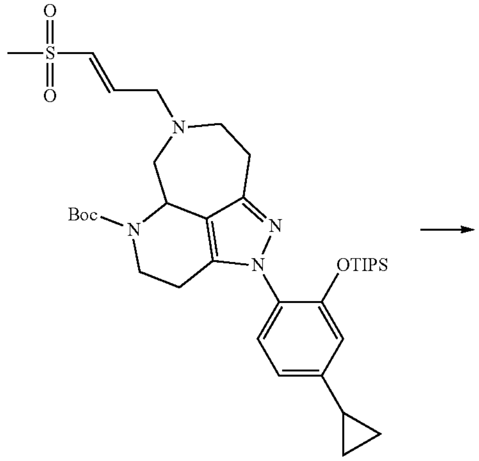
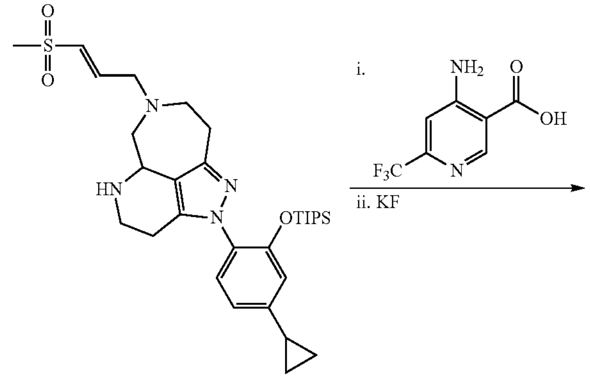
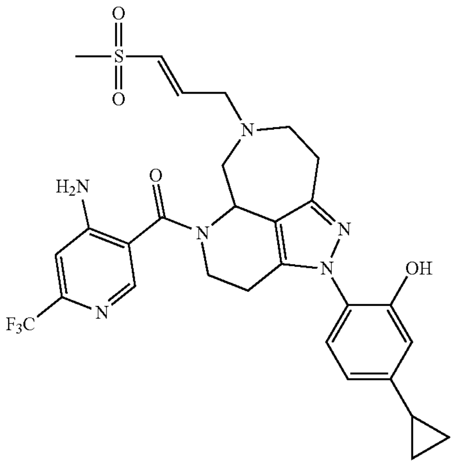

Step 1: Synthesis of Tert-Butyl (R or S)-2-(4-cyclopropyl-2-hydroxyphenyl)-8-oxo-2,3,4,5a,6,7,8,9-octahydro-5H-1,2,5,7-tetraazabenzo[cd]azulene-5-carboxylate (Int. L-F-1)

The racemic Int. L-F was purified by Prep-chiral HPLC with the following conditions: column-DAICEL CHIRALCEL OD(250 mm*30 mm, 10 um); mobile phase: [C02-MeOH(0.1% $NH_3$ in water)]; B %:25%, isocratic elution mode; RT1(min) 1.5; RT2(min) 1.7) to afford terttert-butyl (R or S)-2-(4-cyclopropyl-2-hydroxyphenyl)-8-oxo-2,3,4,5a,6,7,8,9-octahydro-5H-1,2,5,7-tetraazabenzo[cd]azulene-5-carboxylate (Int. L-1-1) (1.67 g) as the first-eluting peak as a yellow solid. LCMS:(ESI, m/z): 425 $[M+1]^+$.

Step 2: Synthesis of Terttert-Butyl (R or S)-2-(4-cyclopropyl-2-((triisopropylsilyl)oxy)phenyl)-8-oxo-2,3,4,5a,6,7,8,9-octahydro-5H-1,2,5,7-tetraazabenzo[cd]azulene-5-carboxylate To a solution of tert-butyl (8(R or S))-3-(4-cyclopropyl-2-hydroxy-phenyl)-11-oxo-2,3,7,10-tetrazatricyclo[6.4.1.04,13]trideca-1,4(13)-diene-7-carboxylate (0.600 g, 1 equiv, 1.41 mmol) in DCM (6 mL) was added TEA (0.286 g, 2 equiv, 2.83 mmol, 0.93 mL) and TIPSCI (300 mg, 1.1 equiv, 1.6 mmol, 0.33 mL) at rt. Then the mixture was stirred at 1 h, after which it was quenched by addition water (60 mL) and extracted with DCM (60 mL×2). The combined organic layers were washed with brine (45 mL), dried over $Na_2SO_4$, filtered and concentrated under reduced pressure to afford terttert-butyl (R or S)-2-(4-cyclopropyl-2-((triisopropylsilyl)oxy)phenyl)-8-oxo-2,3,4,5a,6,7,8,9-octahydro-5H-1,2,5,7-tetraazabenzo[cd]azulene-5-carboxylate (0.79 g) as white solid. LCMS:(ESI, m/z): 581 $[M+1]^+$.

Step 3: Synthesis of Tert-Butyl (R or S)-2-(4-cyclopropyl-2-((triisopropylsilyl)oxy)phenyl)-2,3,4,5a,6,7,8,9-octahydro-5H-1,2,5,7-tetraazabenzo[cd]azulene-5-carboxylate To a solution of tert-butyl (8(R or S))-3-(4-cyclopropyl-2-triisopropylsilyloxy-phenyl)-11-oxo-2,3,7,10-tetrazatricyclo[6.4.1.04,13]trideca-1,4(13)-diene-7-carboxylate (0.75 g, 1 equiv, 1.29 mmol) in THF (7.5 mL) was added $BHr_3$·THF (1M, 4 equiv, 5.17 mL.) at 0° C. under a nitrogen atmosphere. The mixture was heated and stirred at 60° C. for 1 h. The reaction solution was then quenched by the dropwise addition of MeOH (20 ml) at rt, and then the mixture was then heated and stirred at 70° C. for 12 h. The reaction mixture was then concentrated under reduced pressure to tert-butyl (R or S)-2-(4-cyclopropyl-2-((triisopropylsilyl)oxy)phenyl)-2,3,4,5a,6,7,8,9-octahydro-5H-1,2,5,7-tetraazabenzo[cd]azulene-5-carboxylate (1.1 g) a yellow solid which was used in the next step directly without further purification. LCMS:(ESI, m/z): 567 $[M+1]^+$.

Step 4: Synthesis of Tert-Butyl ((R or S),E)-2-(4-cyclopropyl-2-((triisopropylsilyl)oxy)phenyl)-7-(3-(methylsulfonyl)allyl)-2,3,4,5a,6,7,8,9-octahydro-5H-1,2,5,7-tetraazabenzo[cd]azulene-5-carboxylate To a stirred solution of tert-butyl (8(R or S))-3-(4-cyclopropyl-2-triisopropylsilyloxy-phenyl)-2,3,7,10-tetrazatricyclo[6.4.1.04,13]trideca-1,4(13)-diene-7-carboxylate (330 mg, 1 equiv., 583 μmol) and (E)-3-bromo-1-methylsulfonyl-prop-1-ene (116 g, 1 equiv., 582 μmol) in DCM (6 mL) was added DIEA (150 mg, 2 equiv., 1.16 mmol, 202.80 μL) and the reaction solution was stirred at rt for 2 h. The reaction solution was concentrated and the crude product was purified by silica gel column chromatography, eluting with EtOAc/PE (4:1) to tert-butyl ((R or S),E)-2-(4-cyclopropyl-2-((triisopropylsilyl)oxy)phenyl)-7-(3-(methylsulfonyl)allyl)-2,3,4,5a,6,7,8,9-octahydro-5H-1,2,5,7-tetraazabenzo[cd]azulene-5-carboxylate (250 mg) as a light yellow solid. LCMS:(ESI, m/z): 685 $[M+1]^+$.

Step 5: Synthesis of ((R or S),E)-2-(4-cyclopropyl-2-((triisopropylsilyl)oxy)phenyl)-7-(3-(methylsulfonyl)allyl)-3,4,5,5a,6,7,8,9-octahydro-2H-1,2,5,7-tetraazabenzo[cd]azulene To a stirred solution of tert-butyl (8(R or S))-3-(4-cyclopropyl-2-triisopropylsilyloxy-phenyl)-10-[(E)-3-methylsulfonylallyl]-2,3,7,10-tetrazatricyclo[6.4.1.$0^{4,13}$]trideca-1,4(13)-diene-7-carboxylate (210 mg, 1 equiv., 307 μmol) in DCM (4 mL) was added TFA (1.54 g, 1 mL), and the reaction solution was stirred at rt for 0.5 h. The mixture was quenched by slow addition of saturated aqueous sodium bicarbonate (10 mL), and the resulting mixture was extracted with DCM (10 mL×3). The combined organic layers were washed with brine (10 mL), dried over anhydrous $Na_2SO_4$, filtered, and the filtrate was concentrated under reduced pressure to give ((R or S),E)-2-(4-cyclopropyl-2-((triisopropylsilyl)oxy)phenyl)-7-(3-(methylsulfonyl)allyl)-3,4,5,5a,6,7,8,9 -octahydro-2H-1,2,5,7-tetraazabenzo[cd]azulene (170 mg) as a yellow gum which was used in the next step without further purification. LCMS:(ESI, m/z): 585 $[M+1]^+$.

Step 5: Synthesis of [4-amino-6-(trifluoromethyl)-3-pyridyl][(8R)-3-(4-cyclopropyl-2-triisopropylsilyloxy-phenyl)-10-[(E)-3-methylsulfonylallyl]-2,3,7,10-tetrazatricyclo[6.4.1.$0^{4,13}$]trideca-1,4(13)-dien-7-yl]methanone To a stirred solution of ((R or S),E)-2-(4-cyclopropyl-2-((triisopropylsilyl)oxy)phenyl)-7-(3-(methylsulfonyl)allyl)-3,4,5,5a,6,7,8,9-octahydro-2H-1,2,5,7-tetraazabenzo[cd]azulene (170 mg, 1 equiv., 291 gmol) and 4-amino-6-(trifluoromethyl)pyridine-3-carboxylic acid (83.9 mg, 1.4 equiv., 407 μmol) in DMF (3 mL) was added HATU (133 mg, 1.2 equiv., 349 gmol) and DIEA (113 mg, 3 equiv., 872 μmol, 151.88 μL), and the reaction solution was stirred at rt for 1 h. The mixture was then quenched with water (10 mL) and the resulting mixture was extracted with EAOAc (10 mL×3). The combined organic layers were washed with brine (10 mL), dried over anhydrous $Na_2SO_4$, filtered, and the filtrate was concentrated under reduced pressure. The crude product was purified by silica gel column chromatography, eluting with EtOAc/PE (9:1) to afford ((R or S),E)-(4-amino-6-(trifluoromethyl)pyridin-3-yl)(2-(4-cyclopropyl-2-hydroxyphenyl)-7-(3-(methylsulfonyl)allyl)-2,3,4,5a,6,7,8,9-octahydro-5H-1,2,5,7-tetraazabenzo[cd]azulen-5-yl)methanone (150 mg) as a light yellow solid. This residue (130 mg, 1 equiv., 168 gmol) was then dissolved in DMF (2 mL) and KF (195 mg, 20 equiv., 3.36 mmol) was added. The reaction solution was stirred at rt for 0.5 h, and then was filtered by filter membrane, and the crude product was purified by preparative HPLC: (CD01-Phenomenex luna C18 150*25*10 um; flow rate: 15 mL/min; gradient: 18%-48% B over 11 min; mobile phase A: 0.05% aqueous FA, mobile phase B: acetonitrile) to afford ((R or S),E)-(4-amino-6-(trifluoromethyl)pyridin-3-yl)(2-(4-cyclopropyl-2-hydroxyphenyl)-7-(3-(methylsulfonyl)allyl)-3,4,6,7,8,9- hexahydro-2H-1,2,5,7-tetraazabenzo[cd]azulen-5(5aH)-yl) methanone (10.7 mg) as a white solid. LCMS:(ESI, m/z): 617 $[M+1]^+$. $^1H$ NMR: (400 MHz, DMSO-$d_6$) δ=9.99 (s, 1H), 8.13 (br s, 1H), 7.13 (d, J=8.4 Hz, 1H), 7.07 (s, 1H), 7.02-6.89 (m, 1H), 6.77 (td, $J_1$=2.0, $J_2$=3.6 Hz, 1H), 6.69 (d, J=2.0 Hz, 1H), 6.66-6.54 (m, 3H), 5.56-5.27 (m, 1H), 3.73-3.54 (m, 2H), 3.38-3.3 (m, 1H), 3.30-3.20 (m, 1H), 3.06 (s, 5H), 3.01-2.91 (m, 1H), 2.90-2.77 (m, 1H), 2.75-2.56 (m, 3H), 2.39 (br d, J=15.2 Hz, 1H), 1.93-1.82 (m, 1H), 1.01-0.90 (m, 2H), 0.69-0.58 (m, 2H).

Example 2. Biological Activity of the Compounds of the Present Disclosure

The biological activity of the compounds of the present disclosure was determined utilizing the assay described herein.

Protein Production and Purification

Full length Werner helicase construct (Uniprot: Q14191) with a N-terminal FLAG-AVI-TEV tag was expressed using the Sf9 cell/baculovirus expression system. The harvested cell pellet was resuspended and lysed in a glass homogenizer. After insoluble material was removed by centrifugation, the helicase protein was first purified with FLAG affinity resin and then further purified through a size-exclusion chromatography column. Peak fractions containing the purified protein were concentrated, split into aliquots and frozen in liquid nitrogen to be thawed before use.

Biochemical Assay Description (ATPase Activity)—Assay Format A

WRN activity was measured using an ATPase assay. Full length RN protein (aa 2-1432) (production described separately) was used for the biochemical activity assays. The 39-mer ssDNA "C6.18" (CAGCTATGGGACATTTGA-TACCGAGCAACAATTCACTGG) was purchased from IDT and used as a substrate. Quantification of ATP hydrolysis was evaluated using the ADP-Glo assay kit (Promega, Madison, WI).

An enzyme titration time-course was performed to determine the optimal assay conditions. Based on these results, the assay setup included 0.25 nM WRN protein, 100 nM C6.18 ssDNA, and 10 μM ATP in the following assay buffer: 20 mM HEPES, pH 7.5, 100 mM KCl, 1.5 mM $MgCl_2$, 0.01% NP-40, 3% glycerol, 5 mM EGTA, 0.5 mM DTT, 0.1 mg/mL BSA prepared in MilliQ water. To evaluate the inhibitory effects of the compounds, 11-point 3-fold serial dilutions were prepared in DMSO. 50 nL of each concentration in duplicate was preincubated for 30 minutes in a 384-well microplate (Greiner #784075) with 5 μL of 0.5 nM WRN in assay buffer. The reaction was initiated by adding 5 μL of 200 nM C6.18 DNA with 20 M ATP and was allowed to proceed for 30 minutes at room temperature. The reaction was stopped with 10 μL ADP-Glo reagent for 1 hour to remove unreacted ATP. Lastly, 20 μL ATP detection reagent was added and incubated for 1 hour to generate the luminescence signal. Control wells included "high controls" with no inhibition (DMSO, no compound) and "low controls" with maximum inhibition (no WRN). Luminescence was recorded on a PHERAstar (BMG Labtech, Ortenberg, Germany).

Data was fit using the "Smart Fit" method within the Genedata Screener Software (Basel, Switzerland) to obtain IC50 values using four-parameter fits. Reported IC50s are the geometric means of at least two independent trials.

Biochemical Assay Description (ATPase Activity)—Assay Format B

WRN activity was measured using an ATPase assay. Full length WRN protein (aa 2-1432) (production described separately) was used for the biochemical activity assays. The 39-mer ssDNA "C6.18" (CAGCTATGGGACATTTGA-TACCGAGCAACAATTCACTGG) was purchased from IDT and used as a substrate. Quantification of ATP hydrolysis was evaluated using the ADP-Glo assay kit (Promega, Madison, WI).

An enzyme titration time-course was performed to determine the optimal assay conditions. Based on these results, the assay setup included 0.25 nM WRN protein, 100 nM C6.18 ssDNA, and 100 μM ATP in the following assay buffer: 20 mM HEPES, pH 7.5, 100 mM KCl, 1.5 mM MgCl2, 0.01% NP-40, 3% glycerol, 5 mM EGTA, 0.5 mM DTT, 0.1 mg/mL BSA prepared in MilliQ water. To evaluate the inhibitory effects of the compounds, 11-point 3-fold serial dilutions were prepared in DMSO. 50 nL of each concentration in duplicate was preincubated for 60 minutes in a 384-well microplate (Revvity #6007299) with 5 μL of 0.5 nM WRN & 200 μM ATP in assay buffer. The reaction was initiated by adding 5 μL of 200 nM C6.18 DNA and was allowed to proceed for 30 minutes at room temperature. The reaction was stopped with 1 OL ADP Glo reagent for 1 hour to remove unreacted ATP. Lastly, 20 μL ATP detection reagent was added and incubated for 1 hour to generate the luminescence signal. Control wells included "high controls" with no inhibition (DMSO, no compound) and "low controls" with maximum inhibition (no WRN). Luminescence was recorded on an EnSight multimode plate reader (Revvity #HH34000000).

Data was fit using the "Smart Fit" method within the Genedata Screener Software (Basel, Switzerland) to obtain IC50 values using four-parameter fits. Reported IC50s are the geometric means of at least two independent trials.

Cell Assay Description

Compounds were dissolved in DMSO to a concentration of 10 mM. Compounds were then serially diluted in 10 3-fold steps in DMSO using an EVO (Tecan). Plates were then spun down for 1 minute at 1, 000 RPM at room temperature. 50 nL of compounds or DMSO were transferred to 384 white, clear bottom plates (Corning #3765) using Echo665 (Bec an).

The colon carcinoma lines HCT116 (RRID: CVCL_0291) and HT29 (RRID: CVCL 0320) were obtained from ATCC. HCT116 and HT29 cells were cultured in growth media composed of McCoy's 5A medium (Thermo Fisher #16600082) with 10% fetal calf serum (Thermo Fisher #16000044). All cells were maintained at 37° C. with 5% CO2 incubator.

On day of assay, cells were harvested from culture flasks using trypsin-EDTA (Thermo Fisher #25200056). After harvesting, cells were spun down for 5 minutes at 1200 RPM. Cells were resuspended in 10 mL of growth media and counted using Countess (Thermo Fisher). Cell concentrations were adjusted to 50 cells/well for HCT116 and 500 cell/well for HT29. 50 μL of diluted cells were added to compound treated 384 well plates using a 12 channel, 300 uL electronic handheld pipette (Integra). Cell treated plates were placed in 37 C with 5% CO2 incubator for 7 days.

Afterwards, cells were removed from incubator and equilibrated to room temperature for 15 minutes. 35 μL of CellTiter Glo (Promega #G7573) reagent were added to each well using a 12 channel, 300 uL electronic handheld pipette (Integra). Plates were incubated for 20 minutes at room temperature. Luminescence quantification was performed using Envision (PerkinElmer).

For data analysis, the assay background signal was determined in wells containing medium, but no cells. Potencies were calculated by linear least squares fit to the four-parameter logistic IC50 equation. The reported IC50 values are the geometrical mean of at least 2 independent replicates.

The activity values $IC_{50}$ of each compound are shown in Table A below.

Values of Biochemical ATPase ADPGlo—Assay Format A and Format B $AC_{50}$ in Table A are presented in ranges, in which "+"<0.0015 μM, 0.0015 μM≤"++"<0.005 μM, 0.005 μM≤"+++"<0.015 μM, 0.015 μM≤"++++"<0.055 μM, and 0.055 μM≤"+++++."

Values of Viability $AC_{50}$ (μM) HCT116 (MSI) in Table A are presented in ranges, in which 0.001 μM≤"*"<0.100 M, 0.100 μM≤""<0.250 μM, 0.250 μM≤"*"<0.500 μM, 0.500 μM≤"**"<1.000 μM, and 1.000 μM≤"***."

Values of Viability $AC_{50}$ (μM) HT29 (MSS) in Table A are presented in ranges, in which<1.00 μM "#", 1.00 μM≤"##"<3.00 μM, and 3.00 μM≤"###".

TABLE A

| ATPase ADPGlo AC50 (uM)- Assay Format A | ATPase ADPGlo AC50 (uM)- Assay Format B | HCT116 (MSI) Viability 7 Day Abs AC50 (uM) | HT29 (MSS) Viability 7 Day CTGAbs AC50 (uM) | Compound Number | Example Number |
|---|---|---|---|---|---|
| ++ | ++++ | ** | ### | 1 | A-4 |
| + | +++ | * | ### | 2 | A-5 |
| ++ | ++++ | * | ### | 3 | A-6 |
| + | ++++ | * | ### | 4 | A-7 |
| + | +++ | * | ### | 5 | A-8 |
| ++ | ++++ | * | ### | 6 | A-9 |
| + | +++ | * | ### | 7 | B-2 |
| + | +++ | * | ### | 8 | B-3 |
| ++ | ++++ | * | ### | 9 | B-4 |
| + | ++++ | * | ### | 10 | B-5 |
| +++++ | | ***** | ### | 11 | B-6 |
| + | ++++ | * | ### | 12 | B-7 |
| ++ | ++++ | ** | ### | 13 | B-8 |
| ++ | ++++ | * | ### | 14 | B-9 |
| ++++ | +++++ | *** | ### | 15 | B-10 |
| +++++ | | ***** | ### | 16 | B-11 |
| ++++ | +++++ | ***** | ### | 17 | B-12 |
| ++ | ++++ | * | ### | 18 | B-13 |
| ++ | ++++ | * | ### | 19 | C-1 |
| + | +++ | * | ### | 20 | C-2 |
| + | +++ | * | ### | 21 | C-3 |
| ++ | ++++ | *** | ### | 22 | C-4 |
| + | ++ | * | ### | 23 | C-5 |
| + | +++ | * | ### | 24 | C-6 |
| + | +++ | * | ### | 25 | C-7 |
| + | +++ | * | ### | 26 | C-8 |
| + | ++ | * | ### | 27 | C-9 |
| + | ++ | * | ## | 28 | C-10 |
| ++++ | +++++ | ** | ### | 29 | D-1 |
| + | +++ | * | ### | 30 | D-2 |
| ++ | ++++ | *** | ### | 31 | E-2 |
| + | +++ | * | ### | 32 | E-1 |
| ++ | +++ | * | ### | 33 | E-3 |
| ++ | +++ | *** | ### | 34 | E-4 |
| +++ | | ** | ### | 35 | F-1 |
| ++++ | | **** | ### | 36 | F-2 |
| ++++ | | ***** | ### | 37 | F-3 |
| + | +++ | * | ### | 38 | F-4 |
| ++ | ++++ | * | ### | 39 | K-3 |
| + | ++++ | * | ### | 40 | K-4 |
| ++ | ++++ | * | ### | 41 | K-5 |
| + | +++ | * | ### | 42 | K-6 |
| + | +++ | * | ### | 43 | K-7 |
| + | +++ | * | ### | 44 | K-8 |
| ++ | ++++ | ***** | ### | 45 | K-9 |
| ++ | ++++ | * | ### | 46 | K-10 |
| +++ | +++++ | ***** | ### | 47 | K-11 |
| ++ | | ** | ### | 48 | K-12 |
| + | ++++ | * | ### | 49 | K-13 |
| ++ | ++++ | ** | ### | 50 | K-14 |
| ++++ | | ***** | ### | 51 | K-15 |
| +++ | +++++ | *** | ### | 52 | K-16a |
| ++++ | +++++ | **** | ### | 53 | K-16b |
| + | +++ | ***** | ### | 54 | K-17a |
| + | ++++ | ** | ### | 55 | K-17b |
| ++++ | | *** | ### | 56 | K-18 |
| ++ | ++++ | ** | ### | 57 | L-8 |
| ++ | ++++ | ** | ### | 58 | B-9-1 |
| ++ | ++++ | ** | ### | 59 | B-9-3 |
| +++ | +++++ | ***** | ### | 60 | B-15 |
| +++ | +++++ | *** | ### | 61 | B-9-2 |
| ++ | +++++ | ** | ### | 62 | C-6-9 |
| ++ | ++++ | **** | ### | 63 | L-10 |

TABLE A-continued

| ATPase ADPGlo AC50 (uM)- Assay Format A | ATPase ADPGlo AC50 (uM)- Assay Format B | HCT116 (MSI) Viability 7 Day Abs AC50 (uM) | HT29 (MSS) Viability 7 Day CTGAbs AC50 (uM) | Compound Number | Example Number |
|---|---|---|---|---|---|
| | ++++ | * | ### | 64 | L-1-10 |
| + | ++++ | * | ### | 65 | B-9-4 |
| + | +++ | * | ### | 66 | D-4 |
| ++ | +++ | * | ### | 67 | A-4-1 |
| +++++ | +++++ | ***** | ### | 68 | A-4-12 |
| +++ | ++++ | ** | ### | 69 | A-4-3 |
| +++++ | +++++ | ***** | ### | 70 | A-4-6 |
| | +++ | * | ### | 71 | L-4 |
| + | ++ | * | ### | 72 | L-11-2 |
| ++ | ++++ | ** | ### | 73 | |
| + | +++ | * | ### | 74 | C-11-9 |
| + | ++ | * | ### | 75 | C-16 |
| | +++ | * | ### | 76 | C-11-8 |
| +++ | +++++ | **** | ### | 82 | |
| +++ | +++++ | **** | ### | 83 | |
| ++ | ++++ | * | ### | 84 | D-3 |
| + | ++++ | *** | ### | 86 | F-5 |
| + | ++ | * | ### | 87 | C-6-1 |
| | +++ | * | ### | 88 | C-31 |
| + | ++++ | * | ### | 89 | C-32 |
| + | +++ | * | ### | 90 | C-6-2 |
| + | +++ | *** | ### | 91 | L-9-2 |
| + | ++++ | * | ### | 92 | A-29 |
| + | +++ | * | ### | 93 | C-6-3 |
| | ++++ | * | ### | 94 | C-6-4 |
| + | ++ | * | ### | 95 | C-6-5 |
| + | +++ | * | ### | 96 | C-6-6 |
| + | +++ | * | ### | 97 | C-6-7 |
| ++++ | | *** | ### | 98 | A-4-23 |
| ++ | ++++ | ** | ### | 100 | L-1 |
| ++ | ++++ | ** | ### | 101 | L-1-9 |
| +++ | +++++ | **** | ### | 102 | B-2-3 |
| + | ++++ | *** | ### | 103 | K-19 |
| +++ | +++++ | * | ### | 104 | B-14 |
| | | ***** | ### | 105 | K-20 |
| ++ | +++++ | *** | ### | 106 | B-2-4 |
| +++ | ++++ | ** | ### | 107 | C-6-8 |
| +++ | | | | 108 | A-4-13 |
| +++ | ++++ | *** | ### | 109 | A-4-2 |
| +++ | +++++ | ** | ### | 110 | A-4-10 |
| ++++ | | | | 111 | A-4-4 |
| +++ | +++++ | ** | ### | 112 | A-4-9 |
| +++ | | | | 113 | A-4-17 |
| +++ | +++++ | *** | ### | 114 | A-4-15 |
| ++++ | | **** | ### | 115 | A-4-14 |
| +++++ | | ***** | ### | 116 | A-4-5 |
| ++ | +++ | * | ### | 117 | A-4-16 |
| +++++ | | ***** | ### | 118 | A-4-19 |
| ++++ | | ***** | ### | 119 | A-4-22 |
| ++ | | ***** | ### | 120 | A-4-18 |
| ++++ | | | | 121 | A-4-11 |
| ++++ | | **** | ### | 122 | A-4-20 |
| ++++ | | *** | ### | 123 | A-4-21 |
| ++++ | | | | 124 | A-4-7 |
| +++++ | | | | 125 | A-4-8 |
| +++ | | *** | ### | 126 | A-4-24 |
| + | +++ | * | ### | 128 | A-4-25 |
| + | ++ | * | ## | 129 | C-22 |
| + | +++ | * | ### | 130 | E-11 |
| + | +++ | * | ### | 131 | A-34 |
| | ++ | * | ### | 132 | C-11 |
| + | +++ | * | ### | 133 | A-7-1 |
| + | ++ | * | ### | 134 | C-11-1 |
| + | +++ | * | ### | 135 | E-10 |
| ++ | ++++ | ** | ### | 136 | L-9 |
| + | | * | ### | 137 | C-11-10 |
| + | +++ | * | ### | 138 | C-11-2 |
| + | +++ | * | ### | 139 | L-1-7 |
| | +++ | * | ### | 140 | C-11-3 |
| + | +++ | * | ### | 141 | L-1-8 |
| + | ++++ | * | ### | 142 | C-11-4 |
| + | +++ | * | ### | 143 | A-25 |
| + | ++ | * | ### | 144 | C-11-5 |
| + | +++ | * | ### | 145 | C-12-1 |
| + | +++ | * | ### | 146 | C-11-6 |
| | +++ | * | ### | 147 | C-8-3 |

TABLE A-continued

| ATPase ADPGlo AC50 (uM)- Assay Format A | ATPase ADPGlo AC50 (uM)- Assay Format B | HCT116 (MSI) Viability 7 Day Abs AC50 (uM) | HT29 (MSS) Viability 7 Day CTGAbs AC50 (uM) | Compound Number | Example Number |
|---|---|---|---|---|---|
| + | +++ | * | ### | 148 | C-33 |
| + | +++ | *** | ### | 149 | C-11-7 |
| + | +++ | * | ### | 150 | B-2-1 |
| + | | * | ### | 151 | C-13 |
| + | ++++ | * | ### | 152 | A-7-2 |
| + | ++ | * | ### | 153 | C-14 |
| + | | * | ### | 154 | C-34 |
| + | +++ | * | ### | 155 | C-24 |
| ++ | +++ | * | ### | 156 | C-22-2 |
| + | +++ | * | ### | 157 | C-12-2 |
| + | ++ | * | ### | 158 | C-8-4 |
| ++ | ++++ | * | ### | 159 | C-11-12 |
| + | ++ | * | ### | 160 | C-27 |
| + | +++ | * | ### | 161 | C-8-1 |
| + | +++ | * | ### | 162 | A-4-32 |
| + | +++ | * | ### | 163 | A-10 |
| | ++ | * | ### | 164 | C-11-11 |
| | ++++ | * | ### | 165 | C-15 |
| + | +++ | * | ### | 166 | A-4-26 |
| + | ++++ | * | ### | 167 | A-4-27 |
| | +++ | * | ### | 168 | E-8 |
| + | ++++ | * | ### | 169 | C-26 |
| +++++ | | ***** | ### | 170 | B-2-2 |
| | ++++ | * | ### | 171 | C-20 |
| | +++ | * | ### | 172 | A-10-1 |
| | +++ | * | ### | 173 | C-29 |
| + | ++ | * | ### | 174 | C-28 |
| | ++ | ** | ### | 175 | A-25-1 |
| | ++ | * | ### | 176 | C-30 |
| | +++ | * | ### | 177 | A-24 |
| + | +++ | * | ### | 178 | A-4-29 |
| | ++++ | ** | ### | 179 | A-33 |
| | ++++ | * | ### | 180 | A-5-1 |
| + | ++ | * | ### | 181 | A-4-28 |
| + | ++ | * | ### | 182 | A-4-30 |
| + | ++ | * | ### | 183 | A-14 |
| + | +++ | * | ### | 184 | A-22 |
| | ++++ | * | ## | 185 | C-35 |
| + | +++ | * | ### | 186 | A-16 |
| + | +++ | * | ### | 187 | C-22-1 |
| | ++ | * | ### | 188 | A-28 |
| + | +++ | * | ### | 189 | E-6 |
| | +++ | * | ### | 190 | E-7 |
| | +++ | * | ### | 191 | A-10-2 |
| + | +++ | * | ### | 192 | A-10-12 |
| + | +++ | * | ### | 193 | A-10-3 |
| ++ | +++ | * | ### | 194 | A-13 |
| + | +++ | * | ### | 195 | E-5 |
| + | +++ | * | ### | 196 | A-10-4 |
| | +++ | * | ### | 197 | A-10-5 |
| + | +++ | * | ### | 198 | C-25 |
| + | +++ | * | ### | 199 | A-10-6 |
| + | ++++ | * | ### | 200 | A-26 |
| +++++ | + | ***** | ### | 201 | L-6 |
| ++ | ++ | * | ### | 202 | A-10-7 |
| | +++ | * | ### | 203 | L-1-2 |
| | ++++ | * | ### | 204 | A-4-33 |
| | +++ | * | ### | 205 | C-25-6 |
| ++ | ++ | * | ### | 206 | A-12 |
| | +++ | * | ### | 207 | A-10-8 |
| | ++ | * | ### | 208 | A-18 |
| | ++ | * | ### | 209 | A-27 |
| | ++ | * | ### | 210 | A-10-9 |
| | ++ | * | ### | 211 | A-17 |
| | ++ | * | ### | 212 | A-31 |

TABLE A-continued

| ATPase ADPGlo AC50 (uM)- Assay Format A | ATPase ADPGlo AC50 (uM)- Assay Format B | HCT116 (MSI) Viability 7 Day Abs AC50 (uM) | HT29 (MSS) Viability 7 Day CTGAbs AC50 (uM) | Compound Number | Example Number |
|---|---|---|---|---|---|
| | +++ | * | ### | 213 | A-10-10 |
| | +++ | * | ### | 214 | A-30 |
| | ++ | * | ### | 215 | L-1-5 |
| | ++ | * | ### | 216 | A-32 |
| | ++ | * | ### | 217 | L-1-11 |
| | +++ | * | ### | 218 | L-1-1 |
| | +++ | * | ### | 219 | L-7 |
| | ++ | * | ### | 220 | A-15 |
| | +++ | * | ### | 221 | E-9 |
| | ++ | * | ### | 222 | L-11-1 |
| | ++ | * | ### | 223 | A-17-1 |
| | +++ | * | ### | 224 | L-2 |
| | ++++ | ** | ### | 225 | A-19 |
| | +++ | * | ### | 226 | L-5 |
| | +++ | * | # | 227 | L-1-3 |
| | ++ | * | ### | 228 | A-11 |
| | ++++ | * | ### | 229 | L-1-4 |
| | ++++ | * | ### | 231 | A-23 |
| | +++ | * | ### | 232 | L-11 |
| | +++++ | ** | ### | 233 | |
| | ++++ | * | ### | 234 | C-25-7 |
| | +++++ | ** | ### | 235 | C-25-8 |
| | +++ | * | ### | 236 | C-8-2 |
| | ++ | * | ### | 237 | F-6 |
| | +++ | * | ### | 238 | F-7 |
| +++ | +++++ | ** | ### | 239 | C-17 |
| + | ++ | * | ### | 240 | C-19 |
| + | +++ | * | ### | 241 | C-21 |
| ++ | ++++ | * | ### | 242 | C-23 |
| ++ | ++++ | * | ## | 243 | C-18 |
| ++ | ++++ | * | ### | 244 | L-9-1 |
| + | +++ | * | ### | 245 | A-10-11 |
| + | +++ | * | ### | 246 | C-25-5 |
| ++ | +++ | * | ### | 247 | A-10-14 |
| + | ++ | * | ### | 248 | A-35 |
| + | ++ | * | ### | 249 | C-25-3 |
| + | + | * | ### | 250 | C-25-1 |
| + | +++ | * | ### | 251 | C-25-2 |
| ++ | +++ | * | ### | 252 | A-20 |
| | +++ | * | ### | 253 | L-2-1 |
| | ++++ | * | ### | 254 | L-3 |
| + | +++ | * | ### | 255 | C-25-4 |
| ++++ | +++++ | *** | ### | 256 | A-21 |
| +++++ | +++++ | ***** | ### | 257 | L-12 |
| +++ | ++++ | * | ### | 258 | L-1-6 |
| | ++++ | * | ### | 259 | A-10-13 |
| + | ++ | * | ### | 260 | C-25-9 |

EQUIVALENTS

The details of one or more embodiments of the disclosure are set forth in the accompanying description above. Although any methods and materials similar or equivalent to those described herein can be used in the practice or testing of the present disclosure, the preferred methods and materials are now described. Other features, objects, and advantages of the disclosure will be apparent from the description and from the claims. In the specification and the appended claims, the singular forms include plural referents unless the context clearly dictates otherwise. Unless defined otherwise, all technical and scientific terms used herein have the same meaning as commonly understood by one of ordinary skill in the art to which this disclosure belongs. All patents and publications cited in this specification are incorporated by reference.

The foregoing description has been presented only for the purposes of illustration and is not intended to limit the disclosure to the precise form disclosed, but by the claims appended hereto.

The invention claimed is:

1. A compound of Formula (III-a'):

(III-a')

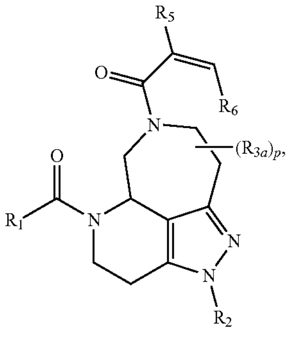

or a pharmaceutically acceptable salt, solvate, hydrate, stereoisomer, or tautomer thereof, wherein:

$R_1$ is $C_3$-$C_{10}$ cycloalkyl, $C_6$-$C_{10}$ aryl, 5- to 10-membered heteroaryl, or 3- to 10-membered heterocyclyl, wherein the $C_3$-$C_{10}$ cycloalkyl, $C_6$-$C_{10}$ aryl, 5- to 10-membered heteroaryl, or 3- to 10-membered heterocyclyl is optionally substituted with one or more $R_{1a}$;

each $R_{1a}$ independently is oxo, halo, cyano, —OH, —$NH_2$, —$NO_2$, —NH($C_1$-$C_6$ alkyl), —N($C_1$-$C_6$ alkyl)$_2$, —NH—C(O)($C_1$-$C_6$ alkyl), —S($C_1$-$C_6$ alkyl), —S(O)$_2$($C_1$-$C_6$ alkyl), —S(O)$_2$($NH_2$), —C(O)(H), —C(O)$NH_2$, —O(3- to 10-membered heterocyclyl), $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, $C_3$-$C_{10}$ cycloalkyl, $C_6$-$C_{10}$ aryl, 5- to 10-membered heteroaryl, or 3-to 10-membered heterocyclyl, wherein the —NH($C_1$-$C_6$ alkyl), —N($C_1$-$C_6$ alkyl)$_2$ —NH—C(O)($C_1$-$C_6$ alkyl), —S($C_1$-$C_6$ alkyl), —S(O)$_2$($C_1$-$C_6$ alkyl), —O(3- to 10-membered heterocyclyl), $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, $C_3$-$C_{10}$ cycloalkyl, $C_6$-$C_{10}$ aryl, 5-to 10-membered heteroaryl, or 3- to 10-membered heterocyclyl is optionally substituted with one or more $R_{1b}$;

each $R_{1b}$ independently is oxo, halo, cyano, —OH, —O($C_1$-$C_6$ alkyl), —O($C_1$-$C_6$ haloalkyl), —O($C_2$-$C_6$ alkenyl), —O($C_2$-$C_6$ alkynyl), —$NH_2$, —NH($C_1$-$C_6$ alkyl), —N($C_1$-$C_6$ alkyl)$_2$, —NH($C_1$-$C_6$ haloalkyl), —S($C_1$-$C_6$ alkyl), —S(O)$_2$($C_1$-$C_6$ alkyl), —C(O)$NH_2$, $C_1$-$C_6$ alkyl, $C_3$-$C_{10}$ cycloalkyl, or 3-to 10-membered heterocyclyl optionally substituted with oxo;

$R_2$ is $C_6$-$C_{10}$ aryl or 5- to 10-membered heteroaryl, wherein the $C_6$-$C_{10}$ aryl or 5- to 10-membered heteroaryl is optionally substituted with one or more $R_{2a}$;

each $R_{2a}$ independently is halo, cyano, —OH, —$NH_2$, —NH($C_1$-$C_6$ alkyl), —N($C_1$-$C_6$ alkyl)$_2$, —SH, —S(O)$_2NH_2$, —$SF_5$, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, —S($C_1$-$C_6$ haloalkyl), —S($C_1$-$C_6$ alkyl), $C_3$-$C_{10}$ cycloalkyl, $C_6$-$C_{10}$ aryl, 5- to 10-membered heteroaryl, or 3- to 10-membered heterocyclyl, wherein the $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, —S($C_1$-$C_6$ haloalkyl), —S($C_1$-$C_6$ alkyl), $C_3$-$C_{10}$ cycloalkyl, $C_6$-$C_{10}$ aryl, 5- to 10-membered heteroaryl, or 3- to 10-membered heterocyclyl is optionally substituted with one or more $R_{2a1}$;

each $R_{2a1}$ independently is oxo, halo, cyano, —OH, —$NH_2$, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, —NH—C(O)($C_1$-$C_6$ alkyl), —C(O)$NH_2$, or —OC(O)($C_1$-$C_6$ alkyl), wherein the $C_1$-$C_6$ alkyl, $C_2$-$C_6$ alkenyl, $C_2$-$C_6$ alkynyl, $C_1$-$C_6$ alkoxy, or $C_1$-$C_6$ haloalkyl is optionally substituted with one or more —OH;

each $R_{3a}$ independently is cyano, halo, —OH, —$NH_2$, —NH($C_1$-$C_6$ alkyl), —N($C_1$-$C_6$ alkyl)$_2$, —N($C_1$-$C_6$ alkyl)($C_1$-$C_6$ haloalkyl), —NH—C(O)($C_1$-$C_6$ alkyl), —O($C_3$-$C_{10}$ cycloalkyl), —O(3- to 10-membered heterocyclyl), $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_1$-$C_6$ haloalkoxy, $C_3$-$C_{10}$ cycloalkyl, 3- to 10-membered heterocyclyl, 5- to 10-membered heteroaryl, —S(O)(=NH)($C_1$-$C_6$ alkyl), —SO$_2$($C_1$-$C_6$ alkyl), —S($C_1$-$C_6$ alkyl), or —S($C_1$-$C_6$ haloalkyl);

p is 0, 1, 2, 3, 4, 5, or 6;

$R_5$ is H, halo, cyano, or $C_1$-$C_6$ alkyl; and $R_6$ is H, halo, cyano, $C_1$-$C_6$ alkyl, or $C_1$-$C_6$ alkoxy, wherein the $C_1$-$C_6$ alkyl or $C_1$-$C_6$ alkoxy is optionally substituted with one or more —$NH_2$, —NH($C_1$-$C_6$ alkyl), or —N($C_1$-$C_6$ alkyl)$_2$, or $R_5$ and $R_6$, together with the atoms to which they are attached, form a $C_4$-$C_{10}$ cycloalkenyl.

2. The compound of claim 1, wherein $R_1$ is 5- or 6-membered heteroaryl substituted with one or more Ria.

3. The compound of claim 2, wherein each $R_{1a}$ independently is halo, —$NH_2$, or $C_1$-$C_6$ haloalkyl.

4. The compound of claim 1, wherein $R_1$ is

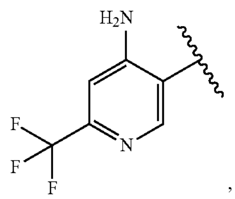,
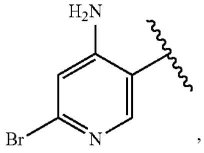,
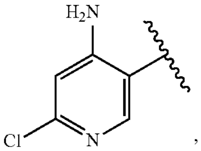,
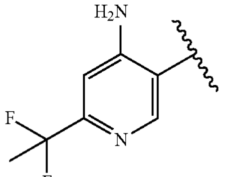,
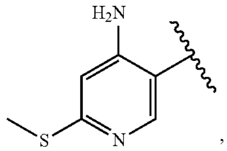,
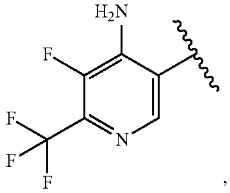,
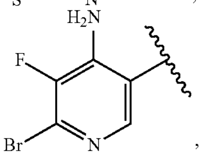,
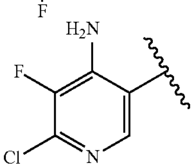,
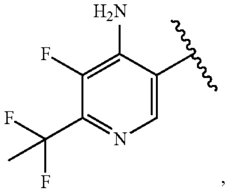,
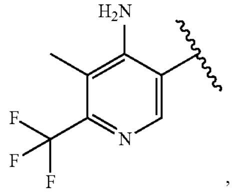,
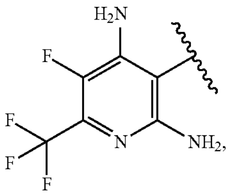, or
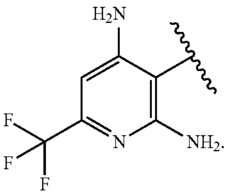.

5. The compound of claim 1, wherein $R_2$ is $C_6$ aryl substituted with one or more $R_{2a}$.

6. The compound of claim 5, wherein each $R_{2a}$ independently is —OH or $C_3$-$C_{10}$ cycloalkyl.

7. The compound of claim 1, wherein p is 0.

8. The compound of claim 1, wherein $R_5$ is H.

9. The compound of claim 1, wherein $R_6$ is H.

10. The compound of claim 1, wherein the compound is a compound of Formula (III-a'''):

(III-a''')

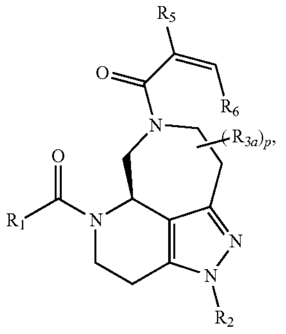

or a pharmaceutically acceptable salt, solvate, hydrate, stereoisomer, or tautomer thereof.

11. The compound of claim 1, wherein the compound is a compound of Formula (IV-a), (IV-d), or (IV-g):

(IV-a)

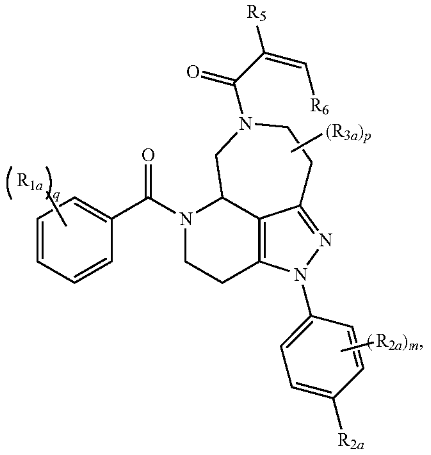

(IV-d)

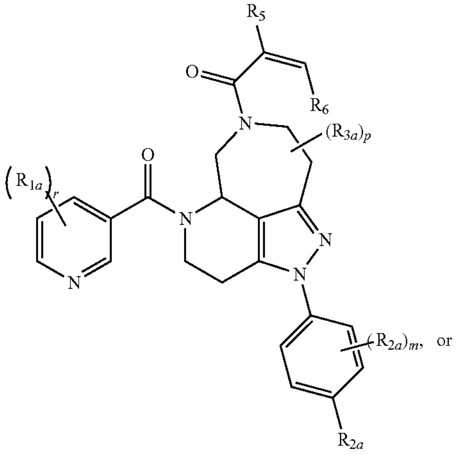

or

-continued (IV-g)

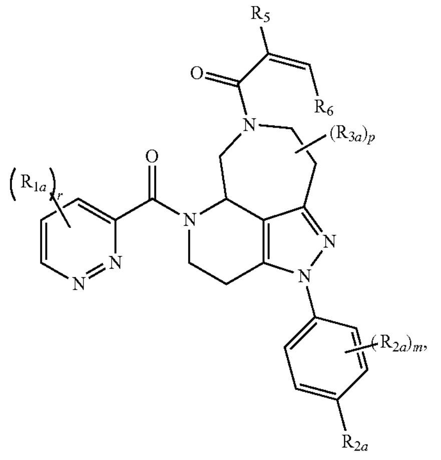

or a pharmaceutically acceptable salt, solvate, hydrate, stereoisomer, or tautomer thereof, wherein m is 0, 1, 2, 3, or 4: q is 0, 1, 2, 3, 4, or 5; and r is 0, 1, 2, 3, or 4.

12. The compound of claim 11, wherein the compound is a compound of Formula (IV-a'), (IV-d'), or (IV-g'):

(IV-a')

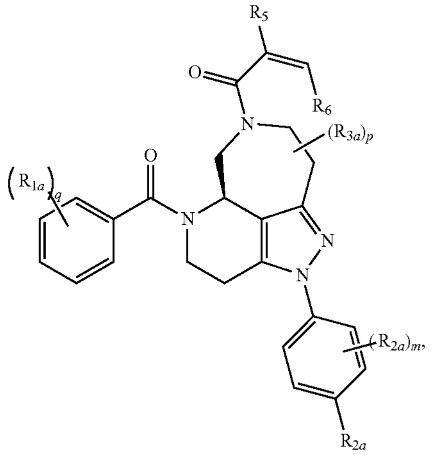

(IV-d')

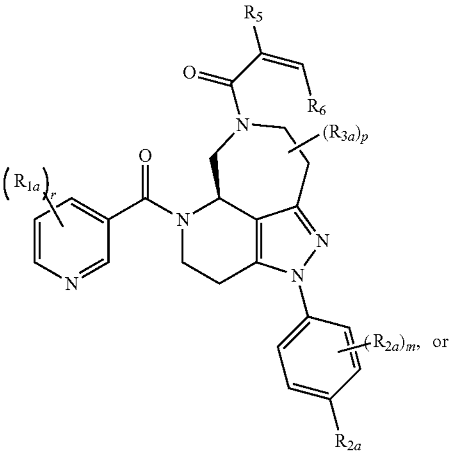

or

-continued (IV-g')

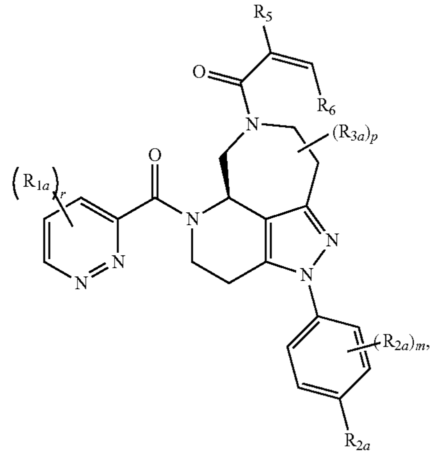

or a pharmaceutically acceptable salt, solvate, hydrate, stereoisomer, or tautomer thereof, wherein m is 0, 1, 2, 3, or 4: q is 0, 1, 2, 3, 4, or 5; and r is 0, 1, 2, 3, or 4.

13. The compound of claim 1, wherein the compound is a compound of Formula (III-c'):

(III-c')

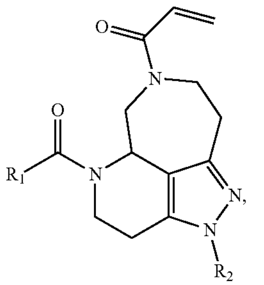

or a pharmaceutically acceptable salt, solvate, hydrate, stereoisomer, or tautomer thereof.

14. The compound of claim 1, wherein the compound is a compound of Formula (III-c):

(III-c)

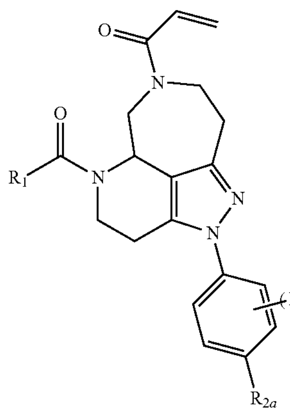

or a pharmaceutically acceptable salt, solvate, hydrate, stereoisomer, or tautomer thereof, wherein m is 0, 1, 2, 3, or 4.

15. The compound of claim 14, wherein the compound is a compound of Formula (III-c"):

(III-c")

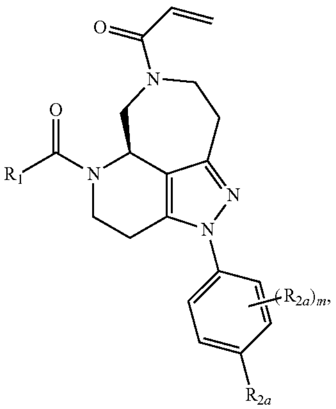

or a pharmaceutically acceptable salt, solvate, hydrate, stereoisomer, or tautomer thereof, wherein m is 0, 1, 2, 3, or 4.

16. The compound of claim 1, wherein the compound is a compound of Formula (IV-f):

(IV-f)

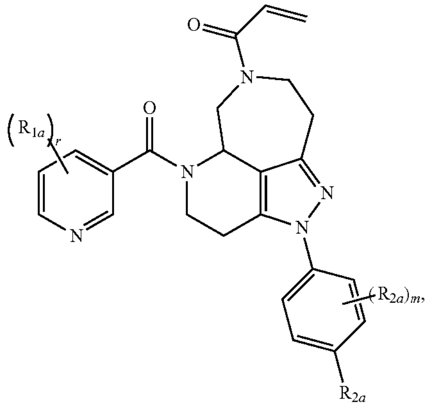

or a pharmaceutically acceptable salt, solvate, hydrate, stereoisomer, or tautomer thereof, wherein m is 0, 1, 2, 3, or 4; and r is 0, 1, 2, 3, or 4.

17. The compound of claim 1, wherein the compound is selected from Compound Nos. 1-35, 57-76, 78-79, 81-84, 87-98, 100-102, 104, 106-126, 128-168, 170-197, 199-200, 202-204, 206-218, 220-221, 223-229, 232, 236, 240-248, 252-254, 256, and 258-259, or a pharmaceutically acceptable salt thereof.

18. The compound of claim 1, wherein the compound is selected from Compound Nos. 1A, 4A-5A, 7A-26A, 62A, 67A-71A, 74A-76A, 87A-98A, 100A-102A, 104A, 106A, 126A, 128A, 131A-134A, 137A-155A, 157A-159A, 161A-167A, 172A-173A, 175A, 177A-179A, 181A-183A, 185A-186A, 191A-194A, 196A-197A, 199A-200A, 202A-204A, 206A-211A, 213A-216A, 218A, 220A, 223A, 227A-229A, 236A, 242A-245A, 247A-248A, and 258A-259A, or a pharmaceutically acceptable salt thereof.

19. A pharmaceutical composition comprising the compound of claim 1, or a pharmaceutically acceptable salt, solvate, hydrate, stereoisomer, or tautomer thereof, and one or more pharmaceutically acceptable diluent or carrier.
20. A compound which is:
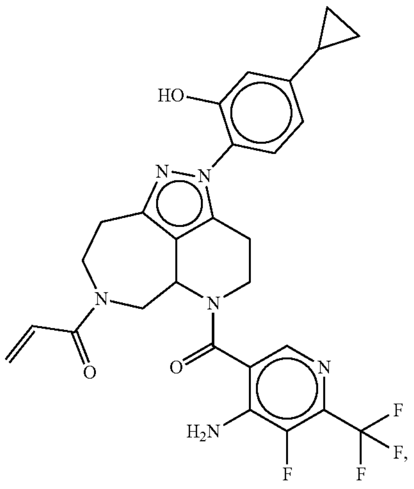
or a pharmaceutically acceptable salt, solvate, hydrate, stereoisomer, or tautomer thereof.
21. A compound which is:
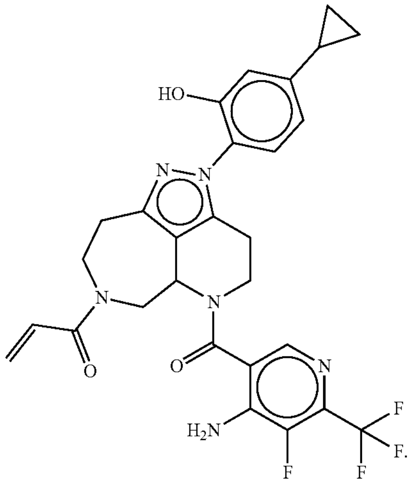
* * * * *